(12) United States Patent
Malcolm et al.

(10) Patent No.: US 7,772,178 B2
(45) Date of Patent: Aug. 10, 2010

(54) PHARMACEUTICAL FORMULATIONS AND METHODS OF TREATMENT USING THE SAME

(75) Inventors: Bruce A. Malcolm, Paoli, PA (US); Prudence K. Bradley, Cranford, NJ (US); Anastasia Pavlovsky, Morris Plains, NJ (US); Wing-Kee Philip Cho, Princeton, NJ (US); Zhihui Qiu, Bridgewater, NJ (US)

(73) Assignee: Schering Corporation, Kenilworth, NJ (US)

( * ) Notice: Subject to any disclaimer, the term of this patent is extended or adjusted under 35 U.S.C. 154(b) by 529 days.

(21) Appl. No.: 11/444,078

(22) Filed: May 31, 2006

(65) Prior Publication Data

US 2007/0010431 A1      Jan. 11, 2007

Related U.S. Application Data

(60) Provisional application No. 60/686,945, filed on Jun. 2, 2005.

(51) Int. Cl.
    *A61K 38/12* (2006.01)
(52) U.S. Cl. .................. 514/2; 514/9; 514/16; 514/17; 514/18
(58) Field of Classification Search .................. None
    See application file for complete search history.

(56) References Cited

U.S. PATENT DOCUMENTS

| | | | |
|---|---|---|---|
| 5,501,969 A | 3/1996 | Hastings et al. | |
| 5,712,145 A | 1/1998 | Houghton et al. | |
| 5,866,684 A | 2/1999 | Attwood et al. | |
| 6,143,715 A | 11/2000 | Llinas-Brunet et al. | |
| 6,265,380 B1 | 7/2001 | Tung et al. | |
| 6,268,207 B1 | 7/2001 | Bailey | |
| 6,323,180 B1 | 11/2001 | Llinas-Brunet et al. | |
| 6,413,974 B1 | 7/2002 | Dumont et al. | |
| 6,608,027 B1 | 8/2003 | Tsantrizos et al. | |
| 6,617,309 B2 | 9/2003 | Tung et al. | |
| 6,767,991 B1 | 7/2004 | Llinas-Brunet et al. | |
| 6,800,434 B2 | 10/2004 | Saksena et al. | |
| 6,894,072 B2 | 5/2005 | Arasappan et al. | |
| 7,173,057 B2 | 2/2007 | Chen et al. | |
| 7,186,747 B2 | 3/2007 | Arasappan et al. | |
| 7,192,957 B2 | 3/2007 | Venkatraman et al. | |
| 7,205,330 B2 | 4/2007 | Bogen et al. | |
| 7,253,160 B2 | 8/2007 | Njoroge et al. | |
| 2002/0010781 A1 | 1/2002 | Tuatini | |
| 2002/0016294 A1 | 2/2002 | Venkatraman et al. | |
| 2002/0068702 A1 | 6/2002 | Lim-Wilby et al. | |
| 2002/0102235 A1 | 8/2002 | Arasappan et al. | |
| 2002/0147139 A1 | 10/2002 | Zhu et al. | |
| 2002/0160962 A1 | 10/2002 | Saksena et al. | |
| 2003/0036501 A1 | 2/2003 | Saksena et al. | |
| 2005/0020689 A1 | 1/2005 | Chen et al. | |
| 2005/0059648 A1 | 3/2005 | Park et al. | |
| 2005/0059800 A1 | 3/2005 | Sudhakar et al. | |
| 2005/0085425 A1 | 4/2005 | Chen et al. | |
| 2005/0119168 A1 | 6/2005 | Venkatraman et al. | |
| 2005/0153900 A1 | 7/2005 | Velazquez et al. | |
| 2005/0197301 A1 | 9/2005 | Njorge et al. | |
| 2005/0209164 A1 | 9/2005 | Bogen et al. | |
| 2005/0272663 A1 | 12/2005 | Arasappan et al. | |
| 2006/0046956 A1 | 3/2006 | Sannigrahi et al. | |
| 2006/0105978 A1 | 5/2006 | Chu et al. | |
| 2006/0252698 A1 | 11/2006 | Malcolm | |
| 2006/0276405 A1 | 12/2006 | Albrecht | |
| 2006/0276406 A1 | 12/2006 | Gupta et al. | |
| 2006/0276407 A1 | 12/2006 | Albrecht et al. | |
| 2006/0281688 A1 | 12/2006 | Zhang et al. | |
| 2006/0281689 A1 | 12/2006 | Malcolm | |
| 2006/0287248 A1 | 12/2006 | Malcolm | |
| 2007/0004653 A1 | 1/2007 | Arosio et al. | |
| 2007/0021351 A1 | 1/2007 | White et al. | |
| 2007/0042968 A1 | 2/2007 | Bennett et al. | |
| 2007/0237818 A1 | 10/2007 | Malcolm et al. | |

FOREIGN PATENT DOCUMENTS

| | | |
|---|---|---|
| EP | 0 423 358 A1 | 4/1991 |
| EP | 0 603 873 A1 | 6/1994 |
| EP | 0 381 216 B1 | 12/1995 |
| WO | WO 89/04669 A1 | 6/1989 |
| WO | WO 94/04172 A1 | 3/1994 |
| WO | WO 98/14181 A1 | 4/1998 |

(Continued)

OTHER PUBLICATIONS

Hinrichsen et al., "Short-term Antiviral Efficacy of BILN 2061, A Hepatitis C Virus Serine Protease Inhibitor, In Hepatitis C Genotype 1 Patients", *Gastroenterology*, 127(5)1347-1355 (2004).

(Continued)

*Primary Examiner*—Christopher R. Tate
*Assistant Examiner*—Roy Teller
(74) *Attorney, Agent, or Firm*—Geraldine Baldwin; Sandy Zaradic; Palaiyur Kalyanaraman

(57) ABSTRACT

Pharmaceutical formulations containing at least one compound of Formulae I-XXVI herein and at least one surfactant. Pharmaceutically acceptable carriers and excipients may also be included in the formulations. The formulations of the present invention are suited for use in single unit dosages.

10 Claims, No Drawings

FOREIGN PATENT DOCUMENTS

| | | | |
|---|---|---|---|
| WO | WO 98/17679 A1 | 4/1998 | |
| WO | WO 98/22496 A2 | 5/1998 | |
| WO | WO 99/07734 A2 | 2/1999 | |
| WO | WO 00/59929 A1 | 10/2000 | |
| WO | WO 02/08187 A1 | 1/2002 | |
| WO | WO 02/08244 A2 | 1/2002 | |
| WO | WO 02/08256 A2 | 1/2002 | |
| WO | WO 02/18369 A2 | 3/2002 | |
| WO | WO 03/062265 | * | 7/2003 |
| WO | WO 03/062265 A2 | 7/2003 | |
| WO | WO 03/066103 A1 | 8/2003 | |
| WO | WO 2005/007681 A2 | 1/2005 | |
| WO | WO 2005/107745 | * | 11/2005 |
| WO | WO 2005/107745 A1 | 11/2005 | |
| WO | WO 2005/123076 A2 | 12/2005 | |
| WO | WO 2006/050250 A2 | 5/2006 | |

OTHER PUBLICATIONS

Jackson A., "Evaluation of a Cmin and a normalized Cmin method for the confirmation of steady-state in bioequivalence studies," *Pharmaceutical Research*, 15(7)1077-1084 (1998).

Mycek, Harvez and Champe, "Lippincott's Illustrated Reviews—Pharmacology," XP002423552, p. 6, chapter IV; Bioavailability, p. 11, end of paragraph 2; (1997) Lipincott-Raven Publishers, Philadelphia, USA.

Naveau et al., "Interleukin-1 Receptor Antagonist Plasma Concentration is Specifically Increased by alpha-2A-interferon Treatment", *Journal of Hepatology*, 27(2):272-275 (1997).

Pang et al., "The Phramacokinetics and Efficacy of Slow-Release Theophylline with Asymmetric Dosing in Asthmatic Chinese*", *Chest*, 93(4):785-789 (1998).

Patel et al., "Week 12 Viral Load Reduction and the Effect of Intra-Assay Variability on Predicting Treatment Response to Combination Therapy in Patients with Chronic Hepatitis C", *Hepatology*, 34(4):604A 2001.

Reesink et al., "Initial Results of a Phase 1B, Multiple-Dose Study of VX-950, A Hepatitis C Virus Protease Inhibitor", *Gastroenterology*, 128(4, Suppl. 2):A-697 (2005).

Richards, P., "Pattern of asymmetric dosing and pain control in long-term use of controlled-release oxycodone for treatment of chronic noncancer pain", *Archives of Physical Medicine and Rehabilitation*, 85(9):E40 (2004).

Sacks et al., "Lessons from HIV and Hepatitis Viruses", *Antiviral Research*1, 63S1:S11-S18 (2004).

Tsuda et al., "Poststatin, A New Inhibitor of Prolyl Endopeptidase V. Endopeptidase Inhibitory, Activity of Poststatin Analogues", *Journal of Antibiotics*, 49(9):890-899 (1996).

Ulrich, J., "Lehrbuch der Klinischen Pharmazie," *Wissenschafiliche Verlagsgesellschaft MBH*, , pp. 56-58, paragraphs 4.1.1, 4.1.2 and 4.1.3; p. 70, paragraph 4.3.3, (1998) Stuttgart.

Ulrich, J., English Translation of "Lehrbuch der Klinischen Pharmazie," *Wissensehaftliche Verlagsgesellschaft MBH*, pp. 56-58, paragraphs 4.1.1, 4.1.2 and 4.1.3; p. 70, Paragraph. 4.3.3, (1998) Stuttgart.

Van Thiel et al., "1220 Potential Early Biomarkers of a Response to Interferon Therapy in Individuals with Chronic Hepatitis C Treated with Pegasys", *Hepatolooy*, 38:748A (2003).

Wong et al., "Update on Chronic Hepatitis C ", *Clinical Gastroenterology and Hepatology*, 3(6):507-520 (2005).

Yip et al., "P4 and P1 optimization of bicycloproline P2 bearing tetrapeptidyl alpha-ketoamides as HCV protease inhibitors", *Bioorganic & Medicinal Chemistry Letters*, 14(19):5007-5011 (2004).

Yip et al., "Discovery of a novel bicycloproline P2 bearing peptidyl alpha-ketoamide LY514962 as HCV protease inhibitor", *Bioorganic & Medicinal Chemistry Letters*, 14:251-256 (2004).

Baldwin et al., "Crystal structures of native and inhibited forms of human cathepsin D: implications for lysosomal targeting and drug design," *Proc Natl Acad Sci*, 90(14):6796-6800 (1993).

Berenguer and Wright, "Hepatitis B and C viruses: molecular identification and targeted antiviral therapies," *Proc Assoc Am Physicians*, 110(2);98-112 (1998).

Bossard et al., "Proteolytic activity of human osteoclast cathepsin K," *J Biol Chem*, 271(21):12517-12524 (1996).

Bromme et al., "Human cathepsin O2, a matrix protein-degrading cysteine protease expressed in osteoclasts," *J. Biol. Chem*, 271(4):2126-2132 (1996).

Colella and Casey, "Decreased activity of cathepsins L+B and decreased invasive ability of PC3 prostate cancer cells," *Biotech Histochem*, 78(2):101-108 (2003).

Dimasi et al., "Characterization of engineered hepatitis C virus NS3 protease inhibitors affinity selected from human pancreatic secretory trypsin inhibitor and minibody repertoires," *J Virol*, 71(10):7461-7469 (1997).

Drake et al., "Cathepsin K, but not cathepsins B, L, or S, is abundantly expressed in human osteoclasts*," *J Biol Chem*, 271(21):12511-12516 (1996).

Elzouki et al., "Serine protease inhibitors in patients with chronic viral hepatitis," *J Hepat*, 27(1):42-48 (1997).

Failla et al., "Redesigning the substrate specificity of the hepatitis C virus NS3 protease," *Fold Des*, 1(1):35-42 (1996).

Friedrich et al., "Cathepsins B, H, L and cysteine protease inhibitors in malignant prostate cell lines, primary cultured prostatic cells and prostatic tissue," *Eur J Cancer*, 35(1):138-144 (1999).

Frohlich et al., "Cathepsins in basal cell carcinomas: activity, immunoreactivity and mRNA staining of cathepsins B, D, H and L," *Arch Dermatol Res*. 295(10):411-421 (2004).

Hoofnagle and Di Bisceglie, "The treatment of chronic viral hepatitis," *N Engl J Med*, 336(5):347-356 (1997).

Ingallinella et al., "Potent peptide inhibitors of human hepatitis C virus NS3 protease are obtained by optimizing the cleavage products," *Biochemistry*, 37(25):8906-8914 (1998).

Isahara et al., "Regulation of a novel pathway for cell death by lysosomal aspartic and cysteine proteinases," *Neuroscience*, 91(1):233-249 (1999).

Jones et al., "Cystatin A expression reduces bile salt-induced apoptosis in a rat hepatoma cell line," *Am J Physiol*, 275(4Pt1):G723-730 (1998).

Katunuma et al., "Structure-based design of specific cathepsin inhibitors and their application to protection of bone metasteses of cancer cells," *Arch Biochem Biophys*, 397(2):305-311 (2002).

Keyszer et al., "Comparative analysis of cathepsin L, cathepsin D, and collagenase messenger RNA expression in synovial tissues of patients with rheumatoid arthritis and osteoarthritis, by in situ hybridization," *Arthritis Rheum*, 38(7):976-984 (1995).

Kolykhalov et al., "Specificity of the hepatitis C virus NS3 serine protease: effects of substitutions at the 3/4A, 4A/4B, 4B/5A, and 5A/5B cleavage sites on polyprotein processing," *J Virol*, 68(11):7525-7533 (1994).

Komoda et al., "Substrate requirements of hepatitis C virus serine proteinase for intermolecular polypeptide cleavage in Escherichia coli," *J Virol*, 68(11):7351-7357 (1994).

Kos and Lah, "Cysteine proteinases and their endogenous inhibitors: target proteins for prognosis, diagnosis and therapy in cancer (review)," *Oncol Rep*, 5(6):1349-1361 (1998).

Krueger et al., "Cathepsin L antisense oligonucleotides in a human osteosarcoma cell line: Effects on the invasive phenotype," *Cancer Gene Ther*, 8(7):522-528 (2001).

Landro et al., "Mechanistic role of an NS4A peptide cofactor with the truncated NS3 protease of hepatitis C Virus: Elucidation of the NS4A stimulatory effect via kinetic analysis and inhibitor mapping," *Biochemistry*, 36(31):9340-9348 (1997).

Levicar et al., "Selective suppression of cathepsin L by antisense cDNA impairs human brain tumor cell invasion in vitro and promotes apoptosis," *Cancer Gene Ther*, 10(2):141 -151 (2003).

Llinas-Brunet et al., "Peptide-based inhibitors of the hepatitis C virus serine protease," *Bioorg Med Chem Lett*, 8(13):1713-1718 (1998).

Martin et al., "Affinity selection of a camelized $V_H$ domain antibody inhibitor of hepatitis C virus NS3 protease," *Protein Eng*, 10(5):607-614 (1997).

Martin et al., "Design of selective eglin inhibitors of HCV NS3 proteinase," *Biochemistry*, 37(33):11459-11468 (1998).

Mizuochi et al., "Both cathepsin B and cathepsin D are necessary for processing of ovalbumin as well as for degradation of class II MHC invariant chain," *Immunol Lett*, 43(3):189-193 (1994).

Mort and Buttle, "Molecules in focus," *Int J Biochem Cell Biol*, 29(5):715-720 (1997).

Osborne, R., Editor, "Other news to note. Ribozyme Pharmaceuticals Inc.," *BioWorld® Today*, 9(217):4 (Nov. 10, 1998); BioWorld® Publishing Group, Atlanta, Georgia.

Pizzi et al., "Molecular model of the specificity pocket of the hepatitis C virus protease: implications for substrate recognition," *Proc Natl Acad Sci (USA)*, 91(3):888-892 (1994).

Potempa et al., "Host and *Porphyromonas gingivalis* proteinases in periodontitis: a biochemical model of infection and tissue destruction," *Perspectives in Drug Discover and Design*, 2:445-458 (1994).

Roberts et al., "Cathepsin B contributes to bile salt-induced apoptosis of rat hepatocytes," *Gastroenterology*, 113(5):1714-1726 (1997).

Rousselet et al., "Inhibition of tumorigenicity and metastasis of human melanoma cells by anti-cathepsin L single chain variable fragment," *Cancer Res*, 64(1):146-151 (2004).

Shibata et al., "Participation of cathepsins B and D in Apoptosis of PC12 cells following serum deprivation," *Biochem Biophys Res Commun*, 251(1):199-203 (1998).

Troy et al., "Expression of cathepsin B and L antigen and activity is associated with early colorectal cancer progression," *Eur J Cancer*, 40(10):1610-1616 (2004).

Wang et al., "Conserved C-terminal threonine of hepatitis C virus NS3 regulates autoproteolysis and prevents product inhibition," *J Virol*, 78(2):700-709 (2004).

Yan et al., "Cathepsin B and Human Tumor Progression*," *Biol Chem*, 379(2):113-123 (1998).

* cited by examiner

PHARMACEUTICAL FORMULATIONS AND METHODS OF TREATMENT USING THE SAME

CROSS-REFERENCE TO PRIORITY APPLICATION

This application claims the benefit of priority from U.S. provisional patent application Ser. No. 60/686,945 filed Jun. 2, 2005.

FIELD OF THE INVENTION

The present invention relates to pharmaceutical formulations that are useful for treating a wide variety of diseases or disorders associated with hepatitis C virus ("HCV") by inhibiting HCV protease (for example HCV NS3/NS4a serine protease), and/or diseases or disorders associated with cathepsin activity and inhibiting cathepsin activity.

BACKGROUND OF THE INVENTION

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Current therapies for hepatitis C include interferon-α ($INF_\alpha$) and combination therapy with ribavirin and interferon. See, e.g., Beremguer et al. (1998) *Proc. Assoc. Am. Physicians* 110(2):98-112. These therapies suffer from a low sustained response rate and frequent side effects. See, e.g., Hoofnagle et al. (1997) *N. Engl. J. Med.* 336:347. Currently, no vaccine is available for HCV infection.

Hepatitis C virus (HCV) is a (+)-sense single-stranded RNA virus that has been implicated as the major causative agent in non-A, non-B hepatitis (NANBH), particularly in blood-associated NANBH (BB-NANBH)(see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) *Proc. Natl. Acad. Sci (USA)* 91:888-892, Failla et al. (1996) *Folding & Design* 1:35-42. The NS3/NS4a cleavage site is also more tolerant of mutagenesis than the other sites. See, e.g., Kollykhalov et al. (1994) *J. Virol.* 68:7525-7533. It has also been found that acidic residues in the region upstream of the cleavage site are required for efficient cleavage. See, e.g., Komoda et al. (1994) *J. Virol.* 68:7351-7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340-9348, Ingallinella et al. (1998) *Biochem.* 37:8906-8914, Llinas-Brunet et al. (1998) *Bioorg. Med. Chem. Lett.* 8:1713-1718), inhibitors based on the 70-amino acid polypeptide eglin c (Martin et al. (1998) *Biochem.* 37:11459-11468, inhibitors affinity selected from human pancreatic secretory trypsin inhibitor (hPSTI-C3) and minibody repertoires (MBip) (Dimasi et al. (1997) *J. Virol.* 71:7461-7469), $cV_HE2$ (a "camelized" variable domain antibody fragment) (Martin et al. (1997) *Protein Eng.* 10:607-614), and α1-antichymotrypsin (ACT) (Elzouki et al.) (1997) *J. Hepat.* 27:42-28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

Pending and copending U.S. patent applications, Ser. No. 60/194,607, filed Apr. 5, 2000, and Ser. No. 60/198,204, filed Apr. 19, 2000, Ser. No. 60/220,110, filed Jul. 21, 2000, Ser. No. 60/220,109, filed Jul. 21, 2000, Ser. No. 60/220,107, filed Jul. 21, 2000, Ser. No. 60/254,869, filed Dec. 12, 2000, Ser. No. 60/220,101, filed Jul. 21, 2000, Ser. No. 60/568,721 filed May 6, 2004, and WO 2003/062265, disclose various types of peptides and/or other compounds as NS-3 serine protease inhibitors of hepatitis C virus.

There is a need for new treatments and therapies for HCV infection to treat or prevent or ameliorate of one or more symptoms of hepatitis C, methods for modulating the activity of serine proteases, particularly the HCV NS3/NS4a serine protease, and methods of modulating the processing of the HCV polypeptide using the compounds provided herein.

Another aspect of the present invention is directed to inhibiting cathepsin activity. Cathepsins (Cats) belong to the papain superfamily of lysosomal cysteine proteases. Cathepsins are involved in the normal proteolysis and turnover of target proteins and tissues as well as in initiating proteolytic cascades by proenzyme activation and in participating in MHC class II molecule expression. Baldwin (1993) Proc. Natl. Acad. Sci., 90: 6796-6800; Mixuochi (1994) Immunol. Lett., 43:189-193.

However, aberrant cathepsin expression has also been implicated in several serious human disease states. Cathepsins have been shown to be abundantly expressed in cancer cells, including breast, lung, prostate, glioblastoma and head/neck cancer cells, (Kos et al. (1998) Oncol. Rep., 5:1349-1361; Yan et al. (1998) Biol. Chem., 379:113-123; Mort et al. (1997) Int. J. Biochem. Cell Biol., 29: 715-720; Friedrick et al. (1999) Eur. J Cancer, 35:138-144) and are associated with poor treatment outcome of patients with breast cancer, lung cancer, brain tumor and head/neck cancer. Kos et al, supra. Additionally, aberrant expression of cathepsin is evident in several inflammatory disease states, including rheumatoid arthritis and osteoarthritis. Keyszer (1995) Arthritis Rheum., 38:976-984.

The molecular mechanisms of cathepsin activity are not completely understood. Recently, it was shown that forced expression of cathepsin B rescued cells from serum deprivation-induced apoptotic death (Shibata et al. (1998) Biochem. Biophys. Res. Commun., 251: 199-203) and that treatment of cells with antisense oligonucleotides of cathepsin B induced apoptosis. Isahara et at. (1999) Neuroscience, 91:233-249. These reports suggest an anti-apoptotic role for the cathepsins that is contrary to earlier reports that cathepsins are mediators of apoptosis. Roberts et al (1997) Gastroenterology, 113: 1714-1726; Jones et al. (1998) Am. J Physiol., 275: G723-730.

Cathepsin K is a member of the family of enzymes which are part of the papain superfamily of cysteine proteases. Cathepsins B, H, L, N and S have been described in the literature. Recently, cathepsin K polypeptide and the cDNA encoding such polypeptide were disclosed in U.S. Pat. No. 5,501,969 (called cathepsin O therein). Cathepsin K has been recently expressed, purified, and characterized. Bossard, M. J., et al., (1996) *J Biol. Chem.* 271, 12517-12524; Drake, F. H., et al., (1996) *J. Biol. Chem.* 271, 12511-12516; Bromme, D., et al., (1996) *J. Biol. Chem.* 271, 2126-2132.

Cathepsin K has been variously denoted as cathepsin O, cathepsin X or cathepsin O2 in the literature. The designation cathepsin K is considered to be the more appropriate one (name assigned by Nomenclature Committee of the International Union of Biochemistry and Molecular Biology).

Cathepsins of the papain superfamily of cysteine proteases function in the normal physiological process of protein degradation in animals, including humans, e.g., in the degradation of connective tissue. However, elevated levels of these enzymes in the body can result in pathological conditions leading to disease. Thus, cathepsins have been implicated in various disease states, including but not limited to, infections by *pneumocystis carinii, trypsanoma cruzi, trypsanoma brucei brucei*, and *Crithidia fusiculata*; as well as in schistosomiasis malaria, tumor metastasis, metachromatic leukodystrophy, muscular dystrophy, amytrophy, and the like. See International Publication Number WO 94/04172, published on Mar. 3, 1994, and references cited therein. See also European Patent Application EP 0 603 873 A1, and references cited therein. Two bacterial cysteine proteases from *P. gingivallis*, called gingipains, have been implicated in the pathogenesis of gingivitis. Potempa, J., et al. (1994) *Perspectives in Drug Discovery and Design*, 2, 445-458.

Cathepsin K is believed to play a causative role in diseases of excessive bone or cartilage loss. Bone is composed of a protein matrix in which spindle- or plate-shaped crystals of hydroxyapatite are incorporated. Type I Collagen represents the major structural protein of bone comprising approximately 90% of the structural protein. The remaining 10% of matrix is composed of a number of non-collagenous proteins, including osteocalcin, proteoglycans, osteopontin, osteonectin, thrombospondin, fibronectin, and bone sialoprotein. Skeletal bone undergoes remodeling at discrete foci throughout life. These foci, or remodeling units, undergo a cycle consisting of a bone resorption phase followed by a phase of bone replacement. Bone resorption is carried out by osteoclasts, which are multinuclear cells of hematopoietic lineage. In several disease states, such as osteoporosis and Paget's disease, the normal balance between bone resorption and formation is disrupted, and there is a net loss of bone at each cycle. Ultimately, this leads to weakening of the bone and may result in increased fracture risk with minimal trauma.

The abundant selective expression of cathepsin K in osteoclasts strongly suggests that this enzyme is essential for bone resorption. Thus, selective inhibition of cathepsin K may provide an effective treatment for diseases of excessive bone loss, including, but not limited to, osteoporosis, gingival diseases such as gingivitis and periodontitis, Paget's disease, hypercalcemia of malignancy, and metabolic bone disease. Cathepsin K levels have also been demonstrated to be elevated in chondroclasts of osteoarthritic synovium. Thus, selective inhibition of cathepsin K may also be useful for treating diseases of excessive cartilage or matrix degradation, including, but not limited to, osteoarthritis and rheumatoid arthritis. Metastatic neoplastic cells also typically express high levels of proteolytic enzymes that degrade the surrounding matrix. Thus, selective inhibition of cathepsin K may also be useful for treating certain neoplastic diseases.

There are reports in the literature of the expression of Cathepsin B and L antigen and that activity is associated with early colorectal cancer progression. Troy et al., (2004) Eur J Cancer, 40(10):1610-6. The findings suggest that cysteine proteases play an important role in colorectal cancer progression.

Cathepsin L has been shown to be an important protein mediating the malignancy of gliomas and it has been suggested that its inhibition may diminish their invasion and lead to increased tumor cell apoptosis by reducing apoptotic threshold. Levicar et al., (2003) Cancer Gene Ther., 10(2): 141-51.

Katunama et al., (2002) Arch Biochem Biophys., 397(2): 305-11 reports on antihypercalcemic and antimetastatic effects of CLIK-148 in vivo, which is a specific inhibitor of cathepsin L. This reference also reports that CLIK-148 treatment reduced distant bone metastasis to the femur and tibia of melanoma A375 tumors implanted into the left ventricle of the heart.

Rousselet et al., (2004) Cancer Res., 64(1): 146-51 reports that anti-cathepsin L single chain variable fragment (ScFv) could be used to inhibit the tumorigenic and metastatic phenotype of human melanoma, depending on procathepsin L secretion, and the possible use of anti-cathepsin L ScFv as a molecular tool in a therapeutic cellular approach.

Colella et al., (2003) Biotech Histochem., 78(2):101-8 reports that the cysteine proteinases cathepsin L and B participate in the invasive ability of the PC3 prostrate cancer cell line, and the potential of using cystein protease inhibitiors such as cystatins as anti-metastatic agents.

Krueger et al., (2001) Cancer Gene Ther., 8(7):522-8 reports that in human osteosarcoma cell line MNNG/HOS, cathepsin L influences cellular malignancy by promoting migration and basement membrane degradation.

Frohlich et al., (2204) Arch Dermatol Res., 295(10):411-21 reports that cathepsins B and L are involved in invasion of basal cell carcinoma (BCC) cells.

U.S. Provisional Patent Application Serial No. Not Yet Assigned, entitled "Compounds for Inhibiting Cathepsin Activity", filed Apr. 20, 2005, discloses various types of peptides and/or other compounds as inhibitors of cathepsin.

Cathepsins therefore are attractive targets for the discovery of novel chemotherapeutics and methods of treatment effective against a variety of diseases. There is a need for compounds and associated formulations useful in the inhibition of cathepsin activity and in the treatment of these disorders.

There is a need for pharmacuetical formulations including inhibitors of HCV protease or cathepsin having good dissolution to facilitate absorption of the inhibitor.

SUMMARY OF THE INVENTION

The present invention provides pharmaceutical formulations comprising (i) at least one surfactant and (ii) at least one compound of Formulae I-XXVI.

In one embodiment, the compound is a compound of structural Formula I

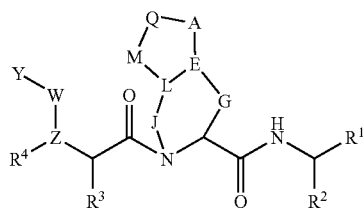

Formula I or a pharmaceutically acceptable salt, solvate or ester thereof; wherein:

Y is selected from the group consisting of the following moieties: alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe optionally substituted with $X^{11}$ or $X^{12}$;

$X^{11}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

$R^1$ is $COR^5$ or $B(OR)_2$, wherein $R^5$ is H, OH, $OR^8$, $NR^9R^{10}$, $CF_3$, $C_2F_5$, $C_3F_7$, $CF_2R^6$, $R^6$, or $COR^7$ wherein $R^7$ is H, OH, $OR^8$, $CHR^9R^{10}$, or $NR^9R^{10}$, wherein $R^6$, $R^8$, $R^9$ and $R^{10}$ are independently selected from the group consisting of H, alkyl, aryl, heteroalkyl, heteroaryl, cycloalkyl, cycloalkyl, arylalkyl, heteroarylalkyl, $[CH(R^{1'})]_p$ $COOR^{11}$, $[CH(R^{1'})]_pCONR^{12}R^{13}$, $[CH(R^{1'})]_pSO_2R^{11'}$, $[CH(R^{1'})]_pCOR^{11}$, $[CH(R^{1'})]_pCH(OH)RCH(R^{1'})CON-HCH(R^{2'})COOR^{11}$, $CH(R^{1'})CONHCH(R^{2'})CONR^{12}R^{13}$, $CH(R^{1'})CONHCH(R^{2'})R'$, $CH(R^{1'})CONHCH(R^{2'})CON-HCH(R^{3'})COOR^{11}$, $CH(R^{1'})CONHCH(R^{2'})CONHCH(R^{3'}) CONR^{12}R^{13}$, $CH(R^{1'})CONHCH(R^{2'})CONHCH(R^{3'}) CONHCH(R^{4'})COOR^{11}$, $CH(R^{1'})CONHCH(R^{2'}) CON-HCH(R^{3'})CONHCH(R^{4'})CONR^{12}R^{13}$, $CH(R^{1'})CONHCH(R^{2'})CONHCH(R^{3'})CONHCH(R^{4'})CONHCH(R^{5'}) COOR^{11}$ and $CH(R^{1'})CONHCH(R^{2'})CONHCH(R^{3'}) CONHCH(R^{4'})CONHCH(R^{5'})CONR^{12}R^{13}$, wherein $R^{1'}$, $R^{2'}$, $R^{3'}$, $R^{4'}$, $R^{5'}$, $R^{11}$, $R^{12}$, $R^{13}$, and $R'$ are independently selected from the group consisting of H, alkyl, aryl, heteroalkyl, heteroaryl, cycloalkyl, alkyl-aryl, alkyl-heteroaryl, aryl-alkyl and heteroaralkyl;

Z is selected from O, N, CH or CR;

W maybe present or absent, and if W is present, W is selected from C=O, C=S, C(=N—CN), or $SO_2$;

Q maybe present or absent, and when Q is present, Q is CH, N, P, $(CH_2)_p$, $(CHR)_p$, $(CRR')_p$, O, NR, S, or $SO_2$; and when Q is absent, M may be present or absent;

when Q and M are absent, A is directly linked to L;

A is O, $CH_2$, $(CHR)_p$, $(CHR—CHR')_p$, $(CRR')_p$, NR, S, $SO_2$ or a bond;

E is CH, N, CR, or a double bond towards A, L or G;

G may be present or absent, and when G is present, G is $(CH_2)_p$, $(CHR)_p$, or $(CRR')_p$; and when G is absent, J is present and E is directly connected to the carbon atom in Formula I as G is linked to;

J maybe present or absent, and when J is present, J is $(CH_2)_p$, $(CHR)_p$, or $(CRR')_p$, $SO_2$, NH, NR or O; and when J is absent, G is present and E is directly linked to N shown in Formula I as linked to J;

L may be present or absent, and when L is present, L is CH, CR, O, S or NR; and when L is absent, then M may be present or absent; and if M is present with L being absent, then M is directly and independently linked to E, and J is directly and independently linked to E;

M may be present or absent, and when M is present, M is O, NR, S, $SO_2$, $(CH_2)_p$, $(CHR)_p(CHR—CHR')_p$, or $(CRR')_p$;

p is a number from 0 to 6; and

R, R', $R^2$, $R^3$ and $R^4$ are independently selected from the group consisting of H; $C_1$-$C_{10}$ alkyl; $C_2$-$C_{10}$ alkenyl; $C_3$-$C_8$ cycloalkyl; $C_3$-$C_8$ heterocycloalkyl, alkoxy, aryloxy, alkylthio, arylthio, amino, amido, ester, carboxylic acid, carbamate, urea, ketone, aldehyde, cyano, nitro, halogen; (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

wherein said alkyl, heteroalkyl, alkenyl, heteroalkenyl, aryl, heteroaryl, cycloalkyl and heterocycloalkyl moieties may be optionally and chemically-suitably substituted, with said term "substituted" referring to optional and chemically-suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate;

further wherein said unit N-C-G-E-L-J-N represents a five-membered or six-membered cyclic ring structure with the proviso that when said unit N-C-G-E-L-J-N represents a five-membered cyclic ring structure, or when the bicyclic ring structure in Formula I comprising N, C, G, E, L, J, N, A, Q, and M represents a five-membered cyclic ring structure, then said five-membered cyclic ring structure lacks a carbonyl group as part of the cyclic ring.

In another embodiment, the compound is a compound of Formula II:

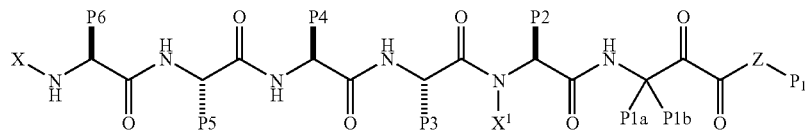

Formula II or a pharmaceutically acceptable salt, solvate or ester thereof; wherein:

Z is O, NH or $NR^{12}$;

X is alkylsulfonyl, heterocyclylsulfonyl, heterocyclylalkyl-sulfonyl, arylsulfonyl, heteroarylsulfonyl, alkylcarbonyl, heterocyclylcarbonyl, heterocyclylalkylcarbonyl, arylcarbonyl, heteroarylcarbonyl, alkoxycarbonyl, heterocyclyloxycarbonyl, aryloxycarbonyl, heteroaryloxycarbonyl, alkyaminocarbonyl, heterocyclylaminocarbonyl, arylaminocarbonyl, or heteroarylaminocarbonyl moiety, with the proviso that X may be additionally optionally substituted with $R^{12}$ or $R^{13}$;

$X^1$ is H; $C_1$-$C_4$ straight chain alkyl; $C_1$-$C_4$ branched alkyl or; $CH_2$-aryl (substituted or unsubstituted);

$R^{12}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl moiety, with the proviso that $R^{12}$ may be additionally optionally substituted with $R^{13}$.

$R^{13}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro moiety, with the proviso that the alkyl, alkoxy, and aryl may be additionally optionally substituted with moieties independently selected from $R^{13}$. P1a, P1b, P2, P3, P4, P5, and P6 are independently:

H; C1-C10 straight or branched chain alkyl; C2-C10 straight or branched chain alkenyl;

C3-C8 cycloalkyl, C3-C8 heterocyclic; (cycloalkyl)alkyl or (heterocyclyl)alkyl, wherein said cycloalkyl is made up of 3 to 8 carbon atoms, and zero to 6 oxygen, nitrogen, sulfur, or phosphorus atoms, and said alkyl is of 1 to 6 carbon atoms;

aryl, heteroaryl, arylalkyl, or heteroarylalkyl, wherein said alkyl is of 1 to 6 carbon atoms;

wherein said alkyl, alkenyl, cycloalkyl, heterocyclyl; (cycloalkyl)alkyl and (heterocyclyl)alkyl moieties may be optionally substituted with $R^{13}$, and further wherein said P1a and P1b may optionally be joined to each other to form a spirocyclic or spiroheterocyclic ring, with said spirocyclic or spiroheterocyclic ring containing zero to six oxygen, nitrogen, sulfur, or phosphorus atoms, and may be additionally optionally substituted with $R^{13}$; and P1' is H, alkyl, alkenyl, alkynyl, cycloalkyl, cycloalkyl-alkyl, heterocyclyl, heterocyclyl-alkyl, aryl, aryl-alkyl, heteroaryl, or heteroaryl-alkyl; with the proviso that said P1' may be additionally optionally substituted with $R^{13}$.

In another embodiment, the compound is a compound of Formula III

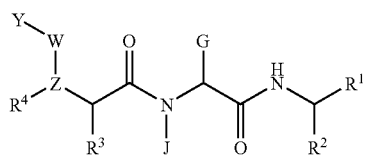

Formula III or a pharmaceutically acceptable salt, solvate or ester thereof; wherein:

G, J and Y may be the same or different and are independently selected from the group consisting of the moieties: H, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe additionally optionally substituted with $X^{11}$ or $X^{12}$;

$X^{11}$ is selected from the group consisting of alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl moiety, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

$R^1$ is $COR^5$ or $B(OR)_2$, wherein $R^5$ is selected from the group consisting of H, OH, $OR^8$, $NR^9R^{10}$, $CF_3$, $C_2F_5$, $C_3F_7$, $CF_2R^6$, $R^6$ and $COR^7$ wherein $R^7$ is selected from the group consisting of H, OH, $OR^8$, $CHR^9R^{10}$, and $NR^9R^{10}$ wherein $R^6$, $R^8$, $R^9$ and $R^{10}$ may be the same or different and are independently selected from the group consisting of H, alkyl, aryl, heteroalkyl, heteroaryl, cycloalkyl, cycloalkyl, arylalkyl, heteroarylalkyl, $CH(R^{1'})COOR^{11}$, $CH(R^{1'})CONR^{12}R^{13}$, $CH(R^{1'})CONHCH(R^{2'})COOR^{11}$, $CH(R^{1'})CONHCH(R^{2'})CONR^{12}R^{13}$, $CH(R^{1'})CONHCH(R^{2'})R'$, $CH(R^{1'})CONHCH(R^{2'})CONHCH(R^{3'})COOR^{11}$, $CH(R^{1'})CONHCH(R^{2'})CONHCH(R^{3'})CONR^{12}R^{13}$, $CH(R^{1'})$ CONHCH(R²')CONHCH(R³')CONHCH(R⁴')COOR¹¹, CH(R¹')CONHCH(R²')CONHCH(R³')CONHCH(R⁴') CONR¹²R¹³, CH(R¹')CONHCH(R²')CONHCH(R³') CONHCH(R⁴')CONHCH(R⁵')COOR¹¹, and CH(R¹') CONHCH(R²')CONHCH(R³')CONHCH(R⁴')CONHCH (R⁵')CONR¹²R¹³, wherein R¹', R²', R³', R⁴', R⁵', R¹¹, R¹², R¹³, and R' may be the same or different and are independently selected from a group consisting of H, alkyl, aryl, heteroalkyl, heteroaryl, cycloalkyl, alkyl-aryl, alkyl-heteroaryl, aryl-alkyl and heteroaralkyl;

Z is selected from O, N, or CH;

W may be present or absent, and if W is present, W is selected from C=O, C=S, or SO₂; and R, R', R², R³ and R⁴ are independently selected from the group consisting of H; C1-C10 alkyl; C2-C10 alkenyl; C3-C8 cycloalkyl; C3-C8 heterocycloalkyl, alkoxy, aryloxy, alkylthio, arylthio, amino, amido, ester, carboxylic acid, carbamate, urea, ketone, aldehyde, cyano, nitro; oxygen, nitrogen, sulfur, or phosphorus atoms (with said oxygen, nitrogen, sulfur, or phosphorus atoms numbering zero to six); (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

wherein said alkyl, heteroalkyl, alkenyl, heteroalkenyl, aryl, heteroaryl, cycloalkyl and heterocycloalkyl moieties may be optionally substituted, with said term "substituted" referring to optional and chemically-suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamide, sulfoxide, sulfone, sulfonylurea, hydrazide, and hydroxamate.

In another embodiment, the compound is a compound of Formula IV

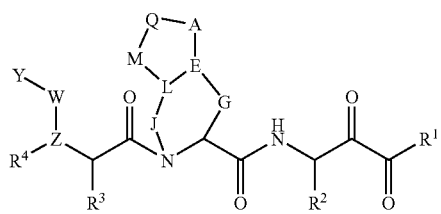

Formula IV or a pharmaceutically acceptable salt, solvate or ester thereof; wherein:

Y is selected from the group consisting of the following moieties: alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe optionally substituted with X¹¹ or X¹²;

X¹¹ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, with the proviso that X¹¹ may be additionally optionally substituted with X¹²;

X¹² is hydroxy, alkoxy, aryloxy, thio, alkylthio, arylthio, amino, alkylamino, arylamino, alkylsulfonyl, arylsulfonyl, alkylsulfonamido, arylsulfonamido, carboxyl, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from X¹²;

R¹ is selected from the following structures:

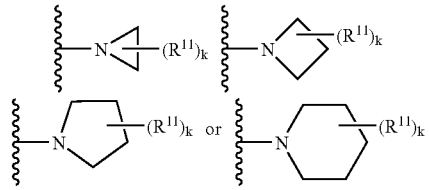

wherein k is a number from 0 to 5, which can be the same or different, R¹¹ denotes optional substituents, with each of said substituents being independently selected from the group consisting of alkyl, alkenyl, alkynyl, aryl, cycloalkyl, alkyl-aryl, heteroalkyl, heteroaryl, aryl-heteroaryl, alkyl-heteroaryl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino, heterocycloalkylamino, hydroxy, thio, alkylthio, arylthio, amino, alkylsulfonyl, arylsulfonyl, alkylsulfonamido, arylsulfonamido, carboxyl, carbalkoxy, carboxamido, alkoxycarbonylamino, alkoxycarbonyloxy, alkylureido, arylureido, halogen, cyano, and nitro, with the proviso that R¹¹ (when R¹¹≠H) maybe optionally substituted with X¹¹ or X¹²;

Z is selected from O, N, CH or CR;

W may be present or absent, and if W is present, W is selected from C=O, C=S, C(=N—CN), or S(O₂);

Q may be present or absent, and when Q is present, Q is CH, N, P, (CH₂)ₚ, (CHR)ₚ, (CRR')ₚ, O, N(R), S, or S(O₂); and when Q is absent, M may be present or absent; when Q and M are absent, A is directly linked to L;

A is O, CH₂, (CHR)ₚ, (CHR—CHR')ₚ, (CRR')ₚ, N(R'), S, S(O₂) or a bond;

E is CH, N, CR, or a double bond towards A, L or G;

G may be present or absent, and when G is present, G is (CH₂)ₚ, (CHR)ₚ, or (CRR')ₚ; and when G is absent, J is present and E is directly connected to the carbon atom in Formula I as G is linked to;

J may be present or absent, and when J is present, J is (CH₂)ₚ, (CHR)ₚ, or (CRR')ₚ, S(O₂), NH, N(R) or O; and when J is absent, G is present and E is directly linked to N shown in Formula I as linked to J;

L may be present or absent, and when L is present, L is CH, C(R), O, S or N(R); and when L is absent, then M may be present or absent; and if M is present with L being absent, then M is directly and independently linked to E, and J is directly and independently linked to E;

M may be present or absent, and when M is present, M is O, N(R), S, S(O₂), (CH₂)ₚ, (CHR)ₚ(CHR—CHR')ₚ, or (CRR')ₚ;

p is a number from 0 to 6; and

R, R', R², R³ and R⁴ can be the same or different, each being independently selected from the group consisting of H; C₁-C₁₀ alkyl; C₂-C₁₀ alkenyl; C₃-C₈ cycloalkyl; C₃-C₈ heterocycloalkyl, alkoxy, aryloxy, alkylthio, arylthio, amino, amido, ester, carboxylic acid, carbamate, urea, ketone, aldehyde, cyano, nitro, halogen, (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

wherein said alkyl, heteroalkyl, alkenyl, heteroalkenyl, aryl, heteroaryl, cycloalkyl and heterocycloalkyl moieties may be optionally substituted, with said term "substituted" referring to substitution with one or more moieties which can be the same or different, each being independently selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate;

further wherein said unit N-C-G-E-L-J-N represents a five-membered cyclic ring structure or six-membered cyclic ring structure with the proviso that when said unit N-C-G-E-L-J-N represents a five-membered cyclic ring structure, or when the bicyclic ring structure in Formula I comprising N, C, G, E, L, J, N, A, Q, and M represents a five-membered cyclic ring structure, then said five-membered cyclic ring structure lacks a carbonyl group as part of said five-membered cyclic ring.

In another embodiment, the compound is a compound of Formula V

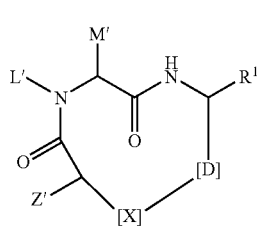

Formula V or a pharmaceutically acceptable salt, solvate or ester of said compound wherein:

(1) $R^1$ is $-C(O)R^5$ or $-B(OR)_2$;

(2) $R^5$ is H, $-OH$, $-OR^8$, $-NR^9R^{10}$, $-C(O)OR^8$, $-C(O)NR^9R^{10}$, $-CF_3$, $-C_2F_5$, $C_3F_7$, $-CF_2R^6$, $-R^6$, $-C(O)R^7$ or $NR^7SO_2R^8$;

(3) $R^7$ is H, $-OH$, $-OR^8$, or $-CHR^9R^{10}$;

(4) $R^6$, $R^8$, $R^9$ and $R^{10}$ are independently selected from the group consisting of H: alkyl, alkenyl, aryl, heteroalkyl, heteroaryl, cycloalkyl, arylalkyl, heteroarylalkyl, $R^{14}$, $-CH(R^{13'})CH(R^{1'})C(O)OR^{11}$, $[CH(R^{1'})]_pC(O)OR^{11}$, $-[CH(R^{1'})]_pC(O)NR^{12}R^{13}$, $-[CH(R^{1'})]_pS(O_2)R^{11}$, $-[CH(R^{1'})]_pC(O)R^{11}$, $-[CH(R^{1'})]_pS(O_2)NR^{12}R^{13}$, $CH(R^{1'})C(O)N(H)CH(R^{2'})(R')$, $CH(R^{1'})CH(R^{1'})C(O)NR^{12}R^{13}$, $-CH(R^{1'})CH(R^{1'})S(O_2)R^{11}$, $-CH(R^{1'})CH(R^{1'})S(O_2)NR^{12}R^{13}$, $-CH(R^{1'})CH(R^{1'})C(O)R^{11}$, $-[CH(R^{1'})]_pCH(OH)R^{11}$, $-CH(R^{1'})C(O)N(H)CH(R^{2'})C(O)OR^{11}$, $C(O)N(H)CH(R^{2'})C(O)OR^{11}$, $-C(O)N(H)CH(R^{2'})C(O)R^{11}$, $CH(R^{1'})C(O)N(H)CH(R^{2'})C(O)NR^{12}R^{13}$, $-CH(R^{1'})C(O)N(H)CH(R^{2'})R'$, $CH(R^{1'})C(O)N(H)CH(R^{2'})C(O)N(H)CH(R^{3'})C(O)OR^{11}$, $CH(R^{1'})C(O)N(H)CH(R^{2'})C(O)CH(R^{3'})NR^{12}R^{13}$, $CH(R^{1'})C(O)N(H)CH(R^{2'})C(O)N(H)CH(R^{3'})C(O)NR^{12}R^{13}$, $CH(R^{1'})C(O)N(H)CH(R^{2'})C(O)N(H)CH(R^{3'})C(O)N(H)CH(R^{4'})C(O)OR^{11}$, $H(R^{1'})C(O)N(H)CH(R^{2'})C(O)N(H)CH(R^{3'})C(O)N(H)CH(R^{4'})C(O)NR^{12}R^{13}$, $CH(R^{1'})C(O)N(H)CH(R^{2'})C(O)N(H)CH(R^{3'})C(O)N(H)CH(R^{4'})C(O)N(H)CH(R^{5'})C(O)OR^{11}$, and $CH(R^{1'})C(O)N(H)CH(R^{2'})C(O)N(H)CH(R^{3'})C(O)N(H)CH(R^{4'})C(O)N(H)CH(R^{5'})C(O)NR^{12}R^{13}$;

wherein $R^{1'}$, $R^{2'}$, $R^{3'}$, $R^{4'}$, $R^{5'}$, $R^{11}$, $R^{12}$ and $R^{13}$ can be the same or different, each being independently selected from the group consisting of: H, halogen, alkyl, aryl, heteroalkyl, heteroaryl, cycloalkyl, alkoxy, aryloxy, alkenyl, alkynyl, alkylaryl, alkyl-heteroaryl, heterocycloalkyl, aryl-alkyl and heteroaralkyl;

or $R^{12}$ and $R^{13}$ are linked together wherein the combination is cycloalkyl, heterocycloalkyl, ary or heteroaryl;

$R^{14}$ is present or not and if present is selected from the group consisting of: H, alkyl, aryl, heteroalkyl, heteroaryl, cycloalkyl, alkyl-aryl, allyl, alkyl-heteroaryl, alkoxy, arylalkyl, alkenyl, alkynyl and heteroaralkyl;

(5) R and R' are present or not and if present can be the same or different, each being independently selected from the group consisting of: H, OH, $C_1$-$C_{10}$ alkyl, $C_2$-$C_{10}$ alkenyl, $C_3$-$C_8$ cycloalkyl, $C_3$-$C_8$ heterocycloalkyl, alkoxy, aryloxy, alkylthio, arylthio, alkylamino, arylamino, amino, amido, arylthioamino, arylcarbonylamino, arylaminocarboxy, alkylaminocarboxy, heteroalkyl, alkenyl, alkynyl, (aryl)alkyl, heteroarylalkyl, ester, carboxylic acid, carbamate, urea, ketone, aldehyde, cyano, nitro, halogen, (cycloalkyl)alkyl, aryl, heteroaryl, (alkyl)aryl, alkylheteroaryl, alkyl-heteroaryl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms;

(6) L' is H, OH, alkyl, heteroalkyl, aryl, heteroaryl, cycloalkyl, or heterocyclyl;

(7) M' is H, alkyl, heteroalkyl, aryl, heteroaryl, cycloalkyl, arylalkyl, heterocyclyl or an amino acid side chain;

or L' and M' are linked together to form a ring structure wherein the portion of structural Formula 1 represented by

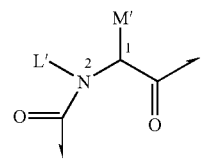

is represented by structural Formula 2:

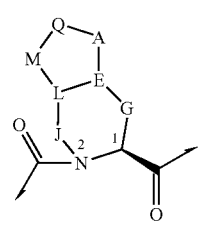

Formula 2 wherein in Formula 2:

E is present or absent and if present is C, CH, N or C(R);

J is present or absent, and when J is present, J is $(CH_2)_p$, $(CHR-CHR')_p$, $(CHR)_p$, $(CRR')_p$, $S(O_2)$, $N(H)$, $N(R)$ or O; when J is absent and G is present, L is directly linked to the nitrogen atom marked position 2;

p is a number from 0 to 6;

L is present or absent, and when L is present, L is C(H) or C(R); when L is absent, M is present or absent; if M is present with L being absent, then M is directly and independently linked to E, and J is directly and independently linked to E;

G is present or absent, and when G is present, G is $(CH_2)_p$, $(CHR)_p$, $(CHR-CHR')_p$ or $(CRR')_p$; when G is absent, J is present and E is directly connected to the carbon atom marked position 1;

Q is present or absent, and when Q is present, Q is NR, PR, (CR=CR), $(CH_2)_p$, $(CHR)_p$, $(CRR')_p$, $(CHR-CHR')_p$, O, NR, S, SO, or $SO_2$; when Q is absent, M is (i) either directly linked to A or (ii) an independent substituent on L, said independent substituent being selected from —OR, —CH(R)(R'), $S(O)_{0-2}R$ or —NRR' or (iii) absent; when both Q and M are absent, A is either directly linked to L, or A is an independent substituent on E, said independent substituent being selected from —OR, —CH(R)(R'), $S(O)_{0-2}R$ or —NRR' or A is absent;

A is present or absent and if present A is O, O(R), $(CH_2)_p$, $(CHR)_p$, $(CHR-CHR')_p$, $(CRR')_p$, N(R), NRR', S, $S(O_2)$, —OR, CH(R)(R') or NRR'; or A is linked to M to form an alicyclic, aliphatic or heteroalicyclic bridge;

M is present or absent, and when M is present, M is halogen, O, OR, N(R), S, $S(O_2)$, $(CH_2)_p$, $(CHR)_p$ $(CHR-CHR')_p$, or $(CRR')_p$; or M is linked to A to form an alicyclic, aliphatic or heteroalicyclic bridge;

(8) Z' is represented by the structural Formula 3:

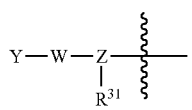

Formula 3 wherein in Formula 3, Y is selected from the group consisting of: H, aryl, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, heteroalkyl-heteroaryl, heteroalkyl-heterocycloalkyl, cycloalkyloxy, alkylamino, arylamino, alkyl-arylamino, arylamino, heteroarylamino, cycloalkylamino and heterocycloalkylamino, and Y is unsubstituted or optionally substituted with one or two substituents which are the same or different and are independently selected from $X^{11}$ or $X^{12}$;

$X^{11}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, and $X^{11}$ is unsubstituted or optionally substituted with one or more of $X^{12}$ moieties which are the same or different and are independently selected;

$X^{12}$ is hydroxy, alkoxy, alkyl, alkenyl, alkynyl, aryl, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkylcarbonyl, arylcarbonyl, heteroalkylcarbonyl, heteroarylcarbonyl, sulfonylurea, cycloalkylsulfonamido, heteroarylcycloalkylsulfonamido, heteroaryl-sulfonamido, alkoxycarbonylamino, alkoxycarbonyloxy, alkylureido, arylureido, halogen, cyano, or nitro, and said alkyl, alkoxy, and aryl are unsubstituted or optionally independently substituted with one or more moieties which are the same or different and are independently selected from alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl;

Z is O, N, C(H) or C(R);

$R^{31}$ is H, hydroxyl, aryl, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, heteroalkyl-heteroaryl, cycloalkyloxy, alkylamino, arylamino, alkyl-arylamino, arylamino, heteroarylamino, cycloalkylamino or heterocycloalkylamino, and $R^{31}$ is unsubstituted or optionally substituted with one or two substituents which are the same or different and are independently selected from $X^{13}$ or $X^{14}$;

$X^{13}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, and $X^{13}$ is unsubstituted or optionally substituted with one or more of $X^{14}$ moieties which are the same or different and are independently selected;

$X^{14}$ is hydroxy, alkoxy, alkyl, alkenyl, alkynyl, aryl, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkylcarbonyl, arylcarbonyl, heteroalkylcarbonyl, heteroarylcarbonyl, cycloalkylsulfonamido, heteroarylcycloalkylsulfonamido, heteroarylsulfonamido, alkoxycarbonylamino, alkoxycarbonyloxy, alkylureido, arylureido, halogen, cyano, or nitro, and said alkyl, alkoxy, and aryl are unsubstituted or optionally independently substituted with one or more moieties which are the same or different and are independently selected from alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl;

W may be present or absent, and if W is present, W is C(=O), C(=S), C(=N—CN), or $S(O_2)$;

(9) X is represented by structural Formula 4:

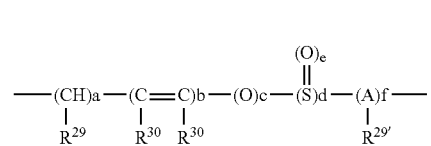

Formula 4 wherein in Formula 4, a is 2, 3, 4, 5, 6, 7, 8 or 9;

b, c, d, e and f are 0, 1, 2, 3, 4 or 5;

A is C, N, S or O;

$R^{29}$ and $R^{29'}$ are independently present or absent and if present can be the same or different, each being independently one or two substituents independently selected from the group consisting of: H, halo, alkyl, aryl, cycloalkyl, cycloalkylamino, cycloalkylaminocarbonyl, cyano, hydroxy, alkoxy, alkylthio, amino, —NH(alkyl), —NH(cycloalkyl), —N(alkyl)$_2$, carboxyl, C(O)O-alkyl, heteroaryl, aralkyl, alkylaryl, aralkenyl, heteroaralkyl, alkylheteroaryl, heteroaralkenyl, hydroxyalkyl, aryloxy, aralkoxy, acyl, aroyl, nitro, aryloxycarbonyl, aralkoxycarbonyl, alkylsulfonyl, arylsulfonyl, heteroarylsulfonyl, alkylsulfinyl, arylsulfinyl, heteroarylsulfinyl, arylthio, heteroarylthio, aralkylthio, heteroaralkylthio, cycloalkenyl, heterocyclyl, heterocyclenyl, $Y_1Y_2$N-alkyl-, $Y_1Y_2$NC(O)— and $Y_1Y_2NSO_2$—, wherein $Y_1$ and $Y_2$ can be the same or different and are independently selected from the group consisting of hydrogen, alkyl, aryl, and aralkyl; or R²⁹ and R²⁹' are linked together such that the combination is an aliphatic or heteroaliphatic chain of 0 to 6 carbons;

R³⁰ is present or absent and if present is one or two substituents independently selected from the group consisting of: H, alkyl, aryl, heteroaryl and cylcoalkyl;

(10) D is represented by structural Formula 5:

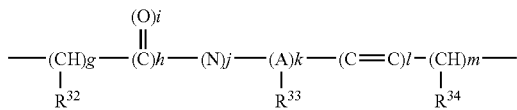

Formula 5 wherein in Formula 5, R³², R³³ and R³⁴ are present or absent and if present are independently one or two substituents independently selected from the group consisting of: H, halo, alkyl, aryl, cycloalkyl, cycloalkylamino, spiroalkyl, cycloalkylaminocarbonyl, cyano, hydroxy, alkoxy, alkylthio, amino, —NH(alkyl), —NH(cycloalkyl), —N(alkyl)₂, carboxyl, —C(O)O-alkyl, heteroaryl, aralkyl, alkylaryl, aralkenyl, heteroaralkyl, alkylheteroaryl, heteroaralkenyl, hydroxyalkyl, aryloxy, aralkoxy, acyl, aroyl, nitro, aryloxycarbonyl, aralkoxycarbonyl, alkylsulfonyl, arylsulfonyl, heteroarylsulfonyl, alkylsulfinyl, arylsulfinyl, heteroarylsulfinyl, arylthio, heteroarylthio, aralkylthio, heteroaralkylthio, cycloalkenyl, heterocyclyl, heterocyclenyl, Y₁Y₂N-alkyl-, Y₁Y₂NC(O)— and Y₁Y₂NSO₂—, wherein Y₁ and Y₂ can be the same or different and are independently selected from the group consisting of hydrogen, alkyl, aryl, and aralkyl; or R³² and R³⁴ are linked together such that the combination forms a portion of a cycloalkyl group;

g is 1, 2, 3, 4, 5, 6, 7, 8 or 9;

h, i, j, k, l and m are 0, 1, 2, 3, 4 or 5; and

A is C, N, S or O,

(11) provided that when structural Formula 2:

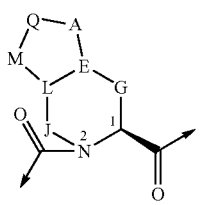

Formula 2 is

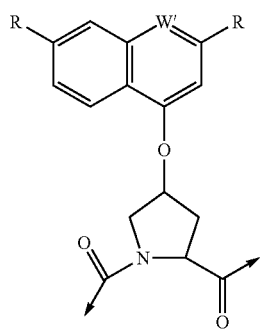

and

W' is CH or N, both the following conditional exclusions (i) and (ii) apply:

conditional exclusion (i): Z' is not —NH—R³⁶, wherein R³⁶ is H, C₆ ₒᵣ ₁₀ aryl, heteroaryl, —C(O)—R³⁷, —C(O)—OR³⁷ or —C(O)—NHR³⁷, wherein R³⁷ is C₁₋₆ alkyl or C₃₋₆ cycloalkyl;

and conditional exclusion (ii): R¹ is not —C(O)OH, a pharmaceutically acceptable salt of —C(O)OH, an ester of —C(O)OH or —C(O)NHR³⁸ wherein R³⁸ is selected from the group consisting of C₁₋₈ alkyl, C₃₋₆ cycloalkyl, C₆ ₜₒ ₁₀ aryl or C₇₋₁₆ aralkyl.

In another embodiment, the compound is a compound of Formula VI

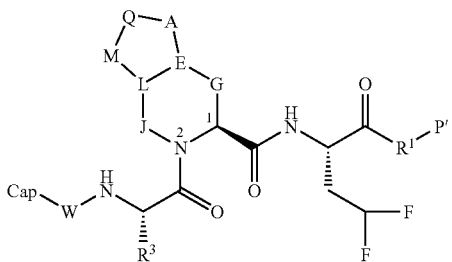

Formula VI or a pharmaceutically acceptable salt, solvate or ester of said compound, wherein:

Cap and P' are independently H, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocyclyloxy, cycloalkyloxy, amino, alkylamino, arylamino, alkyl-arylamino, arylamino, heteroarylamino, cycloalkylamino, carboxyalkylamino, arlylalkyloxy or heterocycylylamino, wherein each of said alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocyclyloxy, cycloalkyloxy, amino, alkylamino, arylamino, alkyl-arylamino, arylamino, heteroarylamino, cycloalkylamino, carboxyalkylamino, arlylalkyloxy or heterocycylylamino can be unsubstituted or optionally independently substituted with one or two substituents which can be the same or different and are independently selected from X¹ and X²;

X¹ is alkyl, alkenyl, alkynyl, cycloalkyl, cycloalkyl-alkyl, heterocyclyl, heterocyclylalkyl, aryl, alkylaryl, arylalkyl, arylheteroaryl, heteroaryl, heterocyclylamino, alkylheteroaryl, or heteroarylalkyl, and X¹ can be unsubstituted or optionally independently substituted with one or more of X² moieties which can be the same or different and are independently selected;

X² is hydroxy, alkyl, aryl, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, keto, ester or nitro, wherein each of said alkyl, alkoxy, and aryl can be unsubstituted or optionally independently substituted with one or more moieties which can be the same or different and are independently selected from alkyl, alkenyl, alkynyl, cycloalkyl, cycloalkyl-alkyl, heterocyclyl, heterocyclylalkyl, aryl, alkylaryl, arylalkyl, arylheteroaryl, heteroaryl, heterocyclylamino, alkylheteroaryl and heteroarylalkyl;

W may be present or absent, and when W is present W is C(=O), C(=S), C(=NH), C(=N—OH), C(=N—CN), S(O) or S(O$_2$);

Q maybe present or absent, and when Q is present, Q is N(R), P(R), CR=CR', (CH$_2$)$_p$, (CHR)$_p$, (CRR')$_p$, (CHR—CHR')$_p$, O, S, S(O) or S(O$_2$); when Q is absent, M is (i) either directly linked to A or (ii) M is an independent substituent on L and A is an independent substituent on E, with said independent substituent being selected from —OR, —CH(R'), S(O)$_{0-2}$R or —NRR'; when both Q and M are absent, A is either directly linked to L, or A is an independent substituent on E, selected from —OR, CH(R)(R'), —S(O)$_{0-2}$R or —NRR';

A is present or absent and if present A is —O—, —O(R)CH$_2$—, —(CHR)$_p$—, —(CHR—CHR')$_p$—, (CRR')$_p$, N(R), NRR', S, or S(O$_2$), and when Q is absent, A is —OR, —CH(R)(R') or —NRR'; and when A is absent, either Q and E are connected by a bond or Q is an independent substituent on M;

E is present or absent and if present E is CH, N, C(R);

G may be present or absent, and when G is present, G is (CH$_2$)$_p$, (CHR)$_p$, or (CRR')$_p$; when G is absent, J is present and E is directly connected to the carbon atom marked position 1;

J may be present or absent, and when J is present, J is (CH$_2$)$_p$, (CHR—CHR')$_p$, (CHR)$_p$, (CRR')$_p$, S(O$_2$), N(H), N(R) or O; when J is absent and G is present, L is directly linked to the nitrogen atom marked position 2;

L may be present or absent, and when L is present, L is CH, N, or CR; when L is absent, M is present or absent; if M is present with L being absent, then M is directly and independently linked to E, and J is directly and independently linked to E;

M may be present or absent, and when M is present, M is O, N(R), S, S(O$_2$), (CH$_2$)$_p$, (CHR)$_p$, (CHR—CHR')$_p$, or (CRR')$_p$;

p is a number from 0 to 6;

R, R' and R$^3$ can be the same or different, each being independently selected from the group consisting of: H, C$_1$-C$_{10}$ alkyl, C$_2$-C$_{10}$ alkenyl, C$_3$-C$_8$ cycloalkyl, C$_3$-C$_8$ heterocyclyl, alkoxy, aryloxy, alkylthio, arylthio, amino, amido, arylthioamino, arylcarbonylamino, arylaminocarboxy, alkylaminocarboxy, heteroalkyl, heteroalkenyl, alkenyl, alkynyl, aryl-alkyl, heteroarylalkyl, ester, carboxylic acid, carbamate, urea, ketone, aldehyde, cyano, nitro, halogen, (cycloalkyl)alkyl, aryl, heteroaryl, alkyl-aryl, alkylheteroaryl, alkyl-heteroaryl and (heterocyclyl)alkyl;

R and R' in (CRR') can be linked together such that the combination forms a cycloalkyl or heterocyclyl moiety; and R$^1$ is N(R) or O.

In another embodiment, the compound is a compound of Formula VII

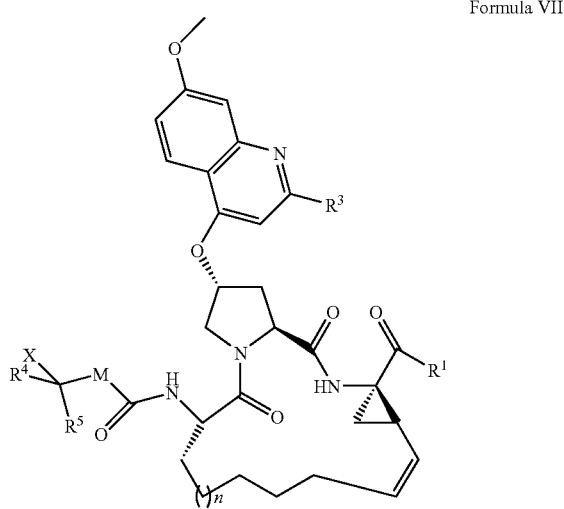

Formula VII or a pharmaceutically acceptable salt, solvate or ester thereof, wherein, M is O, N(H), or CH$_2$;

n is 0-4;

R$^1$ is –OR$^6$, —NR$^6$R$^7$ or

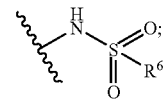

where R$^6$ and R$^7$ can be the same or different, each being independently selected from the group consisting of hydrogen, alkyl, alkenyl, alkynyl, heteroalkyl, cycloalkyl, cycloalkylalkyl, aryl, arylalkyl, heteroaryl, heteroarylalkyl, heterocyclyl, heterocyclylalkyl, hydroxyl, amino, arylamino and alkylamino;

R$^4$ and R$^5$ can be the same or different, each being independently selected from the group consisting of H, alkyl, aryl and cycloalkyl; or alternatively R$^4$ and R$^5$ together form part of a cyclic 5- to 7-membered ring such that the moiety

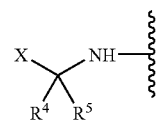

is represented by

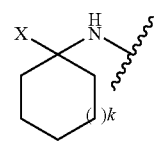

where k is 0 to 2;
X is selected from the group consisting of:

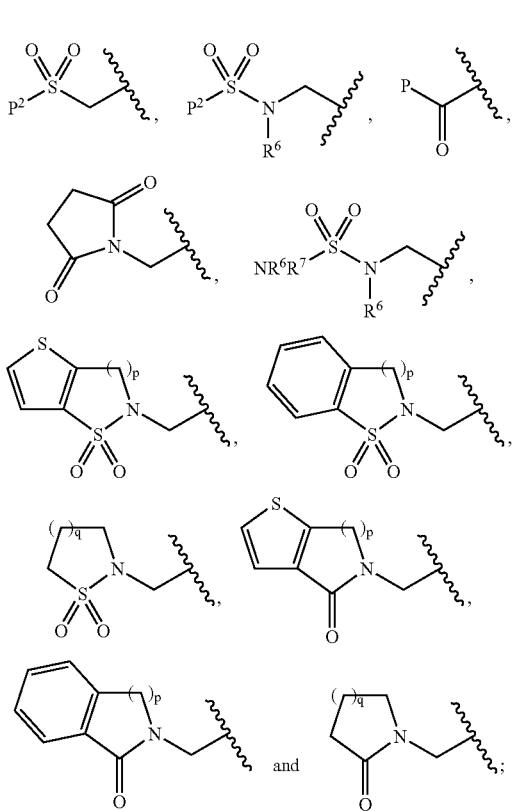

where p is 1 to 2, q is 1-3 and $P^2$ is alkyl, aryl, heteroaryl, heteroalkyl, cycloalkyl, dialkylamino, alkylamino, arylamino or cycloalkylamino;

and $R^3$ is selected from the group consisting of: aryl, heterocyclyl, heteroaryl,

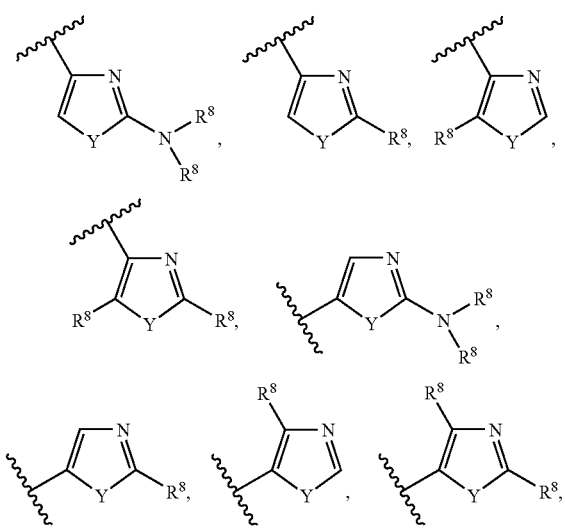

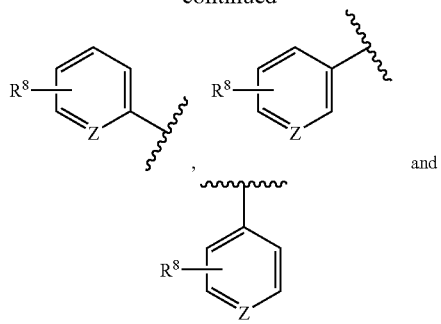

where Y is O, S or NH, and Z is CH or N, and the $R^8$ moieties can be the same or different, each $R^8$ being independently selected from the group consisting of hydrogen, alkyl, heteroalkyl, cycloalkyl, aryl, heteroaryl, heterocyclyl, hydroxyl, amino, arylamino, alkylamino, dialkylamino, halo, alkylthio, arylthio and alkyloxy.

In another embodiment, the compound is a compound of Formula VIII:

Formula VIII

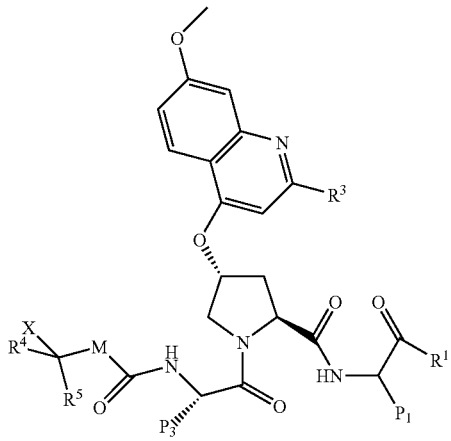

or a pharmaceutically acceptable salt, solvate or ester thereof, wherein,
M is O, N(H), or $CH_2$;
$R^1$ is —$OR^6$, —$NR^6R^7$ or

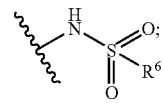

where $R^6$ and $R^7$ can be the same or different, each being independently selected from the group consisting of hydrogen, alkyl, alkenyl, alkynyl, heteroalkyl, cycloalkyl, cycloalkylalkyl, aryl, arylalkyl, heteroaryl, heteroarylalkyl, heterocyclyl, heterocyclylalkyl, hydroxyl, amino, arylamino and alkylamino;
$P_1$ is selected from the group consisting of alkyl, alkenyl, alkynyl, cycloalkyl haloalkyl;
$P_3$ is selected from the group consisting of alkyl, cycloalkyl, aryl and cycloalkyl fused with aryl;

$R^4$ and $R^5$ can be the same or different, each being independently selected from the group consisting of H, alkyl, aryl and cycloalkyl; or alternatively $R^4$ and $R^5$ together form part of a cyclic 5- to 7-membered ring such that the moiety

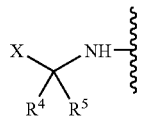

is represented by

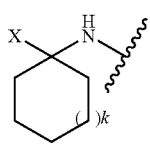

where k is 0 to 2;
X is selected from the group consisting of:

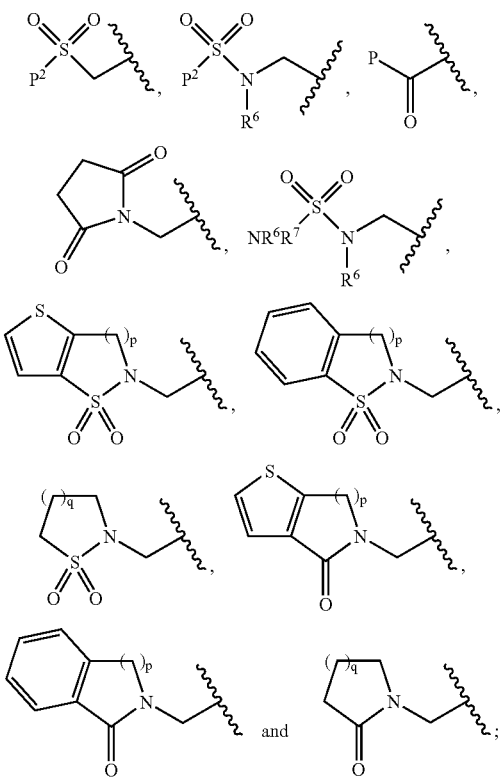

where p is 1 to 2, q is 1 to 3 and $P^2$ is alkyl, aryl, heteroaryl, heteroalkyl, cycloalkyl, dialkylamino, alkylamino, arylamino or cycloalkylamino;

and
$R^3$ is selected from the group consisting of: aryl, heterocyclyl, heteroaryl,

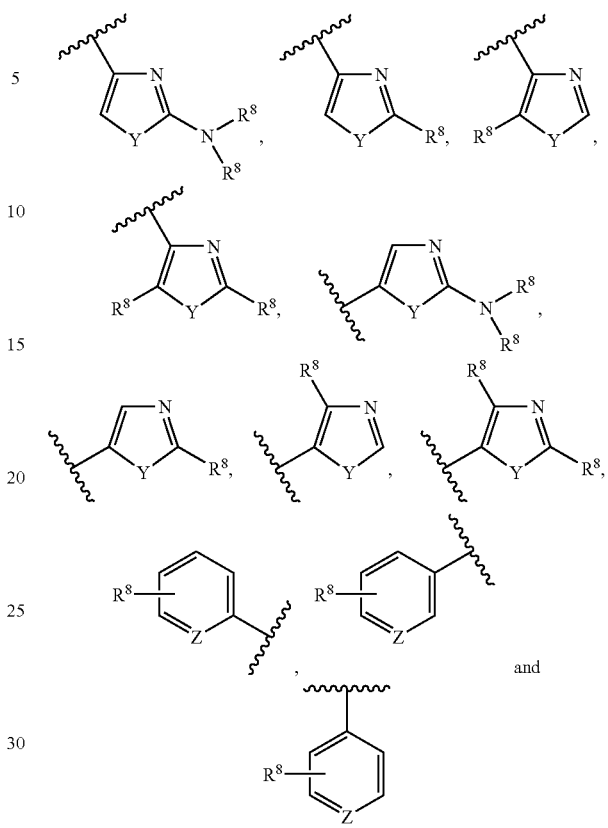

where Y is O, S or NH, and Z is CH or N, and the $R^8$ moieties can be the same or different, each $R^8$ being independently selected from the group consisting of hydrogen, alkyl, heteroalkyl, cycloalkyl, aryl, heteroaryl, heterocyclyl, hydroxyl, amino, arylamino, alkylamino, dialkylamino, halo, alkylthio, arylthio and alkyloxy.

In another embodiment, the compound is a compound of Formula IX:

Formula IX

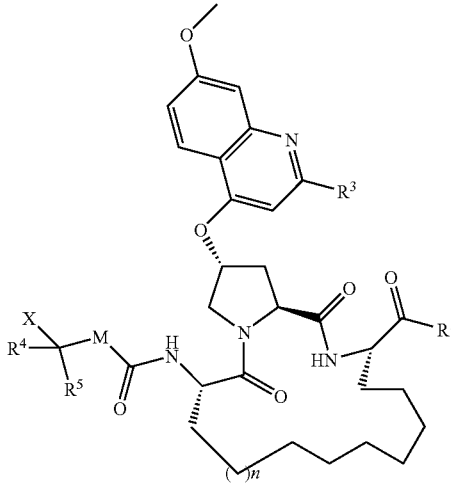

or a pharmaceutically acceptable salt, solvate or ester thereof, wherein,

M is O, N(H), or $CH_2$;
n is 0-4;
$R^1$ is $-OR^6$, $-NR^6R^7$ or

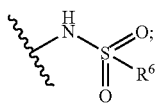

where $R^6$ and $R^7$ can be the same or different, each being independently selected from the group consisting of hydrogen, alkyl, alkenyl, alkynyl, heteroalkyl, cycloalkyl, cycloalkylalkyl, aryl, arylalkyl, heteroaryl, heteroarylalkyl, heterocyclyl, heterocyclylalkyl, hydroxyl, amino, arylamino and alkylamino;

$R^4$ and $R^5$ can be the same or different, each being independently selected from the group consisting of H, alkyl, aryl and cycloalkyl; or alternatively $R^4$ and $R^5$ together form part of a cyclic 5- to 7-membered ring such that the moiety

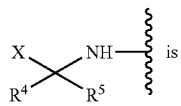 is represented by

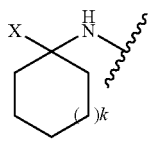

where k is 0 to 2;
X is selected from the group consisting of:

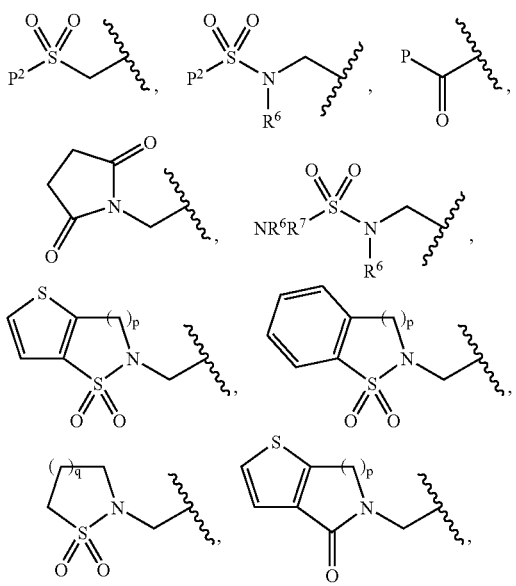

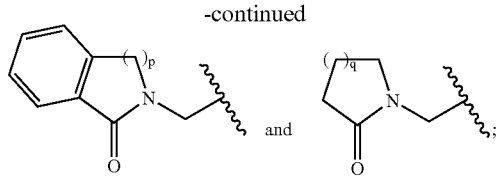

where p is 1 to 2, q is 1 to 3 and $P^2$ is alkyl, aryl, heteroaryl, heteroalkyl, cycloalkyl, dialkylamino, alkylamino, arylamino or cycloalkylamino;

and $R^3$ is selected from the group consisting of: aryl, heterocyclyl, heteroaryl,

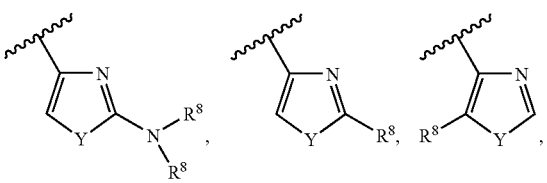

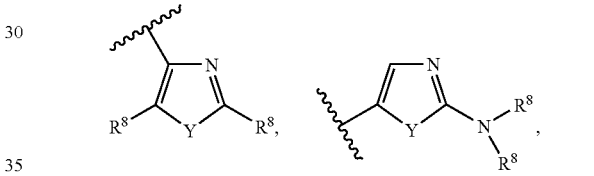

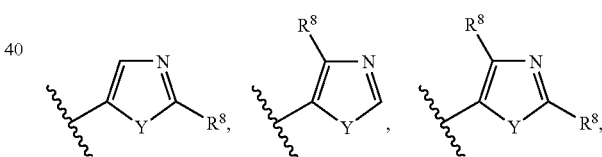

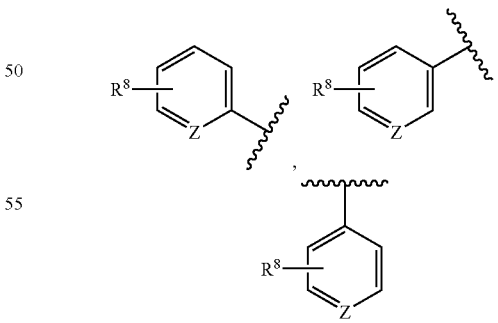

where Y is O, S or NH, and Z is CH or N, and the $R^8$ moieties can be the same or different, each $R^8$ being independently selected from the group consisting of hydrogen, alkyl, heteroalkyl, cycloalkyl, aryl, heteroaryl, heterocyclyl, hydroxyl, amino, arylamino, alkylamino, dialkylamino, halo, alkylthio, arylthio and alkyloxy.

In another embodiment, the compound is a compound of Formula X:

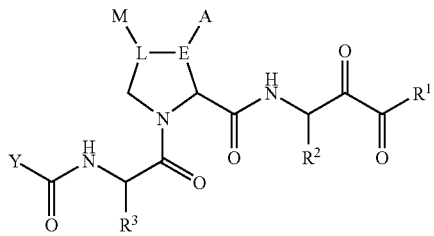

Formula X or a pharmaceutically acceptable salt, solvate or ester thereof; wherein:

$R^1$ is H, $OR^8$, $NR^9R^{10}$, or $CHR^9R^{10}$, wherein $R^8$, $R^9$ and $R^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl;

A and M can be the same or different, each being independently selected from R, OR, NHR, NRR', SR, $SO_2R$, and halo; or A and M are connected to each other such that the moiety:

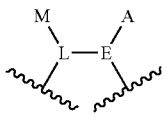

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), $CH_2C(R)$, or $C(R)CH_2$;

R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;

and Y is selected from the following moieties:

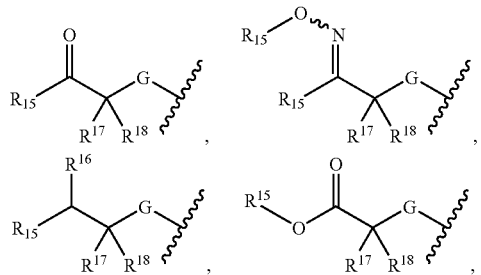

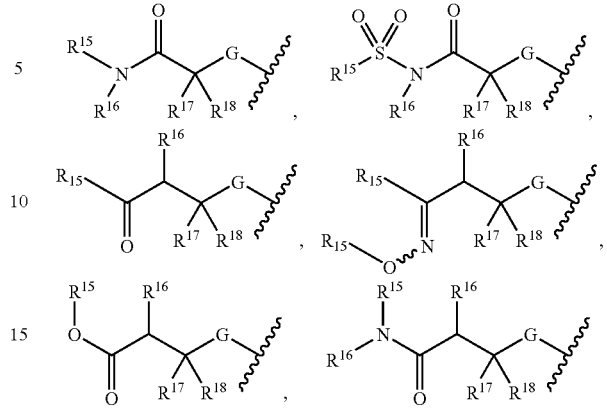

wherein G is NH or O; and $R^{15}$, $R^{16}$, $R^{17}$ and $R^{18}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, $R^{15}$ and $R^{16}$ are connected to each other to form a four to eight-membered cycloalkyl, heteroaryl or heterocyclyl structure, and likewise, independently $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In one embodiment, the compound is a compound of Formula XI:

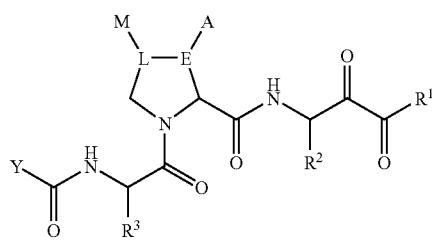

Formula XI or a pharmaceutically acceptable salt, solvate or ester thereof; wherein:

$R^1$ is H, $OR^8$, $NR^9R^{10}$, or $CHR^9R^{10}$, wherein $R^8$, $R^9$ and $R^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl;

A and M can be the same or different, each being independently selected from R, $NR^9R^{10}$, SR, $SO_2R$, and halo; or A and M are connected to each other (in other words, A-E-L-M taken together) such that the moiety:

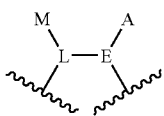

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), $CH_2C(R)$, or $C(R)CH_2$;

R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that $NR^9R^{10}$ forms a four to eight-membered heterocyclyl;

Y is selected from the following moieties:

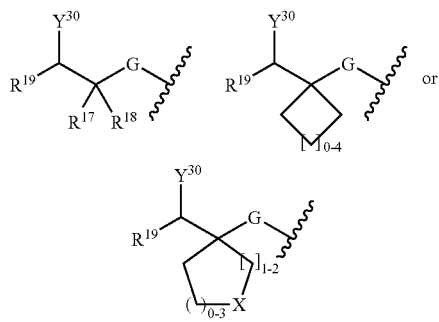

wherein $Y^{30}$ and $Y^{31}$ are selected from

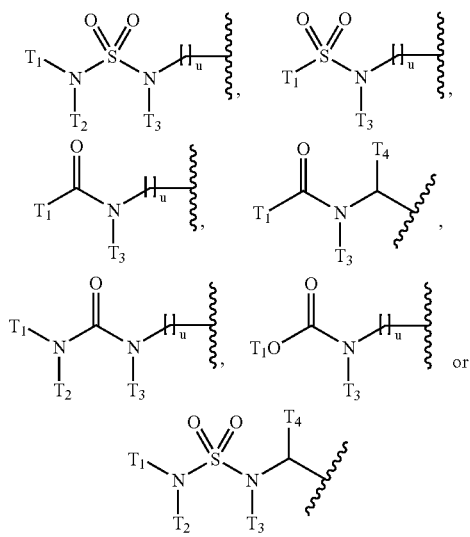

where u is a number 0-6;

X is selected from O, $NR^{15}$, $NC(O)R^{16}$, S, S(O) and $SO_2$;

G is NH or O; and $R^{15}$, $R^{16}$, $R^{17}$, $R^{18}$, $R^{19}$, $T_1$, $T_2$, $T_3$ and $T_4$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In another embodiment, the compound is a compound of Formula XII:

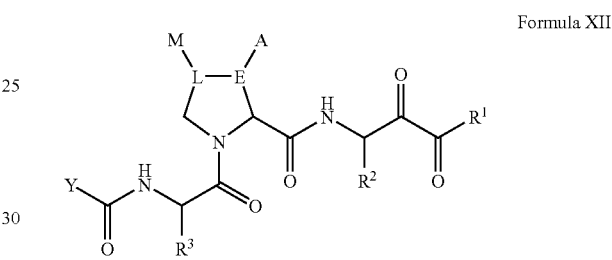

Formula XII or a pharmaceutically acceptable salt, solvate or ester thereof; wherein:

$R^1$ is H, $OR^8$, $NR^9R^{10}$, or $CHR^9R^{10}$, wherein $R^8$, $R^9$ and $R^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl;

A and M can be the same or different, each being independently selected from R, OR, NHR, NRR', SR, $SO_2R$, and halo; or A and M are connected to each other such that the moiety:

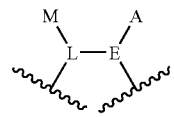

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), $CH_2C(R)$, or $C(R)CH_2$;

R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;

and Y is selected from the following moieties:

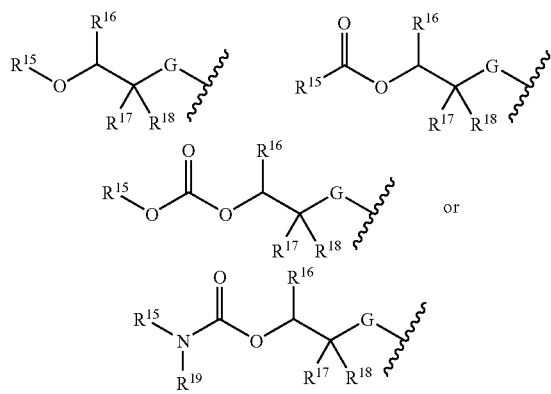

wherein G is NH or O; and $R^{15}$, $R^{16}$, $R^{17}$, $R^{18}$, and $R^{19}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, (i) either $R^{15}$ and $R^{16}$ are connected to each other to form a four to eight-membered cyclic structure, or $R^{15}$ and $R^{19}$ are connected to each other to form a four to eight-membered cyclic structure, and (ii) likewise, independently, $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, alkyl, aryl, heteroaryl, keto, carboxy, carbalkoxy, carboxamido, alkoxycarbonylamino, alkoxycarbonyloxy, alkylureido, arylureido, halo, cyano, and nitro.

In another embodiment, the compound is a compound of Formula XIII:

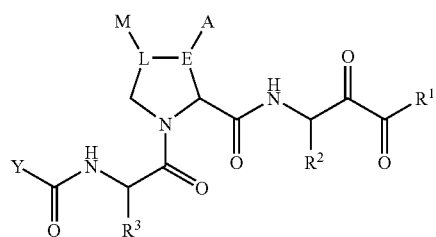

Formula XIII or a pharmaceutically acceptable salt, solvate or ester thereof; wherein:
$R^1$ is H, $OR^8$, $NR^9R^{10}$, or $CHR^9R^{10}$, wherein $R^8$, $R^9$ and $R^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl;
A and M can be the same or different, each being independently selected from R, OR, NHR, NRR', SR, $SO_2R$, and halo; or A and M are connected to each other (in other words, A-E-L-M taken together) such that the moiety:

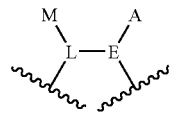

shown above in Formula I forms either a three, four, six, seven or eight-membered cycloalkyl, a four to eight-membered heterocyclyl, a six to ten-membered aryl, or a five to ten-membered heteroaryl;
E is C(H) or C(R);
L is C(H), C(R), $CH_2C(R)$, or $C(R)CH_2$;
R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;
and Y is selected from the following moieties:

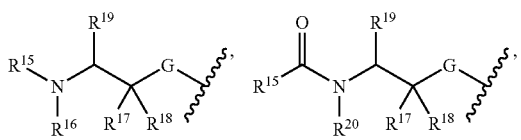

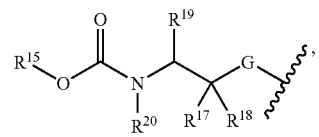

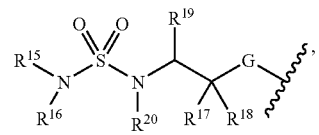

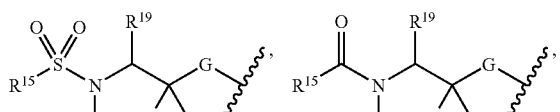

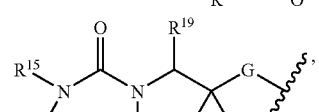

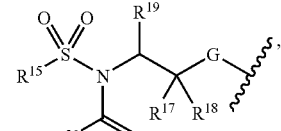

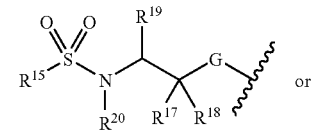

or

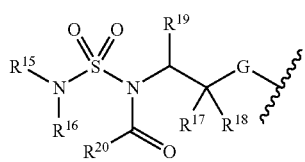

wherein G is NH or O, and $R^{15}, R^{16}, R^{17}, R^{18}, R^{19}$ and $R^{20}$ can be the same or different, each being independently selected from the group consisting of H, $C_1$-$C_{10}$ alkyl, $C_1$-$C_{10}$ heteroalkyl, $C_2$-$C_{10}$ alkenyl, $C_2$-$C_{10}$ heteroalkenyl, $C_2$-$C_{10}$ alkynyl, $C_2$-$C_{10}$ heteroalkynyl, $C_3$-$C_8$ cycloalkyl, $C_3$-$C_8$ heterocyclyl, aryl, heteroaryl, or alternately: (i) either $R^{15}$ and $R^{16}$ can be connected to each other to form a four to eight-membered cycloalkyl or heterocyclyl, or $R^{15}$ and $R^{19}$ are connected to each other to form a five to eight-membered cycloalkyl or heterocyclyl, or $R^{15}$ and $R^{20}$ are connected to each other to form a five to eight-membered cycloalkyl or heterocyclyl, and (ii) likewise, independently, $R^{17}$ and $R^{18}$ are connected to each other to form a three to eight-membered cycloalkyl or heterocyclyl, wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In another embodiment, the compound is a compound of Formula XIV:

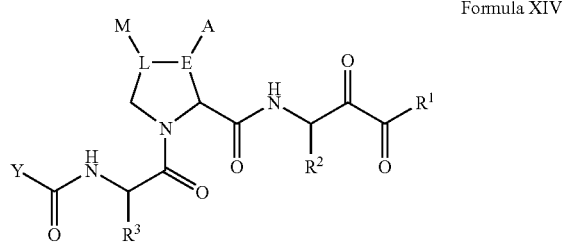

Formula XIV or a pharmaceutically acceptable salt, solvate or ester thereof; wherein:
$R^1$ is H, $OR^8$, $NR^9R^{10}$, or $CHR^9R^{10}$, wherein $R^8, R^9$ and $R^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl;
A and M can be the same or different, each being independently selected from R, OR, NHR, NRR', SR, $SO_2R$, and halo;

or A and M are connected to each other such that the moiety:

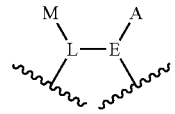

shown above in Formula I forms either a three, four, six, seven or eight-membered cycloalkyl, a four to eight-membered heterocyclyl, a six to ten-membered aryl, or a five to ten-membered heteroaryl;
E is C(H) or C(R);
L is C(H), C(R), $CH_2C(R)$, or $C(R)CH_2$;
R, R', $R^2$, and $R^3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately R and R' in NRR' are connected to each other such that NRR' forms a four to eight-membered heterocyclyl;
and Y is selected from the following moieties:

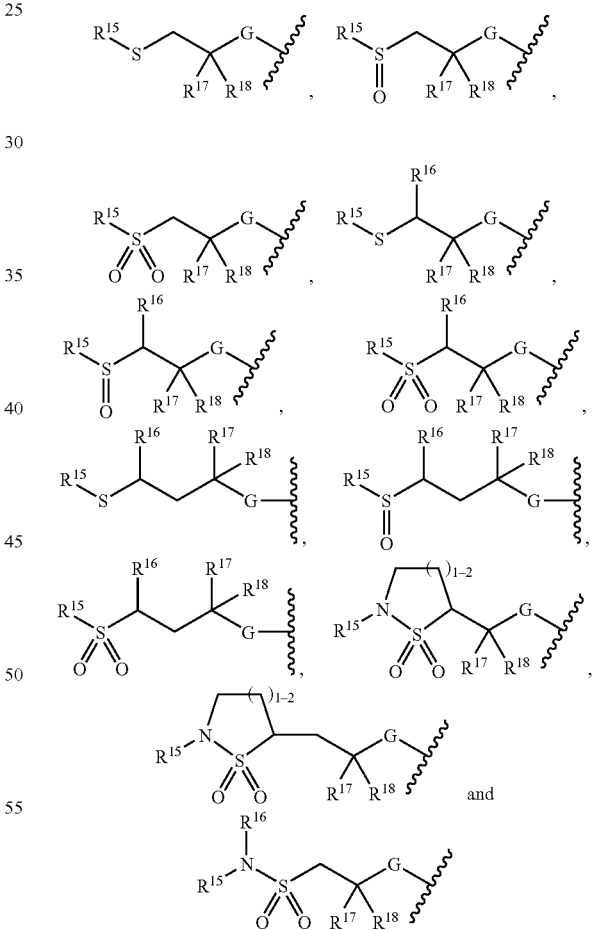

wherein G is NH or O; and $R^{15}, R^{16}, R^{17}$ and $R^{18}$ can be the same or different, each being independently selected from the group consisting of H, alkyl, heteroalkyl, alkenyl, heteroalkenyl, alkynyl, heteroalkynyl, cycloalkyl, heterocyclyl, aryl, and heteroaryl, or alternately, (i) $R^{15}$ and $R^{16}$ are connected to each other to form a four to eight-membered cyclic structure, and (ii) likewise, independently $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, alkyl, aryl, heteroaryl, keto, carboxy, carbalkoxy, carboxamido, alkoxycarbonylamino, alkoxycarbonyloxy, alkylureido, arylureido, halo, cyano, and nitro.

In another embodiment, the compound is a compound of Formula XV:

Formula XV

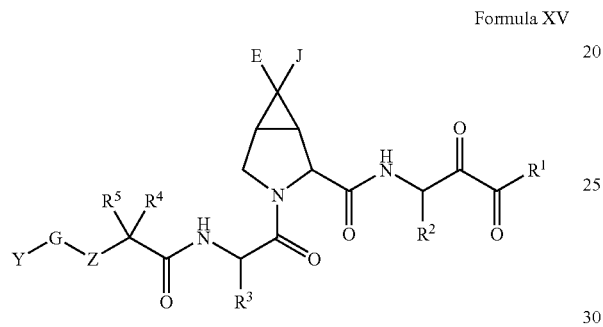

or a pharmaceutically acceptable salt, solvate or ester thereof; wherein:

$R^1$ is H, $OR^8$, $NR^9R^{10}$, or $CHR^9R^{10}$, wherein $R^8$, $R^9$ and $R^{10}$ can be the same or different, each being independently selected from the group consisting of H, alkyl-, aryl-, heteroalkyl-, heteroaryl-, cycloalkyl-, cycloalkyl-, arylalkyl-, and heteroarylalkyl; E and J can be the same or different, each being independently selected from the group consisting of R, OR, NHR, $NRR^7$, SR, halo, and $S(O_2)R$, or E and J can be directly connected to each other to form either a three to eight-membered cycloalkyl, or a three to eight-membered heterocyclyl moiety;

Z is N(H), N(R), or O, with the proviso that when Z is O, G is present or absent and if G is present with Z being O, then G is C(=O);

G maybe present or absent, and if G is present, G is C(=O) or $S(O_2)$, and when G is absent, Z is directly connected to Y;

Y is selected from the group consisting of:

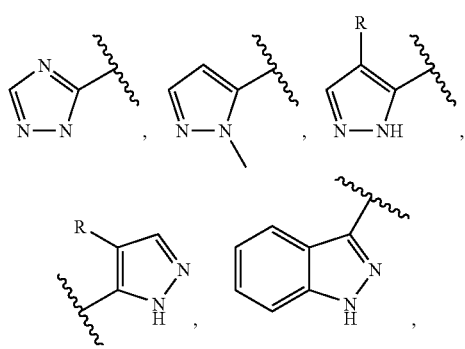

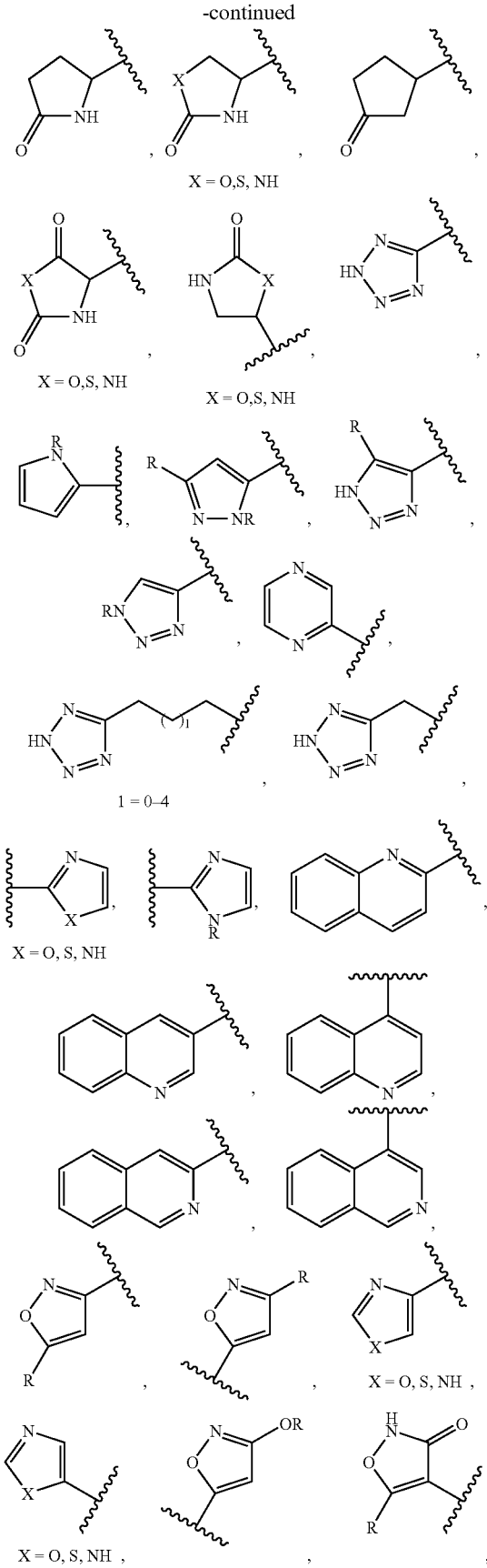

-continued

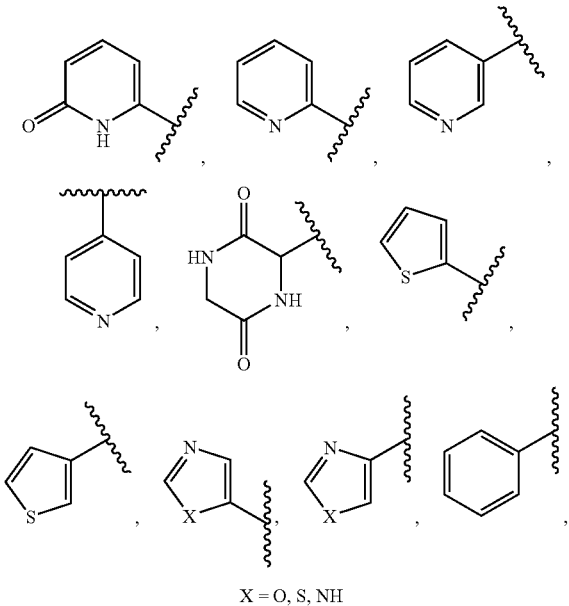

X = O, S, NH

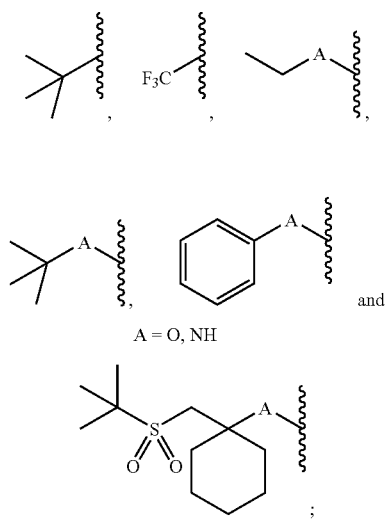

A = O, NH and

R, R$^7$, R$^2$, R$^3$, R$^4$ and R$^5$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-, wherein each of said heteroalkyl, heteroaryl and heterocyclyl independently has one to six oxygen, nitrogen, sulfur, or phosphorus atoms;

wherein each of said alkyl, heteroalkyl, alkenyl, alkynyl, aryl, heteroaryl, cycloalkyl and heterocyclyl moieties can be unsubstituted or optionally independently substituted with one or more moieties selected from the group consisting of alkyl, alkenyl, alkynyl, aryl, aralkyl, cycloalkyl, heterocyclyl, halo, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate.

In another embodiment, the compound is a compound of Formula XVI:

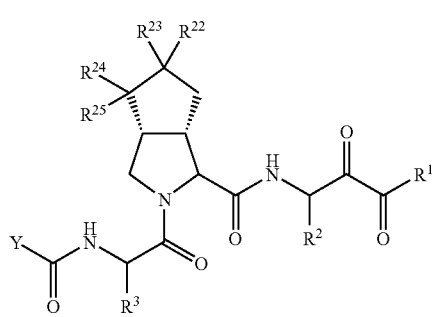

Formula XVI or a pharmaceutically acceptable salt, solvate or ester thereof; wherein:

R$^1$ is H, OR$^8$, NR$^9$R$^{10}$, or CHR$^9$R$^{10}$, wherein R$^8$, R$^9$ and R$^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl, or alternately R$^9$ and R$^{10}$ in NR$^9$R$^{10}$ are connected to each other such that NR$^9$R$^{10}$ forms a four to eight-membered heterocyclyl, and likewise independently alternately R$^9$ and R$^{10}$ in CHR$^9$R$^{10}$ are connected to each other such that CHR$^9$R$^{10}$ forms a four to eight-membered cycloalkyl;

R$^2$ and R$^3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl;

Y is selected from the following moieties:

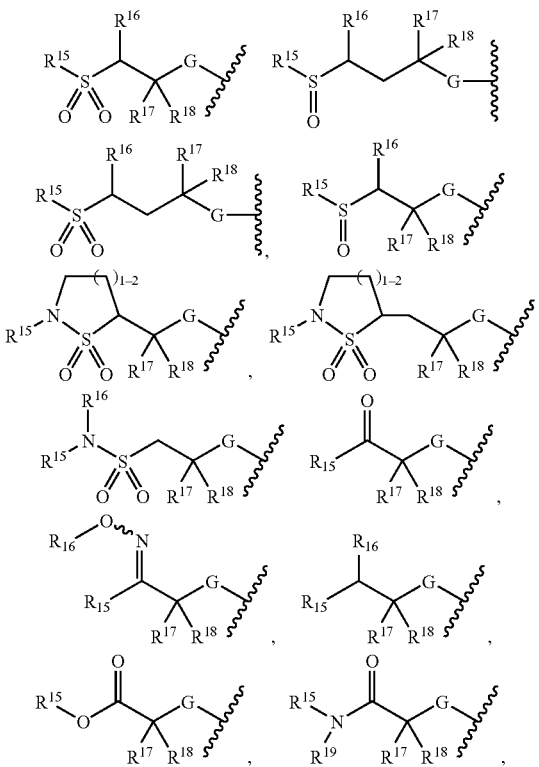

-continued

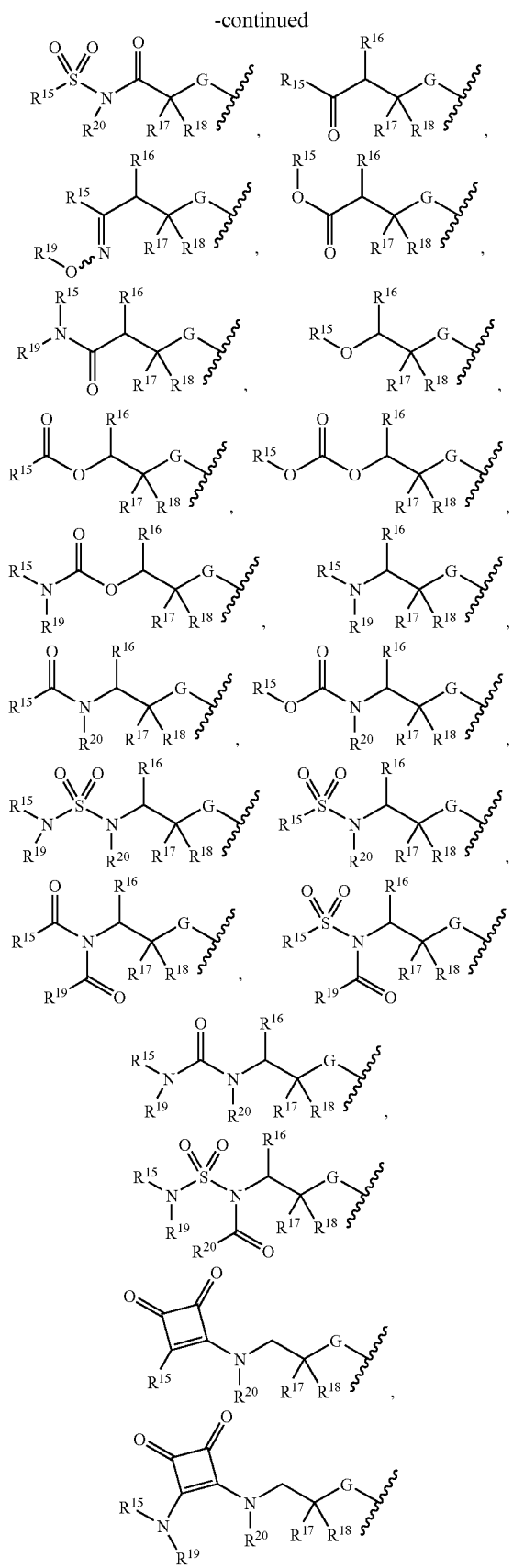

wherein G is NH or O; and $R^{15}$, $R^{16}$, $R^{17}$, $R^{18}$, $R^{19}$, $R^{20}$, $R^{21}$, $R^{22}$, $R^{23}$, $R^{24}$ and $R^{25}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; (iv) likewise independently $R^{15}$ and $R^{20}$ are connected to each other to form a four to eight-membered heterocyclyl; (v) likewise independently $R^{22}$ and $R^{23}$ are connected to each other to form a three to eight-membered cycloalkyl or a four to eight-membered heterocyclyl; and (vi) likewise independently $R^{24}$ and $R^{25}$ are connected to each other to form a three to eight-membered cycloalkyl or a four to eight-membered heterocyclyl;

wherein each of said alkyl, aryl, heteroaryl, cycloalkyl or heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In another embodiment, the compound is a compound of Formula XVII:

Formula XVII

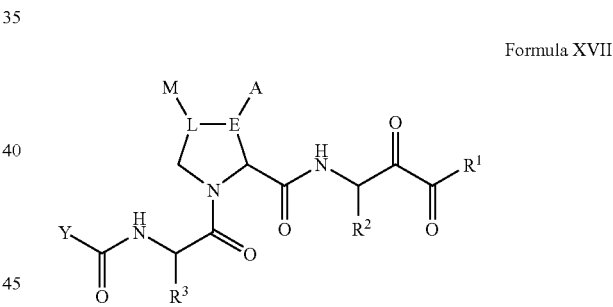

or a pharmaceutically acceptable salt, solvate or ester thereof; wherein:

$R^1$ is H, $OR^8$, $NR^9R^{10}$, or $CHR^9R^{10}$, wherein $R^8$, $R^9$ and $R^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl;

A and M can be the same or different, each being independently selected from R, OR, NHR, NRR', SR, $SO_2R$, and halo; or A and M are connected to each other such that the moiety:

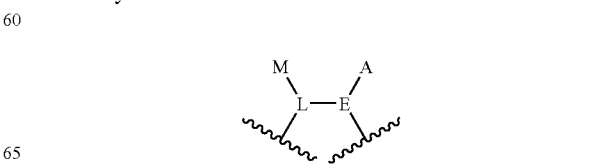

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), CH$_2$C(R), or C(R)CH$_2$;

R, R', R$^2$, and R$^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;

Y is selected from the following moieties:

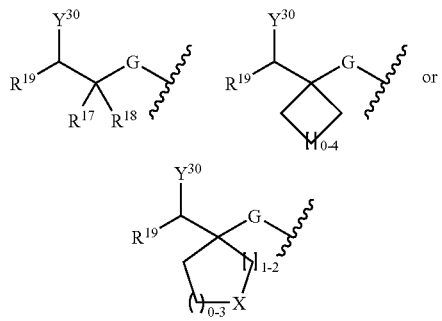

wherein Y$^{30}$ is selected from

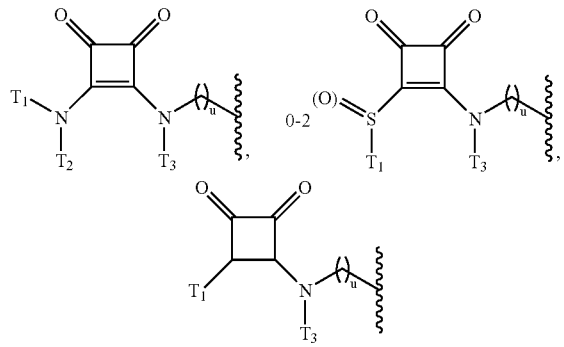

where u is a number 0-1;

X is selected from O, NR$^{15}$, NC(O)R$^{16}$, S, S(O) and SO$_2$;

G is NH or O; and

R$^{15}$, R$^{16}$, R$^{17}$, R$^{18}$, R$^{19}$, T$_1$, T$_2$, and T$_3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, R$^{17}$ and R$^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In another embodiment, the compound is a compound of Formula XVIII:

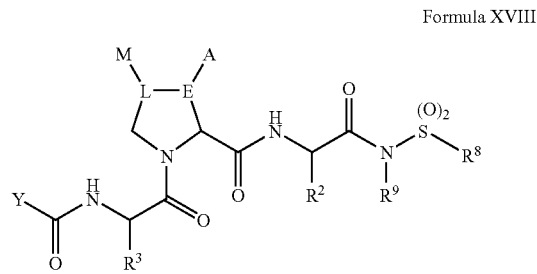

Formula XVIII or a pharmaceutically acceptable salt, solvate or ester thereof, wherein:

R$^8$ is selected from the group consisting of alkyl-, aryl-, heteroalkyl-, heteroaryl-, cycloalkyl-, heterocyclyl-, arylalkyl-, heteroarylalkyl-, and heterocyclylalkyl-;

R$^9$ is selected from the group consisting of H, alkyl, alkenyl, alkynyl, aryl and cycloalkyl;

A and M can be the same or different, each being independently selected from R, OR, N(H)R, N(RR'), SR, S(O$_2$)R, and halo; or A and M are connected to each other (in other words, A-E-L-M taken together) such that the moiety:

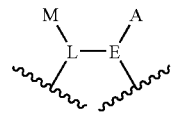

shown above in Formula I forms either a three, four, five, six, seven or eight-membered cycloalkyl, a four to eight-membered heterocyclyl, a six to ten-membered aryl, or a five to ten-membered heteroaryl;

E is C(H) or C(R);

L is C(H), C(R), CH$_2$C(R), or C(R)CH$_2$;

R and R' can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in N(RR') are connected to each other such that N(RR') forms a four to eight-membered heterocyclyl;

R$^2$ and R$^3$ can be the same or different, each being independently selected from the group consisting of H, alkyl, heteroalkyl, alkenyl, heteroalkenyl, alkynyl, heteroalkynyl, cycloalkyl, spiro-linked cycloalkyl, heterocyclyl, aryl, arylalkyl, heteroaryl, and heteroarylalkyl;

Y is selected from the following moieties:

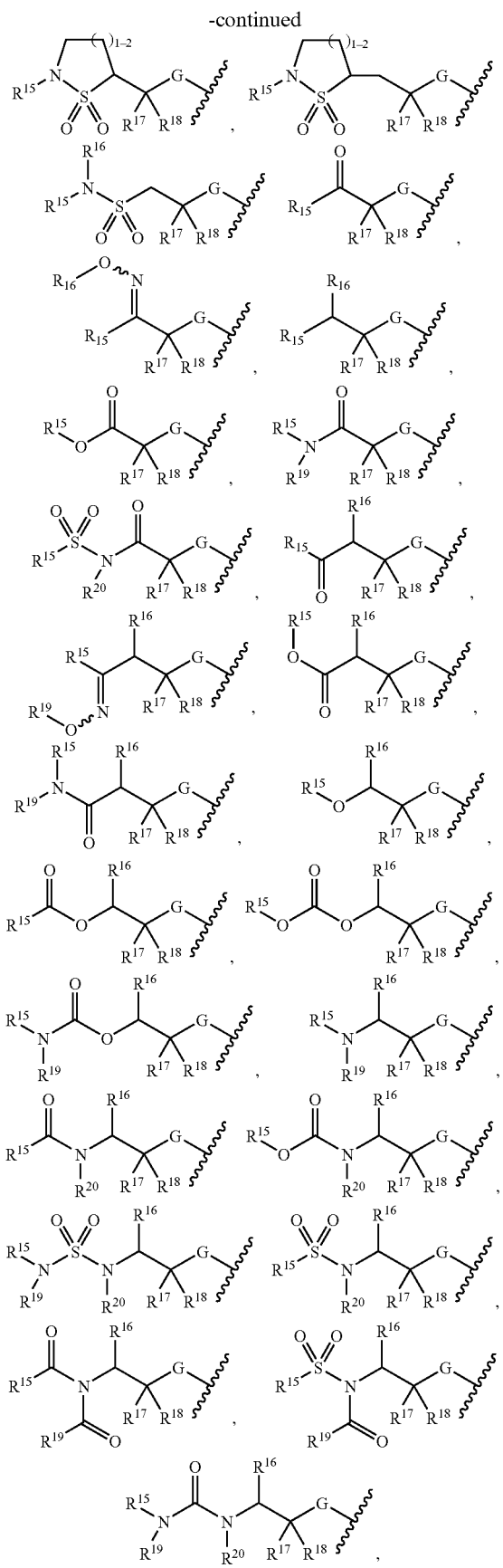

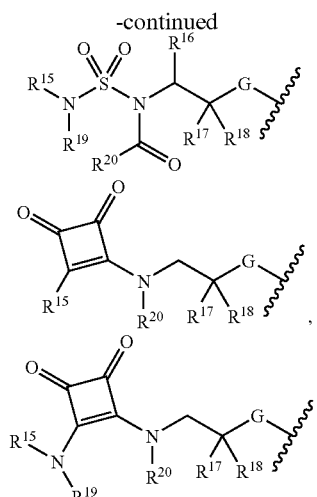

wherein G is NH or O; and $R^{15}$, $R^{16}$, $R^{17}$, $R^{18}$, $R^{19}$ and $R^{20}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl, spiro-linked cycloalkyl, and heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, alkenyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In another embodiment, the compound is a compound of Formula XIX:

Formula XIX

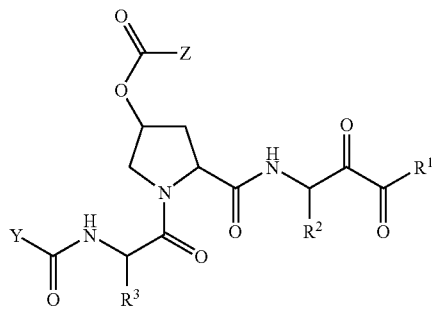

wherein:
Z is selected from the group consisting of a heterocyclyl moiety, N(H)(alkyl), —N(alkyl)$_2$, —N(H)(cycloalkyl), —N(cycloalkyl)$_2$, —N(H)(aryl), —N(aryl)$_2$, —N(H)(heterocyclyl), —N(heterocyclyl)$_2$, —N(H)(heteroaryl), and —N(heteroaryl)$_2$;

$R^1$ is H, $OR^8$, $NR^9R^{10}$, or $CHR^9R^{10}$, wherein $R^8$, $R^9$ and $R^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl, or alternately $R^9$ and $R^{10}$ in $NR^9R^{10}$ are connected to each other such that $NR^9R^{10}$ forms a four to eight-membered heterocyclyl, and likewise independently alternately $R^9$ and $R^{10}$ in $CHR^9R^{10}$ are connected to each other such that $CHR^9R^{10}$ forms a four to eight-membered cycloalkyl;

$R^2$ and $R^3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl;

Y is selected from the following moieties:

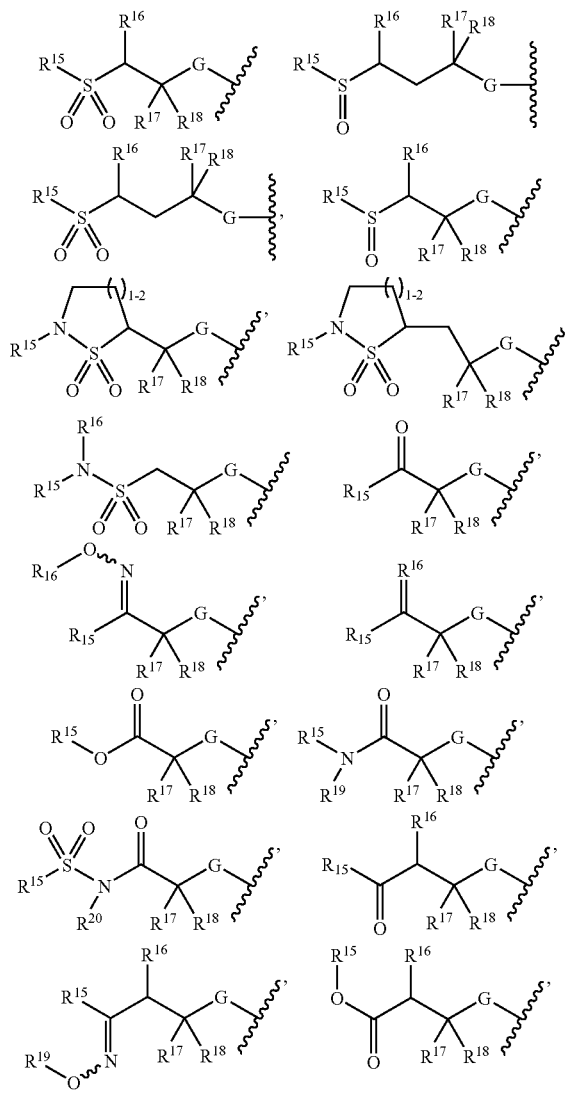

-continued

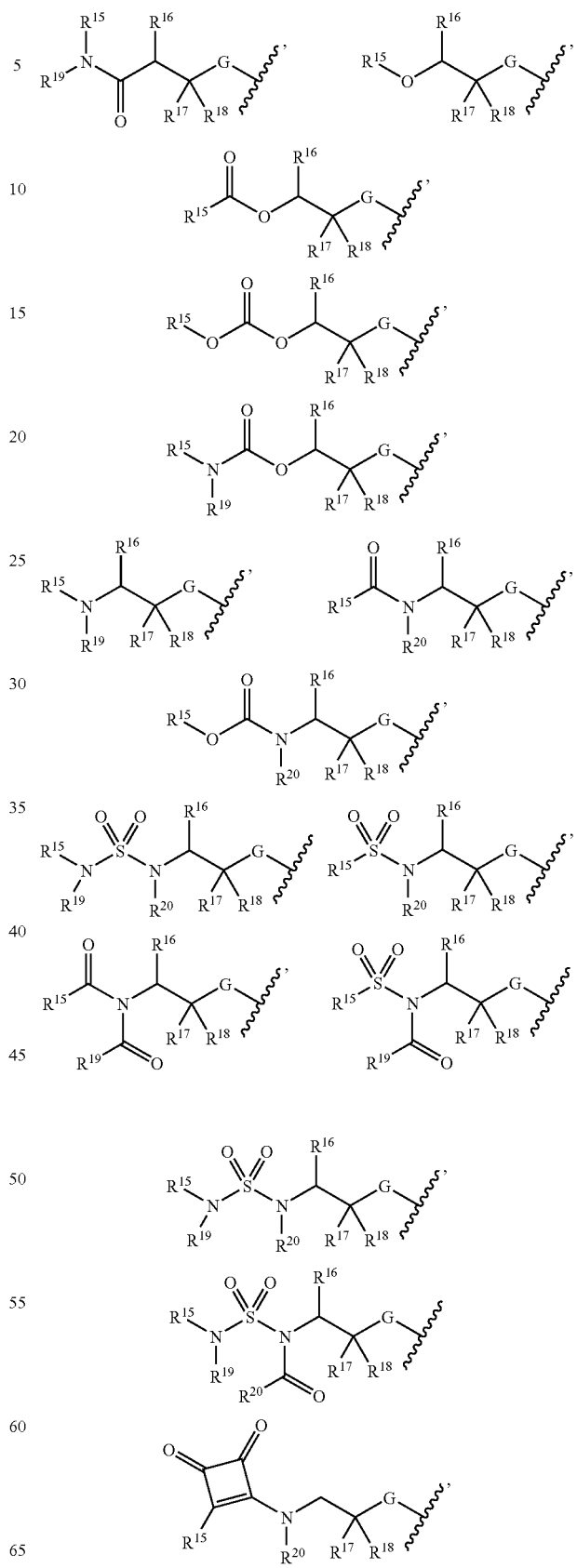

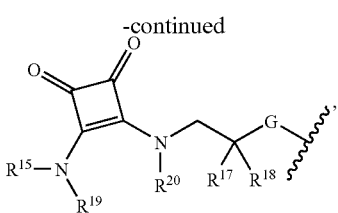

wherein G is NH or O; and $R^{15}$, $R^{16}$, $R^{17}$, $R^{18}$, $R^{19}$, $R^{20}$ and $R^{21}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In another embodiment, the compound is a compound of formula XX

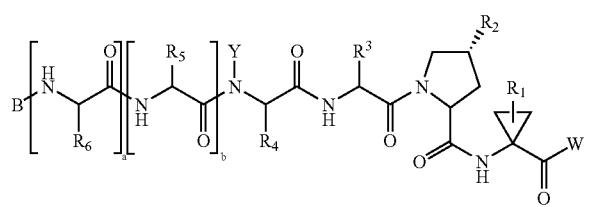

Formula XX or a pharmaceutically acceptable salt, solvate or ester thereof; wherein: a is 0 or 1; b is 0 or 1; Y is H or $C_{1-6}$ alkyl;

B is H, an acyl derivative of formula $R_7$—C(O)— or a sulfonyl of formula $R_7$—SO2 wherein R7 is (i) $C_{1-10}$ alkyl optionally substituted with carboxyl, $C_{1-6}$ alkanoyloxy or $C_{1-6}$ alkoxy;
(ii) $C_{3-7}$ cycloalkyl optionally substituted with carboxyl, ($C_{1-6}$ alkoxy)carbonyl or phenylmethoxycarbonyl;
(iii) $C_6$ or $C_{10}$ aryl or $C_{7-16}$ aralkyl optionally substituted with $C_{1-6}$ alkyl, hydroxy, or amino optionally substituted with $C_{1-6}$ alkyl; or
(iv) Het optionally substituted with $C_{1-6}$ alkyl, hydroxy, amino optionally substituted with $C_{1-6}$ alkyl, or amido optionally substituted with $C_{1-6}$ alkyl;

$R_6$, when present, is $C_{1-6}$ alkyl substituted with carboxyl;
$R_5$, when present, is $C_{1-6}$ alkyl optionally substituted with carboxyl;
$R_4$ is $C_{1-10}$ alkyl, $C_{3-7}$ cycloalkyl or $C_{4-10}$ (alkylcycloalkyl);
$R_3$ is $C_{1-10}$ alkyl, $C_{3-7}$ cycloalkyl or $C_{4-10}$ (alkylcycloalkyl);
$R_2$ is $CH_2$—$R_{20}$, NH—$R_{20}$, O-$R_{20}$ or S—$R_{20}$, wherein $R_{20}$ is a saturated or unsaturated $C_{3-7}$ cycloalkyl or $C_{4-10}$ (alkyl cycloalkyl) being optionally mono-, di- or tri-substituted with $R_{21}$, or $R_{20}$ is a $C_6$ or $C_{10}$ aryl or $C_{7-16}$ aralkyl optionally mono-, di- or tri-substituted with $R_{21}$, or $R_{20}$ is Het or (lower alkyl)-Het optionally mono-, di- or tri-substituted with $R_{21}$, wherein each $R_{21}$ is independently $C_{1-6}$ alkyl; $C_{1-6}$alkoxy; amino optionally mono- or di-substituted with $C_{1-6}$ alkyl; sulfonyl; $NO_2$; OH; SH; halo; haloalkyl; amido optionally mono-substituted with $C_{1-6}$ alkyl, $C_6$ or $C_{10}$ aryl, $C_{7-16}$ aralkyl, Het or (lower alkyl)-Het; carboxyl; carboxy(lower alkyl); $C_6$ or $C_{10}$ aryl, $C_{7-16}$ aralkyl or Het, said aryl, aralkyl or Het being optionally substituted with $R_{22}$;

wherein $R_{22}$ is $C_{1-6}$alkyl; $C_{1-6}$ alkoxy; amino optionally mono- or di-substituted with $C_{1-6}$ alkyl; sulfonyl; $NO_2$; OH; SH; halo; haloalkyl; carboxyl; amide or (lower alkyl)amide;
$R_1$ is $C_{1-6}$ alkyl or $C_{2-6}$ alkenyl optionally substituted with halogen; and W is hydroxy or a N-substituted amino.

In another embodiment, the compound is a compound of Formula XXI

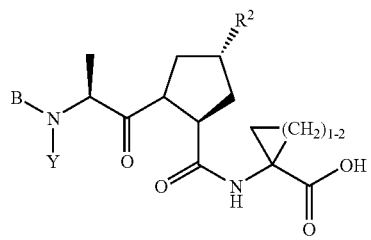

Formula XXI or a pharmaceutically acceptable salt, solvate or ester thereof; wherein:

B is H, a $C_6$ or $C_{10}$ aryl, $C_{7-16}$ aralkyl; Het or (lower alkyl)-Het, all of which optionally substituted with $C_{1-6}$ alkyl; $C_{1-6}$ alkoxy; $C_{1-6}$ alkanoyl; hydroxy; hydroxyalkyl; halo; haloalkyl; nitro; cyano; cyanoalkyl; amino optionally substituted with $C_{1-6}$ alkyl; amido; or (lower alkyl)amide;

or B is an acyl derivative of formula $R_4$—C(O)—; a carboxyl of formula $R_4$—O—-C(O)—; an amide of formula $R_4$—N($R_5$)—C(O)—; a thioamide of formula $R_4$—N($R_5$)—C(S)—; or a sulfonyl of formula $R_4$—SO2 wherein $R_4$ is (i) $C_{1-10}$ alkyl optionally substituted with carboxyl, $C_{1-6}$ alkanoyl, hydroxy, $C_{1-6}$ alkoxy, amino optionally mono- or di-substituted with $C_{1-6}$ alkyl, amido, or (lower alkyl) amide;

(ii) $C_{3-7}$ cycloalkyl, $C_{3-7}$ cycloalkoxy, or $C_{4-10}$ alkylcycloalkyl, all optionally substituted with hydroxy, carboxyl, ($C_{1-6}$ alkoxy)carbonyl, amino optionally mono- or di-substituted with $C_{1-6}$ alkyl, amido, or (lower alkyl) amide;

(iii) amino optionally mono- or di-substituted with $C_{1-6}$ alkyl; amido; or (lower alkyl)amide;

(iv) $C_6$ or $C_{10}$ aryl or $C_{7-16}$ aralkyl, all optionally substituted with $C_{1-6}$ alkyl, hydroxy, amido, (lower alkyl)amide, or amino optionally mono- or di-substituted with $C_{1-6}$ alkyl; or (v) Het or (lower alkyl)-Het, both optionally substituted with $C_{1-6}$ alkyl, hydroxy, amido, (lower alkyl) amide, or amino optionally mono- or di-substituted with $C_{1-6}$ alkyl;

$R_5$ is H or $C_{1-6}$ alkyl;

with the proviso that when $R_4$ is an amide or a thioamide, $R_4$ is not (ii) a cycloalkoxy;

Y is H or $C_{1-6}$ alkyl;

$R_3$ is $C_{1-8}$ alkyl, $C_{3-7}$ cycloalkyl, or $C_{4-10}$ alkylcycloalkyl, all optionally substituted with hydroxy, $C_{1-6}$ alkoxy, $C_{1-6}$ thioalkyl, amido, (lower alkyl)amido, $C_6$ or $C_{10}$ aryl, or $C_{7-16}$ aralkyl;

$R_2$ is $CH_2-R_{20}$, $NH-R_{20}$, $O-R_{20}$ or $S-R_{20}$, wherein $R_{20}$ is a saturated or unsaturated $C_{3-7}$ cycloalkyl or $C_{4-10}$ (alkylcycloalkyl), all of which being optionally mono-, di- or tri-substituted with $R_{21}$, or $R_{20}$ is a $C_6$ or $C_{10}$ aryl or $C_{7-14}$ aralkyl, all optionally mono-, di- or tri-substituted with $R_{21}$, or $R_{20}$ is Het or (lower alkyl)-Het, both optionally mono-, di- or tri-substituted with $R_{21}$, wherein each $R_{21}$ is independently $C_{1-6}$ alkyl; $C_{1-6}$ alkoxy; lower thioalkyl; sulfonyl; $NO_2$; OH; SH; halo; haloalkyl; amino optionally mono- or di-substituted with $C_{1-6}$ alkyl, $C_6$ or $C_{10}$ aryl, $C_{7-14}$ aralkyl, Het or (lower alkyl)-Het; amido optionally mono-substituted with $C_{1-6}$ alkyl, $C_6$ or $C_{10}$ aryl, $C_{7-14}$ aralkyl, Het or (lower alkyl)-Het; carboxyl; carboxy (lower alkyl); $C_6$ or $C_{10}$ aryl, $C_{7-14}$ aralkyl or Het, said aryl, aralkyl or Het being optionally substituted with $R_{22}$;

wherein $R_{22}$ is $C_{1-6}$ alkyl; $C_{3-7}$ cycloalkyl; $C_{1-6}$ alkoxy; amino optionally mono- or di-substituted with $C_{1-6}$ alkyl; sulfonyl; (lower alkyl)sulfonyl; $NO_2$; OH; SH; halo; haloalkyl; carboxyl; amide; (lower alkyl)amide; or Het optionally substituted with $C_{1-6}$ alkyl;

R1 is H; $C_{1-6}$ alkyl, $C_{3-7}$ cycloalkyl, $C_{2-6}$ alkenyl, or $C_{2-6}$ alkynyl, all optionally substituted with halogen.

In another embodiment, the compound is a compound of Formula XXII

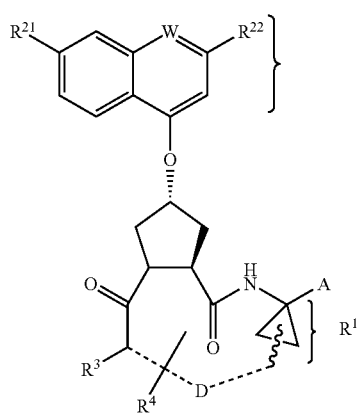

Formula XXII or a pharmaceutically acceptable salt, solvate or ester thereof; wherein W is CH or N, $R^{21}$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$, wherein each $R^{23}$ is independently H, $C_{1-6}$ alkyl or $C_{3-6}$ cycloalkyl;

$R^{22}$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{3-6}$ cycloalkyl, $C_{6\ or\ 10}$ aryl or Het, wherein Het is a five-, six-, or seven-membered saturated or unsaturated heterocycle containing from one to four heteroatoms selected from nitrogen, oxygen and sulfur;

said cycloalkyl, aryl or Het being substituted with $R^{24}$, wherein $R^{24}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{25})_2$, $NH-C(O)-R^{25}$ or $NH-C(O)-NH-R^{25}$, wherein each $R^{25}$ is independently: H, $C_{1-6}$ alkyl or $C_{3-6}$ cycloalkyl;

or $R^{24}$ is $NH-C(O)-OR^{26}$ wherein $R^{26}$ is $C_{1-6}$ alkyl or $C_{3-6}$ cycloalkyl;

$R^3$ is hydroxy, $NH_2$, or a group of formula $-NH-R^{31}$, wherein $R^{31}$ is $C_{6\ or\ 10}$ aryl, heteroaryl, $-C(O)-R^{32}$, $-C(O)-NHR^{32}$ or $-C(O)-OR^{32}$, wherein $R^{32}$ is $C_{1-6}$ alkyl or $C_{3-6}$ cycloalkyl;

D is a 5 to 10-atom saturated or unsaturated alkylene chain optionally containing one to three heteroatoms independently selected from: O, S, or $N-R^{41}$, wherein $R^{41}$ is H, $C_{1-6}$ alkyl, $C_{3-6}$ cycloalkyl or $-C(O)-R^{42}$, wherein $R^{42}$ is $C_{1-6}$ alkyl, $C_{3-6}$ cycloalkyl or $C_{6\ or\ 10}$ aryl; $R^4$ is H or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio and C 1-6 thioalkyl, and A is an amide of formula $-C(O)-NH-R^5$, wherein $R^5$ is selected from the group consisting of: $C_{1-8}$ alkyl, $C_{3-6}$ cycloalkyl, $C_{6\ or\ 10}$ aryl and $C_{7-16}$ aralkyl;

or A is a carboxylic acid.

In another embodiment, the compound is a compound of Formula XXIII

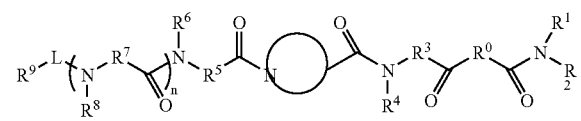

Formula XXIII a pharmaceutically acceptable salt, solvate or ester thereof; wherein:

$R^0$ is a bond or difluoromethylene;

$R^1$ is hydrogen, optionally substituted aliphatic group, optionally substituted cyclic group or optionally substituted aromatic group;

$R^2$ and $R^9$ are each independently optionally substituted aliphatic group, optionally substituted cyclic group or optionally substituted aromatic group;

R3, R5 and R7 are each independently:
optionally substituted (1,1- or 1,2-)cycloalkylene; or
optionally substituted (1,1- or 1,2-)heterocyclylene; or
methylene or ethylene), substituted with one substituent selected from the group consisting of an optionally substituted aliphatic group, an optionally substituted cyclic group or an optionally substituted aromatic group, and wherein the methylene or ethylene is further optionally substituted with an aliphatic group substituent; or;

R4, R 6, R8 and $R^{10}$ are each independently hydrogen or optionally substituted aliphatic group;

is substituted monocyclic azaheterocyclyl or optionally substituted multicyclic azaheterocyclyl, or optionally substituted multicyclic azaheterocyclenyl wherein the unsaturatation is in the ring distal to the ring bearing the $R^9$-L-(N(R$^8$)—R$^7$—C(O)—)$_n$N(R$^6$)—R$^5$—C(O)—N moiety and to which the —C(O)—N(R$^4$)—R$^3$—C(O)C (O)NR$^2$R$^1$ moiety is attached; L is —C(O)—, —OC(O)—, —NR$^{10}$C(O)—, —S(O)$_2$—, or —NR$^{10}$S(O)$_2$—; and n is 0 or 1, provided when

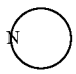

is substituted

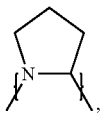

then L is —OC(O)— and R$^9$ is optionally substituted aliphatic; or at least one of R$^3$, R$^5$ and R$^7$ is ethylene, substituted with one substituent selected from the group consisting of an optionally substituted aliphatic group, an optionally substituted cyclic group or an optionally substituted aromatic group and wherein the ethylene is further optionally substituted with an aliphatic group substituent; or R$^4$ is optionally substituted aliphatic.

In another embodiment, the compound is a compound of Formula XXIV

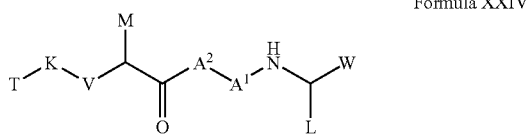

Formula XXIV or a pharmaceutically acceptable salt, solvate or ester thereof; wherein:

W is:

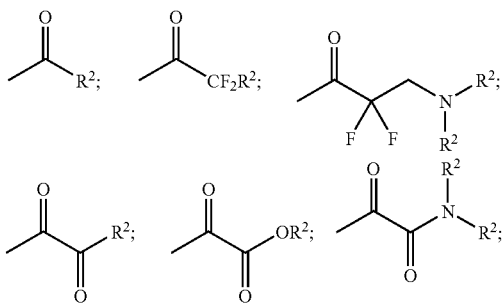

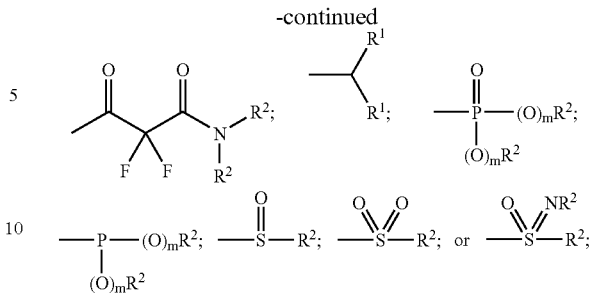

m is 0 or 1;

each R$^1$ is hydroxy, alkoxy, or aryloxy, or each R$^1$ is an oxygen atom and together with the boron, to which they are each bound, form a 5-7 membered ring, wherein the ring atoms are carbon, nitrogen, or oxygen;

each R$^2$ is independently hydrogen, alkyl, alkenyl, aryl, aralkyl, aralkenyl, cycloalkyl, cycloalkylalkyl, cycloalkenyl, cycloalkenylalkyl, heterocyclyl, heterocyclylalkyl, heterocyclylalkenyl, heteroaryl, or heteroaralkyl, or two R$^2$ groups, which are bound to the same nitrogen atom, form together with that nitrogen atom, a 5-7 membered monocyclic heterocyclic ring system; wherein any R$^2$ carbon atom is optionally substituted with J;

J is alkyl, aryl, aralkyl, alkoxy, aryloxy, aralkoxy, cycloalkyl, cycloalkoxy, heterocyclyl, heterocyclyloxy, heterocyclylalkyl, keto, hydroxy, amino, alkylamino, alkanoylamino, aroylamino, aralkanoylamino, carboxy, carboxyalkyl, carboxamidoalkyl, halo, cyano, nitro, formyl, acyl, sulfonyl, or sulfonamido and is optionally substituted with 1-3 J$^1$ groups;

J$^1$ is alkyl, aryl, aralkyl, alkoxy, aryloxy, heterocyclyl, heterocyclyloxy, keto, hydroxy, amino, alkanoylamino, aroylamino, carboxy, carboxyalkyl, carboxamidoalkyl, halo, cyano, nitro, formyl, sulfonyl, or sulfonamido;

L is alkyl, alkenyl, or alkynyl, wherein any hydrogen is optionally substituted with halogen, and wherein any hydrogen or halogen atom bound to any terminal carbon atom is optionally substituted with sulfhydryl or hydroxy;

A$^1$ is a bond;

R$^4$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups;

R$^5$ and R$^6$ are independently hydrogen, alkyl, alkenyl, aryl, aralkyl, aralkenyl, cycloalkyl, cycloalkylalkyl, cycloalkenyl, heterocyclyl, heterocyclylalkyl, heteroaryl, or heteroaralkyl, and is optionally substituted with 1-3 J groups;

X is a bond, —C(H)(R7)—, —O—, —S—, or —N(R8)—;

R$^7$ is hydrogen, alkyl, alkenyl, aryl, aralkyl, heterocyclyl, heterocyclylalkyl, heteroaryl, or heteroaralkyl, and is optionally substititued with 1-3 J groups;

R$^8$ is hydrogen alkyl, aryl, aralkyl, heterocyclyl, heterocyclylalkyl, heteroaryl, heteroaralkyl, aralkanoyl, heterocyclanoyl, heteroaralkanoyl, —C(O)R$^{14}$, —SO$_2$R$^{14}$, or carboxamido, and is optionally substititued with 1-3 J groups; or R$^8$ and Z, together with the atoms to which they are bound, form a nitrogen containing mono- or bicyclic ring system optionally substituted with 1-3 J groups;

R$^{14}$ is alkyl, aryl, aralkyl, heterocyclyl, heterocyclylalkyl, heteroaryl, or heteroaralkyl;

Y is a bond, —CH$_2$—, —C(O)—, —C(O)C(O)—, —S(O)—, —S(O)$_2$—, or —S(O)(NR$^7$)—, wherein R$^7$ is as defined above;

Z is alkyl, aryl, aralkyl, cycloalkyl, cycloalkylalkyl, heterocyclyl, heterocyclylalkyl, heteroaryl, heteroaralkyl, —$OR^2$, or —$N(R^2)_2$, wherein any carbon atom is optionally substituted with J, wherein $R^2$ is as defined above;

$A^2$ is a bond or

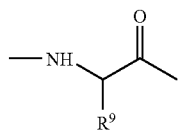

$R^9$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups;

M is alkyl, cycloalkyl, aryl, aralkyl, heterocyclyl, heterocyclylalkyl, heteroaryl, or heteroaralkyl, optionally substituted by 1-3 J groups, wherein any alkyl carbon atom may be replaced by a heteroatom;

V is a bond, —$CH_2$—, —$C(H)(R^{11})$—, —O—, —S—, or —$N(R^{11})$—;

$R^{11}$ is hydrogen or $C_{1-3}$ alkyl;

K is a bond, —O—, —S—, —C(O)—, —S(O)—, —$S(O)_2$—, or —$S(O)(NR^{11})$—, wherein $R^{11}$ is as defined above;

T is —$R^{12}$, -alkyl-$R^{12}$, -alkenyl-$R^{12}$, -alkynyl-$R^{12}$, —$OR^{12}$, —$N(R^{12})_2$, —$C(O)R^{12}$, —$C(=NOalkyl)R^{12}$, or

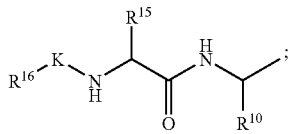

$R^{12}$ is hydrogen, aryl, heteroaryl, cycloalkyl, heterocyclyl, cycloalkylidenyl, or heterocycloalkylidenyl, and is optionally substituted with 1-3 J groups, or a first $R^{12}$ and a second $R^{12}$, together with the nitrogen to which they are bound, form a mono- or bicyclic ring system optionally substituted by 1-3 J groups;

$R^{10}$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 hydrogens J groups;

$R^{15}$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups; and $R^{16}$ is hydrogen, alkyl, aryl, heteroaryl, cycloalkyl, or heterocyclyl.

In another embodiment, the compound is a compound of Formula XXV

Formula XXV

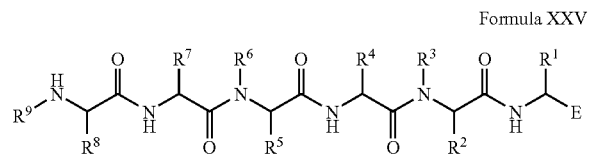

or a pharmaceutically acceptable salt, solvate or ester thereof;

wherein

E represents CHO or $B(OH)_2$;

$R^1$ represents lower alkyl, halo-lower alkyl, cyano-lower alkyl, lower alkylthio-lower alkyl, aryl-lower alkylthio-lower alkyl, aryl-lower alkyl, heteroaryllower alkyl, lower alkenyl or lower alkynyl;

$R^2$ represents lower alkyl, hydroxy-lower alkyl, carboxy-lower alkyl, aryl-lower alkyl, aminocarbonyl-lower alkyl or lower cycloalkyl-lower alkyl; and $R^3$ represents hydrogen or lower alkyl;

or $R^2$ and $R^3$ together represent di- or trimethylene optionally substituted by hydroxy;

$R^4$ represents lower alkyl, hydroxy-lower alkyl, lower cycloalkyl-lower alkyl, carboxy-lower alkyl, aryllower alkyl, lower alkylthio-lower alkyl, cyano-lower alkylthio-lower alkyl, aryl-lower alkylthio-lower alkyl, lower alkenyl, aryl or lower cycloalkyl;

$R^5$ represents lower alkyl, hydroxy-lower alkyl, lower alkylthio-lower alkyl, aryl-lower alkyl, aryl-lower alkylthio-lower alkyl, cyano-lower alkylthio-lower alkyl or lower cycloalkyl;

$R^6$ represents hydrogen or lower alkyl;

$R^7$ represent lower alkyl, hydroxylower alkyl, carboxy-lower alkyl, aryl-lower alkyl, lower cycloalkyl-lower alkyl or lower cycloalkyl;

$R^8$ represents lower alkyl, hydroxy-lower alkyl, carboxy-lower alkyl or aryl-lower alkyl; and $R^9$ represents lower alkylcarbonyl, carboxy-lower alkylcarbonyl, arylcarbonyl, lower alkylsulphonyl, arylsulphonyl, lower alkoxycarbonyl or aryl-lower alkoxycarbonyl.

In another embodiment, the compound is a compound of Formula XXVI

Formula XXVI

P6   P5   P4   P3   P2   P1

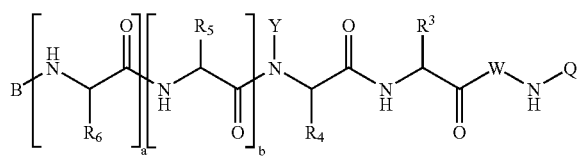

or a pharmaceutically acceptable salt, solvate or ester thereof; wherein

B is an acyl derivative of formula $R_{11}$—C(O)— wherein $R_{11}$ is C1-10 alkyl optionally substituted with carboxyl; or $R_{11}$ is $C_6$ or $C_{10}$ aryl or $C_{7-16}$ aralkyl optionally substituted with a $C_{1-6}$ alkyl;

a is 0 or 1;

$R_6$, when present, is carboxy(lower)alkyl;

b is 0 or 1;

$R_5$, when present, is $C_{1-6}$ alkyl, or carboxy(lower)alkyl;

Y is H or $C_{1-6}$alkyl;

$R_4$ is $C_{1-10}$ alkyl; $C_{3-10}$ cycloalkyl;

$R_3$ is C1-10 alkyl; $C_{3-10}$ cycloalkyl;

W is a group of formula:

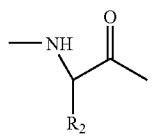

wherein R$_2$ is C$_{1-10}$ alkyl or C$_{3-7}$ cycloalkyl optionally substituted with carboxyl; C$_6$ or C$_{10}$ aryl; or C$_{7-16}$ aralkyl; or W is a group of formula:

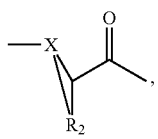

wherein X is CH or N; and
R$_2$' is C$_{3-4}$ alkylene that joins X to form a 5- or 6-membered ring, said ring optionally substituted with OH; SH; NH2; carboxyl; R$_{12}$; OR$_{12}$, SR$_{12}$, NHR$_{12}$ or NR$_{12}$R$_{12}$' wherein R$_{12}$ and R$_{12}$' are independently:

cyclic C$_{3-16}$ alkyl or acyclic C$_{1-16}$ alkyl or cyclic C$_{3-16}$ alkenyl or acyclic C$_{2-16}$ alkenyl, said alkyl or alkenyl optionally substituted with NH$_2$, OH, SH, halo, or carboxyl; said alkyl or alkenyl optionally containing at least one heteroatom selected independently from the group consisting of: 0, S, and N; or R$_{12}$ and R$_{12}$' are independently C$_6$ or C$_{10}$ aryl or C$_{7-16}$ aralkyl optionally substituted with C$_{1-6}$ alkyl, NH$_2$, OH, SH, halo, carboxyl or carboxy(lower)alkyl; said aryl or aralkyl optionally containing at least one heteroatom selected independently from the group consisting of: 0, S, and N;

said cyclic alkyl, cyclic alkenyl, aryl or aralkyl being optionally fused with a second 5-, 6-, or 7-membered ring to form a cyclic system or heterocycle, said second ring being optionally substituted with NH$_2$. OH, SH, halo, carboxyl or carboxy(lower)alkyl; C$_6$ or C$_{10}$ aryl, or heterocycle; said second ring optionally containing at least one heteroatom selected independently from the group consisting of: 0, S, and N;

Q is a group of the formula:

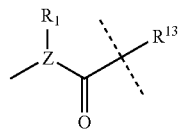

wherein Z is CH or N;
X is 0 or S;
R$_1$ is H, C$_{1-6}$ alkyl or C$_{1-6}$ alkenyl both optionally substituted with thio or halo;
and
when Z is CH, then R$_{13}$ is H; CF$_3$; CF$_2$CF$_3$; CH$_2$—R$_{14}$; CH(F)—R$_{14}$; CF$_2$—R$_{14}$; NR$_{14}$R$_{14}$'; S—R$_{14}$; or CO—NH—R$_{14}$ wherein R$_{14}$ and R$_{14}$' are independently hydrogen, cyclic C$_{3-10}$ alkyl or acyclic C$_{1-10}$ alkyl or cyclic C$_{3-10}$ alkenyl or acyclic C$_{2-10}$ alkenyl, said alkyl or alkenyl optionally substituted with NH$_2$, OH, SH, halo or carboxyl; said alkyl or alkenyl optionally containing at least one heteroatom selected independently from the group consisting of: 0, S, and N; or R$_{14}$ and R$_{14}$' are independently C$_6$ or C$_{10}$ aryl or C$_{7-16}$ aralkyl optionally substituted with C$_{1-6}$ alkyl, NH$_2$, OH, SH, halo, carboxyl or carboxy(lower)alkyl or substituted with a further C$_{3-7}$ cycloalkyl, C$_6$ or C$_{10}$ aryl, or heterocycle; said aryl or aralkyl optionally containing at least one heteroatom selected independently from the group consisting of: 0, S, and N;

said cyclic alkyl, cyclic alkenyl, aryl or aralkyl being optionally fused with a second 5-, 6-, or 7-membered ring to form a cyclic system or heterocycle, said second ring being optionally substituted with NH$_2$, OH, SH, halo, carboxyl or carboxy(lower)alkyl or substituted with a further C$_{3-7}$ cycloalkyl, C$_6$ or C$_{10}$ aryl, or heterocycle; said second ring optionally containing at least one heteroatom selected independently from the group consisting of: 0, S, and N;

or R$_{14}$ and R$_{14}$' are independently C$_{1-4}$ alkyl which when joined together with N form a 3 to 6-membered nitrogen-containing ring which is optionally fused with a further C$_{3-7}$ cycloalkyl, C$_6$ or C$_{10}$ aryl or heterocycle;

with the proviso that when Z is CH, then R$_{13}$ is not an α-amino acid or an ester thereof;

when Z is N, then R$_{13}$ is H; carboxy; C$_{1-6}$ alkyl optionally substituted with carboxy; CH$_2$—R$_{14}$; CHR$_{14}$R$_{14}$'; CH(F)—R$_{14}$; O—R$_{14}$; NR$_{14}$R$_{14}$' or S—R$_{14}$ wherein R$_{14}$ and R$_{14}$' are as defined above; or Q is a phosphonate group of the formula:

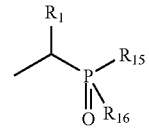

wherein R$_{15}$ and R$_{16}$ are independently C$_{6-20}$ aryloxy; and R$_1$ is as defined above.

In the above-shown structure of the compound of Formula XXVI, the terms P6, P5, P4, P3, P2 and P1 denote the respective amino acid moieties as is conventionally known to those skilled in the art. Thus, the actual structure of the compound of Formula XXVI is:

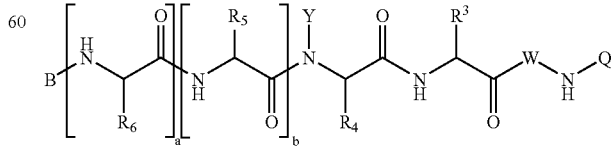

In another embodiment, the compound is selected from the group consisting of:
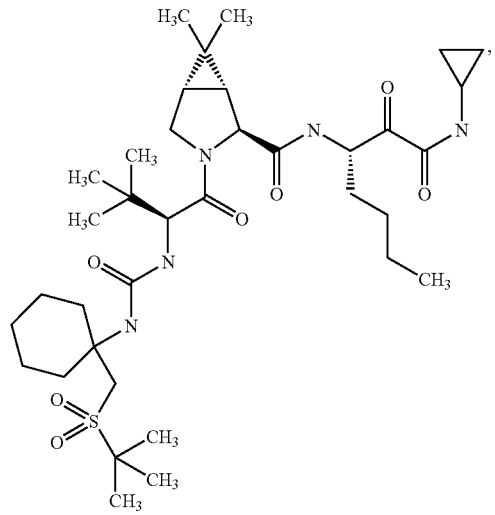
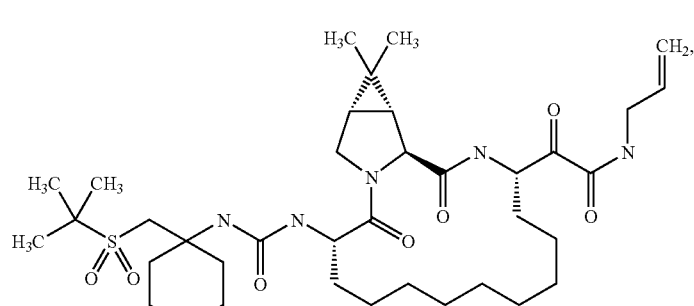
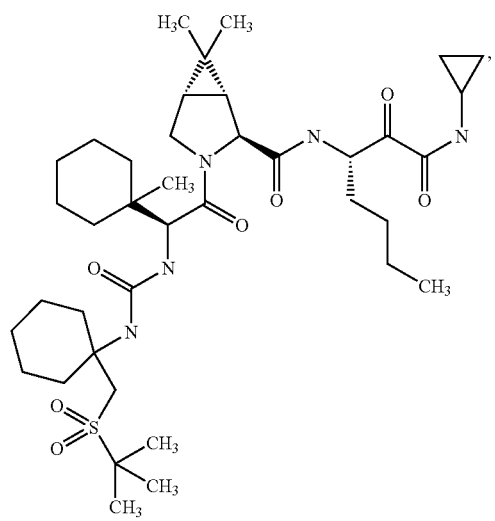
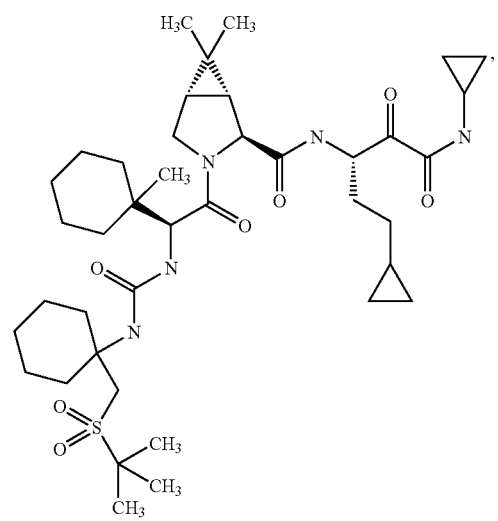
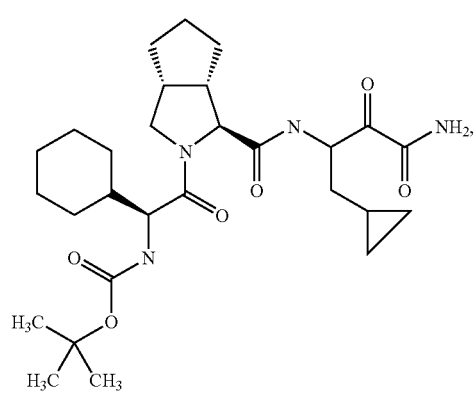
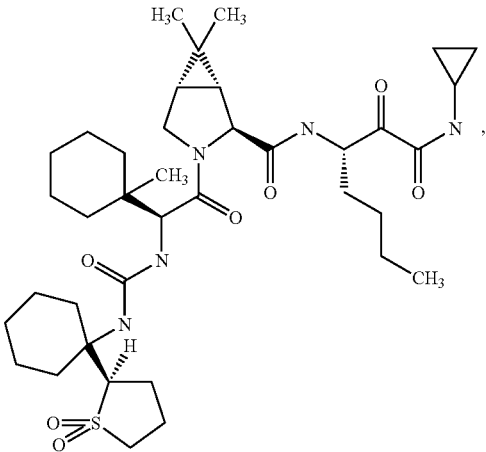

-continued
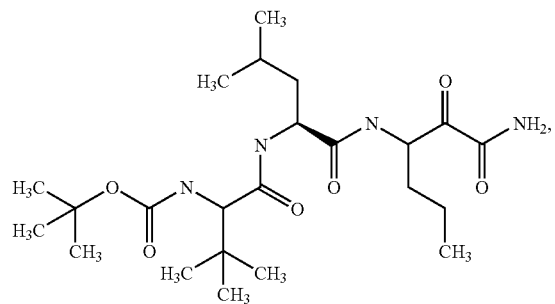
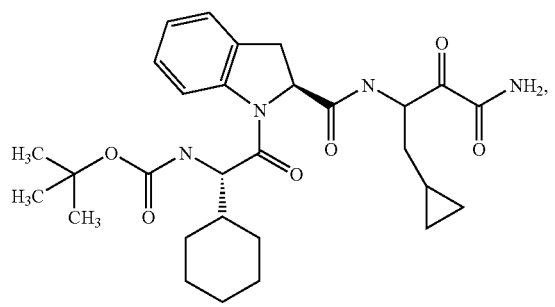
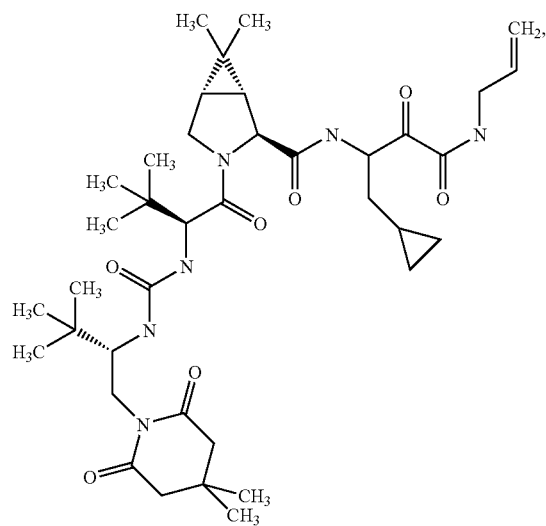
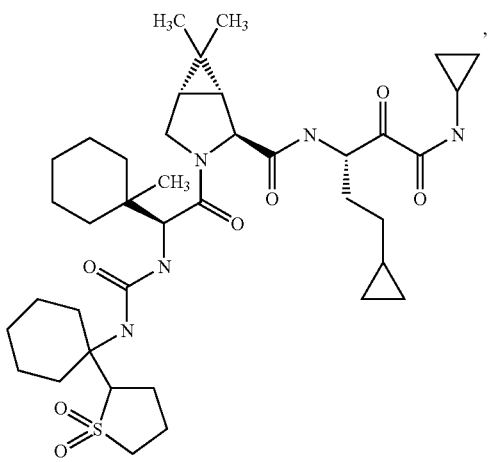
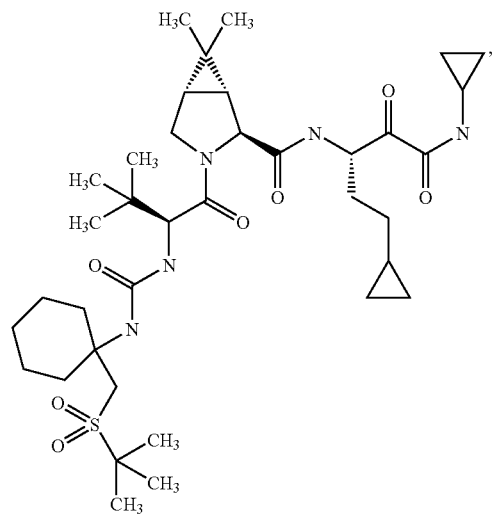
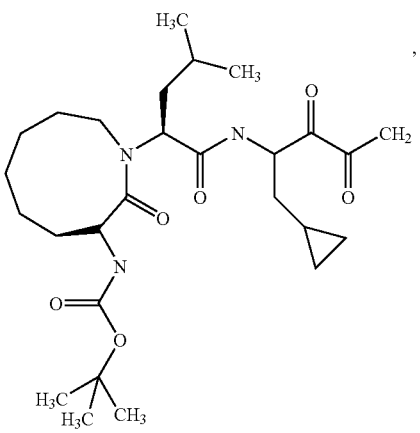

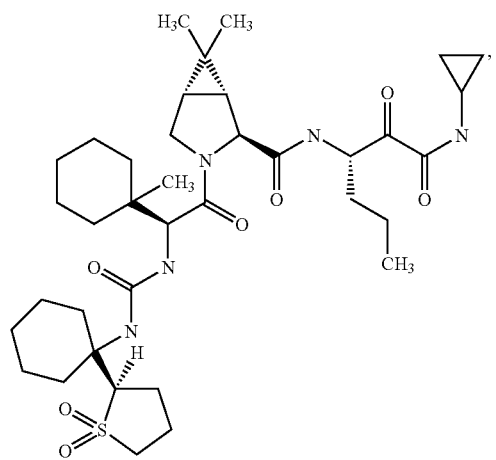
,
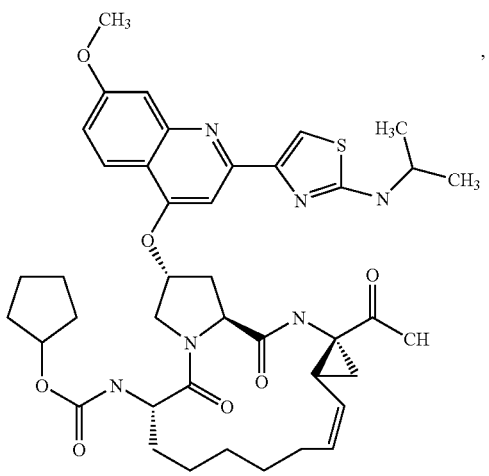
,
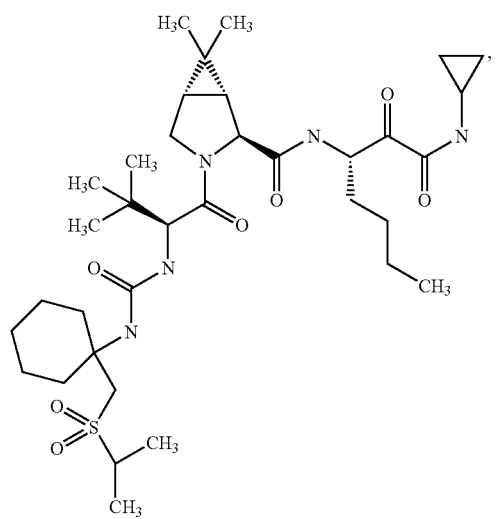
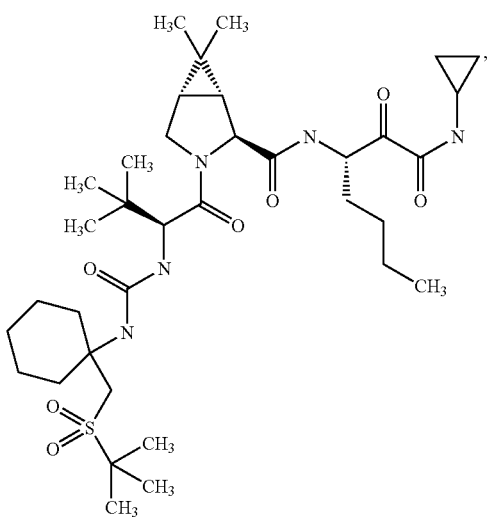
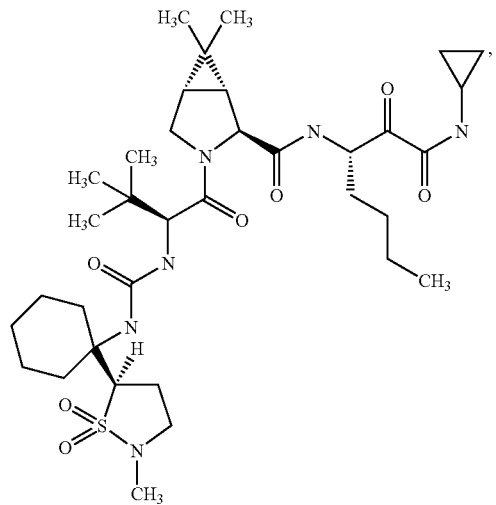
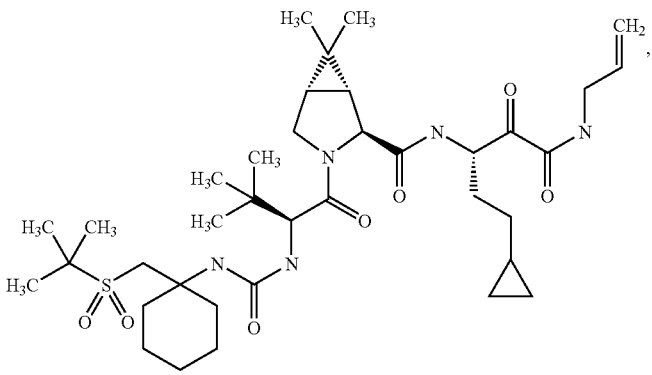

-continued
61
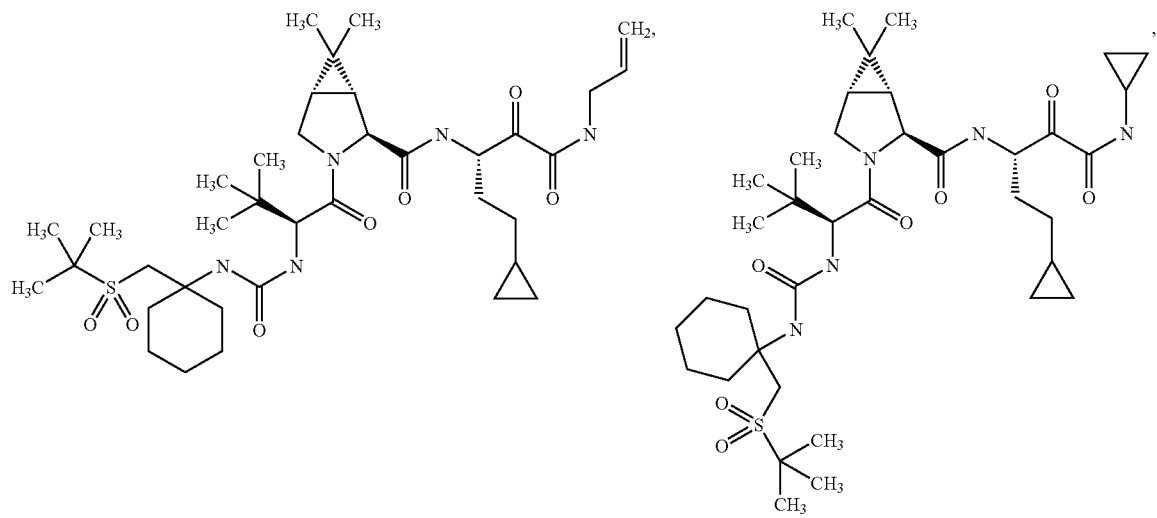
62

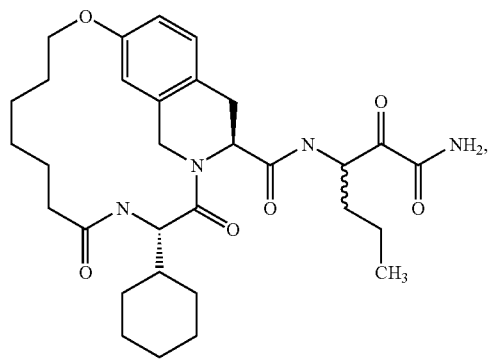
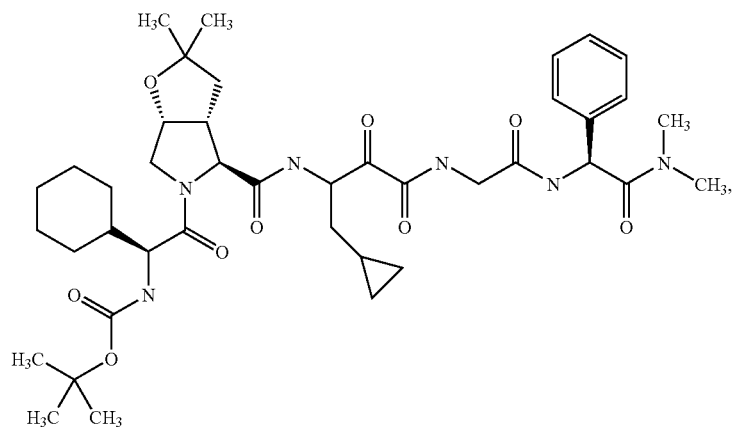
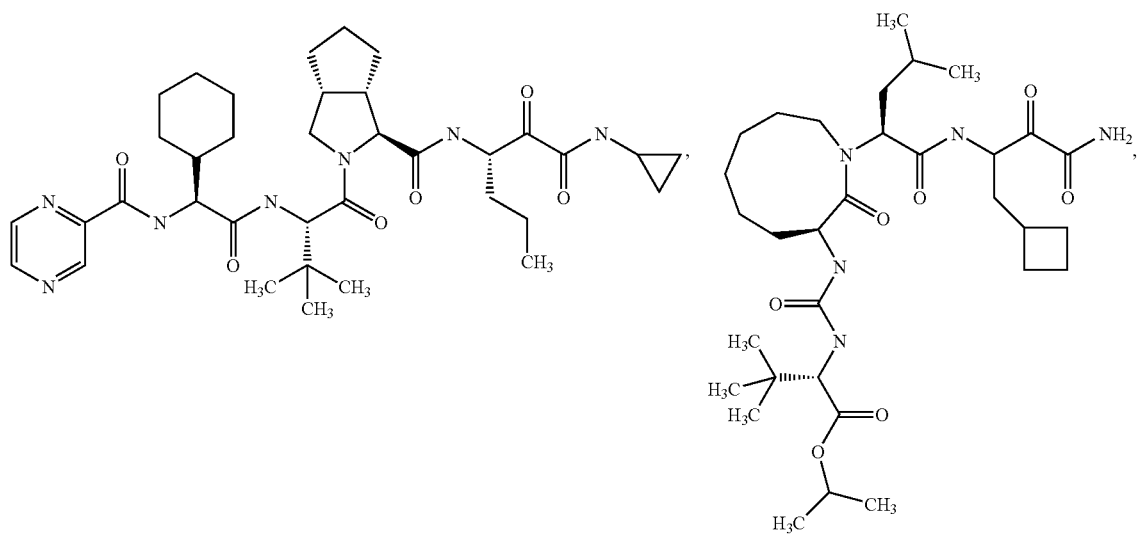

-continued
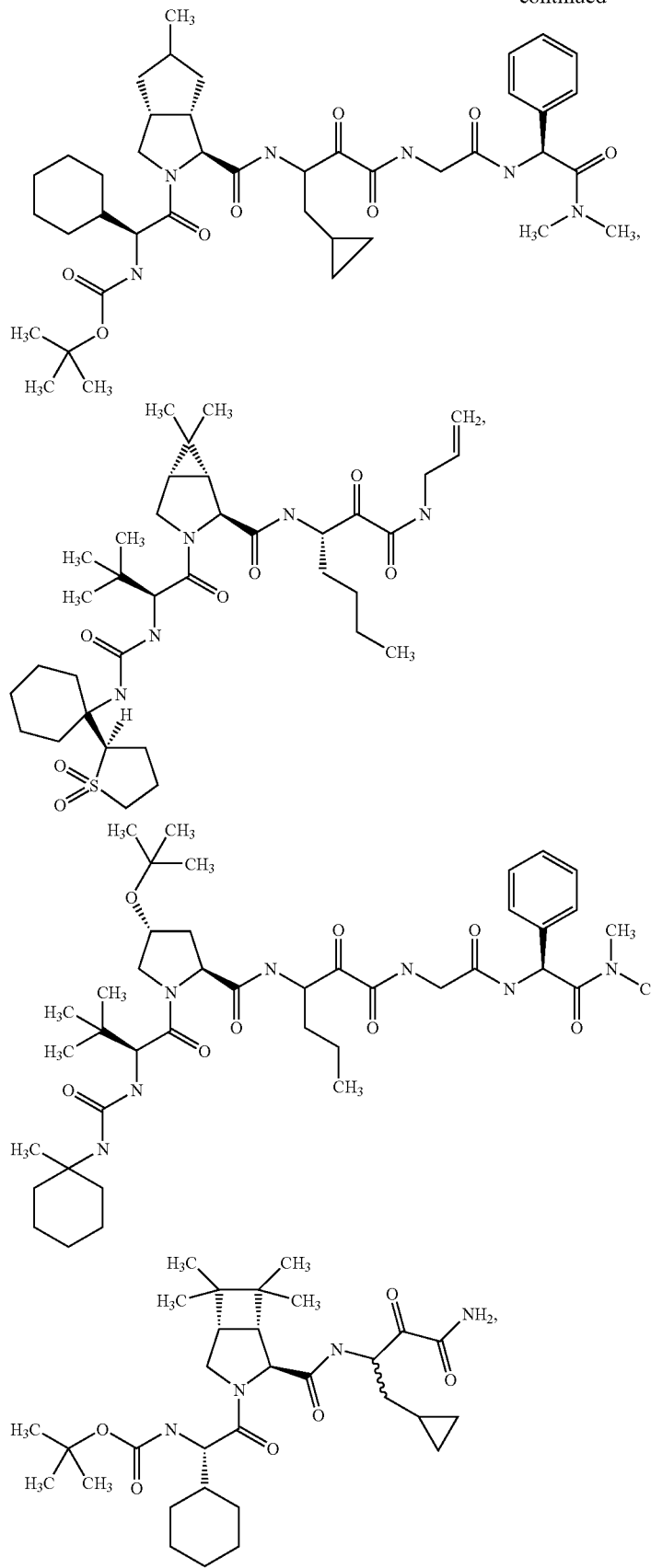

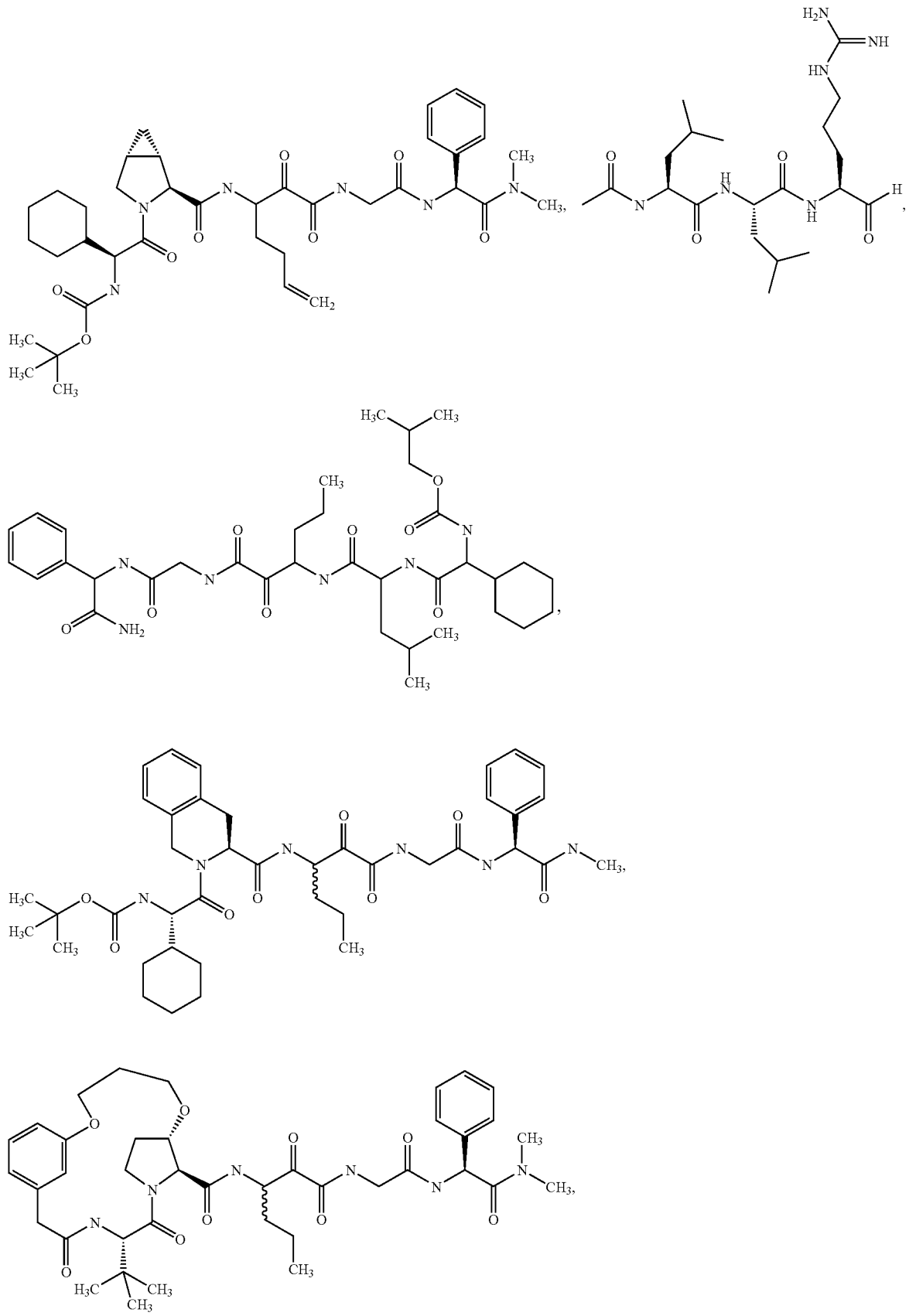

-continued
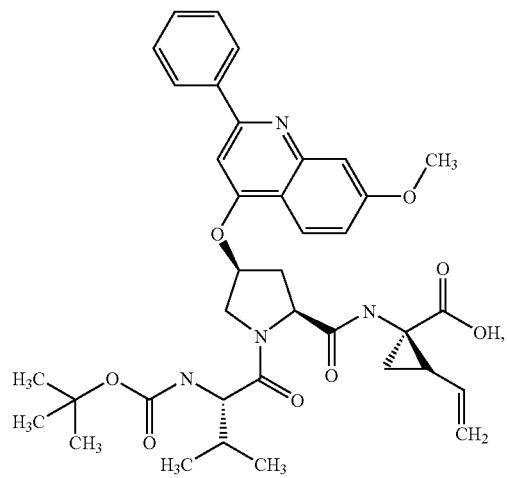
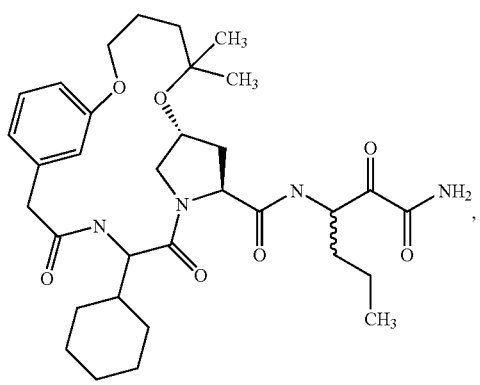
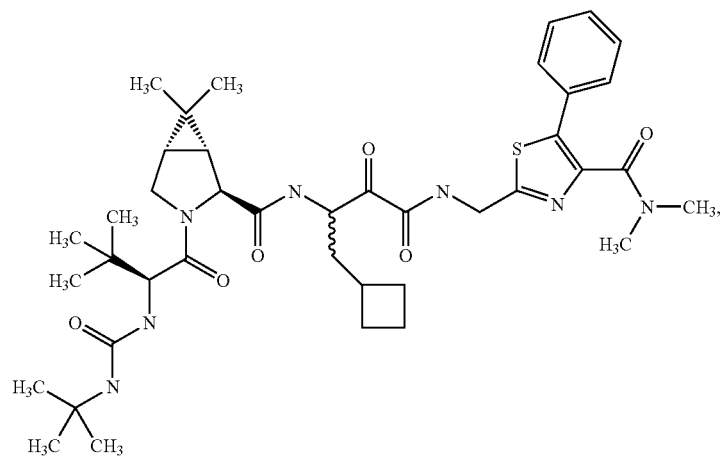
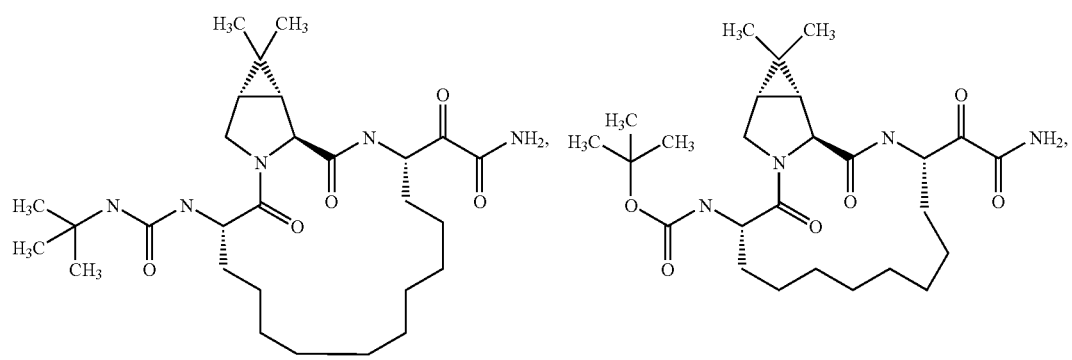

-continued
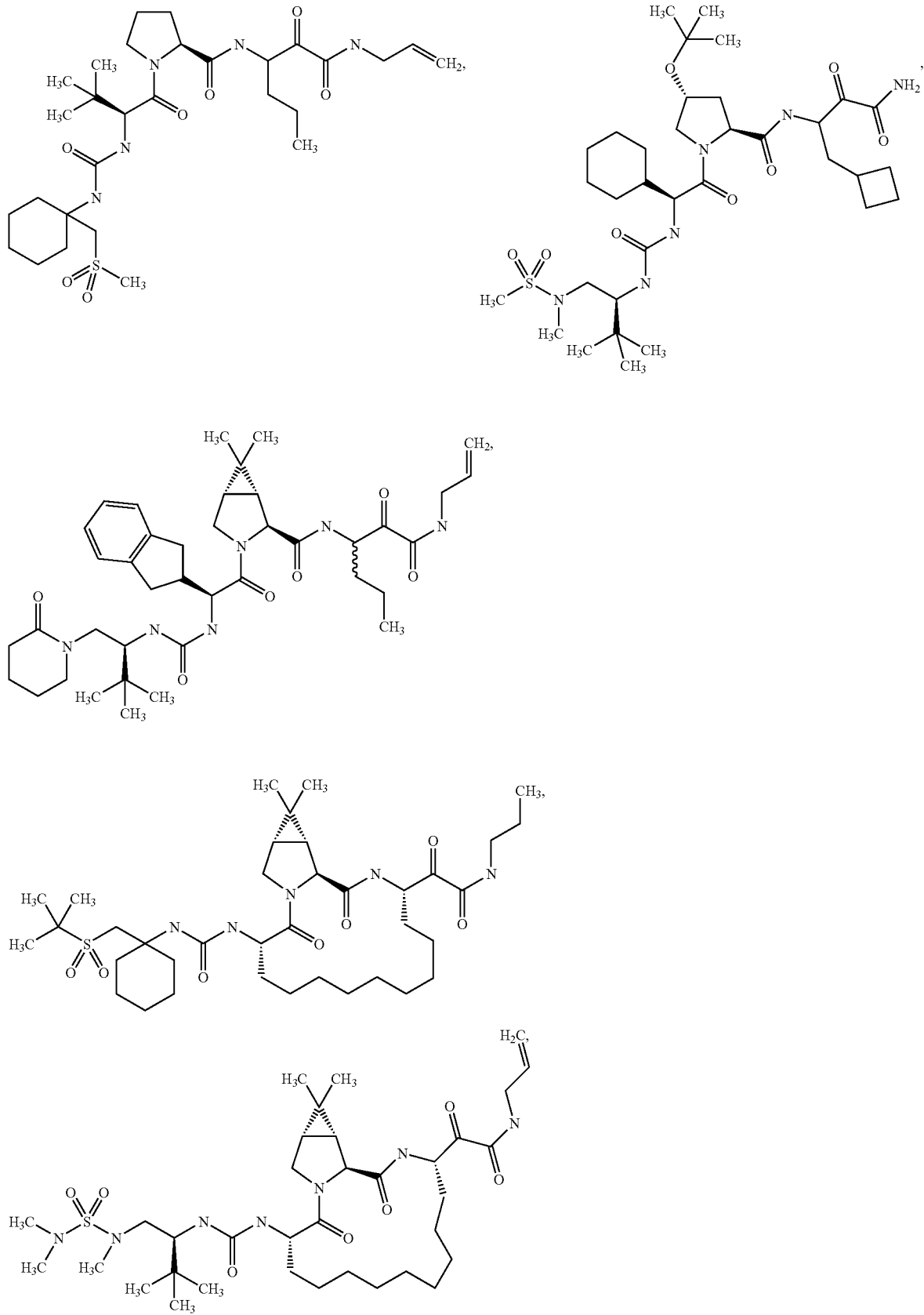

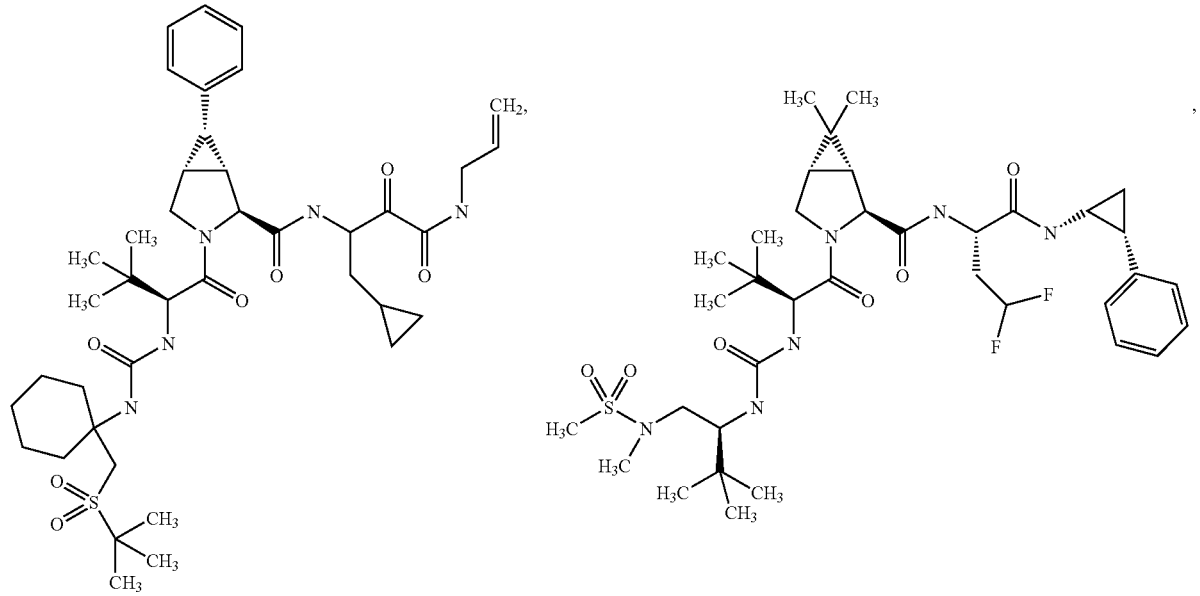
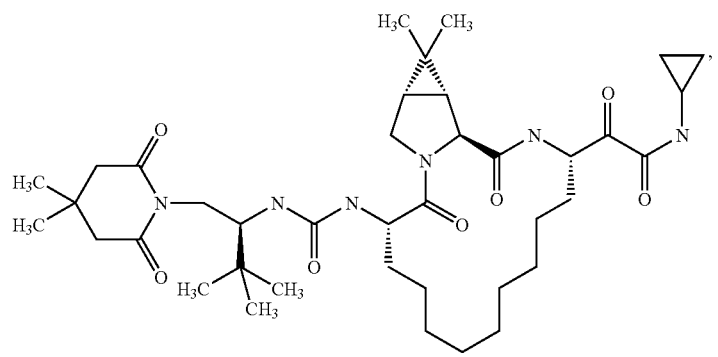
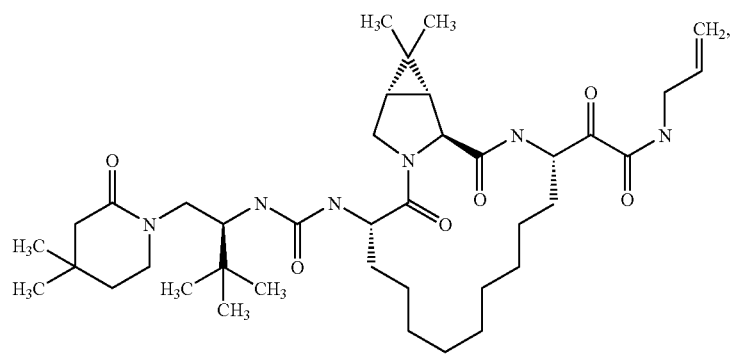

-continued

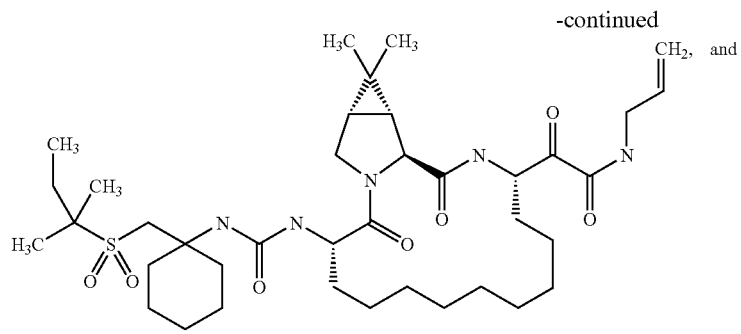

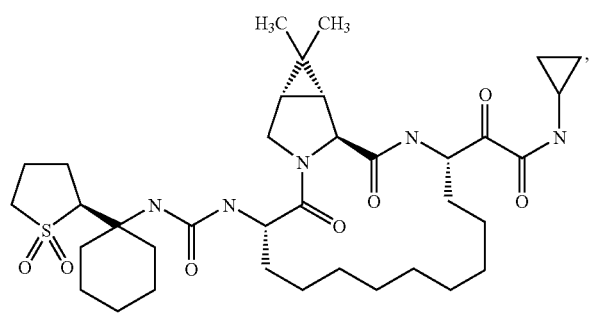

or a pharmaceutically acceptable salt, solvate or ester thereof.

The surfactant in the pharmaceutical formulations of the present invention enhances wetting of the present compounds by aqueous systems (as in a mammal) and improves the dissolution rate of the compounds to render a greater quantity of the compound available for absorption than is available in a formulation of the present compounds that does not include a surfactant. Any pharmaceutically acceptable surfactant that improves wetting of the present compounds may be used. Non-limiting examples of suitable surfactants include sodium lauryl sulfate, stearic acid, monoethanolamine, docusate sodium, sorbitan fatty acid esters, polyoxyethylene sorbitan fatty acid esters, ethoxylated aliphatic alcohols, propylene glycol monocaprylate, glycerol monostearate, medium chain triglycerides, polyoxyethylene alkyl ethers, and polyoxyethylene stearates. Additional suitable surfactants are discussed later.

The pharmaceutical formulations of the present invention may be used in treating HCV and other diseases/disorders, including those associated with cathepsin activity and/or for inhibiting cathepsin activity in a subject. One example of such disorders is proliferative diseases, such as cancer, autoimmune diseases, viral diseases, fungal diseases, neurological/neurodegenerative disorders, arthritis, inflammation, antiproliferative (e.g., ocular retinopathy), neuronal, alopecia and cardiovascular disease. Many of these diseases and disorders are listed in U.S. Pat. No. 6,413,974, the disclosure of which is incorporated herein.

Another example of a disease that can be treated using the pharmaceutical formulations of the present invention is an inflammatory disease, such as organ transplant rejection, graft v. host disease, arthritis, rheumatoid arthritis, inflammatory bowel disease, atopic dermatitis, psoriasis, asthma, allergies, multiple sclerosis, fixed drug eruptions, cutaneous delayed-type hypersentitivity responses, tuberculoid leprosy, type I diabetes, and viral meningitis. Another example of a disease that can be treated using the pharmaceutical formulations of the present invention is a cardiovascular disease. Another example of a disease that can be treated using the pharmaceutical formulations of the present invention is a central nervous system disease, such as depression, cognitive function disease, neurodegenerative disease such as Parkinson's disease, senile dementia such as Alzheimer's disease, and psychosis of organic origin.

Other examples of diseases that can be treated using the pharmaceutical formulations of the present invention are diseases characterized by bone loss, such as osteoporosis; gingival diseases, such as gingivitis and periodontitis; and diseases characterized by excessive cartilage or matrix degradation, such as osteoarthritis and rheumatoid arthritis.

Other than in the operating examples, or where otherwise indicated, all numbers expressing quantities of ingredients, reaction conditions, and so forth used in the specification and claims are to be understood as being modified in all instances by the term "about."

DETAILED DESCRIPTION

The present invention provides pharmaceutical formulations comprising at least one (one or more) compound of Formulae I-XXVI and at least one surfactant. Such formulations can be useful for inhibiting HCV protease and/or capthesin activity and have good dissolution characteristics to facilitate absorption of the compounds of Formulae I-XXVI.

Suitable compounds of formula I are disclosed in PCT International publication WO03/062265 published Jul. 31, 2003. Non-limiting examples of certain compounds disclosed in this publication include:

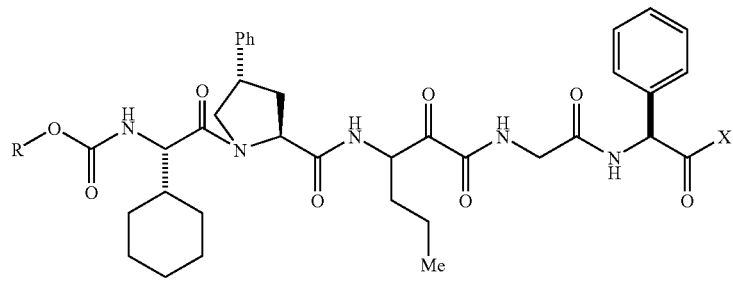
(R = t-butyl, X = NH₂)
(R = Isobutyl, X = NH₂)
(R = t-butyl, X = OH)
(R = Trichloroethyl, X = OH)
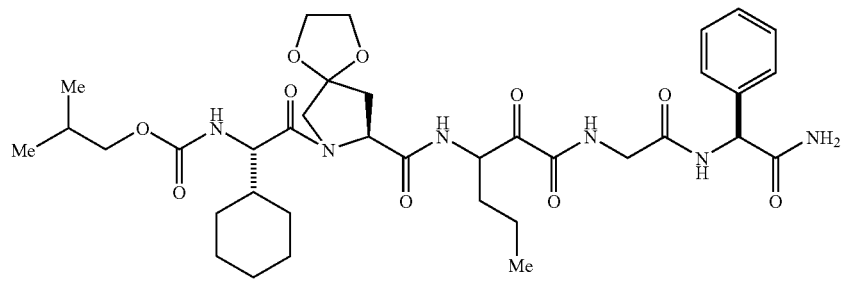
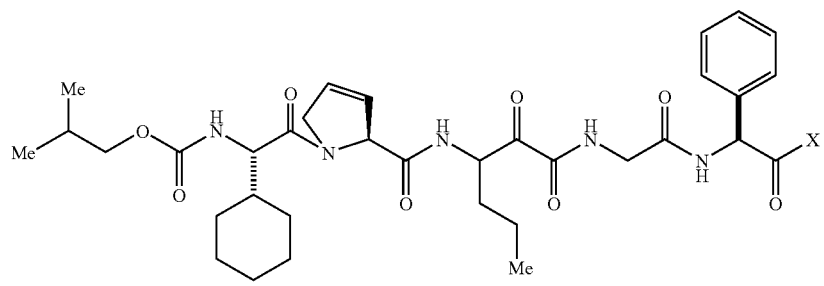
(X = OᵗBu)
(X = OH)
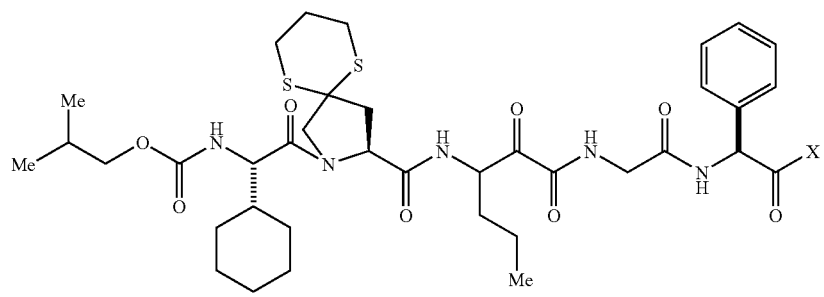
(X = OH)
(X = OᵗBu)
(X = NH₂)
(X = NHMe)
(X = NMe₂)

-continued
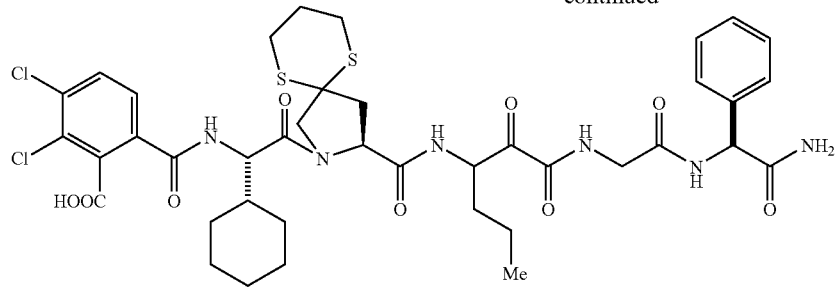
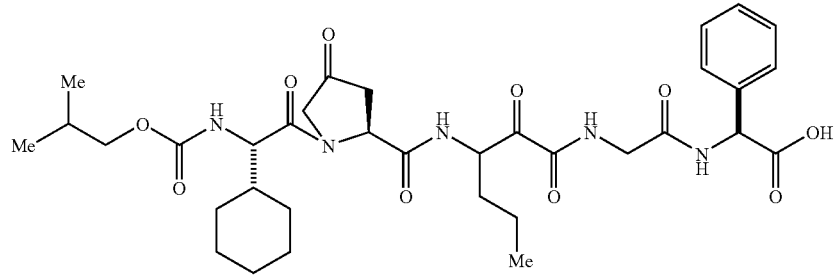
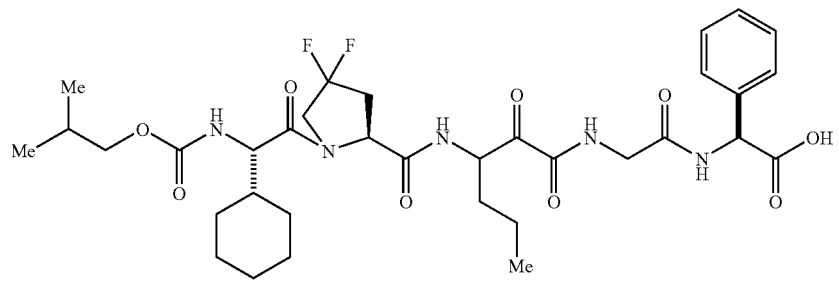
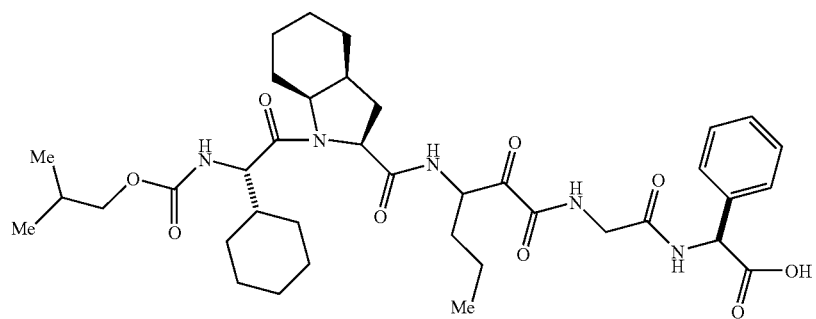
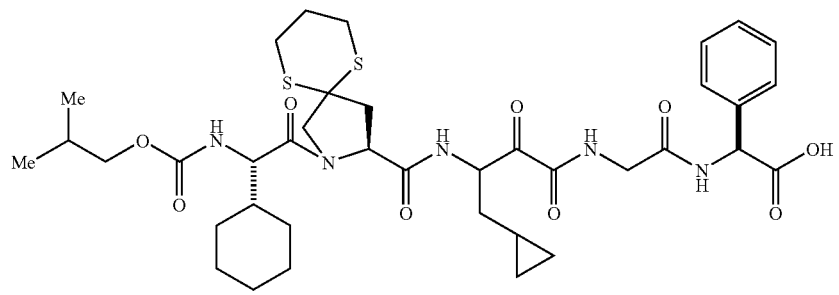

-continued
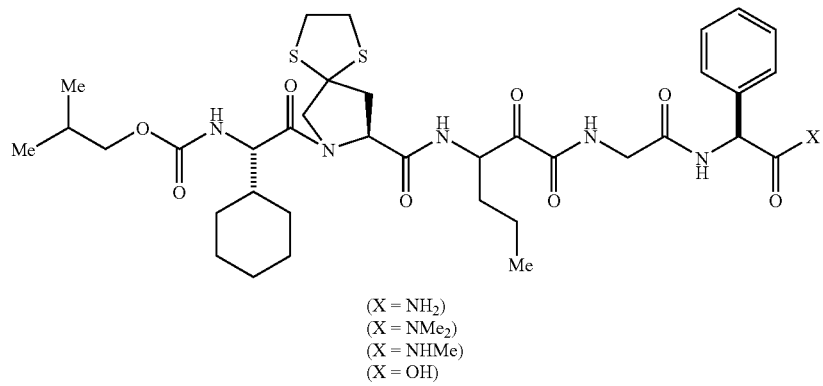
(X = NH₂)
(X = NMe₂)
(X = NHMe)
(X = OH)
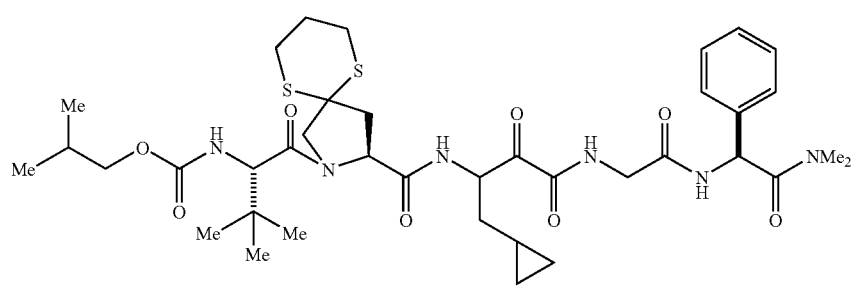
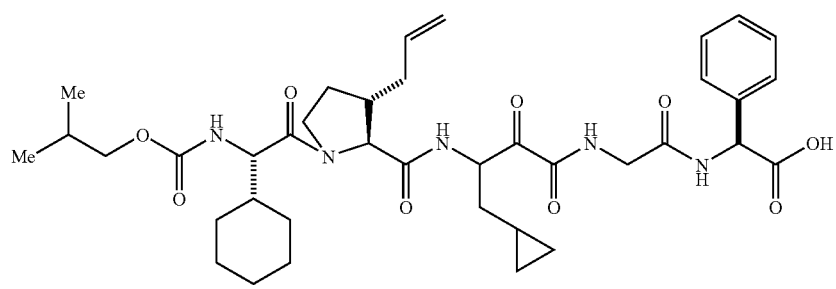
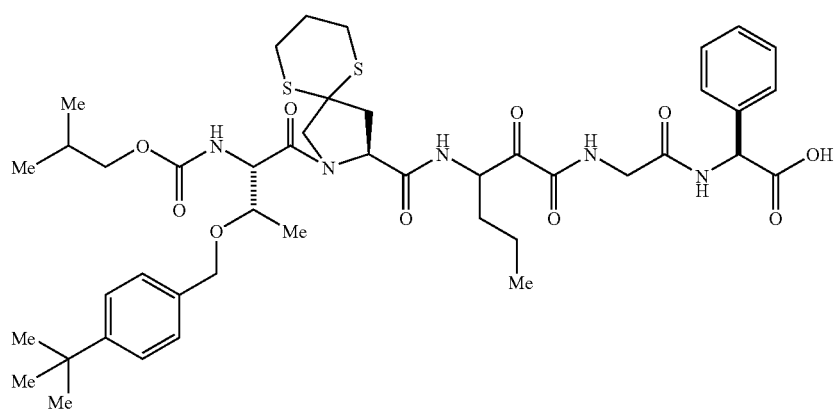

-continued
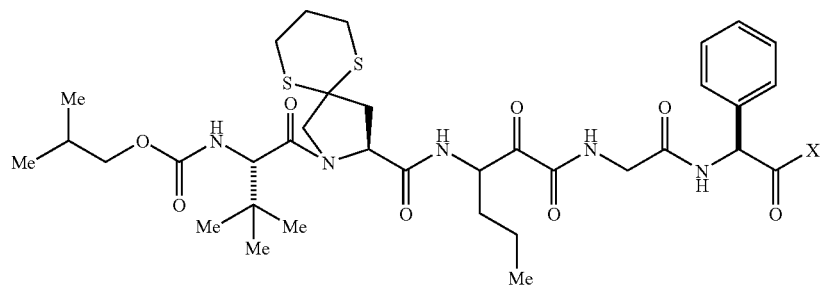
(X = O^tBu)
(X = OH)
(X = NH$_2$)
(X = NMe$_2$)
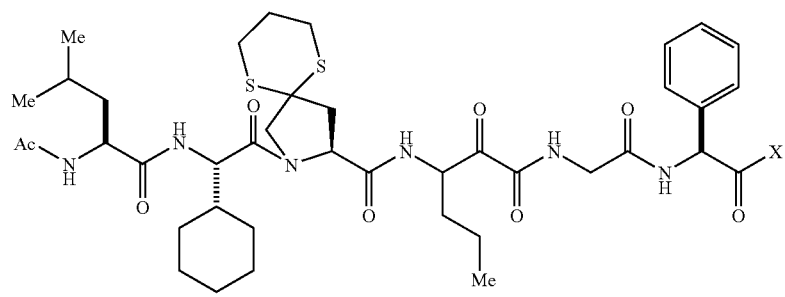
(X = O^tBu)
(X = OH)
(X = NH$_2$)
(X = NMe$_2$)
(X = NMeOMe)
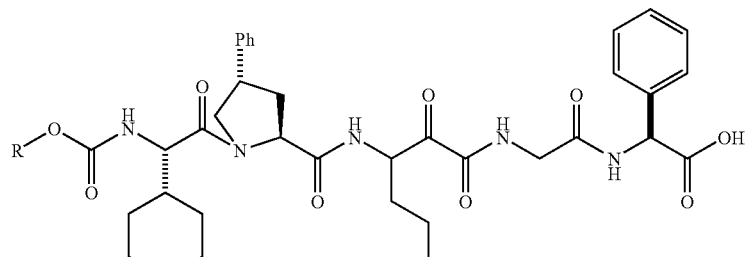
(R = t-butyl)
(R = Isobutyl)
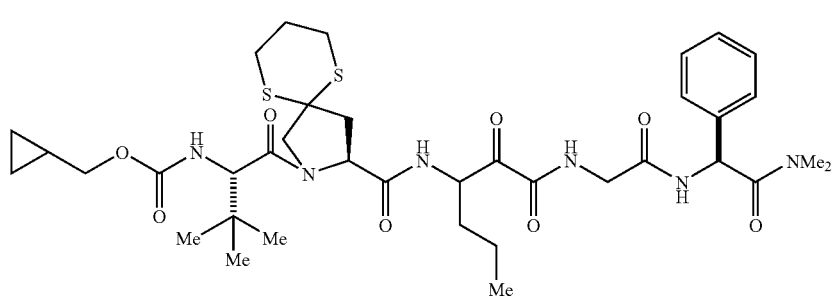

-continued
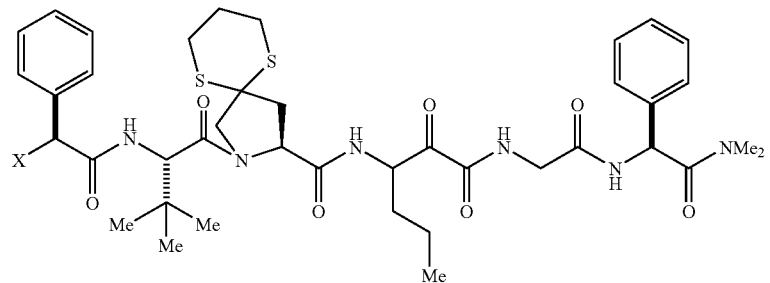
(X = Me, Y = CH₂Me)
(X = OAc, Y = Me)
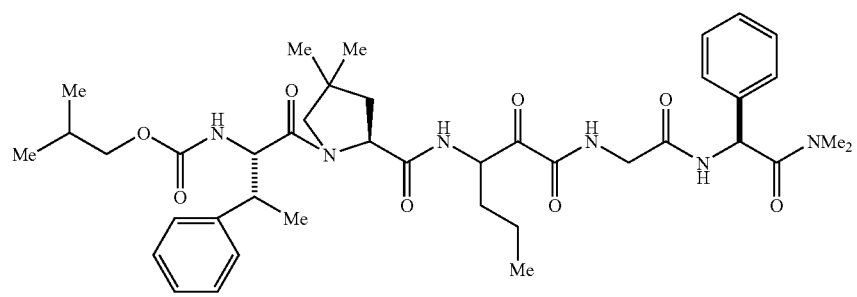
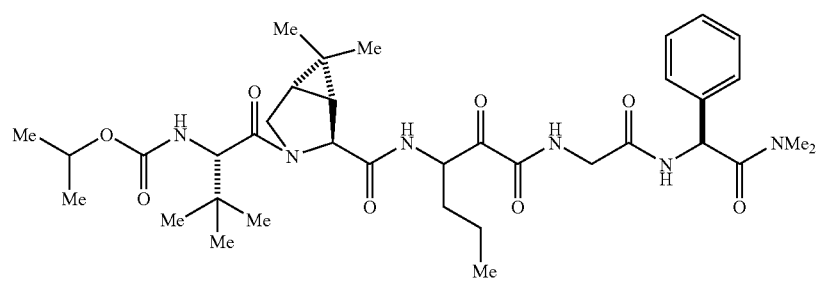
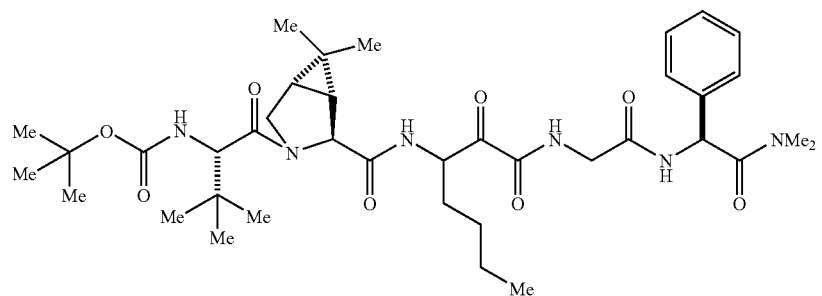
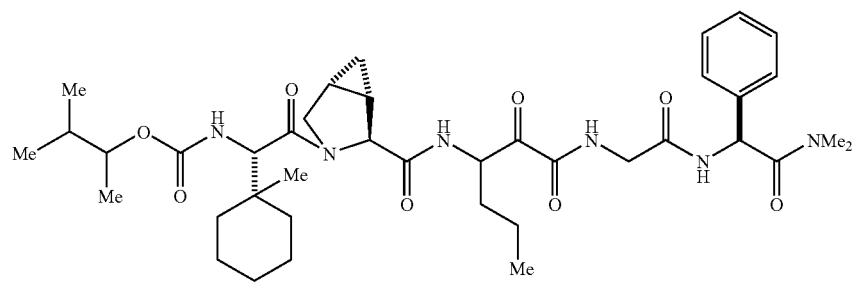

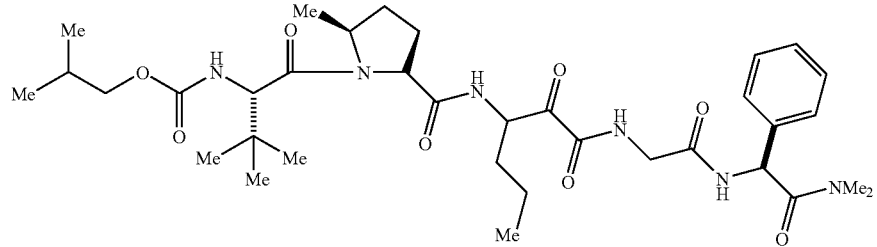
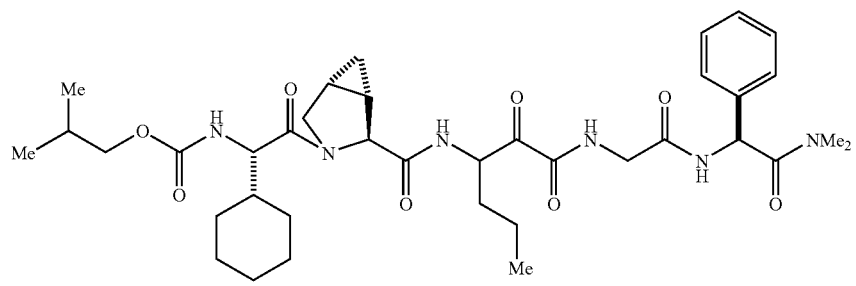
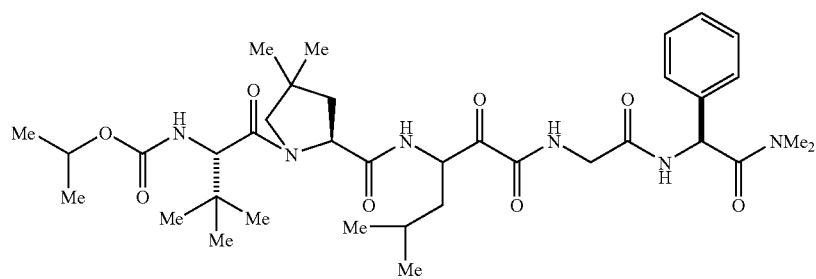
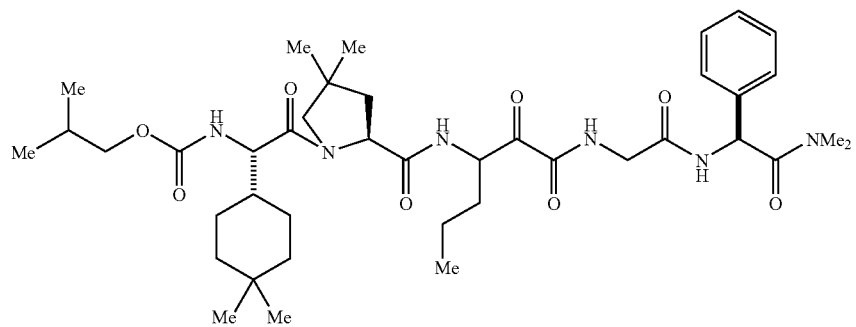
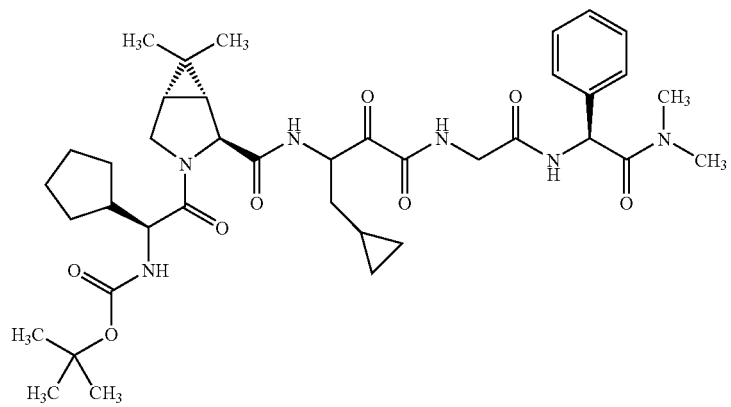

-continued
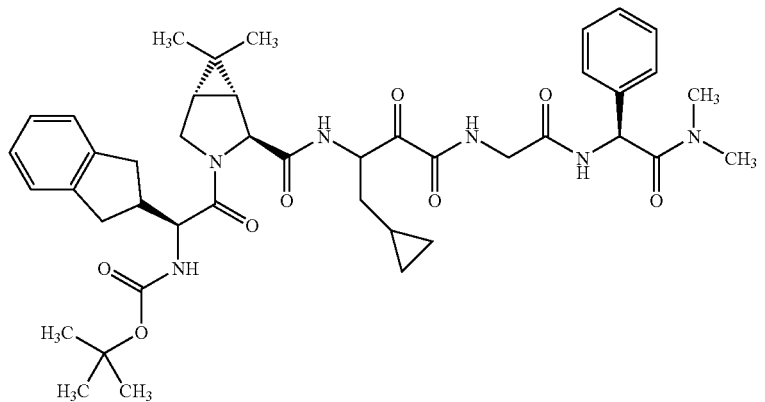
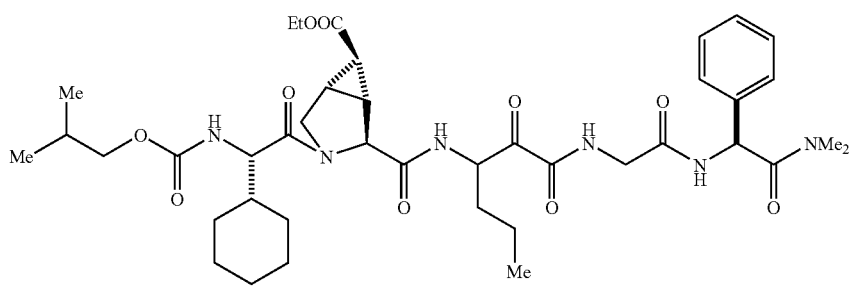
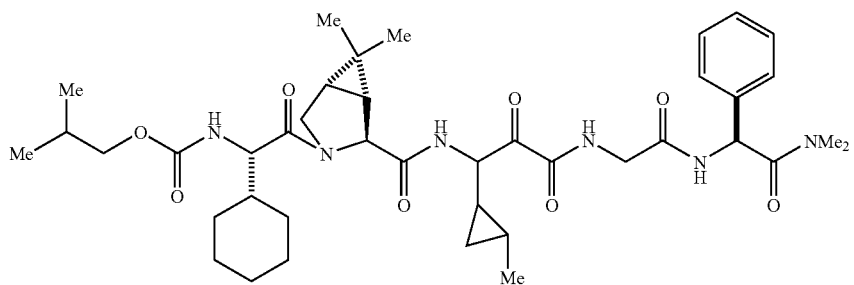
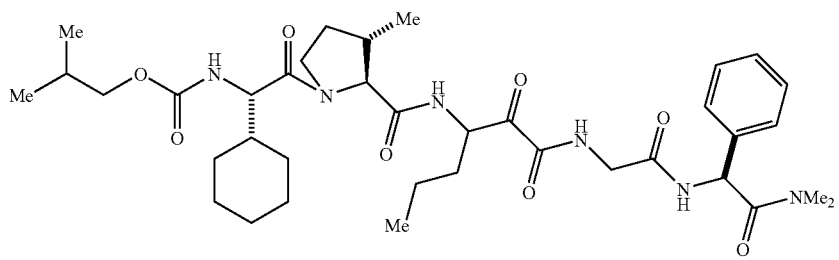
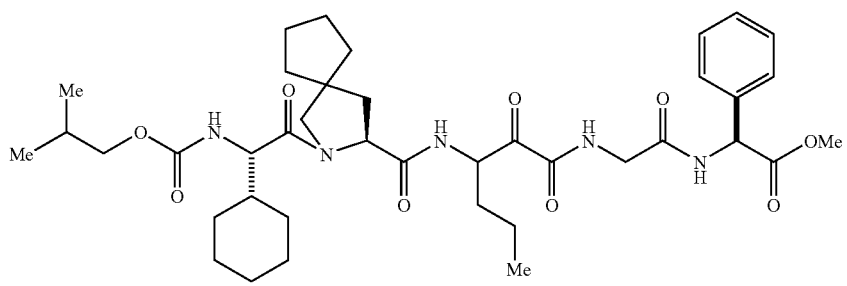

-continued
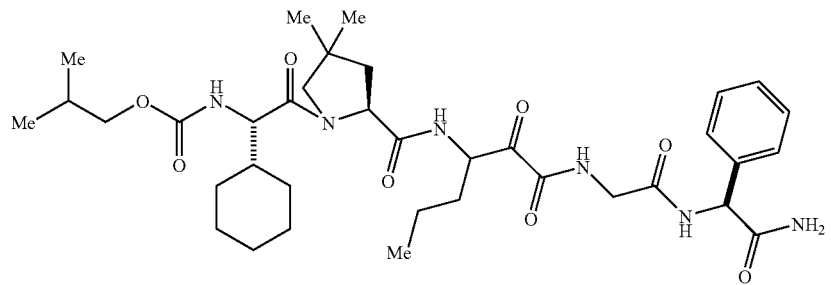
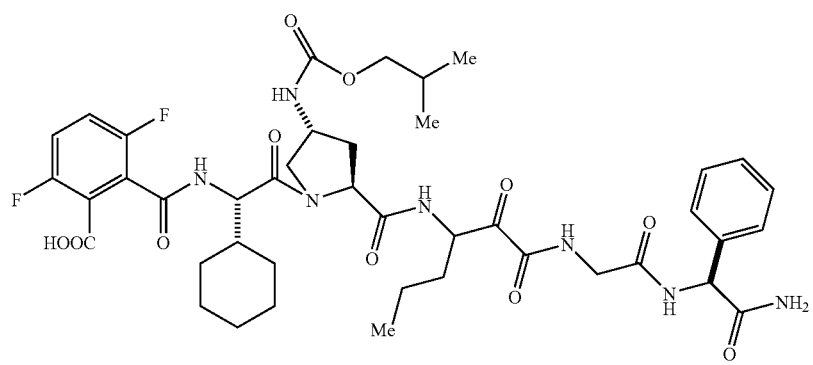
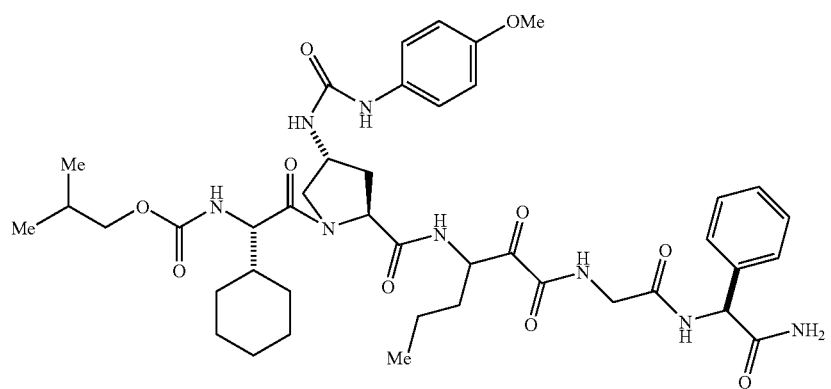
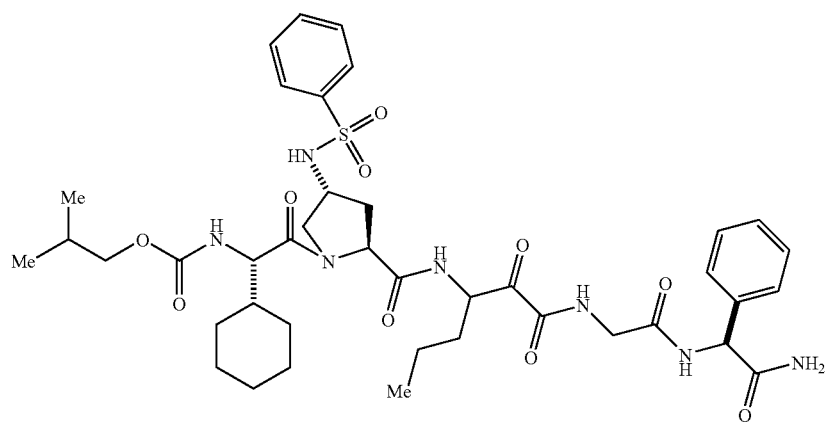

-continued
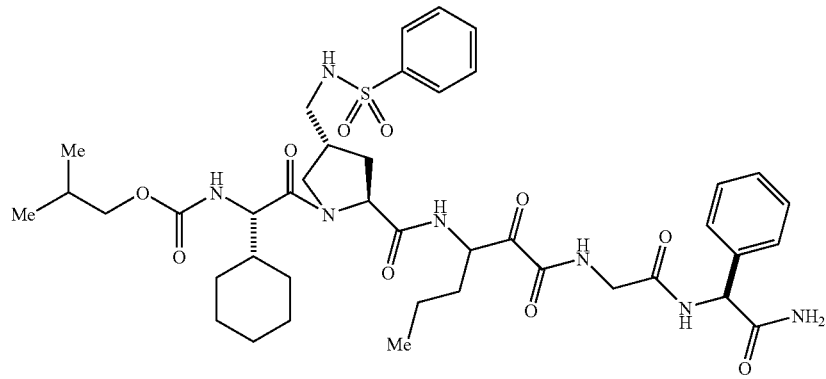
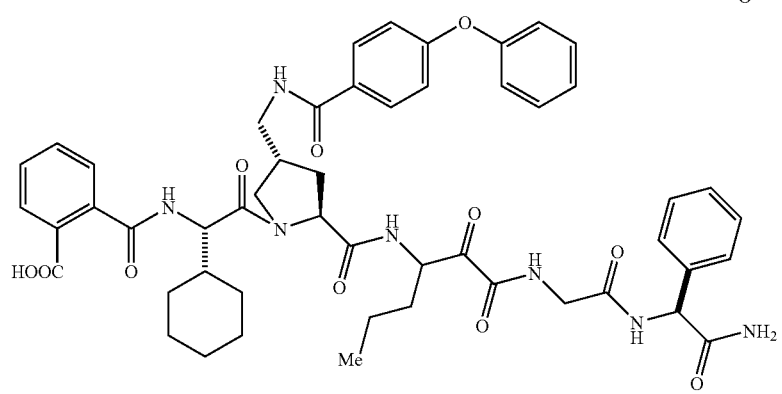
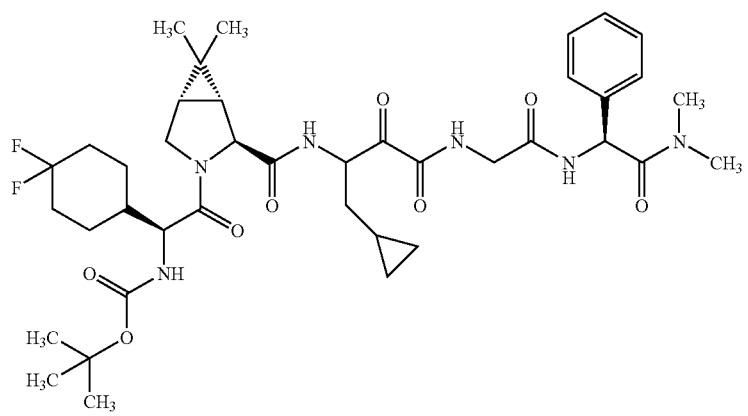
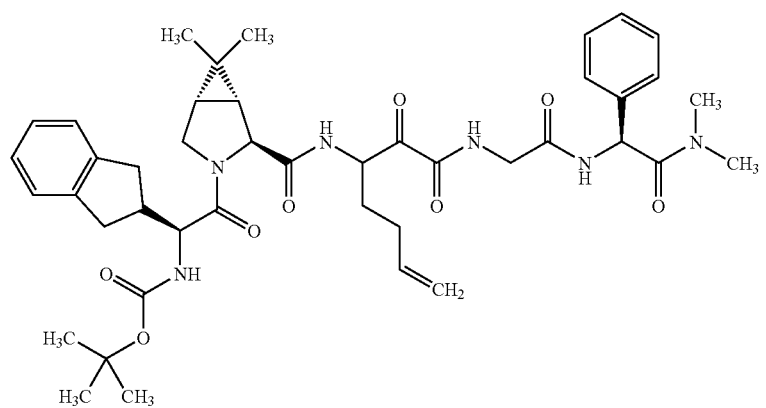

-continued
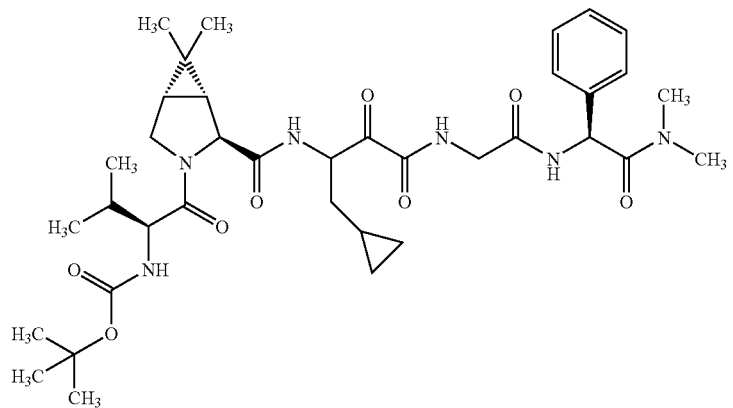
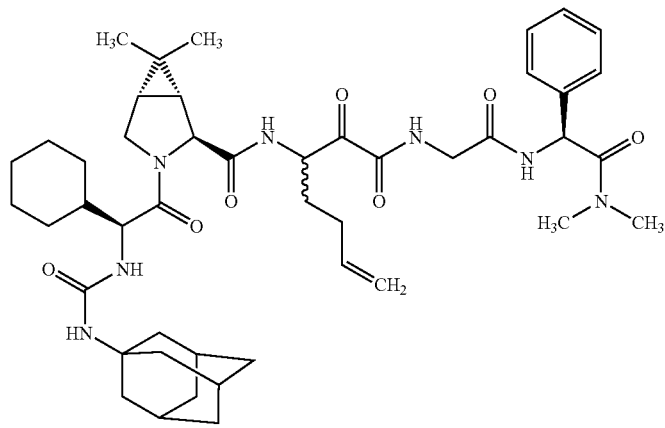
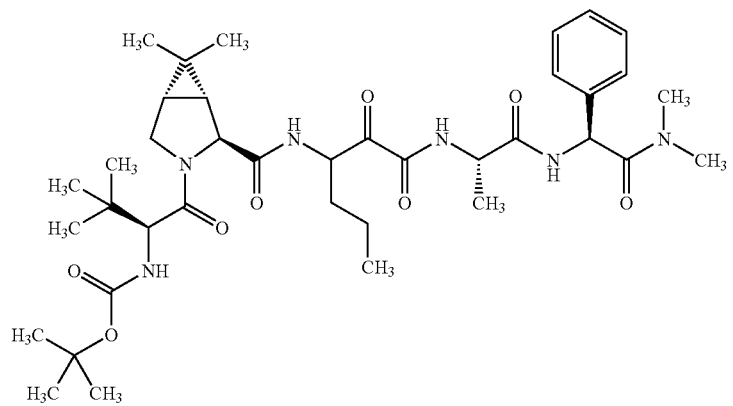
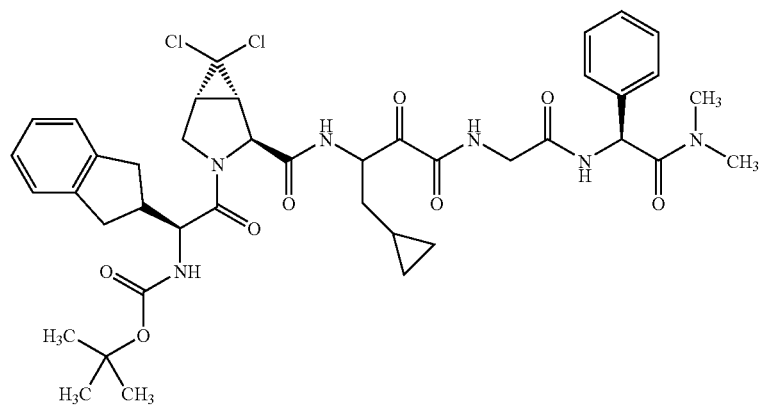

-continued
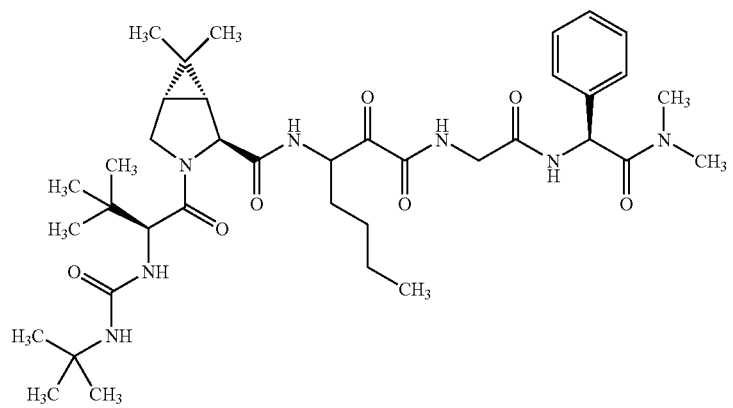
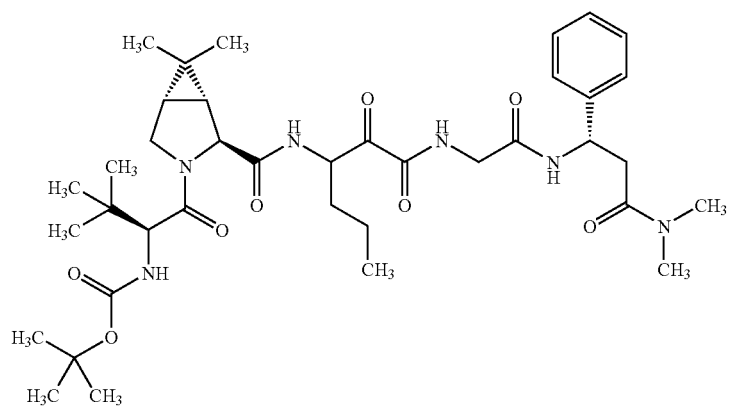
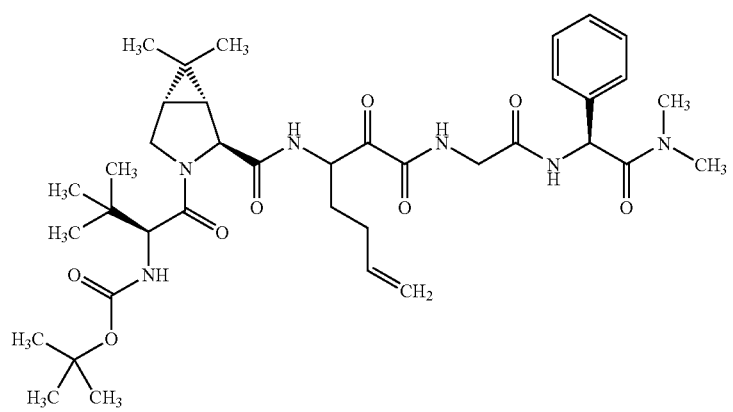
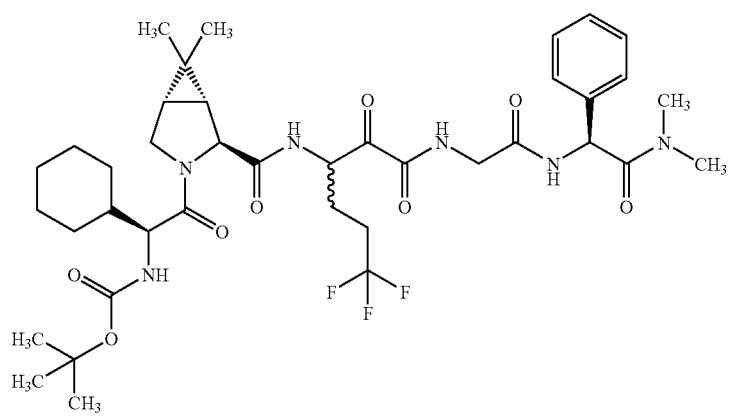

-continued
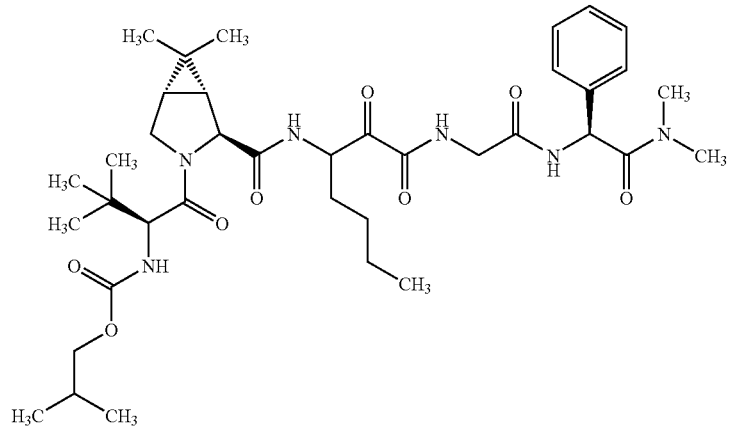
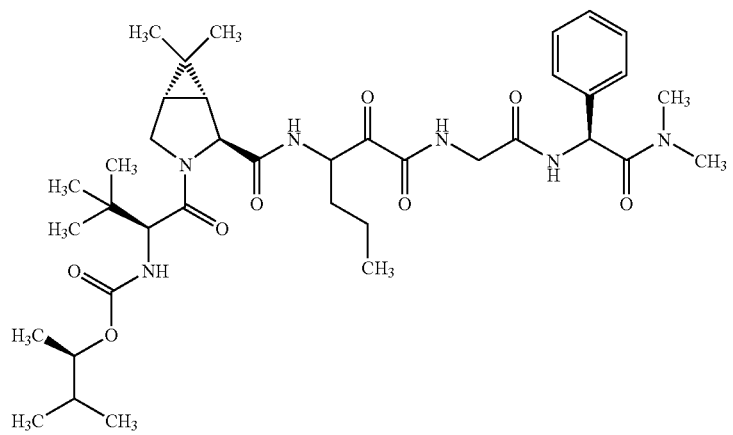
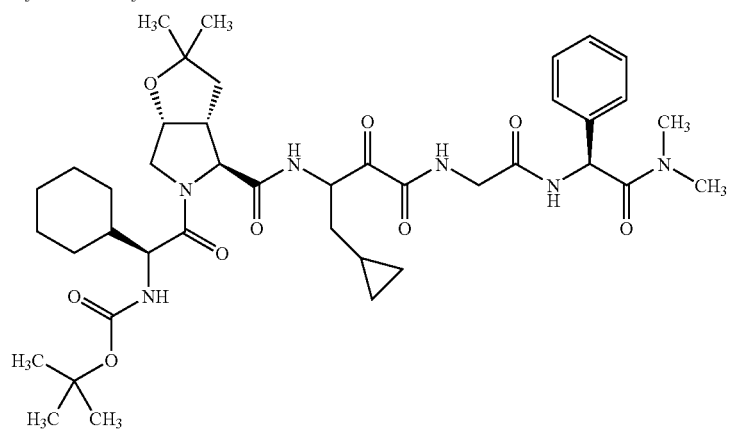
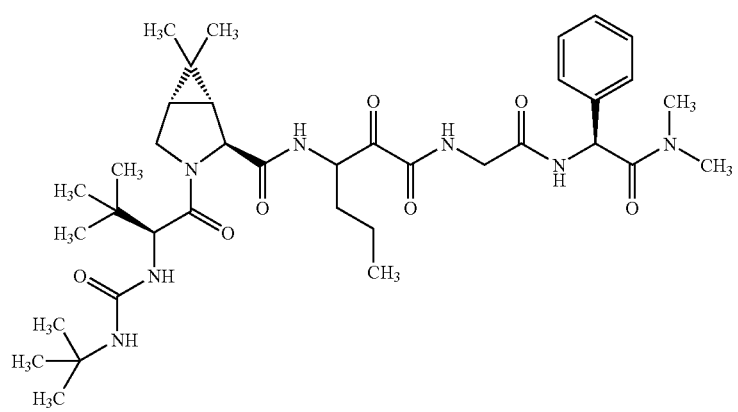

-continued
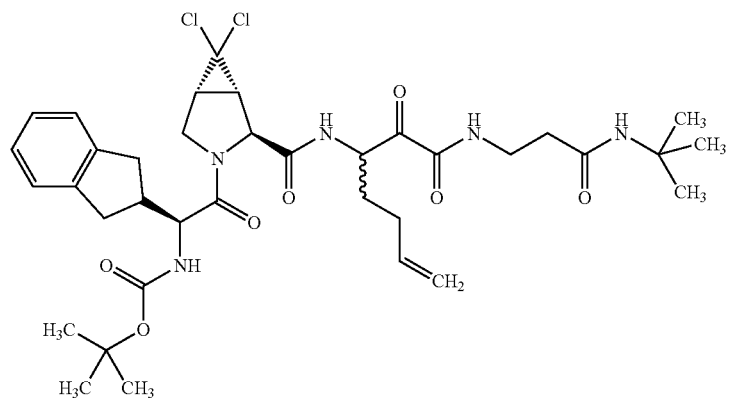
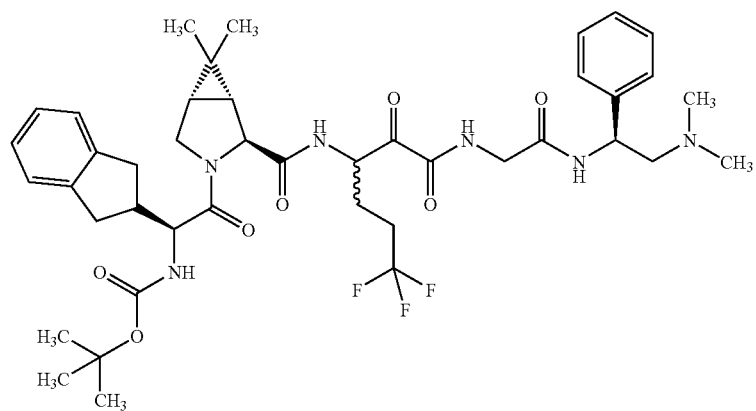
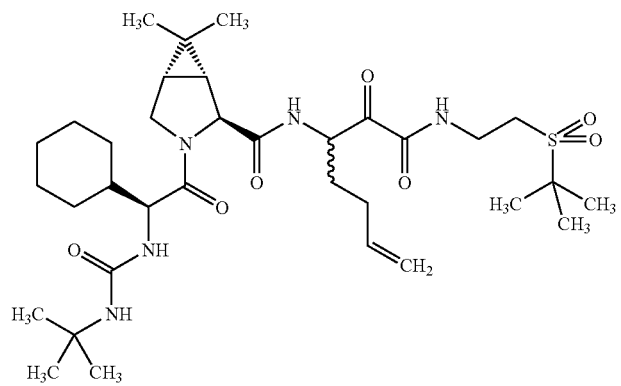
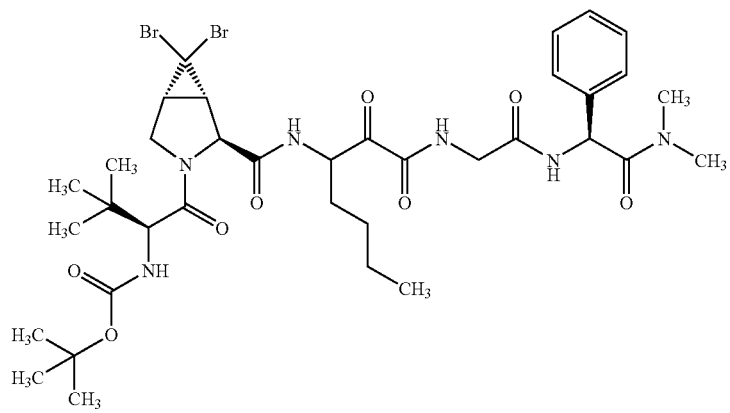

-continued
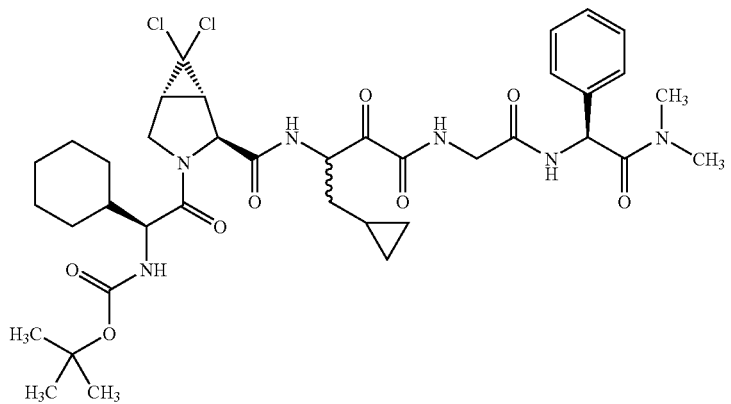
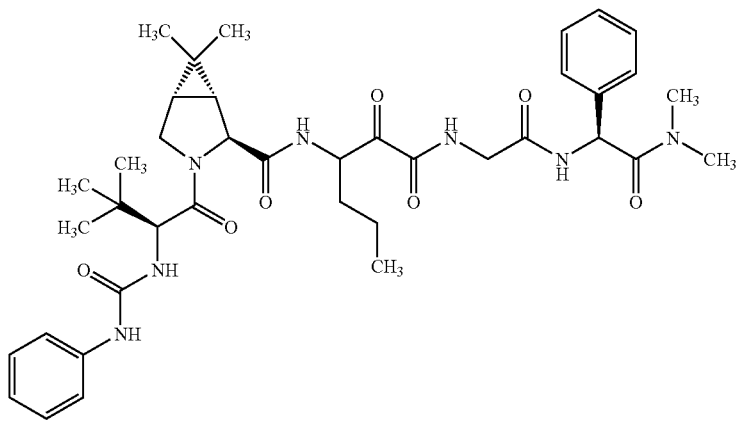
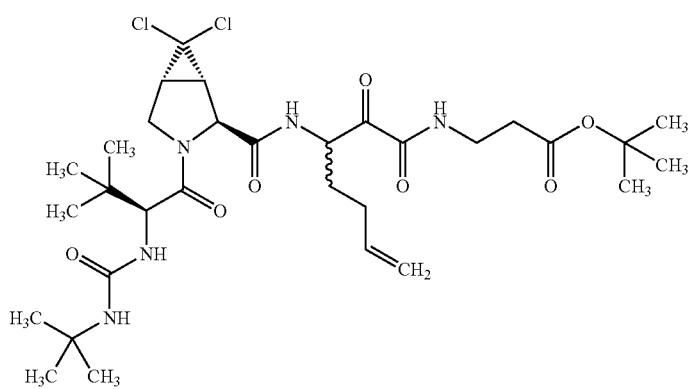
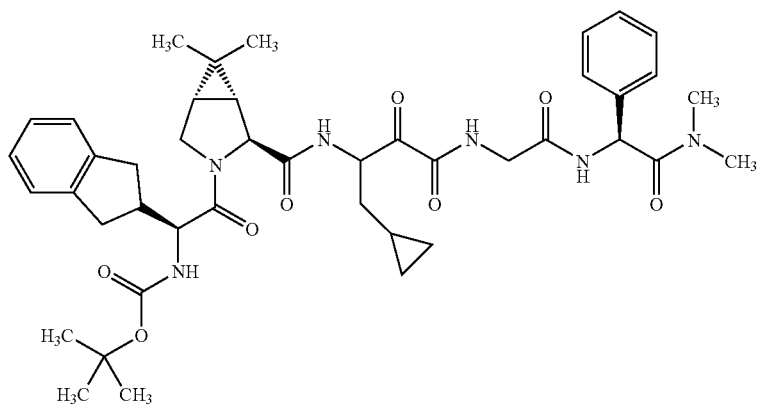

-continued
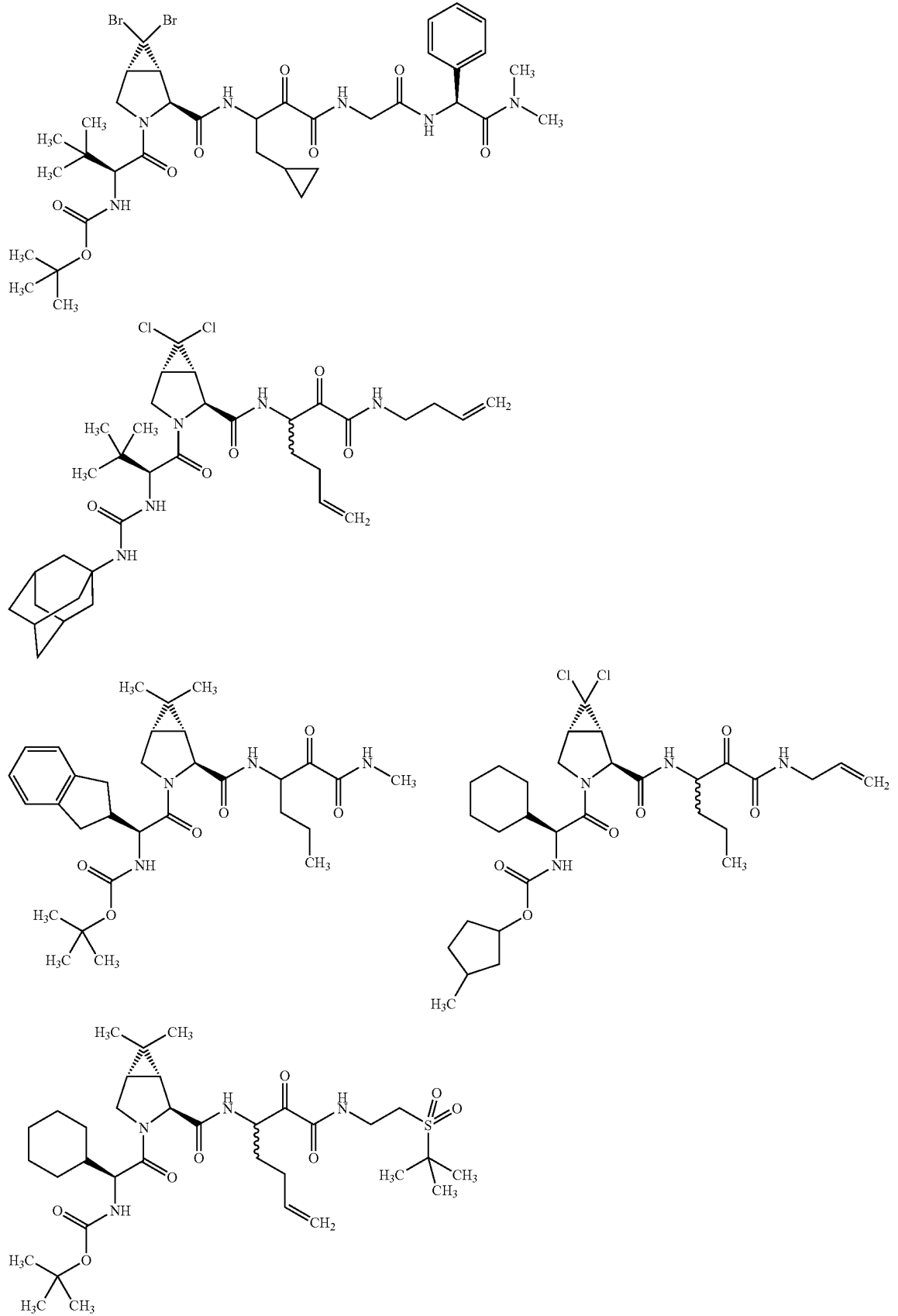

-continued
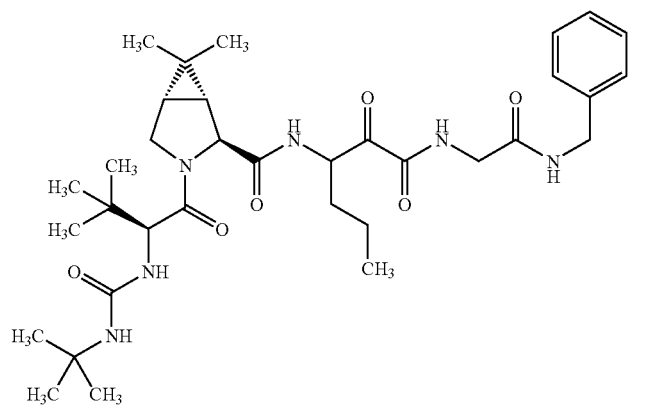
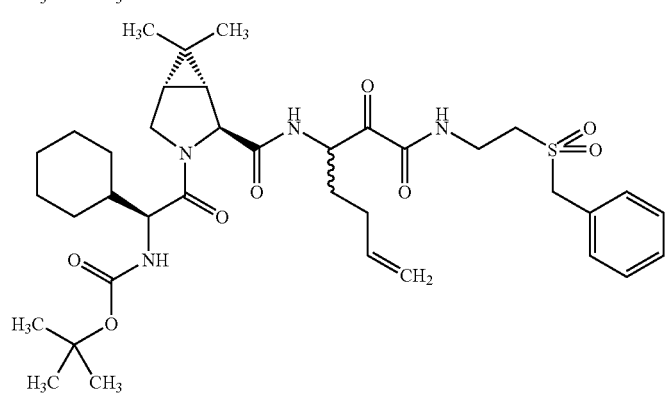
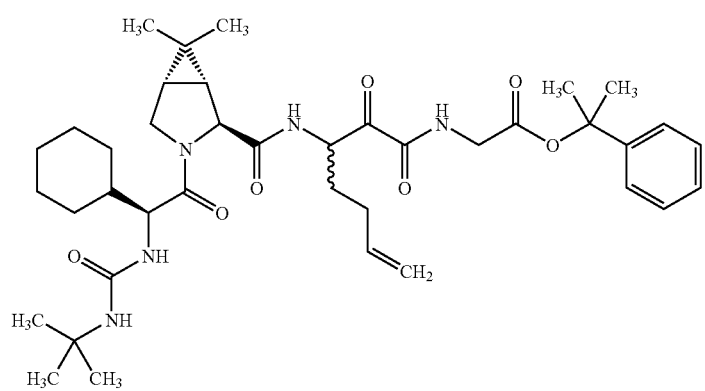
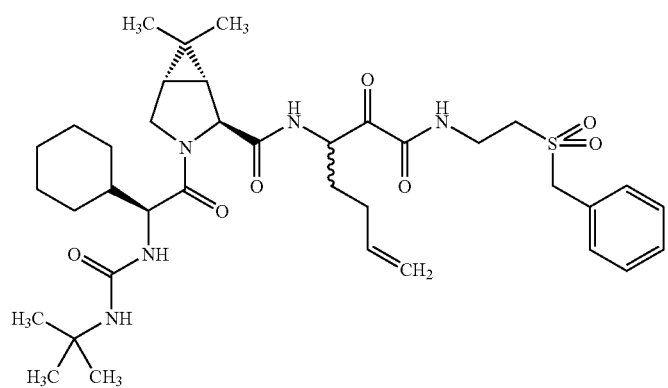

-continued
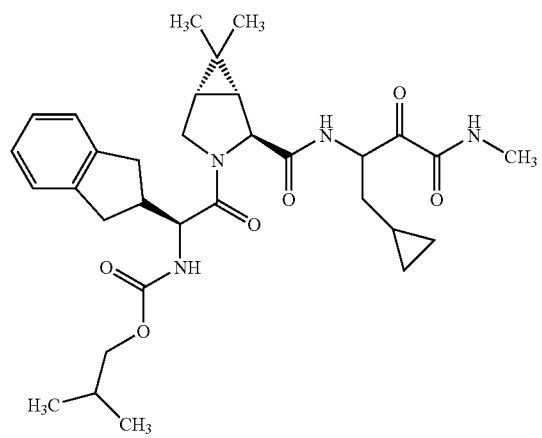
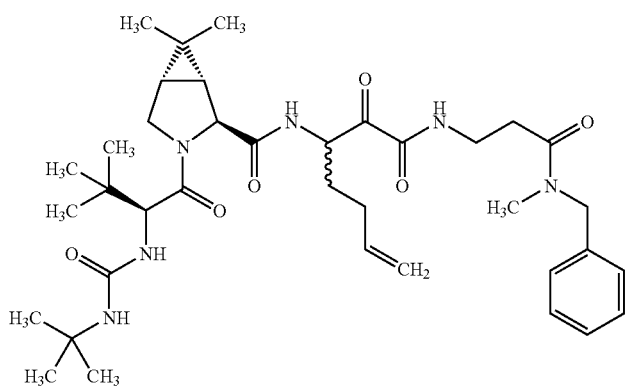
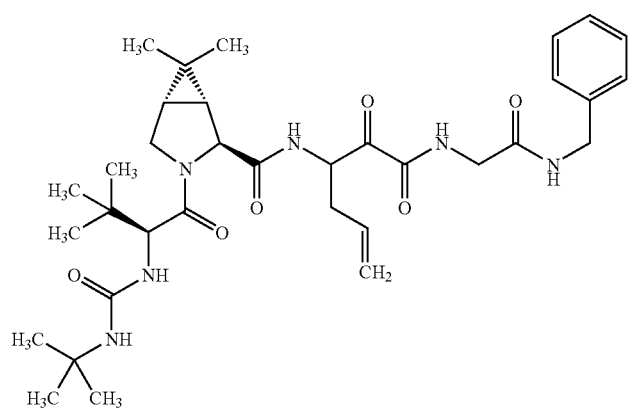
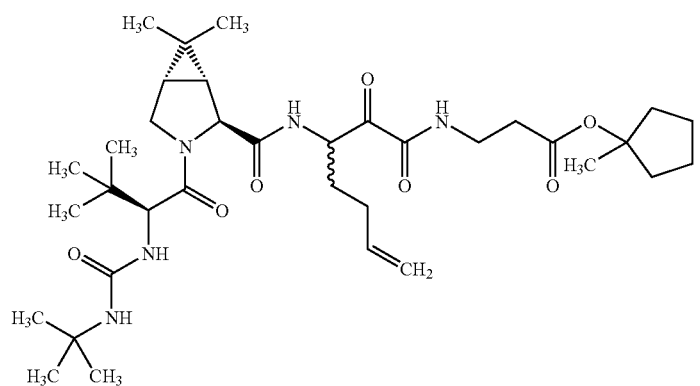
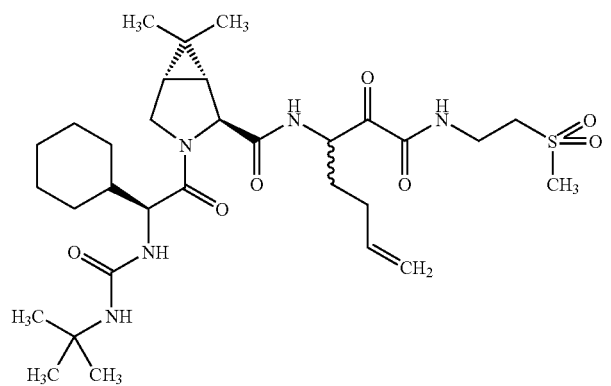

-continued
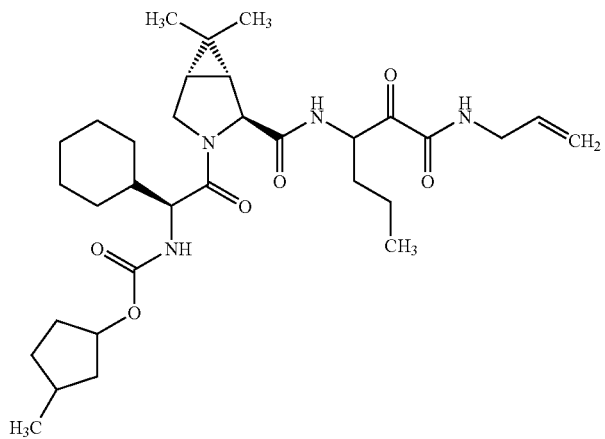
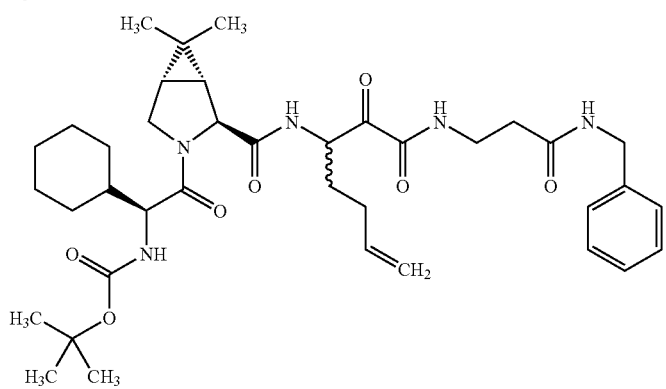
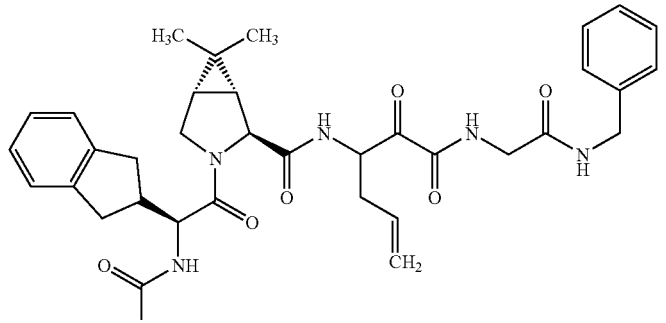
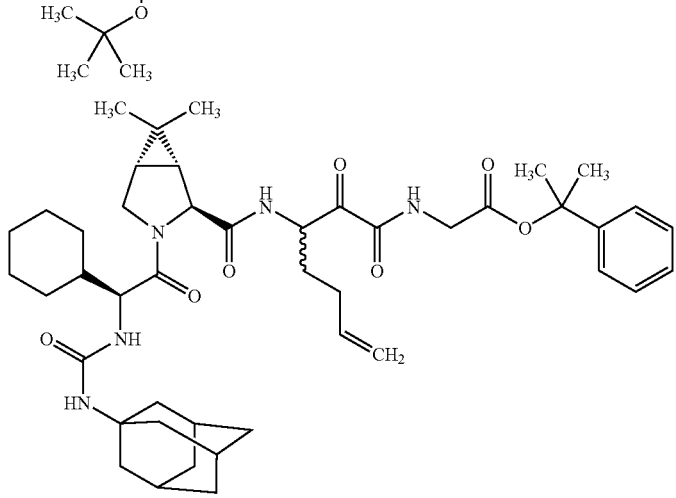

113
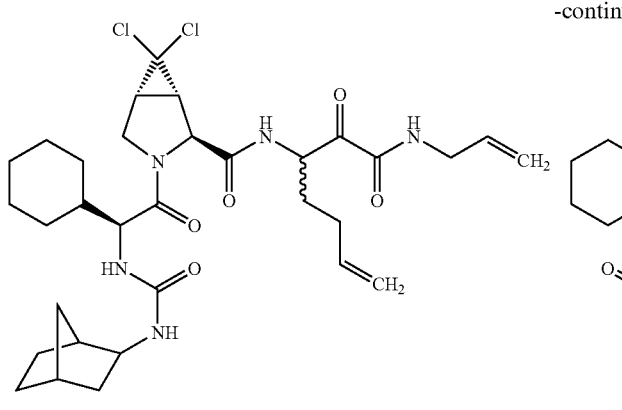
114
-continued
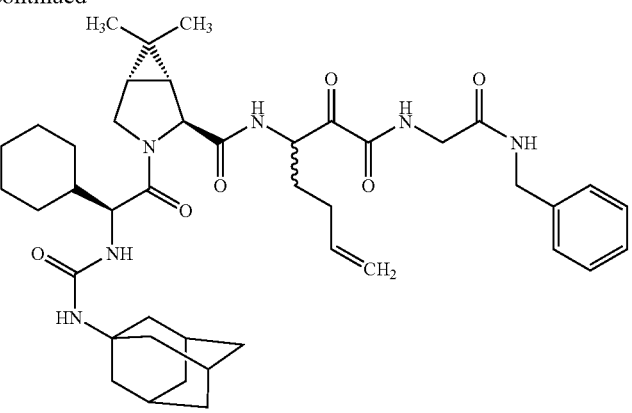
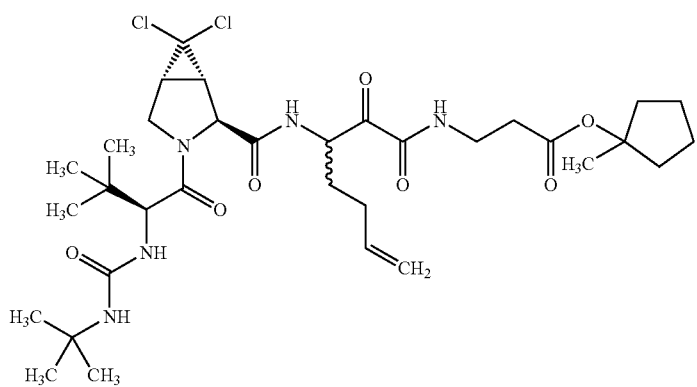
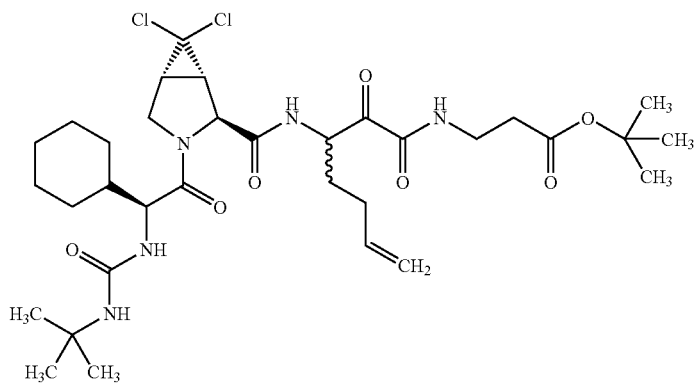
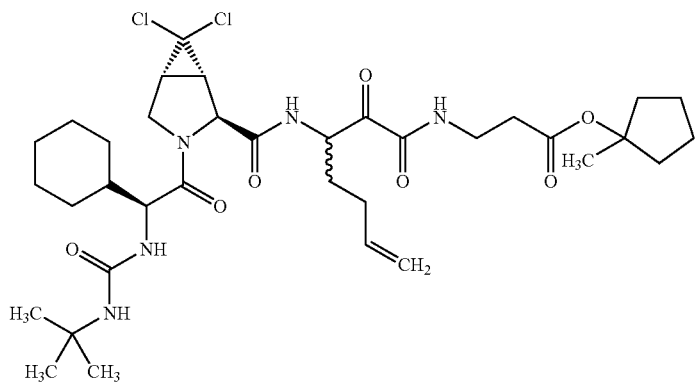

-continued
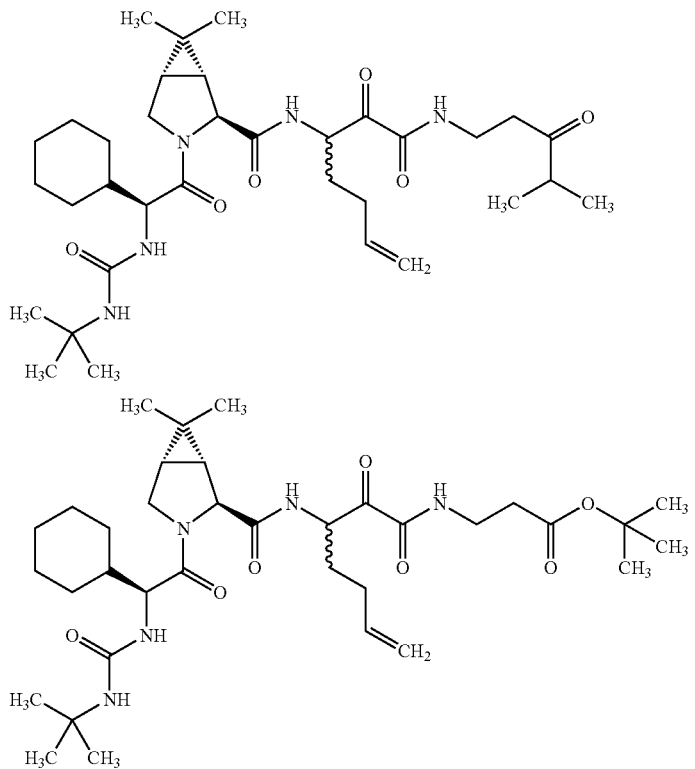
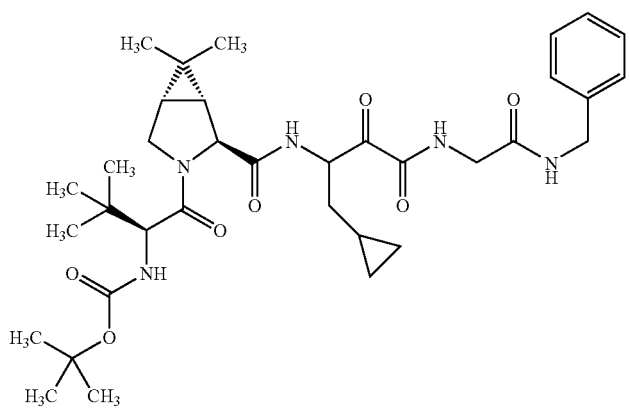
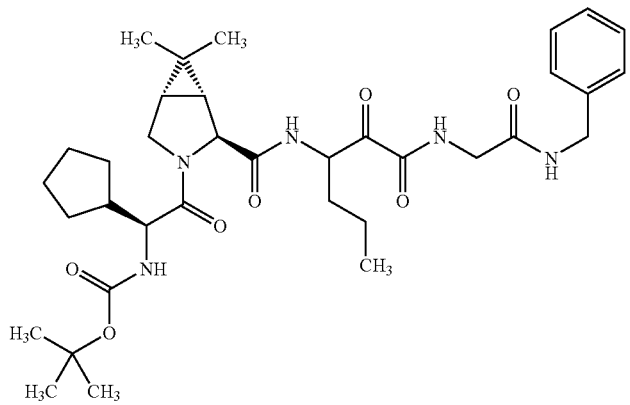

117 118
-continued
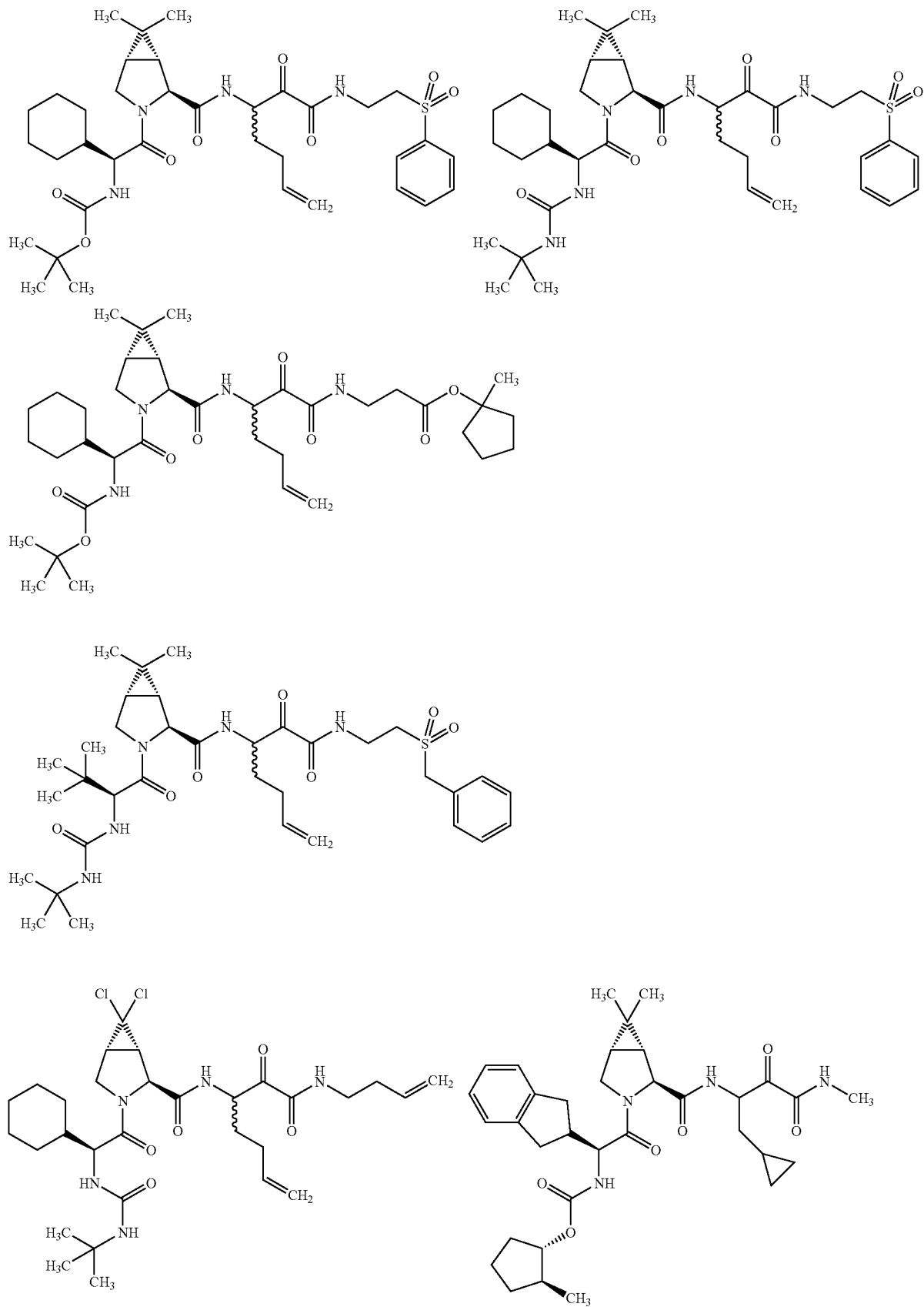

-continued
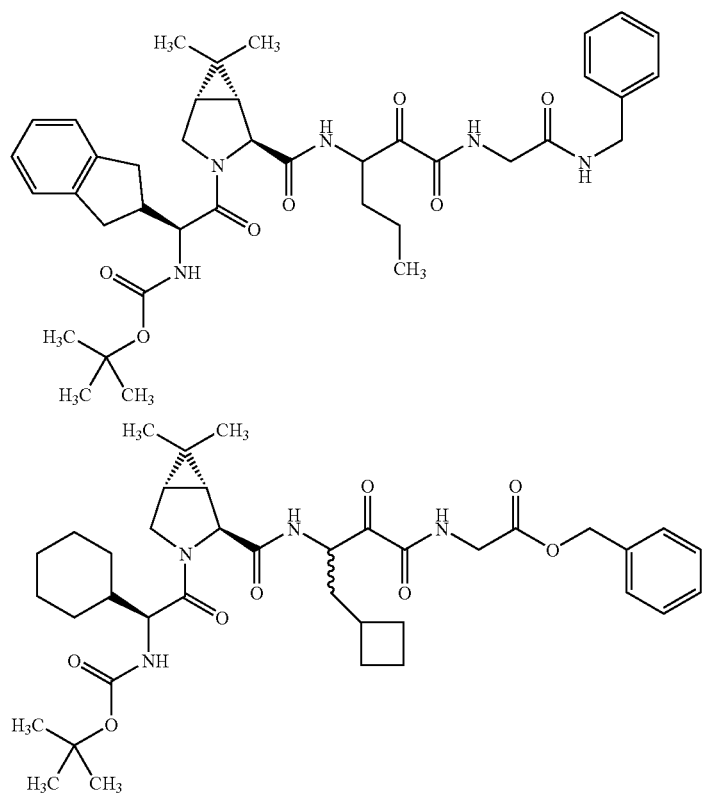
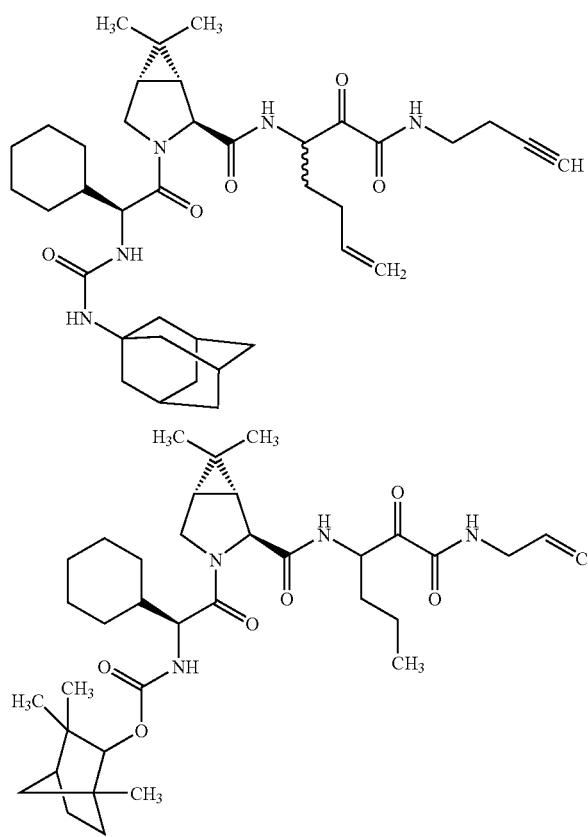

-continued
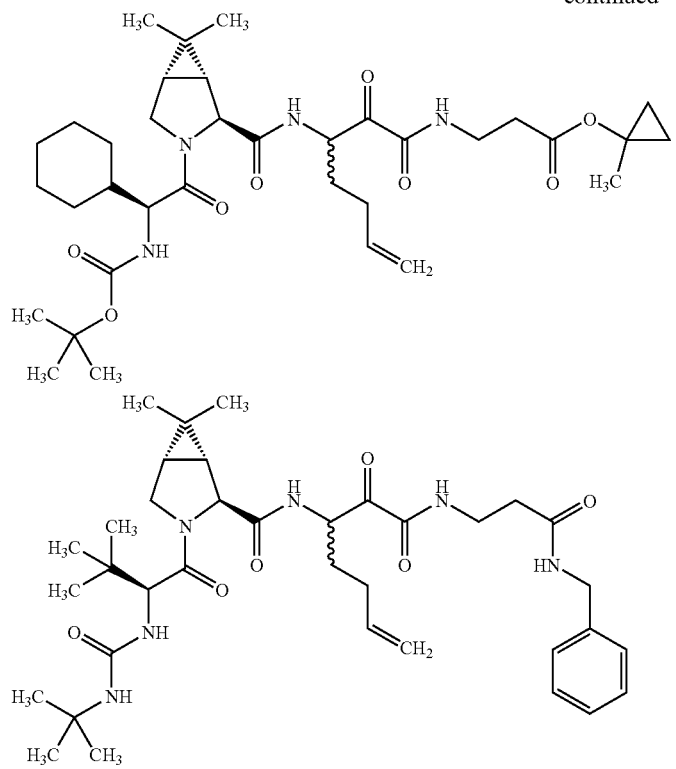
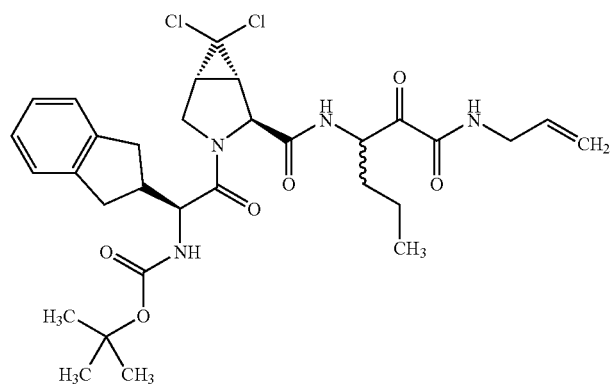
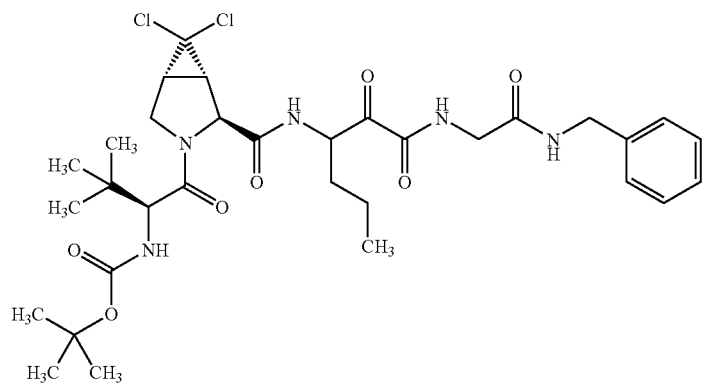

-continued
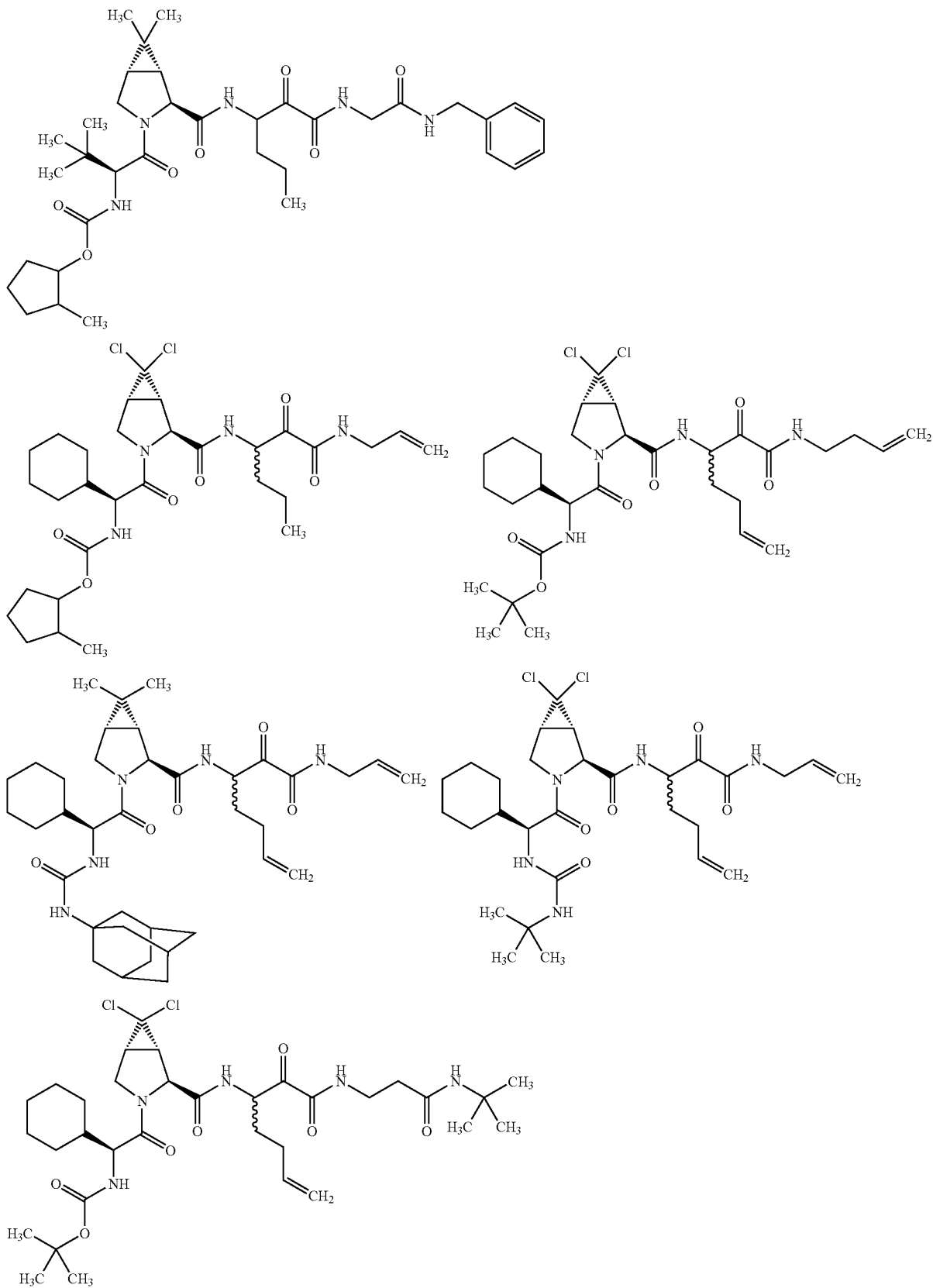

-continued
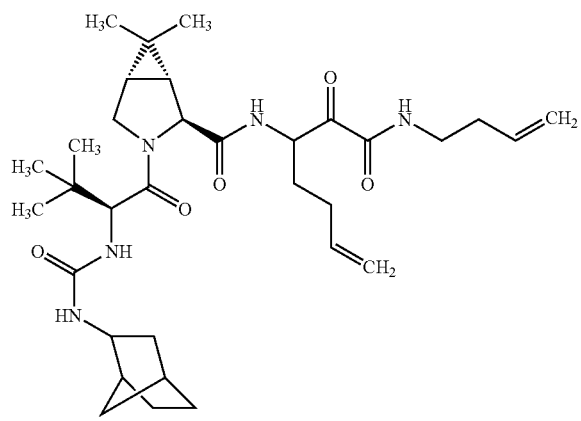
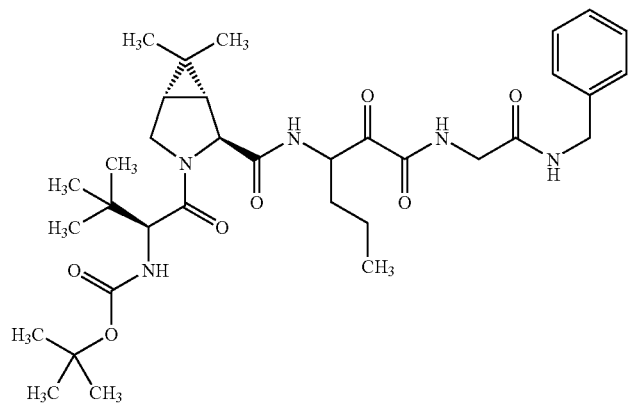
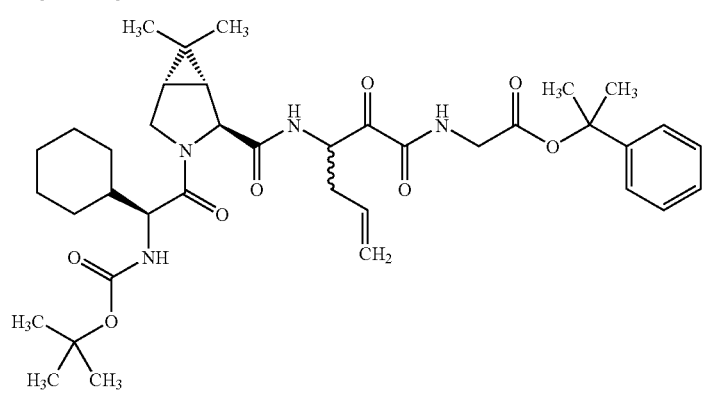
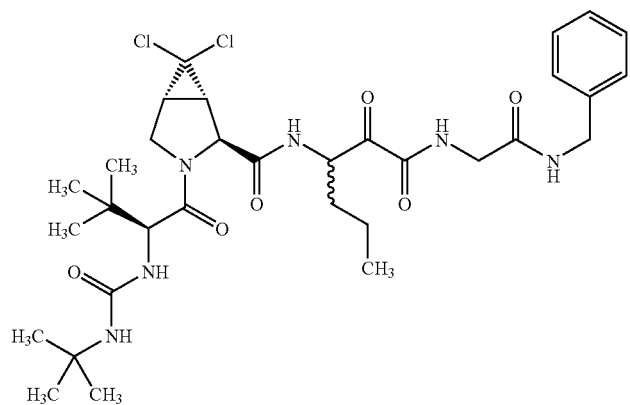

-continued
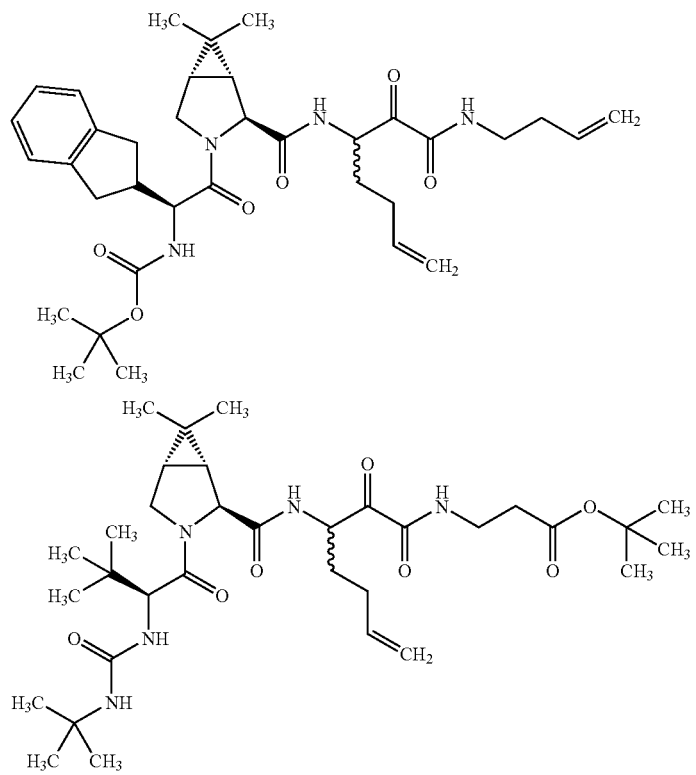
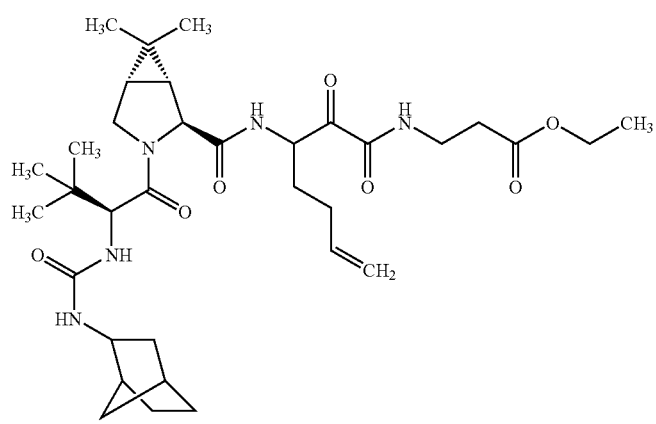
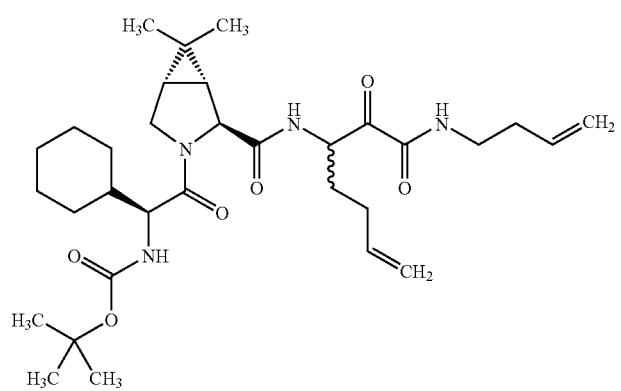

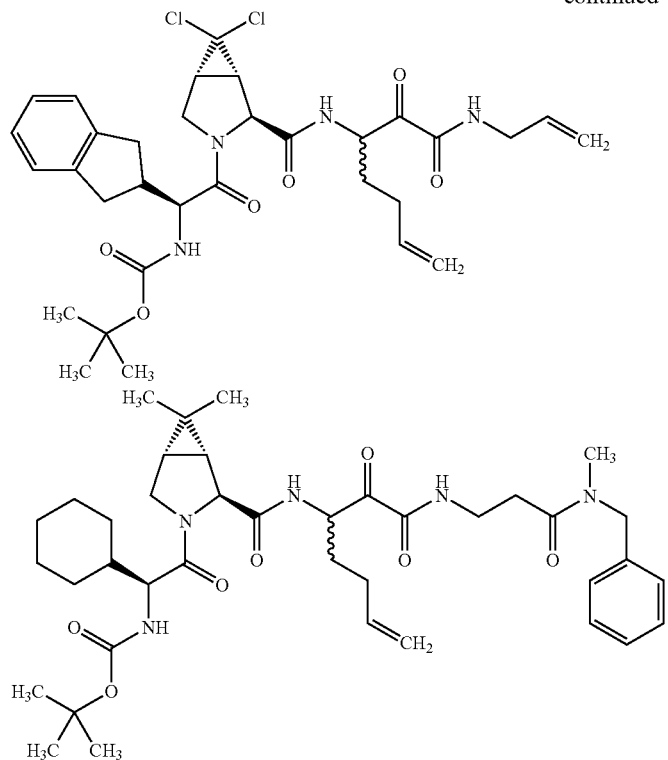
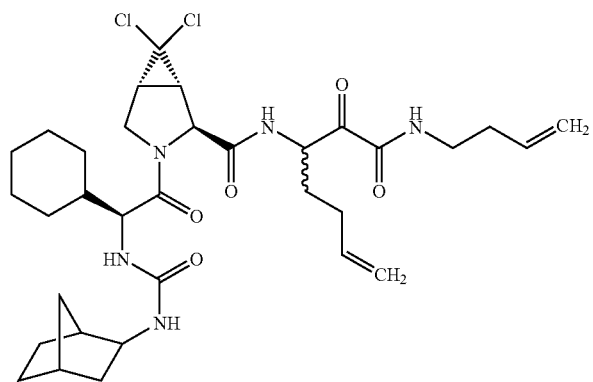
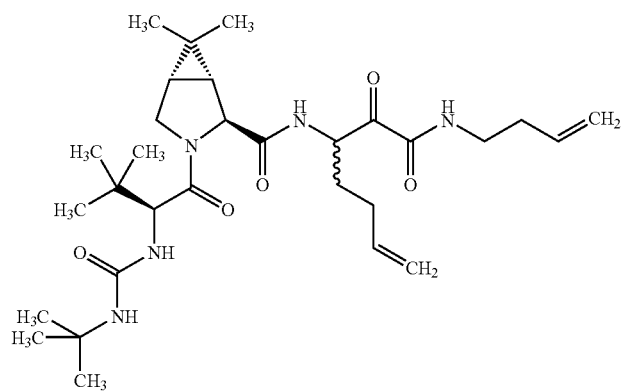

-continued
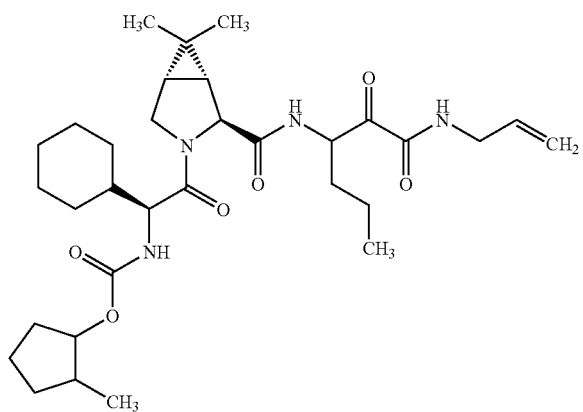
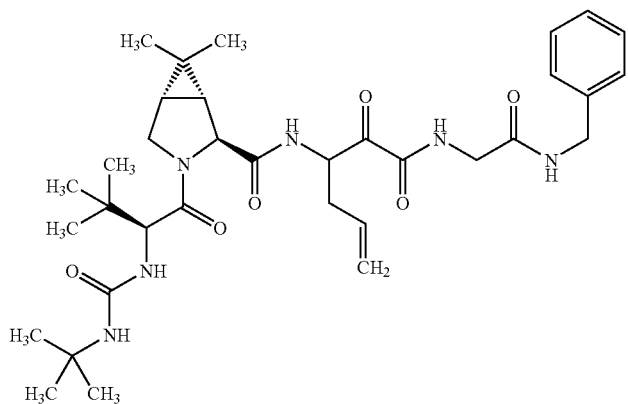
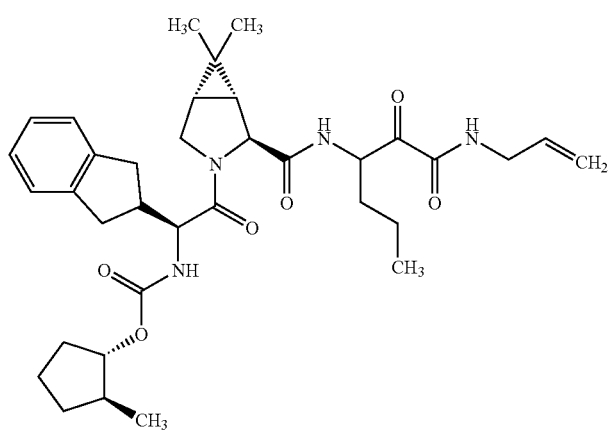
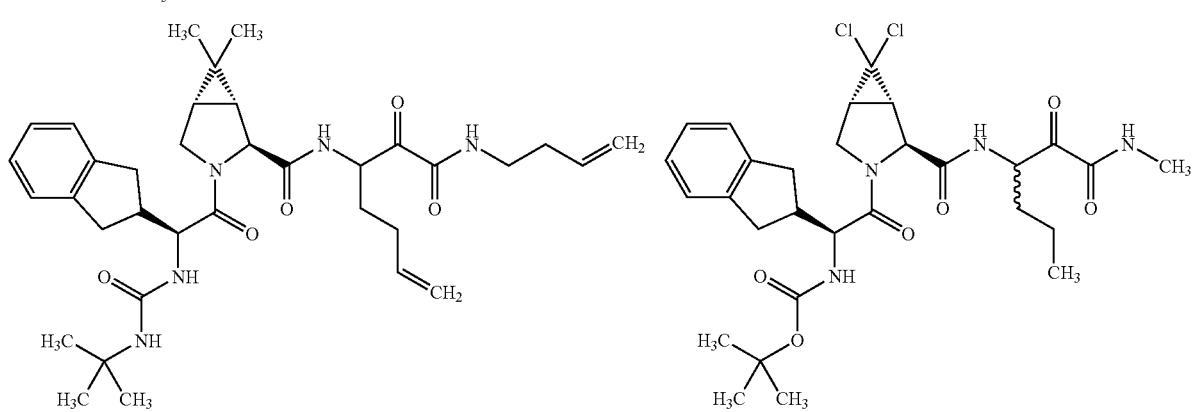

-continued
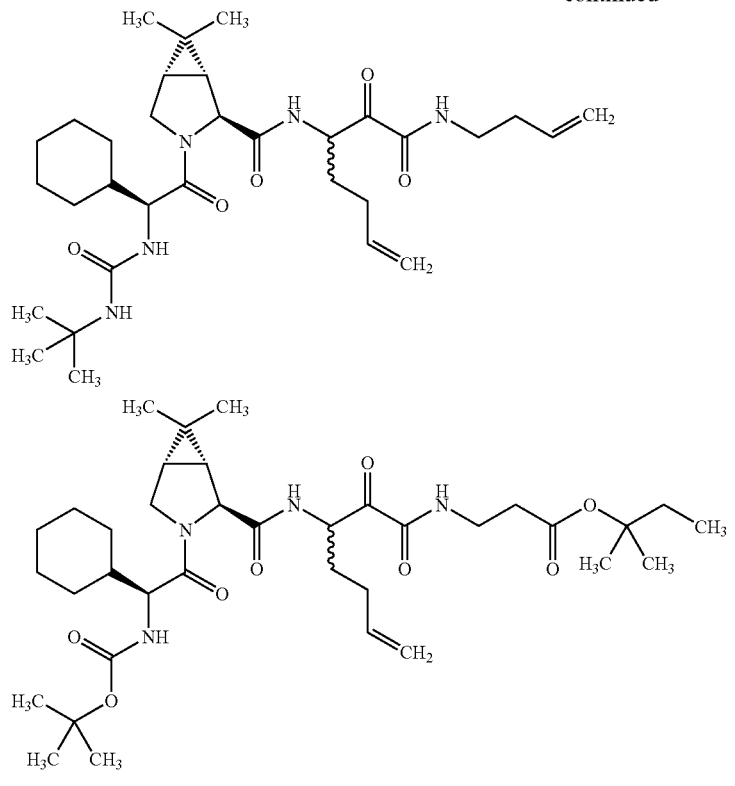
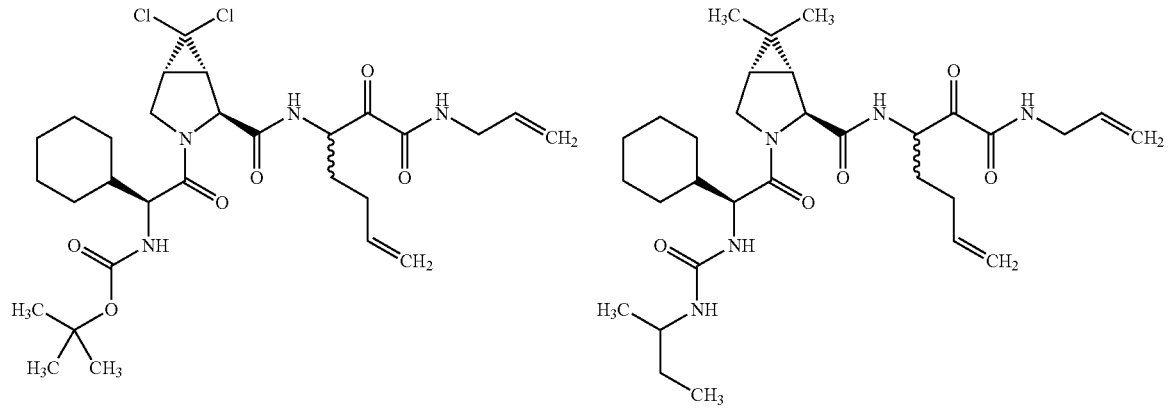
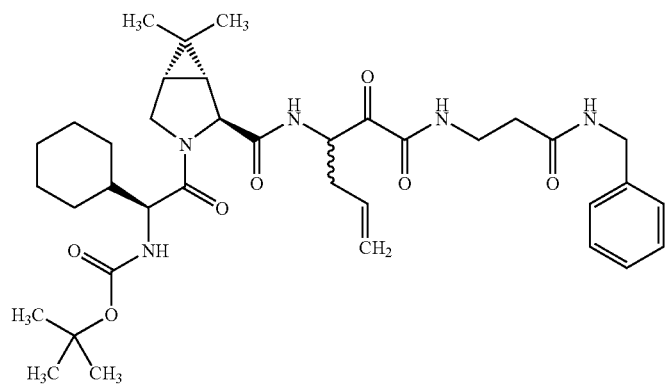

-continued
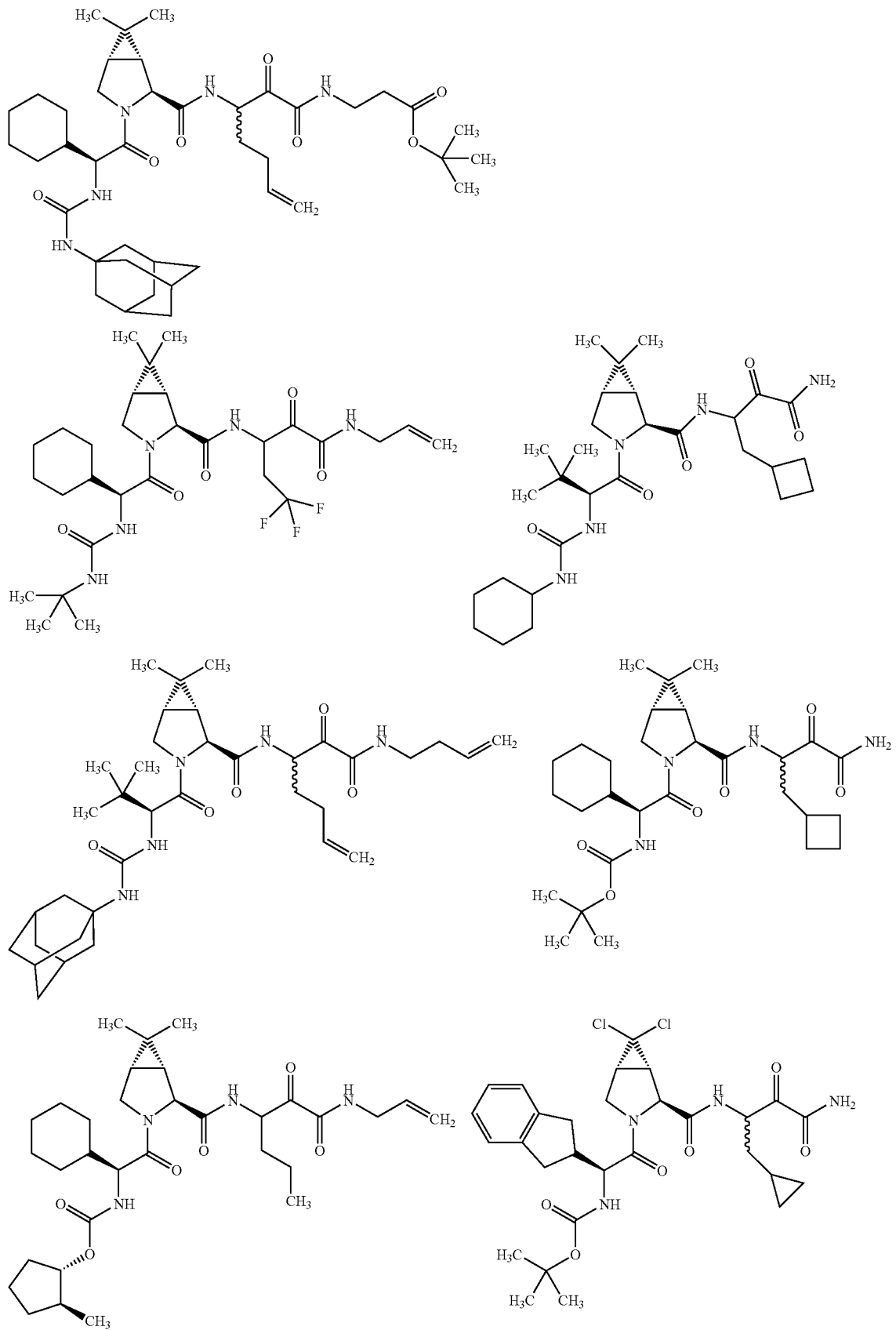

-continued
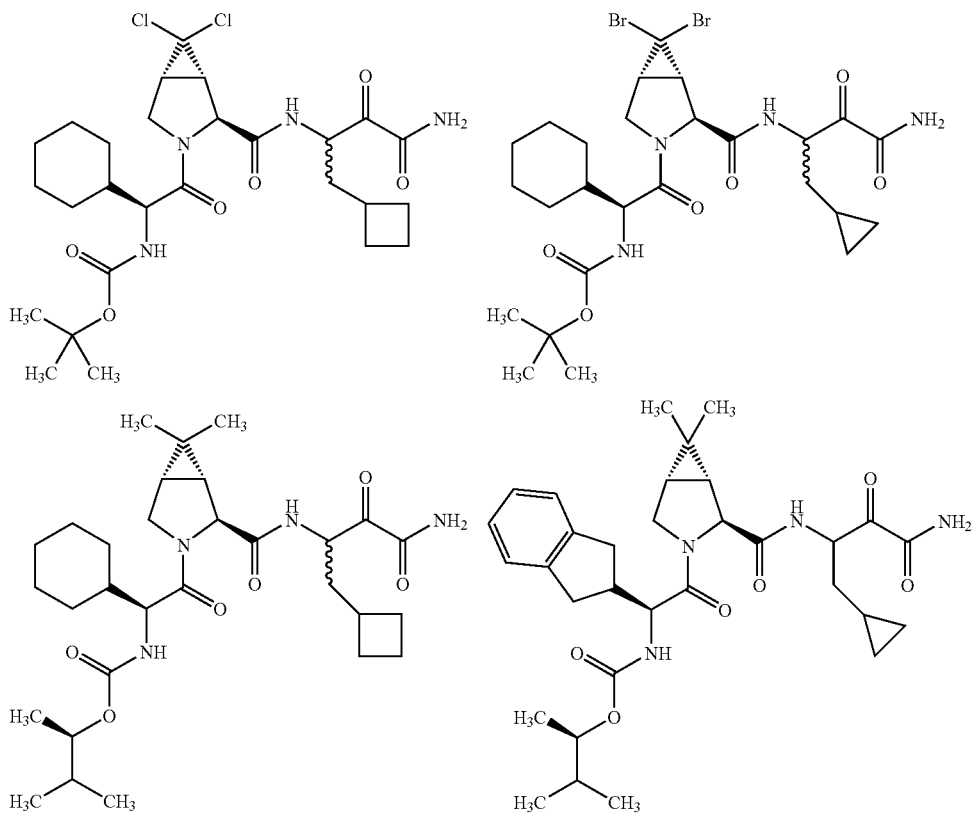
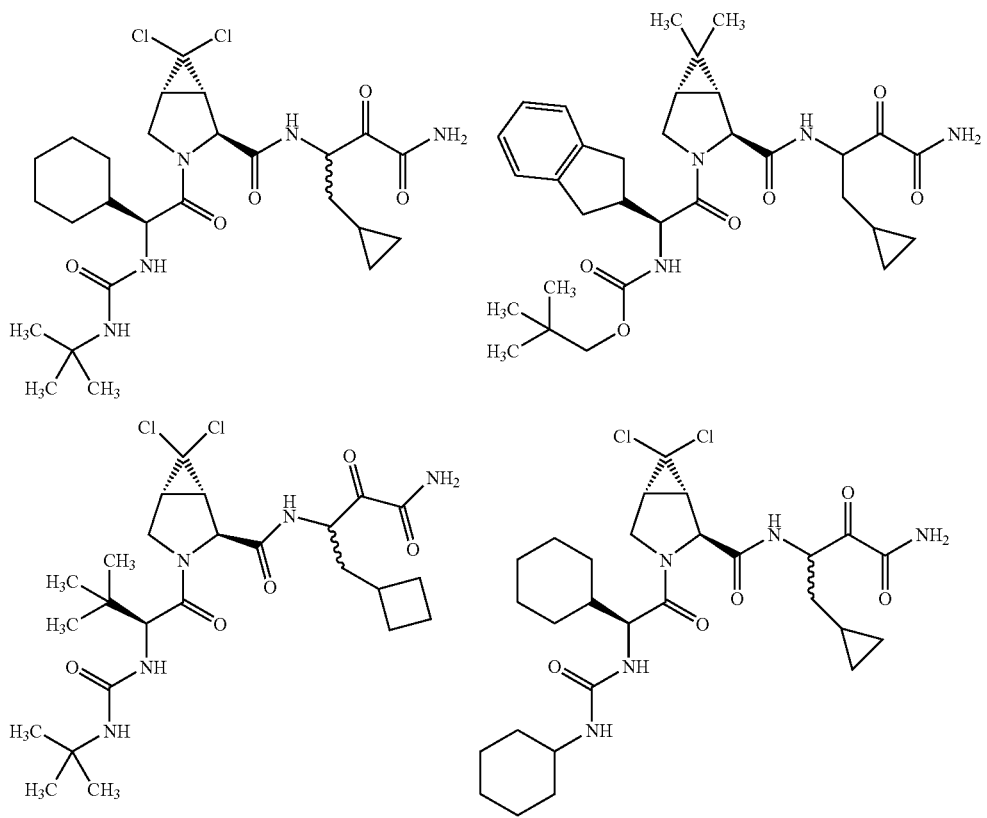

-continued
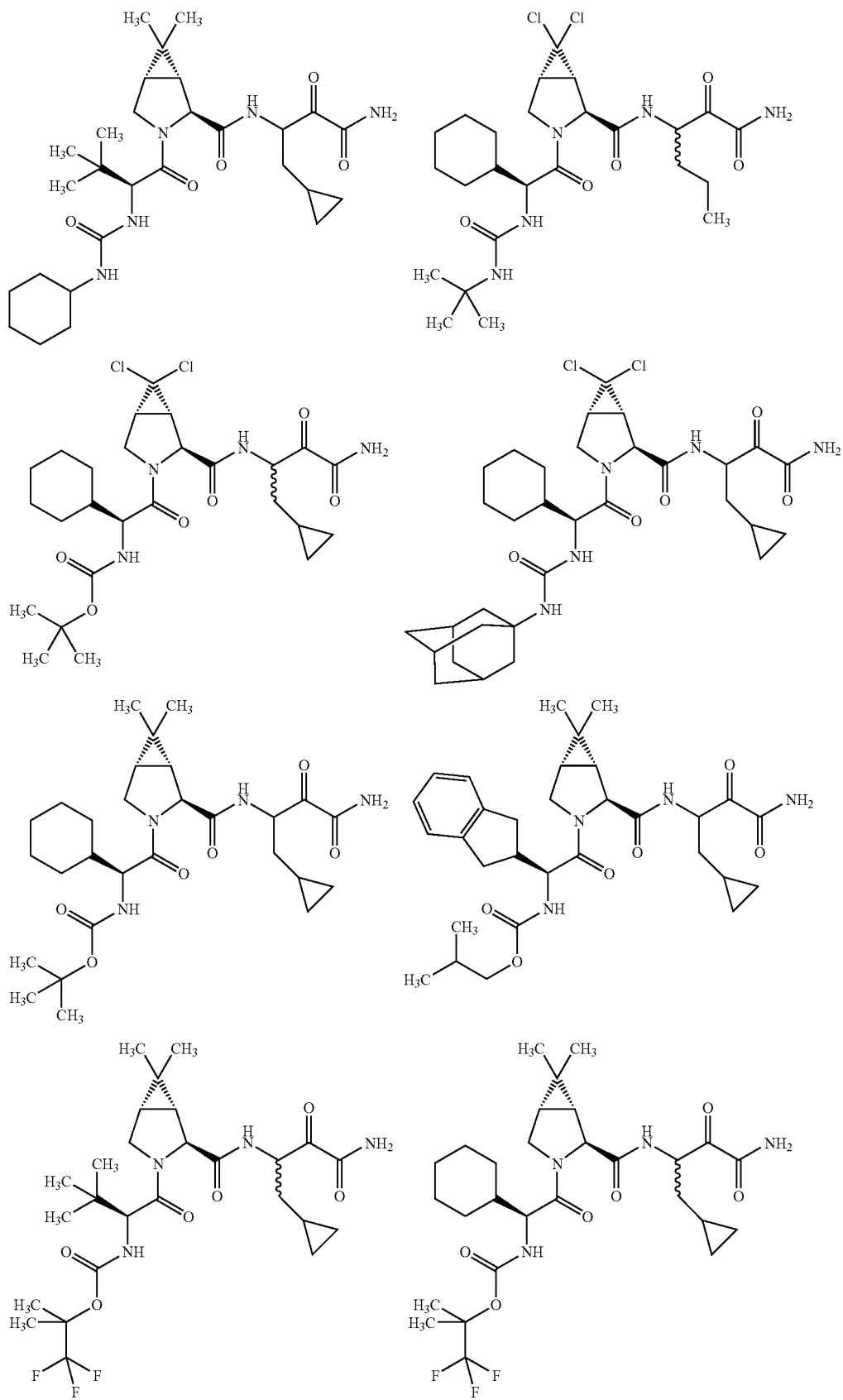

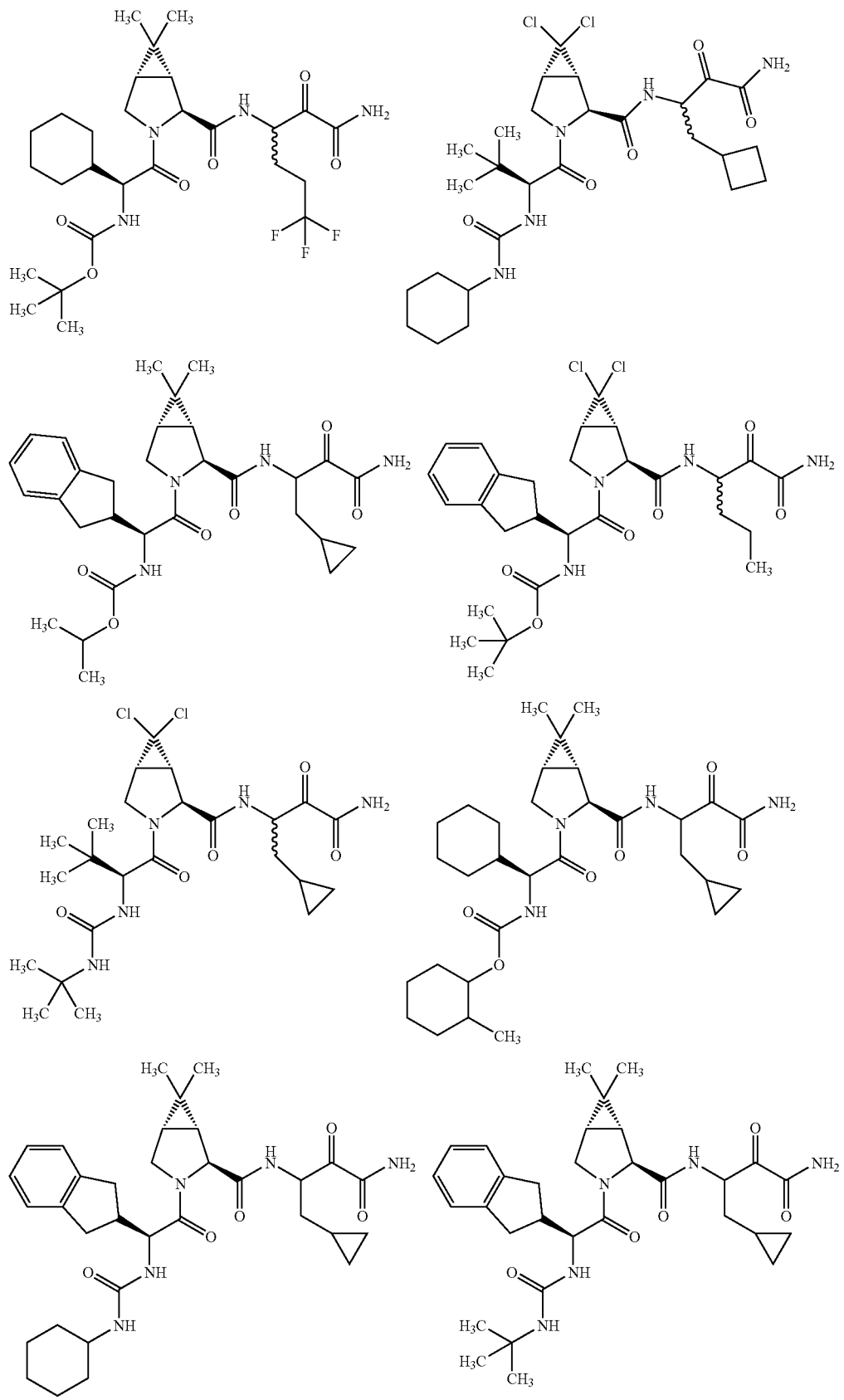

-continued
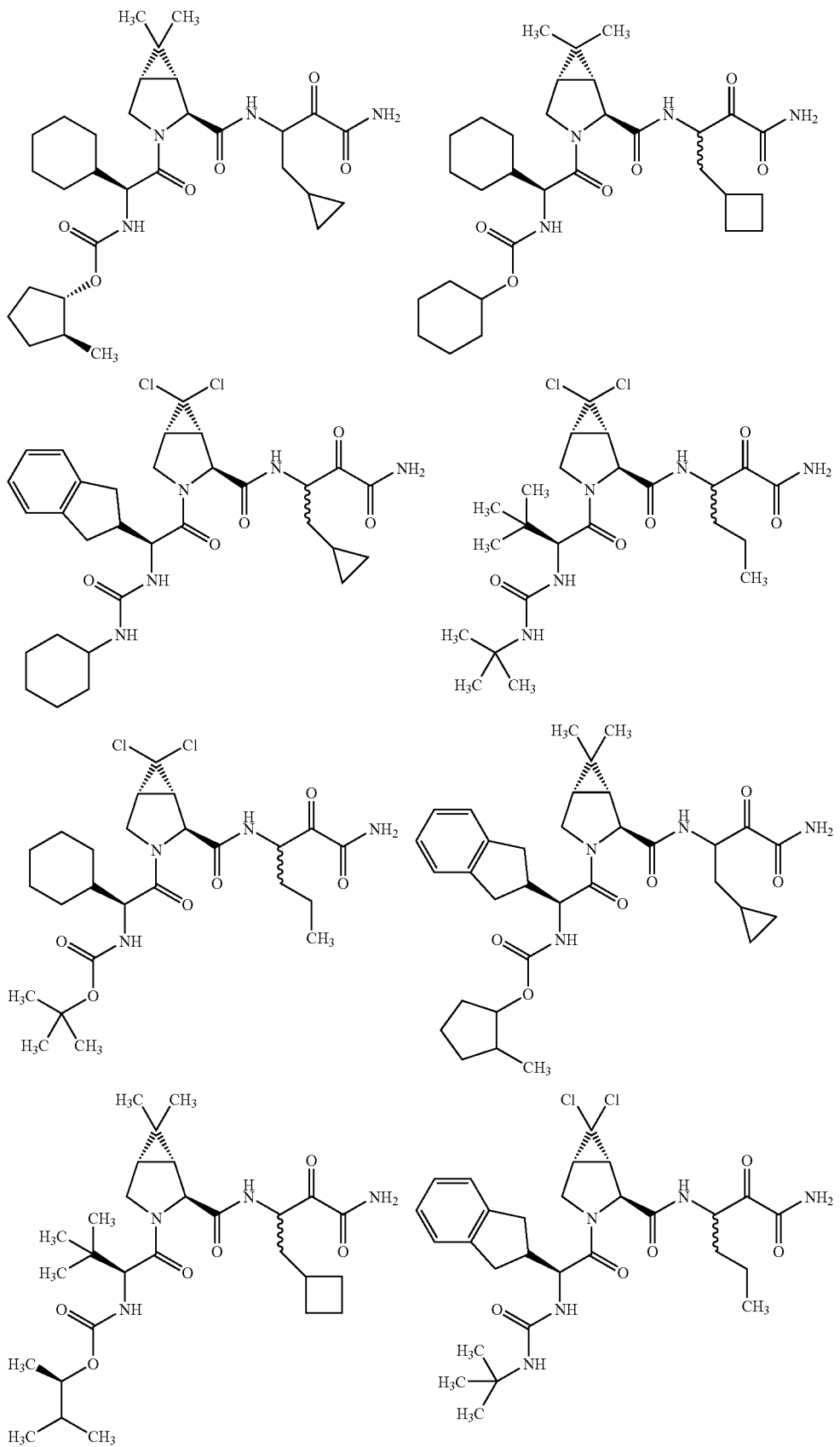

-continued
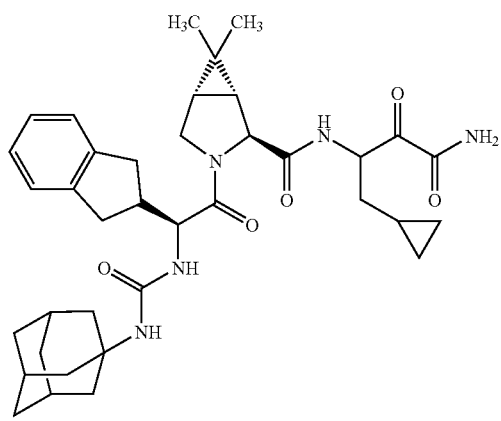
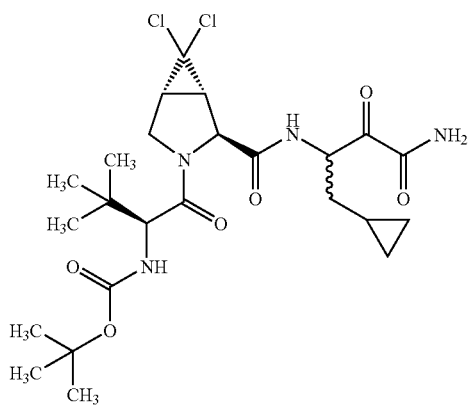
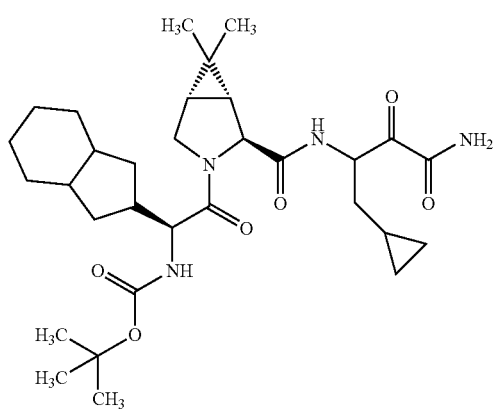
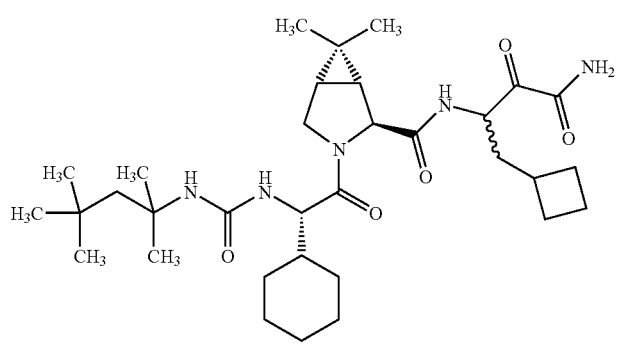
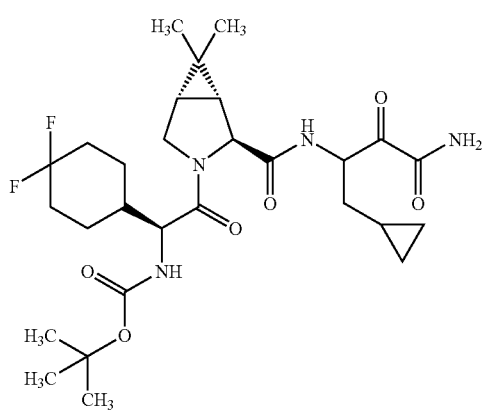
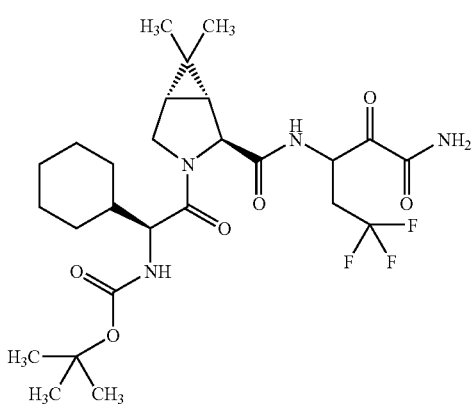
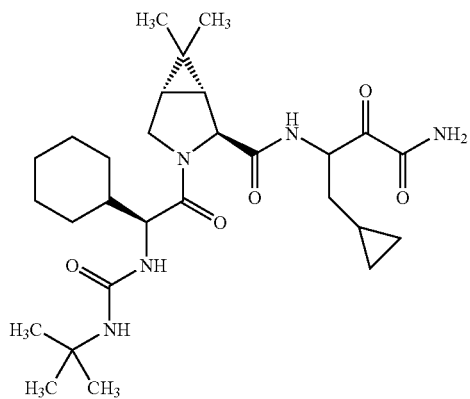
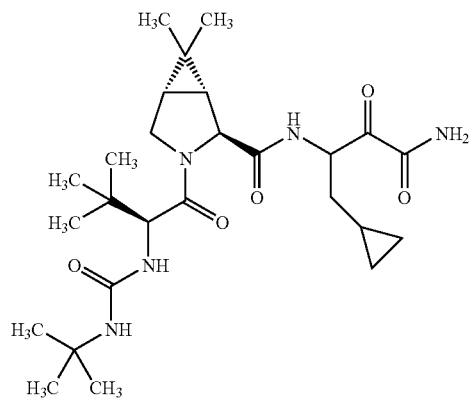

-continued
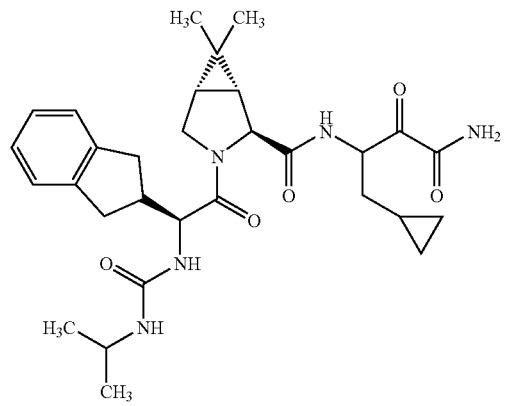
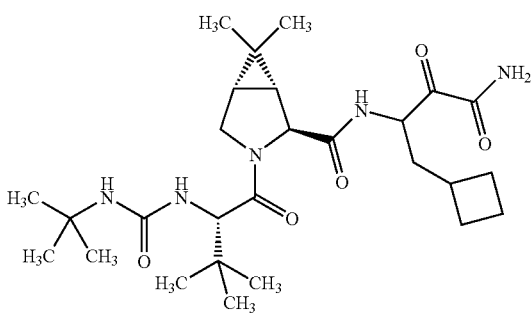
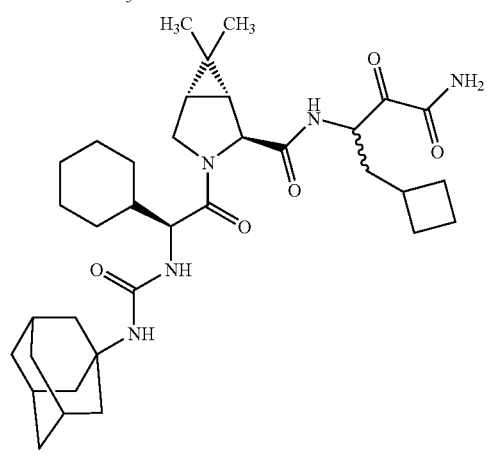
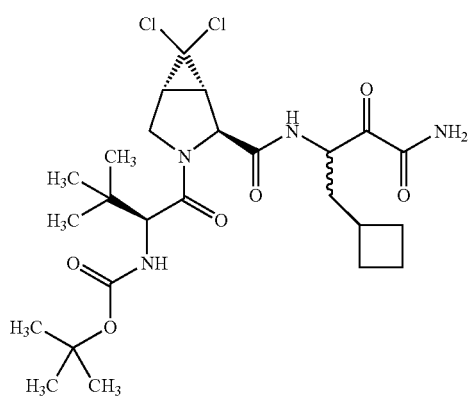
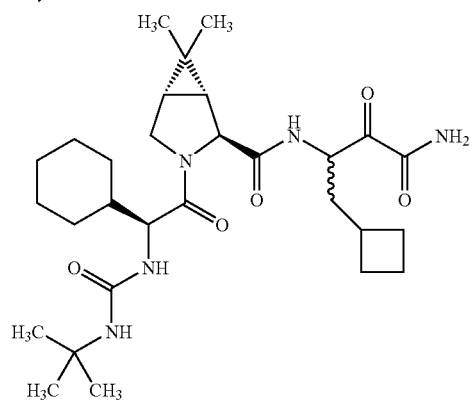
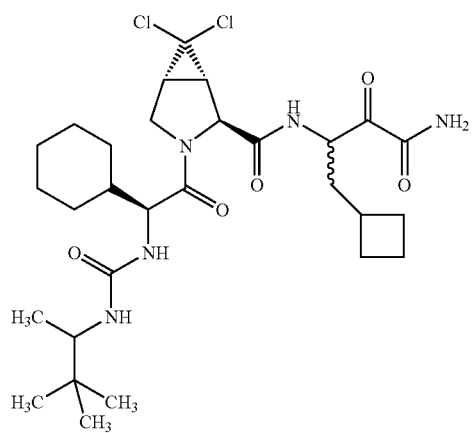
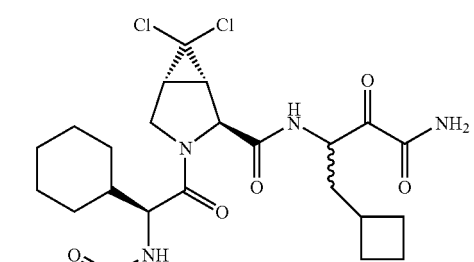
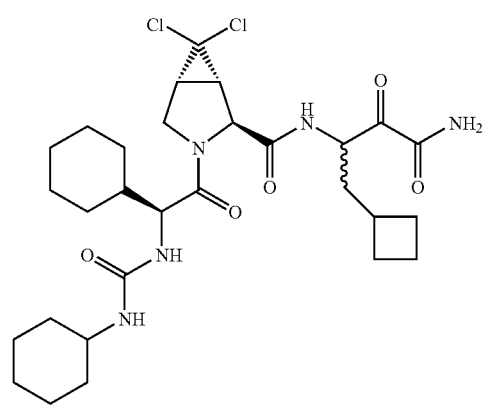

-continued
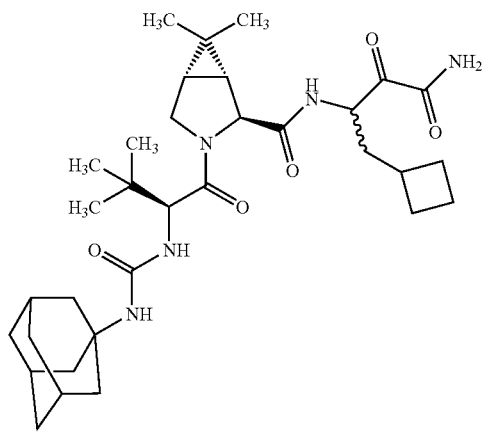
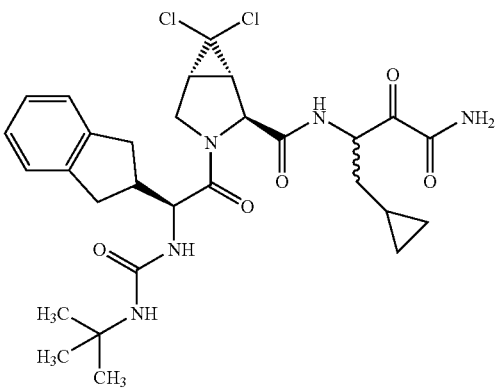
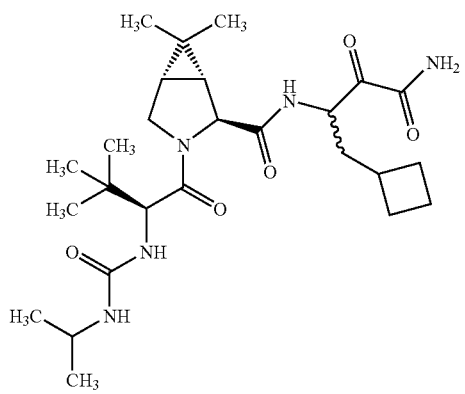
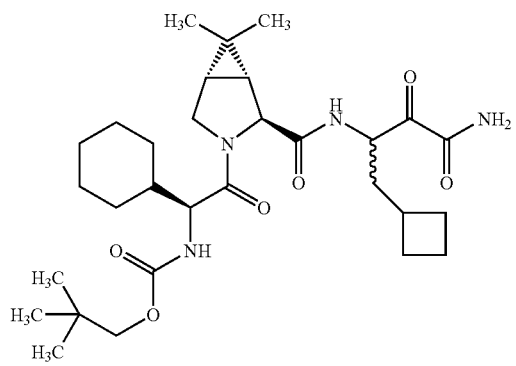
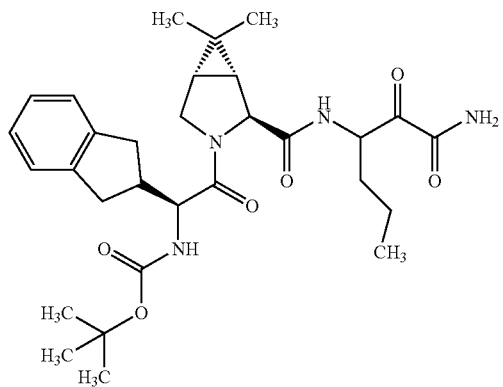
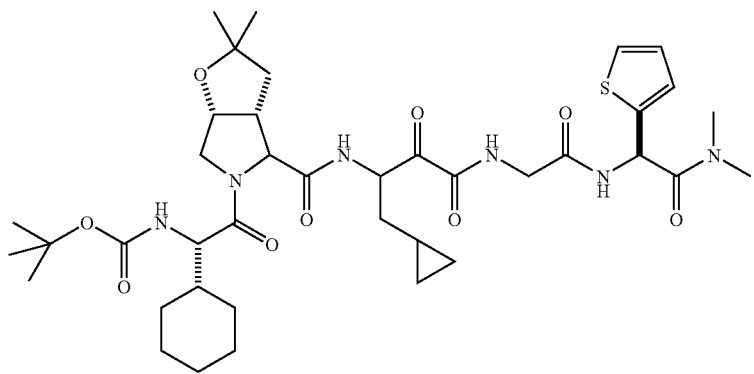

-continued
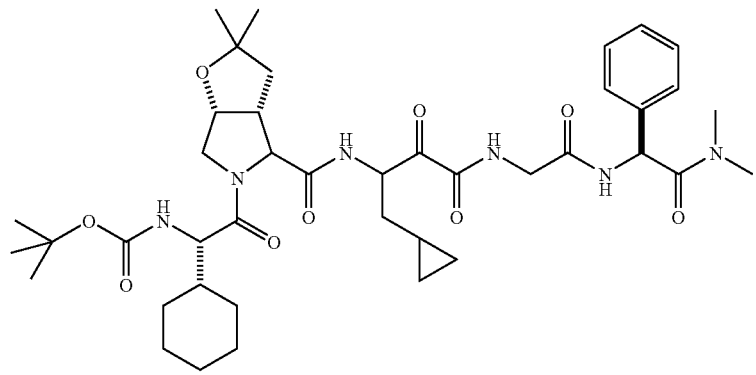
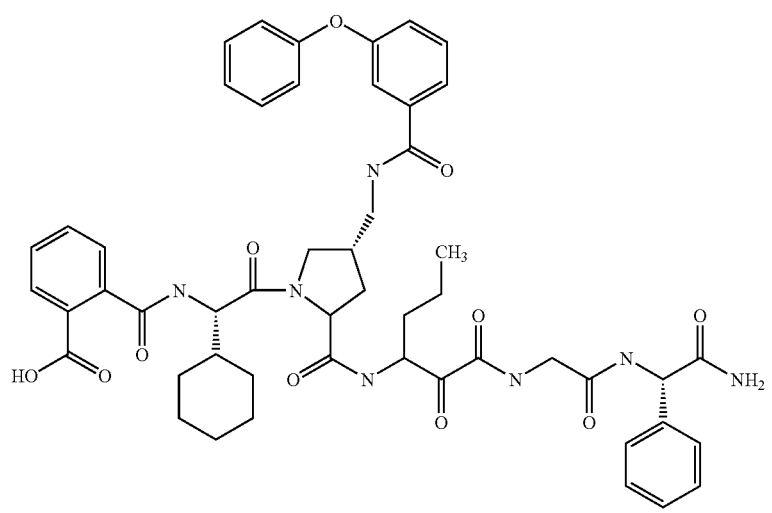
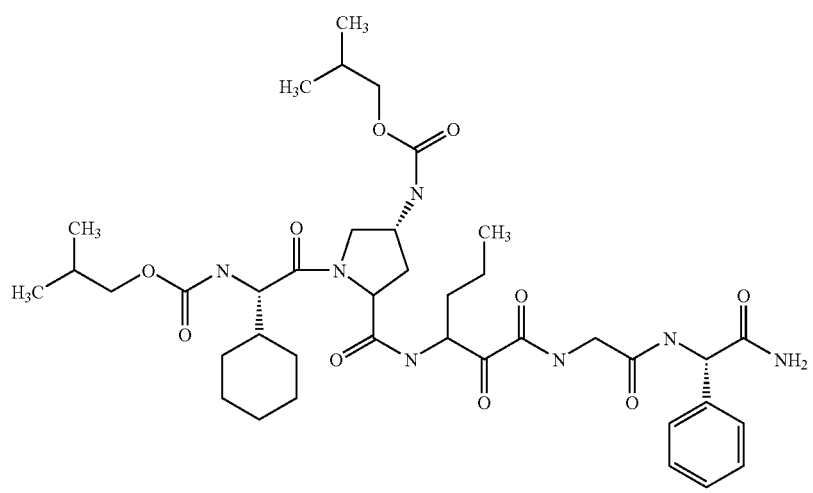

-continued
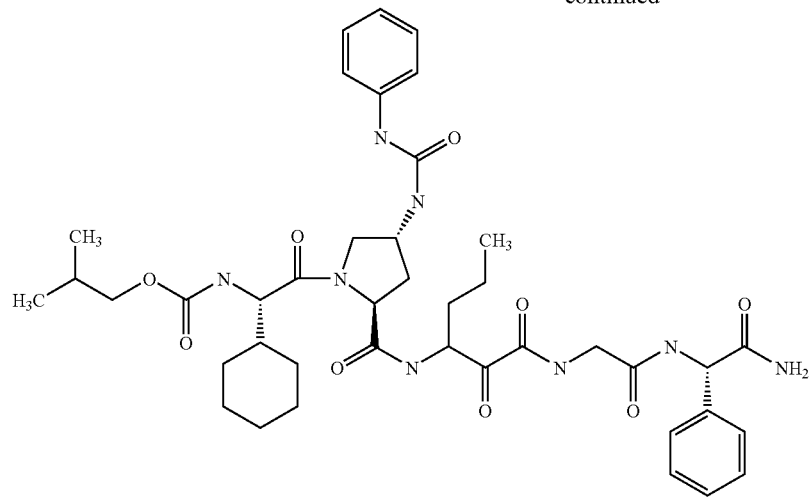
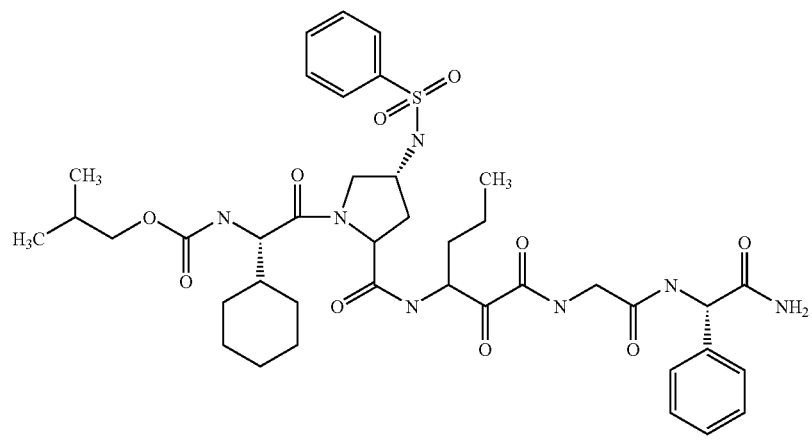
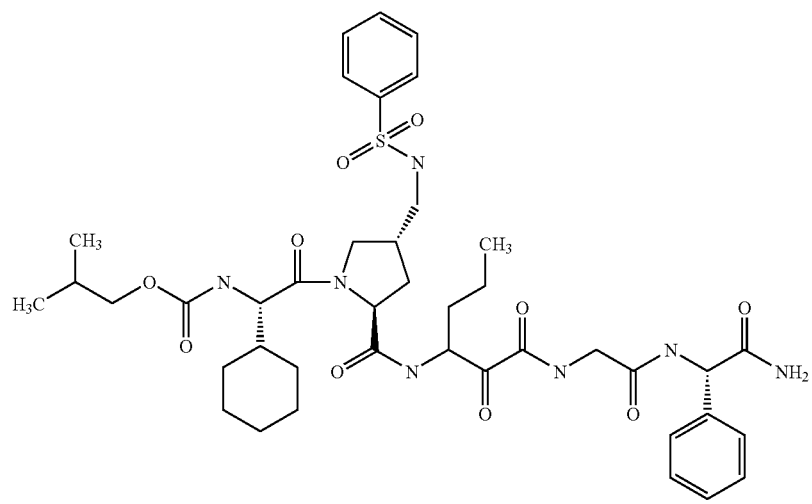

-continued
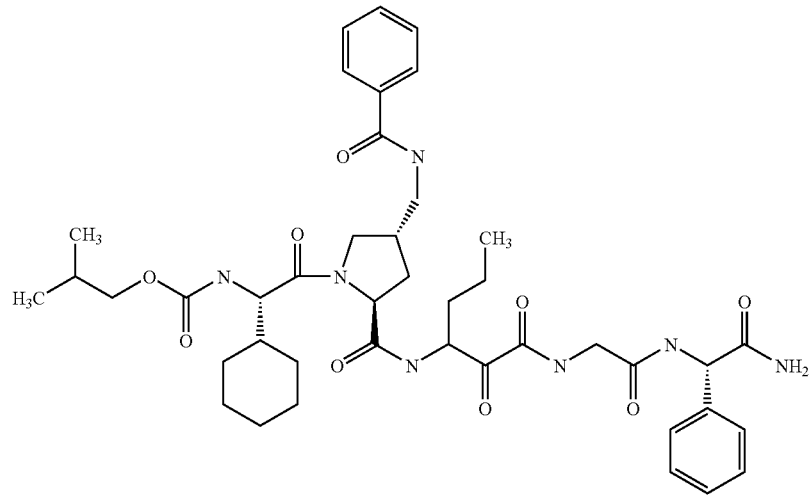
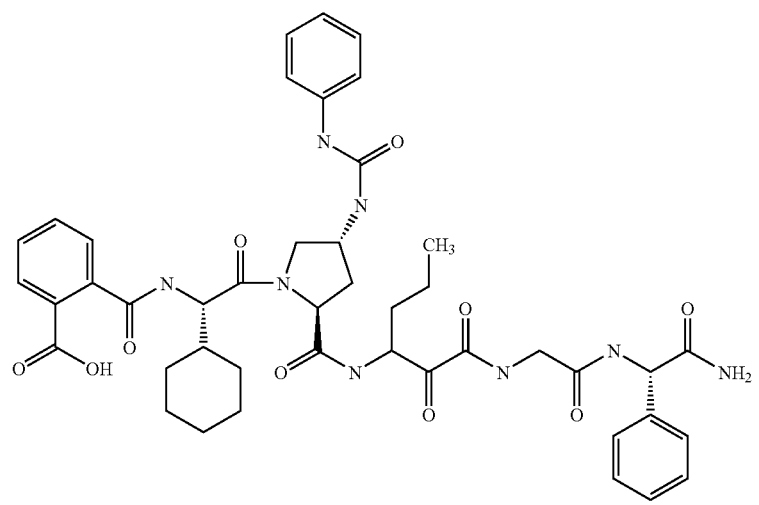
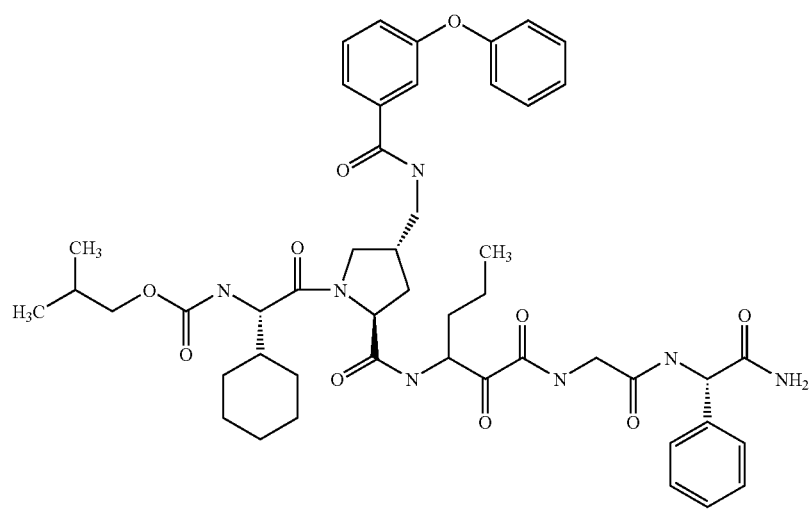

-continued
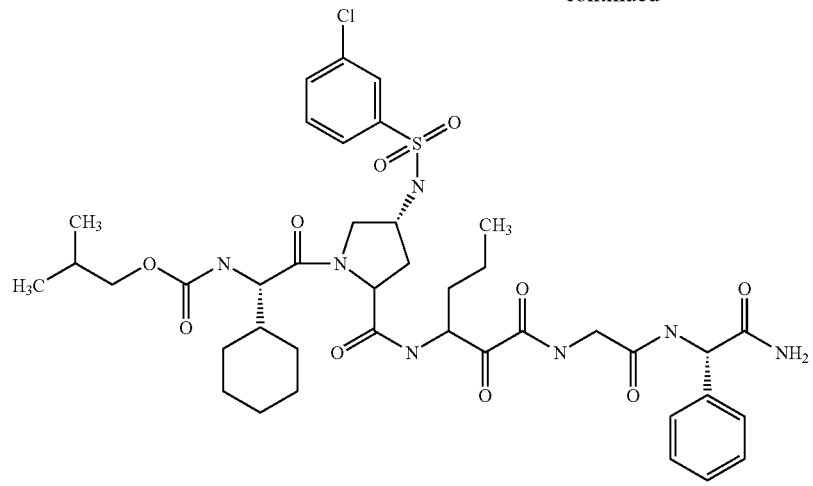
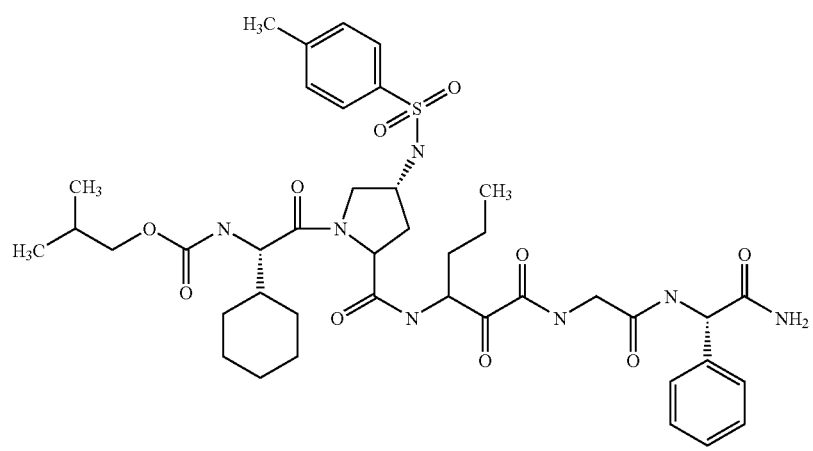
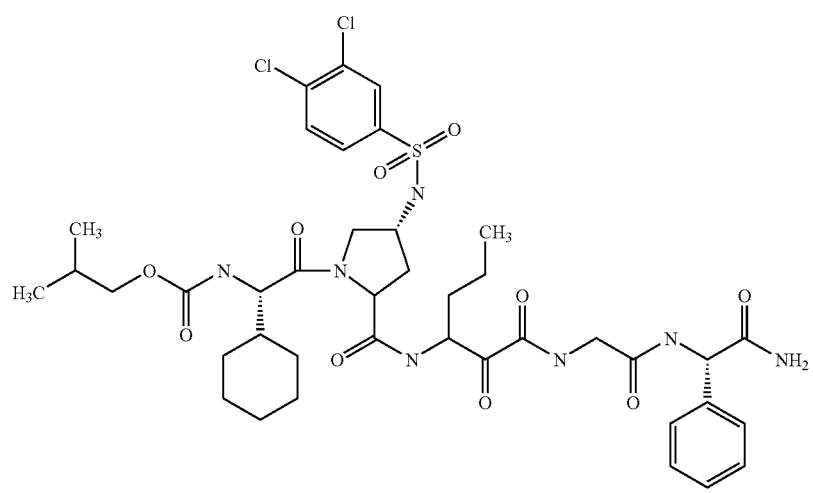

-continued
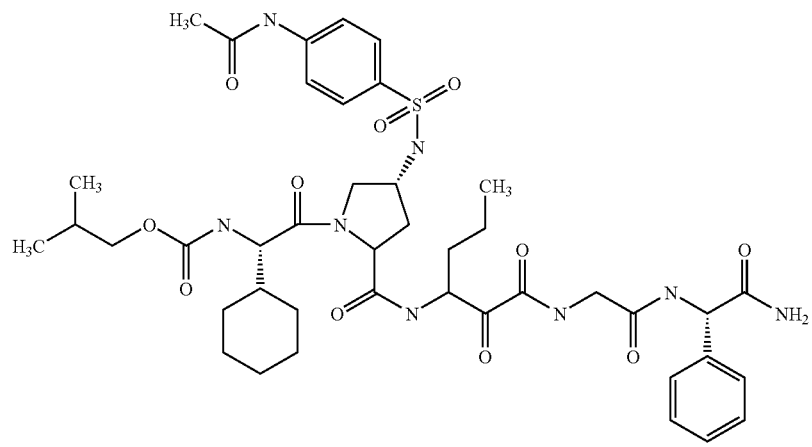
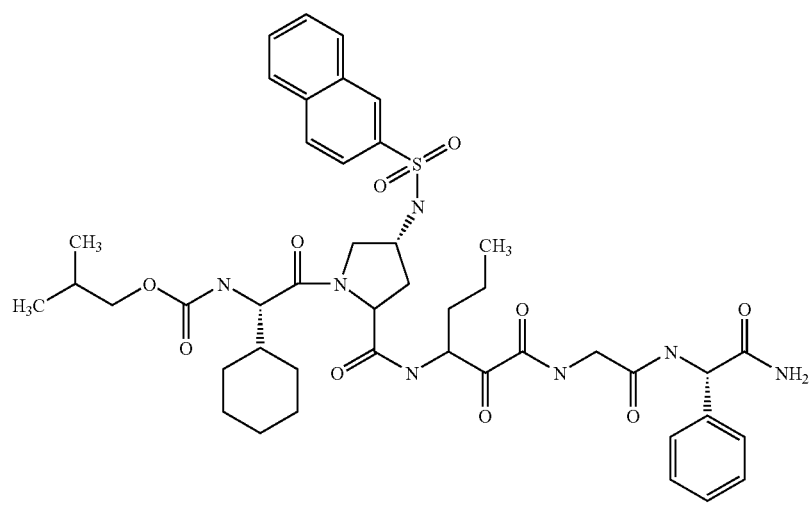
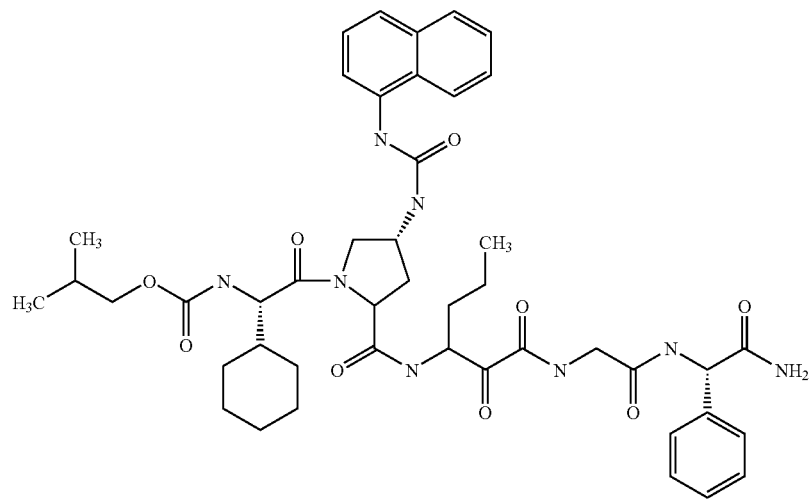

-continued
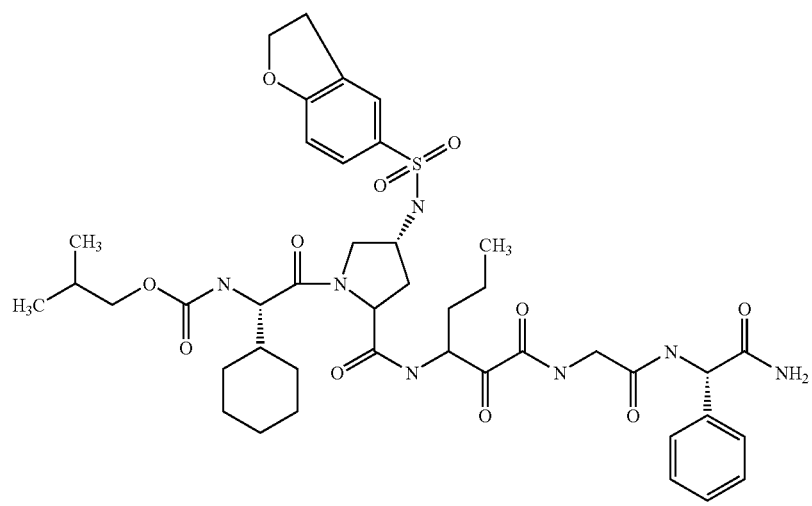
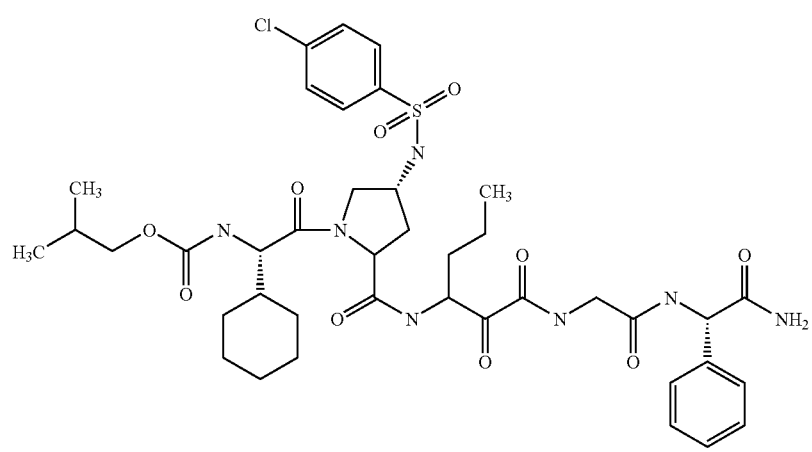
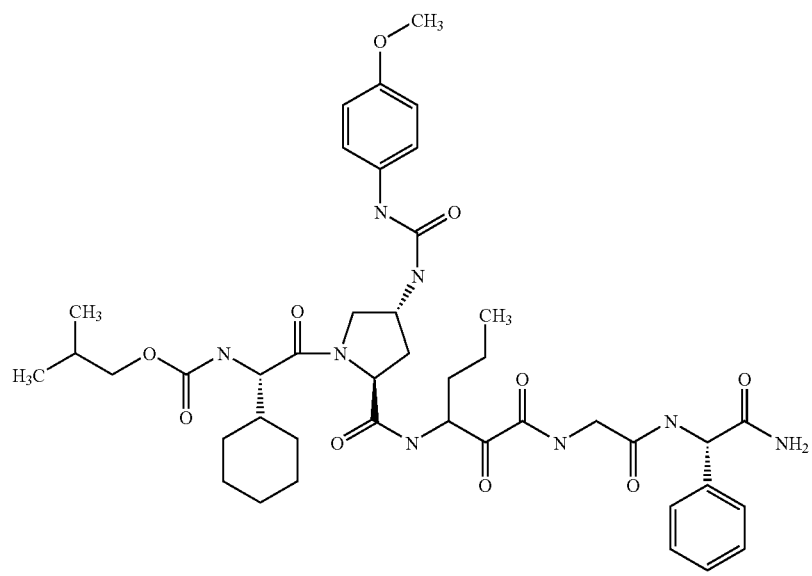

-continued
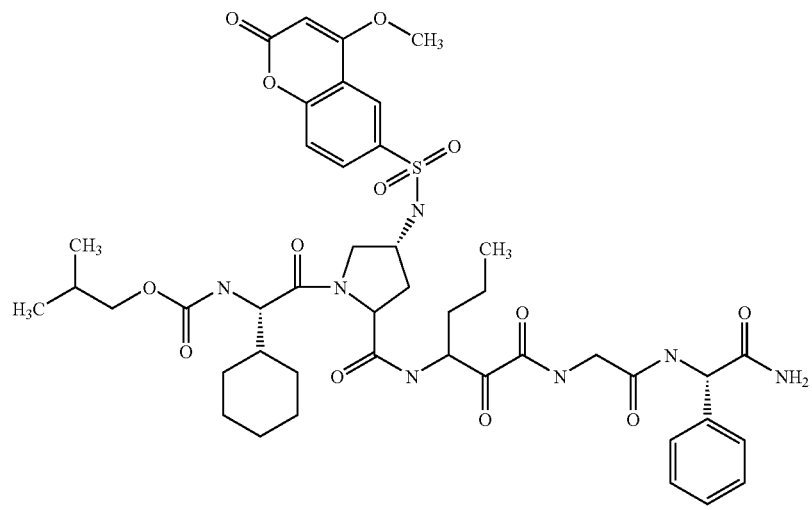
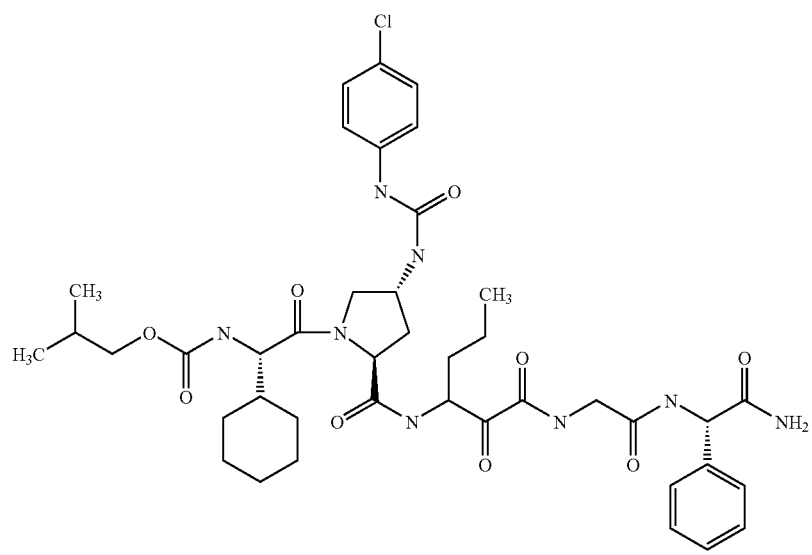
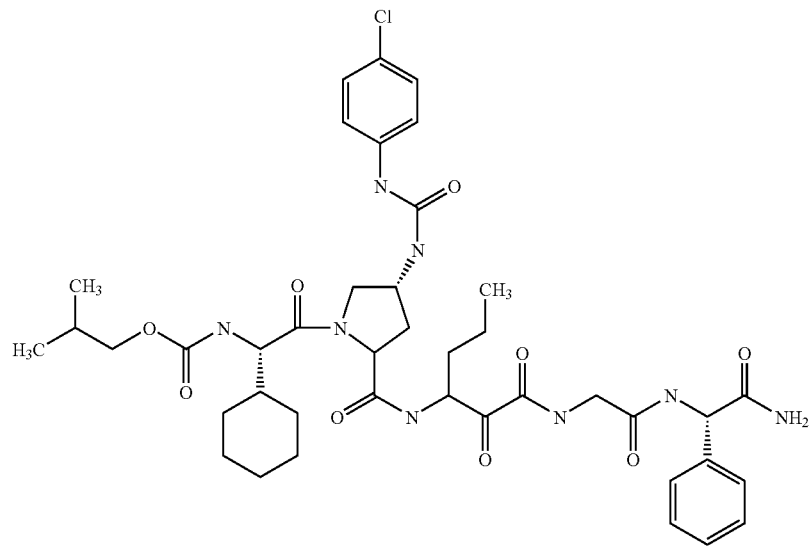

-continued
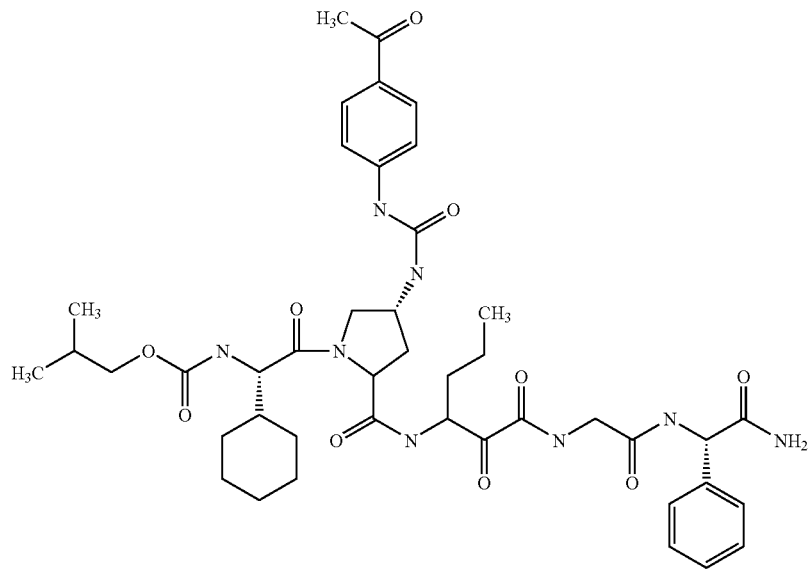
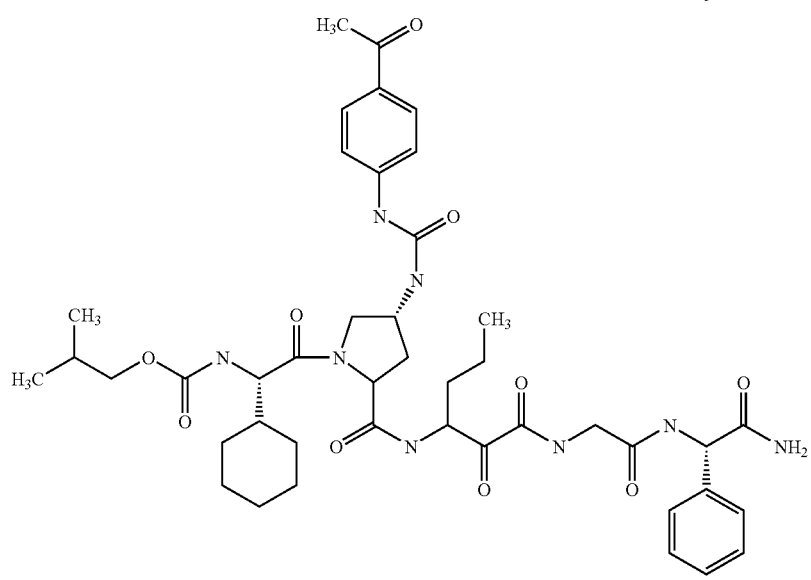
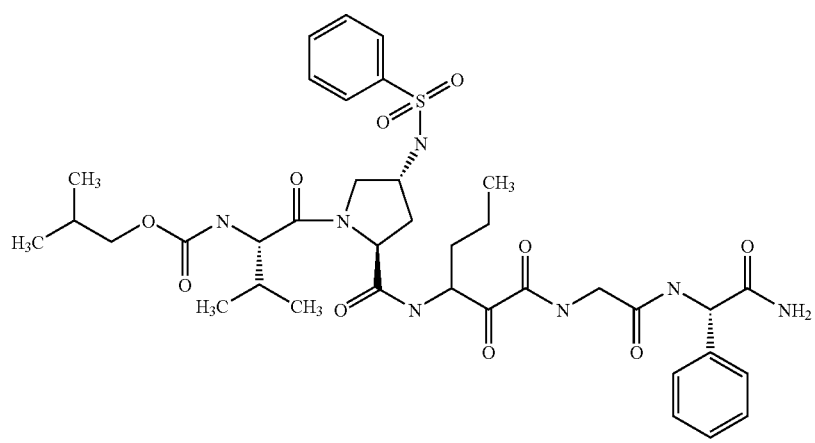

-continued
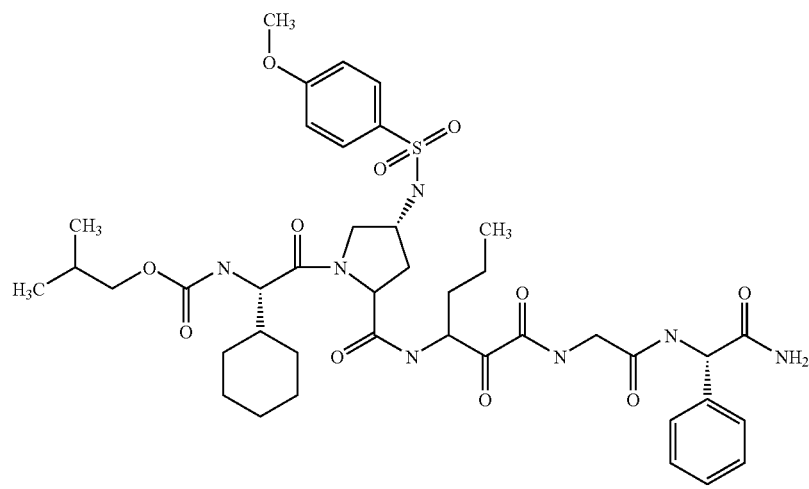
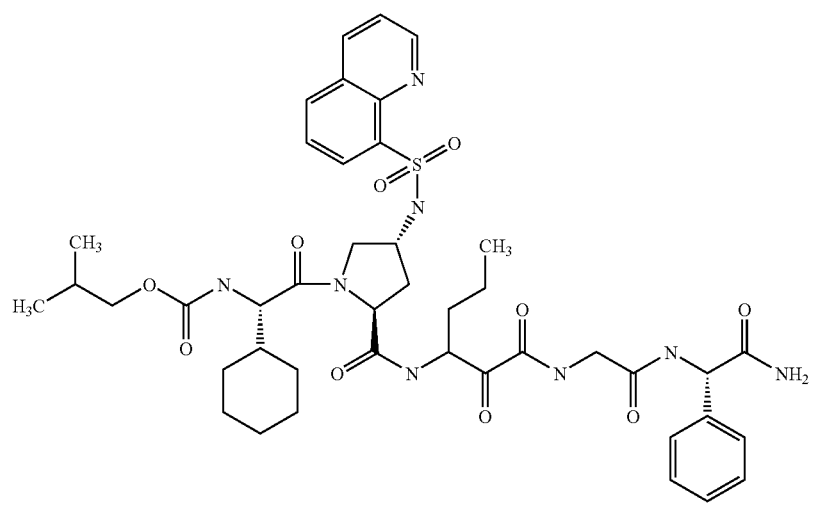
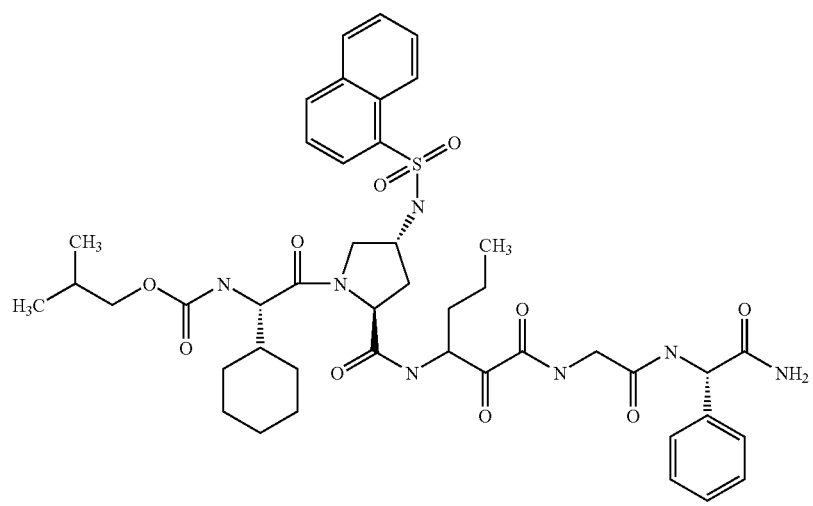

-continued
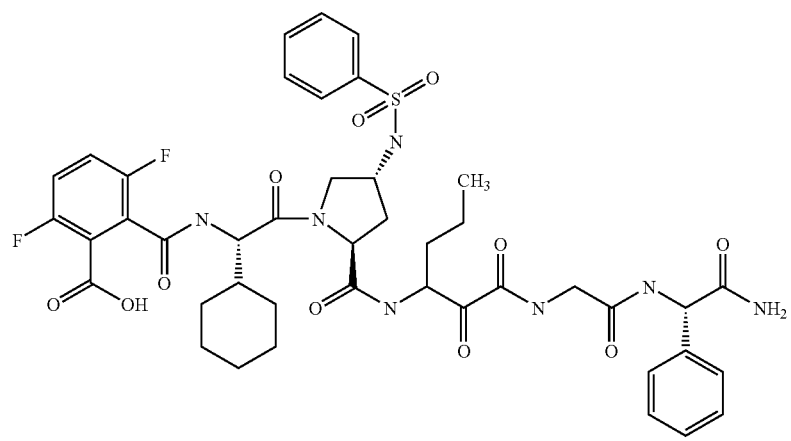
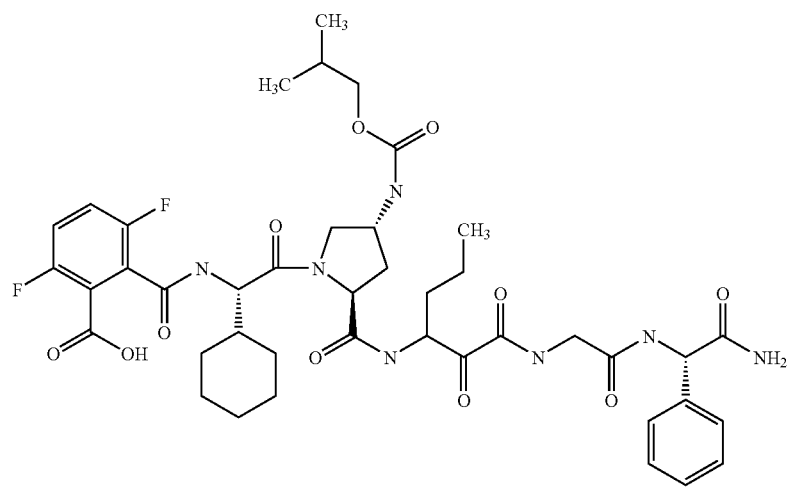
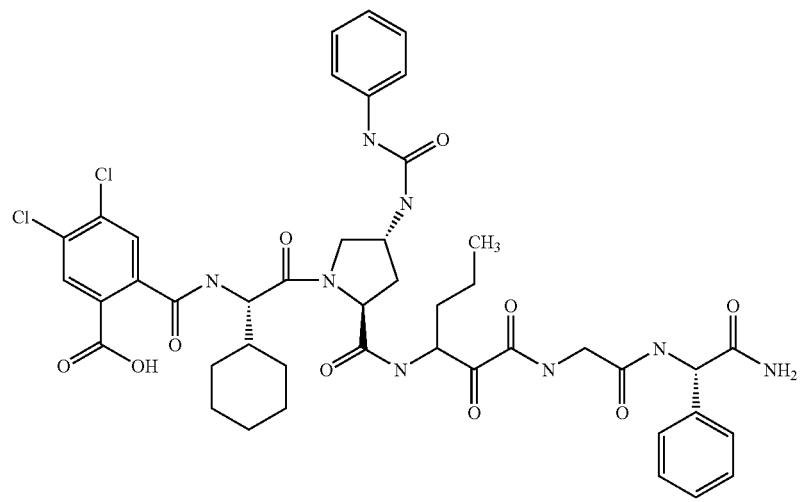

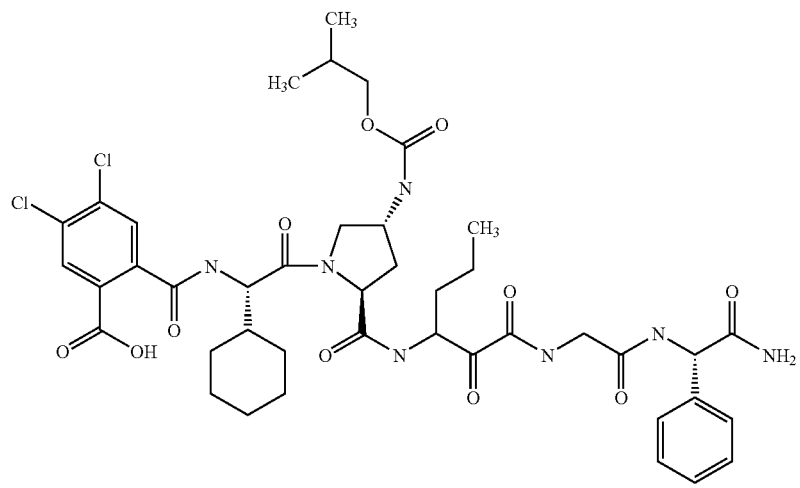
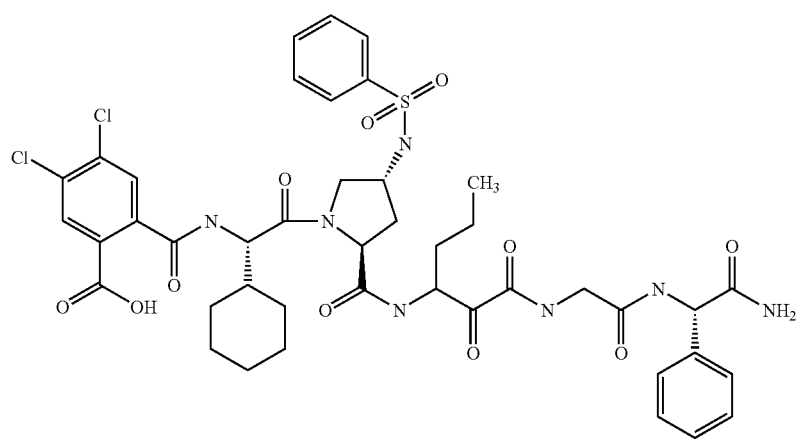
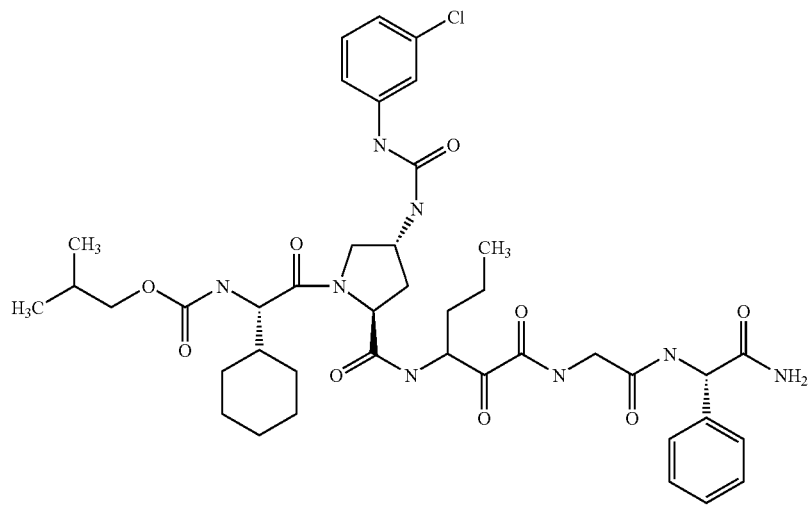

-continued
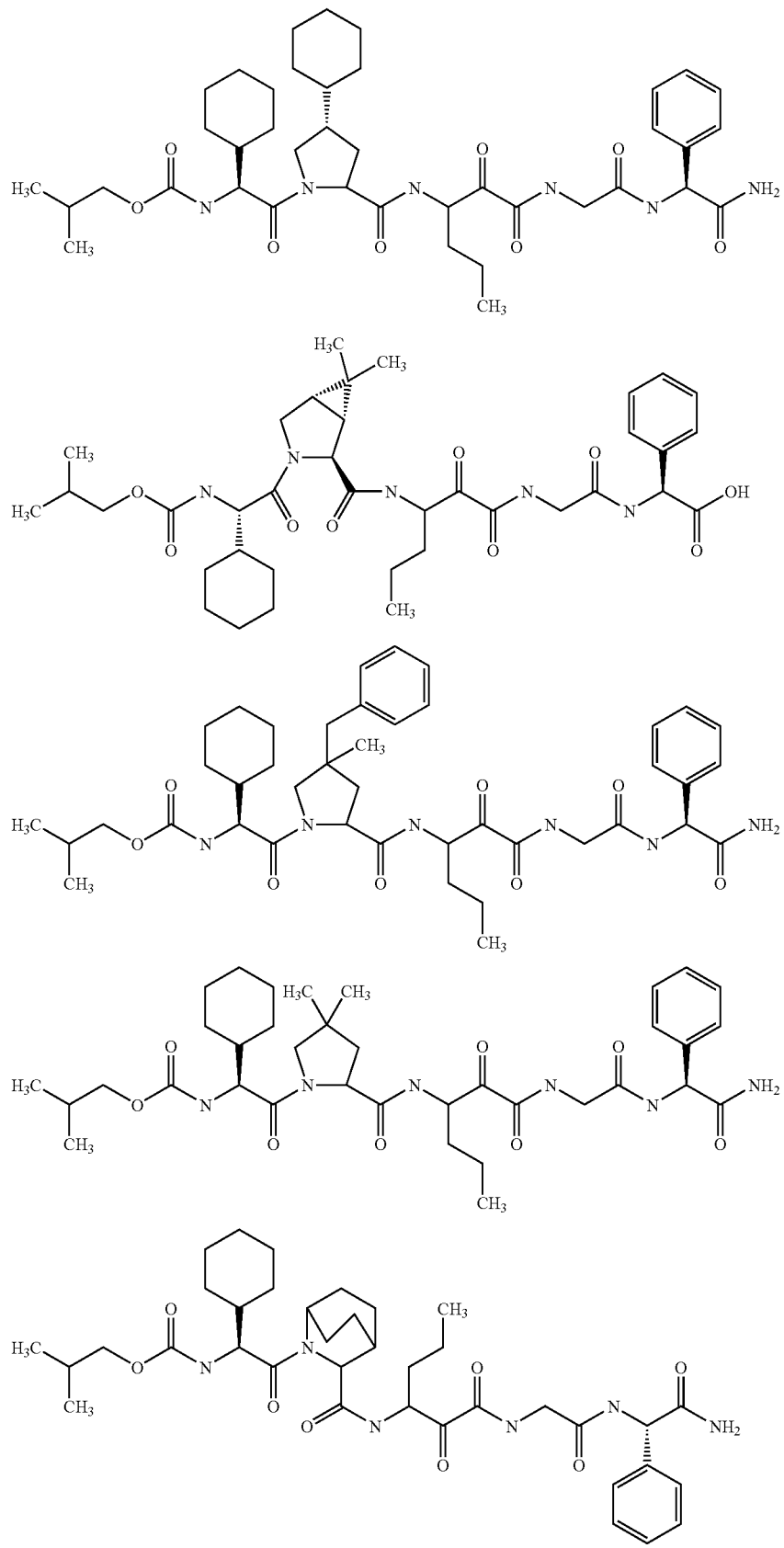

-continued
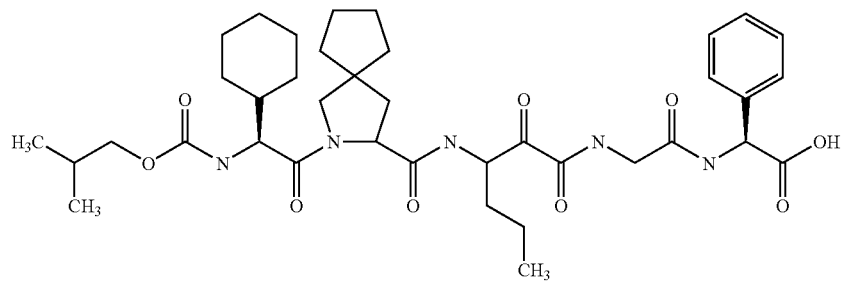
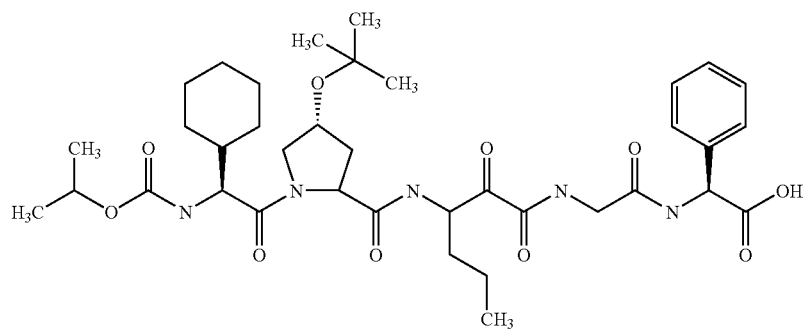
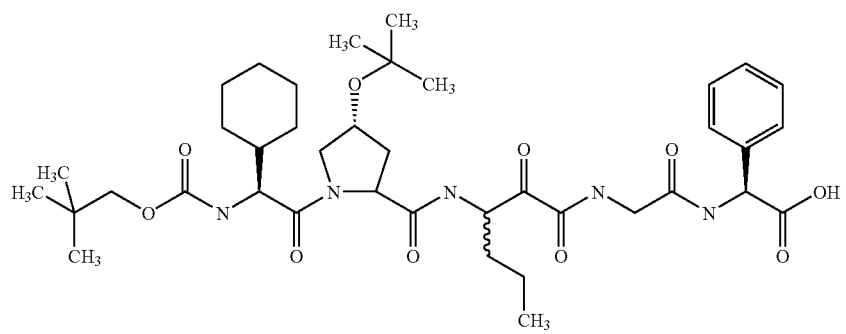
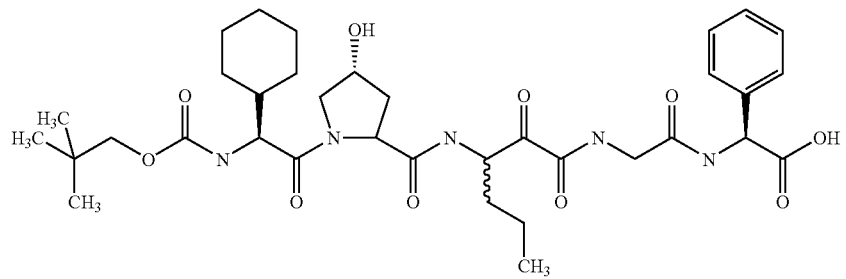
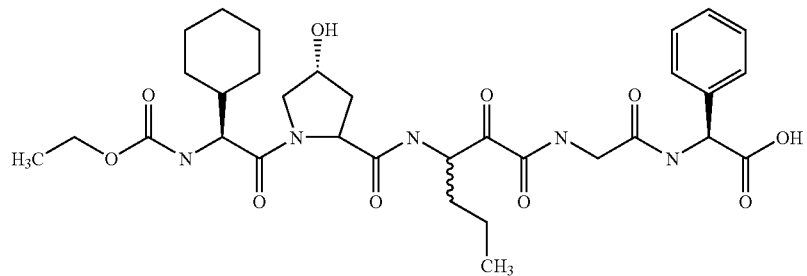

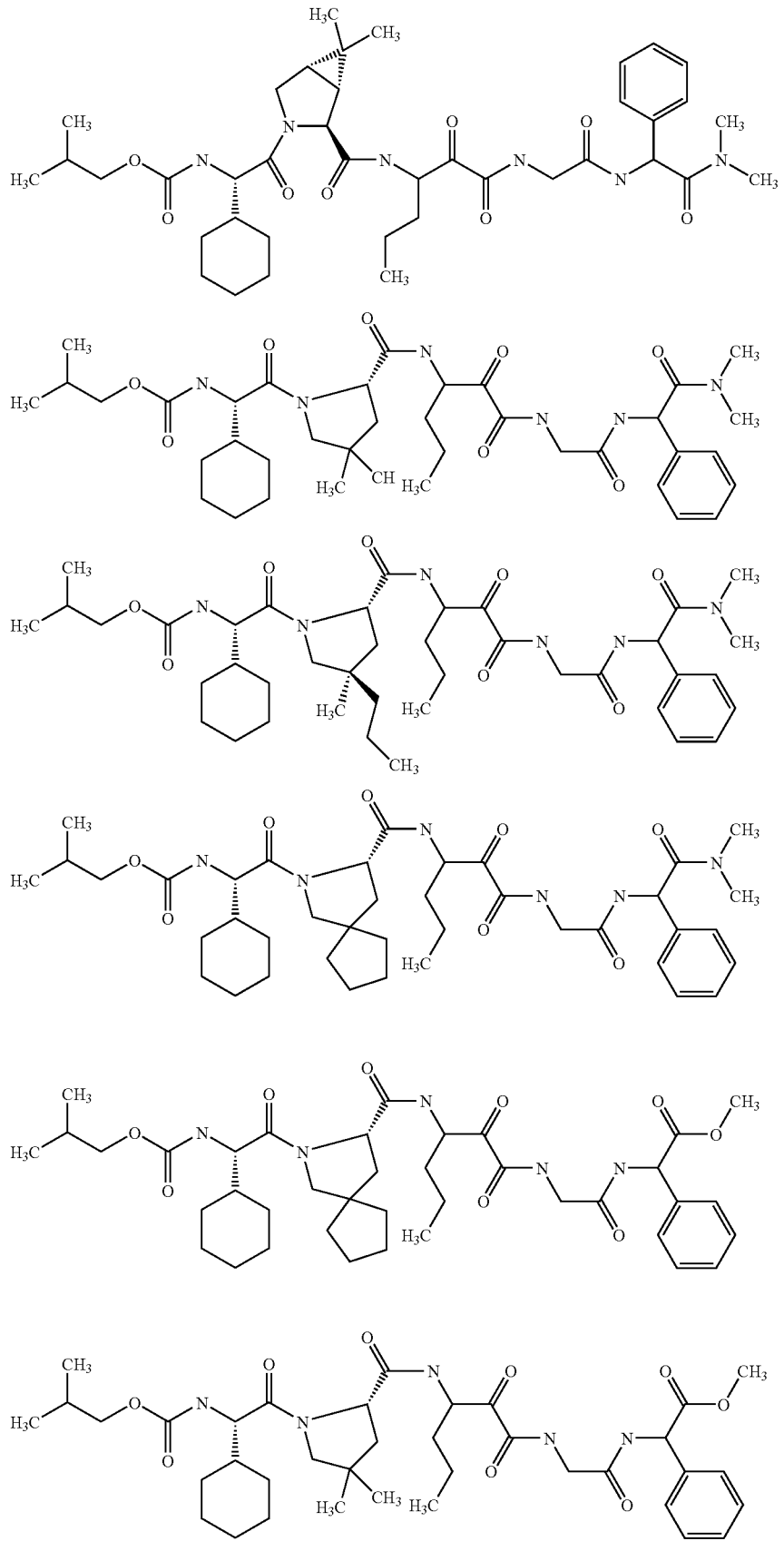

-continued
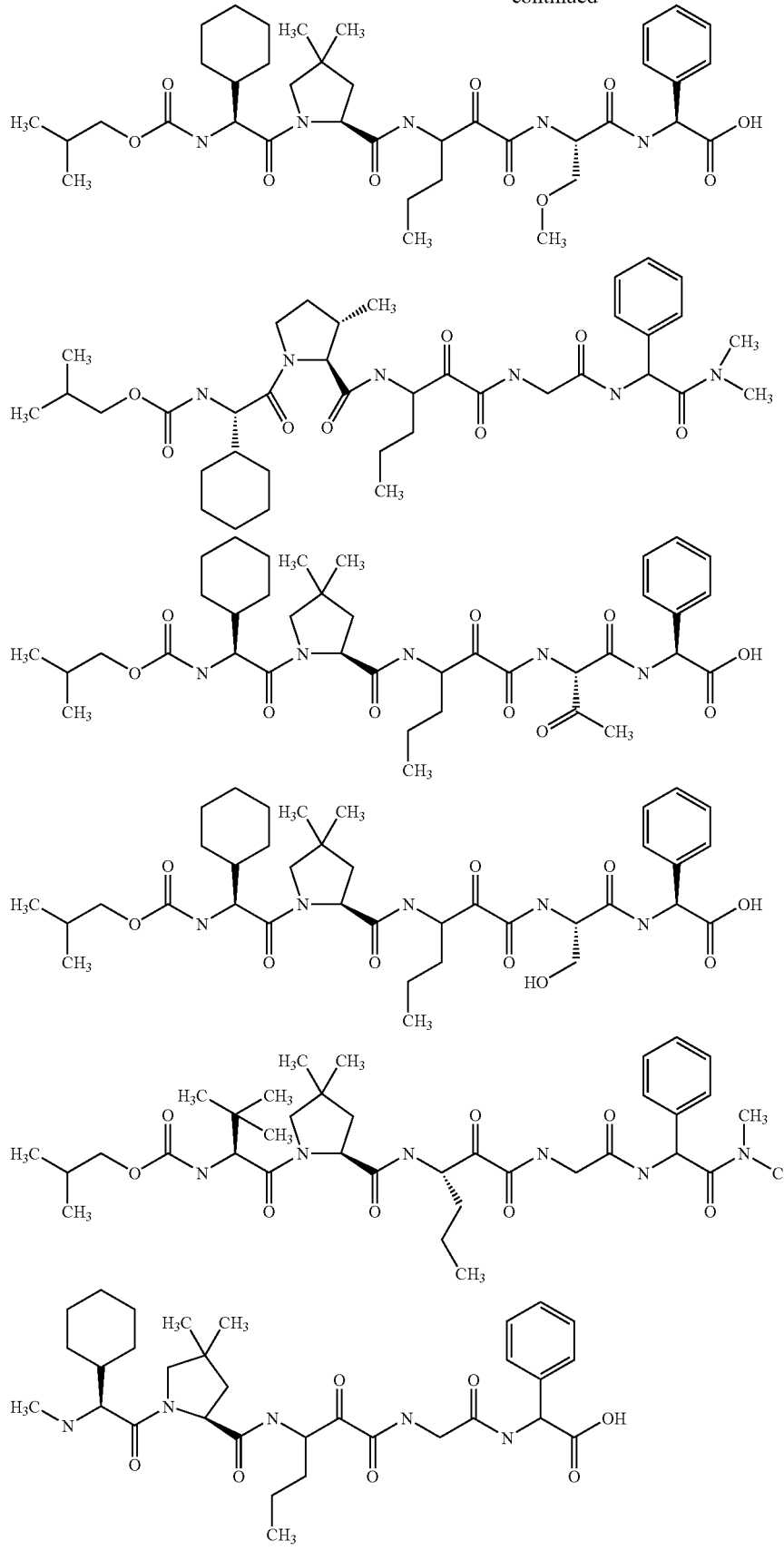

-continued
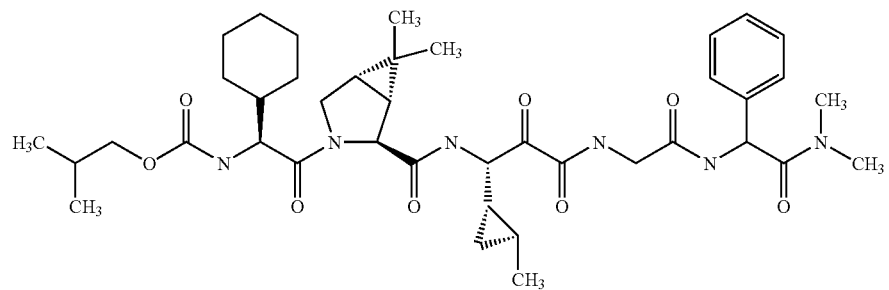
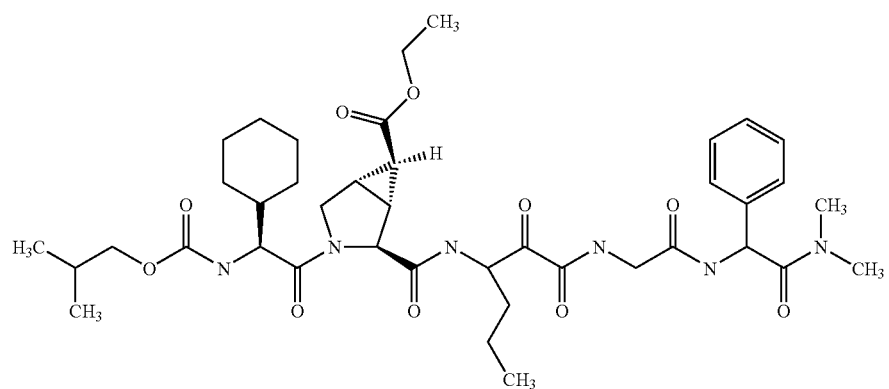
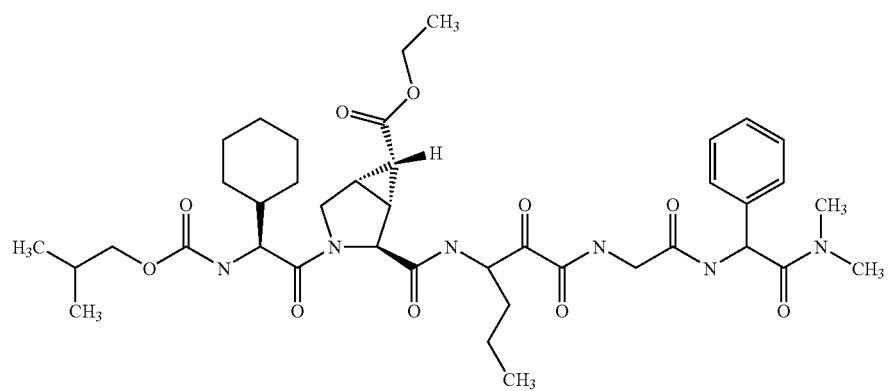
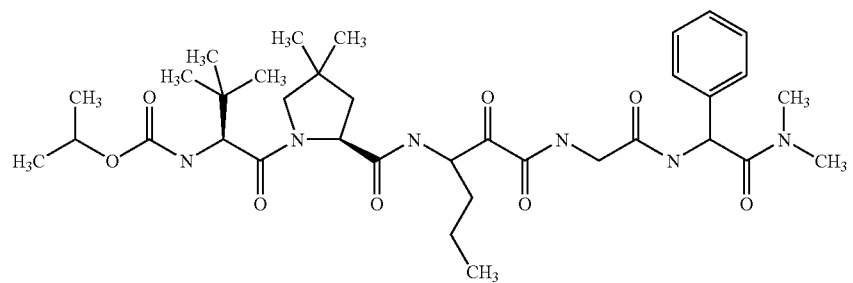
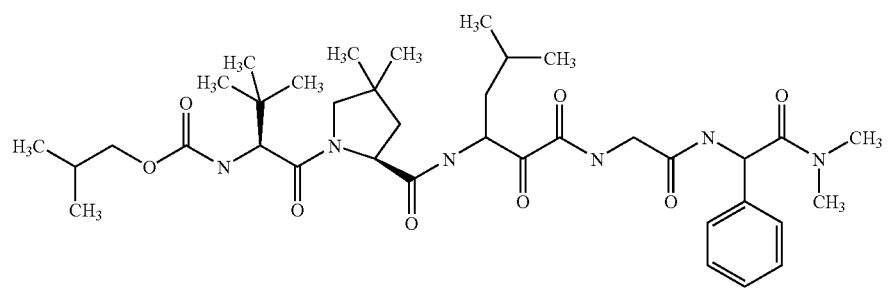

-continued
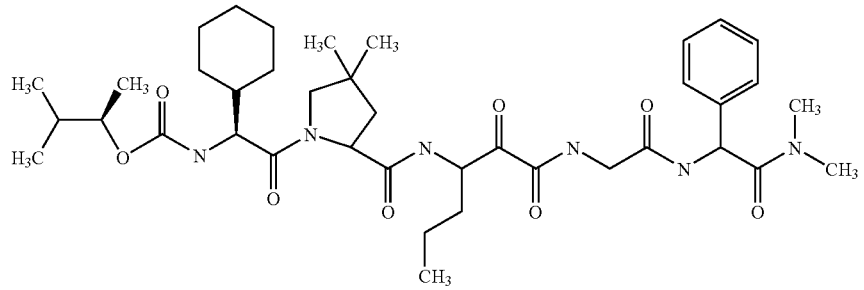
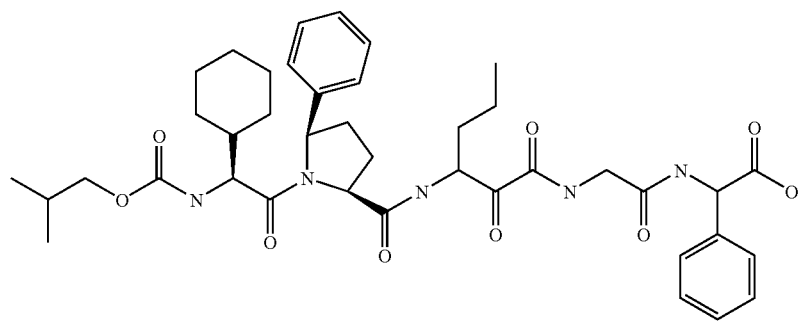
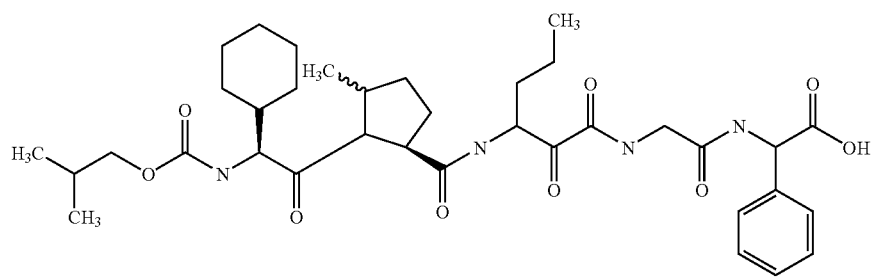
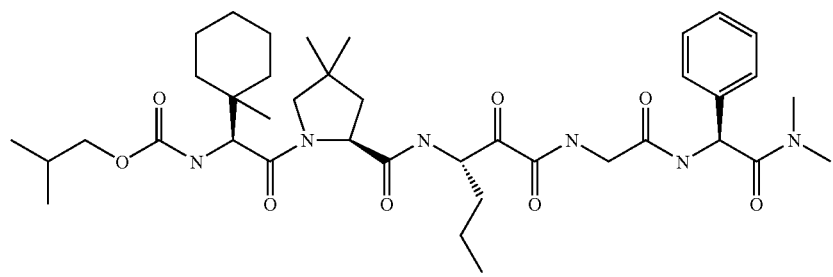
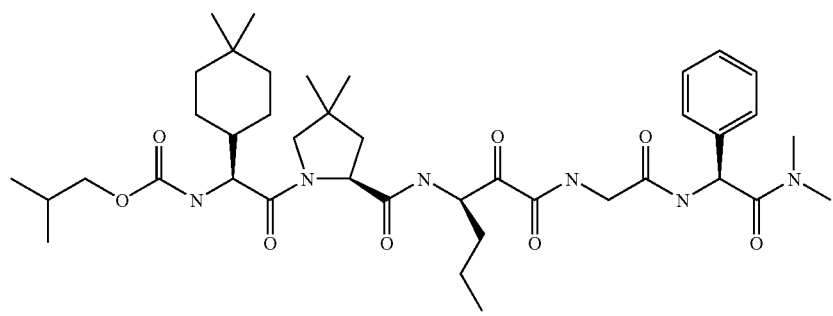

-continued
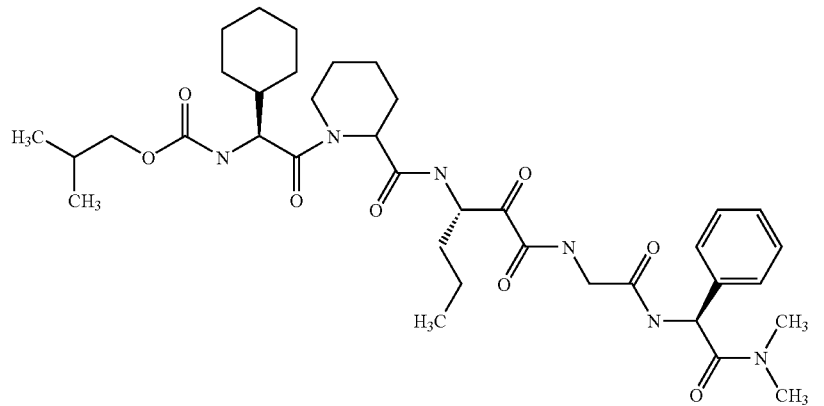
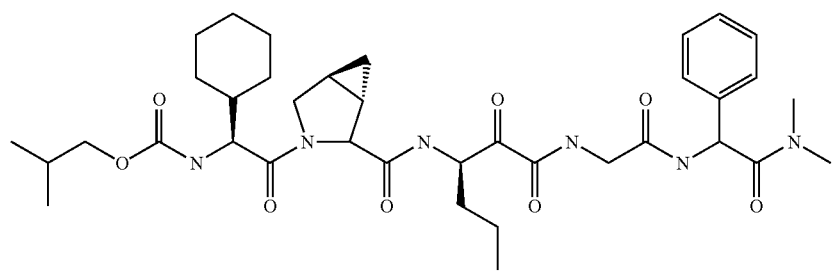
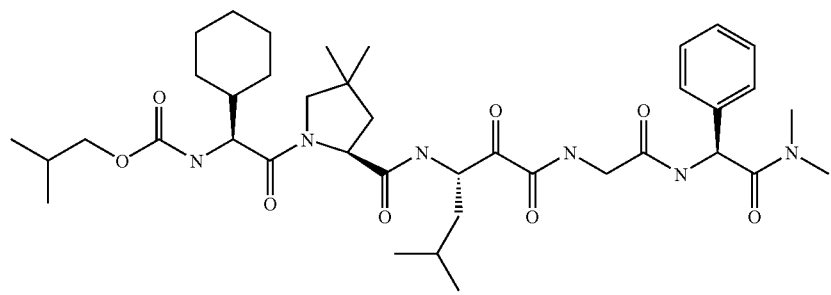
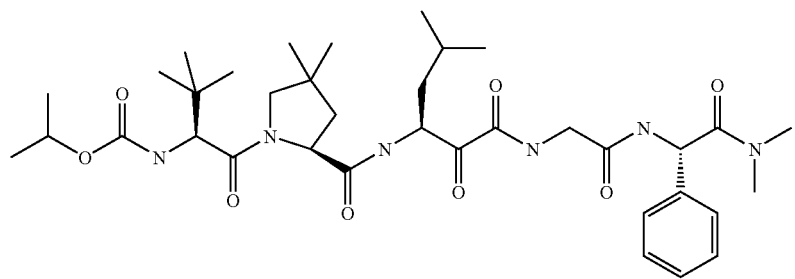
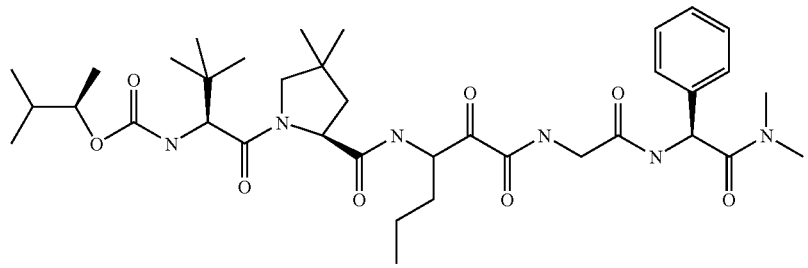

-continued
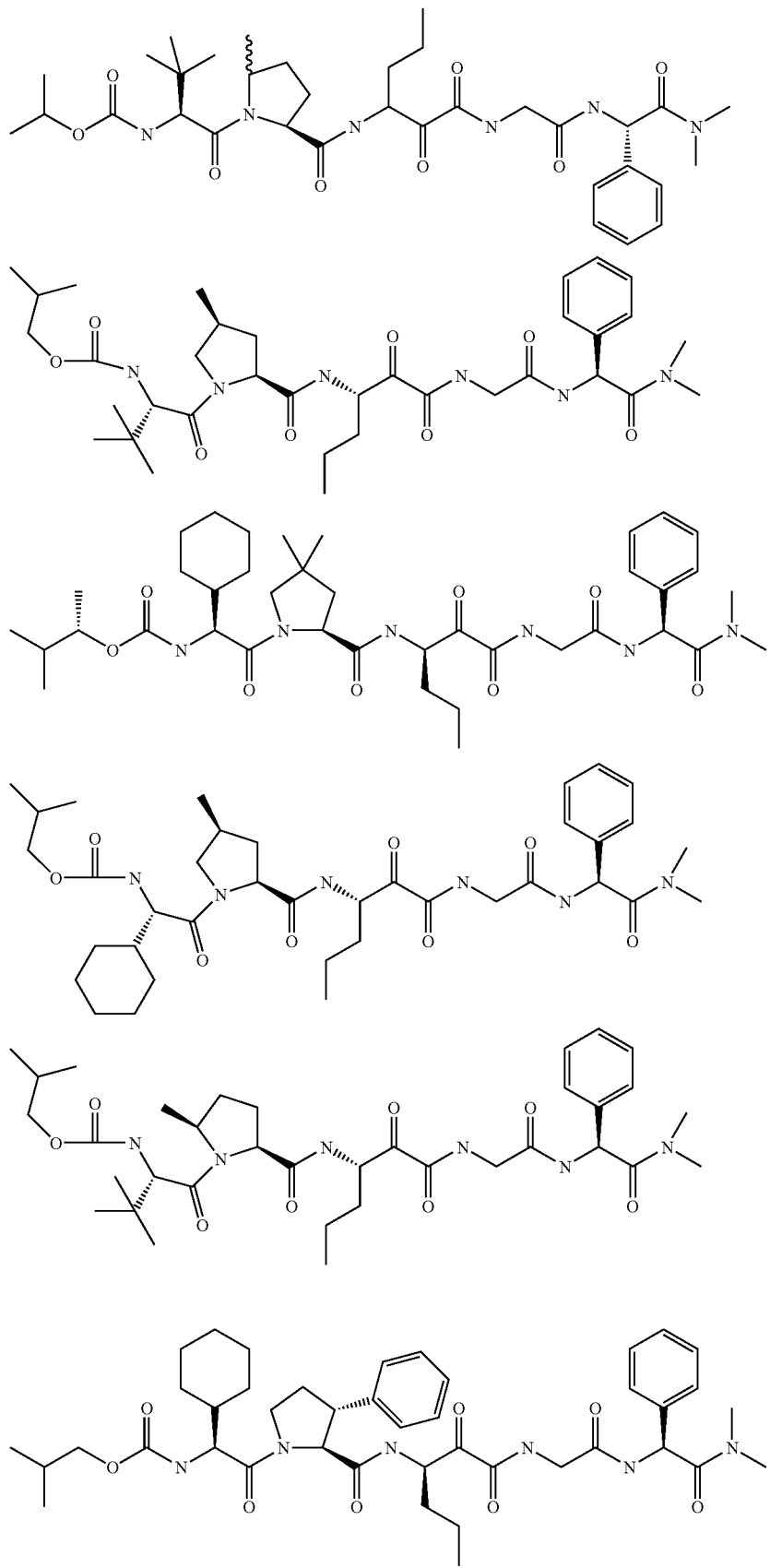

-continued
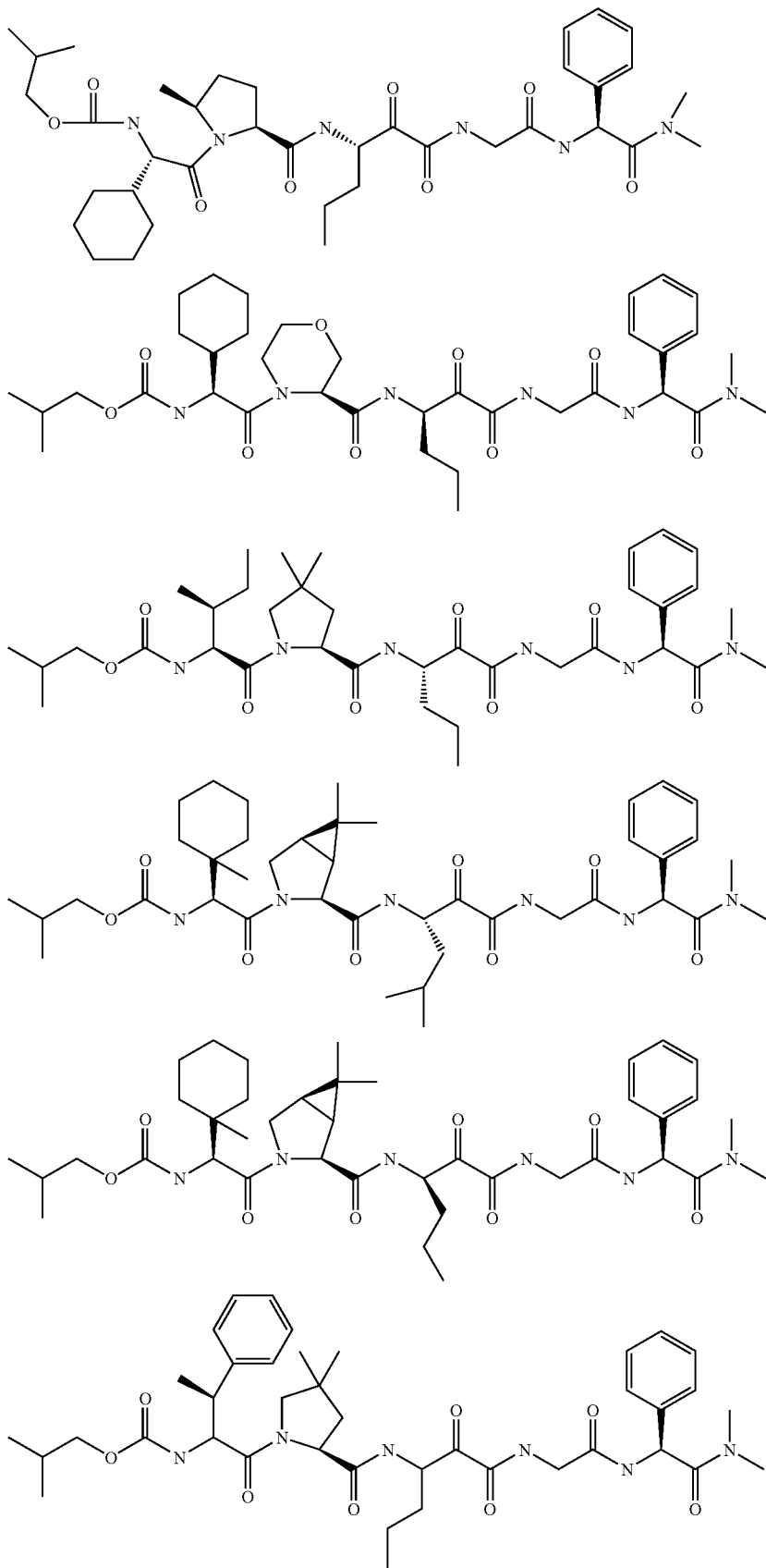

-continued
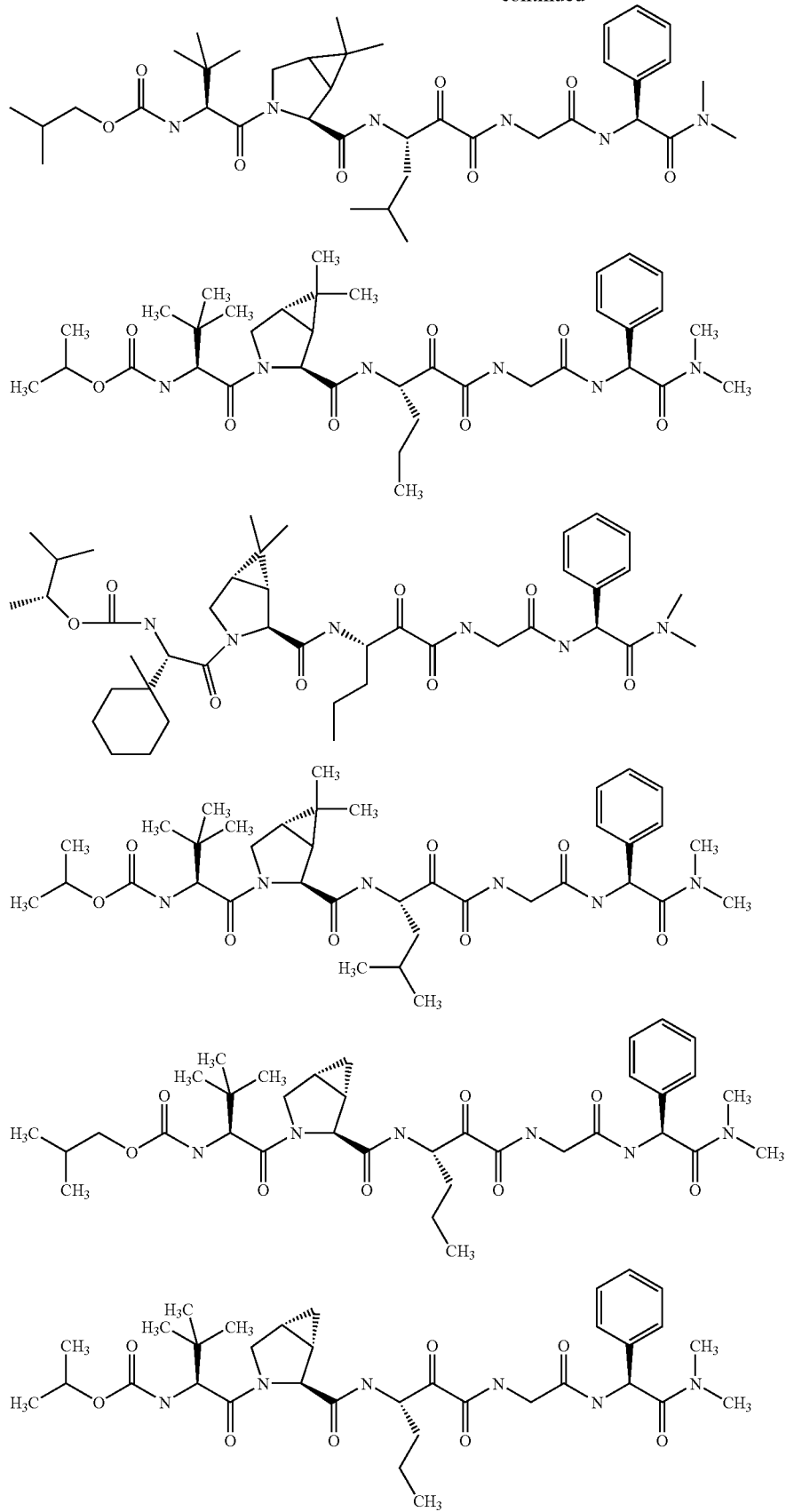

-continued
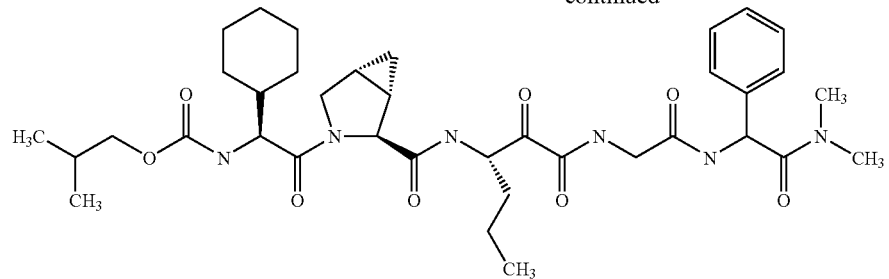
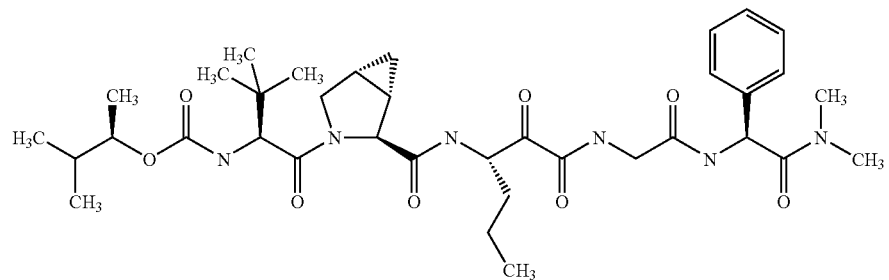
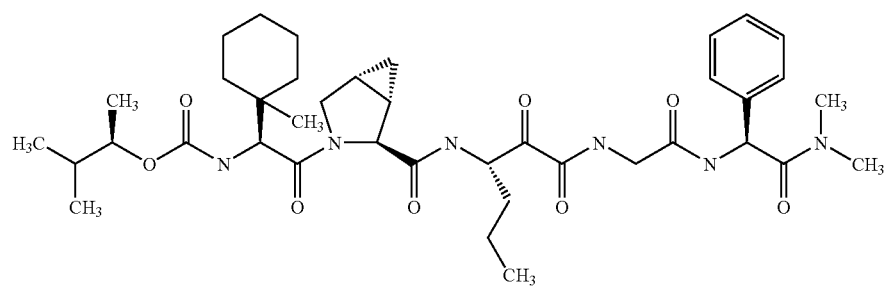
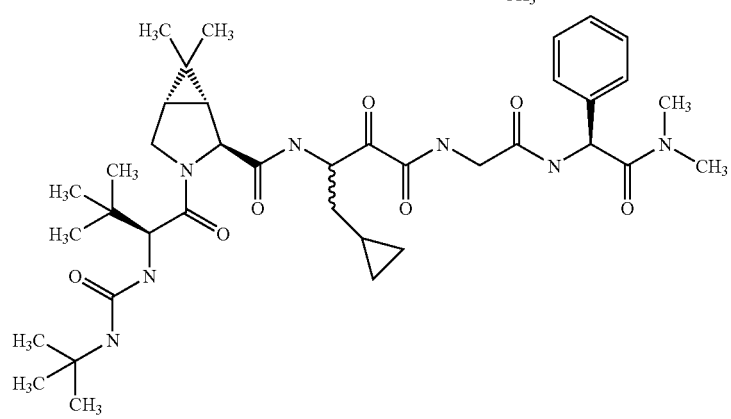
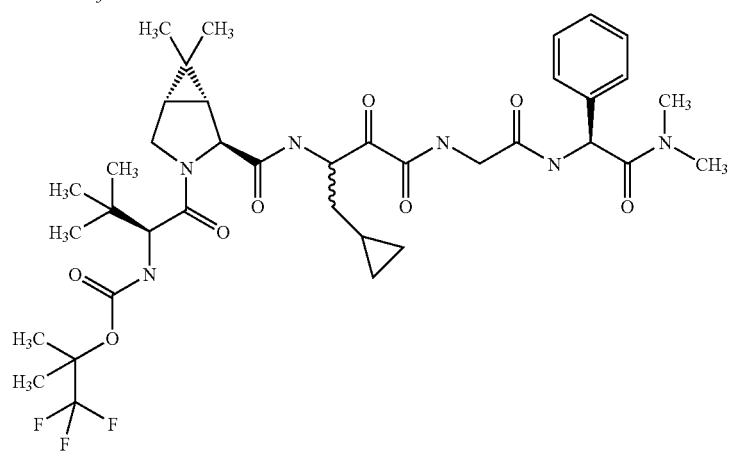

-continued
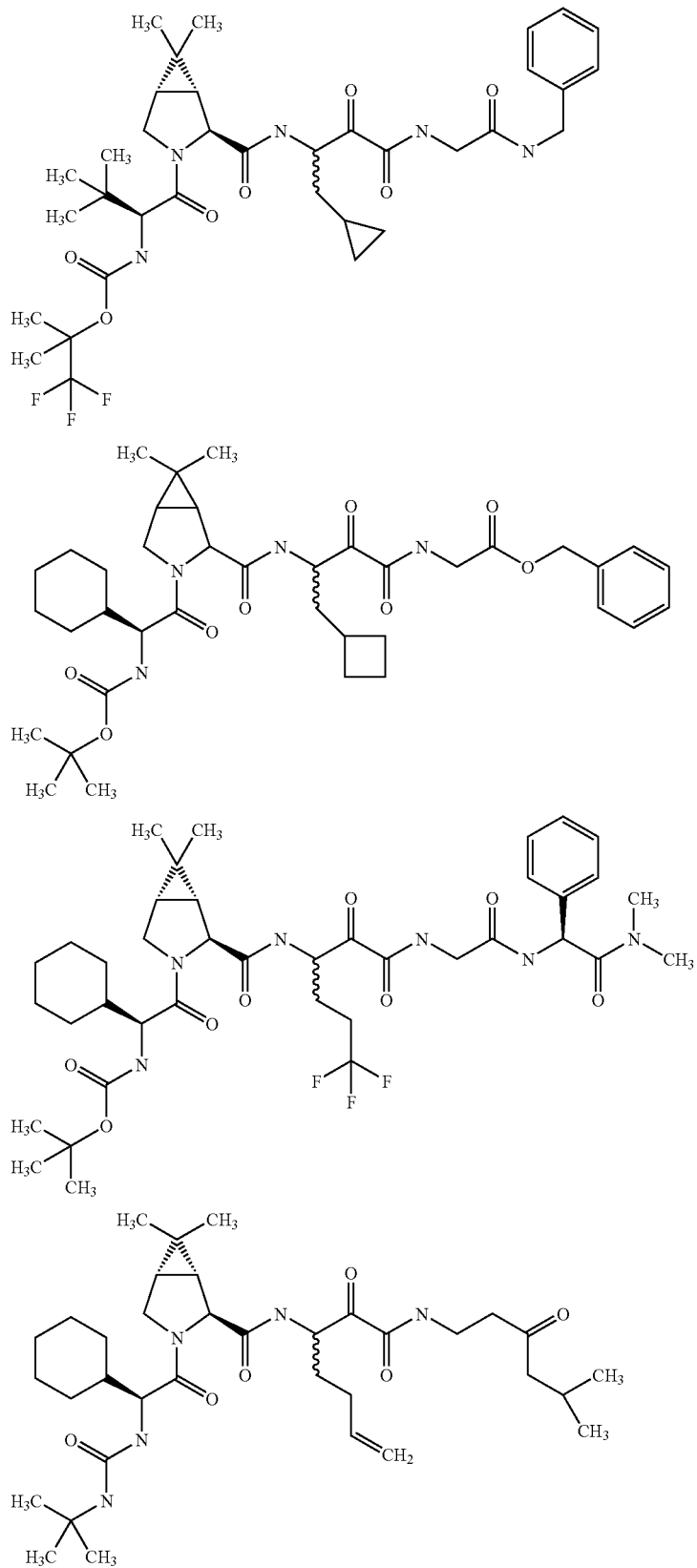

-continued
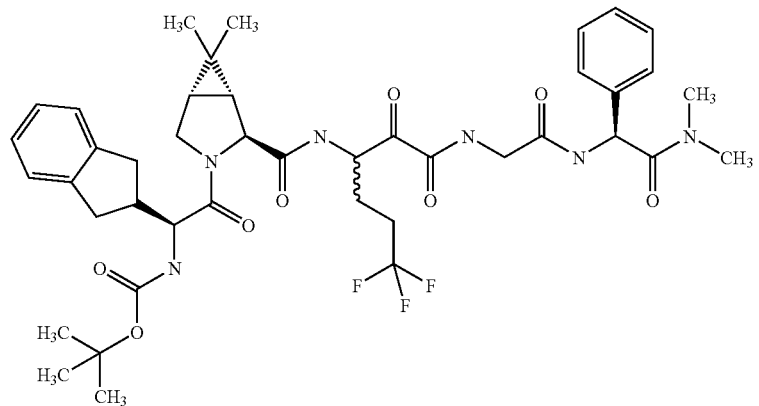
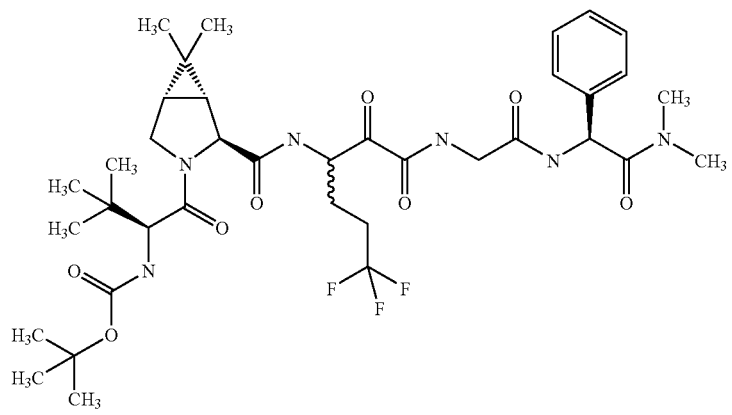
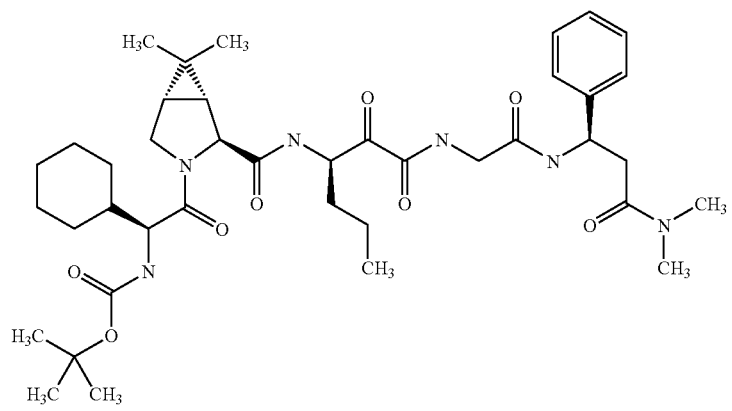
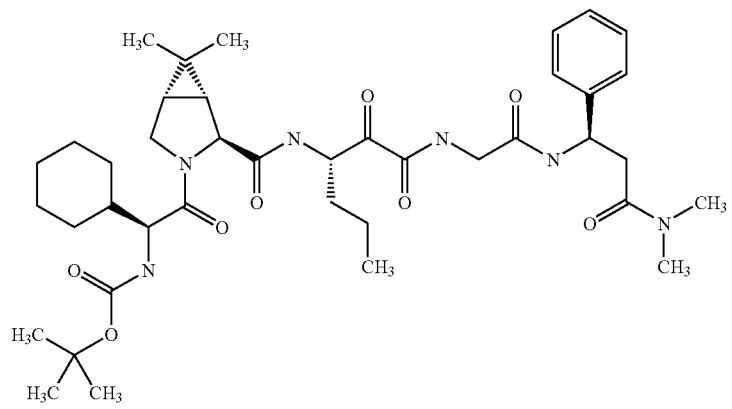

-continued
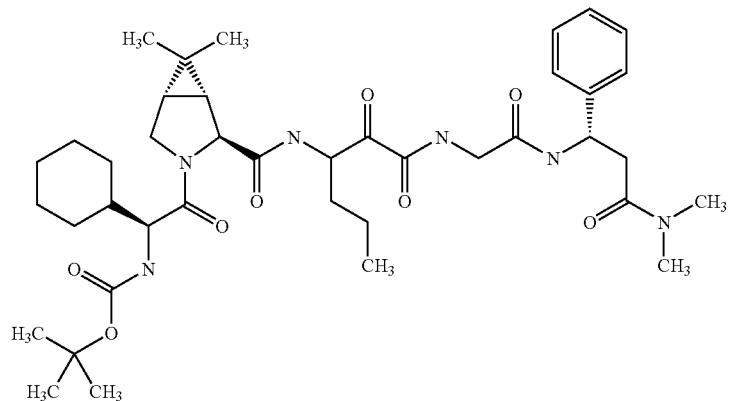
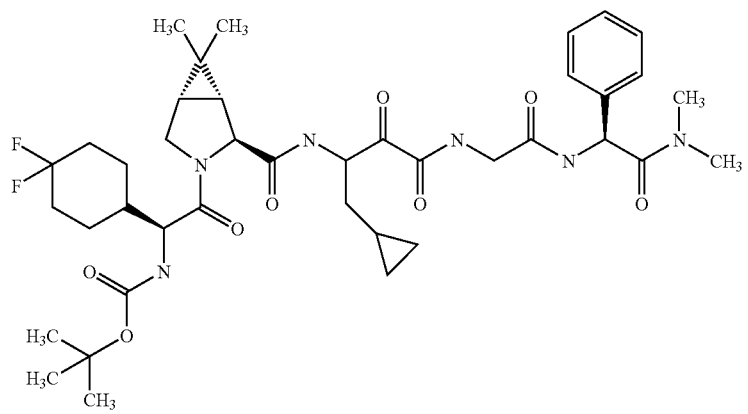
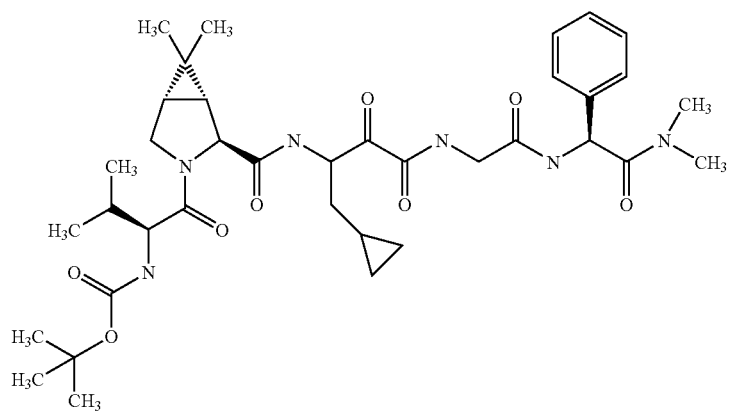
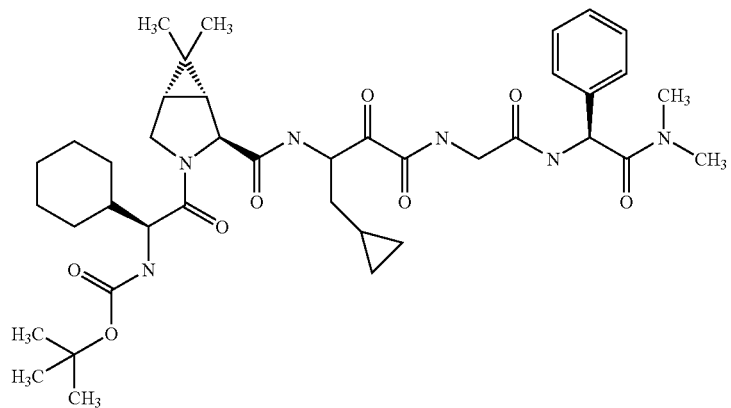

-continued
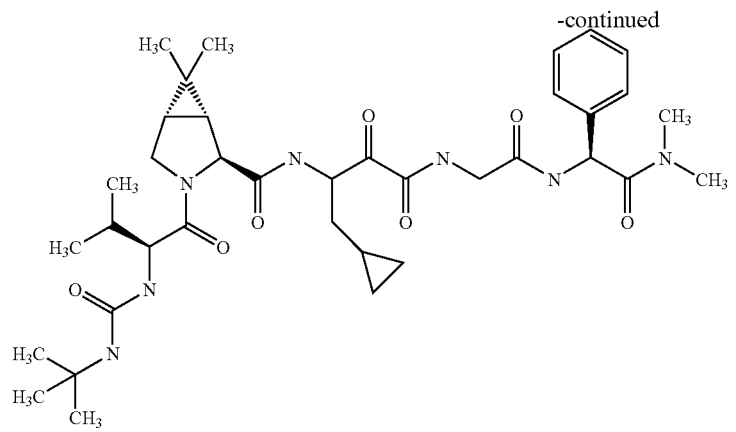
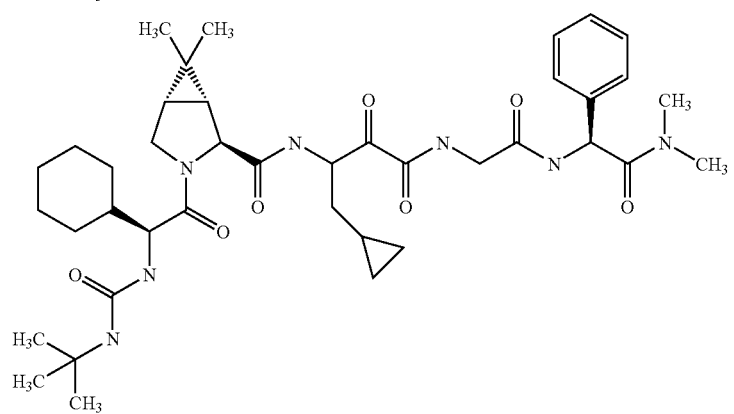
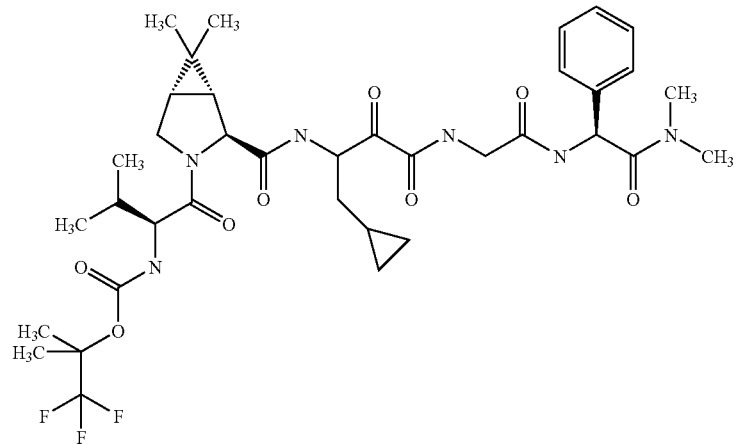
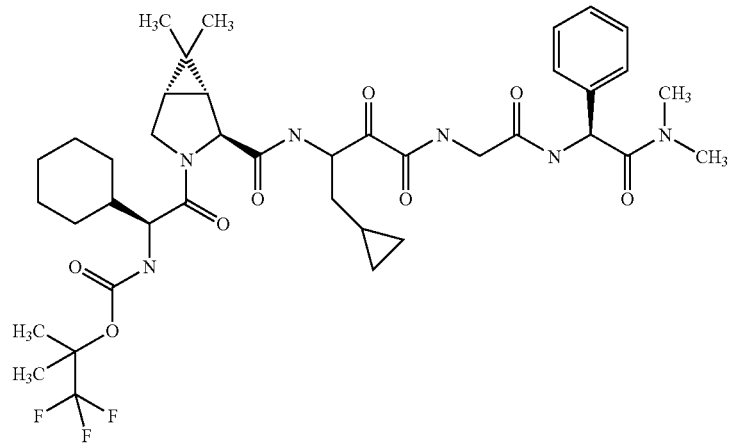

-continued
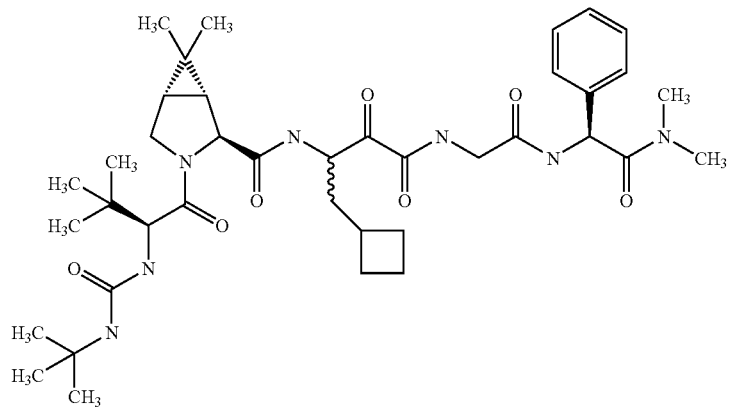
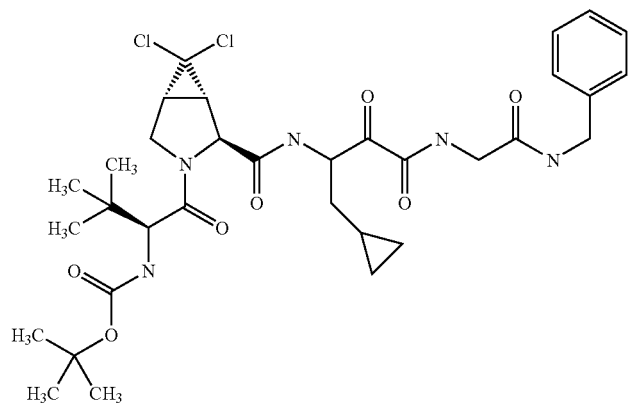
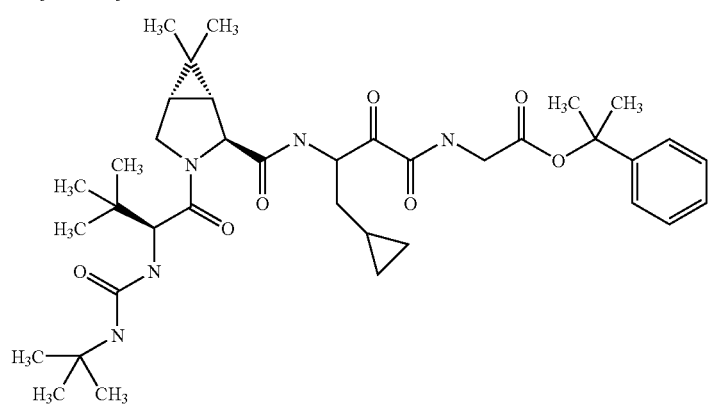
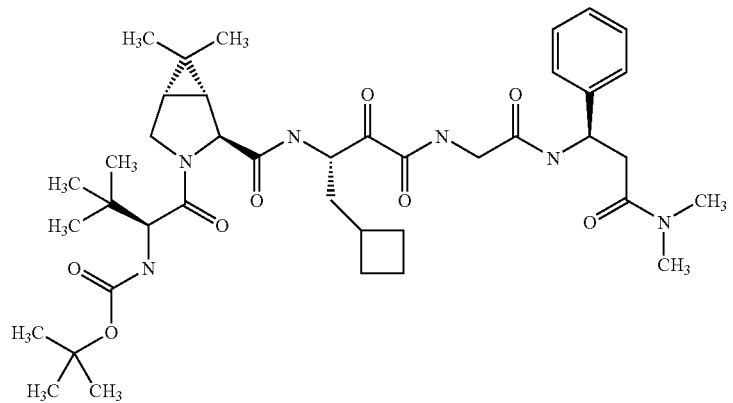

205 206
-continued
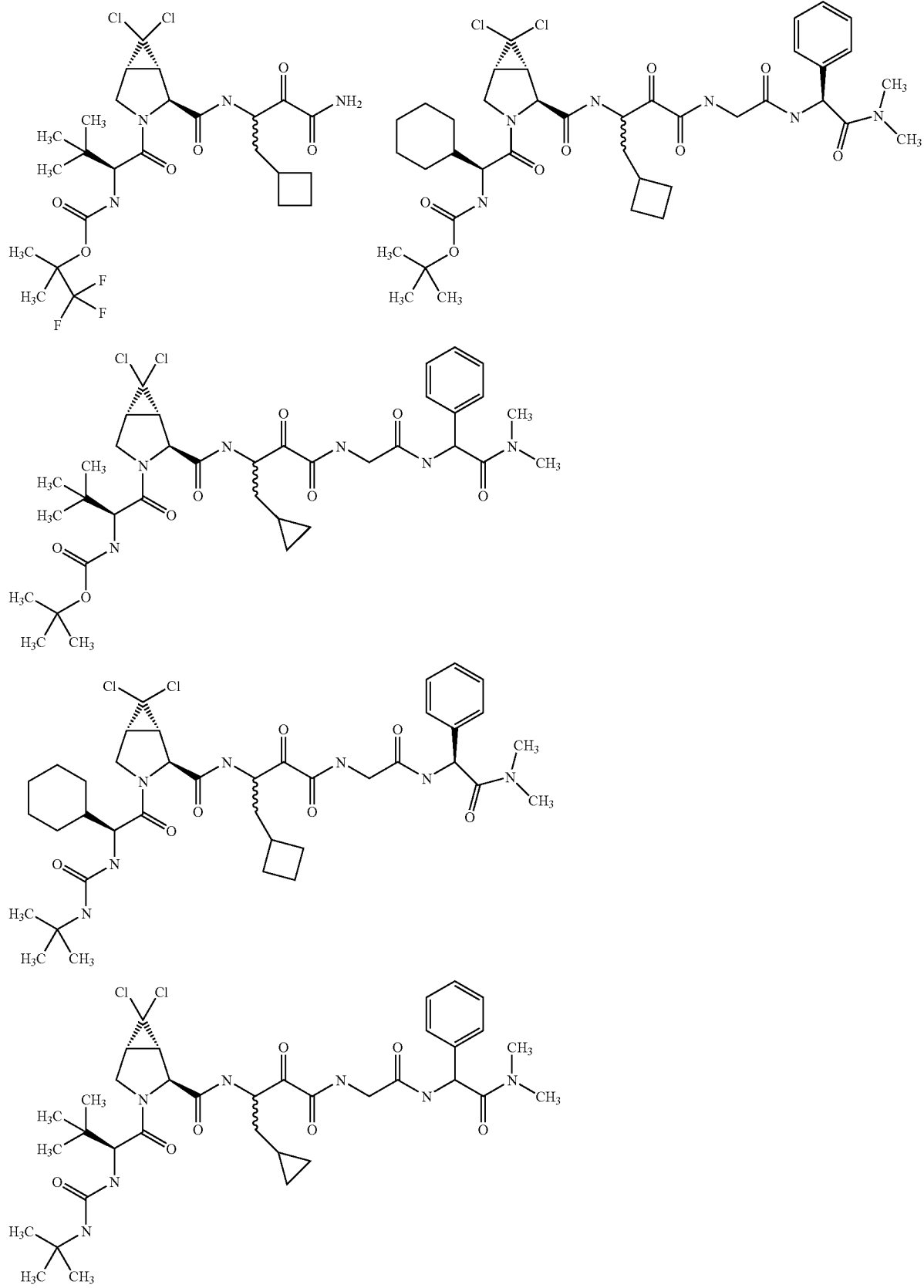

-continued
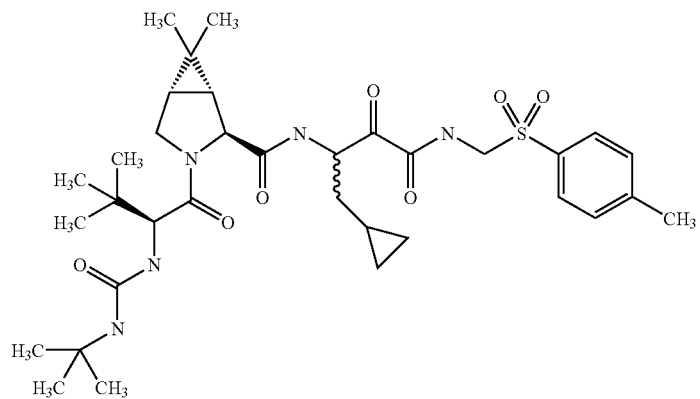
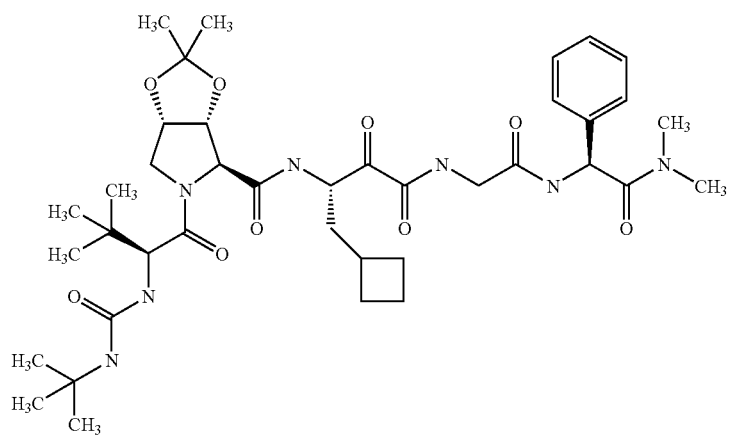
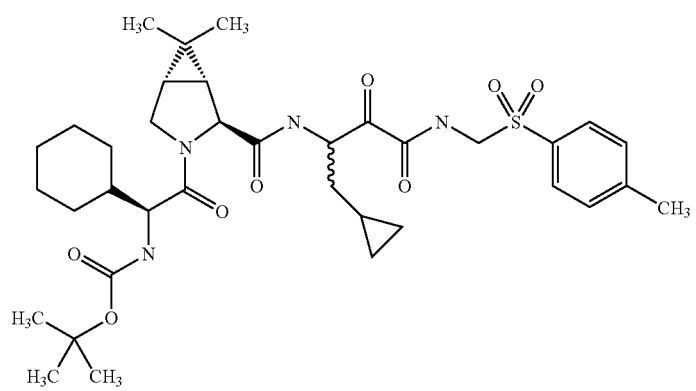
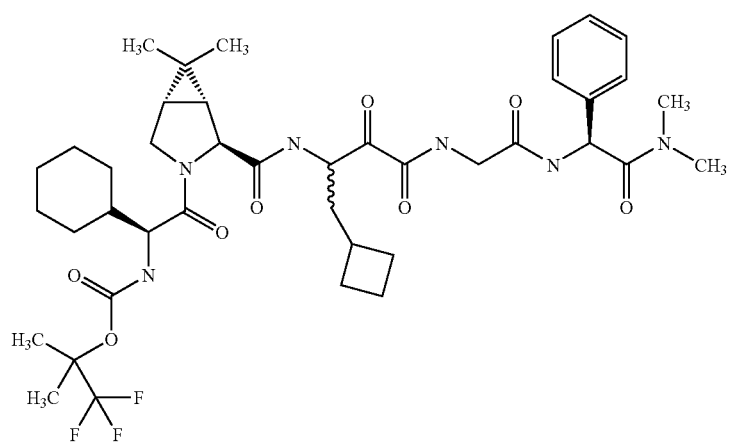

209
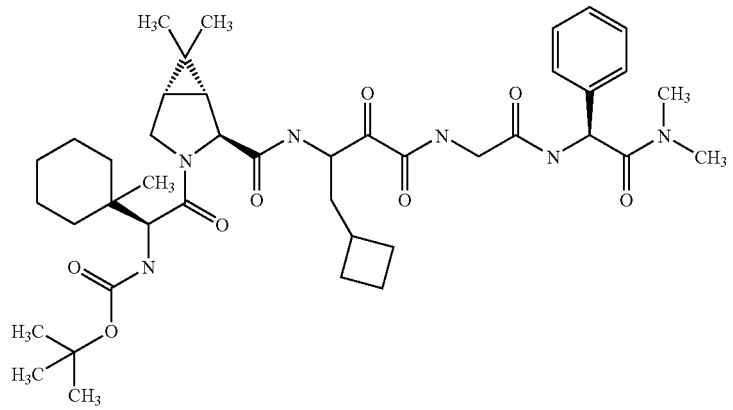
-continued
210
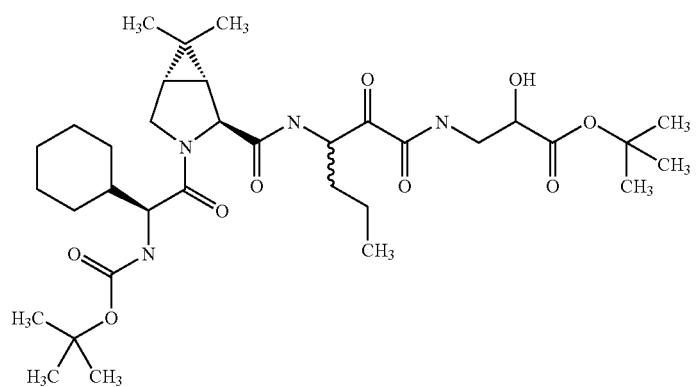
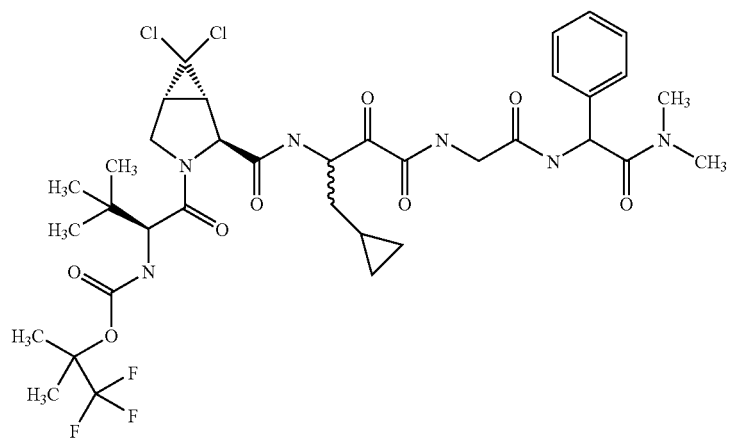
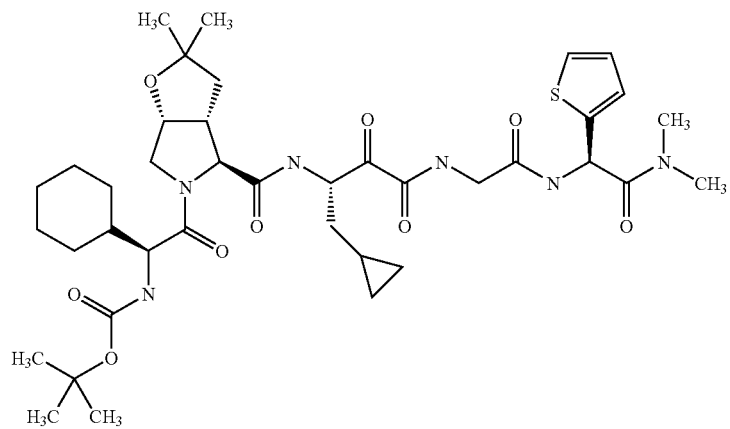
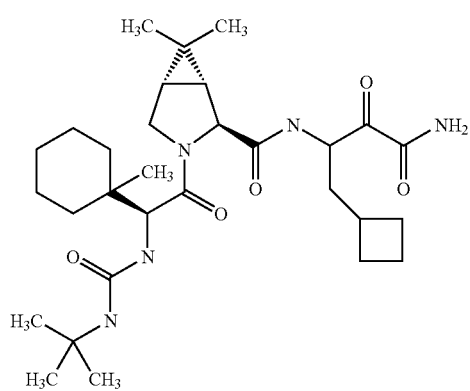

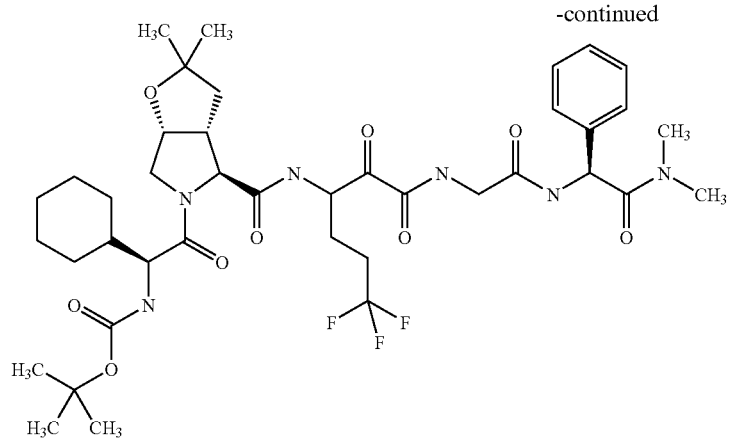
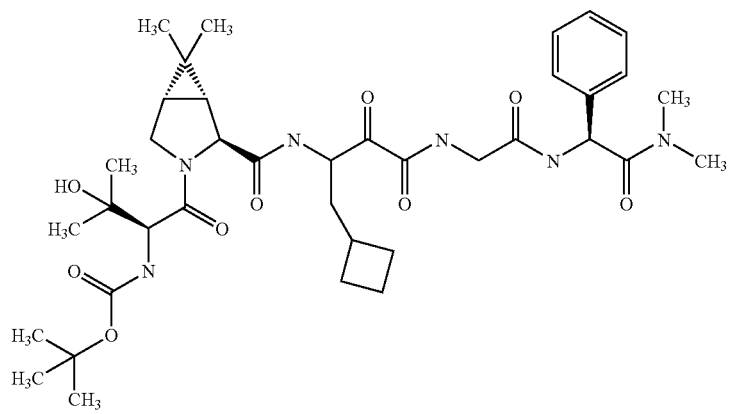
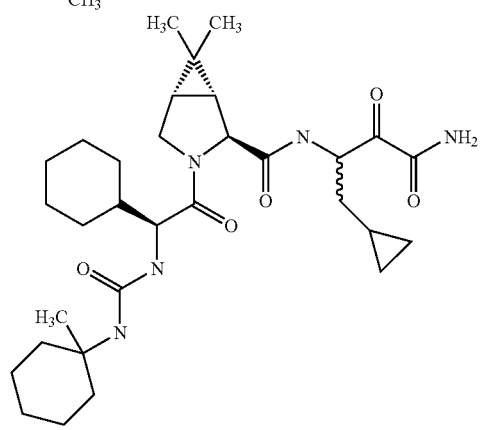
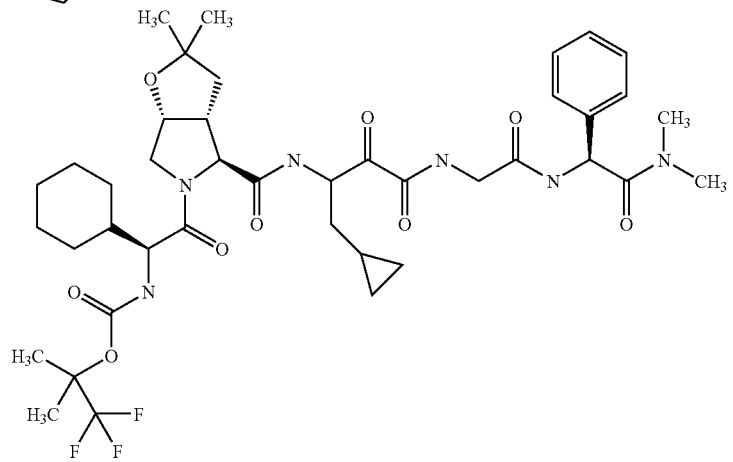

-continued
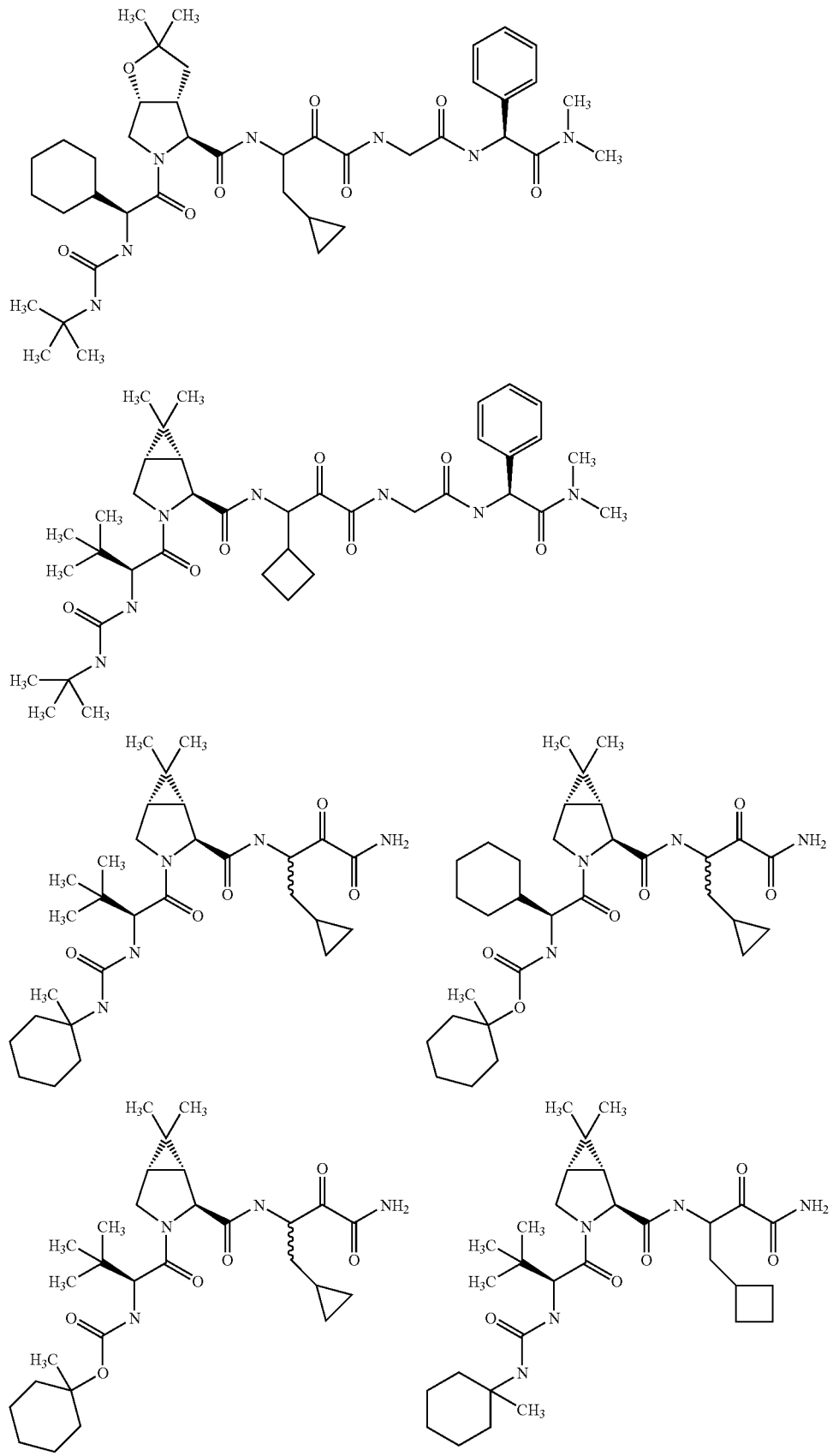

-continued
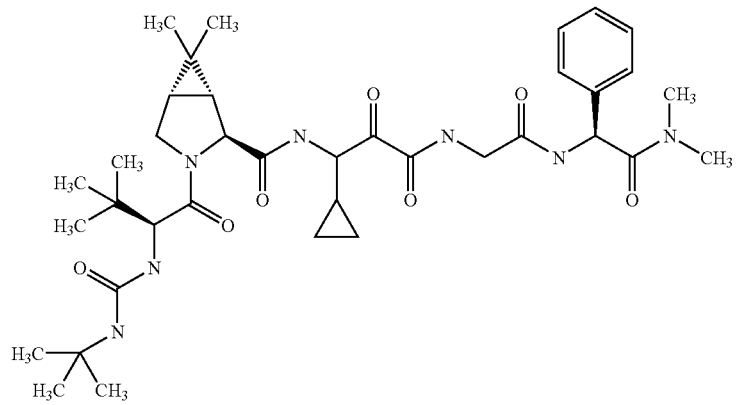
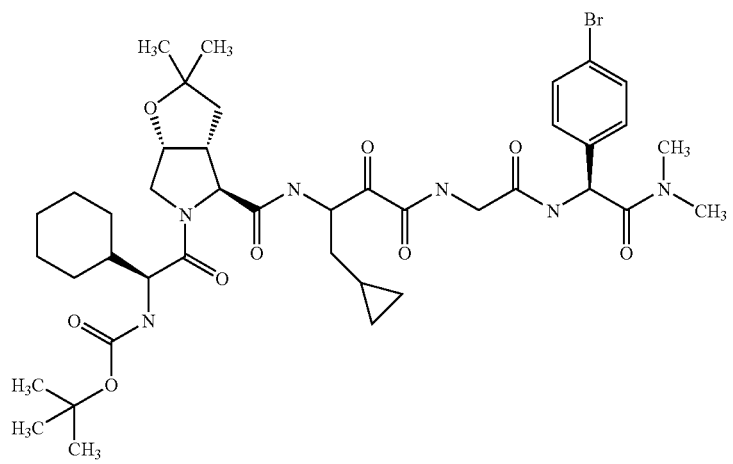
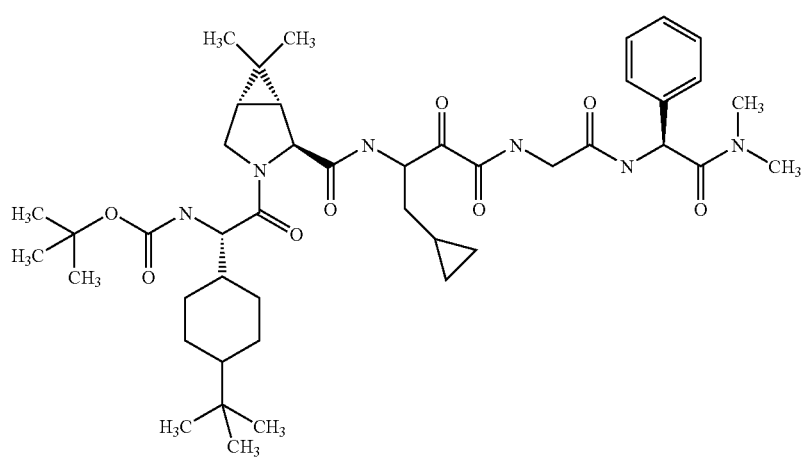

-continued
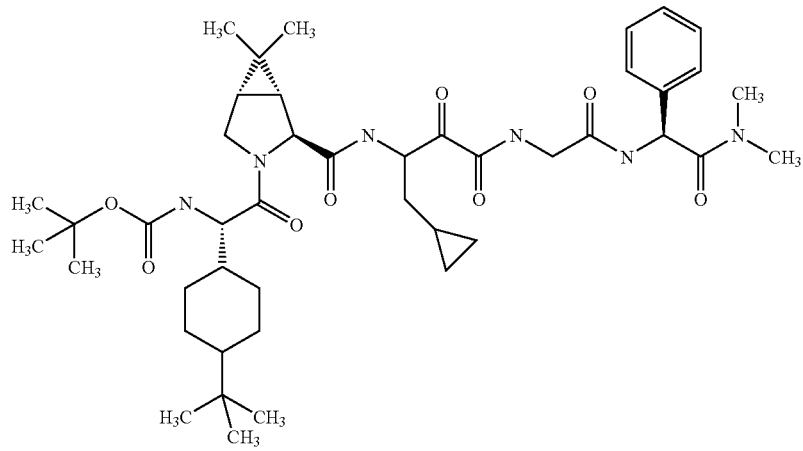
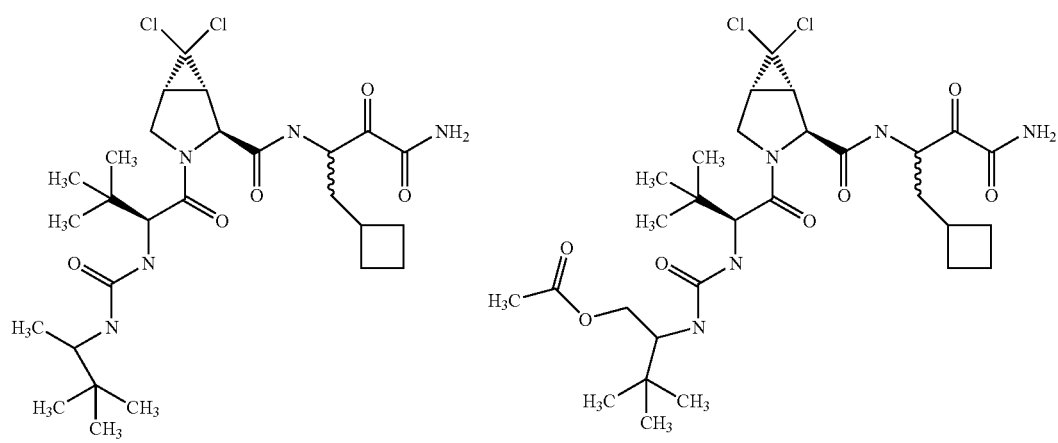
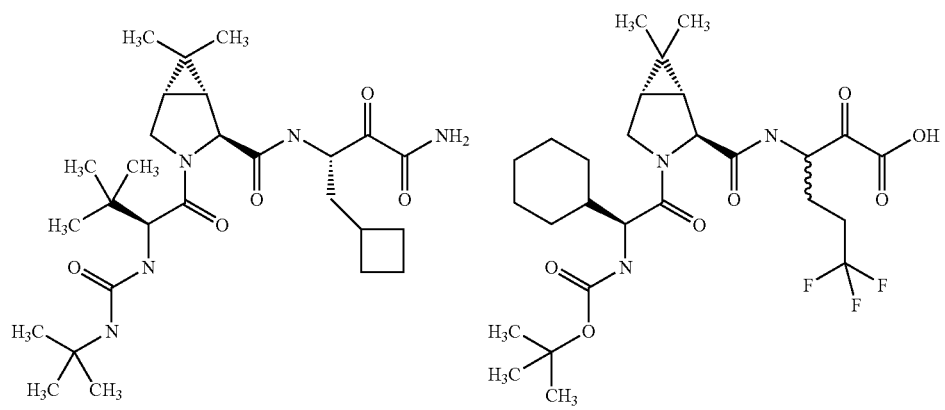

219
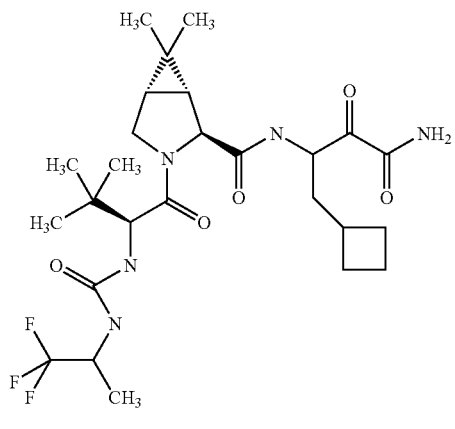
220
-continued
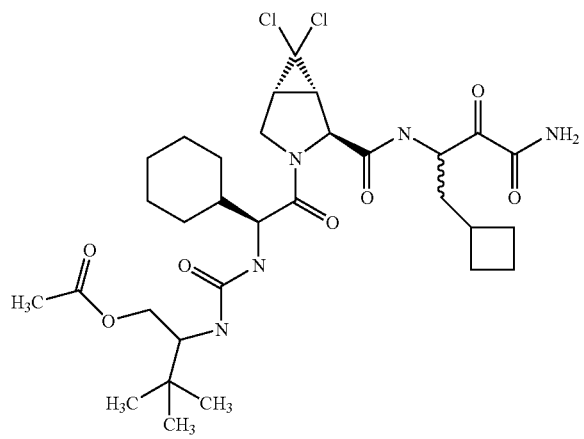
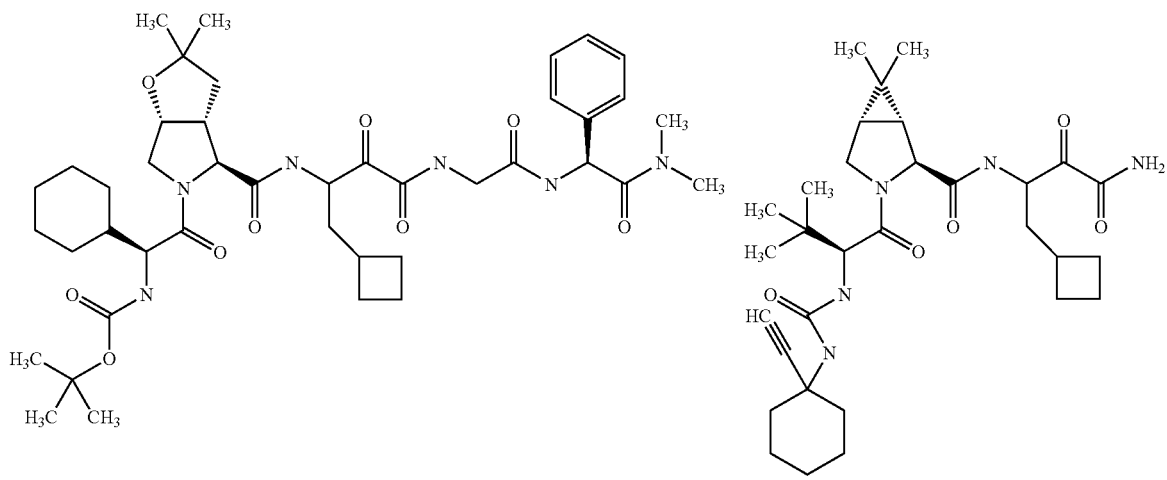
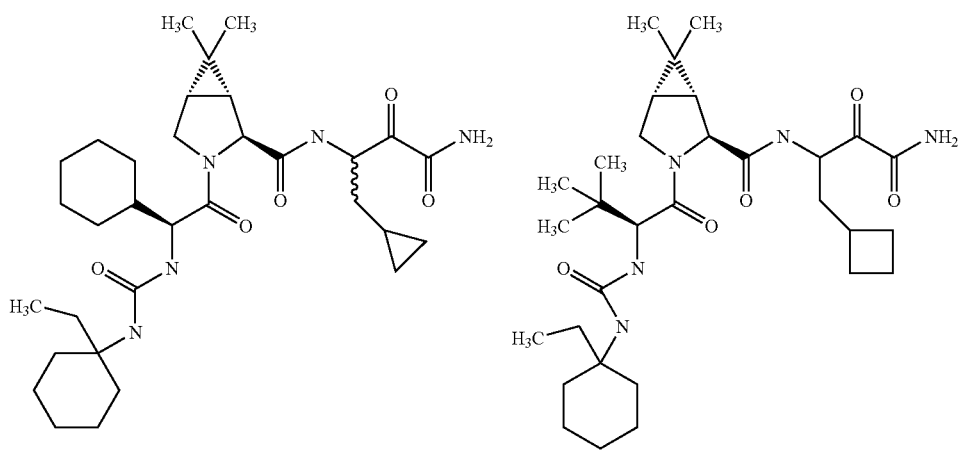

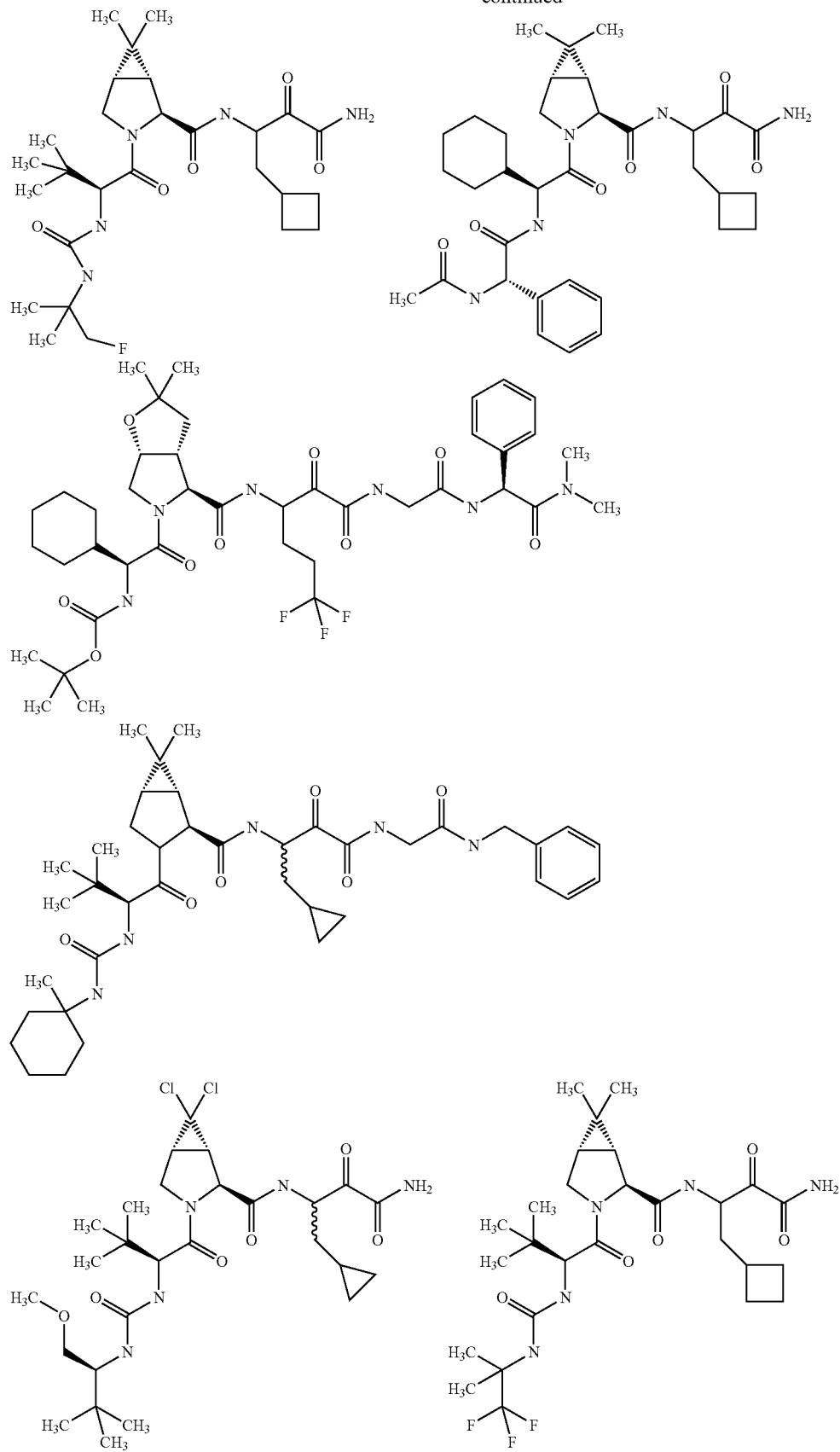

-continued
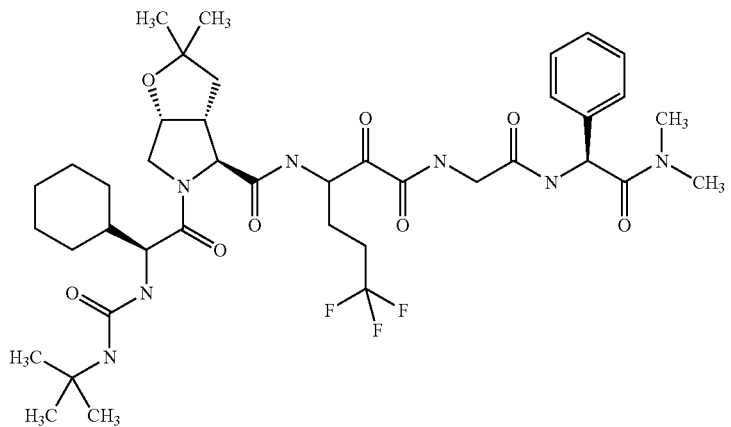
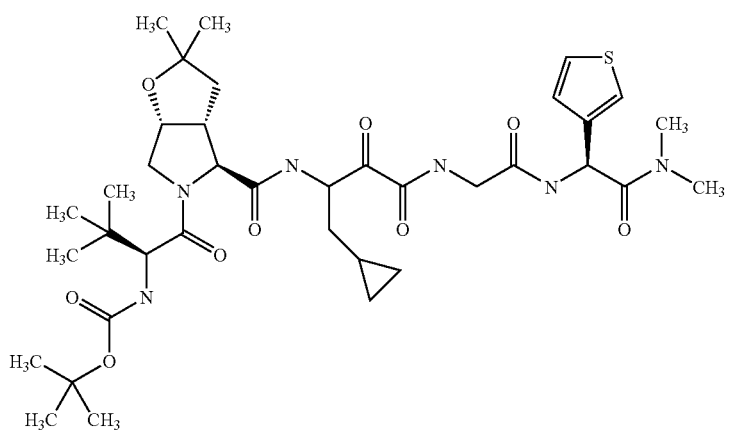
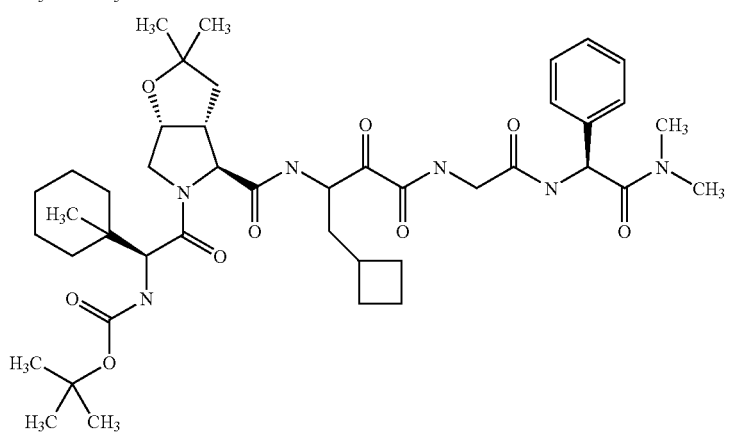
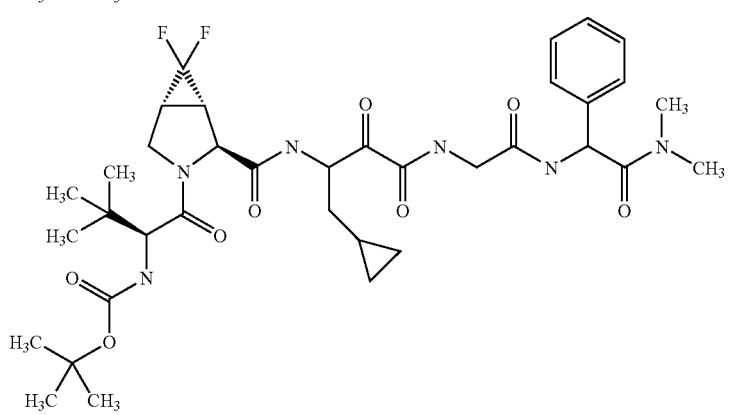

-continued
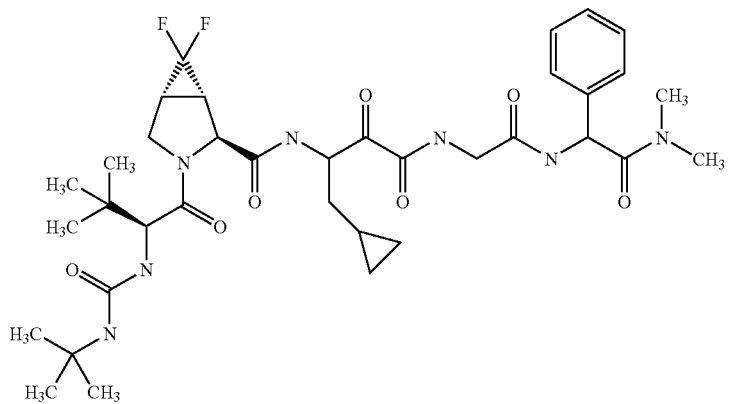
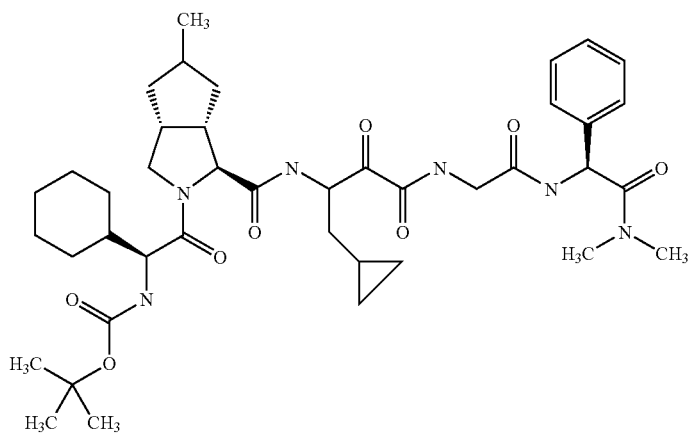
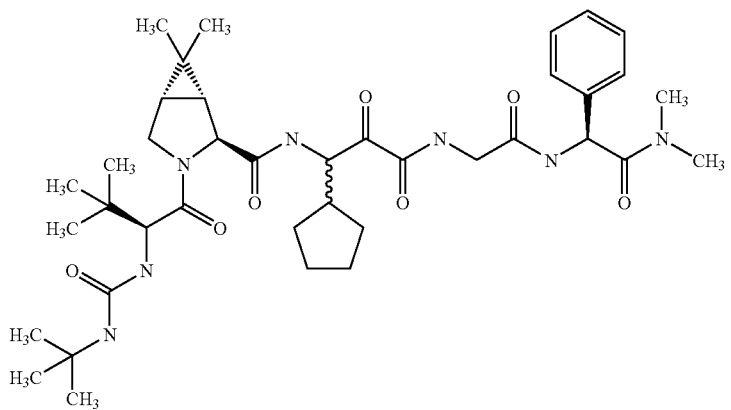
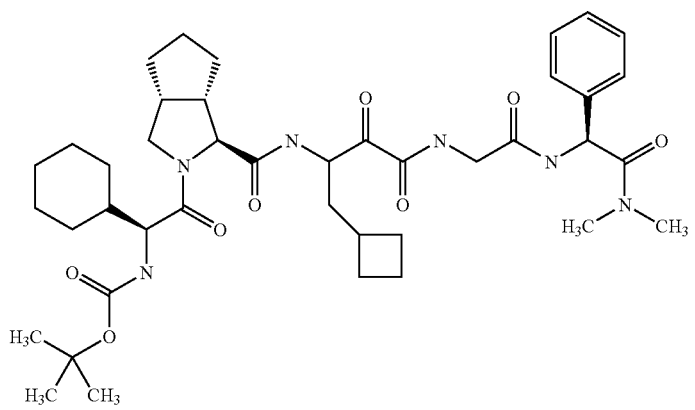

-continued
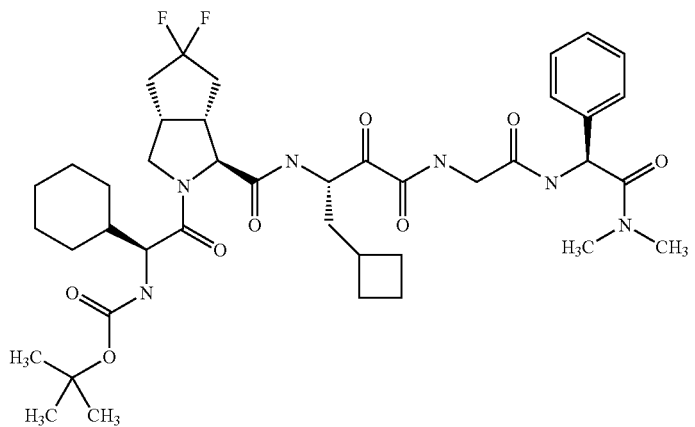
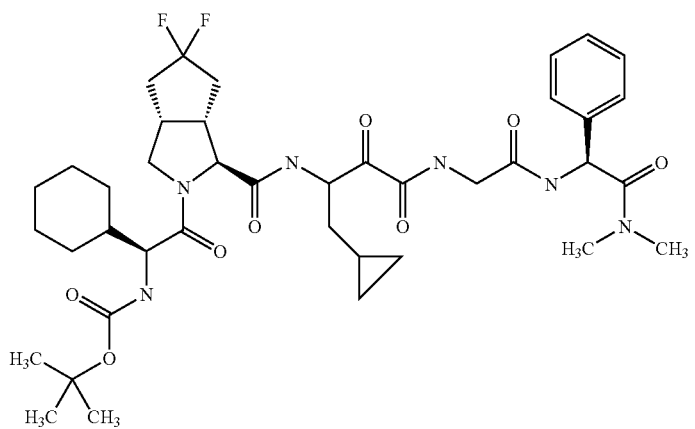
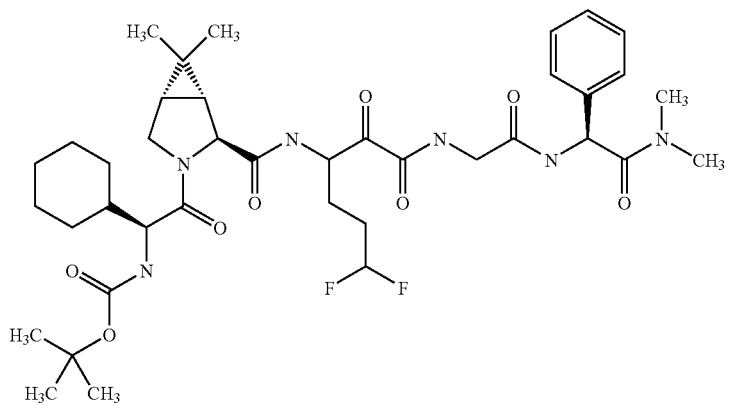
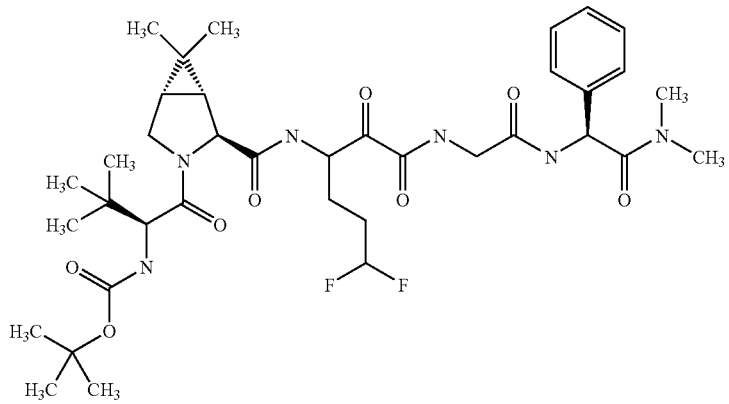

-continued
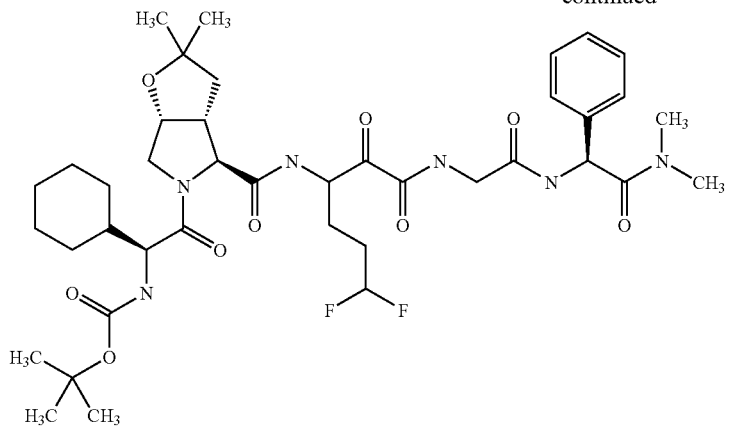
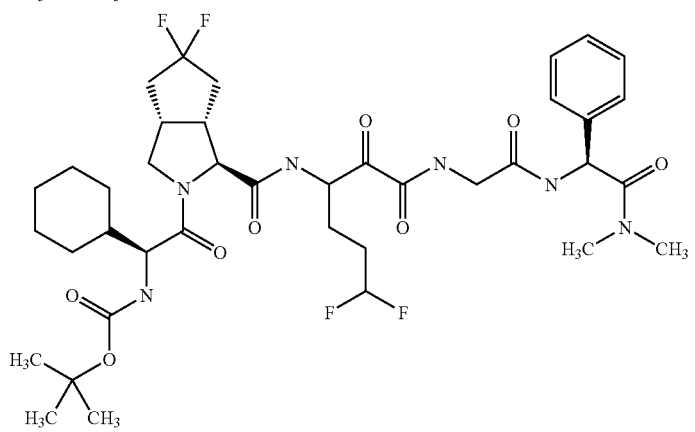
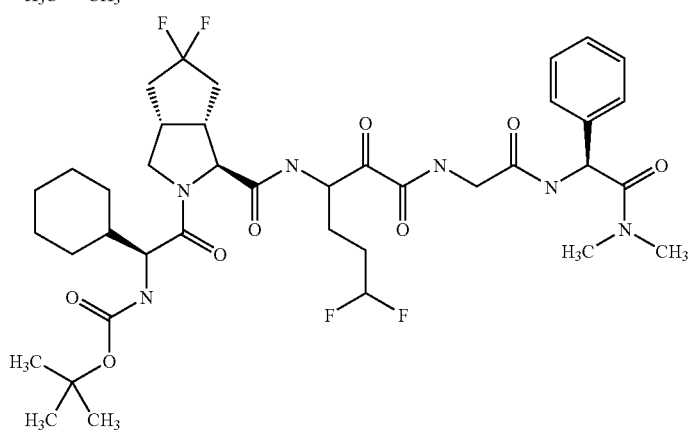
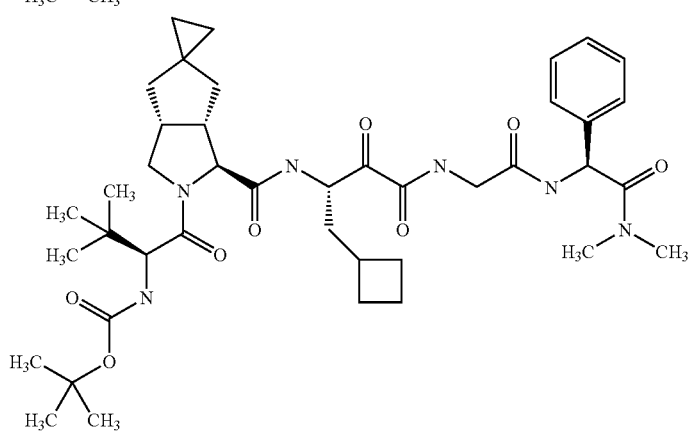

-continued
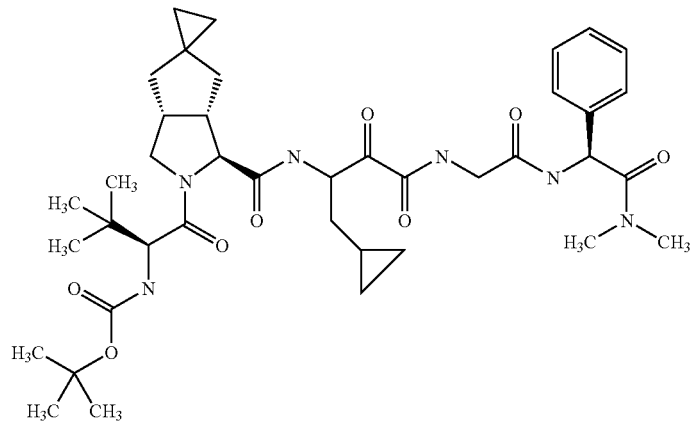
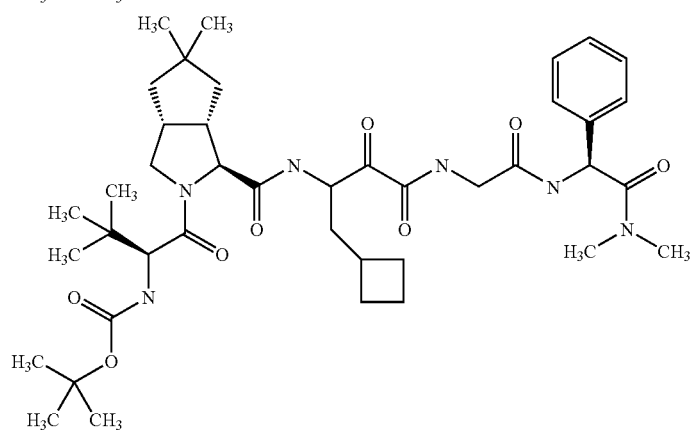
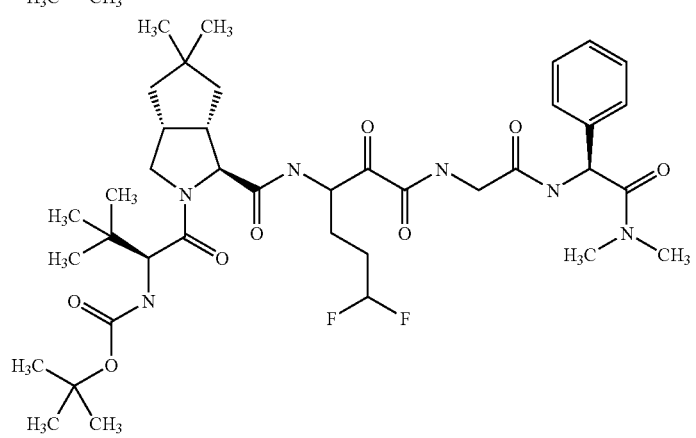
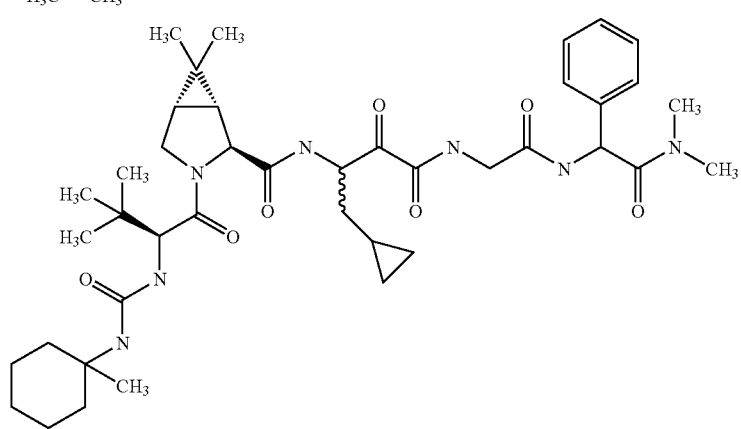

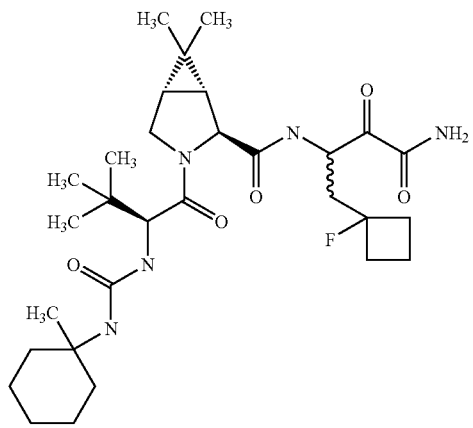
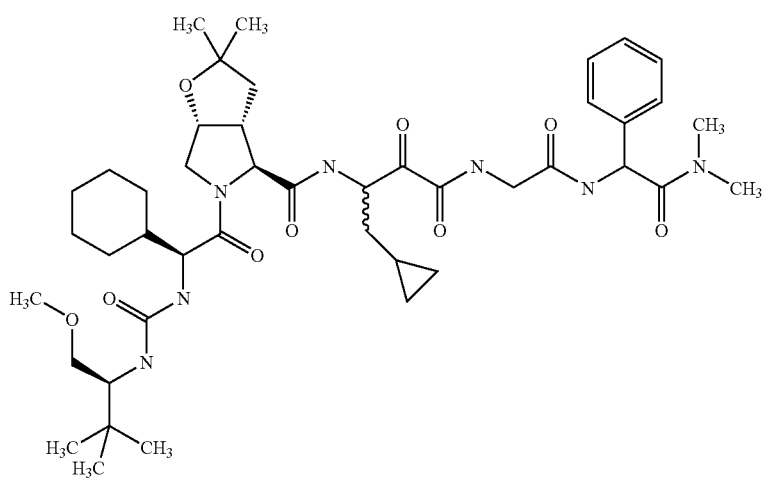
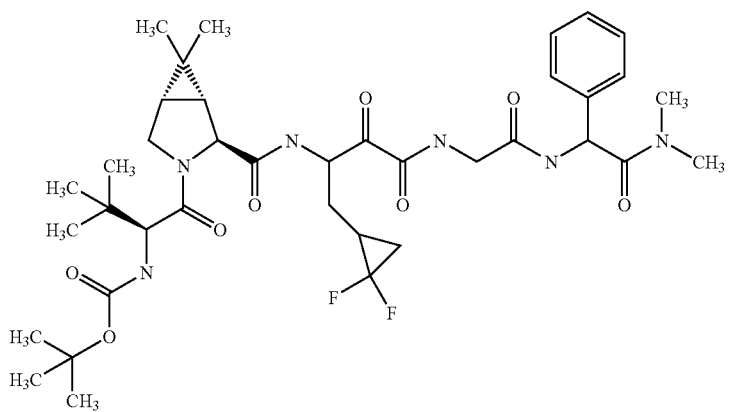

-continued
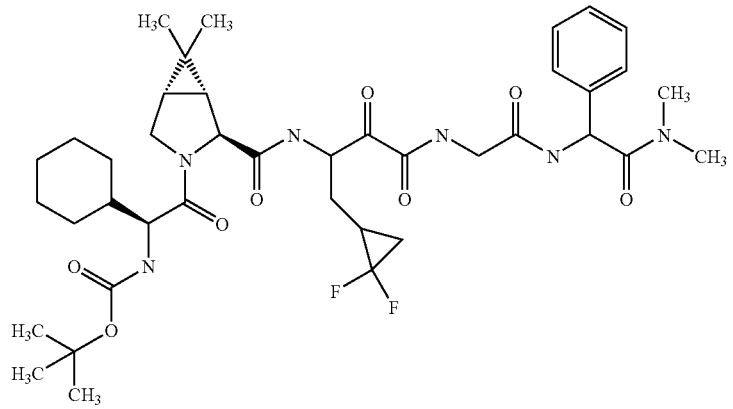
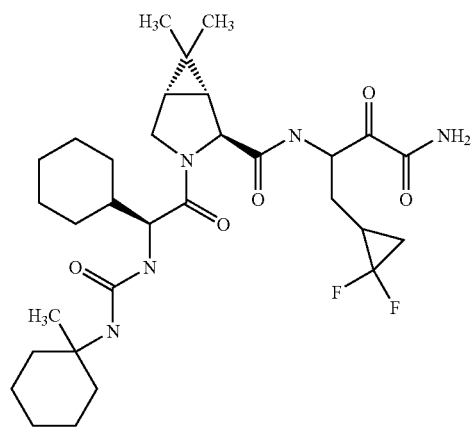
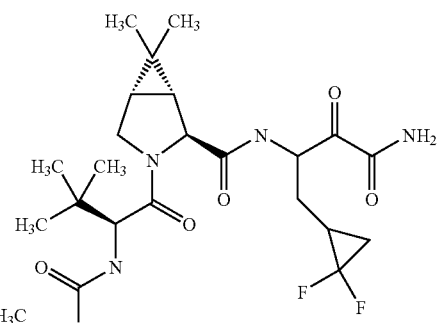
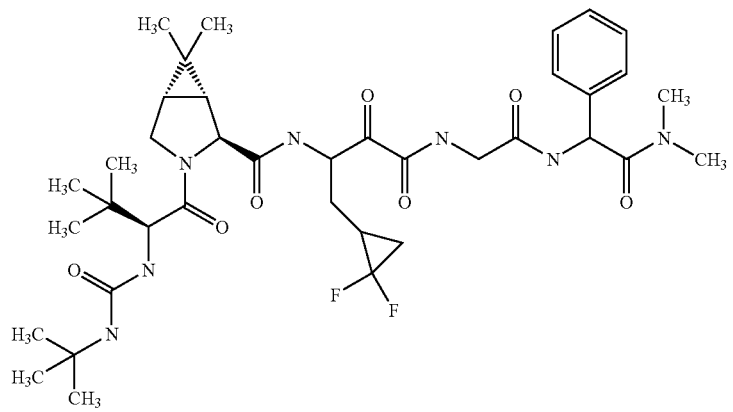
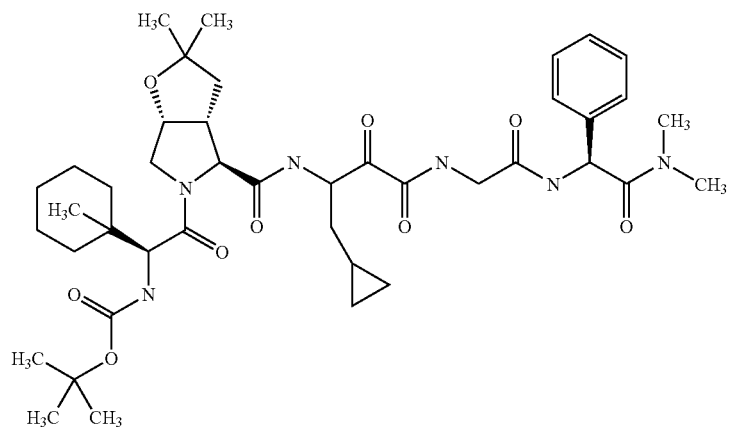

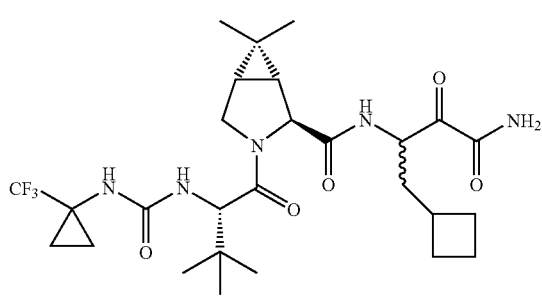

or a pharmaceutically acceptable salt, solvate or ester thereof.

In one embodiment, the HCV protease inhibitor is selected from the group consisting of Formula Ia

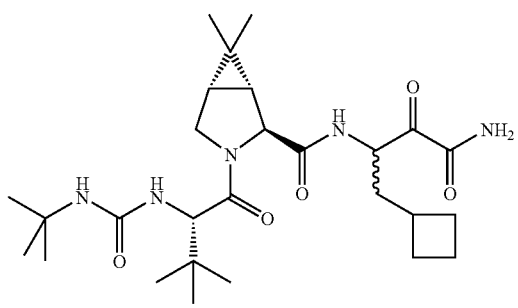

and pharmaceutically acceptable salts or solvates thereof.

The compound of formula Ia has recently been separated into its isomer/diastereomers of Formulas Ib and Ic. In one embodiment, the HCV protease inhibitor is selected from the group consisting of the compound of Formula Ic and pharmaceutically acceptable salts or solvates thereof as a potent inhibitor of HCV NS3 serine protease.

Formula Ib

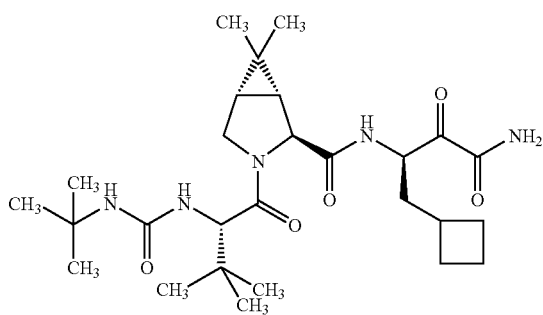

Formula Ic

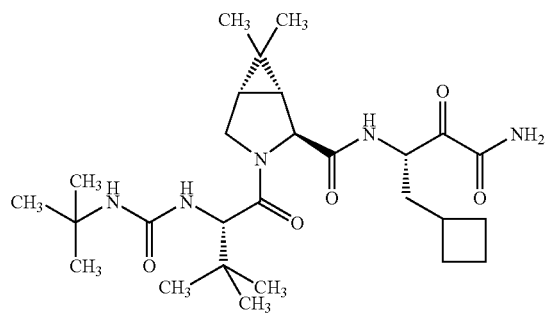

The chemical name of the compound of Formula Ic is (1R, 2S,5S)-N-[(1S)-3-amino-1-(cyclobutylmethyl)-2,3-dioxo-propyl]-3-[(2S)-2-[[[(1,1-dimethylethyl)amino]carbonyl] amino]-3,3-dimethyl-1-oxobutyl]-6,6-dimethyl-3-azabicyclo[3.1.0]hexane-2-carboxamide.

Processes for making compounds of Formula I are disclosed in U.S. Patent Publication Nos. 2005/0059648, 2005/0020689 and 2005/0059800, incorporated by reference herein.

Non-limiting examples of suitable compounds of formula III and methods of making the same are disclosed in WO02/08256 and in U.S. Pat. No. 6,800,434, at col. 5 through col. 247, incorporated herein by reference.

Non-limiting examples of suitable compounds of formula III and methods of making the same are disclosed in International Patent Publication WO02/08187 and in U.S. Patent Publication 2002/0160962 at page 3, paragraph 22 through page 132, incorporated herein by reference.

Non-limiting examples of suitable compounds of formula IV and methods of making the same are disclosed in International Patent Publication WO03/062228 and in U.S. Patent Publication 2003/0207861 at page 3, paragraph 25 through page 26, incorporated herein by reference.

Non-limiting examples of suitable compounds of formula V and methods of making the same are disclosed in U.S. patent application Ser. No. 10/948,367 filed Sep. 23, 2004, and the preparation of the compounds are detailed in the experimental section of this application set forth hereinbelow.

Non-limiting examples of suitable compounds of formula VI and methods of making the same are disclosed in U.S. Patent Publication Ser. No. 2005/0085425 at page 3, paragraph 0023 through page 139, incorporated herein by reference.

Compounds of formula VII-IX are disclosed in U.S. patent application Ser. No. 10/993,394 filed Nov. 19, 2004, and the preparation of the compounds are detailed in the experimental section of this application set forth hereinbelow.
Non-limiting examples of certain compounds of formula VII disclosed in U.S. patent application Ser. No. 10/993,394 are:
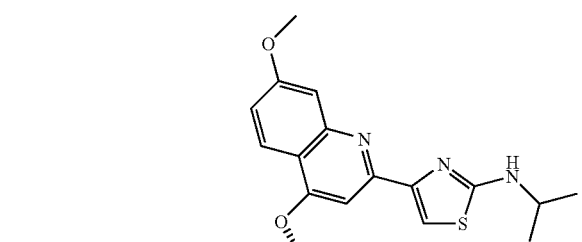
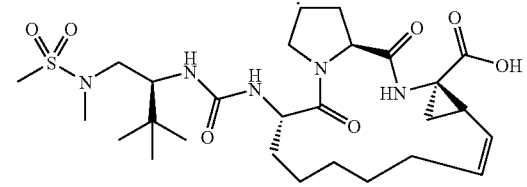
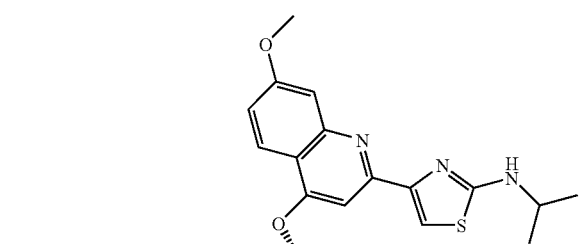
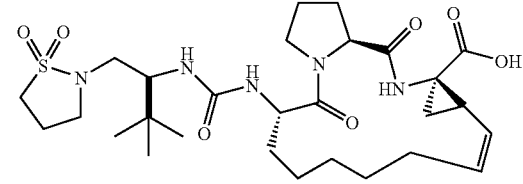
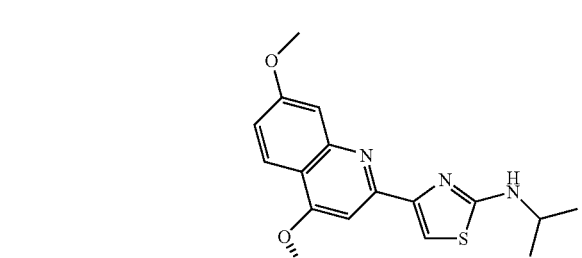
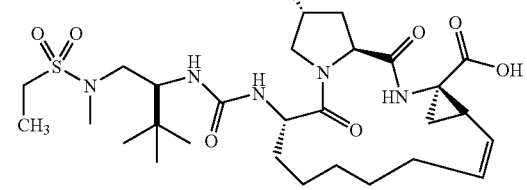
-continued
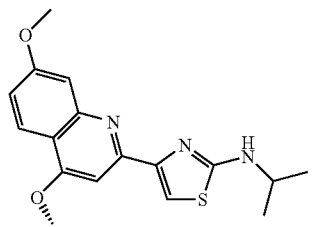
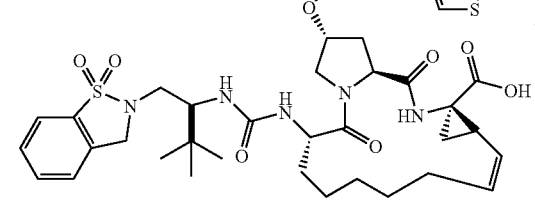
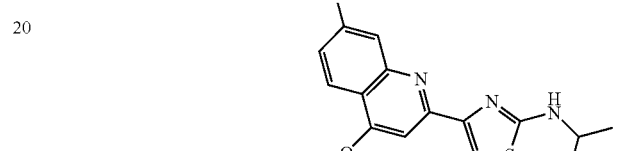
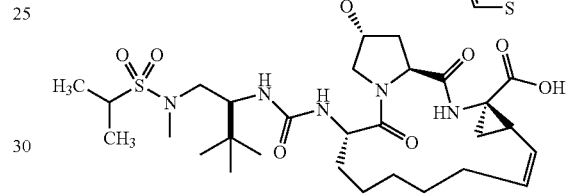
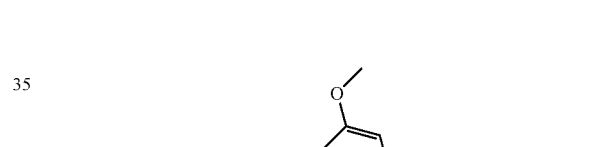
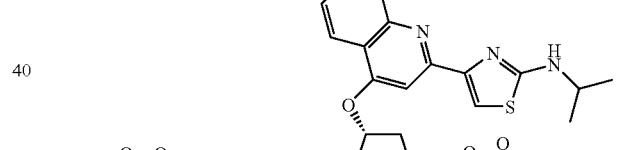
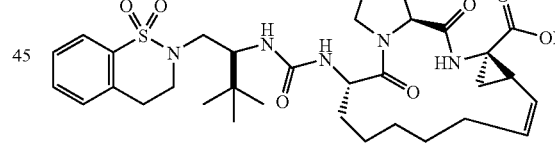
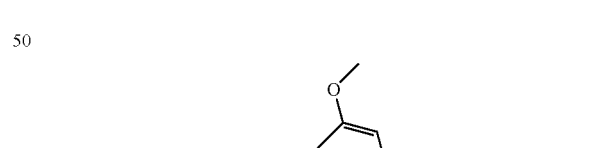
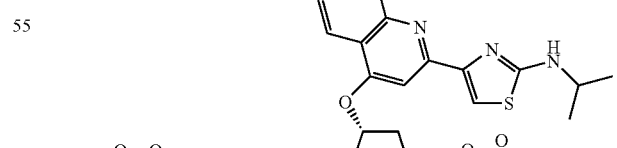
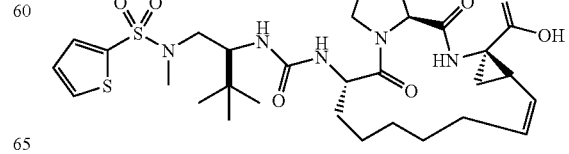

241
-continued
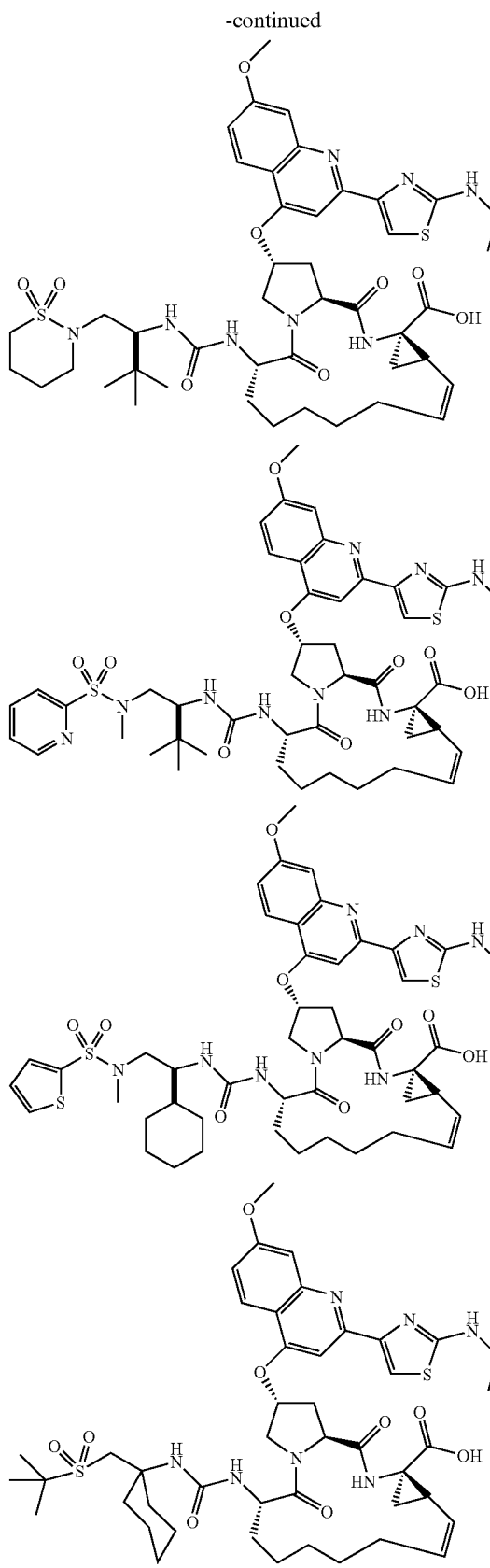
242
-continued
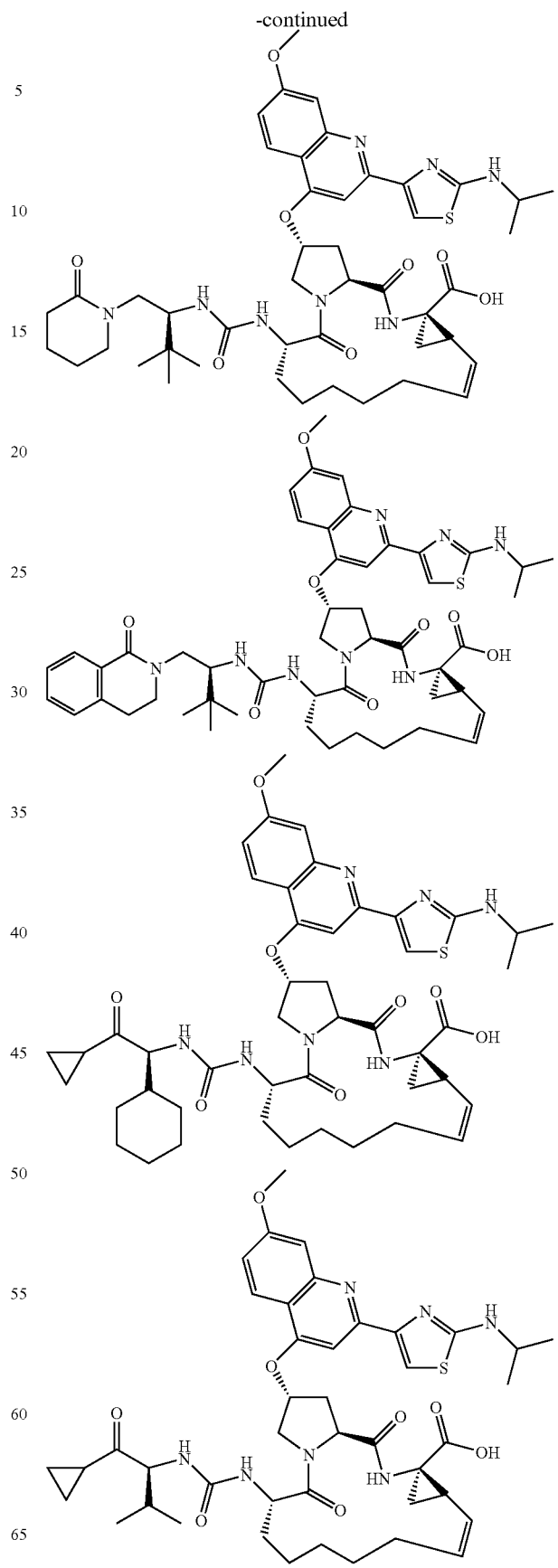

243 244
-continued
-continued
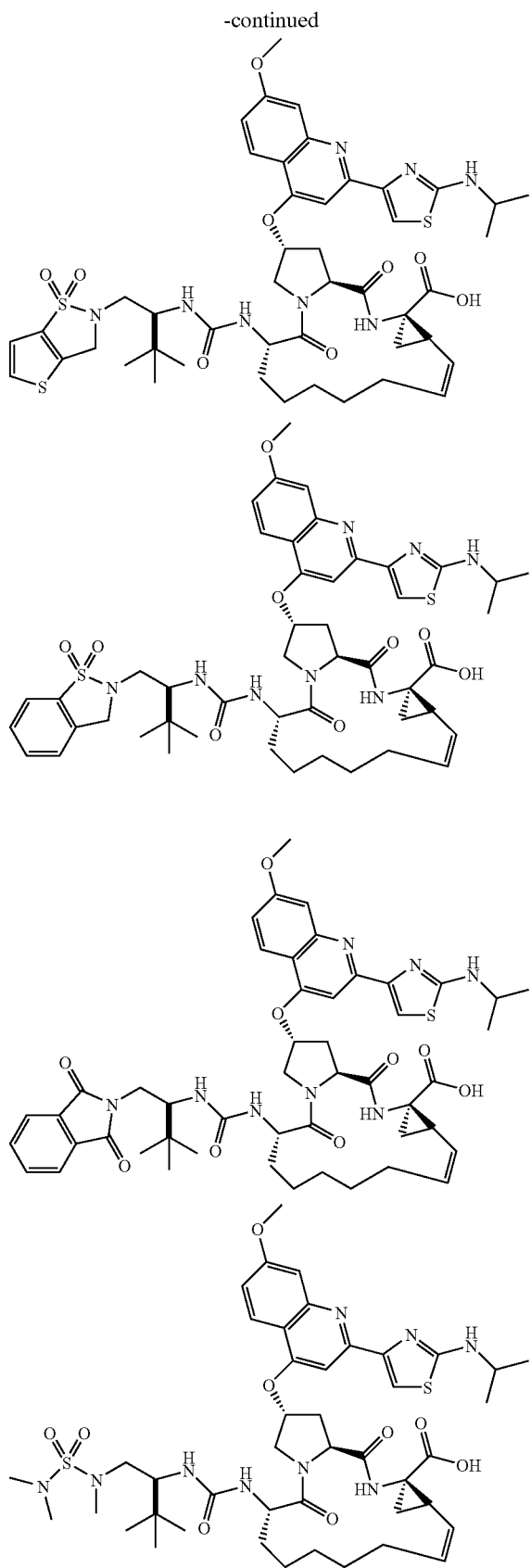
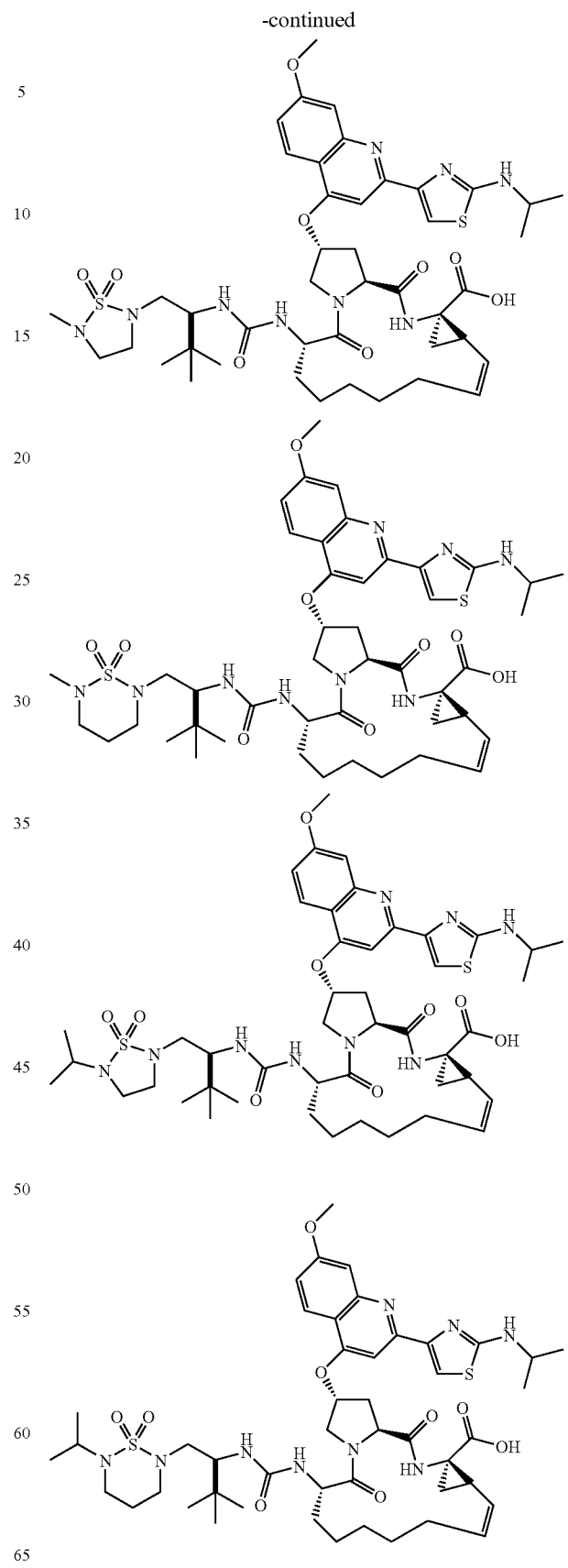

245 246
-continued -continued
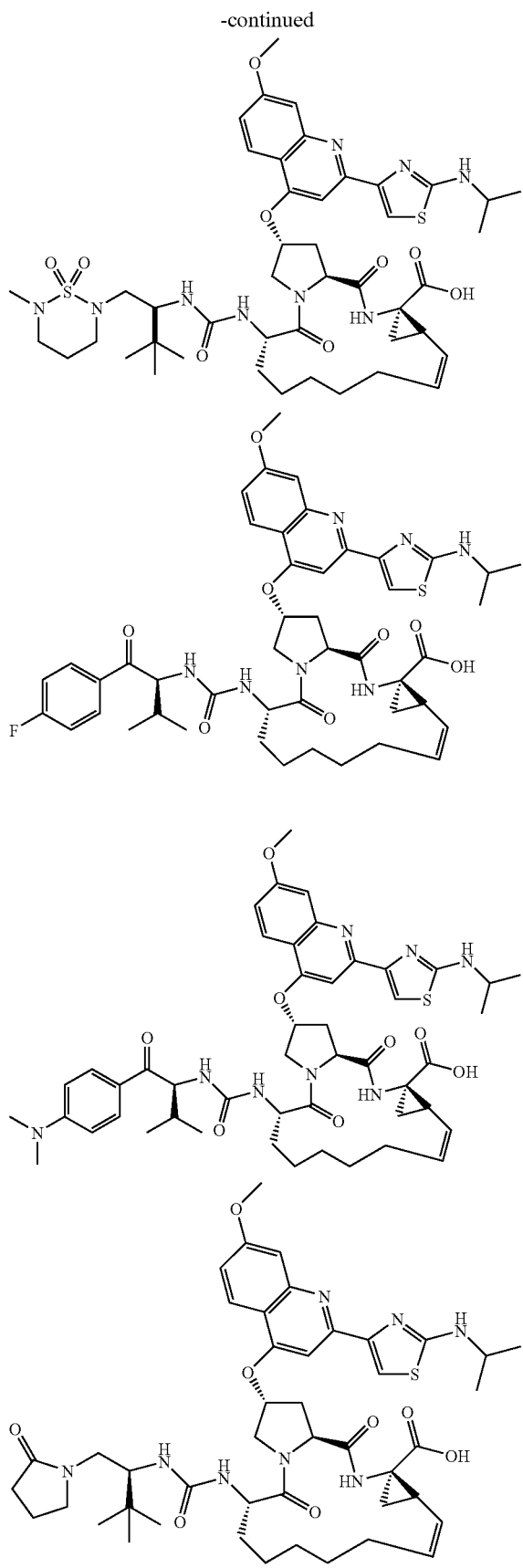
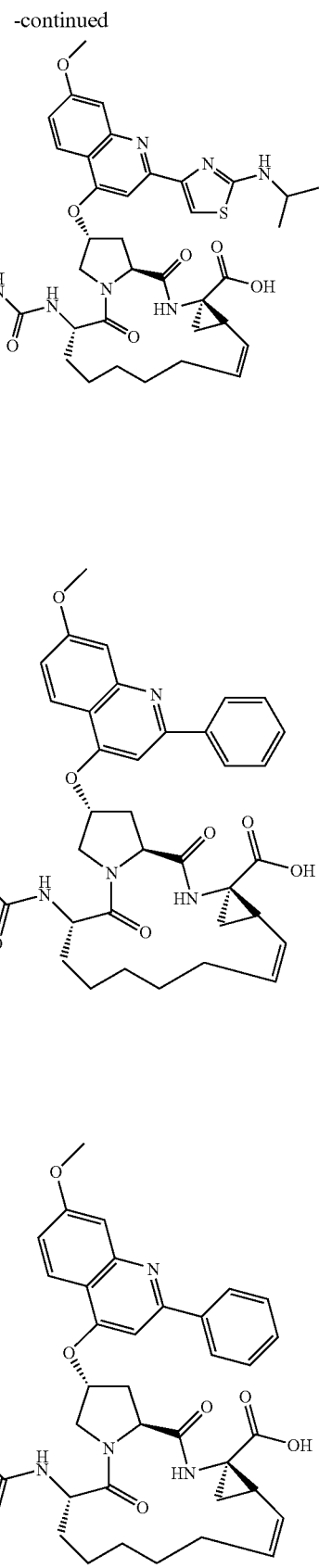

-continued
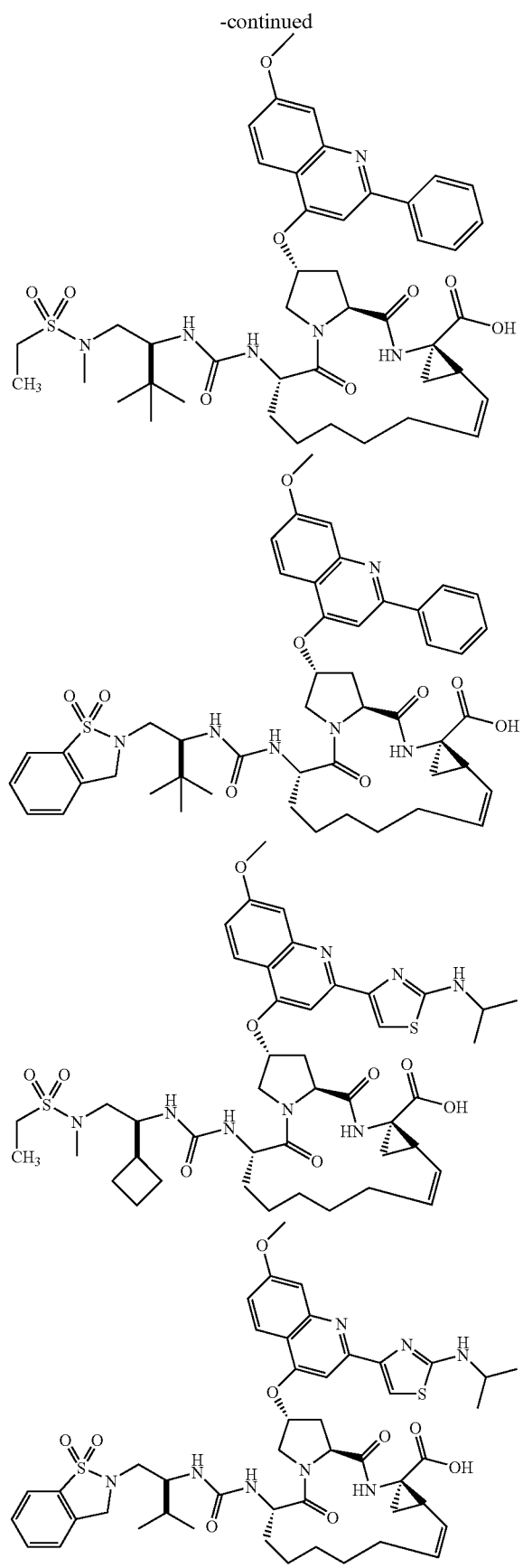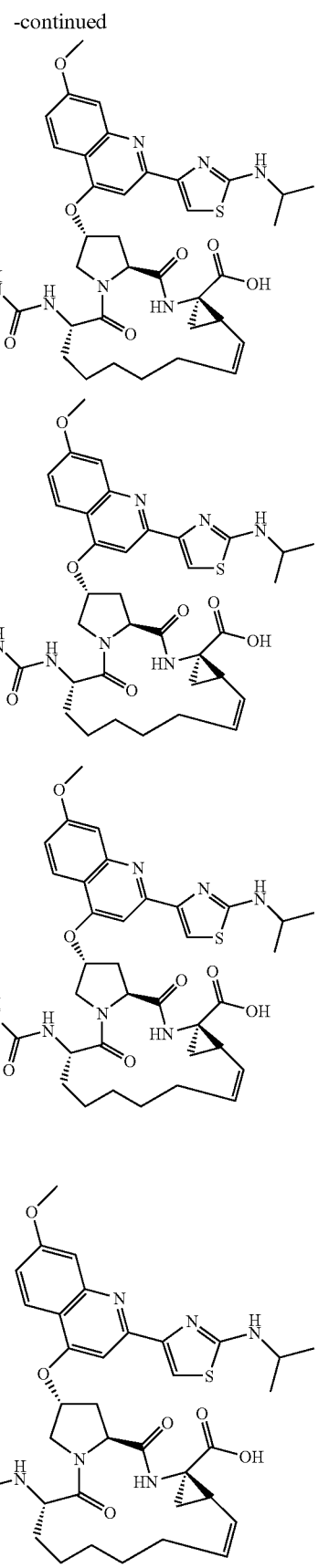

249
-continued
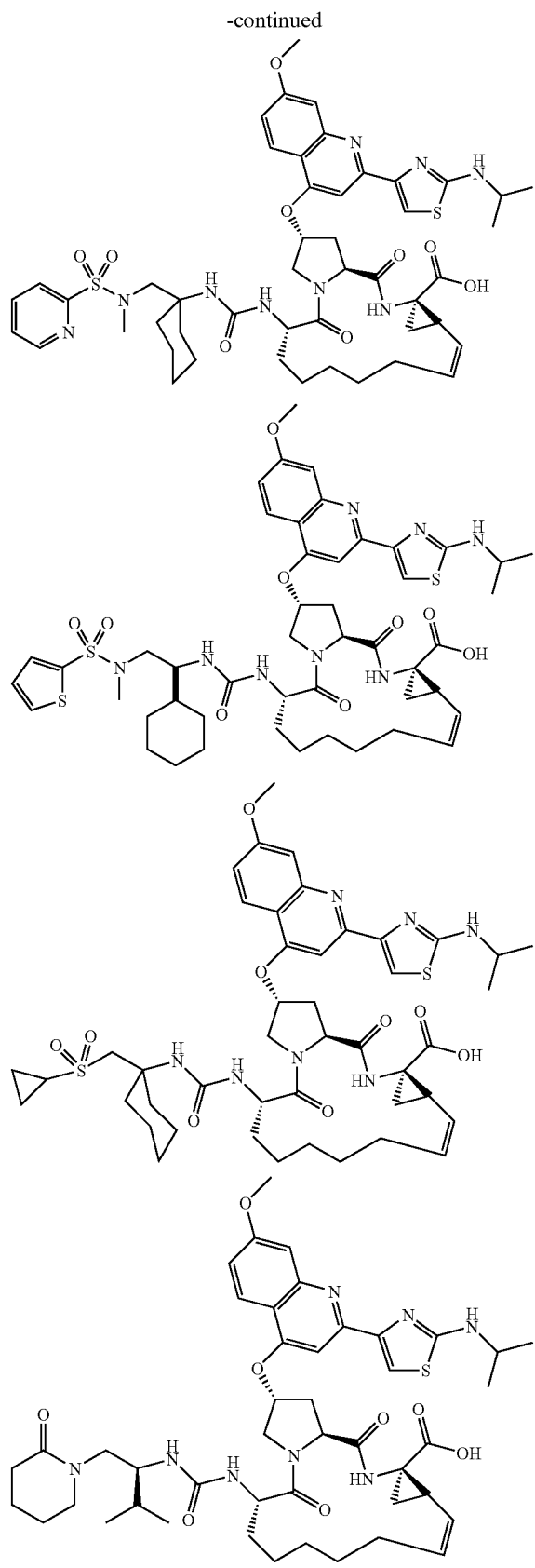
250
-continued
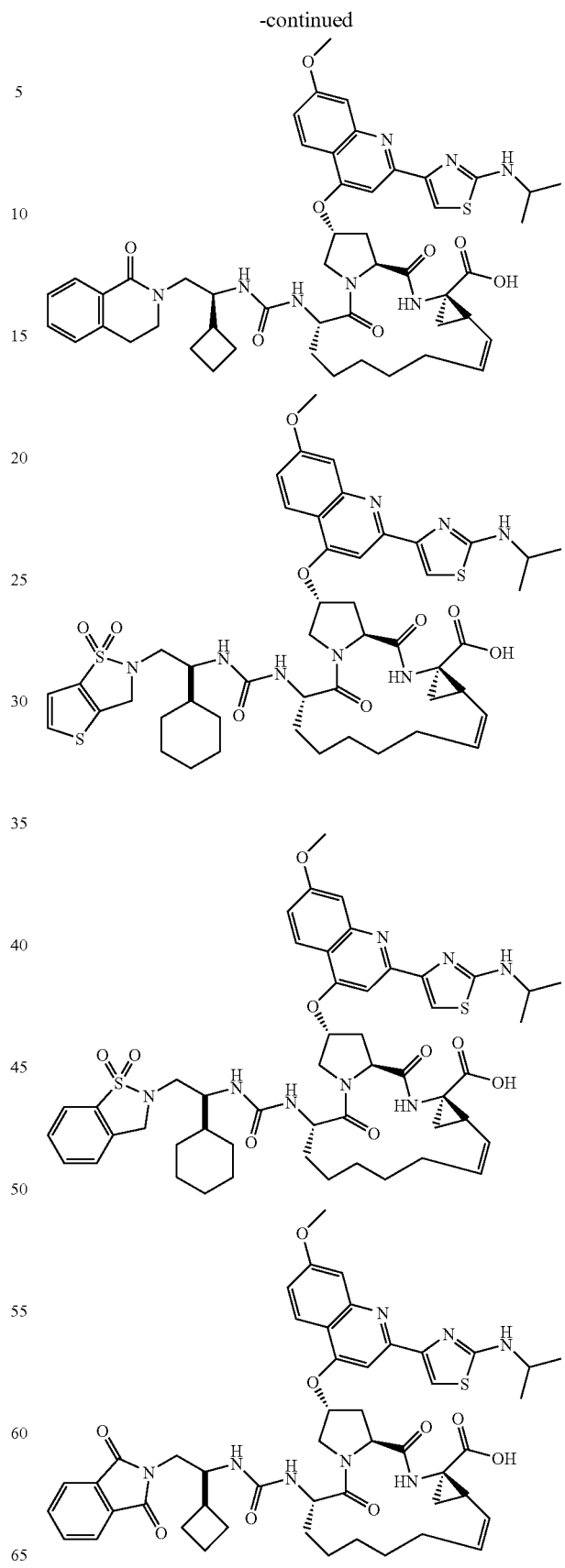

251
-continued
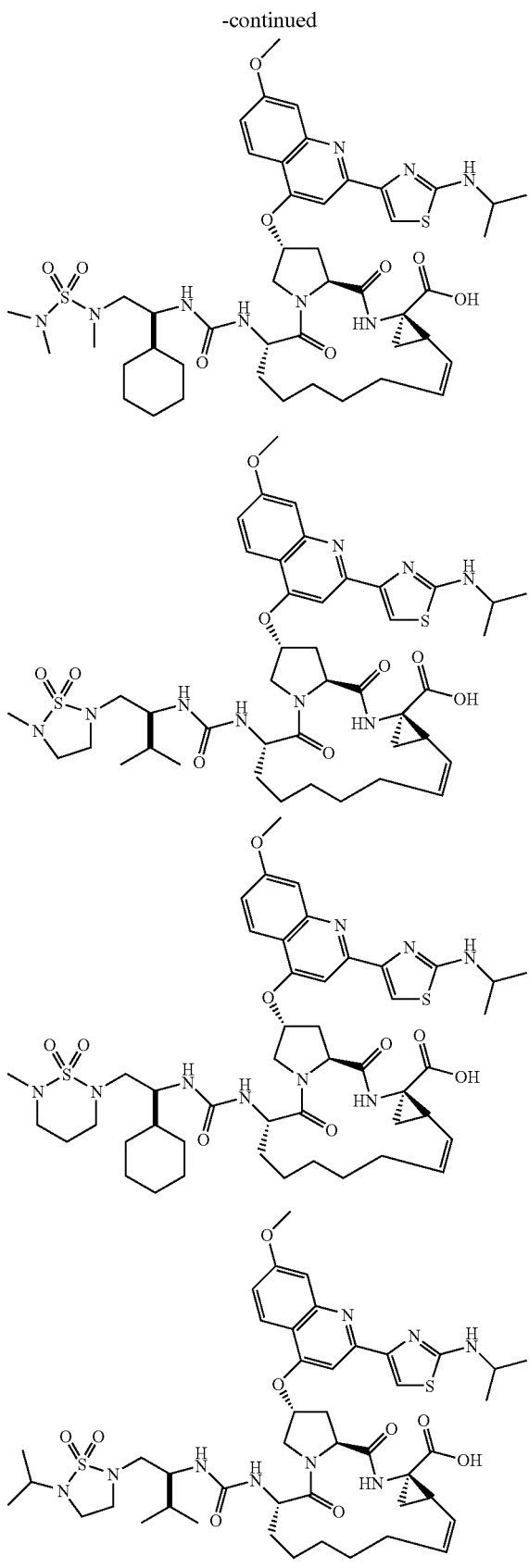
252
-continued
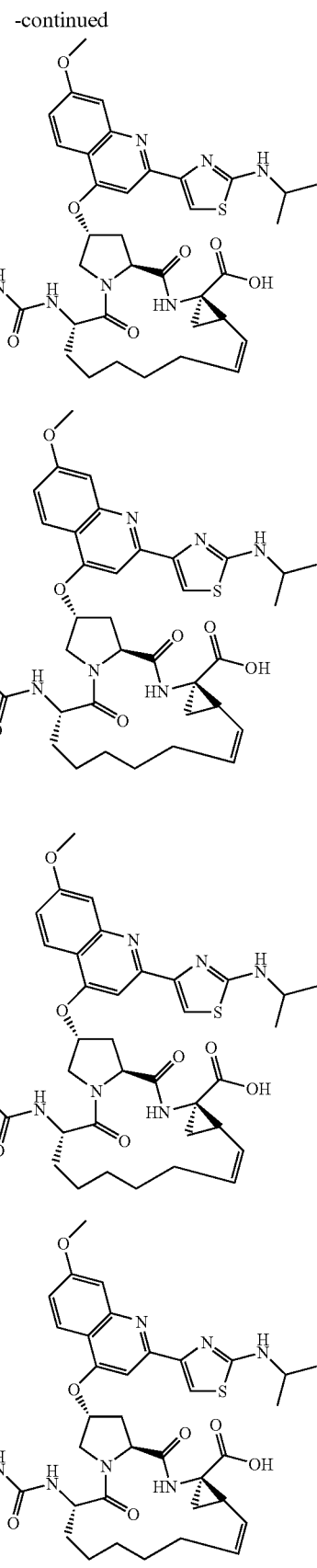

253
-continued
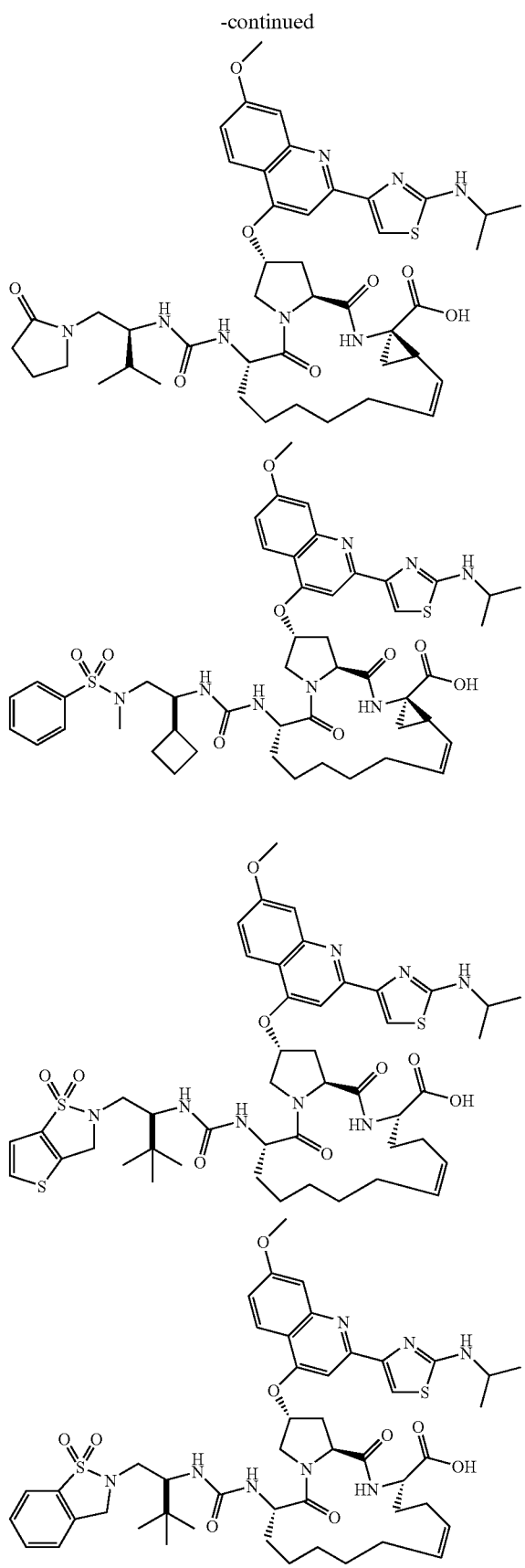
254
-continued
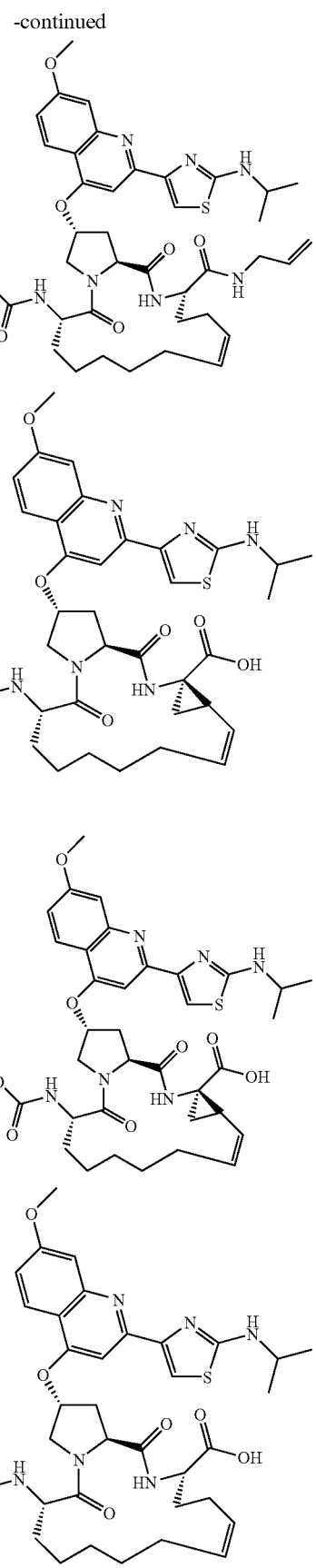

255
-continued
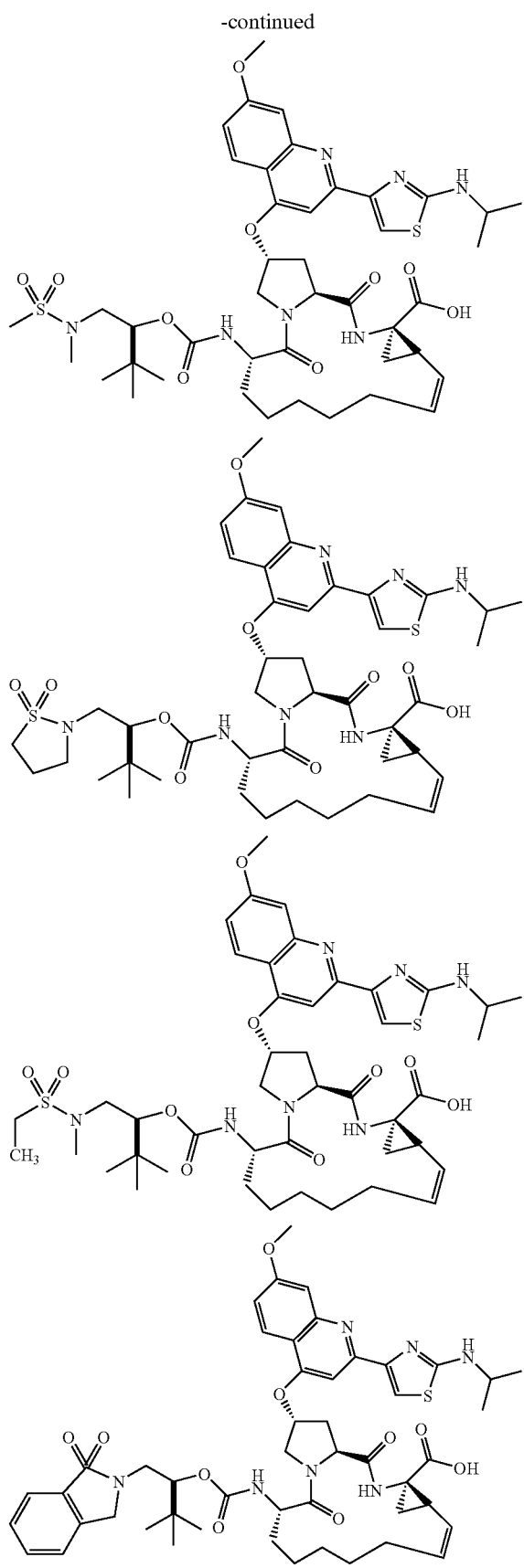
256
-continued
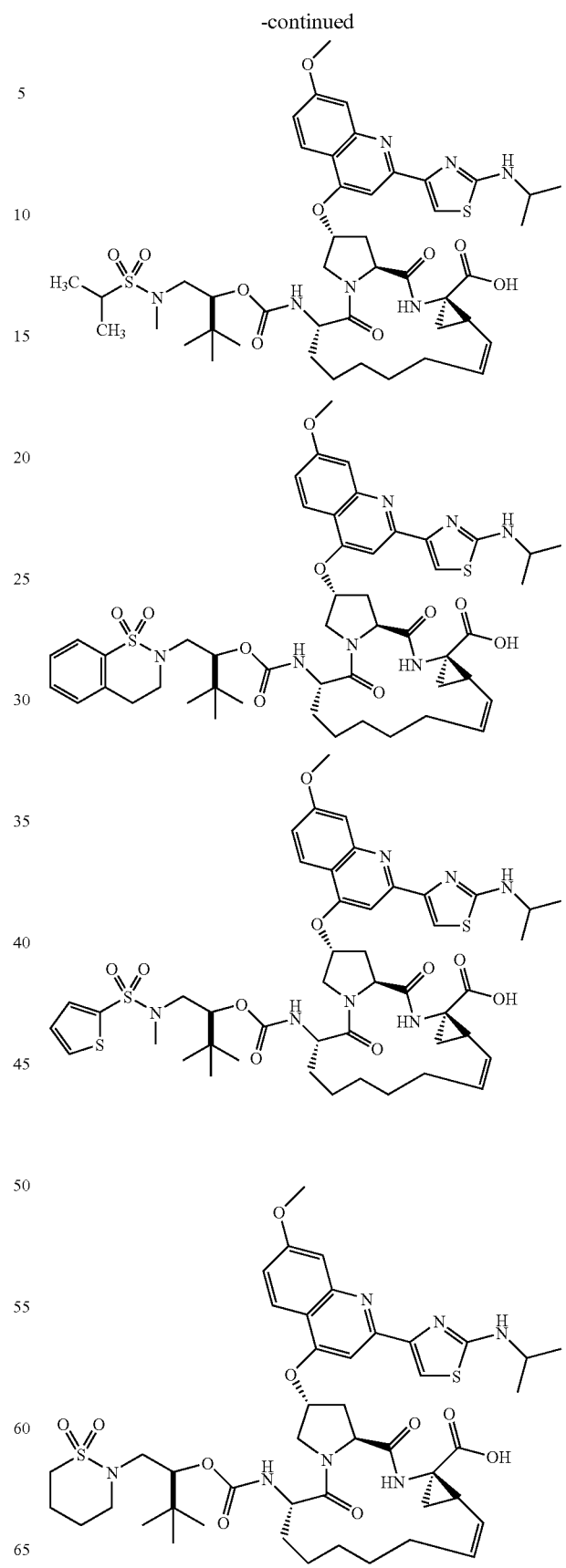

257
-continued
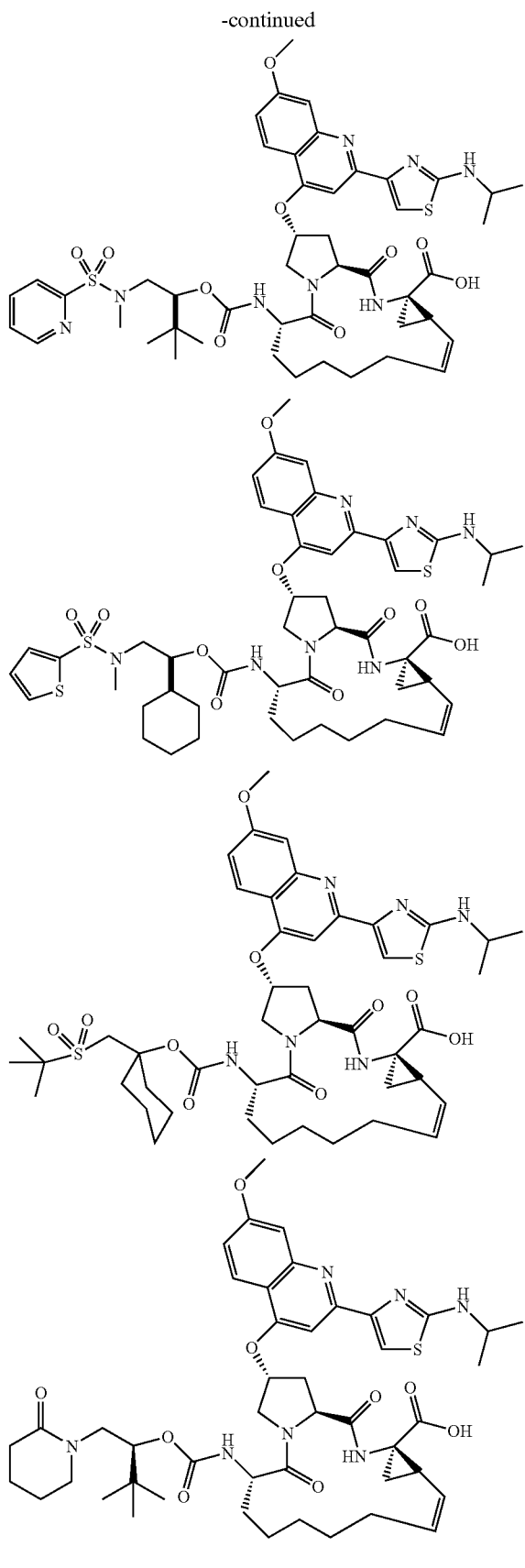
258
-continued
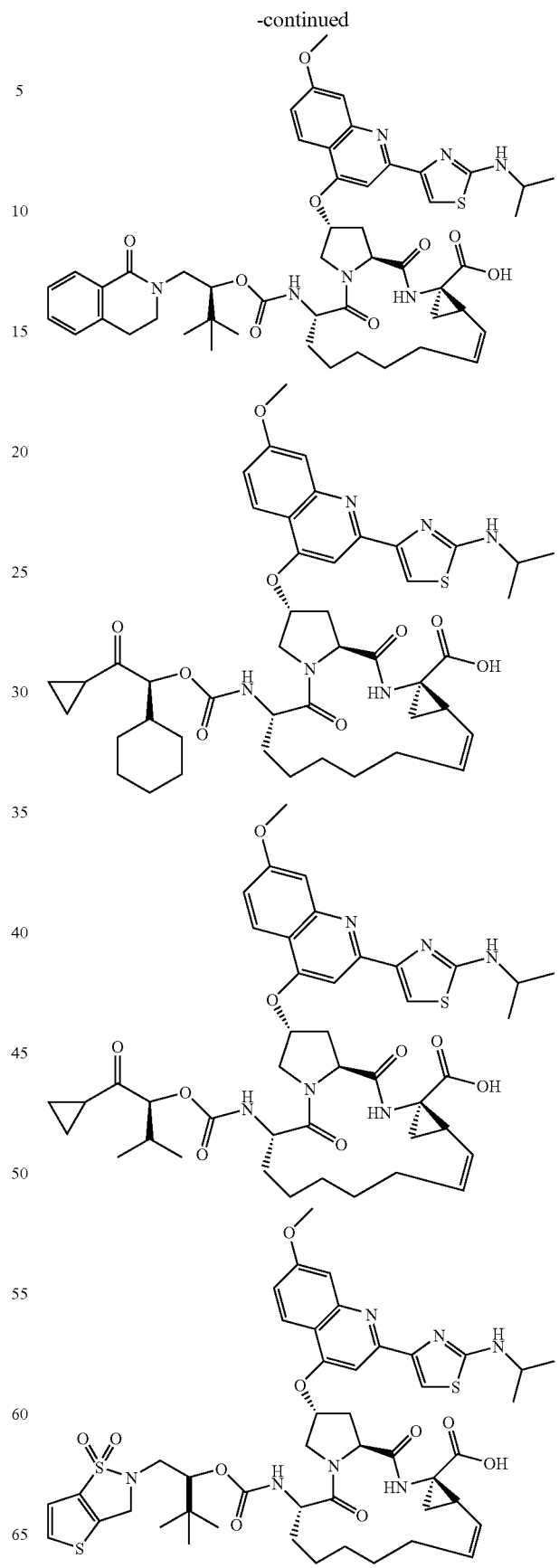

259
-continued
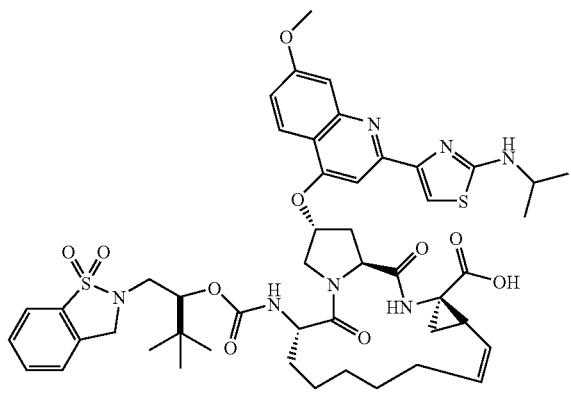
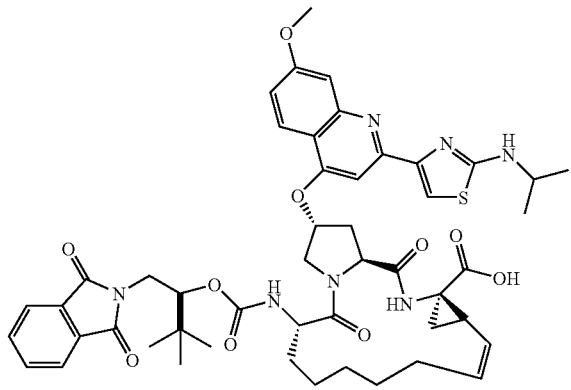
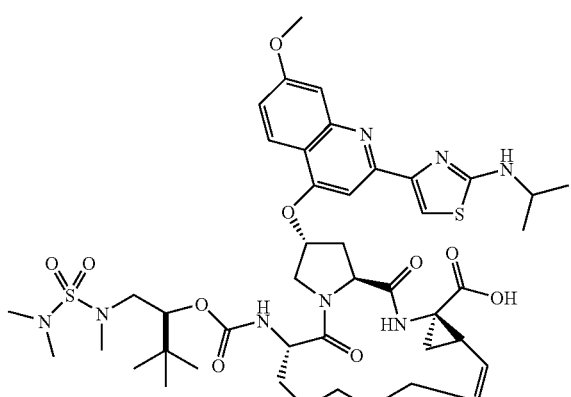
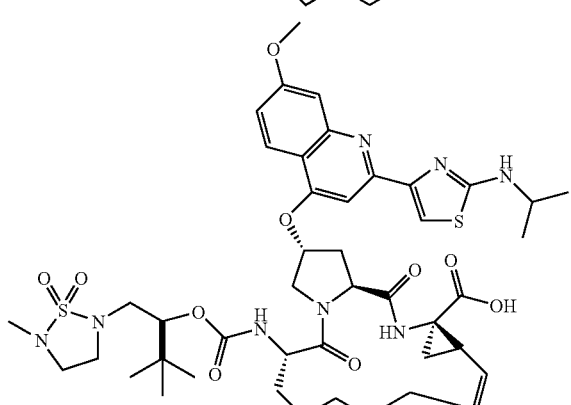
260
-continued
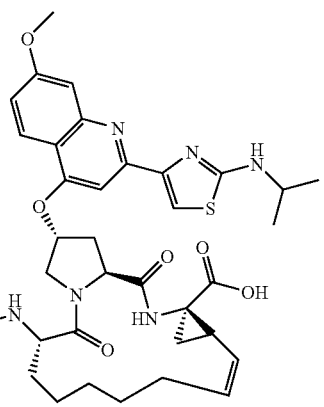

-continued

or a pharmaceutically acceptable salt, solvate or ester thereof.
Nonlimiting examples of certain compounds of formula VIII disclosed in U.S. patent application Ser. No. 10/993,394 are:

and

263
-continued

264
-continued

265
-continued
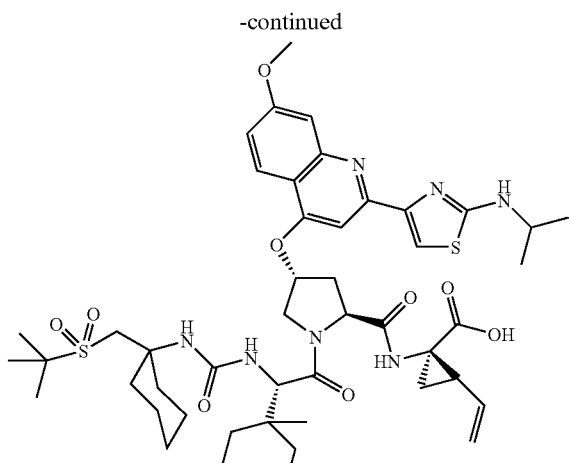
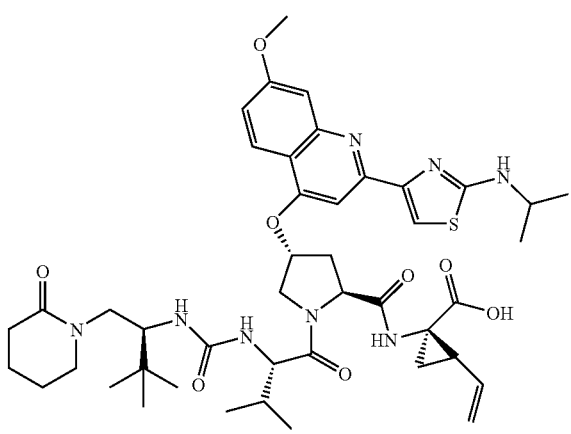
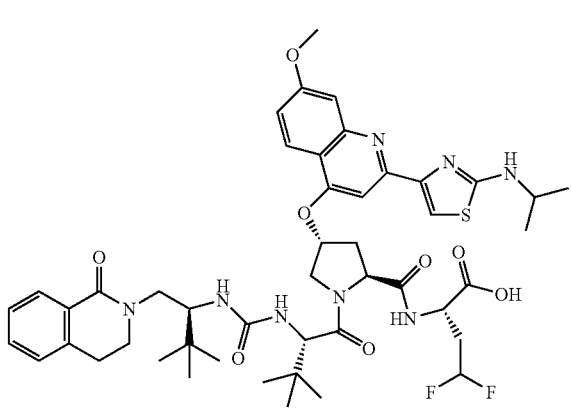
266
-continued
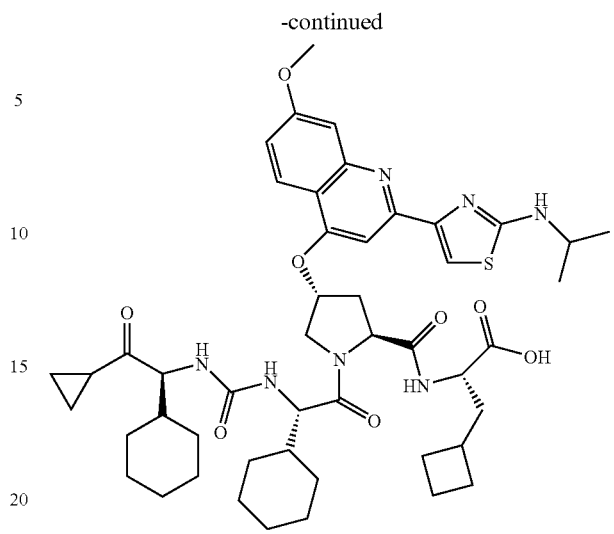
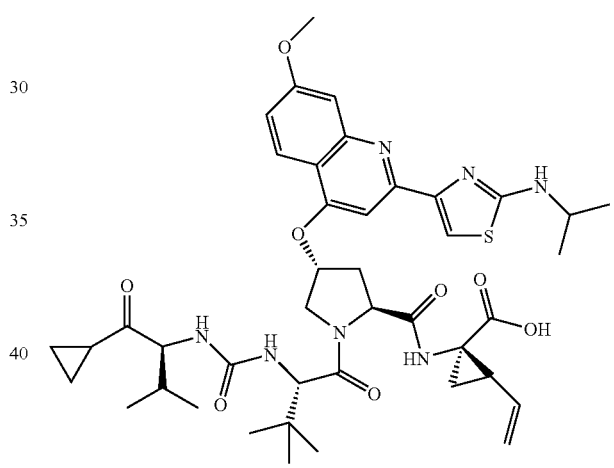
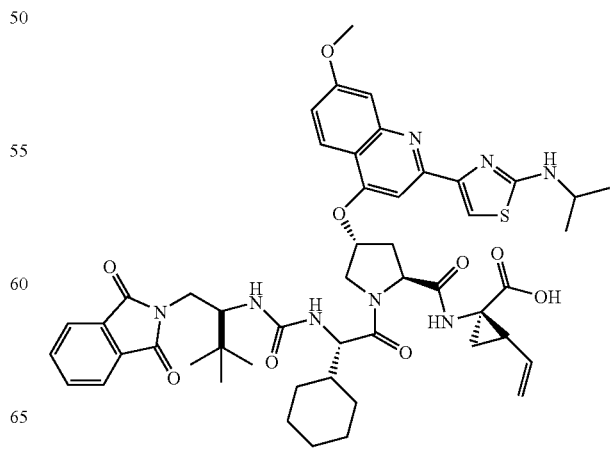

267
-continued
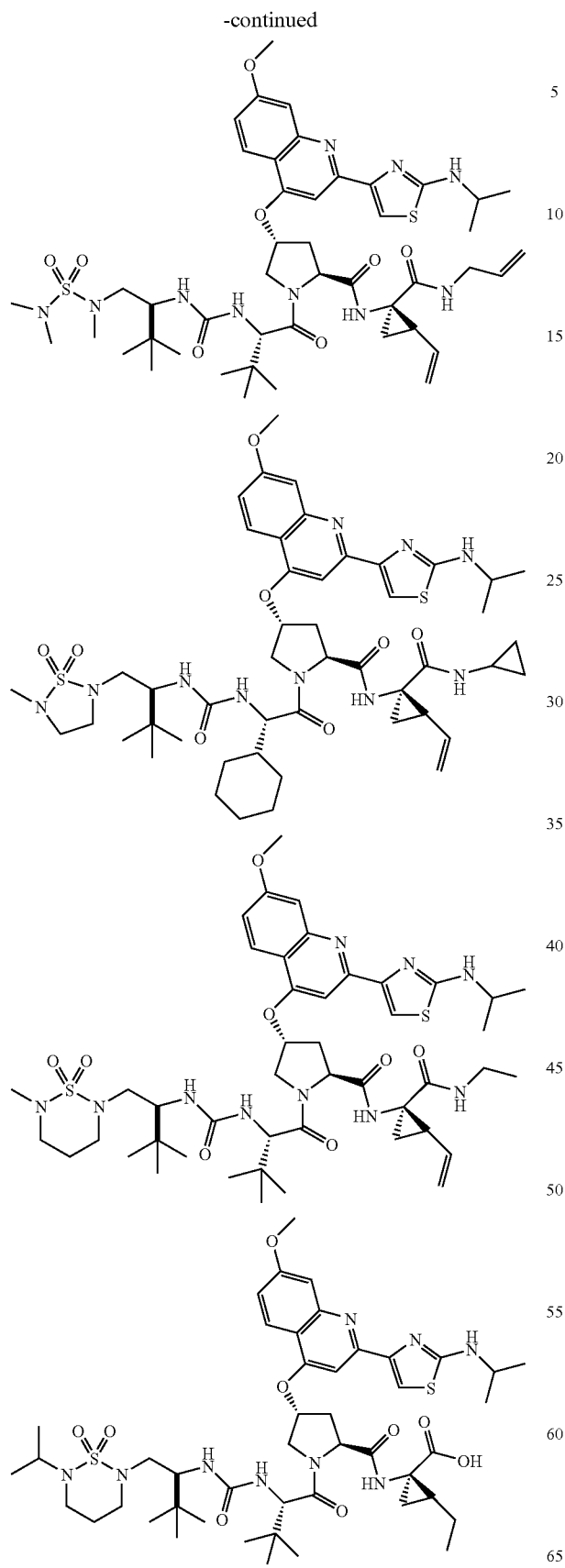
268
-continued
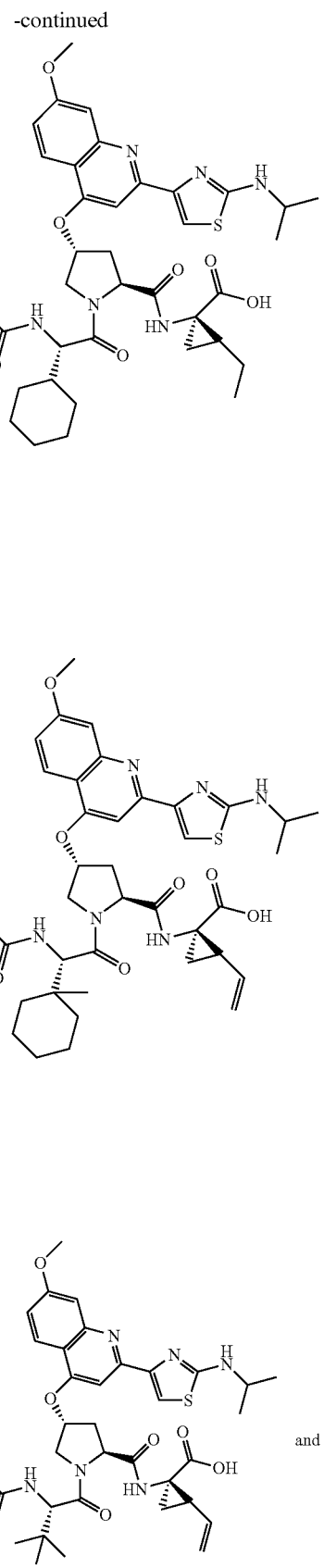
and

-continued
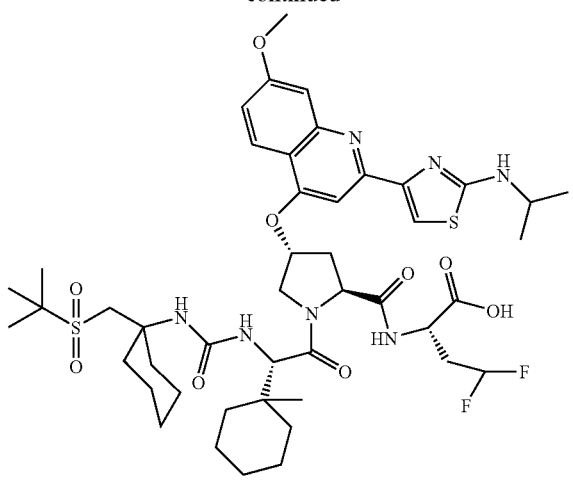
or a pharmaceutically acceptable salt, solvate or ester thereof.
Nonlimiting examples of certain compounds of formula IX disclosed in U.S. patent application Ser. No. 10/993,394 are:
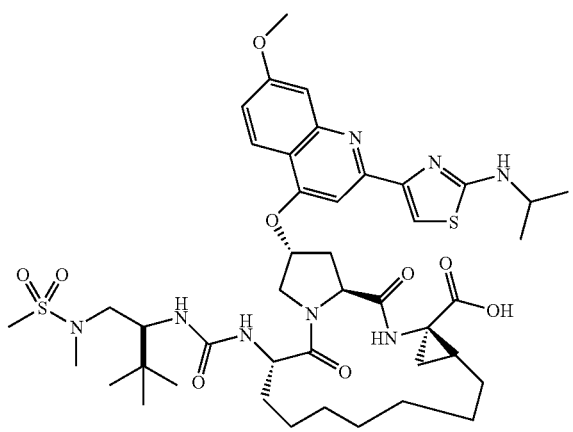
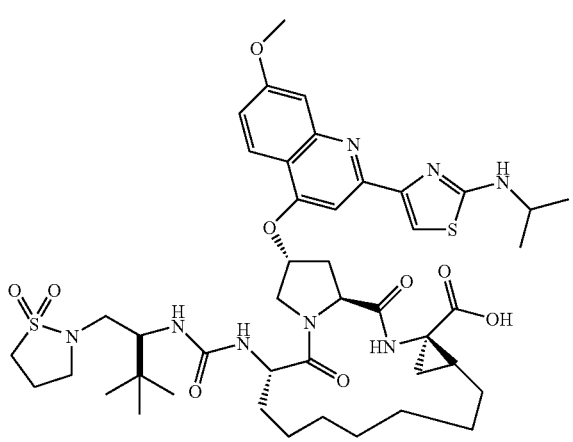
-continued
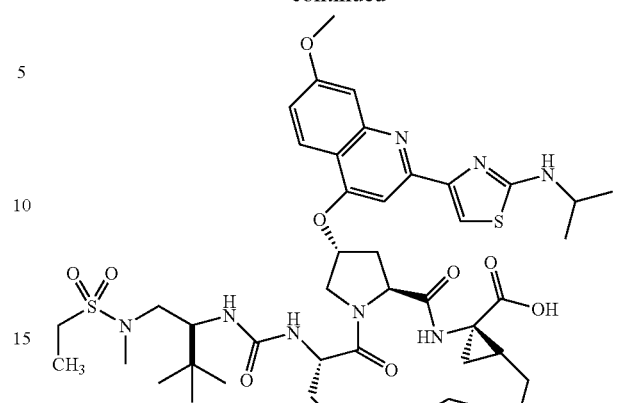
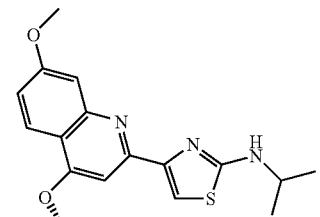
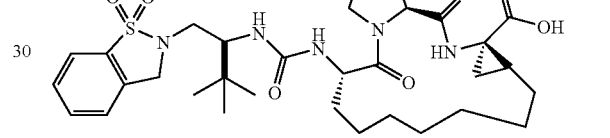
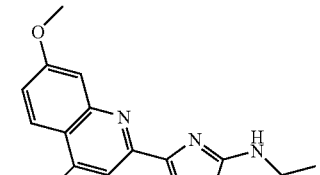
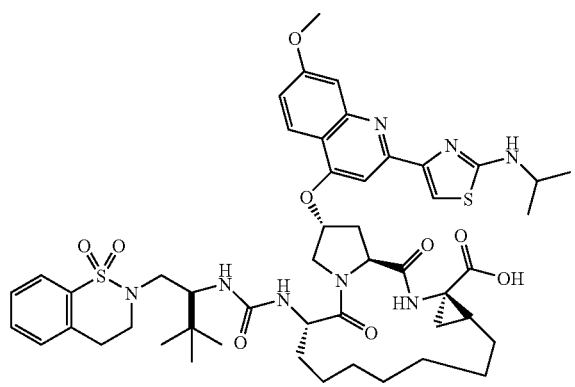

271
-continued
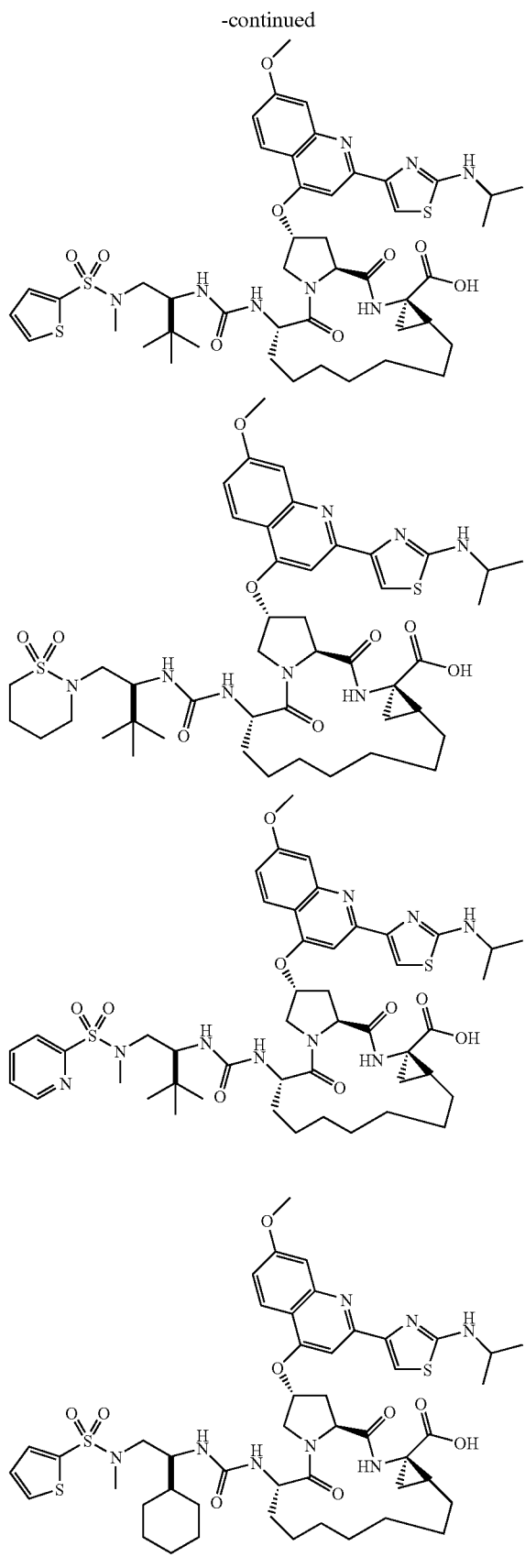
272
-continued
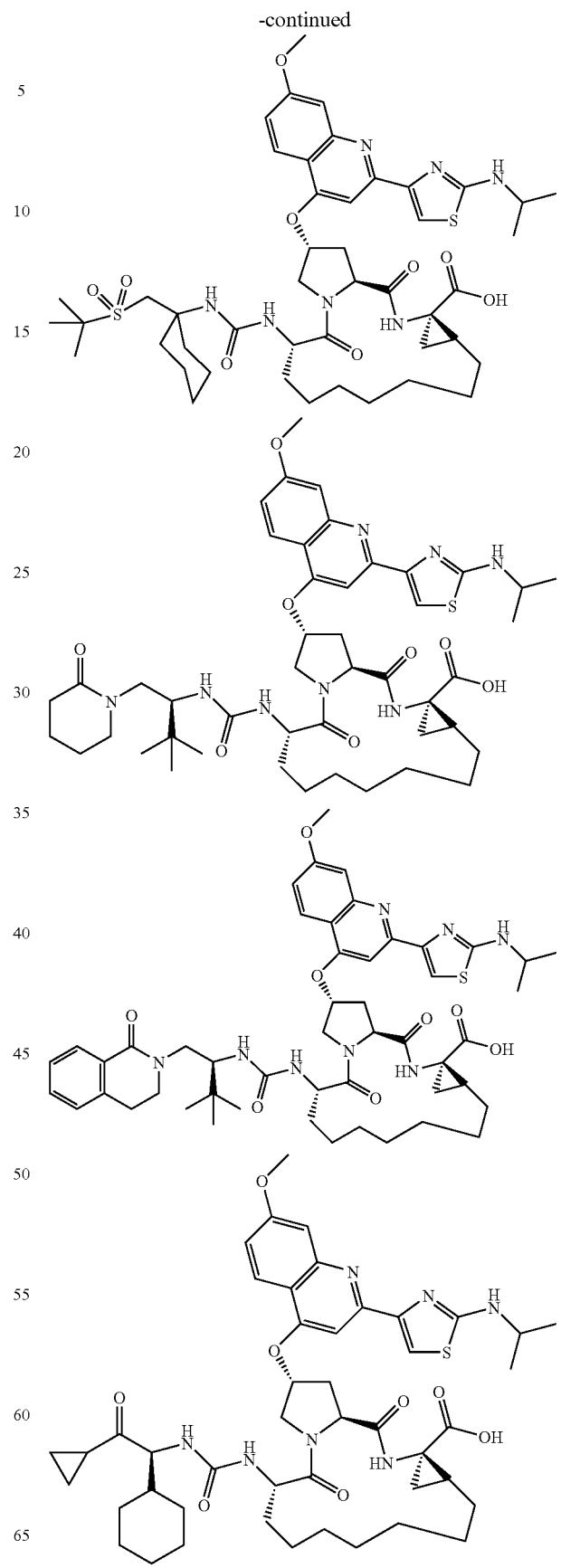

273
-continued
274
-continued
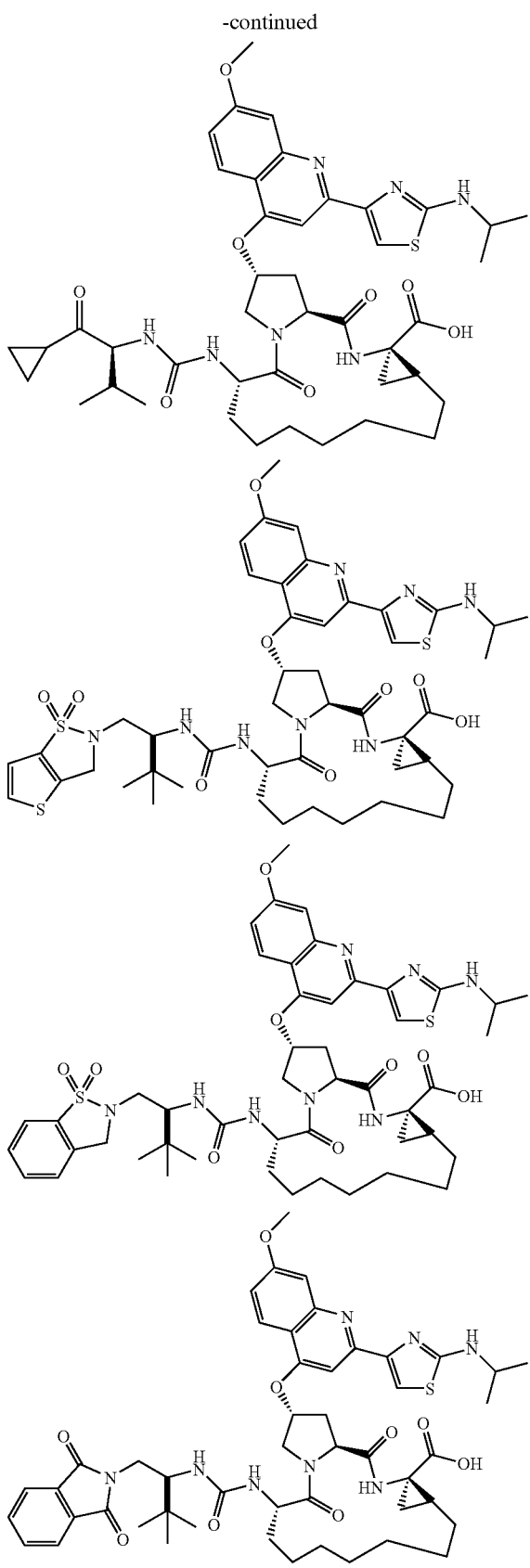
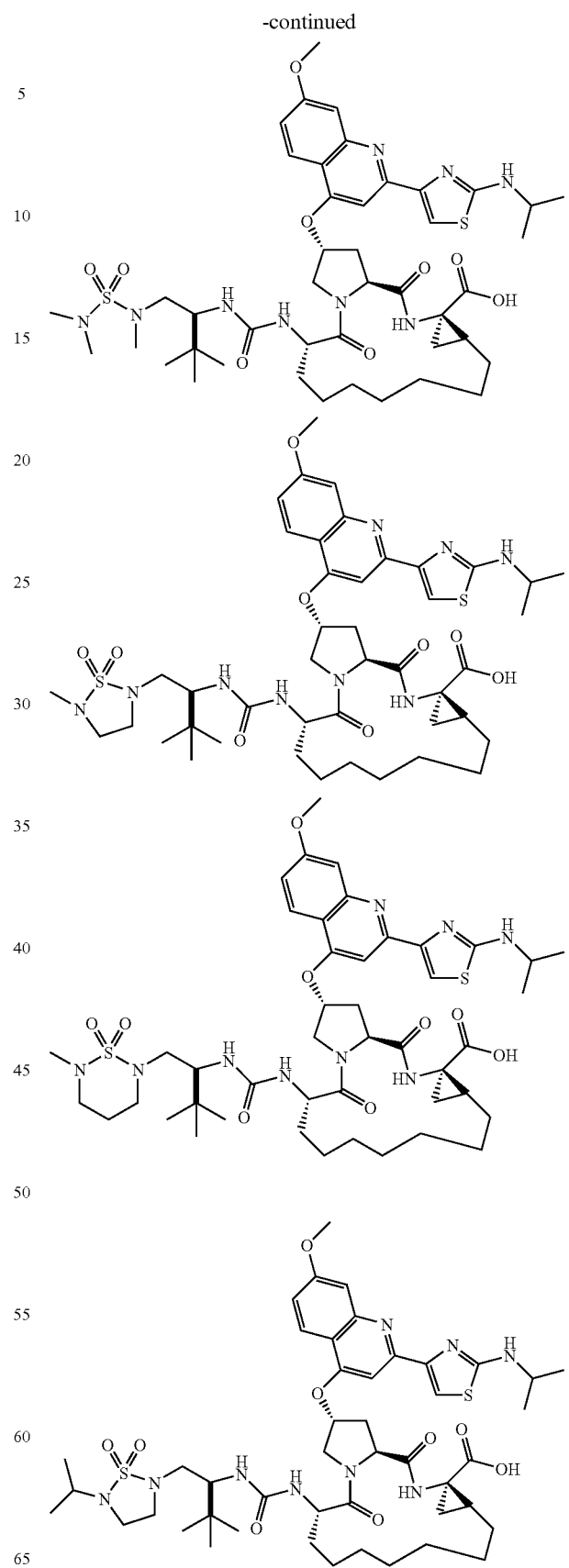

275
-continued
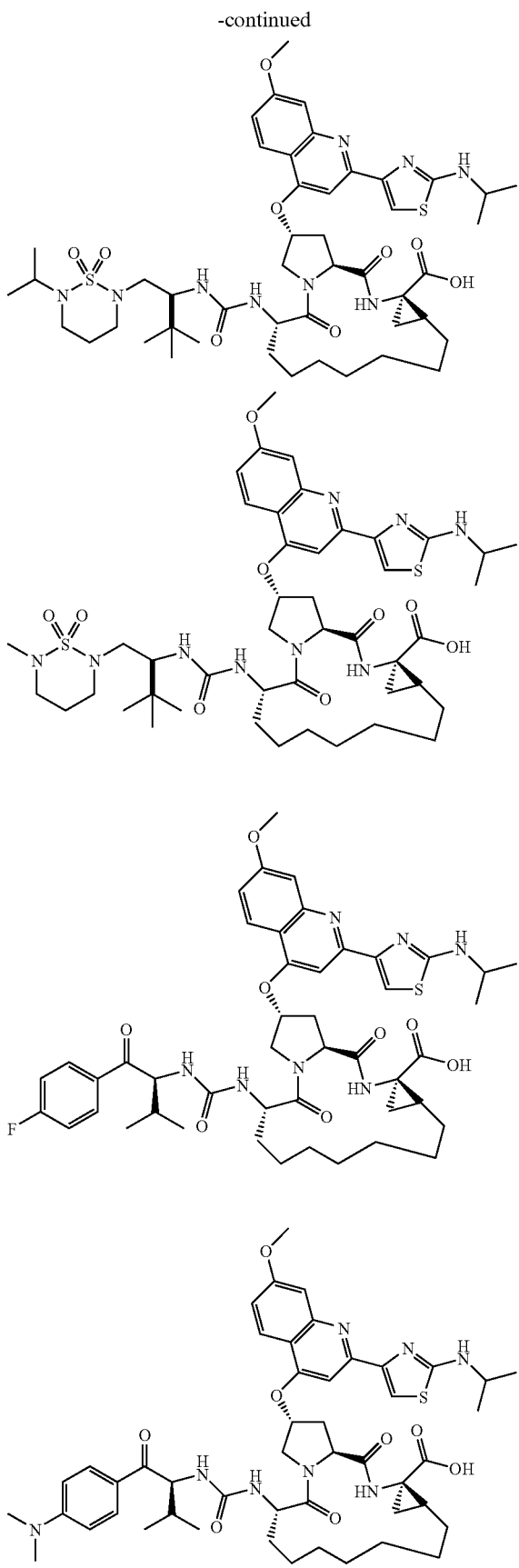
276
-continued
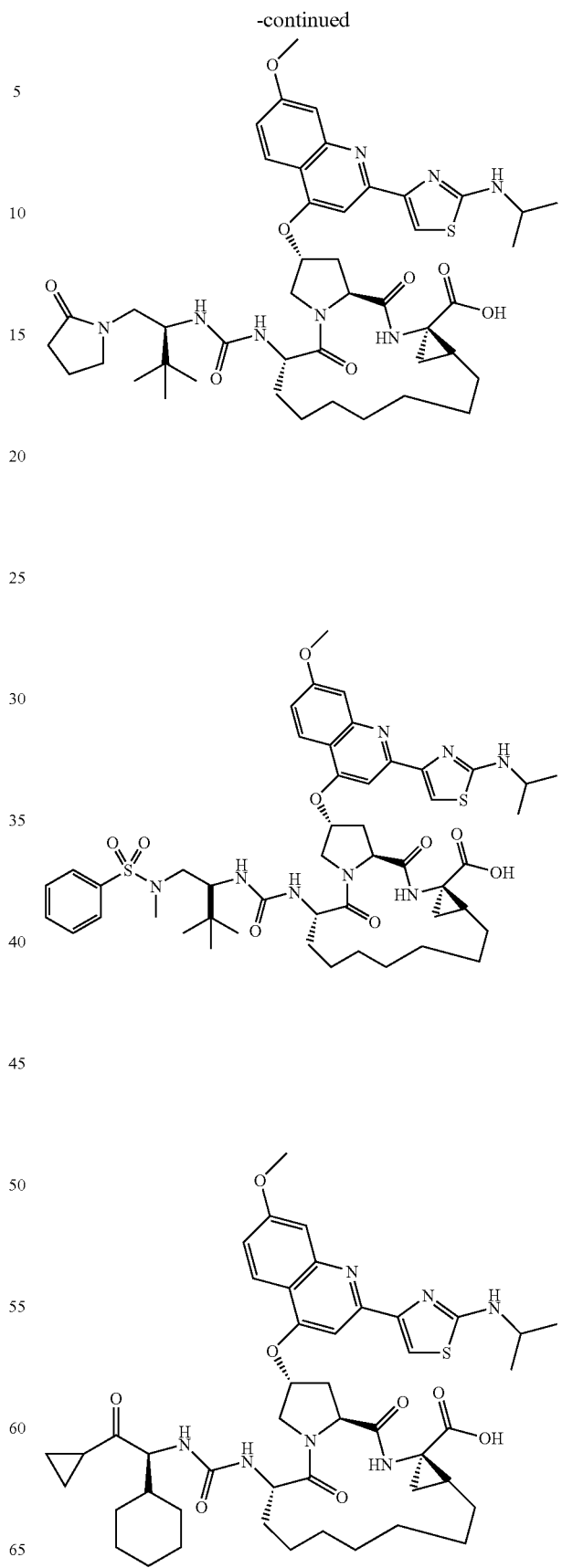

277
-continued
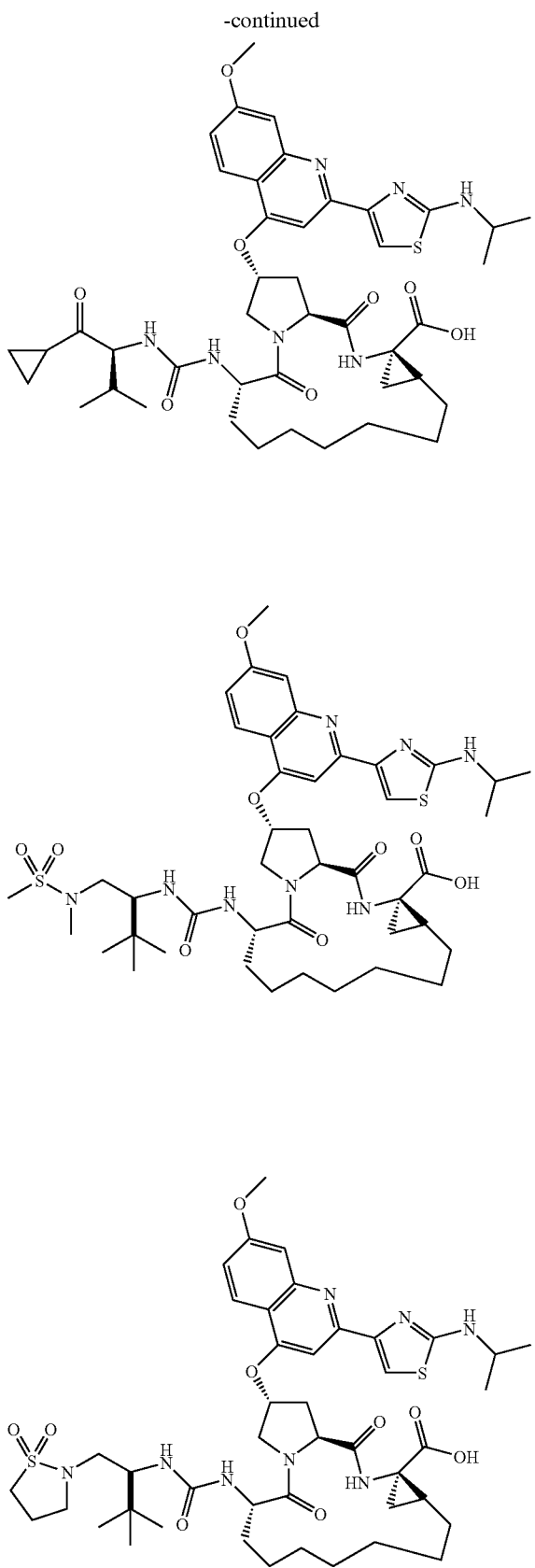
278
-continued
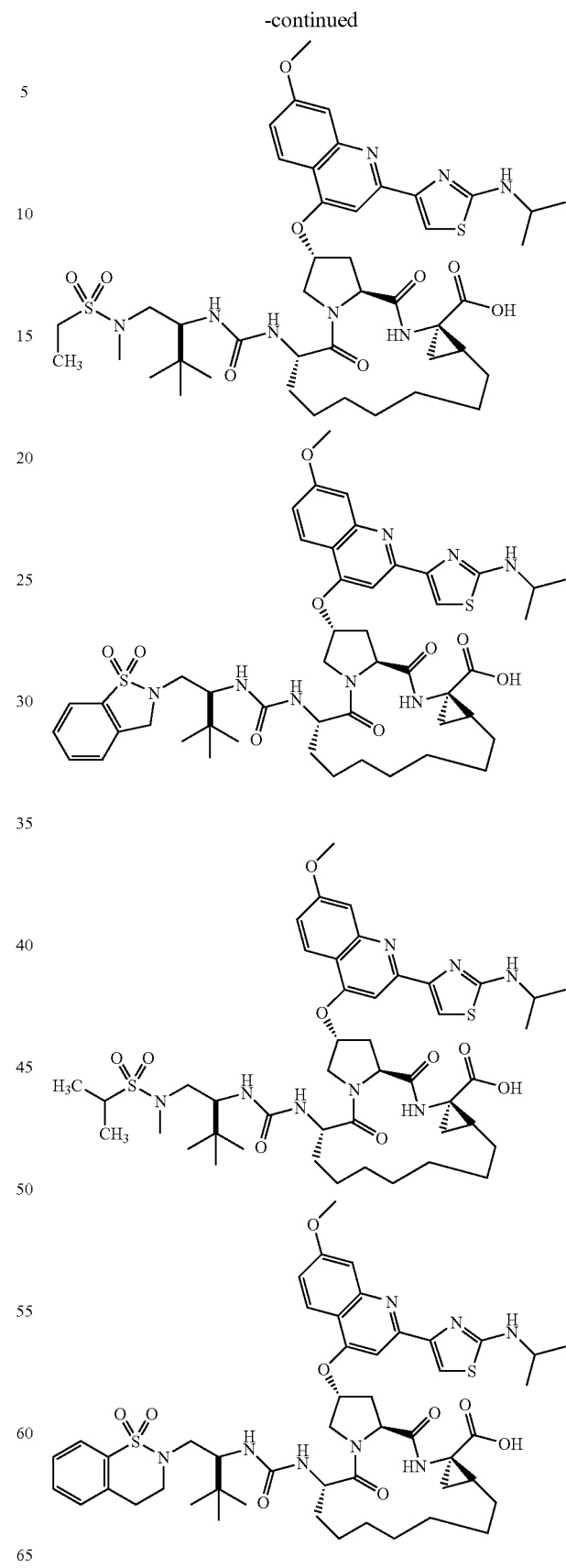

279
-continued
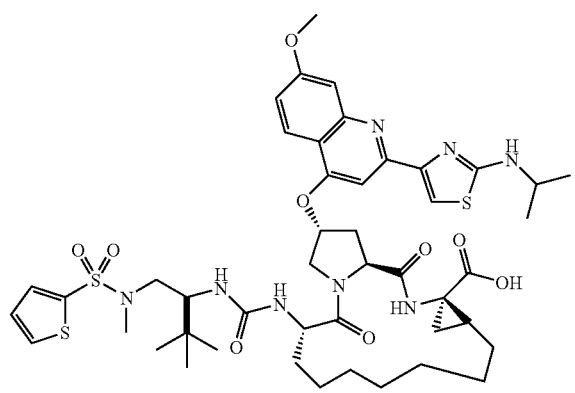
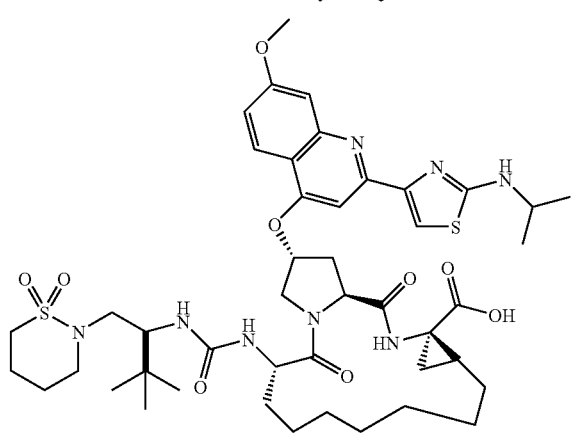
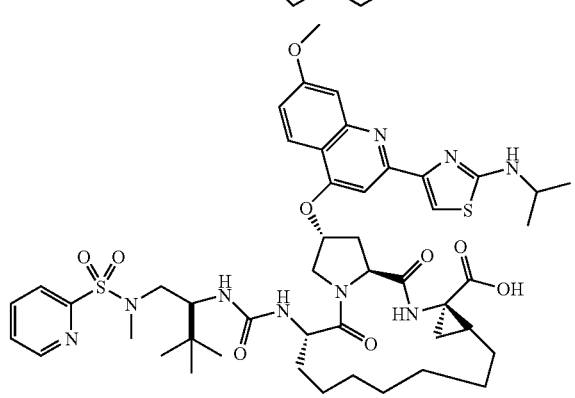
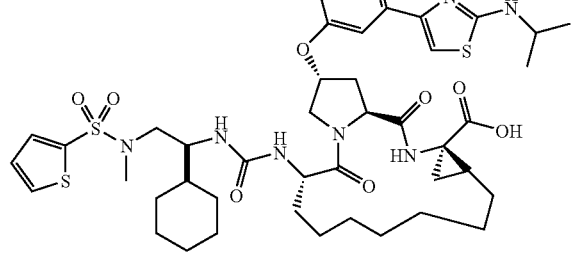
280
-continued
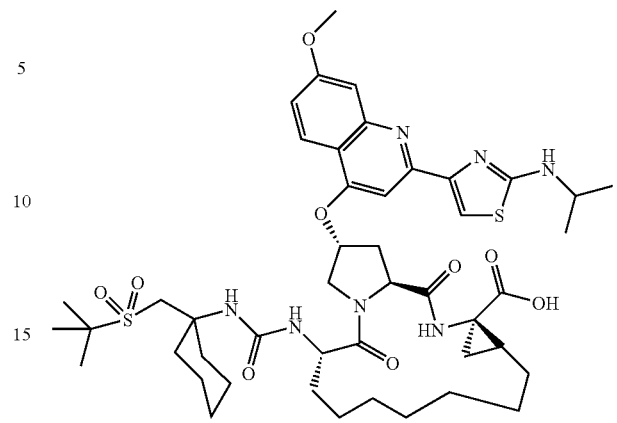
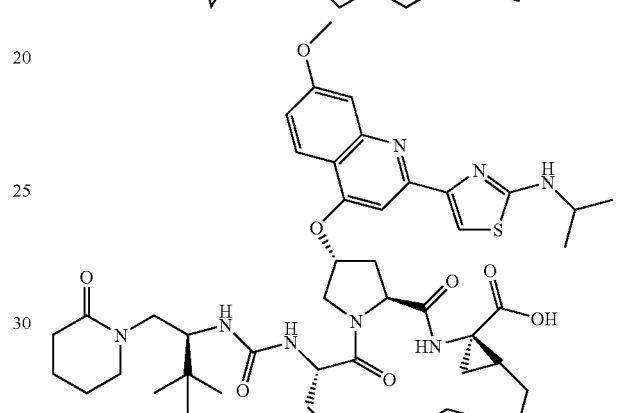
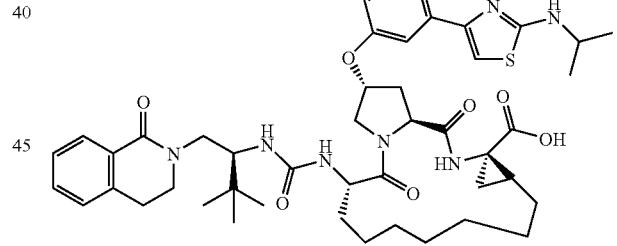
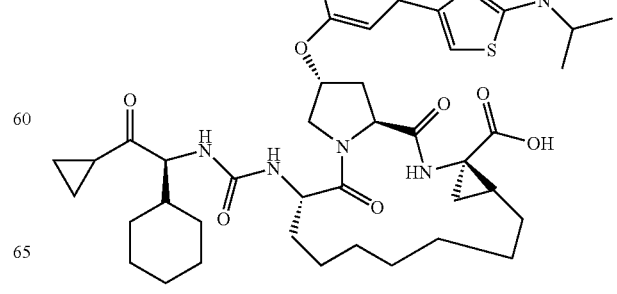

281
-continued
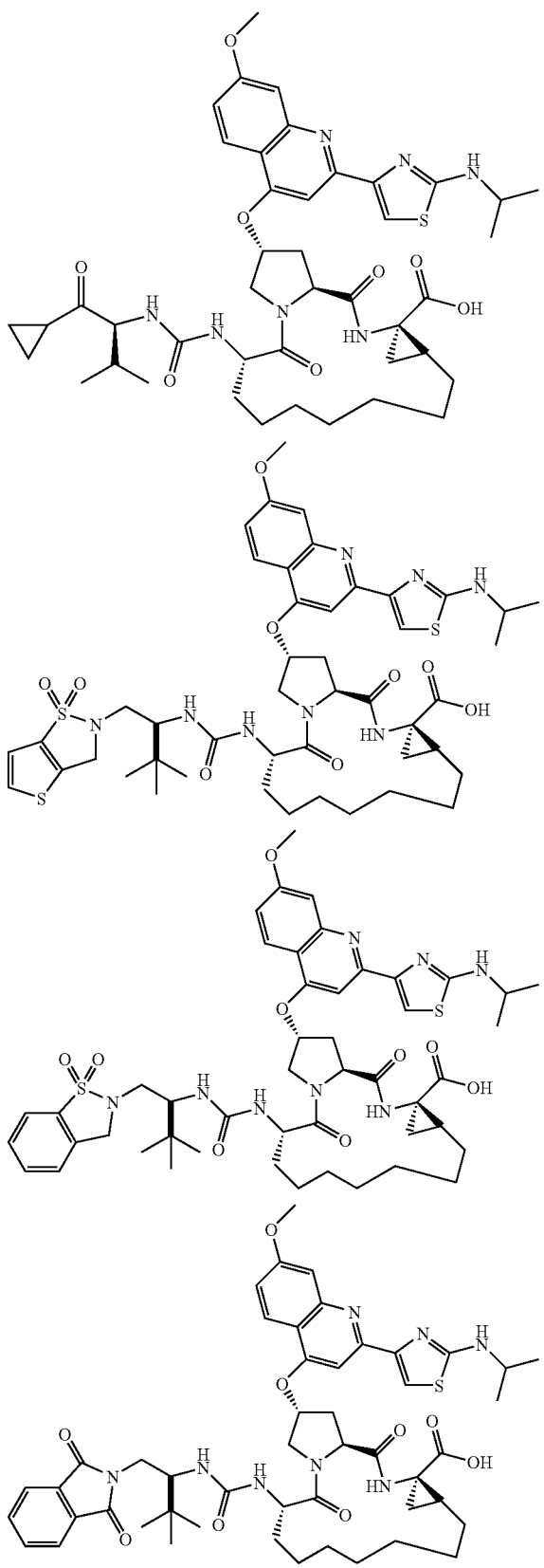
282
-continued
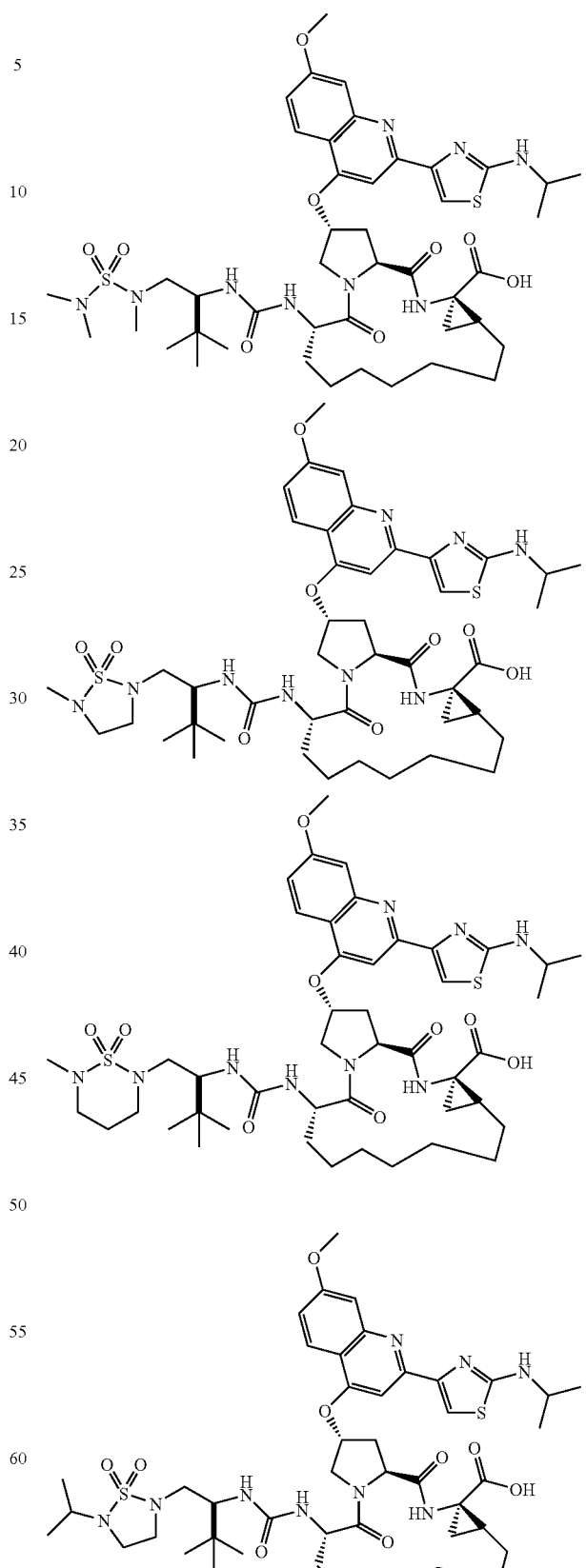

283 284
-continued
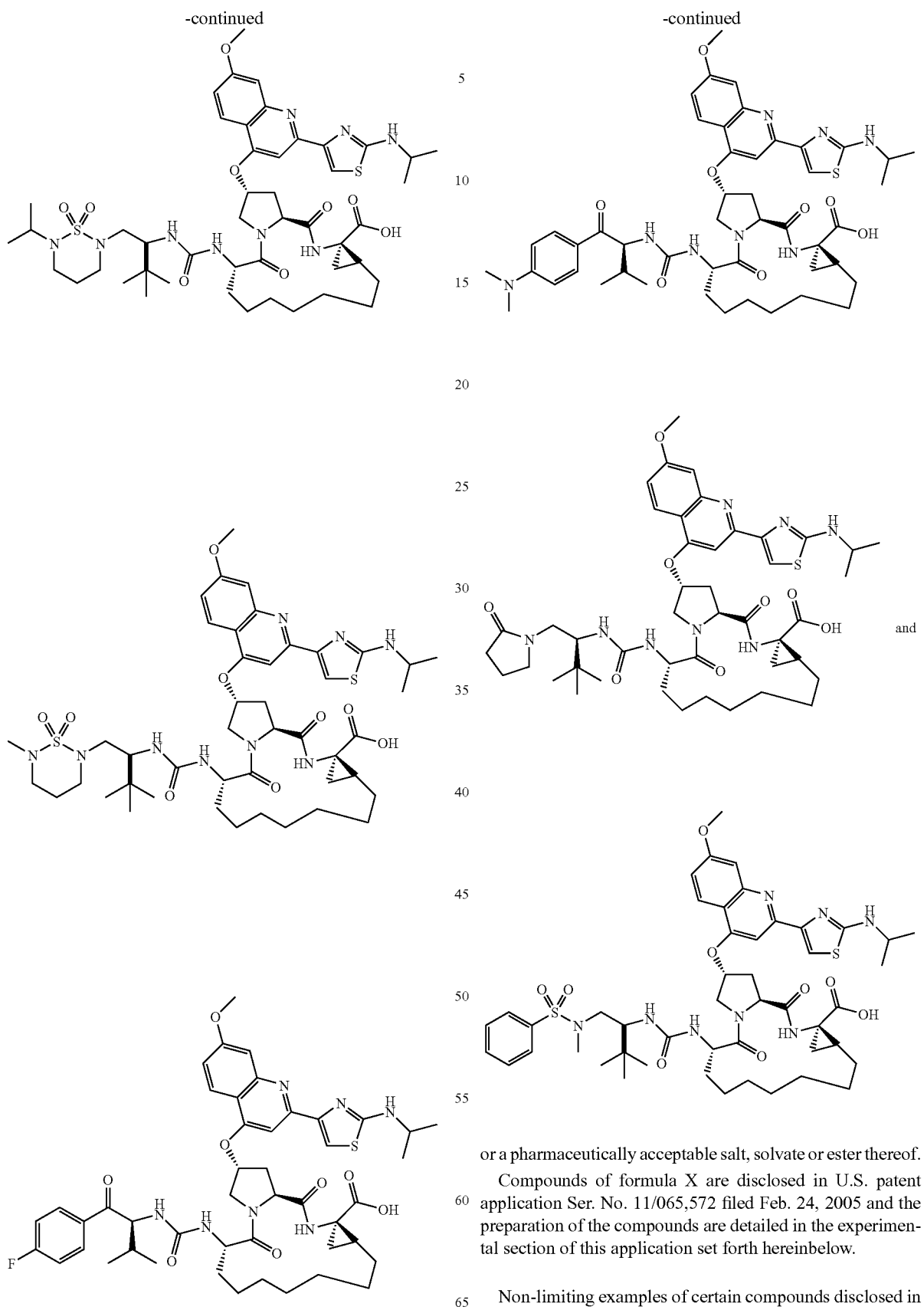
or a pharmaceutically acceptable salt, solvate or ester thereof.
Compounds of formula X are disclosed in U.S. patent application Ser. No. 11/065,572 filed Feb. 24, 2005 and the preparation of the compounds are detailed in the experimental section of this application set forth hereinbelow.
Non-limiting examples of certain compounds disclosed in U.S. patent application Ser. No. 11/065,572 filed Feb. 24, 2005 are:

285 286
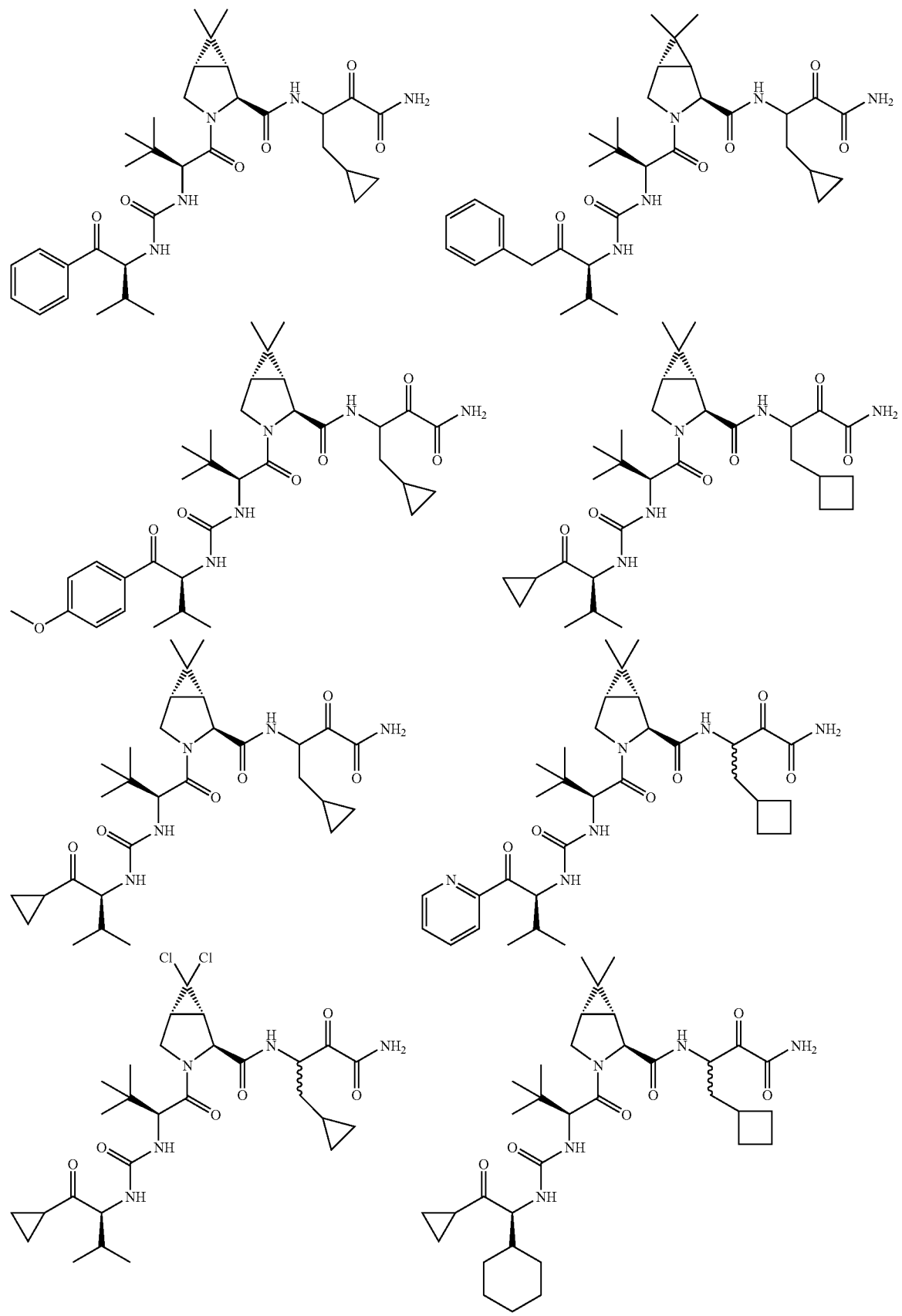

-continued
287
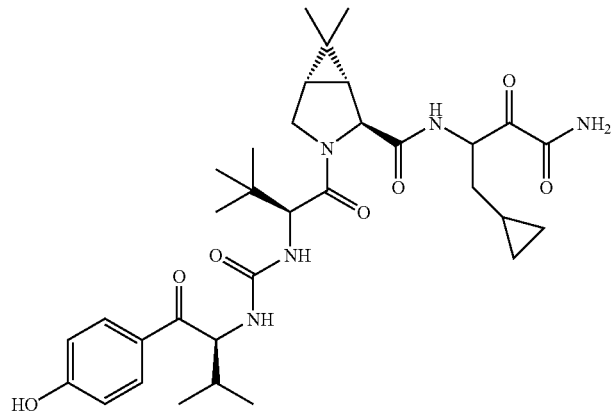
288
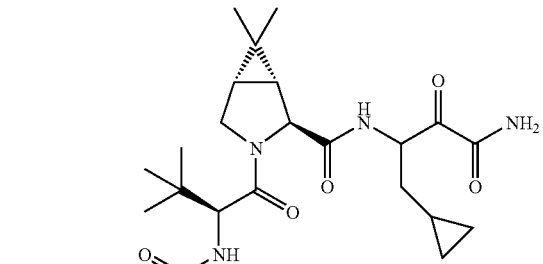
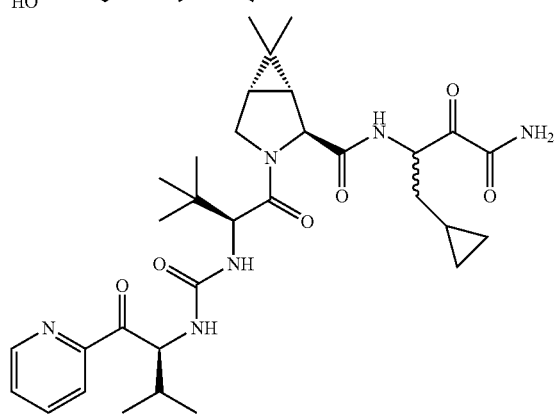
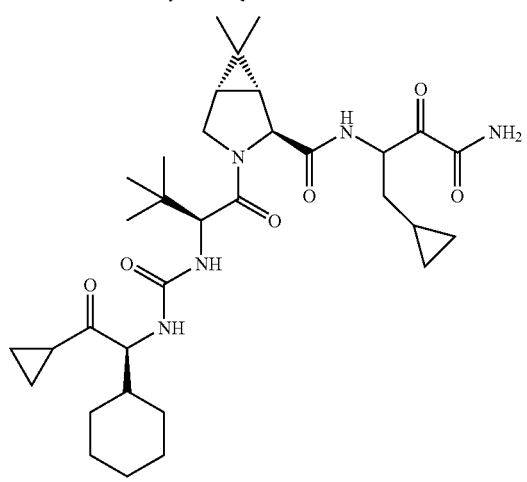
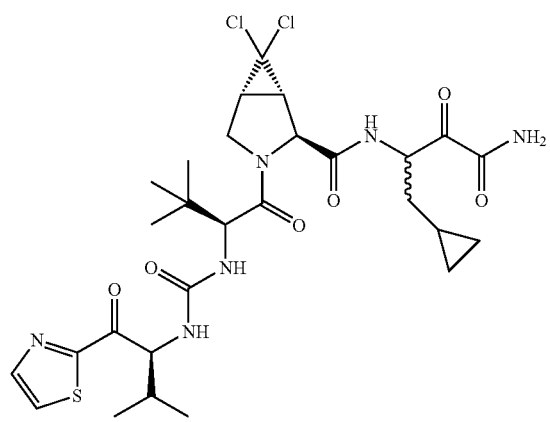
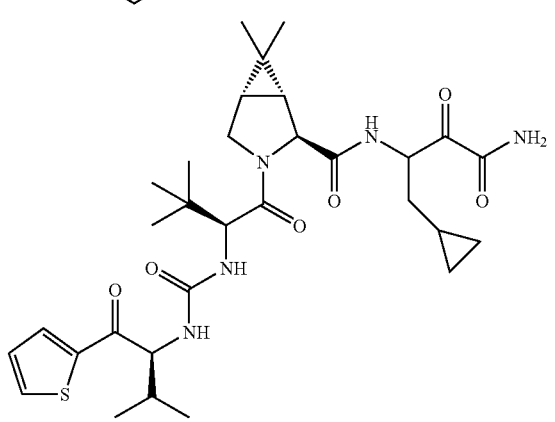
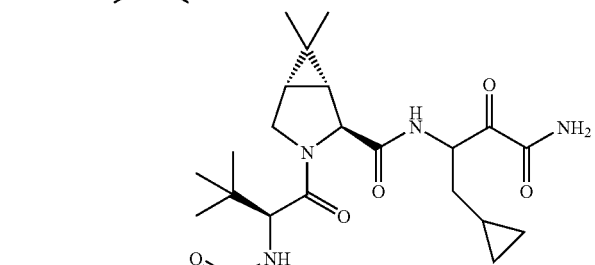
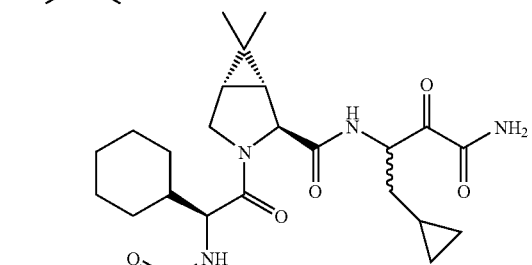

289 290
-continued
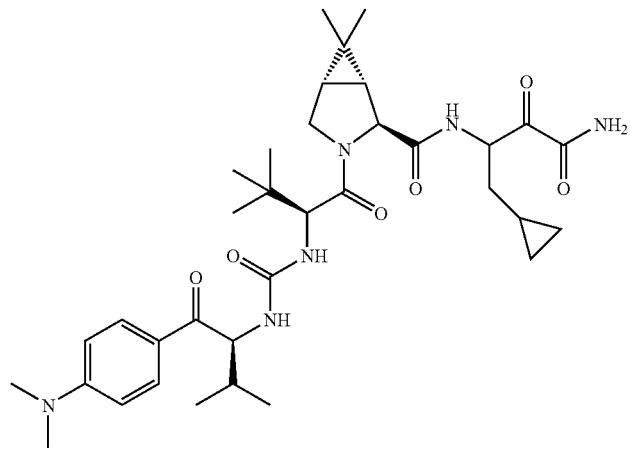
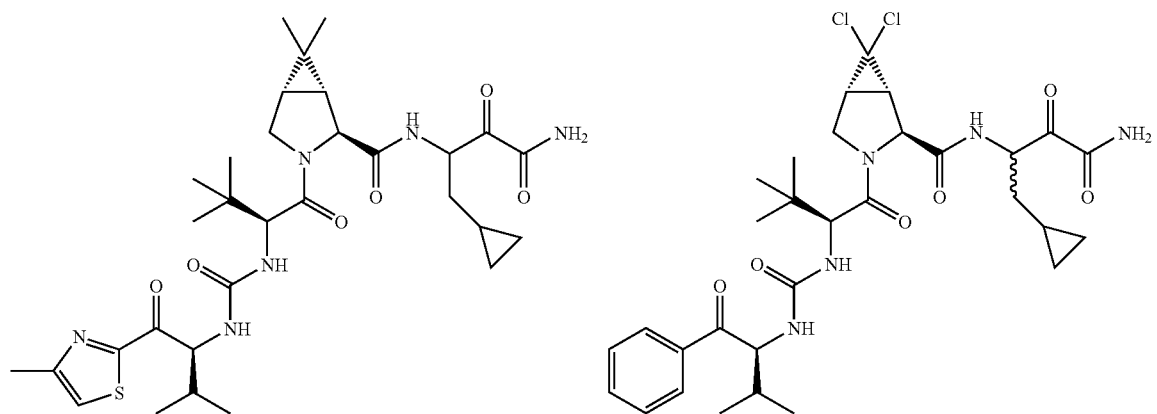
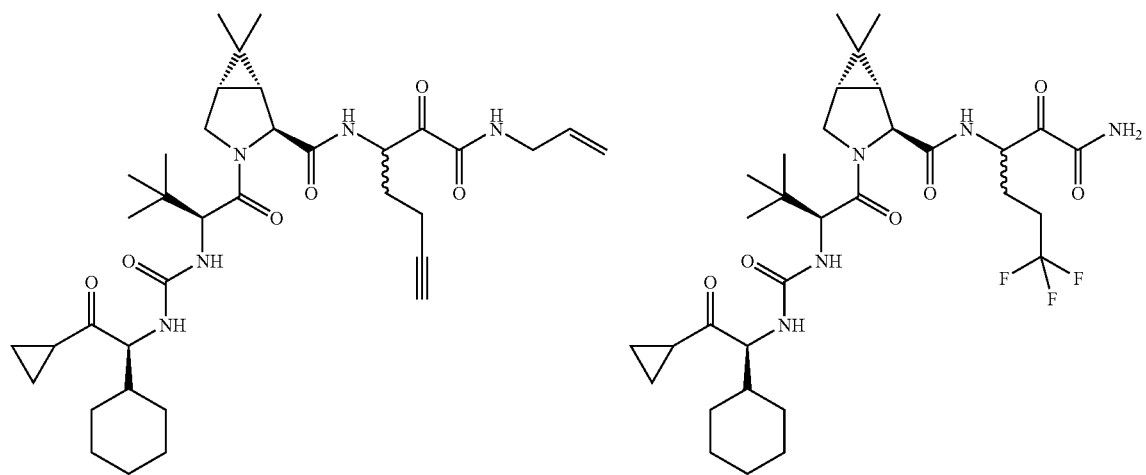

291
-continued
292
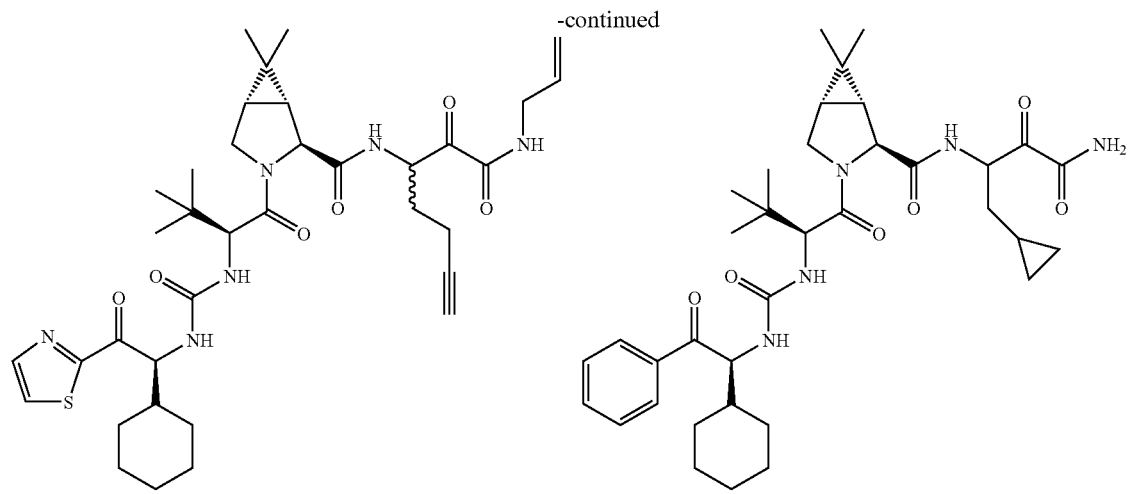
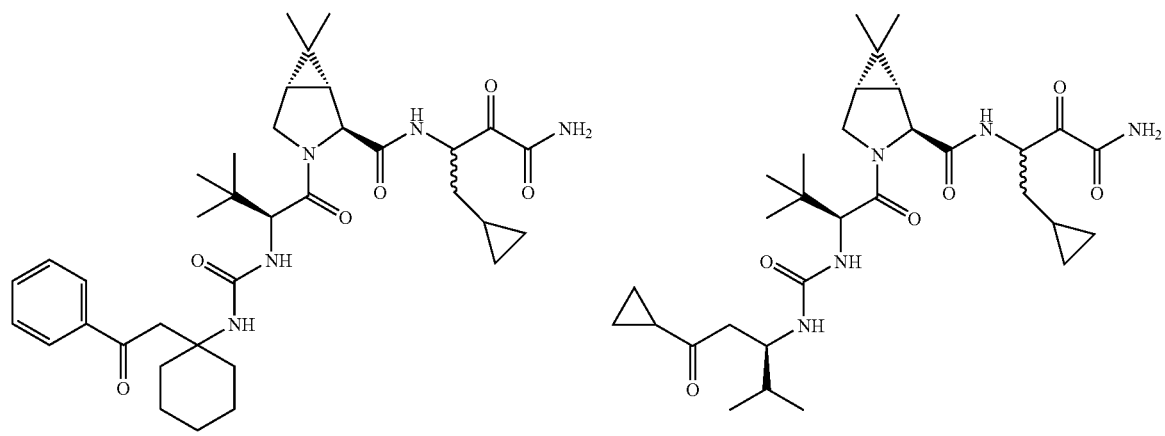
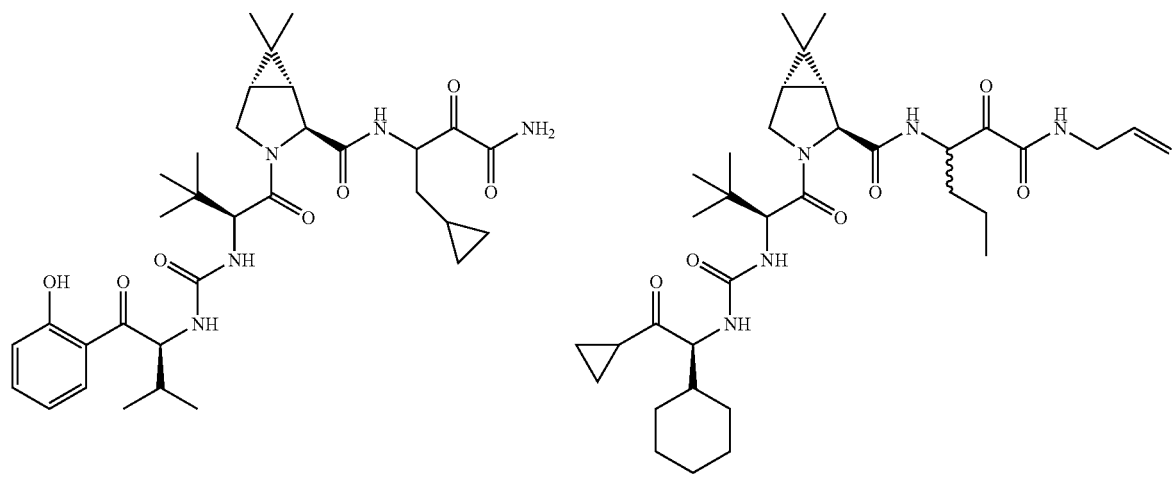

293 294
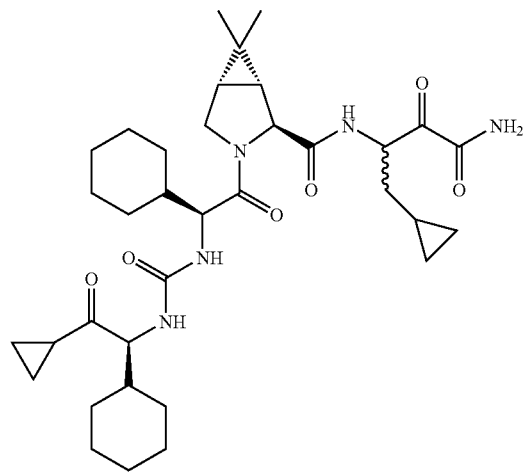
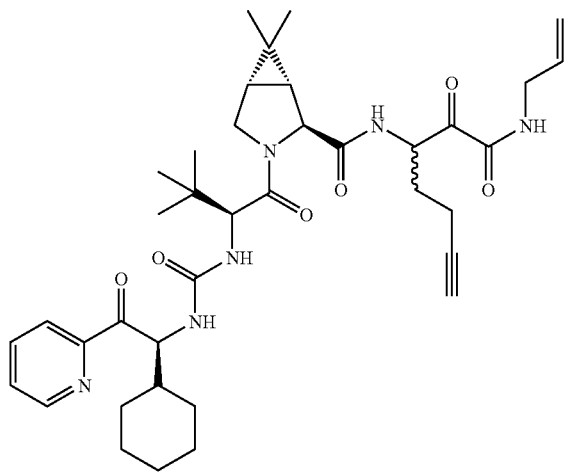
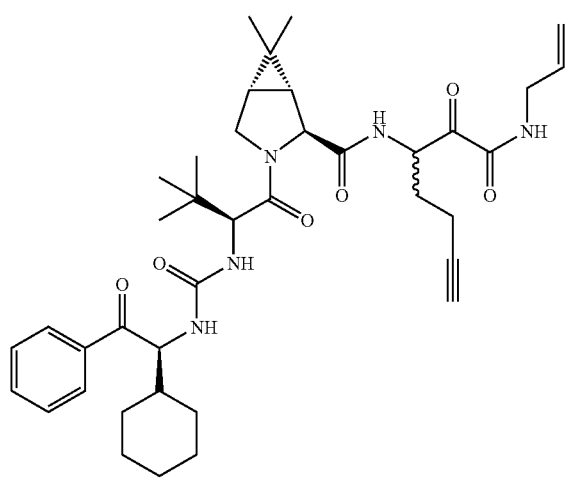
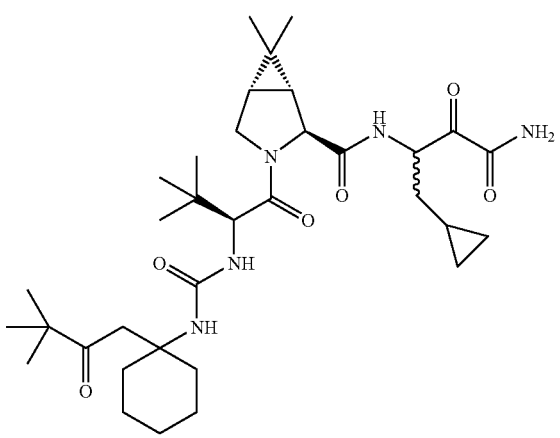
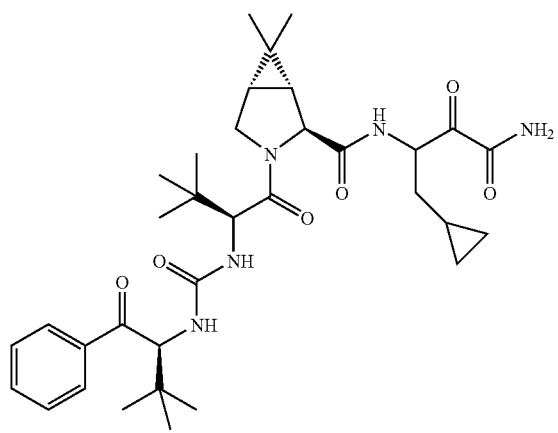
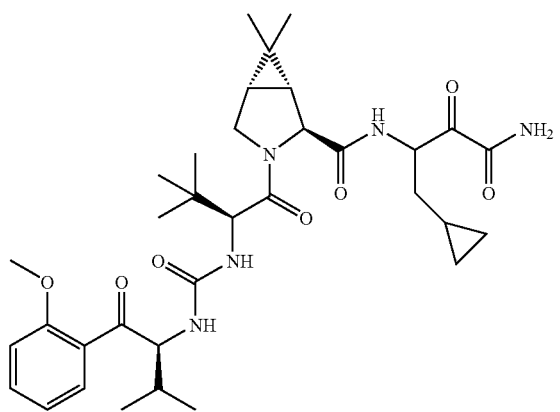

295 296
-continued
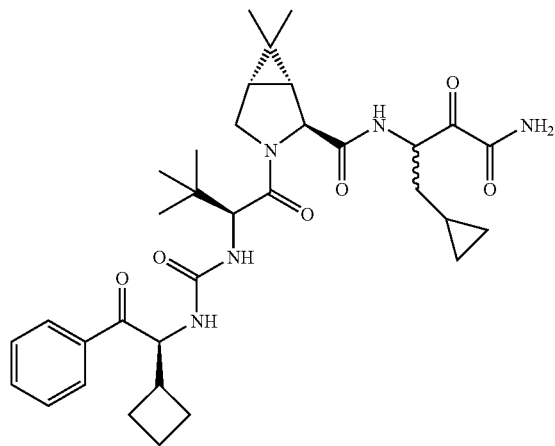
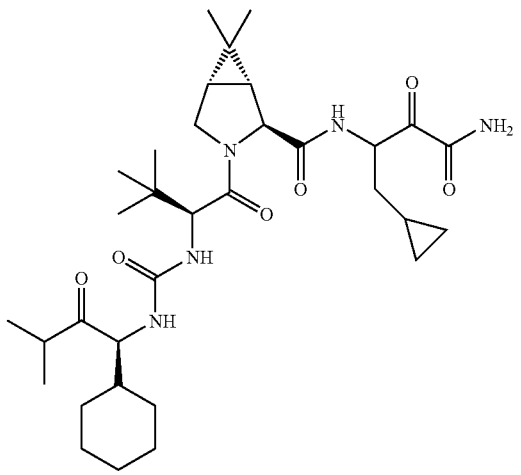
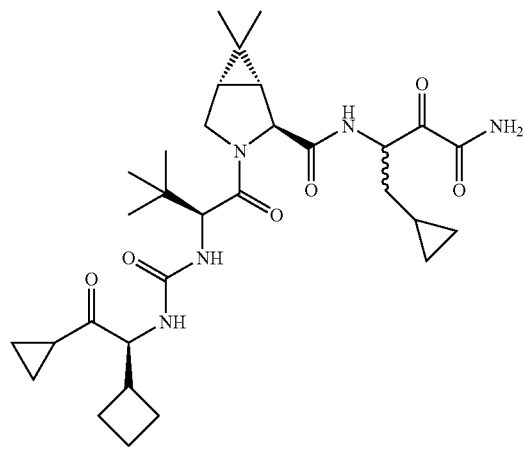
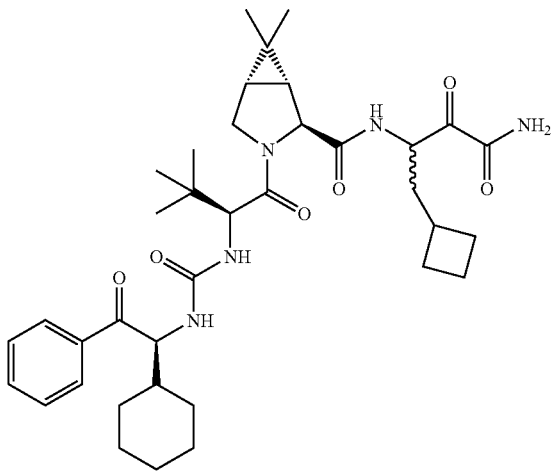
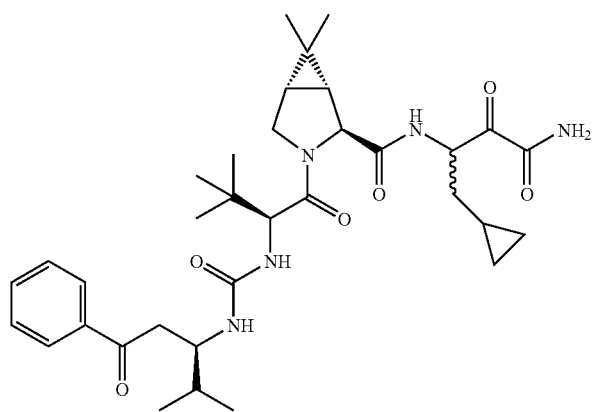
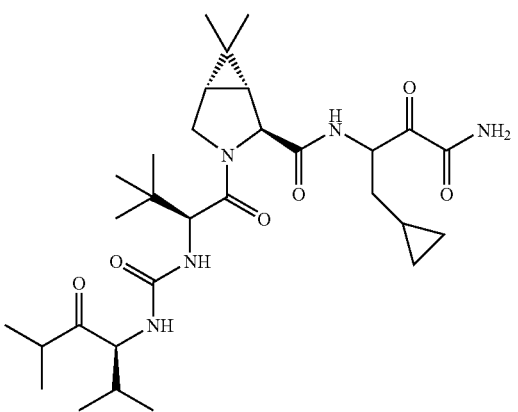

297
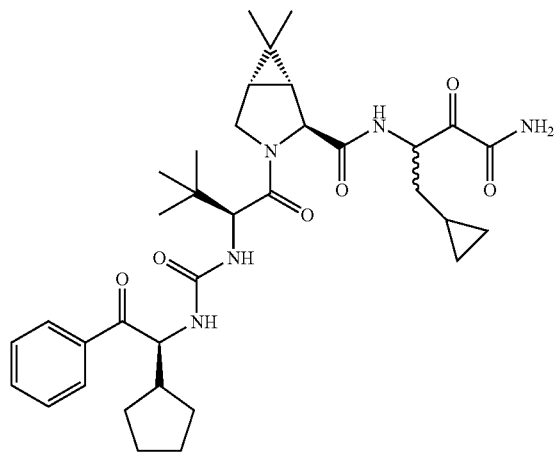
298
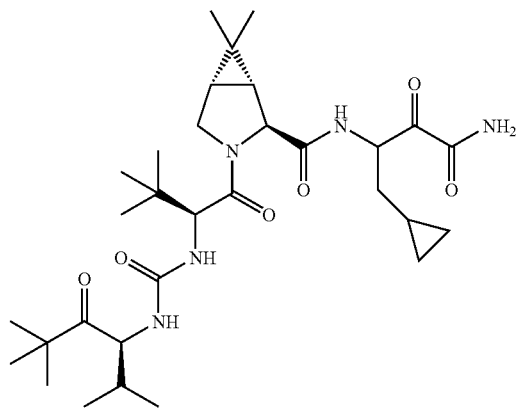
-continued
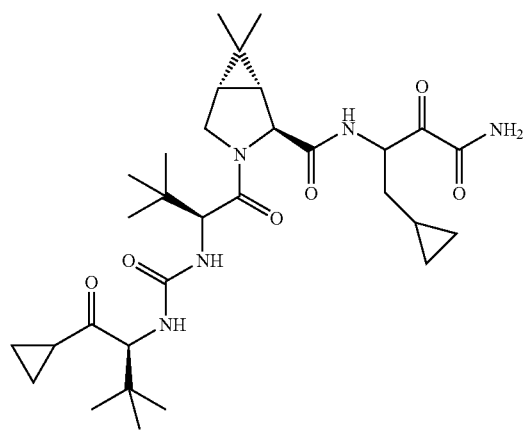
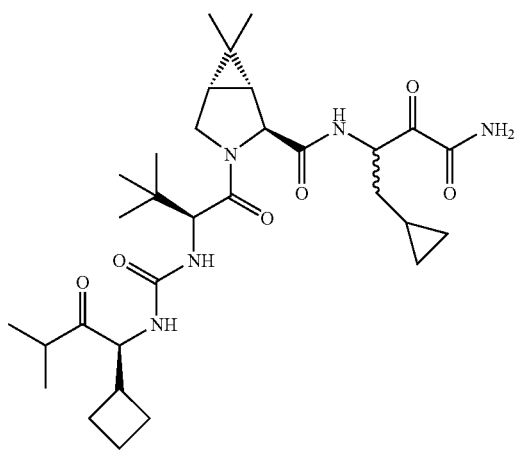
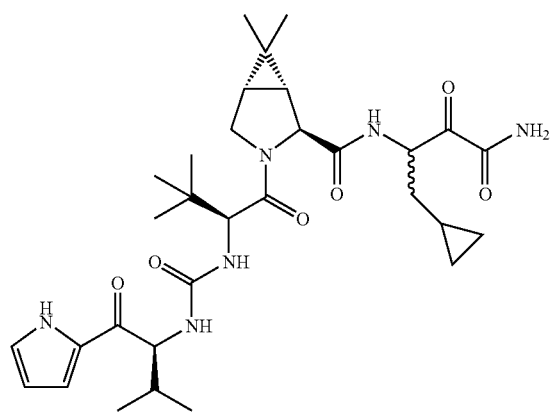
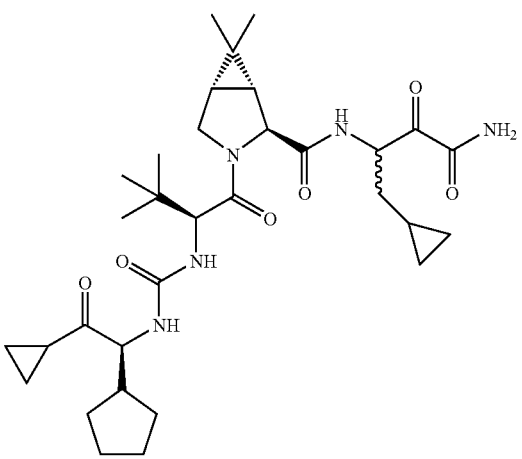

-continued
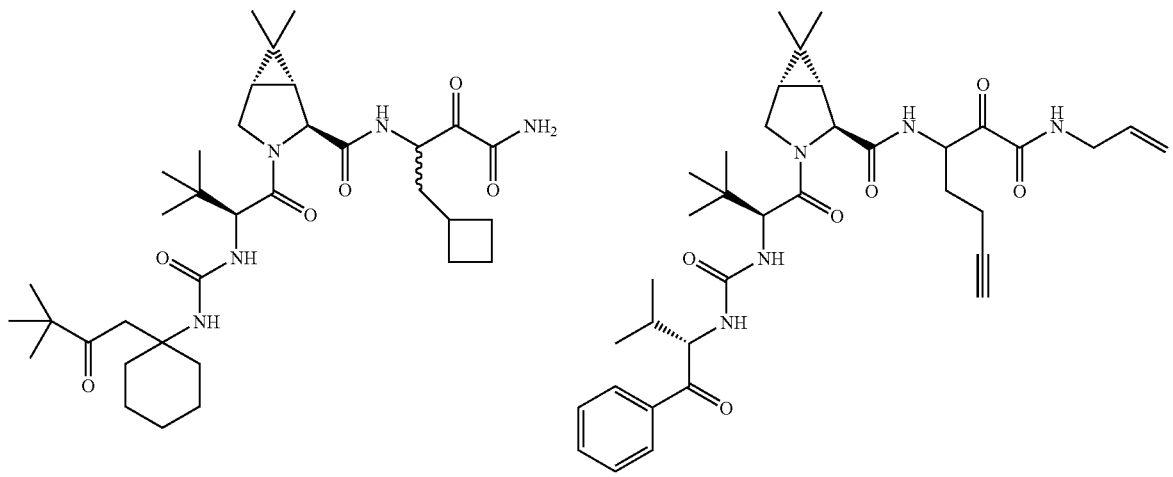
299
300
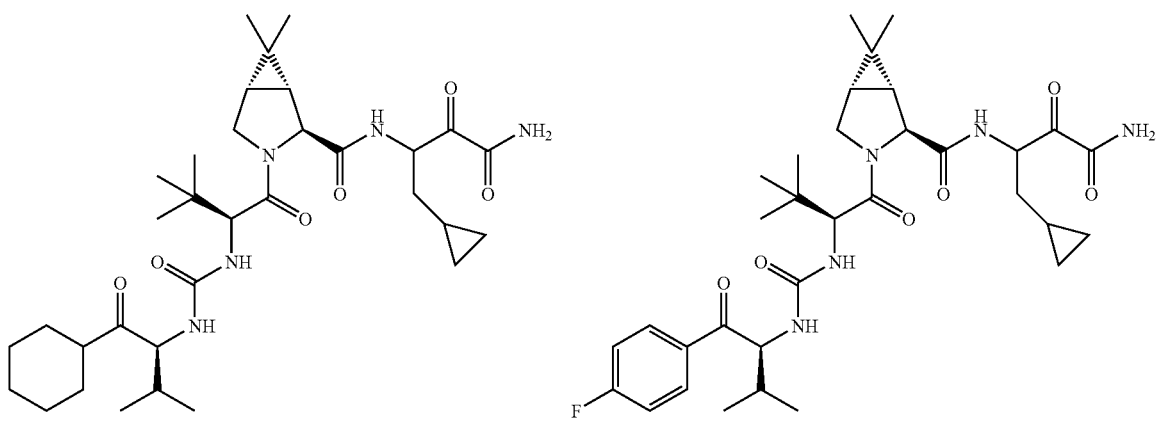
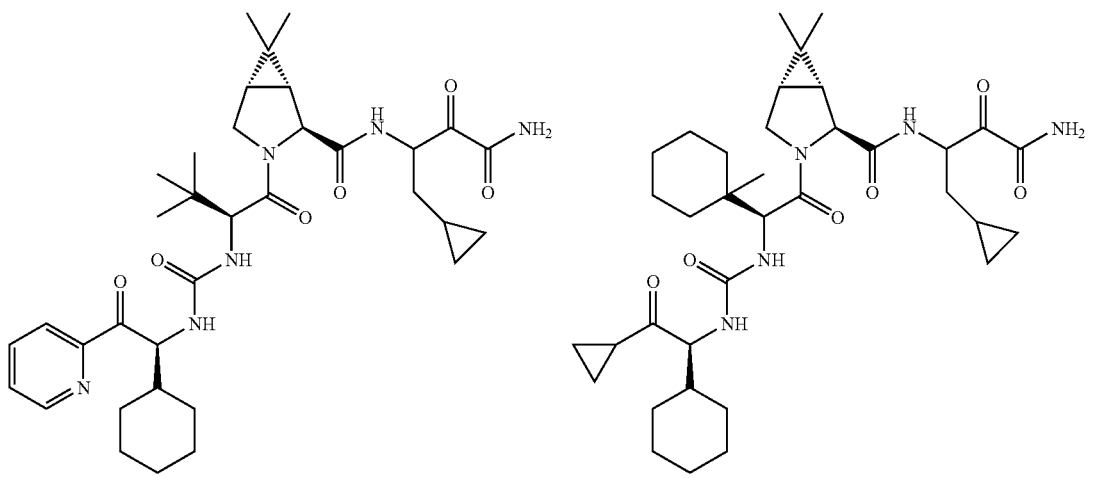

-continued
| 301 | 302 |
|---|---|
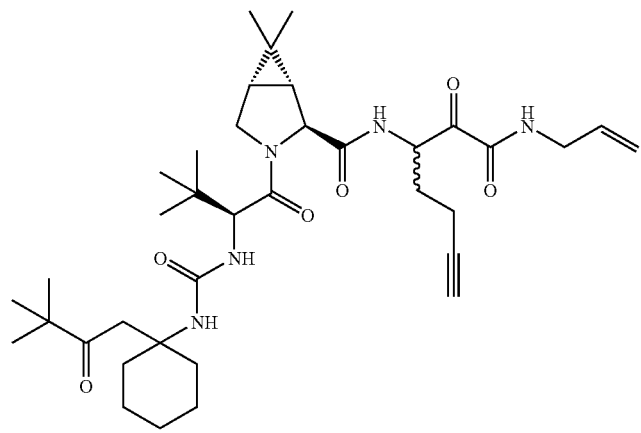
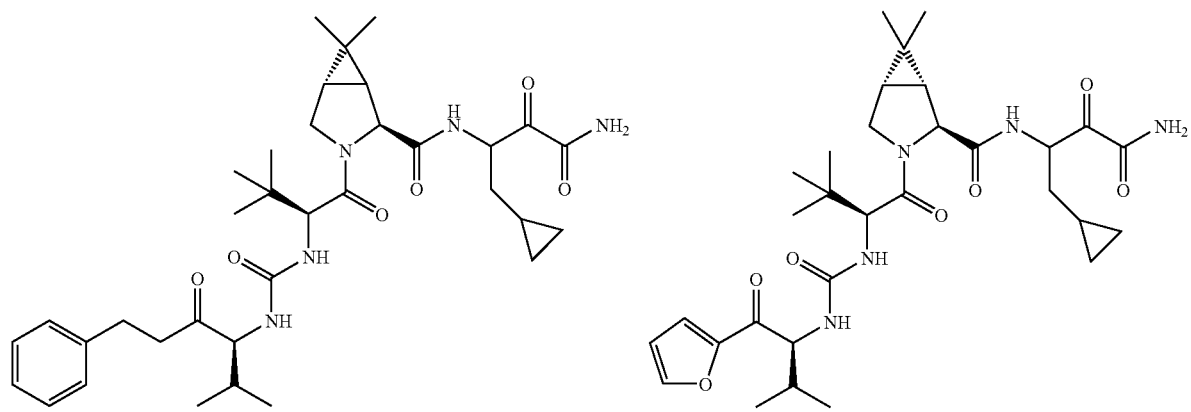
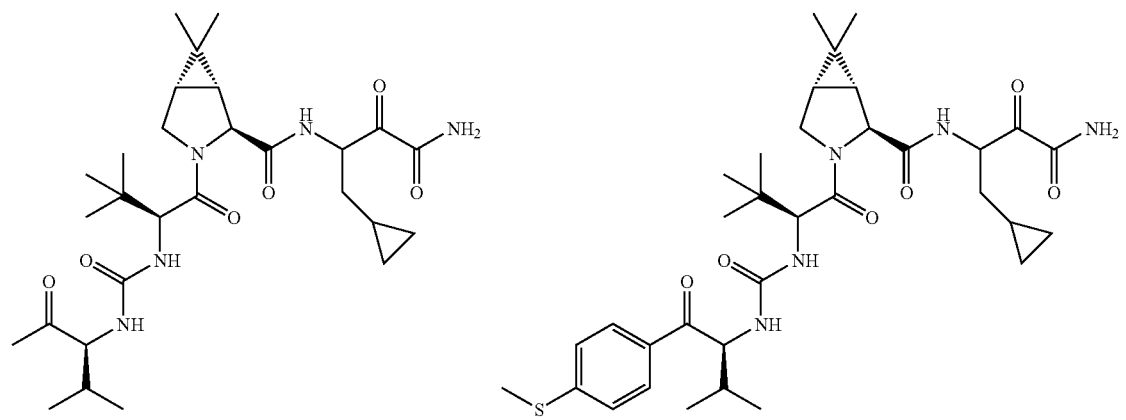

303
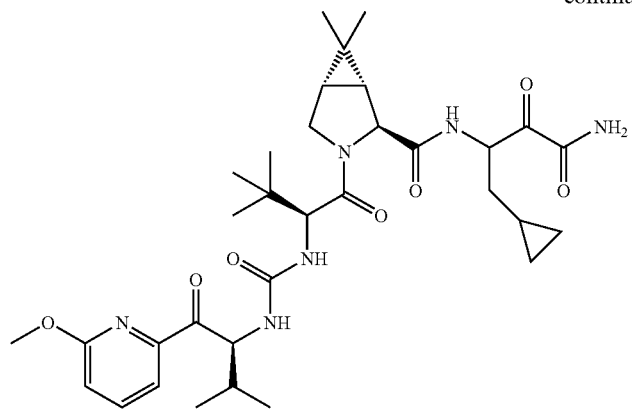
304
-continued
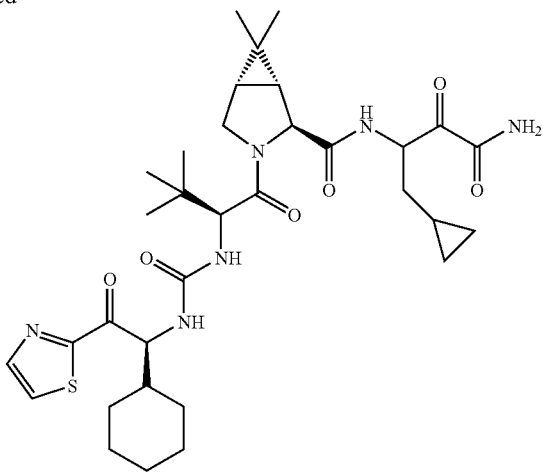
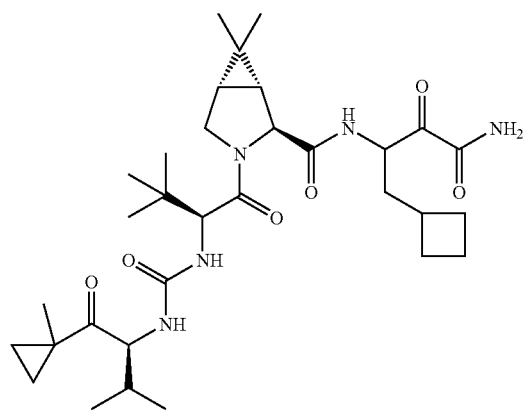
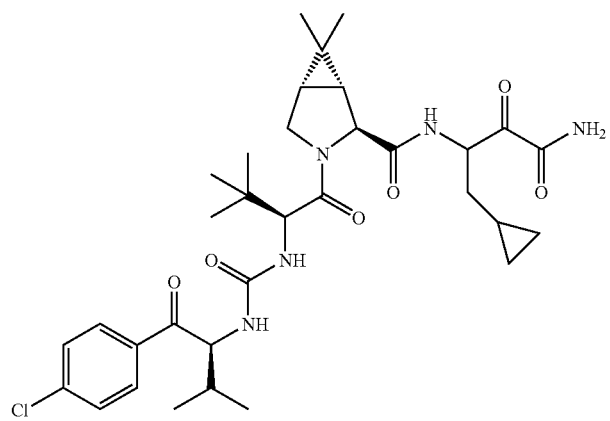
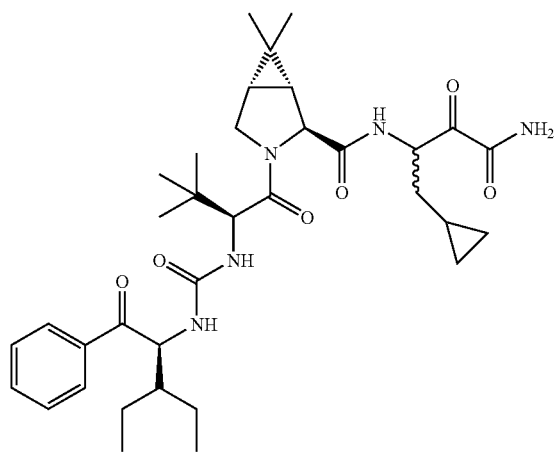
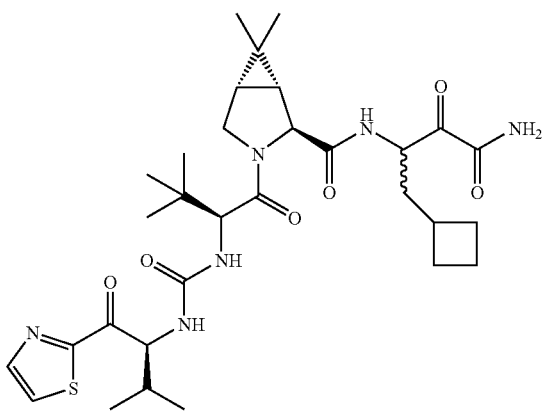

305 306
-continued
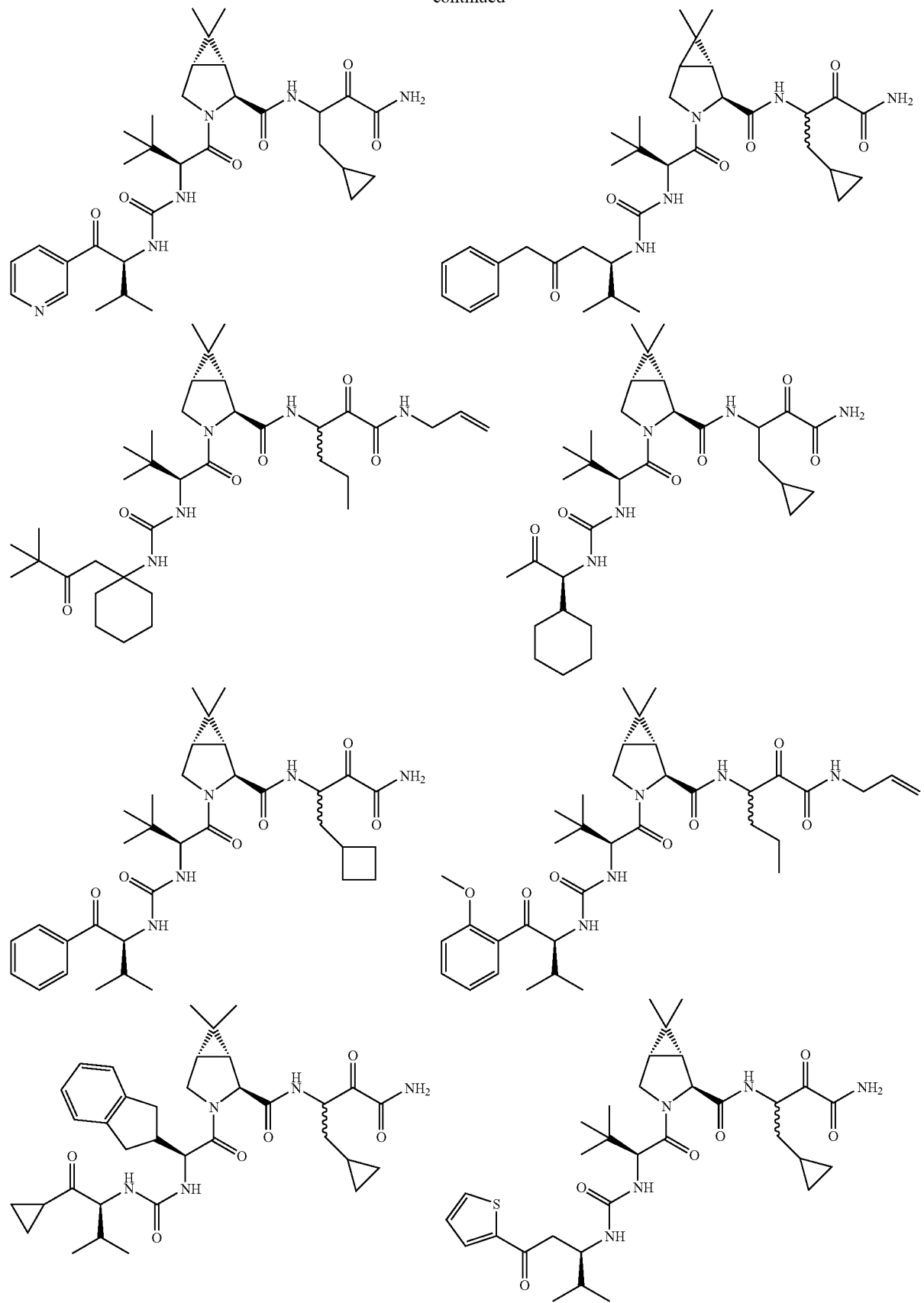

307
308
-continued
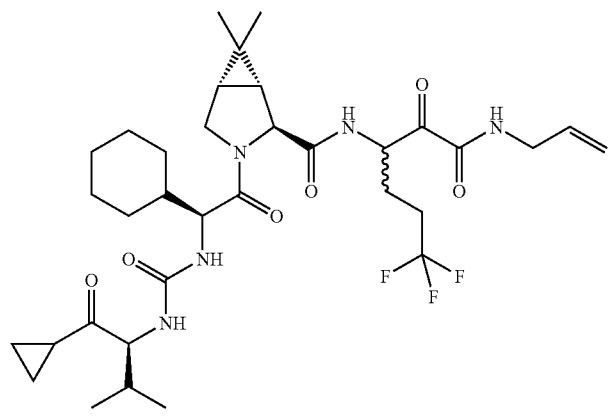
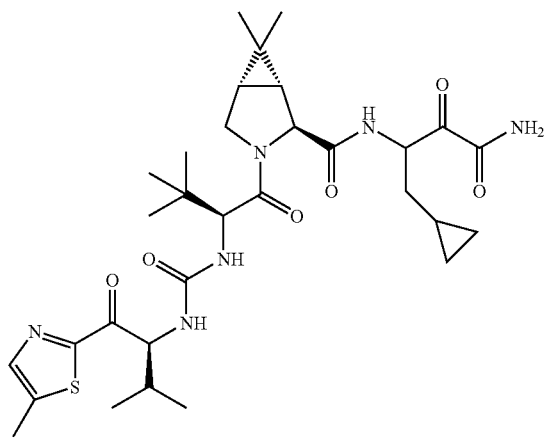
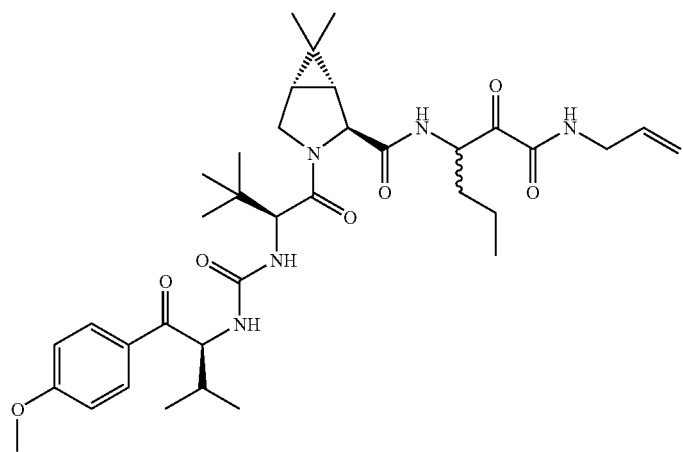
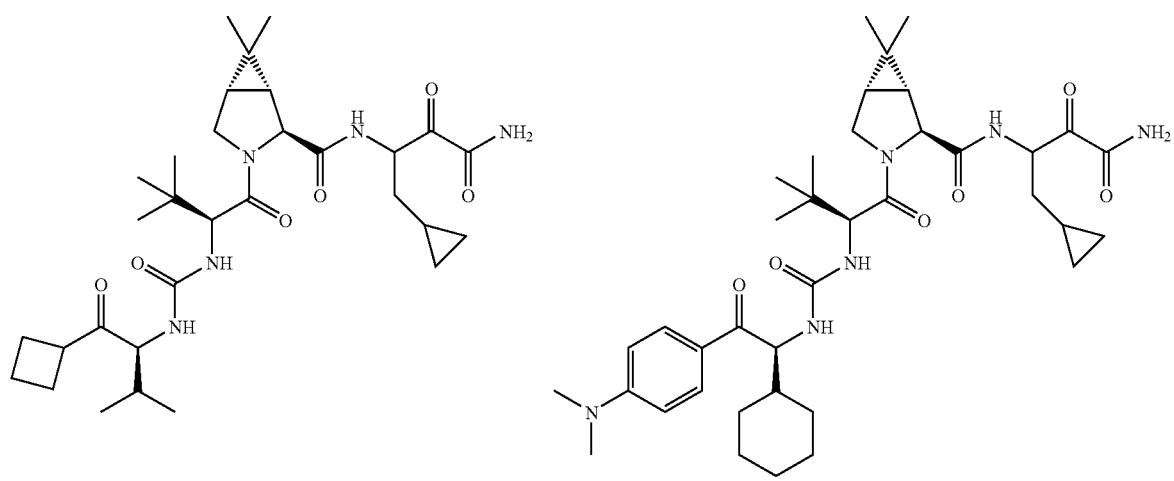

-continued
309
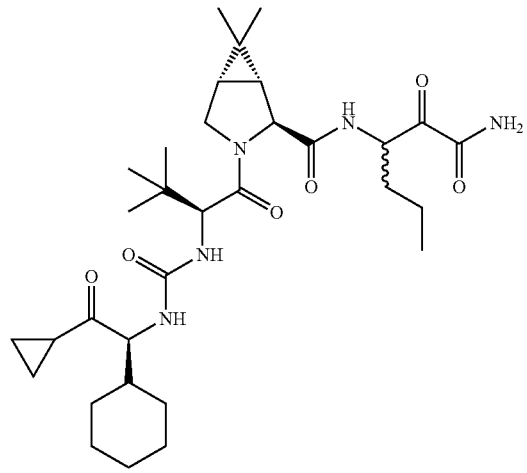
310
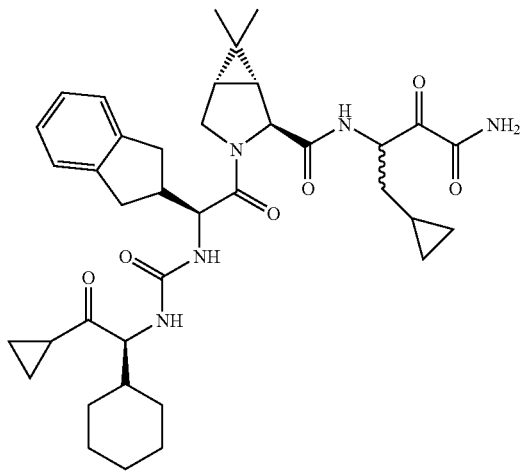
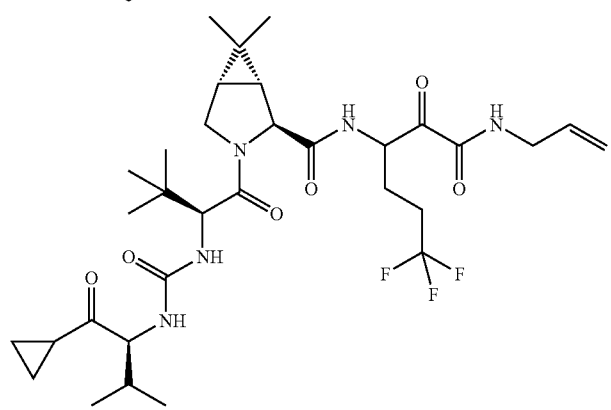
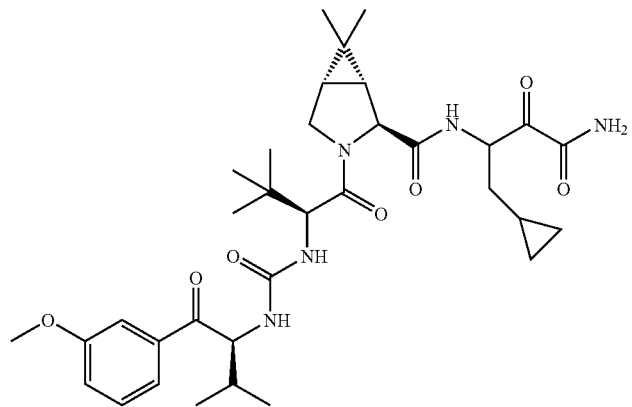
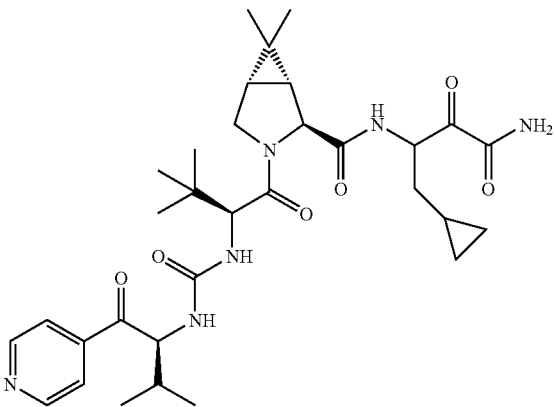
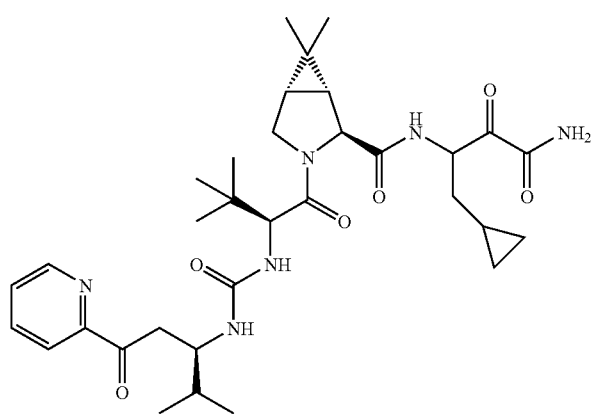

-continued
| 311 | 312 |
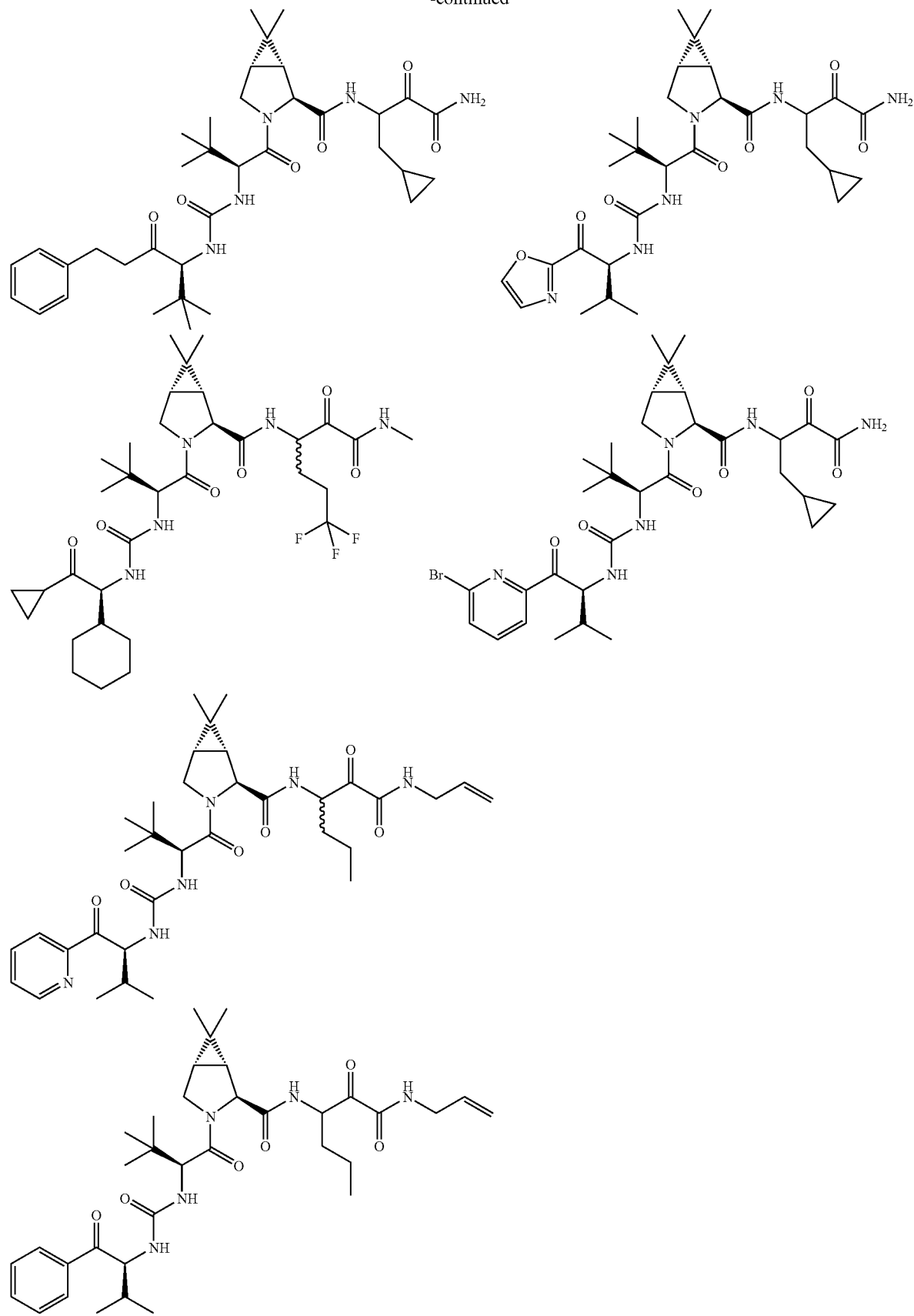

-continued
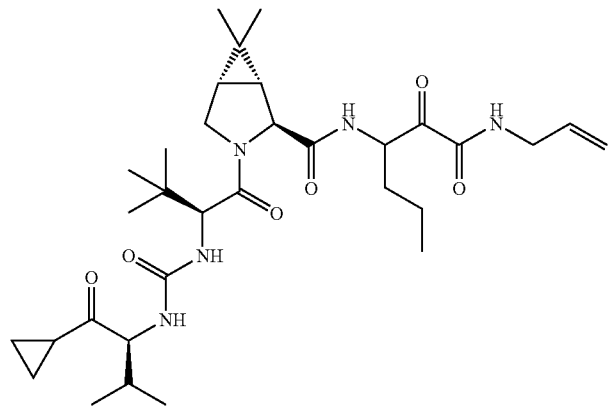
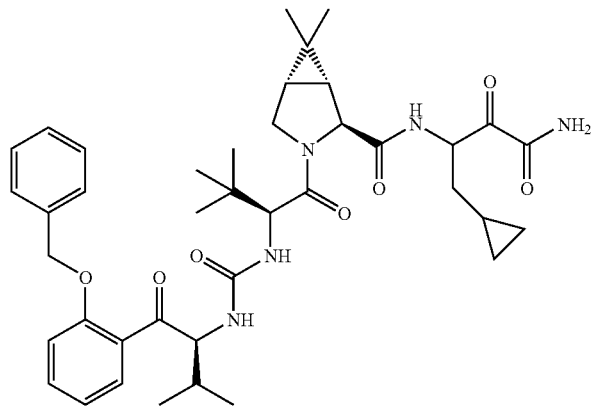
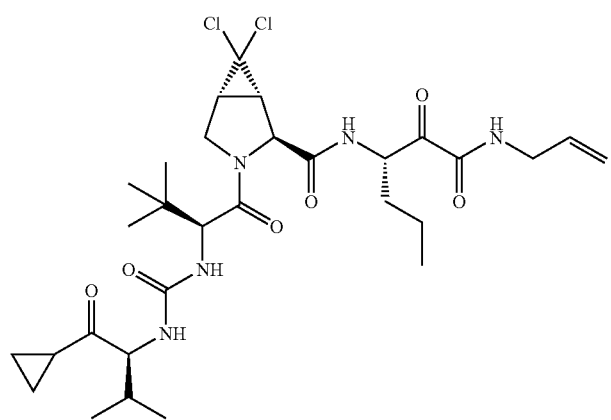
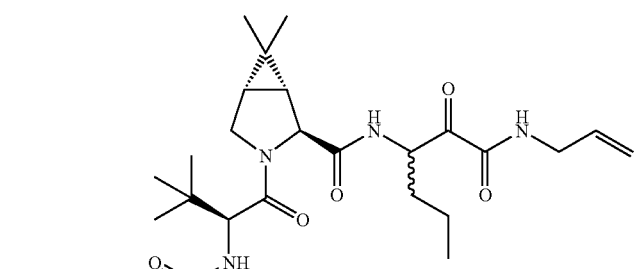

315 316
-continued
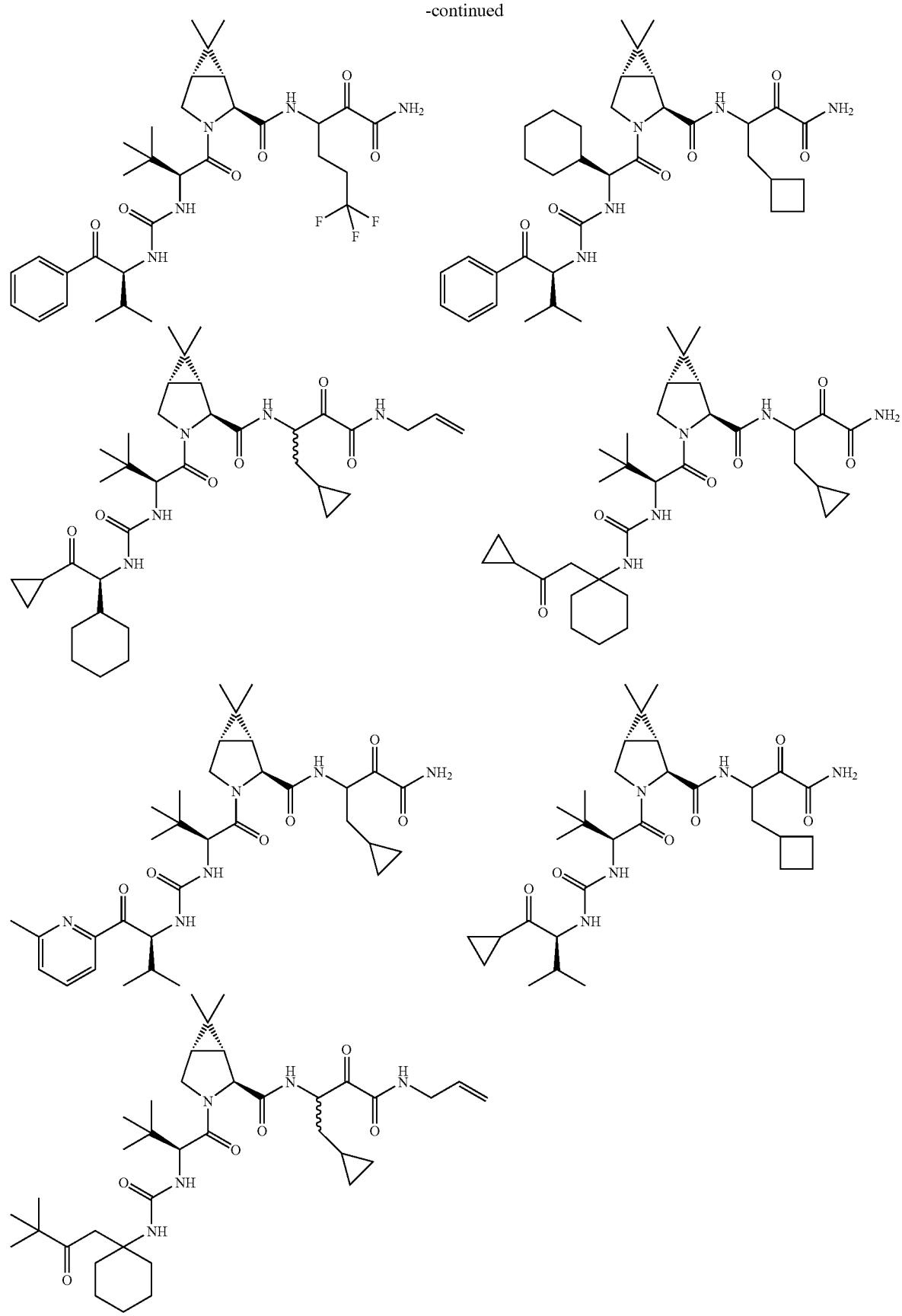

-continued
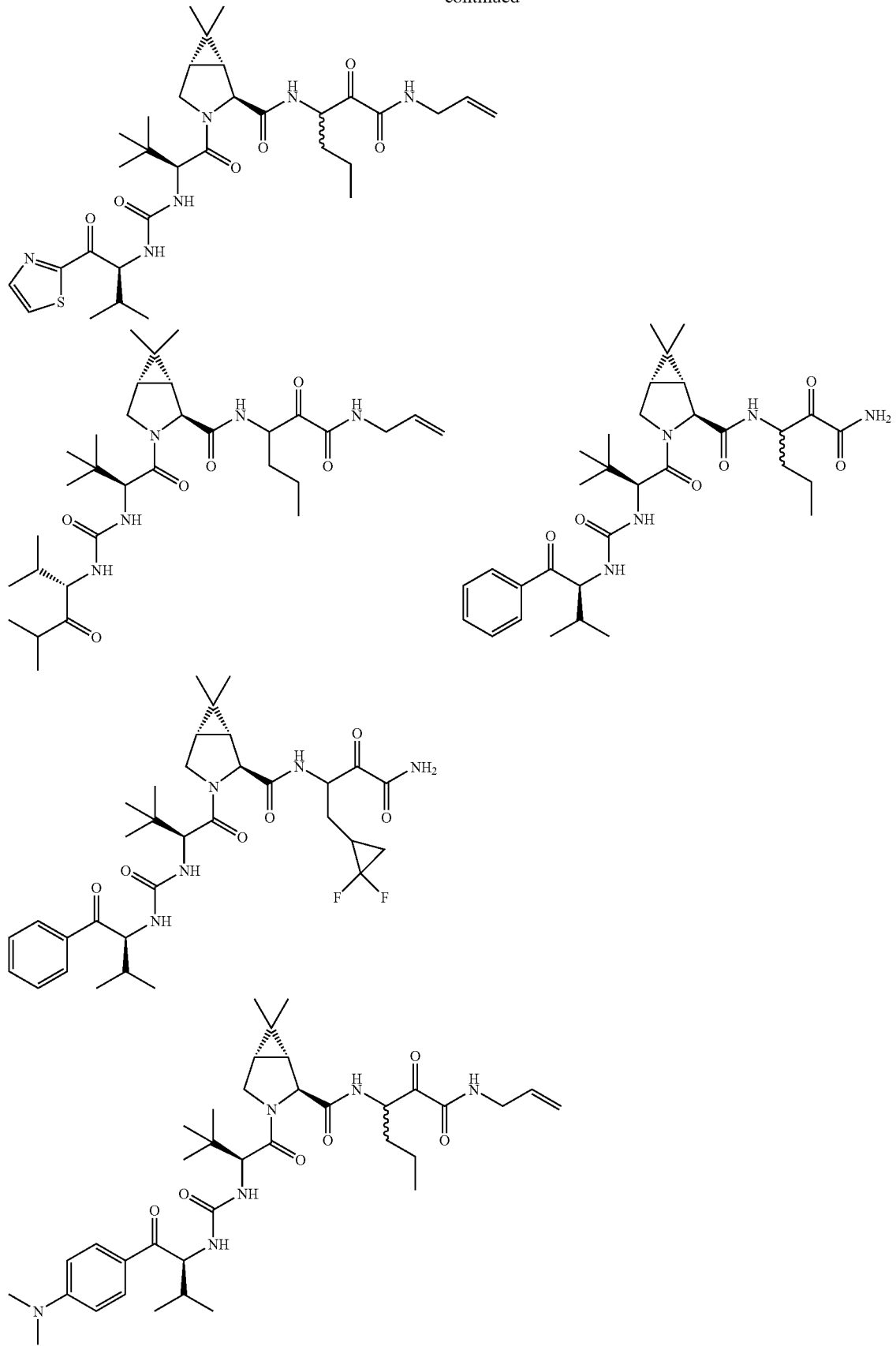

-continued
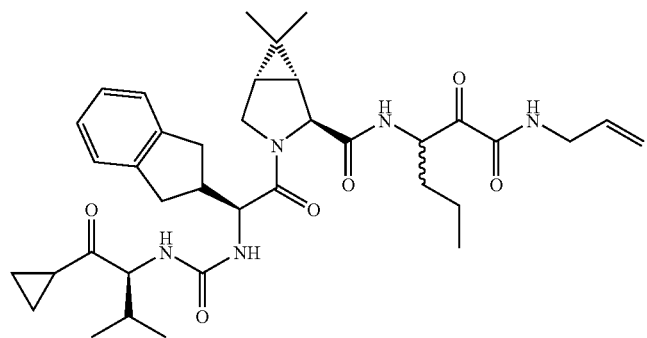
319
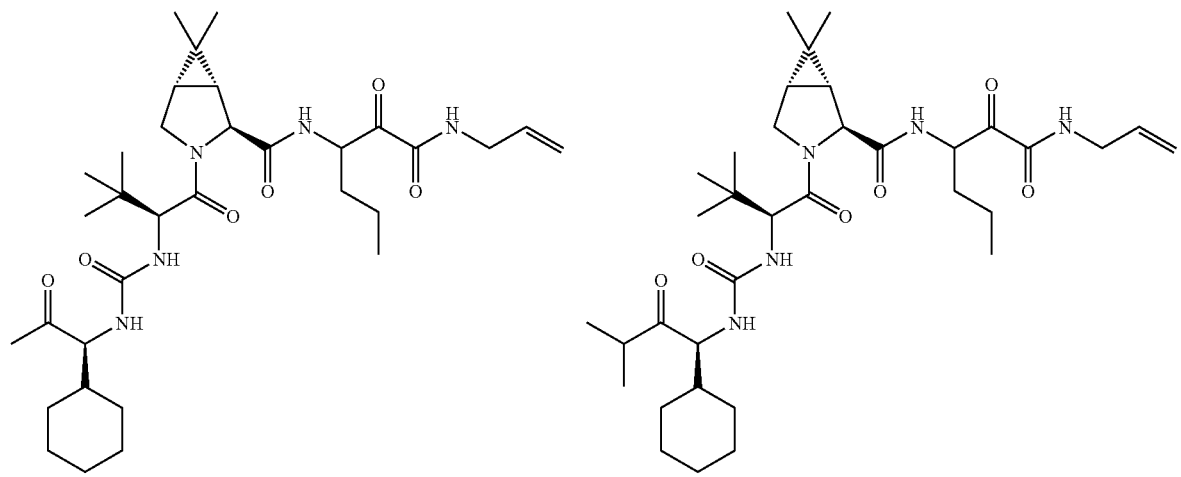
320
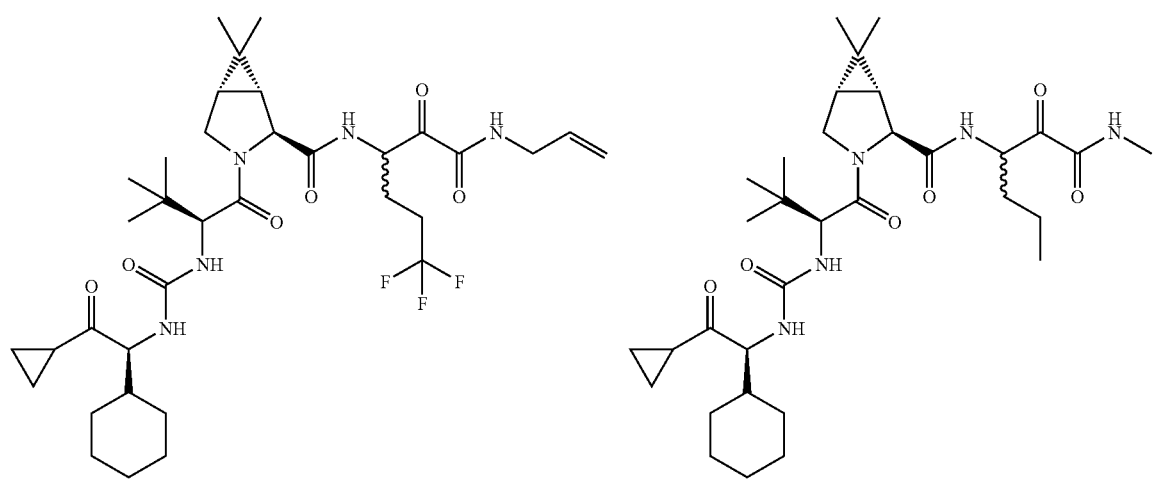

321                                             322
-continued
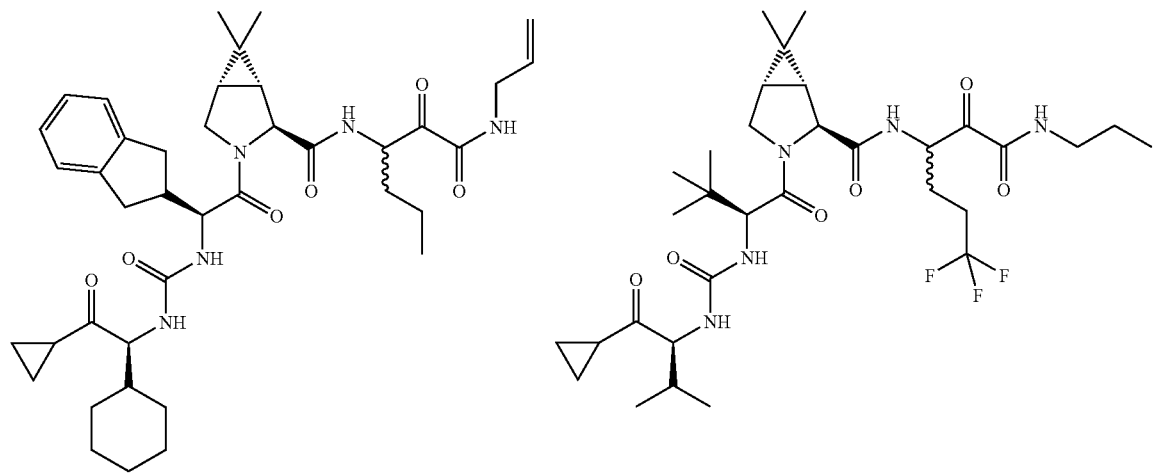
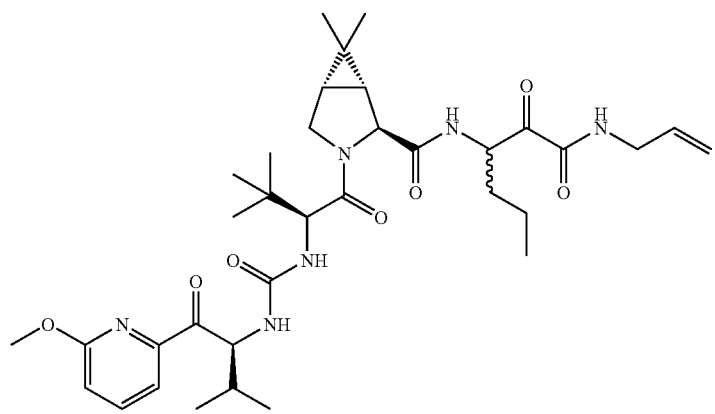
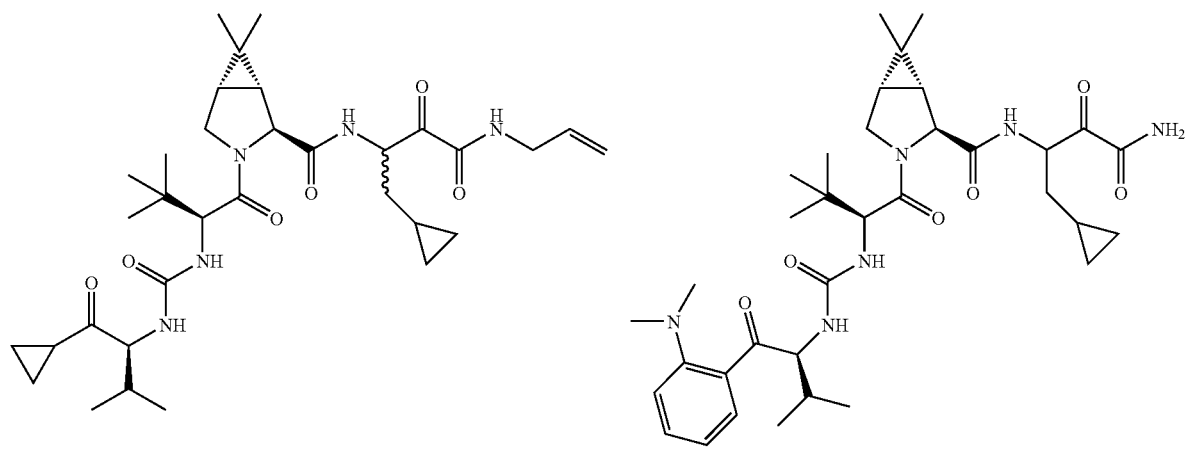

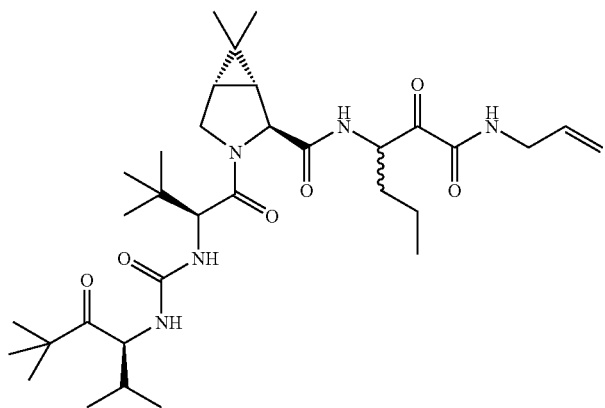
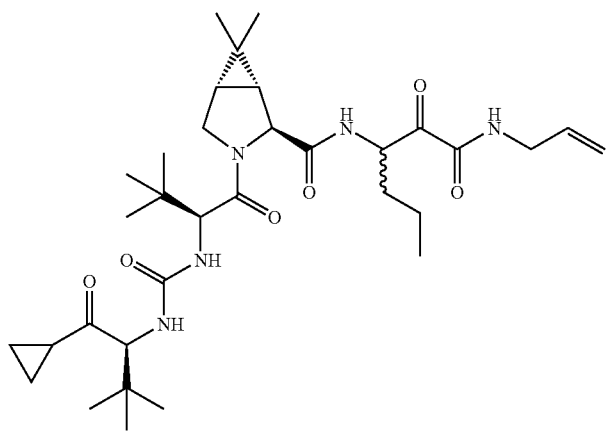
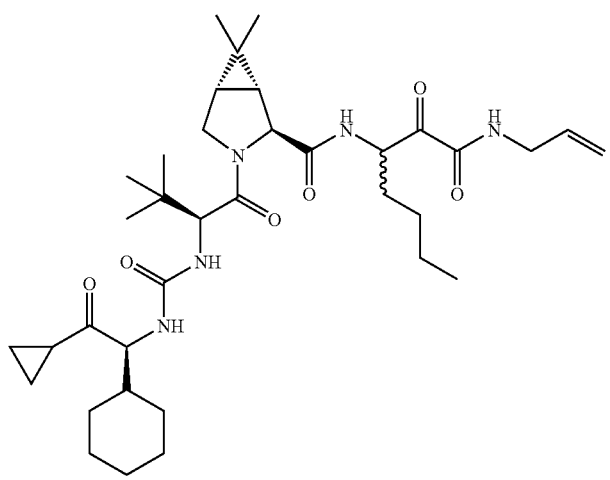

-continued
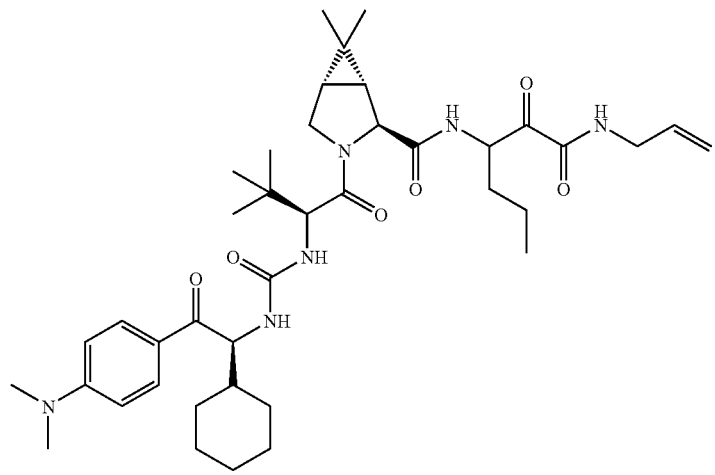
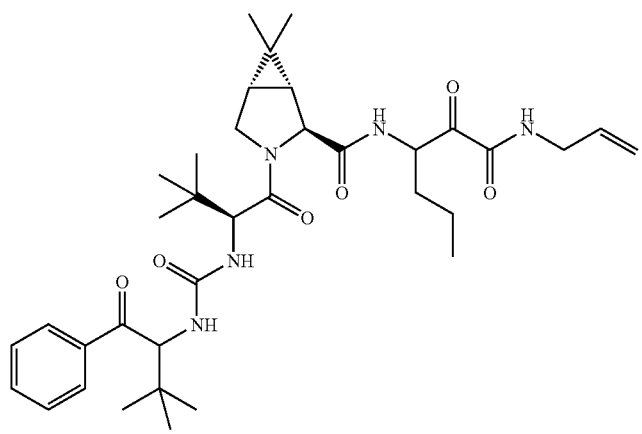
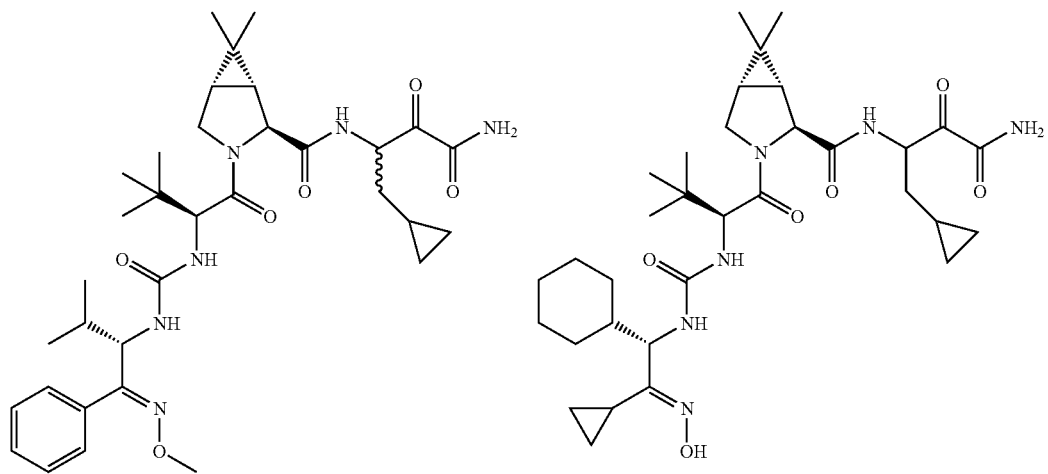

-continued
| 327 | 328 |
|---|---|
| 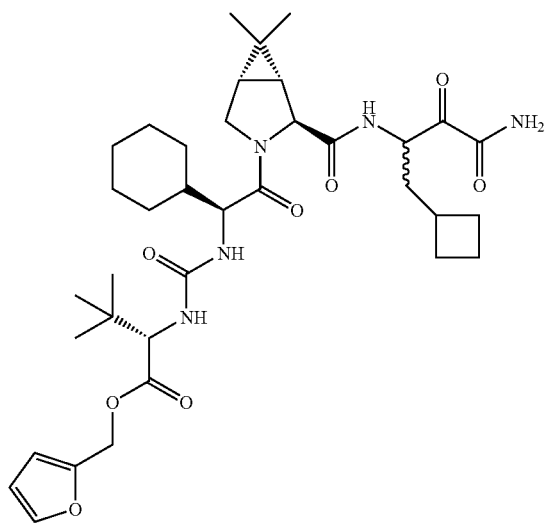 | 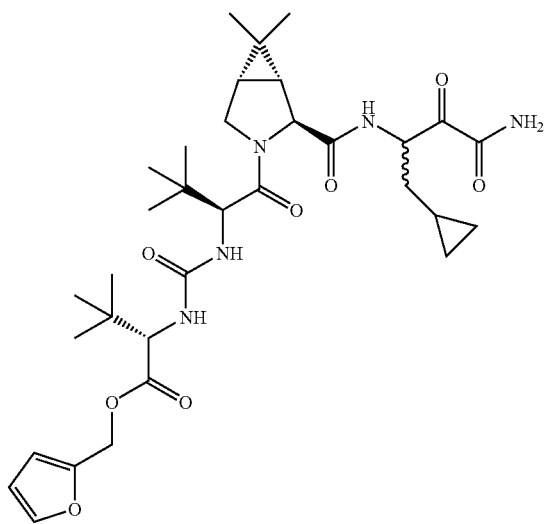 |
| 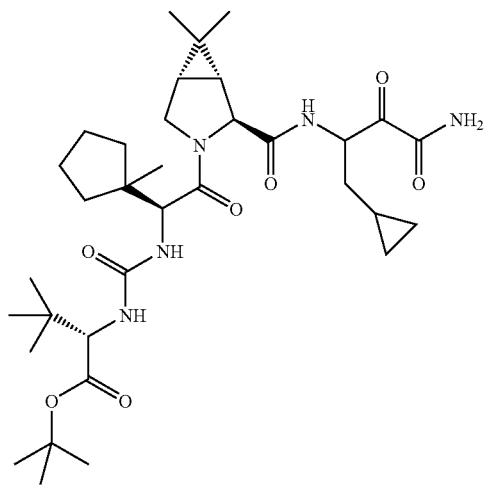 | 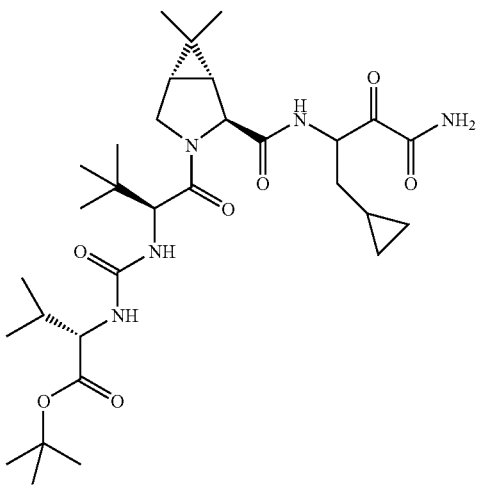 |
| 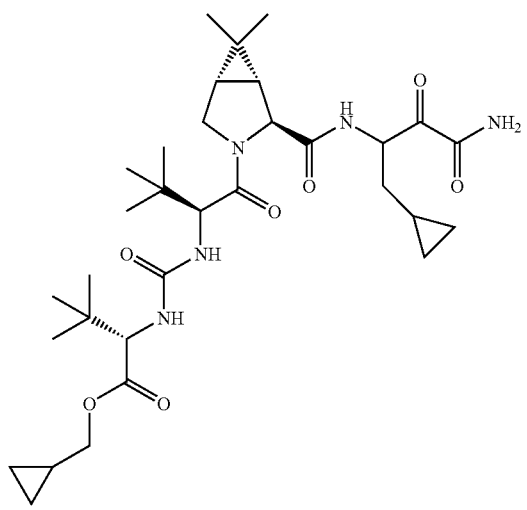 | 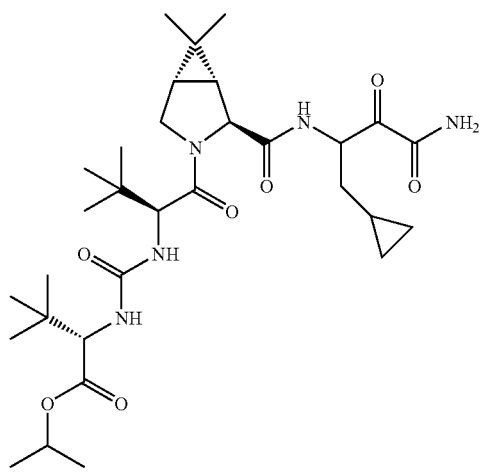 |

-continued
329
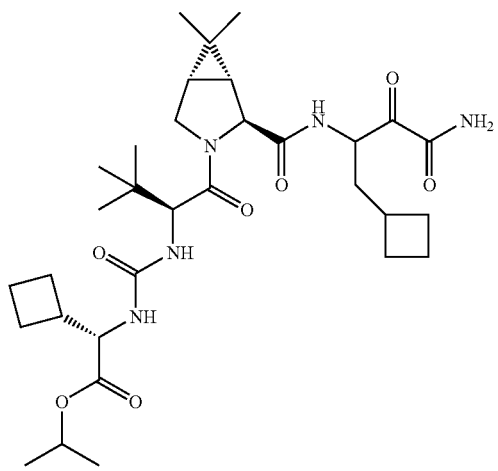
330
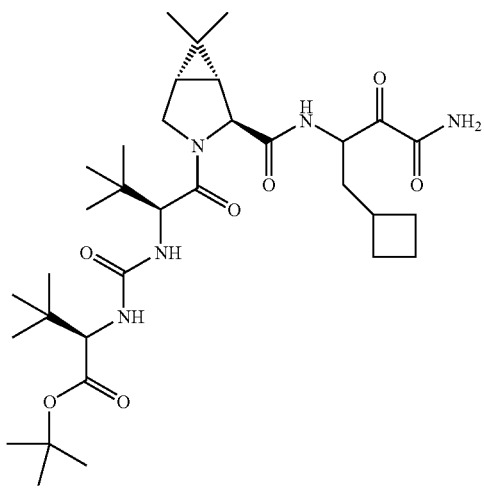
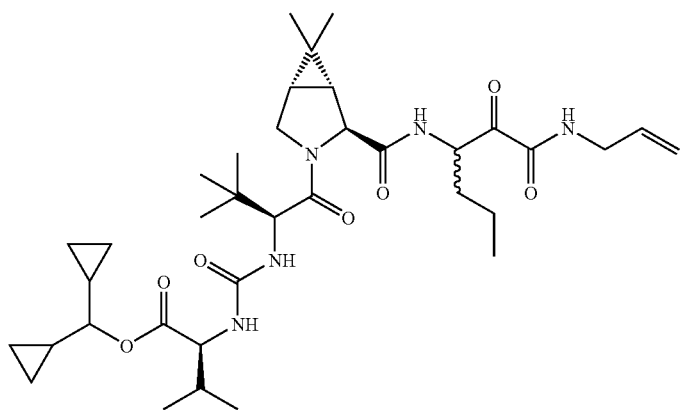
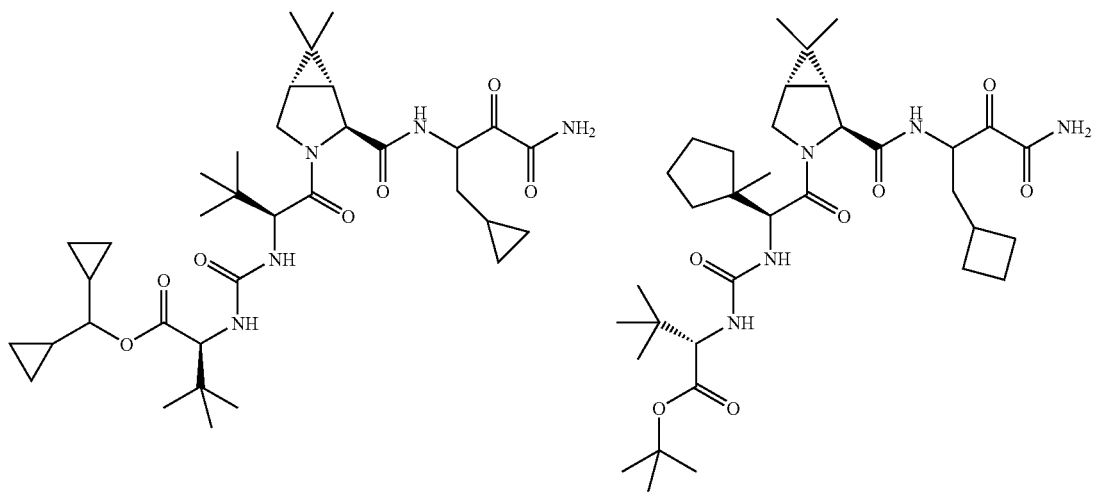

331 332
-continued
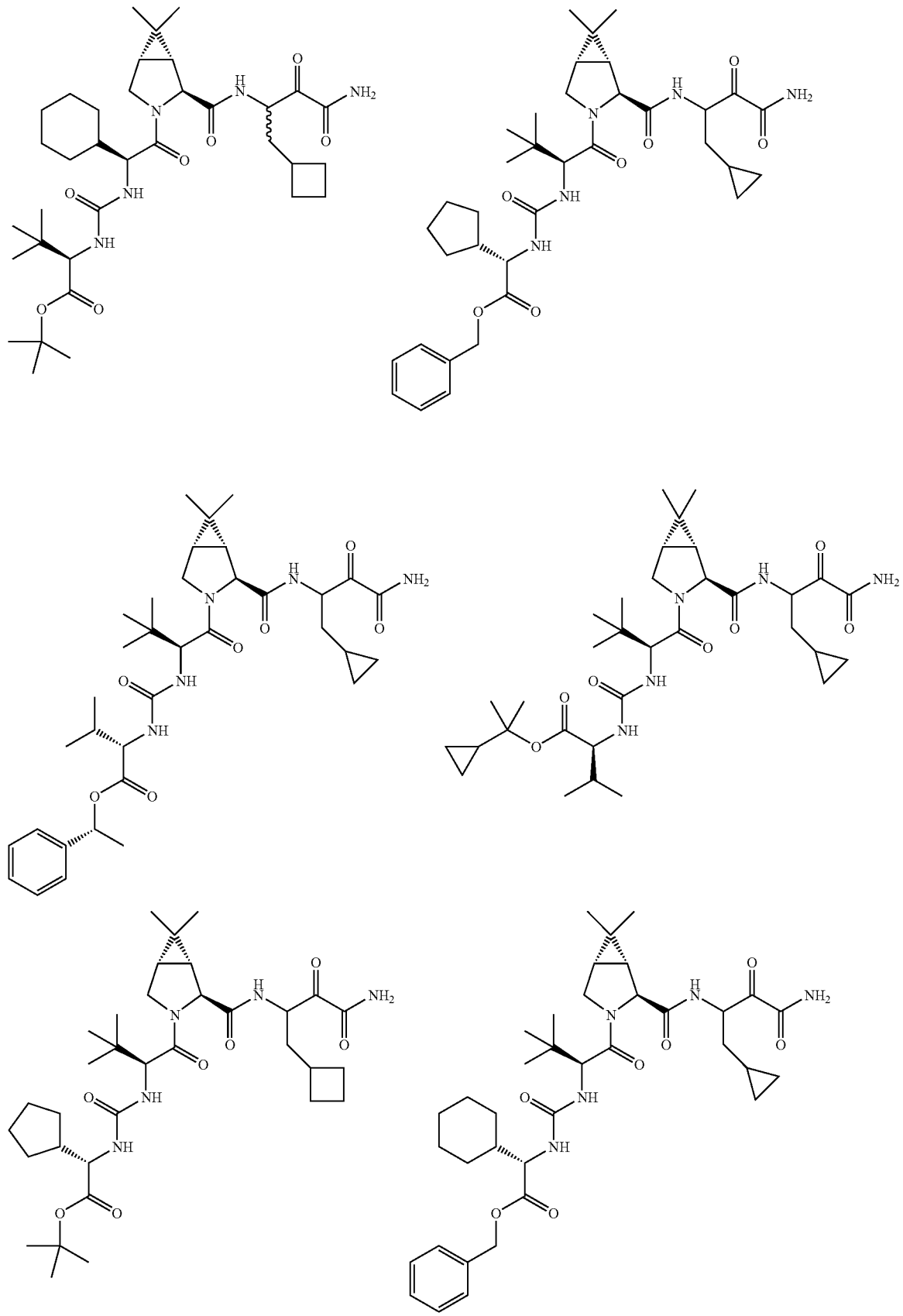

-continued
| 333 | 334 |
|---|---|
| 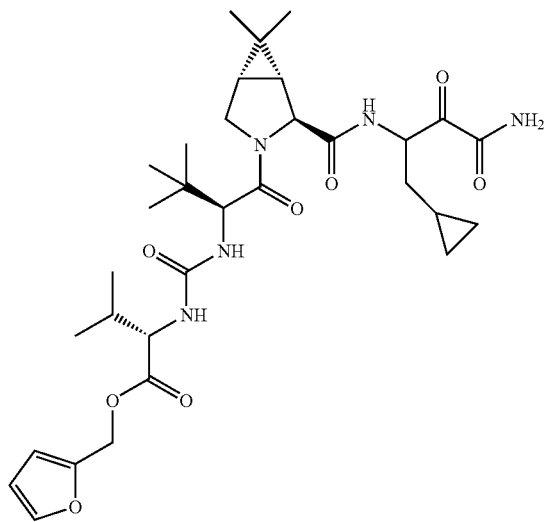 | 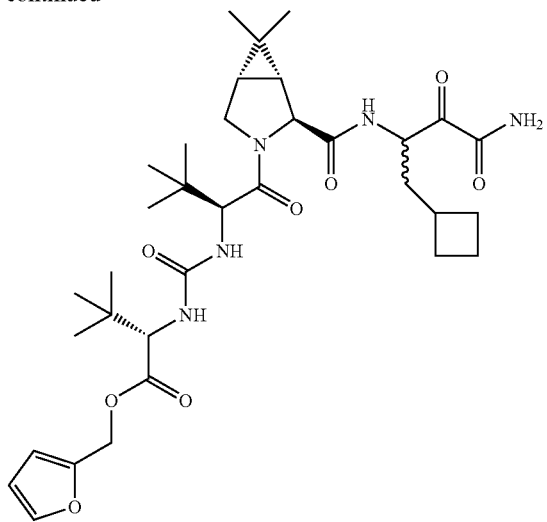 |
| 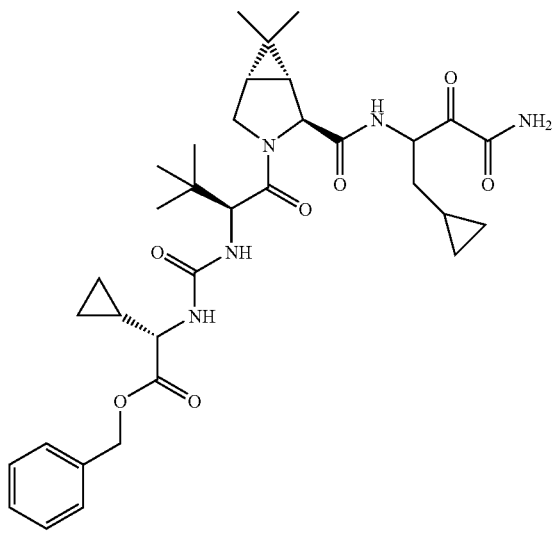 | 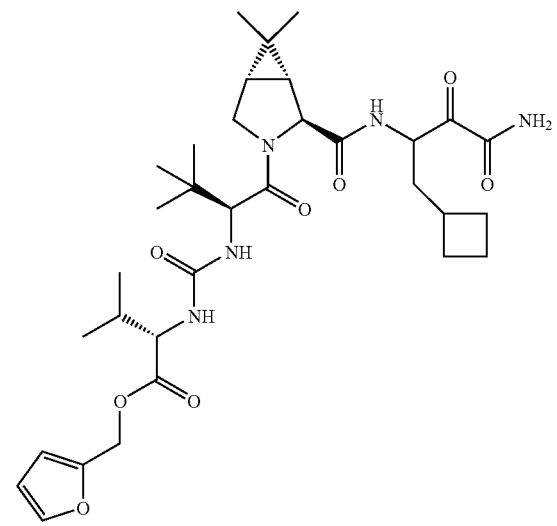 |
| 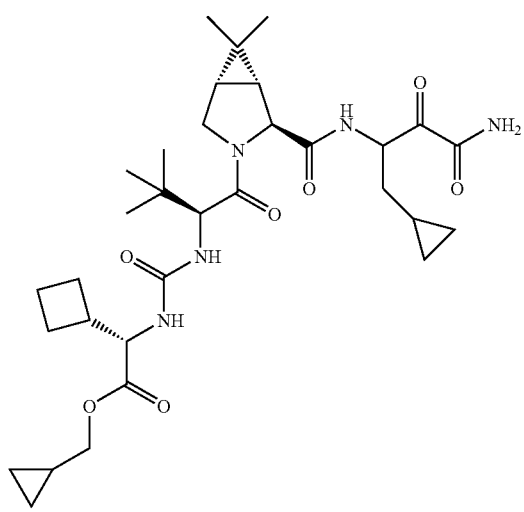 | 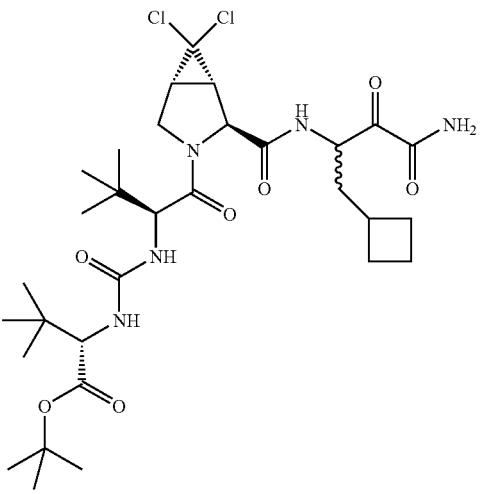 |

335 336
-continued
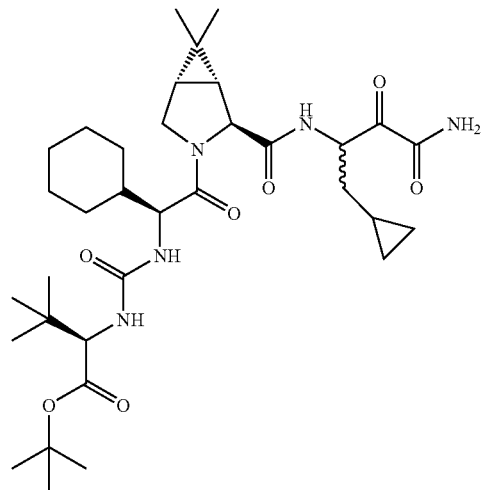
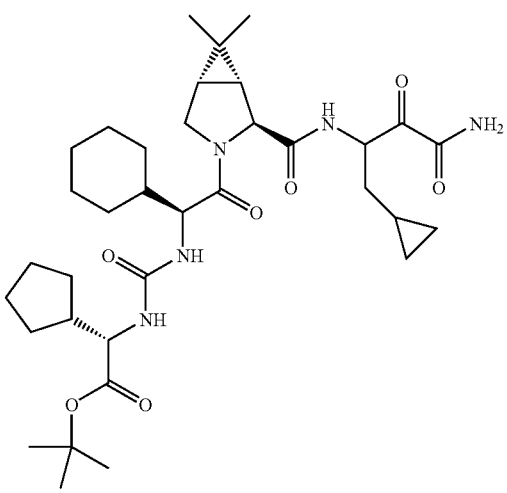
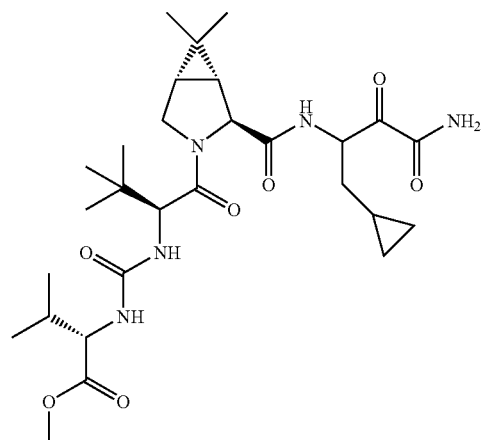
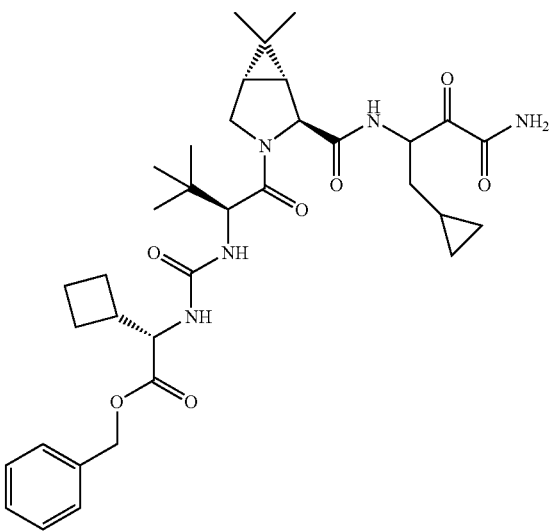
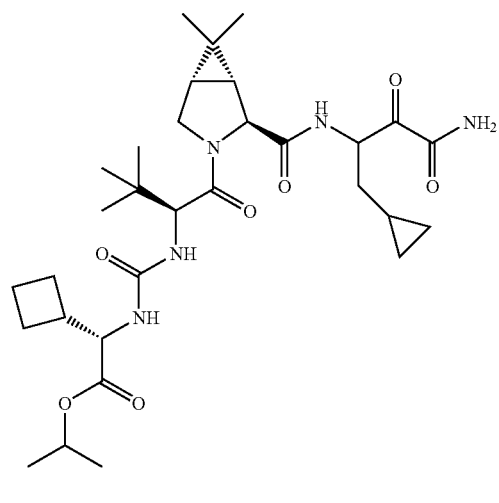
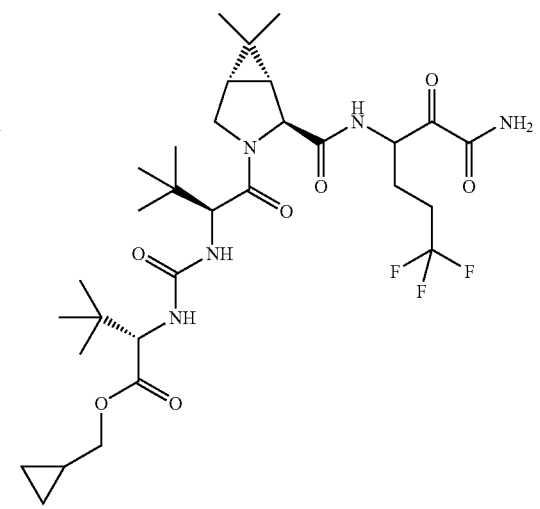

337
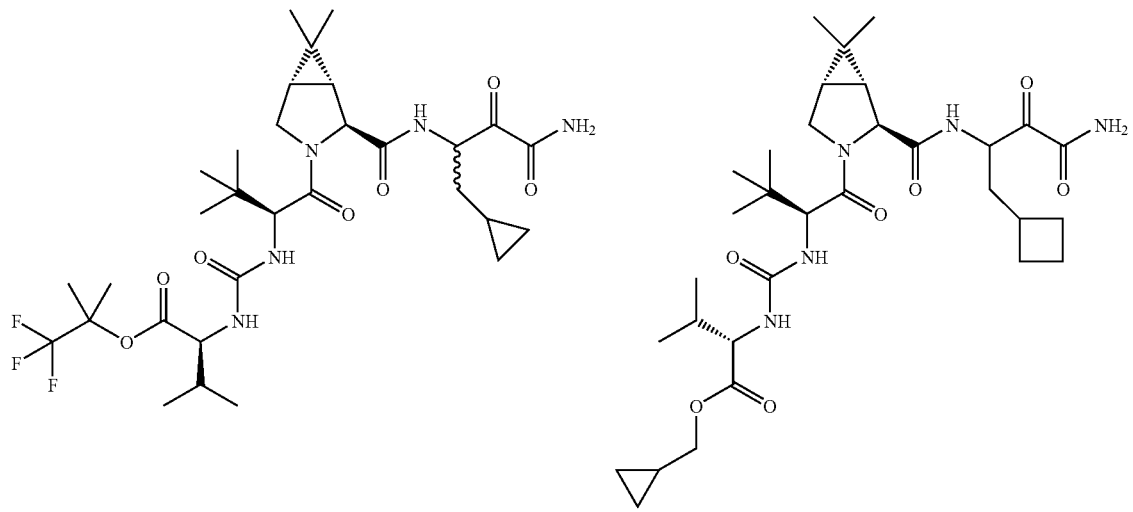
338
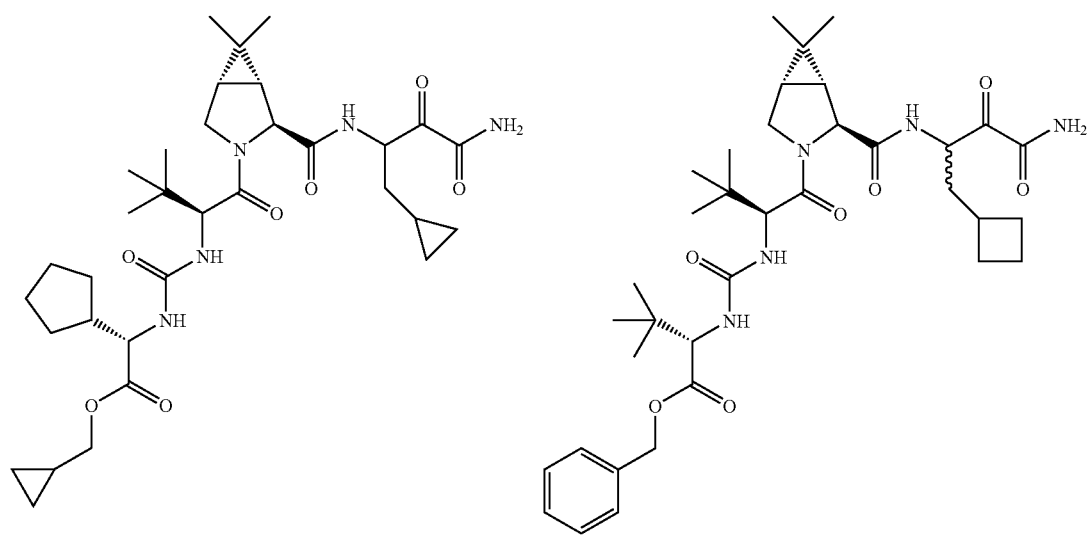
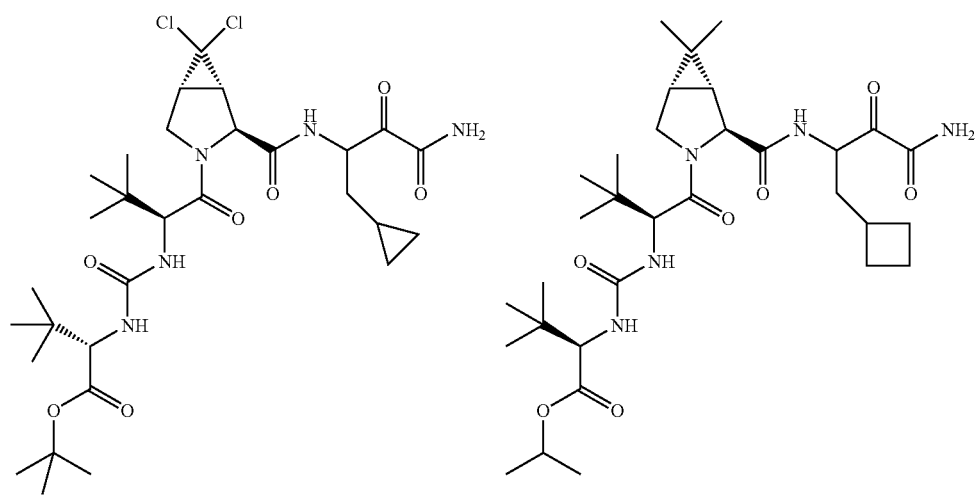

-continued
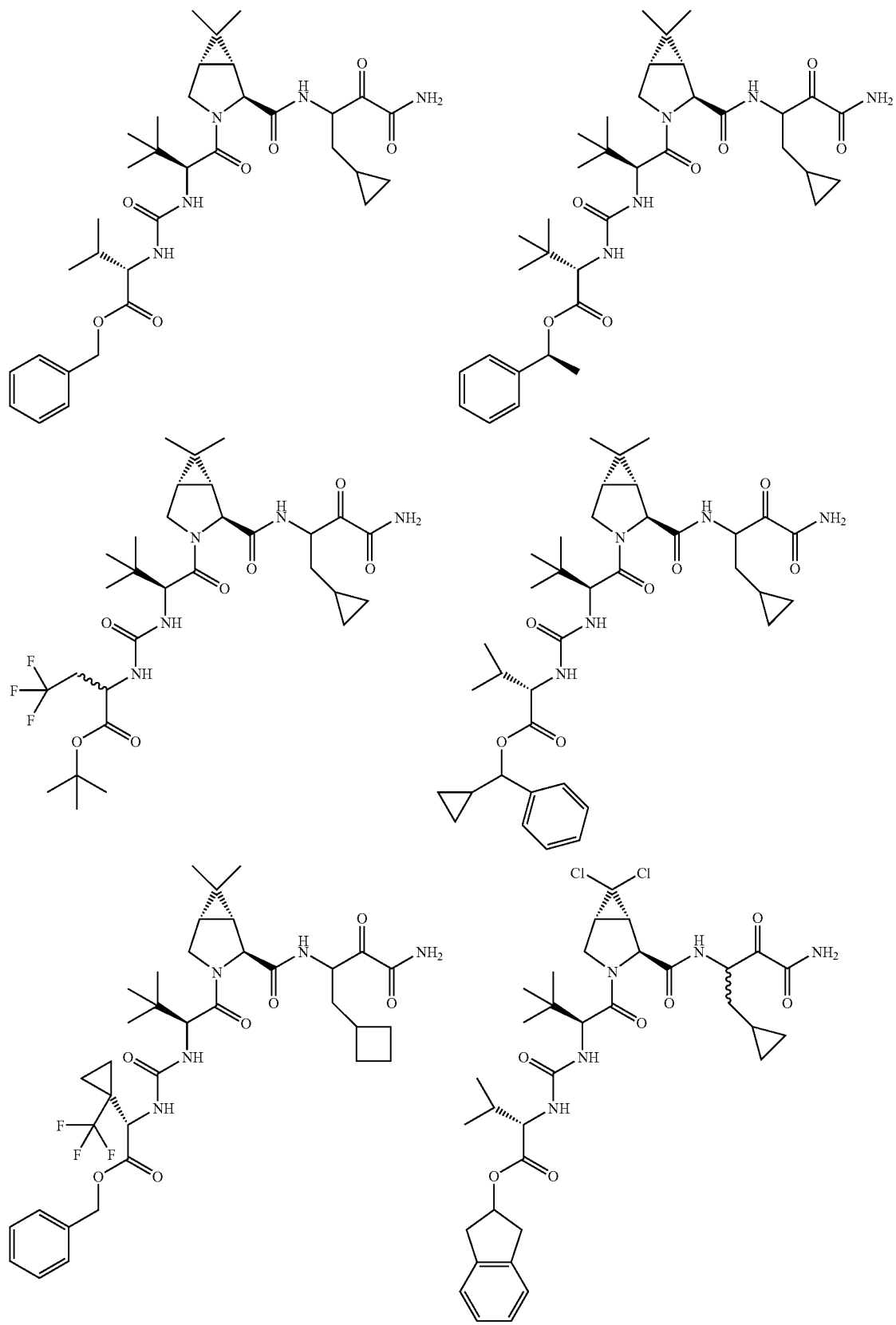

341   342
-continued
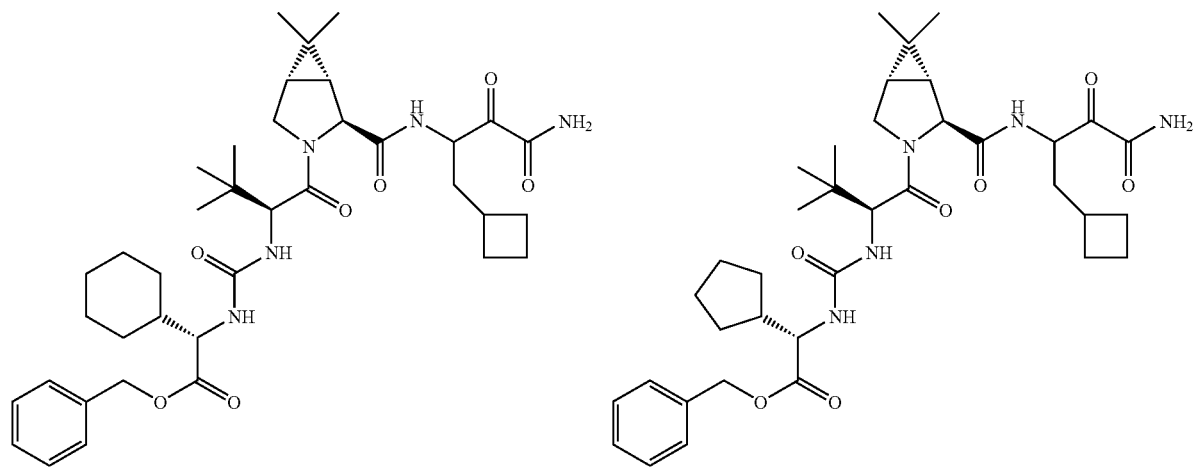
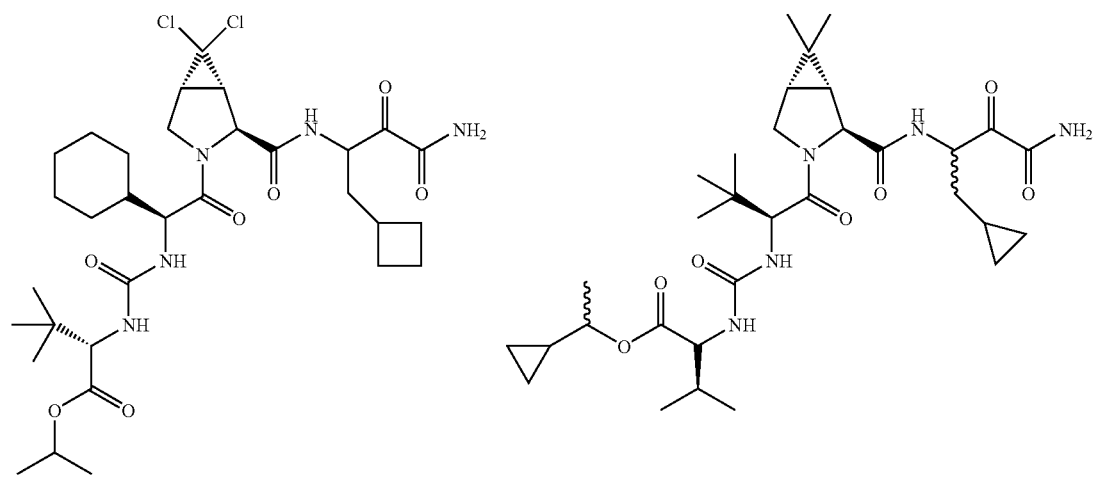
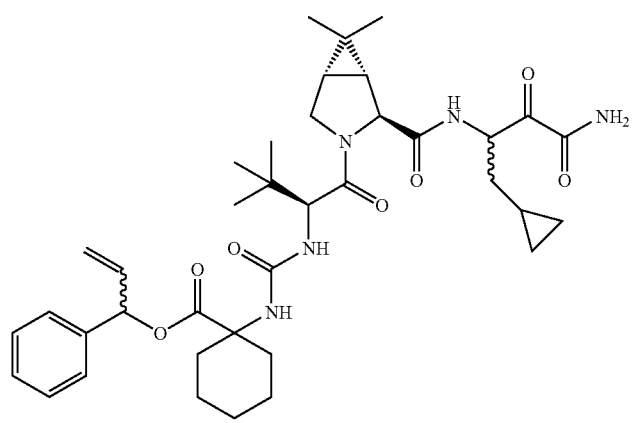

-continued
343
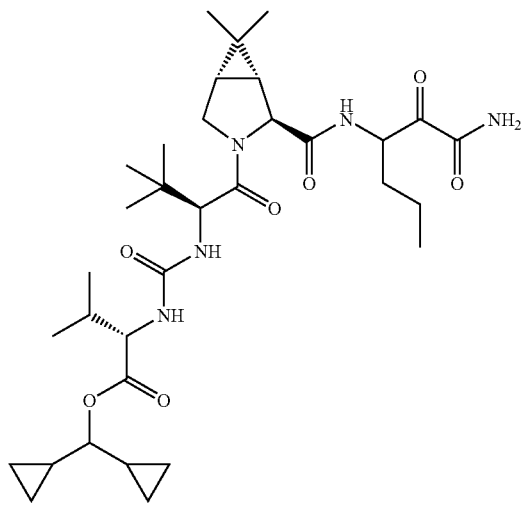
344
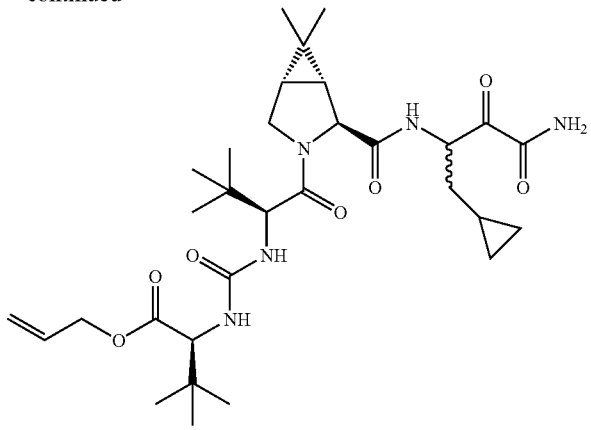
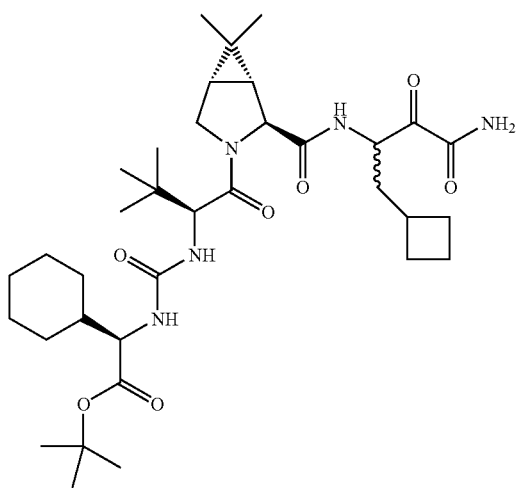
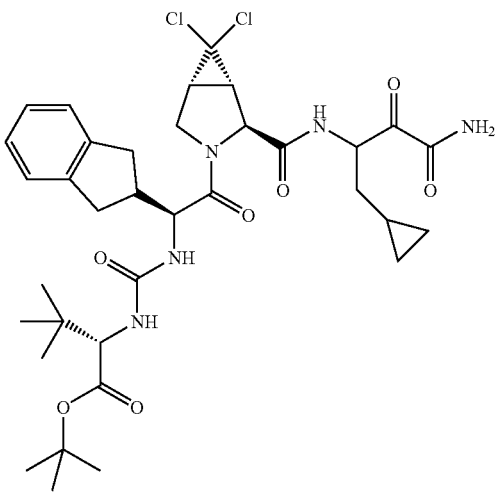
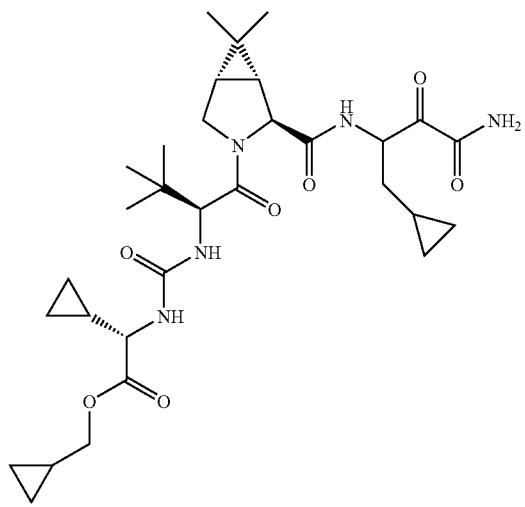

-continued
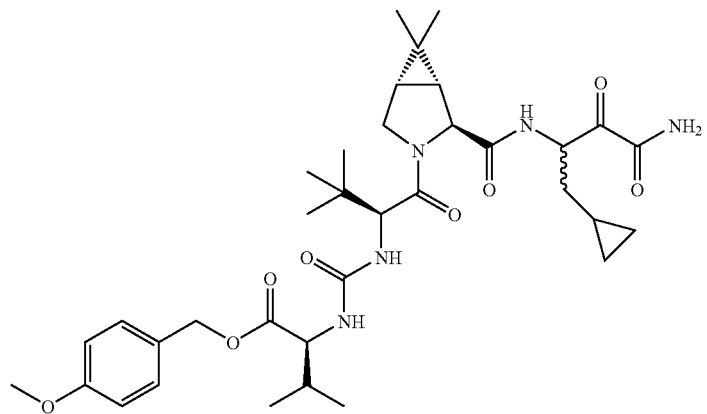
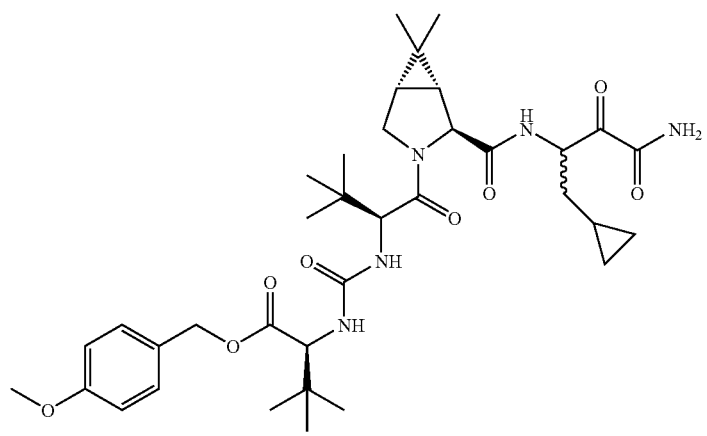
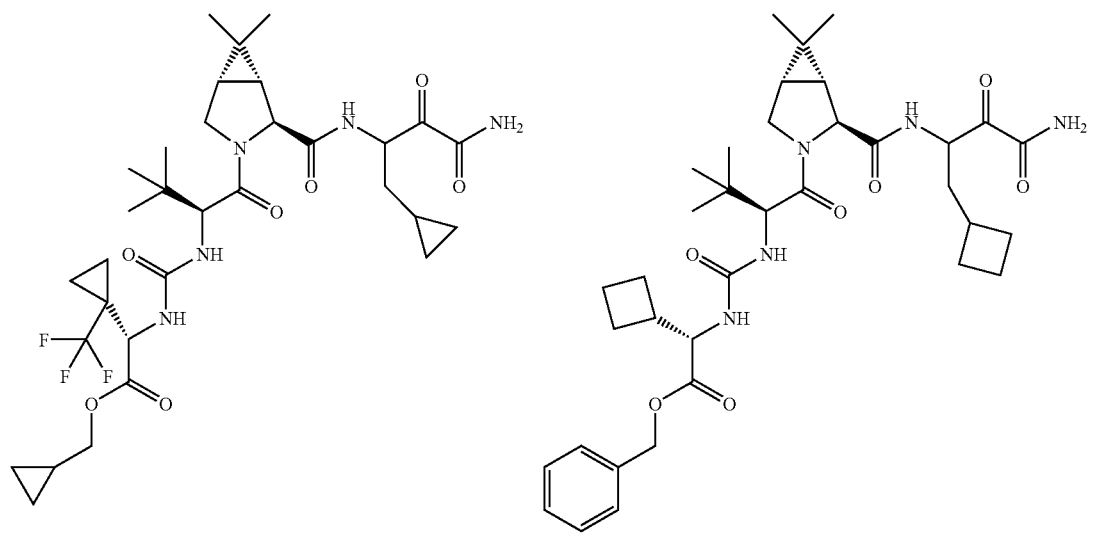

347 348
-continued
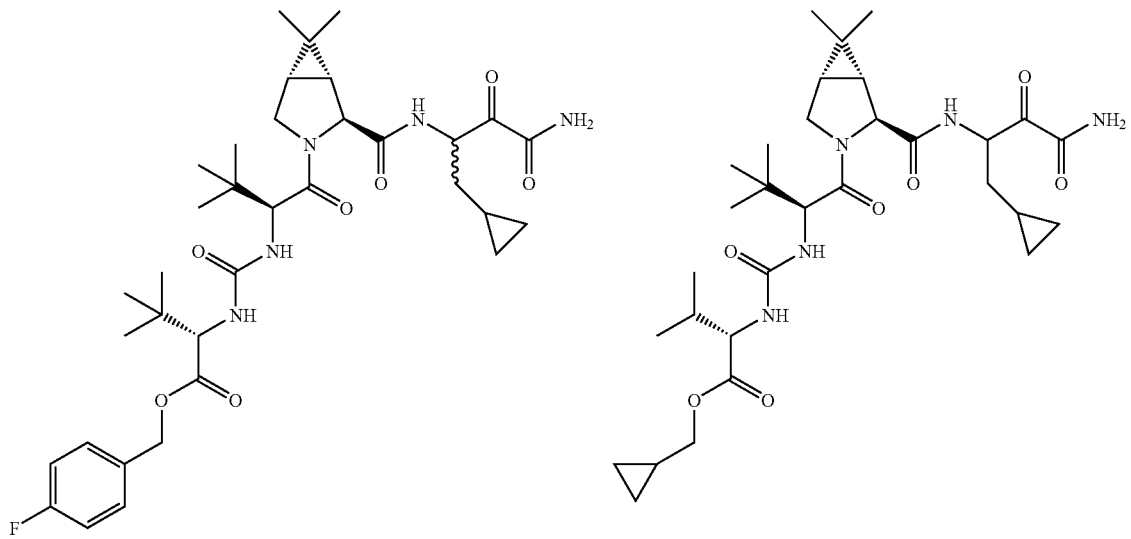
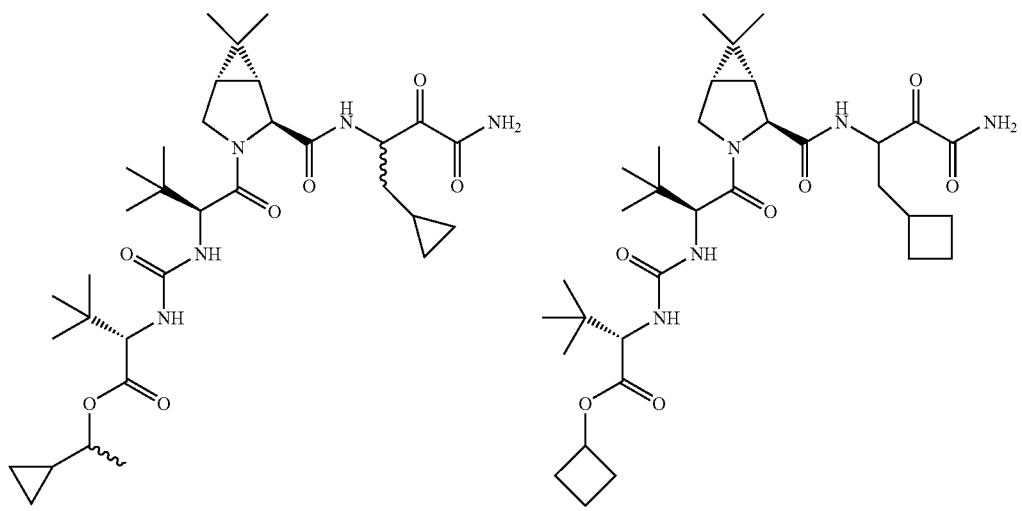
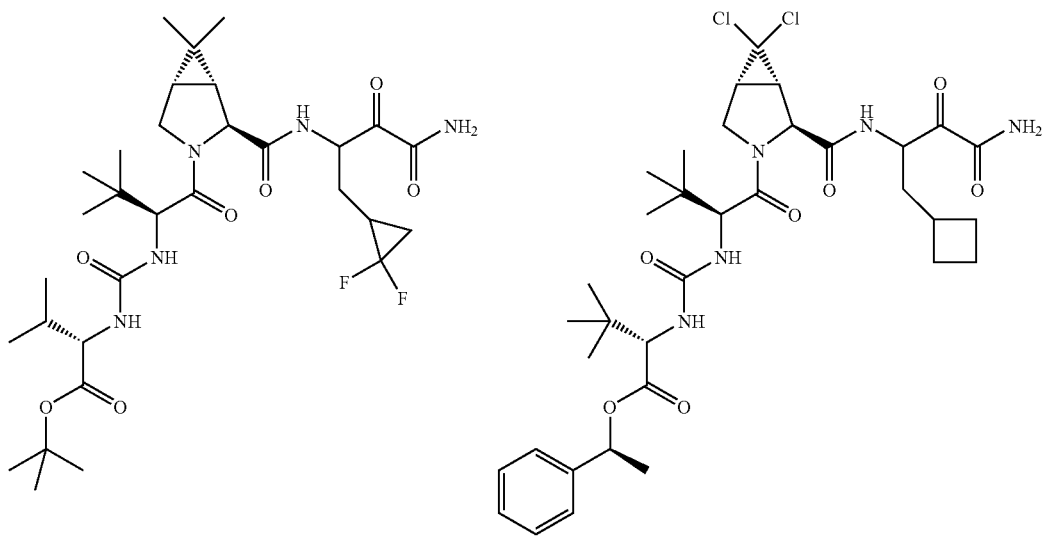

-continued
| 349 | 350 |
|---|---|
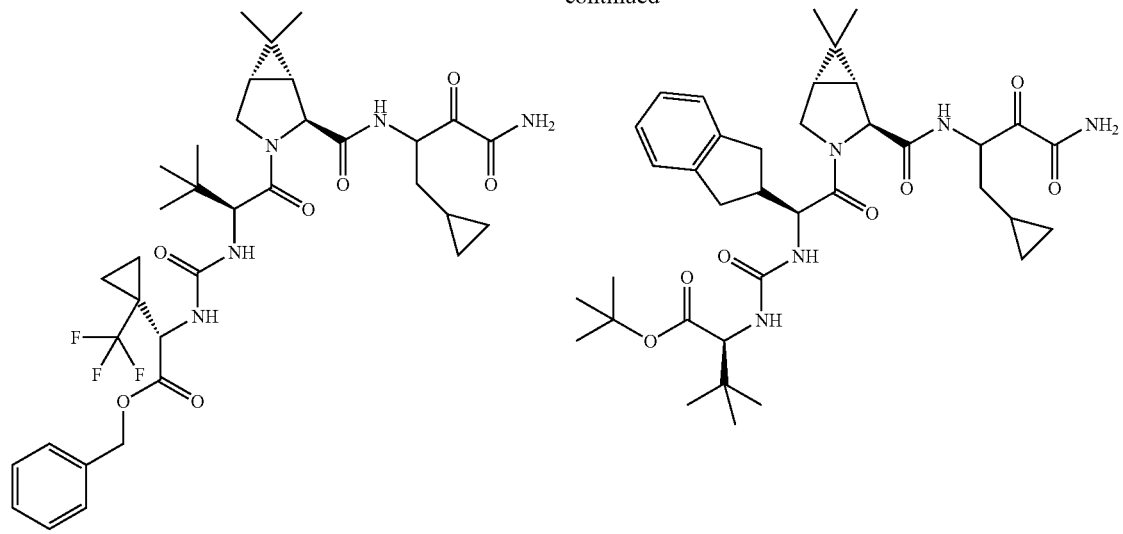
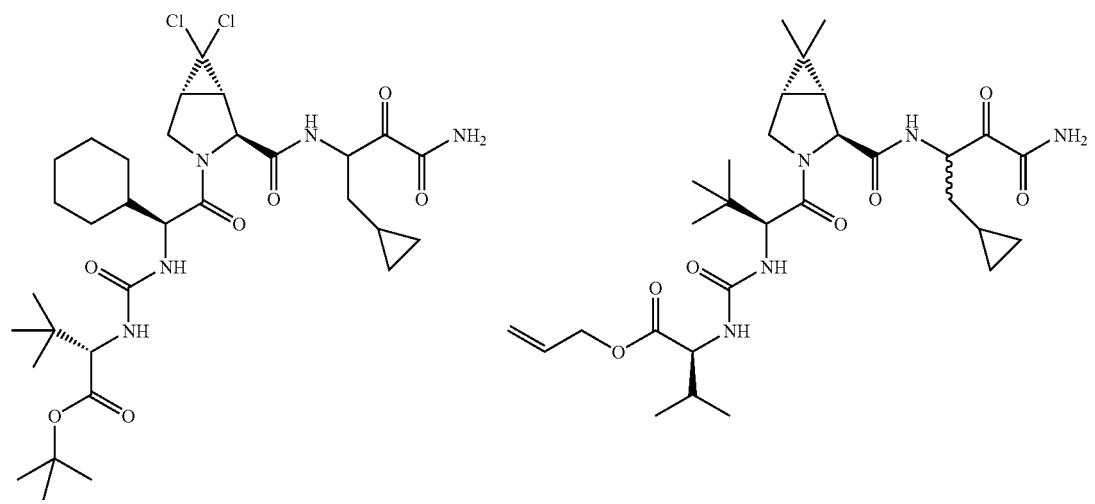
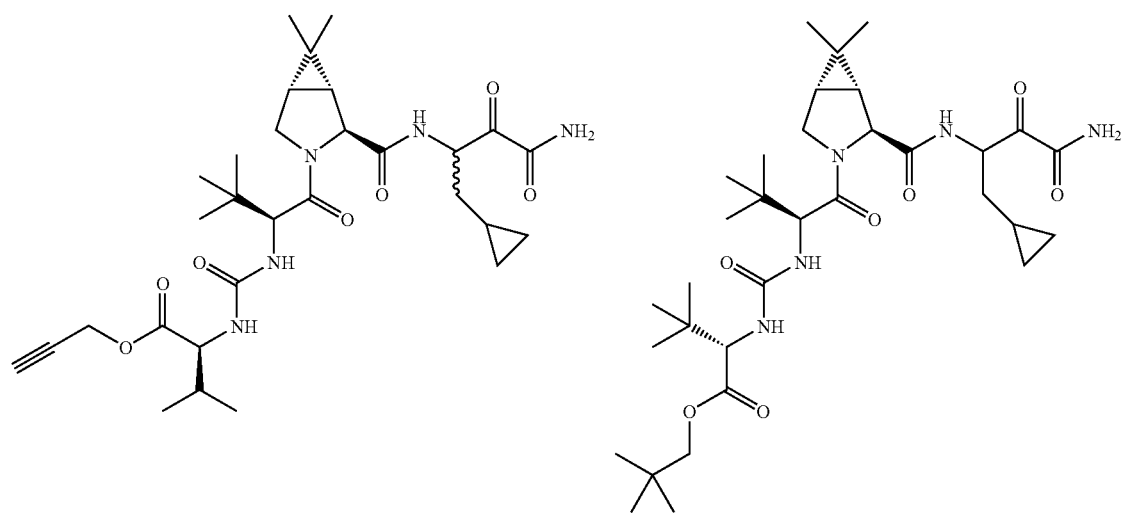

351 352
-continued
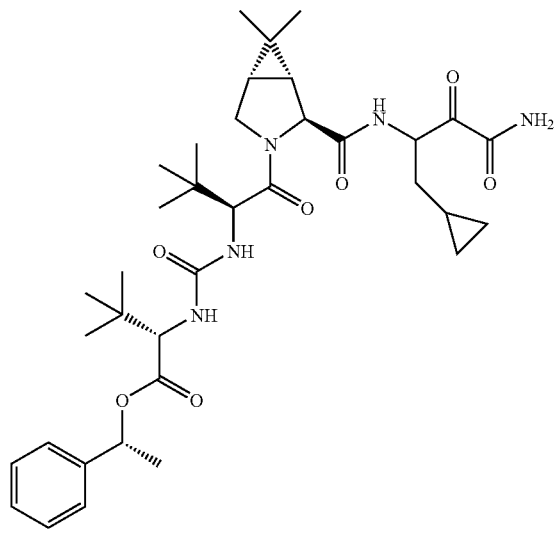
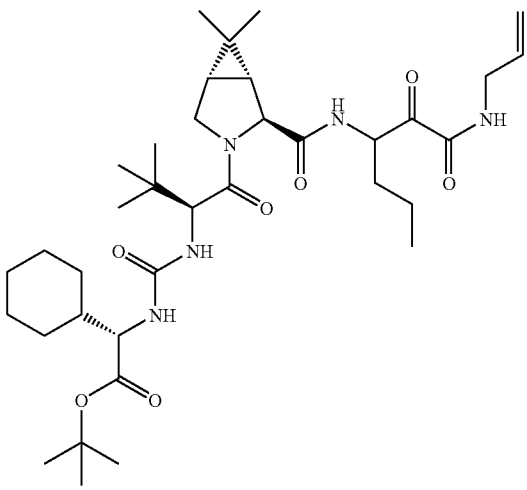
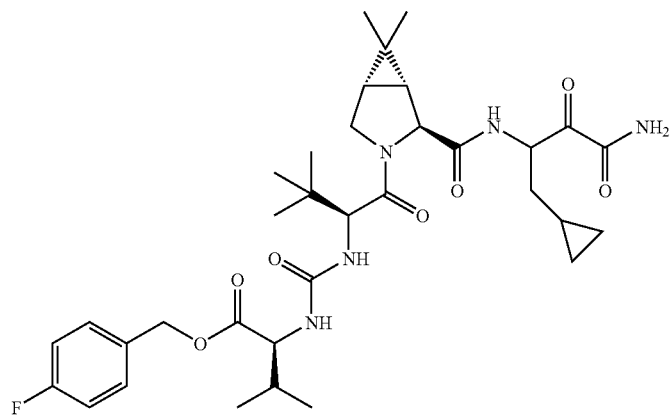
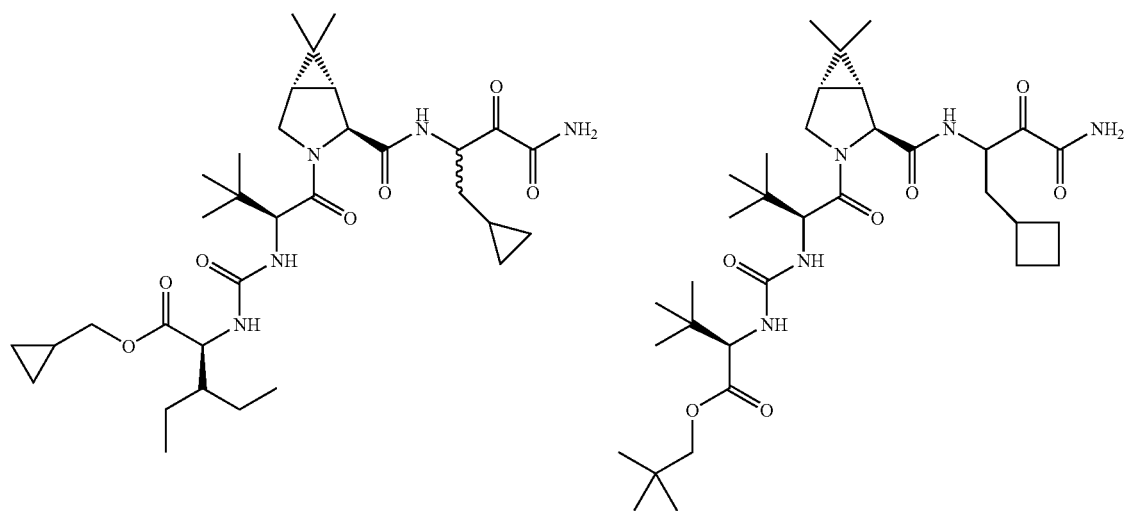

353 354
-continued
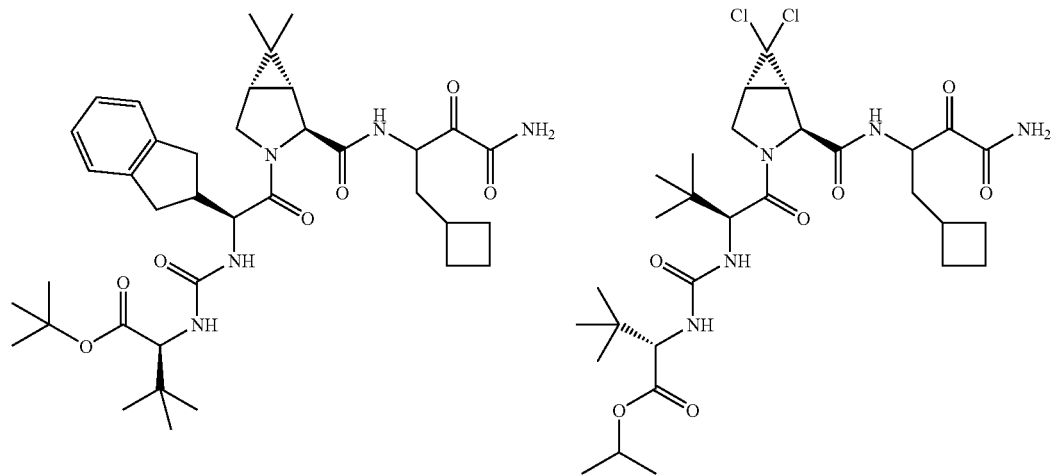
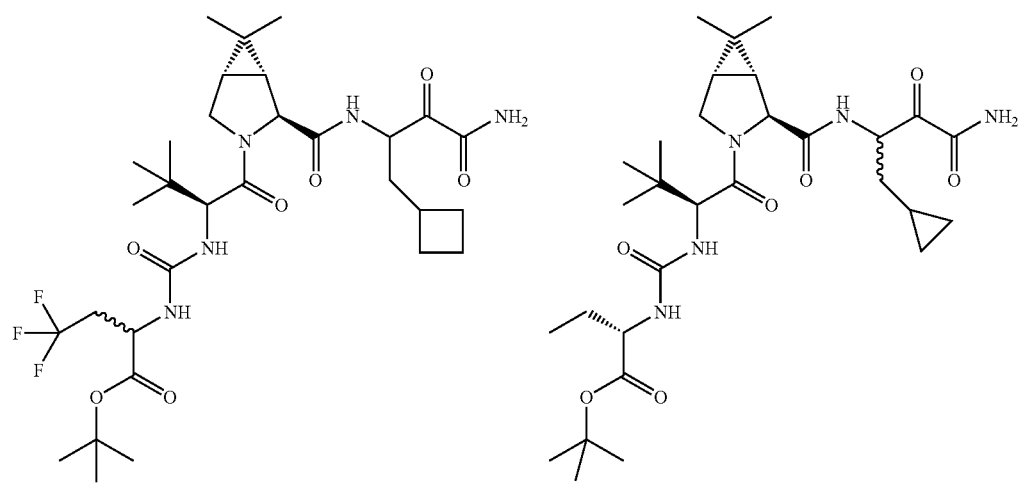
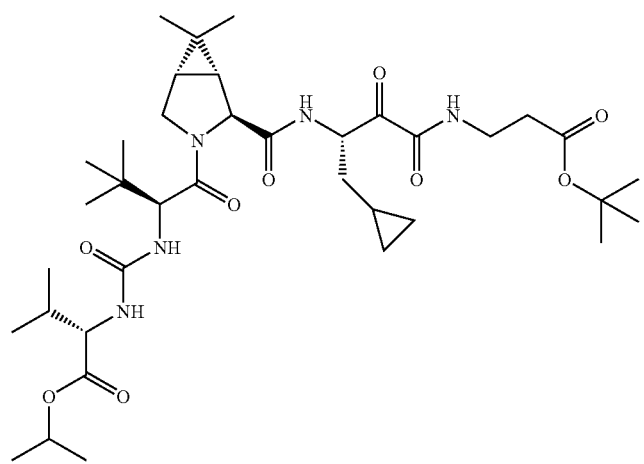

355 356
-continued
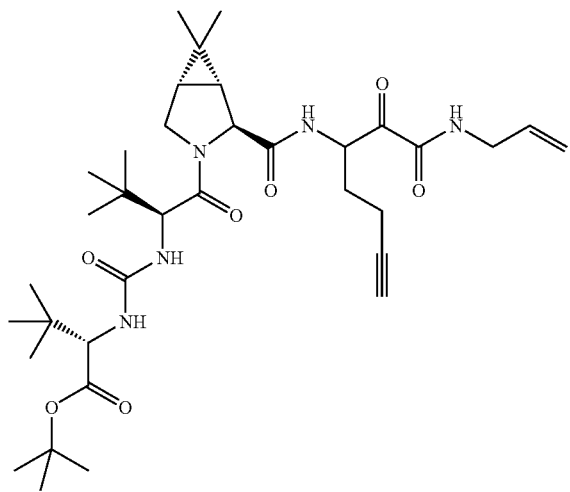
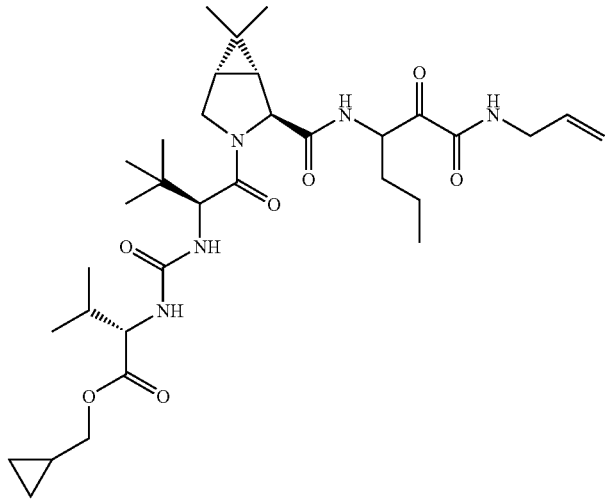
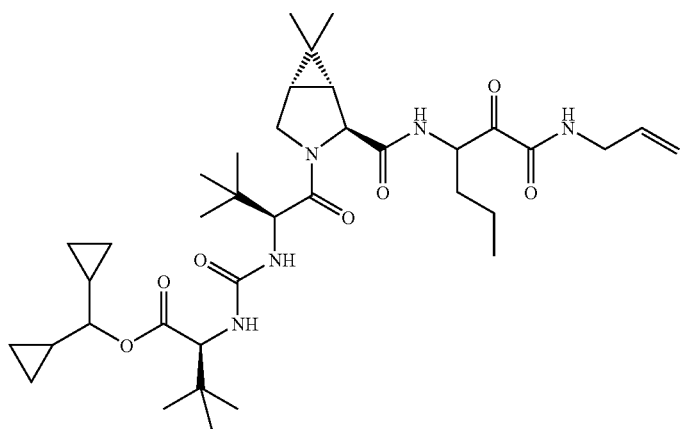
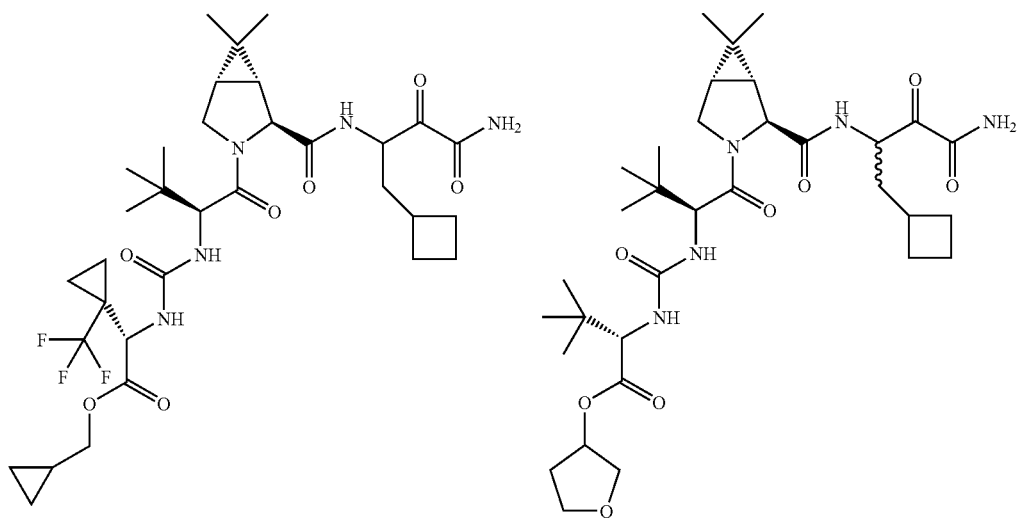

-continued
357
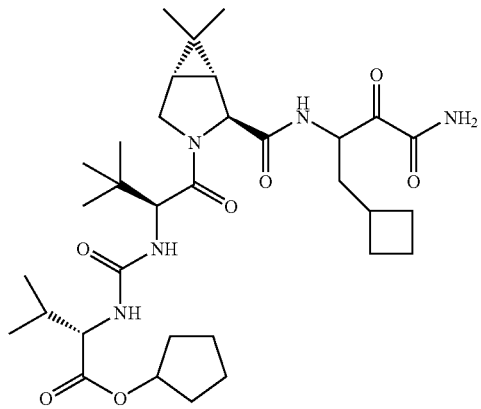
358
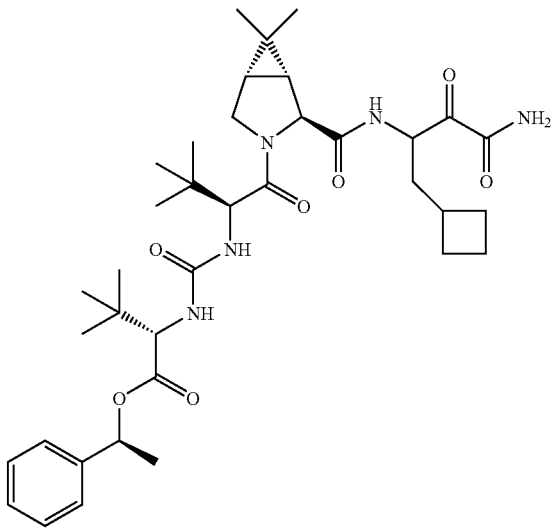
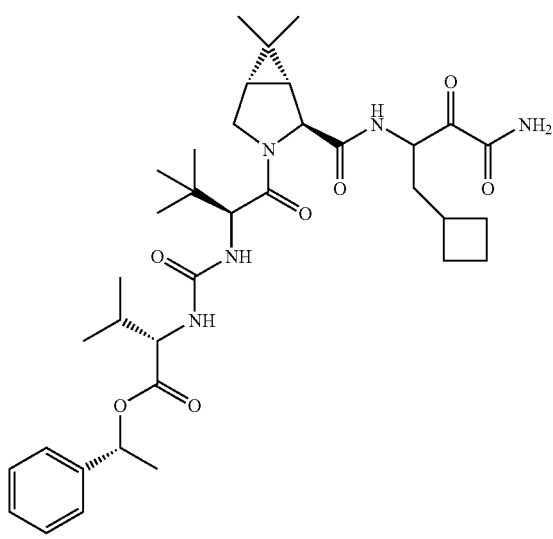
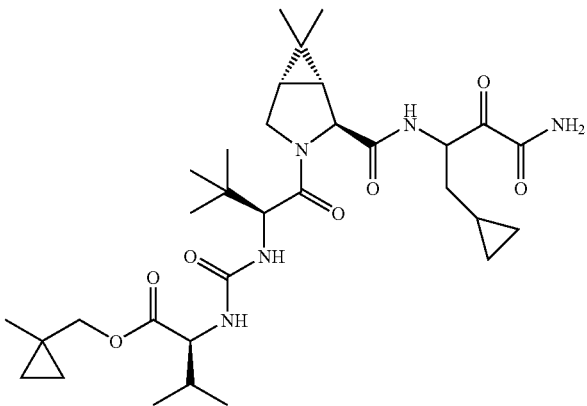
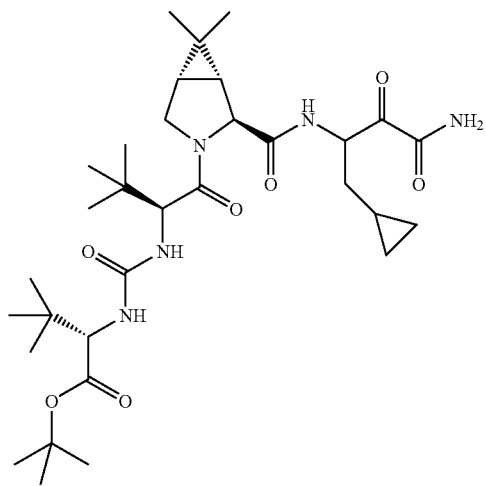
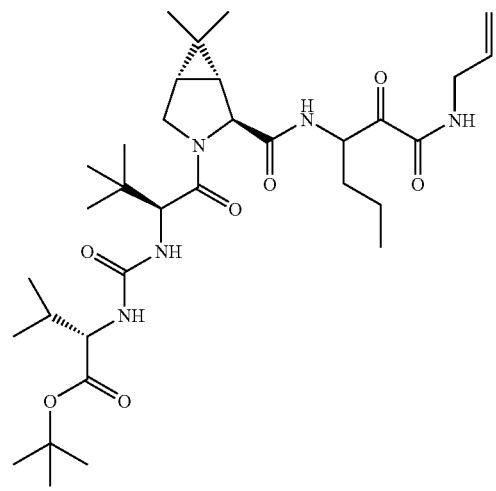

359 360
-continued
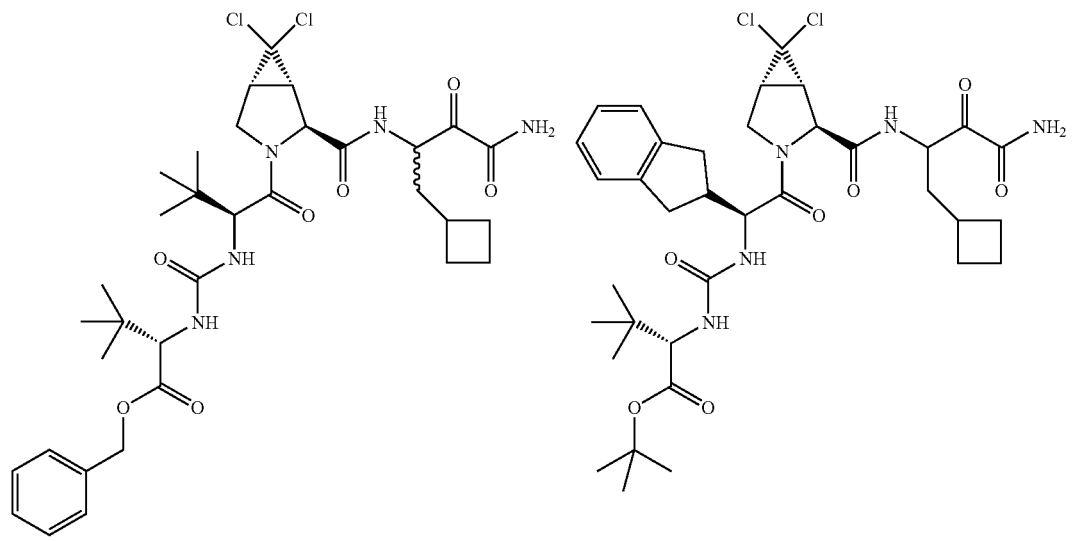
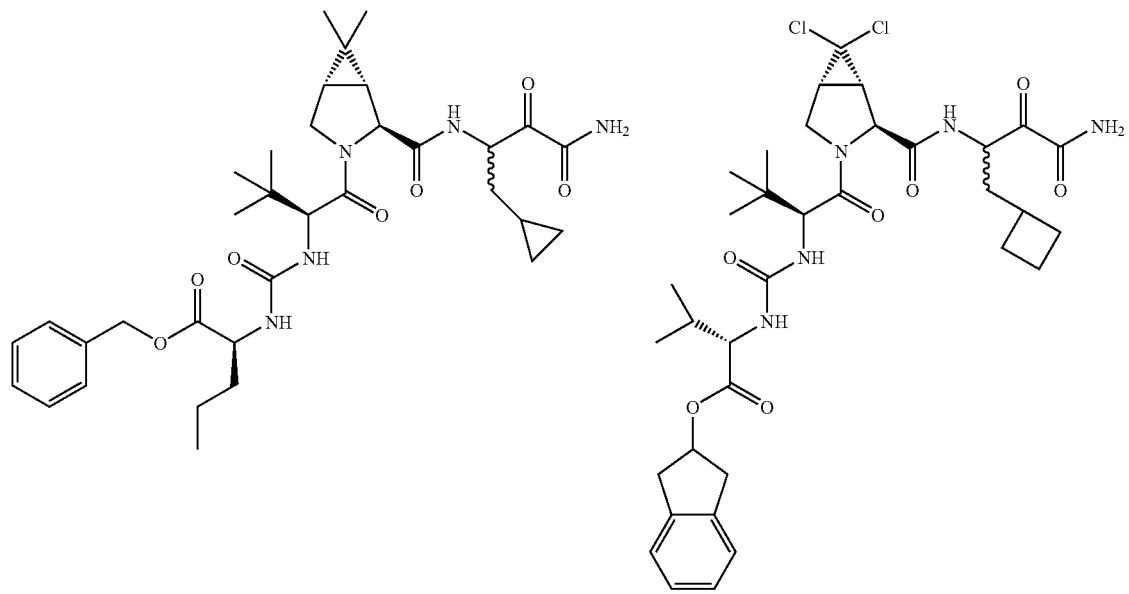
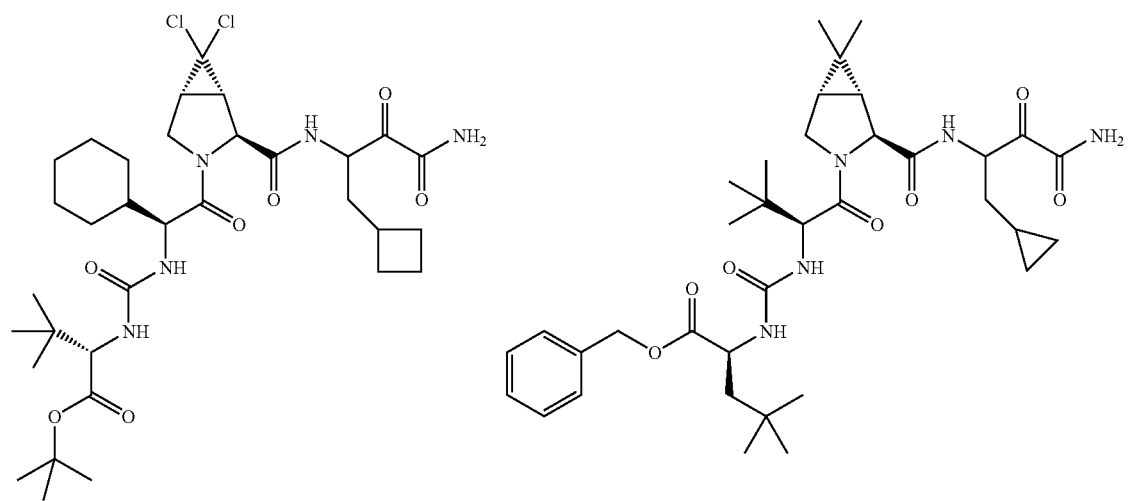

| 361 | 362 |
|---|---|
-continued
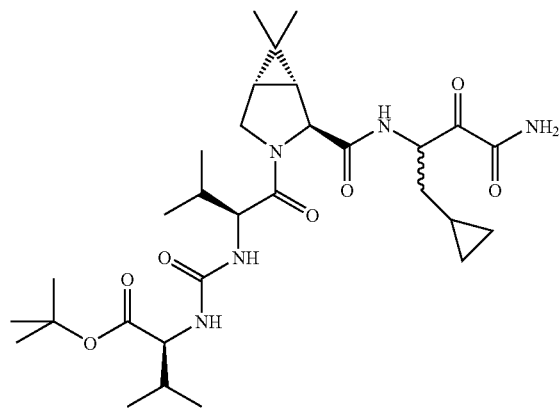
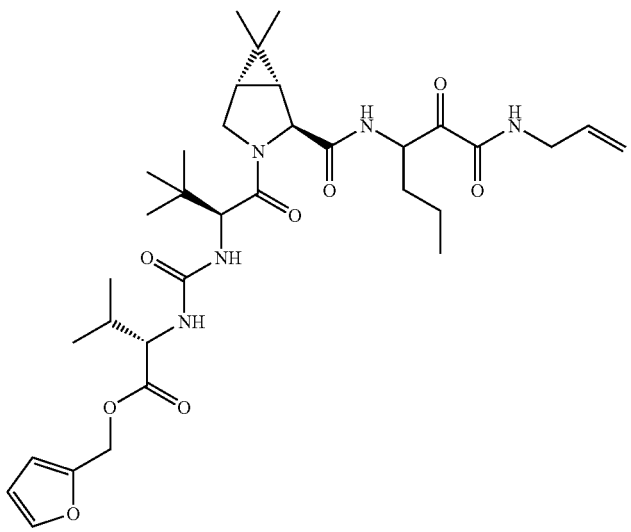
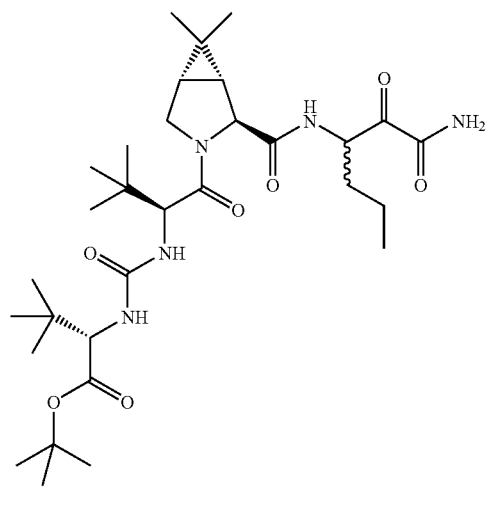
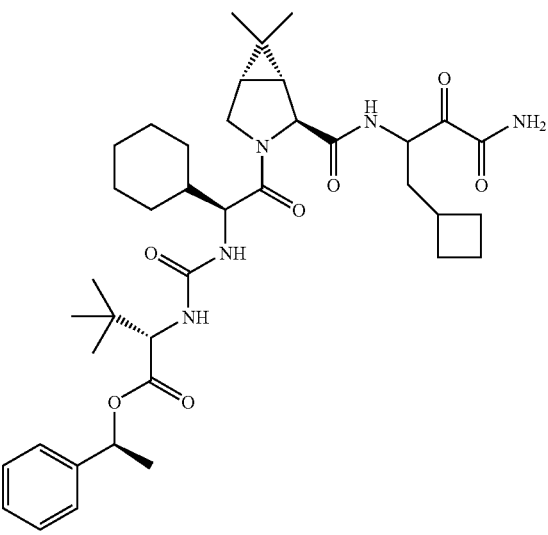
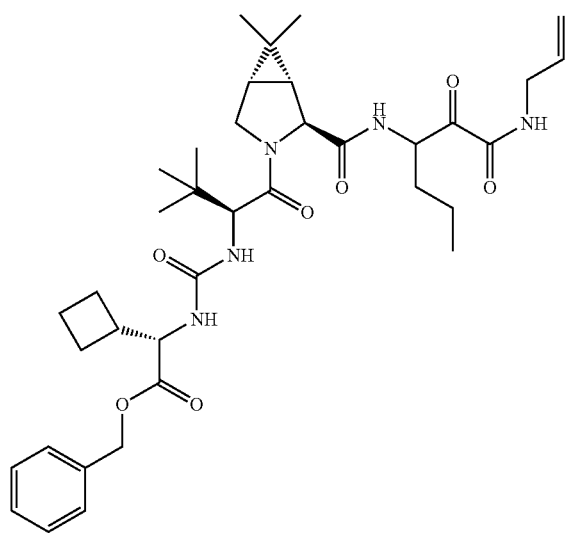
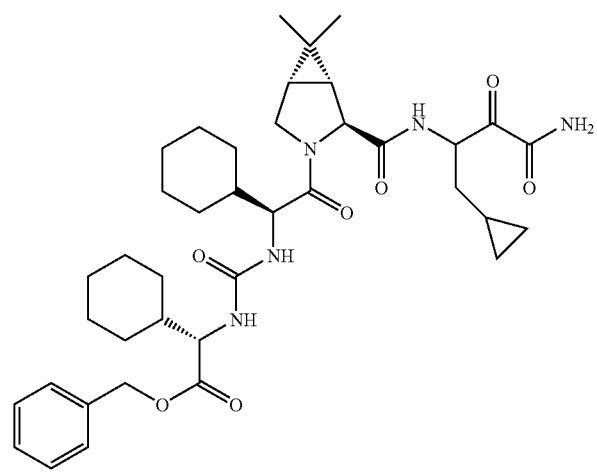

363
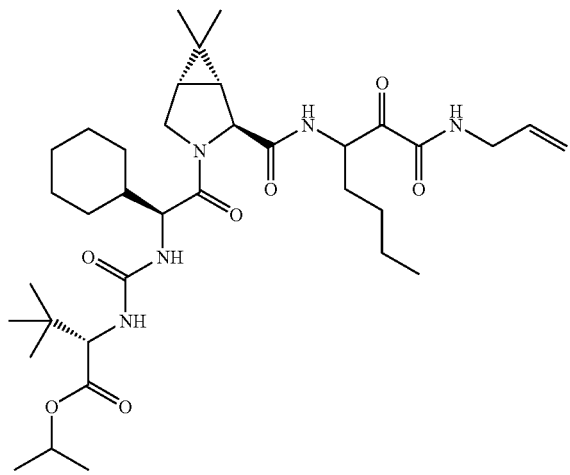
364
-continued
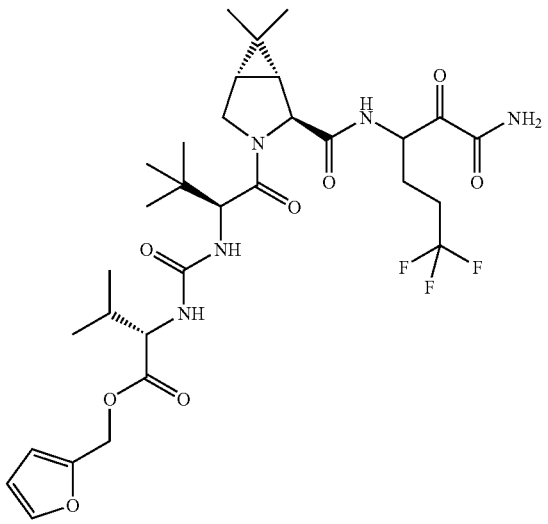
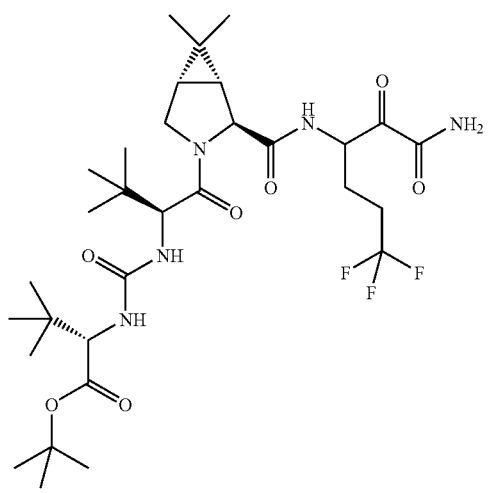
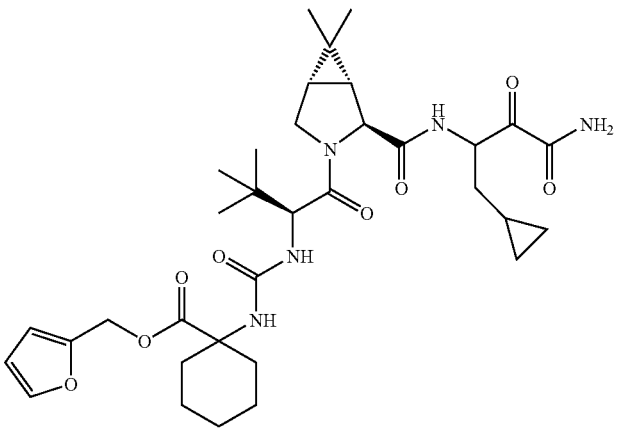
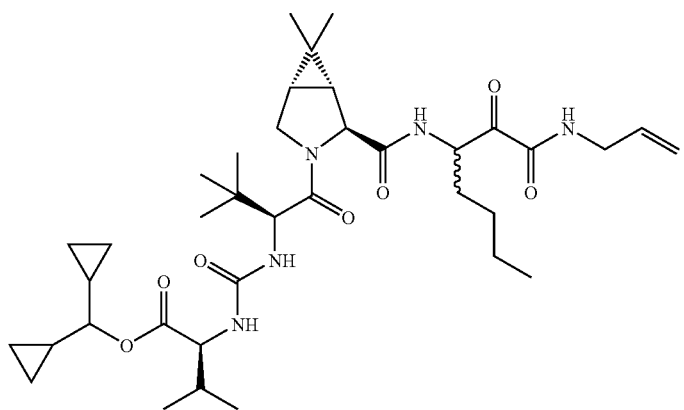

365
-continued
366
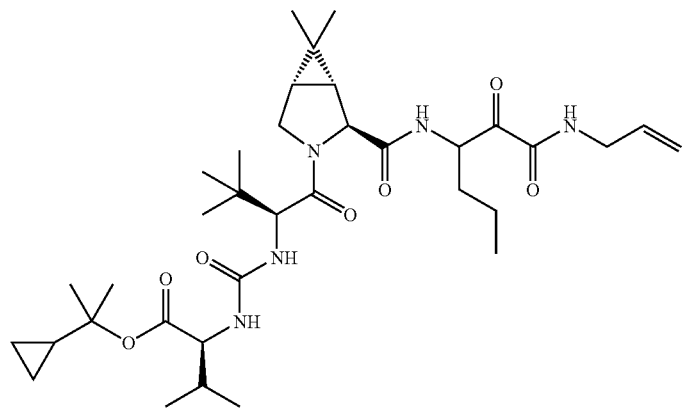
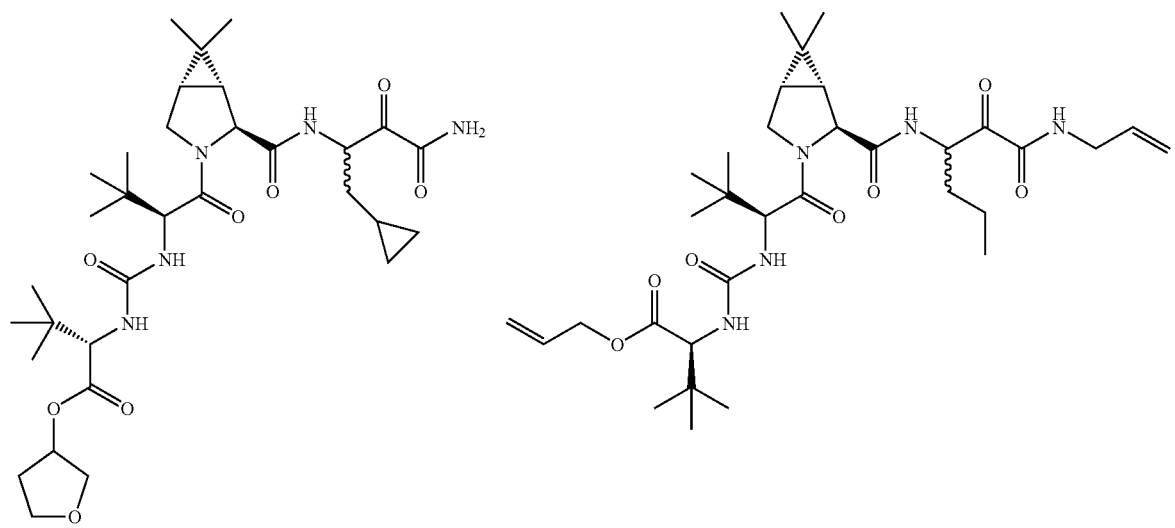
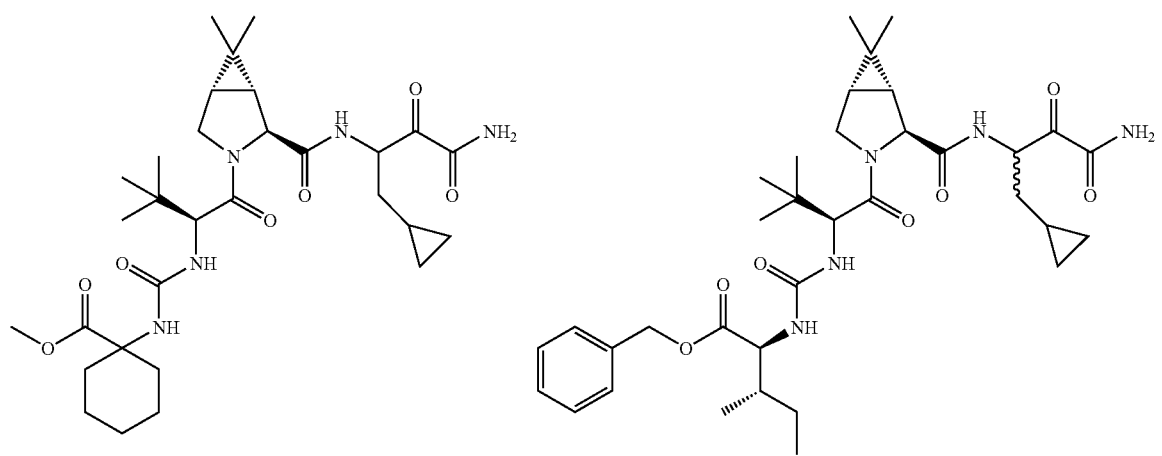

-continued
| 367 | 368 |
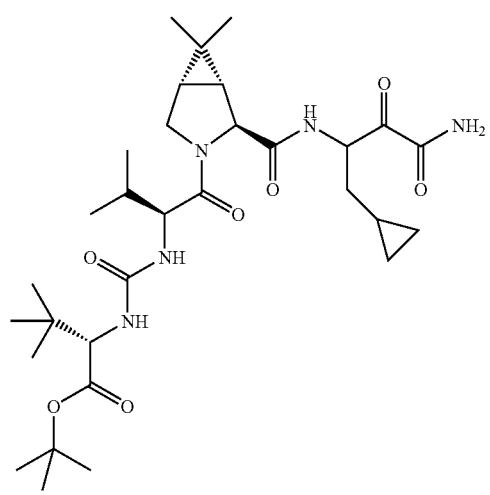
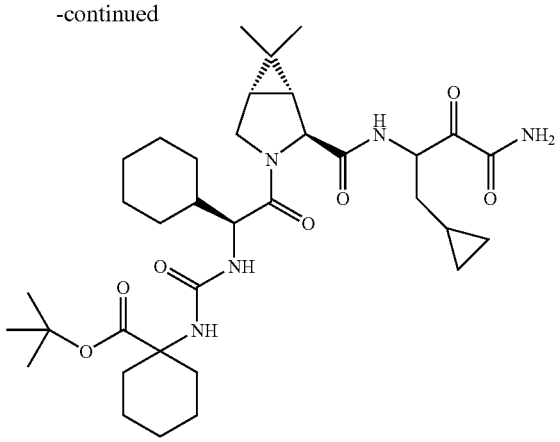
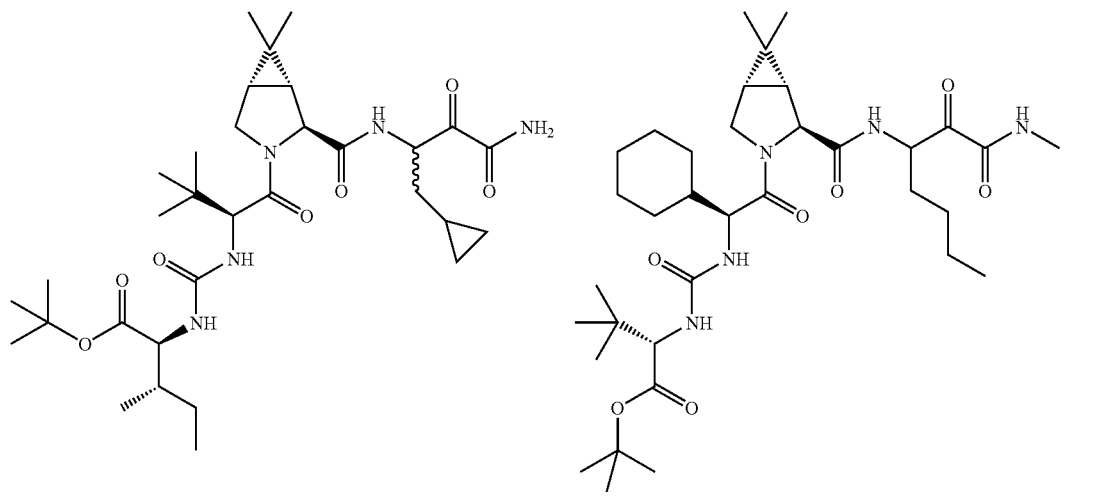
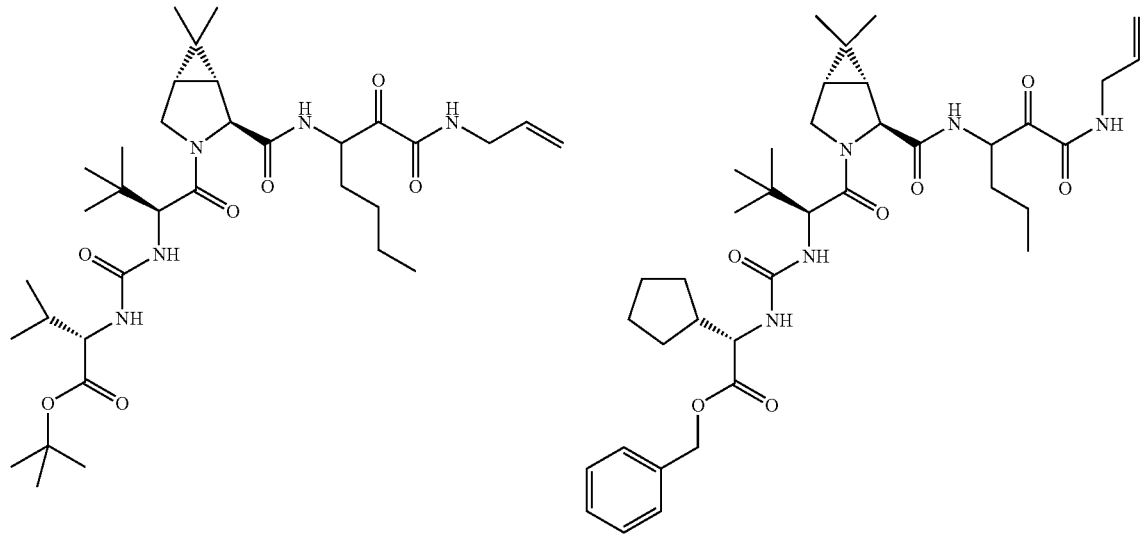

369
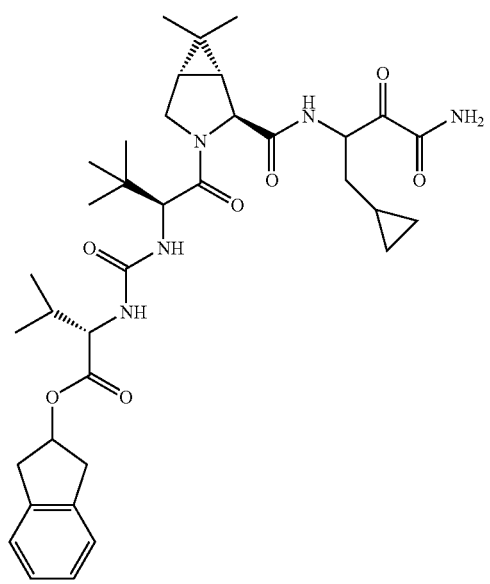
-continued
370
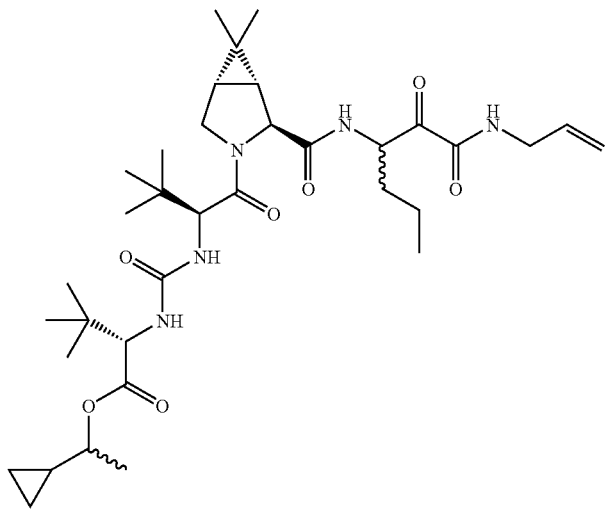
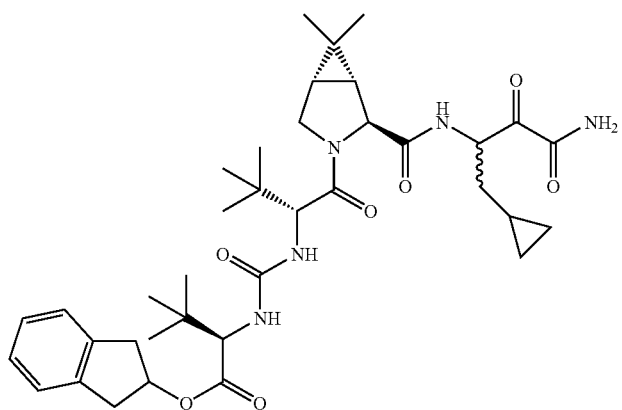
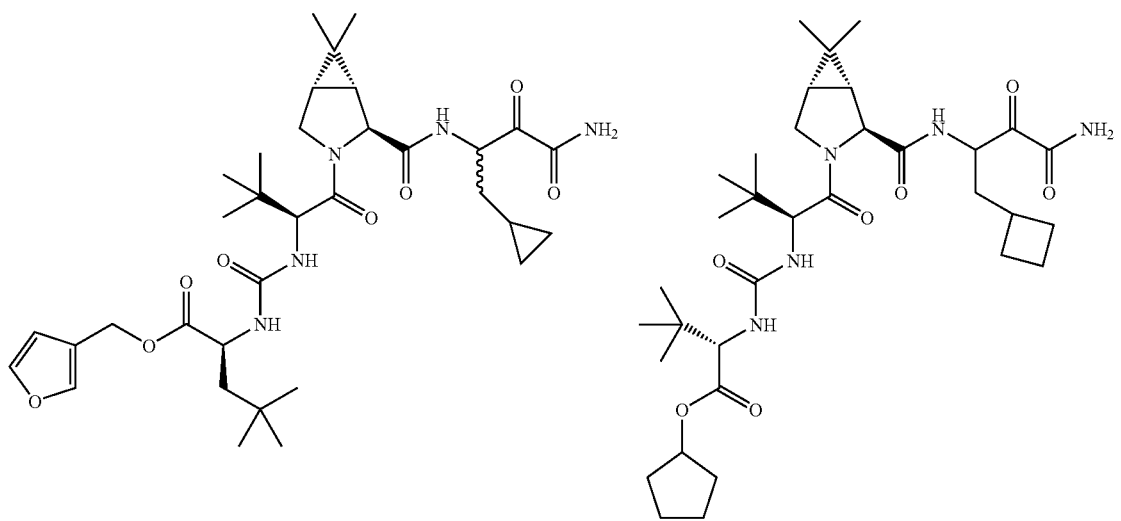

371 372
-continued
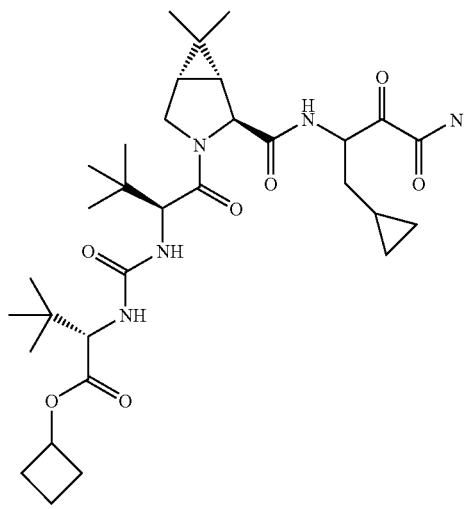
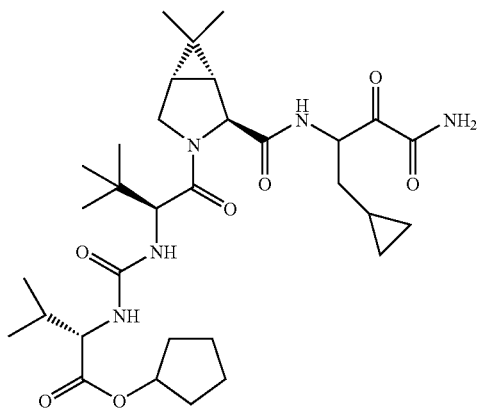
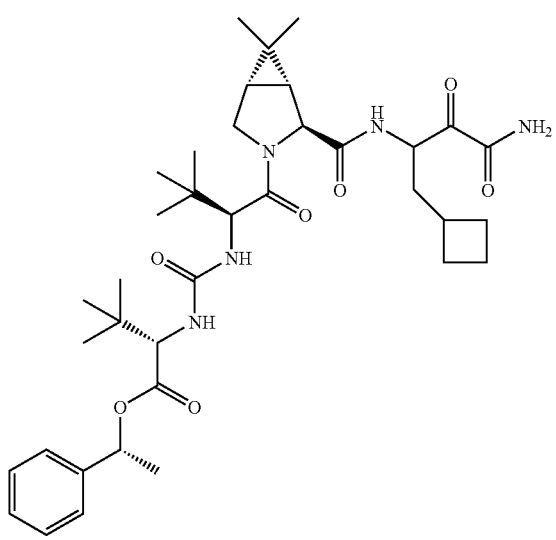
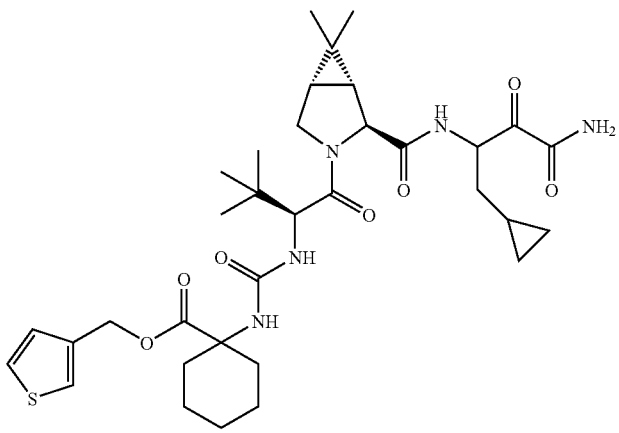
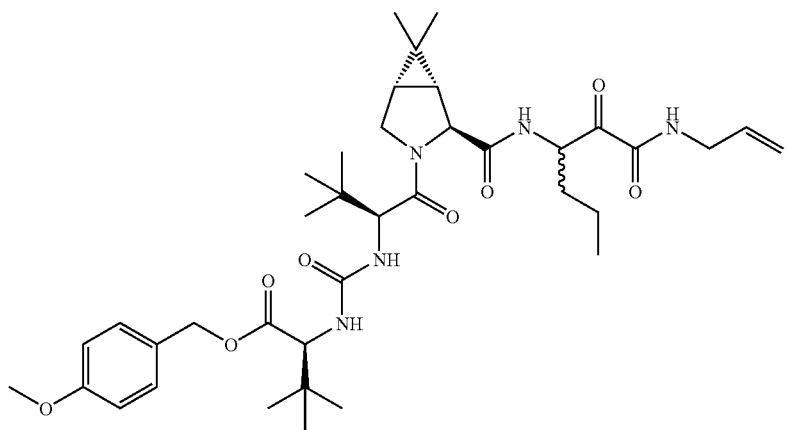

373 374
-continued
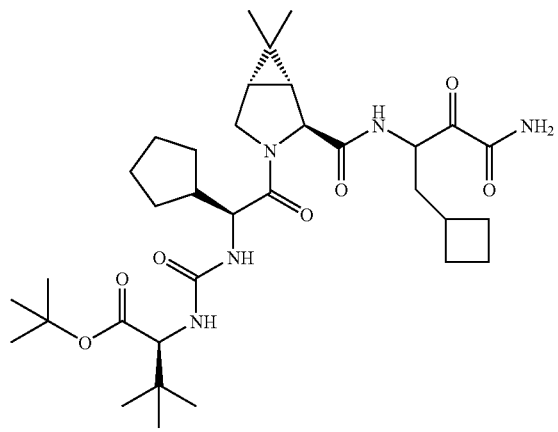
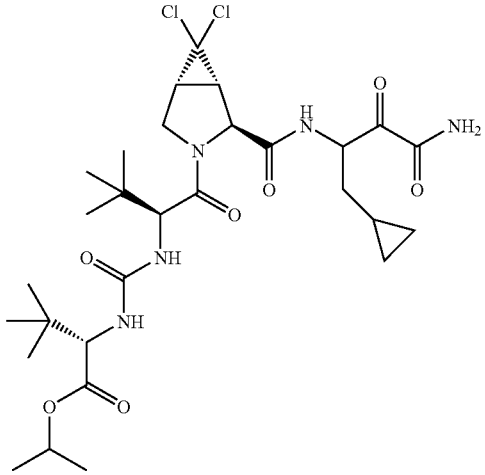
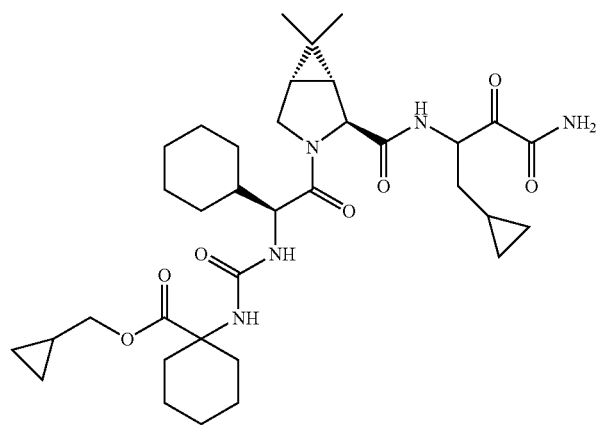
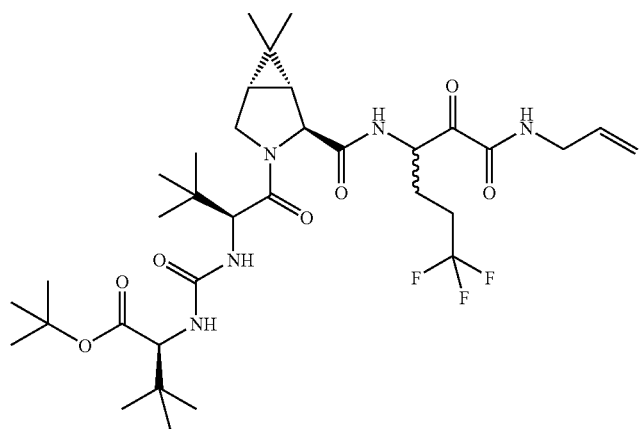

-continued
| 375 | 376 |
|---|---|
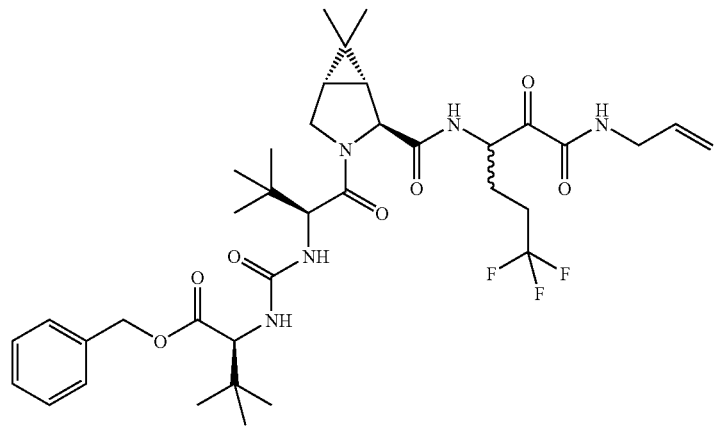
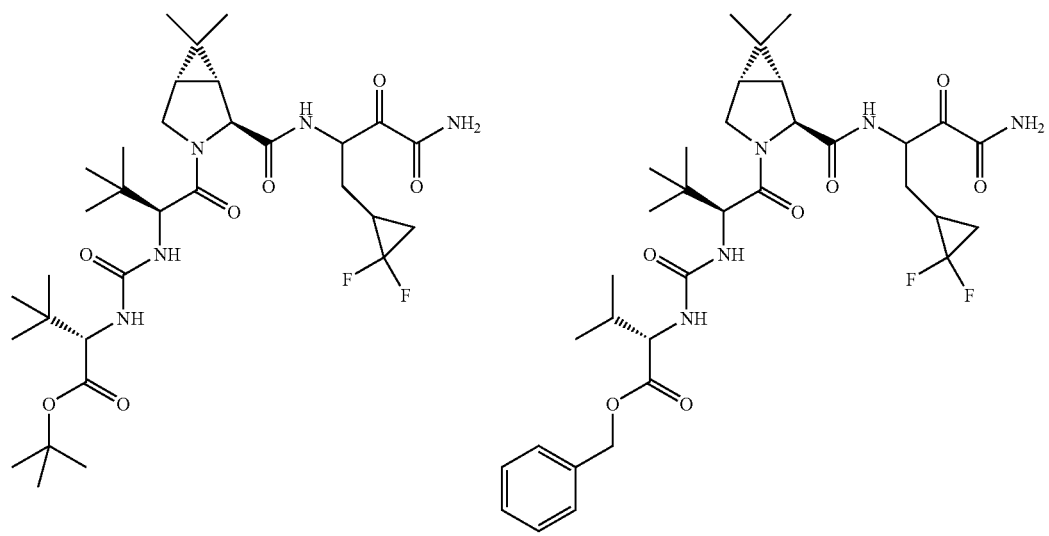
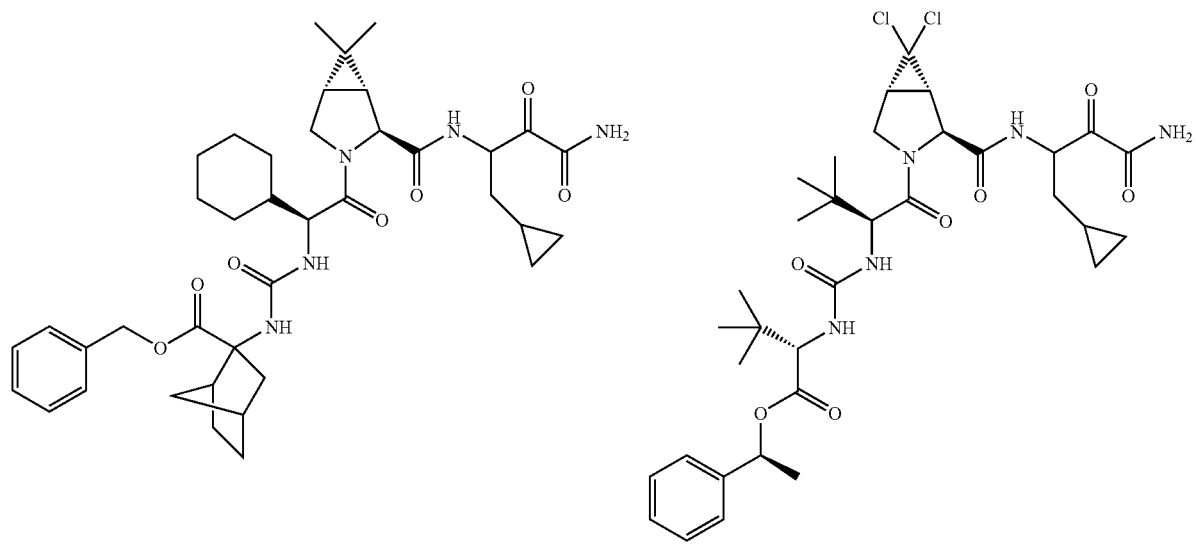

377 378
-continued
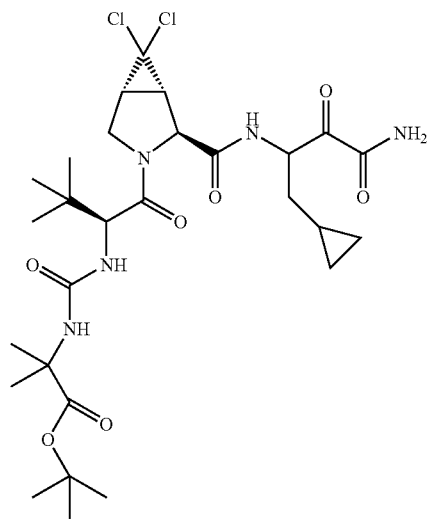
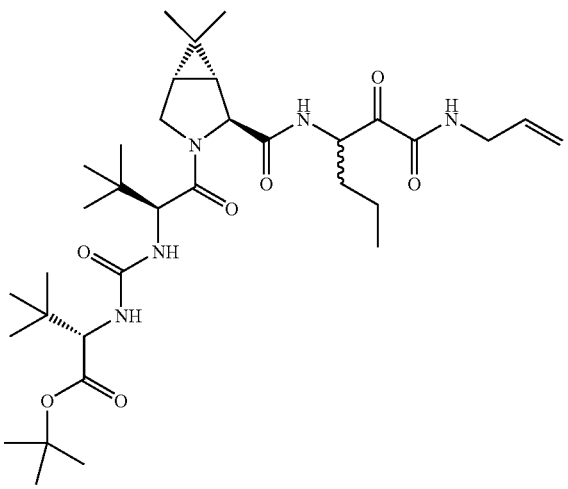
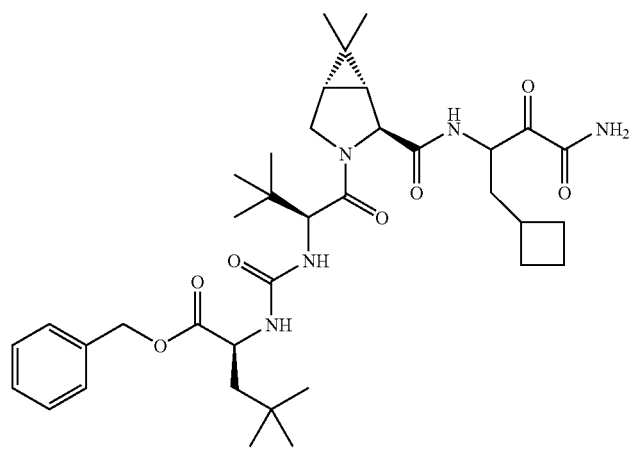
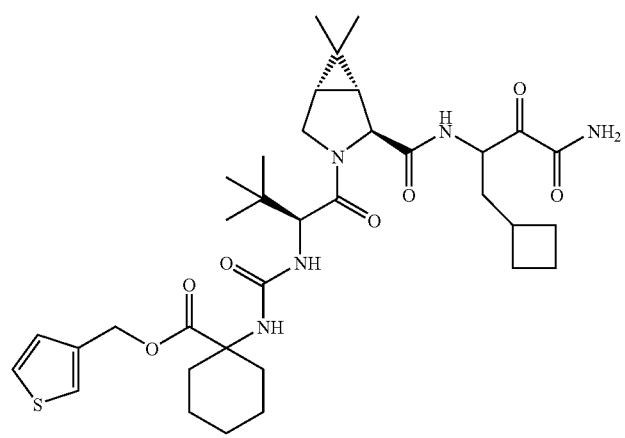

-continued
| 379 | 380 |
|---|---|
| 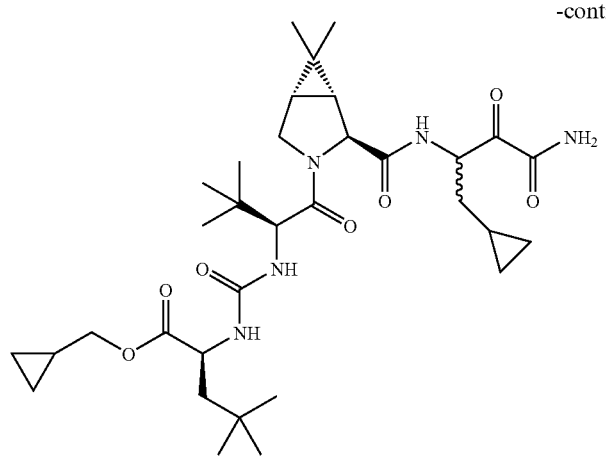 | 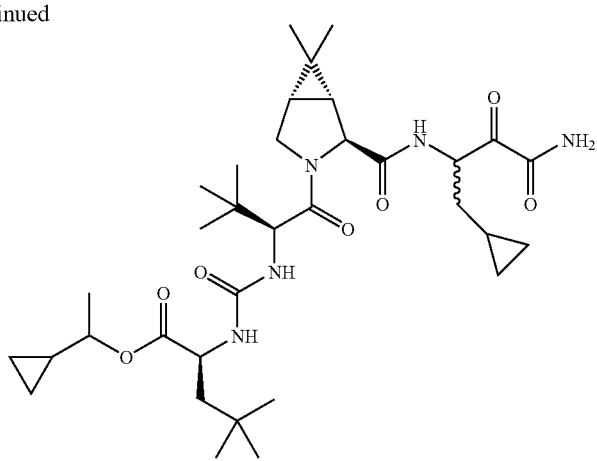 |
| 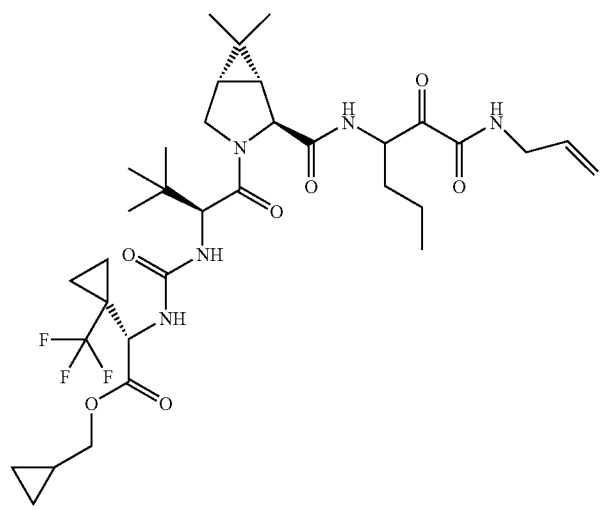 | 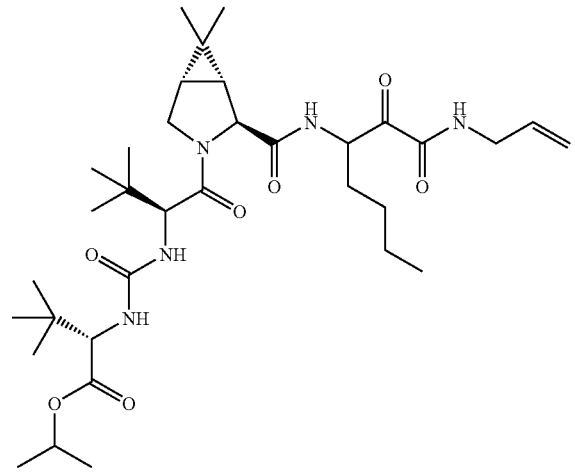 |
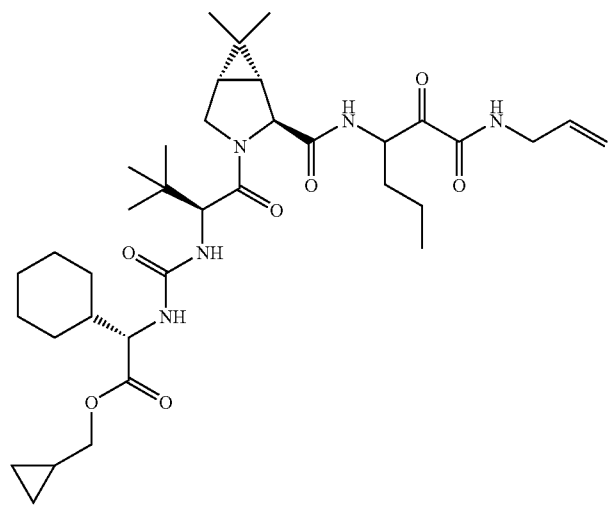

-continued
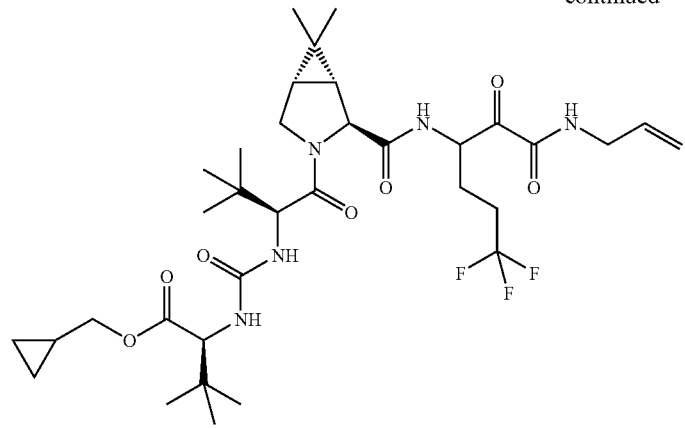
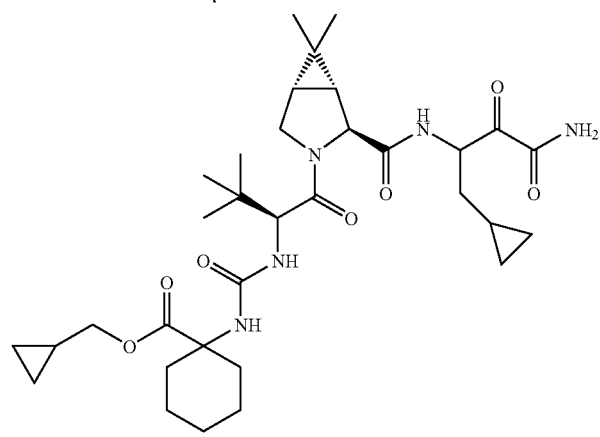
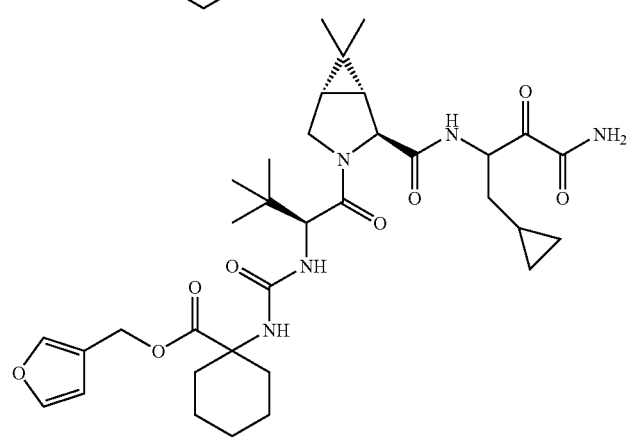
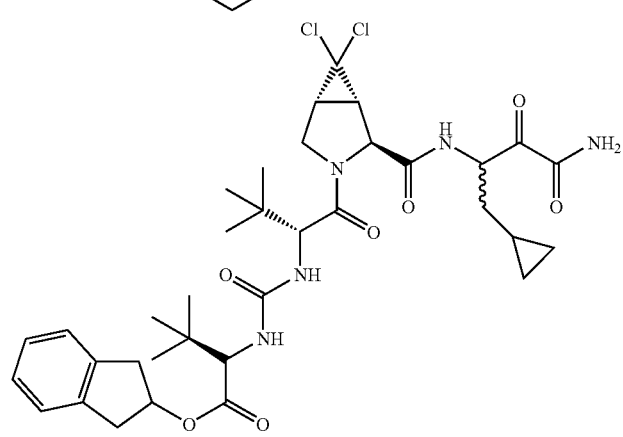

-continued
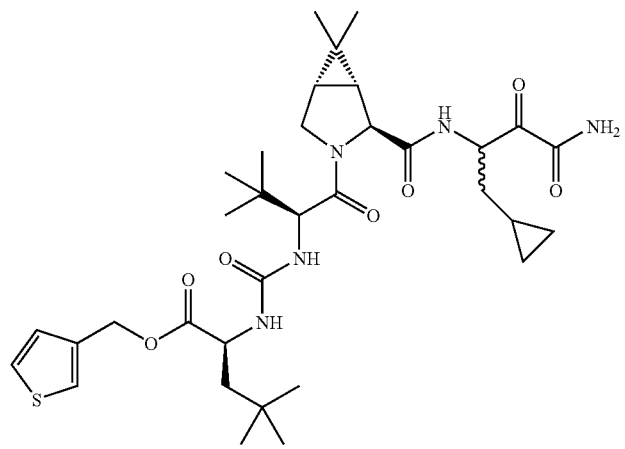
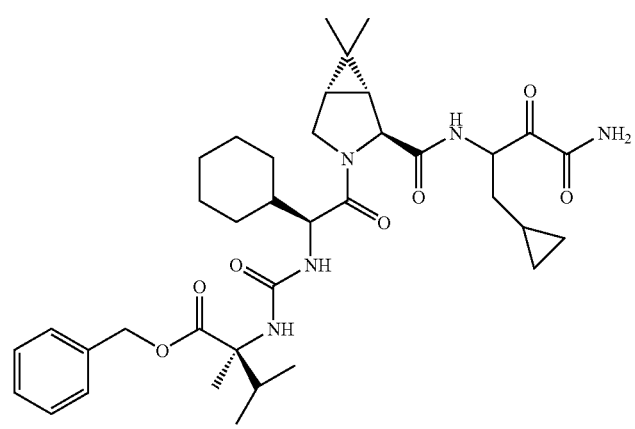
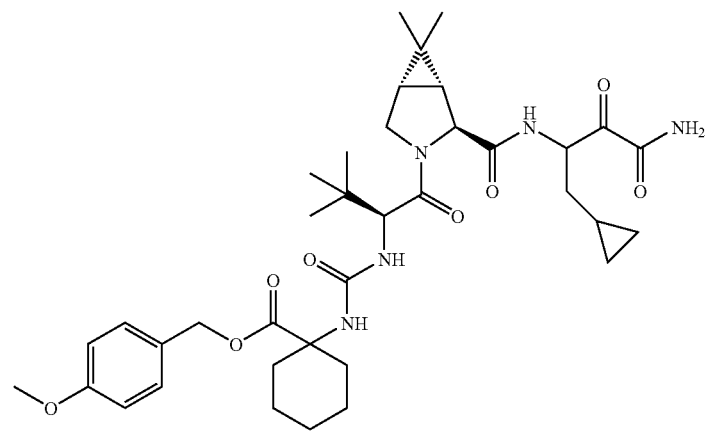

-continued
| 385 | 386 |
|---|---|
| 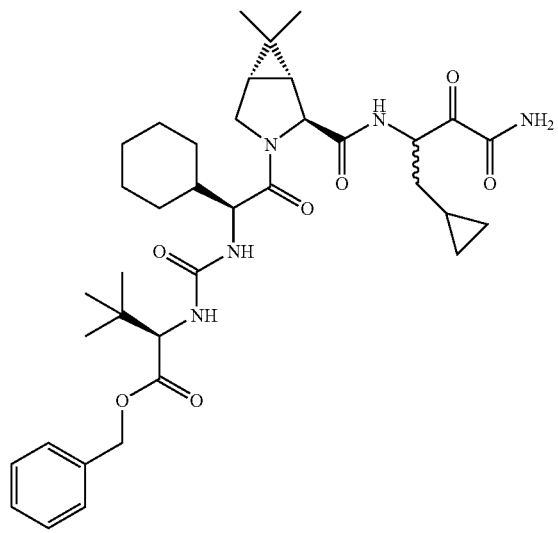 | 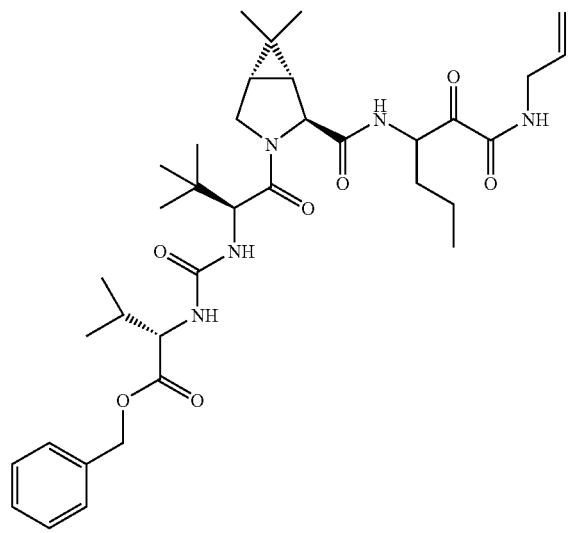 |
| 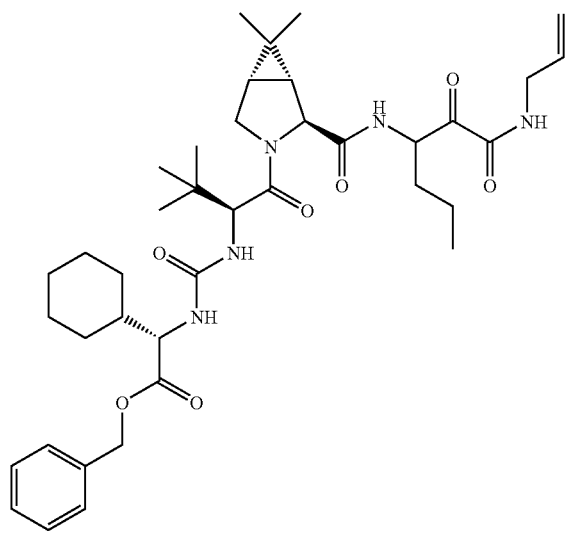 | 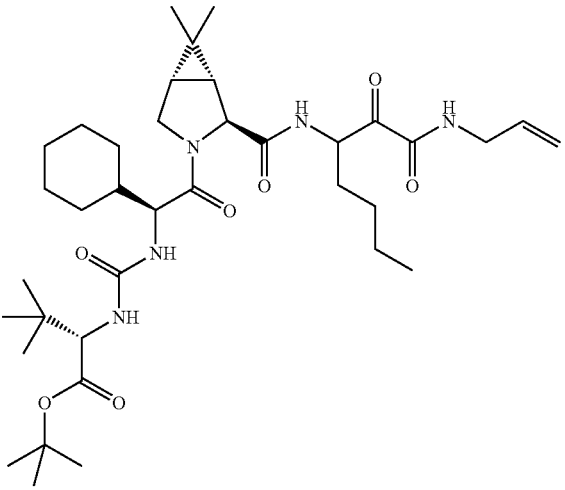 |
| 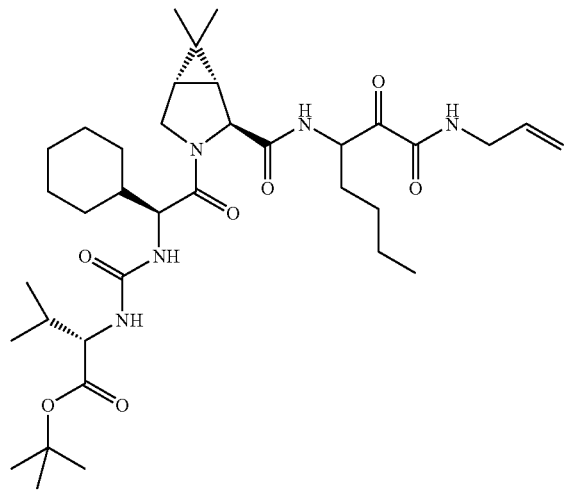 | 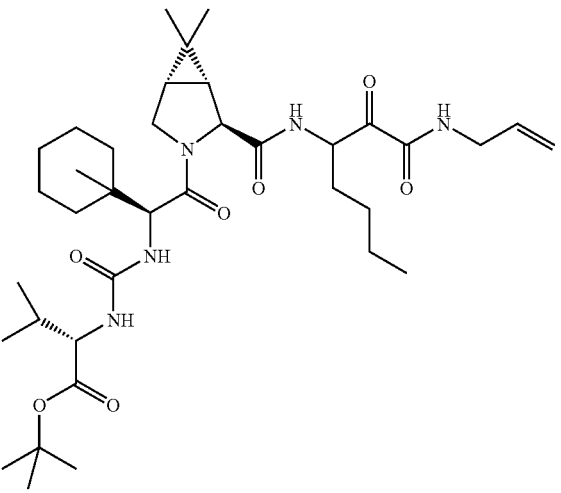 |

-continued
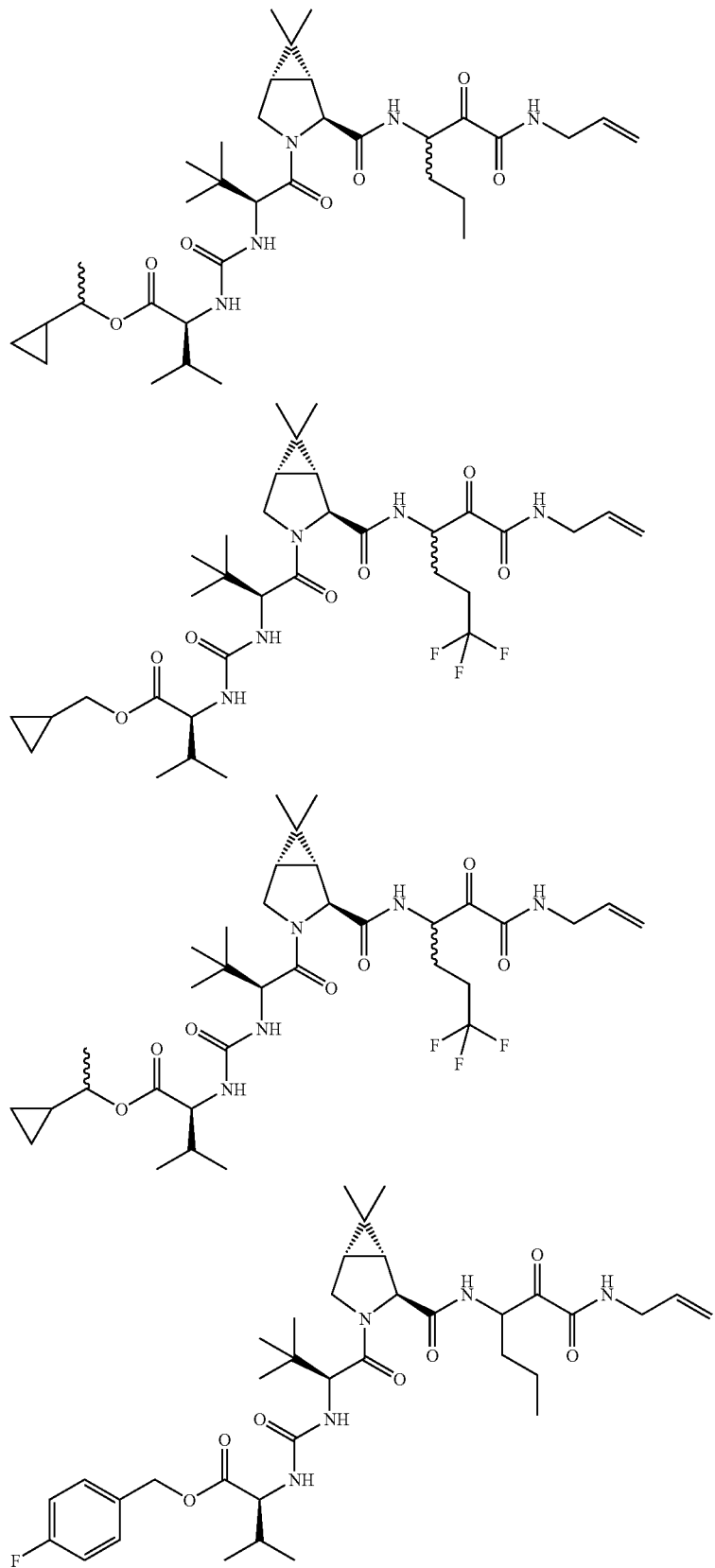

-continued
| 389 | 390 |
|---|---|
| 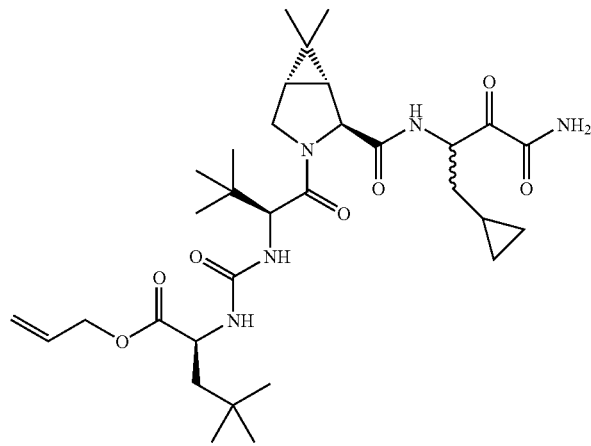 | 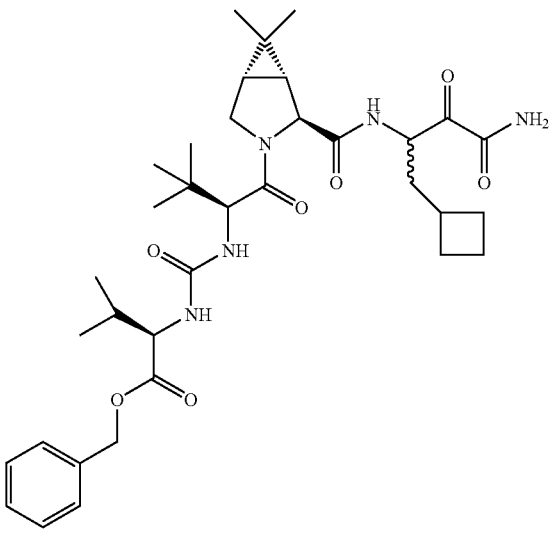 |
| 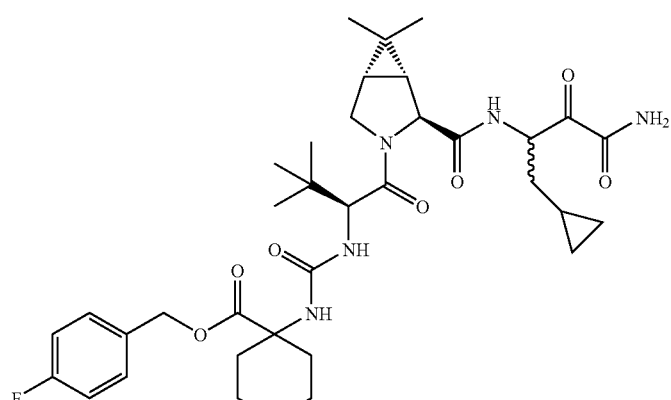 | 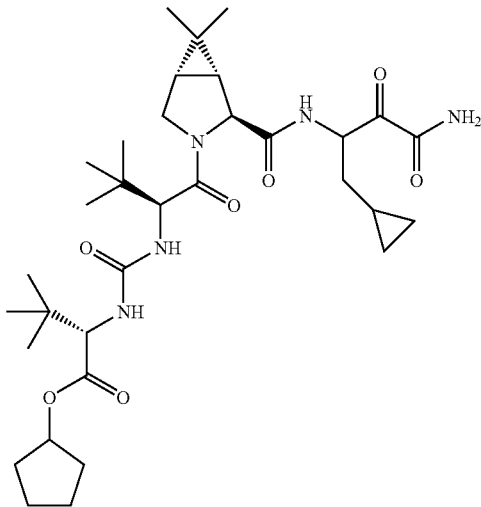 |
| 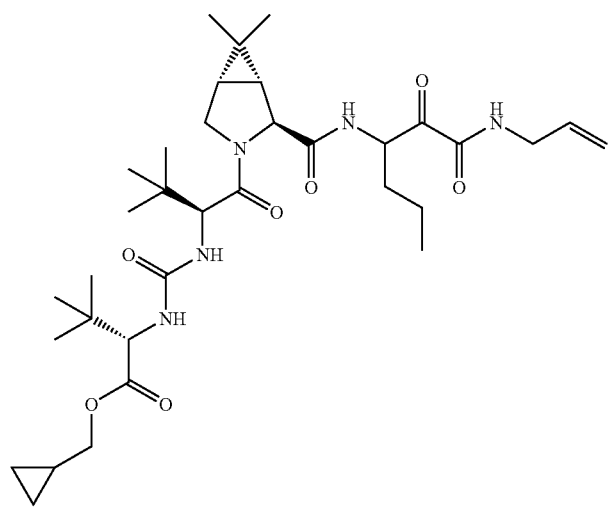 | 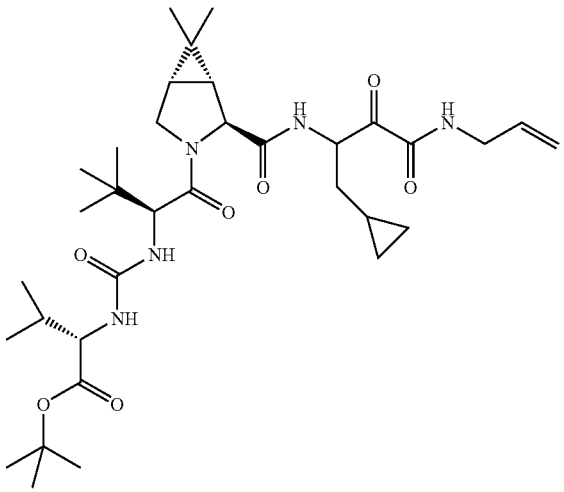 |

391
-continued
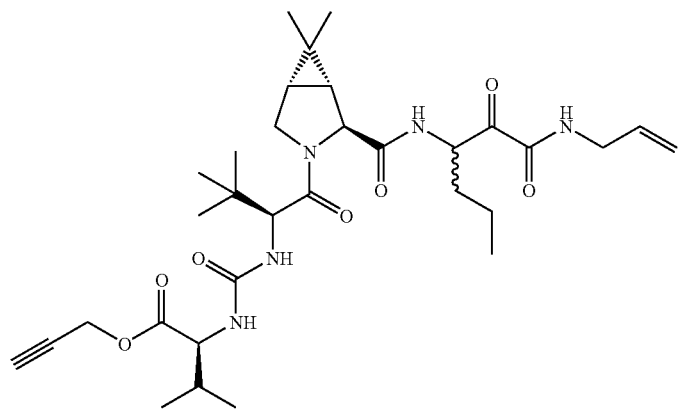
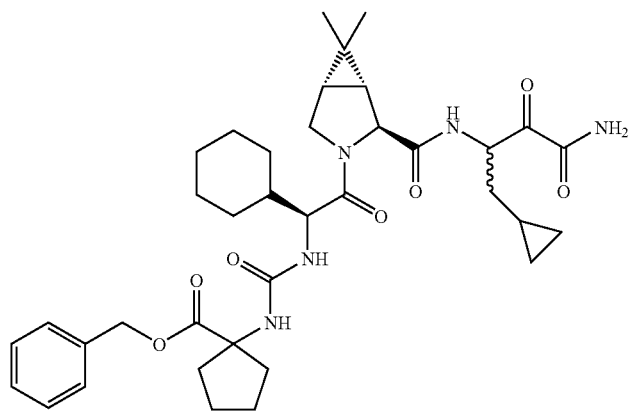
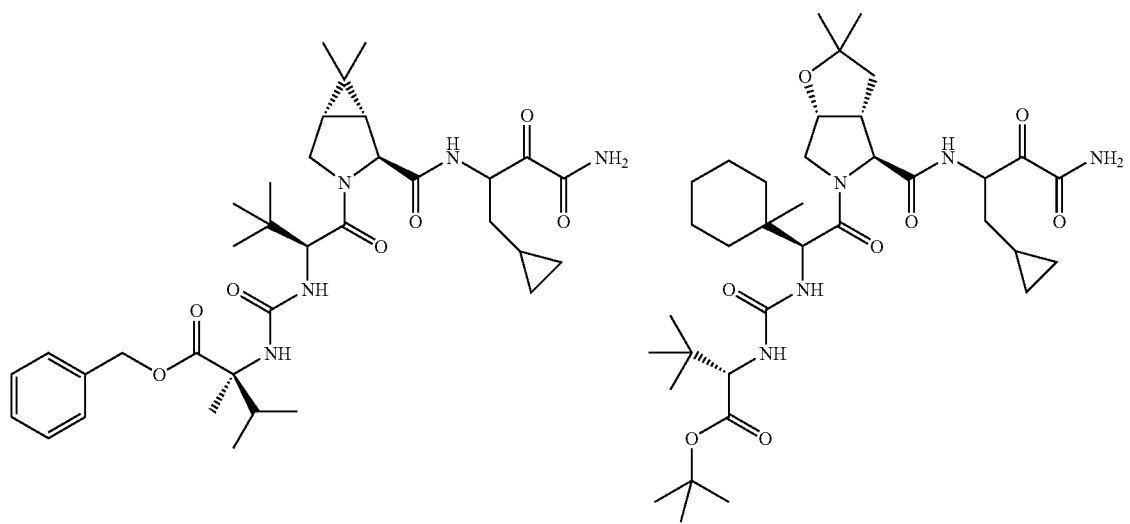

-continued
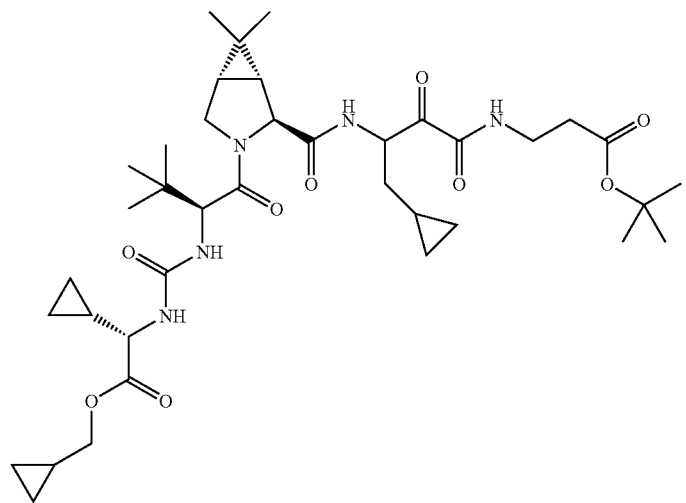
393
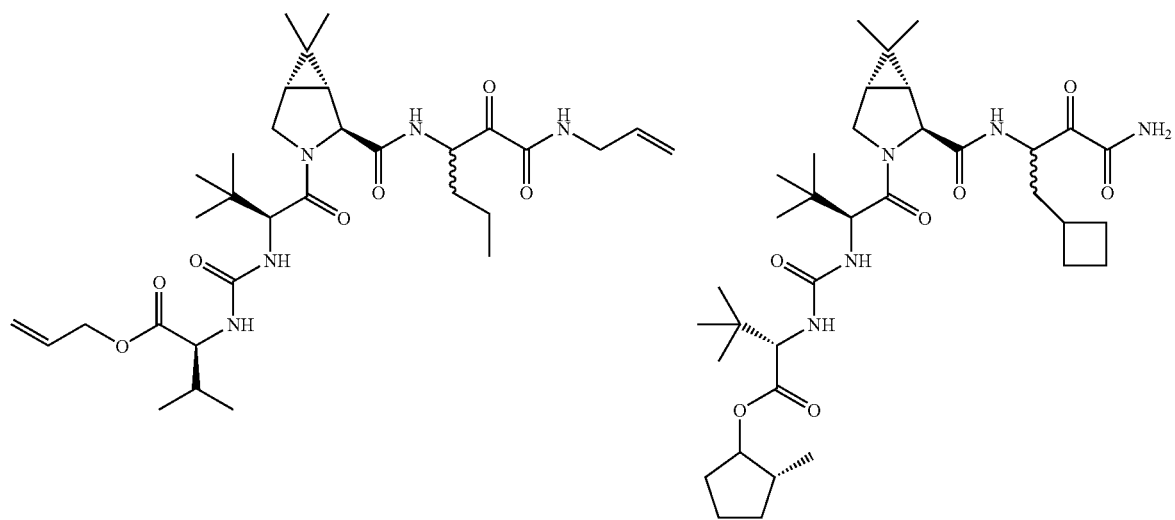
394
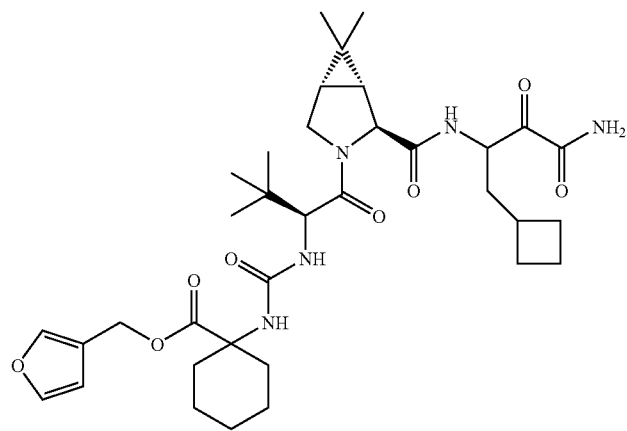

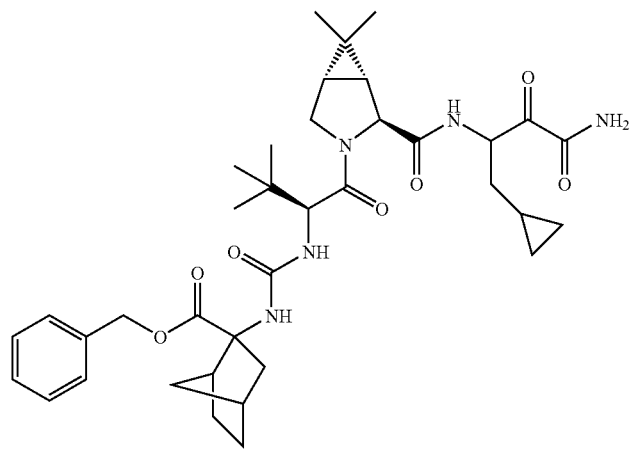
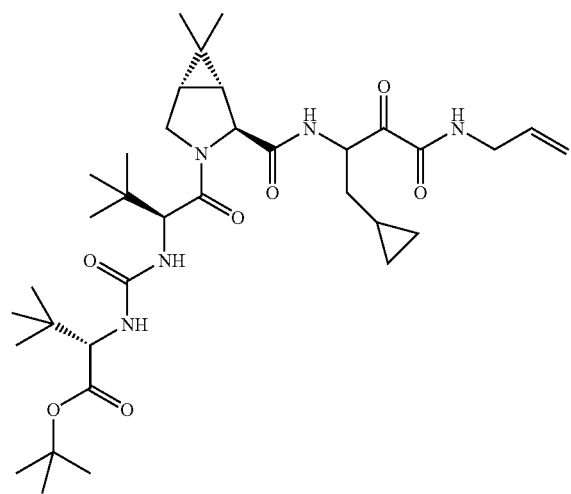
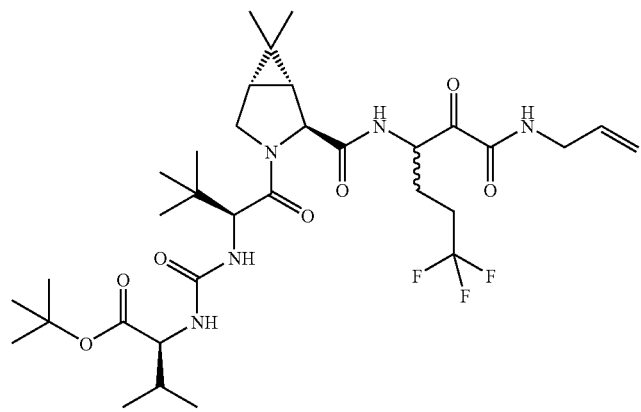

-continued
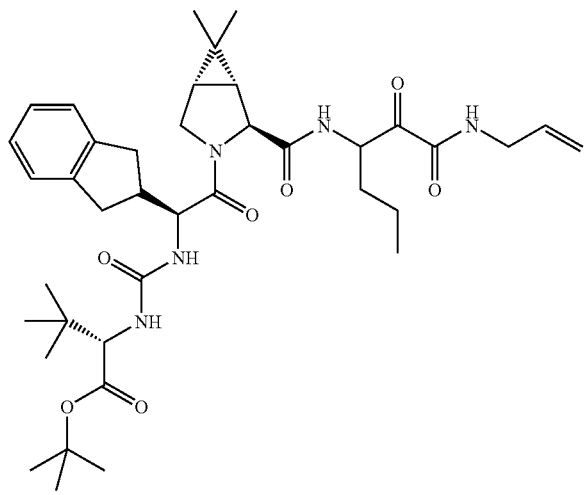
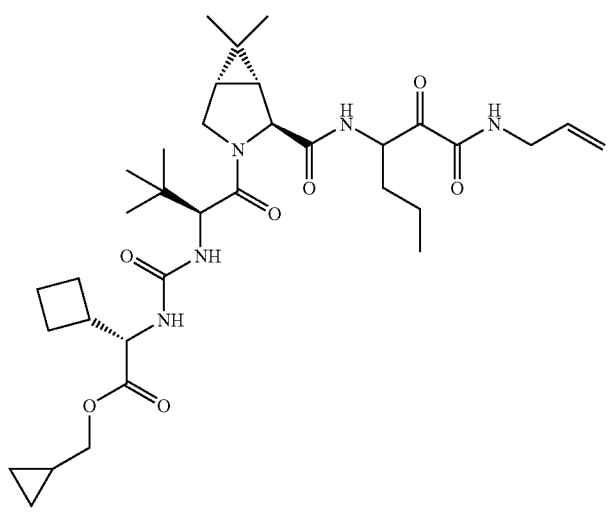
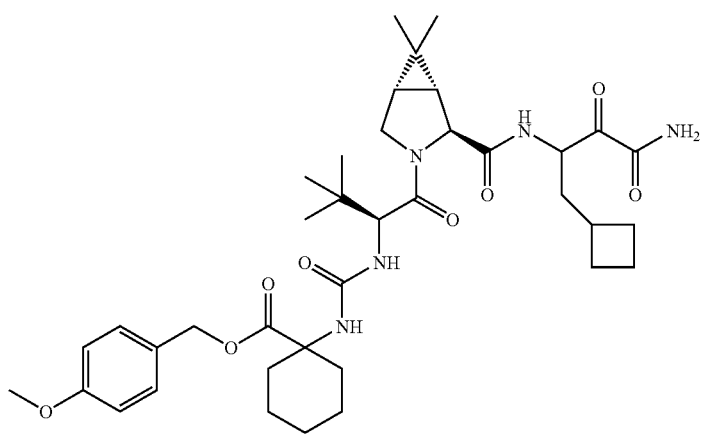

399 400
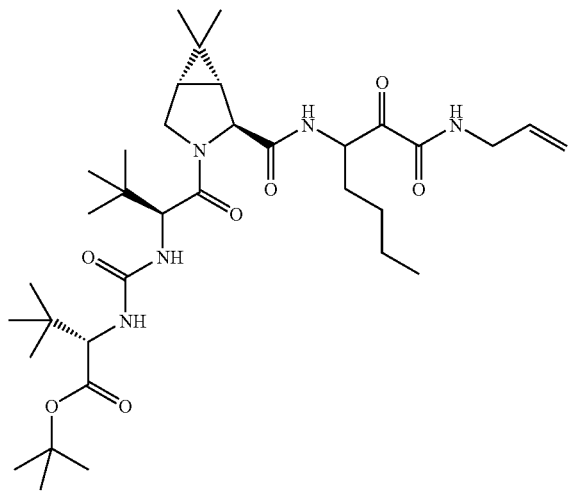
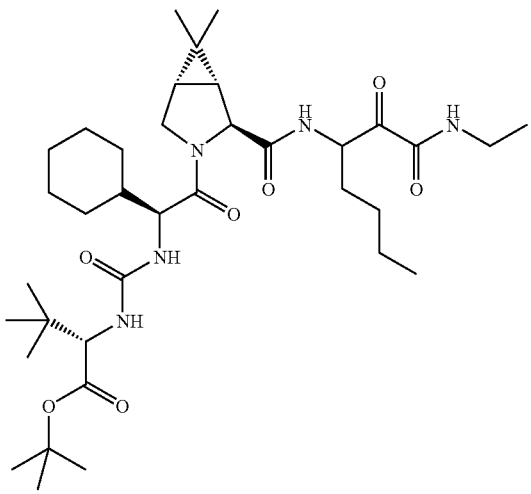
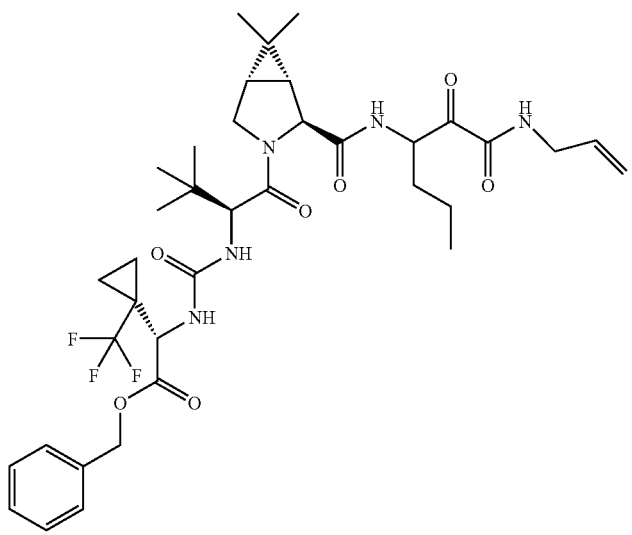
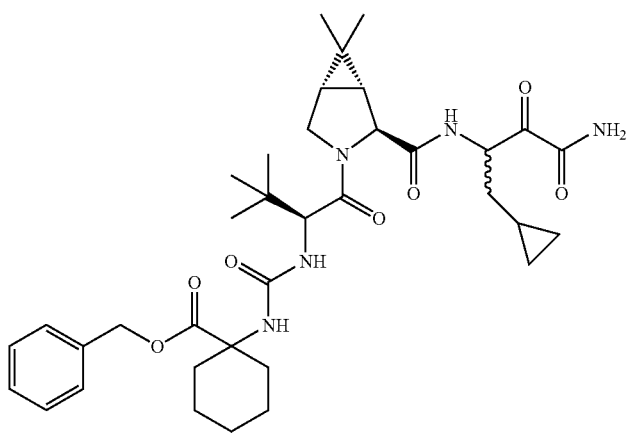

-continued
| 401 | 402 |
|---|---|
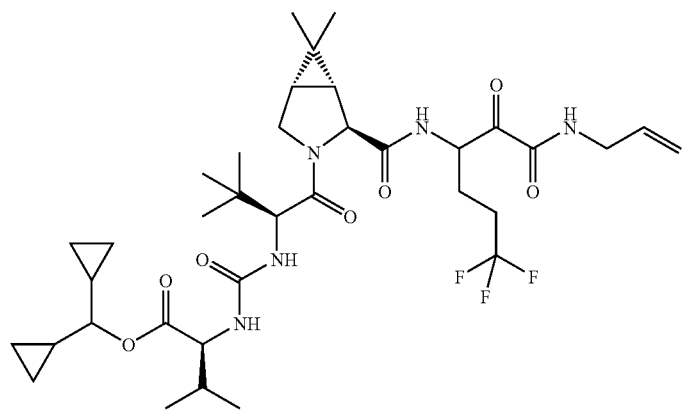
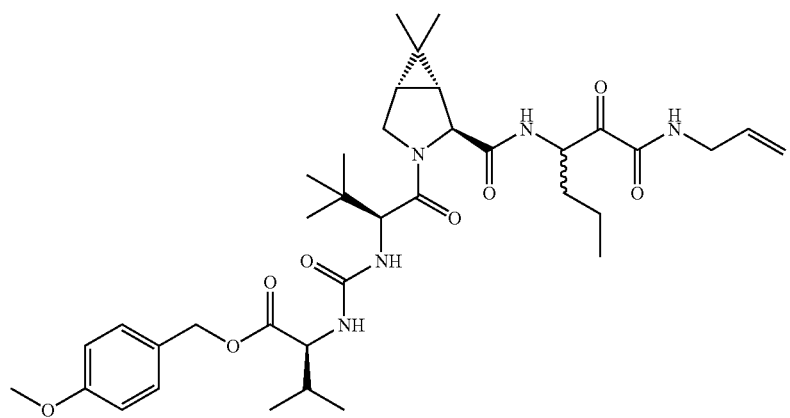
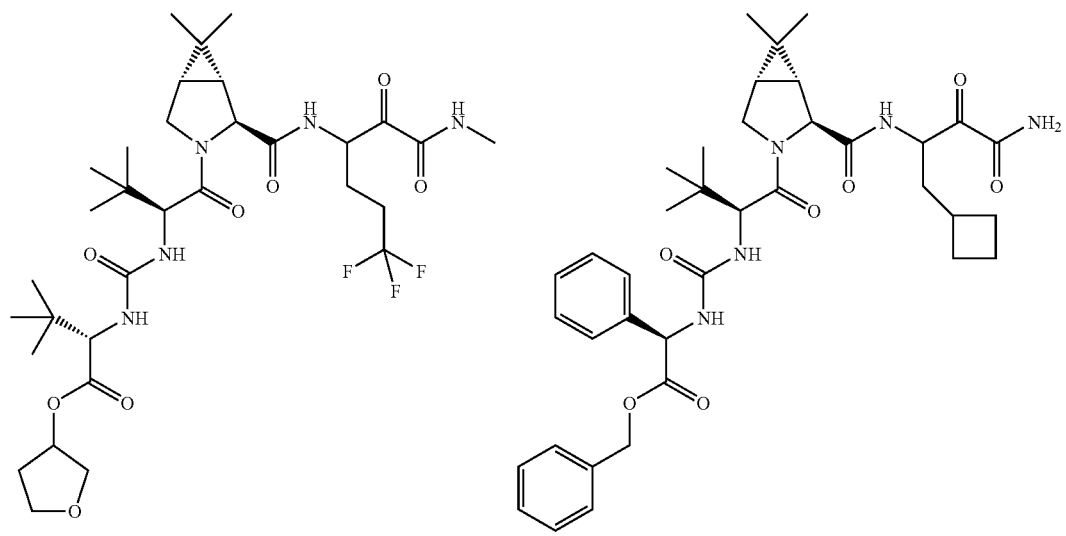

-continued
| 403 | 404 |
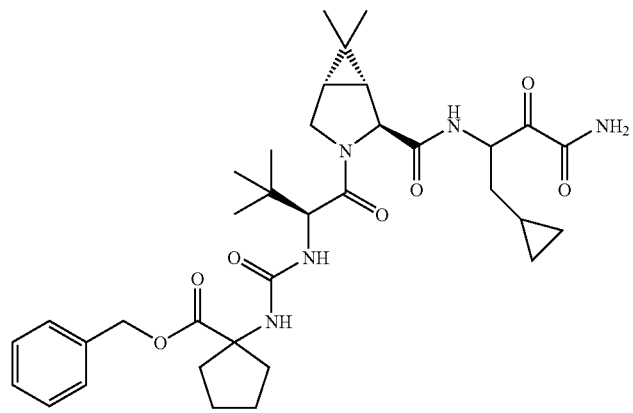
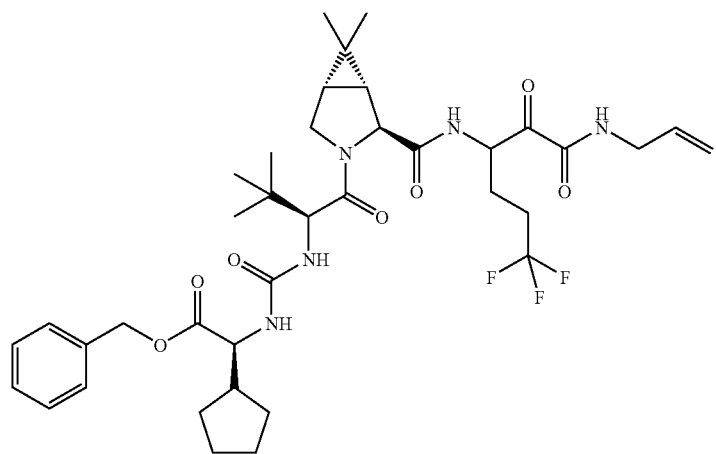
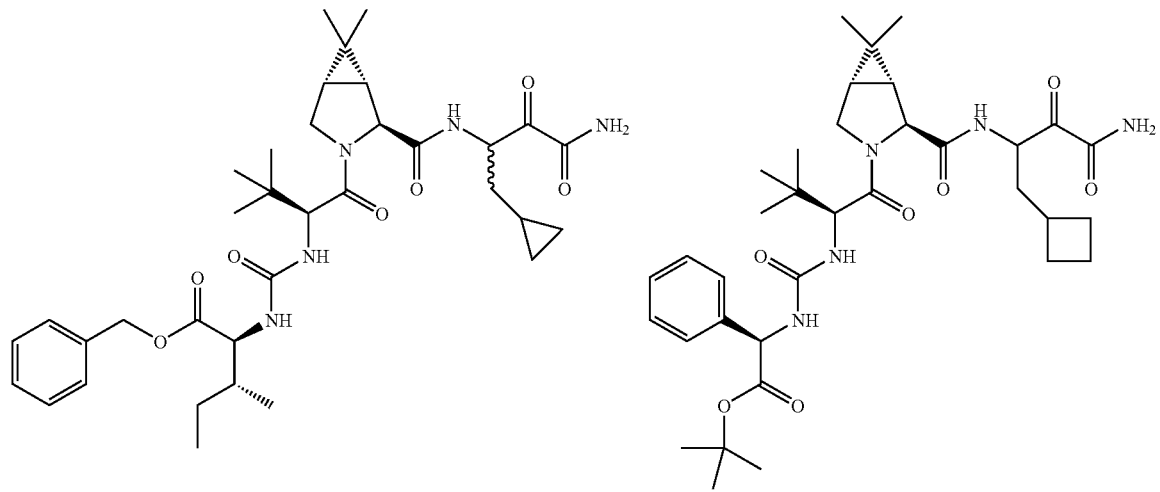

-continued
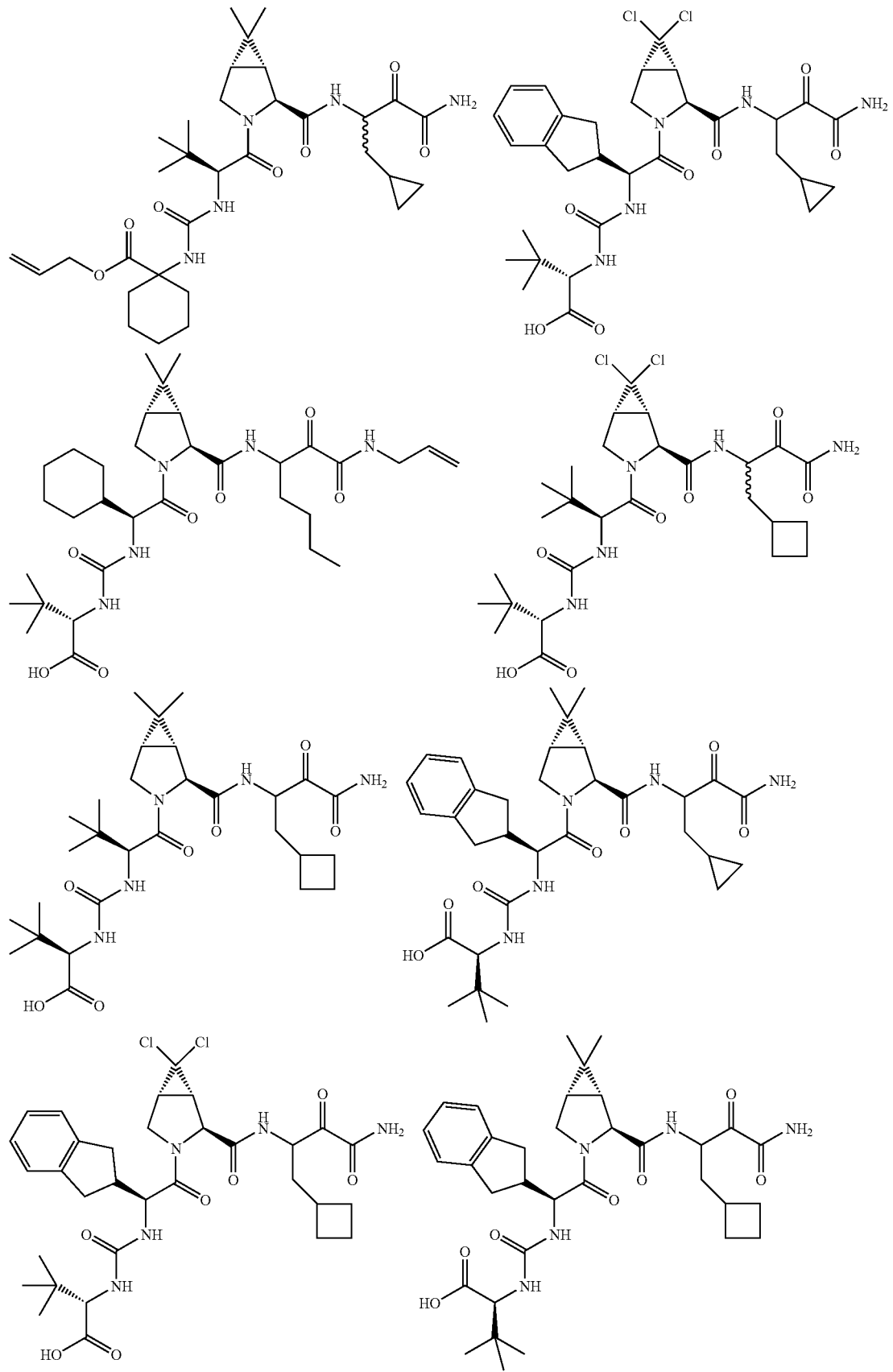

-continued
| 407 | 408 |
|---|---|
| 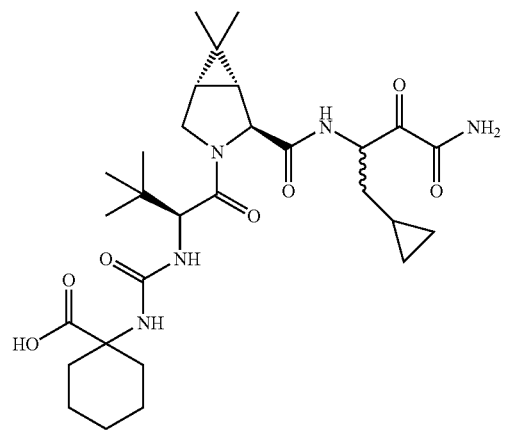 |  |
| 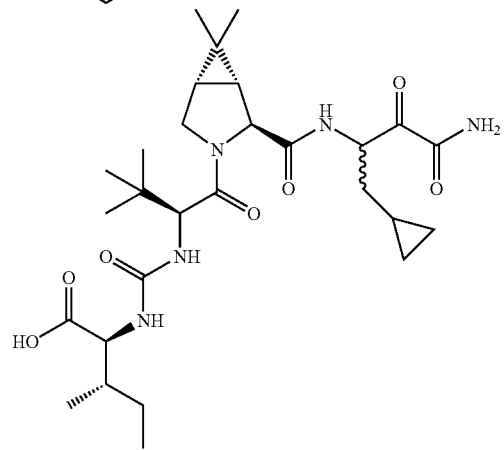 | 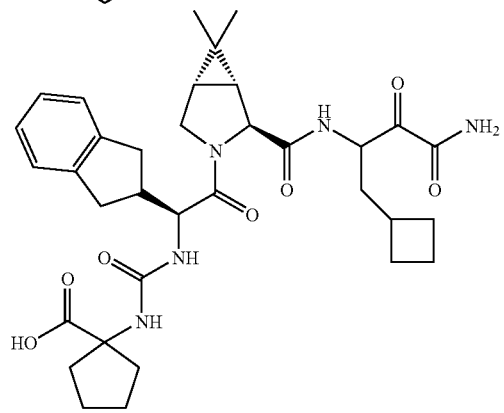 |
| 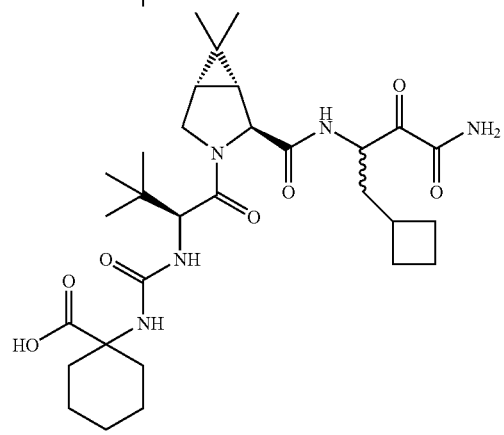 | 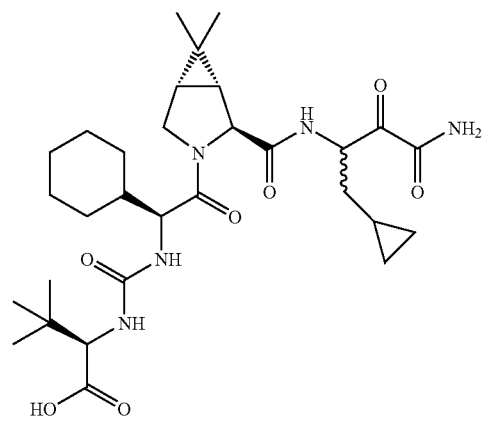 |
| 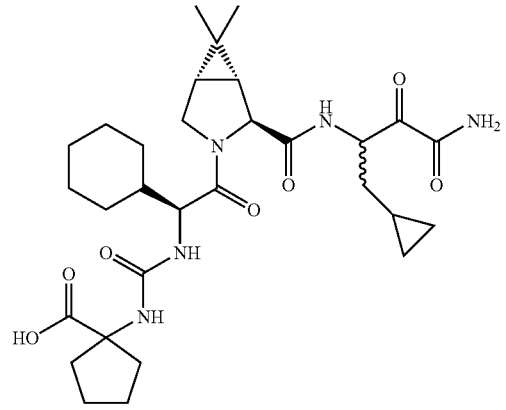 | 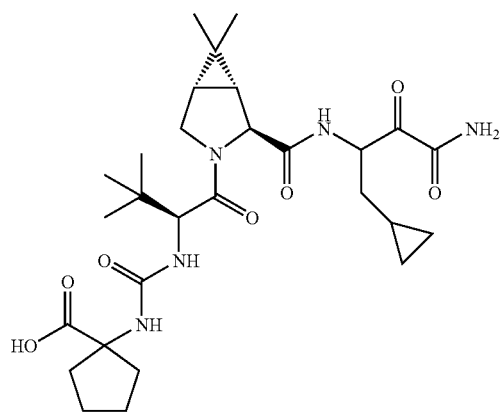 |

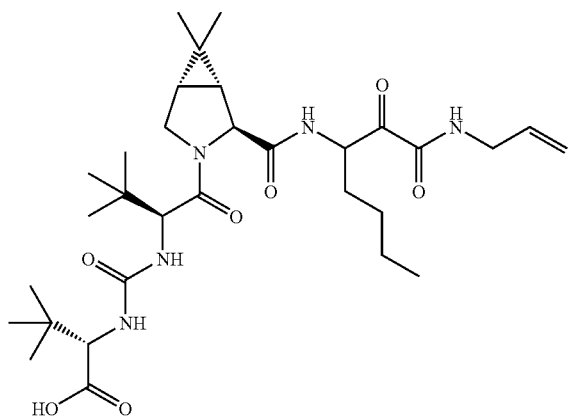
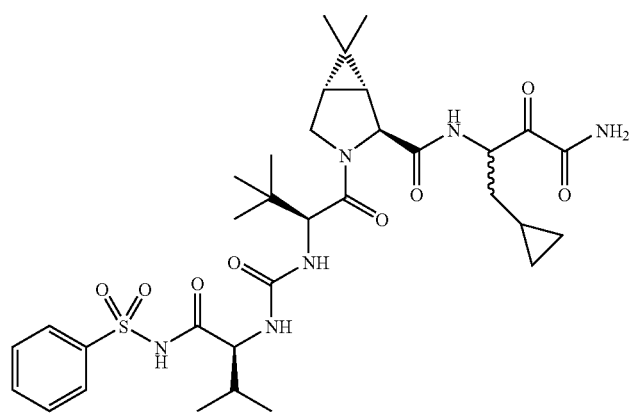
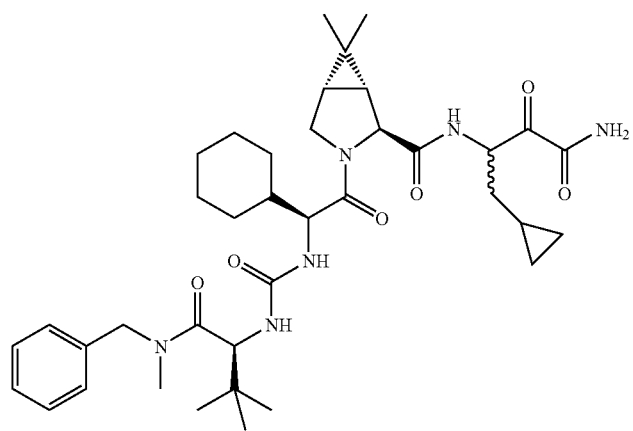

411 412
-continued
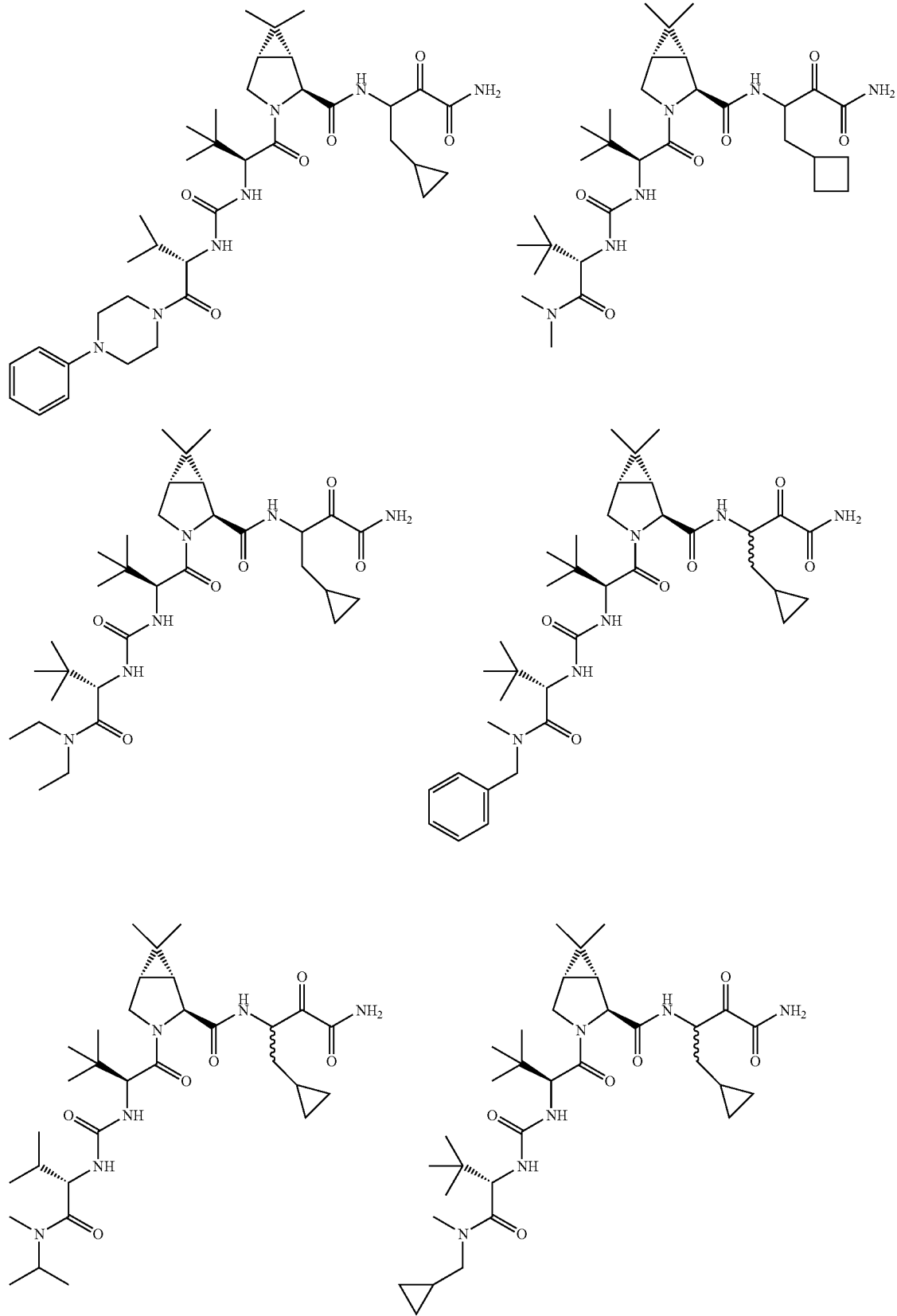

-continued
| 413 | 414 |
|---|---|
| 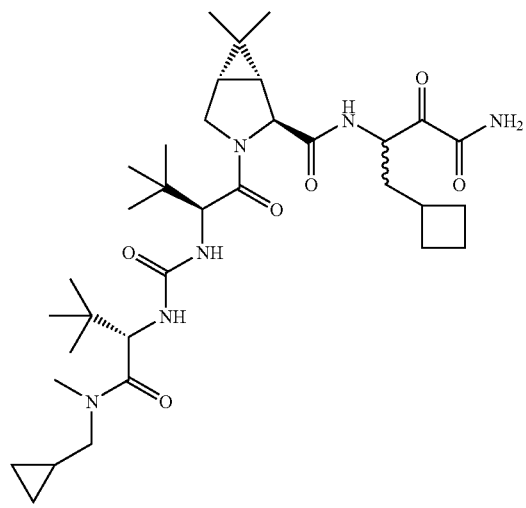 | 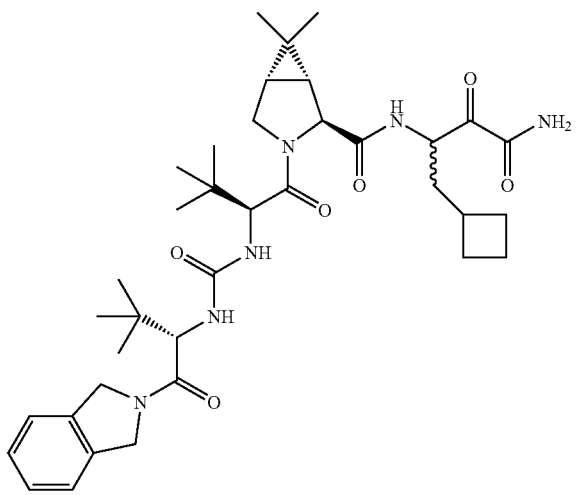 |
| 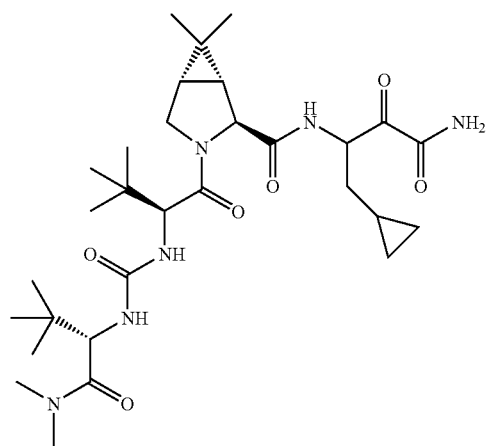 | 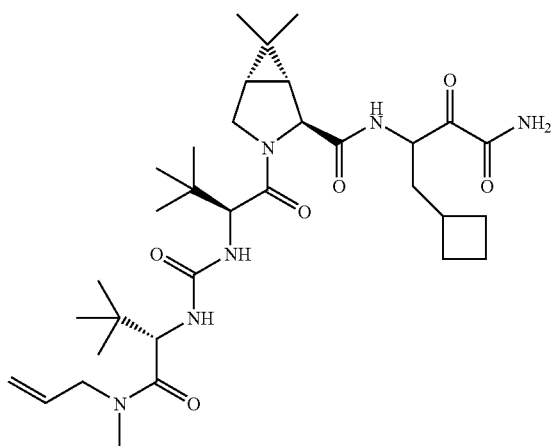 |
| 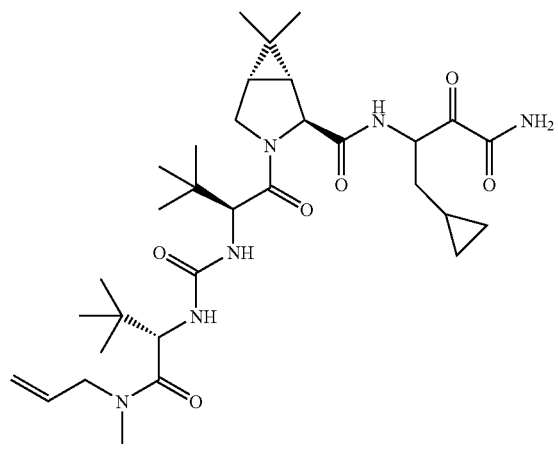 | 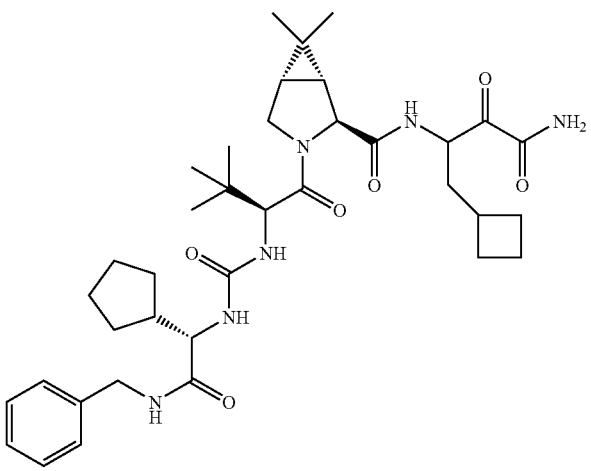 |

-continued
415
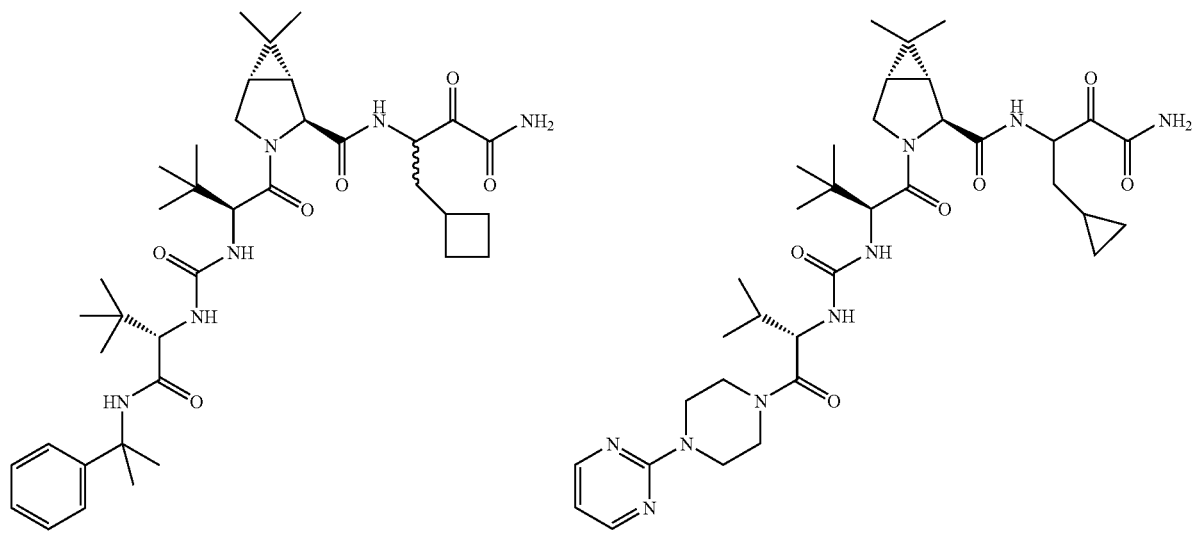
416
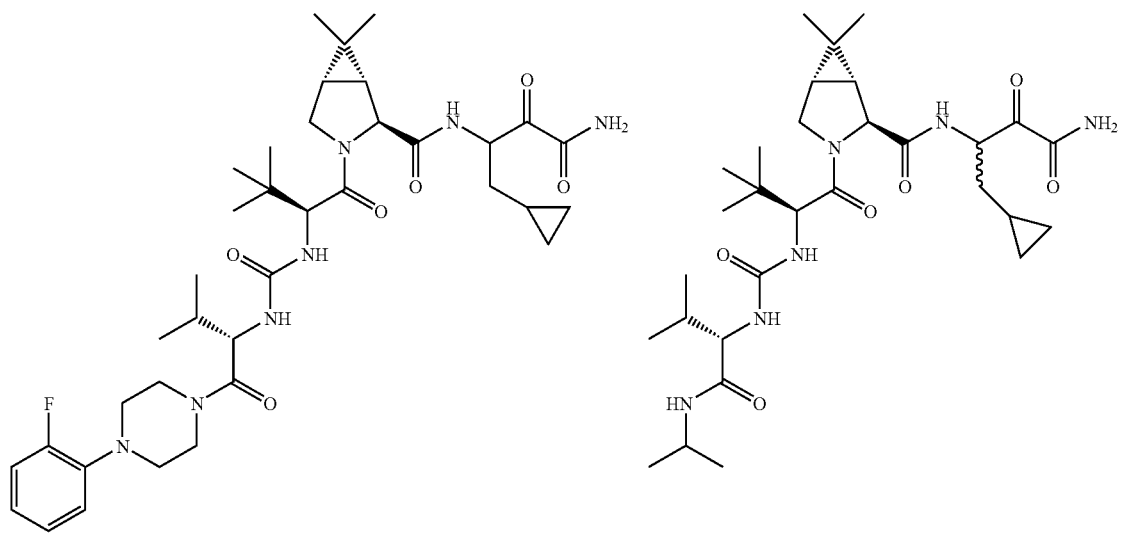
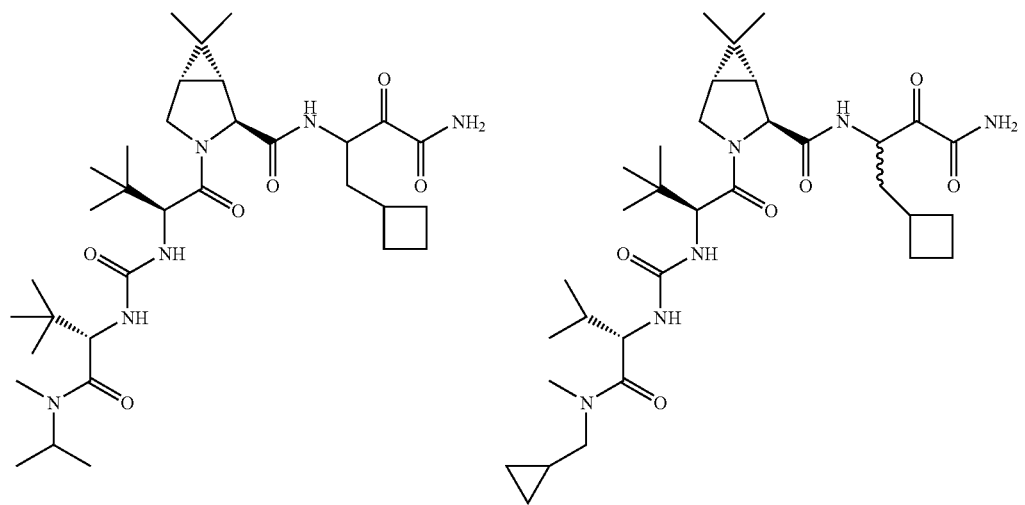

-continued
| 417 | 418 |
|---|---|
| 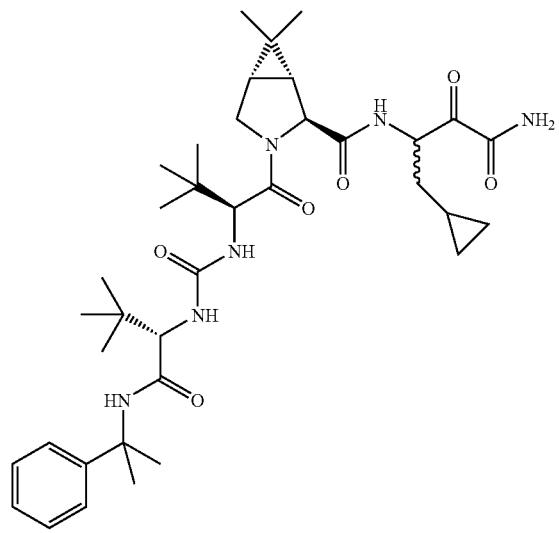 | 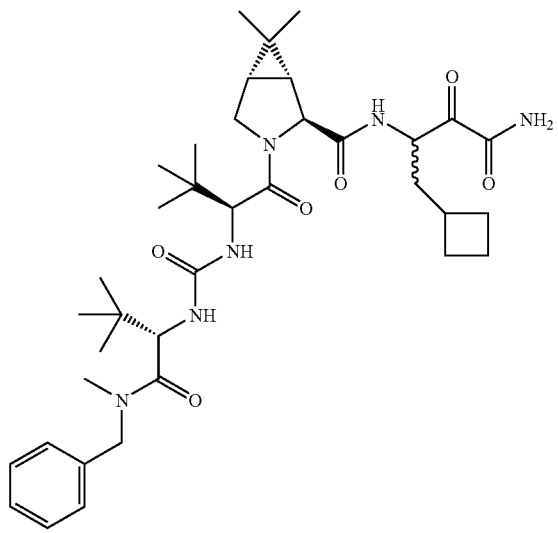 |
| 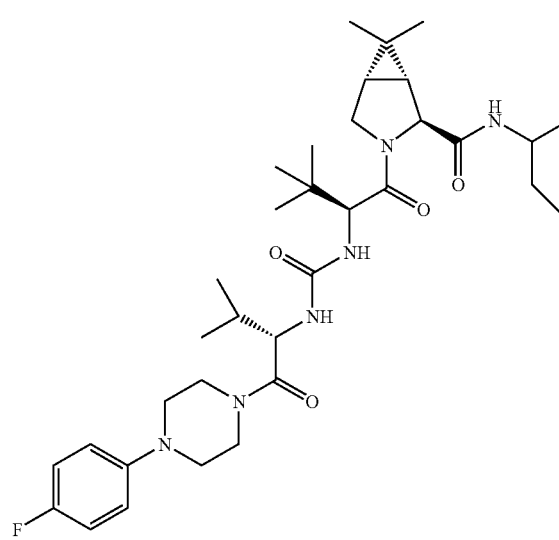 | 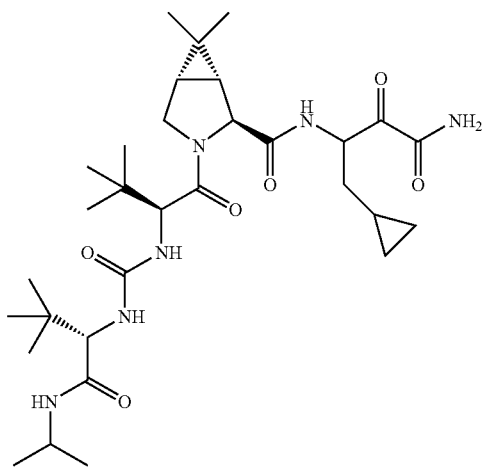 |
| 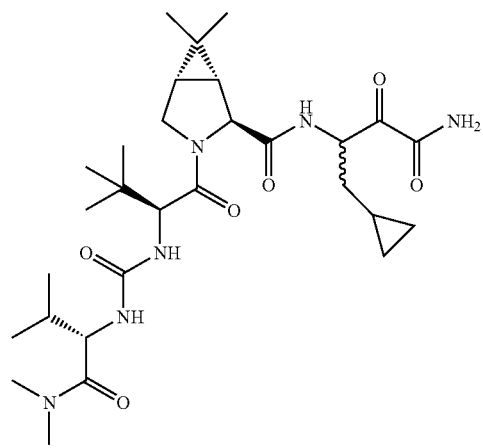 | 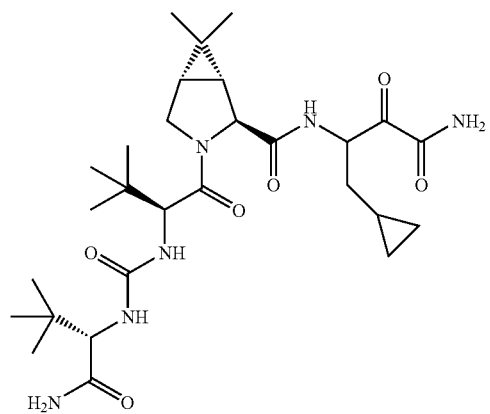 |

-continued
| 419 | 420 |
|---|---|
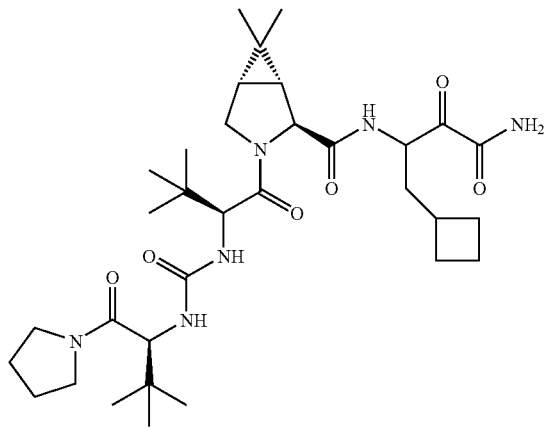
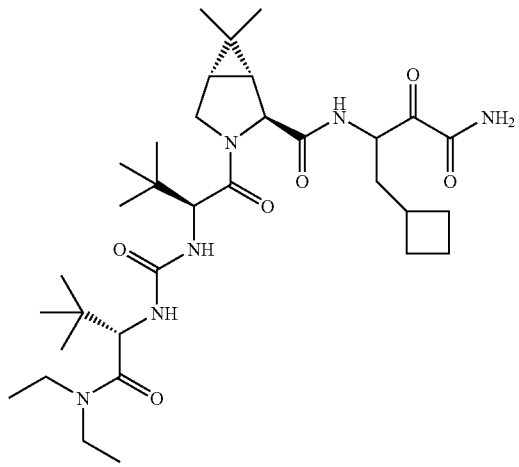
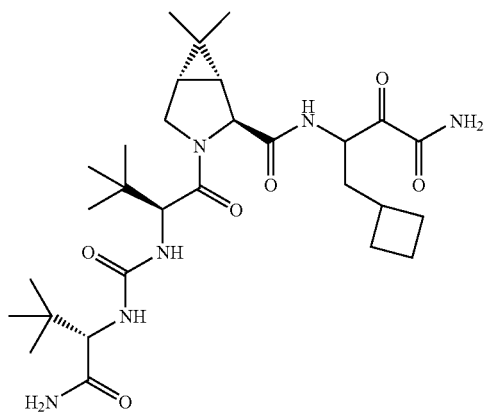
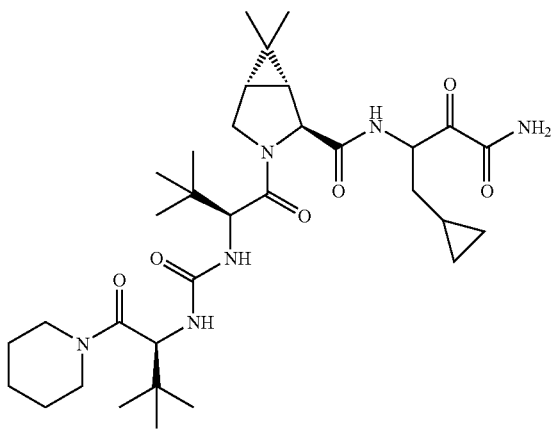
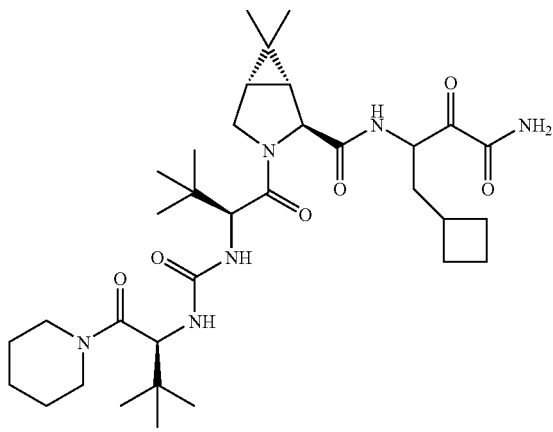
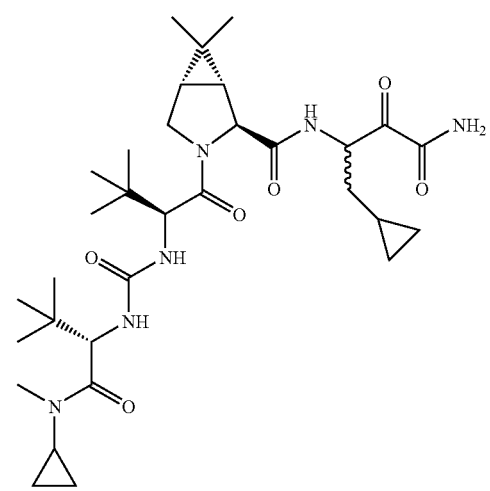

-continued
| 421 | 422 |
|---|---|
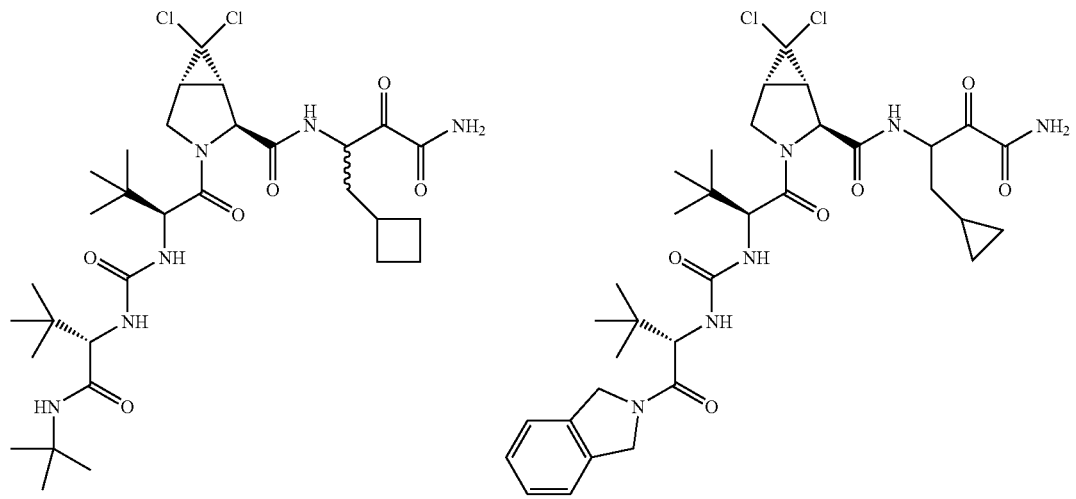
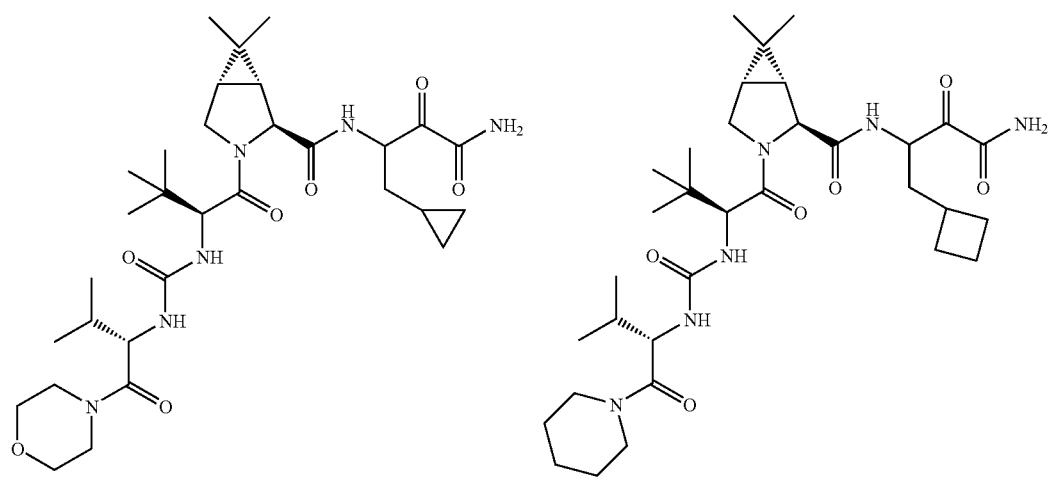
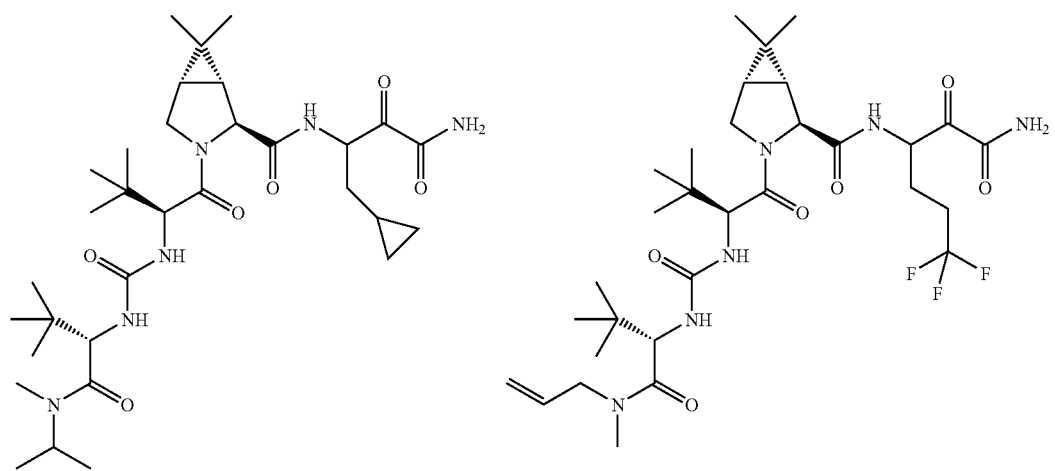

-continued
423 424
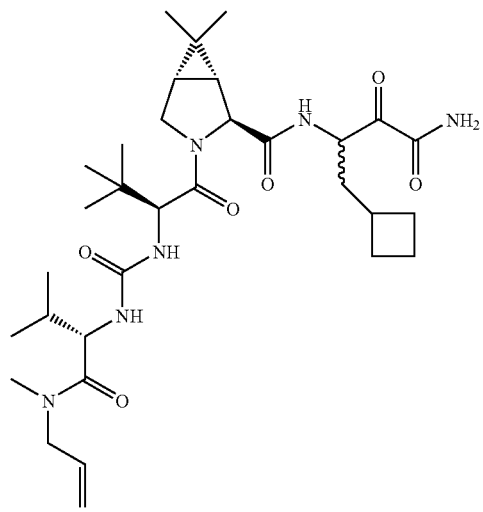 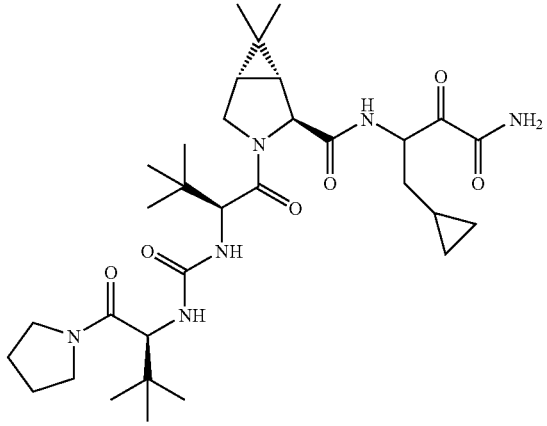
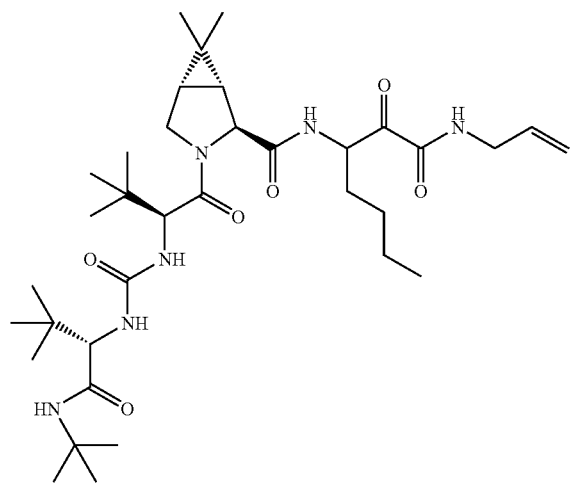 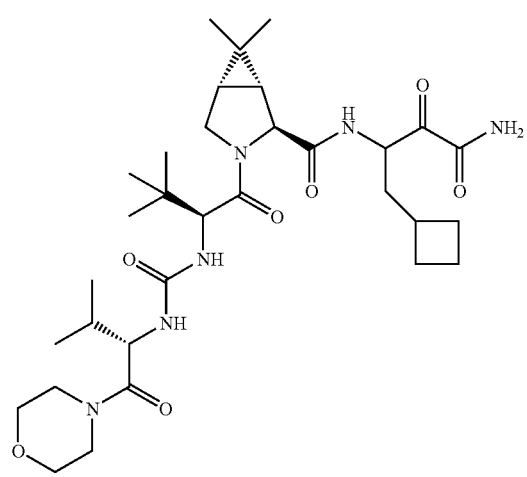
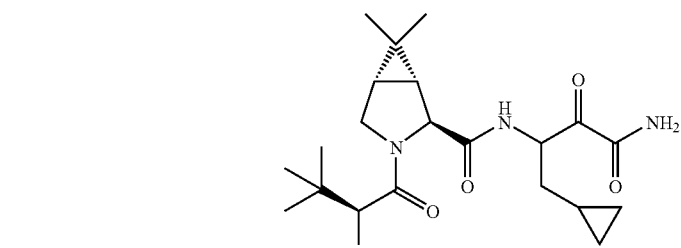 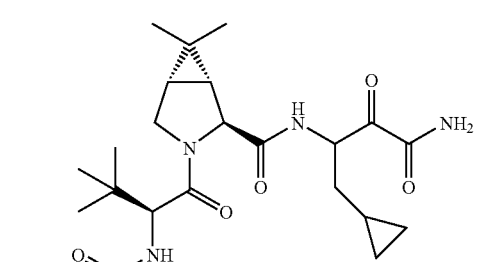
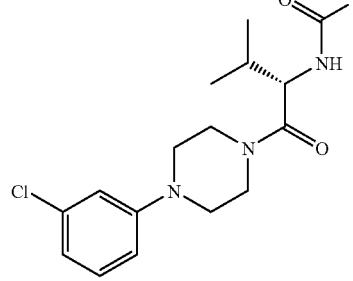 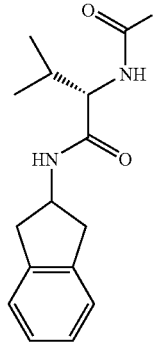

-continued
| 425 | 426 |
|---|---|
| 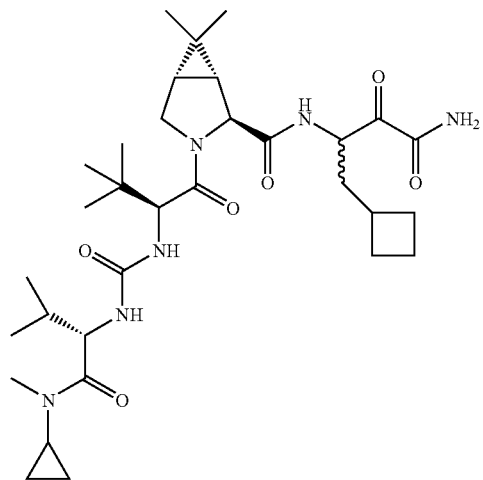 | 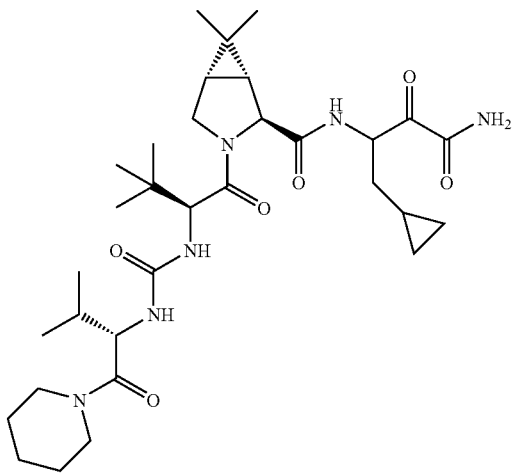 |
| 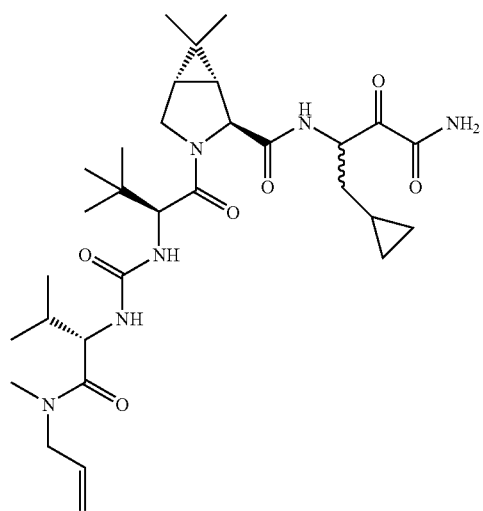 | 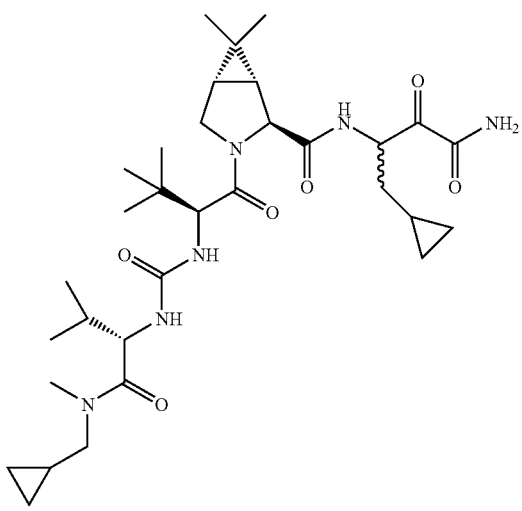 |
| 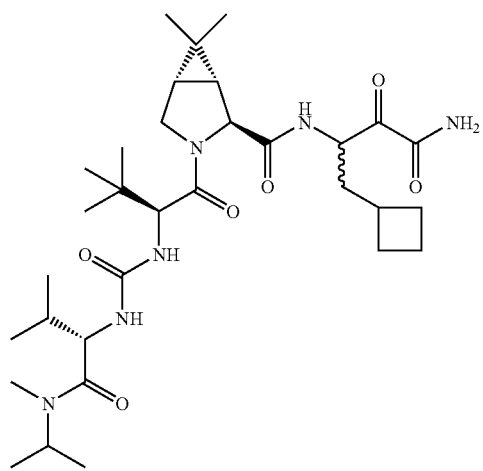 | 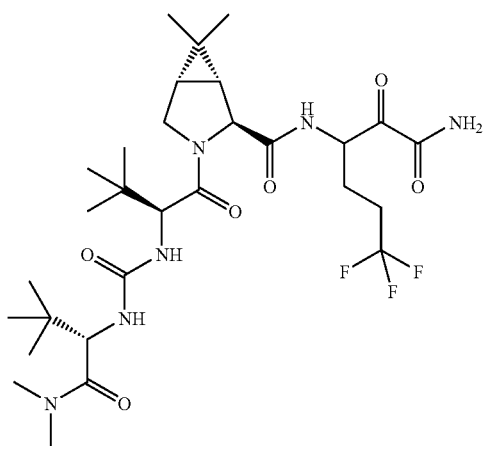 |

427
-continued
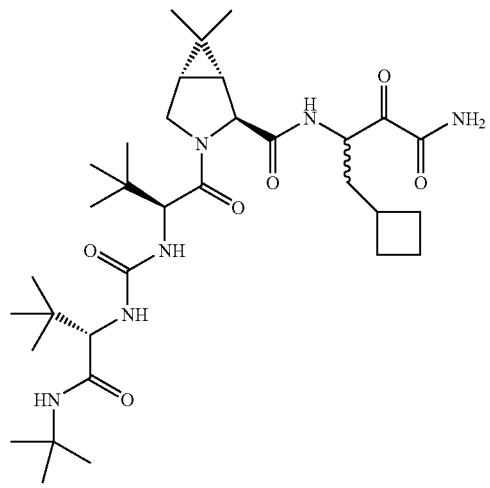
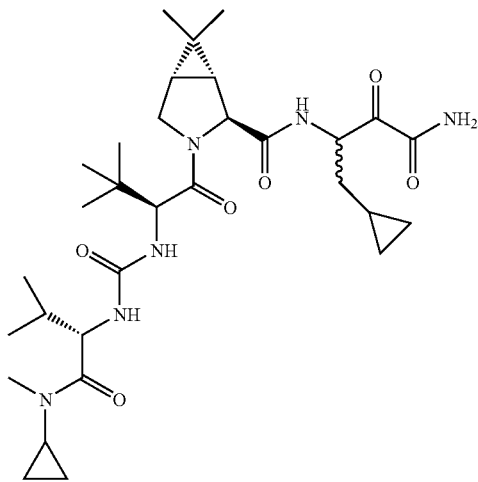
428
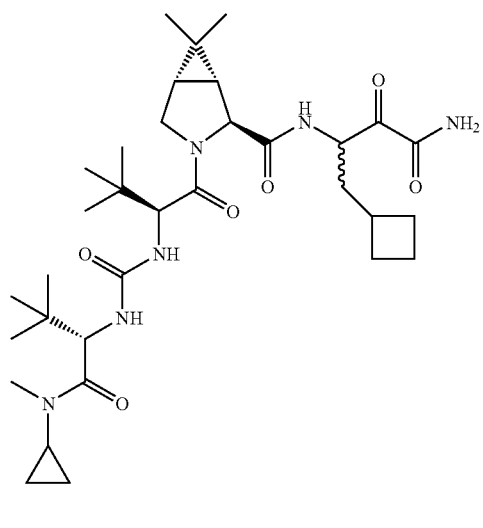
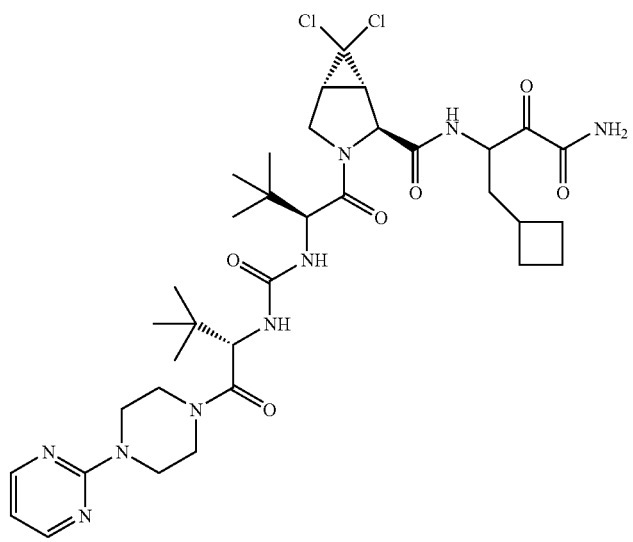
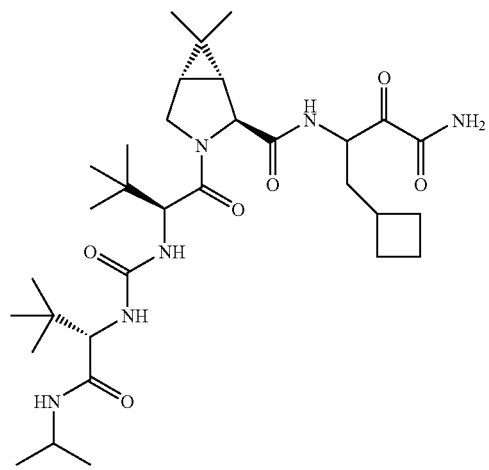
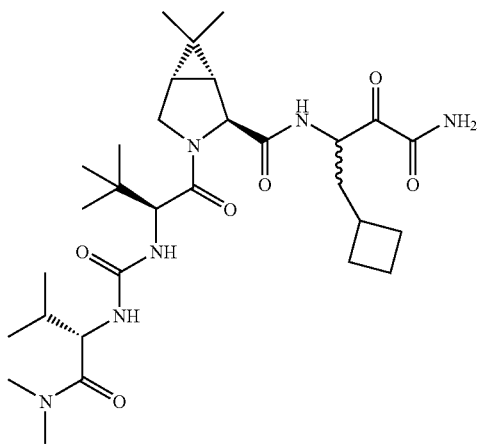

-continued
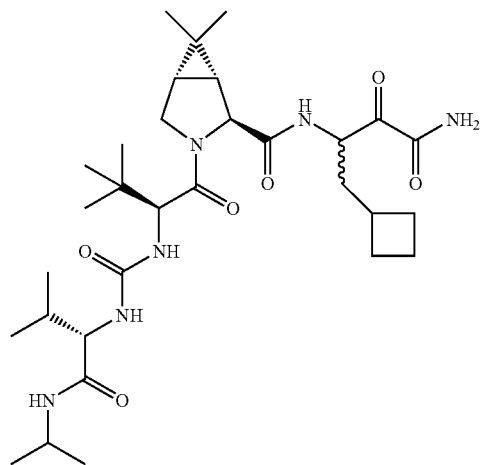
429
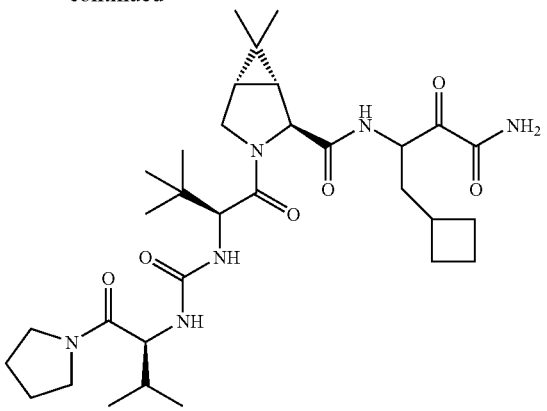
430
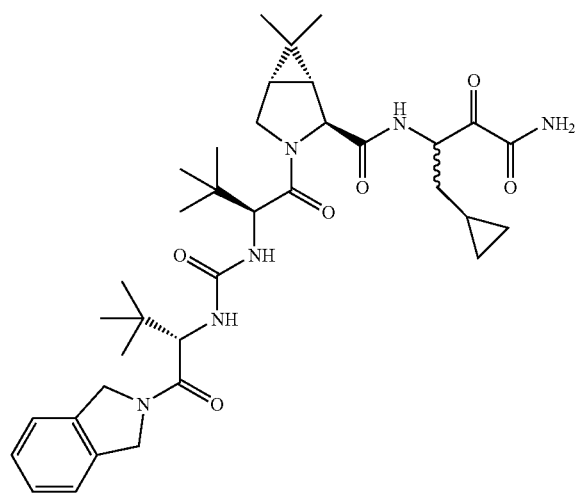
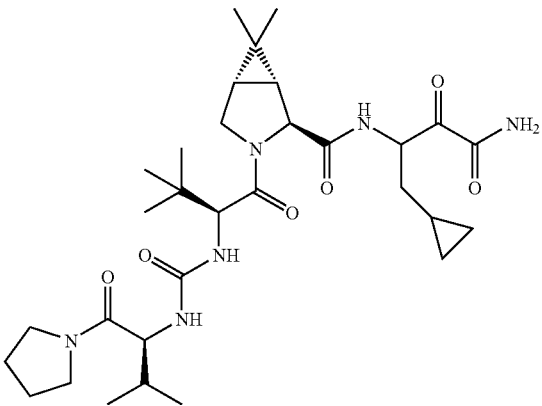
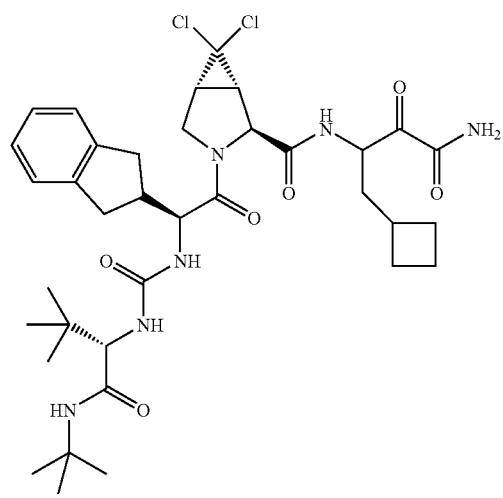
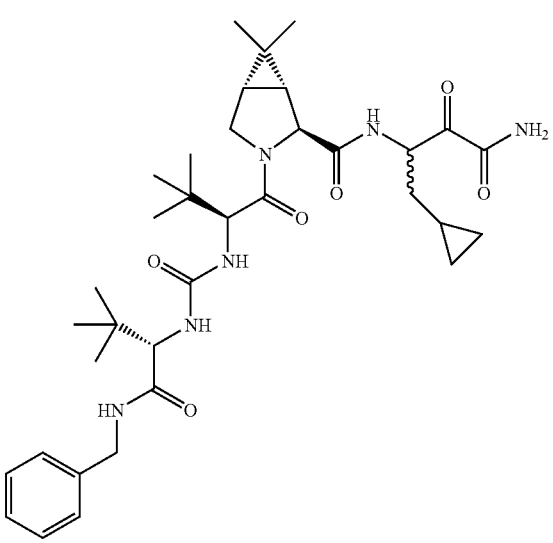

-continued
| 431 | 432 |
|---|---|
| 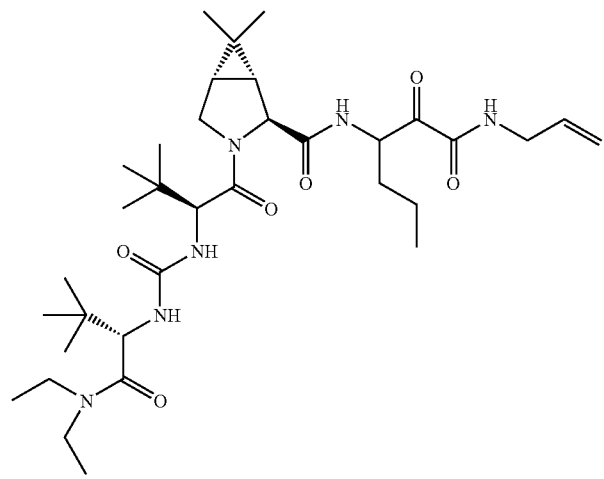 | |
| 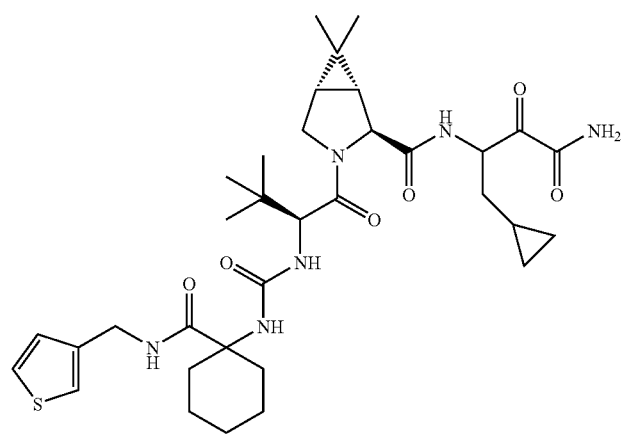 | |
| 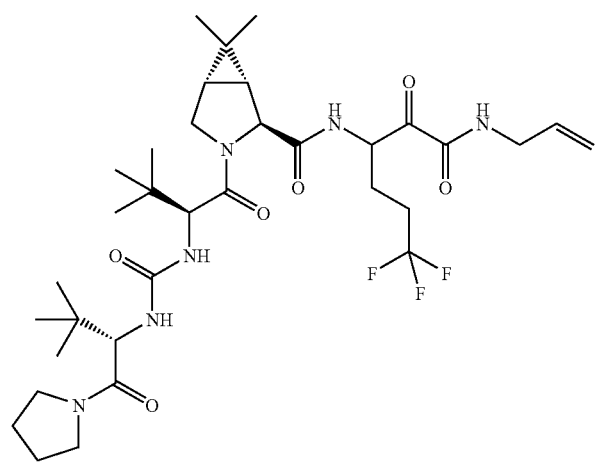 | 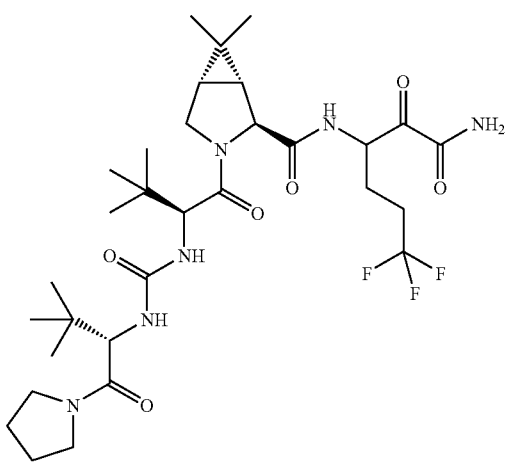 |

433
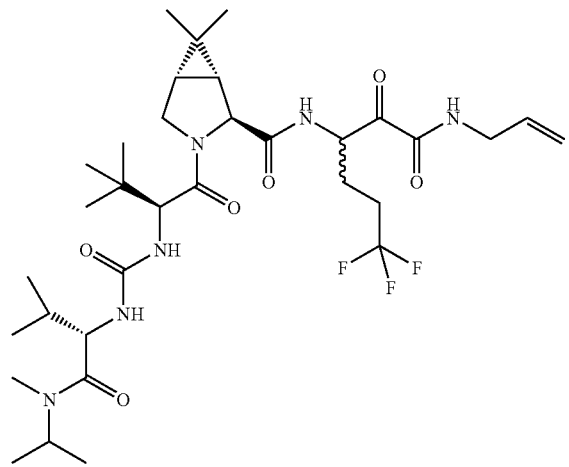
434
-continued
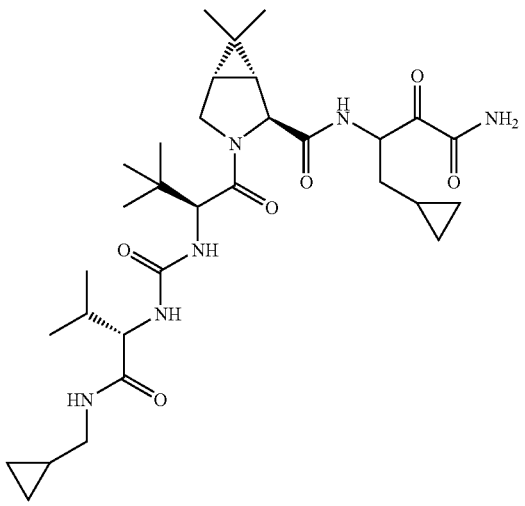
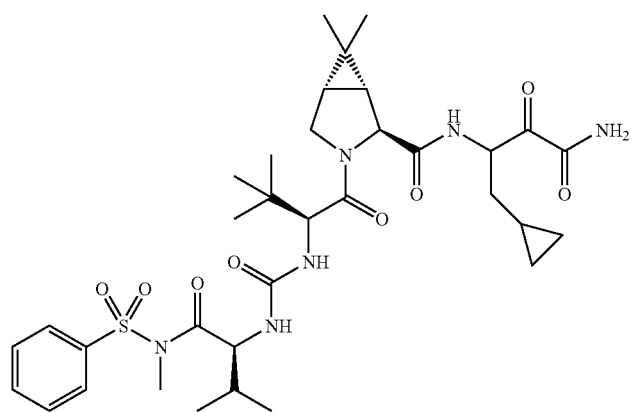
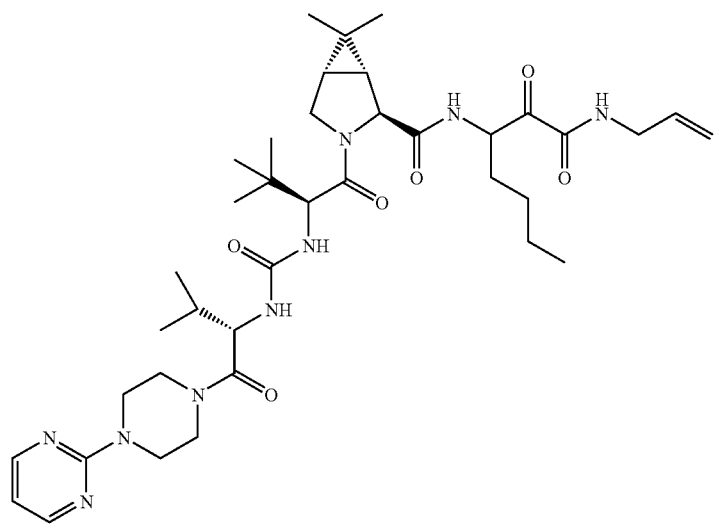

-continued
| 435 | 436 |
|---|---|
| 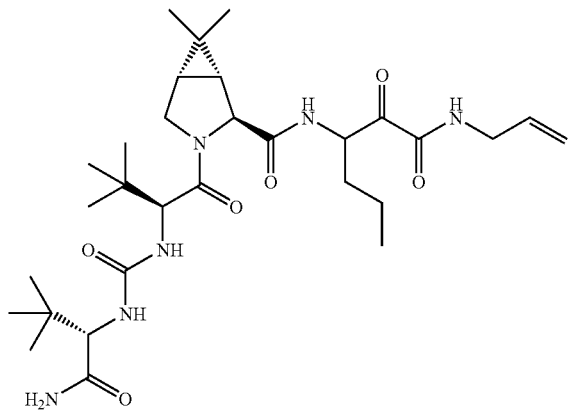 | 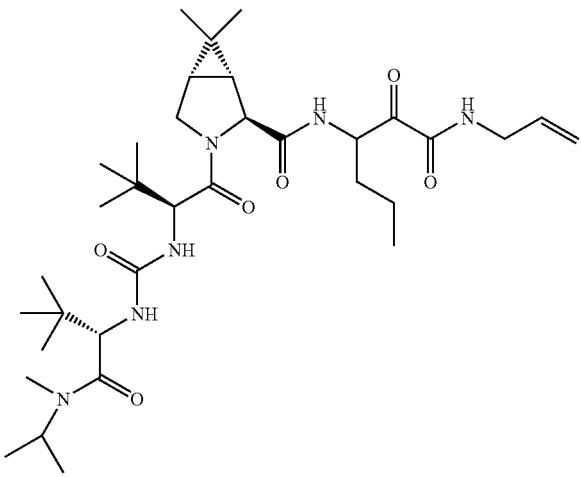 |
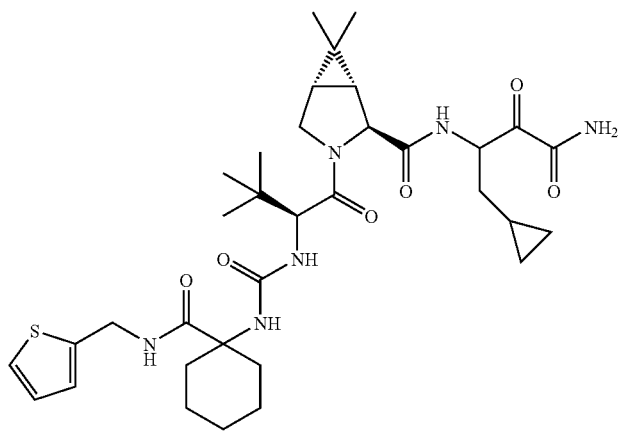
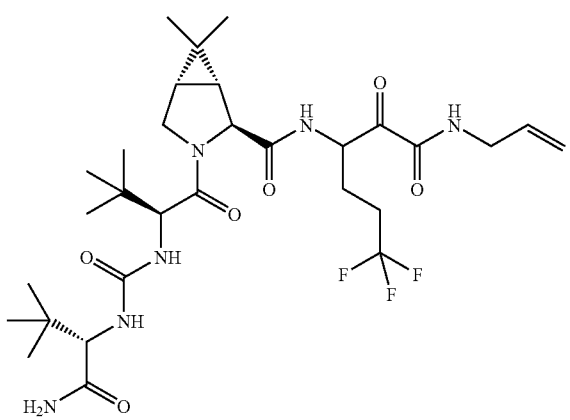
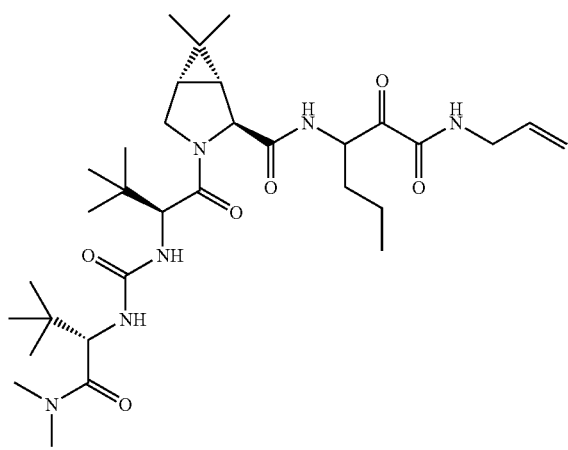

437
-continued
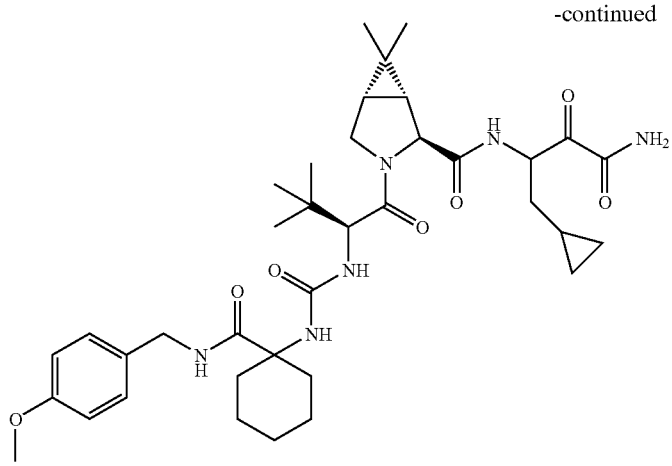
438
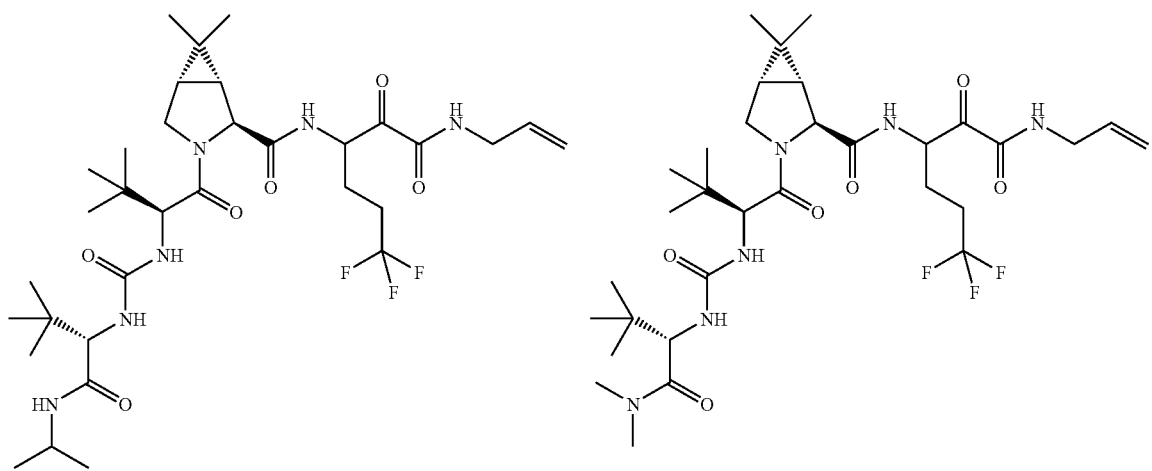
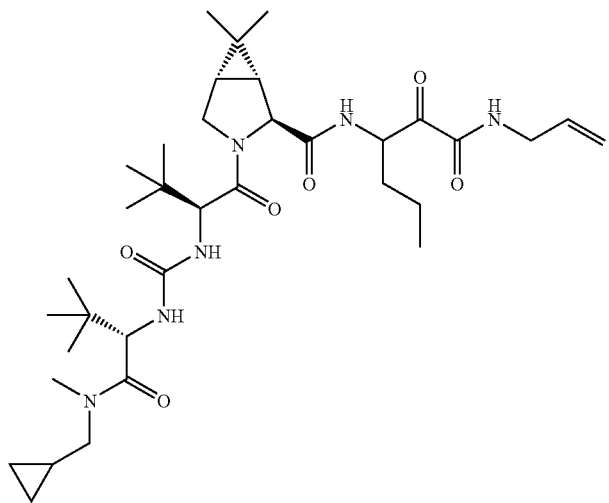

-continued
439
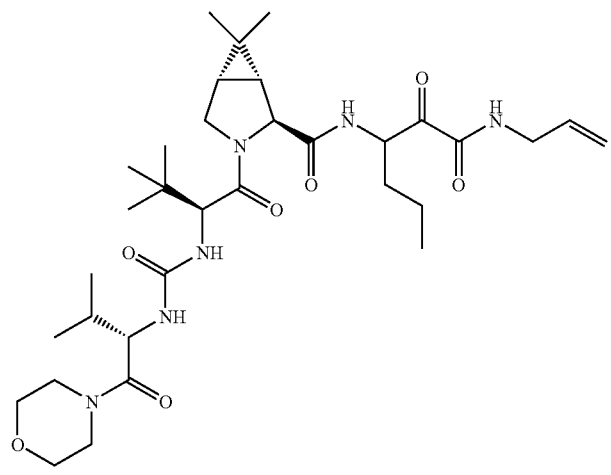
440
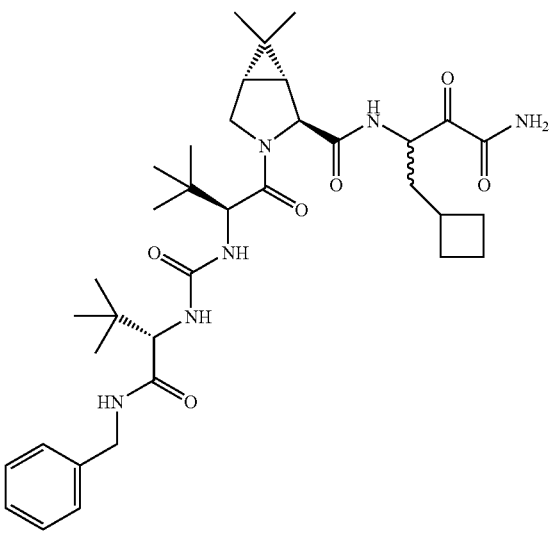
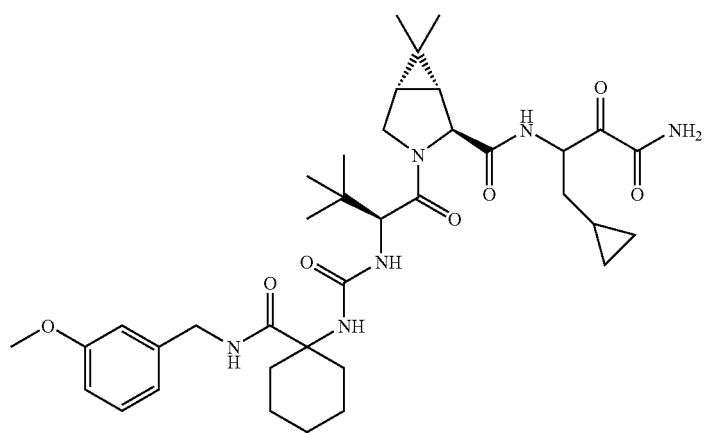
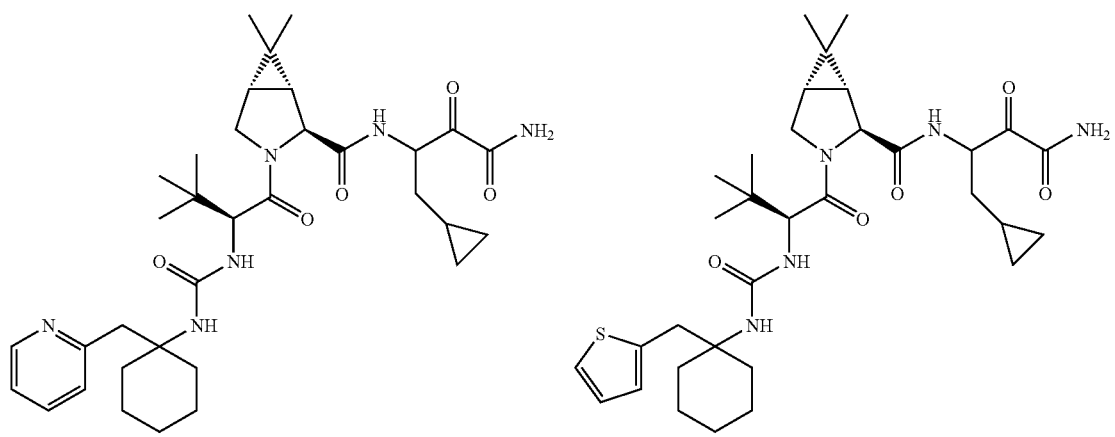

-continued
| 441 | 442 |
|---|---|
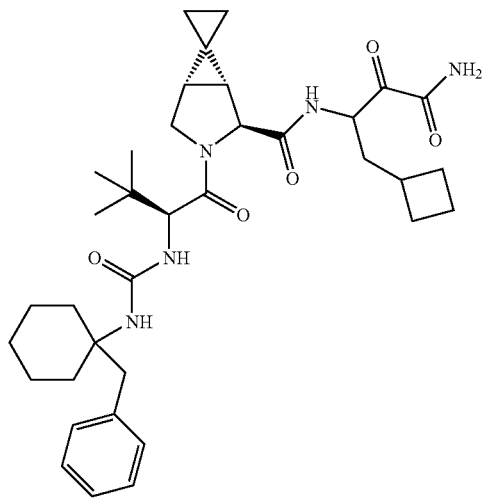
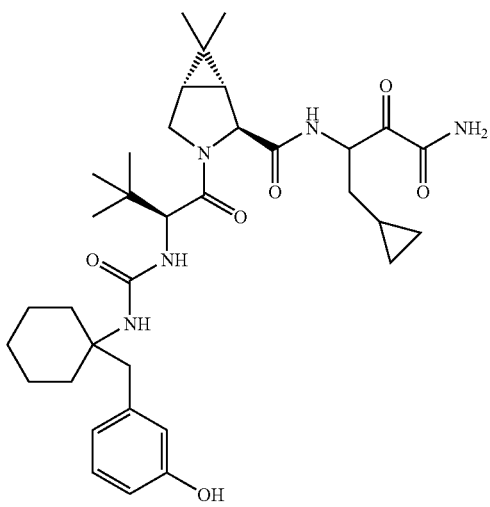
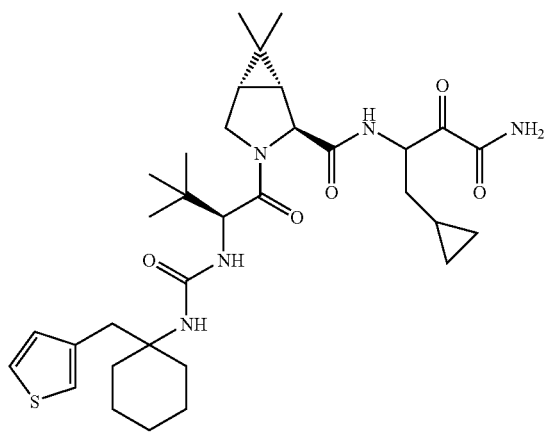
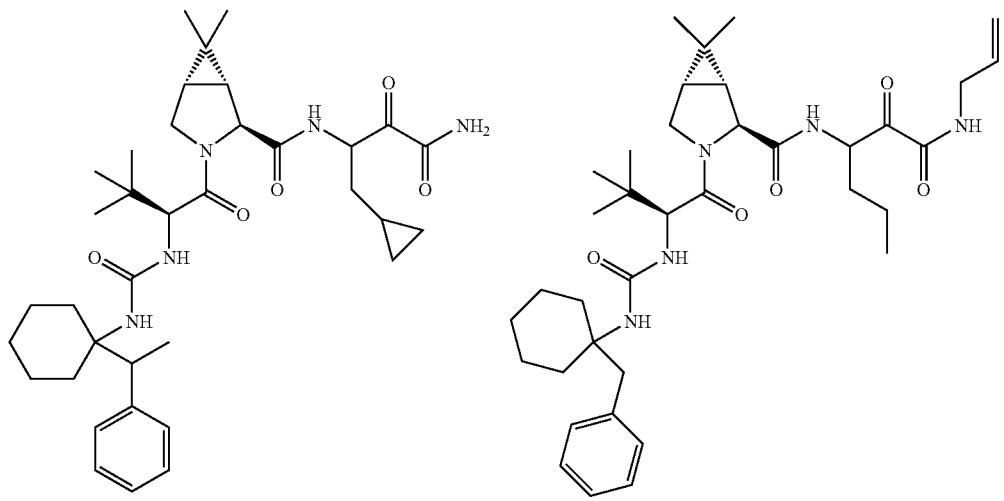

-continued
| 443 | 444 |
|---|---|
| 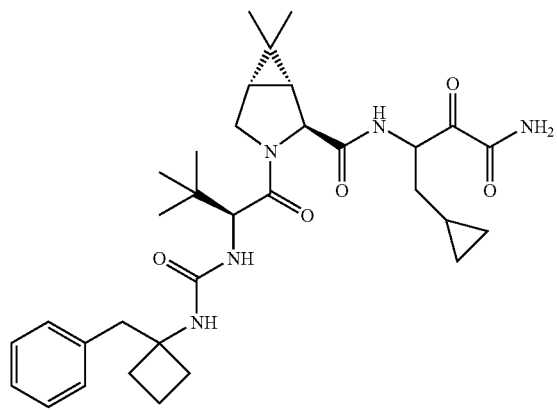 | 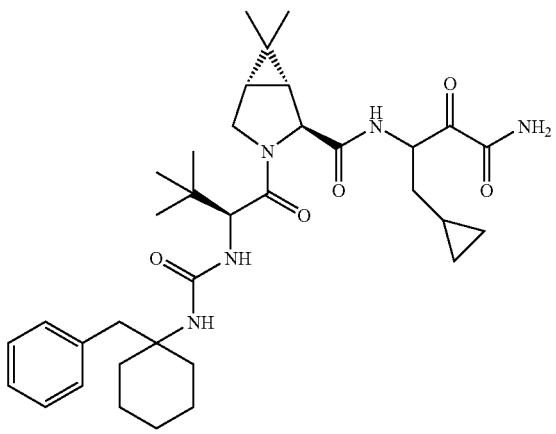 |
| 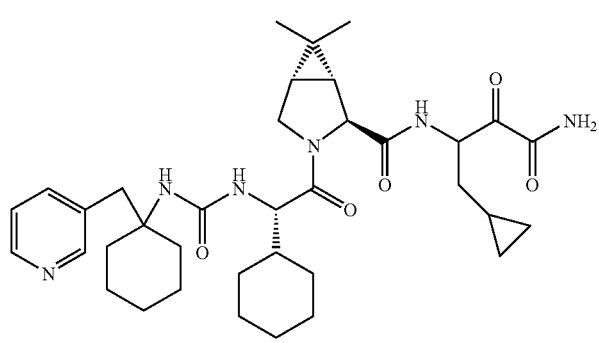 | 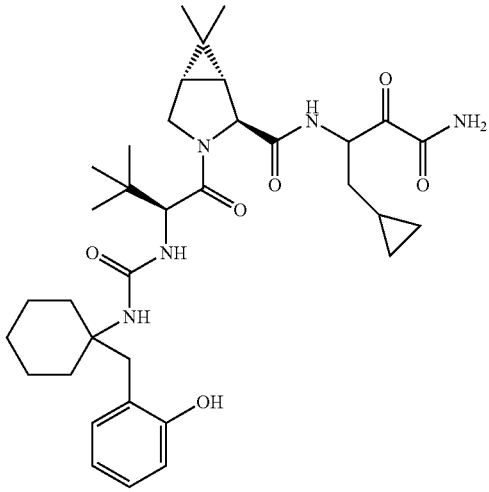 |
| 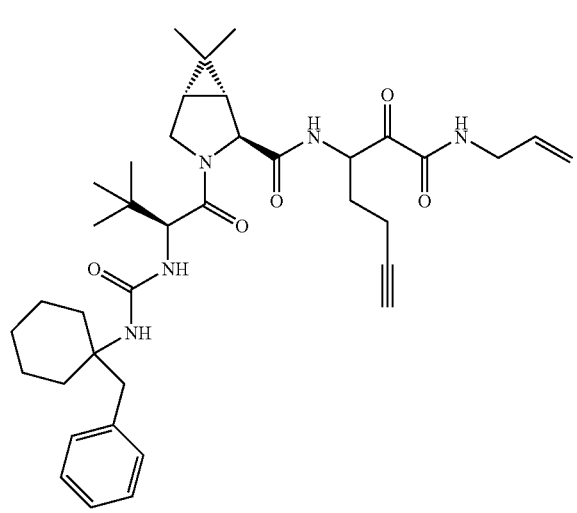 | 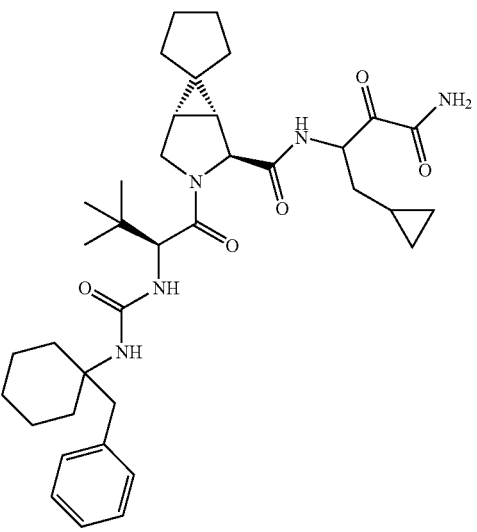 |

-continued
| 445 | 446 |
|---|---|
| 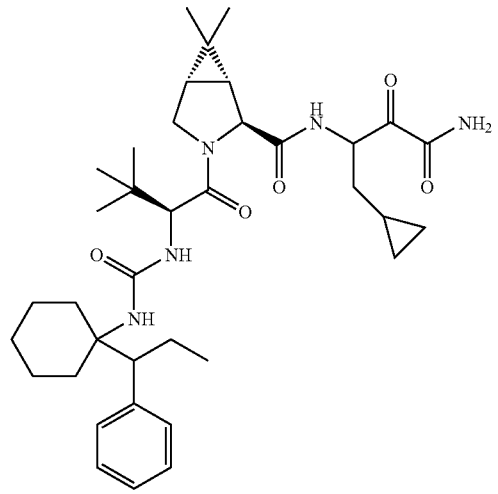 | 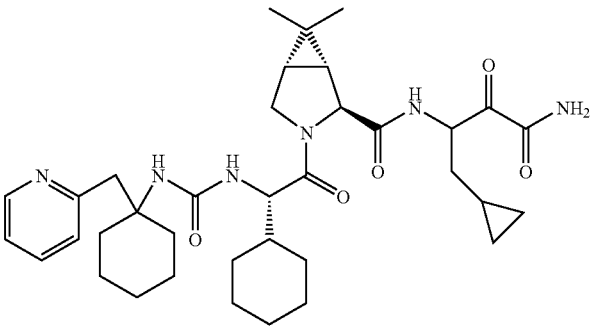 |
| 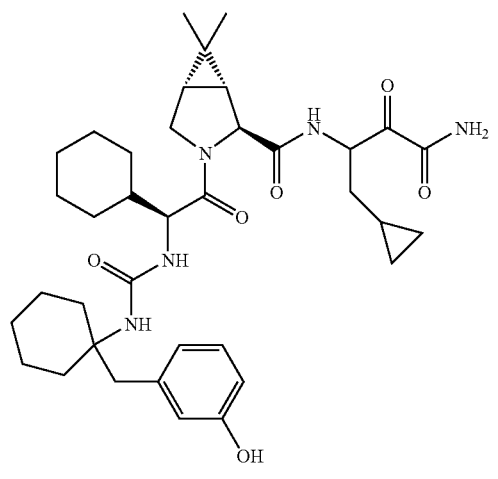 | 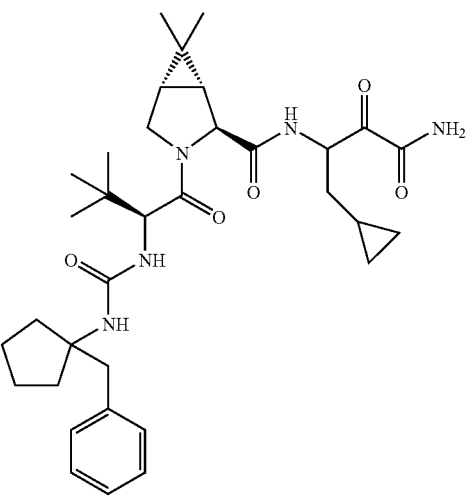 |
| 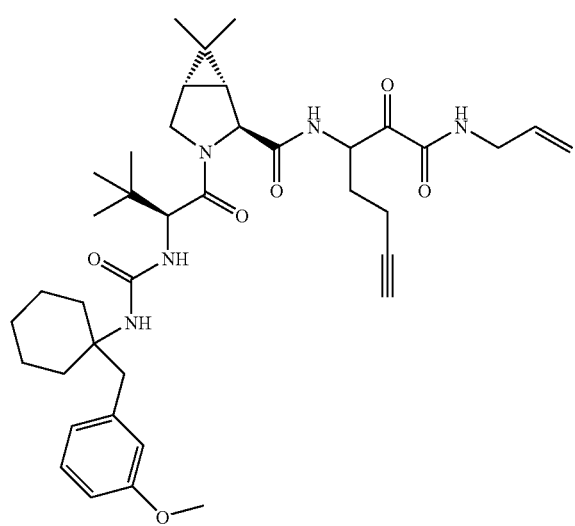 | 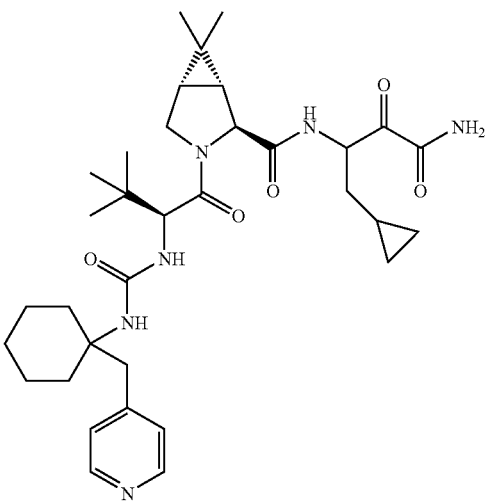 |

447 448
-continued
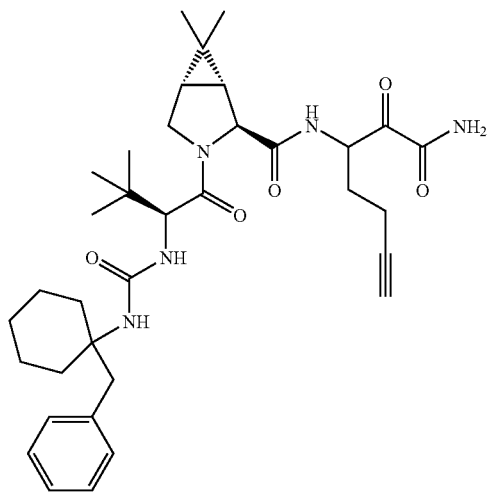
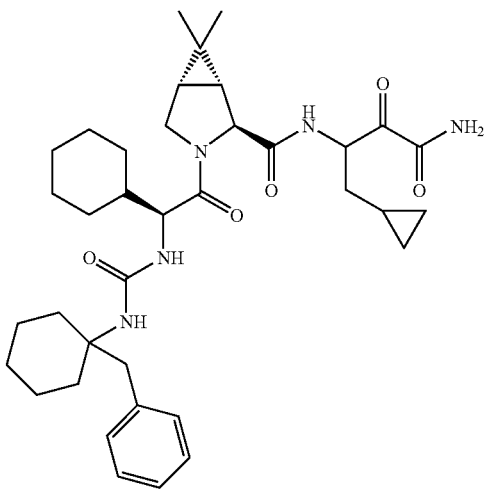
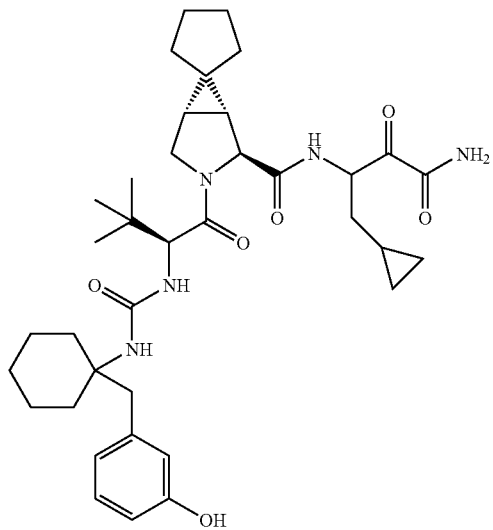
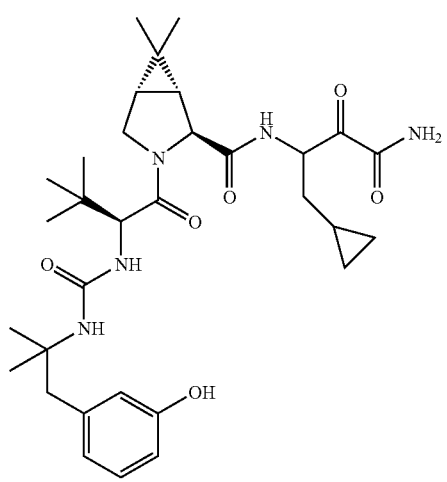
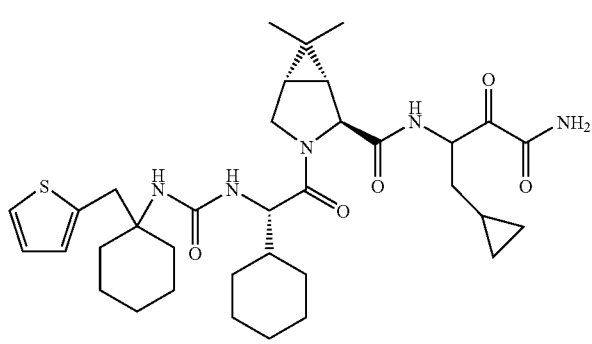
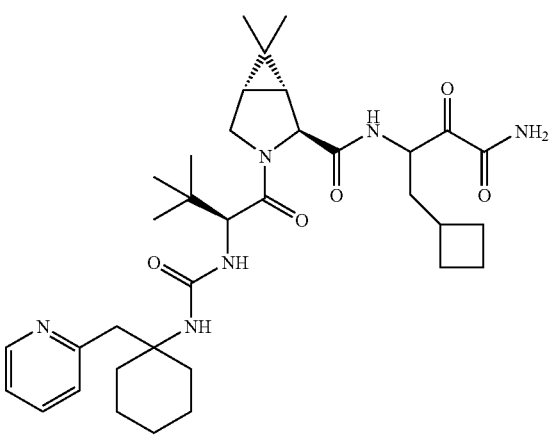

449
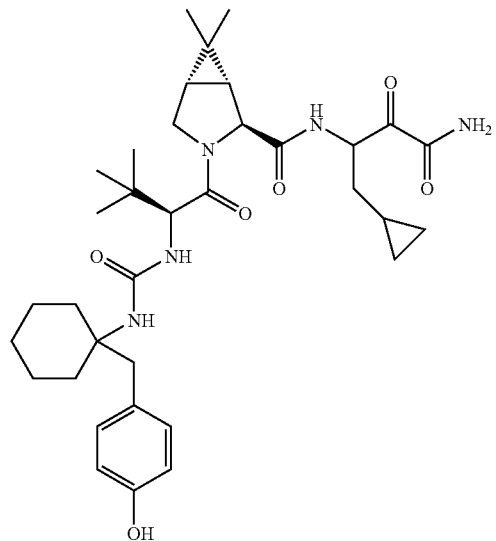
450
-continued
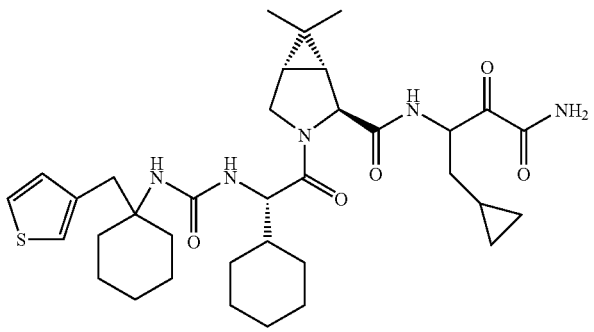
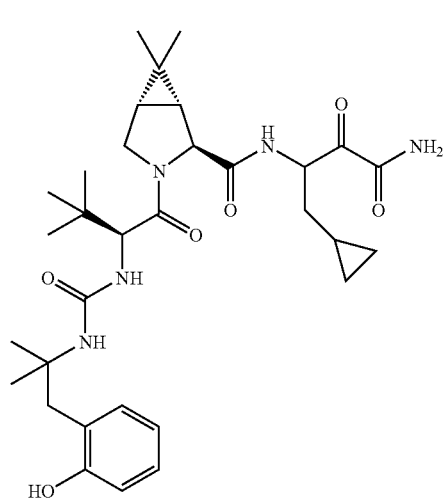
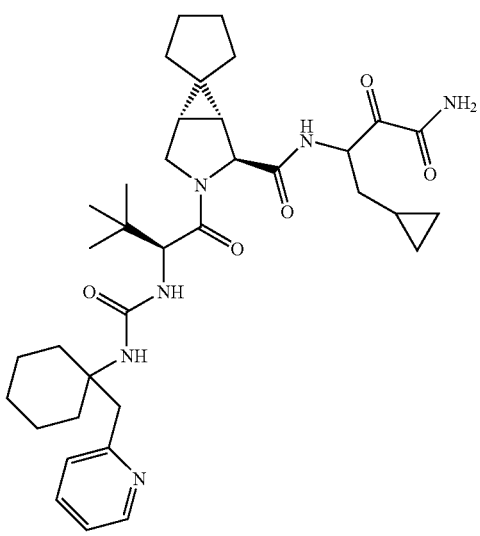
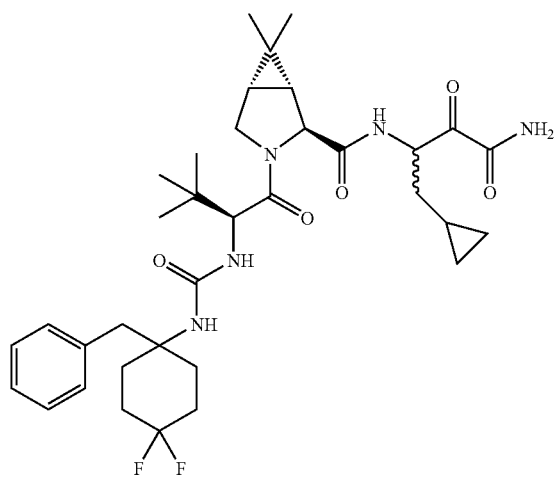
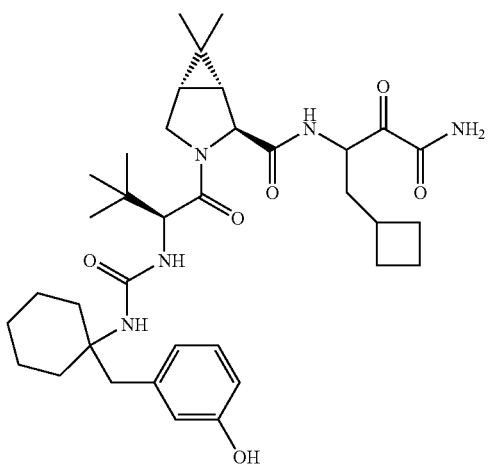

-continued
| 451 | 452 |
|---|---|
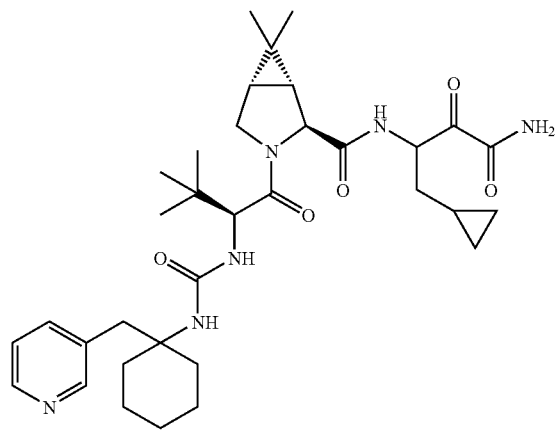
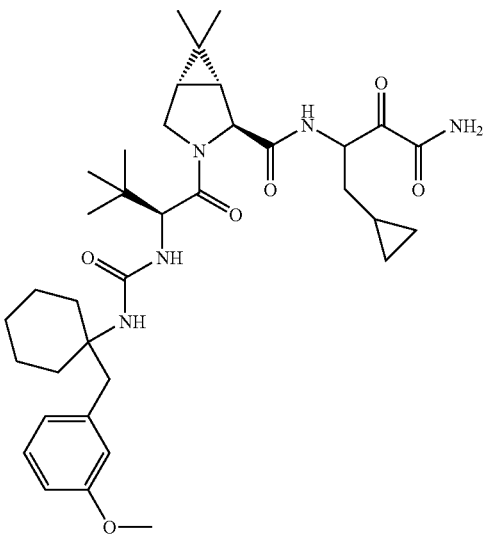
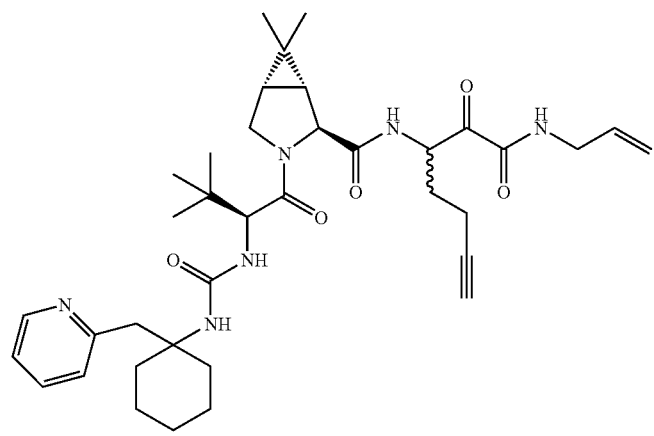
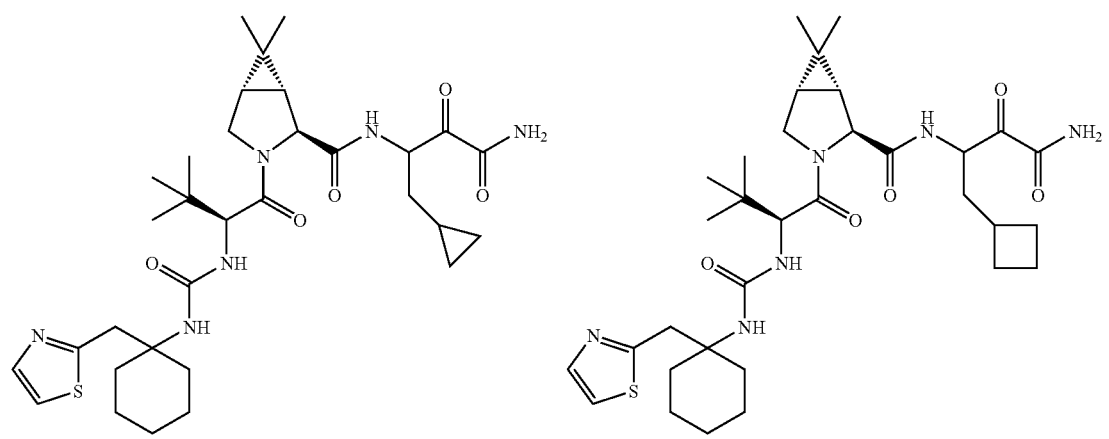

453 454
-continued
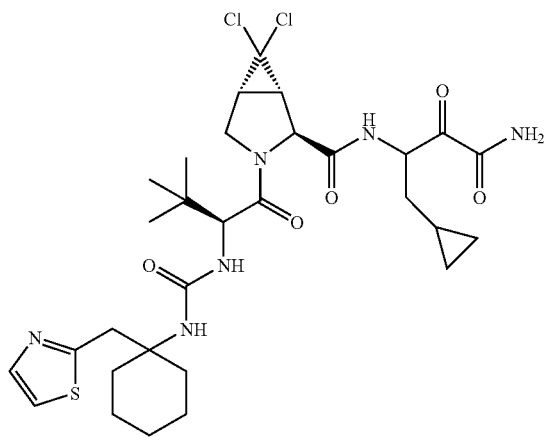
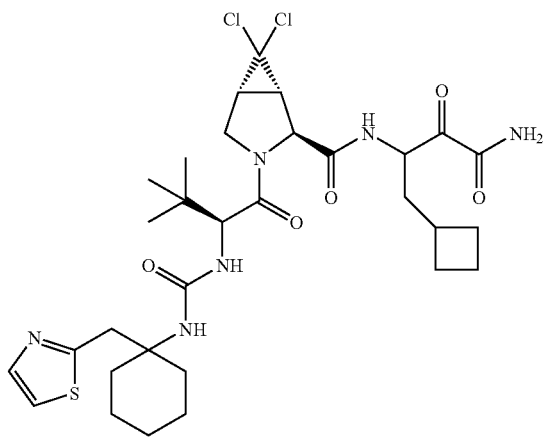
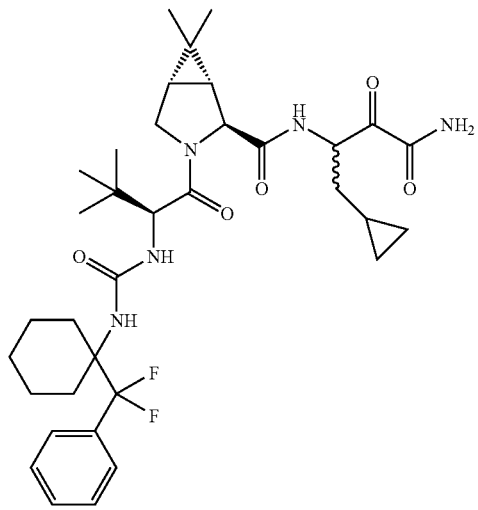
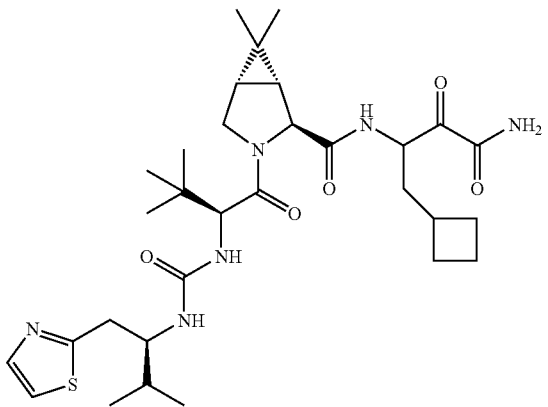
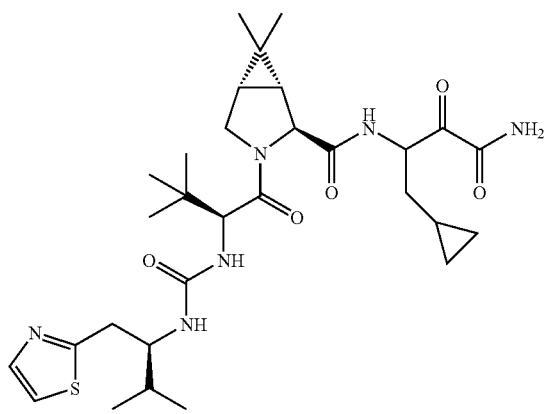
or
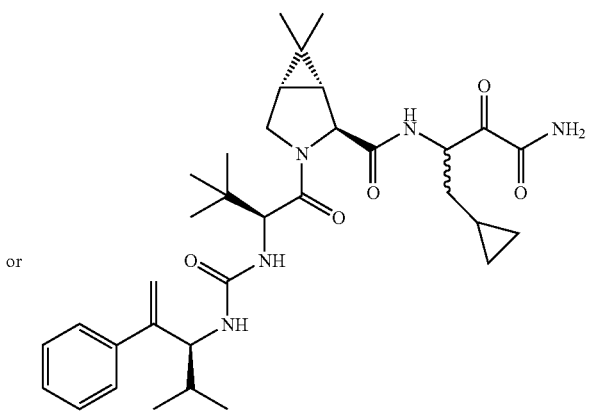

Compounds of formula XI are disclosed in U.S. application Ser. No. 11/065,509 filed Feb. 24, 2005. The preparation of these compounds is disclosed in the experimental section of this application set forth hereinbelow.
Non-limiting examples of certain compounds disclosed in U.S. application Ser. No. 11/065,509 are:
-continued
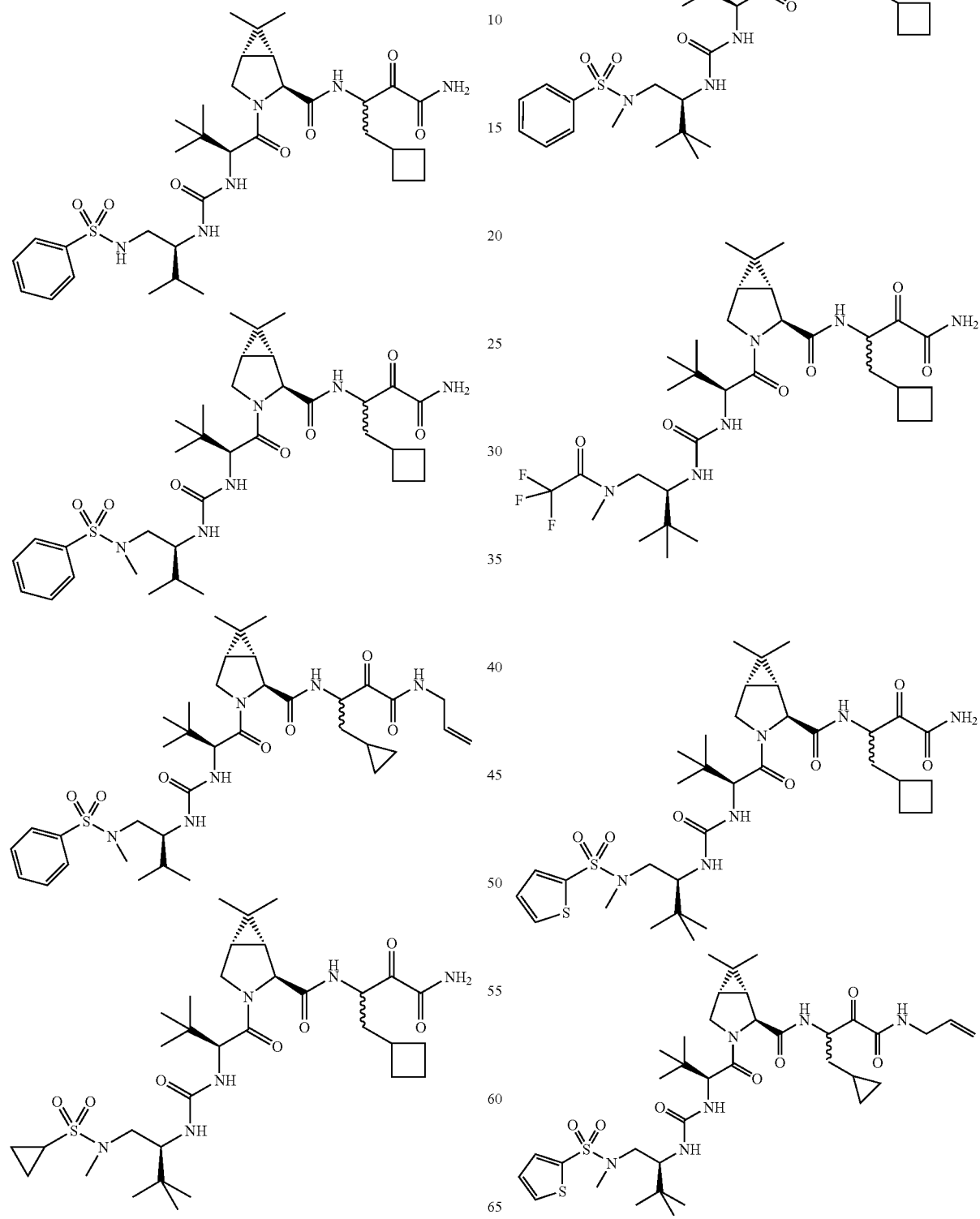

457
-continued
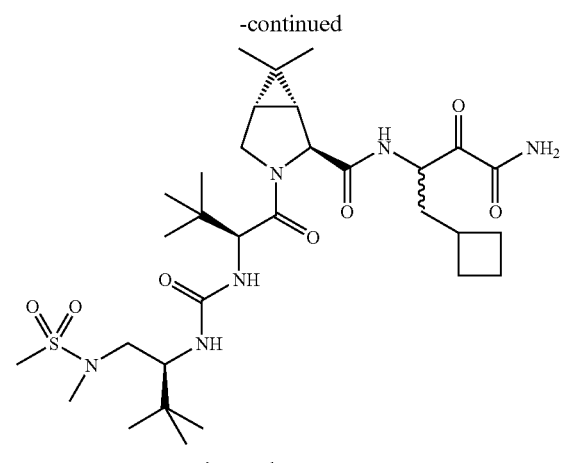
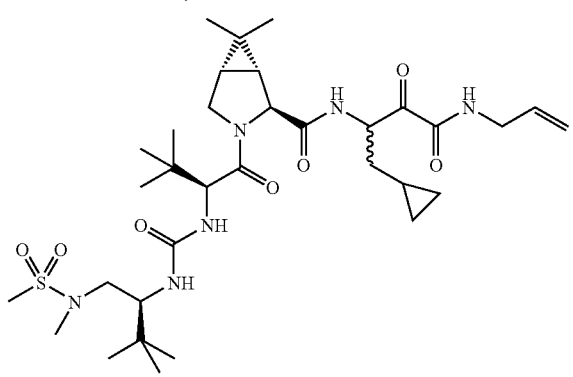
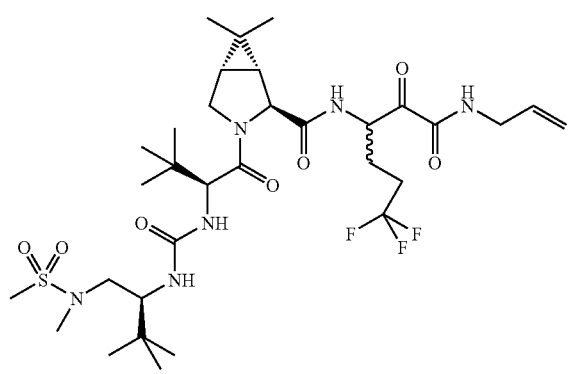
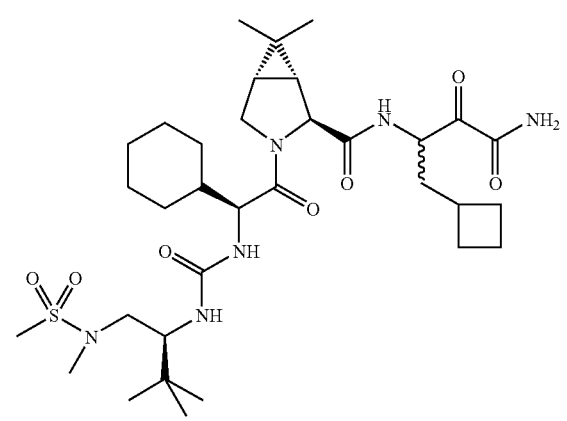
458
-continued
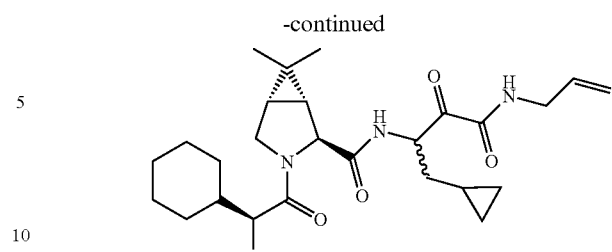
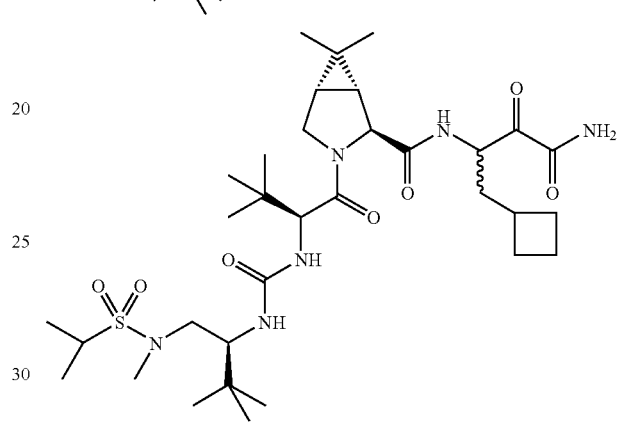
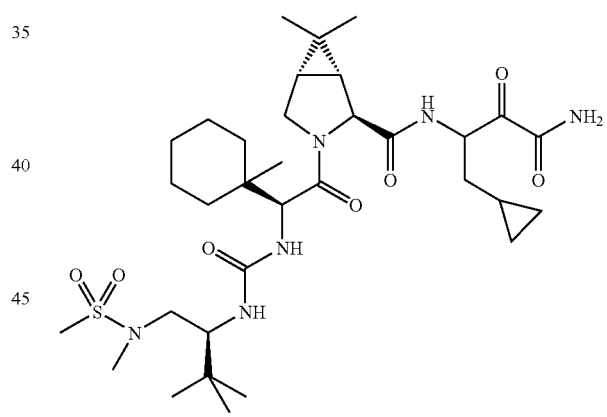
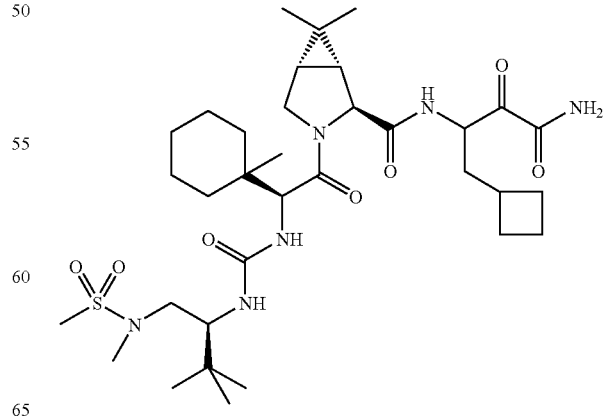

459
-continued
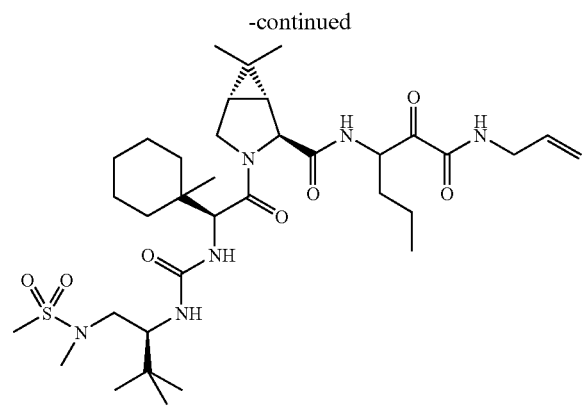
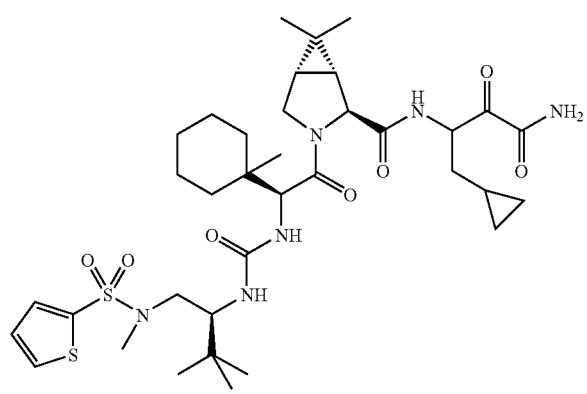
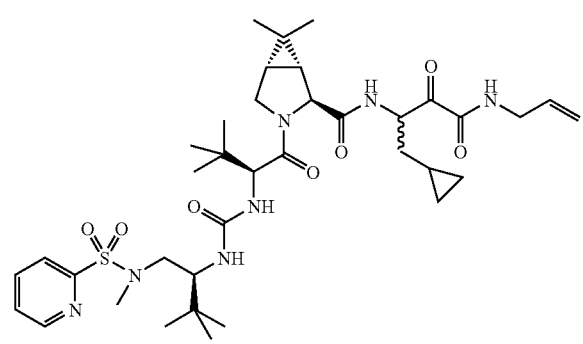
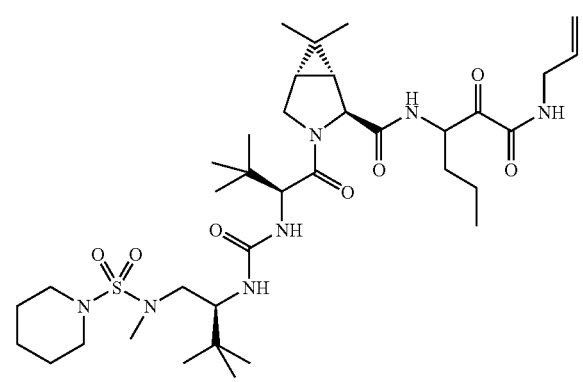
460
-continued
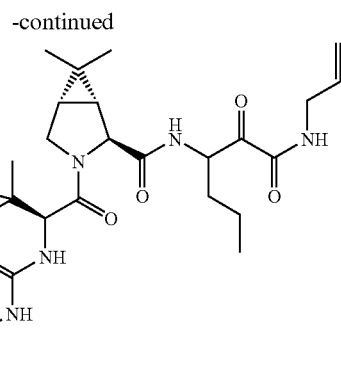
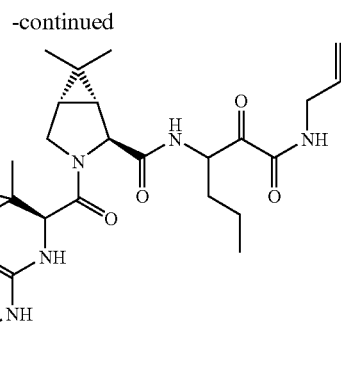
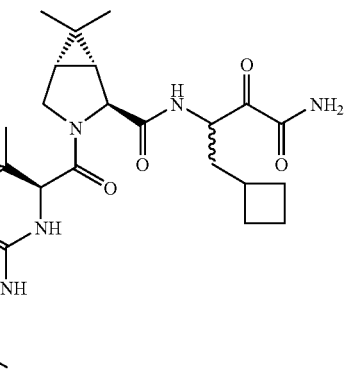
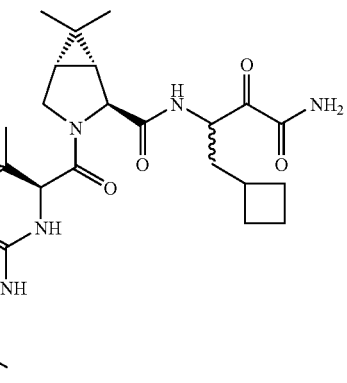

461 -continued
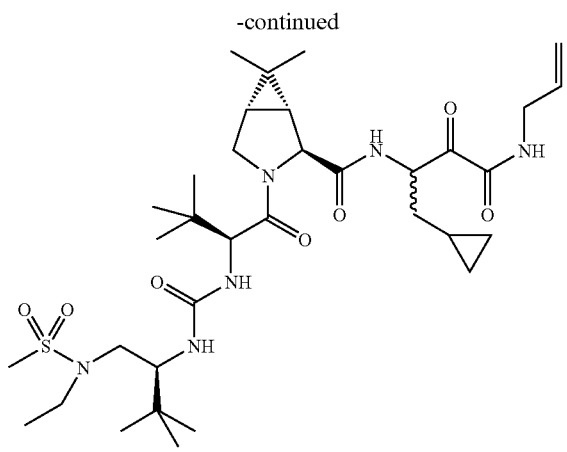
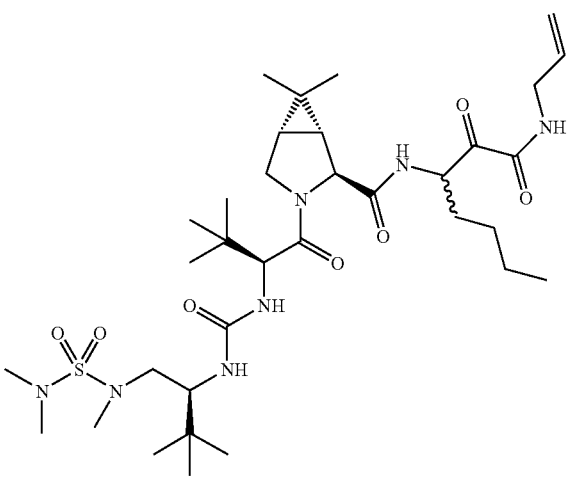
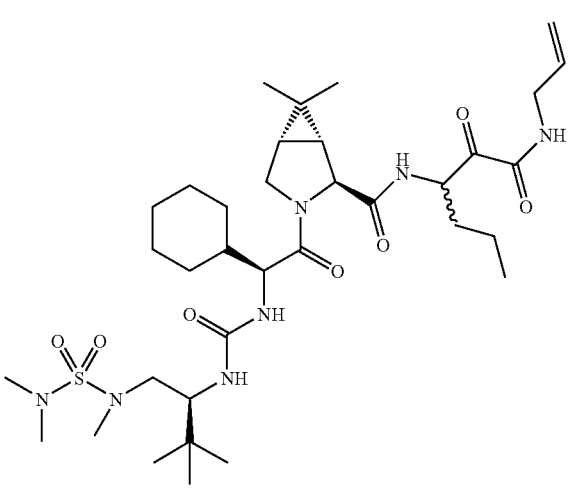
462 -continued
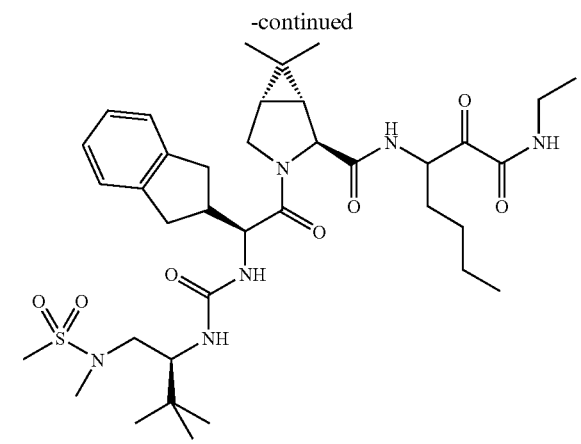

463
-continued
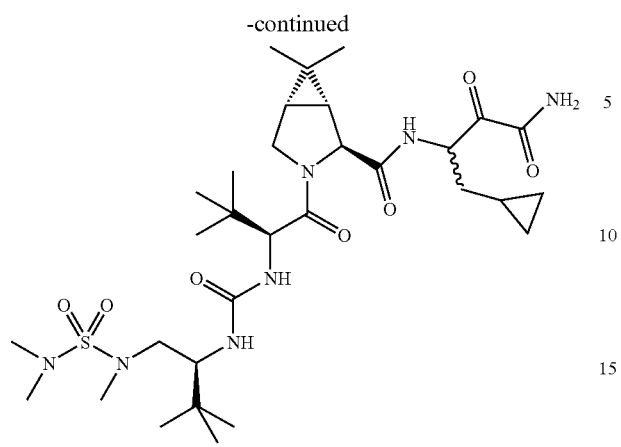
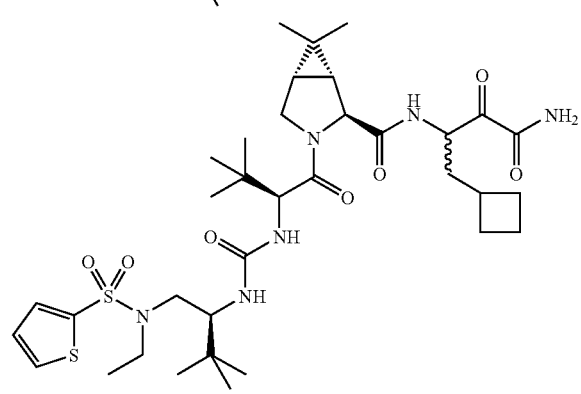
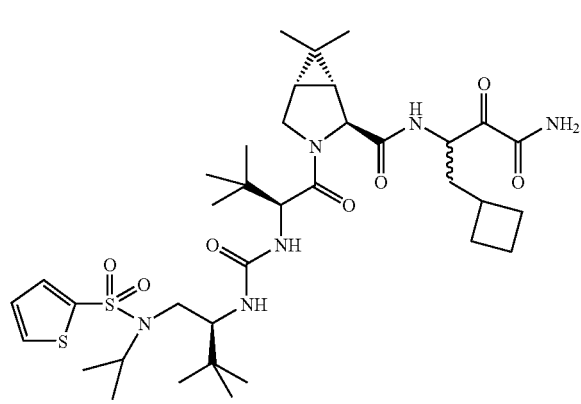
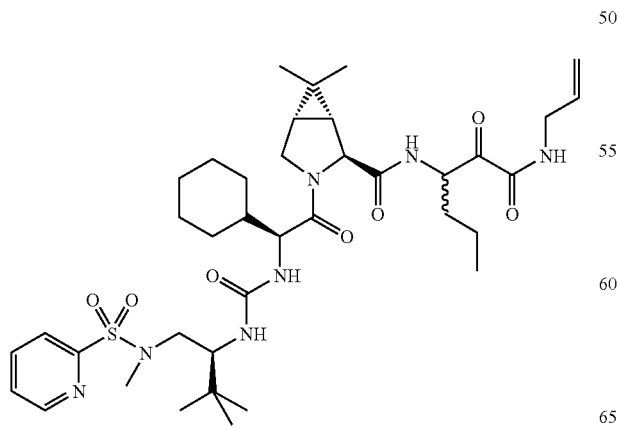
464
-continued
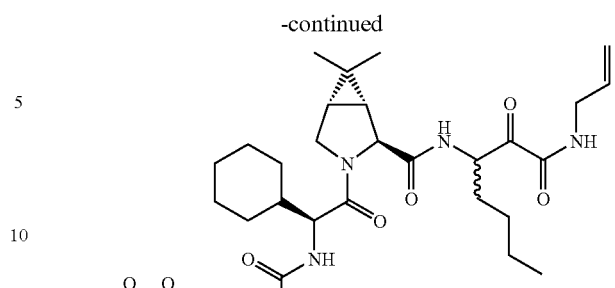
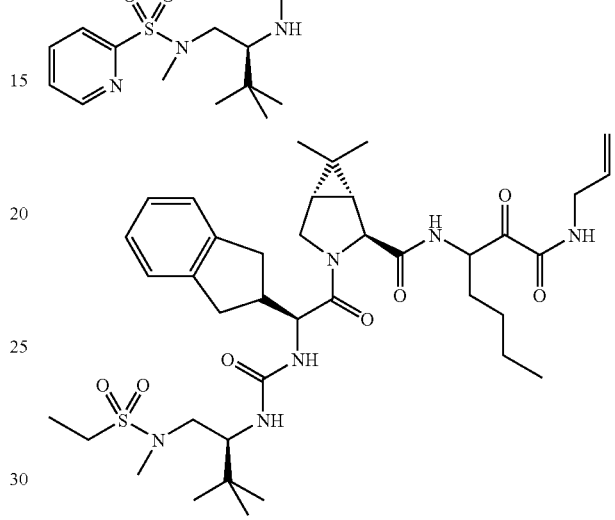
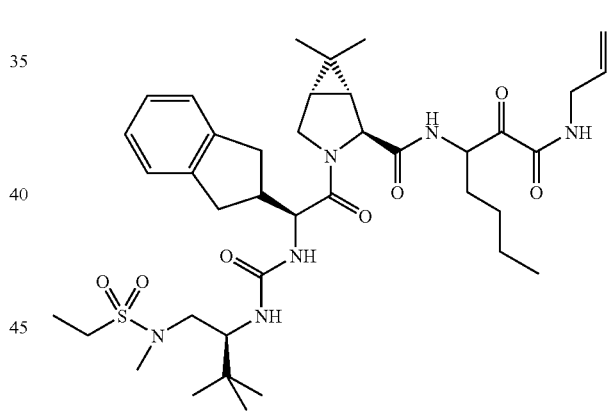
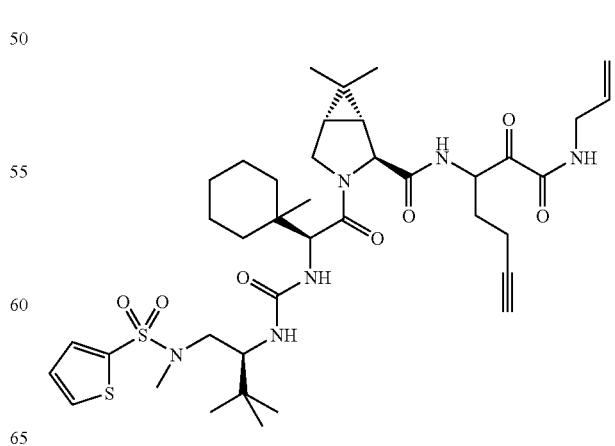

-continued
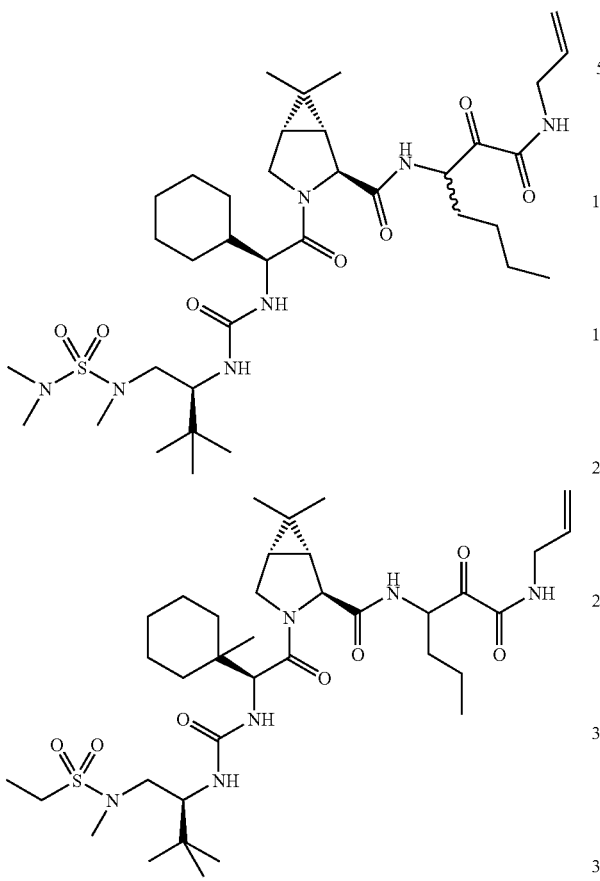
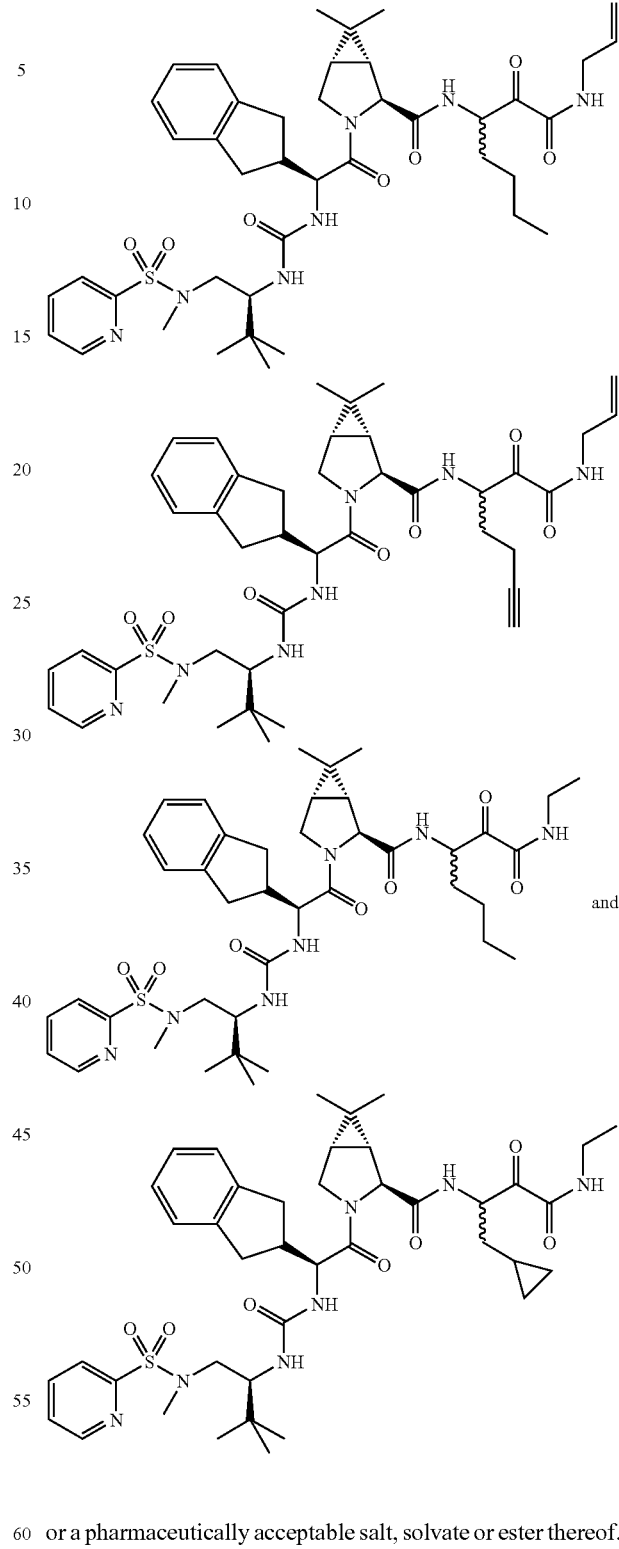
or a pharmaceutically acceptable salt, solvate or ester thereof.
Compounds of formula XII are disclosed in U.S. patent application Ser. No. 11/065,531 filed Feb. 24, 2005. The preparation of these compounds is disclosed in the experimental section of this application set forth hereinbelow.
Non-limiting examples of certain compounds disclosed in U.S. patent application Ser. No. 11/065,531 are:

467 468
-continued
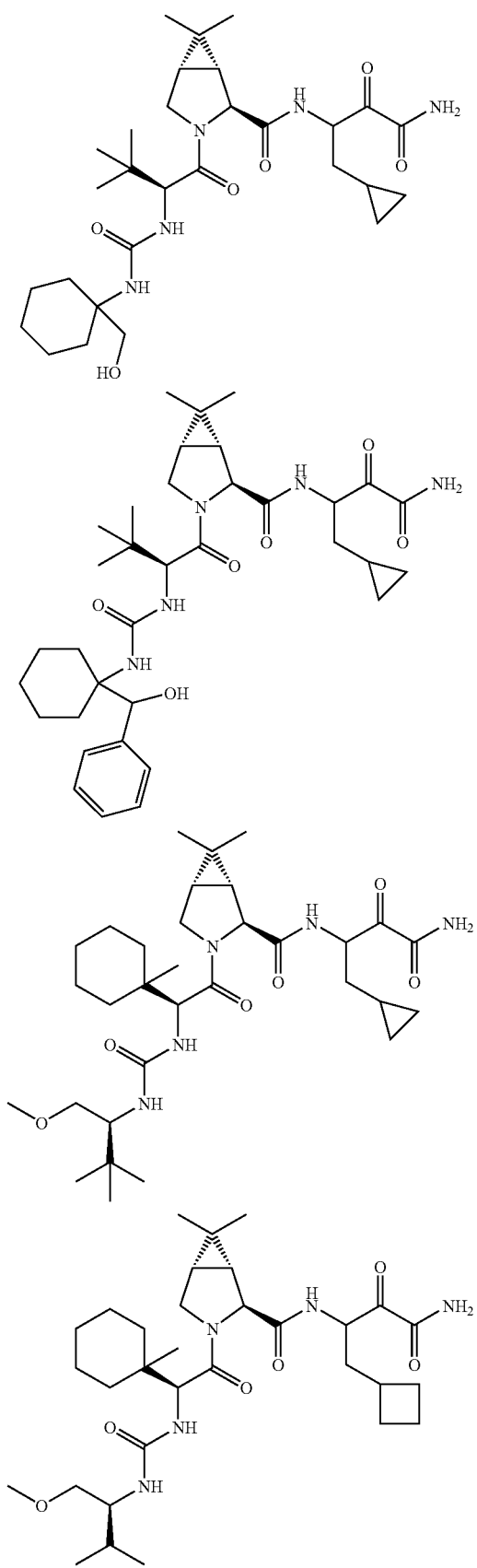
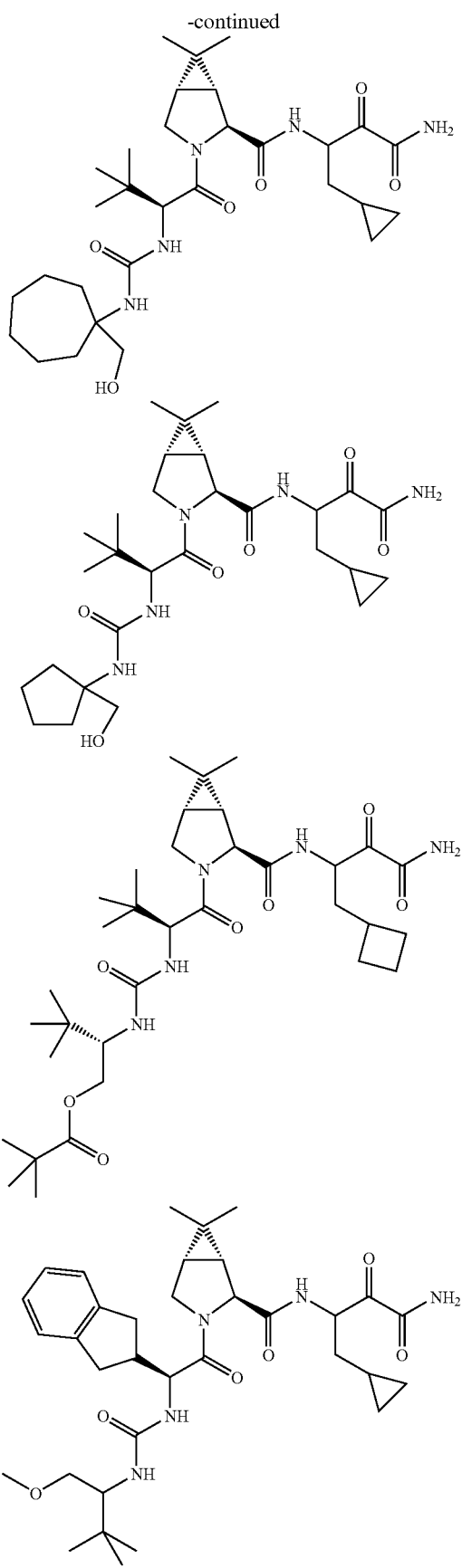

-continued
469
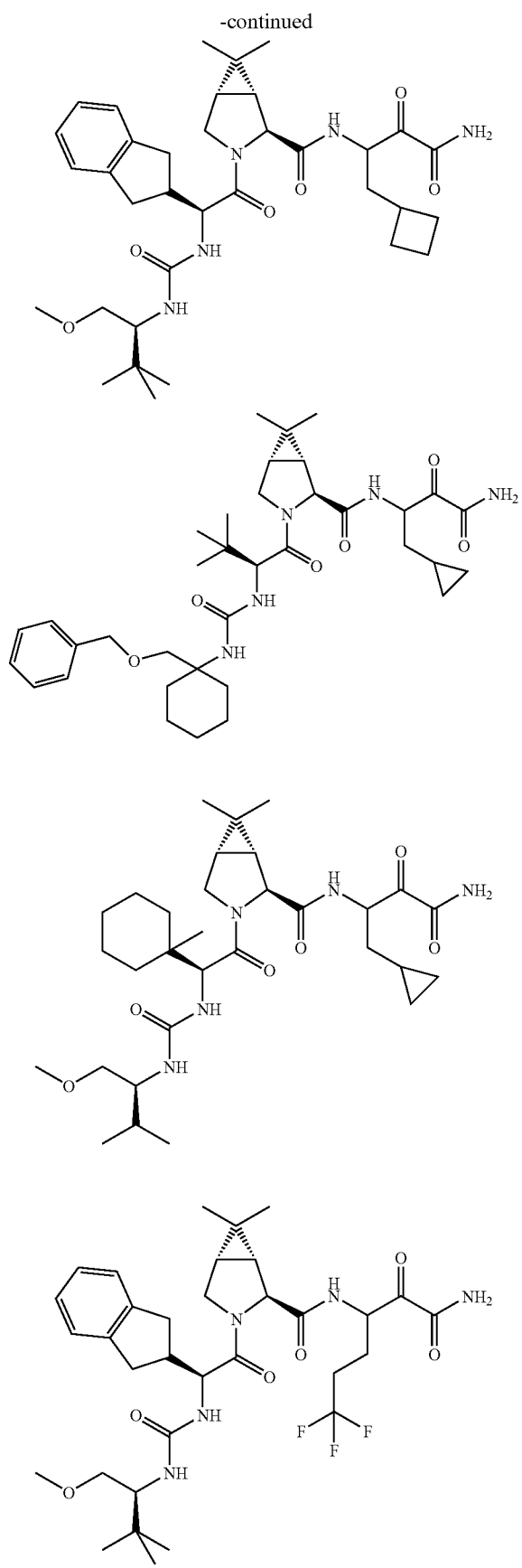
470
-continued
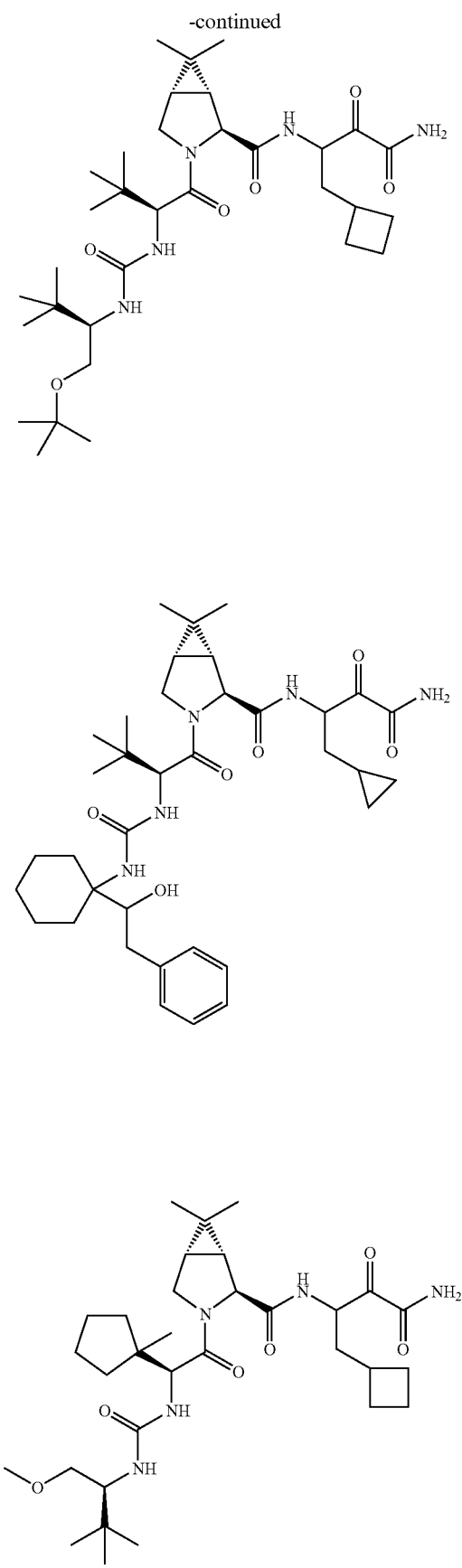

471
-continued
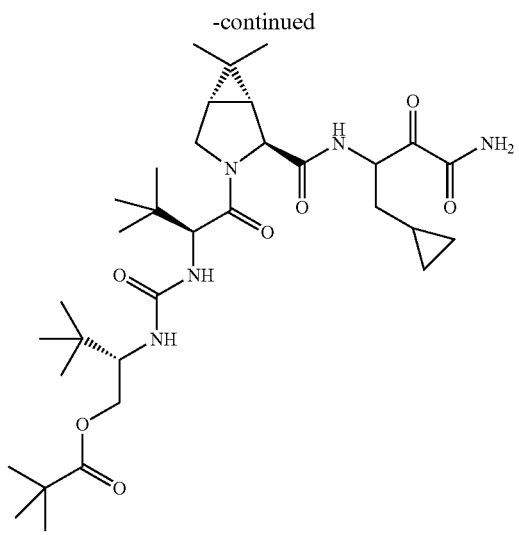
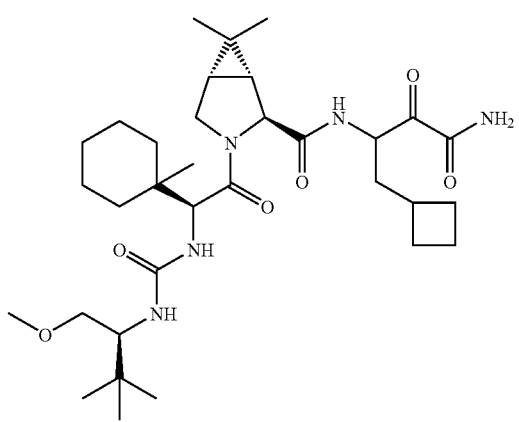
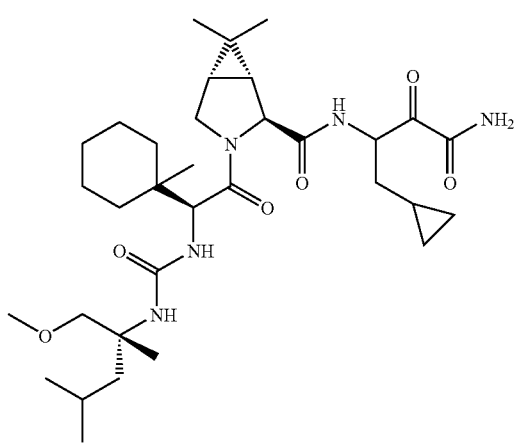
472
-continued
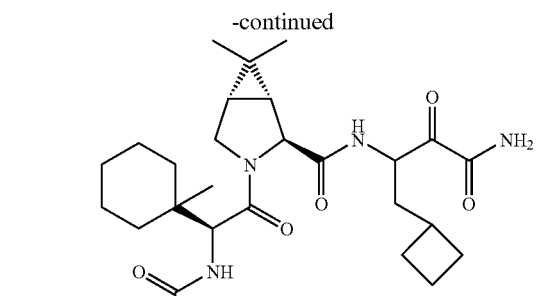
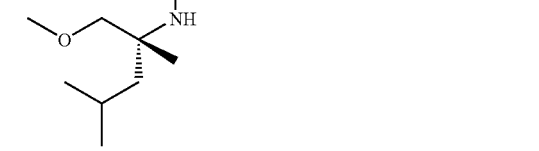
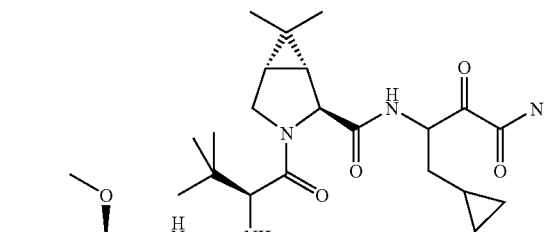
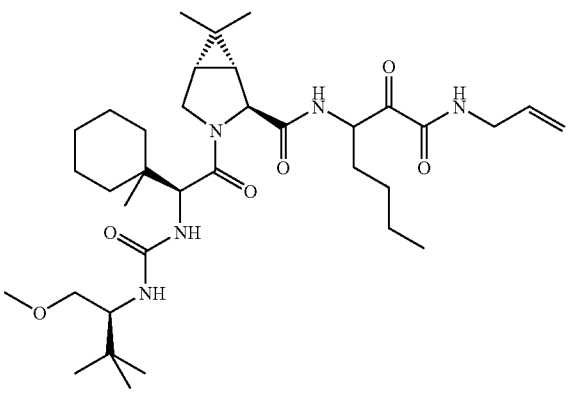
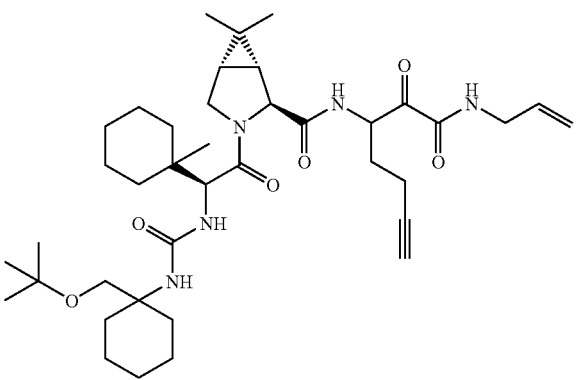

473
-continued
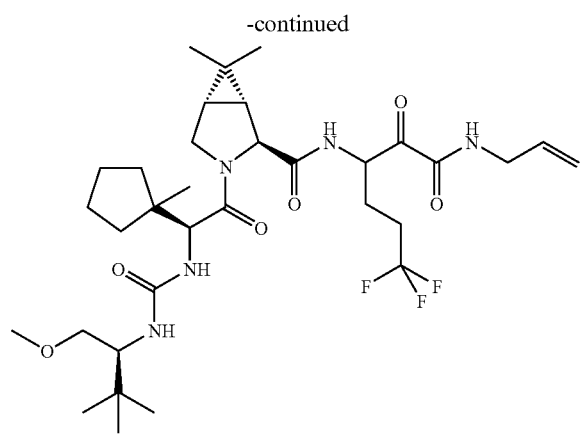
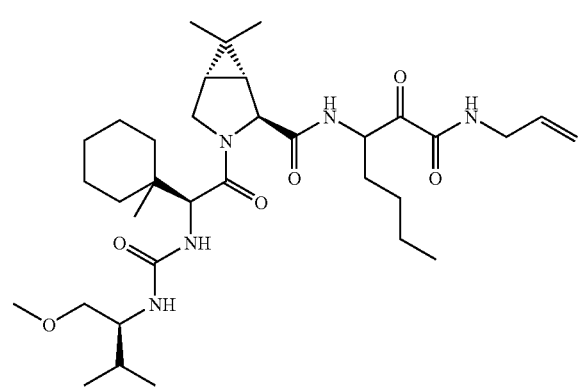
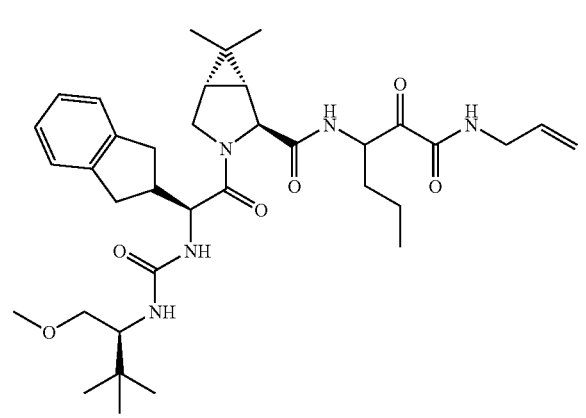
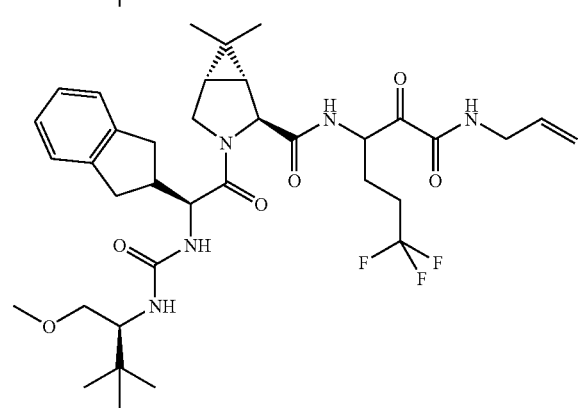
474
-continued
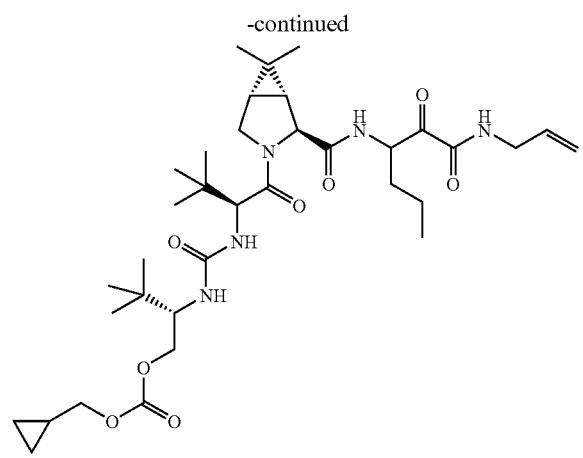
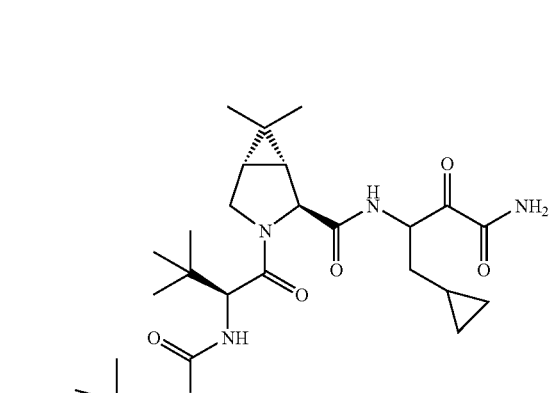
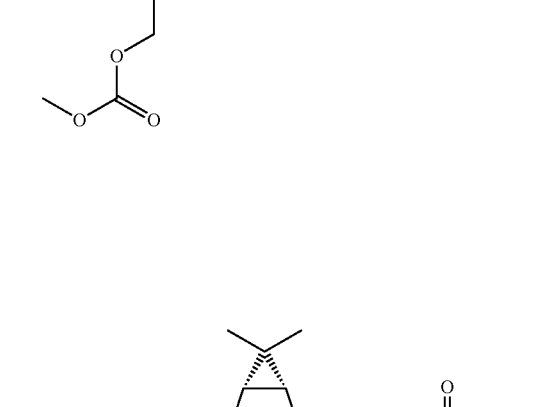
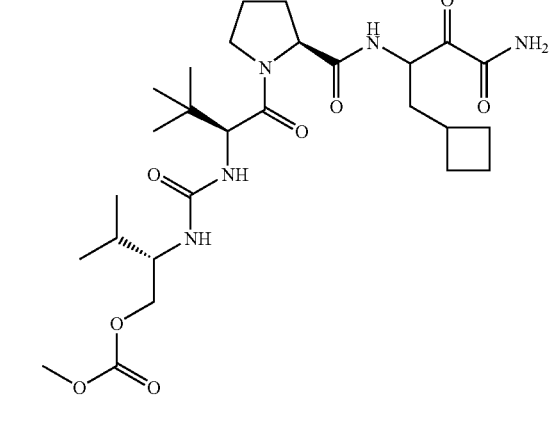

475
-continued
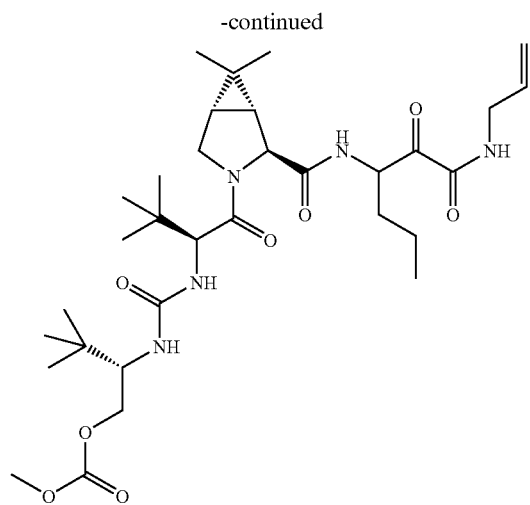
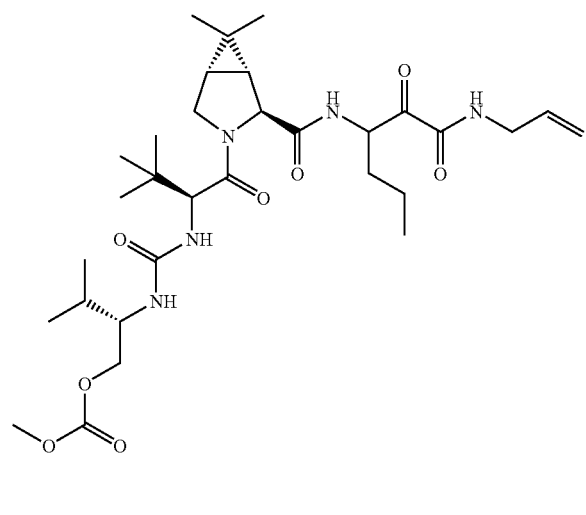
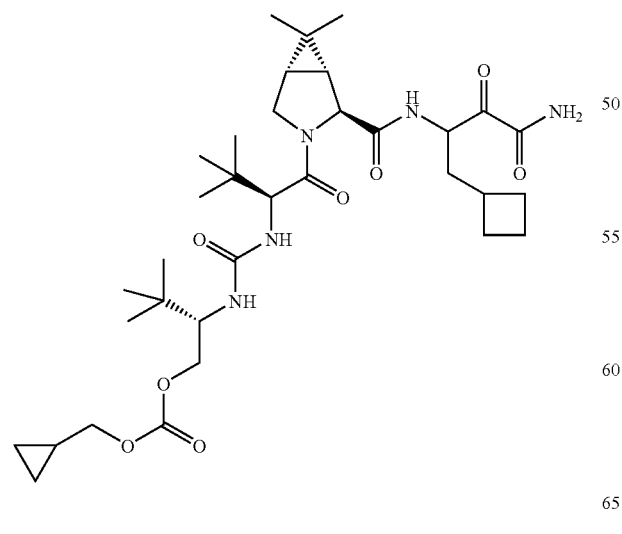
476
-continued
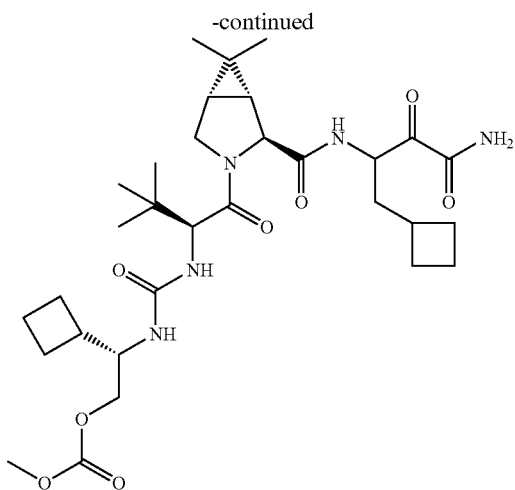
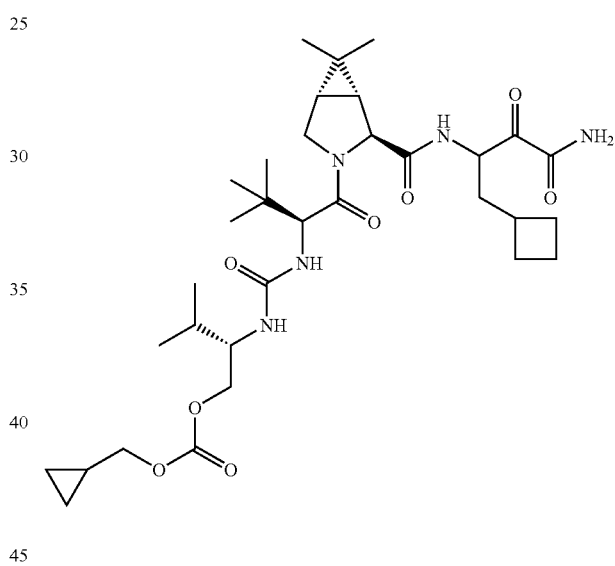
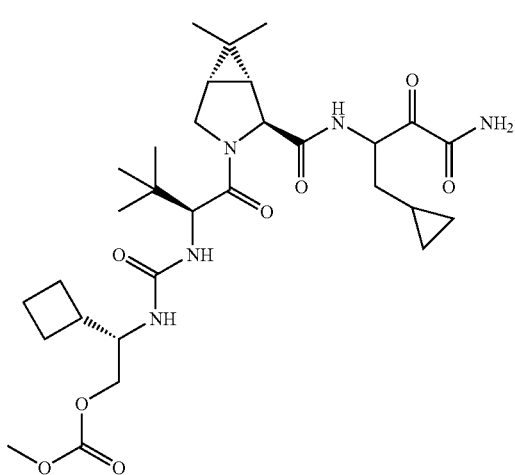

477 478
-continued -continued
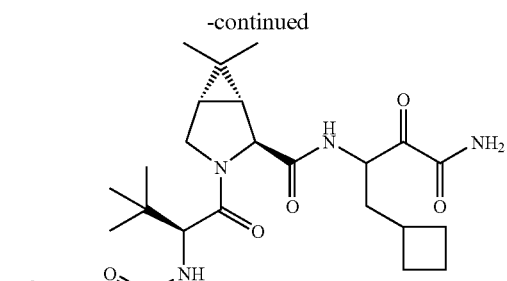
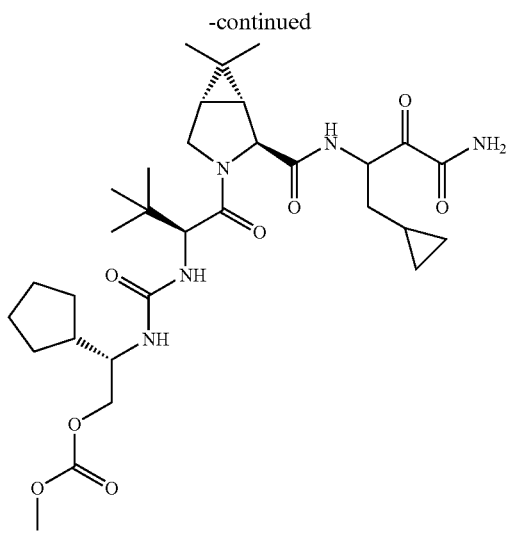
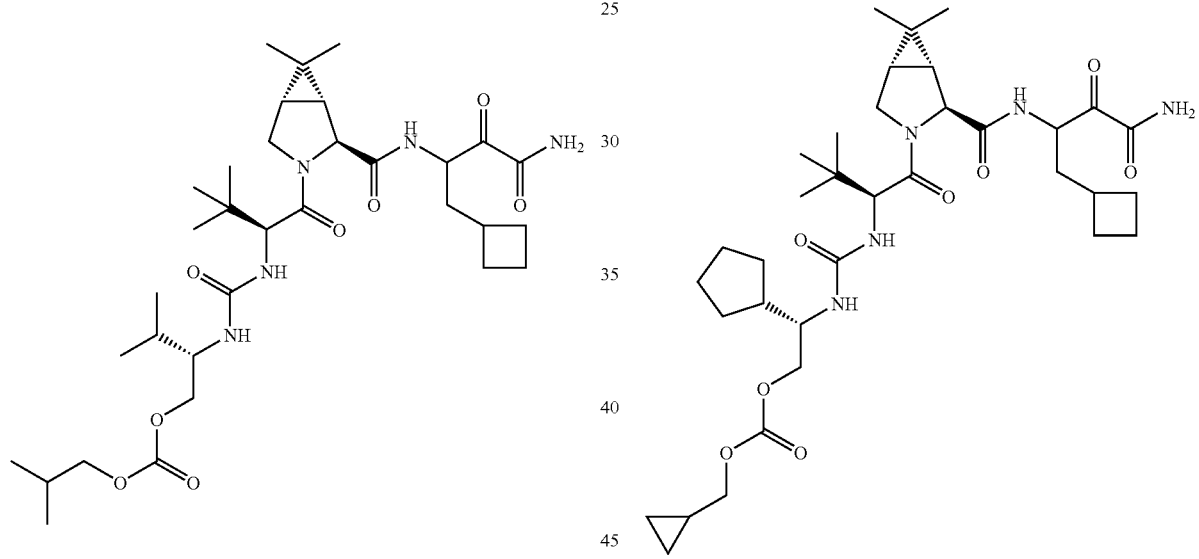
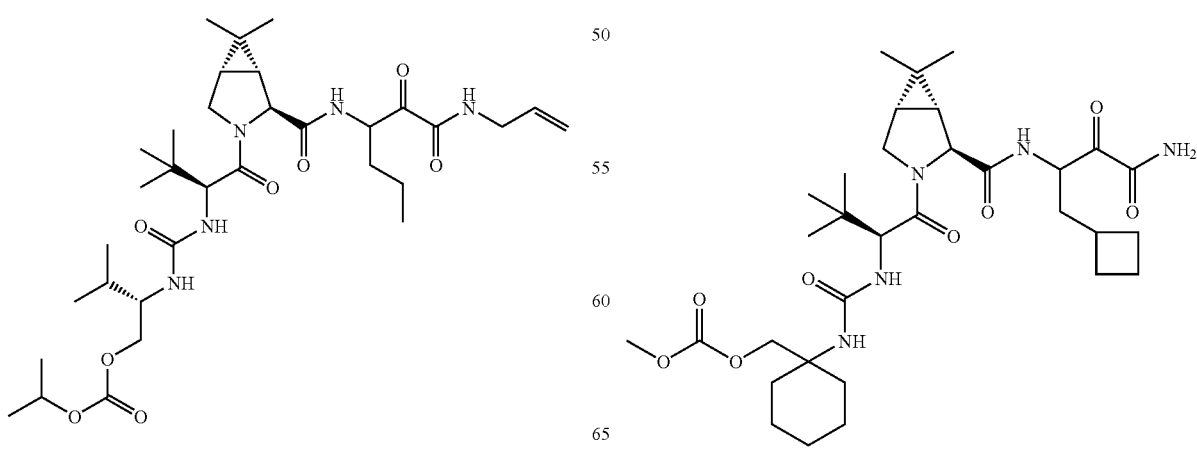

479
-continued
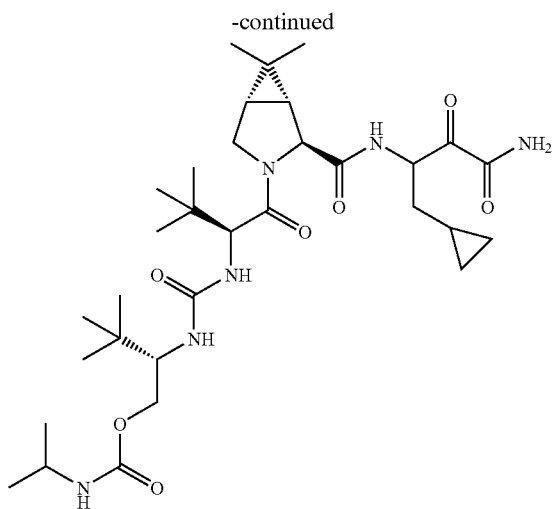
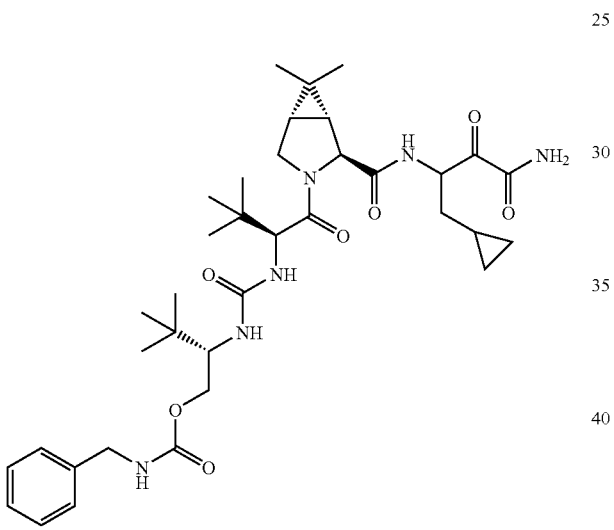
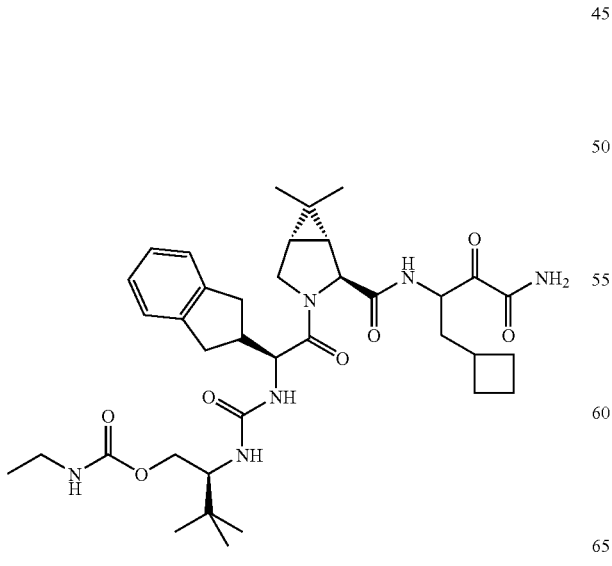
480
-continued
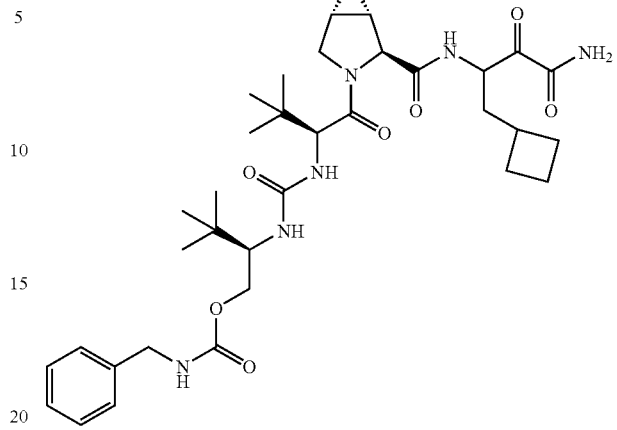
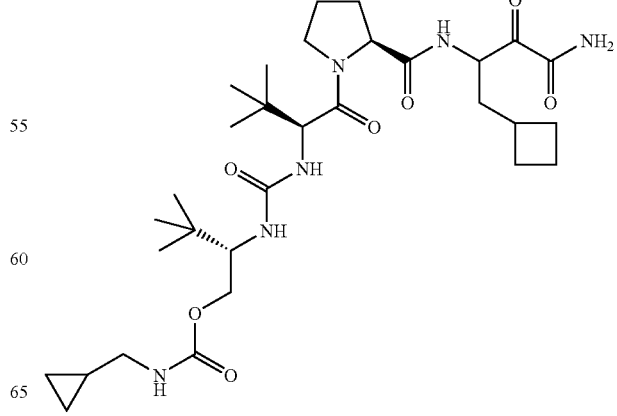

481
-continued
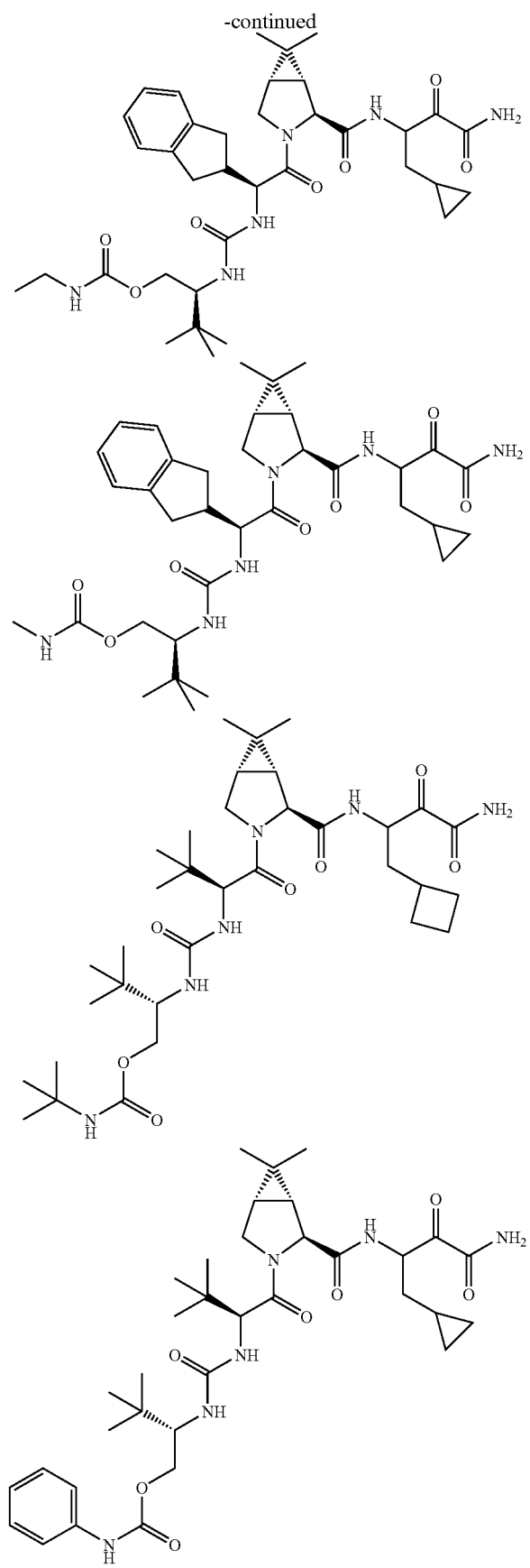
482
-continued
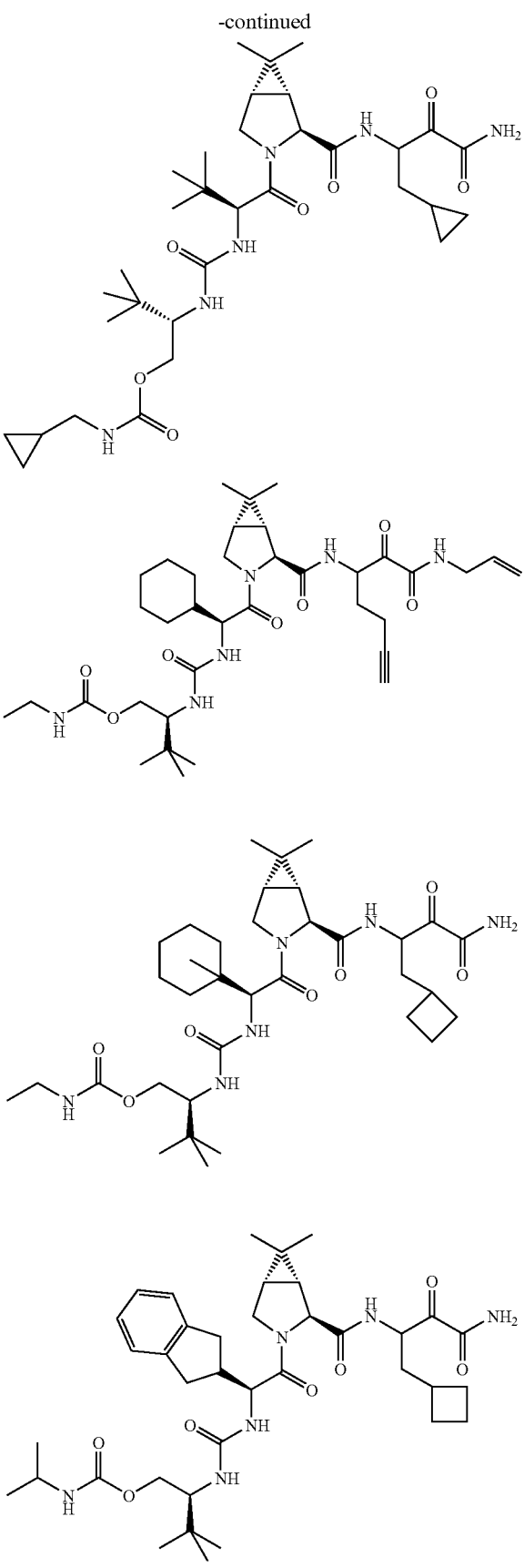

483
-continued
484
-continued
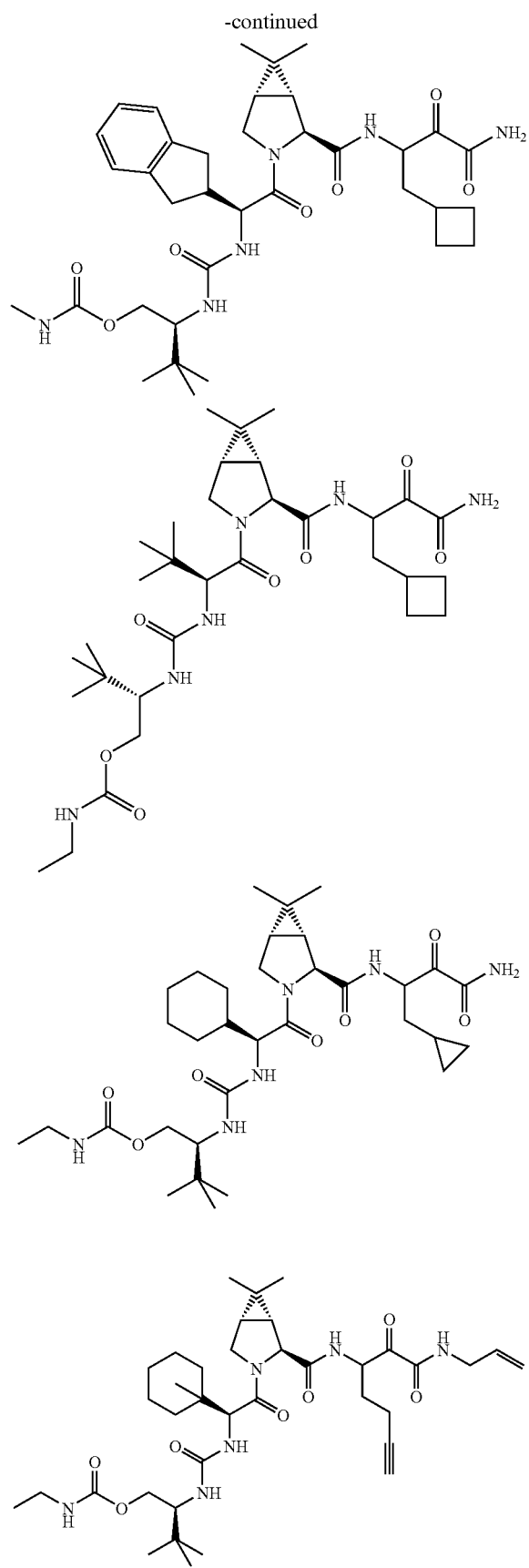
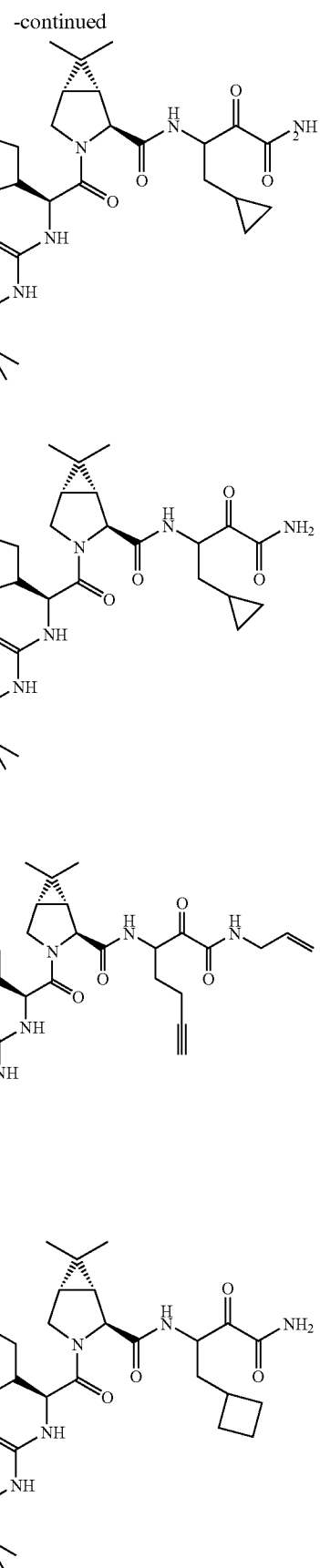

485
-continued
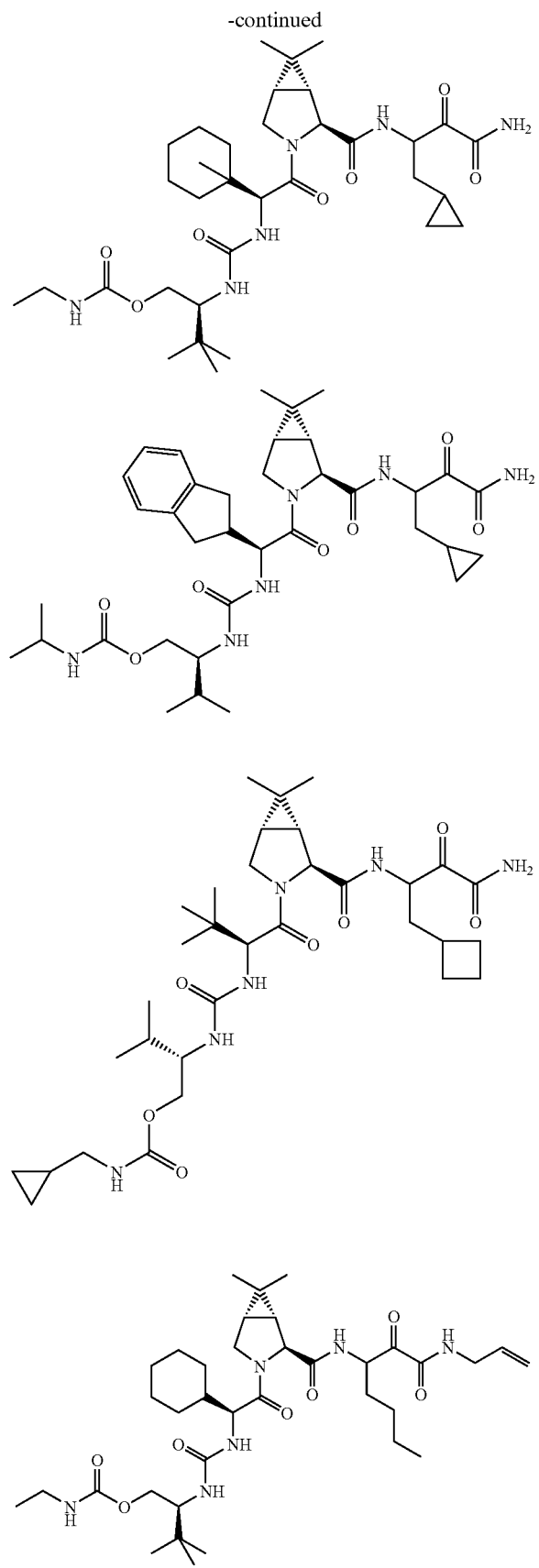
486
-continued
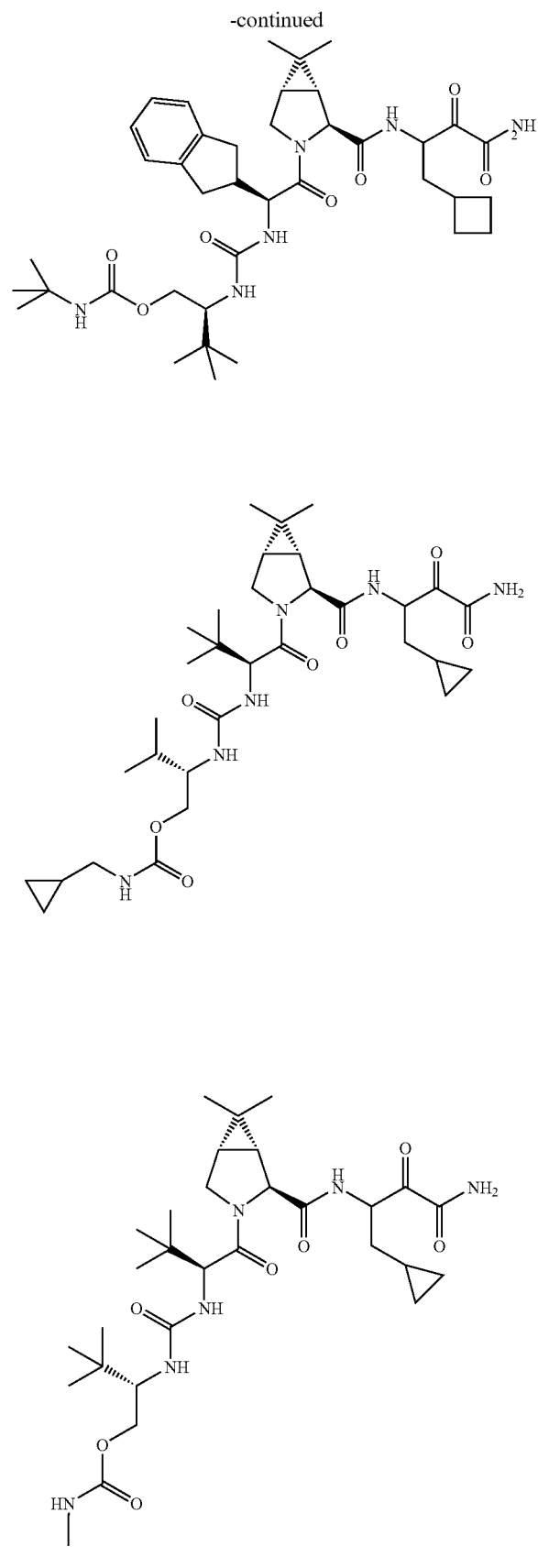

487
-continued
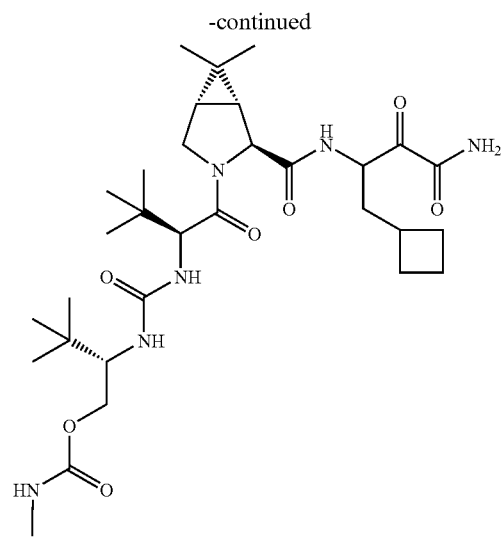
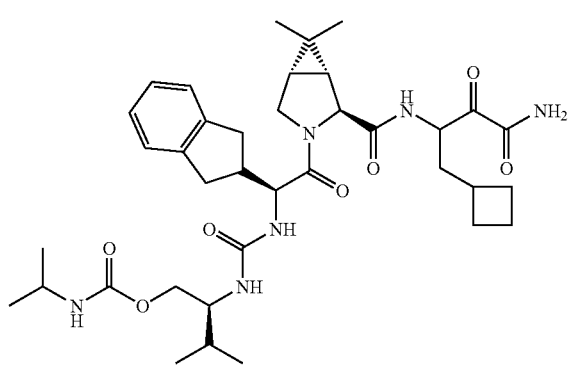
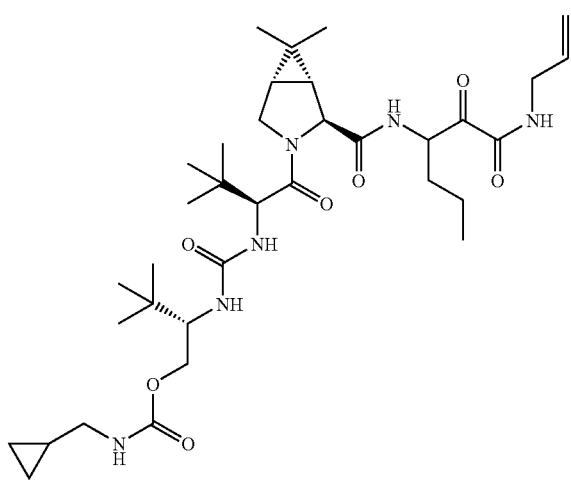
488
-continued
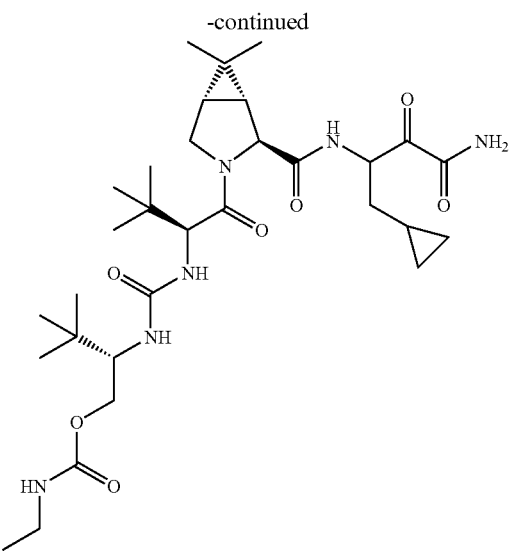
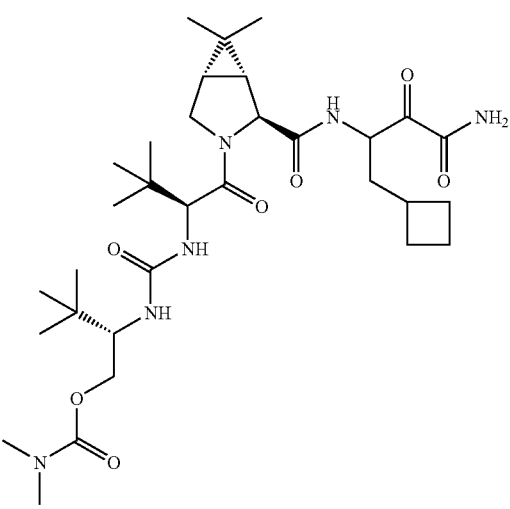
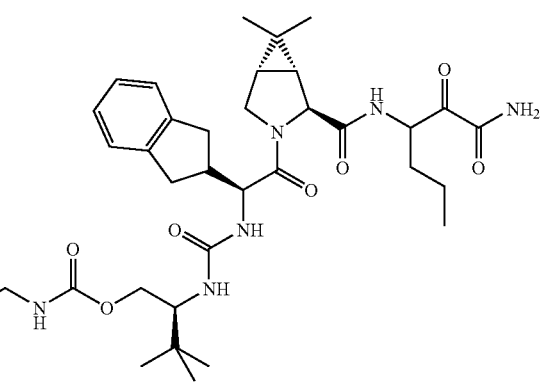

489
-continued
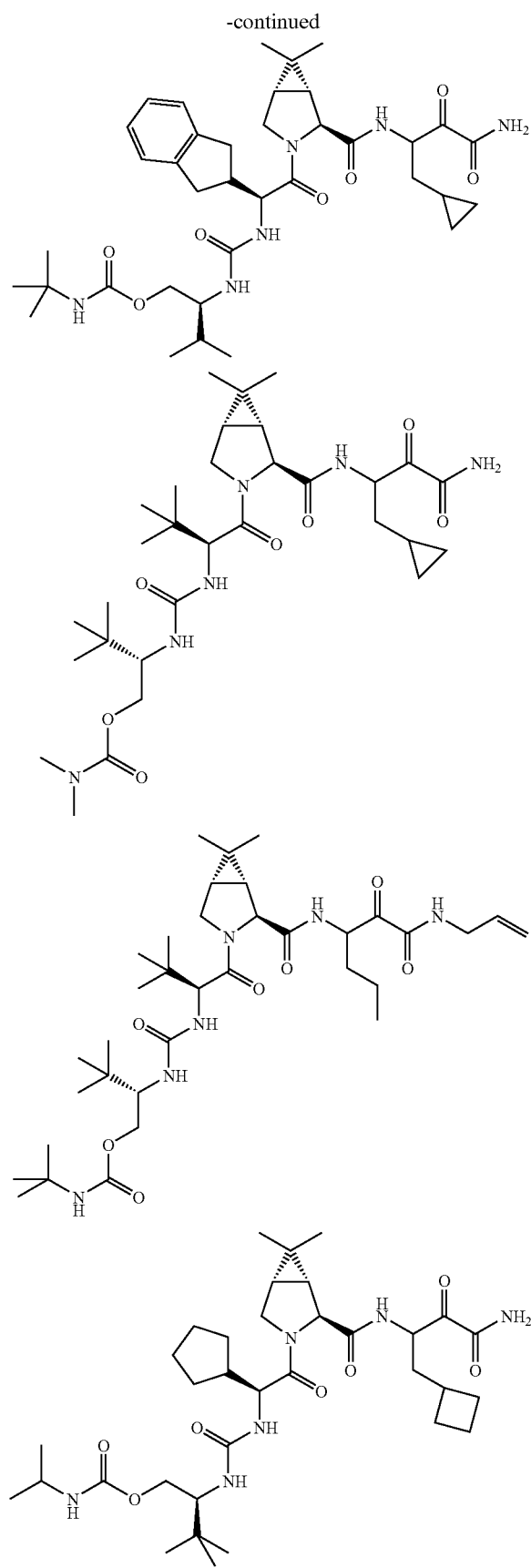
490
-continued
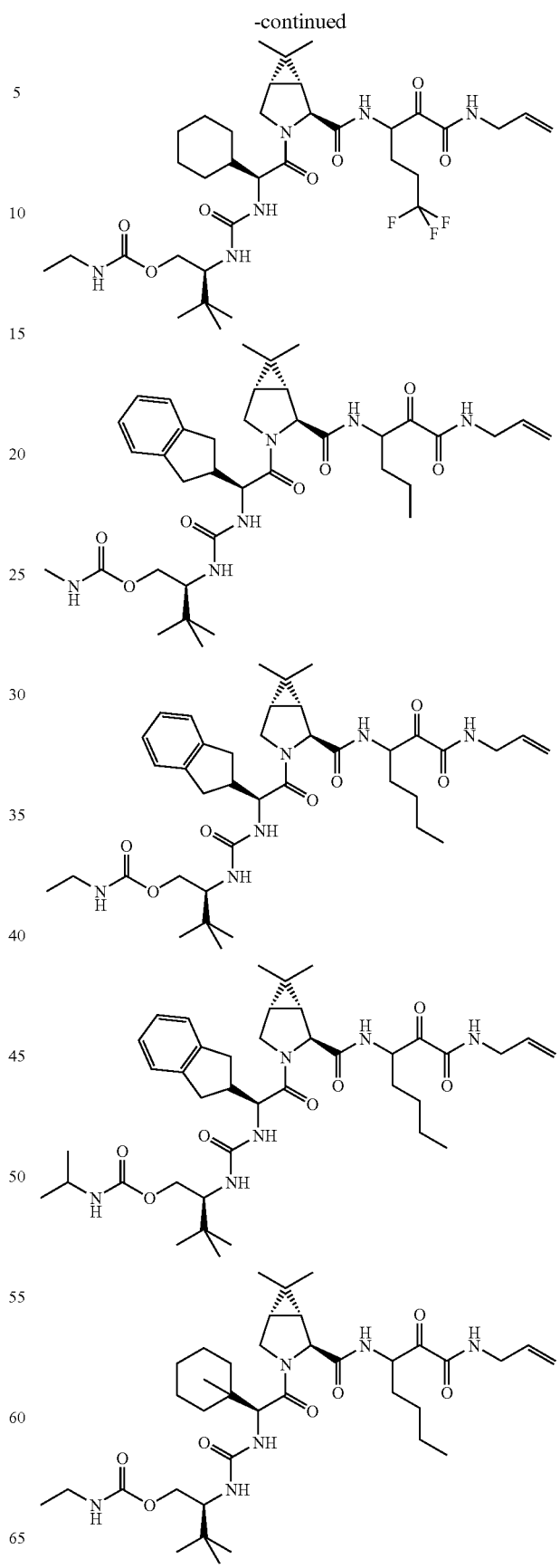

491
-continued
492
-continued
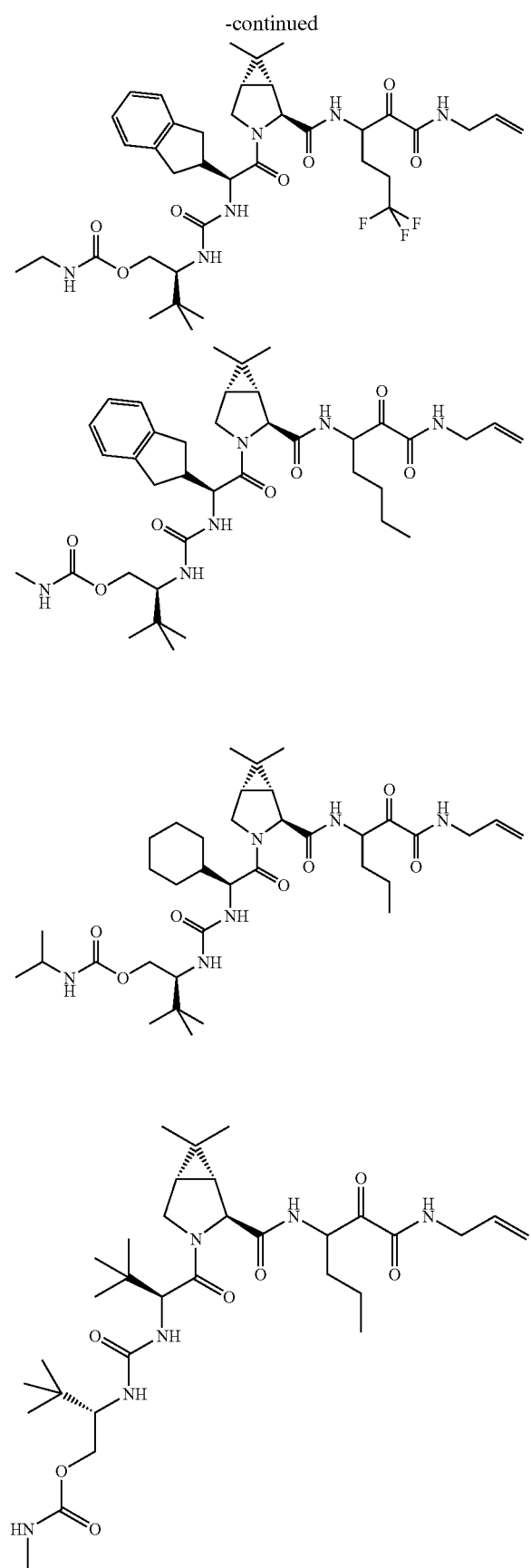
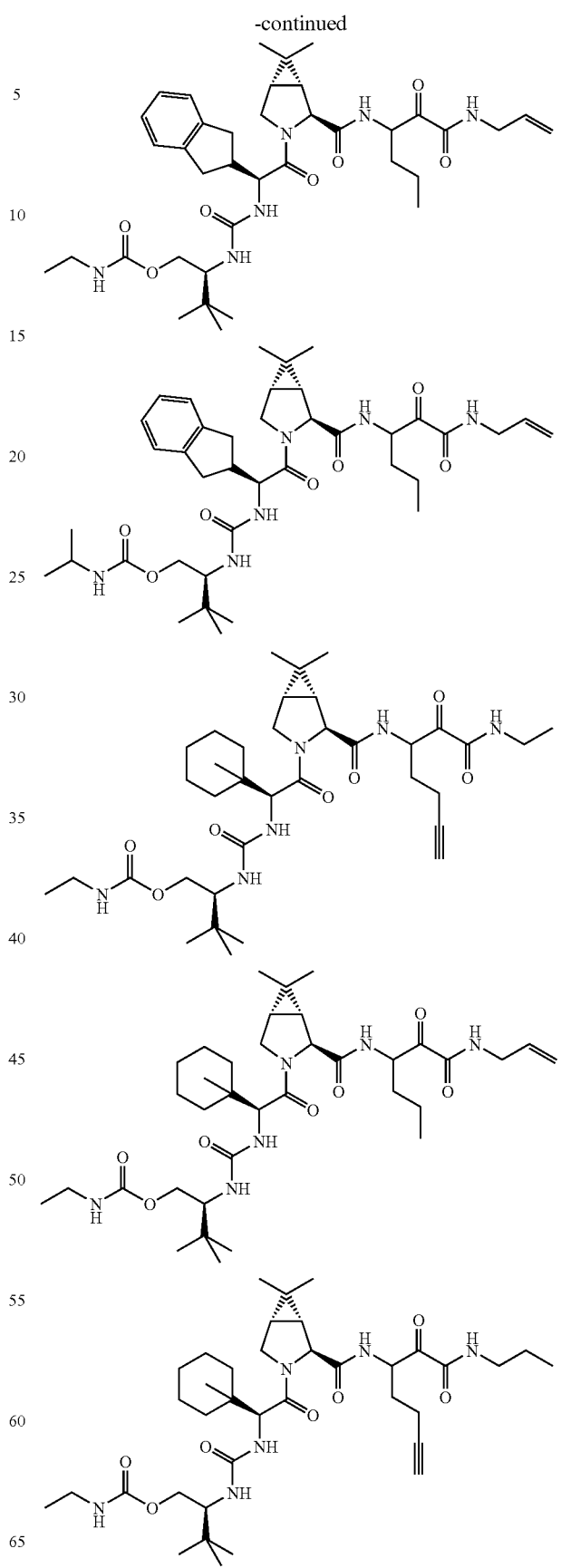

493
-continued
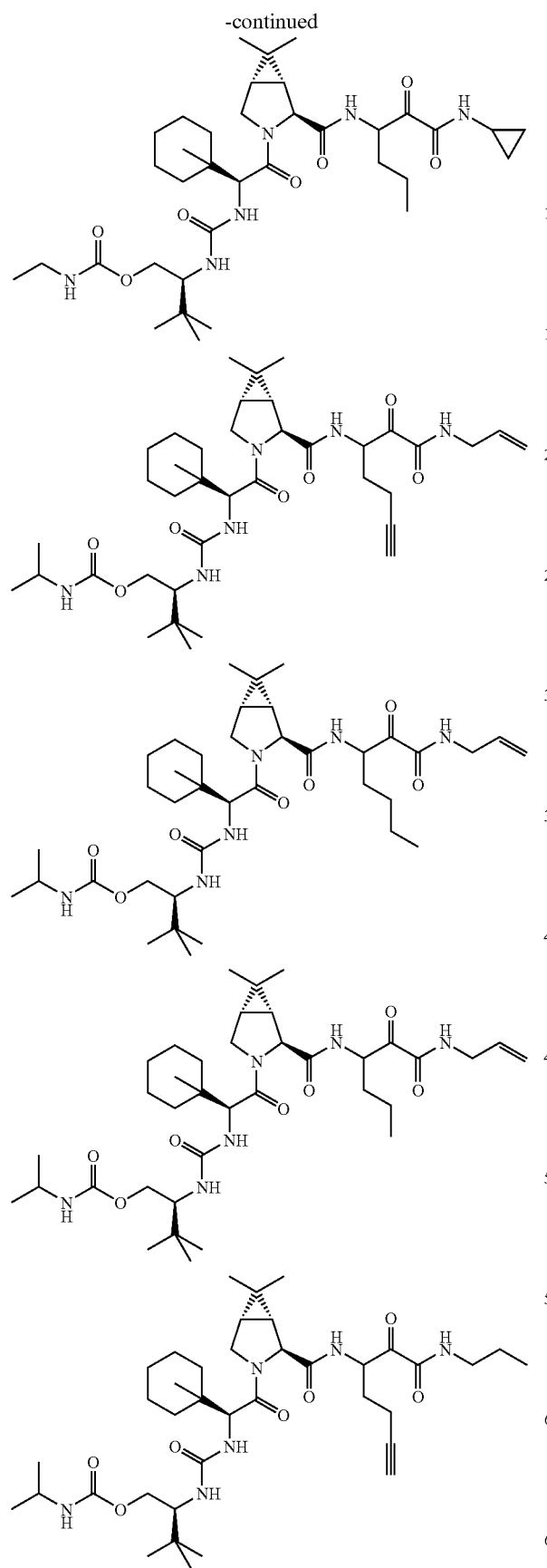
494
-continued
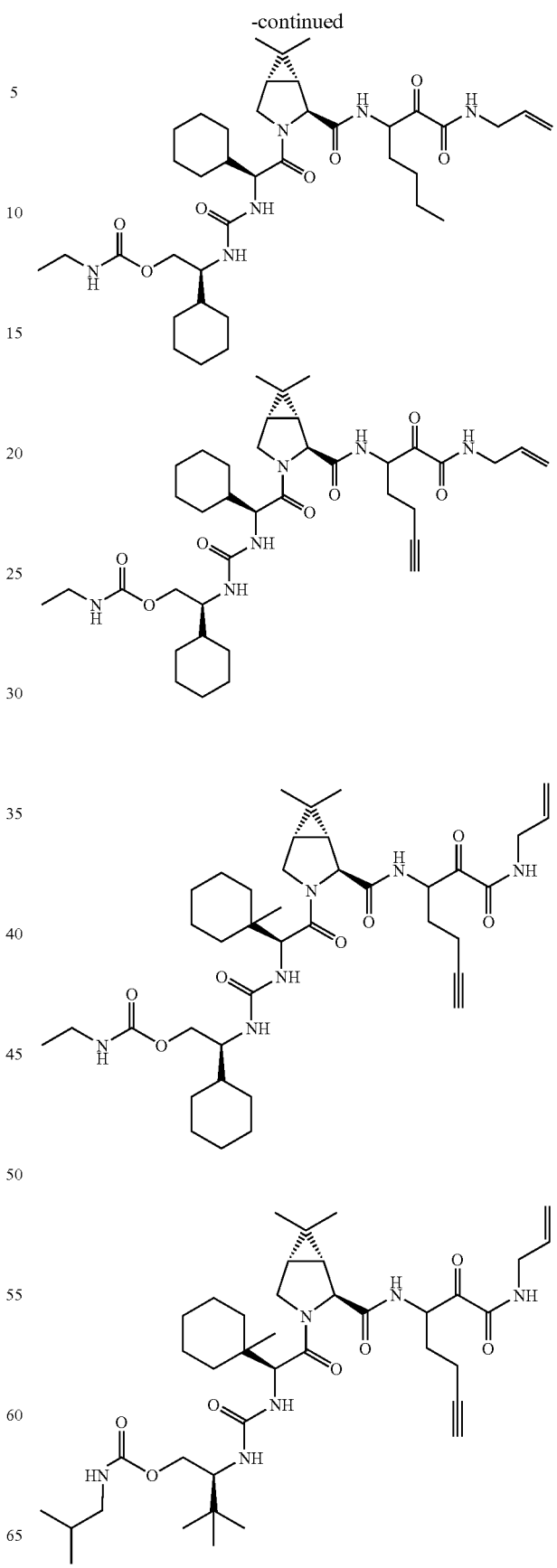

495
-continued
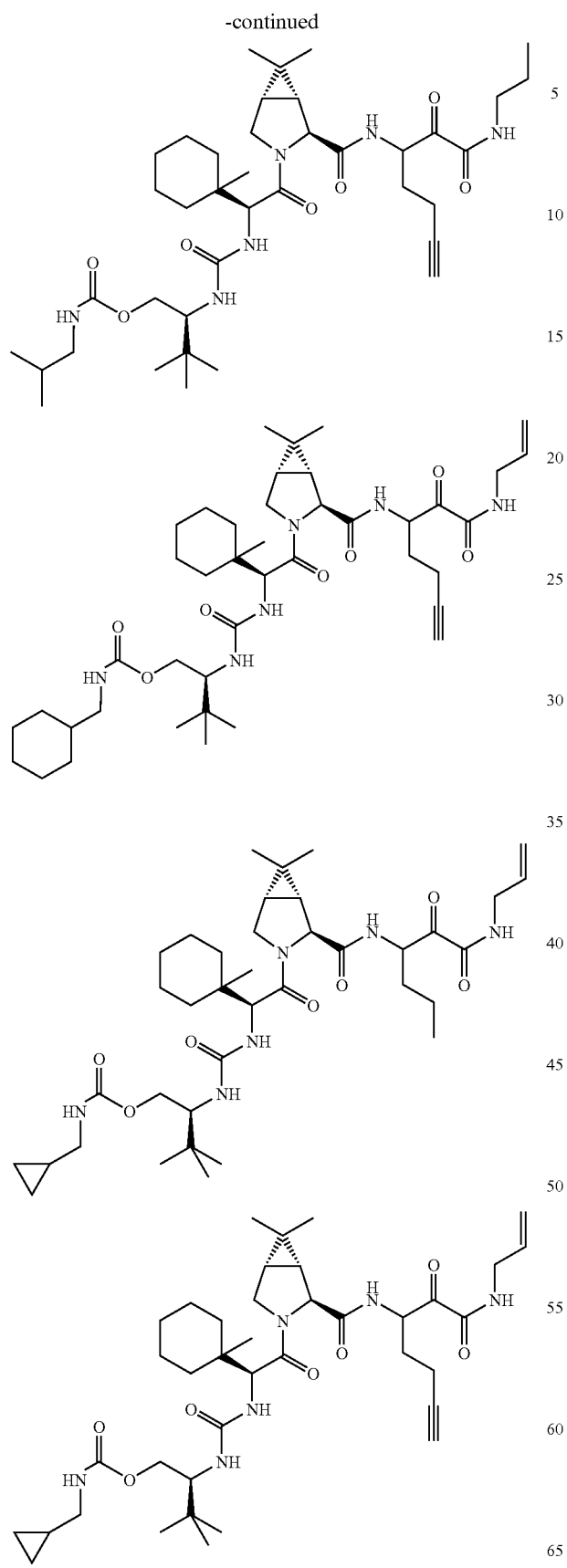
496
-continued
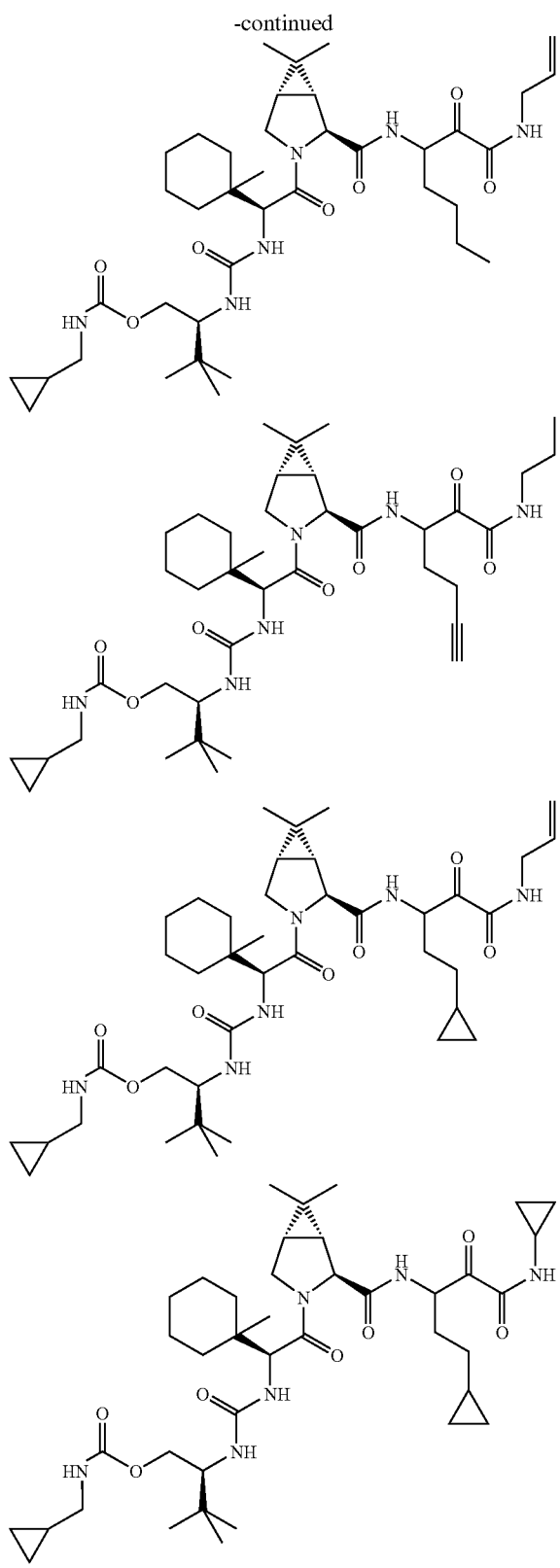
or a pharmaceutically acceptable salt, solvate or ester thereof.
Compounds of formula XIII are disclosed in U.S. patent application Ser. No. 11/065,647 filed Feb. 24, 2005. The

497
preparation of these compounds is disclosed in the experimental section of this application set forth hereinbelow.
498
Non-limiting examples of certain compounds disclosed in U.S. patent application Ser. No. 11/065,647 are:
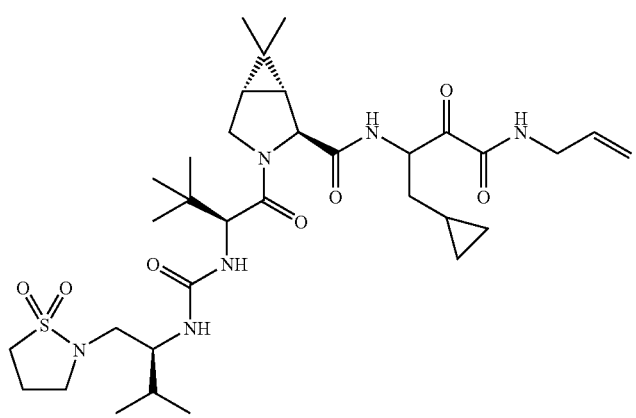
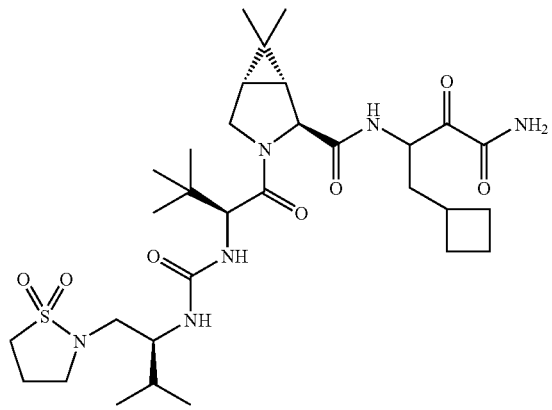
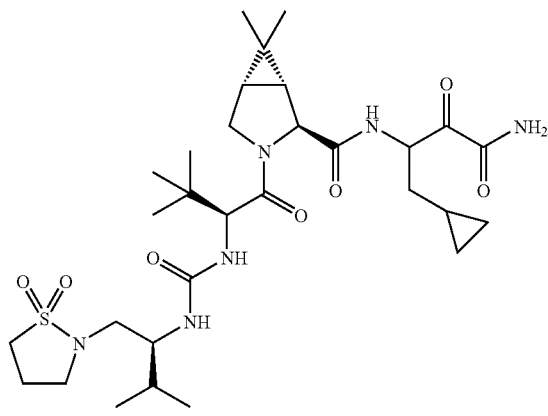
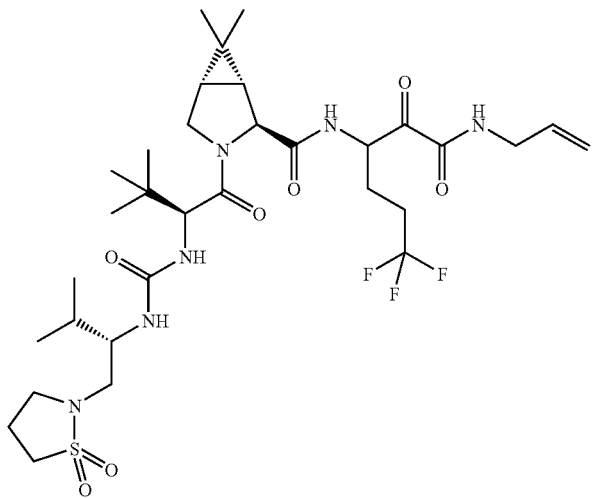
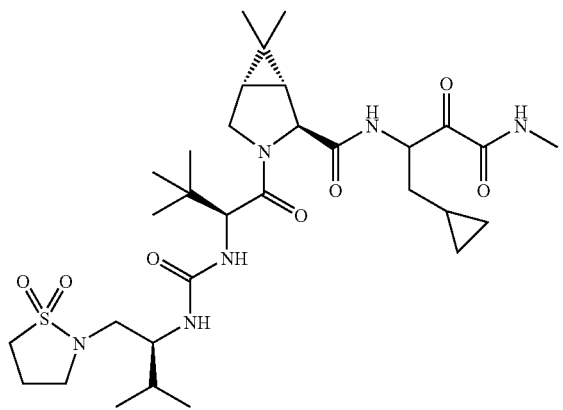

-continued
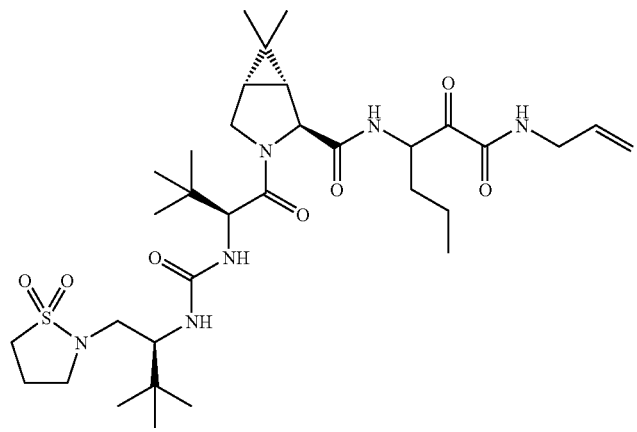
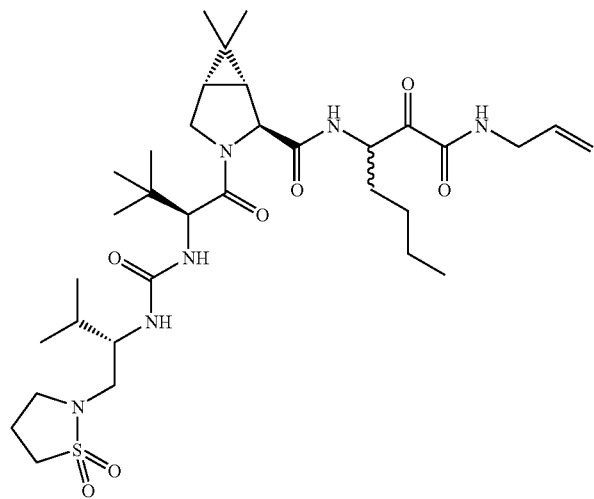
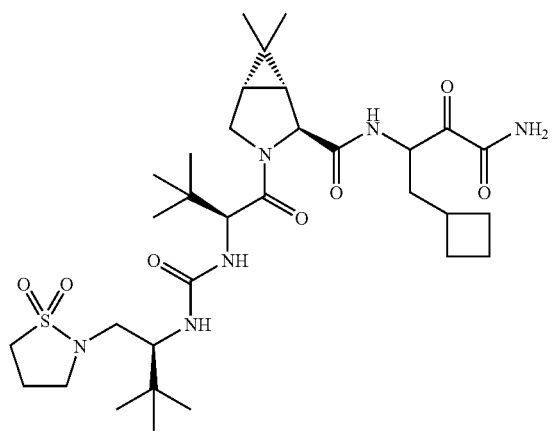
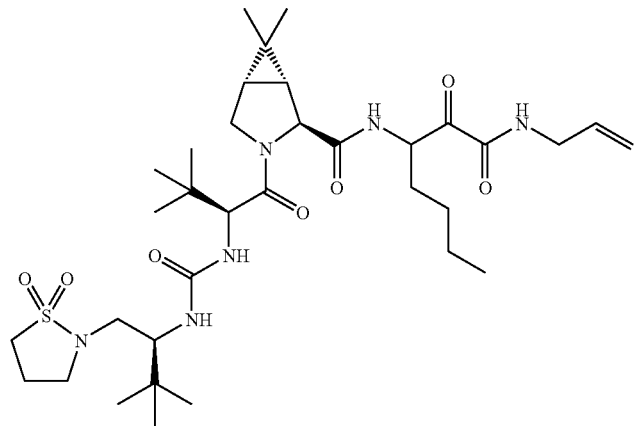

501 502
-continued
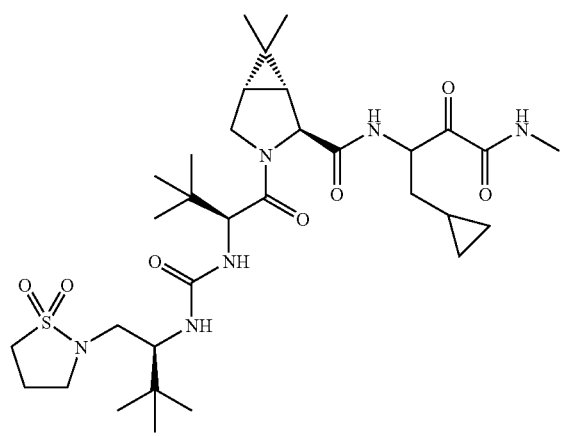
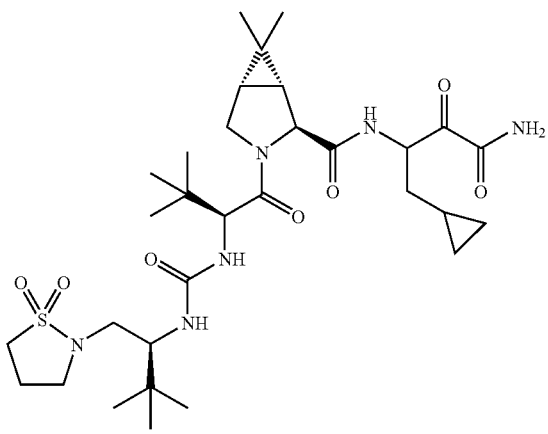
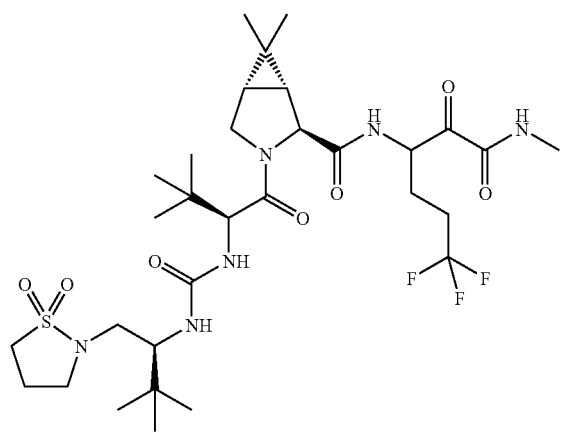
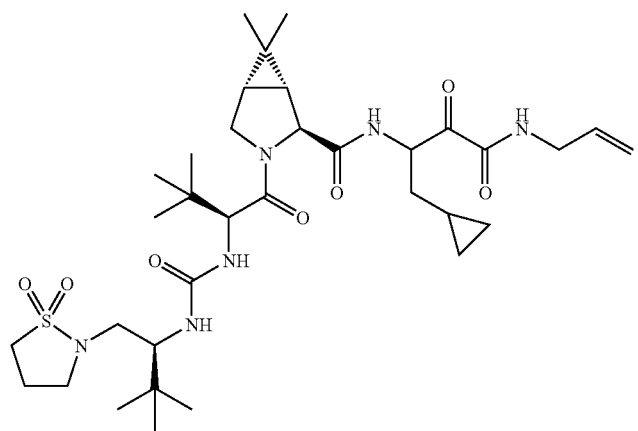

503
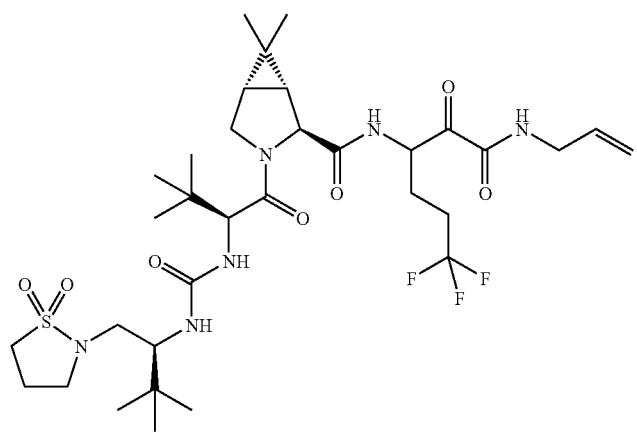
504
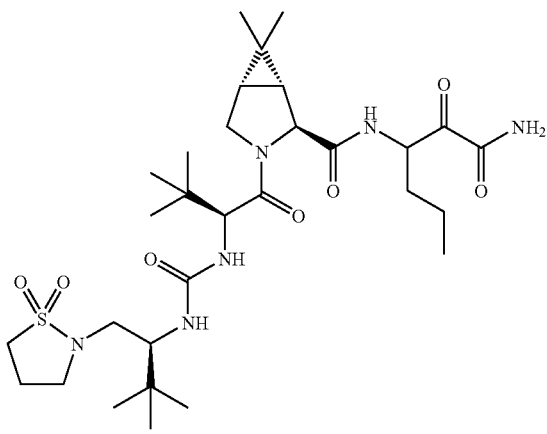
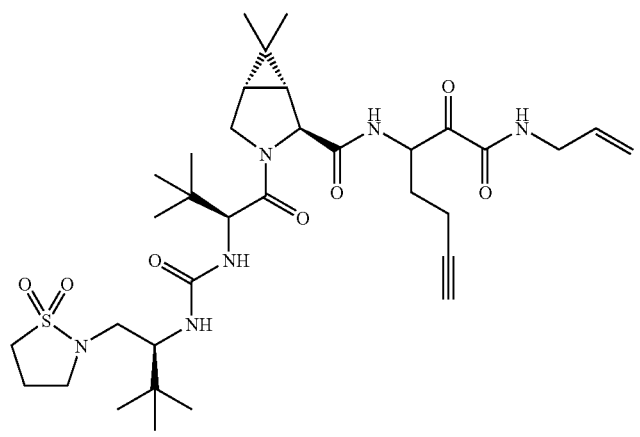
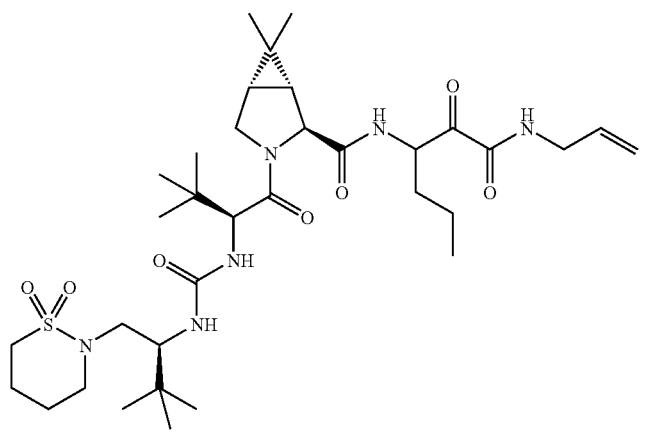

505
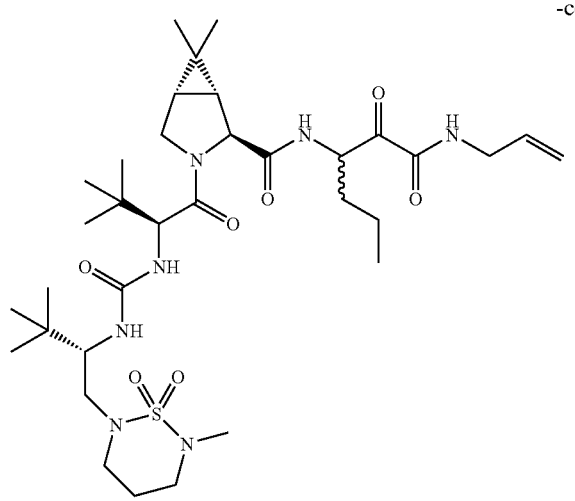
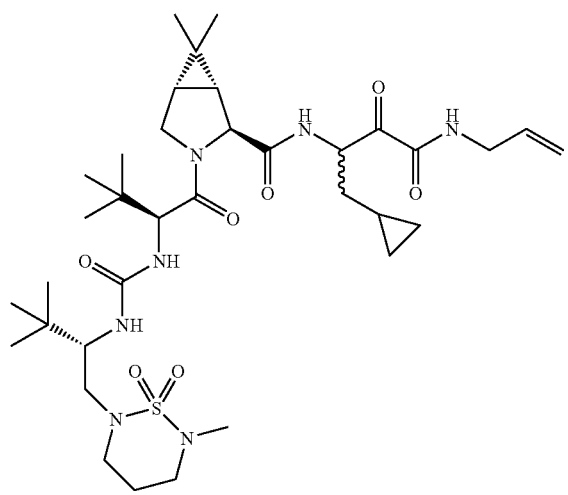
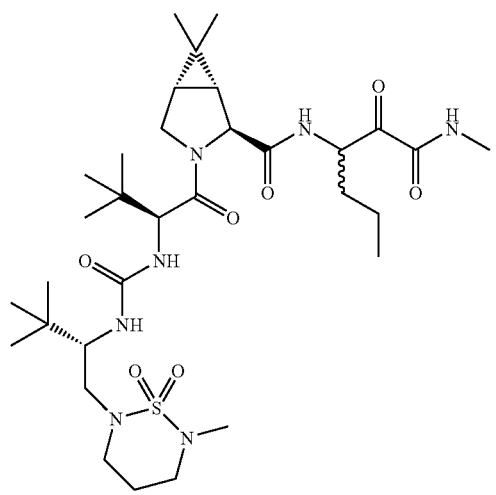
-continued
506
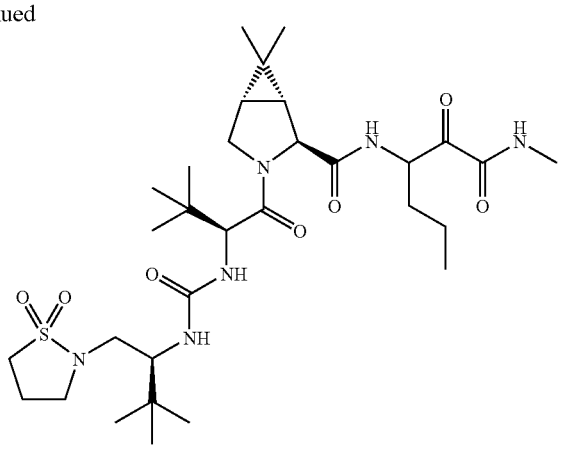
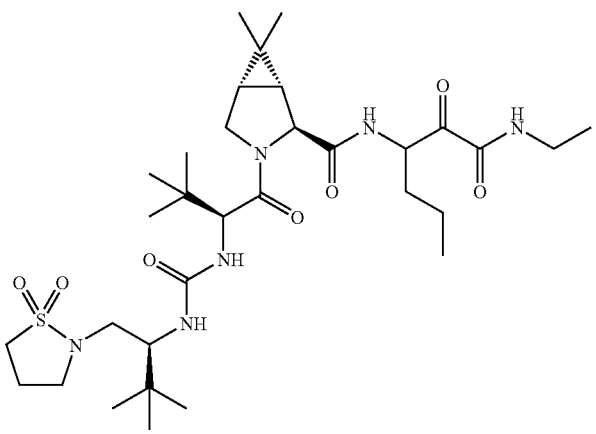
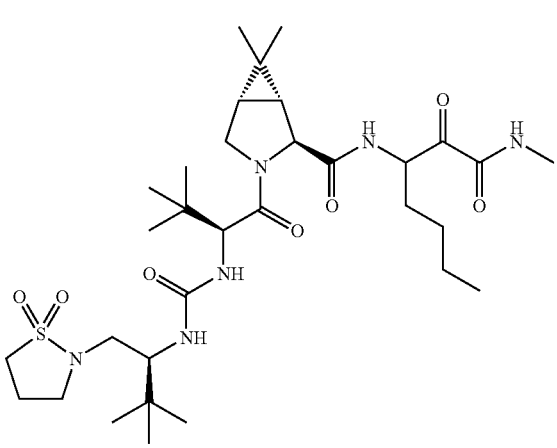

-continued
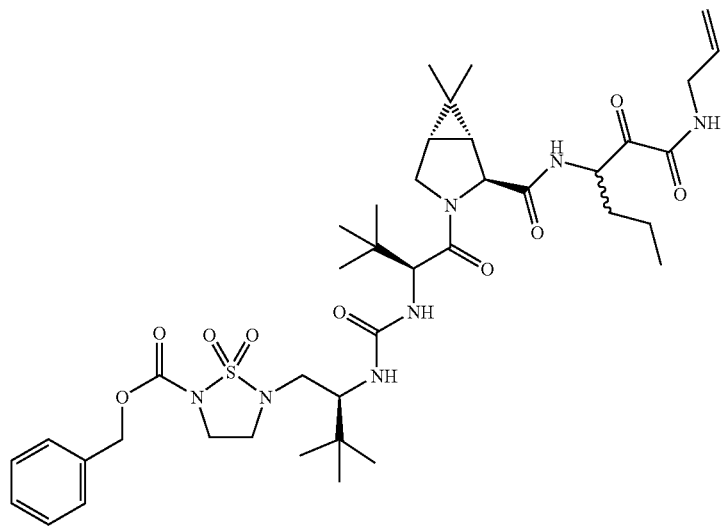
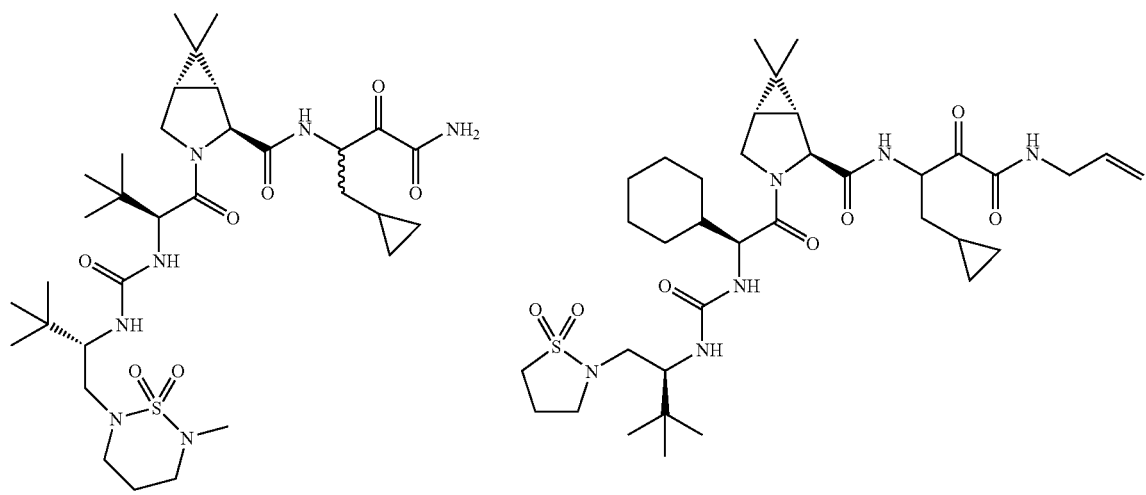
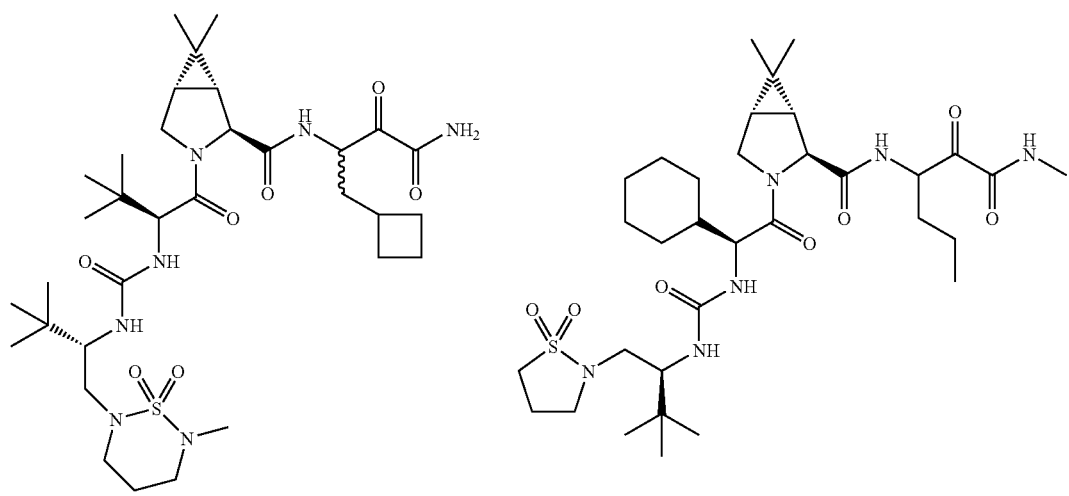

-continued
509
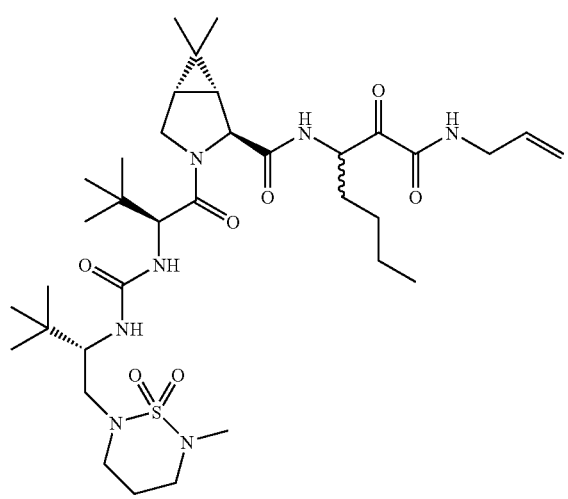
510
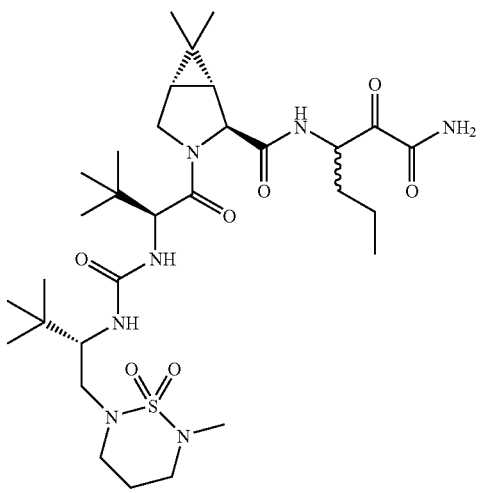
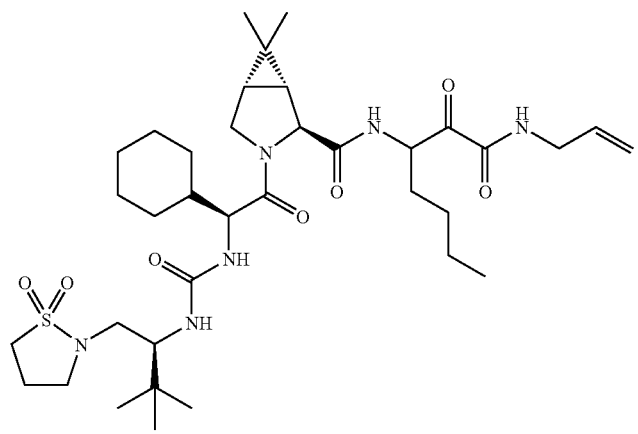
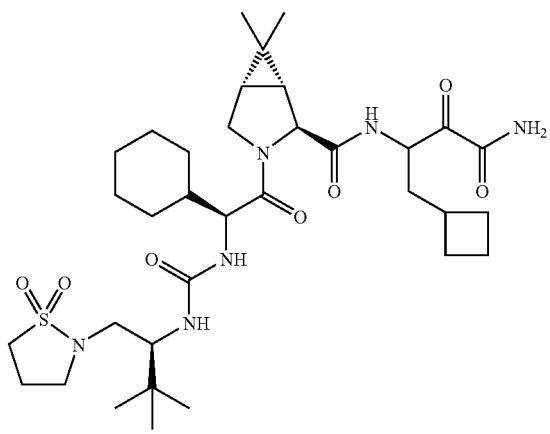
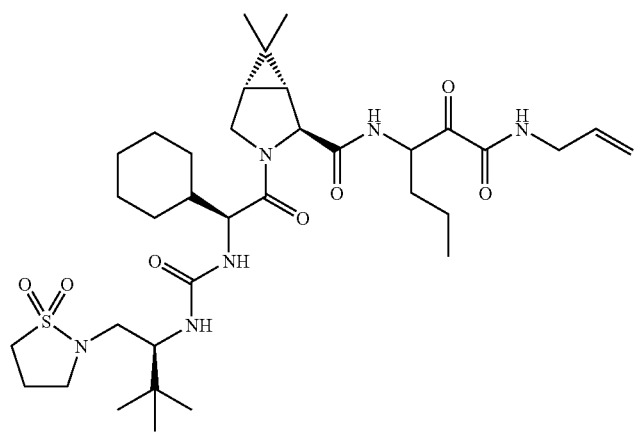

511 512
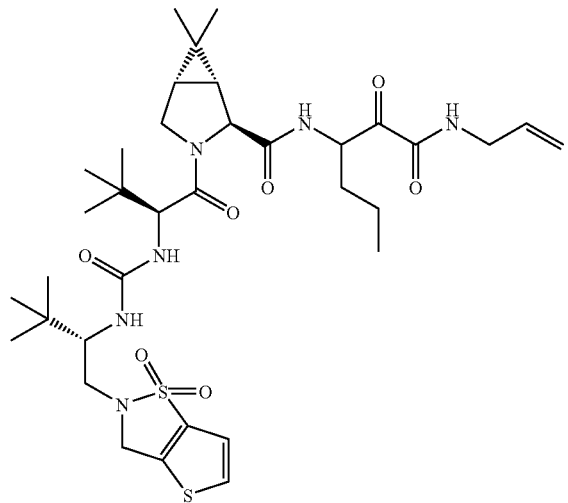 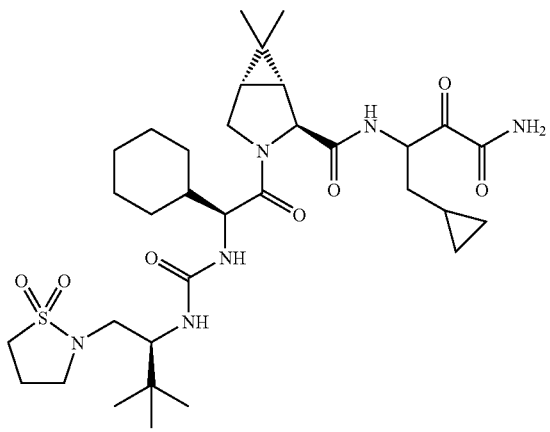
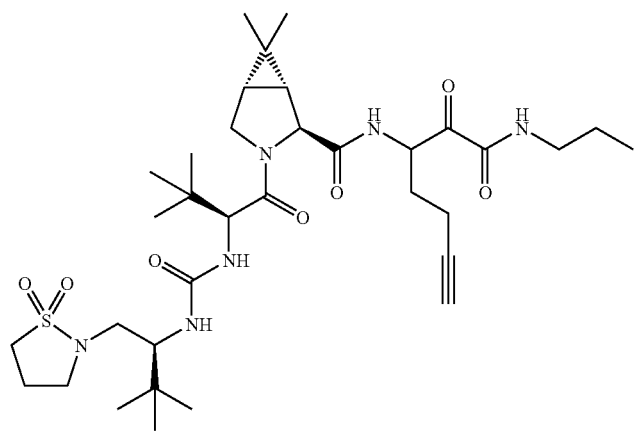
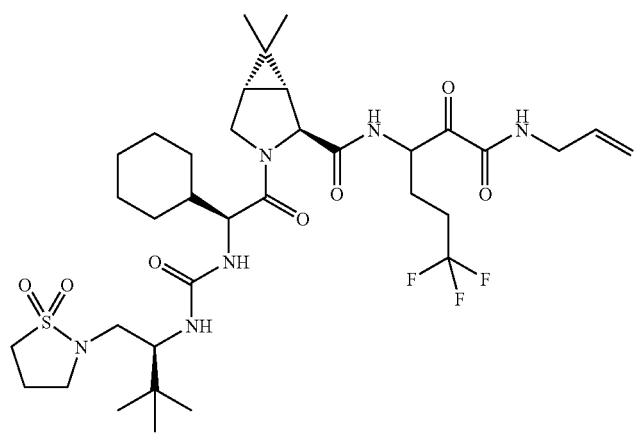

513 514
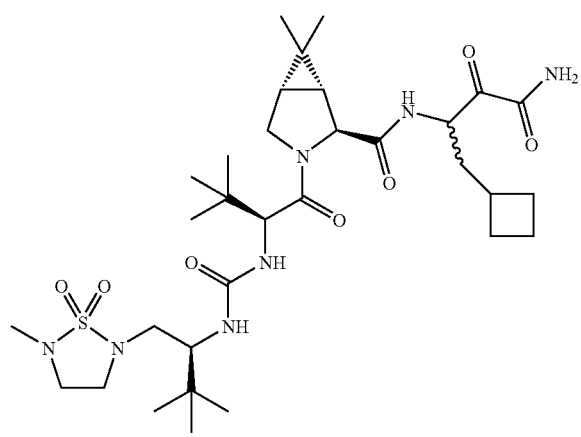
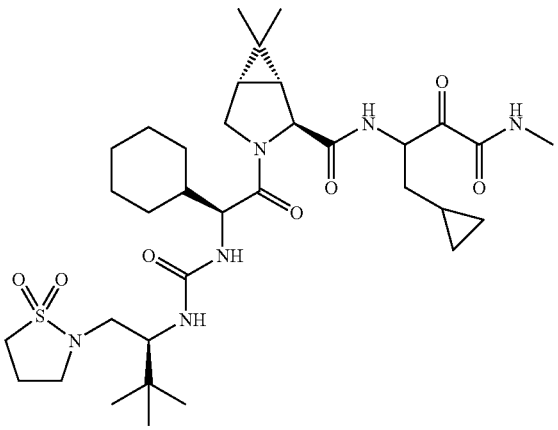
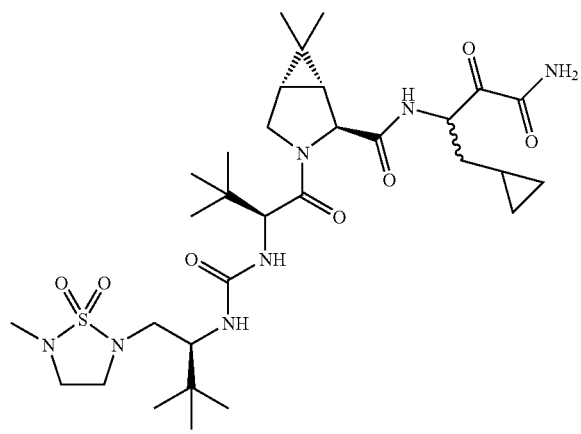
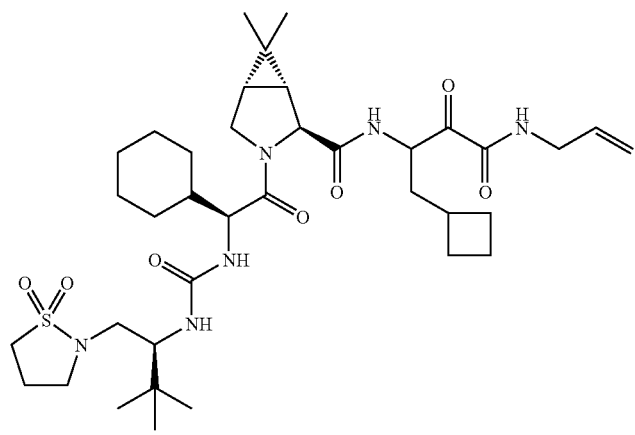

-continued
515
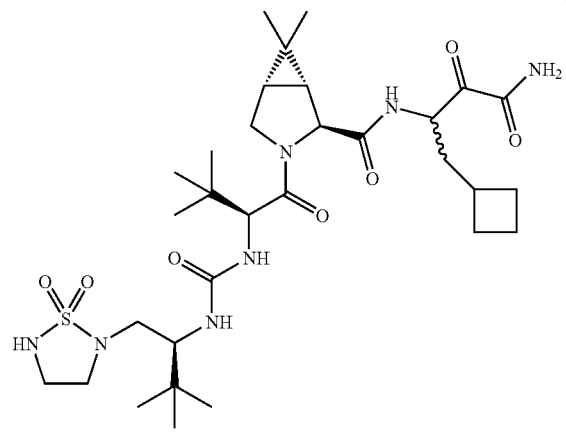
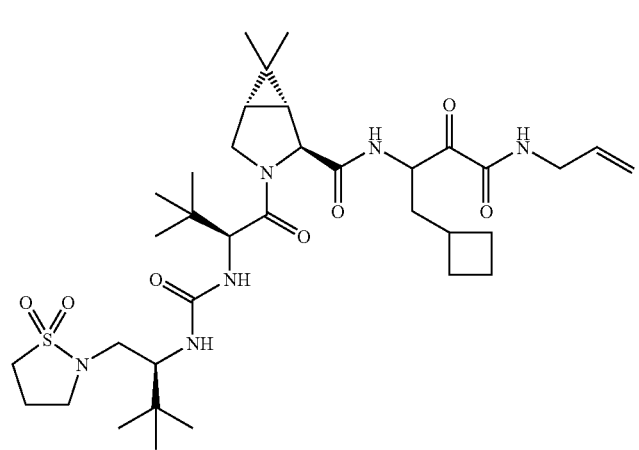
516
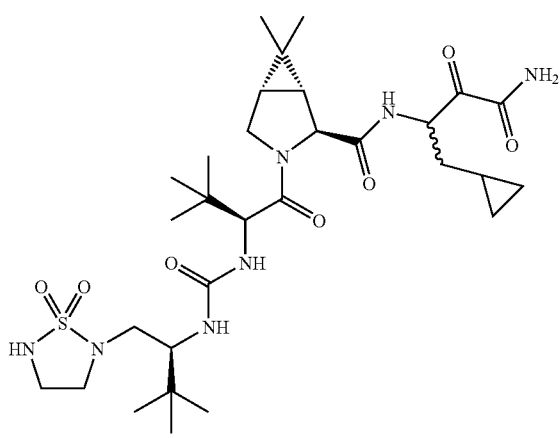
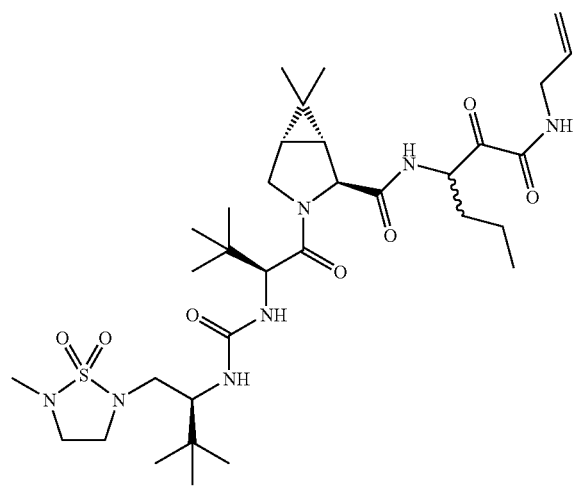

517
518
-continued
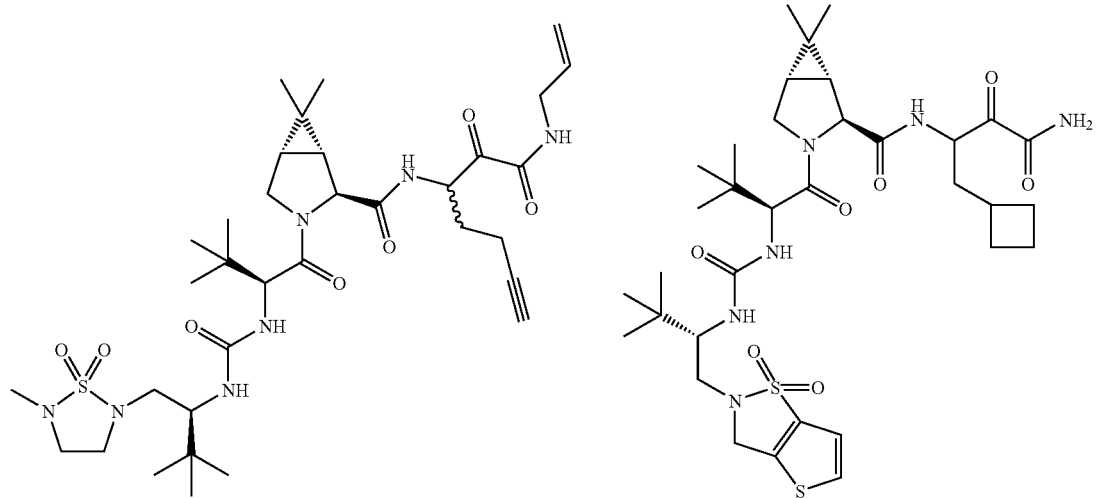
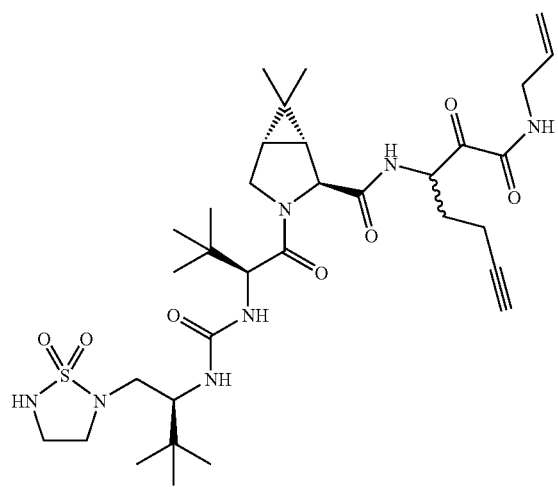
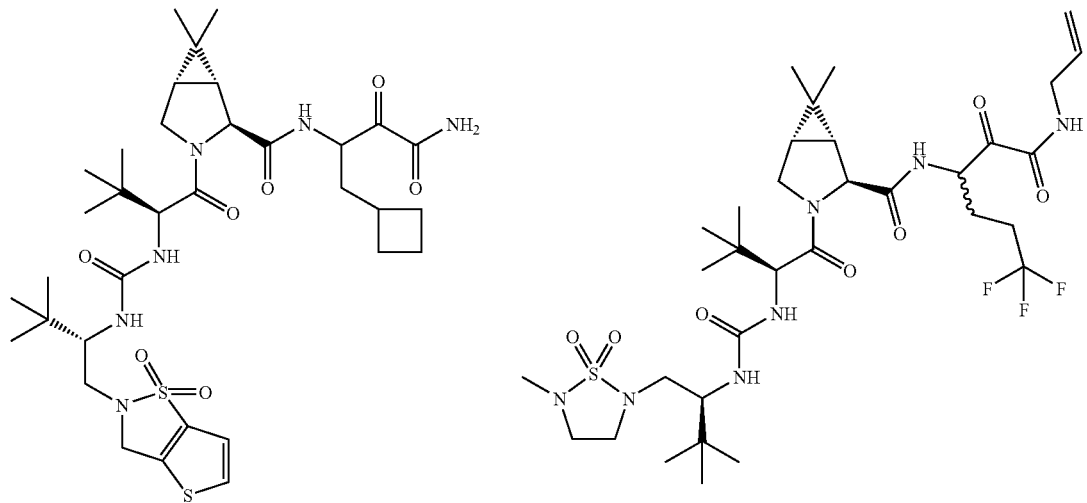

-continued
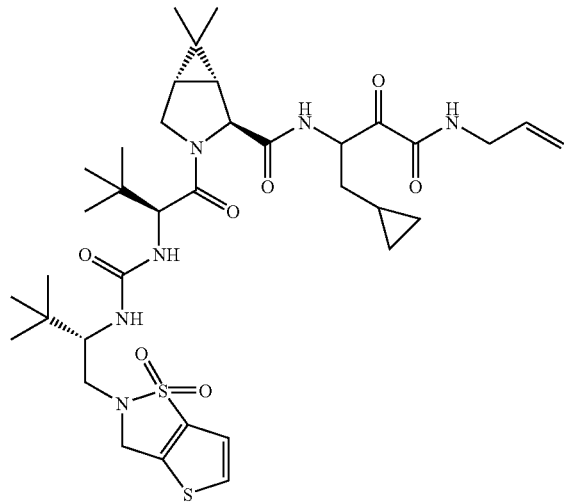
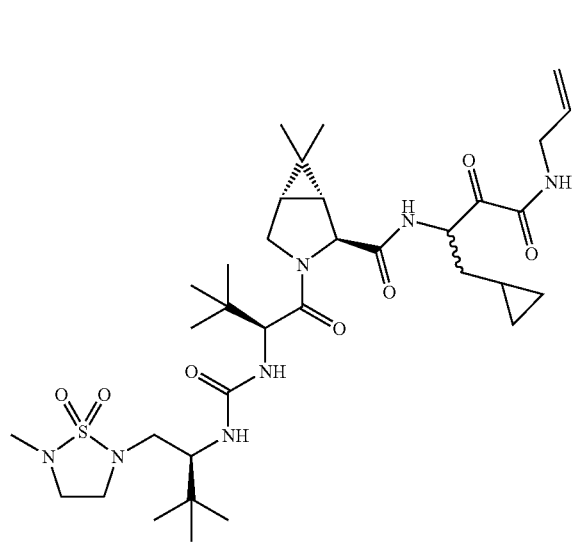
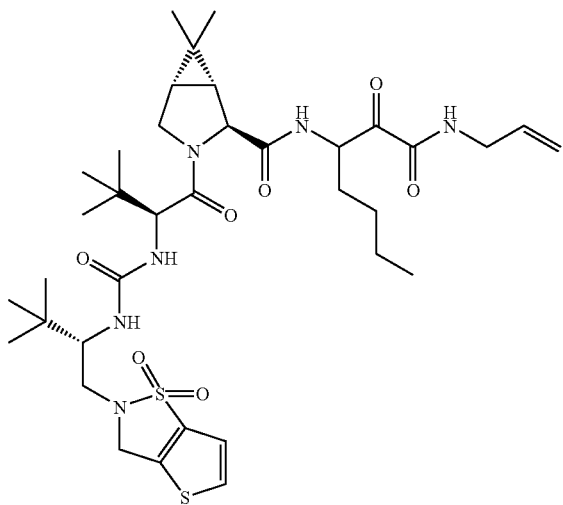
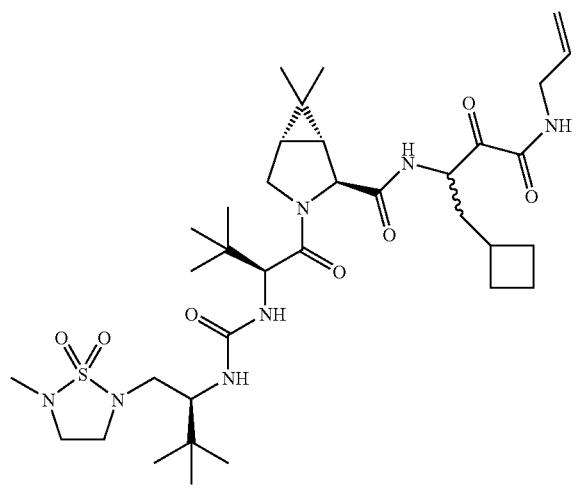

-continued
521
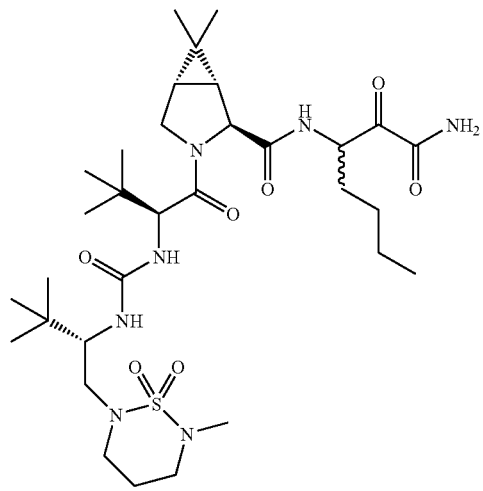
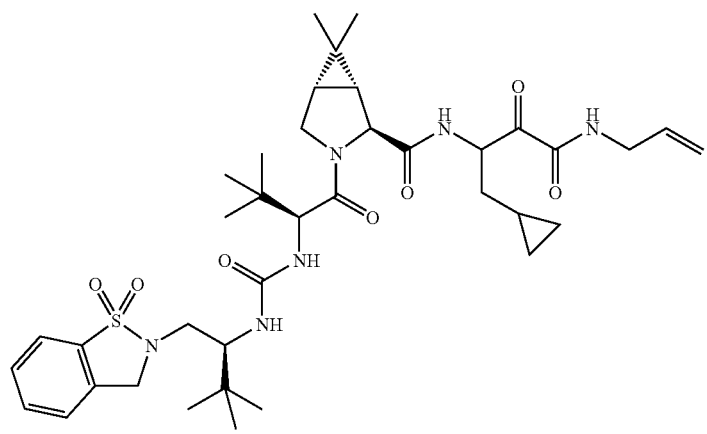
522
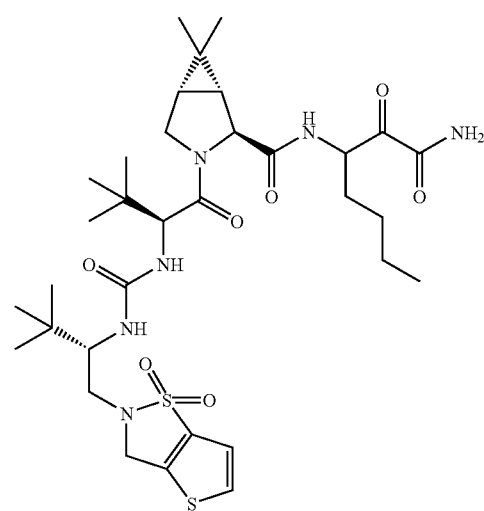
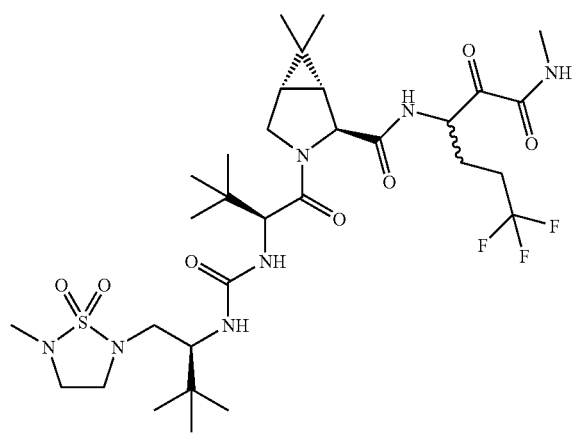

-continued
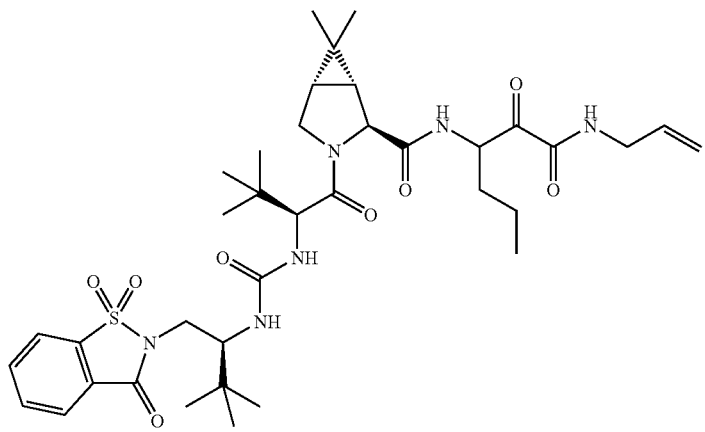
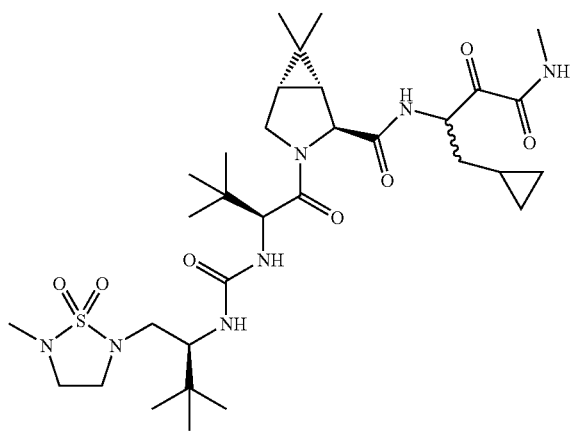
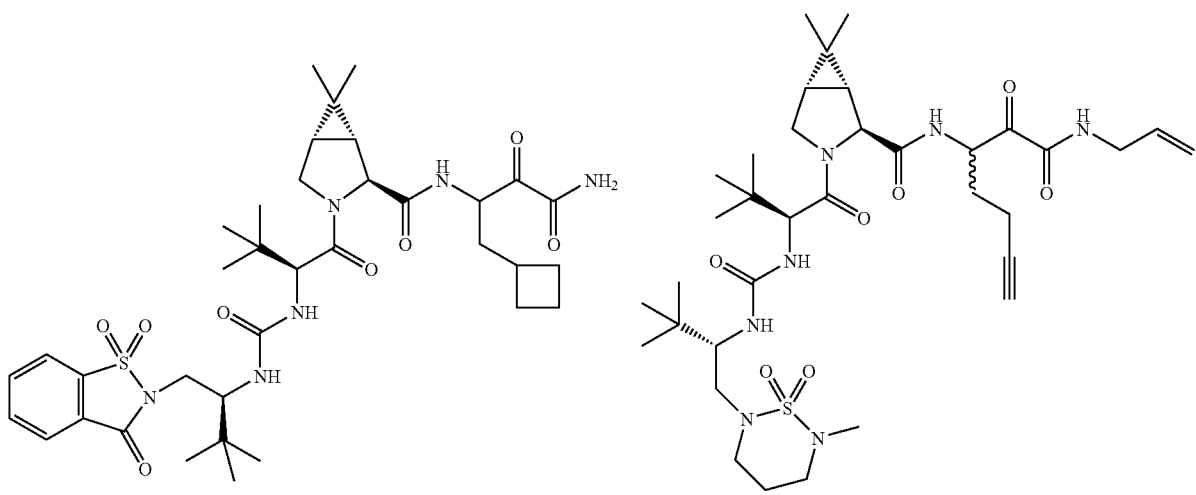

-continued
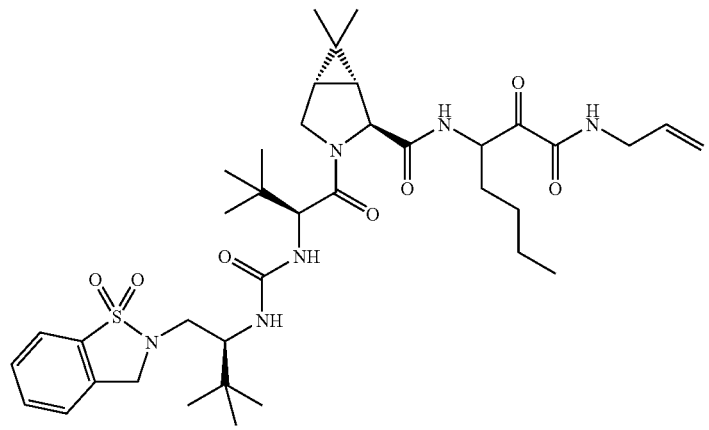
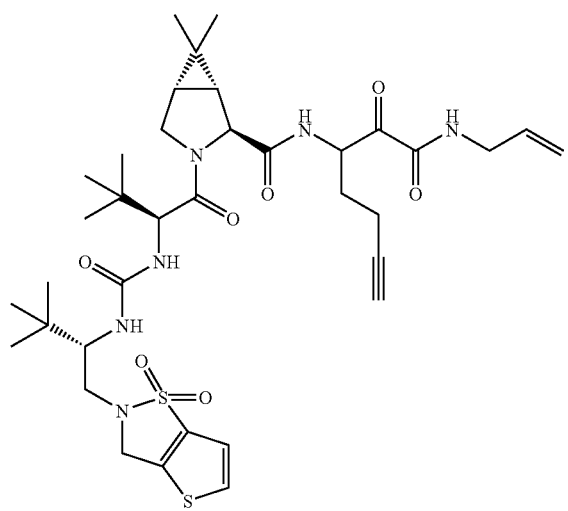
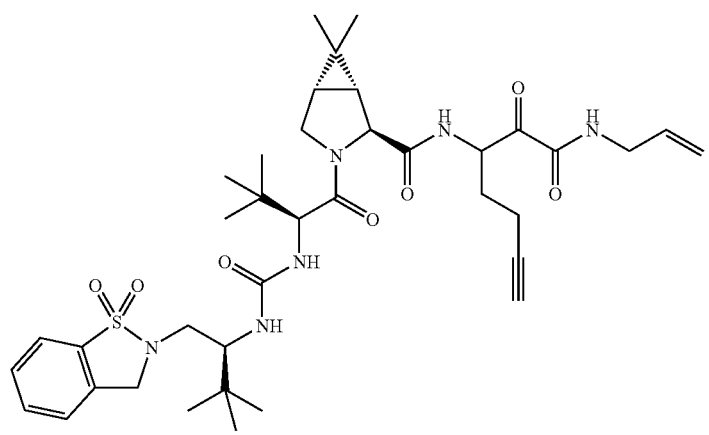

-continued
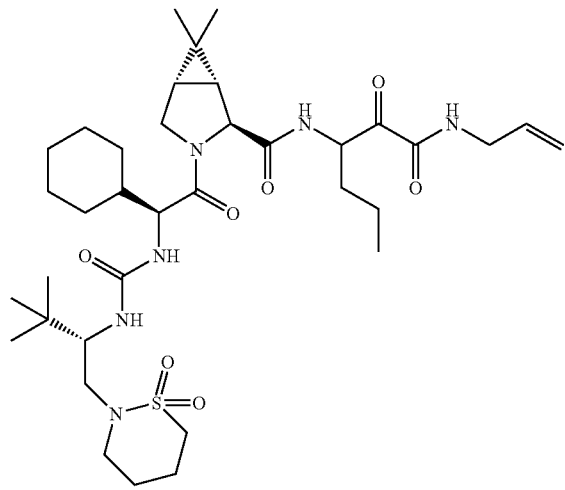
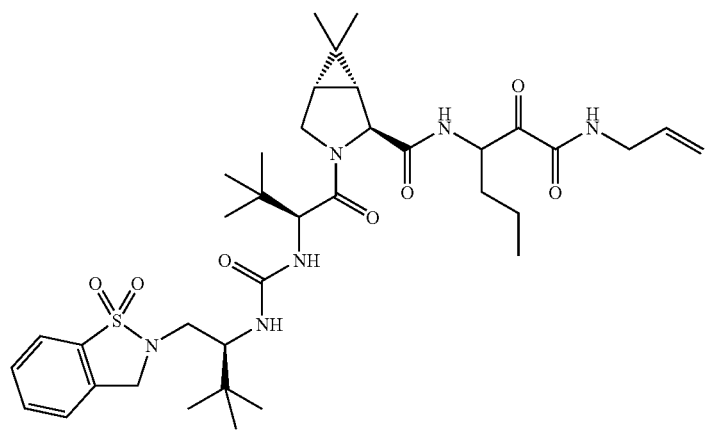
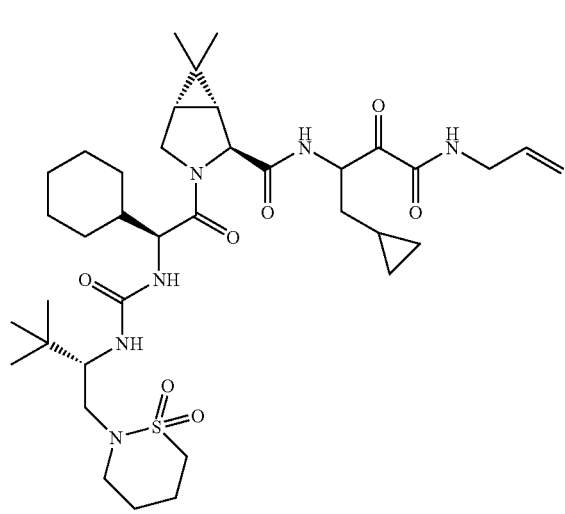
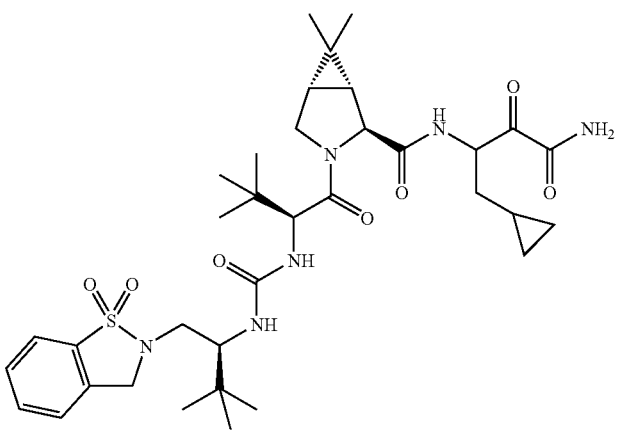

-continued
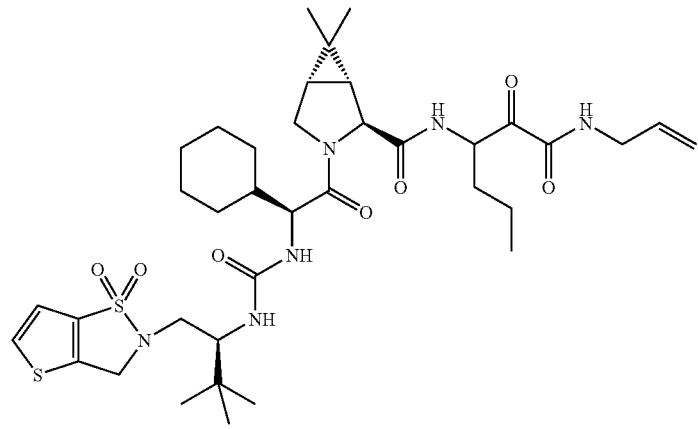
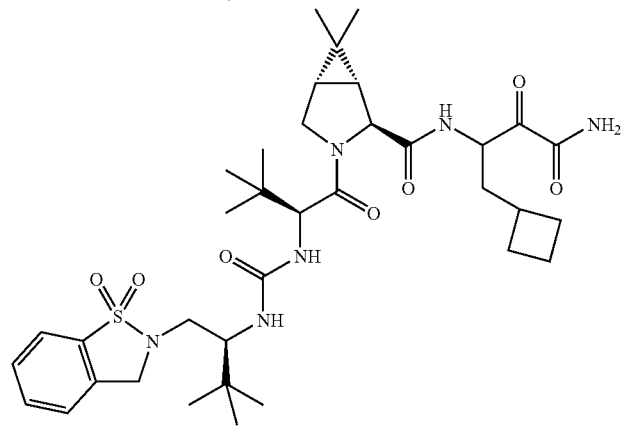
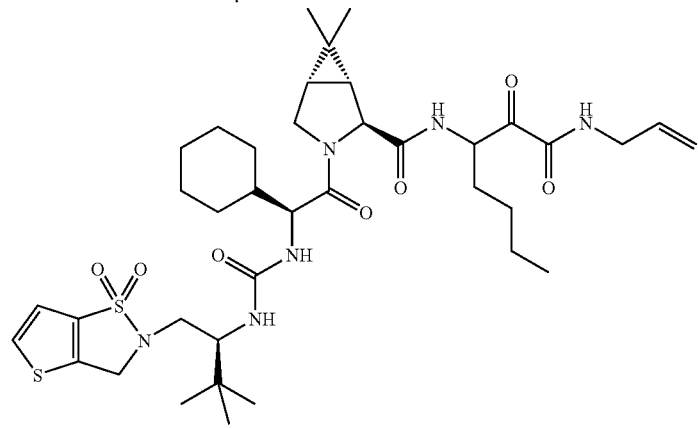
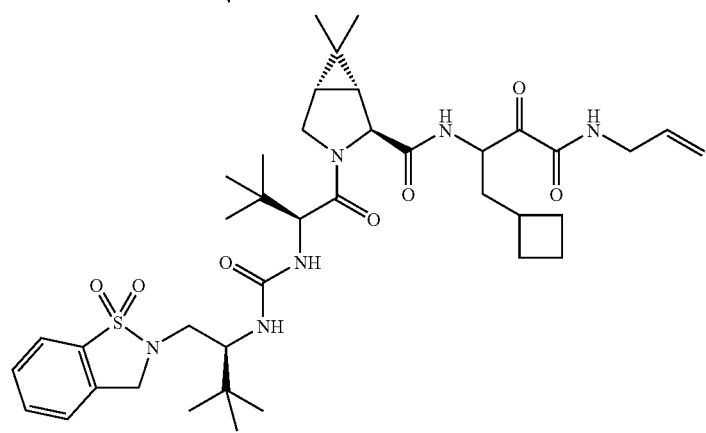

-continued
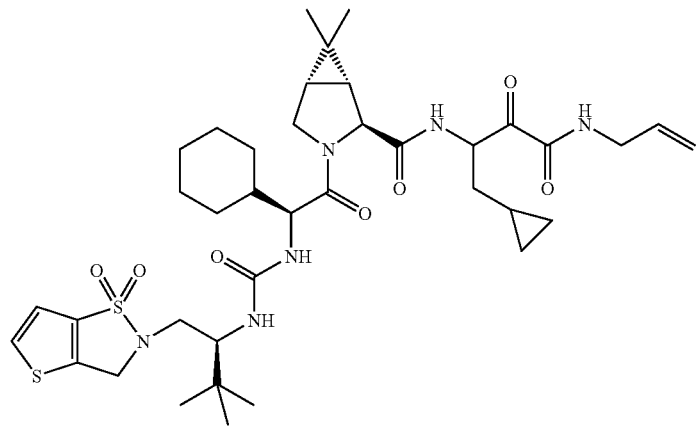
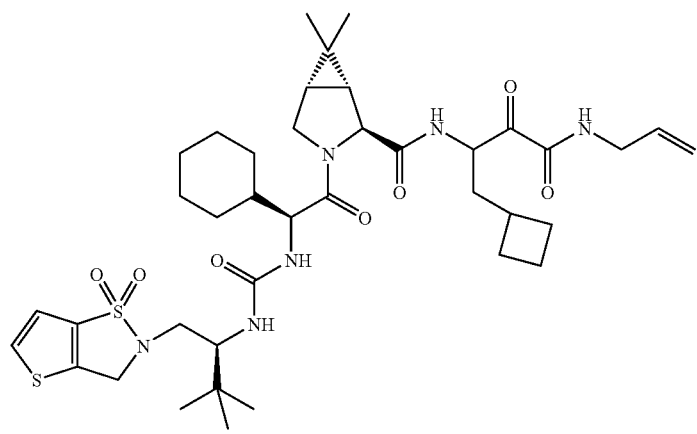
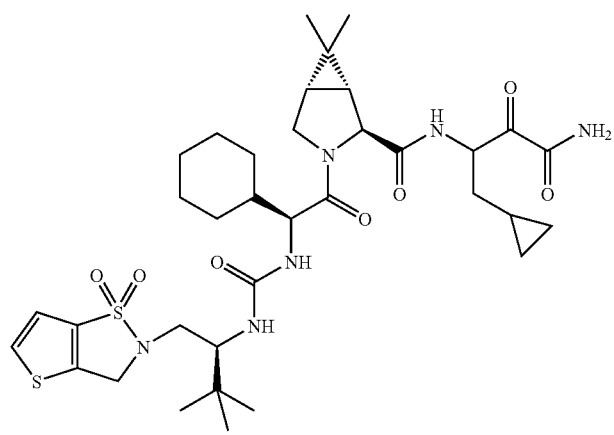

-continued
533
534
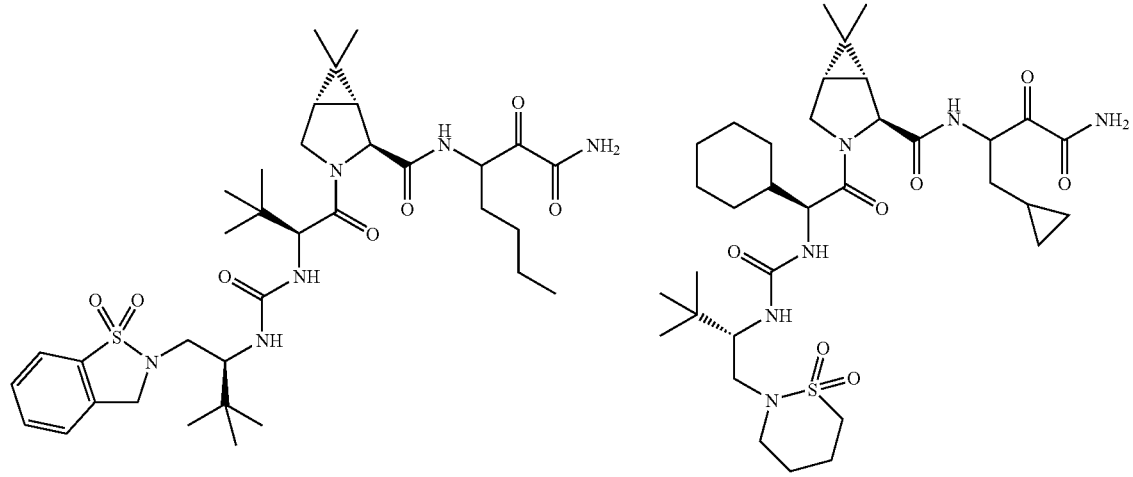
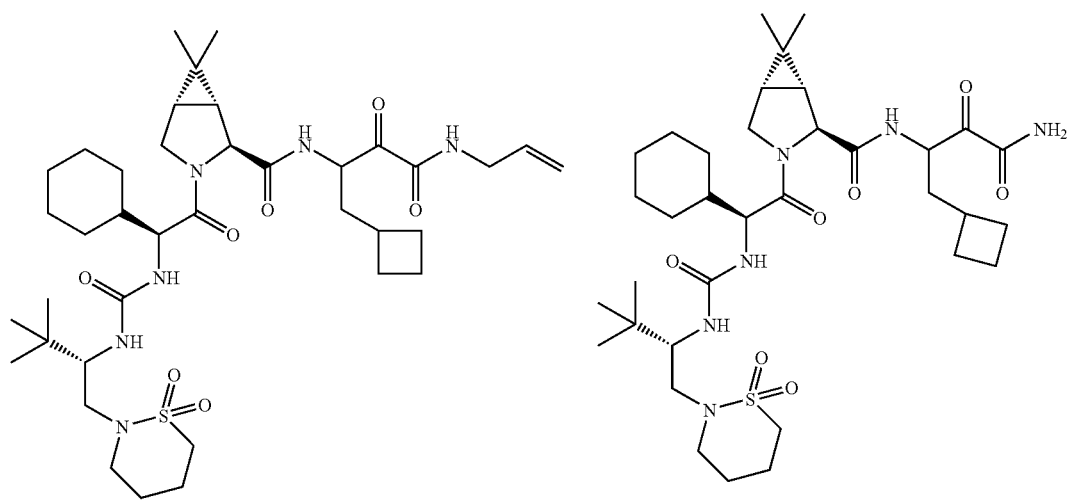
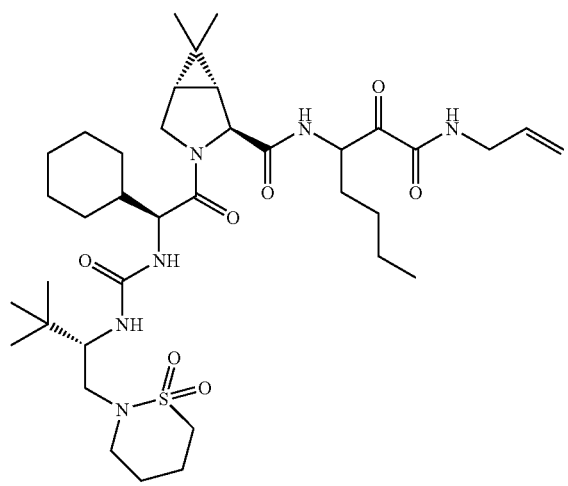

535
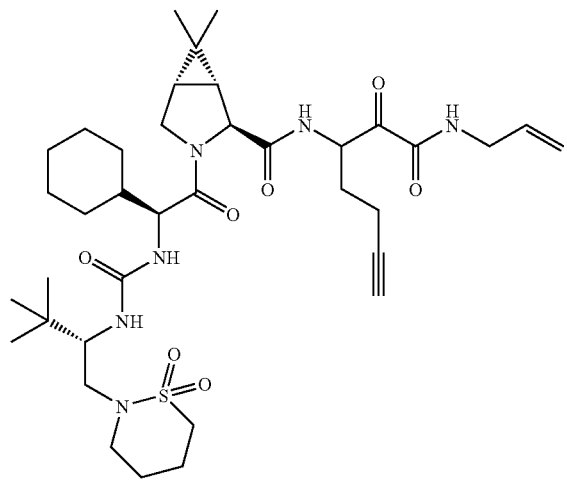
536
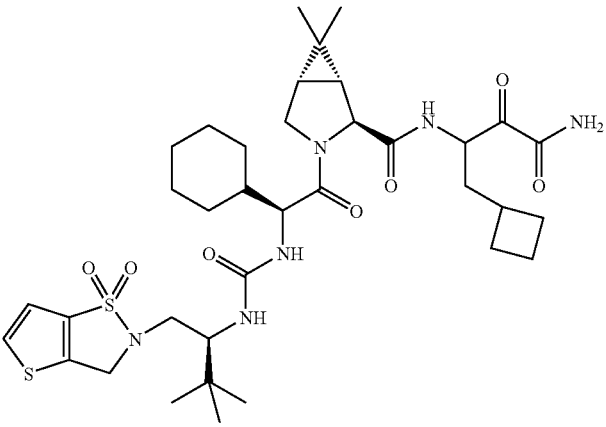
-continued
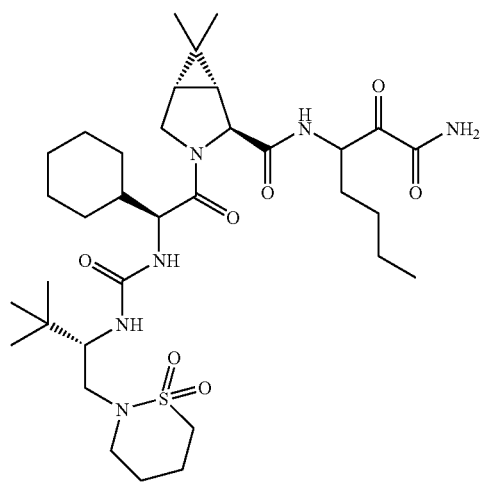
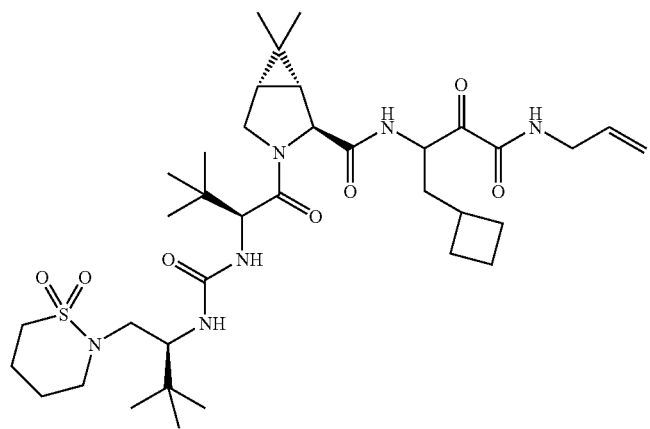

-continued
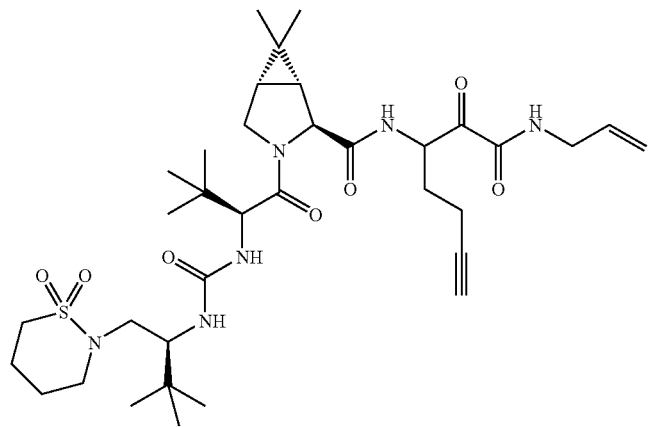
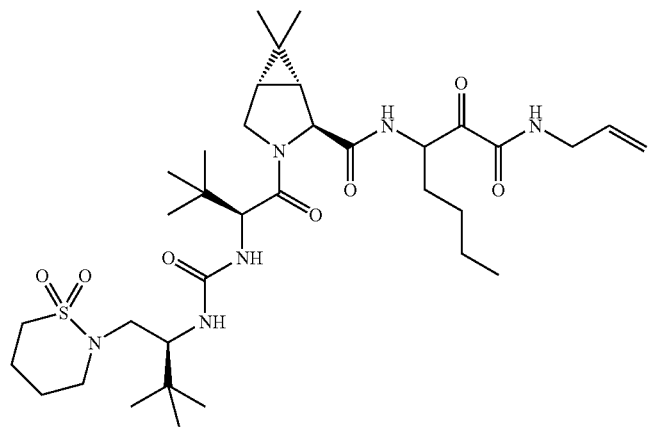
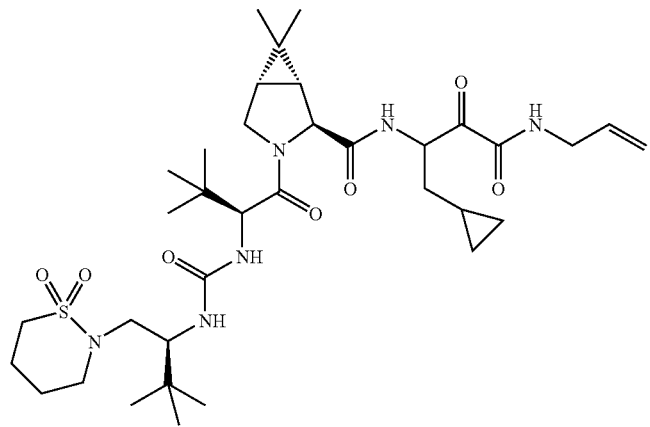

539 540
-continued
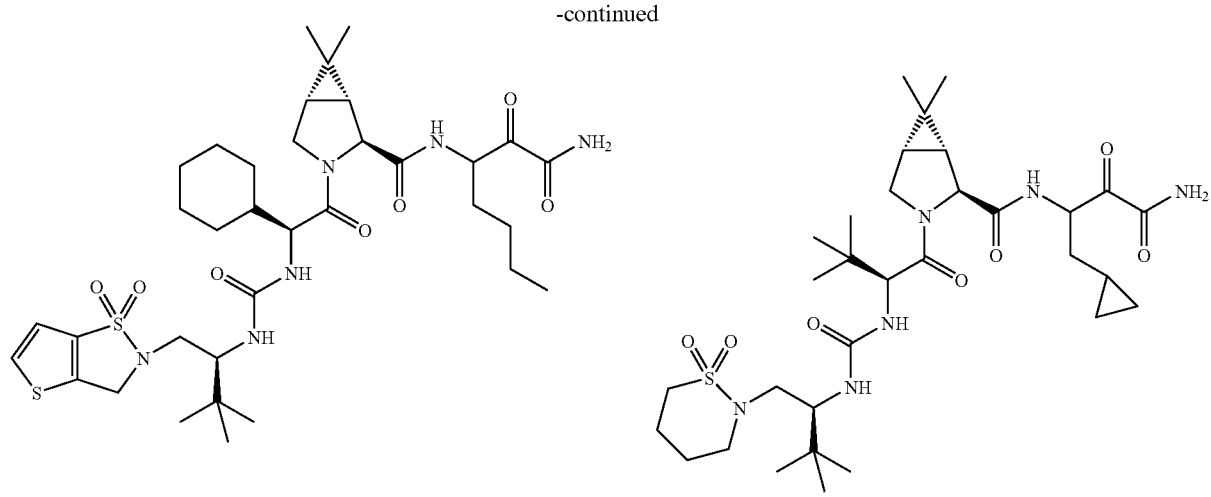
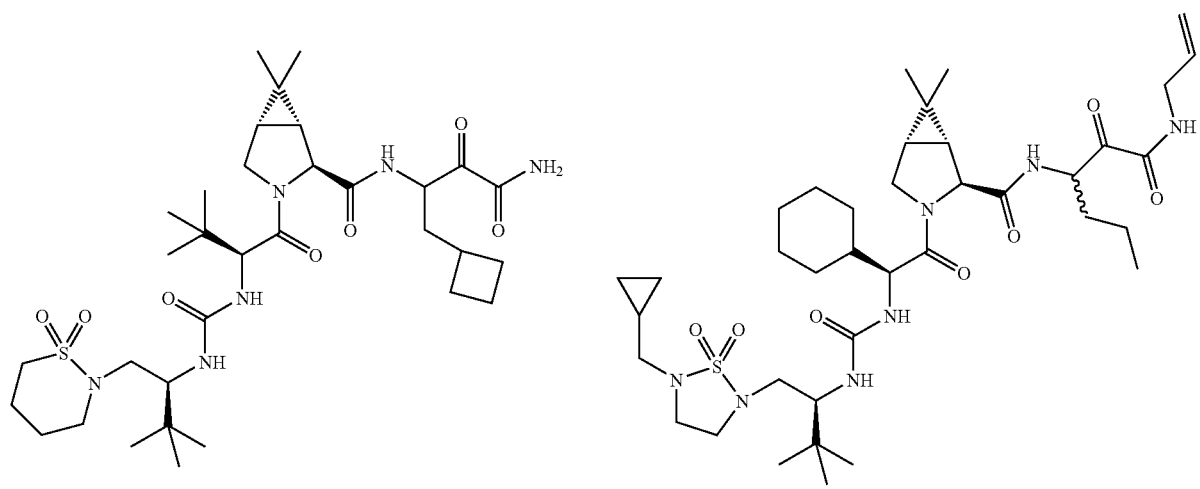
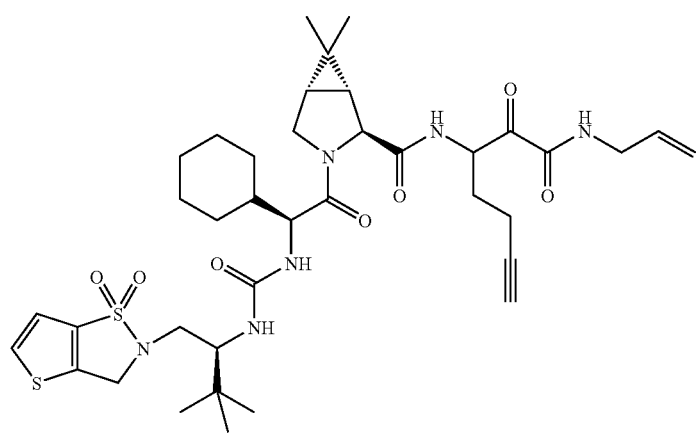

-continued
541
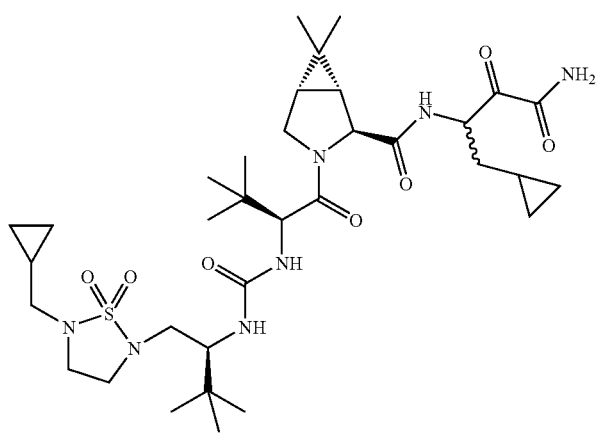
542
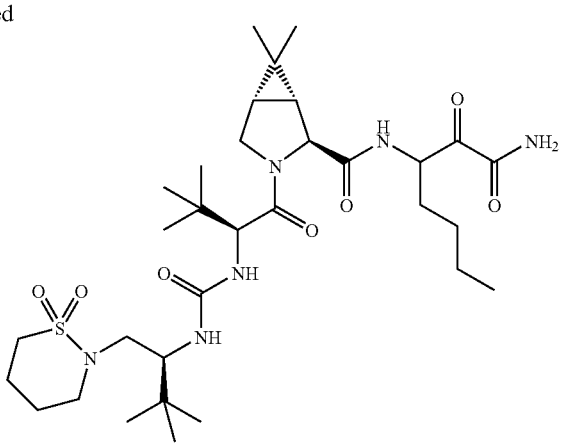
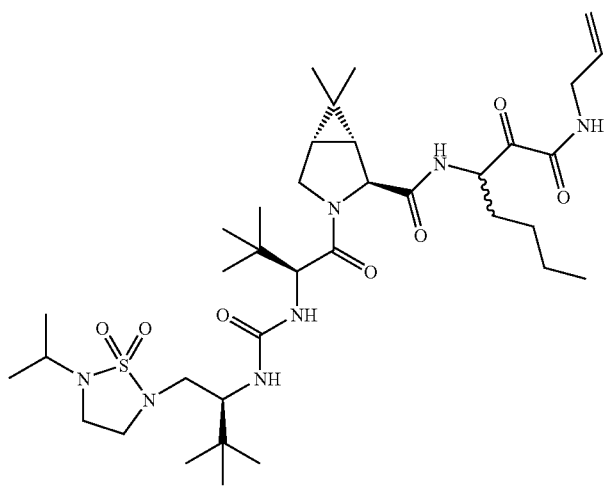
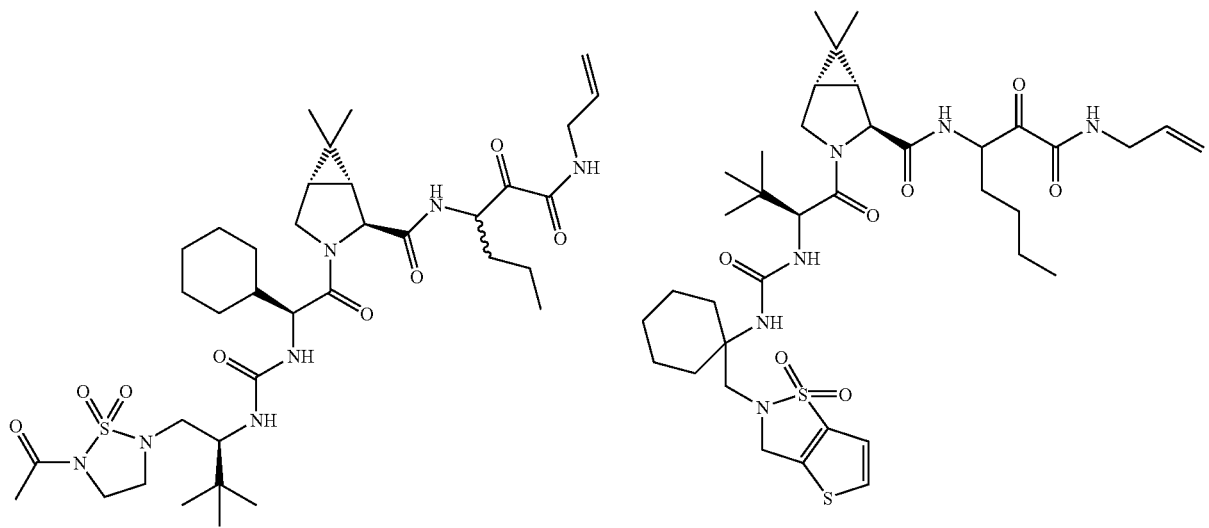

543
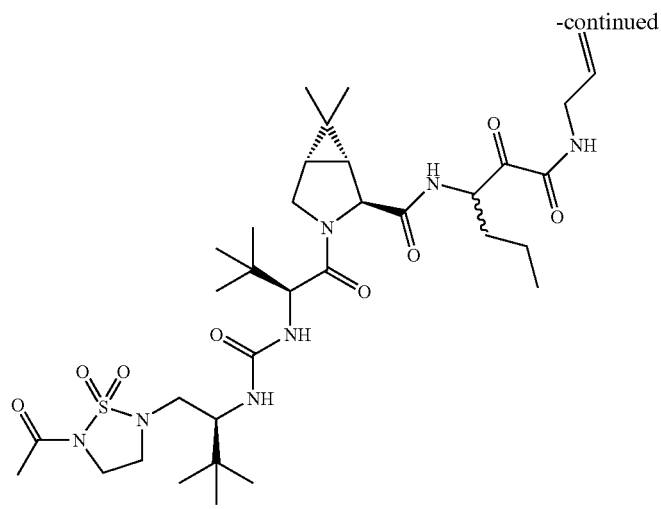
-continued
544
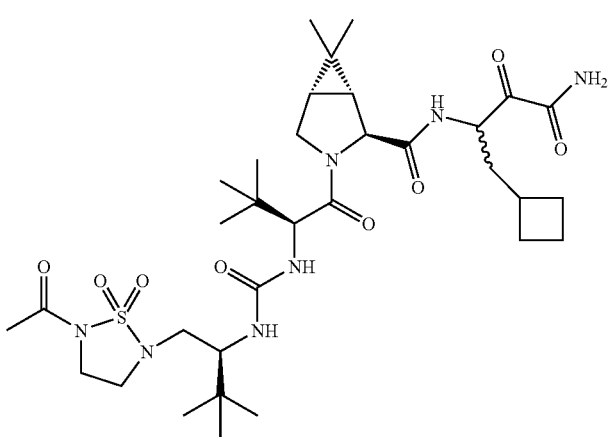
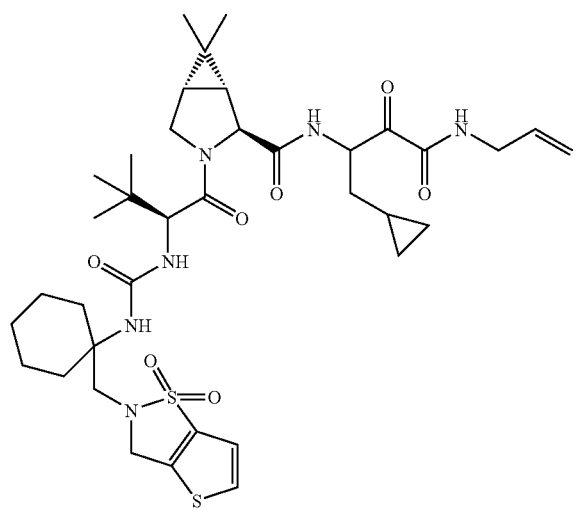
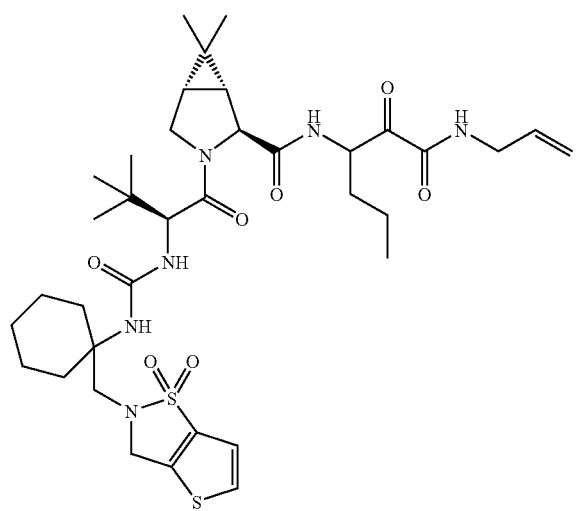

545 546
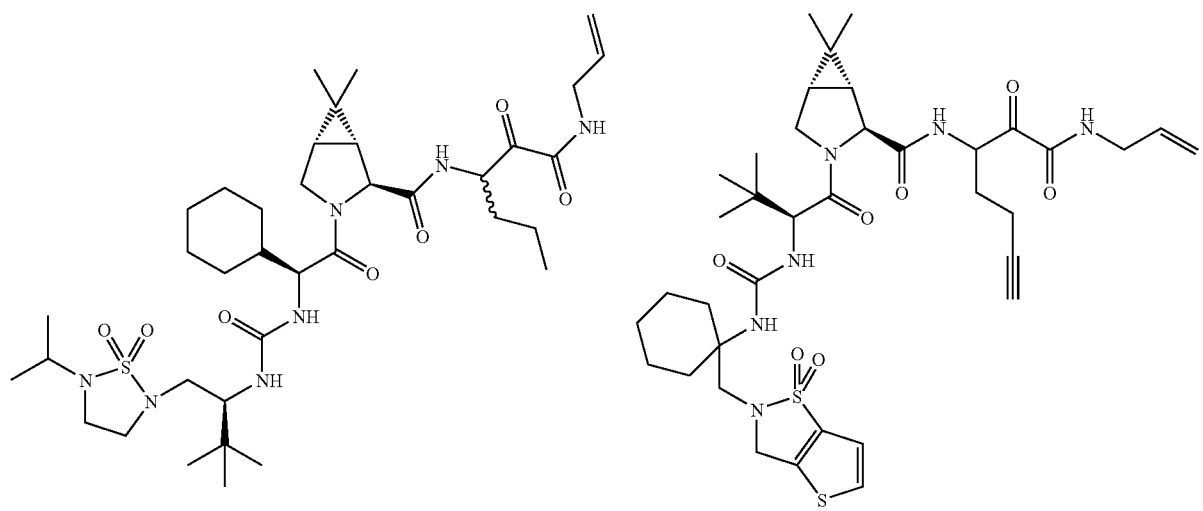
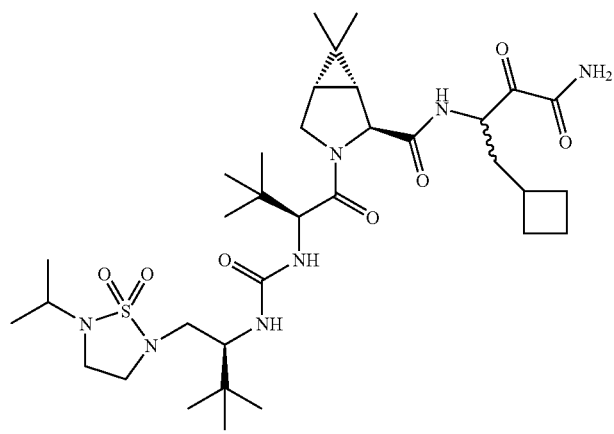
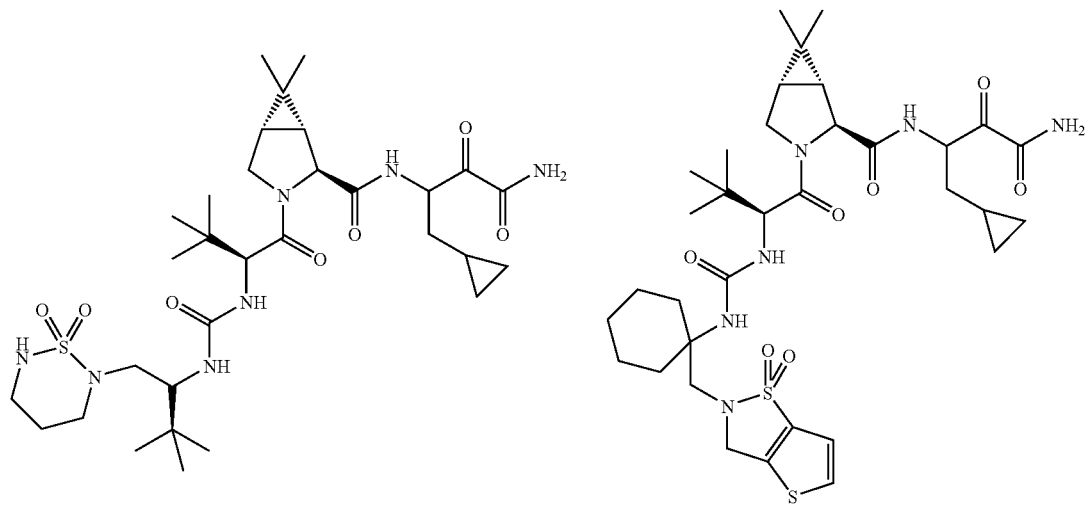

-continued
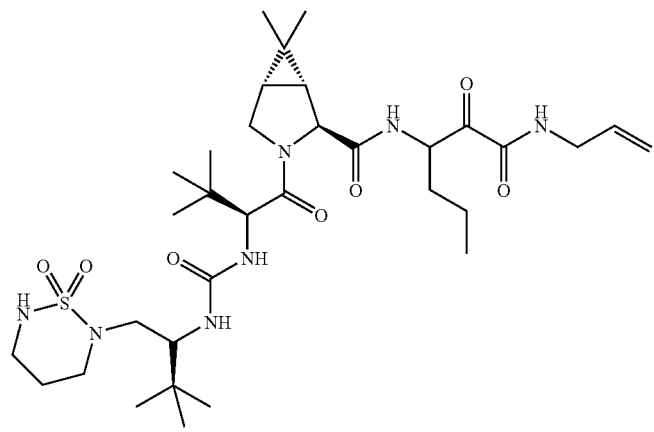
547
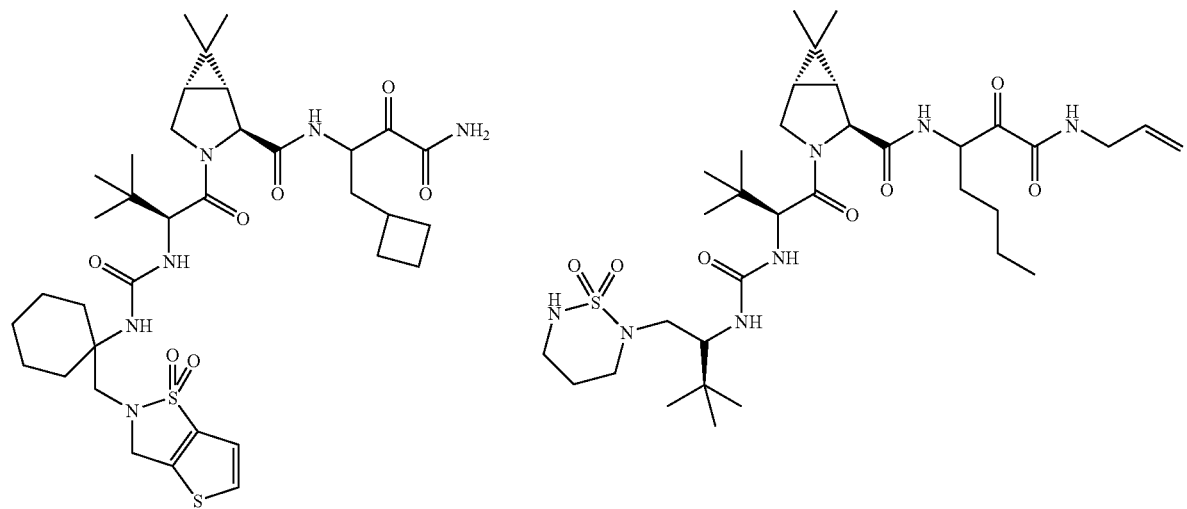
548
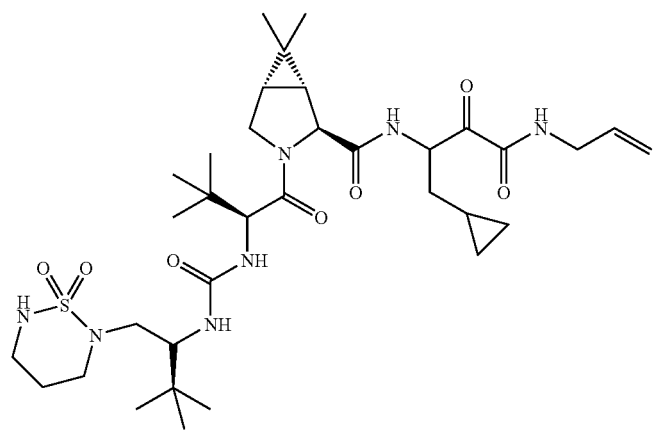

| 549 | 550 |
|---|---|
-continued
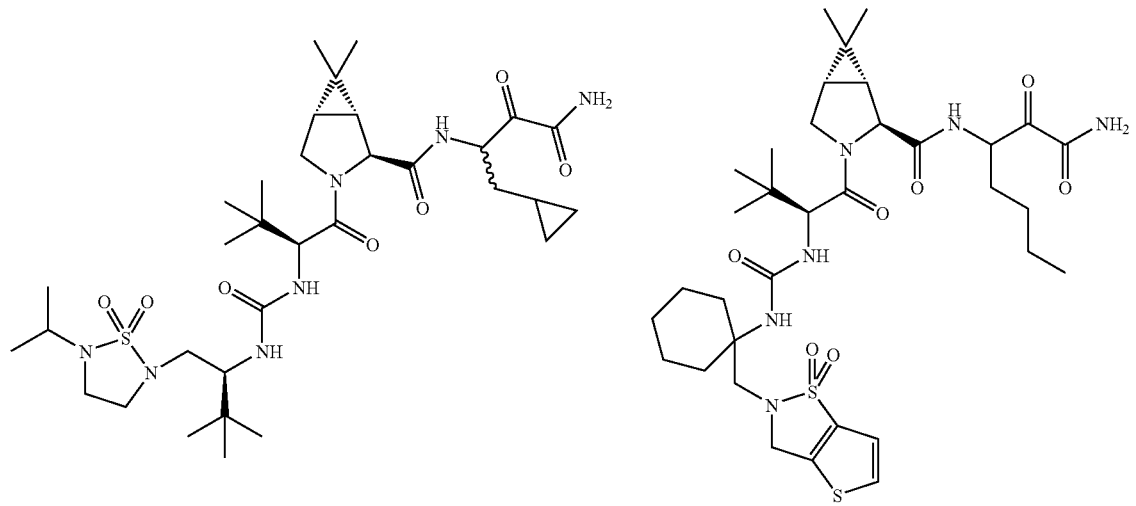
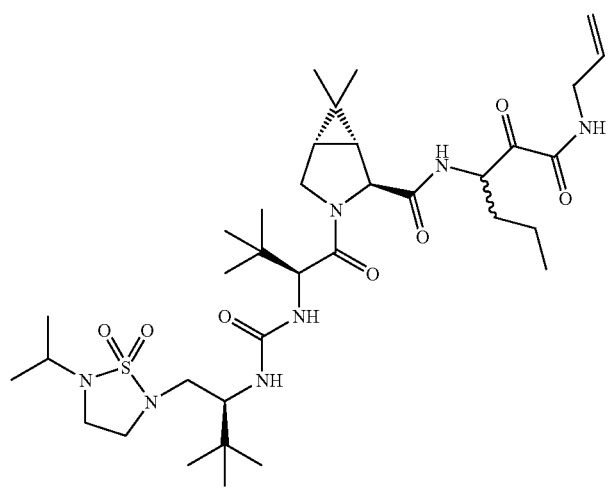
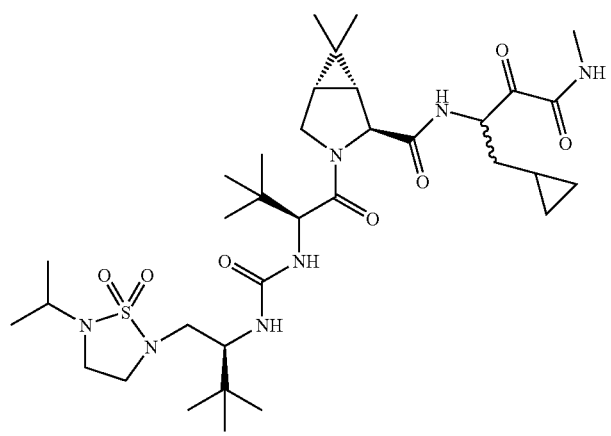

551
552
-continued
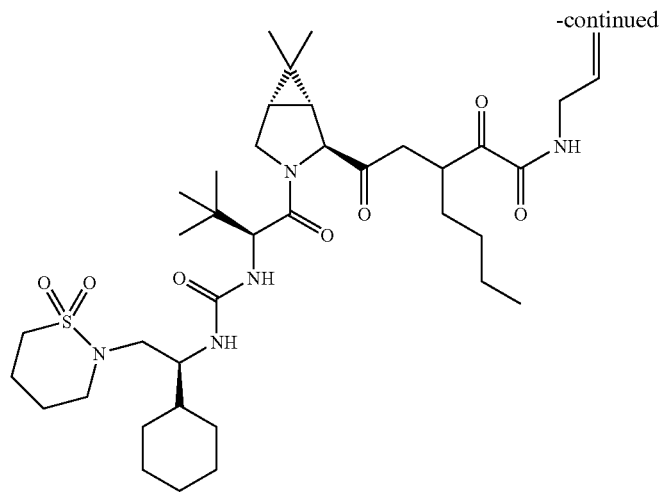
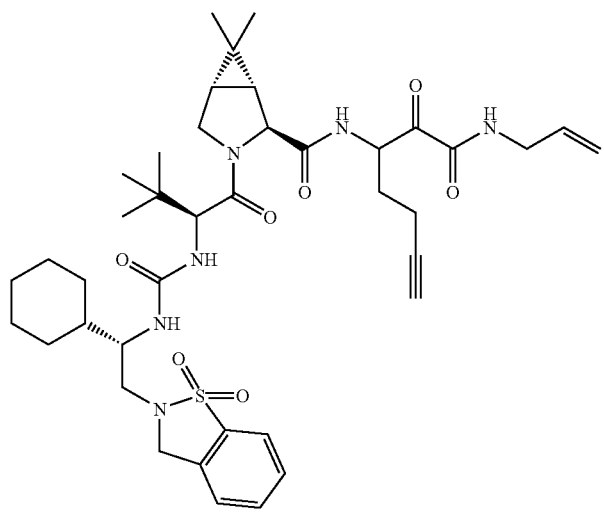
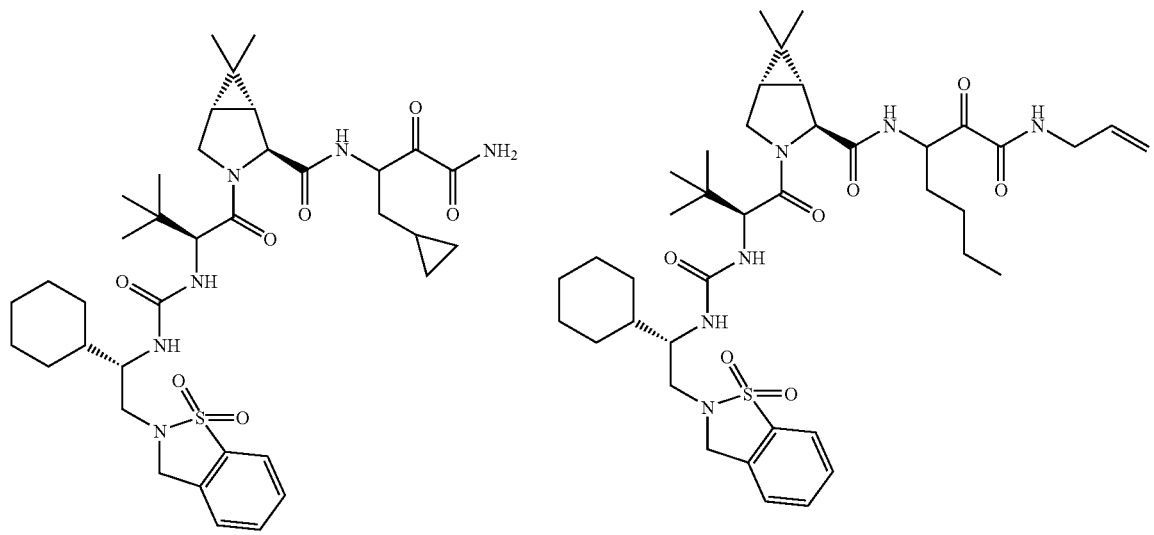

-continued
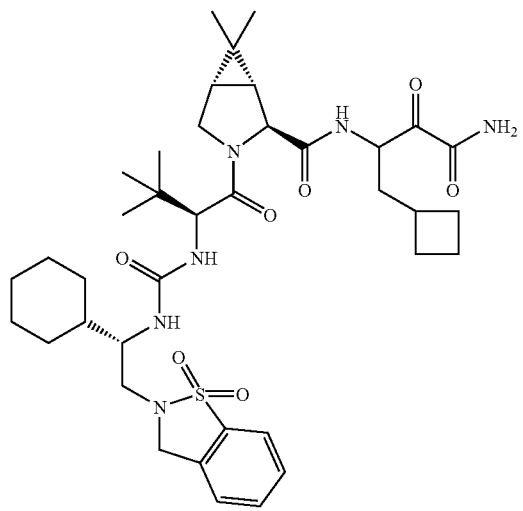
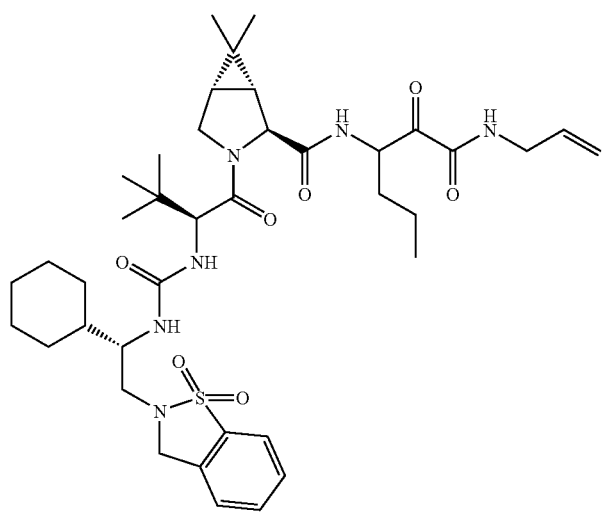
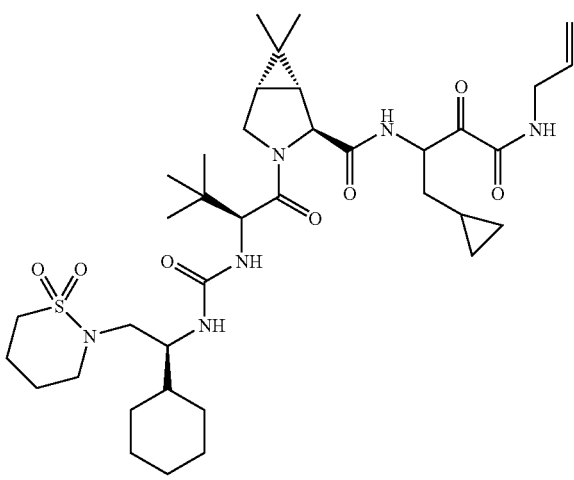
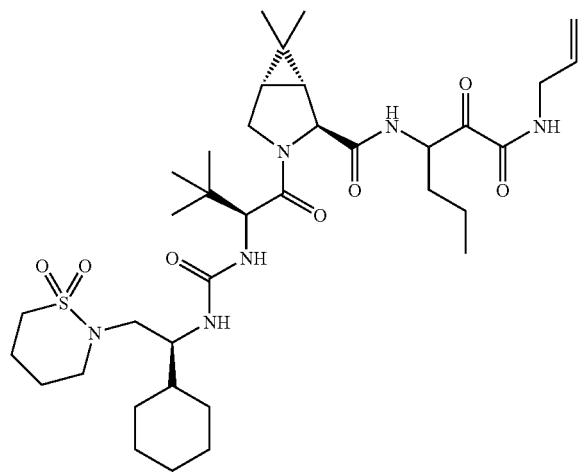

555 556
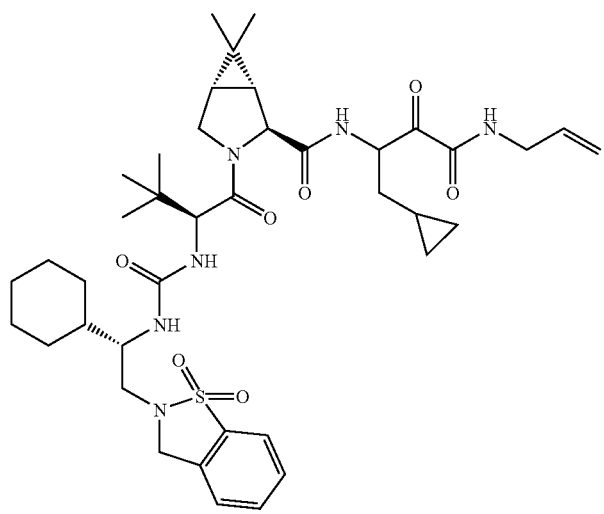 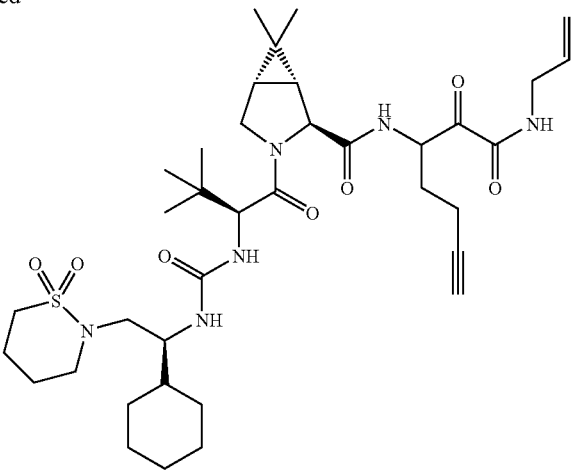
-continued
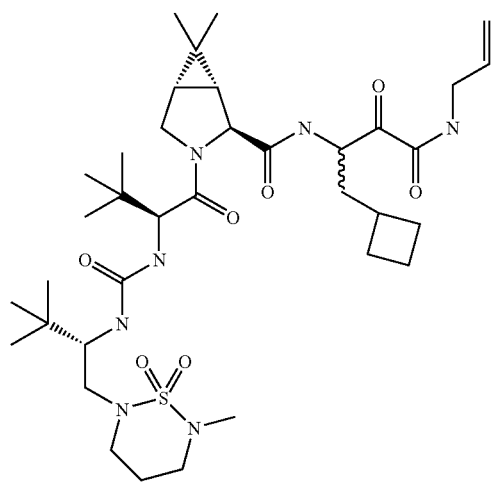
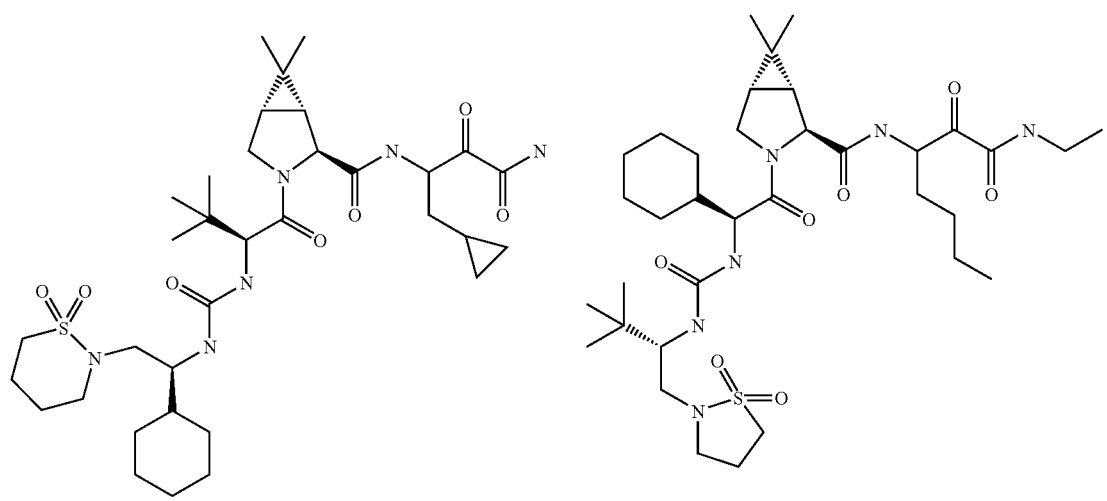

-continued
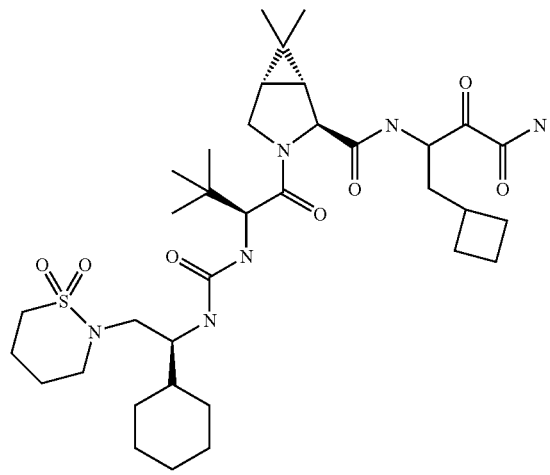
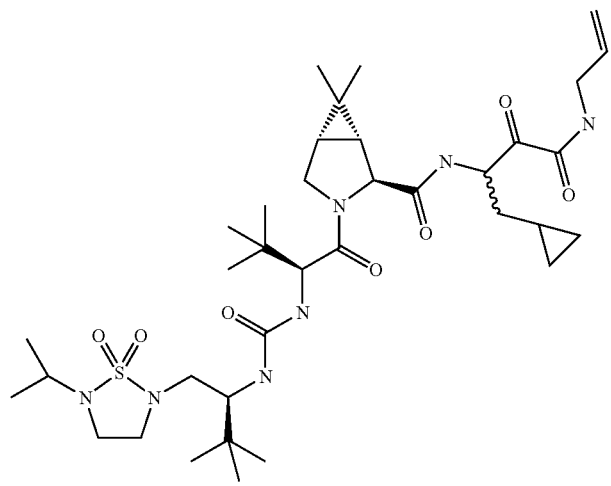
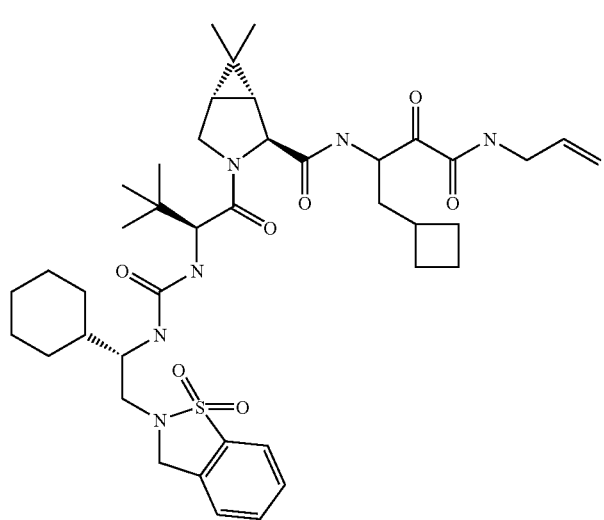
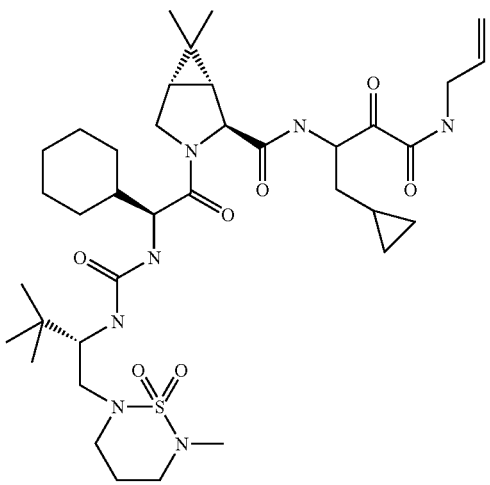

| 559 | 560 |
|---|---|
| 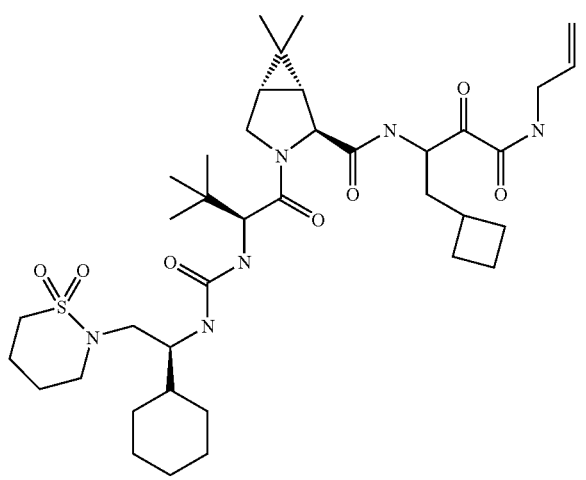 | 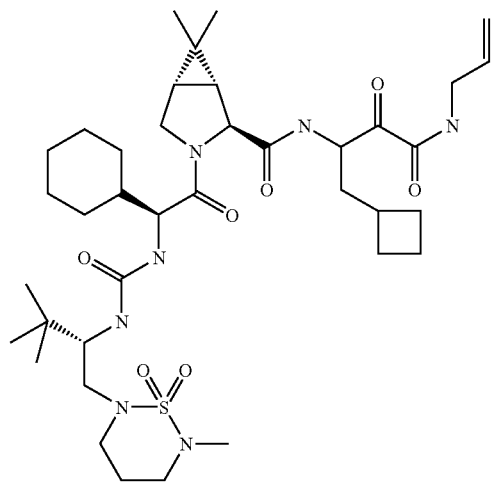 |
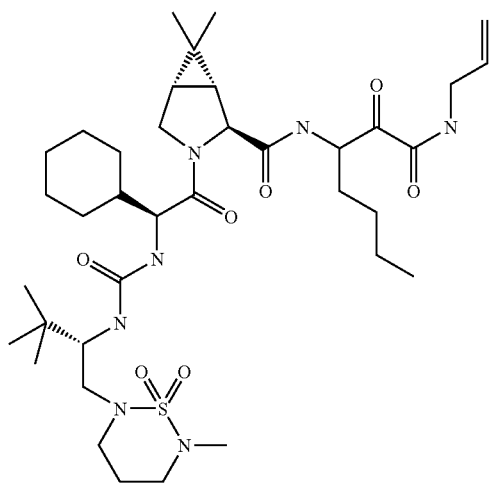
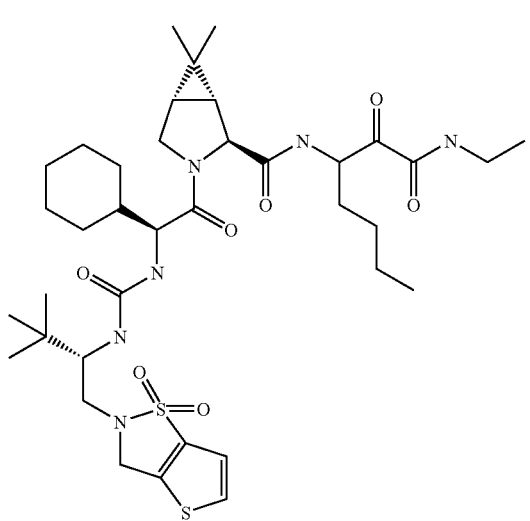
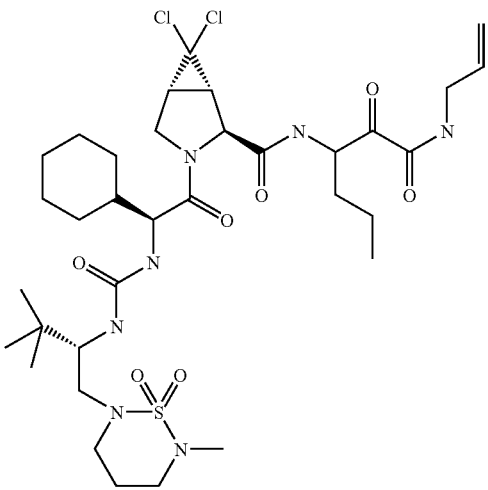

561
562
-continued
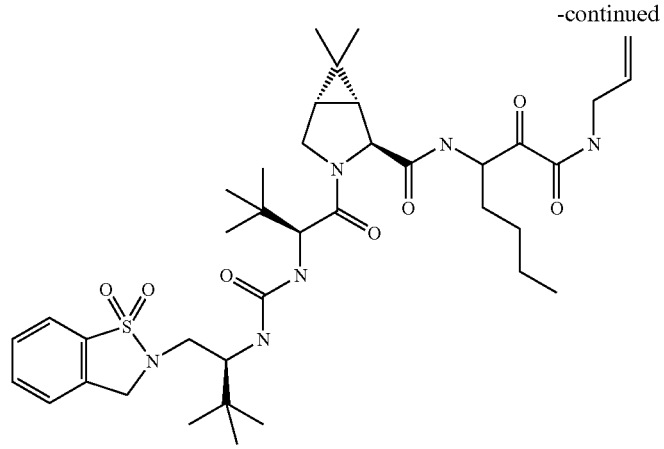
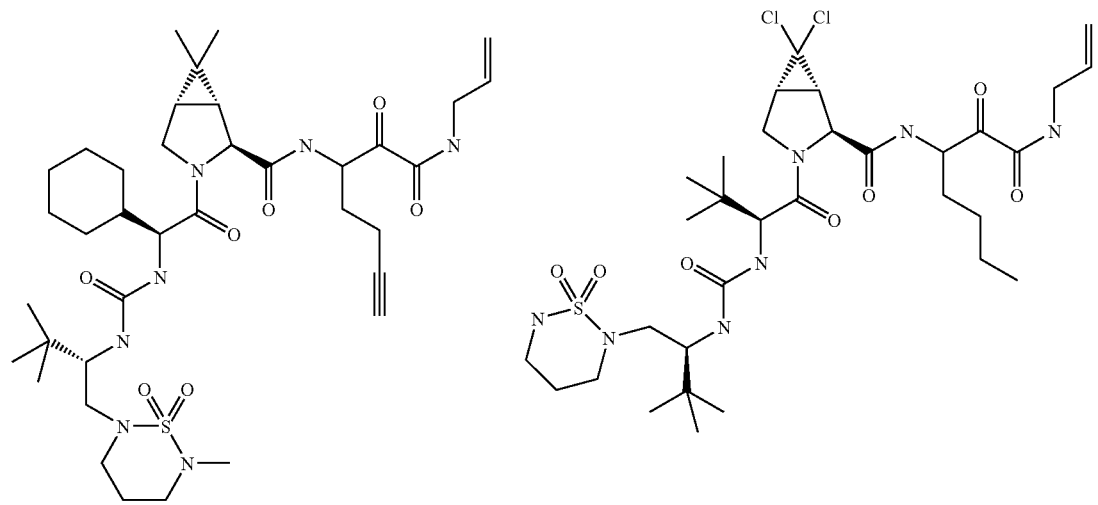
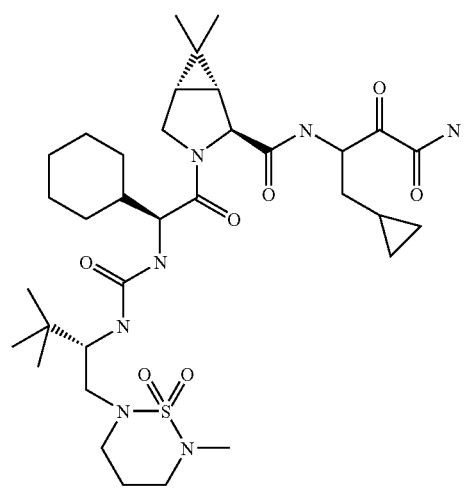

563
564
-continued
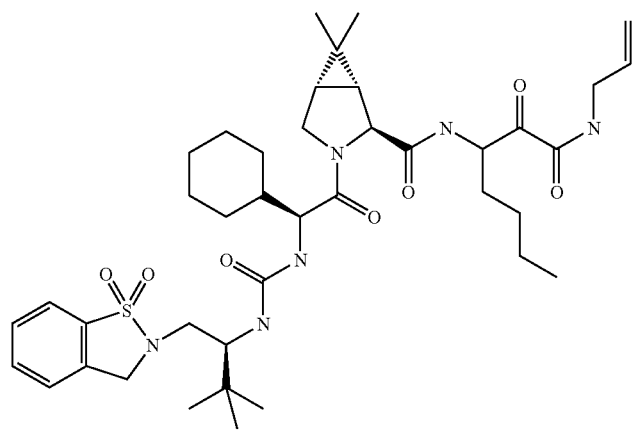
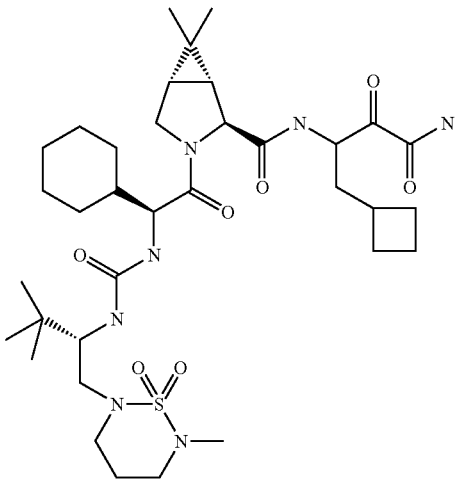
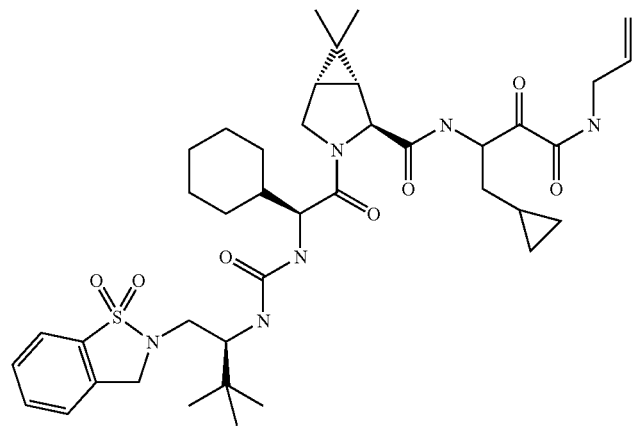
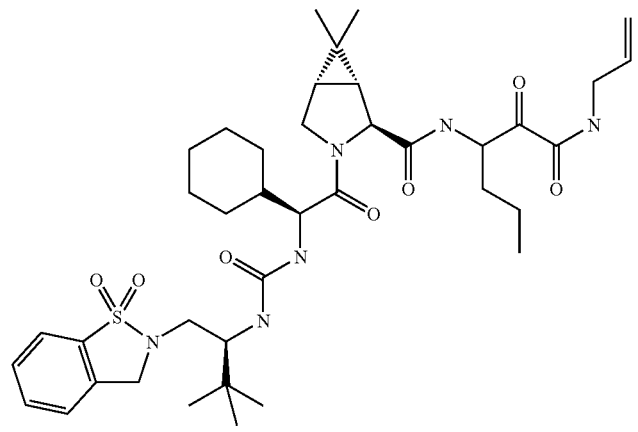

-continued
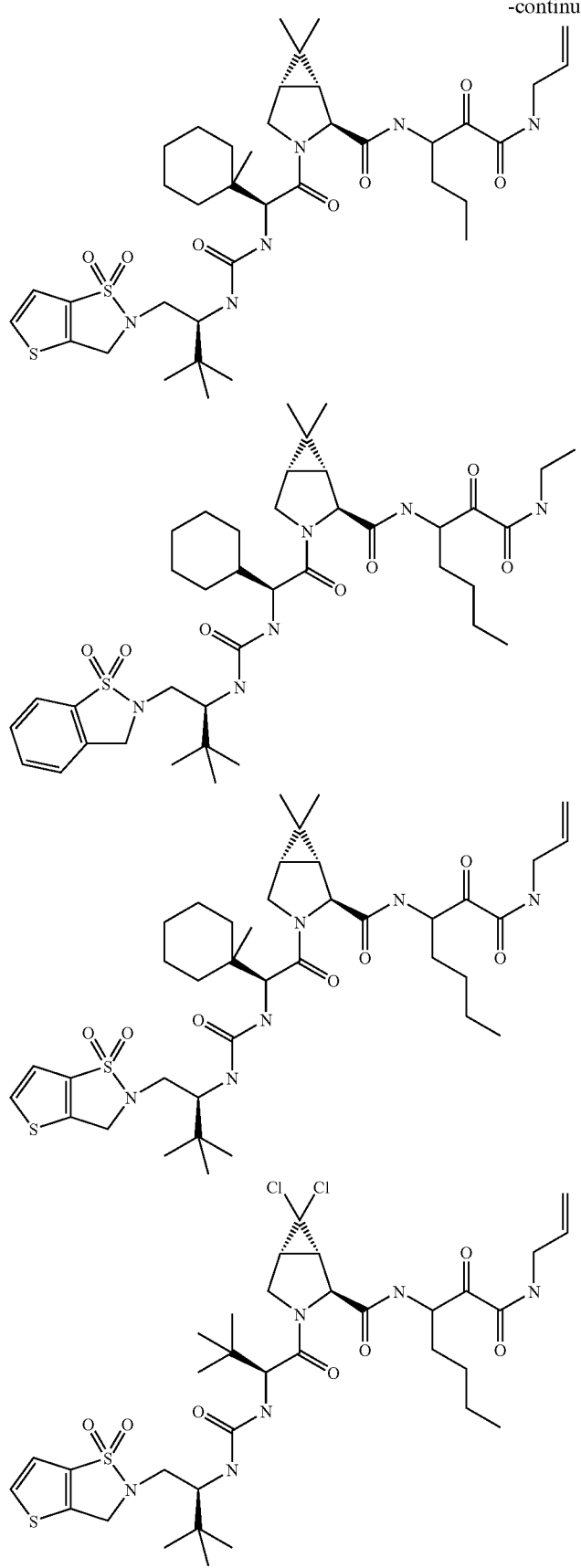

-continued
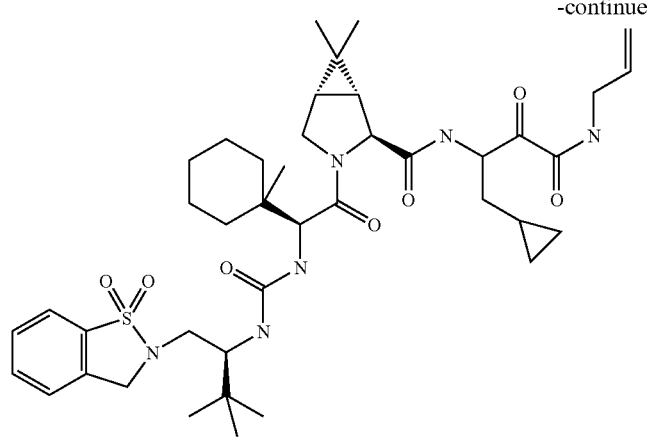
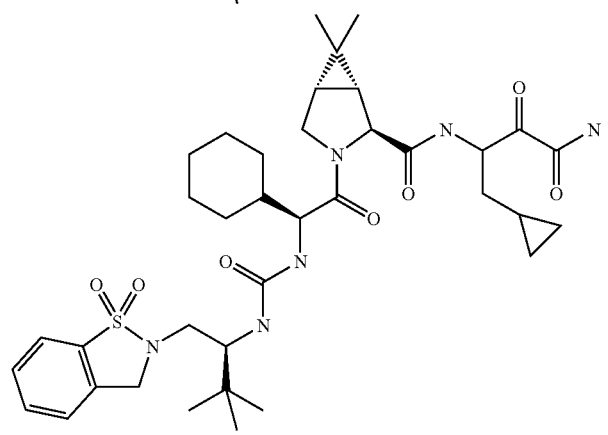
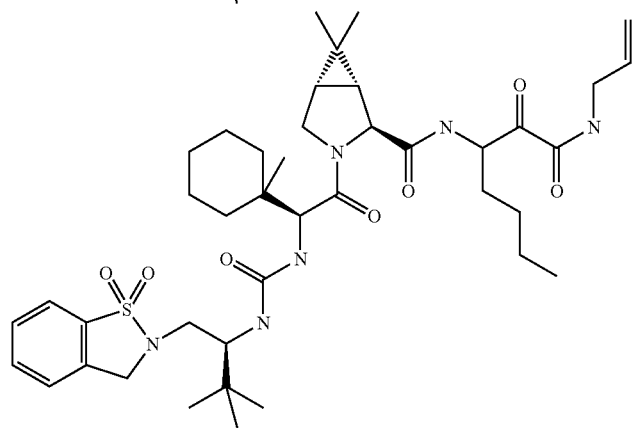
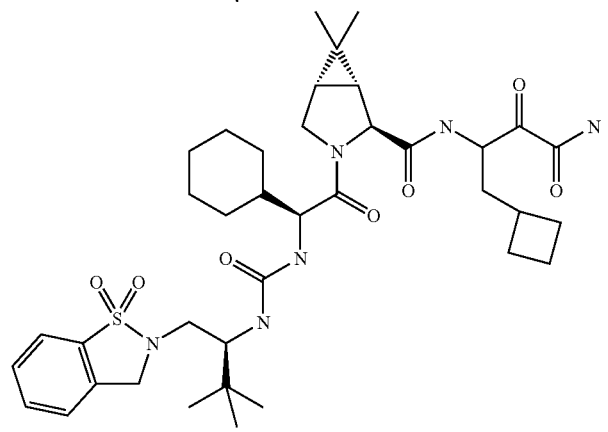

569
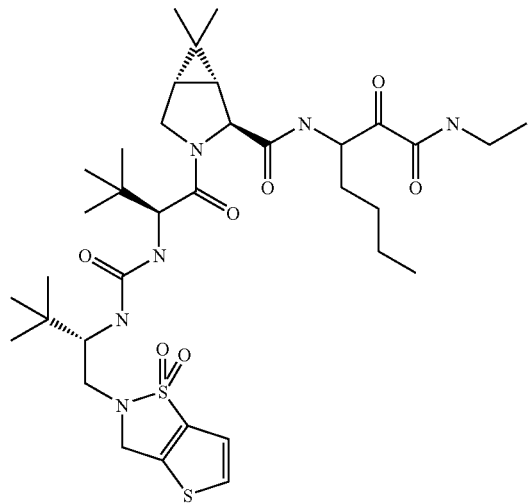
570
-continued
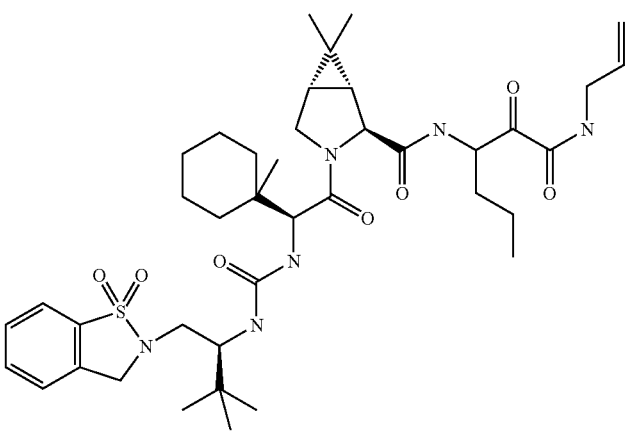
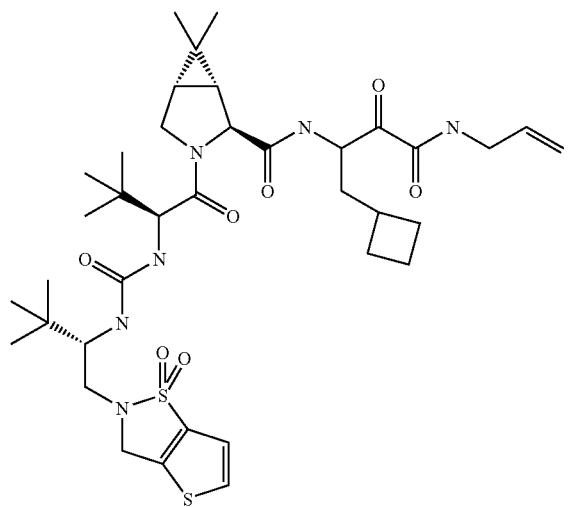
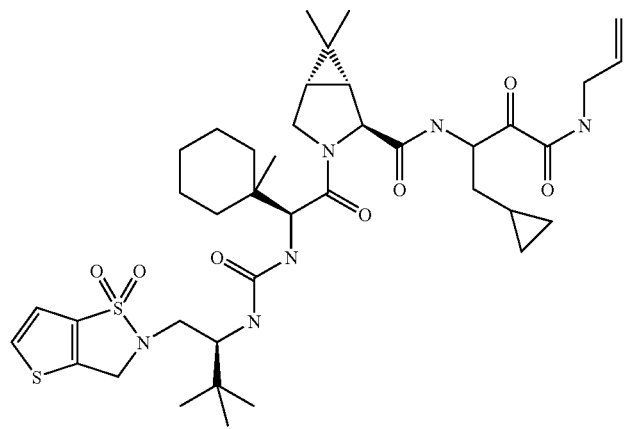

571
-continued
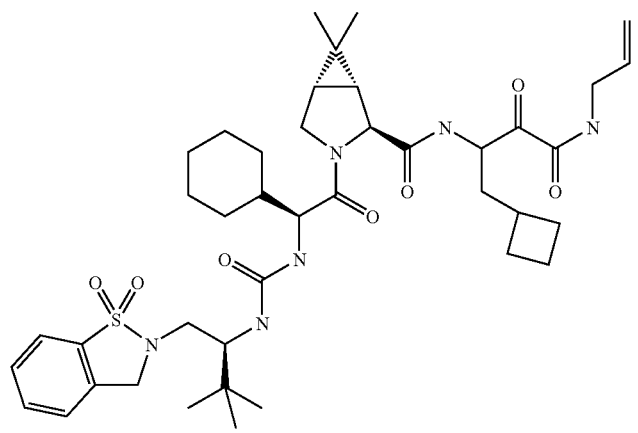
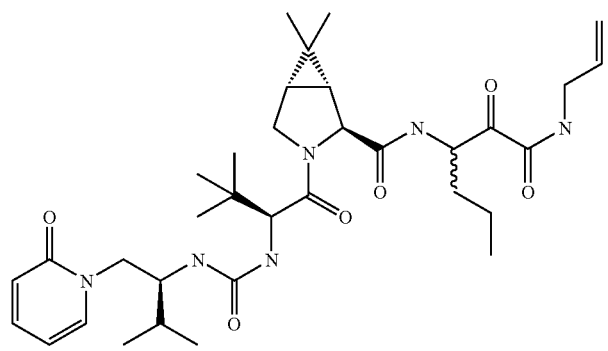
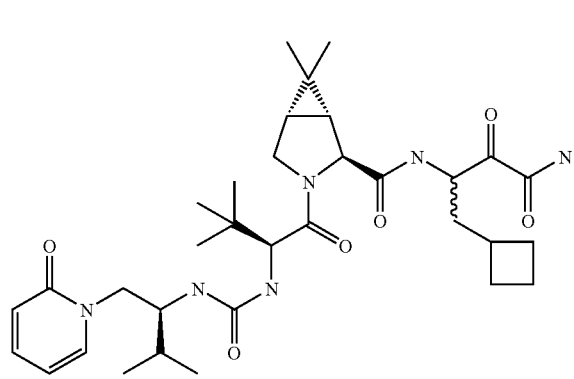
572
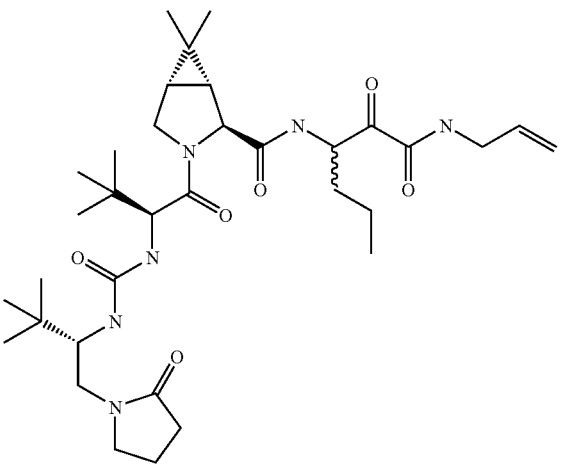
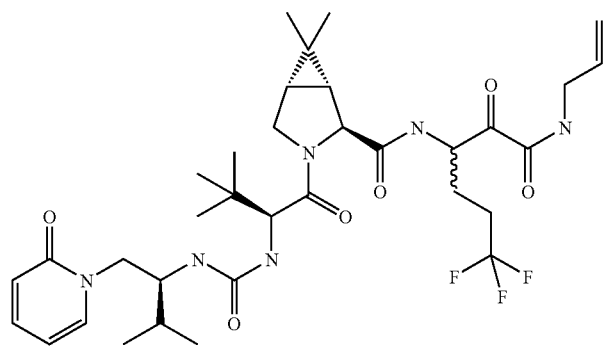

573                               574
-continued
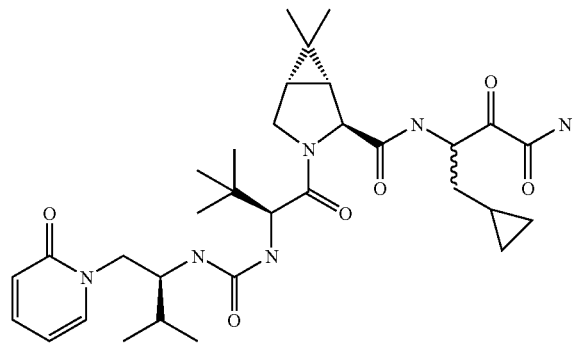
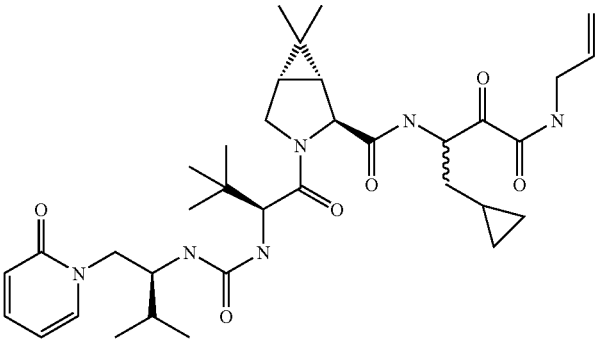
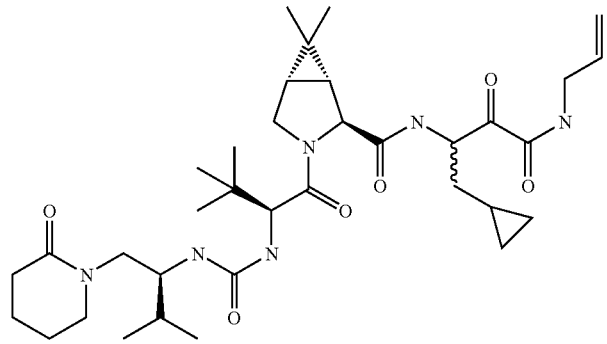
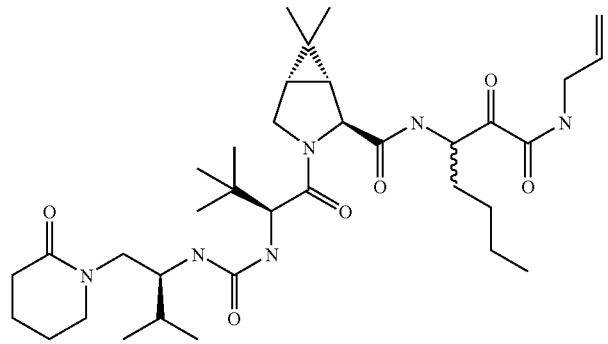
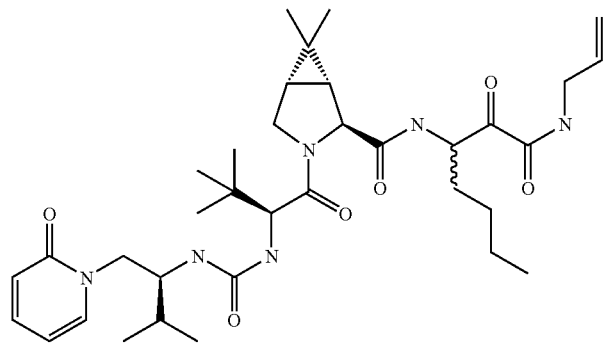

575
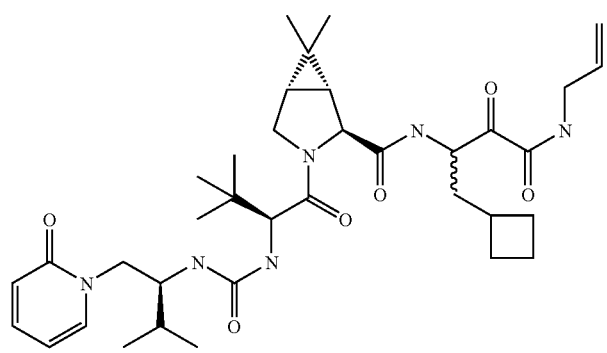
576
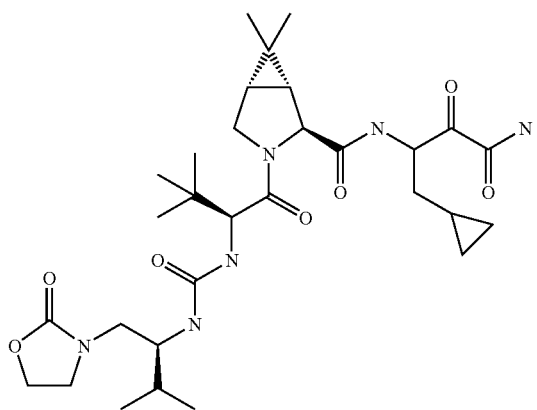
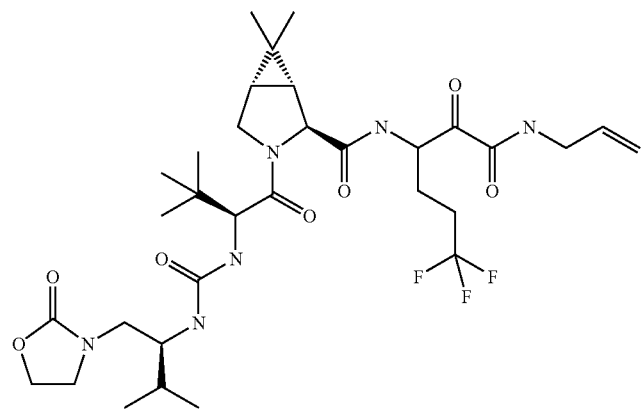
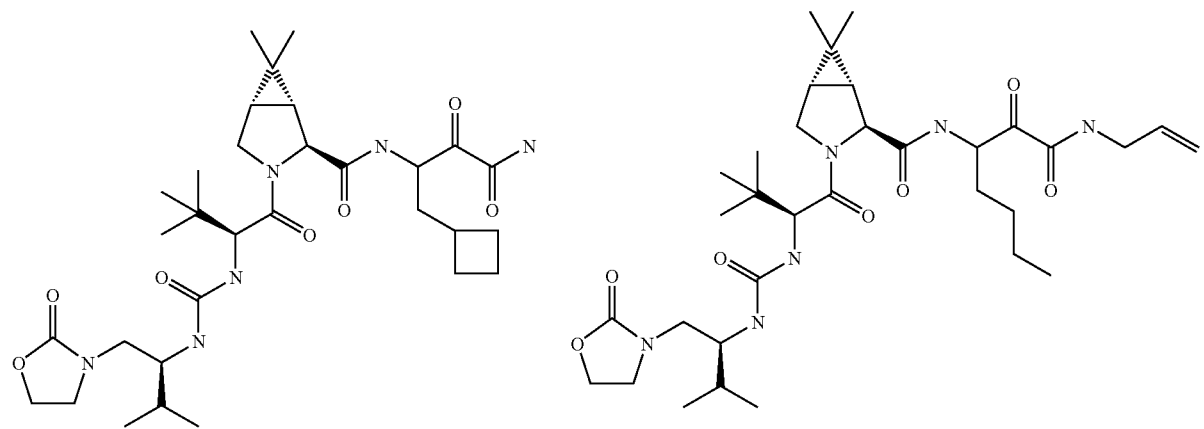

-continued
577
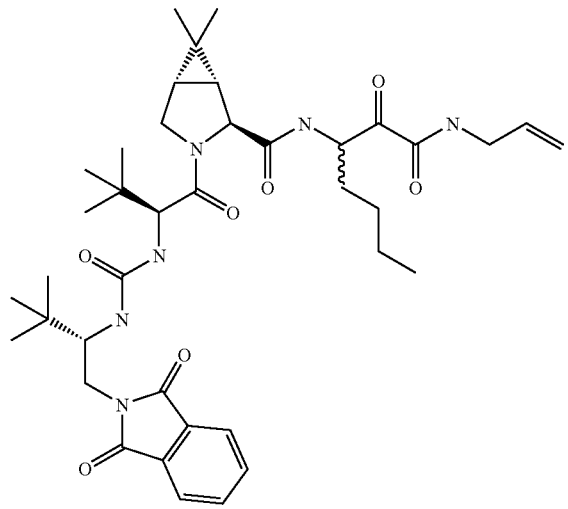
578
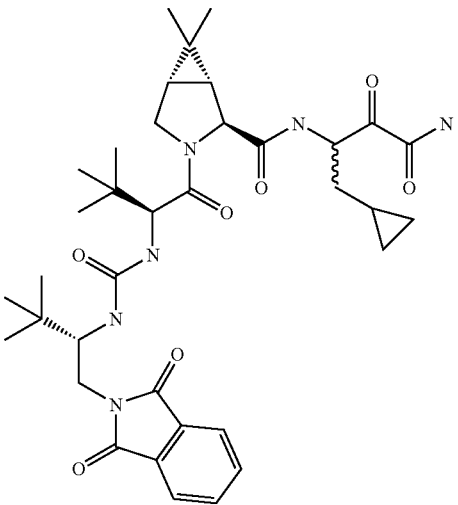
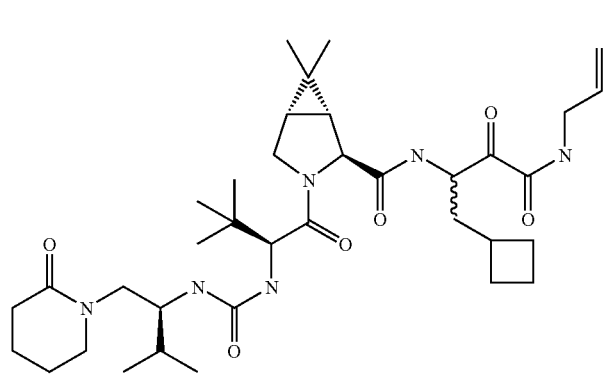
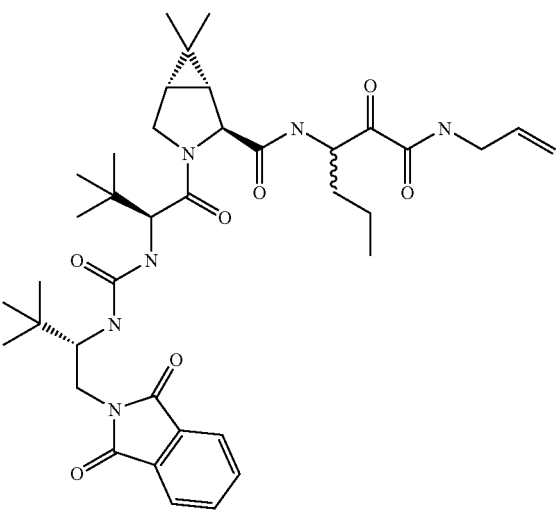
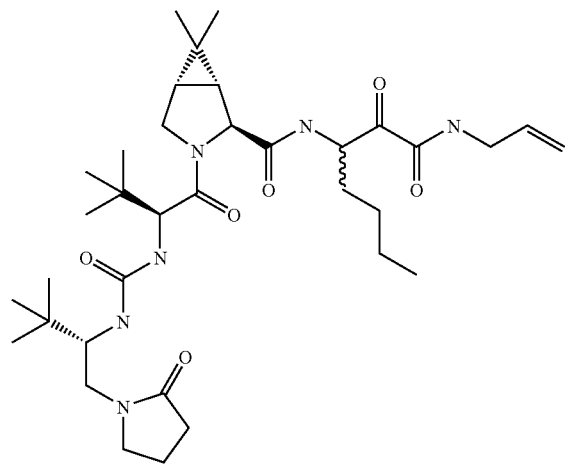

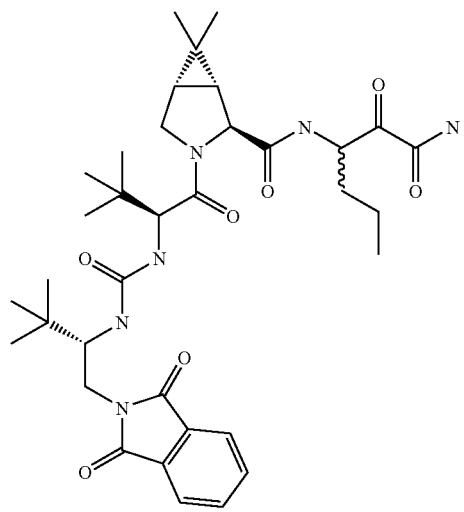
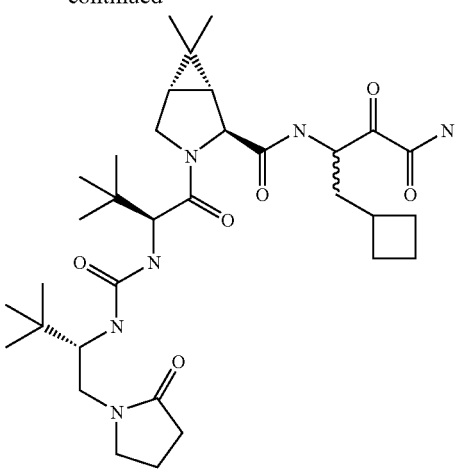
-continued
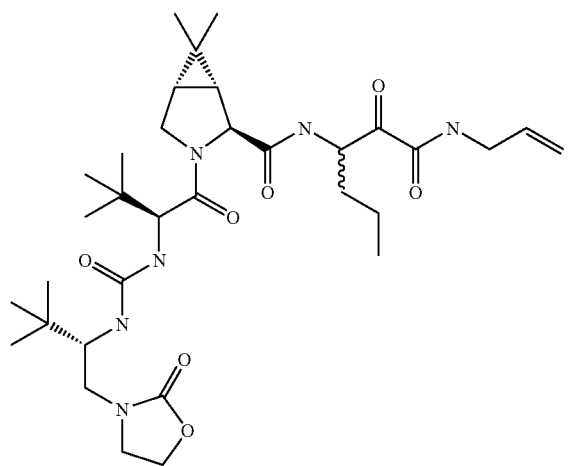
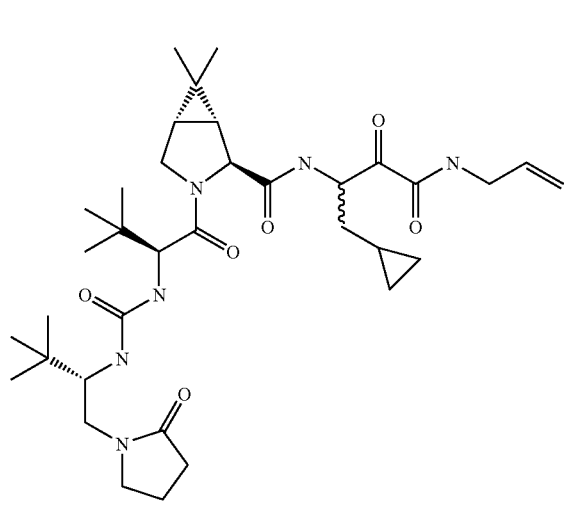
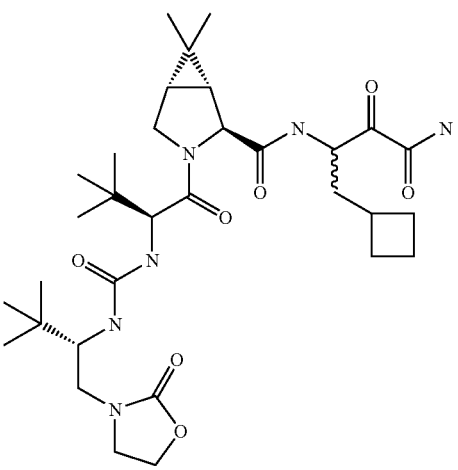

581
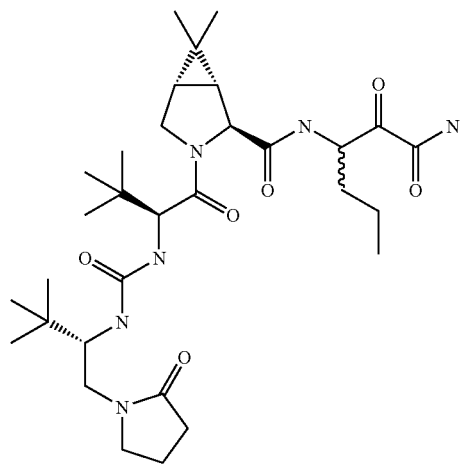
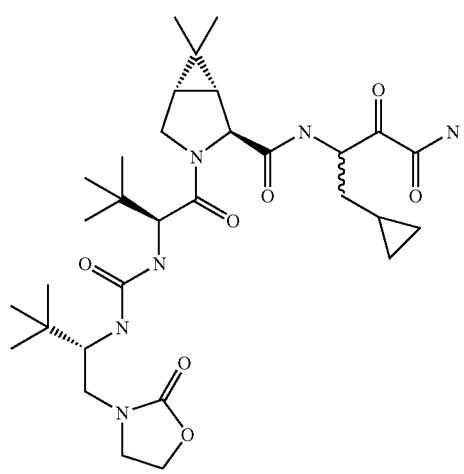
582
-continued
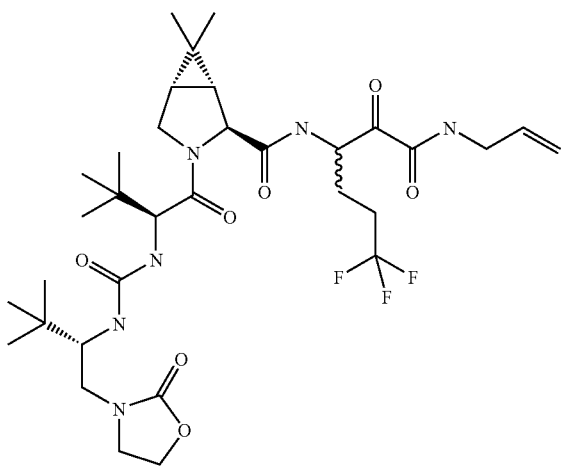
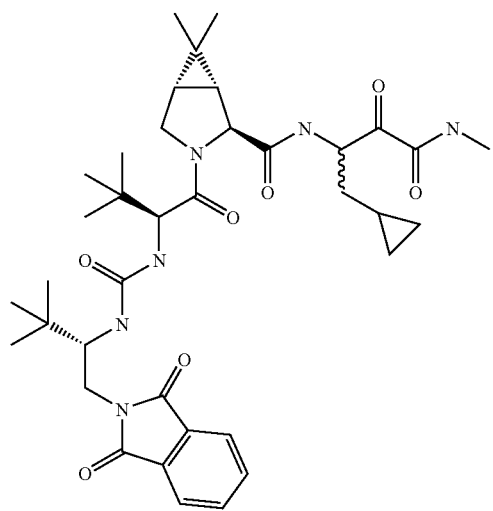

583
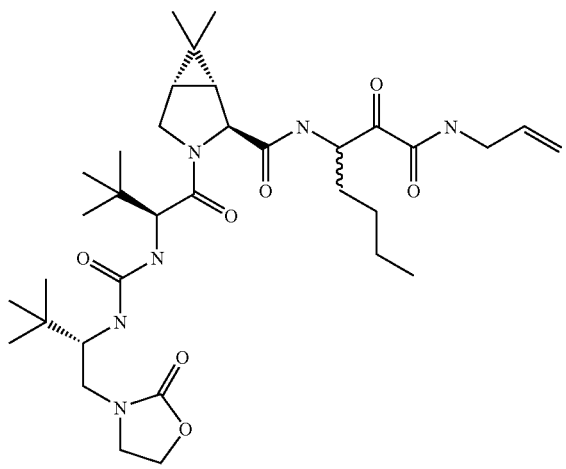
584
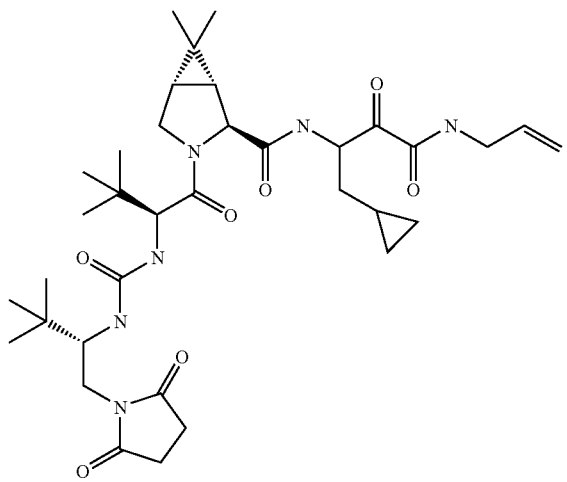
-continued
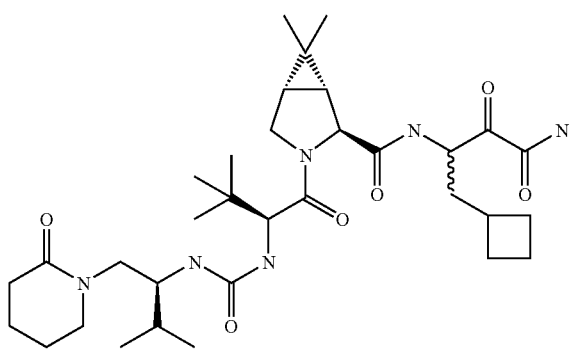
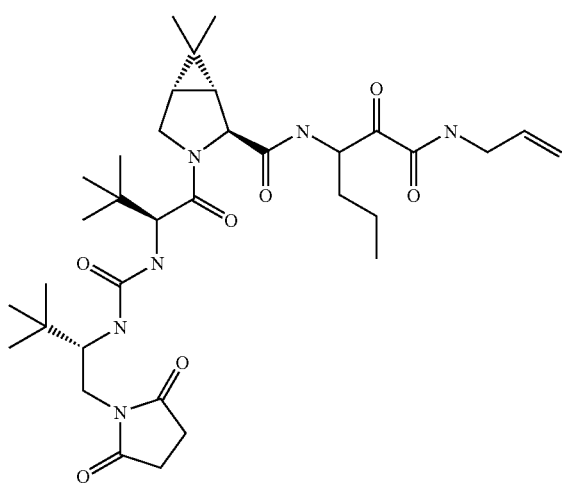
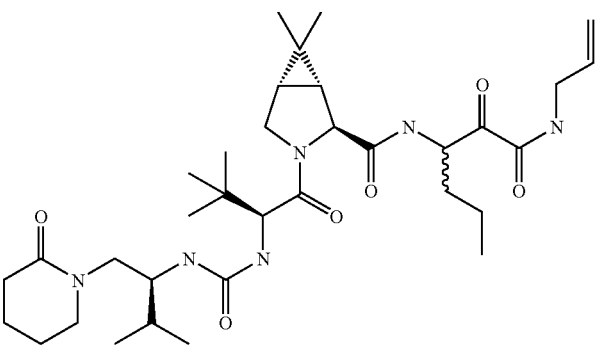

-continued
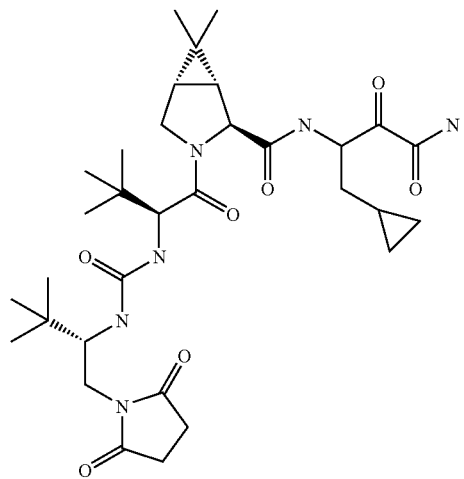
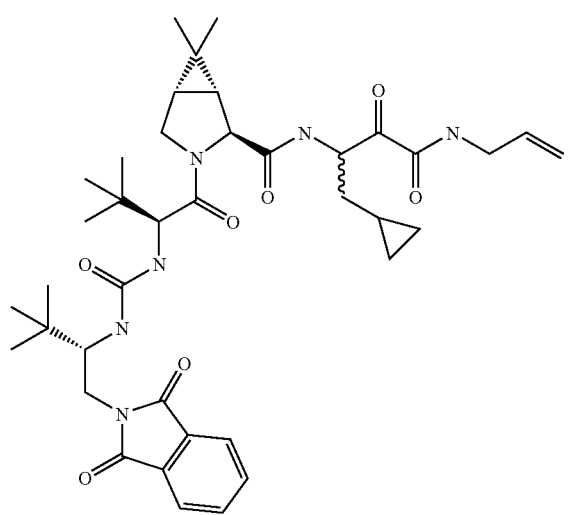
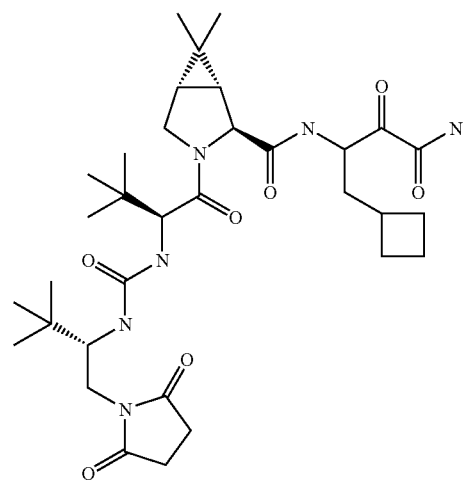
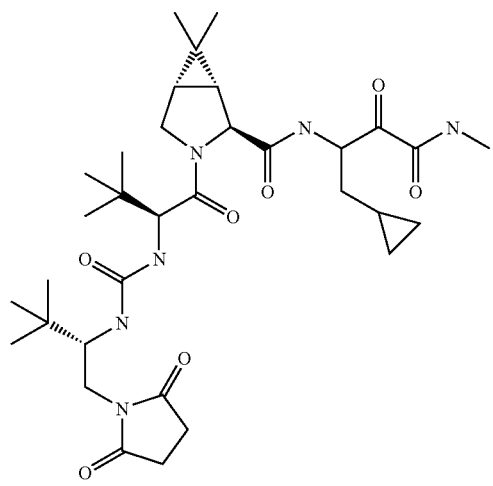

587
-continued
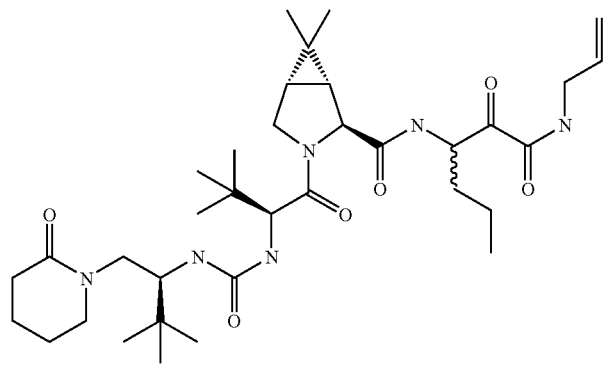
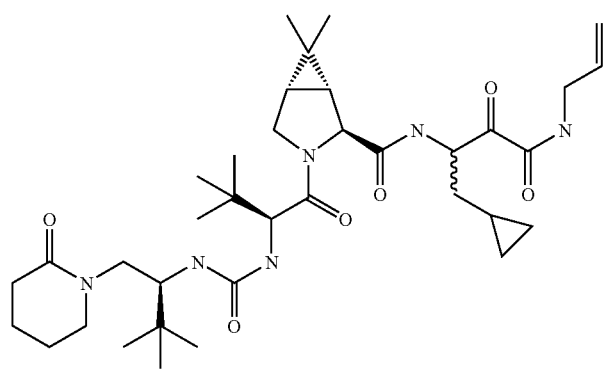
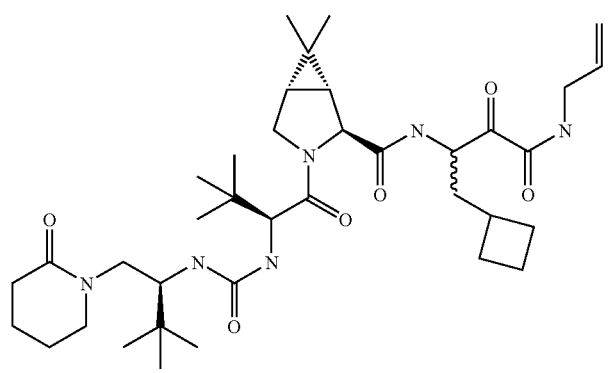
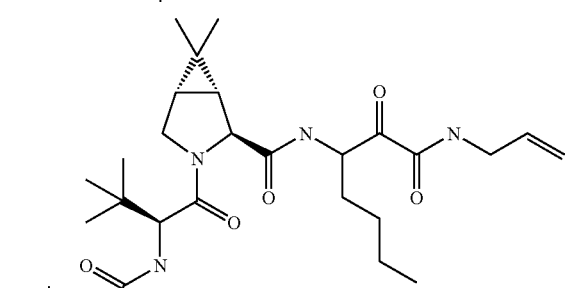
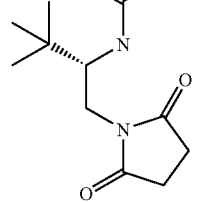
588
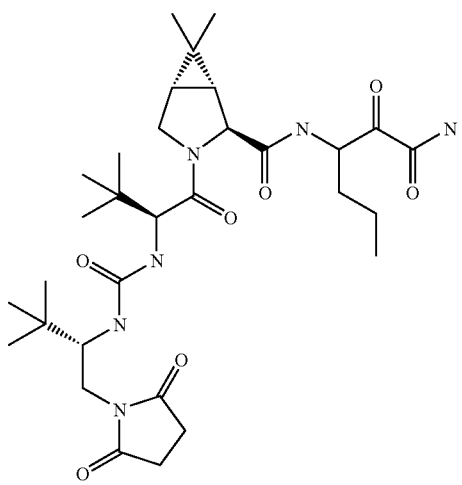
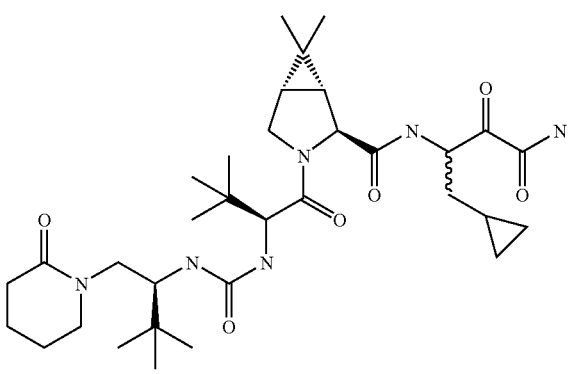

589
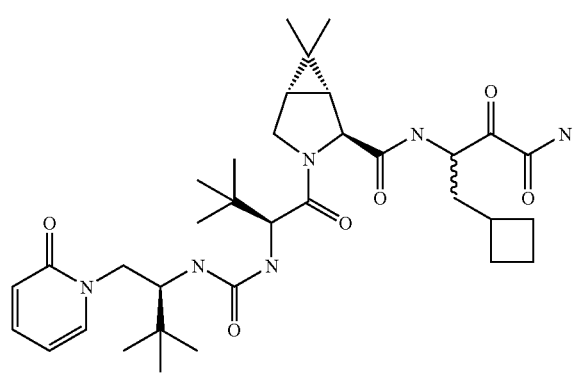
590
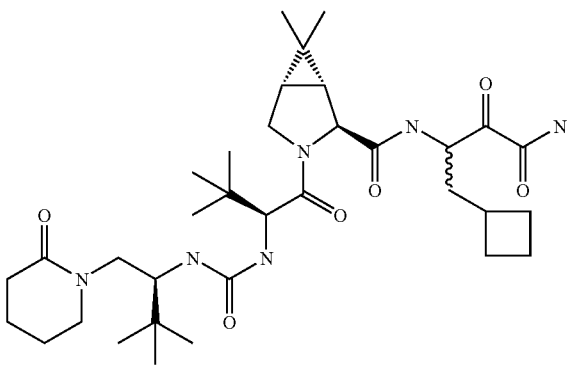
-continued
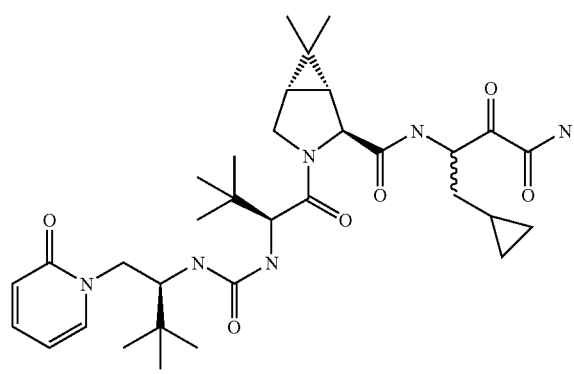
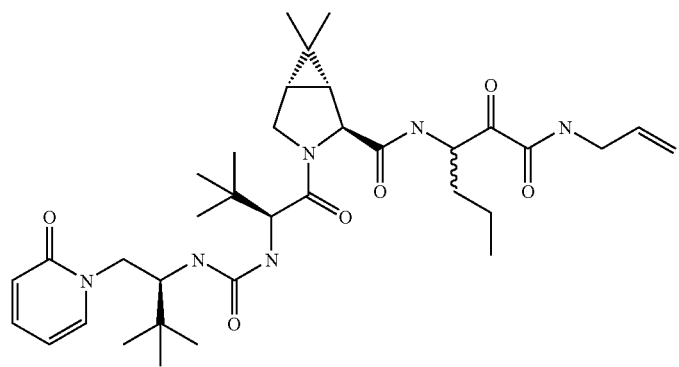
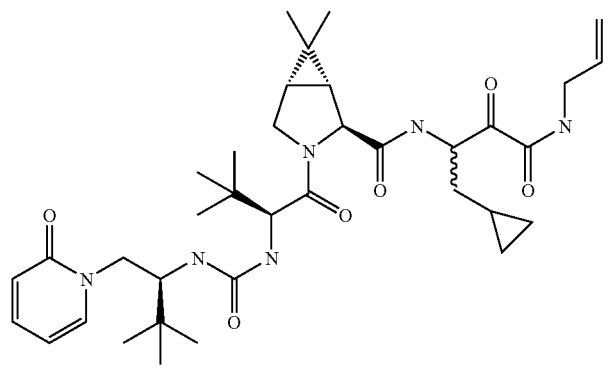

-continued
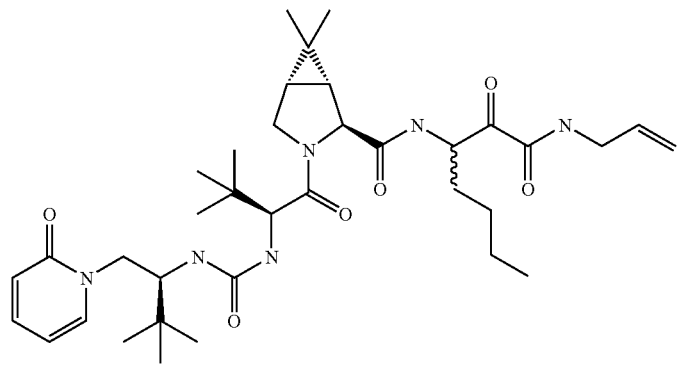
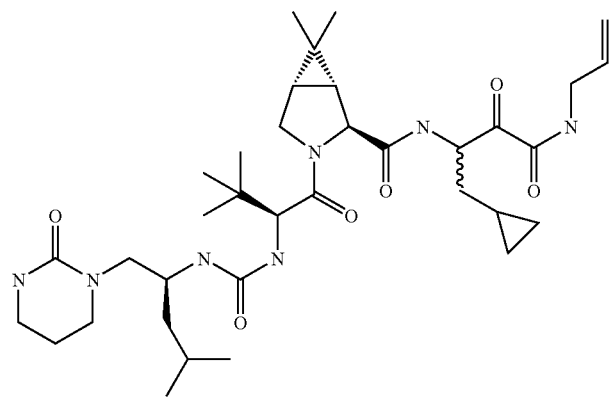
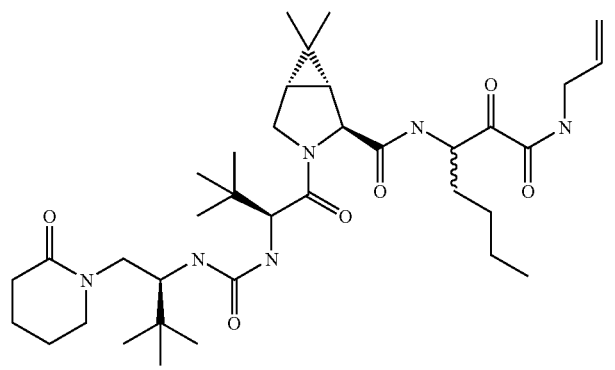
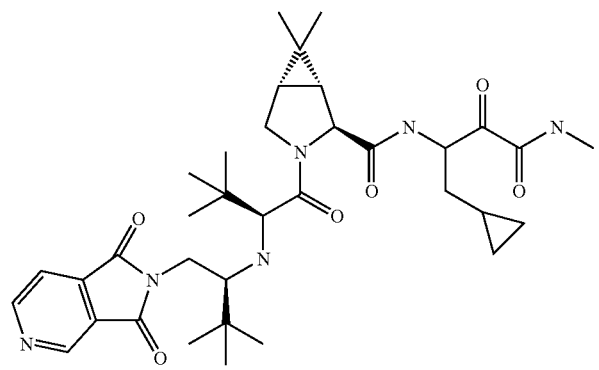

-continued
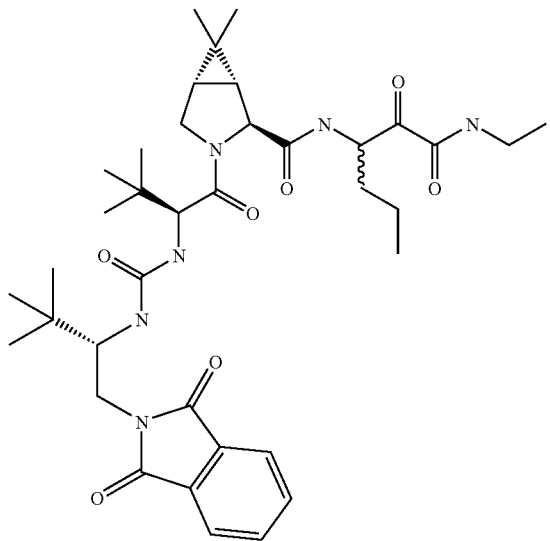
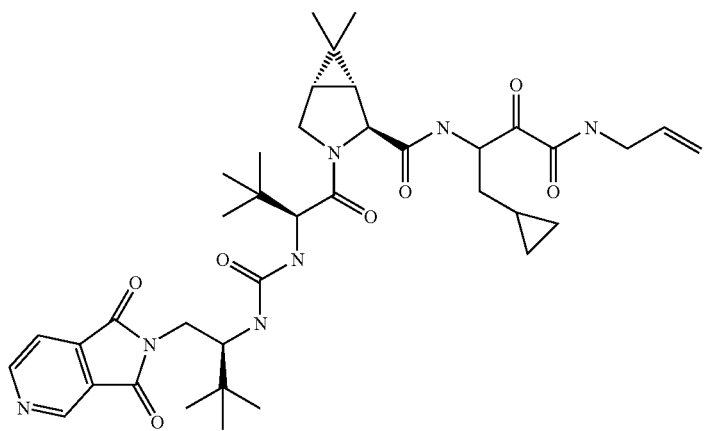
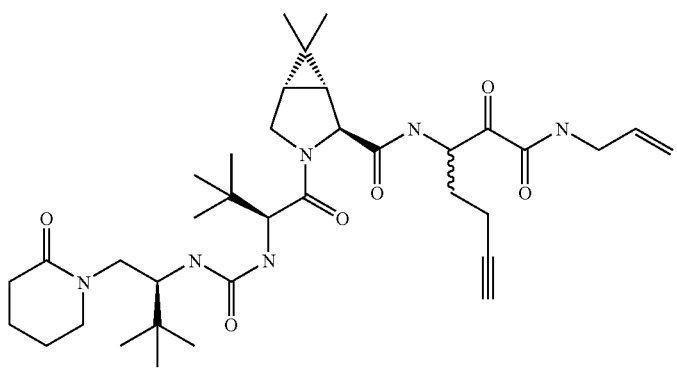

-continued
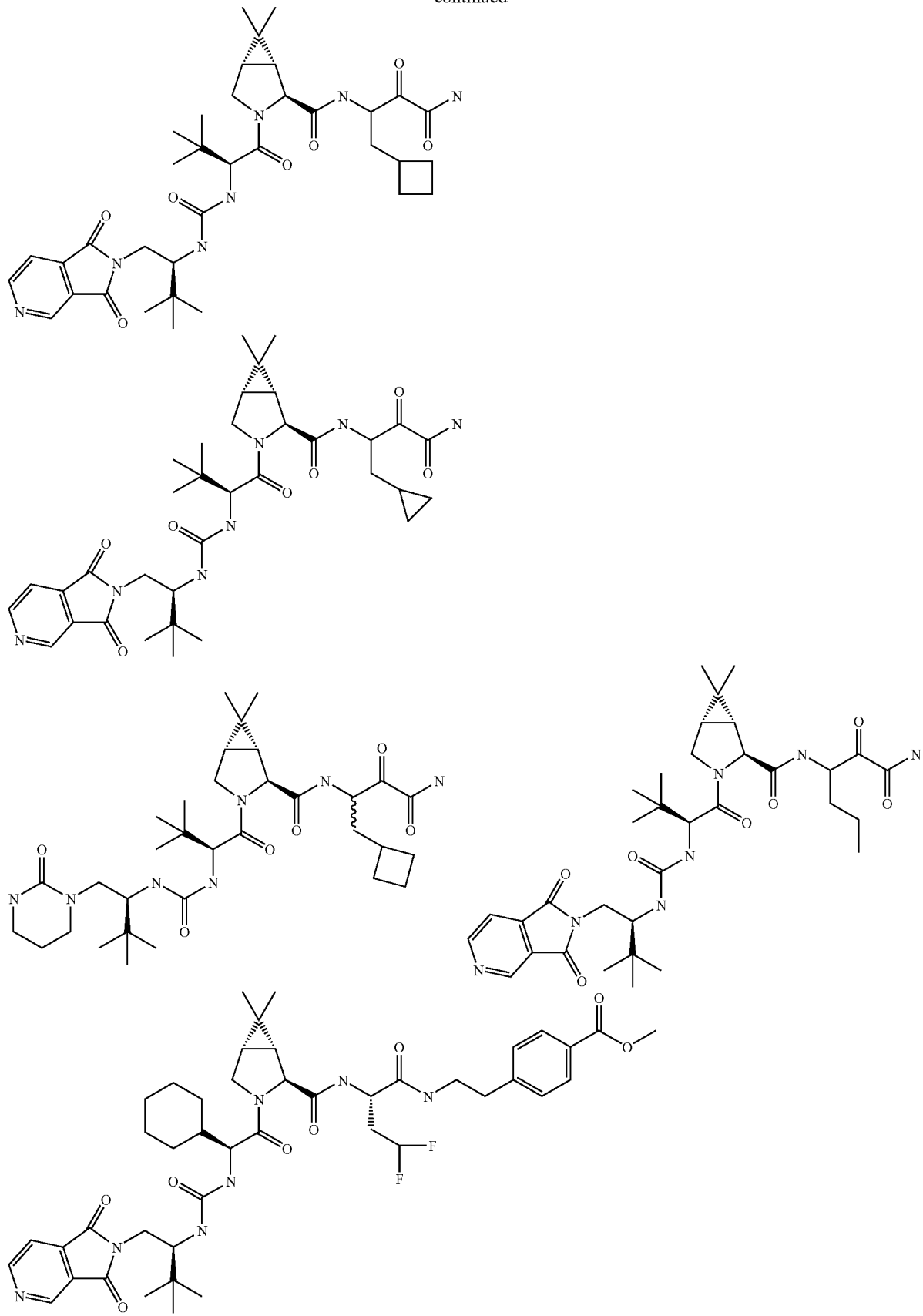

-continued
| 597 | 598 |
|---|---|
| 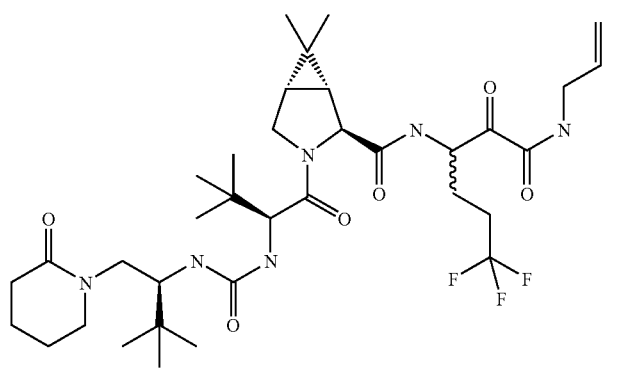 | 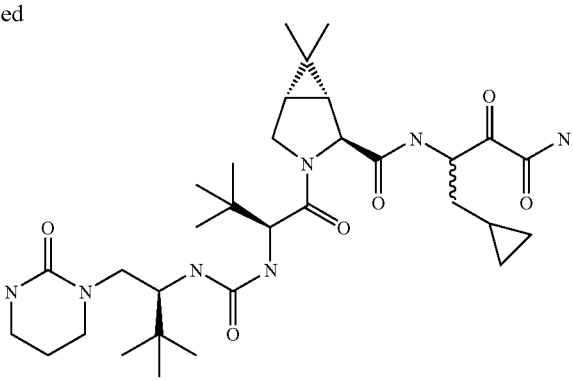 |
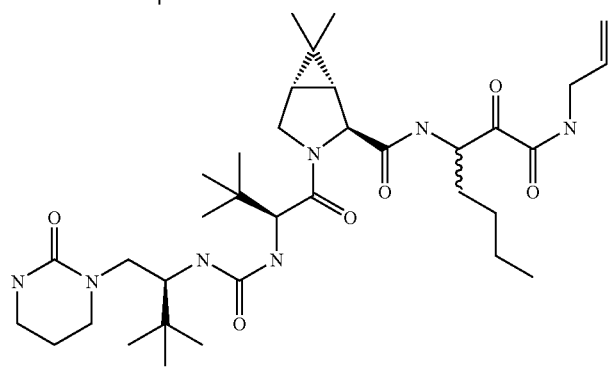
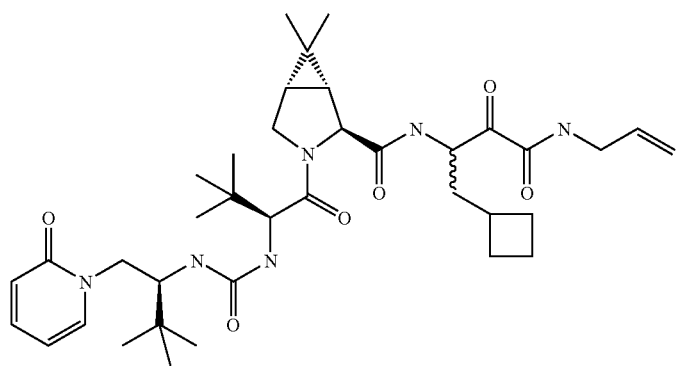
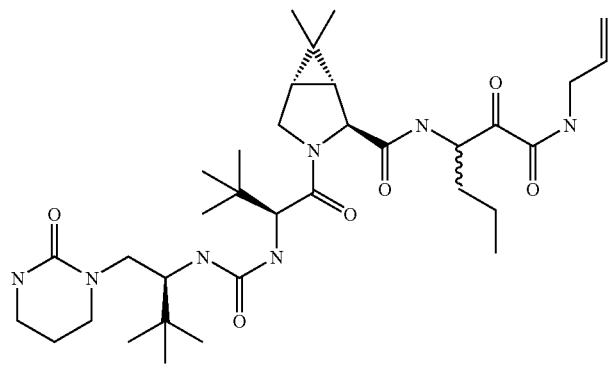

| 599 | 600 |
|---|---|
| 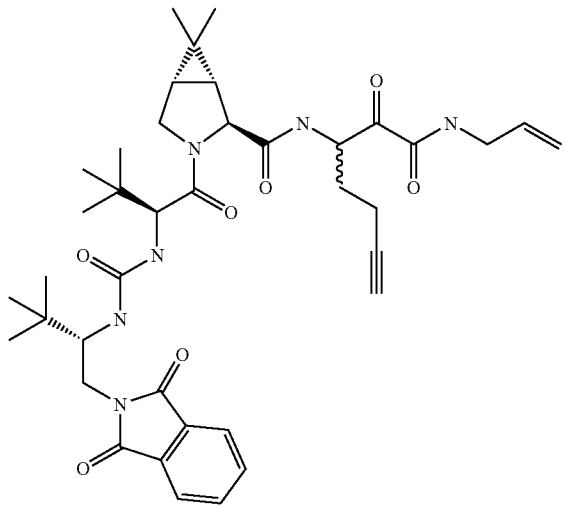 | 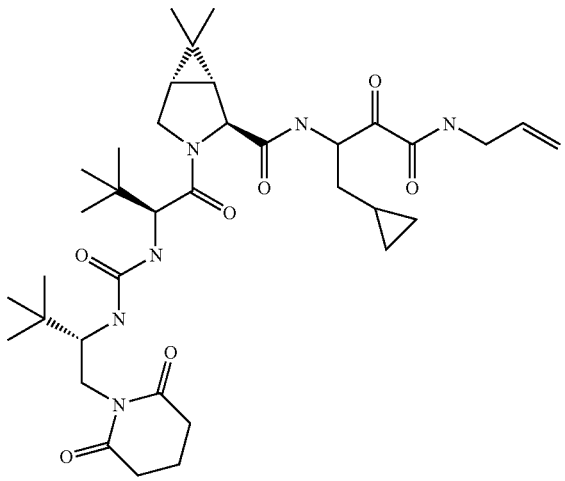 |
| 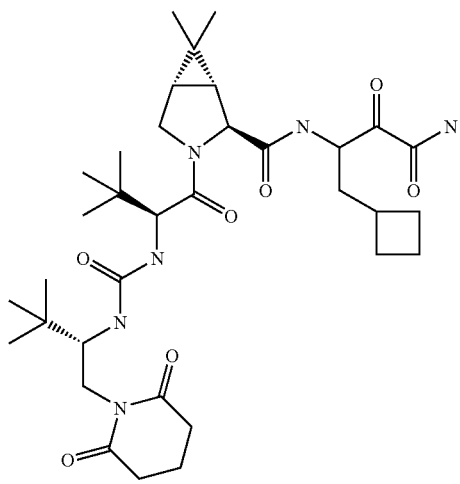 | 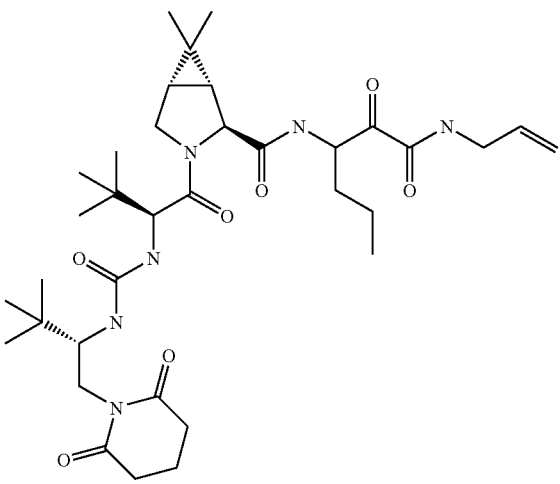 |
| 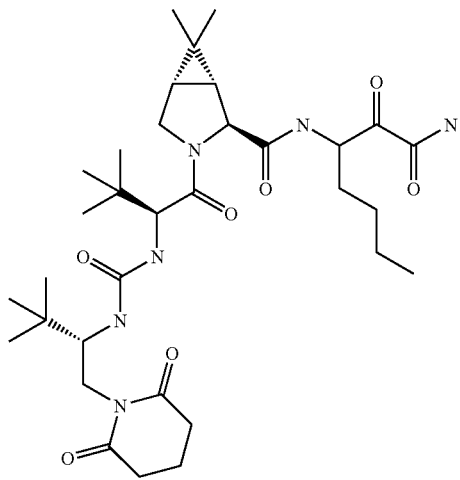 | 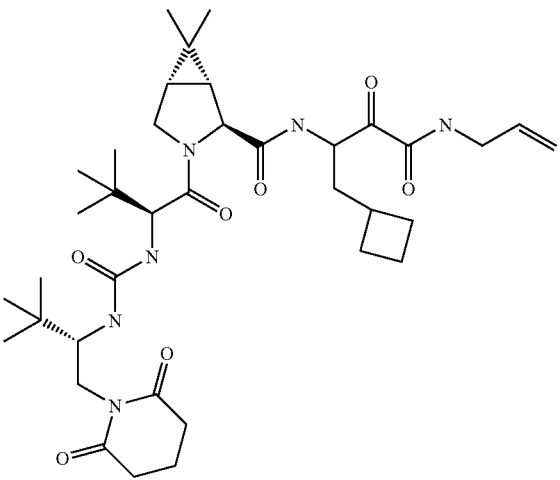 |

-continued
| 601 | 602 |
|---|---|
| 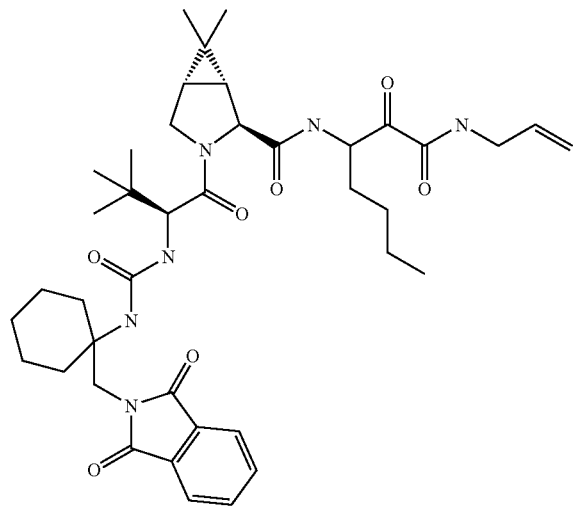 | 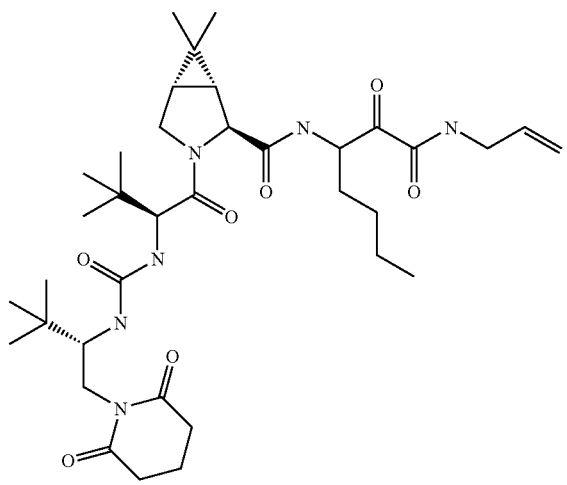 |
| 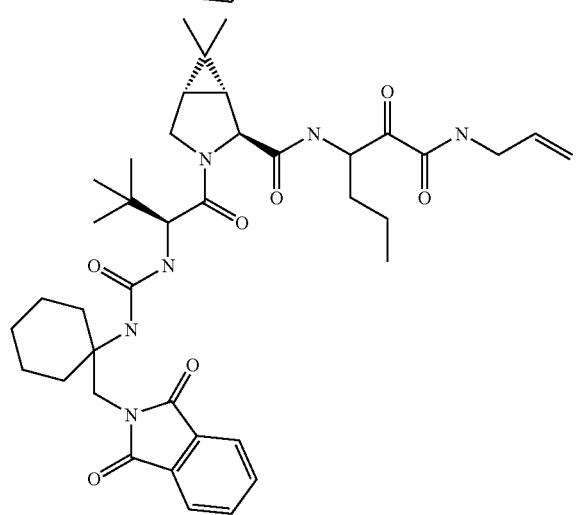 | 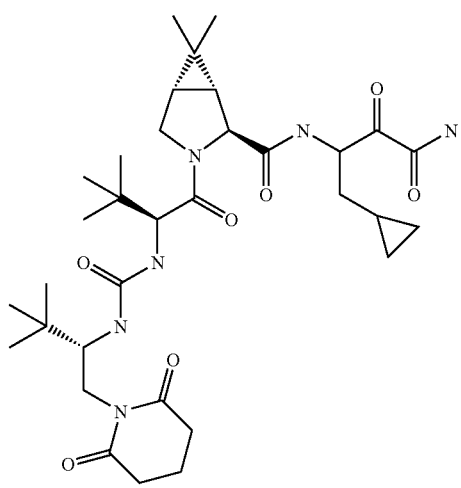 |
| 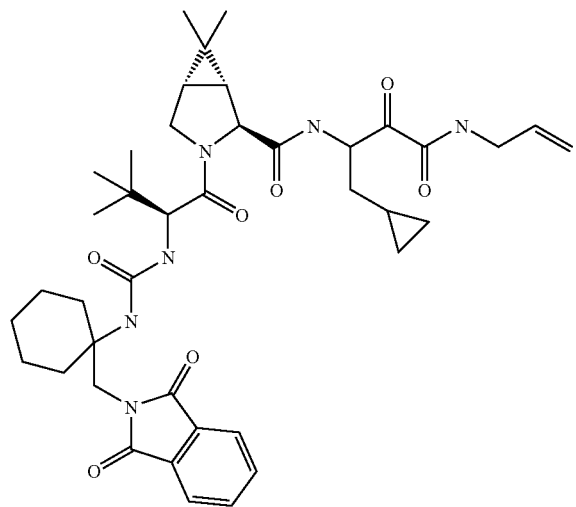 | 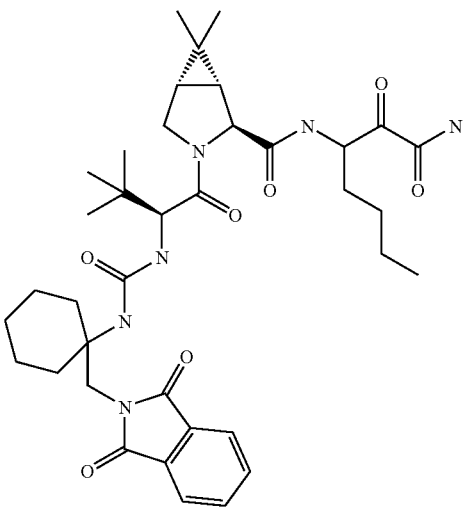 |

603 604
-continued
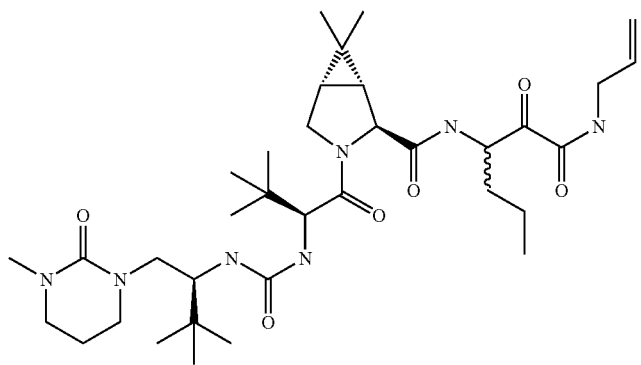
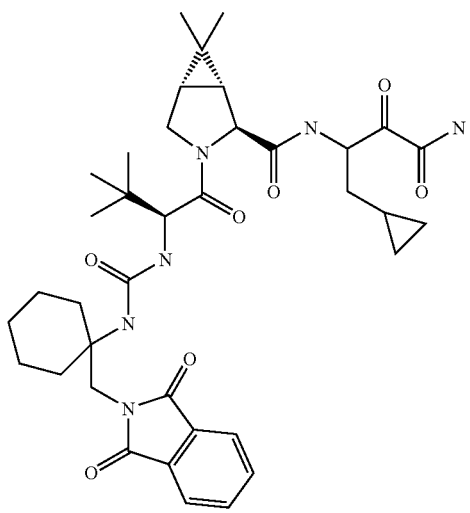
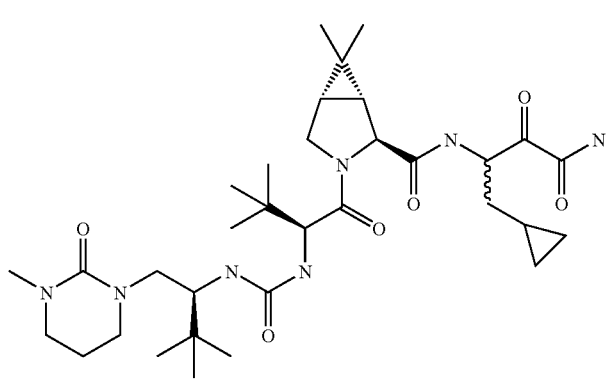
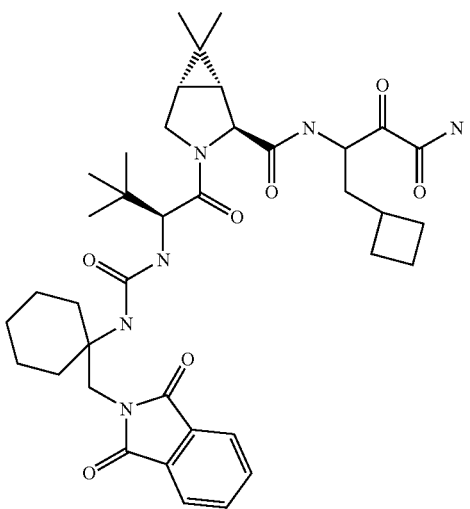
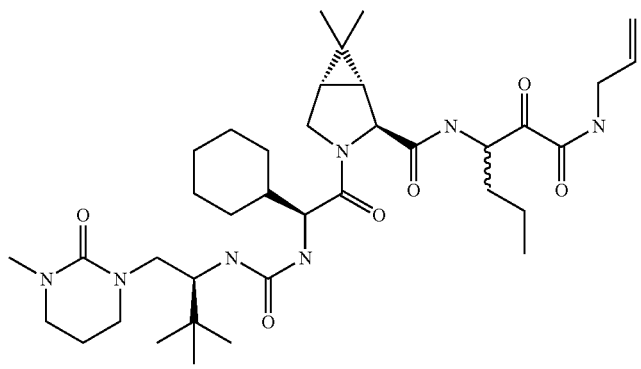

-continued
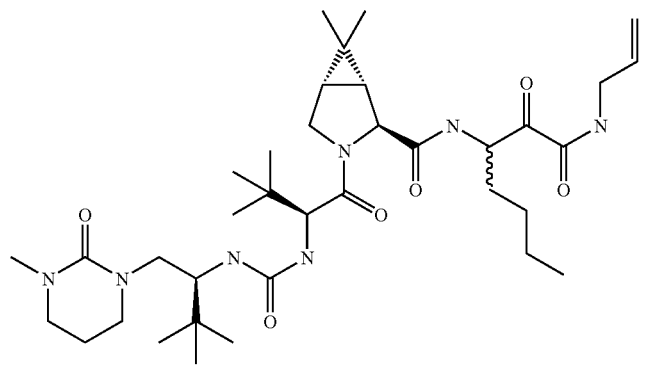
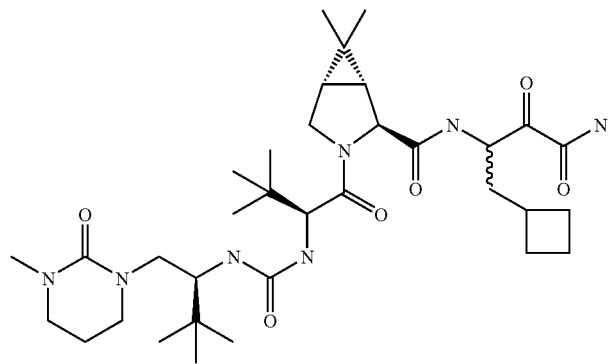
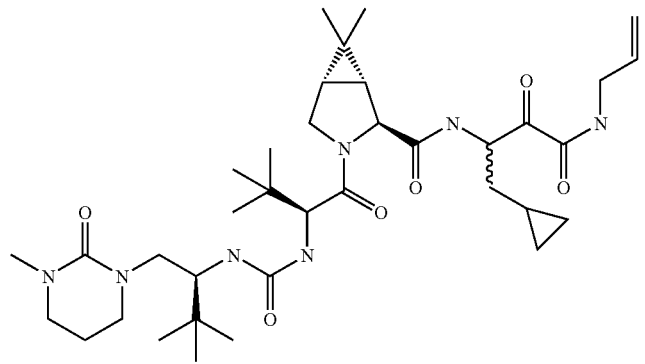
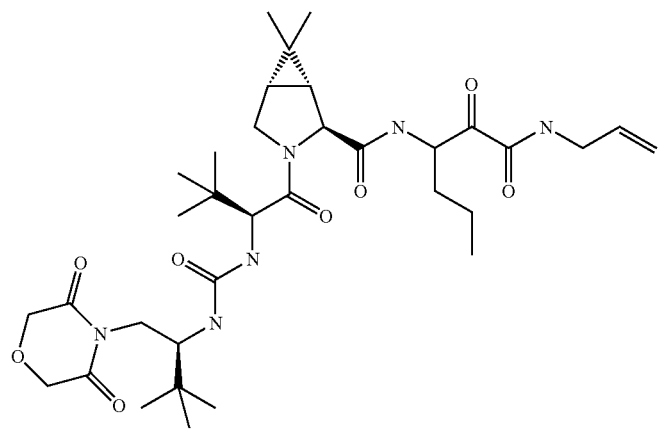

-continued
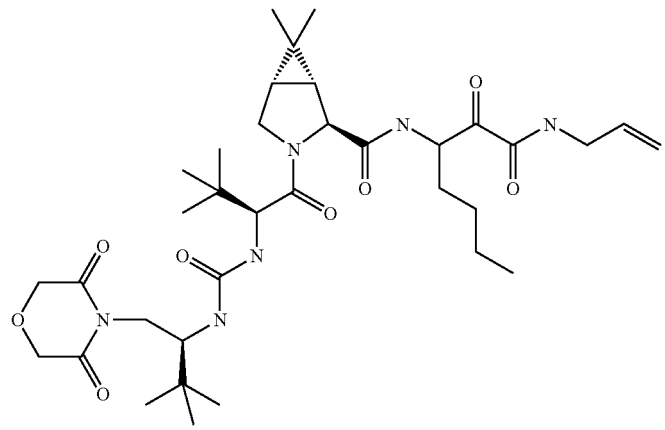
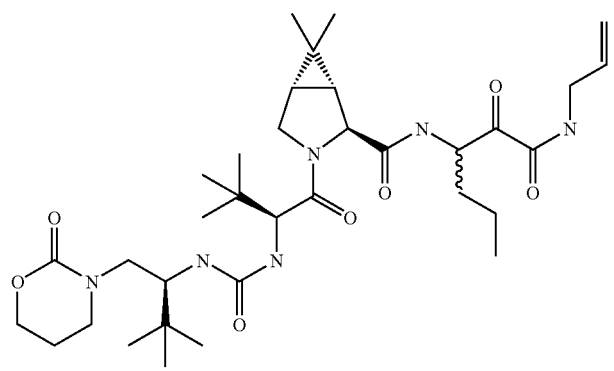
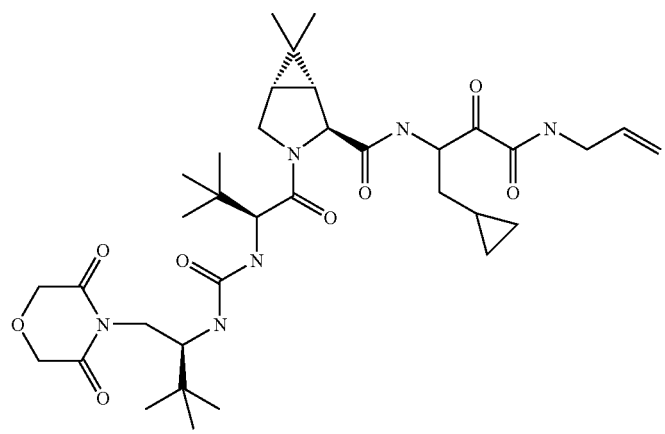

609 610
-continued
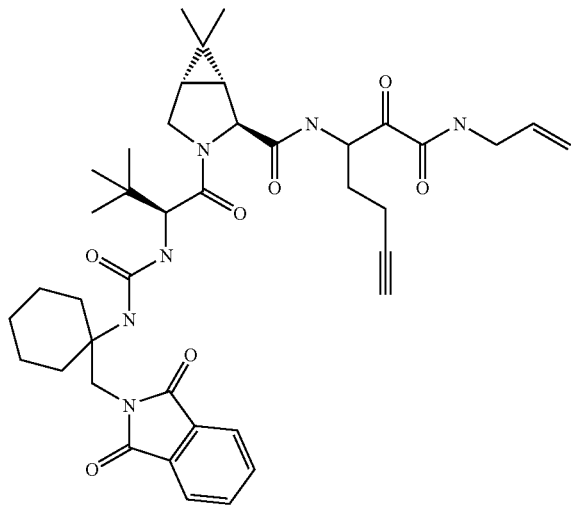
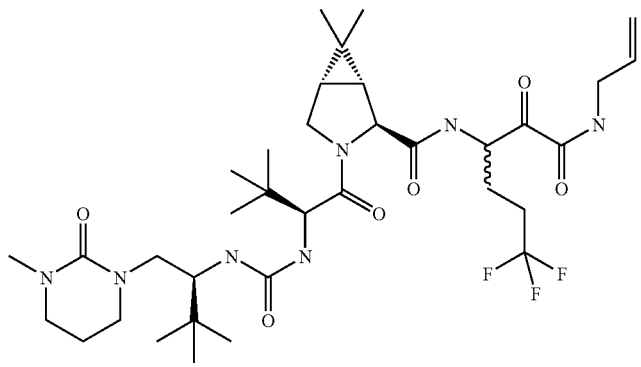
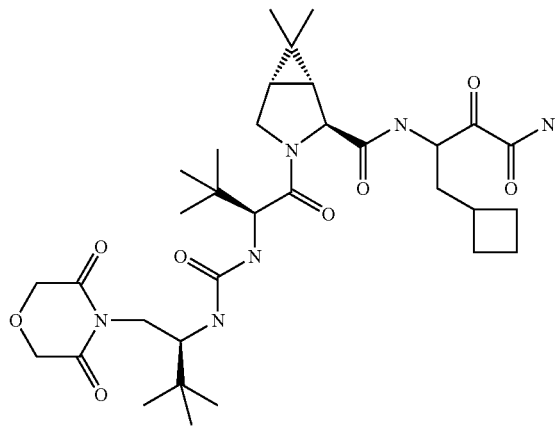
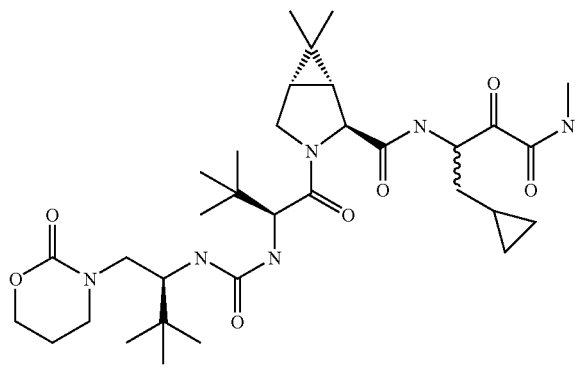

611 612
-continued
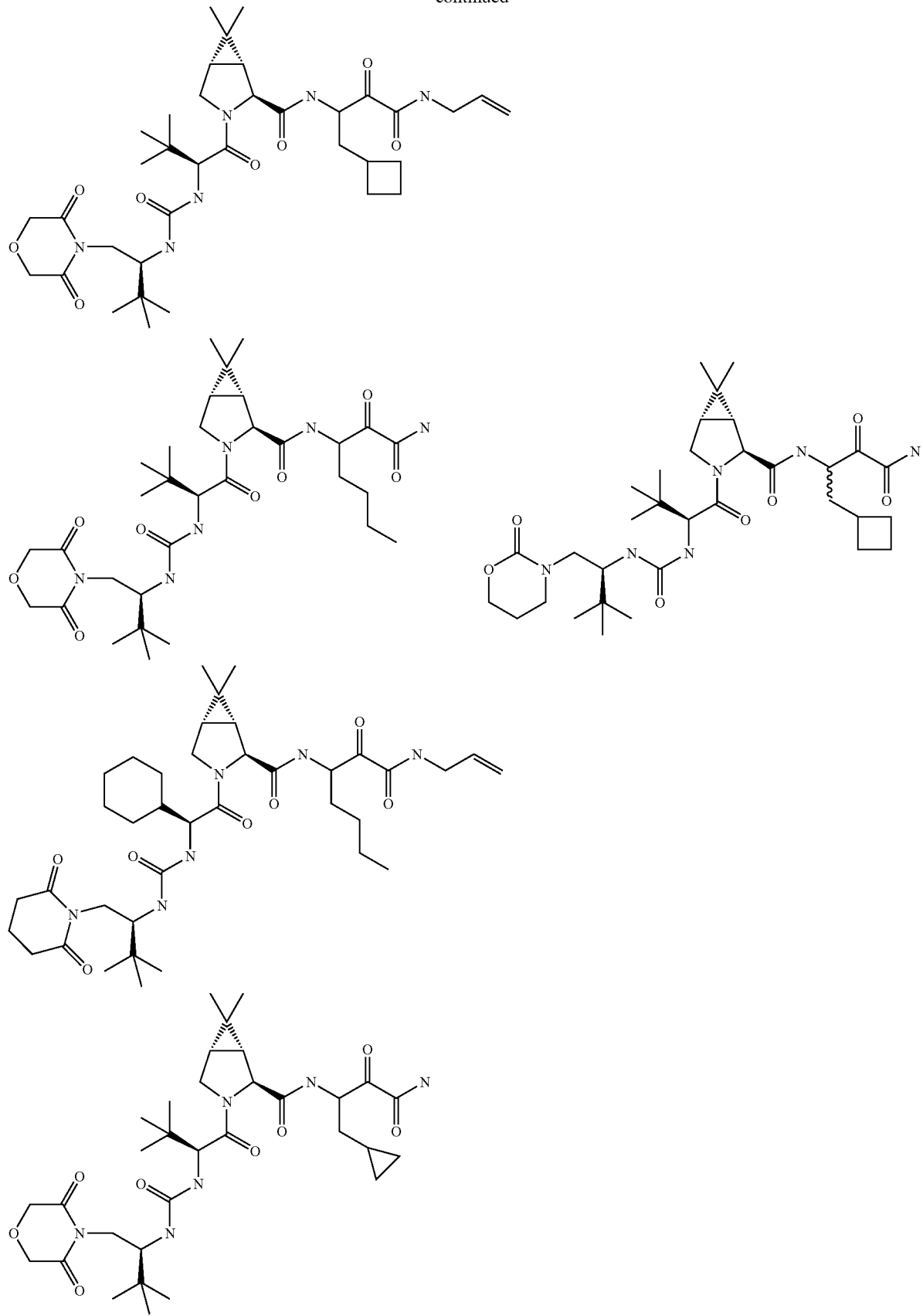

613
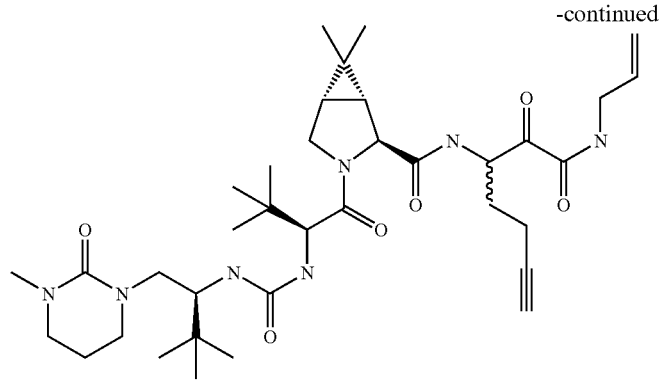
-continued
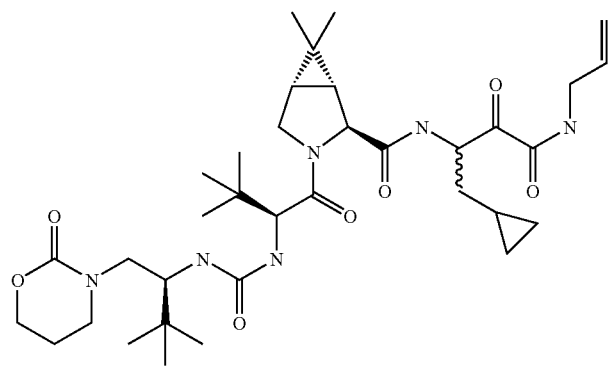
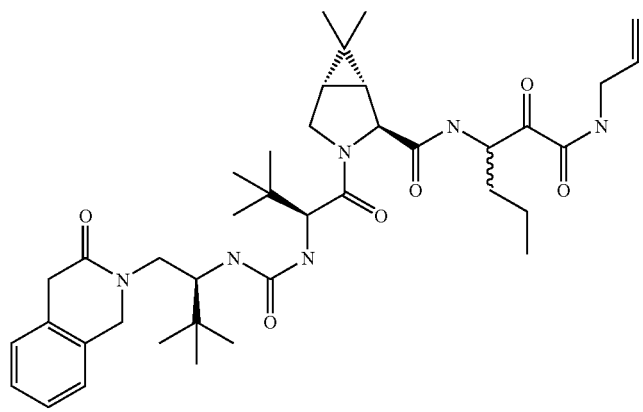
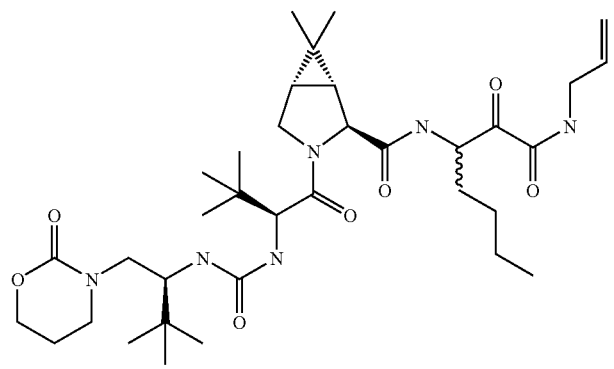

615 616
-continued
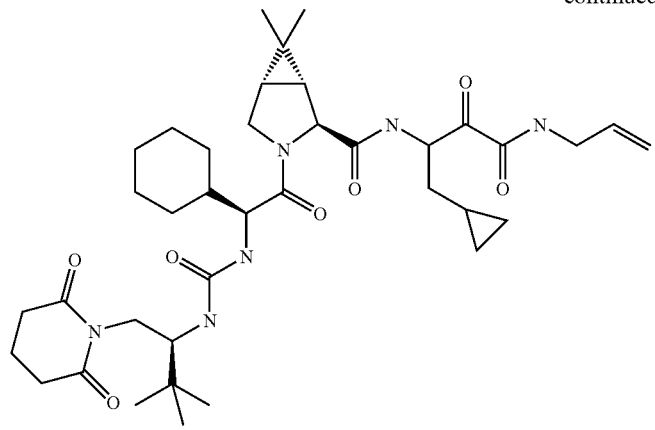
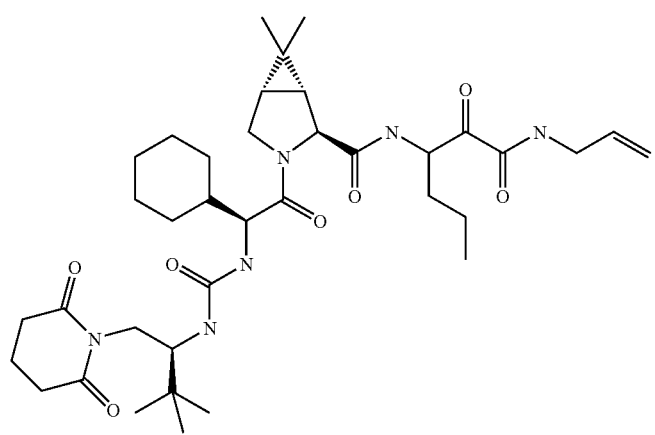
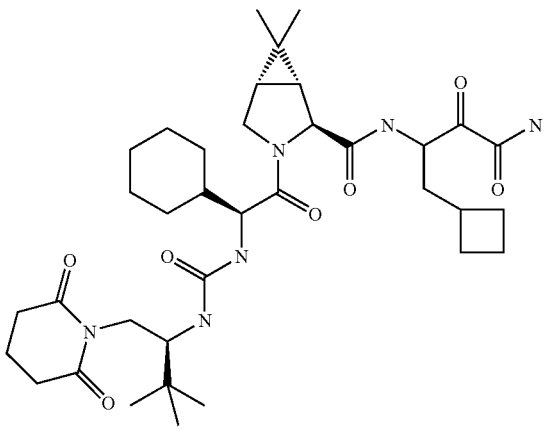
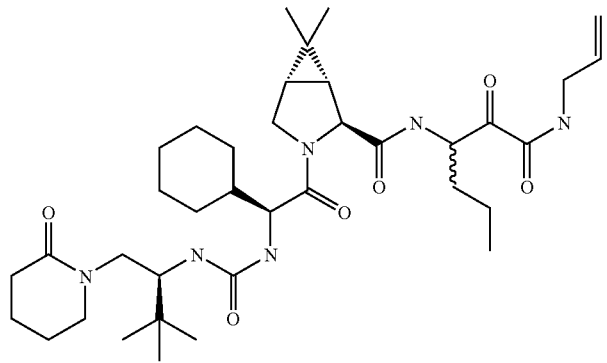
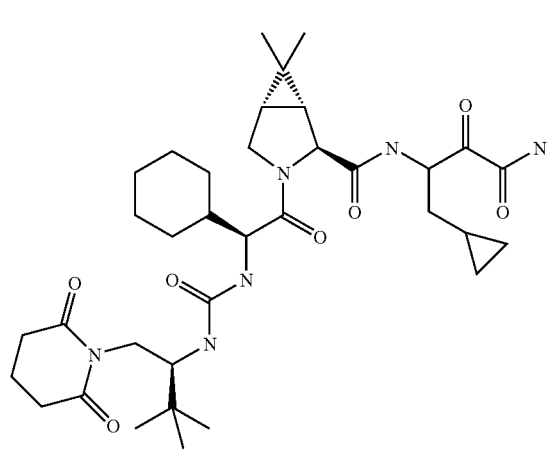
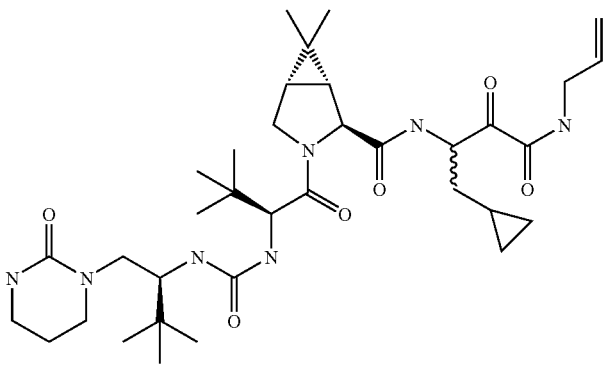

-continued
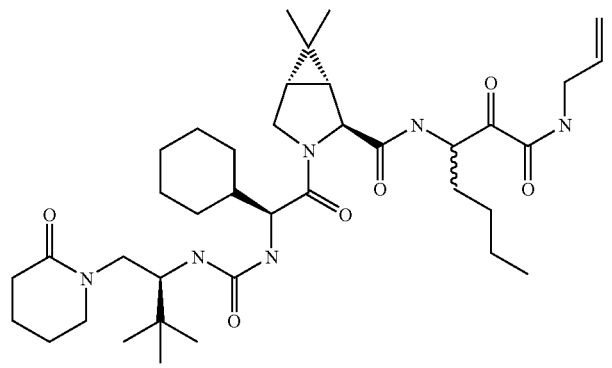
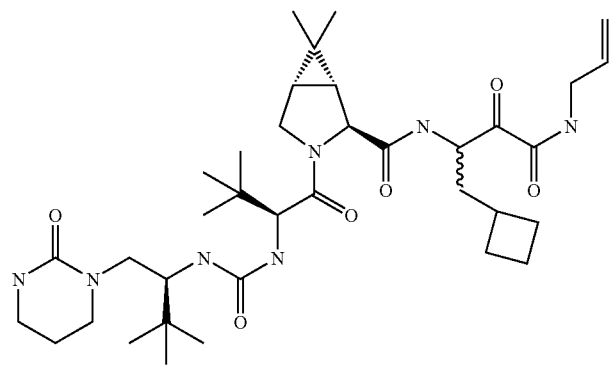
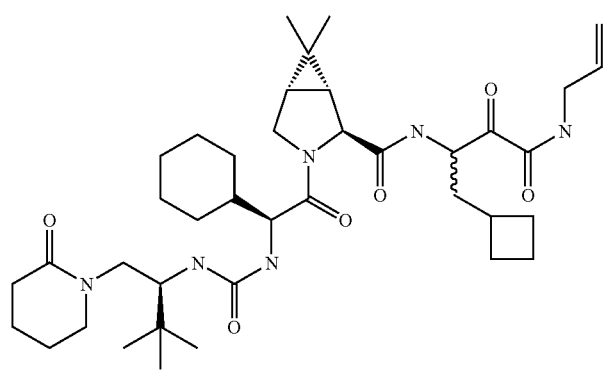
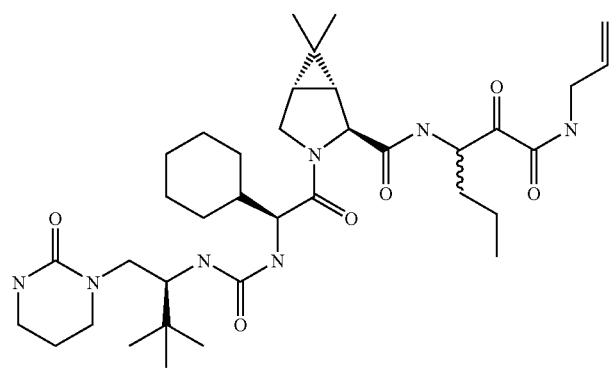

-continued
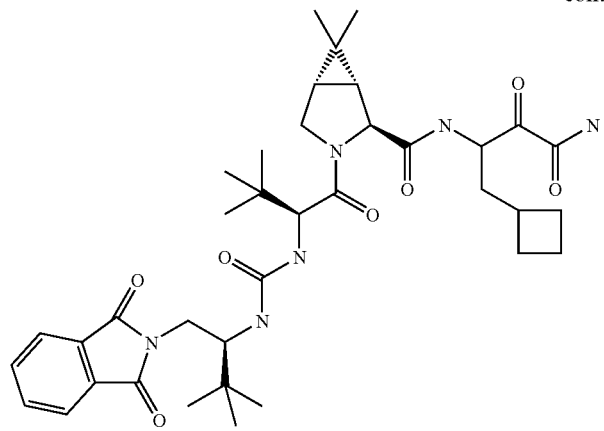
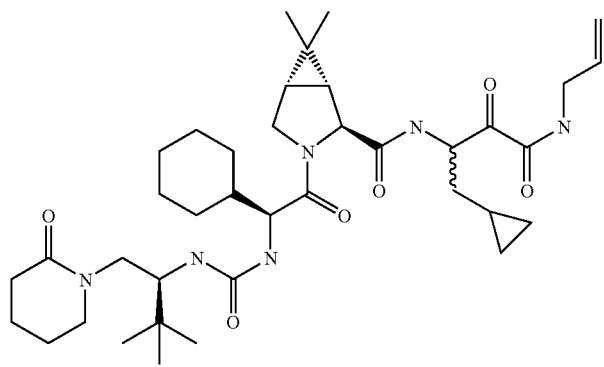
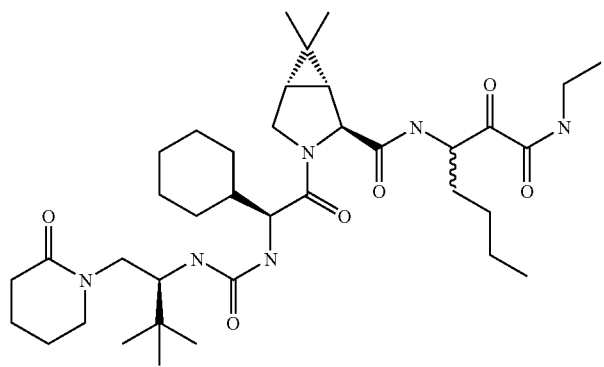
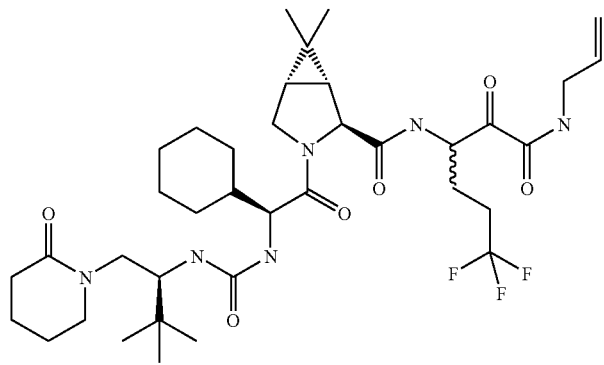

-continued
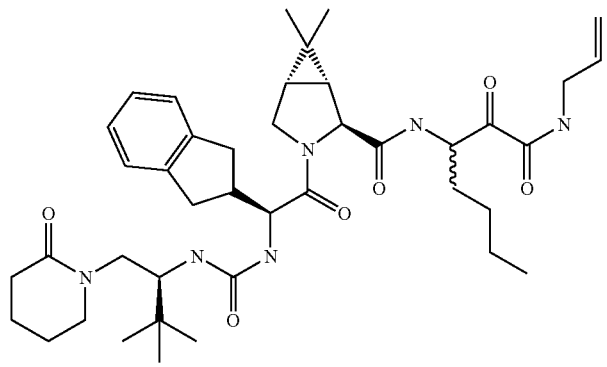
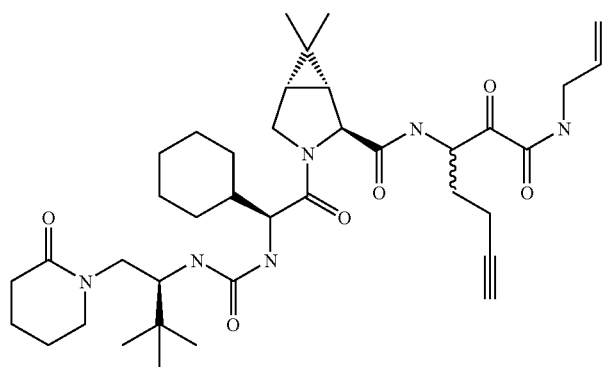
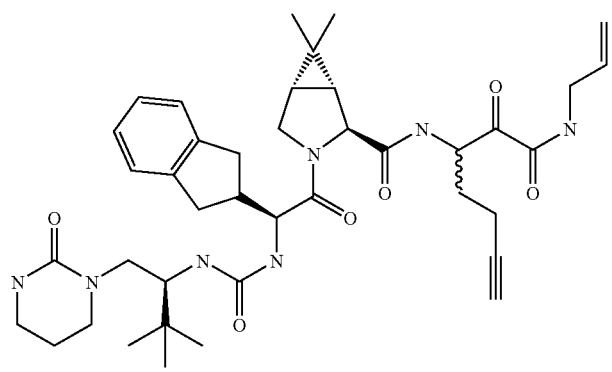
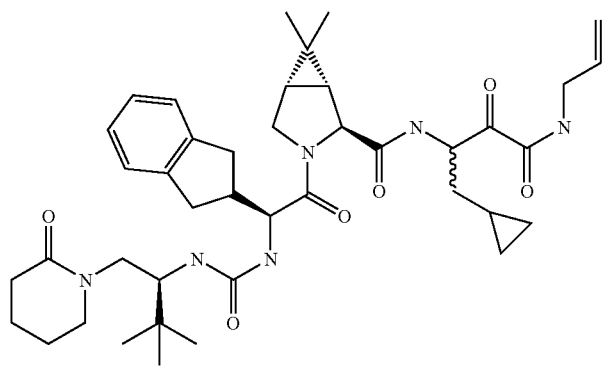

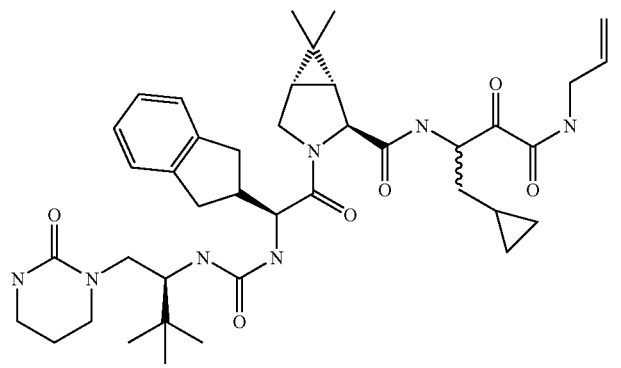
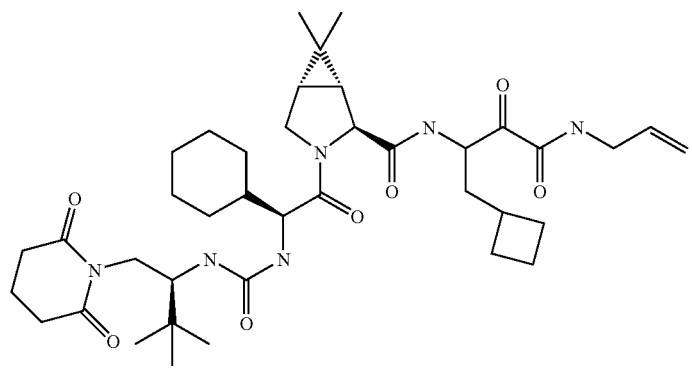
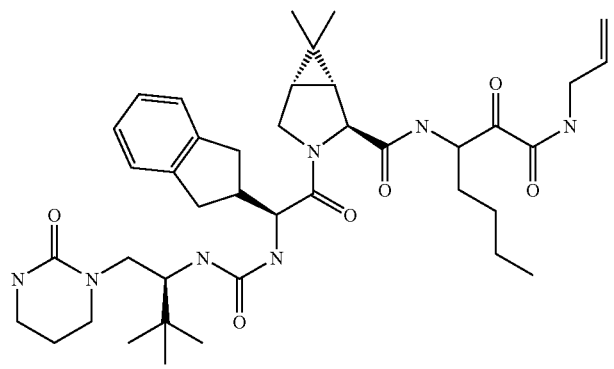
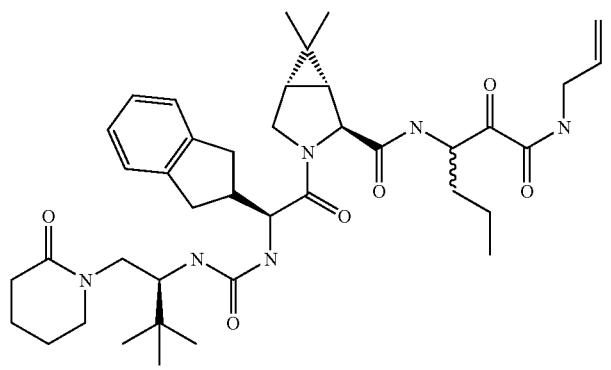

-continued
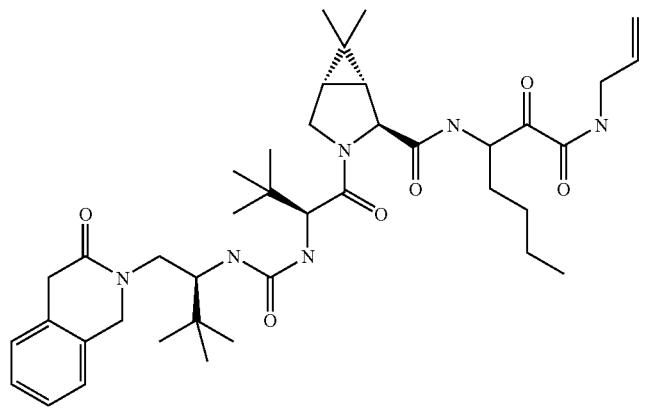
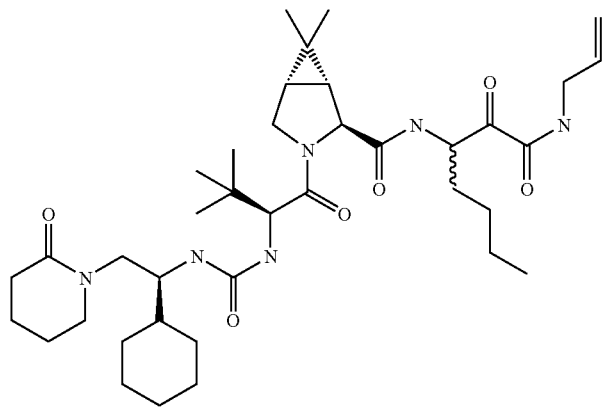
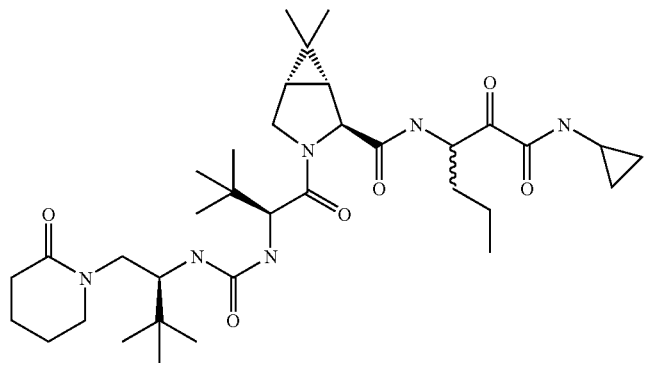
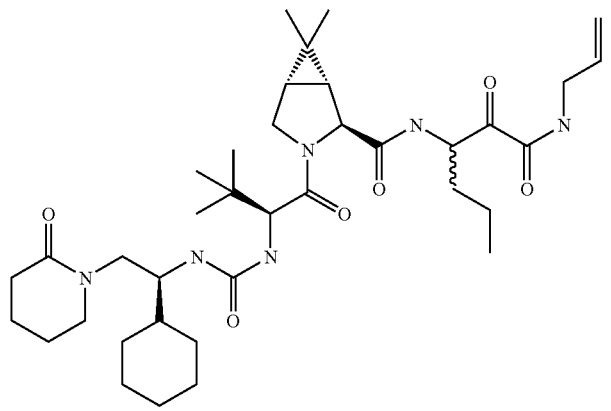

-continued
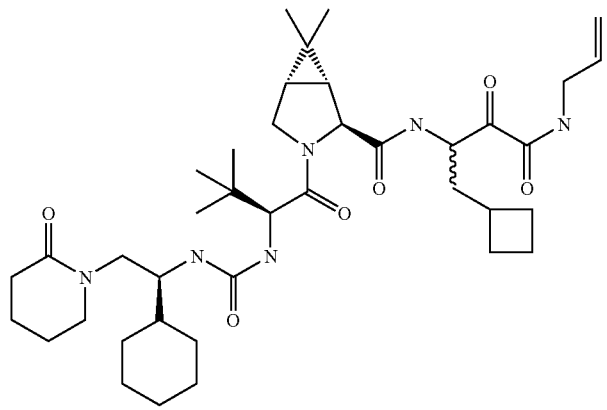
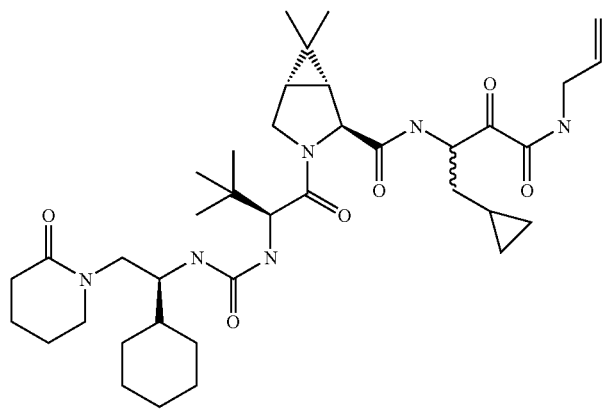
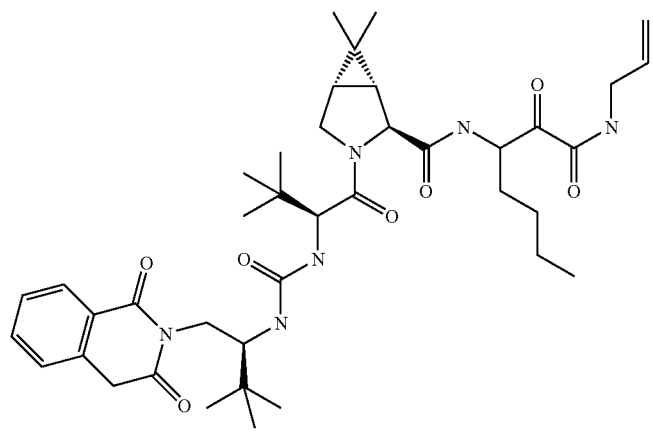
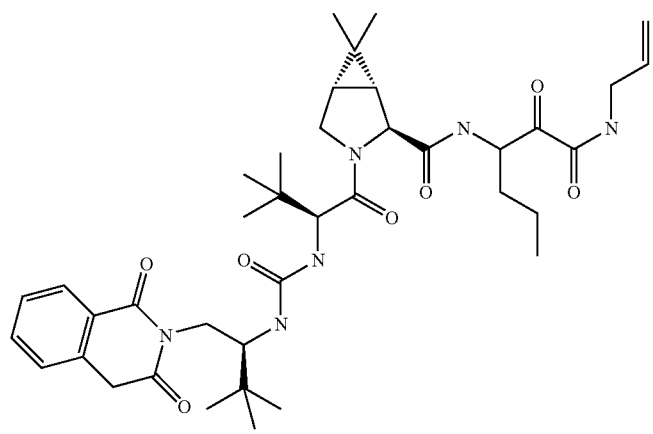

-continued
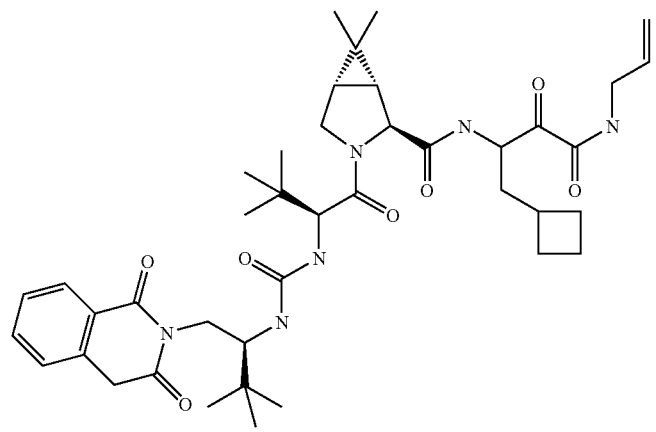
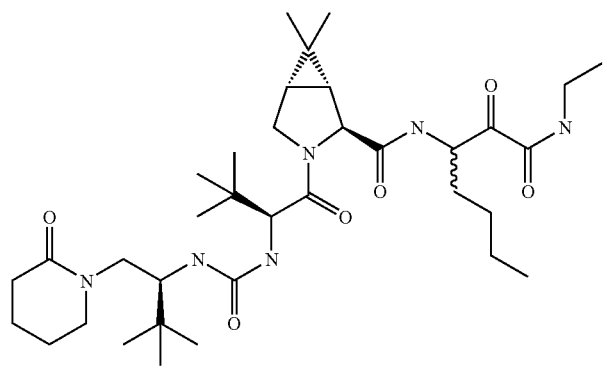
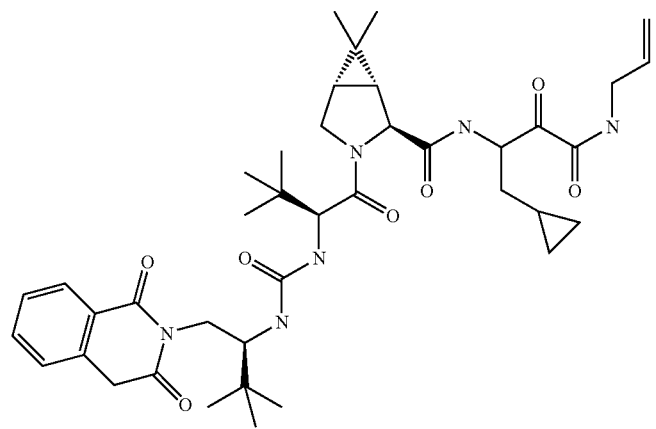

-continued
| 631 | 632 |
|---|---|
| 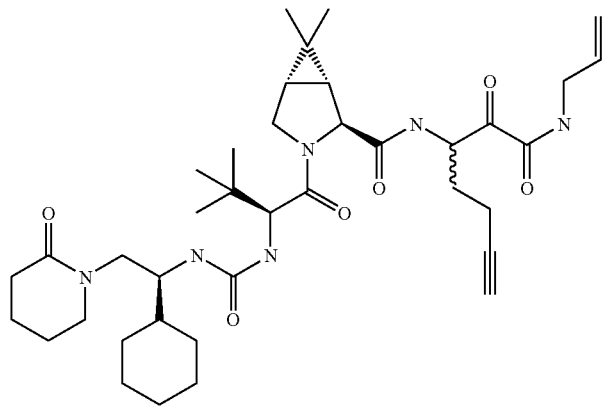 | 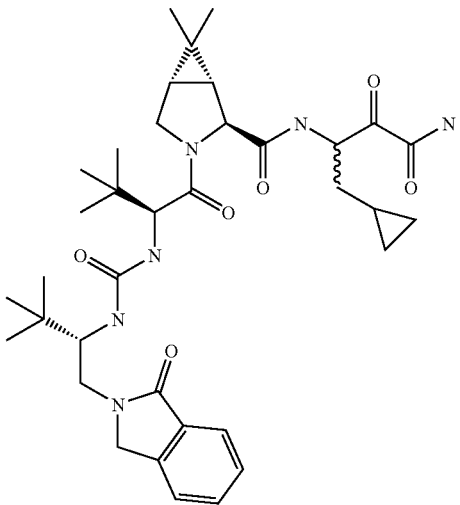 |
| 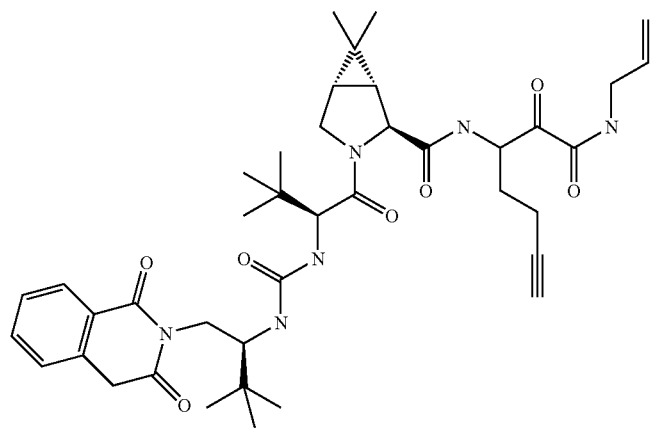 | 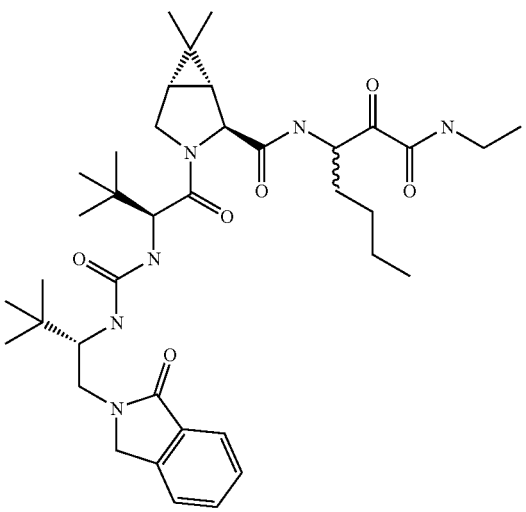 |
| 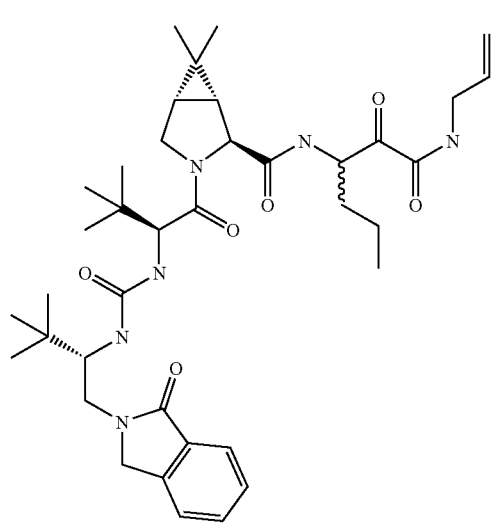 | 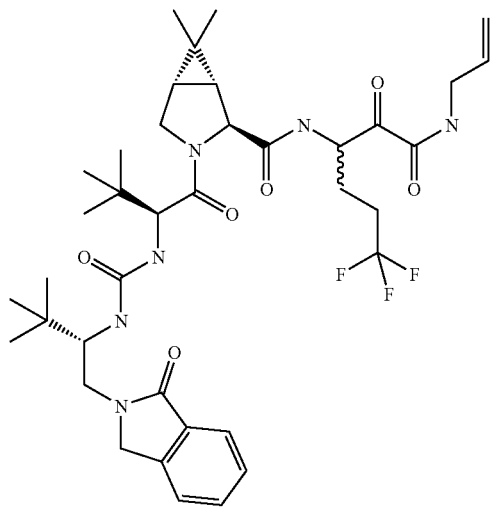 |

-continued
| 633 | 634 |
|---|---|
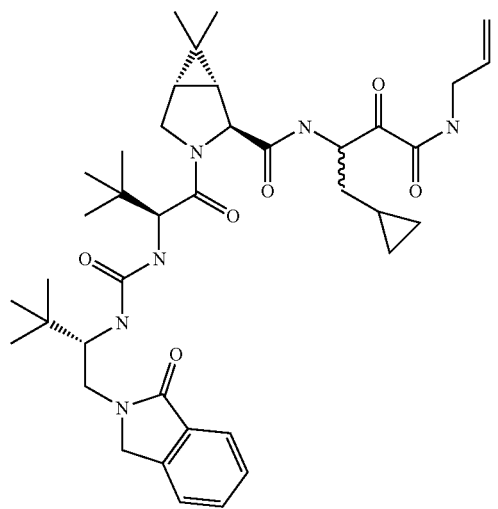
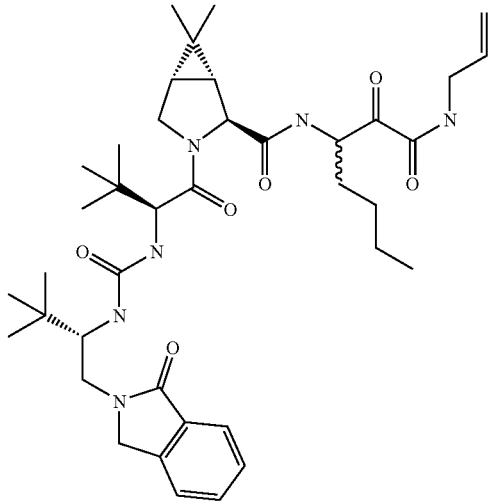
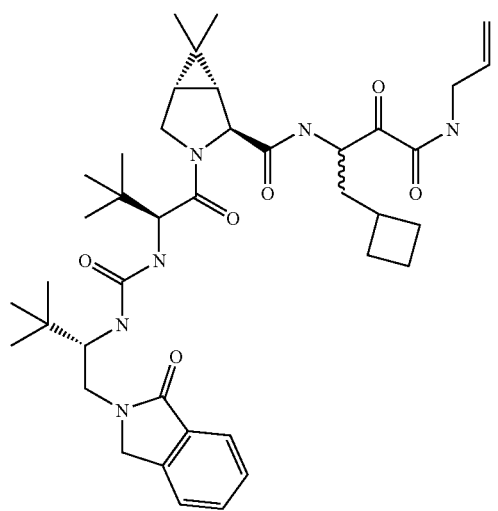
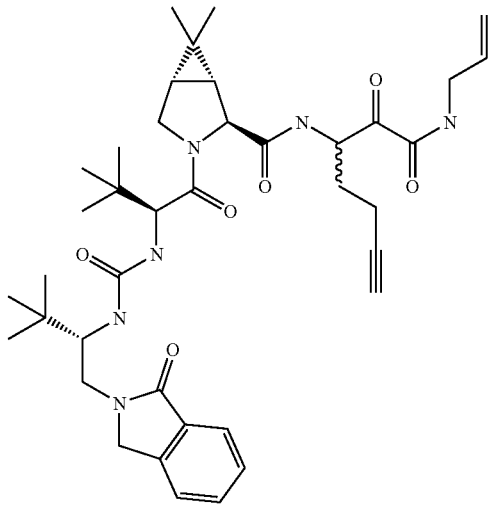
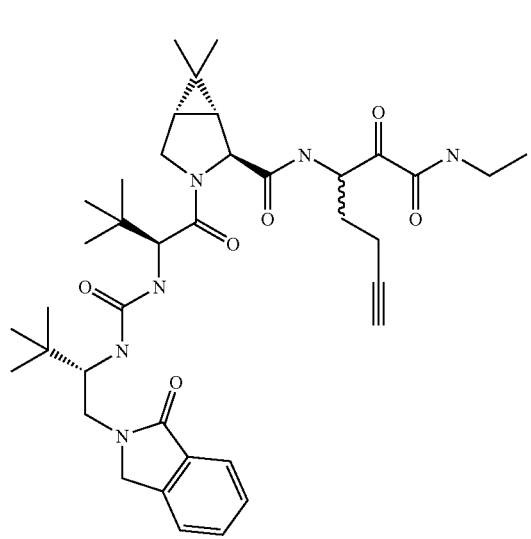
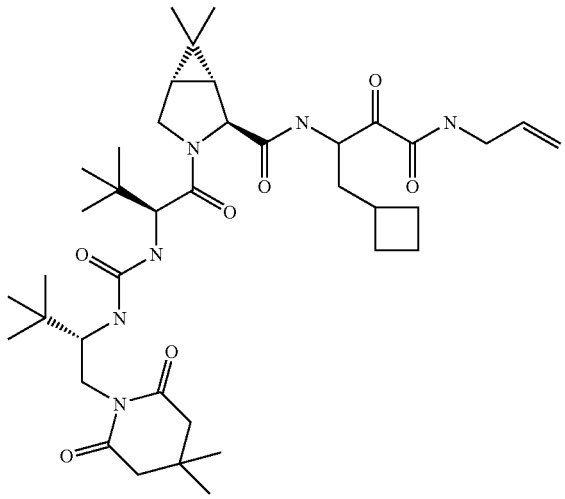

-continued
| 635 | 636 |
|---|---|
| 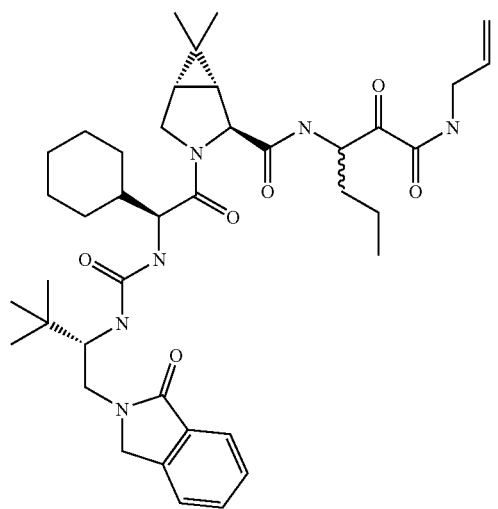 | 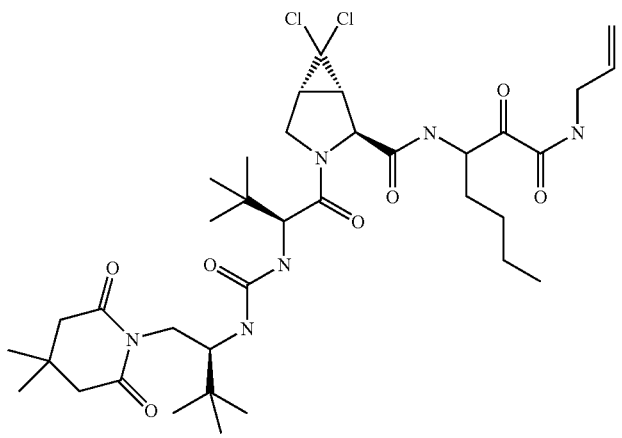 |
| 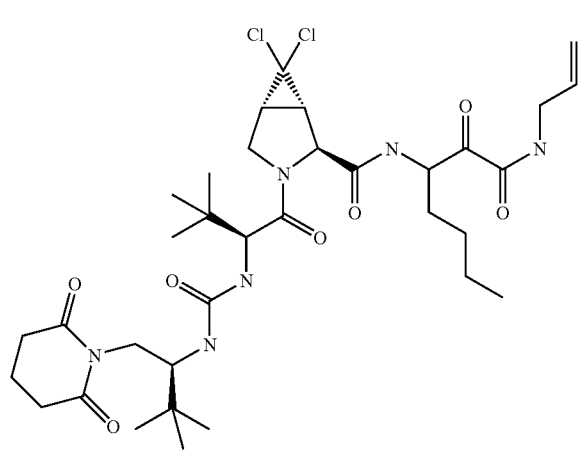 | 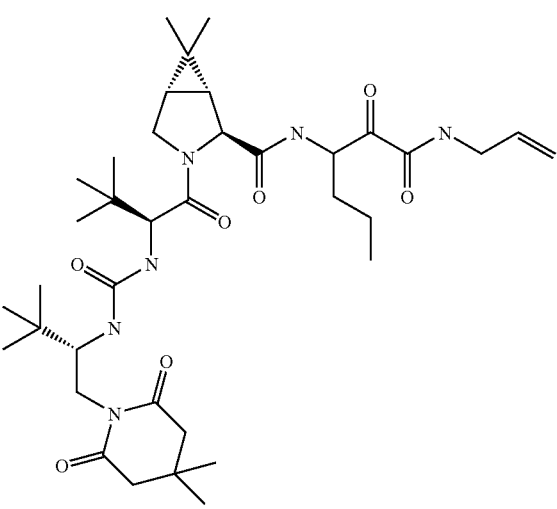 |
| 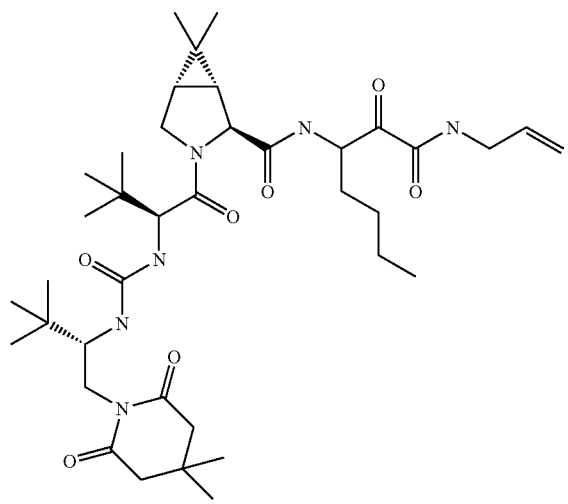 | 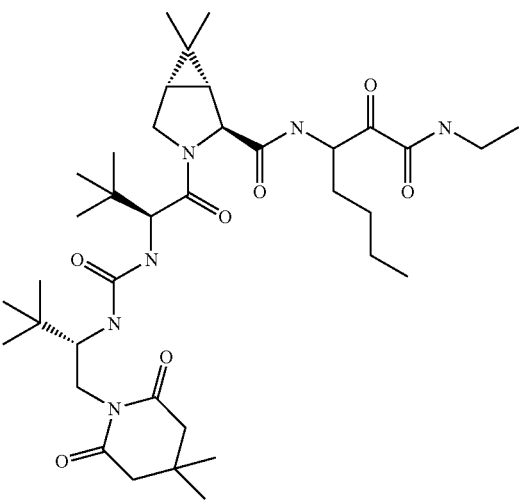 |

637    638
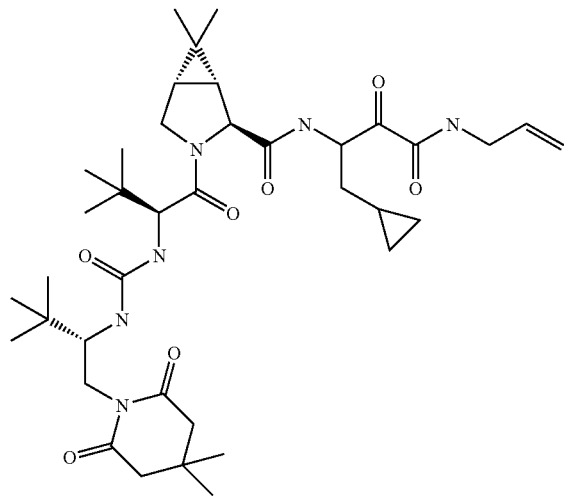
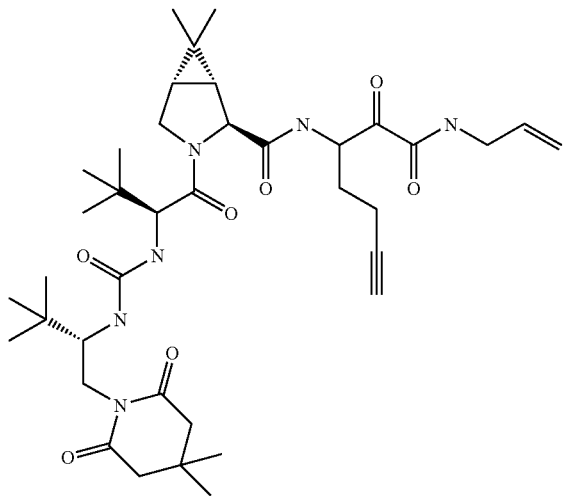
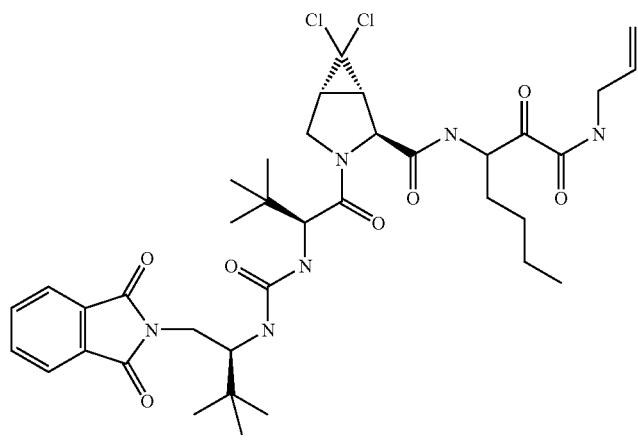
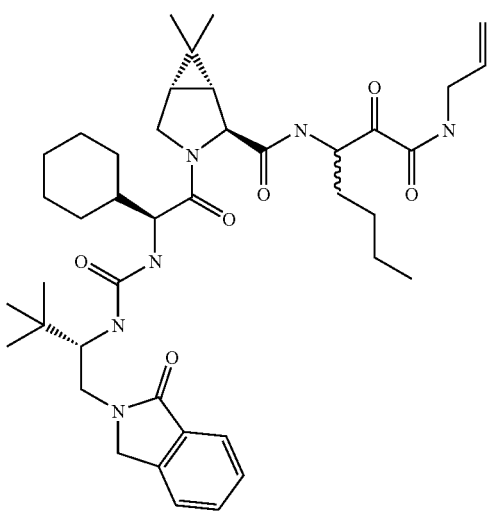
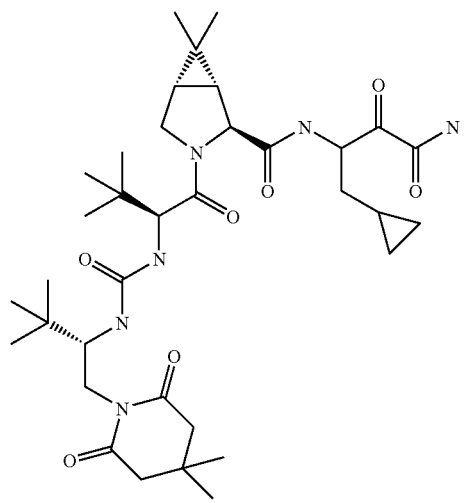
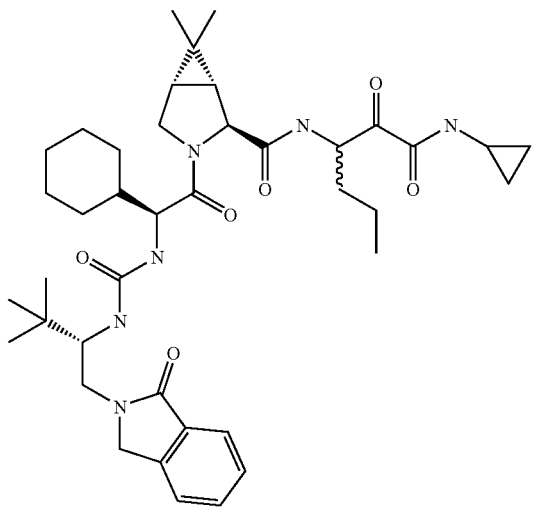

-continued
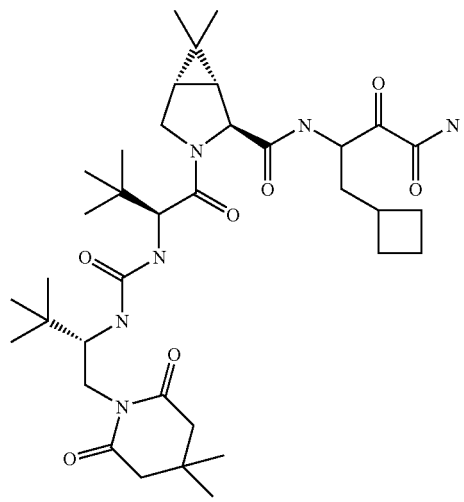
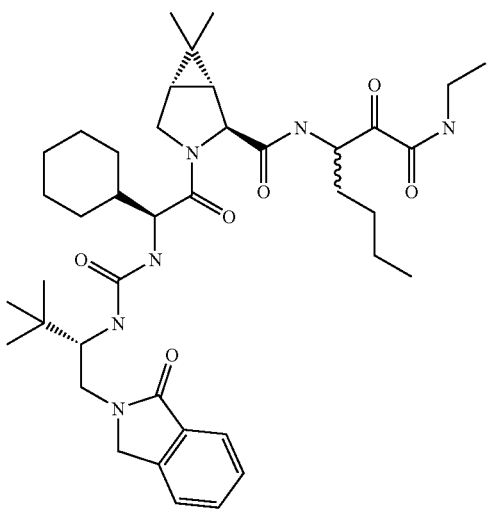
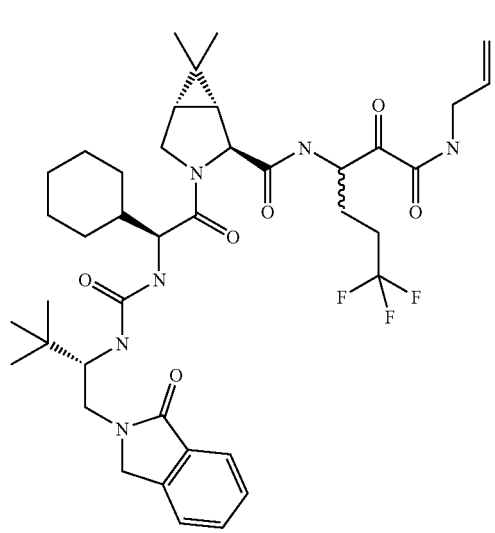
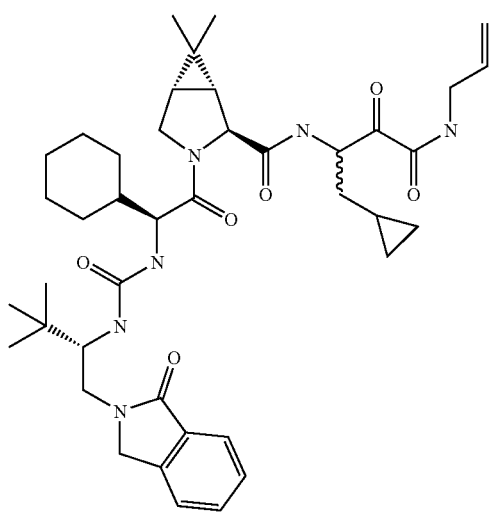
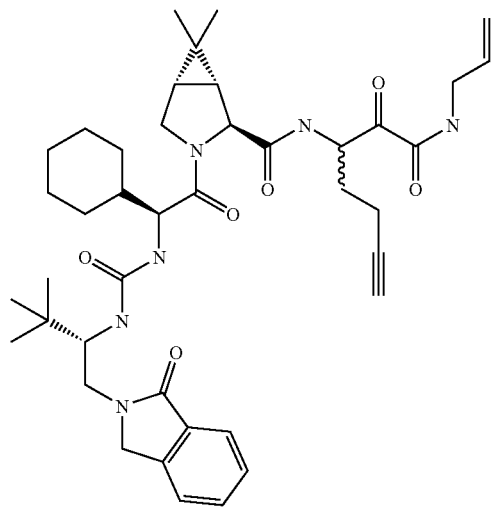
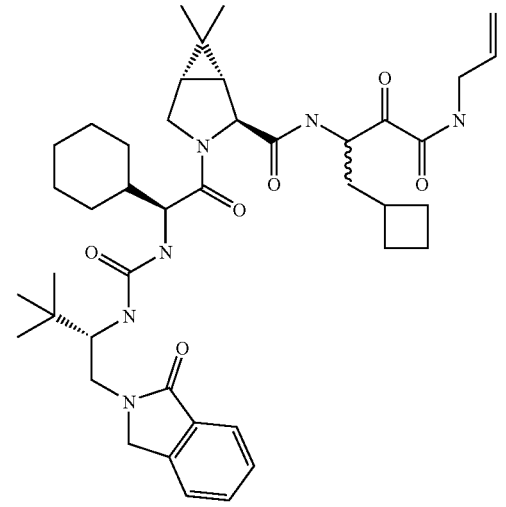

-continued
| 641 | 642 |
|---|---|
| 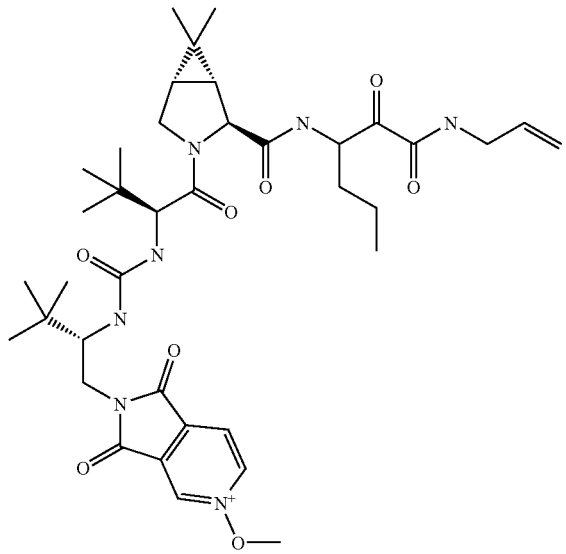 | 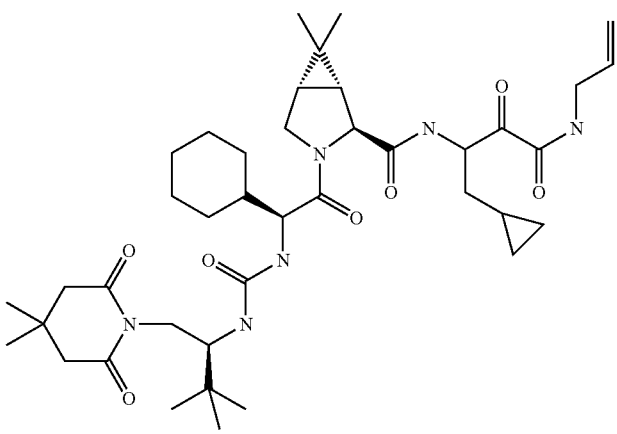 |
| 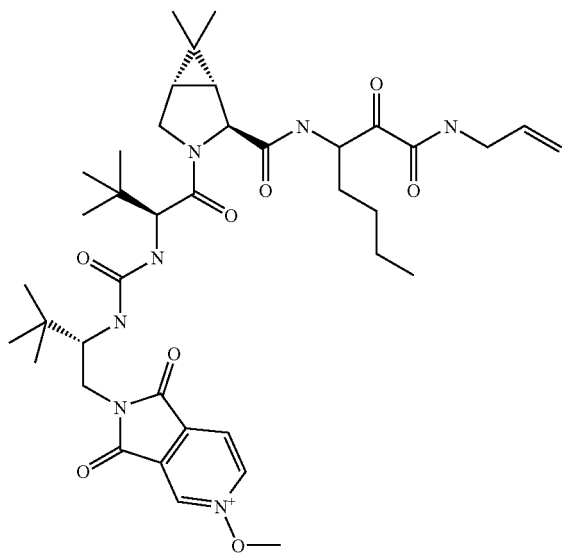 | 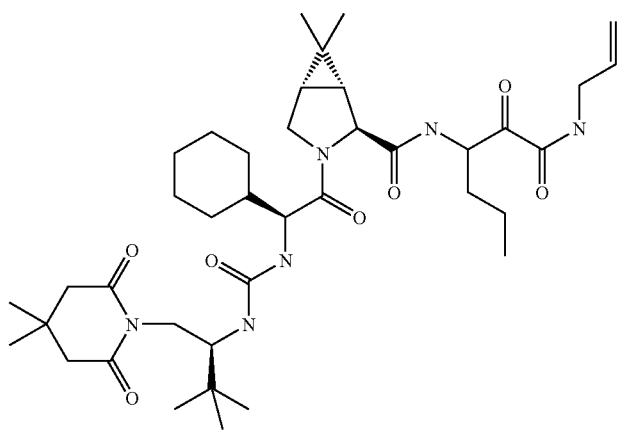 |
| 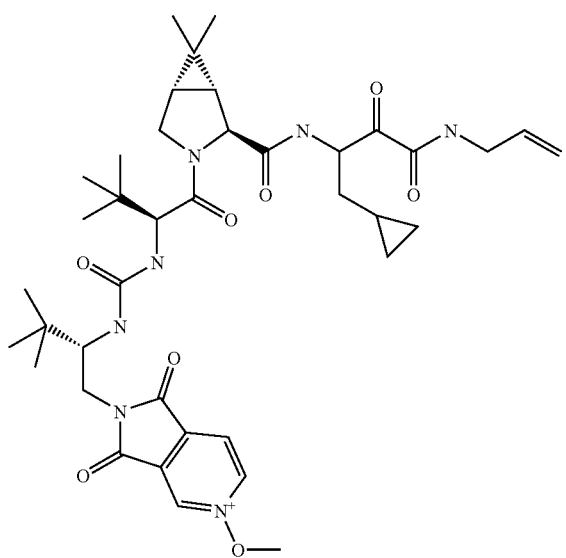 | 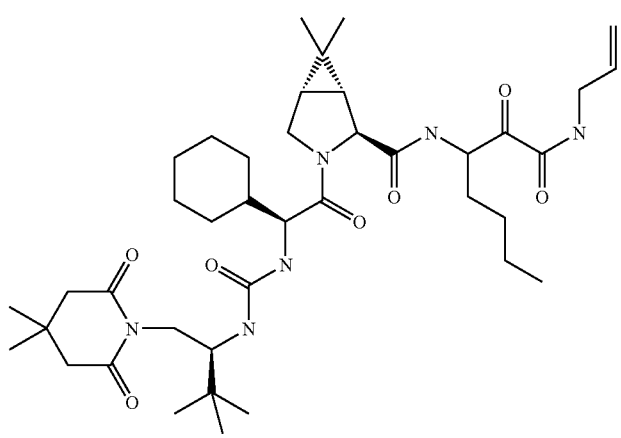 |

643                    644
-continued
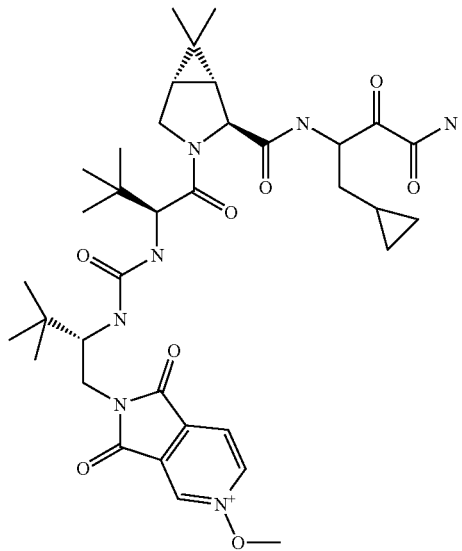
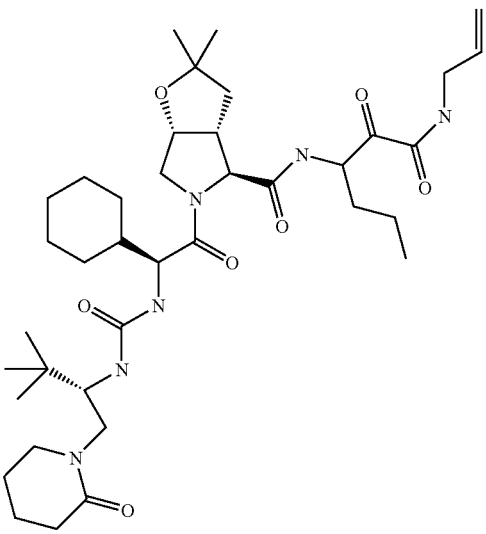
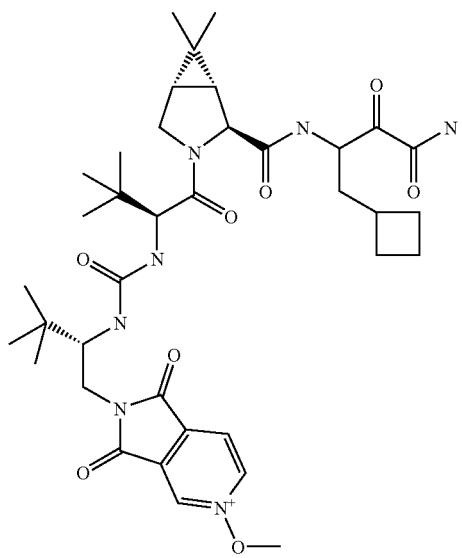
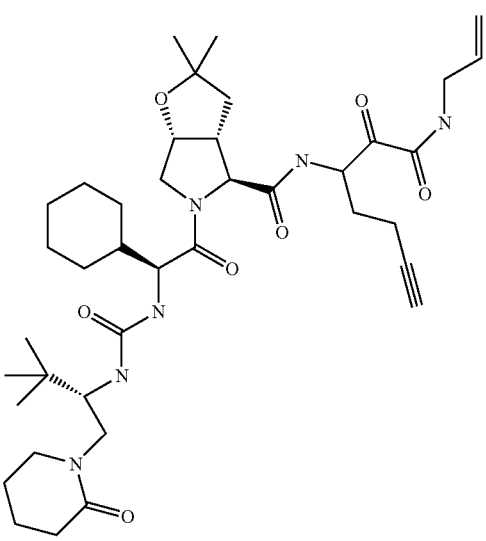
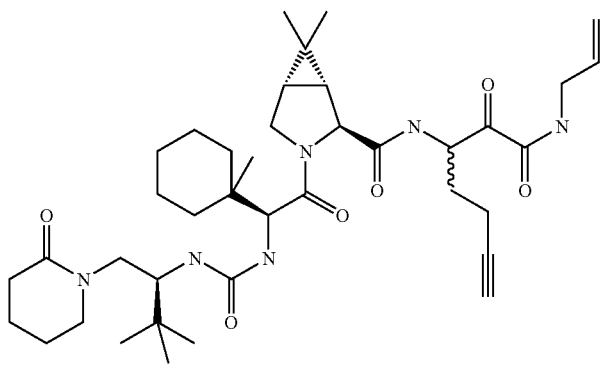

645
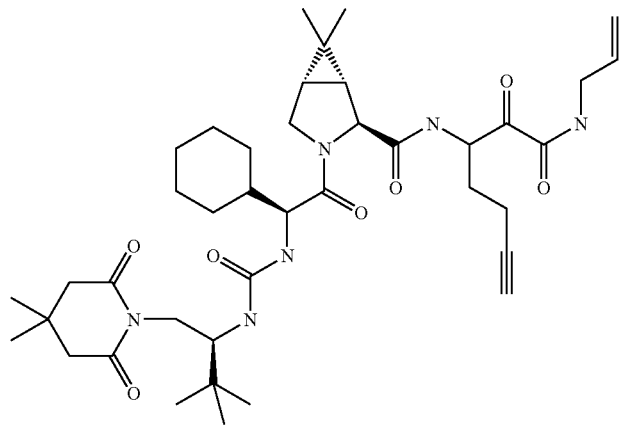
-continued
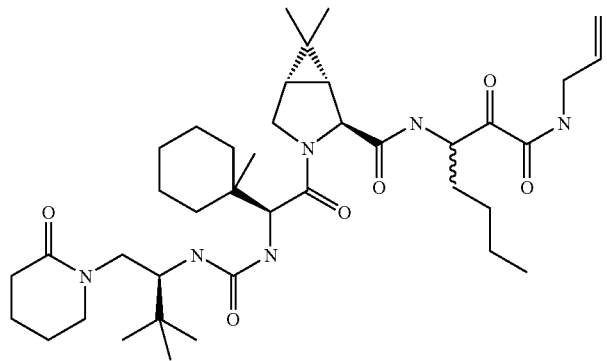
646
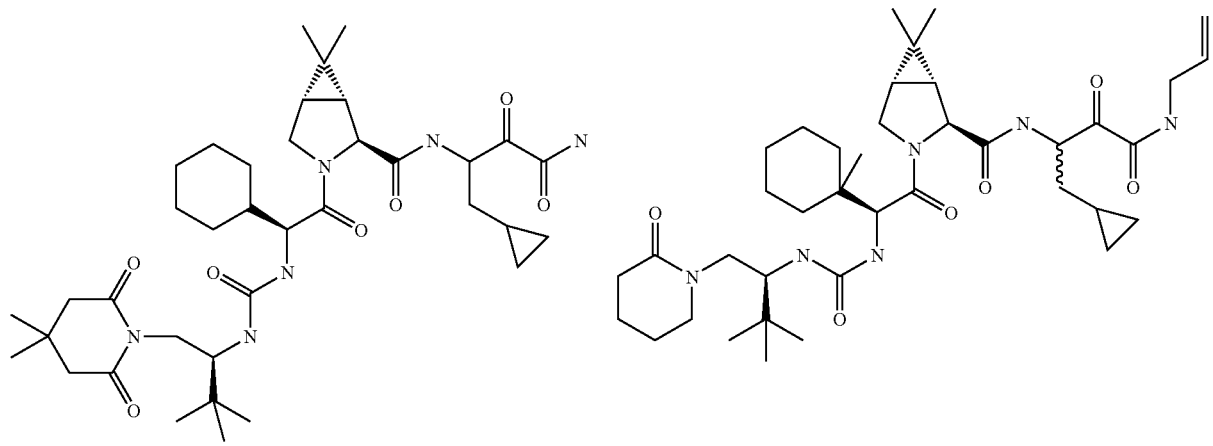
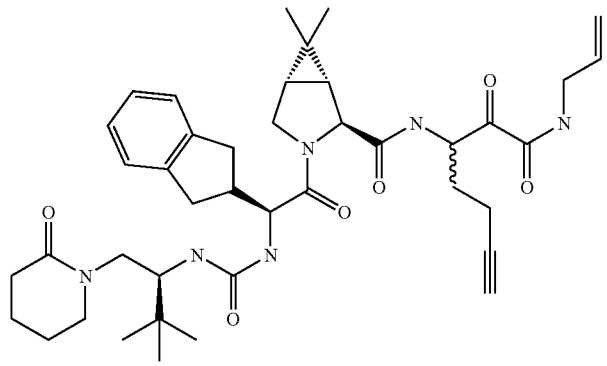

647                                    648
-continued
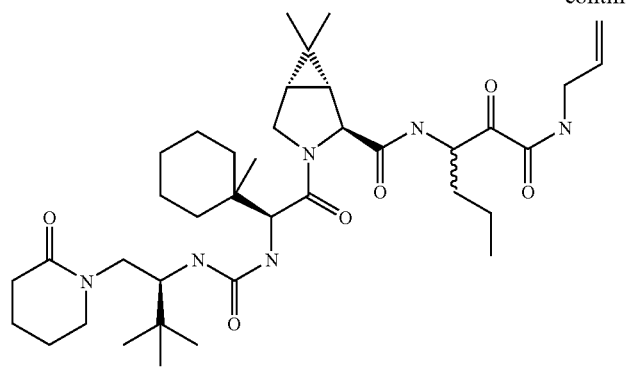
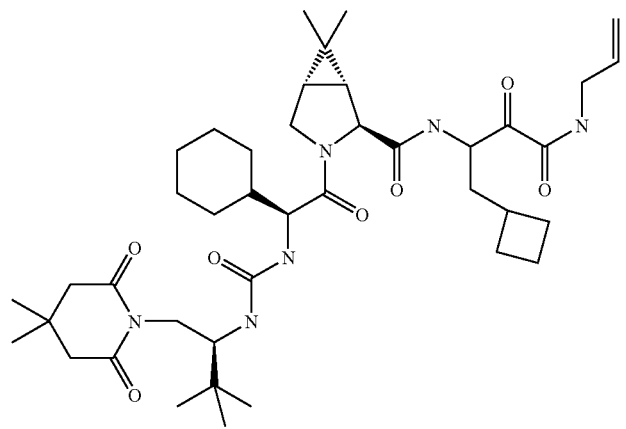
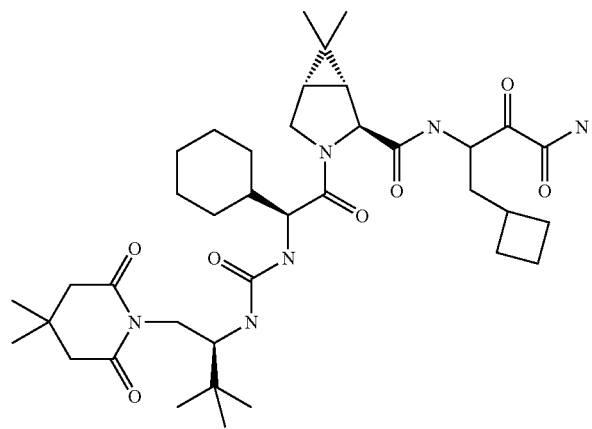
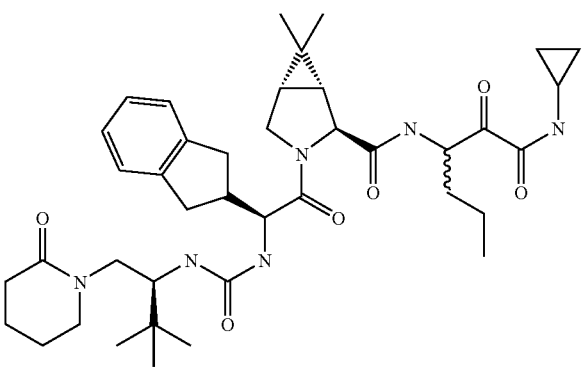
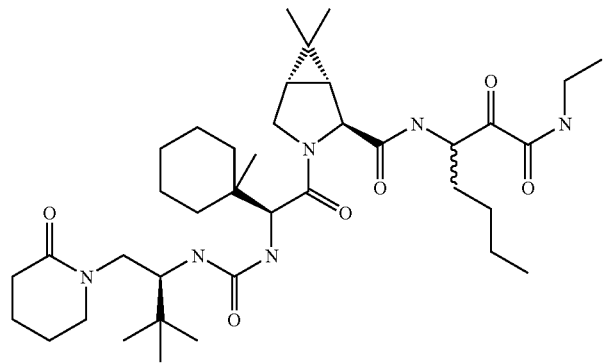

-continued
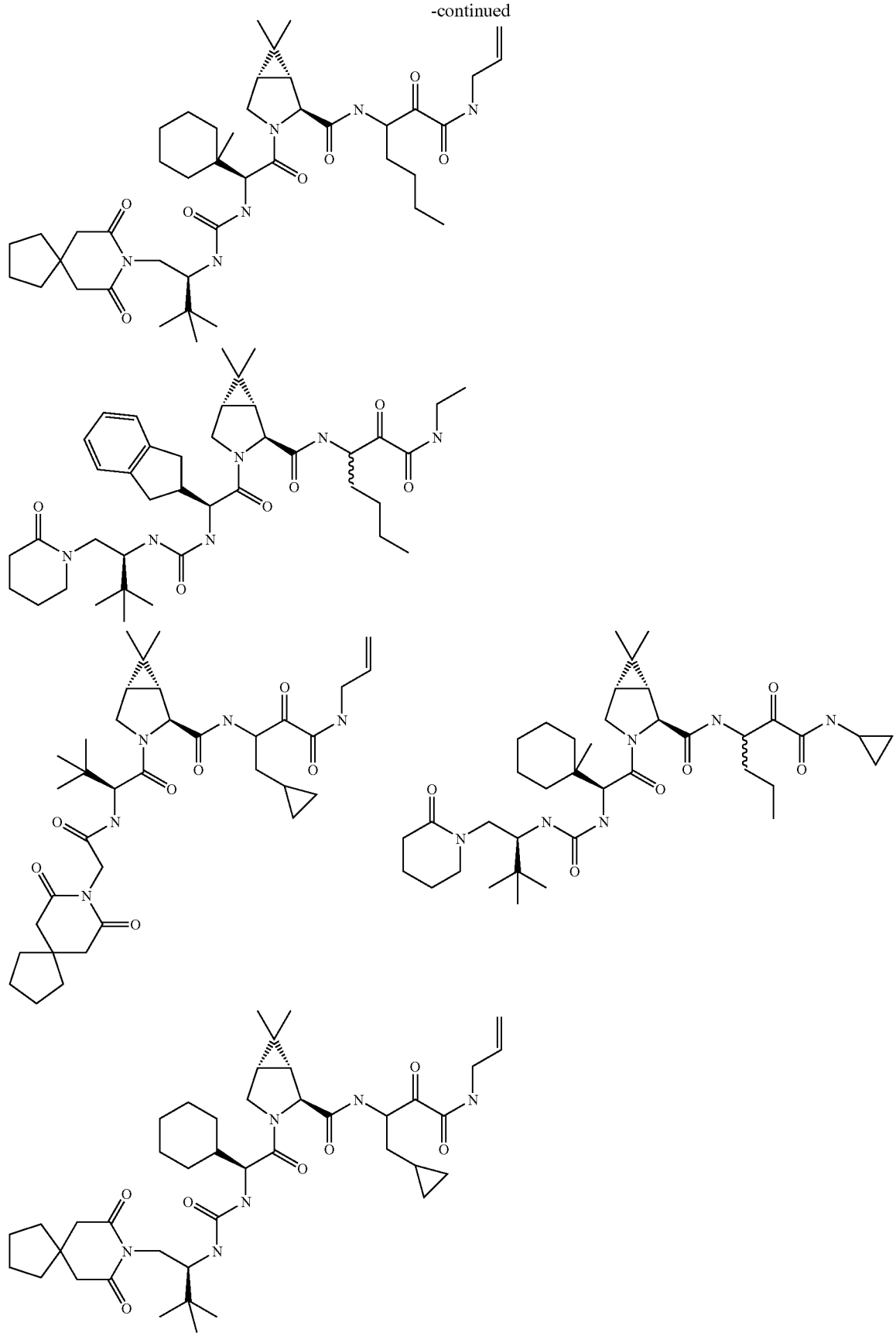

651
652
-continued
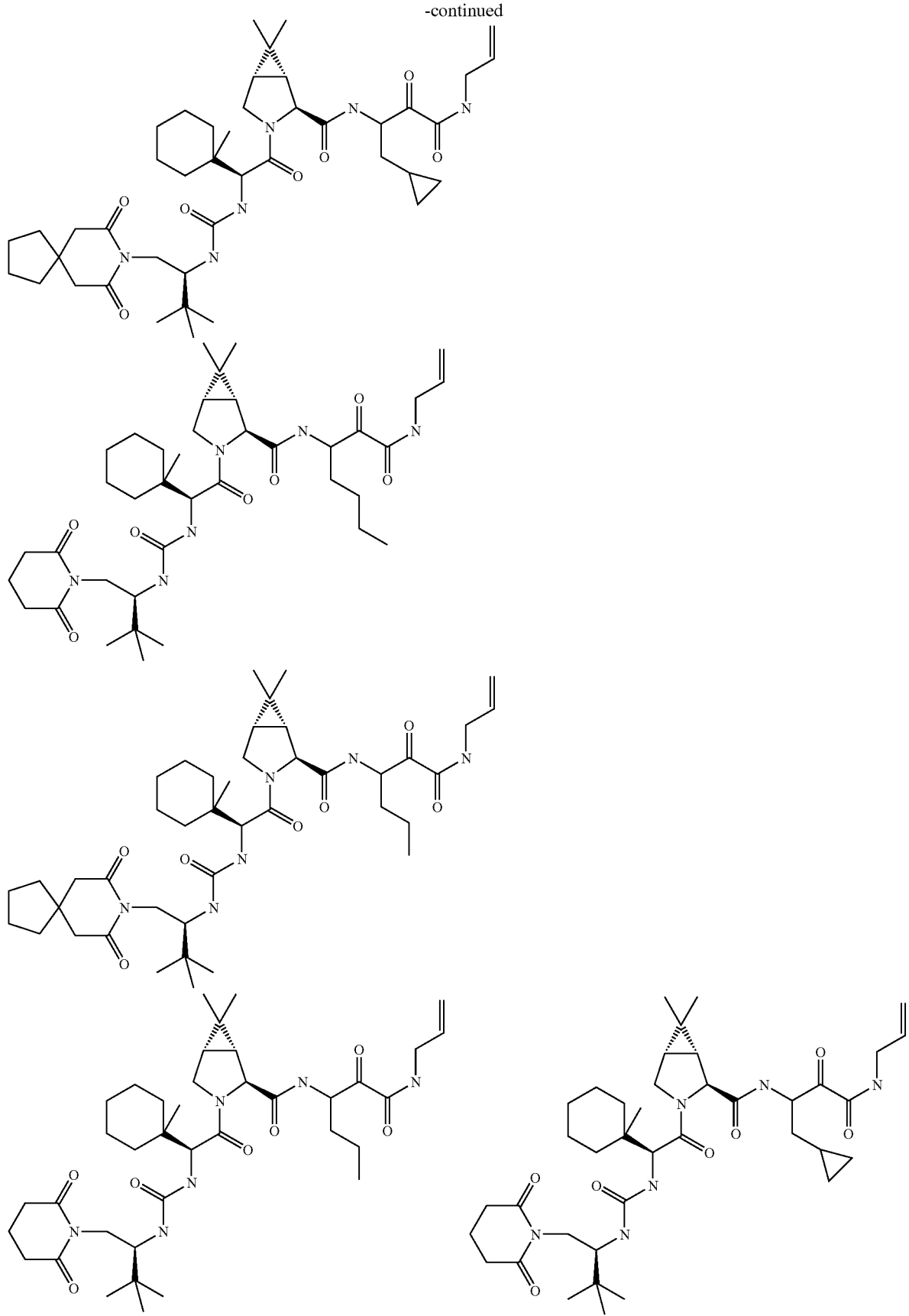

653
-continued
654
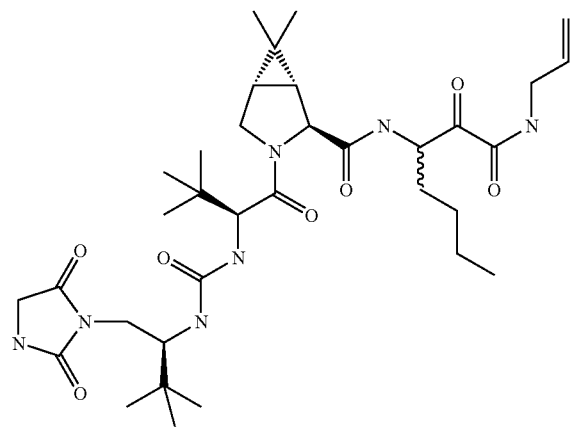
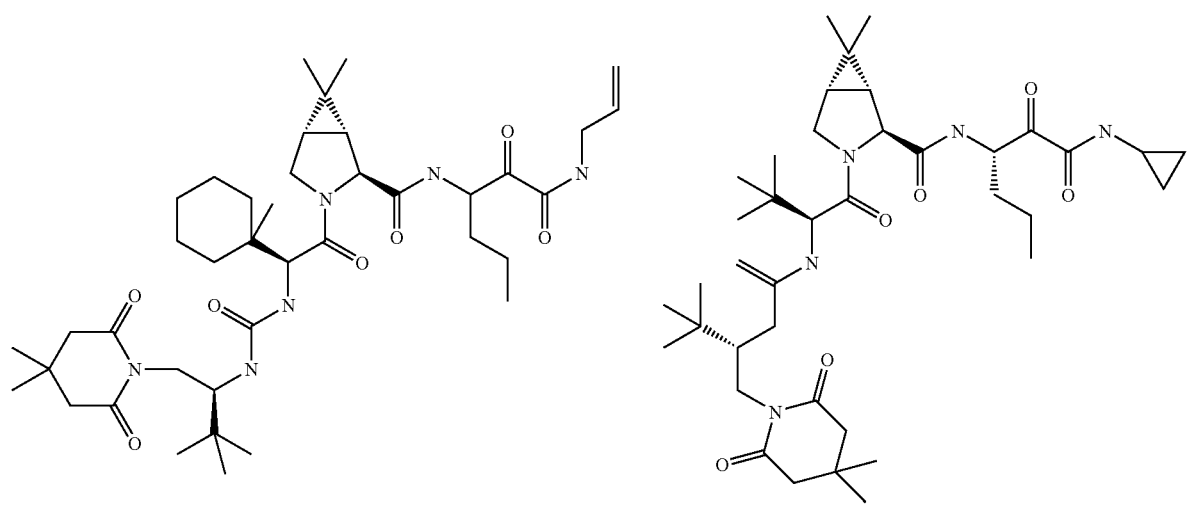
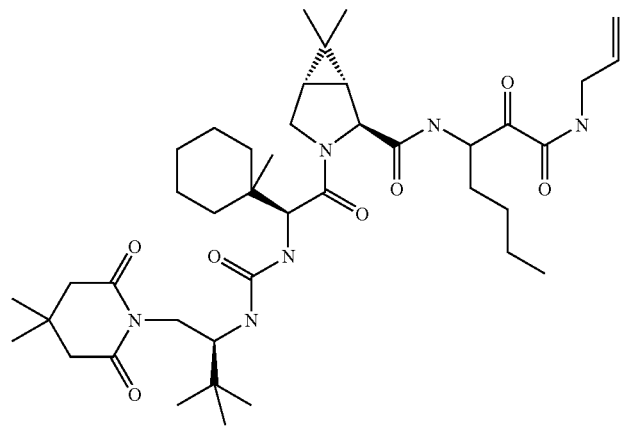

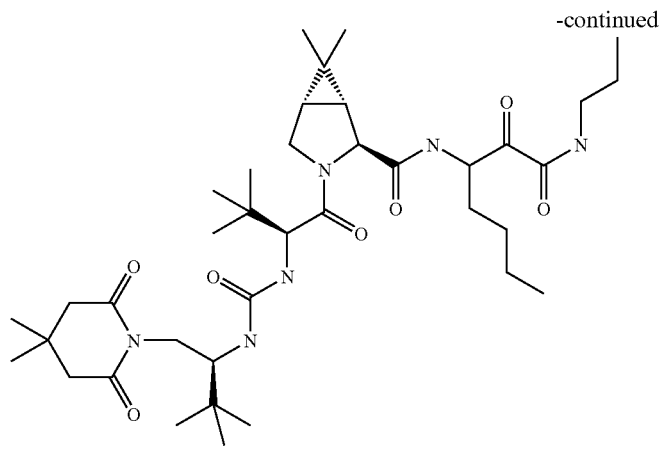
or a pharmaceutically acceptable salt, solvate or ester thereof.
Compounds of formula XIV are disclosed in U.S. patent application Ser. No. 11/064,673 filed Feb. 24, 2005. The preparation of these compounds is disclosed in the experimental section of this application set forth hereinbelow.
Non-limiting examples of certain compounds disclosed in U.S. patent application Ser. No. 11/064,673 are:
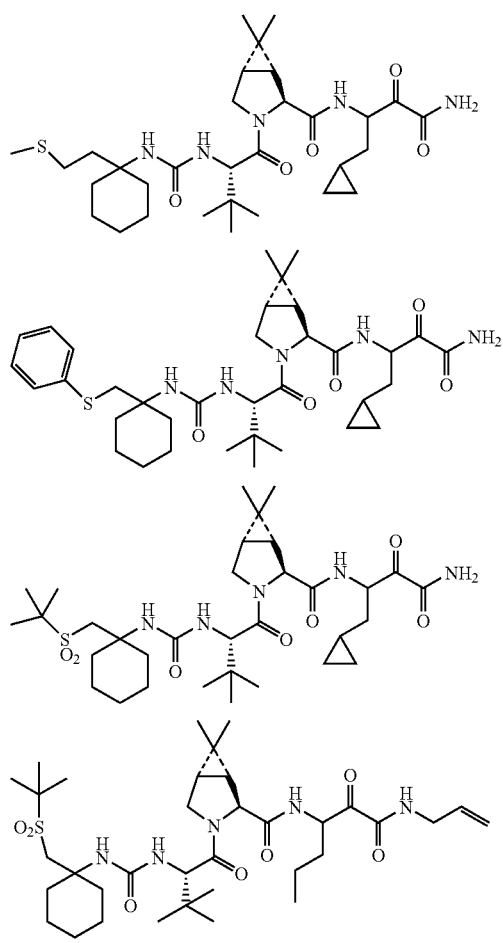
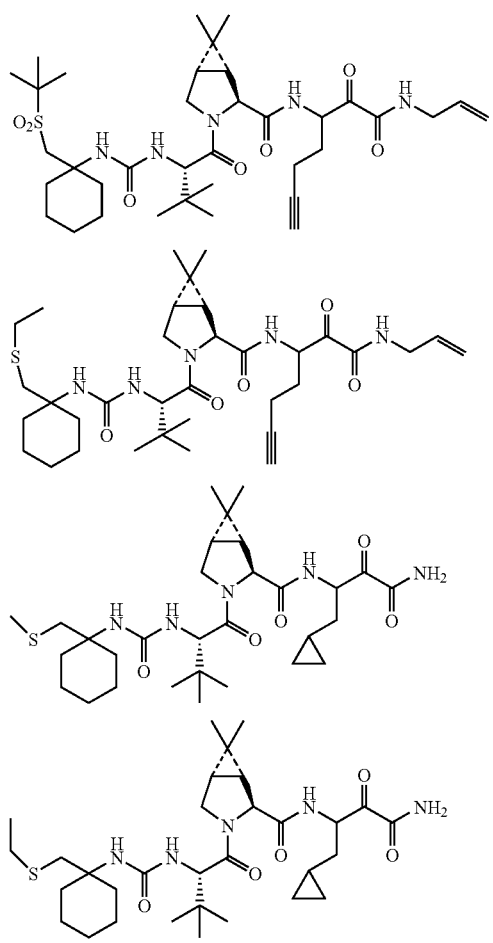

657 658
-continued
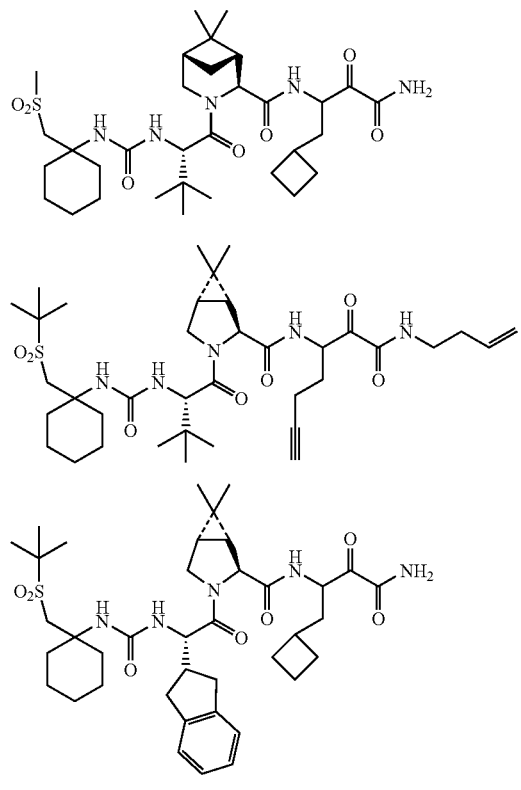
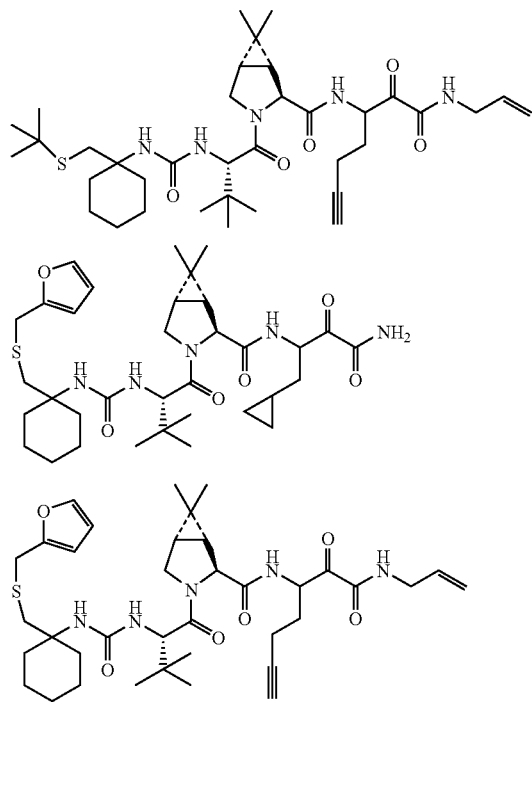
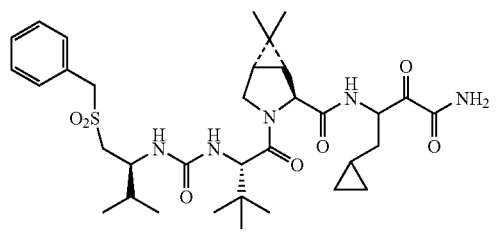
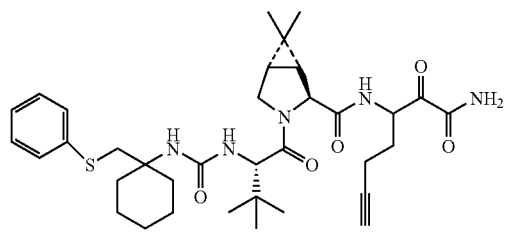
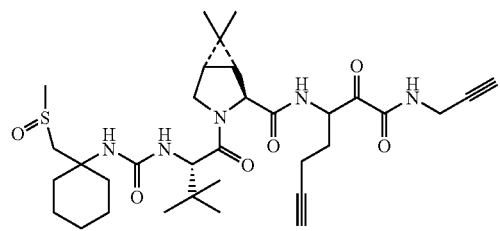
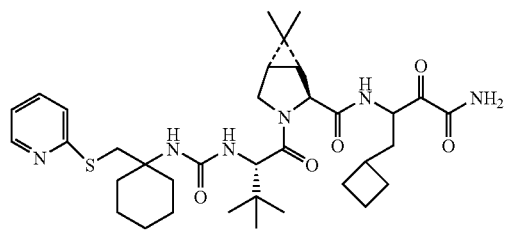
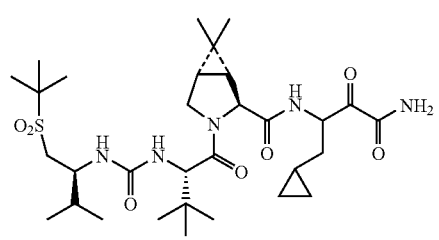
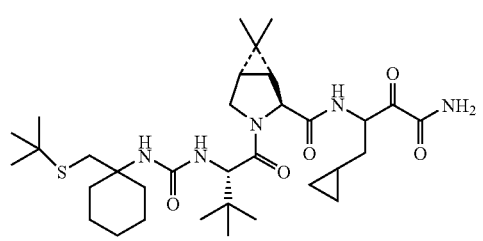

659 660
-continued
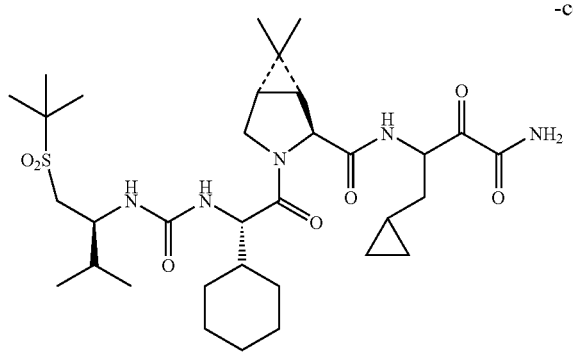
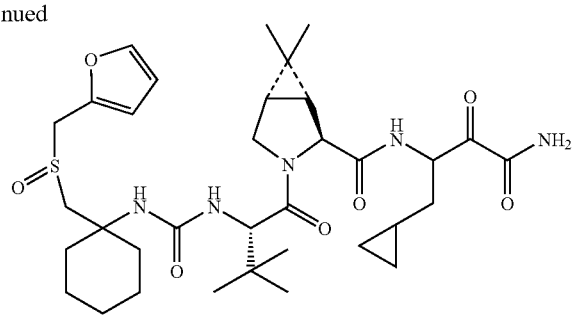
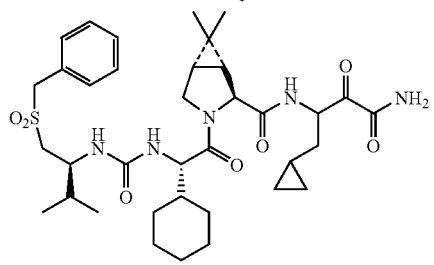
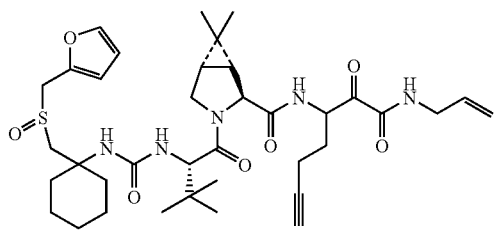
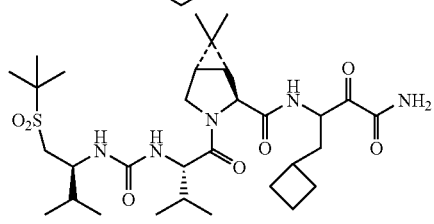
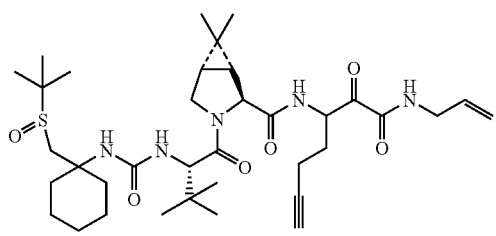
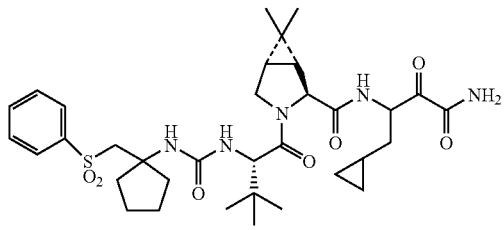
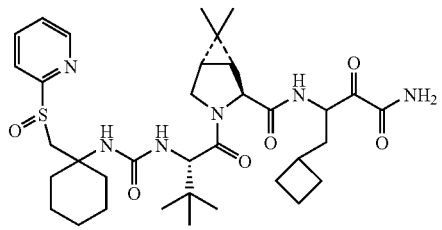
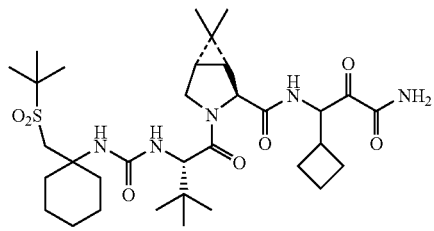
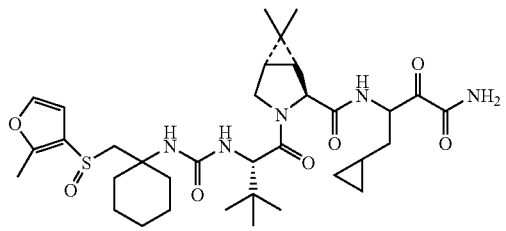
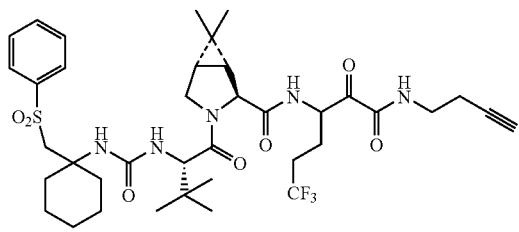
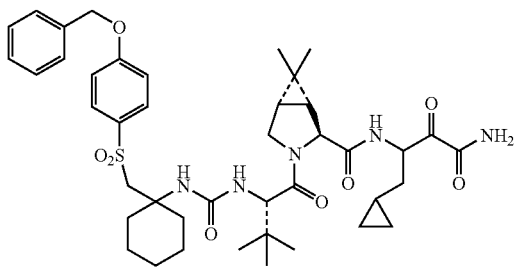

661
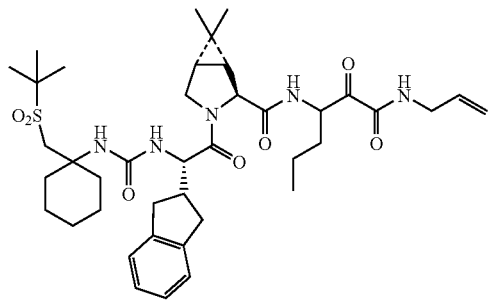
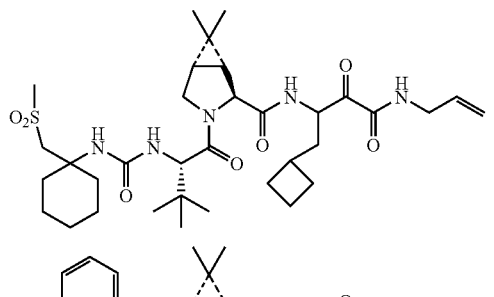
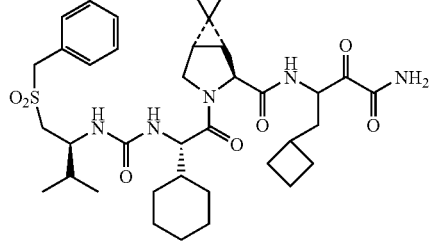
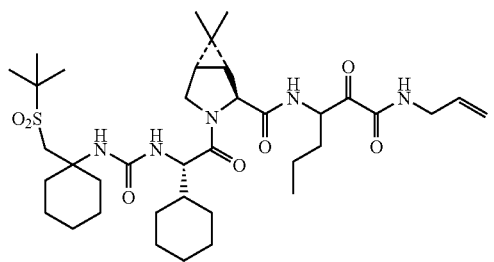
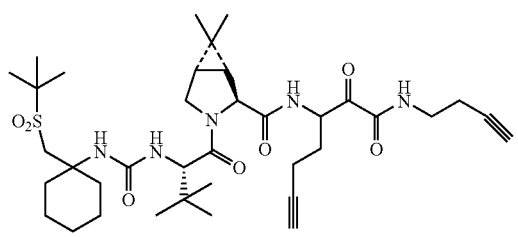
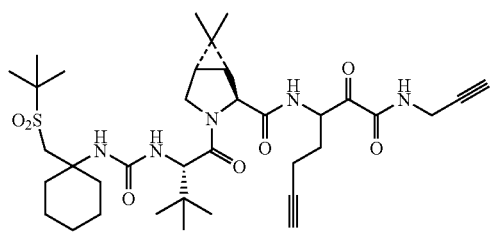
662
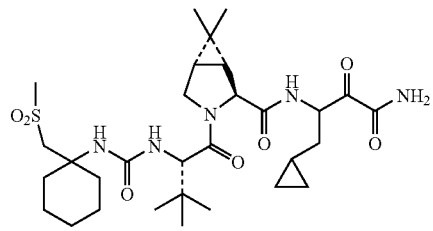
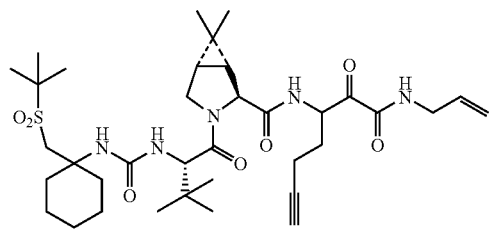
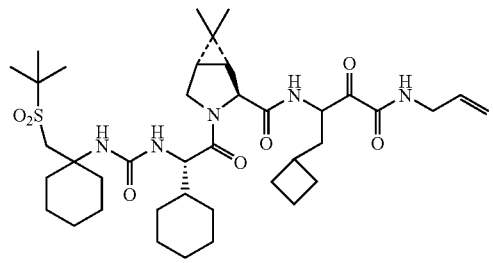
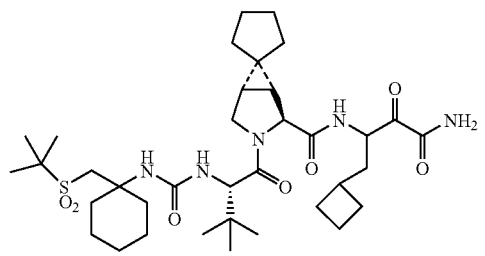
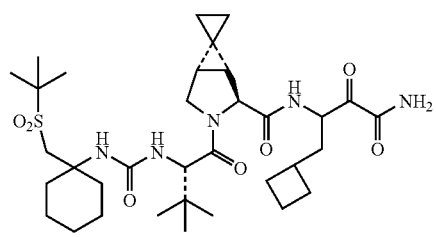
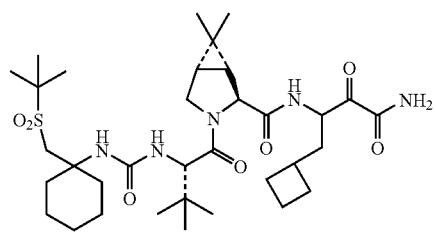

-continued
| 663 | 664 |
|---|---|
| 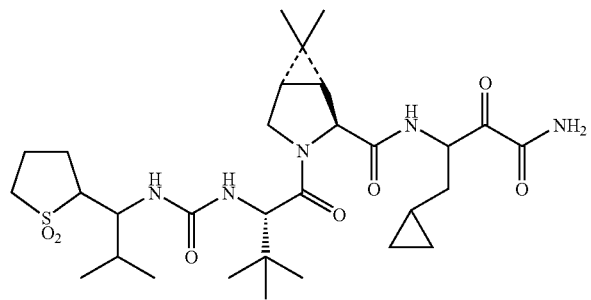 | 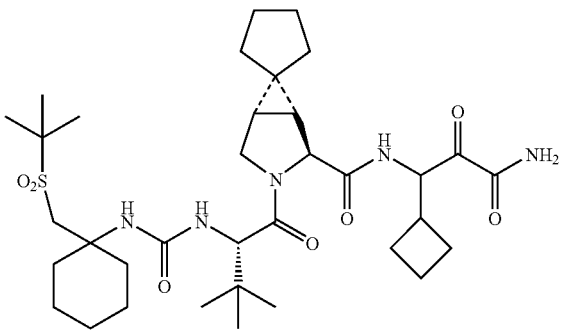 |
| 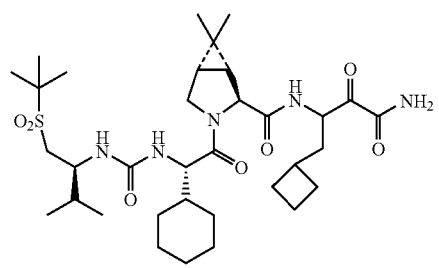 | 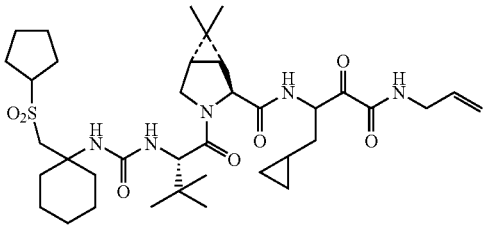 |
| 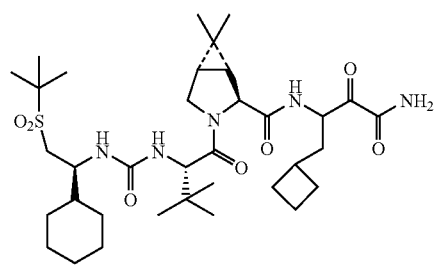 | 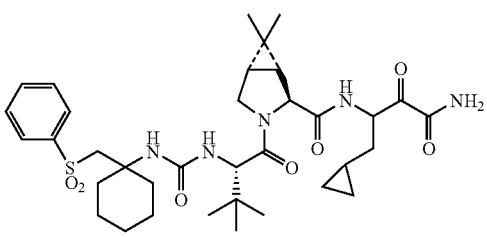 |
| 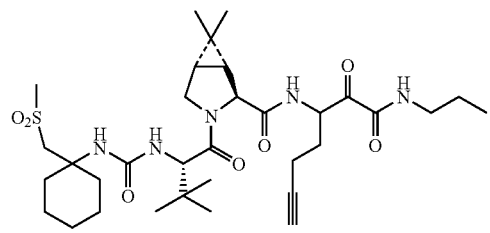 | 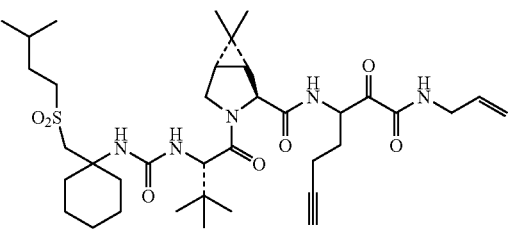 |
| 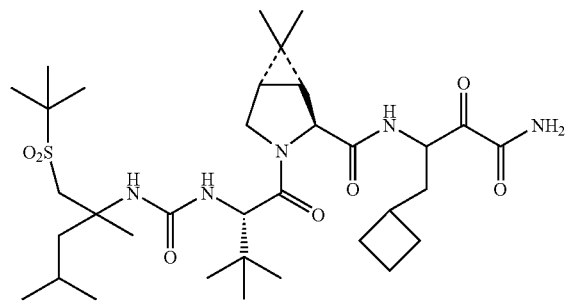 | 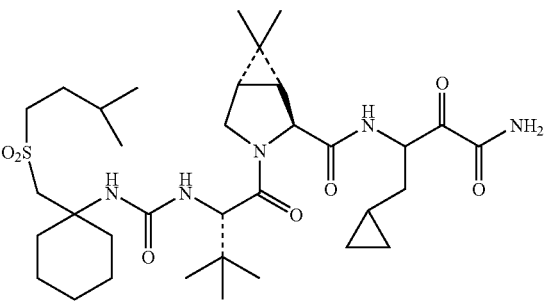 |
| 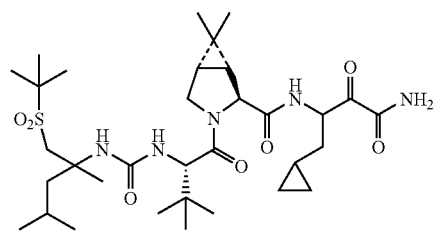 | 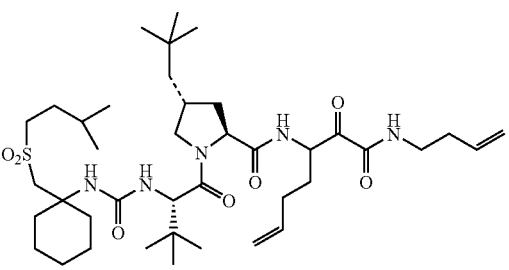 |

665
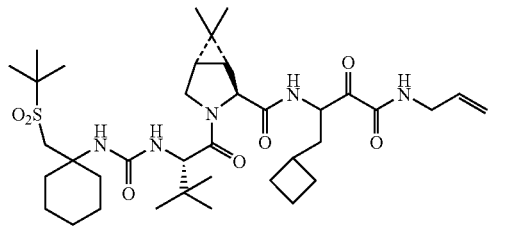
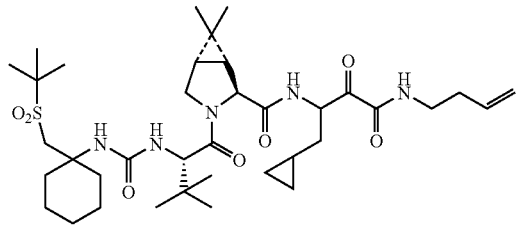
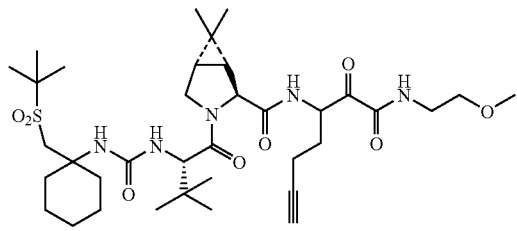
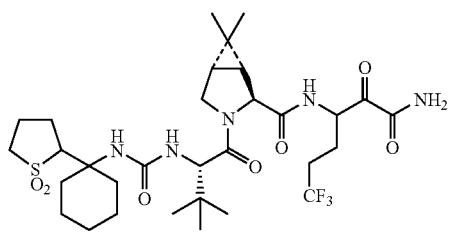
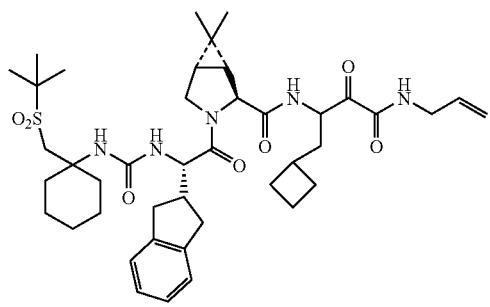
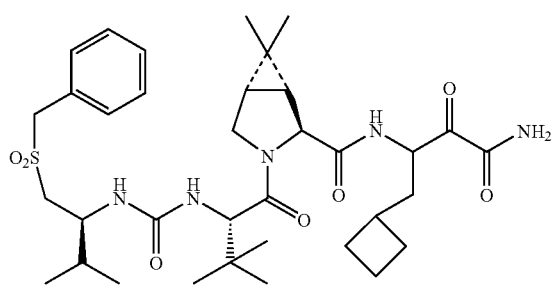
666
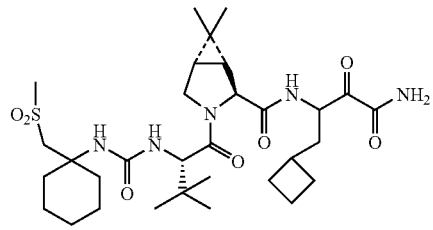
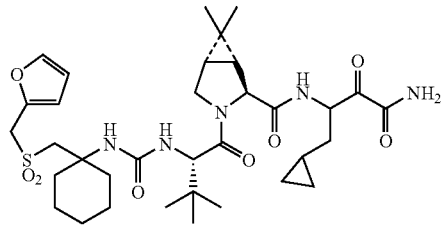
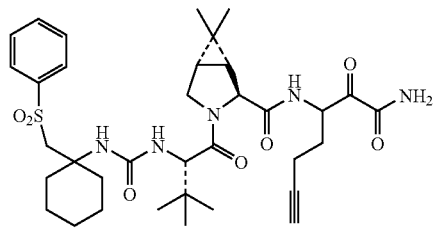
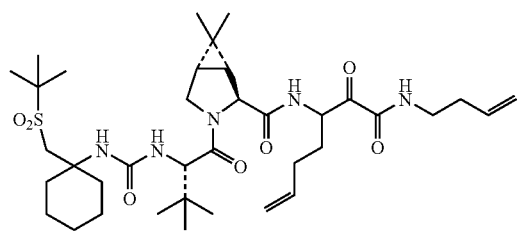
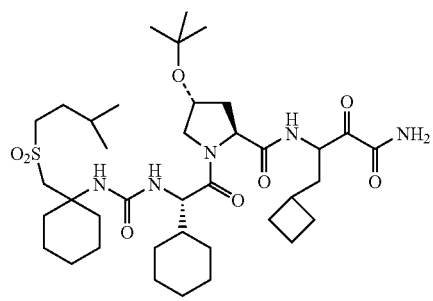
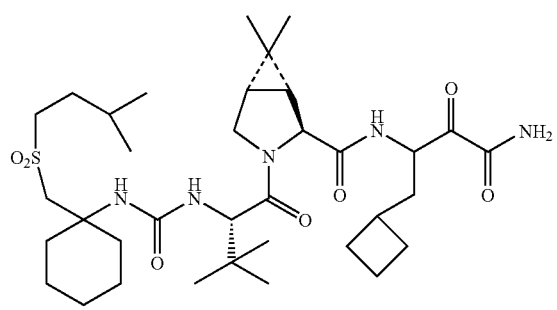

667 668
-continued
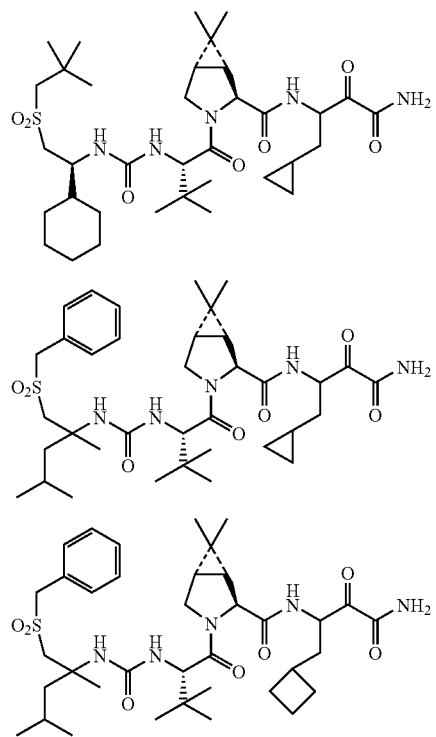
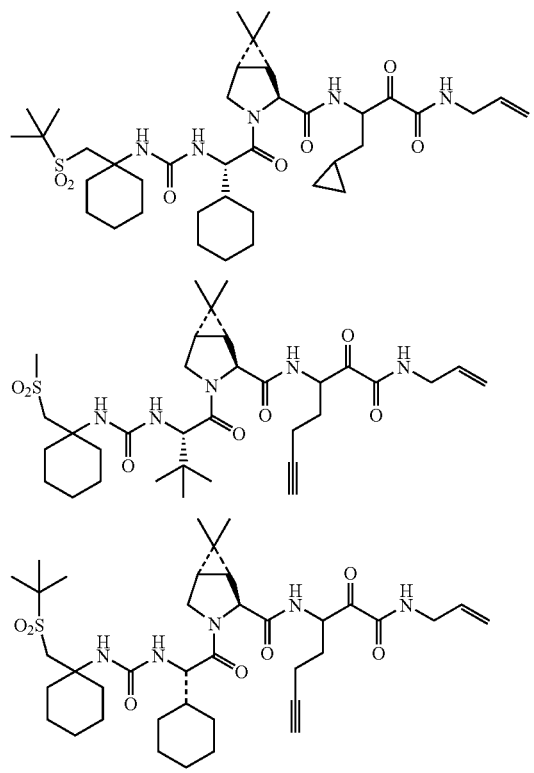
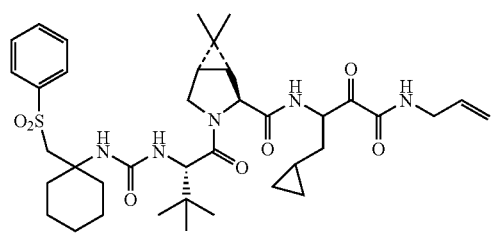
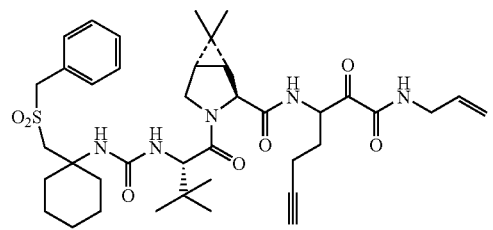
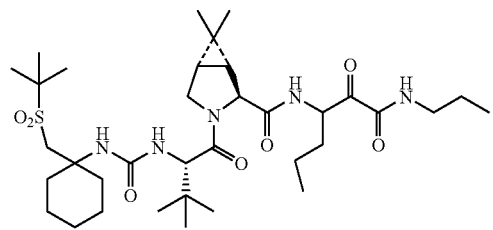
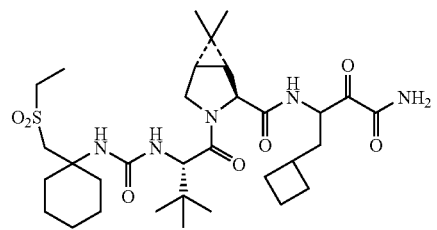
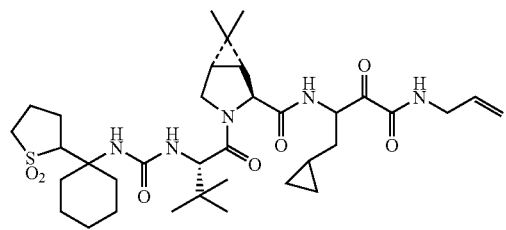

669
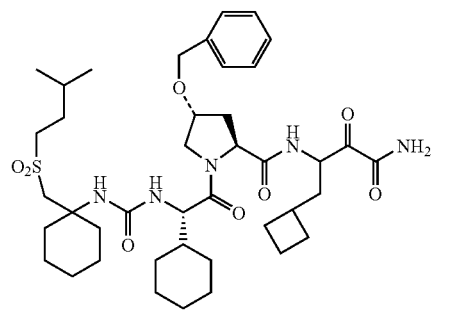
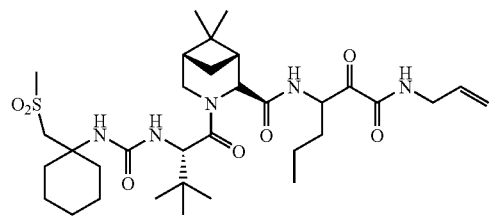
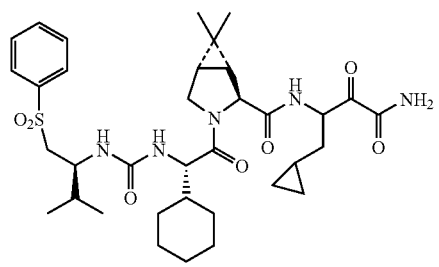
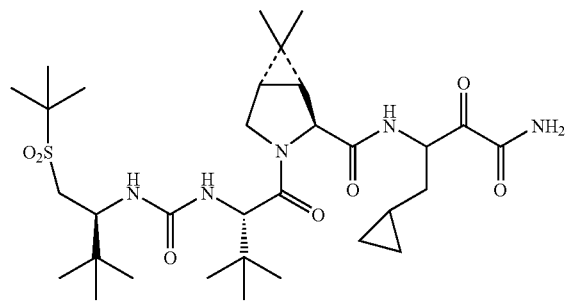
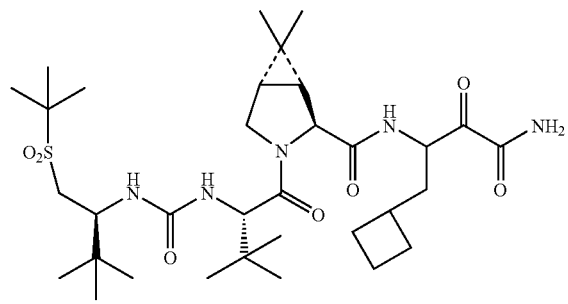
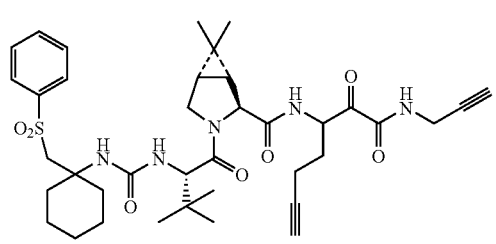
670
-continued
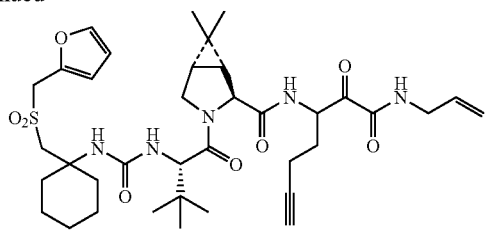
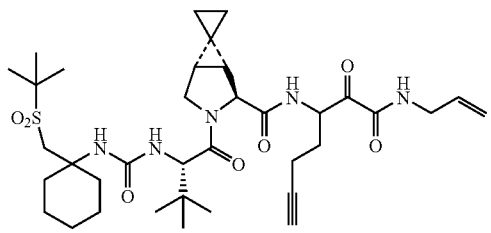
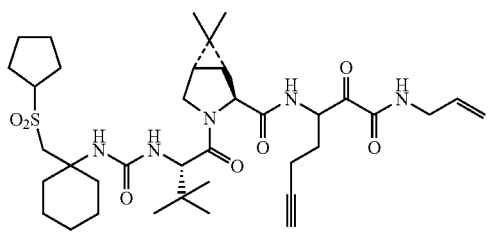
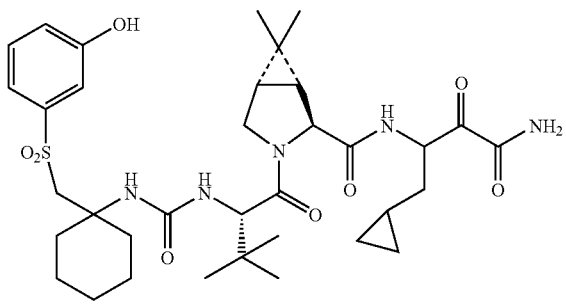
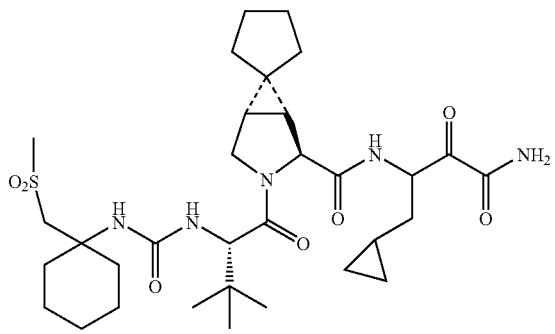
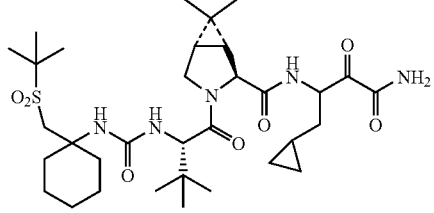

-continued
| 671 | 672 |
|---|---|
| 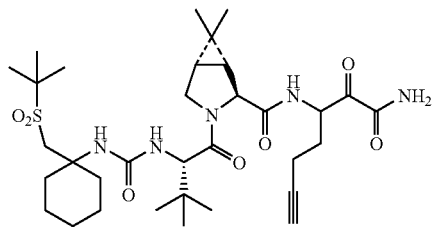 | 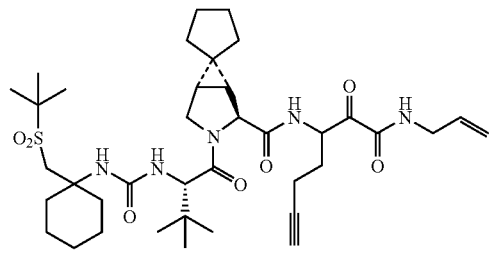 |
| 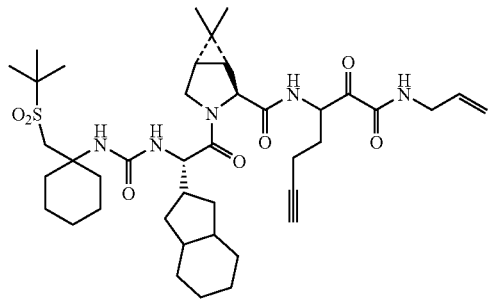 | 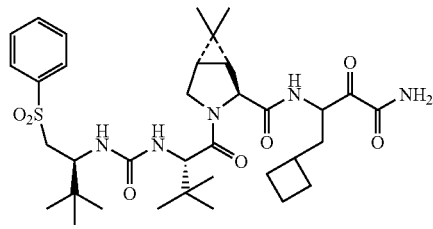 |
| 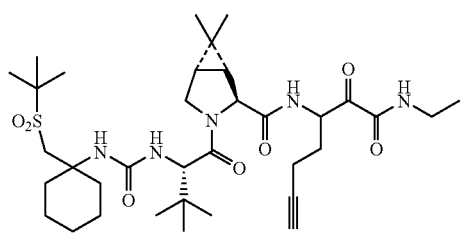 | 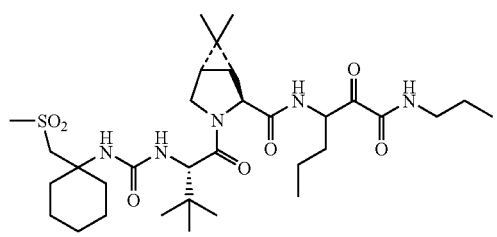 |
| 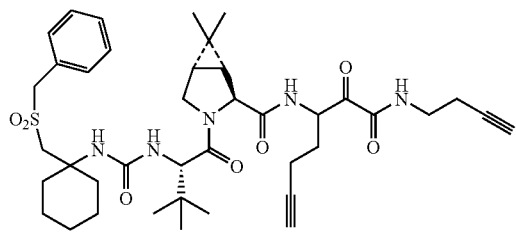 | 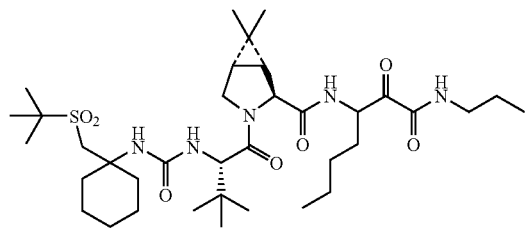 |
| 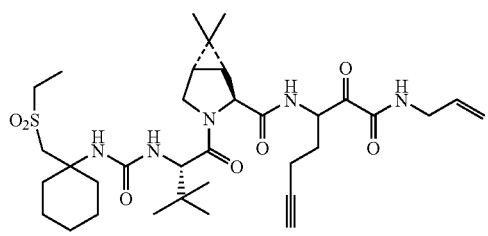 | 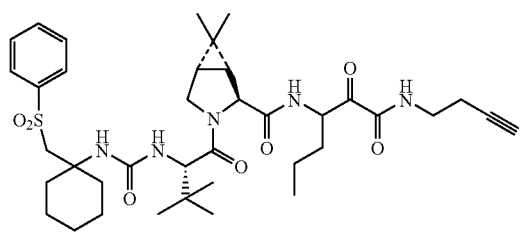 |
| 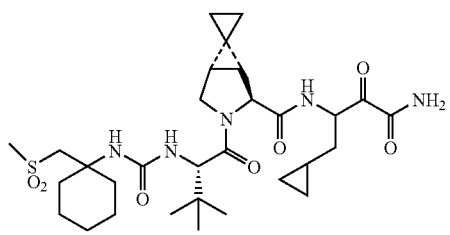 | 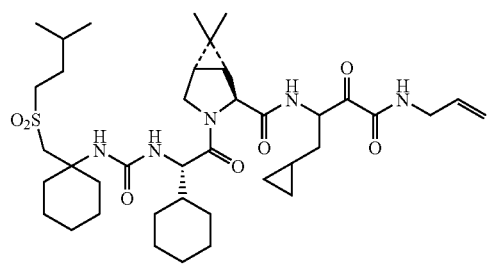 |

673 674
-continued
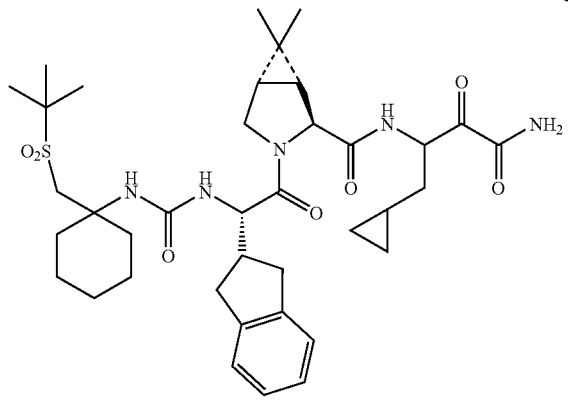 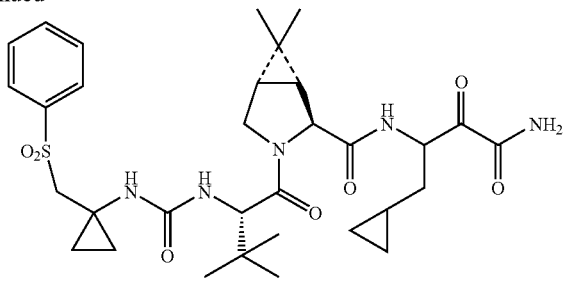
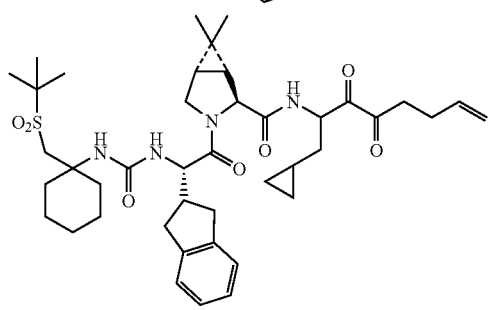 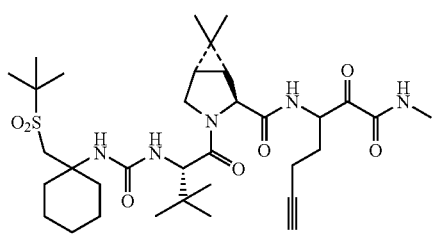
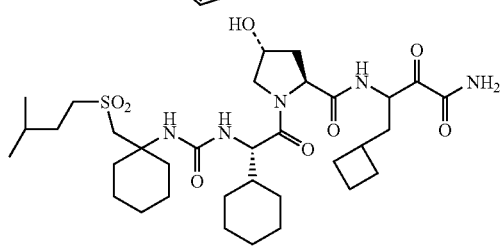 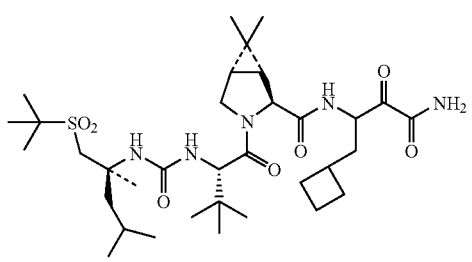
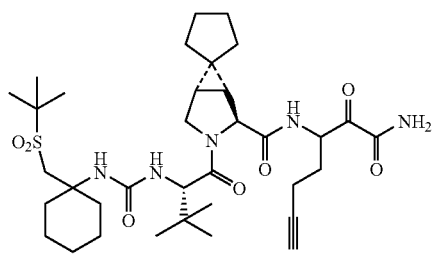 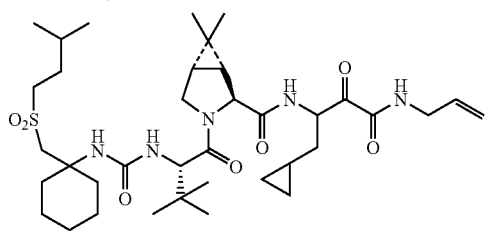
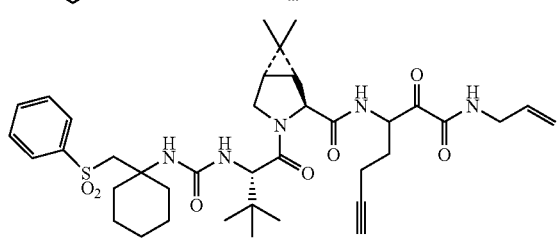 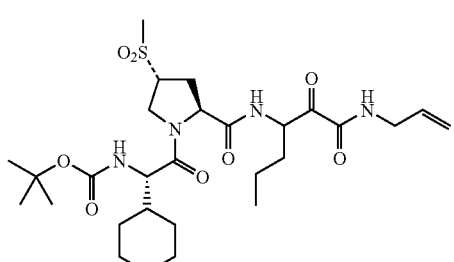
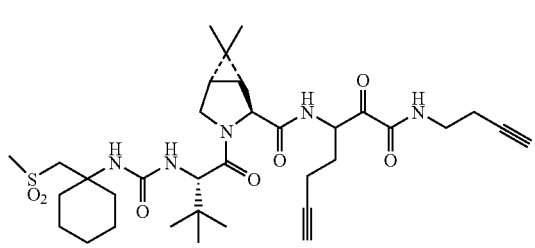 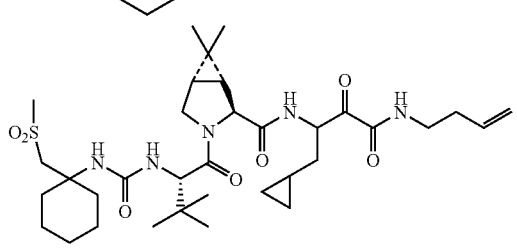

| 675 | 676 |
|---|---|
| 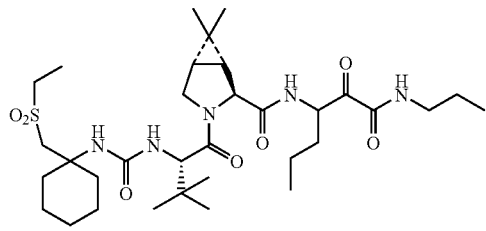 | 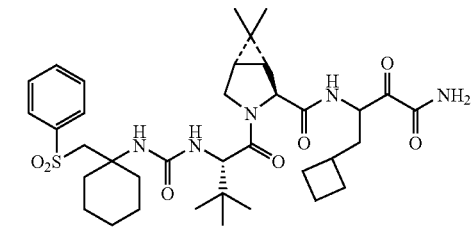 |
| 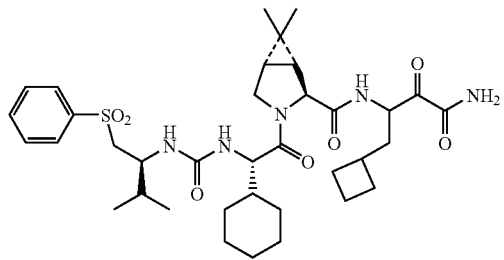 | 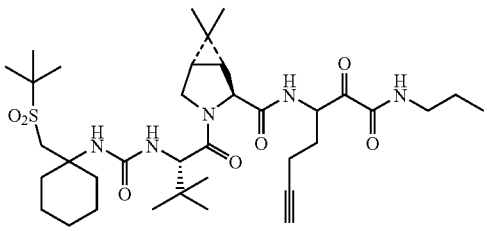 |
| 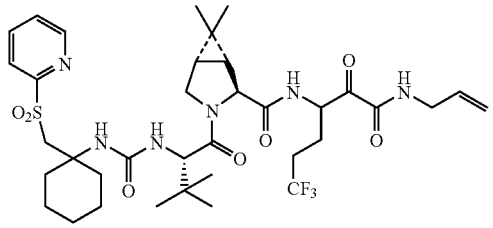 | 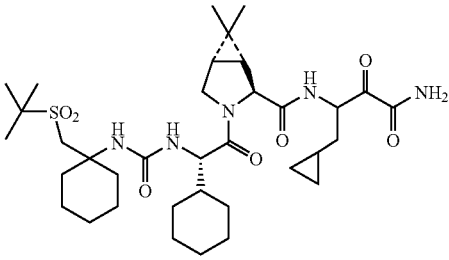 |
| 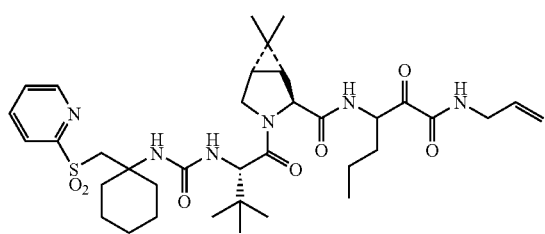 | 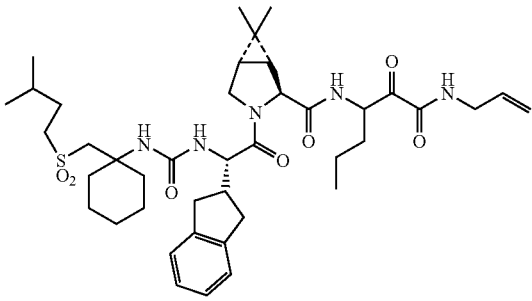 |
| 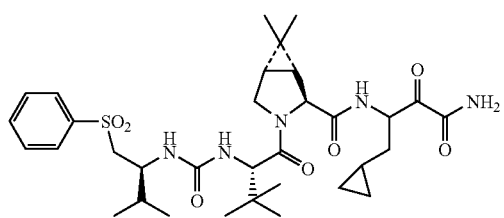 | 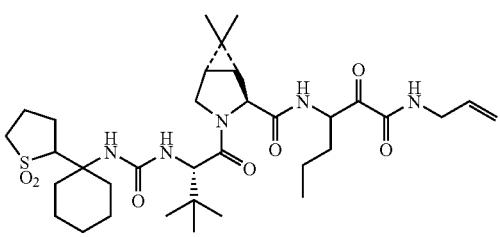 |
| 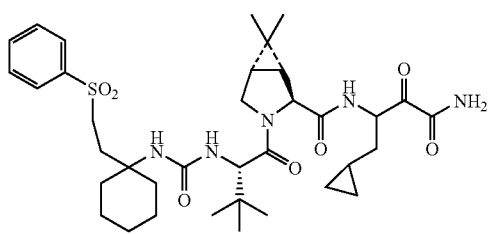 | 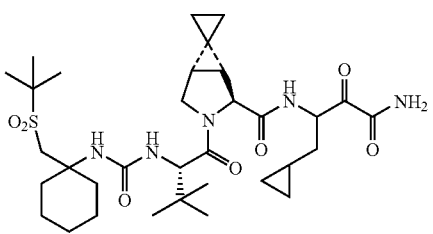 |

677 678
-continued
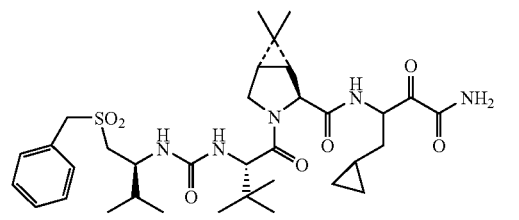
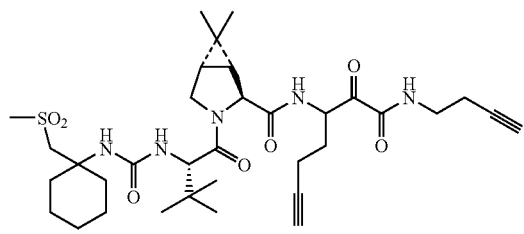
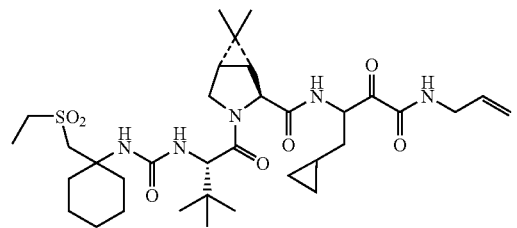
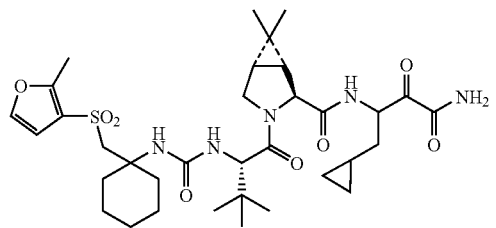
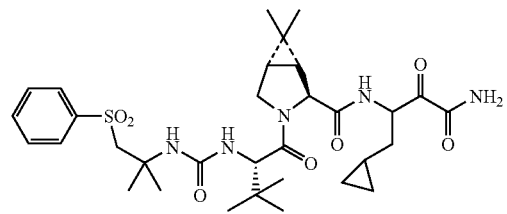
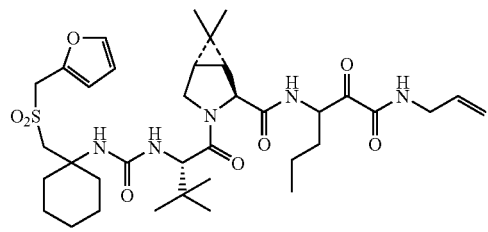
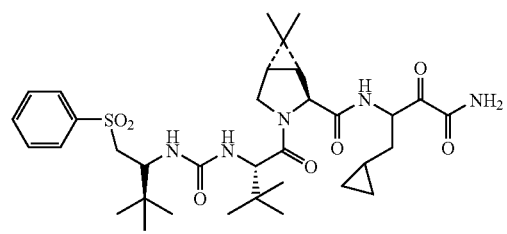
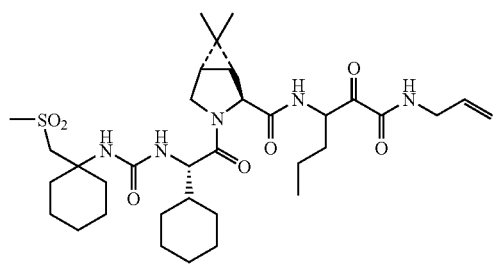
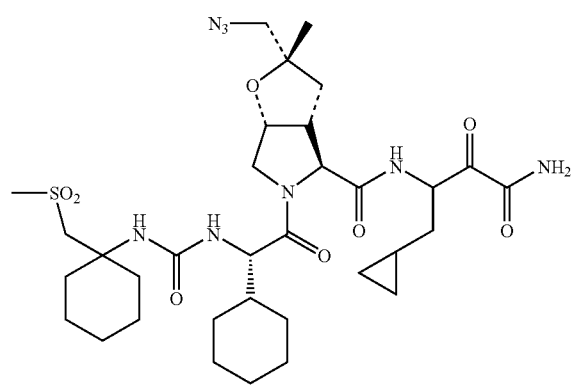
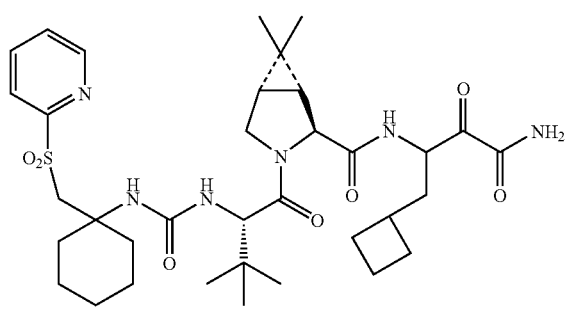
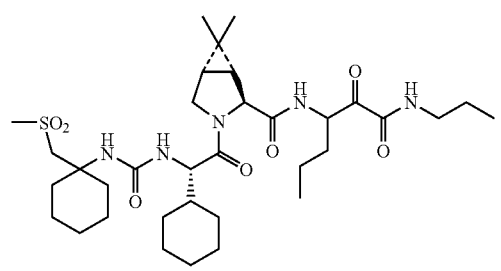
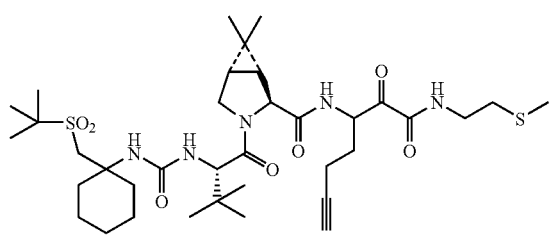

-continued
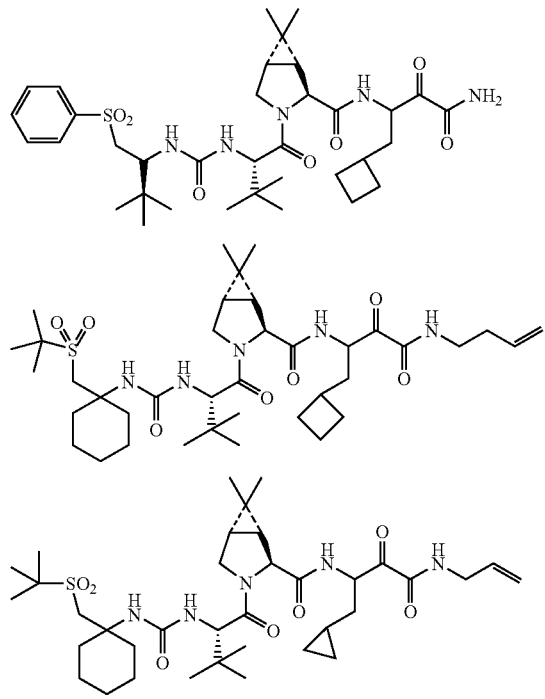
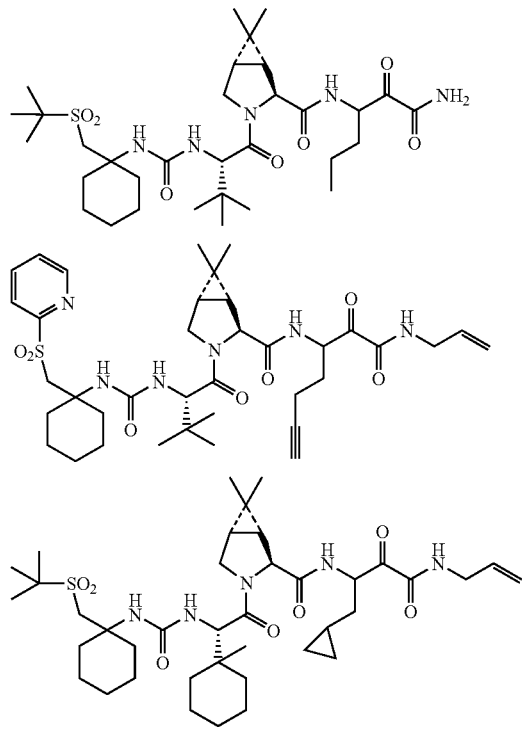
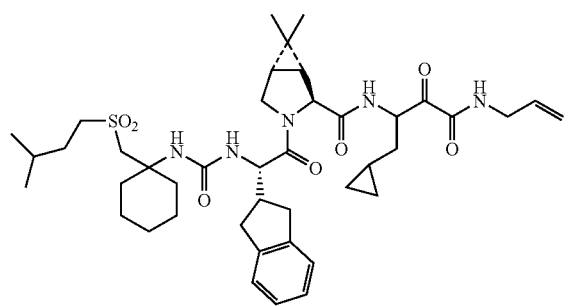
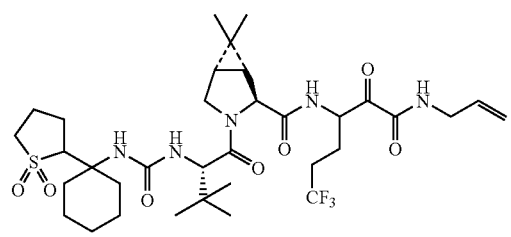
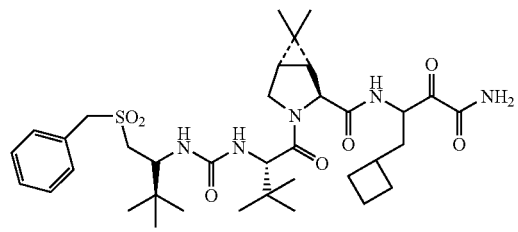
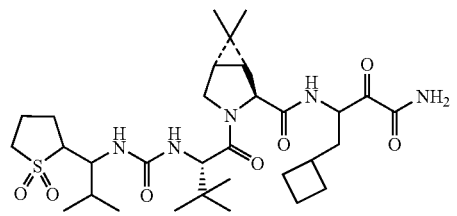
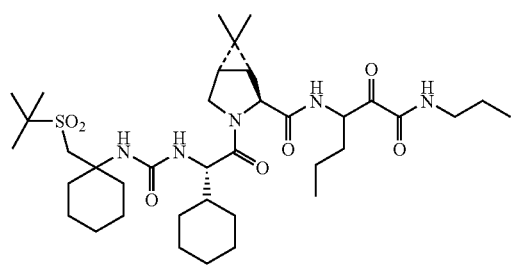
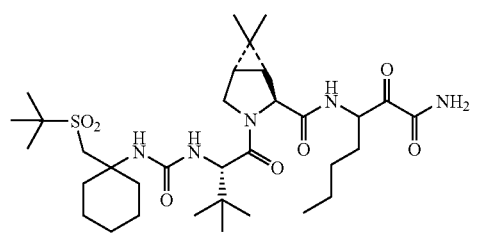

681　　　　　　　　　　　　　　682
-continued
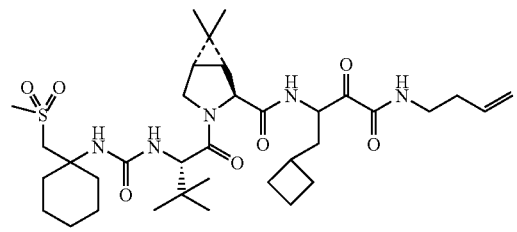
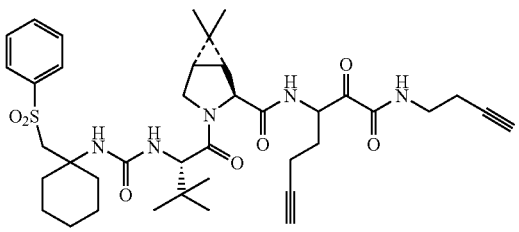
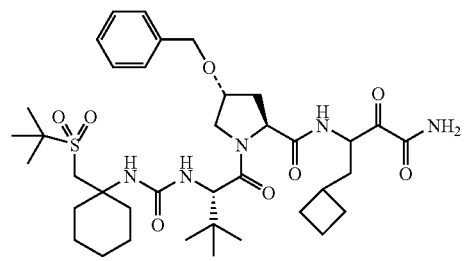
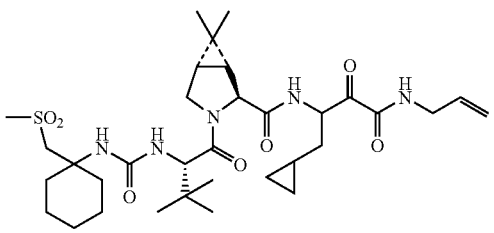
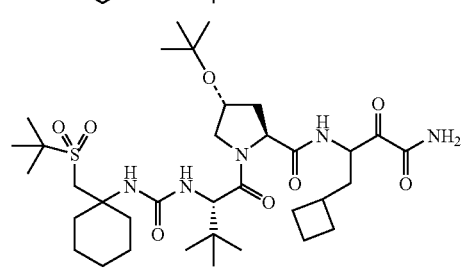
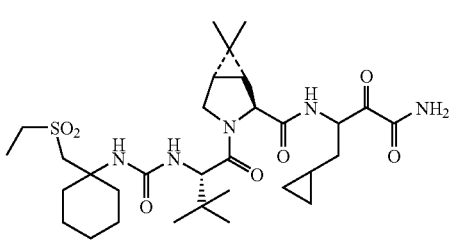
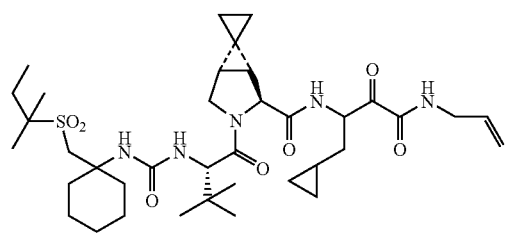
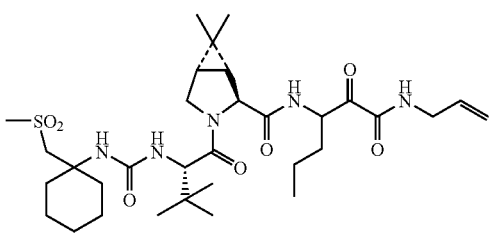
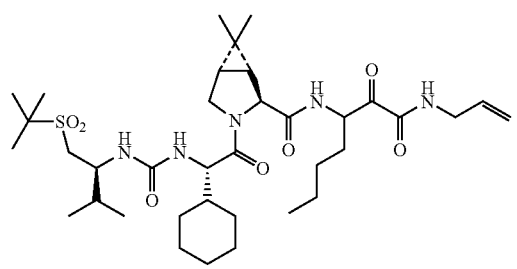
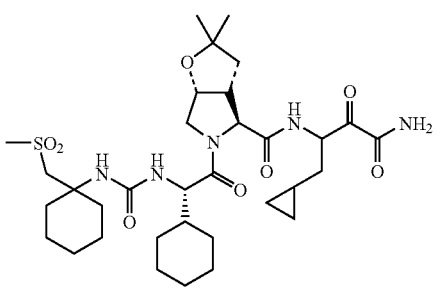
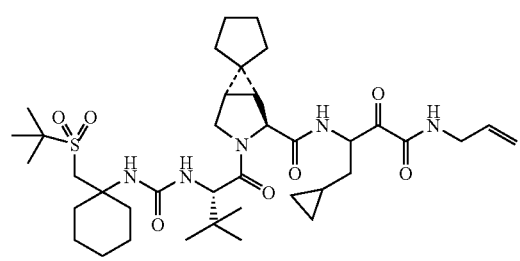
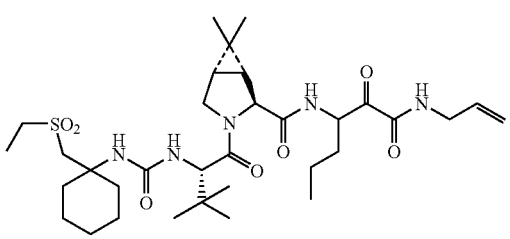

683
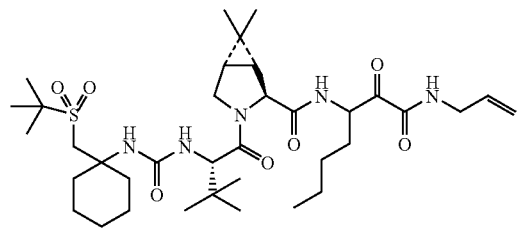
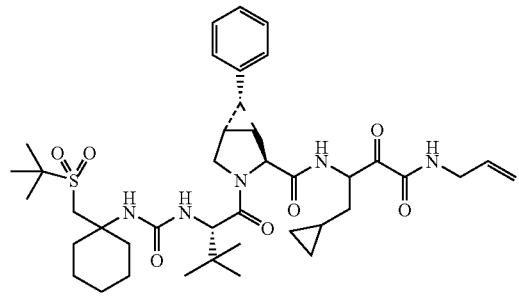
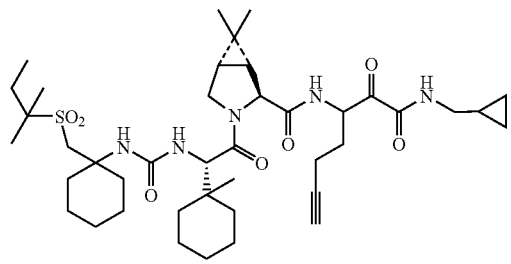
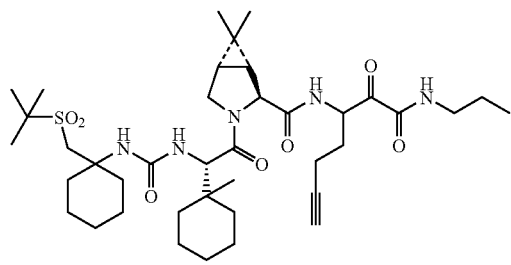
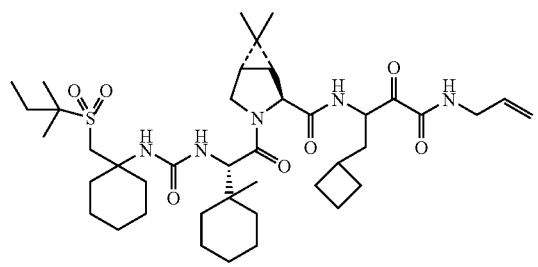
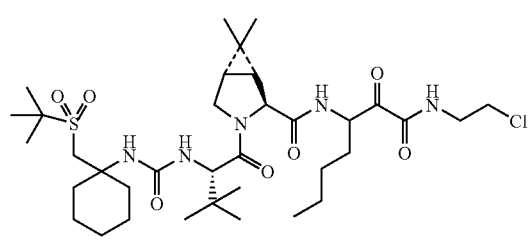
684
-continued
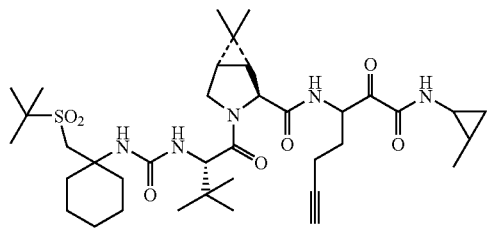
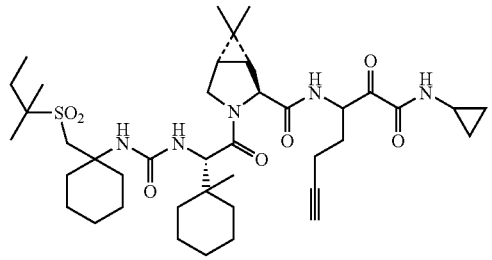
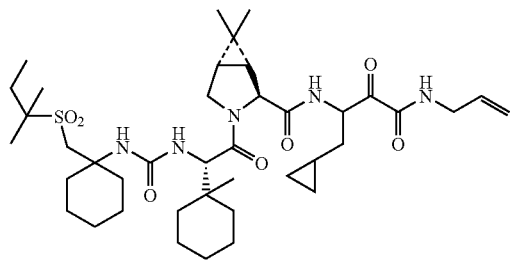
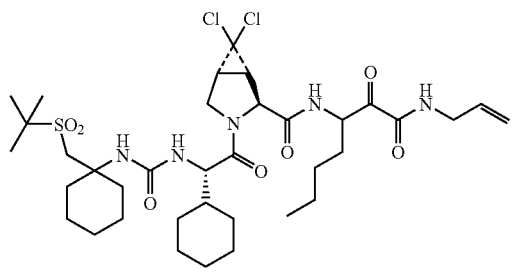
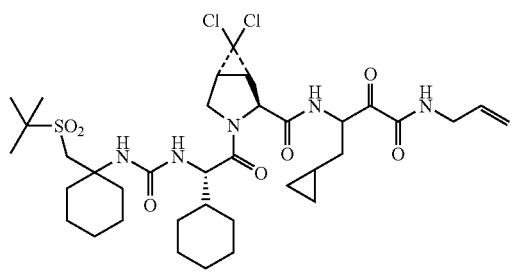
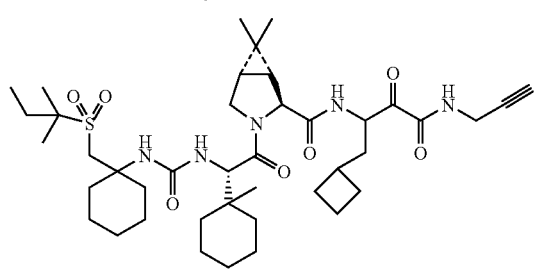

-continued
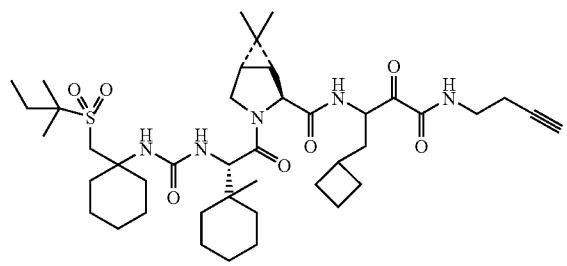
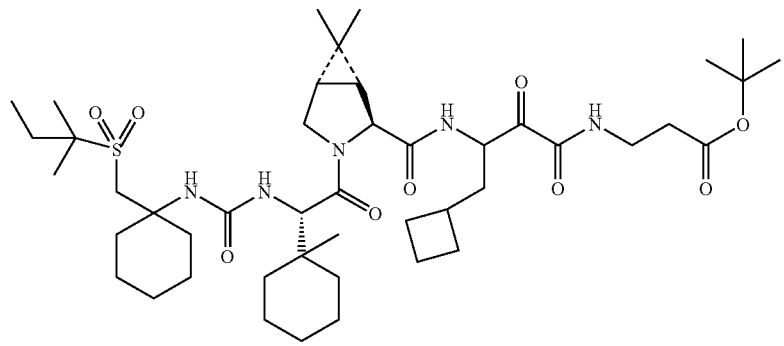
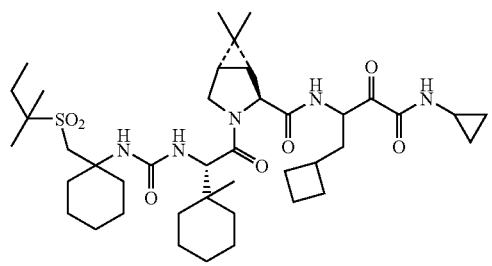
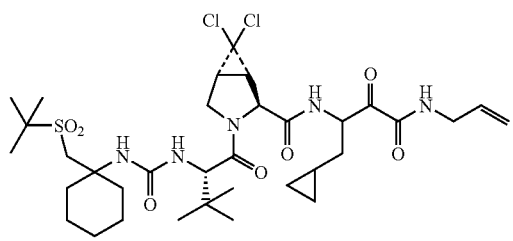
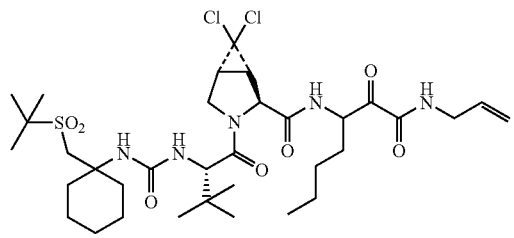
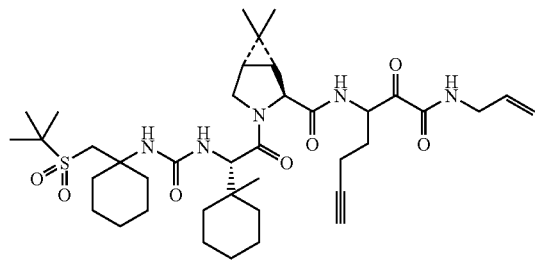
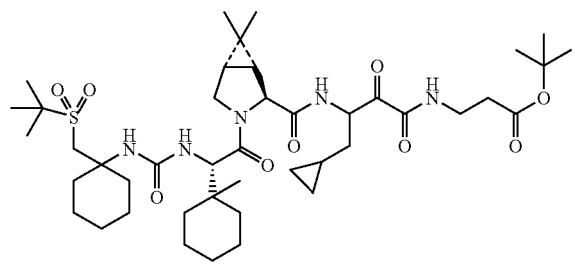

-continued
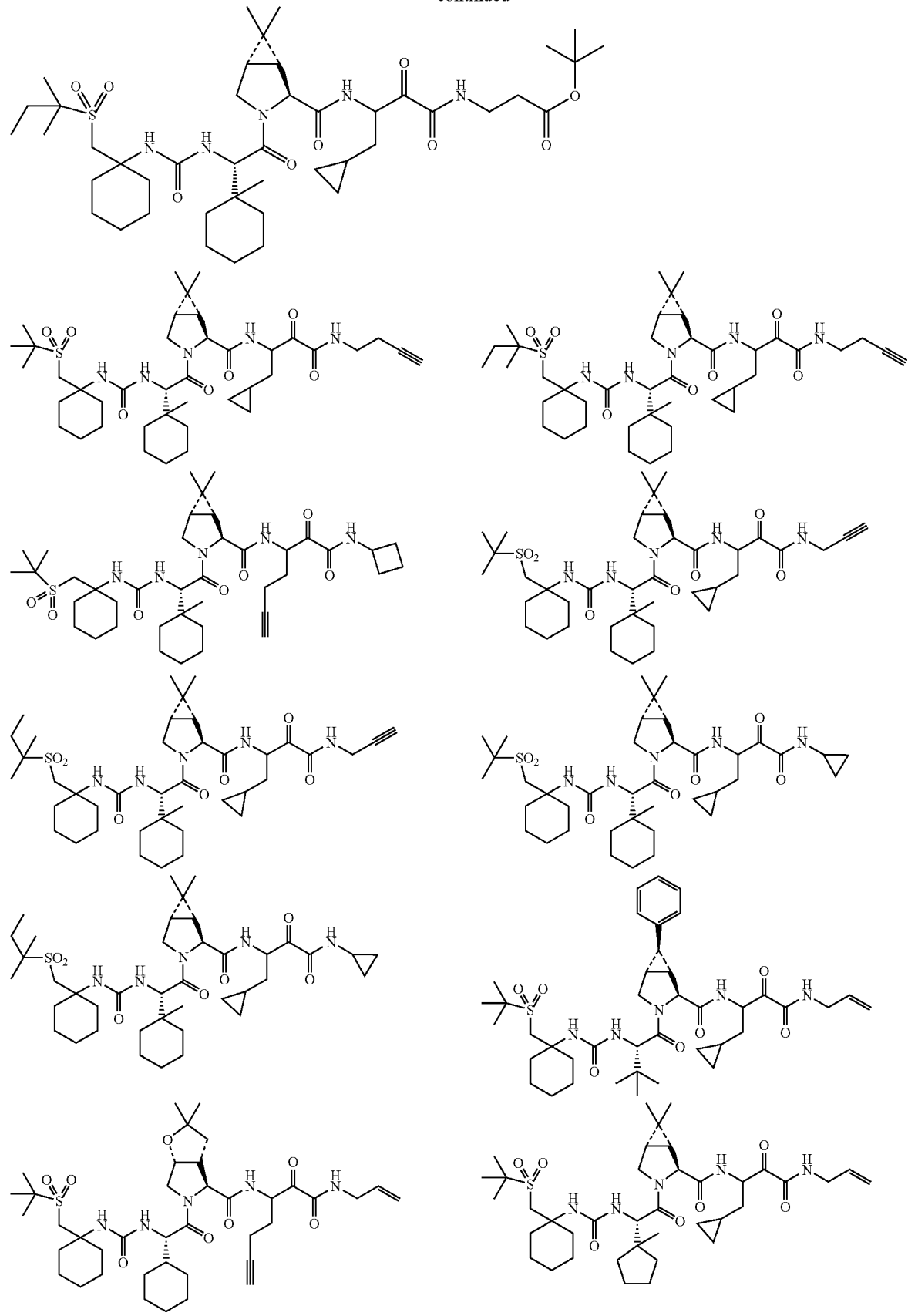

689
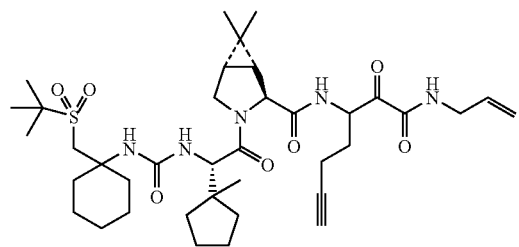
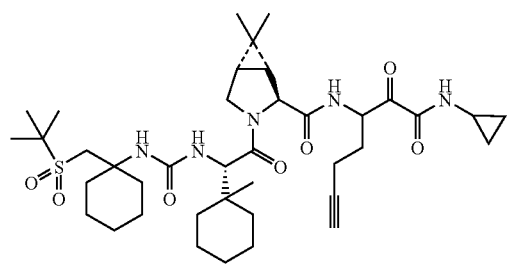
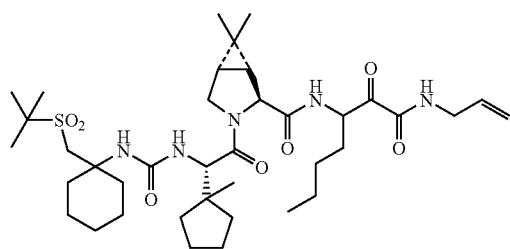
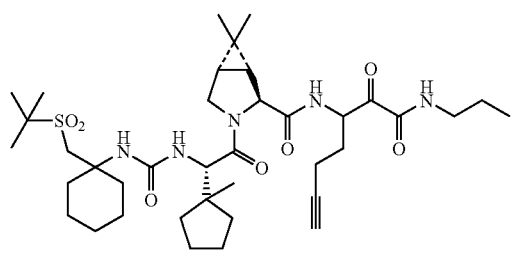
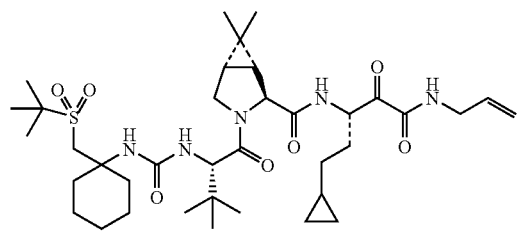
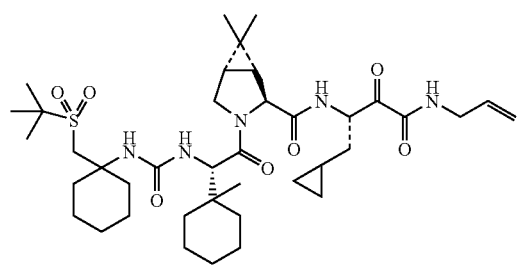
690
-continued
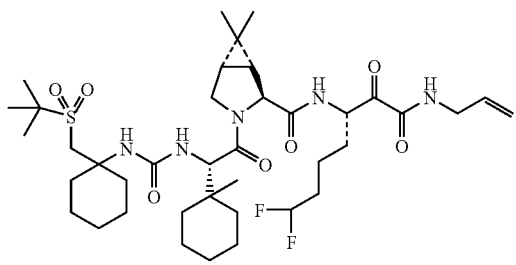
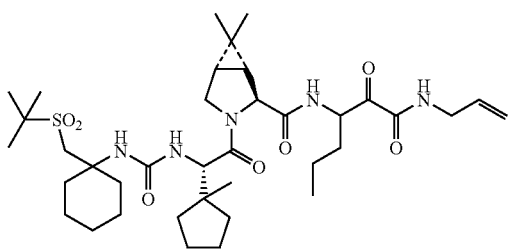
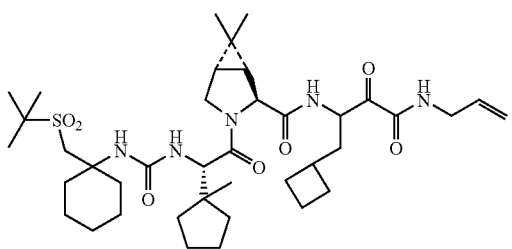
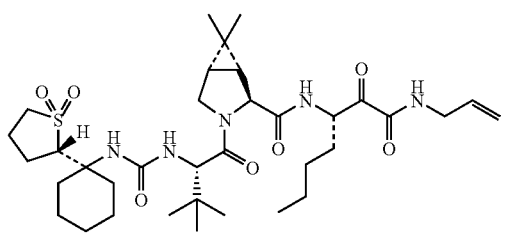
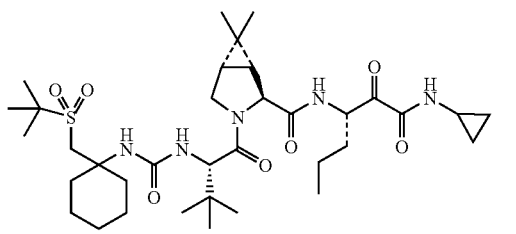
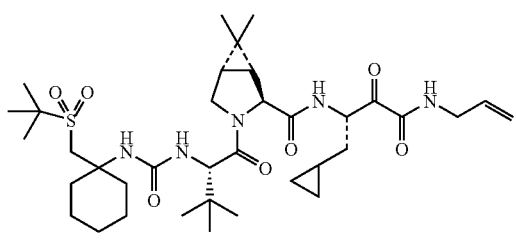

691
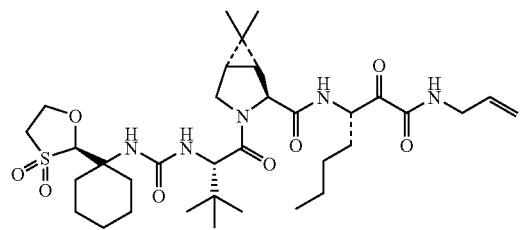
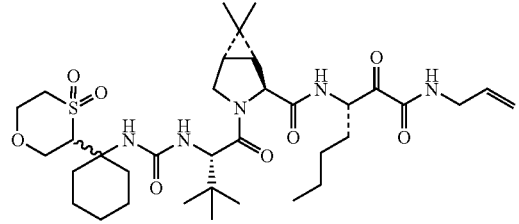
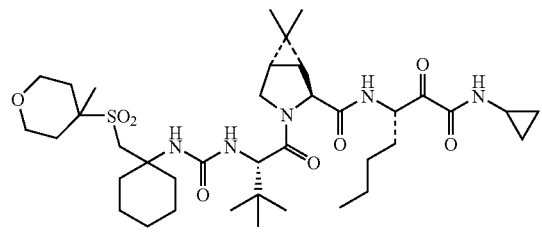
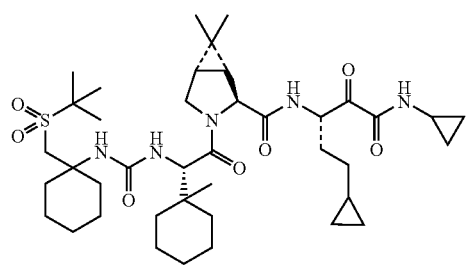
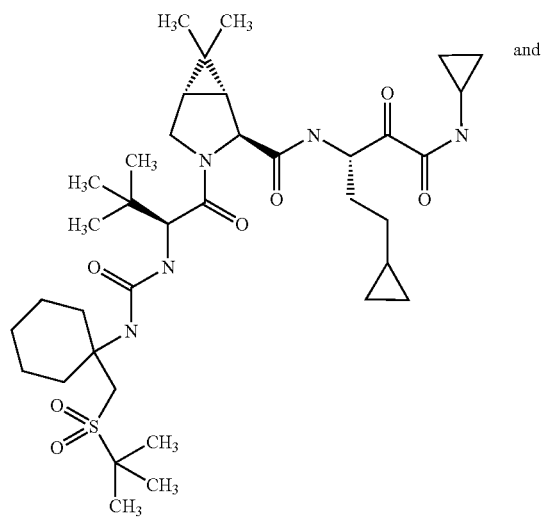
-continued
692
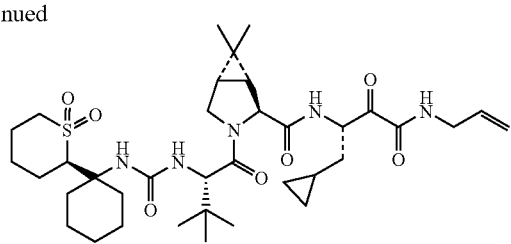
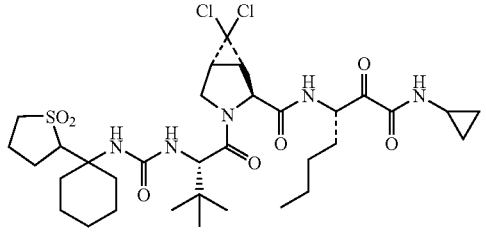
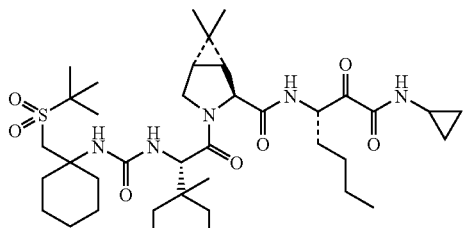
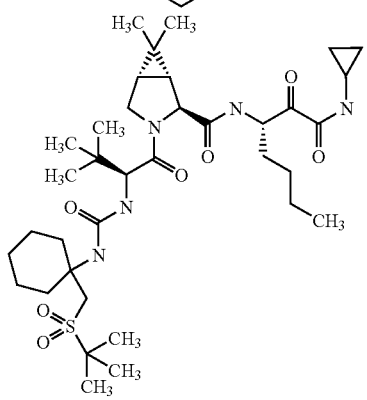
and
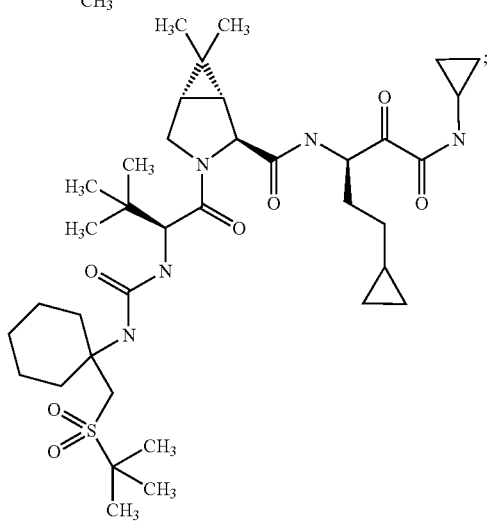
;
pharmaceutically acceptable salt, solvate or ester thereof.

Compounds of formula XV are disclosed in U.S. patent application Ser. No. 11/007,910 filed Dec. 9, 2004. The preparation of these compounds is disclosed in the experimental section of this application set forth hereinbelow.
Non-limiting examples of certain compounds disclosed in U.S. patent application Ser. No. 11/007,910 are:
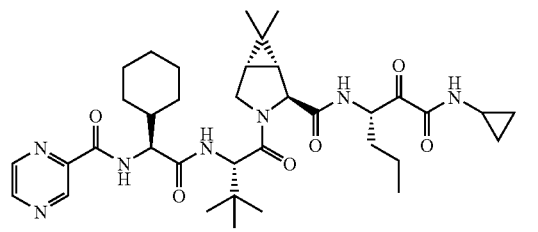
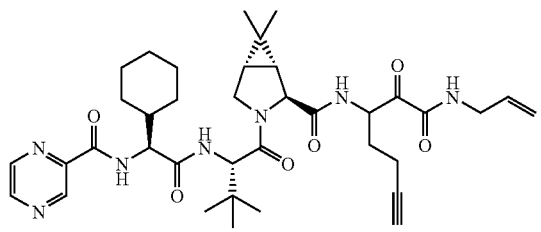
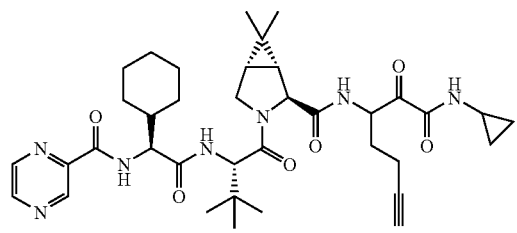
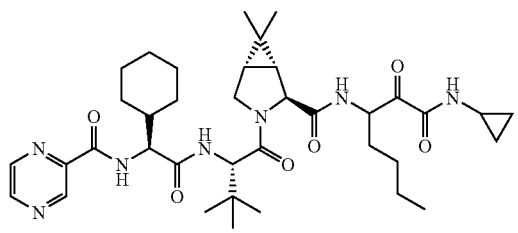
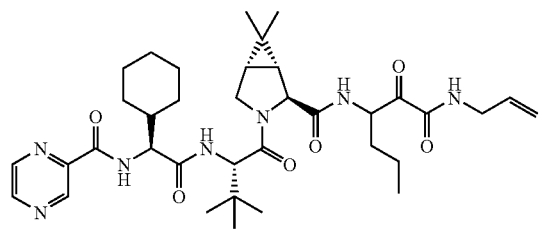
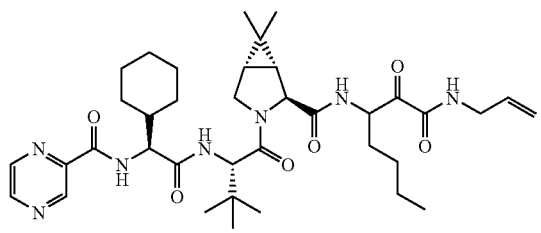
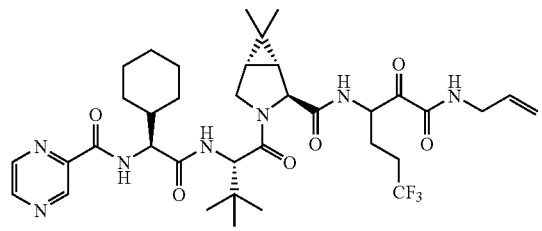
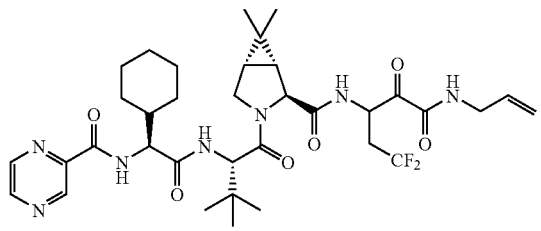
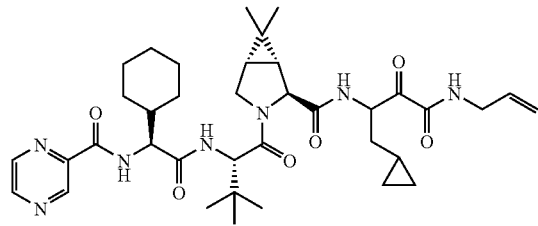
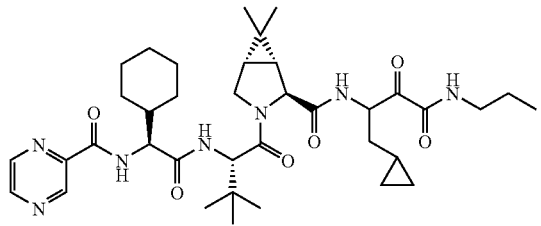
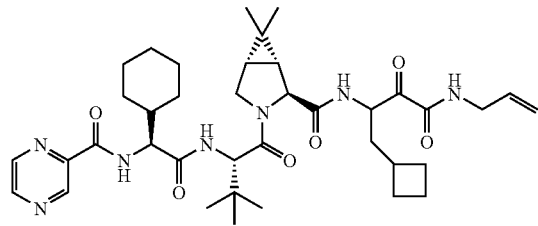
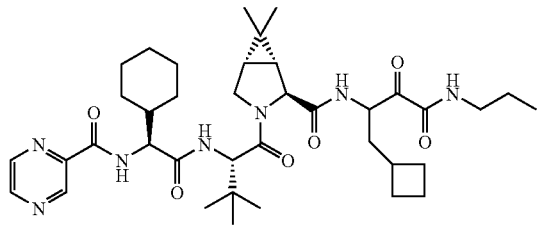

695
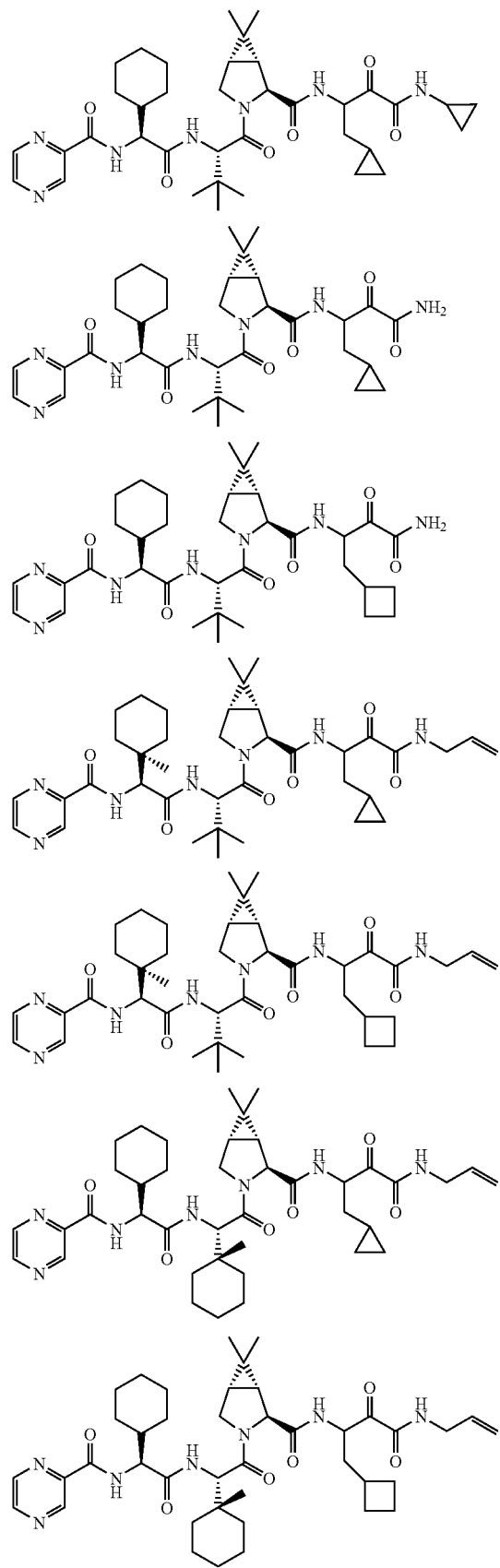
696
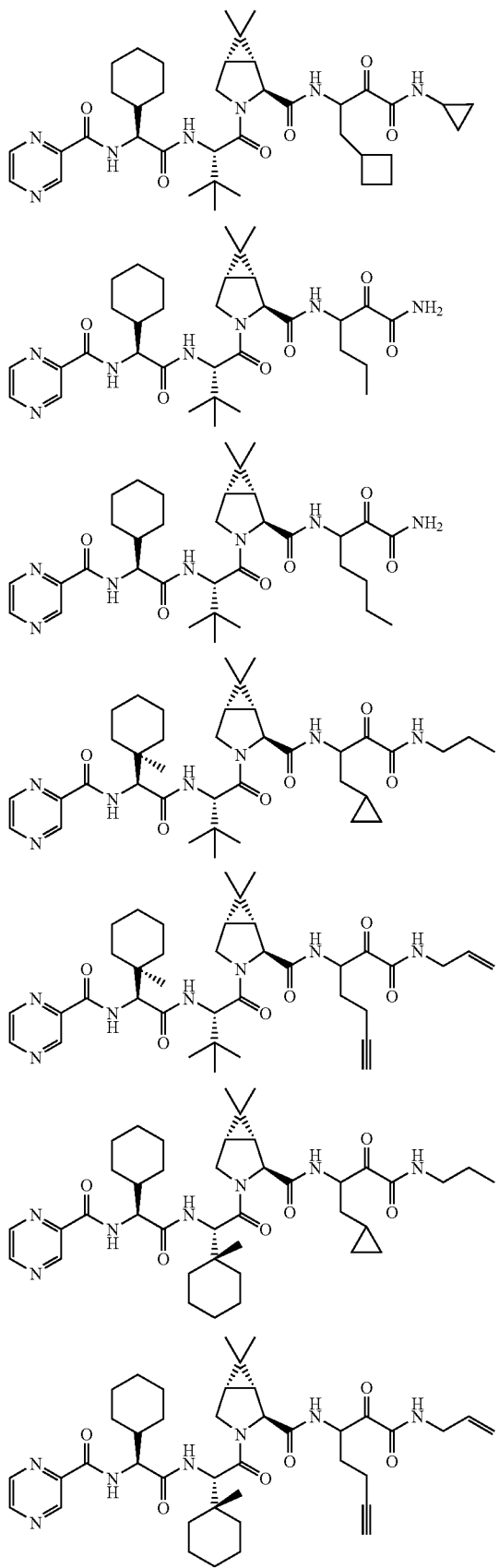

697 698
-continued
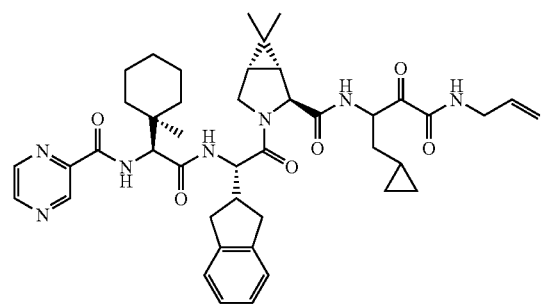
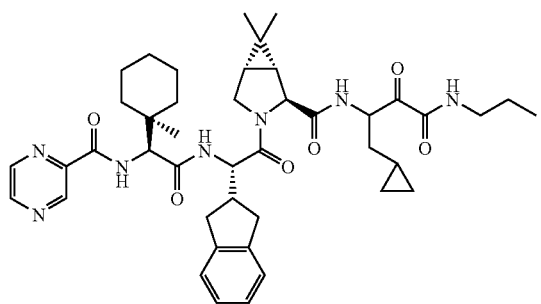
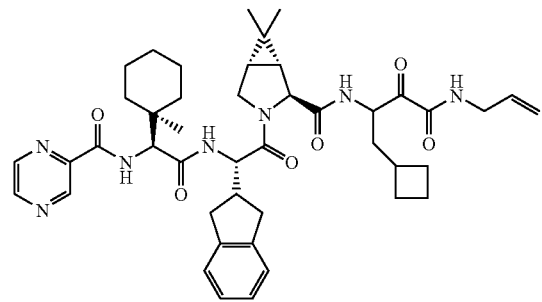
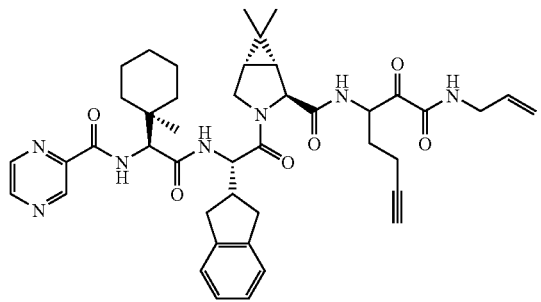
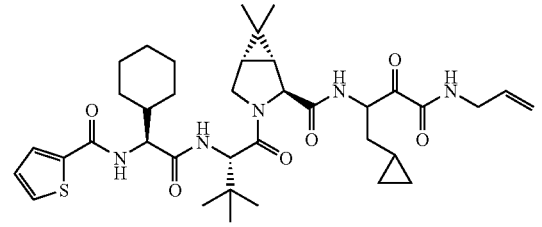
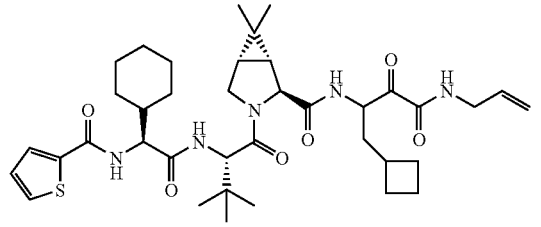
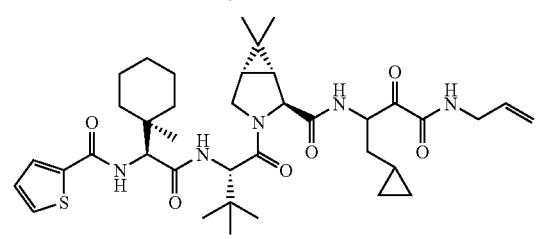
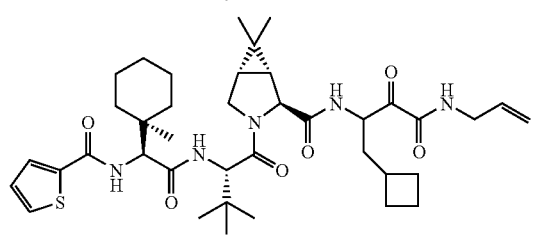
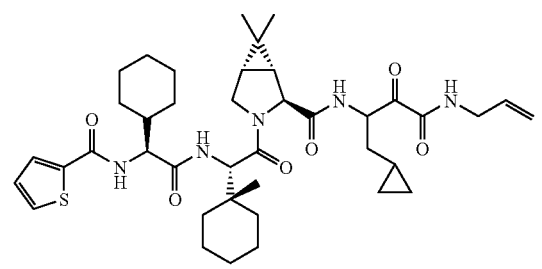
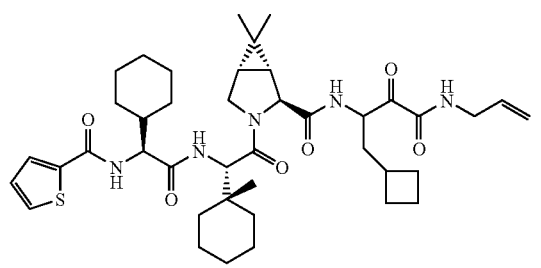
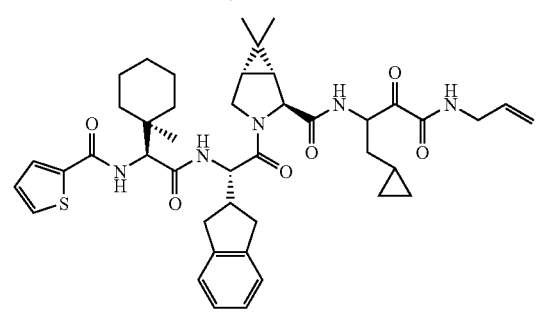
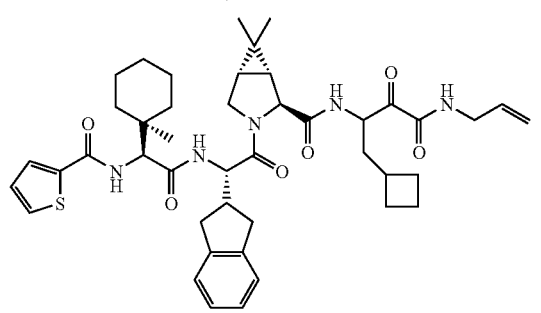

699 700
-continued
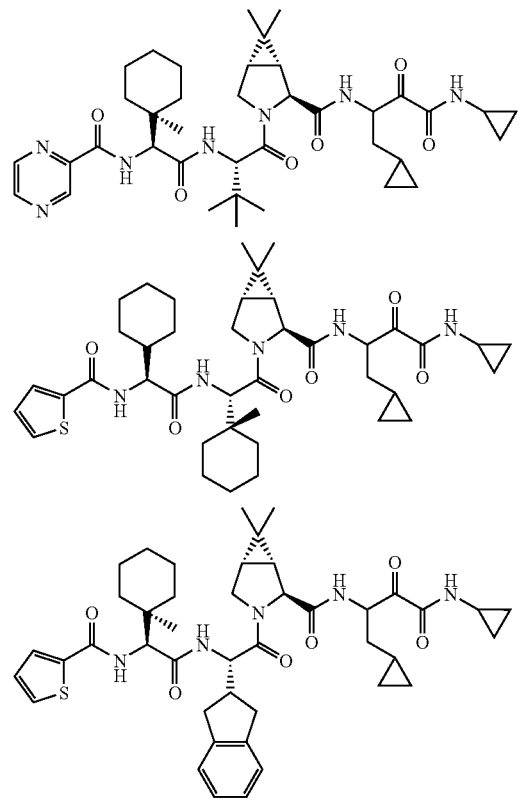
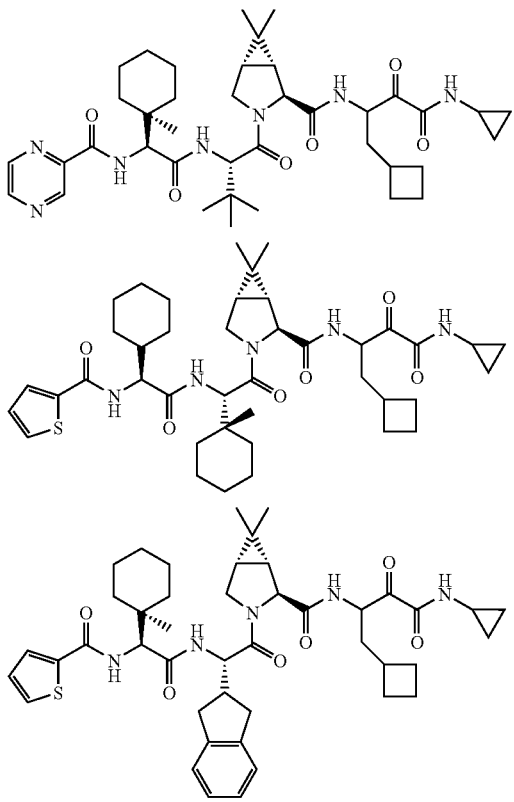
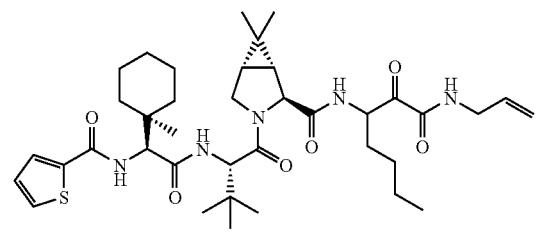
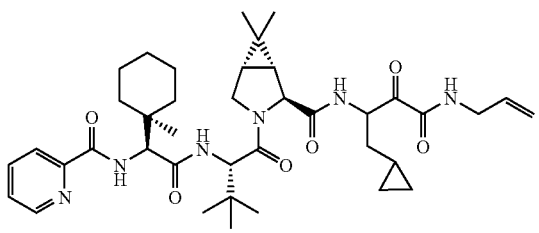
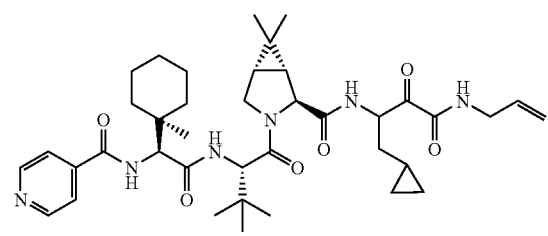
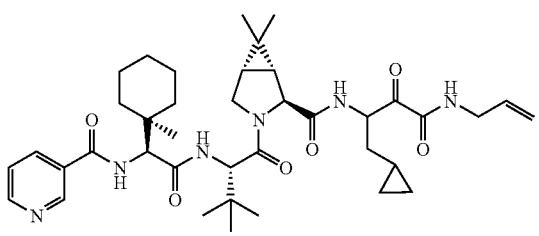
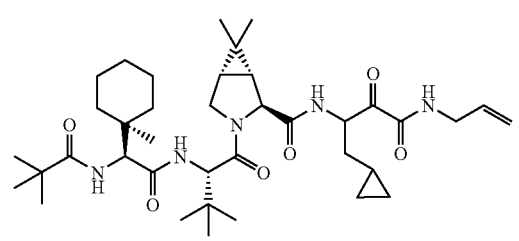
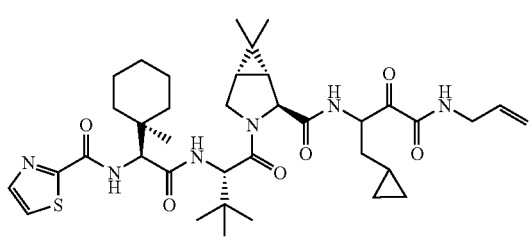

-continued
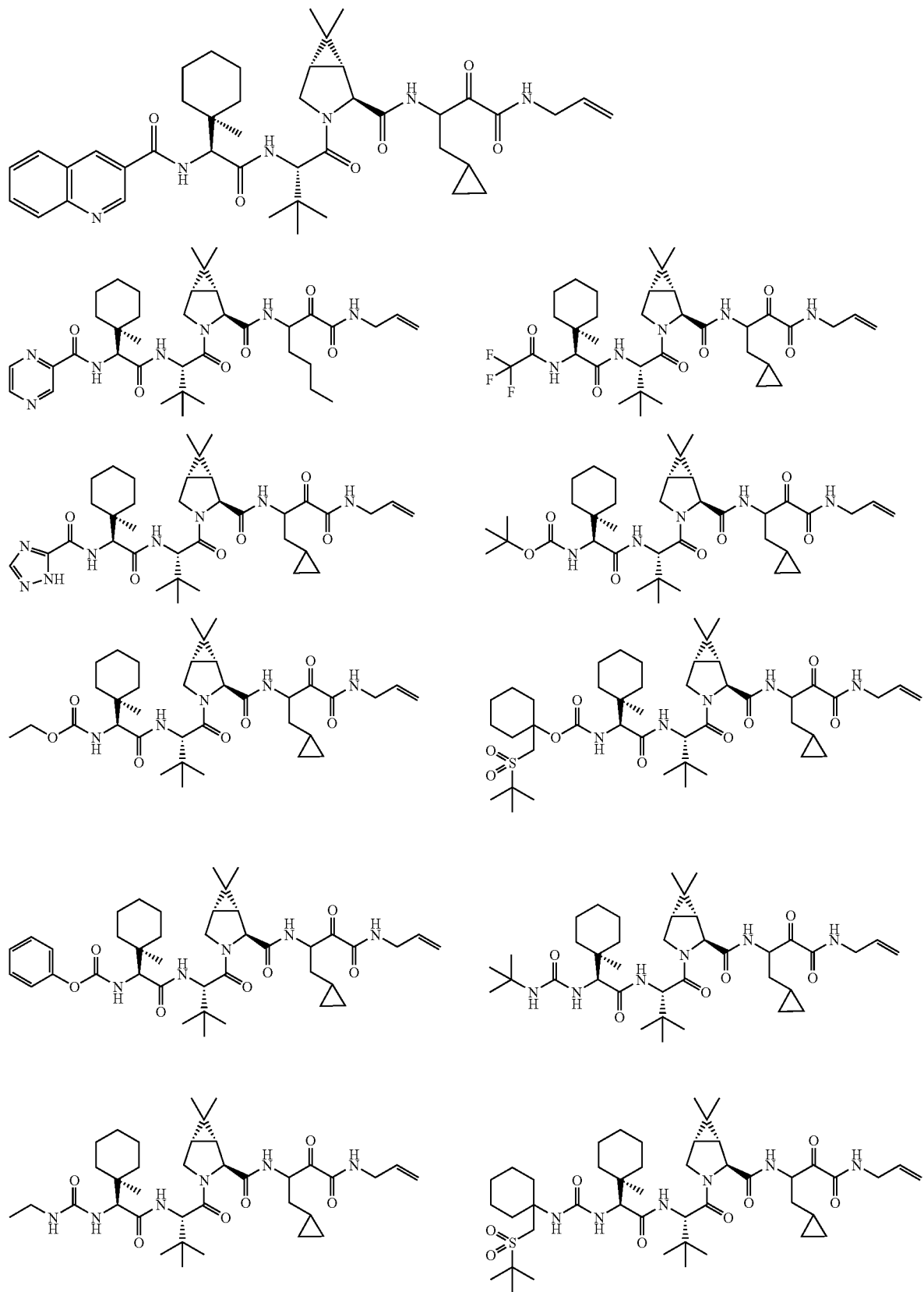

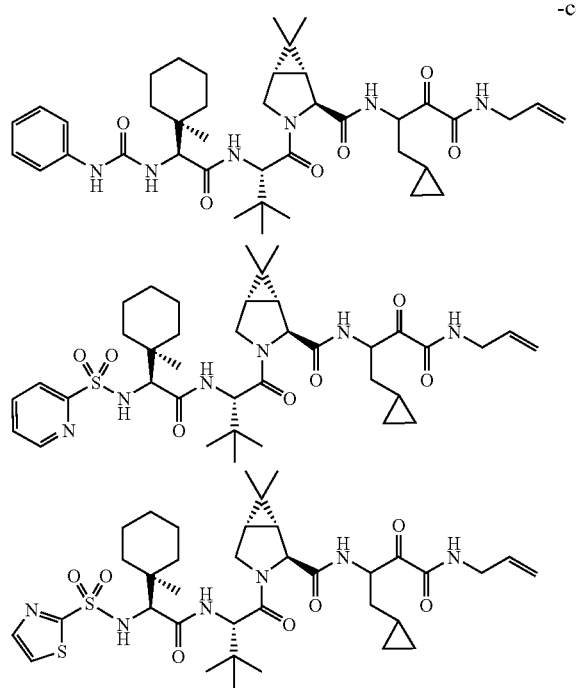
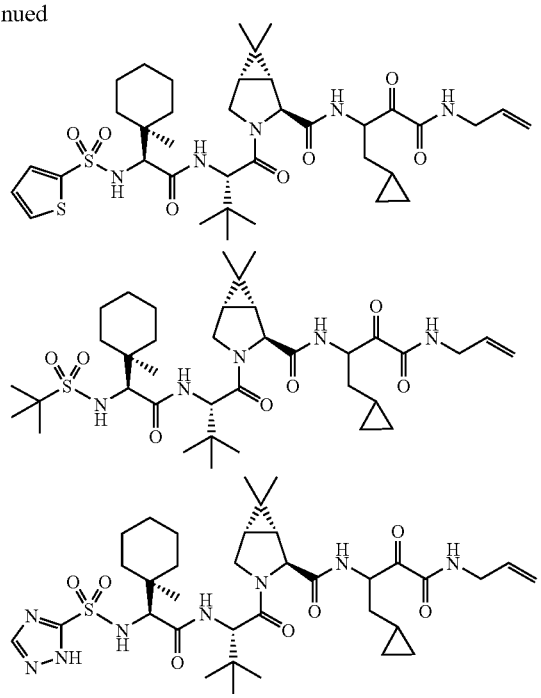
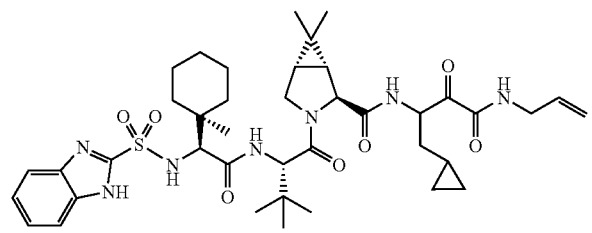
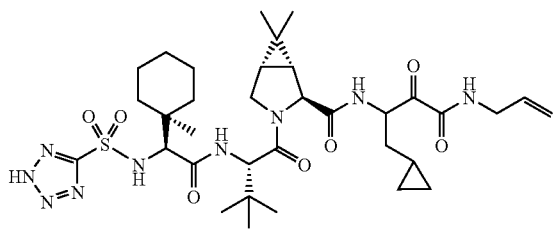
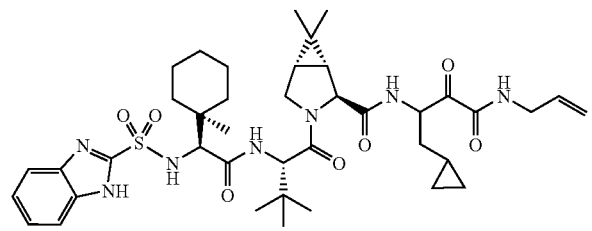
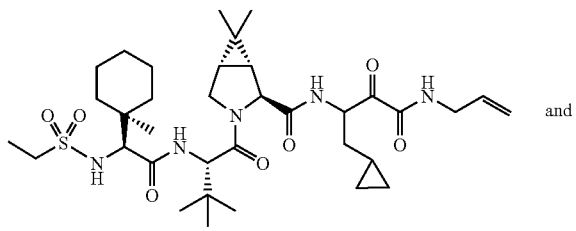
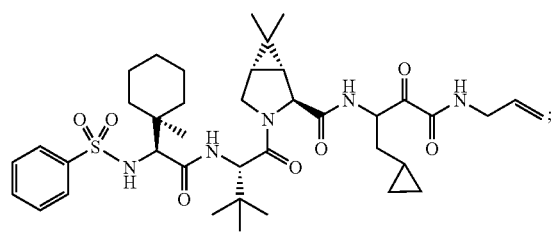
or a pharmaceutically acceptable salt, solvate or ester thereof.

Compounds of formula XVI are disclosed in U.S. patent application Ser. No. 11/064,757 filed Feb. 24, 2005. The preparation of these compounds is disclosed in the experimental section of this application set forth hereinbelow.
Non-limiting examples of certain compounds disclosed in U.S. patent application Ser. No. 11/064,757 are:
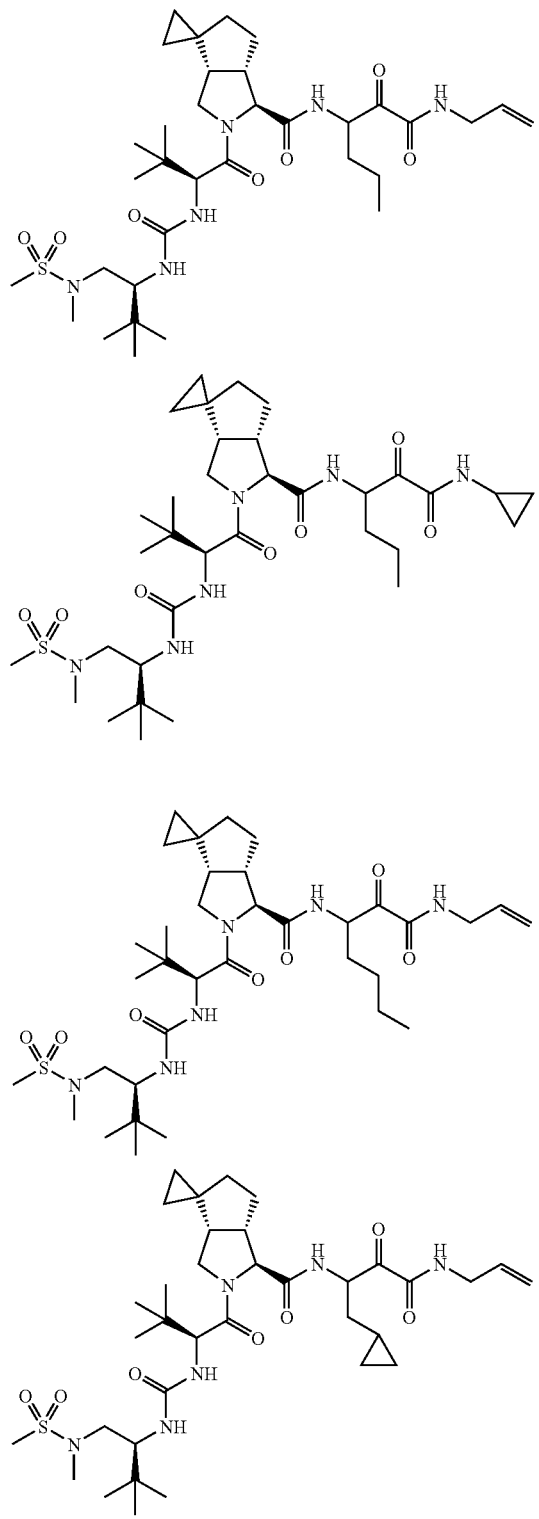
-continued
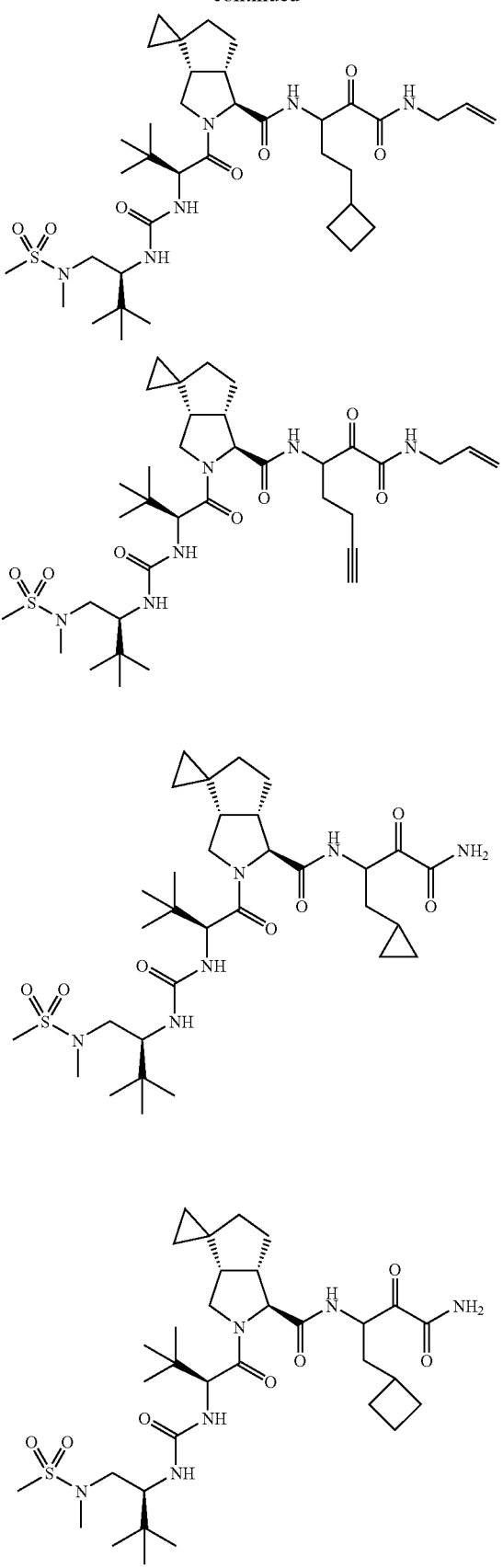

707
-continued
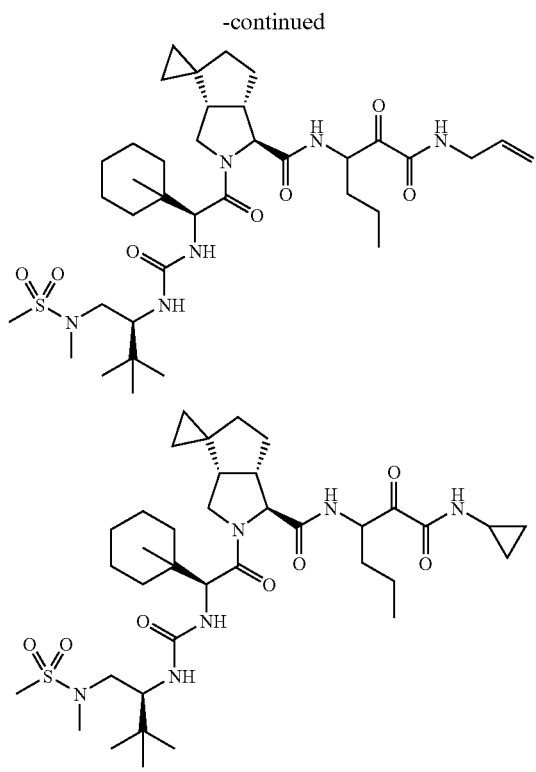
708
-continued
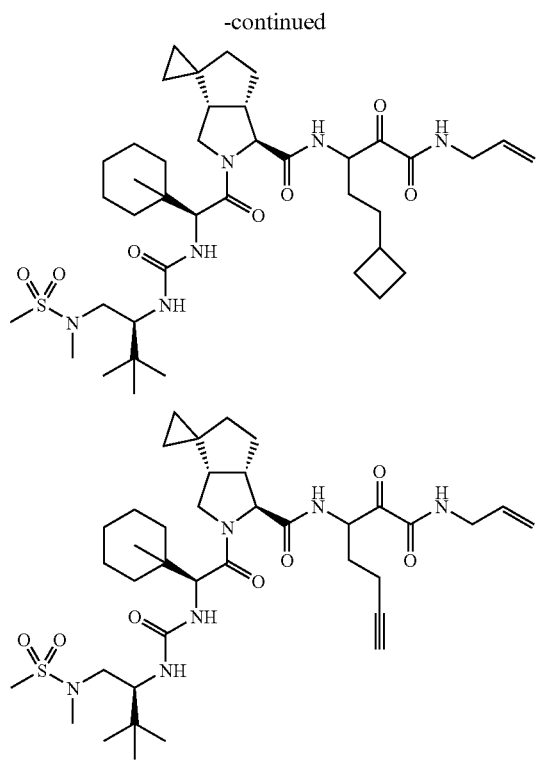
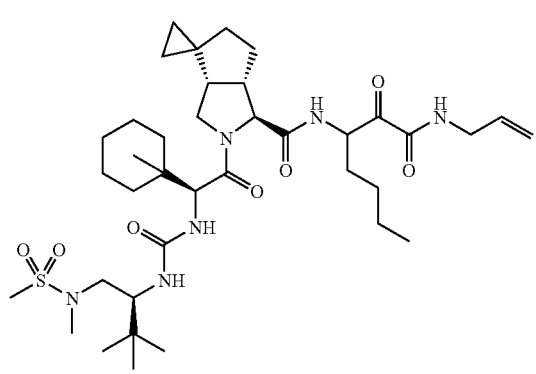
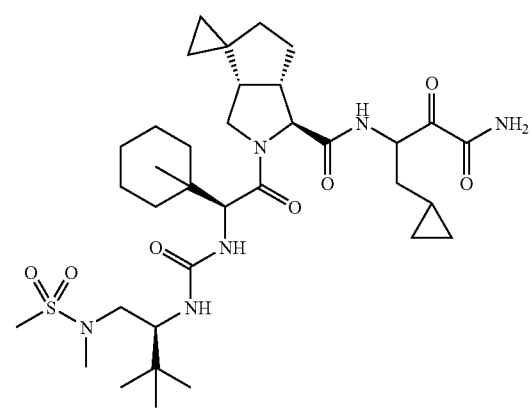
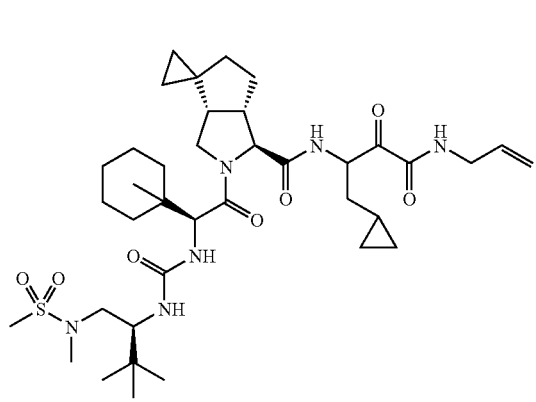
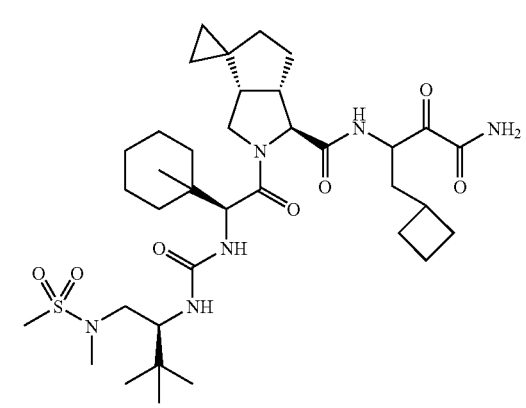

709
-continued
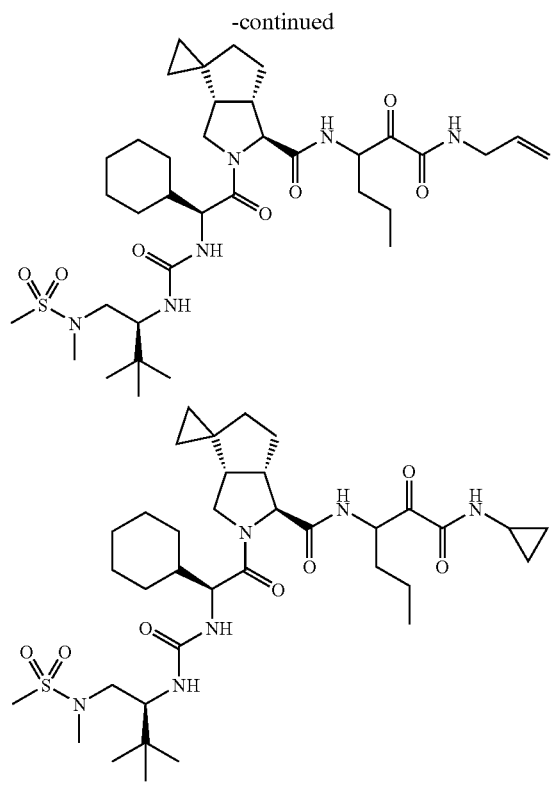
710
-continued
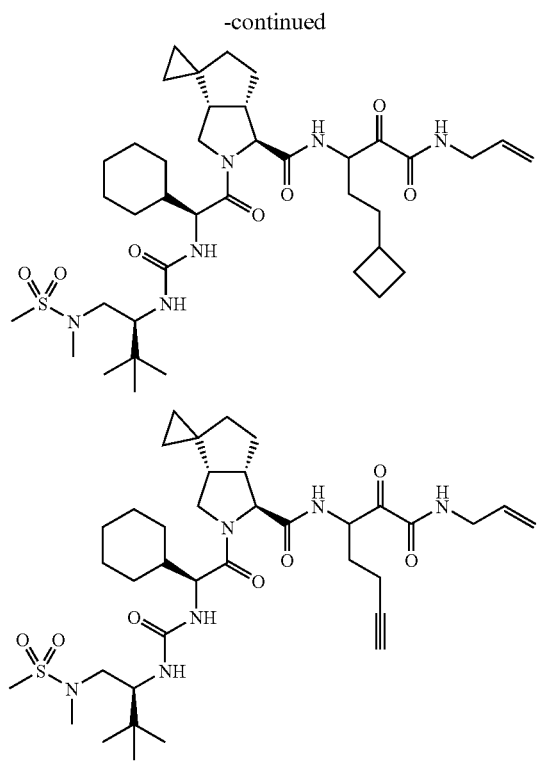
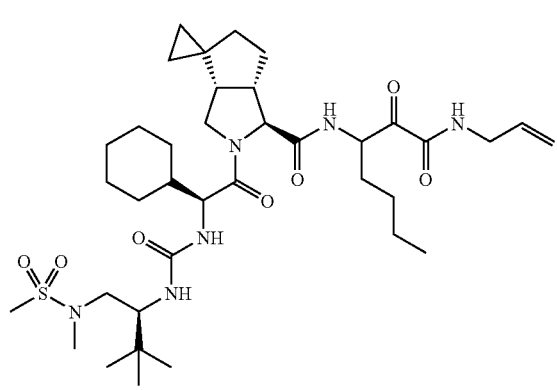
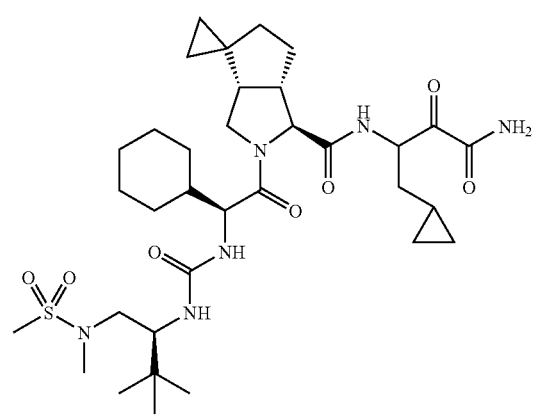
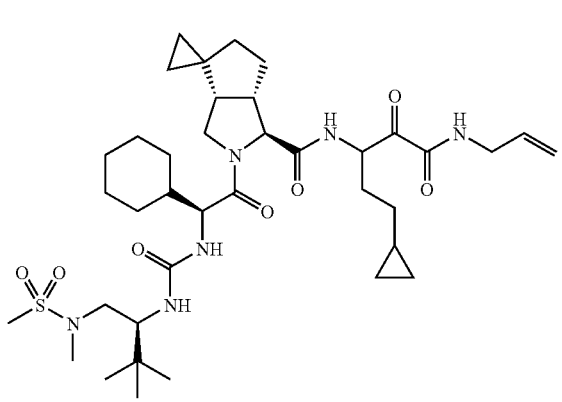
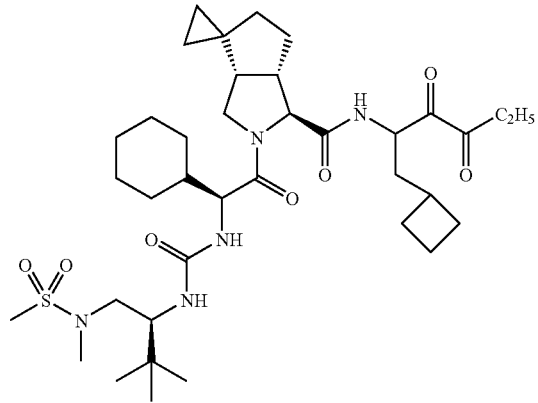

711                                          712
-continued                                  -continued
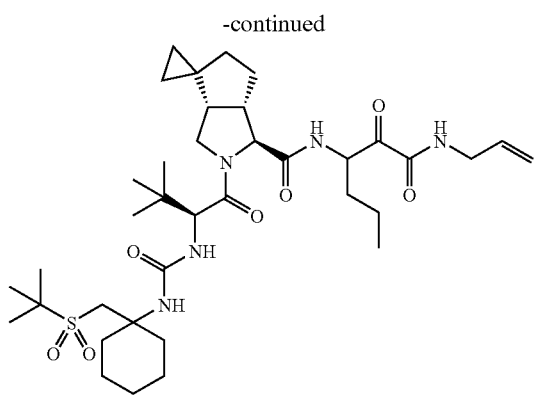
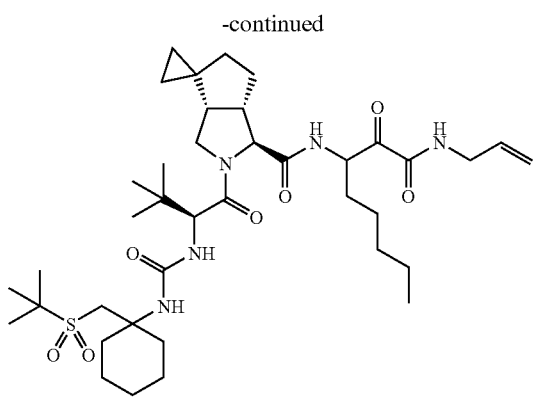
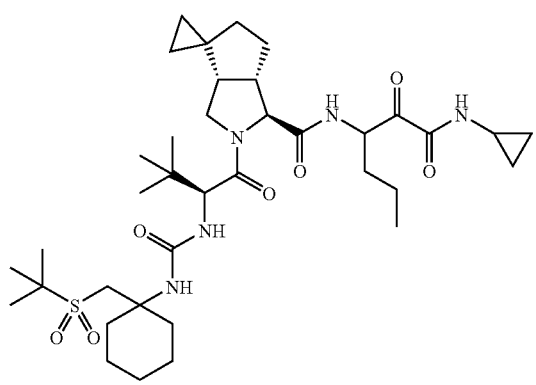
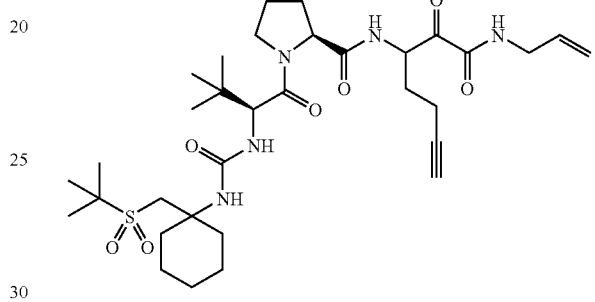
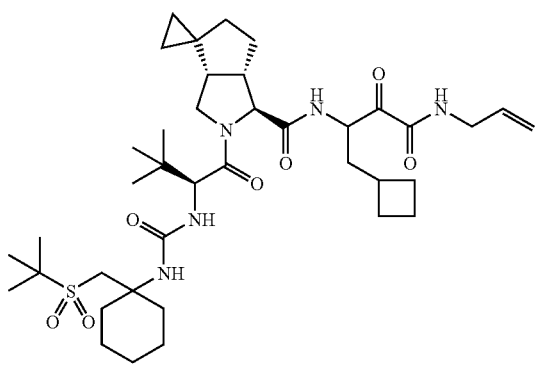
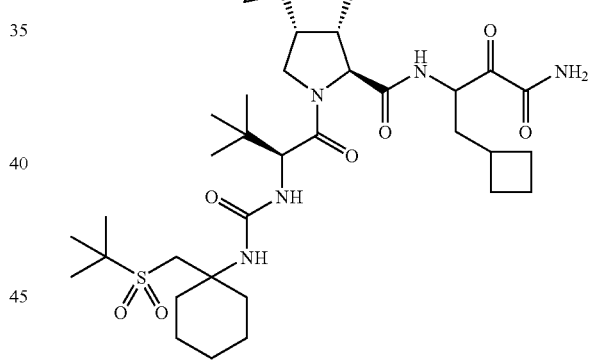
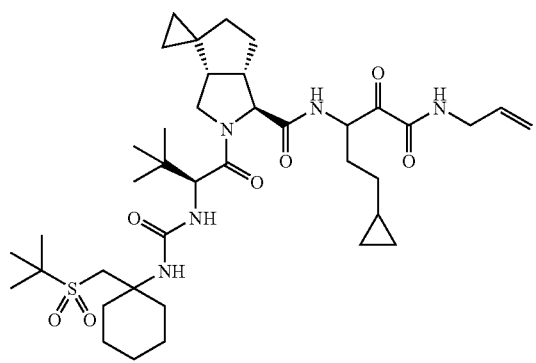
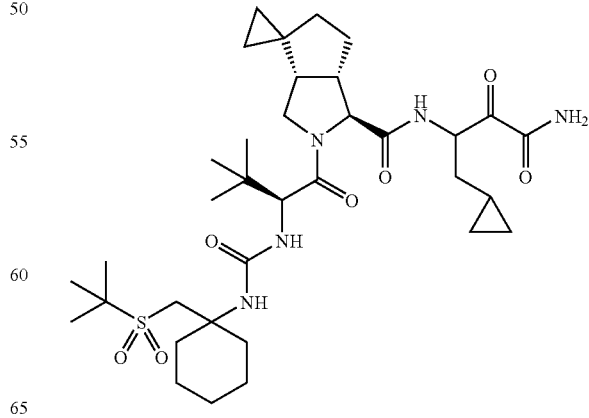

713
-continued
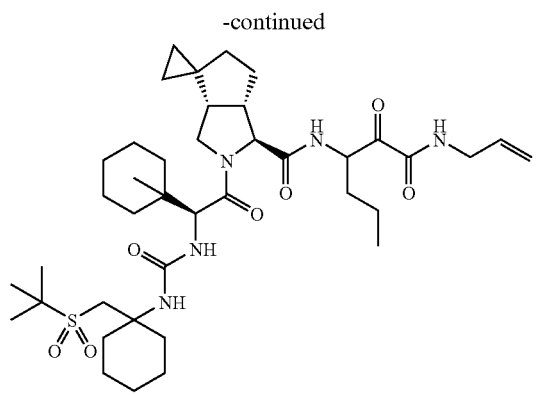
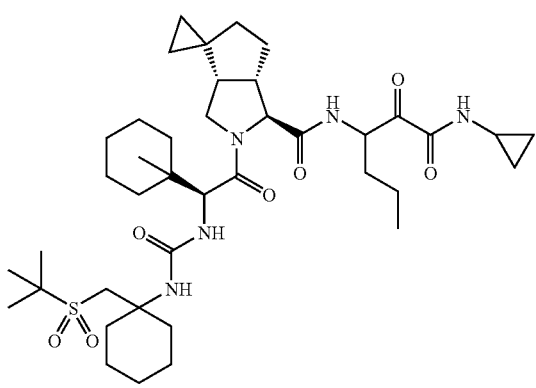
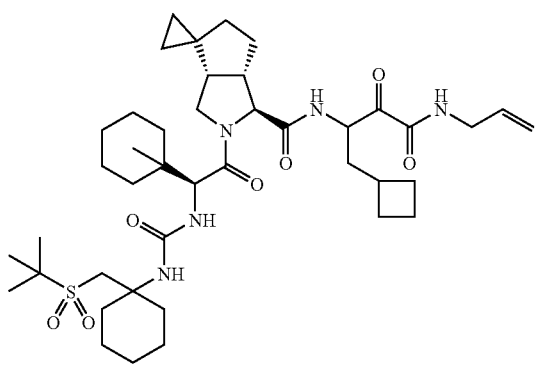
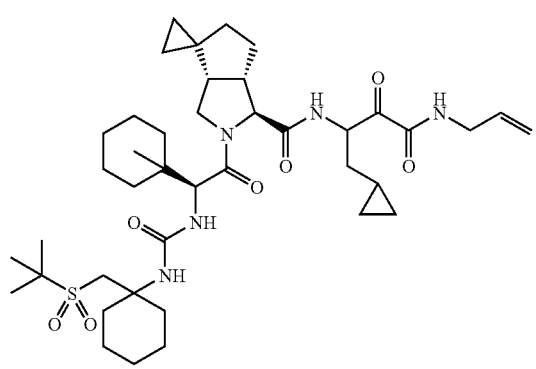
714
-continued
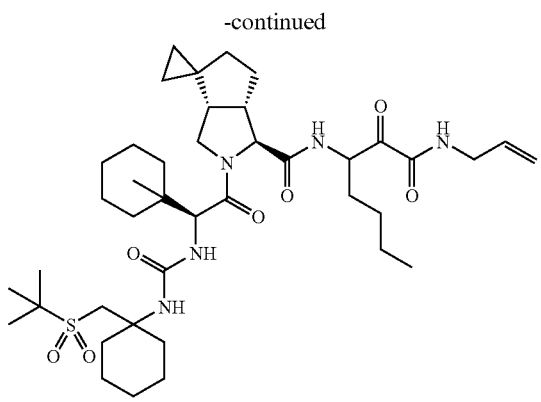
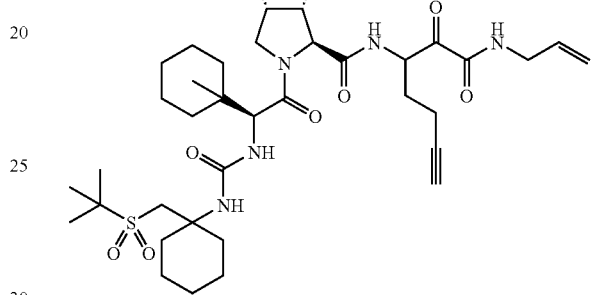
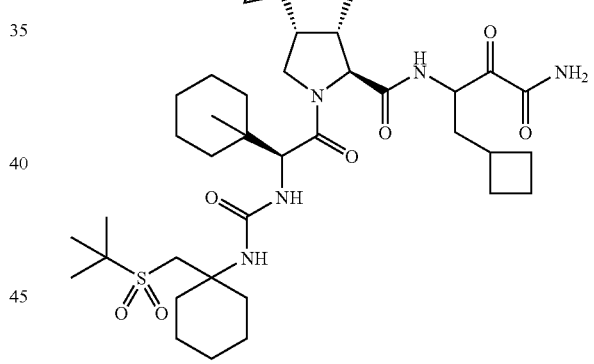
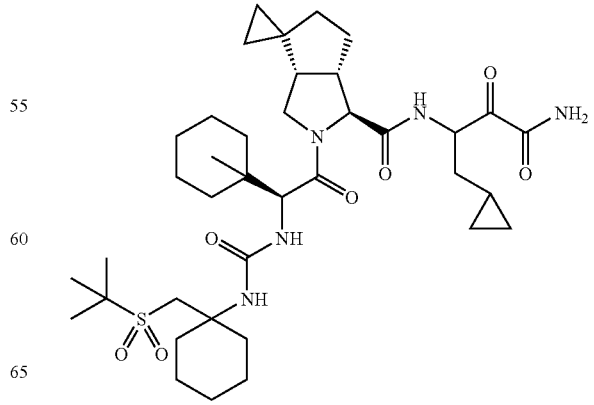

715 716
-continued -continued
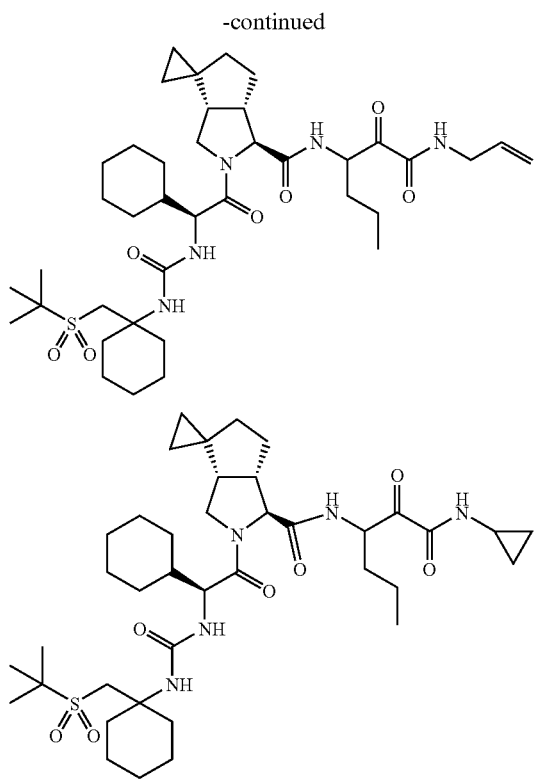
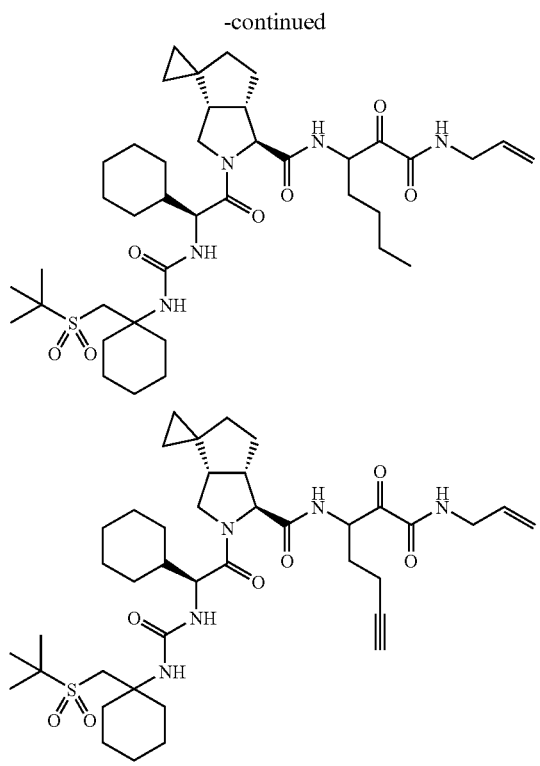
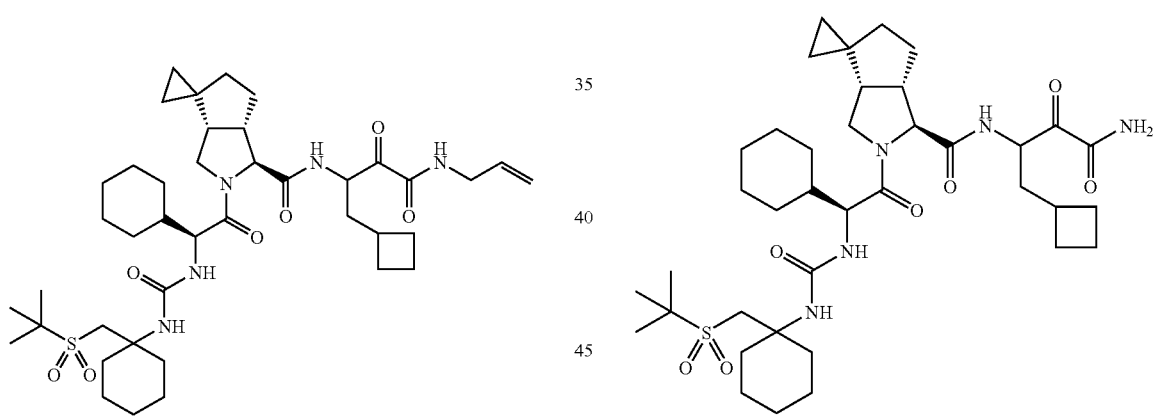
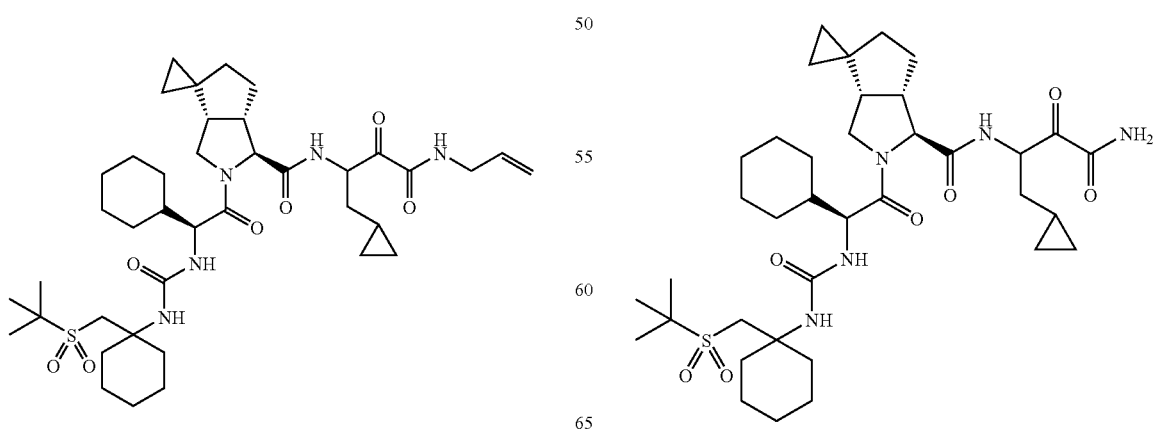

717
-continued
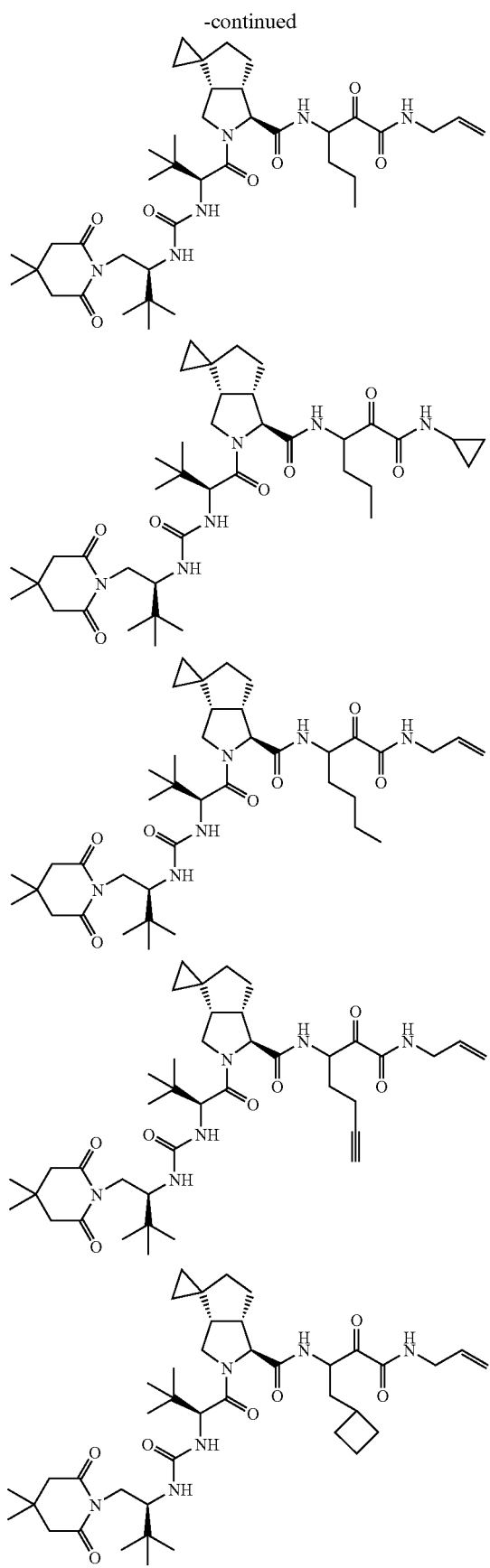
718
-continued
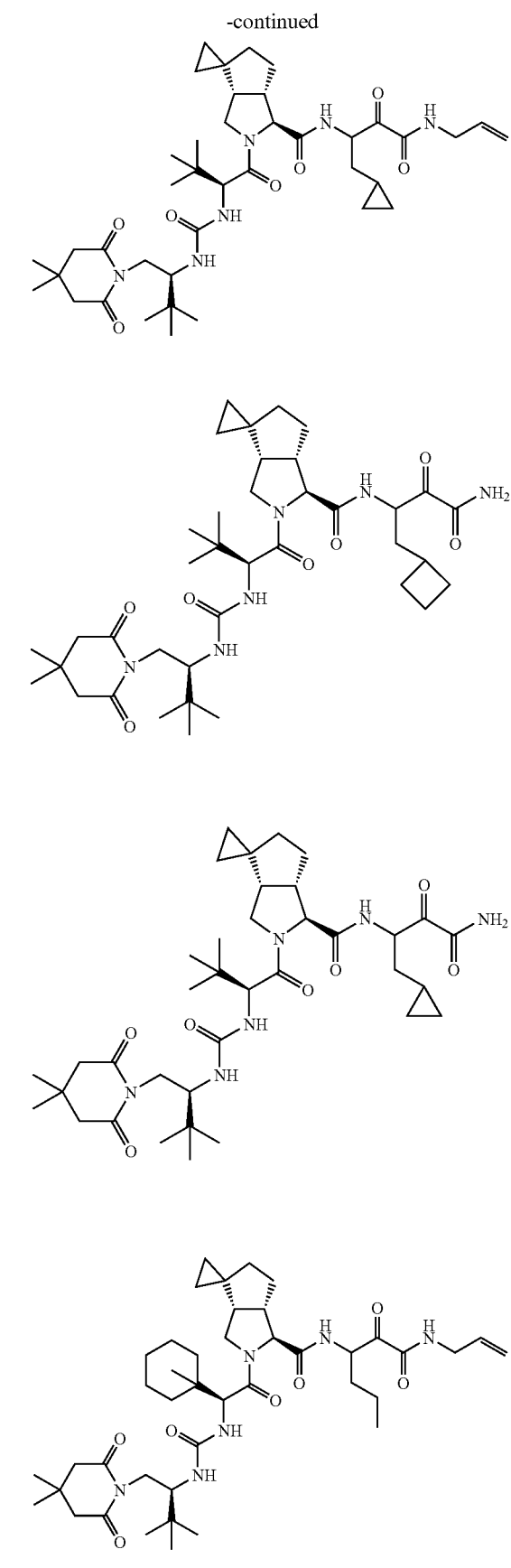

719
-continued
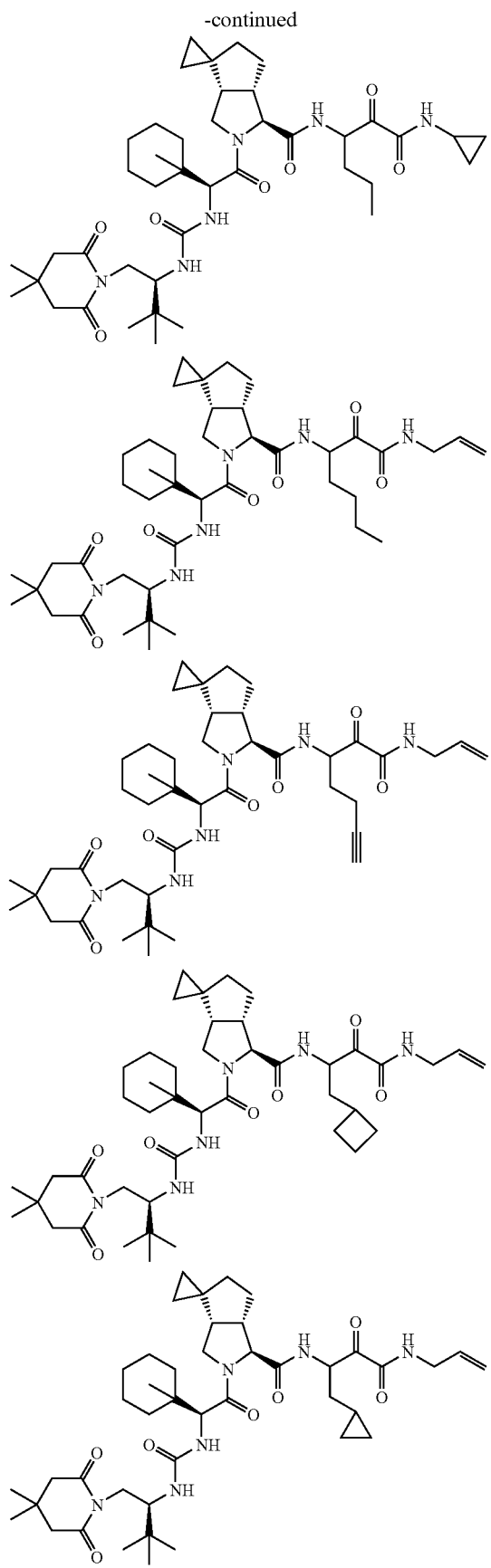
720
-continued
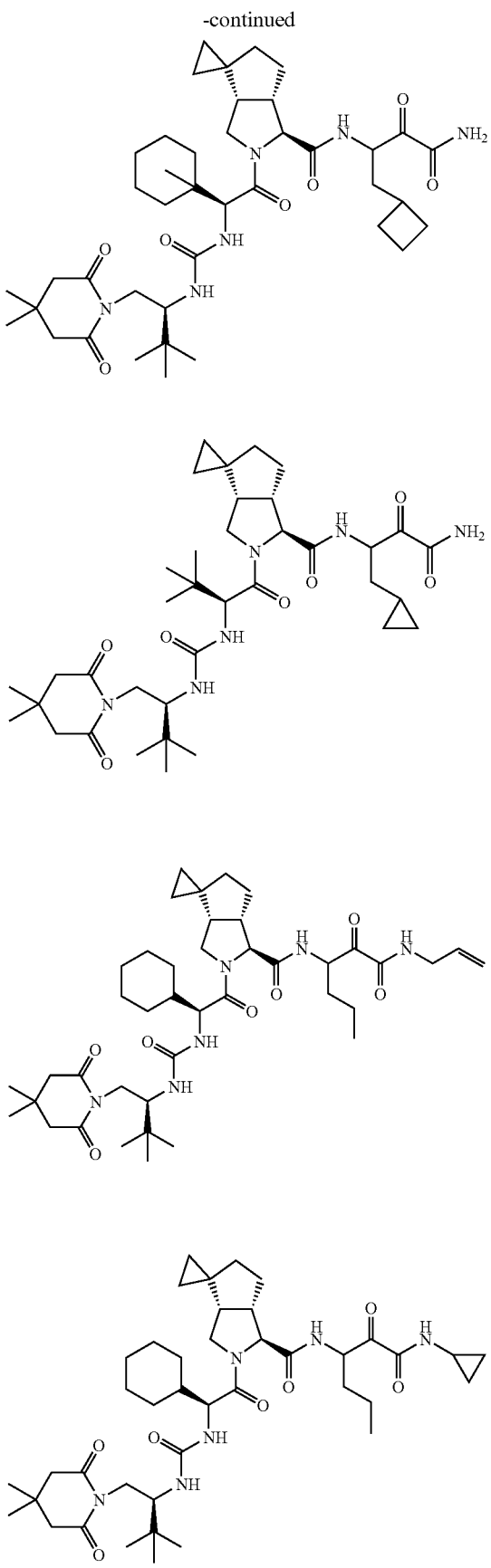

721
-continued
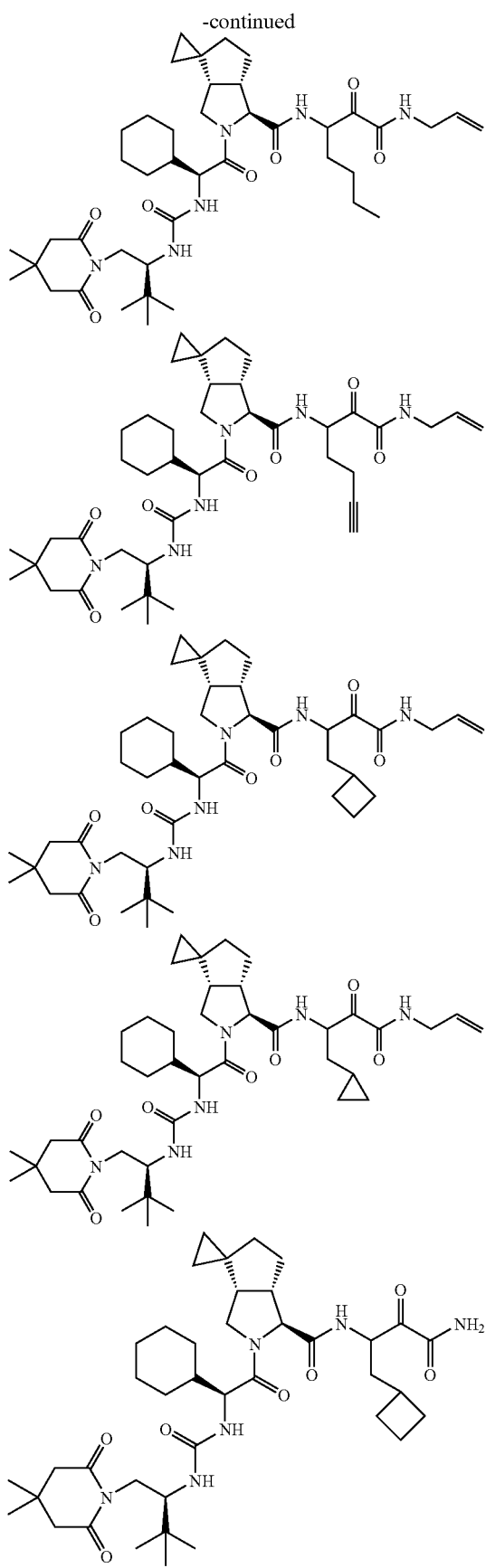
722
-continued
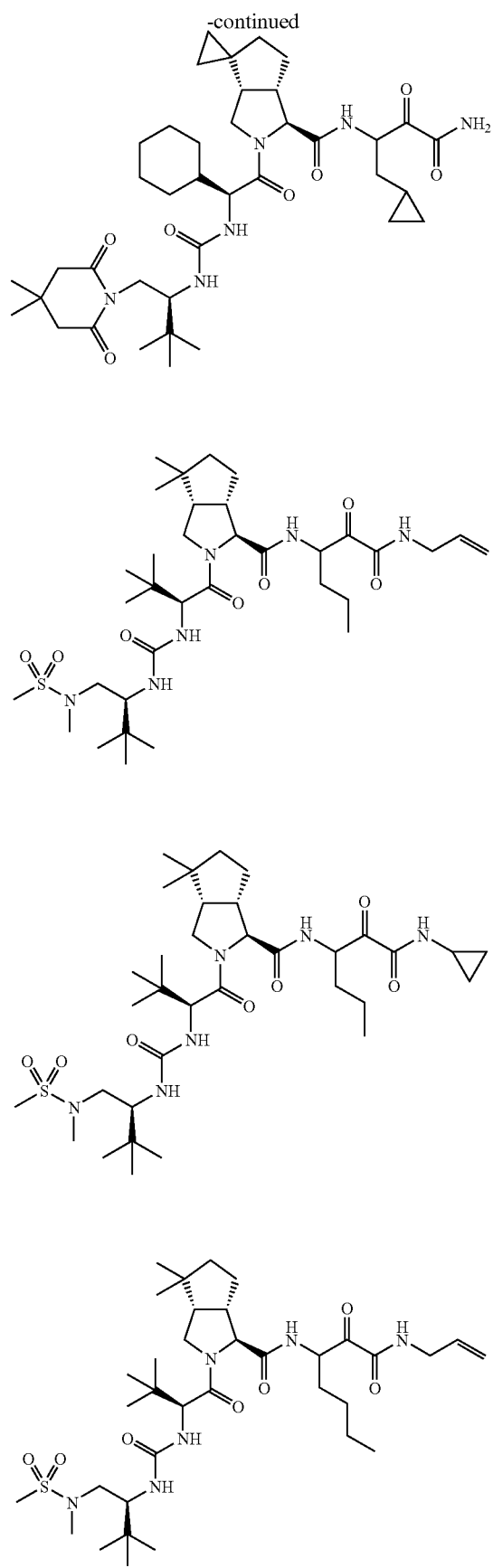

723
-continued
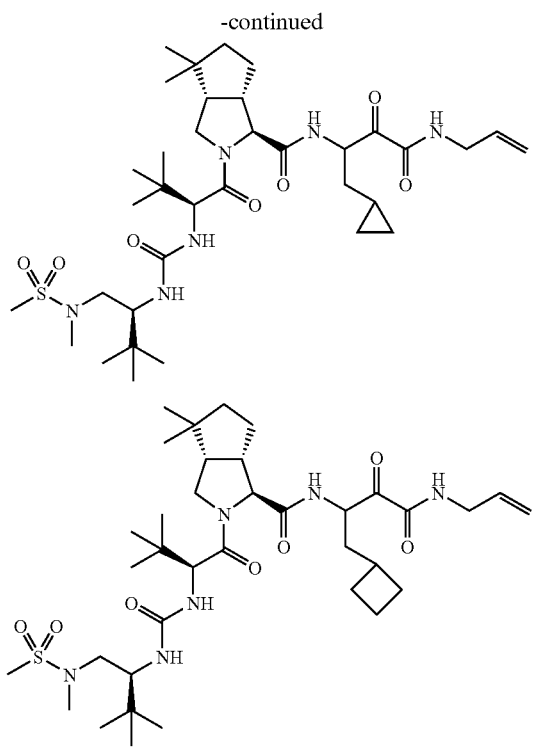
724
-continued
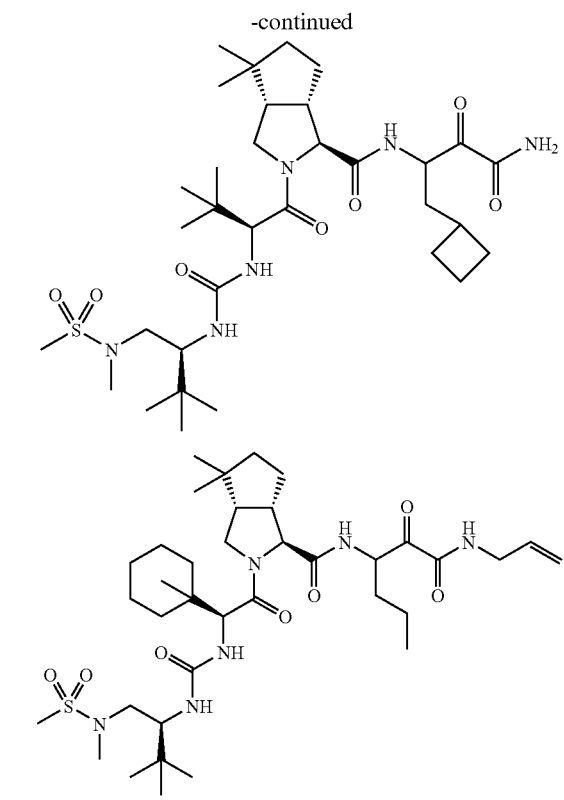
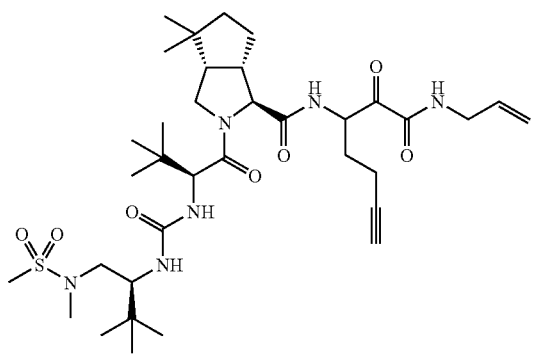
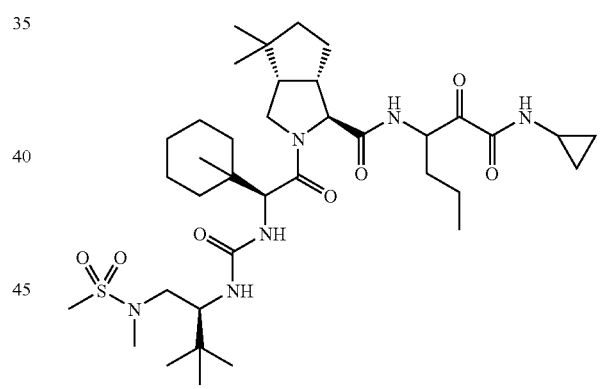
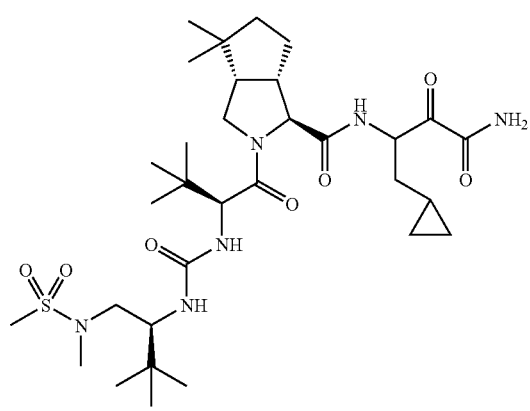
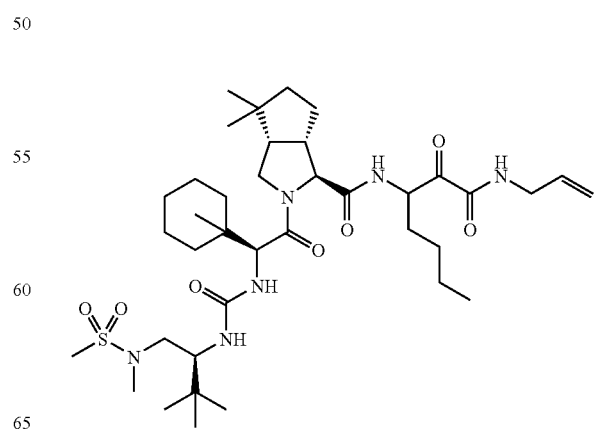

725
-continued
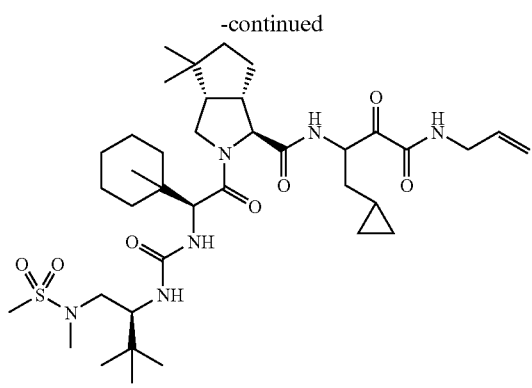
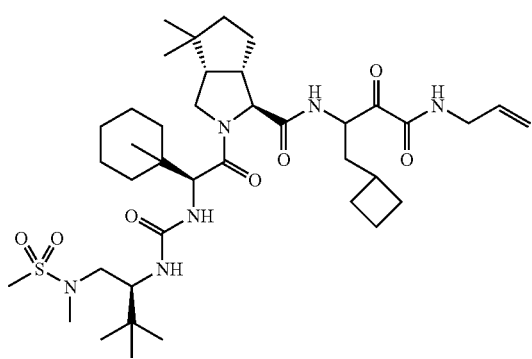
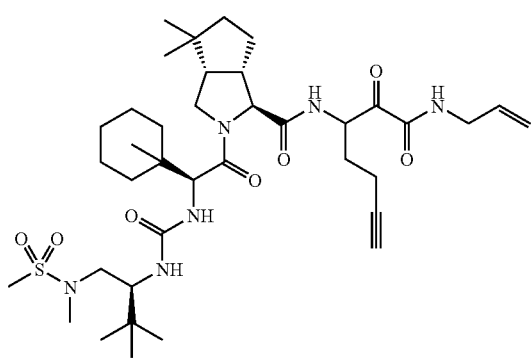
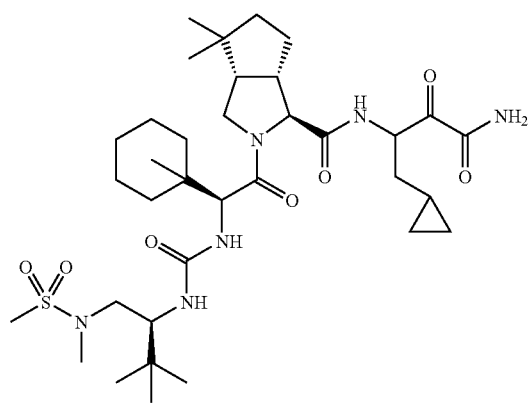
726
-continued
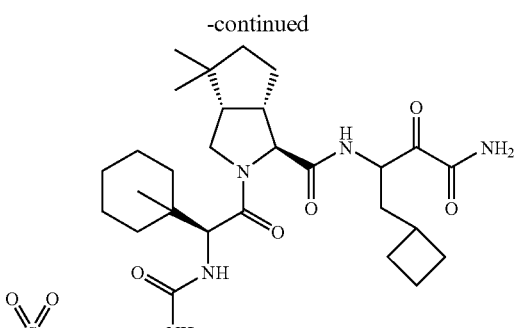
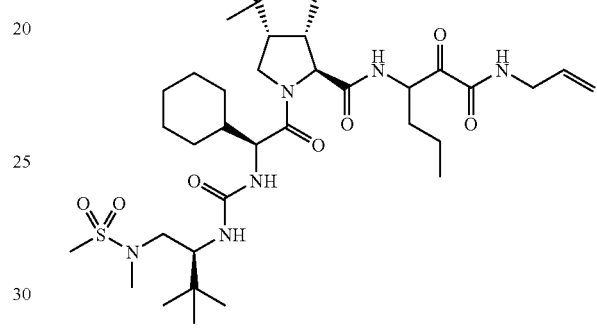
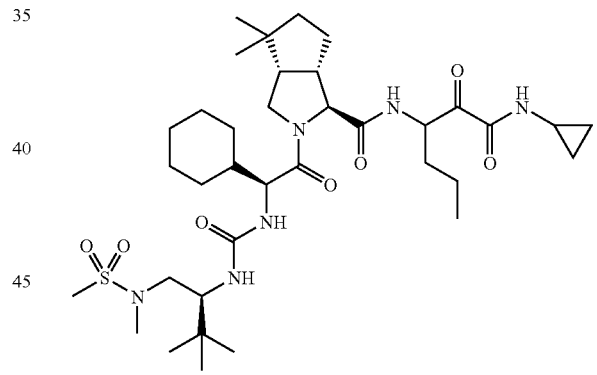
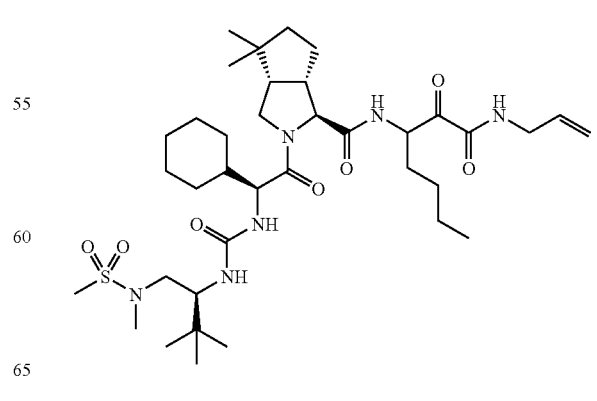

727
-continued
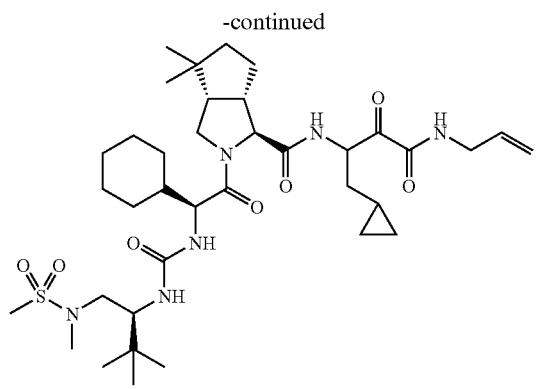
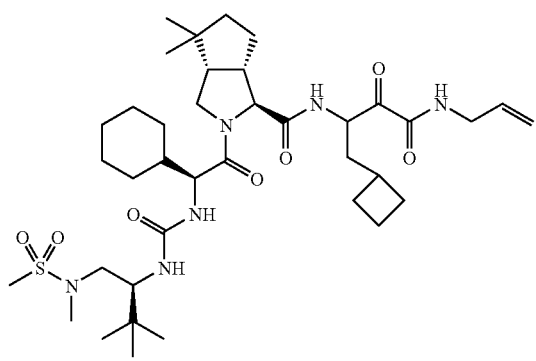
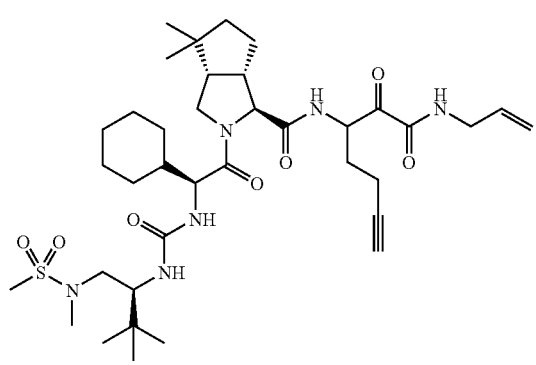
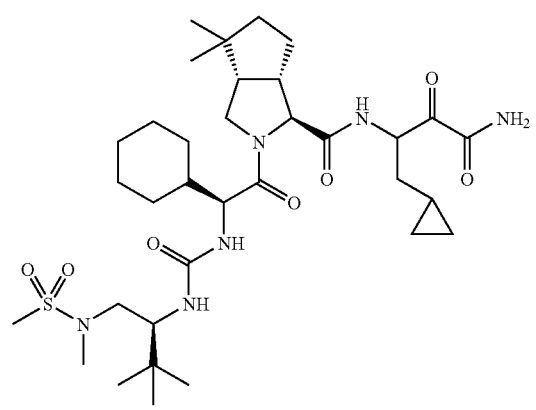
728
-continued
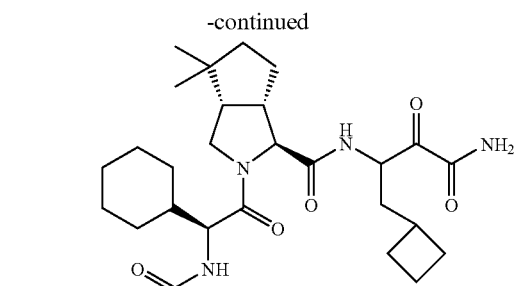
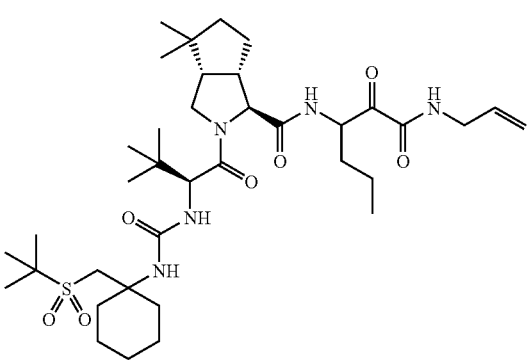
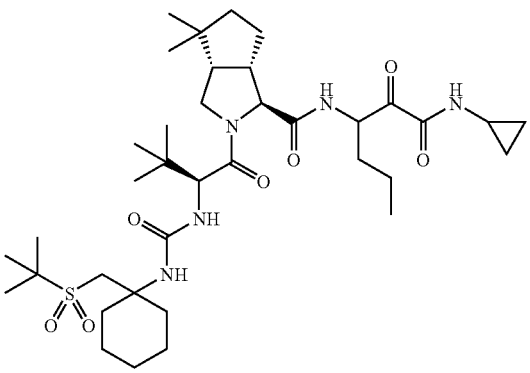
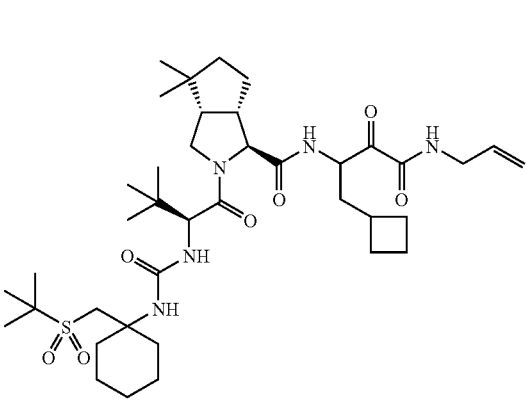

729                                              730
-continued                                       -continued
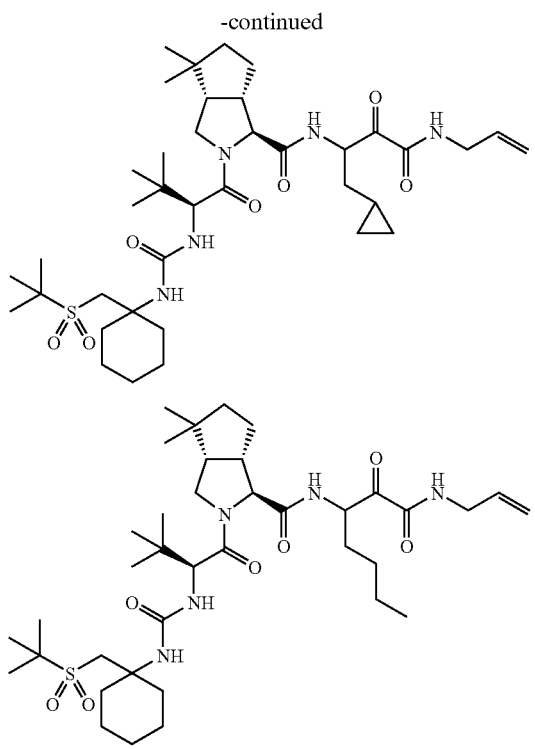
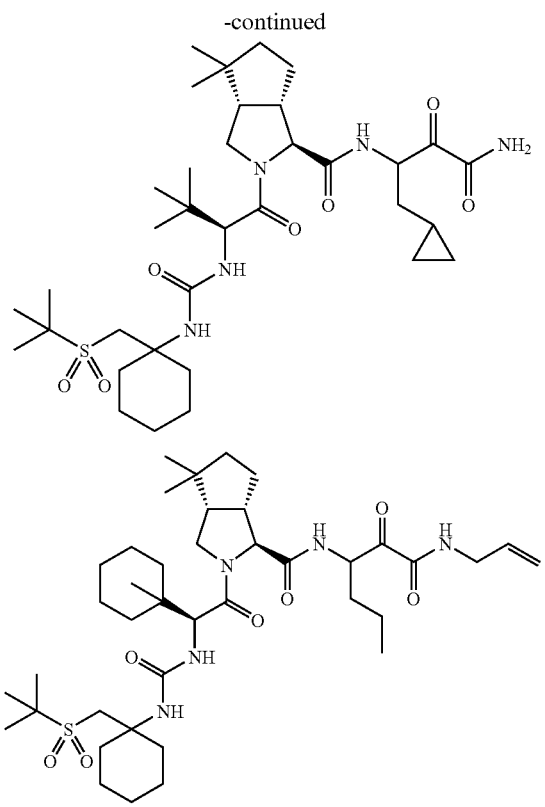

731
-continued
732
-continued
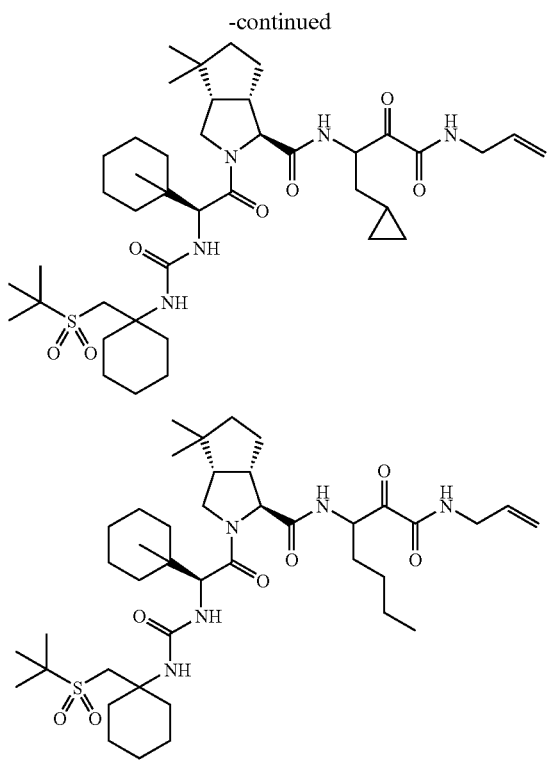
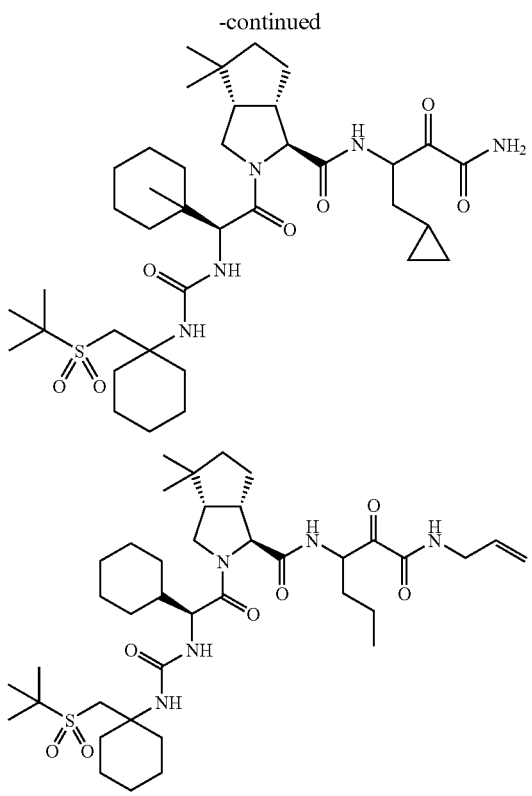
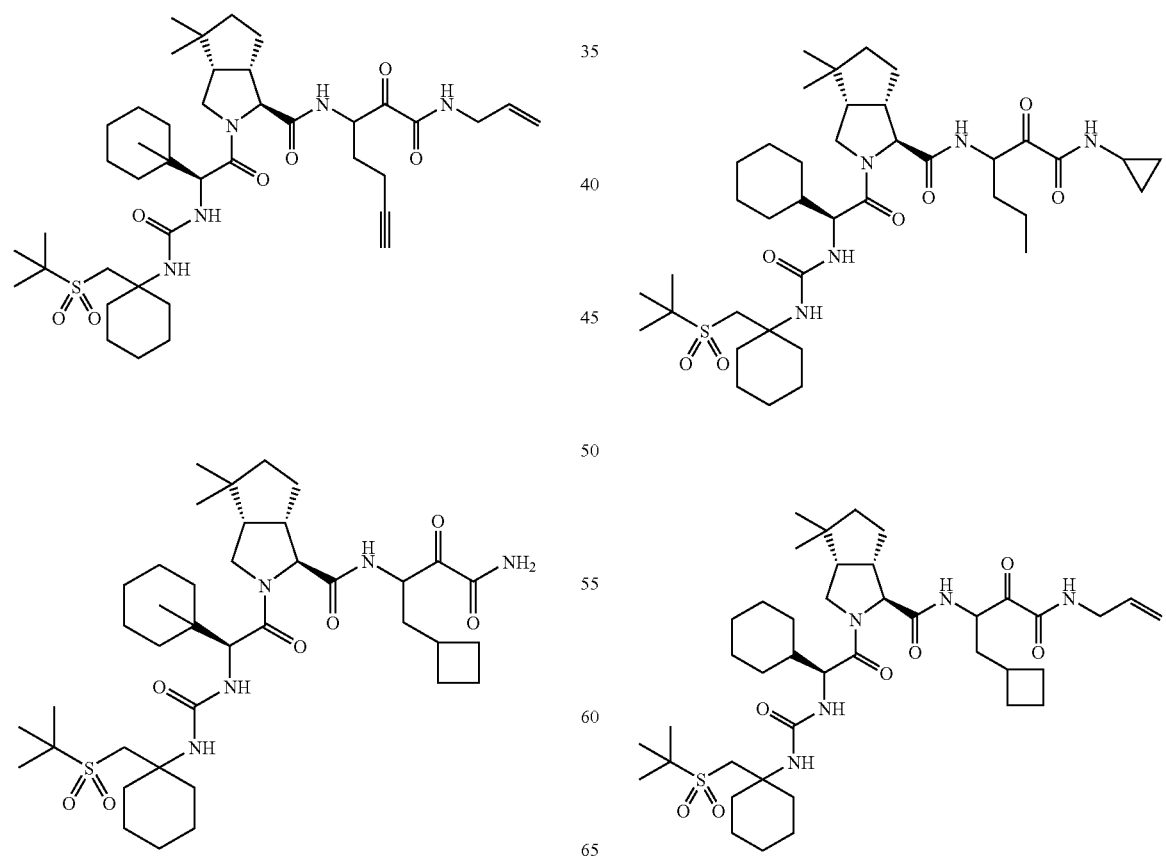

733
-continued
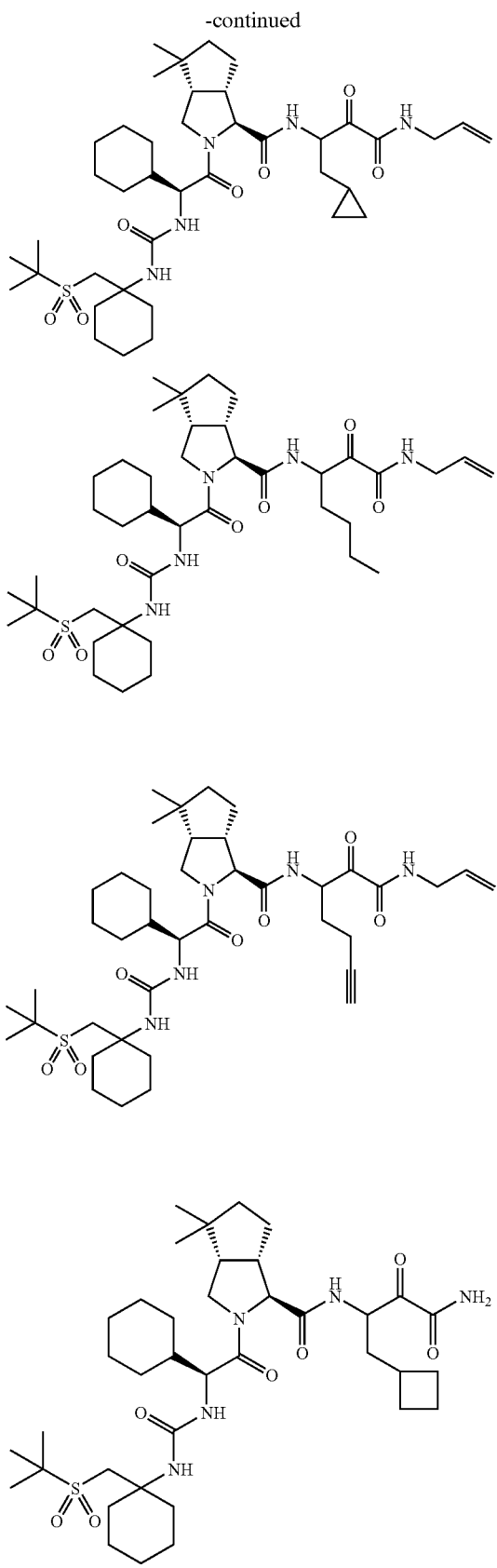
734
-continued
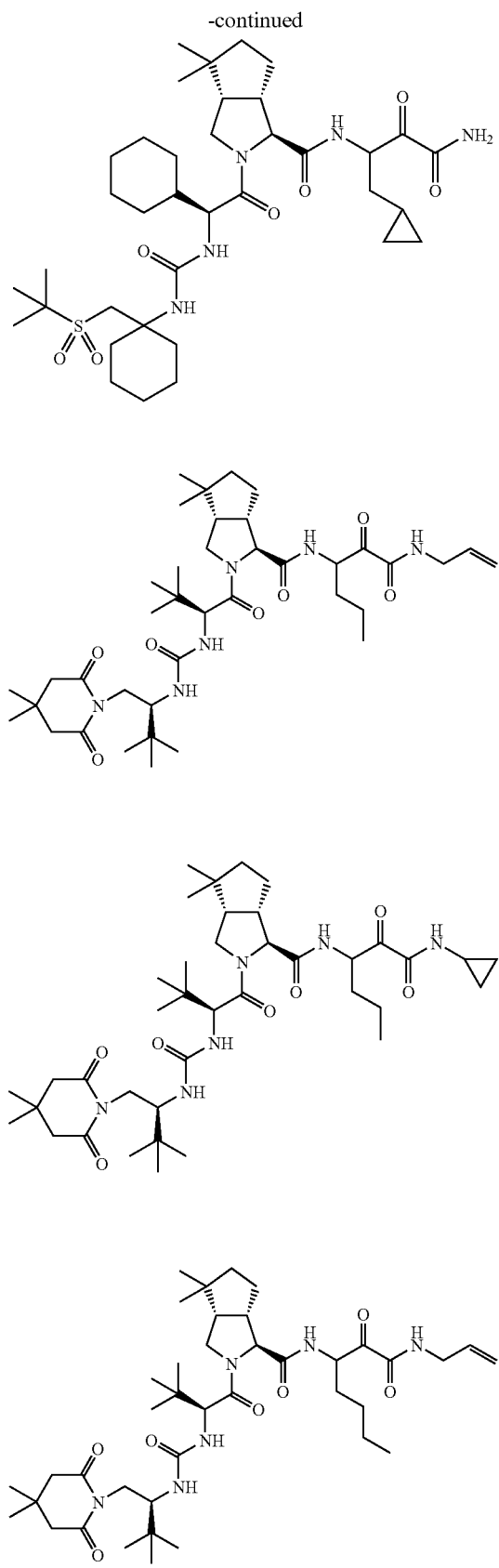

-continued
735
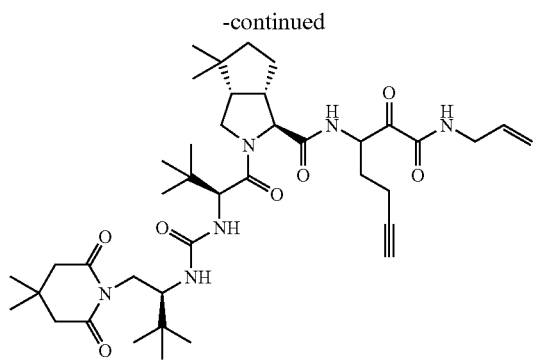
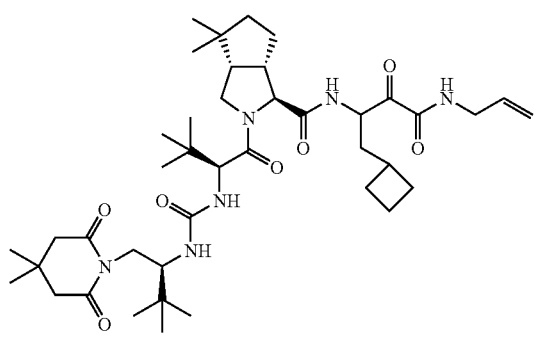
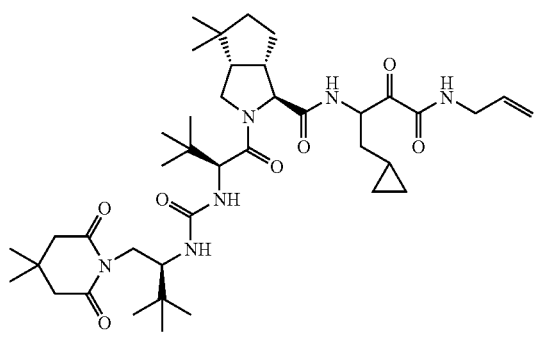
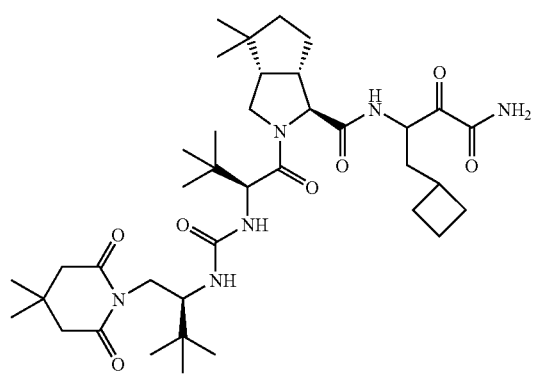
736
-continued
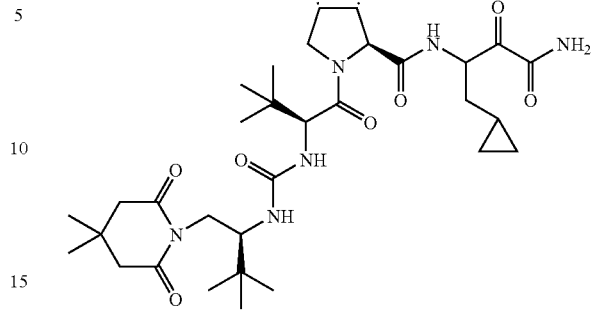
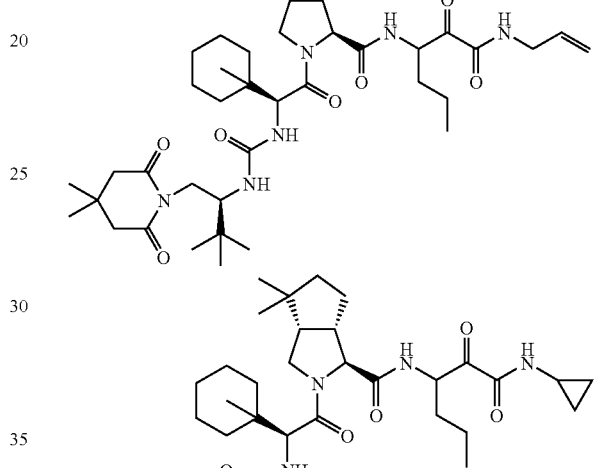
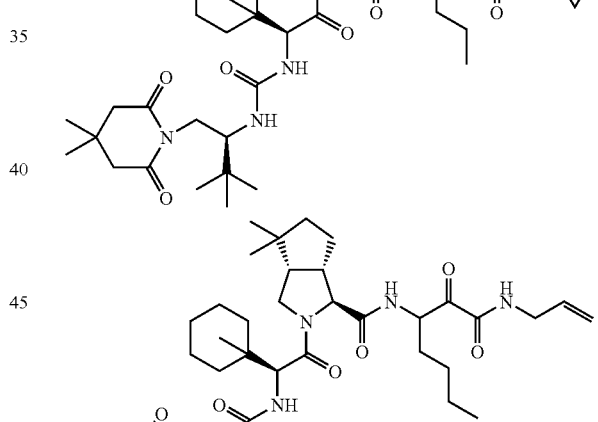
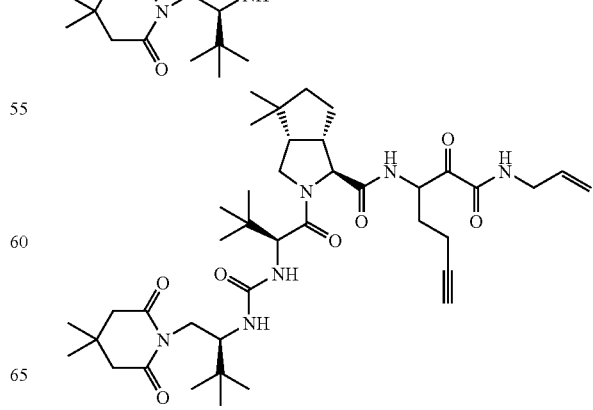

737
-continued
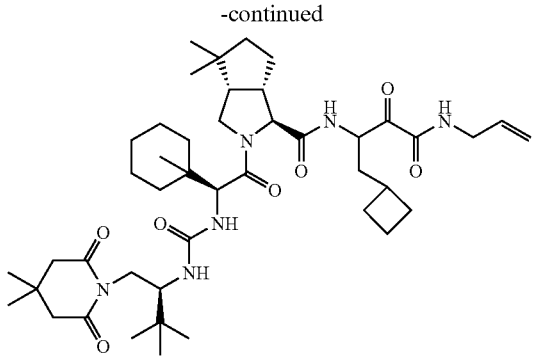
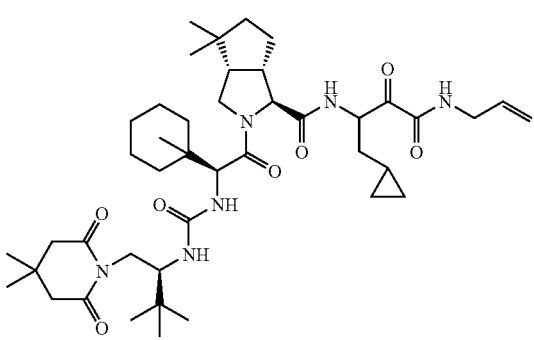
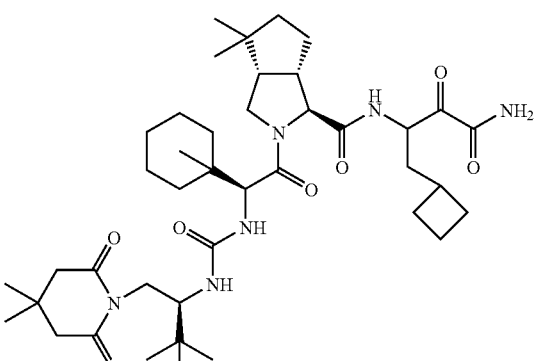
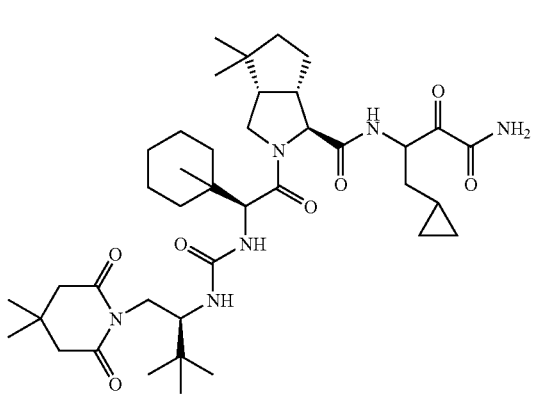
738
-continued
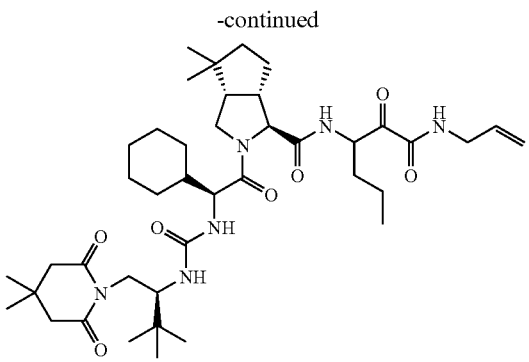
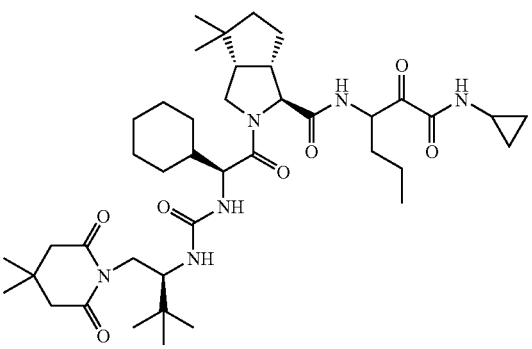
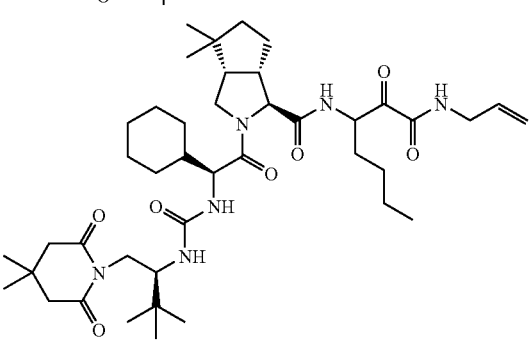
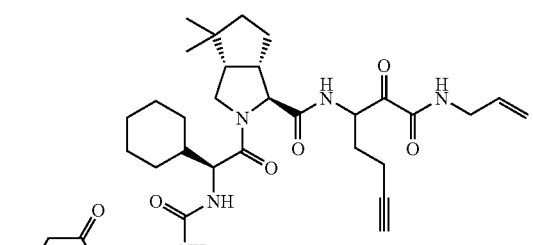
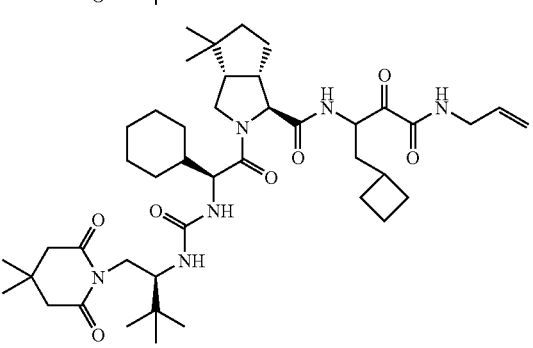

739
-continued
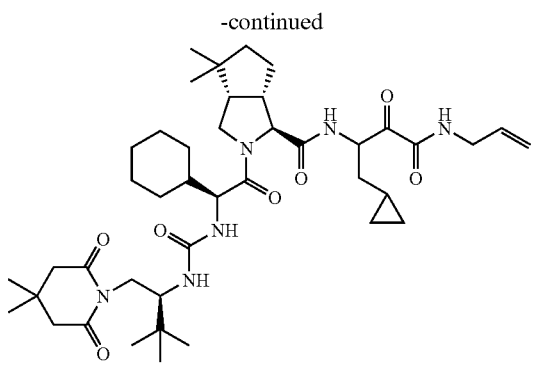
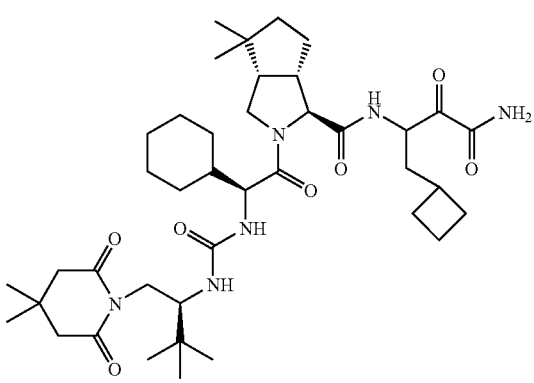
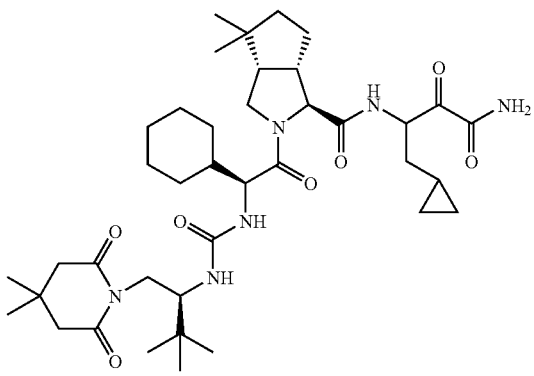
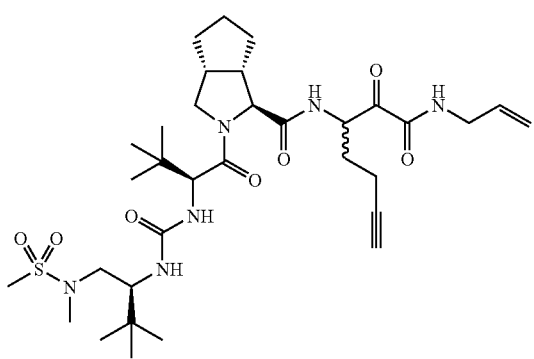
740
-continued
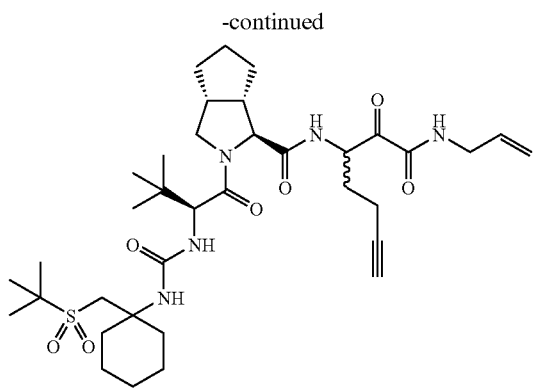
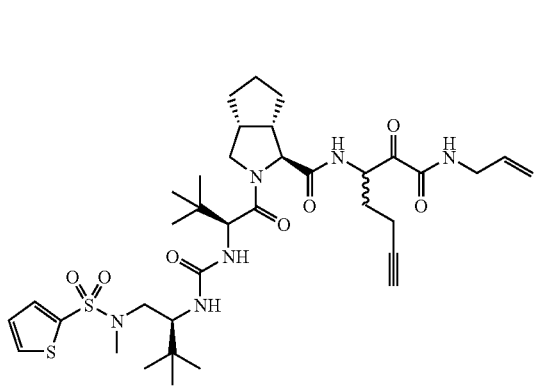
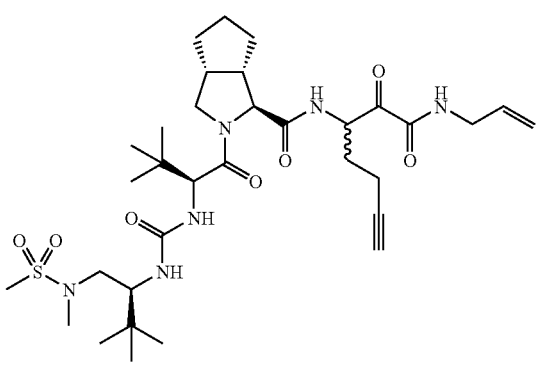
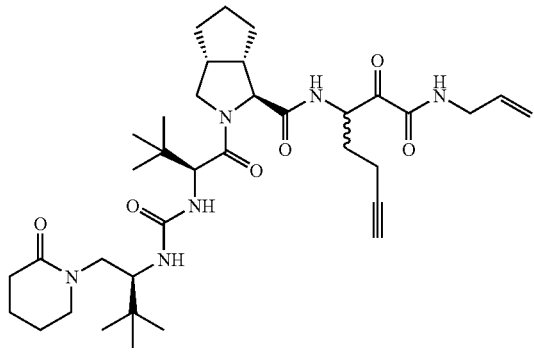

741
-continued
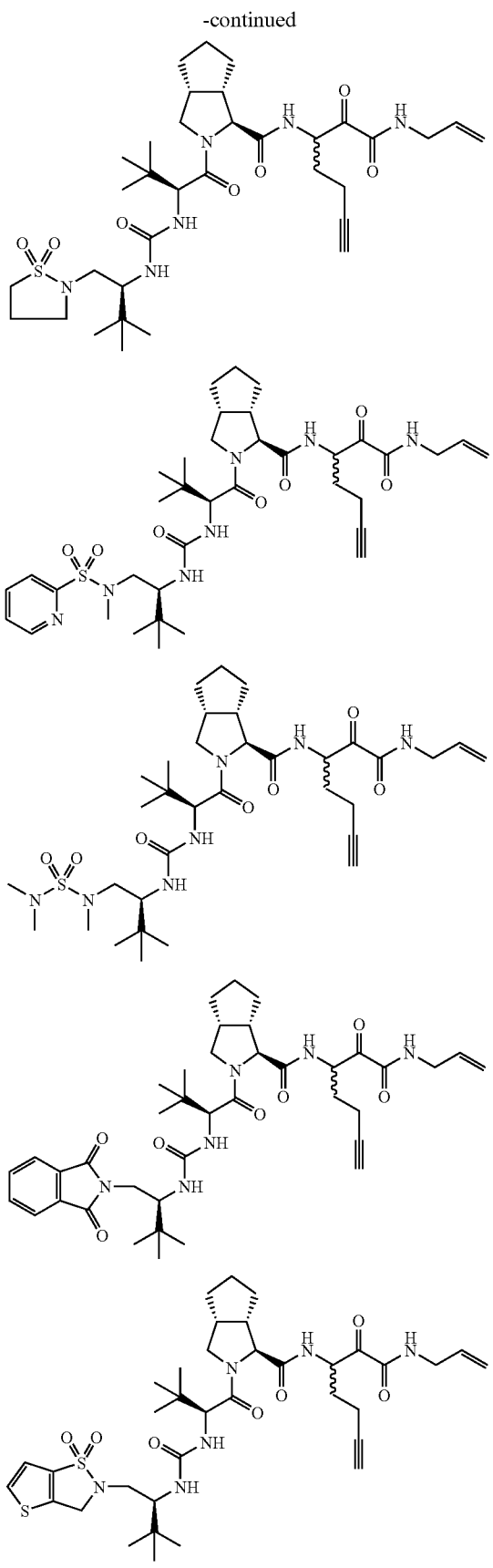
742
-continued
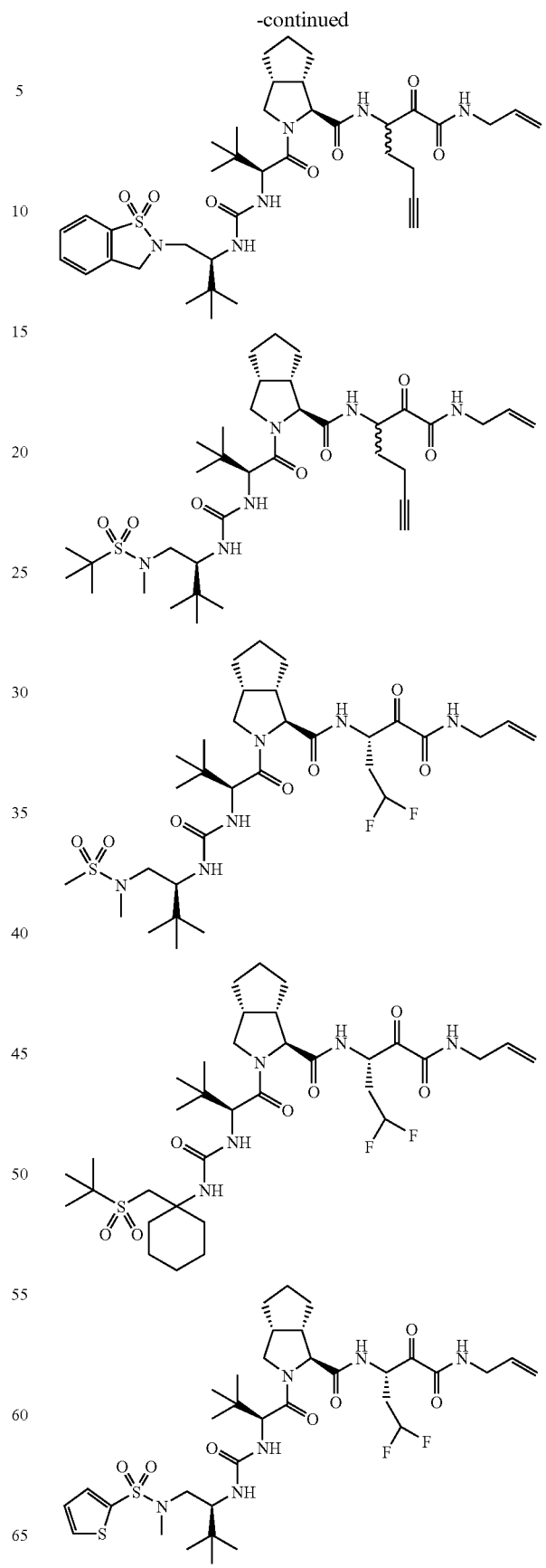

743
-continued
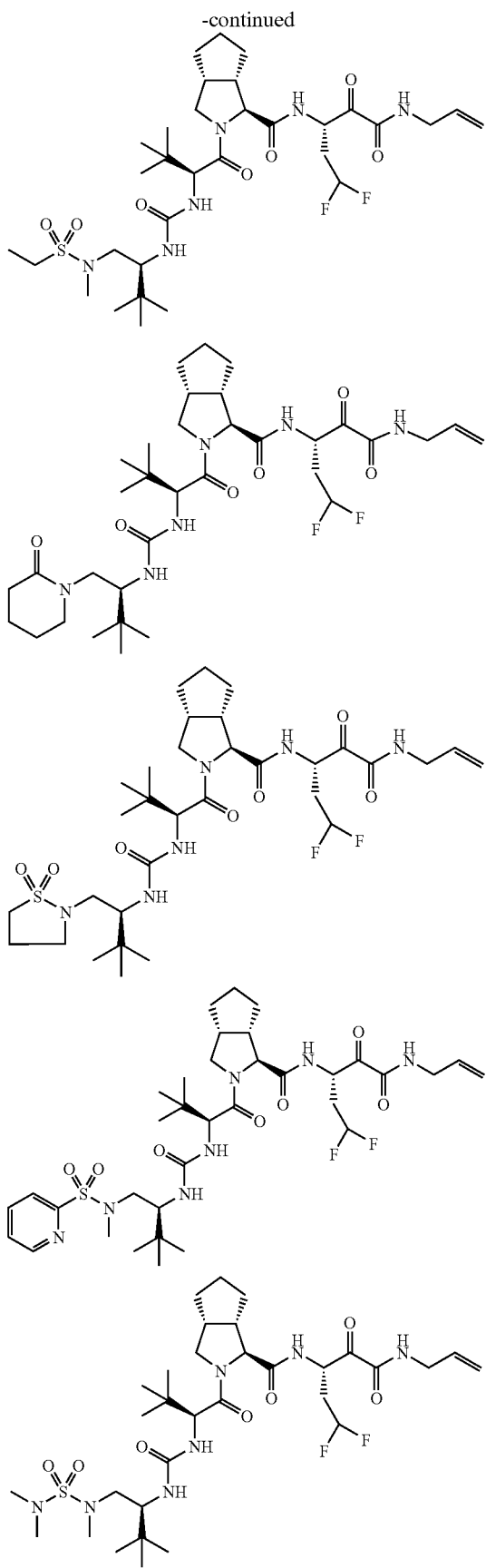
744
-continued
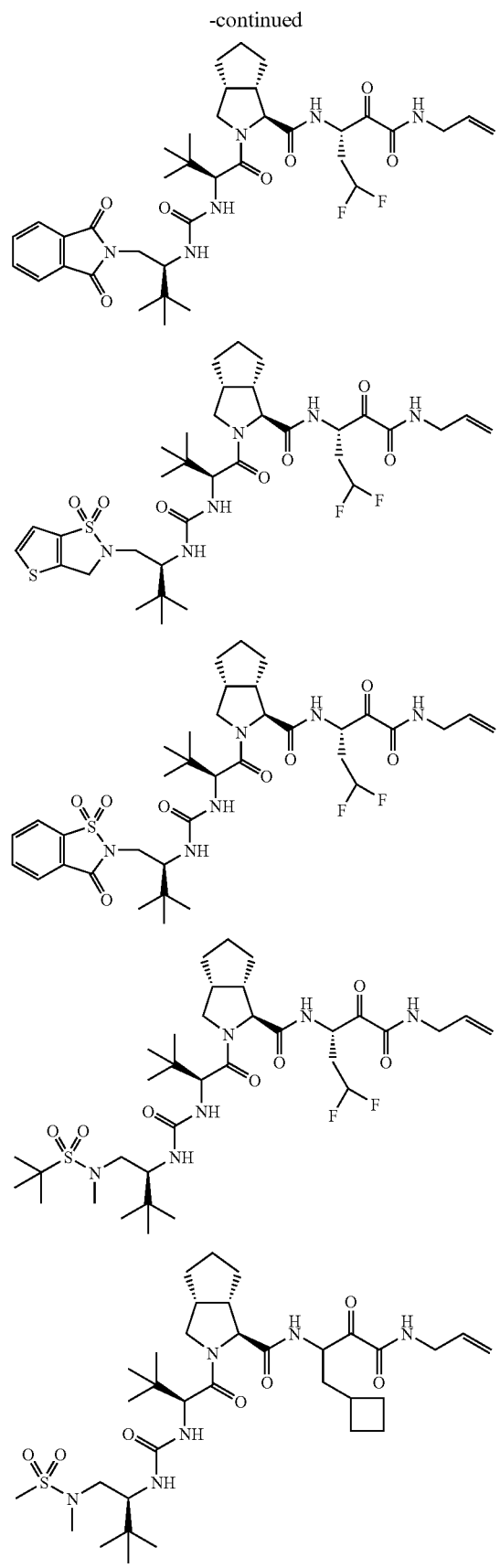

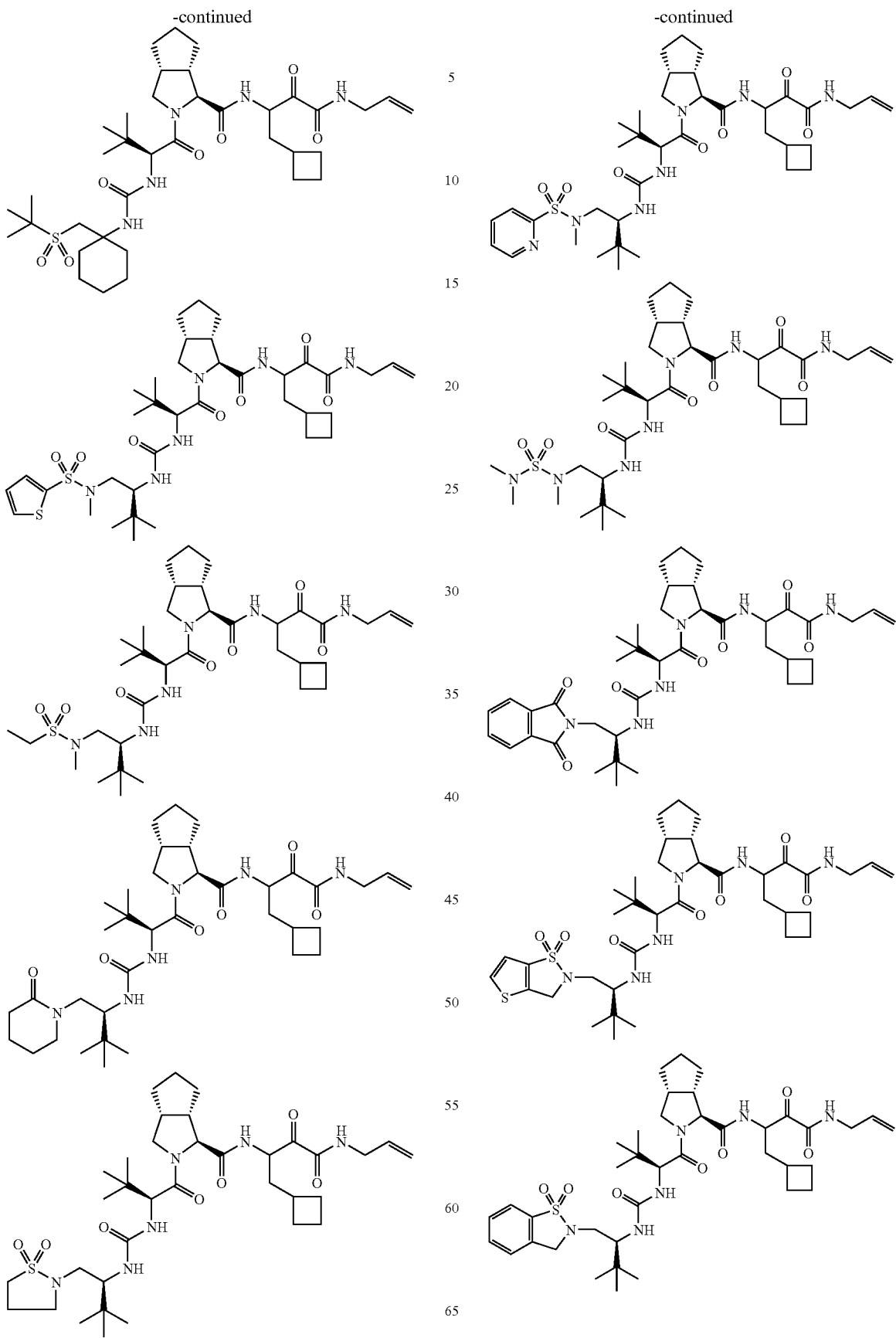

-continued
| 747 | 748 |
|---|---|
| 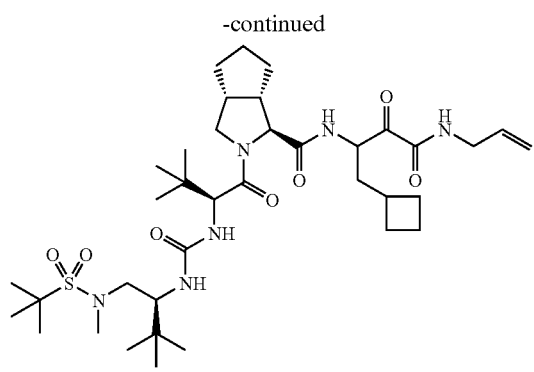 | 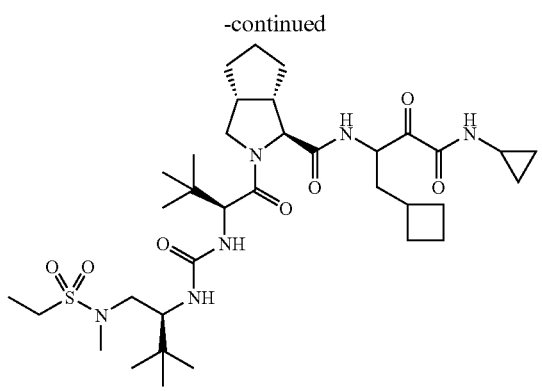 |
| 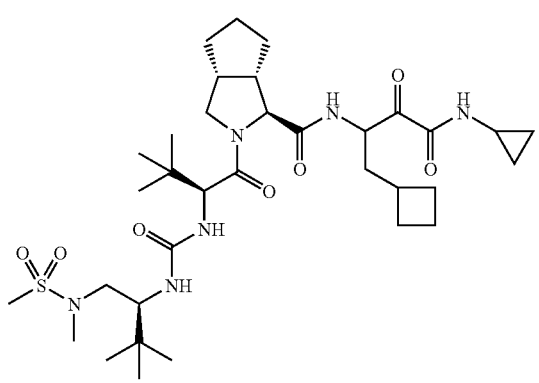 | 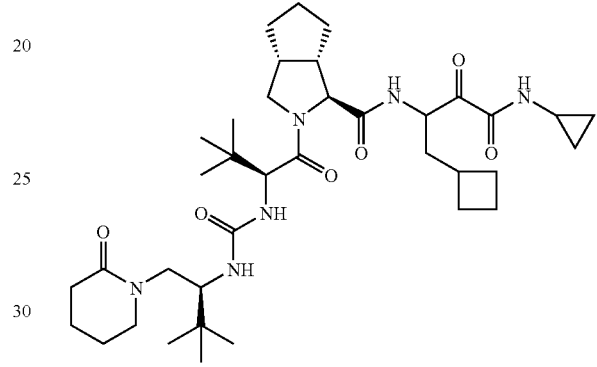 |
| 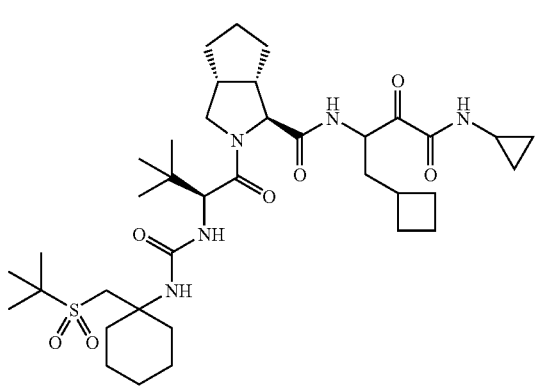 | 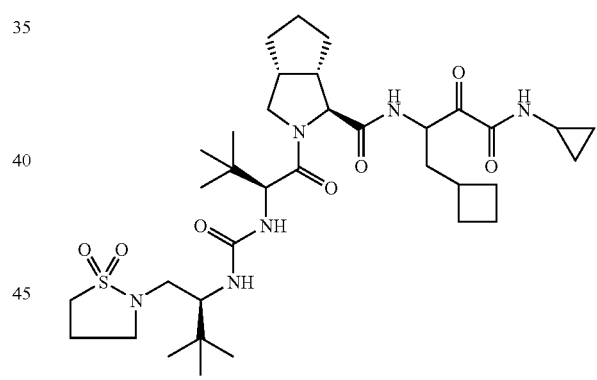 |
| 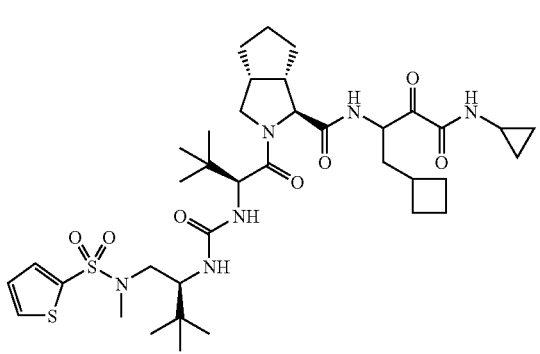 | 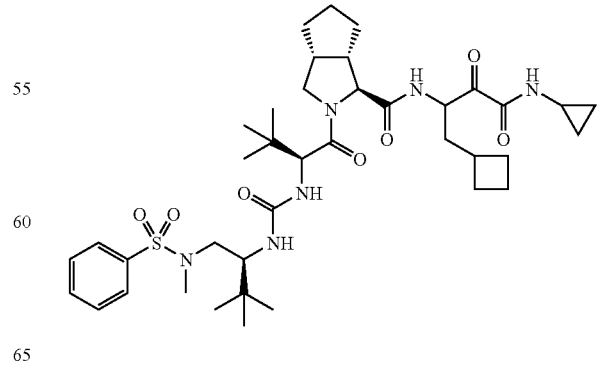 |

749
-continued
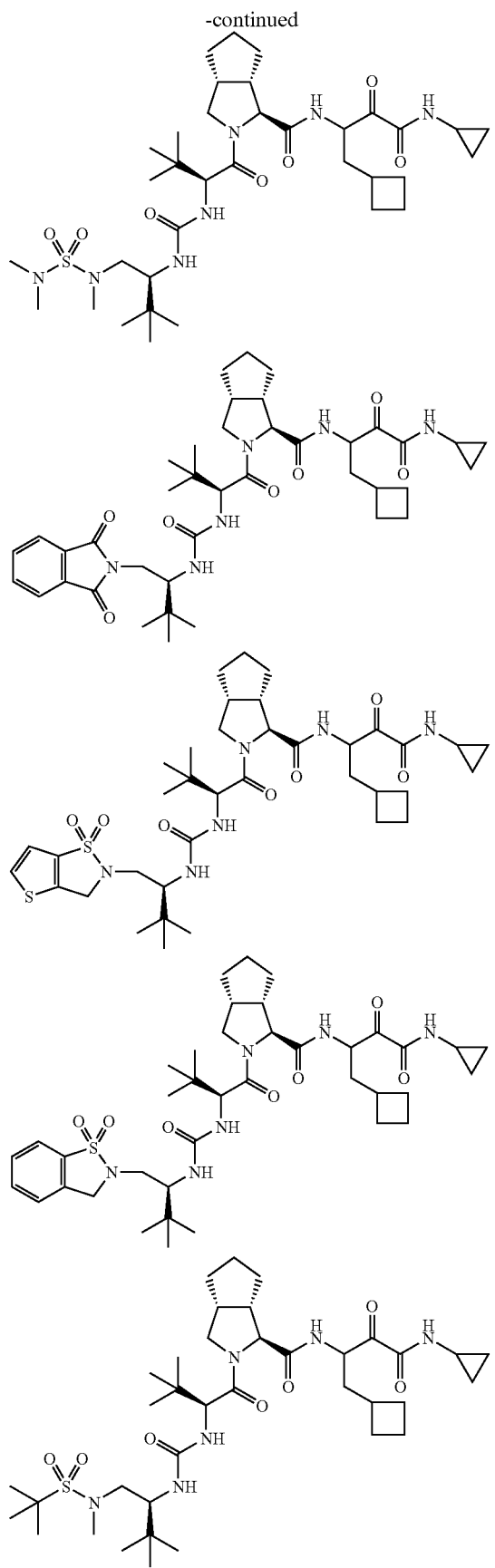
750
-continued
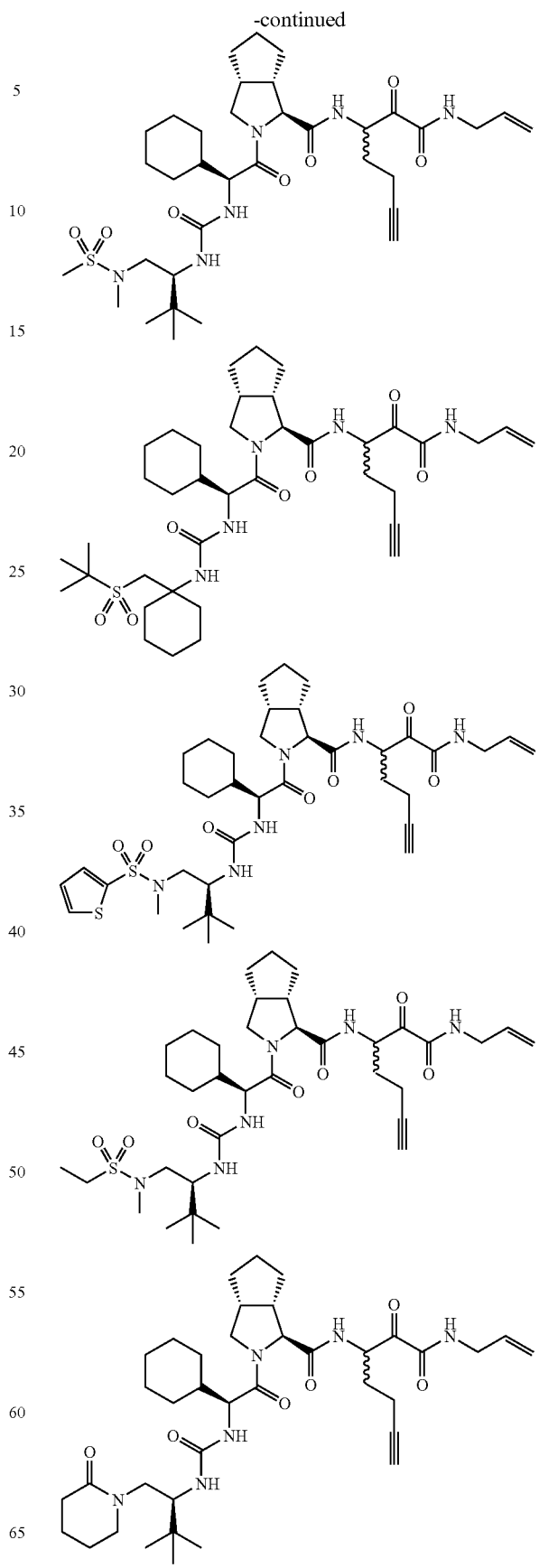

751
-continued
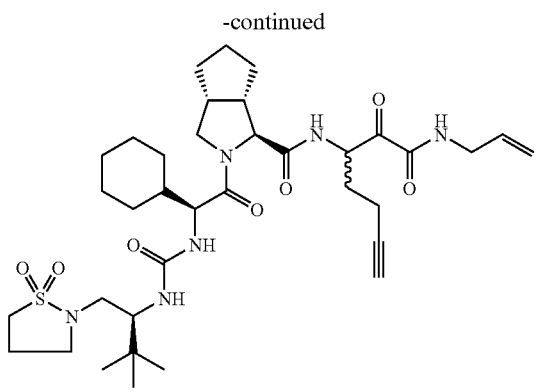
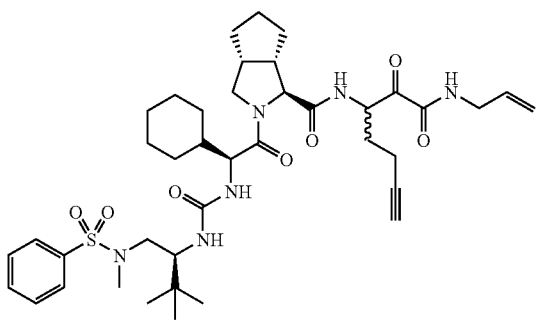
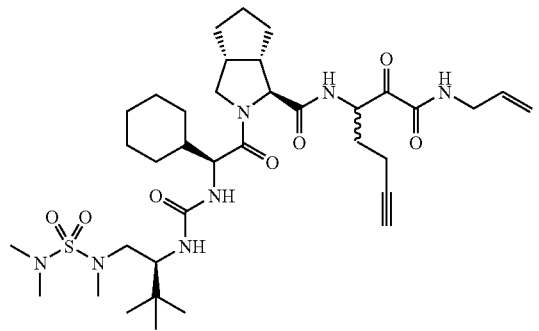
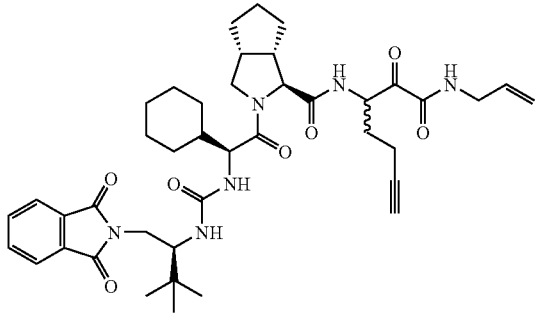
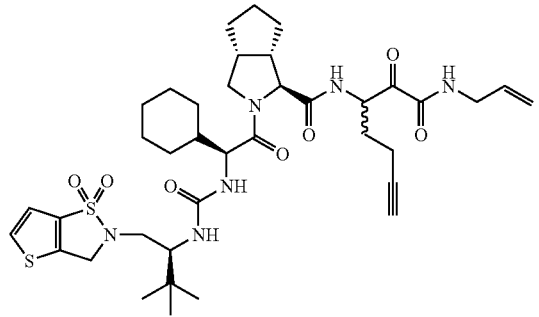
752
-continued
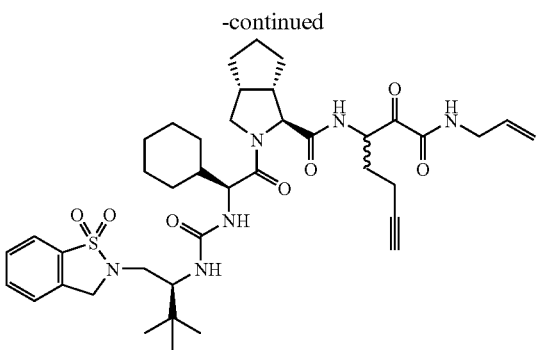
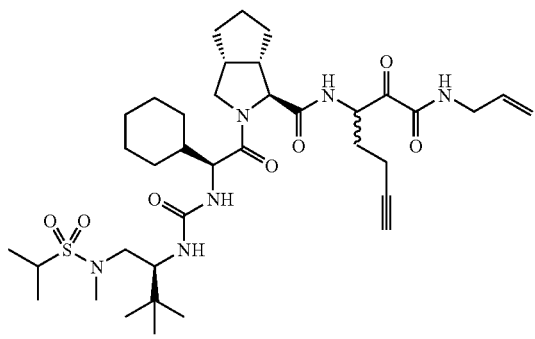
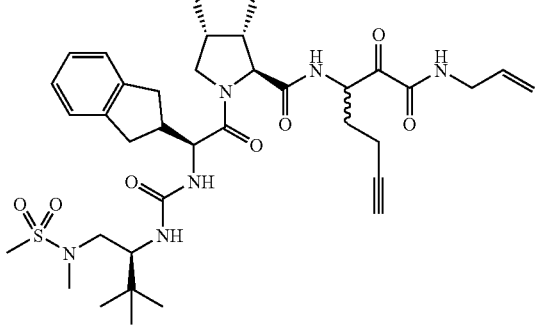
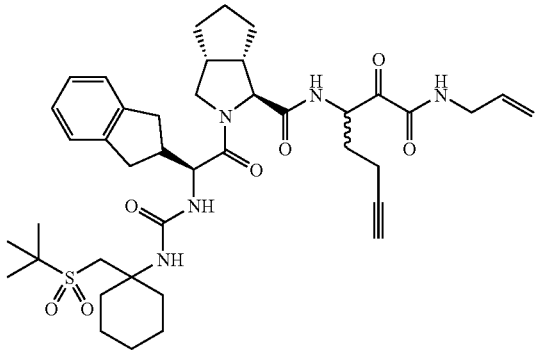
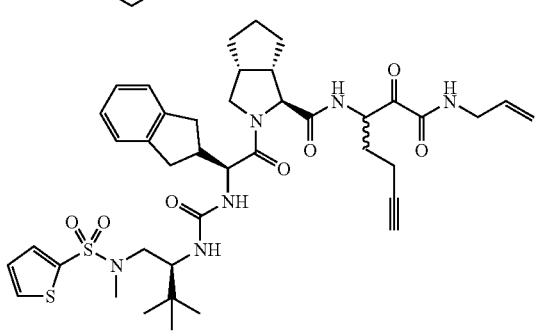

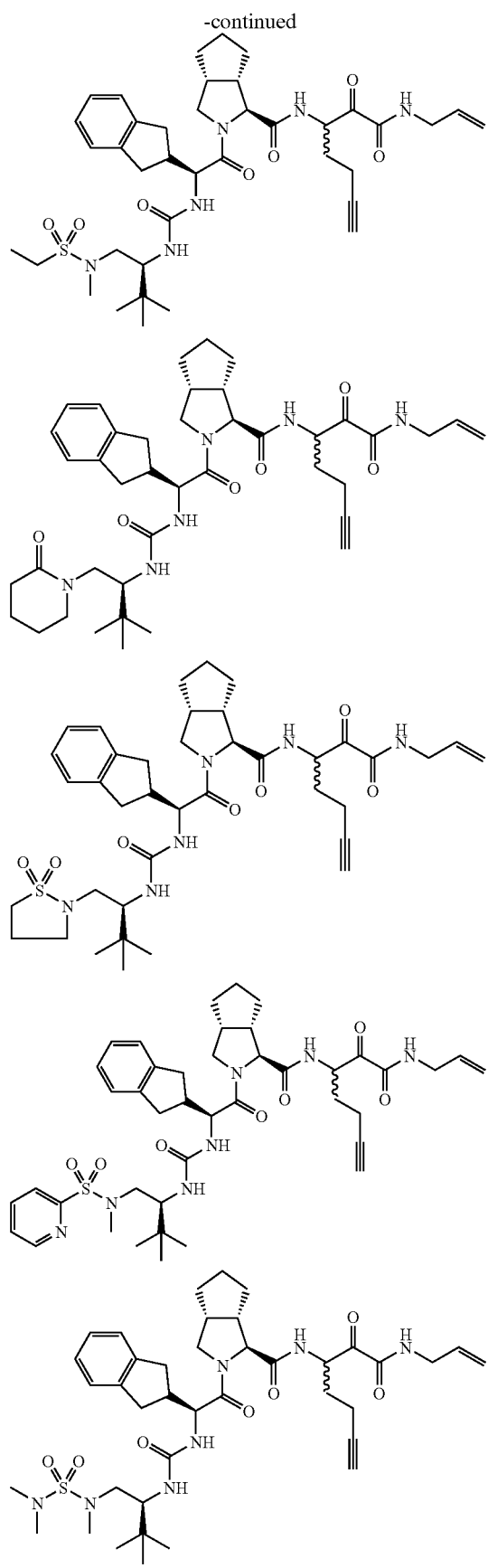

755 756
-continued -continued
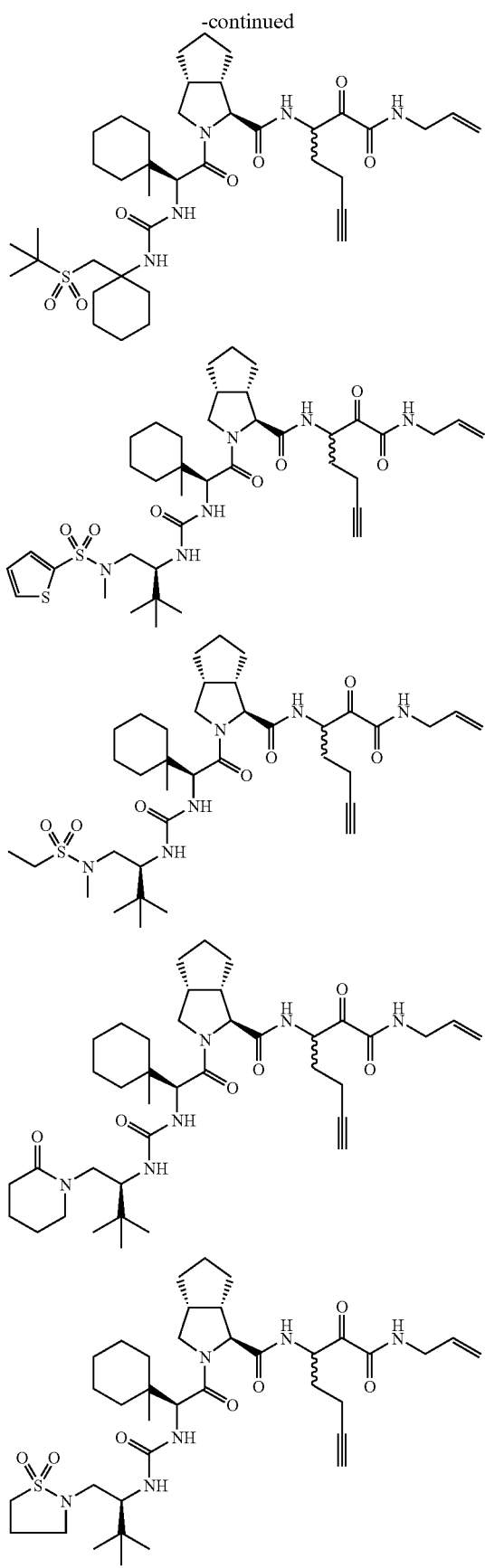
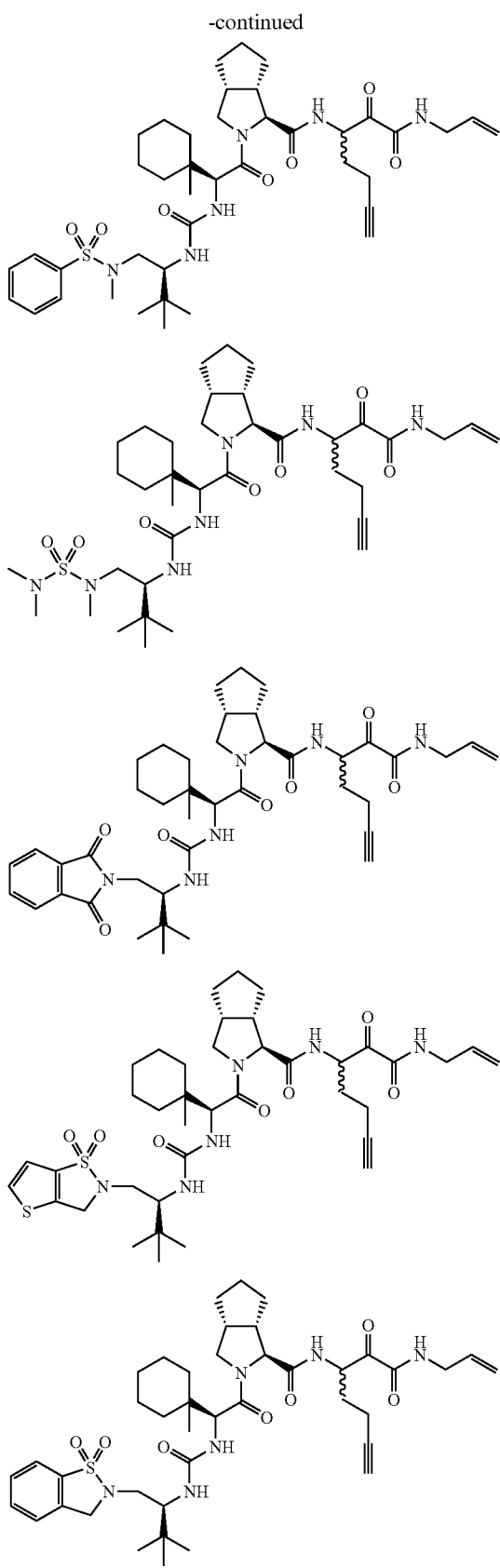

-continued
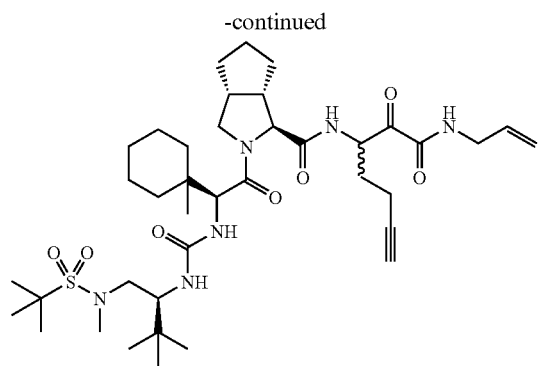
or a pharmaceutically acceptable salt, solvate or ester thereof.
Compounds of formula XVII are disclosed in U.S. patent application Ser. No. 11/064,574 filed Feb. 24, 2005. The preparation of these compounds is disclosed in the experimental section of this application set forth hereinbelow.
Non-limiting examples of certain compounds disclosed in U.S. patent application Ser. No. 11/064,574 are:
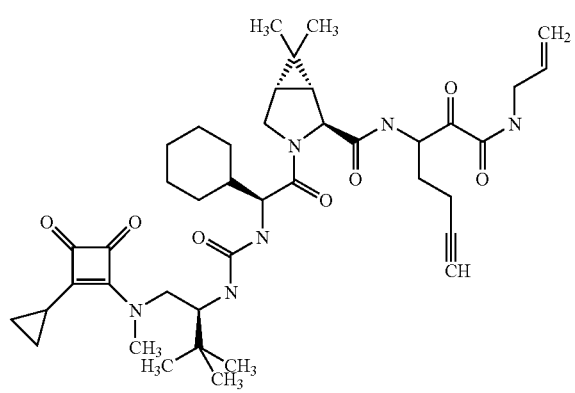
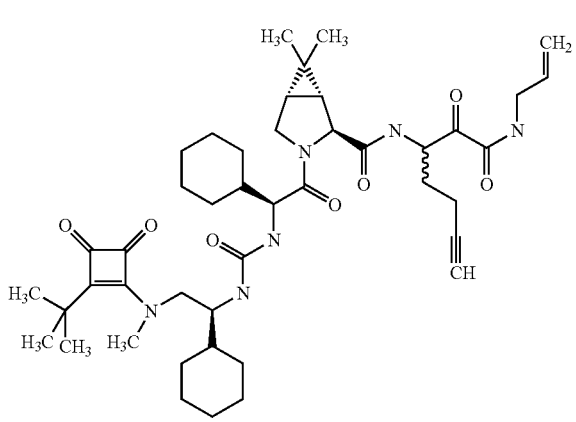
-continued
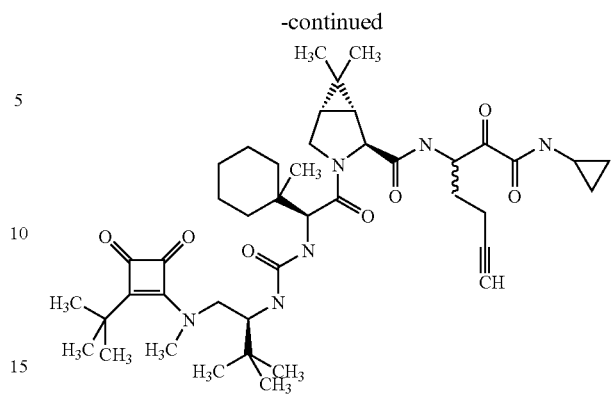
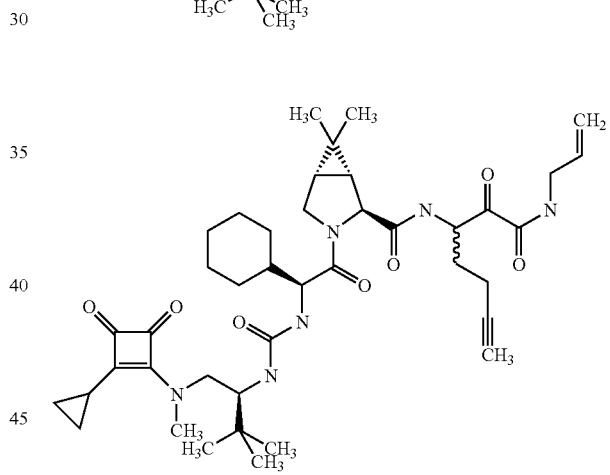
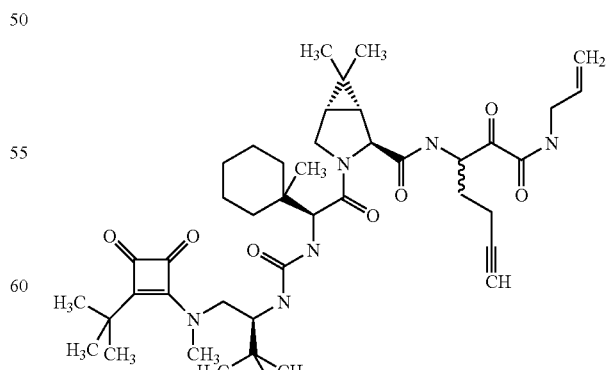

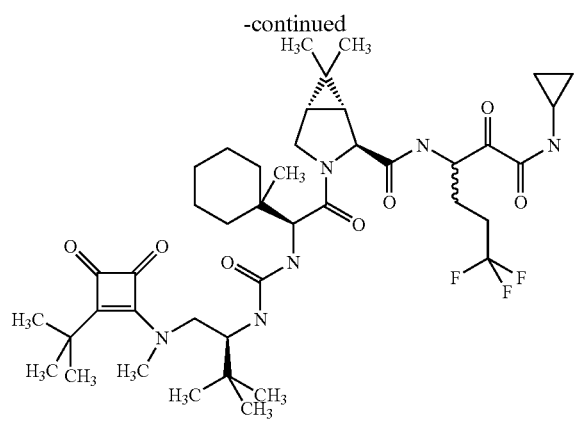

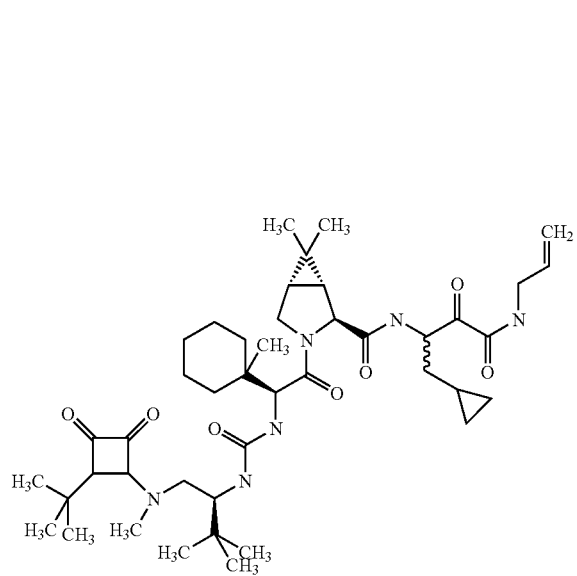

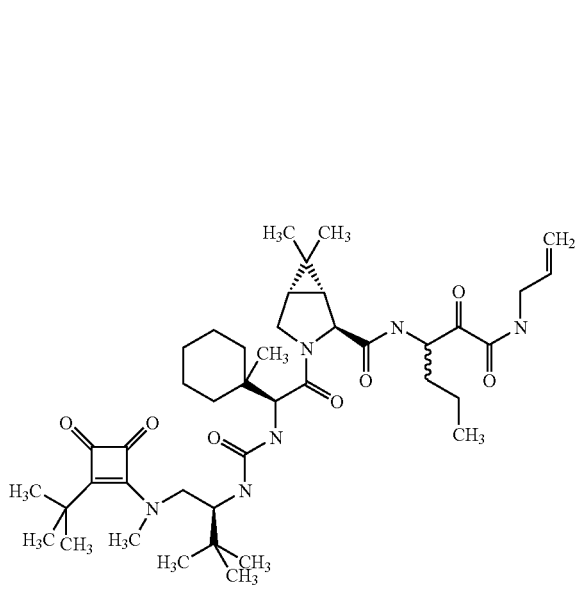

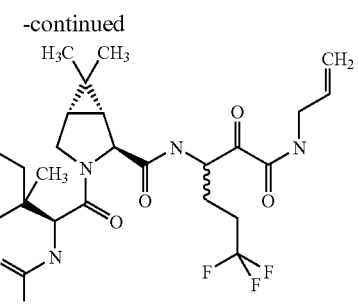

or a pharmaceutically acceptable salt, solvate or ester thereof.

Compounds of formula XVIII are disclosed in U.S. Provisional Patent Application Ser. No. 60/605,234 filed Aug. 27, 2004. The preparation of these compounds is disclosed in the experimental section of this application set forth hereinbelow.

Non-limiting examples of certain compounds disclosed in U.S. Provisional Patent Application Ser. No. 60/605,234 are:

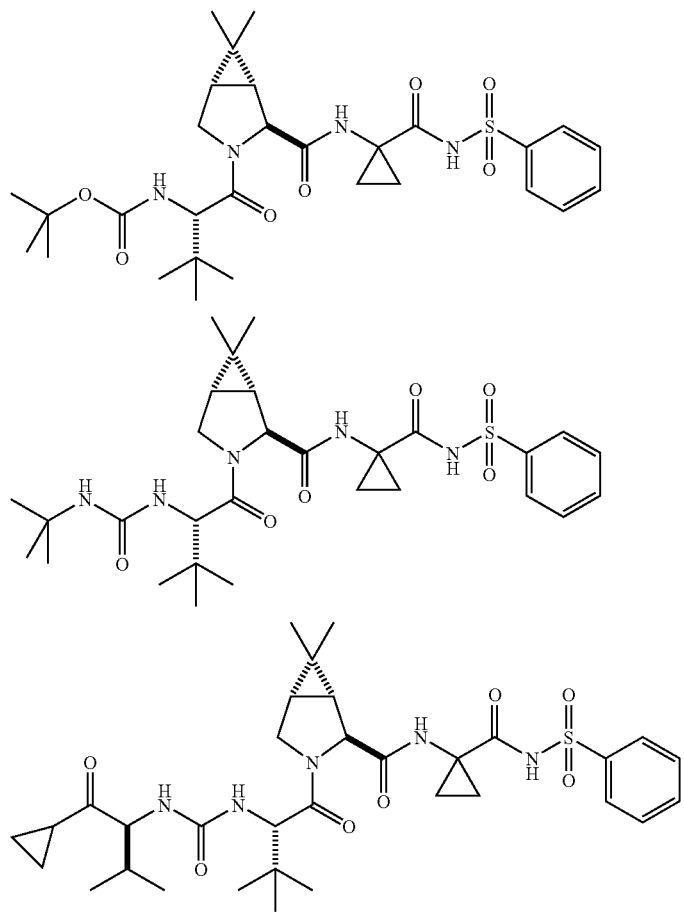
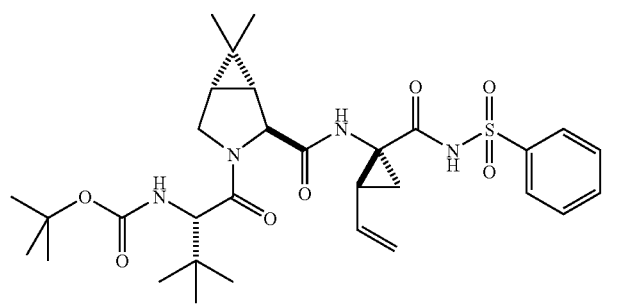
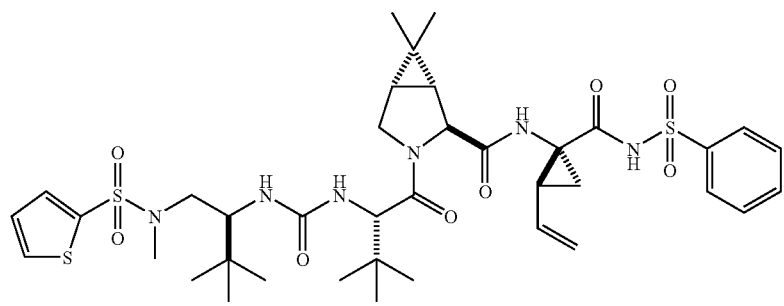

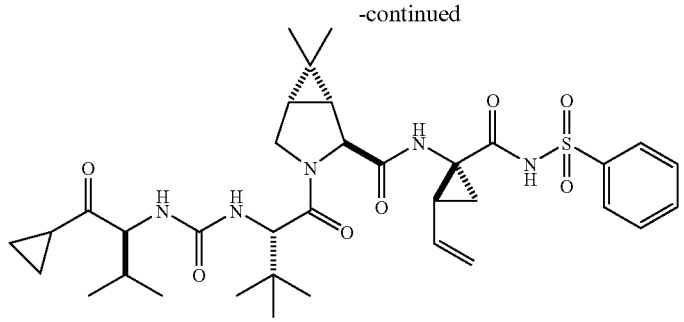
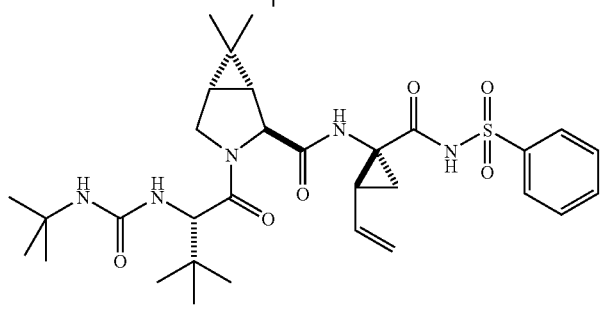
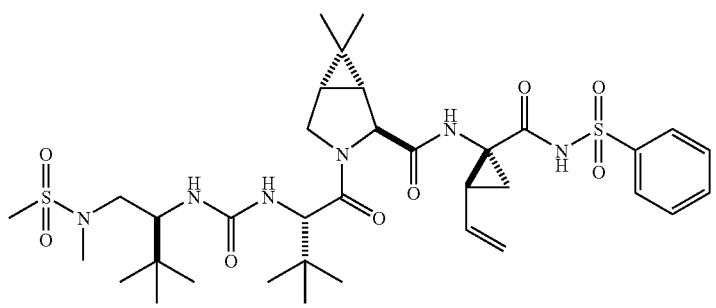
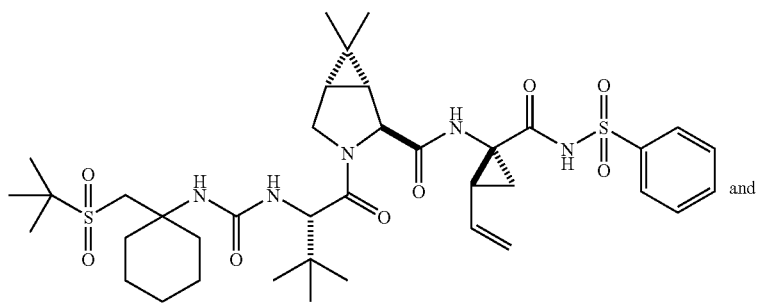
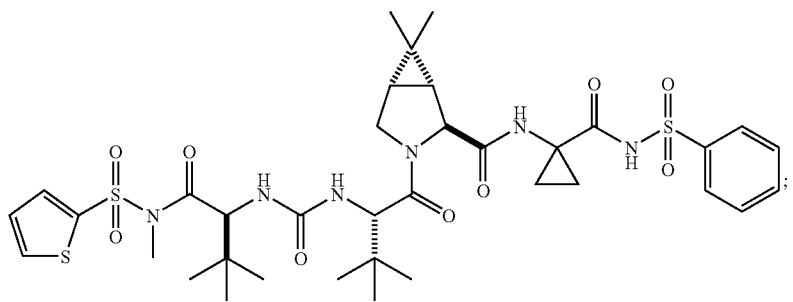
or a pharmaceutically acceptable salt, solvate or ester thereof.

Compounds of formula XIX are disclosed in U.S. Provisional Patent Application Ser. No. 60/573,191 filed May 20, 2004. The preparation of these compounds is disclosed in the experimental section of this application set forth hereinbelow.
Non-limiting examples of certain compounds disclosed in U.S. Provisional Patent Application Ser. No. 60/573,191 are:
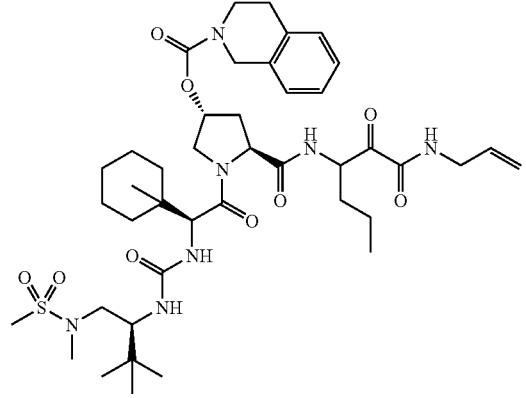
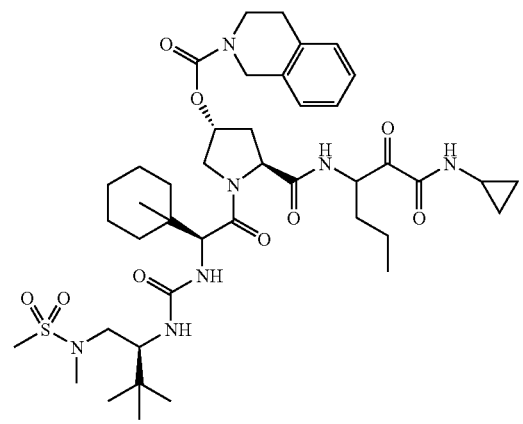
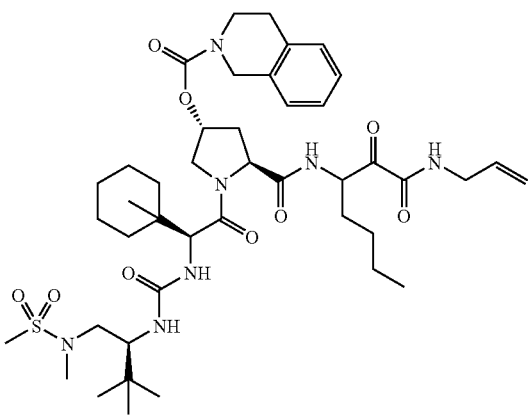
-continued
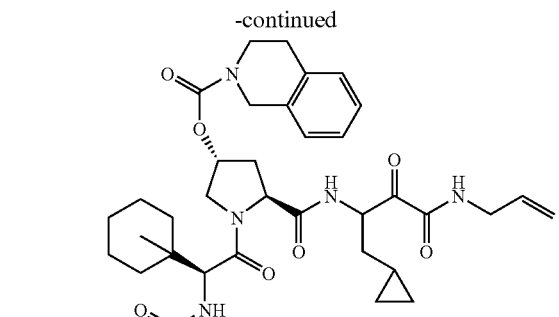
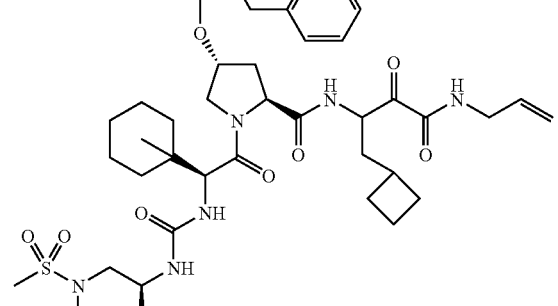
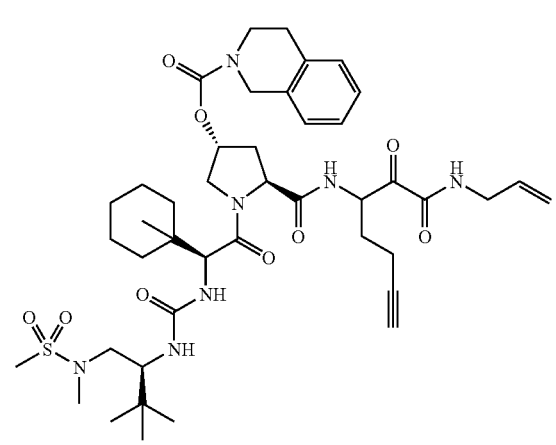

767 768
-continued
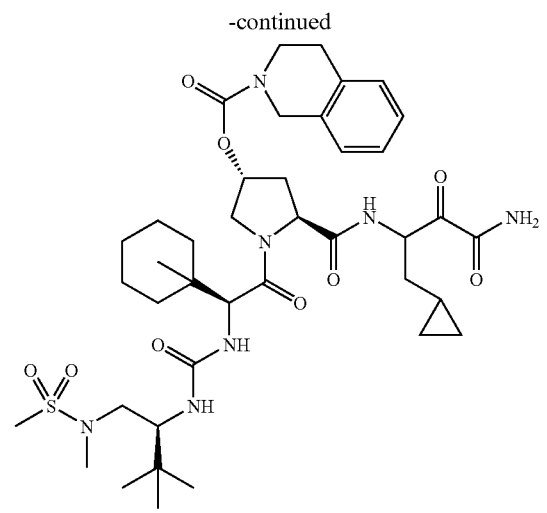
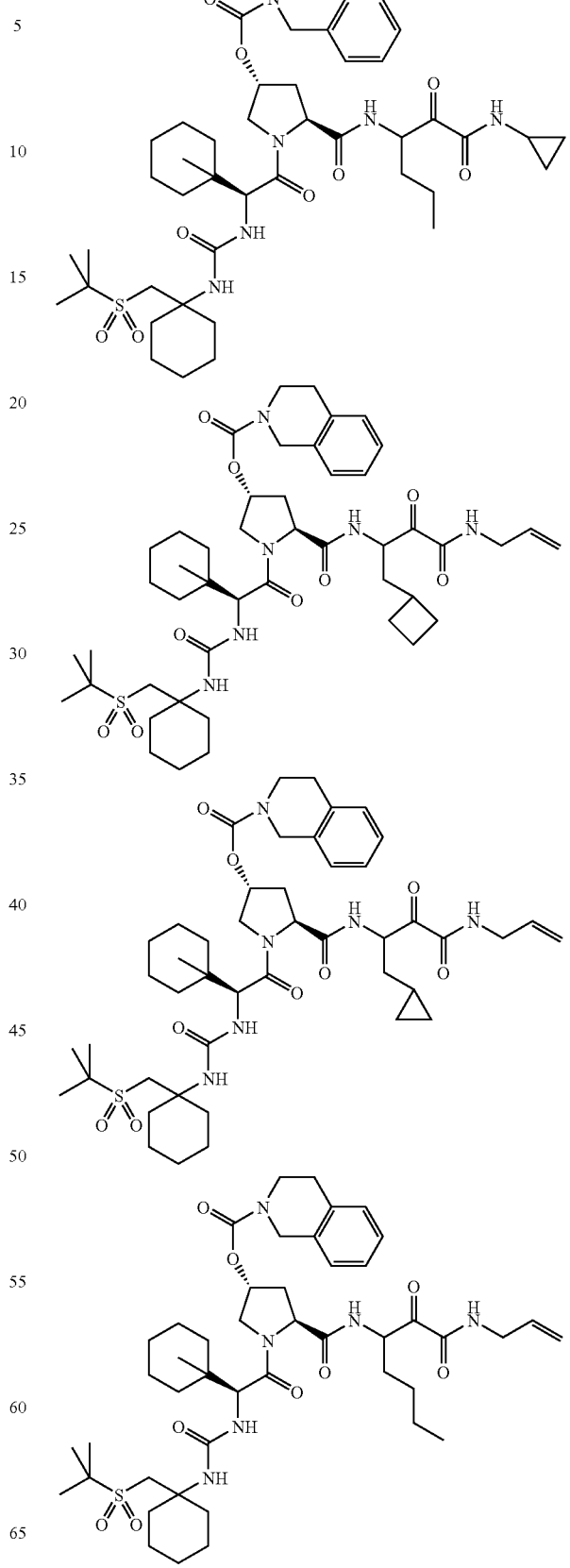

769                                    770
-continued                            -continued
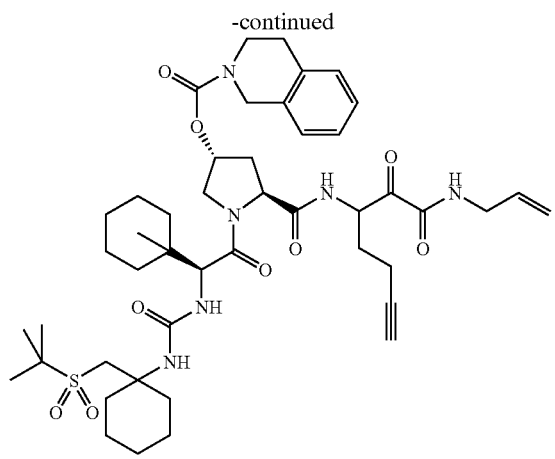
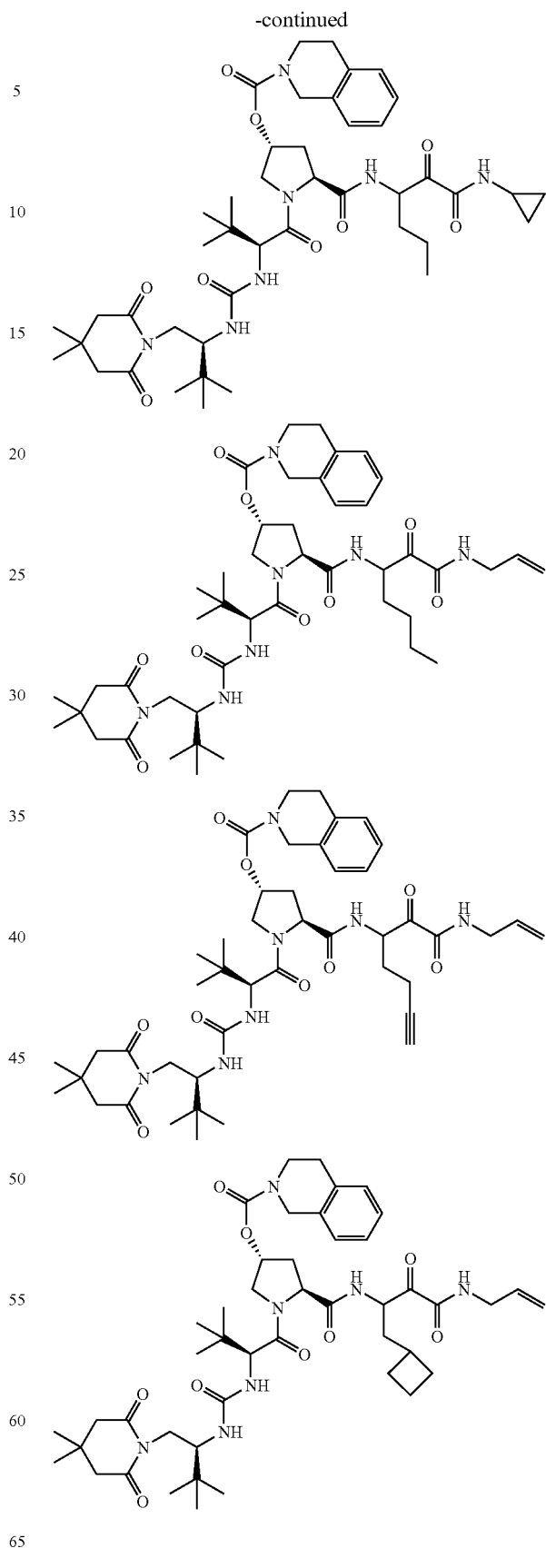

771
-continued
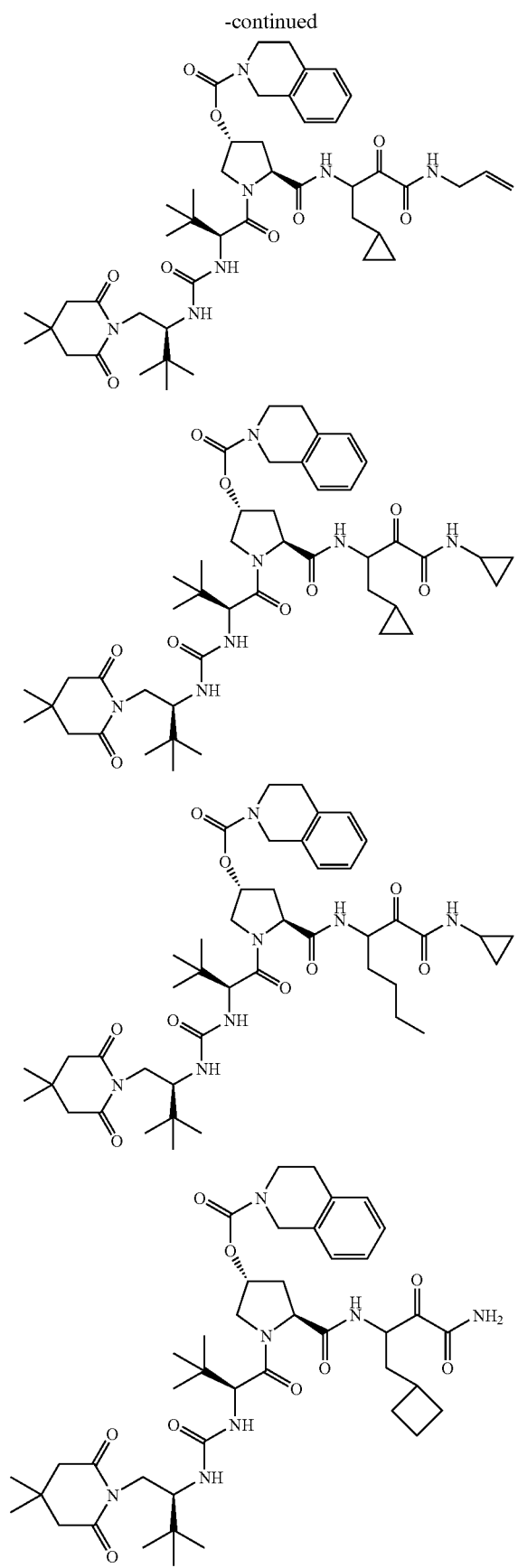
772
-continued
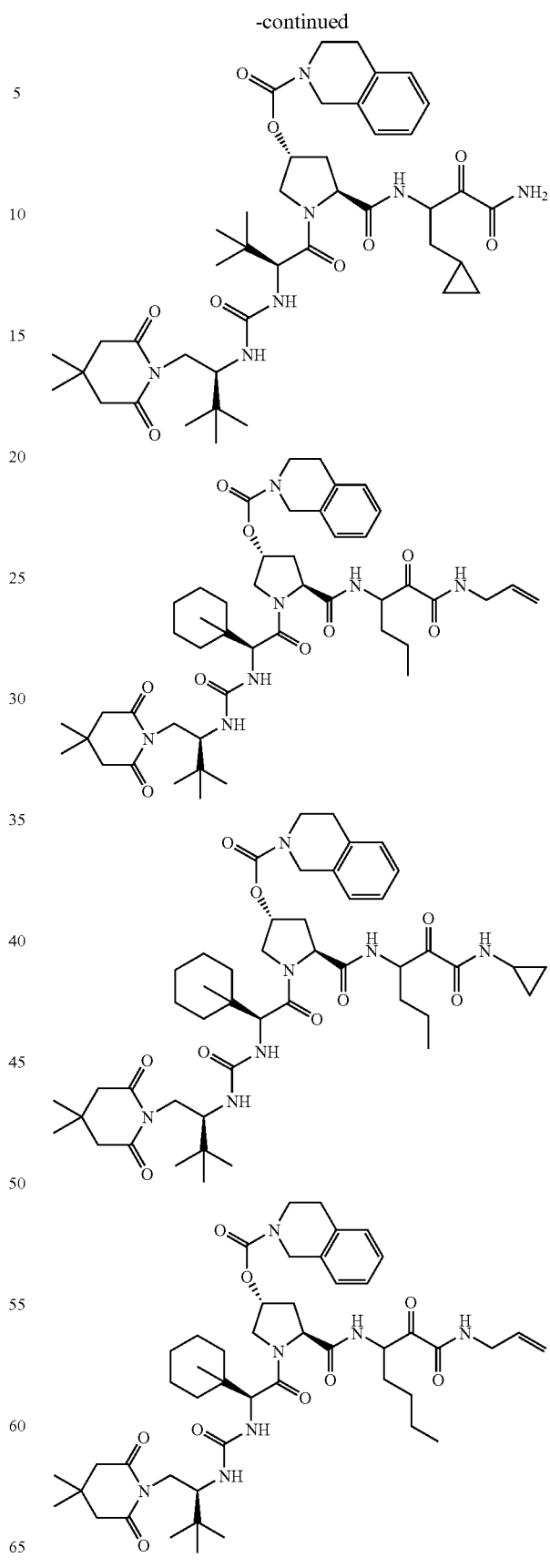

-continued
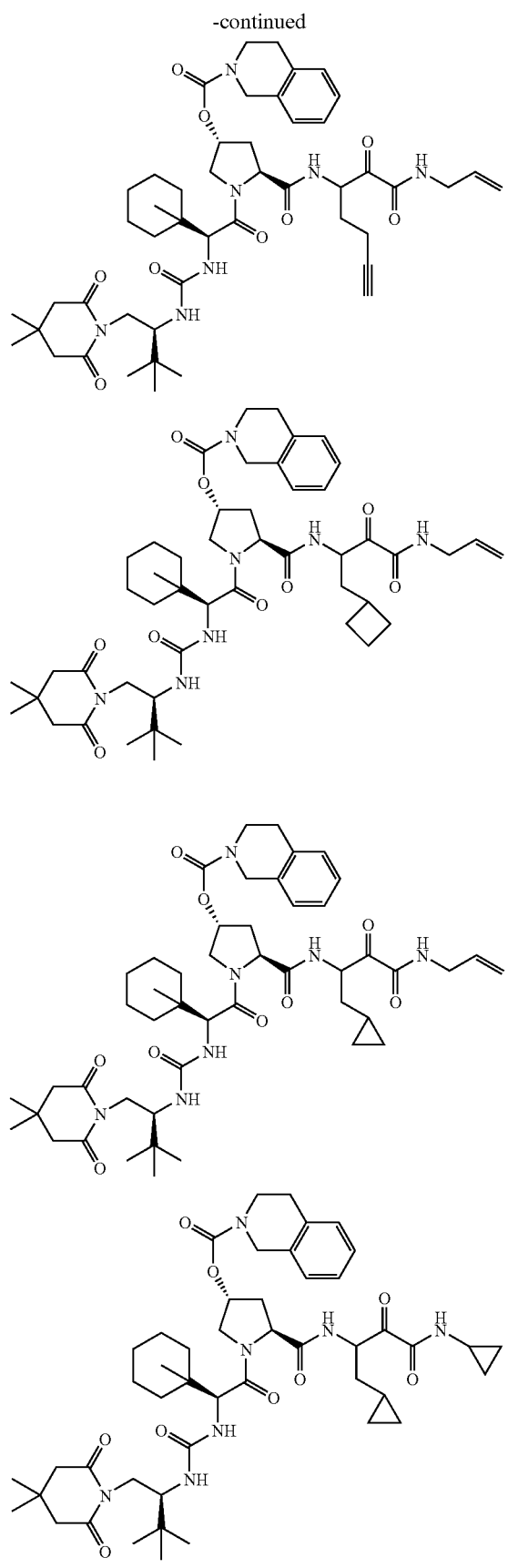
-continued
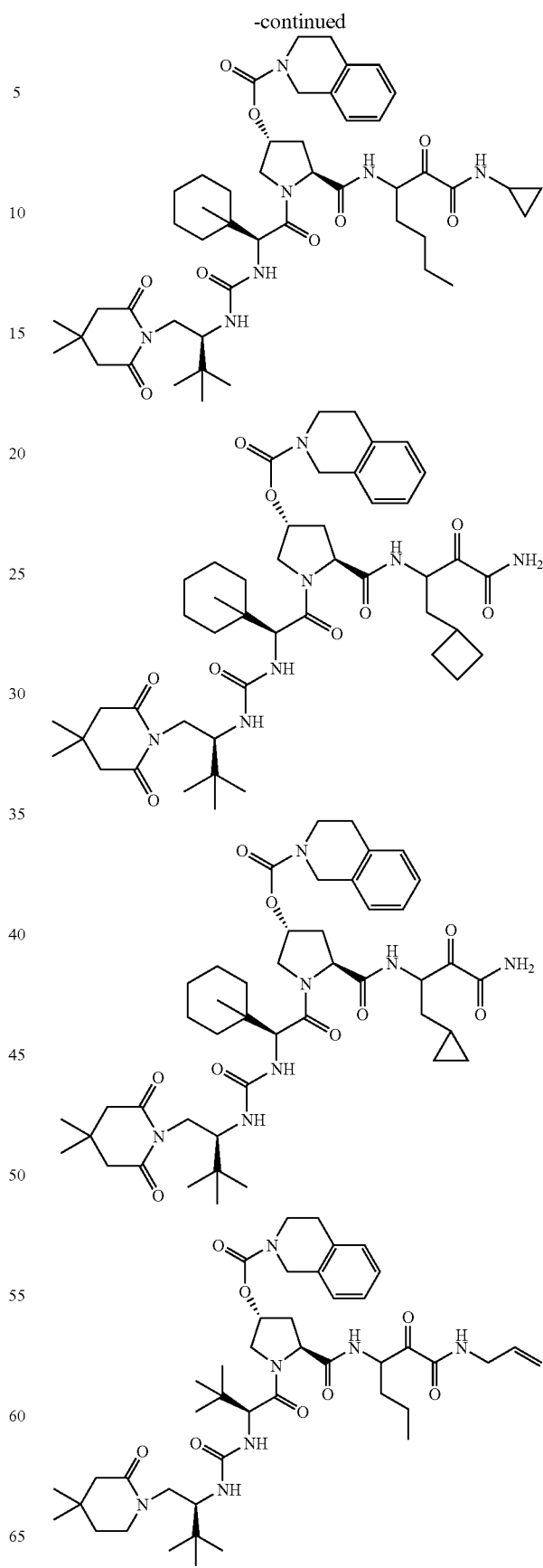

775
-continued
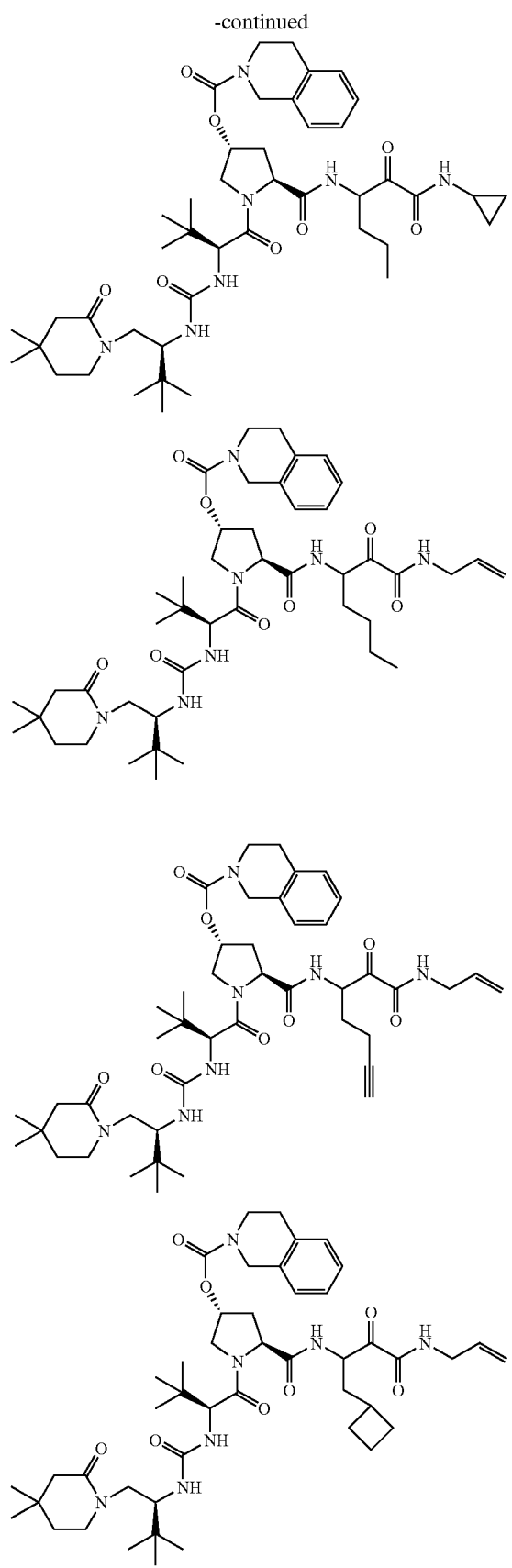
776
-continued
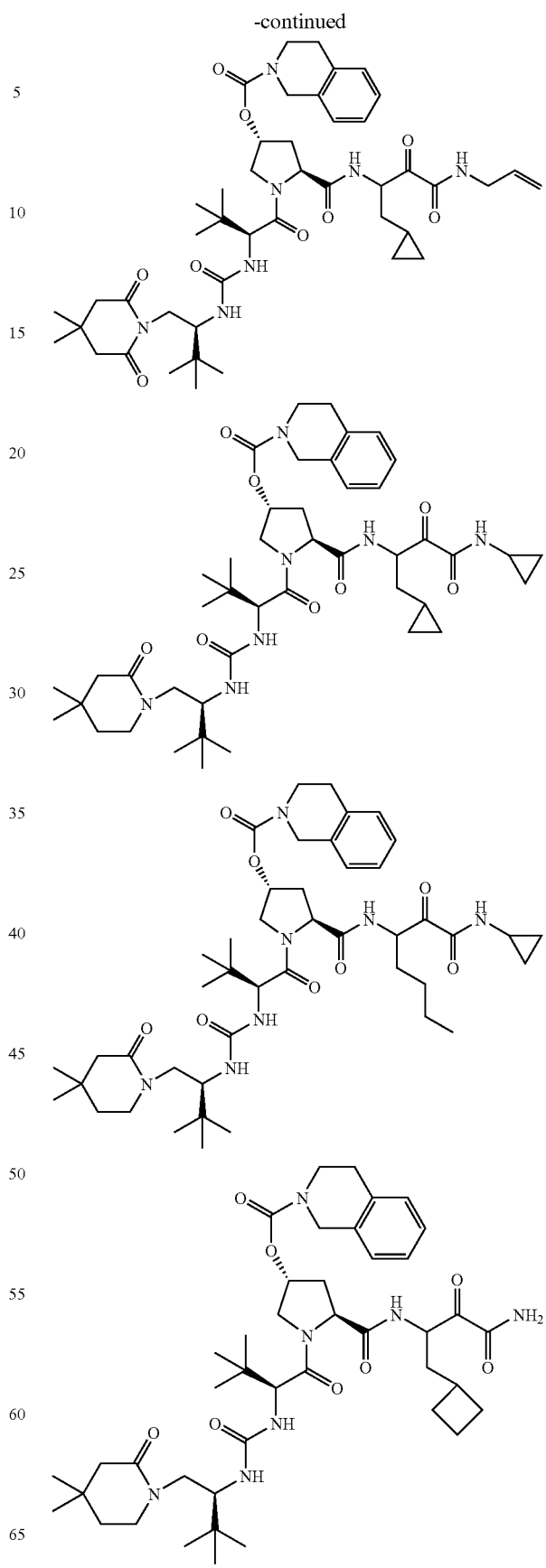

777 778
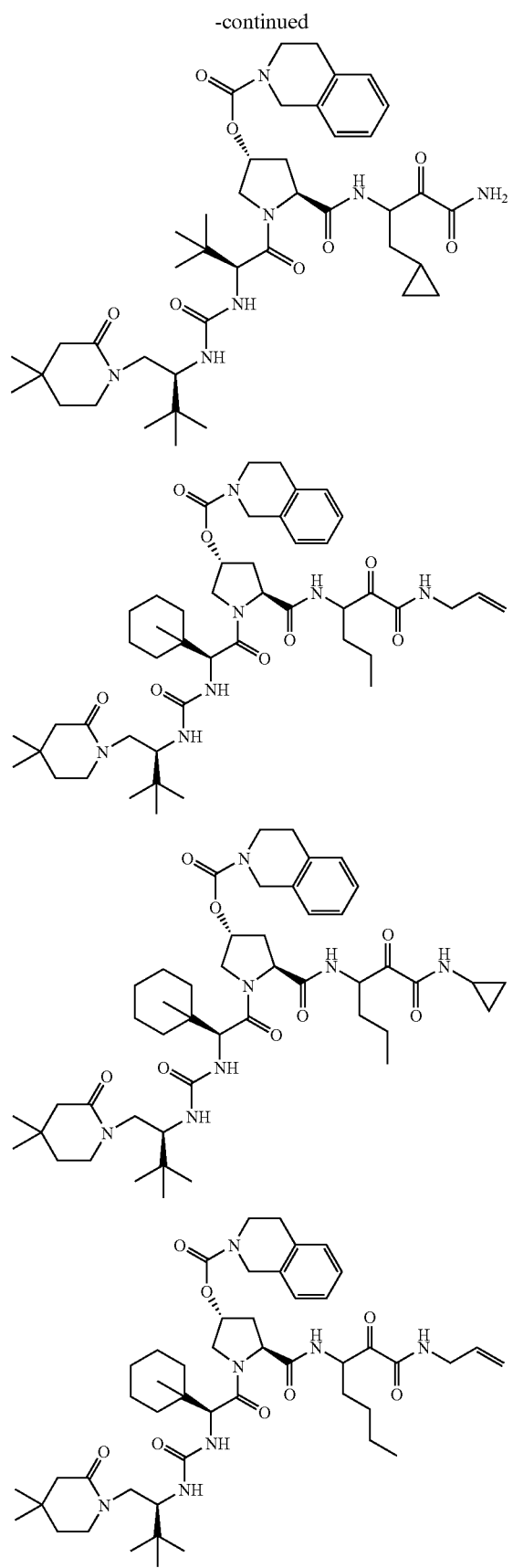
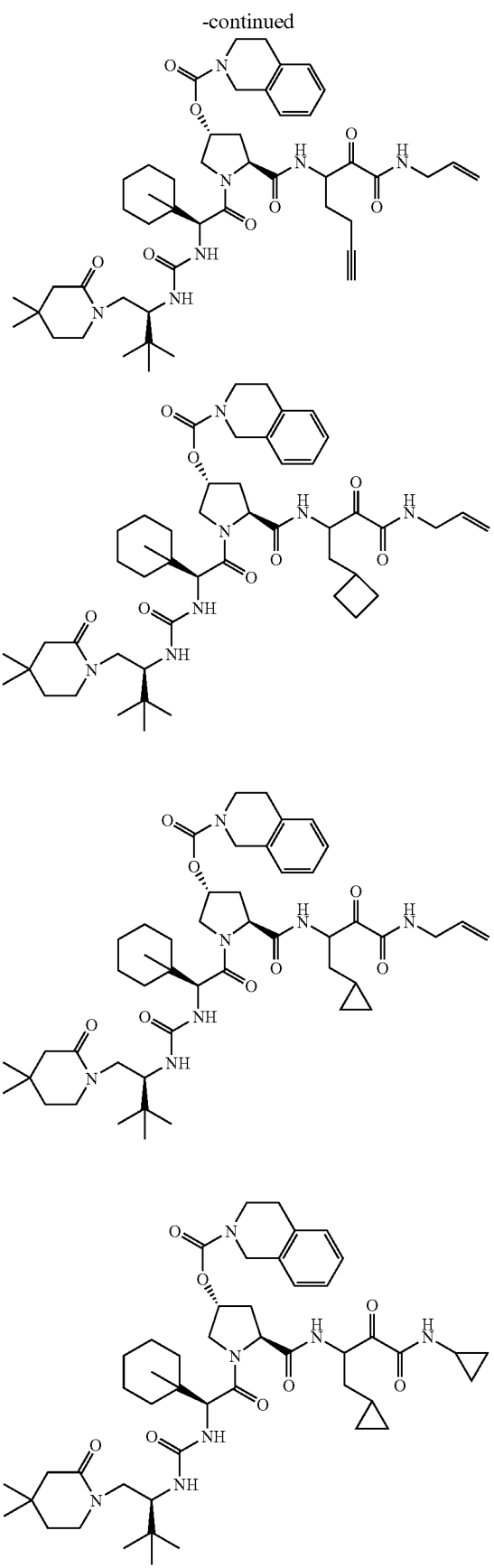

779
-continued
780
-continued
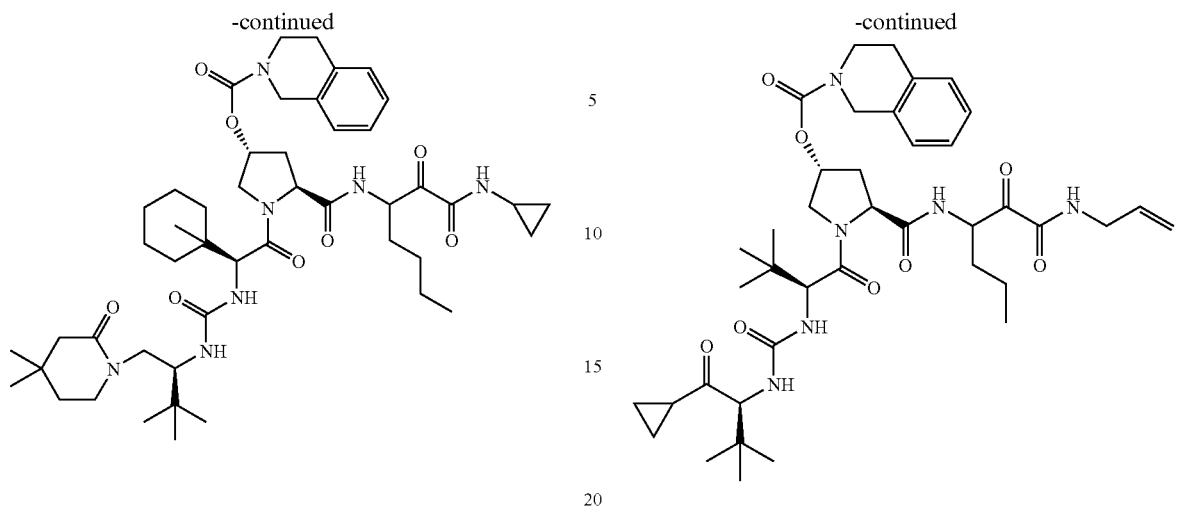
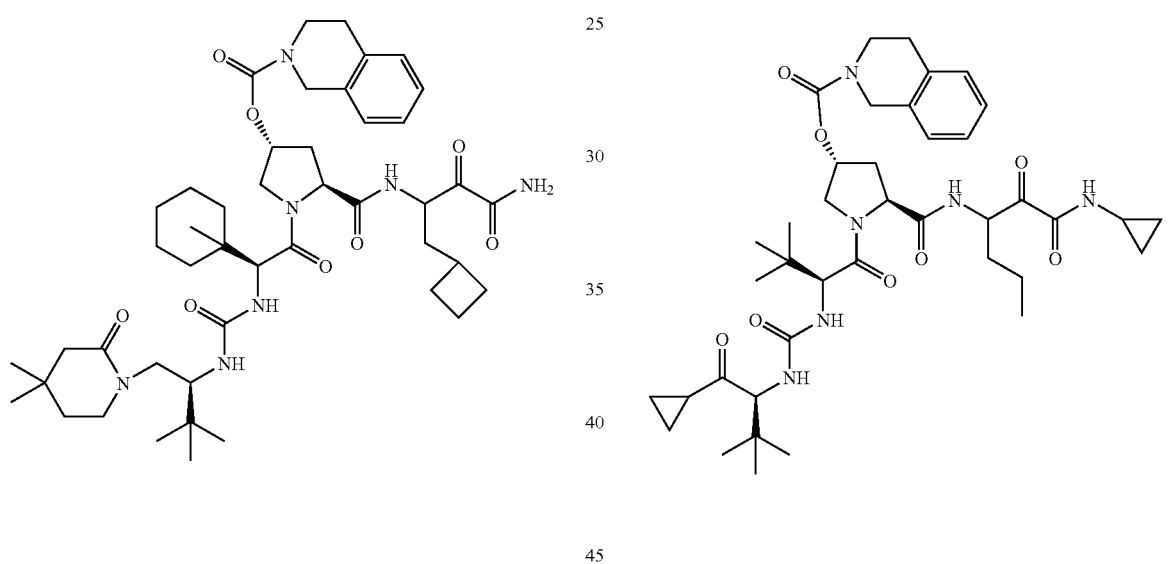
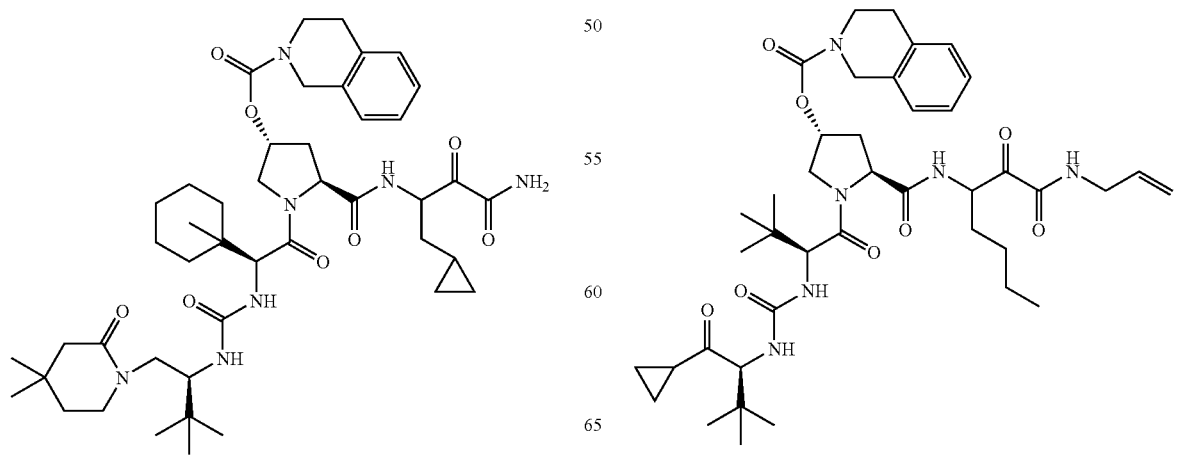

781
-continued
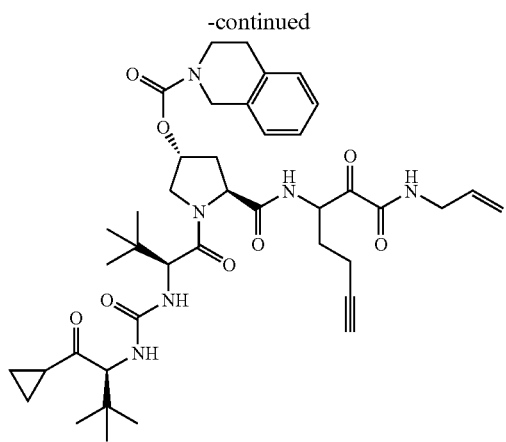
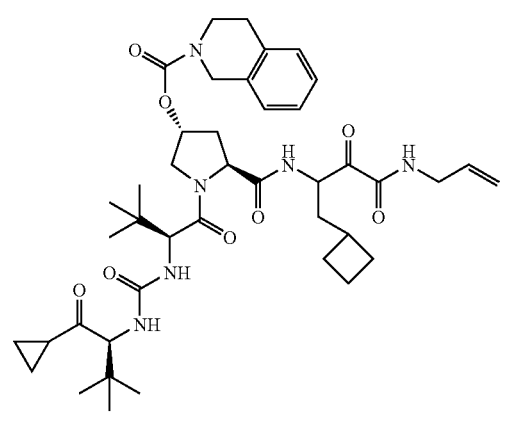
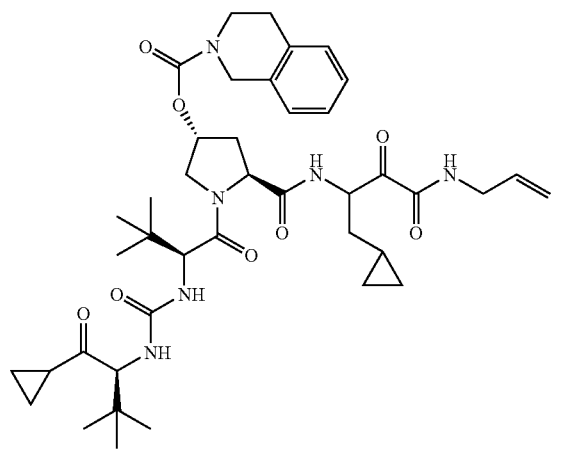
782
-continued
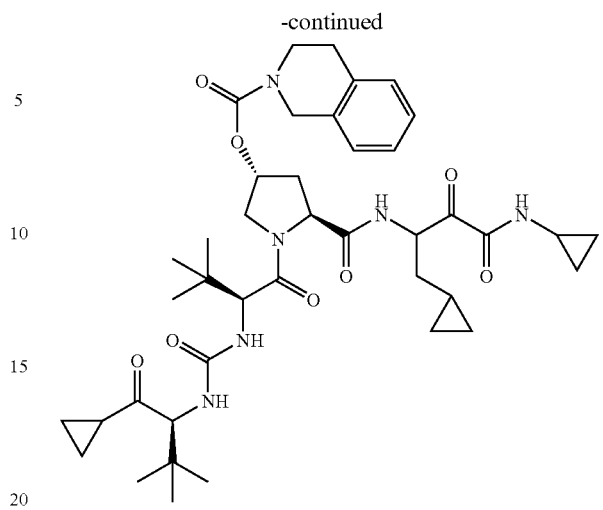
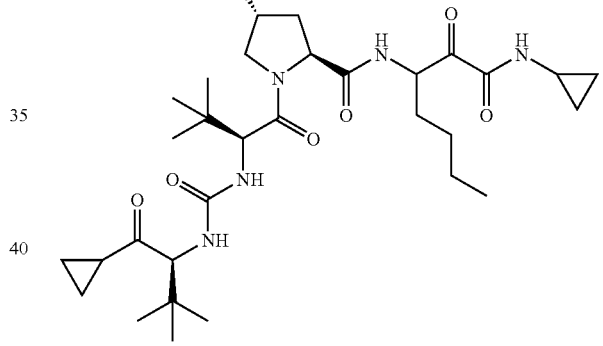
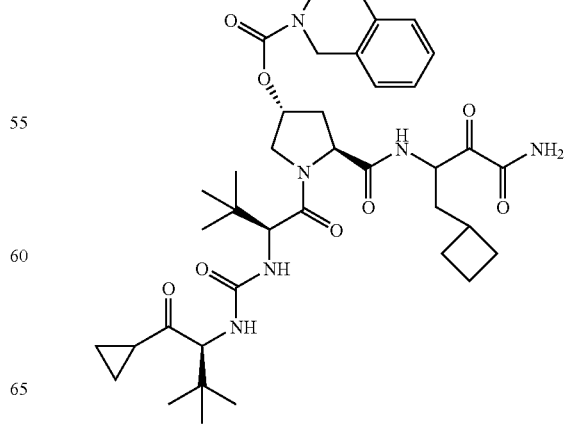

783 -continued
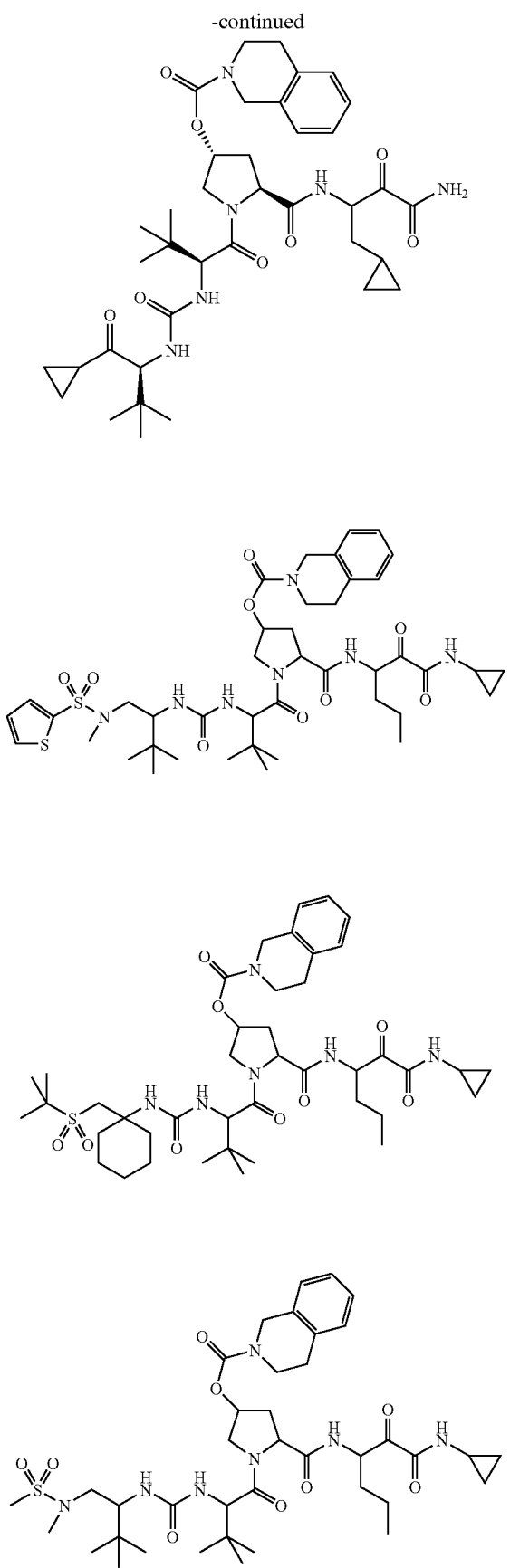
784 -continued
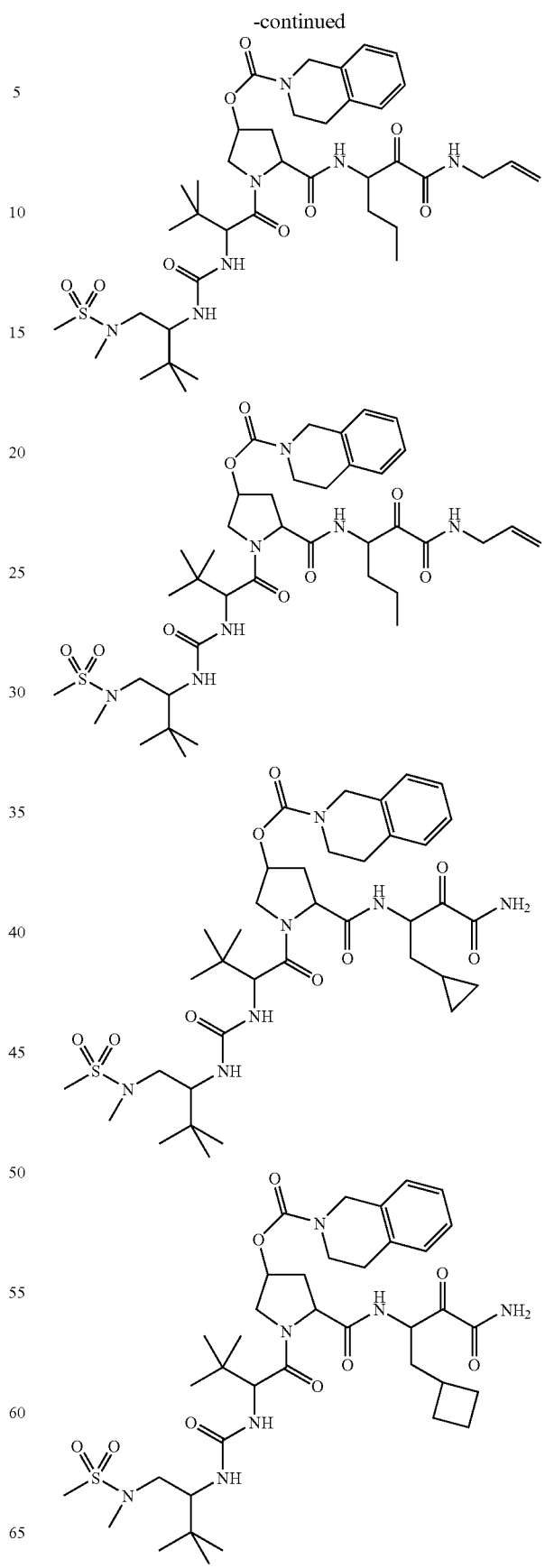

785
-continued
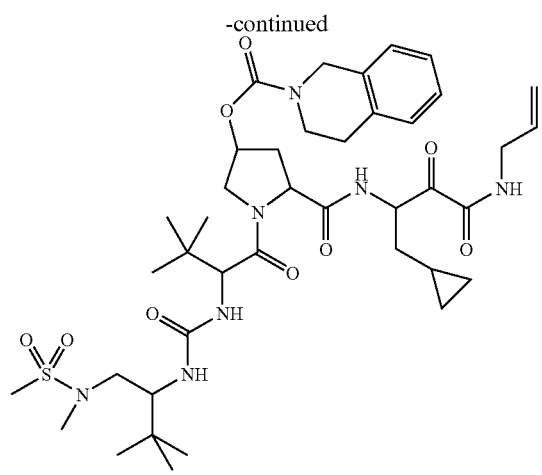
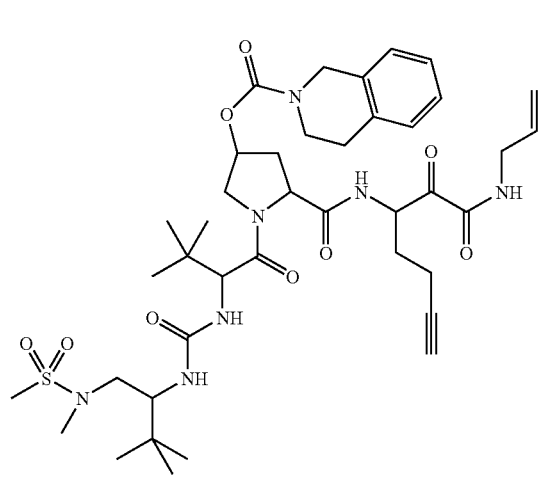
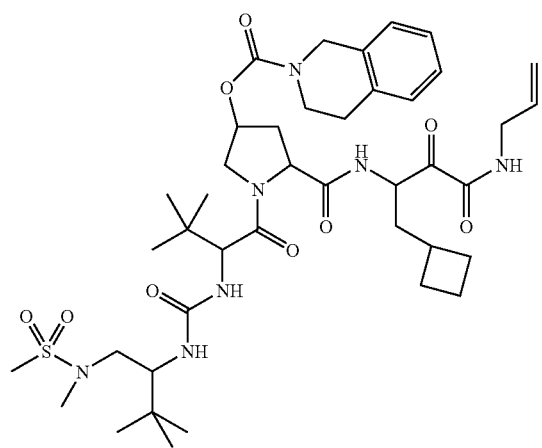
786
-continued
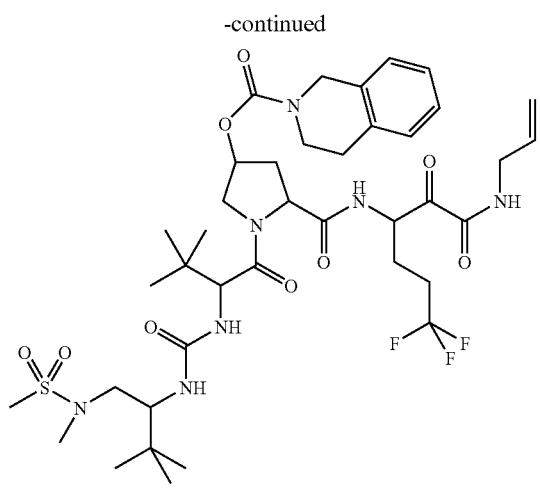
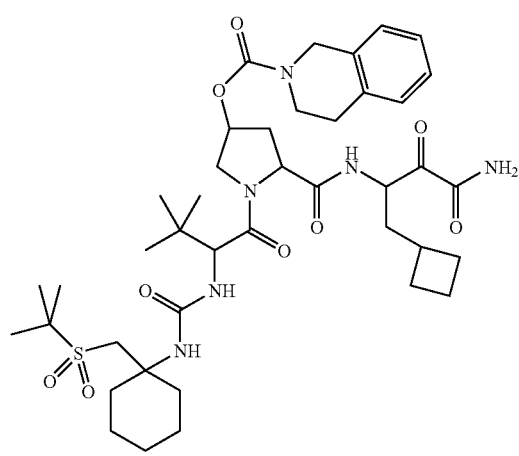
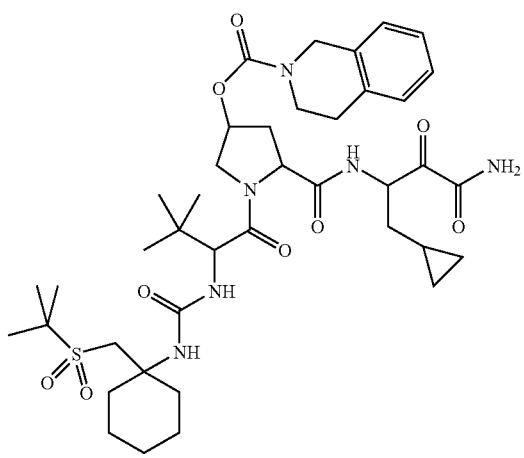

-continued

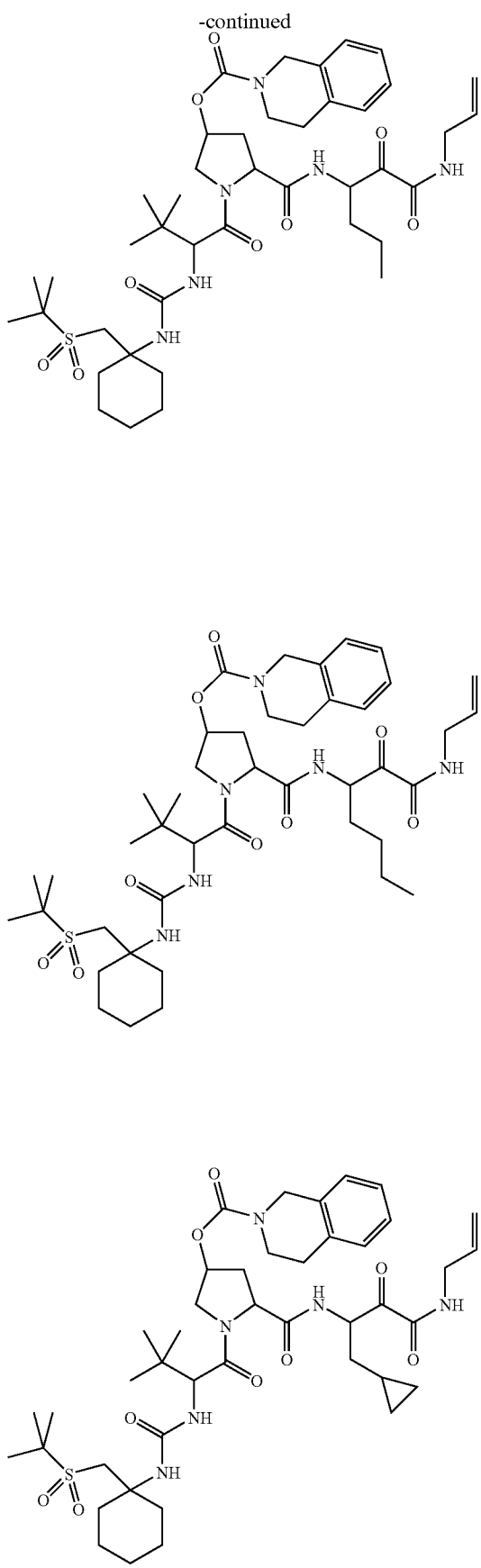

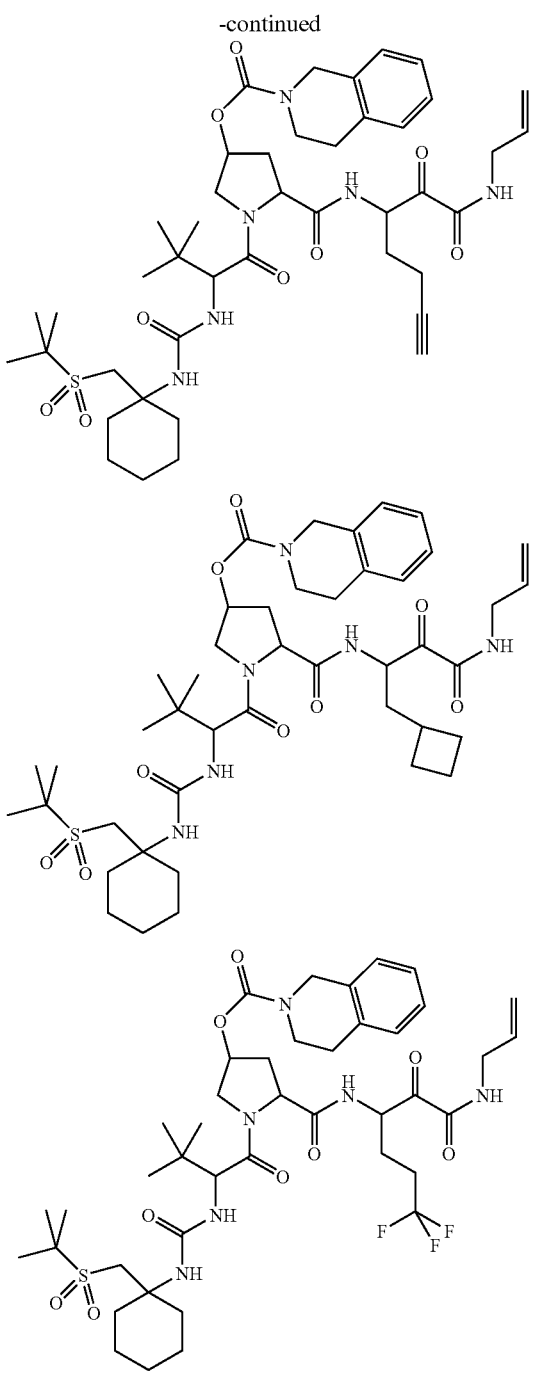

or a pharmaceutically acceptable salt, solvate or ester thereof.

Compounds of formula (XX) have been disclosed in U.S. Pat. No. 6,767,991 at col. 3, line 48 through col. 147, incorporated herein by reference.

Compounds of formula (XXI) have been disclosed in U.S. Patent Publication Nos. 2002/0016442, 2002/0037998 and U.S. Pat. Nos. 6,268,207, 6,323,180 at col. 3, line 28 through col. 141, line 60, U.S. Pat. No. 6,329,379 at col. 3, line 28 through col. 147, line 27, U.S. Pat. No. 6,329,417 at col. 3, line 25 through col. 147, line 30, U.S. Pat. No. 6,410,531 at col. 3, line 28 through col. 141, U.S. Pat. No. 6,534,523 at col.

3, line 34 through col. 139, line 29, and U.S. Pat. No. 6,420,380 at col. 3, line 28 through col. 141, line 65, each incorporated herein by reference.

Compounds of formula (XXII) have been disclosed in PCT International Patent Publication WO00/59929 published on Oct. 12, 2000, U.S. Patent Publication No. 2004/0002448 and U.S. Pat. No. 6,608,027 at col. 4 through col. 137, incorporated herein by reference.

Compounds of formula (XXIII) have been disclosed in PCT International Patent Publication WO02/18369 published on Mar. 7, 2002.

Compounds of formula (XXIV) have been disclosed U.S. Patent Publication Nos. 2002/0032175, 2004/0266731 and U.S. Pat. No. 6,265,380 at col. 3, line 35 through col. 121 and U.S. Pat. No. 6,617,309 at col. 3, line 40 through col. 121, each incorporated herein by reference.

Compounds of formula (XXV) have been disclosed U.S. Pat. No. 5,866,684 at col. 1 through col. 72 and U.S. Pat. No. 6,018,020 at col. 1 through col. 73, each incorporated herein by reference.

Compounds of formula (XXVI) have been disclosed in U.S. Pat. No. 6,143,715 at col. 3, line 6 through col. 62, line 20, incorporated herein by reference.

Isomers of the various present compounds (where they exist), including enantiomers, stereoisomers, rotamers, tautomers and racemates are also contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of the present invention. Isomers may also include geometric isomers, e.g., when a double bond is present. Polymorphous forms of the present compounds, whether crystalline or amorphous, also are contemplated as being part of this invention. The (+) isomers of the present compounds are preferred compounds used in the present invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are also within the scope of this invention.

It will be apparent to one skilled in the art that certain of the present compounds may exist in alternative tautomeric forms. All such tautomeric forms of the present compounds are within the scope of the invention. Unless otherwise indicated, the representation of either tautomer is meant to include the other. For example, both isomers (1) and (2) are contemplated:

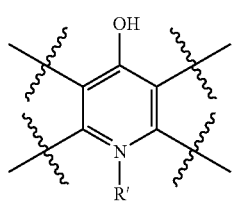

(1)

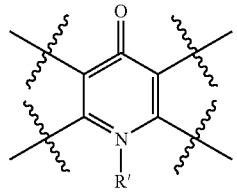

(2)

wherein R' is H or $C_{1-6}$ unsubstituted alkyl.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy$(C_1-C_6)$alkyl, amino $(C_1-C_4)$alkyl or mono-N- or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more of the present compounds may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving a compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

"Effective amount" or "therapeutically effective amount" is meant to describe an amount of a compound or a composition used in the present invention effective in inhibiting HCV protease and/or cathepsins, and thus producing the desired therapeutic, ameliorative, inhibitory or preventative effect in a suitable subject.

The present compounds form salts that are also within the scope of this invention. Reference to a compound of the present invention herein is understood to include reference to salts, esters and solvates thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the present compounds of the various formulae disclosed herein may be formed, for example, by reacting the present compounds with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention. All acid and base salts, as well as esters and solvates, are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

In such esters, unless otherwise specified, any alkyl moiety present preferably contains from 1 to 18 carbon atoms, particularly from 1 to 6 carbon atoms, more particularly from 1 to 4 carbon atoms. Any cycloalkyl moiety present in such esters preferably contains from 3 to 6 carbon atoms. Any aryl moiety present in such esters preferably comprises a phenyl group.

The compounds of Formulae I-XXVI can exhibit HCV inhibitory activity and/or capthesin inhibitory activity. Pharmaceutical formulations containing these compounds can possess utility in treating hepatitis C and related disorders and/or capthesin-associated disorders and may be used by administering a therapeutically effective amount of the inventive pharmaceutical formulation to a patient having such a disease or diseases and in need of such a treatment.

The pharmaceutical formulations of the present invention are suited for treatment of infection by any of the genotypes of HCV. HCV types and subtypes may differ in their antigenicity, level of viremia, severity of disease produced, and response to interferon therapy. (Holland, J. et al., "Hepatitis C genotyping by direct sequencing of the product from the Roche Amplicor Test: methodology and application to a South Australian population," Pathology, 30:192-195, 1998). The nomenclature of Simmonds, P. et al. ("Classification of hepatitis C virus into six major genotypes and a series of subtypes by phylogenetic analysis of the NS-5 region," J. Gen. Virol., 74:2391-9, 1993) is widely used and classifies isolates into six major genotypes, 1 through 6, with two or more related subtypes, e.g., 1a, 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3. (Lamballerie, X. et al., "Classification of hepatitis C variants in six major types based on analysis of the envelope 1 and nonstructural 5B genome regions and complete polyprotein sequences," J. Gen. Virol., 78:45-51, 1997). The major genotypes have been defined as having sequence similarities of between 55 and 72% (mean 64.5%), and subtypes within types as having 75%-86% similarity (mean 80%) when sequenced in the NS-5 region. (Simmonds, P. et al., "Identification of genotypes of hepatitis C by sequence comparisons in the core, E1 and NS-5 regions," J. Gen. Virol., 75:1053-61, 1994).

The formulations of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP 50406™ (from Viropharma, Incorporated, Exton, Pa.), ISIS 14803™ (from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-lntron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

The formulations of the present invention can be administered in combination with interferon alpha, PEG-interferon alpha conjugates or consensus interferon concurrently or consecutively at recommended dosages for the duration of HCV treatment. The commercially available forms of interferon alpha include interferon alpha 2a and interferon alpha 2b and also pegylated forms of both aforementioned interferon alphas. The recommended dosage of INTRON-A interferon alpha 2b (commercially available from Schering-Plough Corp.) as administered by subcutaneous injection at 3MIU (12 mcg)/0.5 mL/TIW is for 24 weeks or 48 weeks for first time treatment. The recommended dosage of PEG-INTRON interferon alpha 2b pegylated (commercially available from Schering-Plough Corp.) as administered by subcutaneous injection at 1.5 mcg/kg/week, within a range of 40 to 150 mcg/week, is for at least 24 weeks. The recommended dosage of ROFERON A inteferon alpha 2a (commercially available from Hoffmann-La Roche) as administered by subcutaneous or intramuscular injection at 3MIU (11.1 mcg/mL) ITIW is for at least 48 to 52 weeks, or alternatively 6MIU/TIW for 12 weeks followed by 3MIU/TIW for 36 weeks. The recommended dosage of PEGASUS interferon alpha 2a pegylated (commercially available from Hoffmann-La Roche) as administered by subcutaneous injection at 180 mcg/1 mL or 180 mcg/0.5 mL is once a week for at least 24 weeks. The recommended dosage of INFERGEN interferon alphacon-1 (commercially available from Amgen) as administered by subcutaneous injection at 9 mcg/TIW is for 24 weeks for first time treatment and up to 15 mcg/TIW for 24 weeks for non-responsive or relapse treatment. Optionally, Ribavirin, a synthetic nucleoside analogue with activity against a broad spectrum of viruses including HCV, can be included in combination with the interferon and the HCV protease inhibitor. The recommended dosage of ribavirin is in a range from 600 to 1400 mg per day for at least 24 weeks (commercially available as REBETOL ribavirin from Schering-Plough or COPEGUS ribavirin from Hoffmann-La Roche).

The formulations of the present invention comprise at least one compound of Formulae I-XXVI, as defined above, together with one or more surfactant. The formulation can further comprises one or more pharmaceutically acceptable adjuvants and optionally other therapeutic agents and pharmaceutically acceptable carriers and excipients. Each excipient must be acceptable in the sense of being compatible with the other ingredients of the formulation and not injurious to the mammal in need of treatment.

In one embodiment, the adjuvant is at least one pharmaceutically acceptable surfactant or at least one acidifying agent or both. When desired or needed, suitable carriers and other excipients (such as binders, glidents, lubricants, and disintegrants) may also be incorporated in the formulation. These adjuvants, carriers and excipients as well as others are described hereinafter.

"Surfactant", as used herein, refers to an adjuvant material that reduces the contact angle between the active drug component and the environment of its use in a mammal and may also be referred to as a wetting agent. Treatment of diseases requiring high dosages of the present compounds, such as HCV, is enhanced by improving the absorption rate of the compounds thereby improving the extent of absorption of the compounds in a mammal. The surfactant in the pharmaceutical formulations of the present invention enhances wetting of the present compounds by aqueous systems (as in a mammal) and improves the dissolution rate of the compounds to render a greater quantity of the compound available for absorption than is available in a formulation of the present compounds that does not include a surfactant. Any pharmaceutically acceptable surfactant that improves wetting of the present compounds may be used. Particularly suitable surfactants include sodium lauryl sulfate, stearic acid, monoethanolamine, docusate sodium, sorbitan fatty acid esters, polyoxyethylene sorbitan fatty acid esters, ethoxylated aliphatic alcohols, propylene glycol monocaprylate, glycerol monostearate, medium chain triglycerides, polyoxyethylene alkyl ethers, and polyoxyethylene stearates. In one embodiment, the surfactant is sodium lauryl sulfate. In another embodiment, the surfactant is a polyoxyethylene sorbitan fatty acid ester. In yet another embodiment, the surfactant is PEG-1-PEG-9-lauryl glycol ether. These surfactants may be used alone in or combination in the pharmaceutical formulations of the present invention in a total amount of about 0.1 to about 10% by weight or about 1 to about 5% by weight.

Acidifying agent refers to an adjuvant material that lowers the pH of the formulation. An acidic pH environment may improve the stability of the present compounds. Any pharmaceutically acceptable acidifying agent that improves stability of the present compounds may be used. Particularly suitable acidifying agents include tartaric acid, ascorbic acid, citric acid, malic acid, lactic acid and succinic acid. In one embodiment, the acidifying agent is tartaric acid. These acidifying agents may be used alone in or combination in the pharmaceutical formulations of the present invention in a total amount of about 0 to about 10% by weight or about 1 to 5% by weight.

Carrier refers to a substance that usually makes up the major portion of the composition or dosage form. Suitable carriers include celluloses such as microcrystalline cellulose; sugars such as lactose, sucrose, mannitol and sorbitol; and starches such as are derived from wheat, corn, rice and potato. The amount of carrier in the formulation can range from about 10 to about 90% by weight of the total formulation, or about 25 to about 75% by weight, or about 30 to about 60% by weight, or about 12 to about 60% by weight. In one embodiment, the carrier is microcrystalline cellulose.

Binders refers to substances that bind or "glue" powders together and make them cohesive by forming granules, thus serving as the "adhesive" in the formulation. Binders add cohesive strength already available in the diluent or bulking agent. Suitable binders include sugars such as lactose, sucrose and corn sweeteners; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; polyethylene glycol; waxes and inorganics such as magnesium aluminum silicate. The amount of binder in the formulation can range from about 10 to about 90% by weight of the total formulation, or about 25 to about 75% by weight, or about 30 to about 60% by weight, or about 12 to about 60% by weight. In one embodiment, the binder is anhydrous lactose.

Glidents refers to material that prevents caking and improves the flow characteristics of granulations, so that flow is smooth and uniform. Suitable glidents include silicon dioxide and talc. The amount of glident in the formulation can range from about 0.1% to about 5% by weight of the total formulation, or from about 0.5 to about 3% by weight.

Lubricants are substances added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as boric acid sodium chloride, sodium benzoate, sodium acetate, sodium chloride sodium oleate, polyethylene glycols and d'l-leucine. Lubricants are usually added at the very last step before compression, since they must be present on the surfaces of the granules and in between them and the parts of the tablet press. The amount of lubricant in the formulation can range from about 0.1 to about 10% by weight of the formulation, or from about 0.5 to about 5% by weight.

Disintegrant refers to materials added to the formulation to help it break apart (disintegrate) and release the drug. Suitable disintegrants include starches; "cold water soluble" modified starches such as sodium carboxymethyl starch; natural and synthetic gums such as locust bean, karaya, guar gum, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the formulation, or from about 2 to about 10% by weight.

Coloring agents provide coloration to the formulation or the dosage form. Such excipients can include food grade dyes and food grade dyes adsorbed onto a suitable adsorbent such as clay or aluminum oxide. The amount of the coloring agent can vary from about 0.1 to about 5% by weight of the formulation, or from about 0.1 to about 1%.

Sweetening agents, flavoring agents, stabilizers, antioxidants and preservatives may also be included where appropriate.

The term pharmaceutical formulation encompasses both the bulk formulation and individual unit dosage forms. The bulk composition is material that has not yet been formed into individual dosage units. An illustrative dosage unit is an oral dosage unit such as tablets, capsules and the like.

The formulations of the present invention may be administered orally, intravenously, subcutaneously, or transdermally. Preferably, the pharmaceutical formulation is in a unit dosage form. In such form, the preparation is subdivided into suitably sized unit doses containing appropriate quantities of the active components, e.g., an effective amount to achieve the desired purpose. Suitable unit dosage forms are solids, gels, or fluids including elixirs, dispersible granules, syrups, suspensions. Solid form preparations include powders, tablets, dispersible granules, capsules, cachets and suppositories.

The powders, tablets and capsules may be comprised of from about 5 to about 95 percent active ingredient. Tablets, powders, cachets and capsules can be used as solid dosage forms suitable for oral administration. Other examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa. The formulations of the present invention may be produced via a dry blend processor a wet granulation process and filled or compressed into capsules or tablets.

Capsules (either solid-filled, semi-solid filled or liquid filled) are special containers or enclosures, often made of methyl cellulose, polyvinyl alcohols, or denatured gelatins or starch for holding or containing the pharmaceutical formulation. (Hard shell capsules are typically made of blends of relatively high gel strength bone and pork skin gelatins. The capsule itself may contain small amounts of dyes, opaquing agents, plasticizers and preservatives.

Tablet refers to a compressed or molded solid dosage form containing the pharmaceutical formulation. The tablet can be prepared by compression of mixtures or granulations obtained by wet granulation, dry granulation or by compaction.

A gel, such as an oral gel refers to the formulations dispersed or solubilized in a hydrophillic semi-solid matrix.

Suppositories containing the formulations of the present invention may be prepared by melting a low melting wax such as a mixture of fatty acid glycerides such as cocoa butter, and dispersing the components of the formulations homogeneously therein by stirring or similar mixing. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Fluid forms may be liquids including solutions, suspensions and emulsions containing the formulations. Non-limiting examples include water or water-propylene glycol solutions for parenteral injections or addition of sweeteners and pacifiers for oral solutions, suspensions and emulsions. Liquid form preparations may also include solutions for intranasal administration.

Also included are aerosol preparations of the present invention that are suitable for inhalation. Aerosols may include solutions and solids in powder form, which may be in combination with a pharmaceutically acceptable carrier such as inert compressed gas, e.g. nitrogen.

Also included are solid form preparations which are intended to be converted, shortly before use, to liquid form preparations for either oral or parenteral administration. Such liquid forms include solutions, suspensions and emulsions. Alternatively, the formulations of the present invention may be prepared in powder blends that can be suspended in water or juices.

Transdermal formulations may take the form of creams, lotions, aerosols and/or emulsions and can be included in a transdermal patch of the matrix or reservoir type as are conventional in the art for this purpose.

Bioavailability refers to the rate and extent to which the active drug ingredient or therapeutic moiety is absorbed into the systemic circulation from an administered dosage form as compared to a standard or control.

The present invention discloses methods for preparing the pharmaceutical formulations of the present invention. Conventional methods for preparing tablets and capsules are known. Such methods include dry methods such as direct compression and compression of granulation produced by compaction, or wet methods or other special procedures. In one embodiment, a capsule containing the pharmaceutical formulation of the present invention is produced by blending the active drug component with some excipients, compacting the mixture such as with a roller compactor, milling the compacted mixture, blending the milled material with any remaining excipients and filling the final blend into capsules.

In one embodiment, the pharmaceutical formulation of the present is administered orally and is in a unit dosage form. In such form, the preparation is subdivided into suitably sized unit doses containing appropriate quantities of the active component, e.g., an effective amount to achieve the desired purpose.

The amount and frequency of administration of the formulations of the present invention will be regulated according to the judgment of the attending clinician considering such factors as age, condition and size of the patient as well as severity of the symptoms being treated. A typical recommended daily dosage regimen for oral administration can range from about 50 mg/day to about 3000 mg/day, in two to four divided doses.

The quantity of active compound in a unit dose of preparation may be varied or adjusted from about 1 mg to about 1000 mg, or from about 50 mg to about 800 mg, or from about 50 mg to about 600 mg, or from about 50 mg to about 400 mg, or from about 50 mg to about 200 mg according to the particular application. In one embodiment, the dosage form contains about 200 mg of the active compound. In another embodiment, the dosage form contains about 200 mg of the active compound.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The following formulations exemplify some of the dosage forms of the present invention. In the formulation, the "Active Compound" designates any of the compounds of Formulae I-XXVI, as defined above, or a pharmaceutically acceptable sale, solvate or ester thereof.

EXAMPLE 1

Dry Blend

| Ingredient | Amount |
| --- | --- |
| Active Compound | 200 mg |
| Microcrystalline cellulose | 0-60 wt. % |
| Lactose, anhydrous | 0-60 wt. % |
| Sodium croscarmellose | 2-10 wt. % |
| Sodium lauryl sulfate | 0-10 wt. % |
| Tartaric acid | 0-10 wt. % |
| Silicon dioxide | 0-3 wt. % |
| Magnesium stearate | 1-10 wt. % |
| Capsule shell | 1 unit |
| TOTAL FILL WEIGHT | 350-500 mg |

In one embodiment, the powdery Active Compound can be blended with some of the ingredients and compacted with a roller compactor to densify the powder. The resulting compact is milled, and the milled compact is blended with the remaining ingredients and filled into a capsule or pressed into a tablet.

EXAMPLE 2

Wet Blend

| Ingredient | Amount |
| --- | --- |
| Active Compound | 200 mg |
| Microcrystalline cellulose | 0-60 wt. % |

-continued

| Ingredient | Amount |
| --- | --- |
| Lactose, anhydrous | 0-60 wt. % |
| Sodium croscarmellose | 2-10 wt. % |
| Sodium lauryl sulfate | 0-10 wt. % |
| Tartaric acid | 0-10 wt. % |
| Pregelatinized starch | 0-15 wt. % |
| Hydroxypropylmethylcellulose | 0-6 wt. % |
| Magnesium stearate | 1-10 wt. % |
| Capsule shell | 1 unit |
| TOTAL FILL WEIGHT | 350-500 mg |

In one embodiment, the powdery Active Compound can be blended with some of the ingredients, granulated with a solution of binders and dried. The dry granules are milled and blended with the remaining ingredients and filled into a capsule or pressed into a tablet.

The Following Experimental Section Applies for the Preparation of the Compounds of Formula XI:

Abbreviations which are used in the descriptions of the schemes, preparations and the examples that follow are:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et$_2$O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
iBoc: isobutoxycarbonyl
iPr: isopropyl
'Bu or Bu$^t$: tert-Butyl
Boc: tert-Butyloxycarbonyl
Cbz: Benzyloxycarbonyl
Cp: Cylcopentyldienyl
Ts: p-toluenesulfonyl
MCPBA: 3-chloroperbenzoic acid.
Me: Methyl
HATU: O-(7-azabenzotriazol-1-yl)-1,1,3,3-tetramethyluronium hexafluorophosphate
DMAP: 4-N,N-Dimethylaminopyridine
Bop: Benzotriazol-1-yl-oxy-tris(dimethylamino)hexafluorophosphate
PCC: Pyridiniumchlorochromate Other abbreviations are commonly used abbreviations Such as according to the guidelines published by *Journal of Organic Chemistry*.

General Schemes for Preparation of Target Compounds

Compounds of the present invention were synthesized using the general schemes (Methods A-E) described below.

Method A

Deprotection of the N-Boc functionality of 1.01 under acidic conditions provided the hydrochloride salt 1.02 which was subsequently coupled with N-Boc-tert-leucine under peptide coupling methodology (Louis A Carpino et al. "Preparation of uronium and immonium salts for peptide coupling", WO 2002094822, pp. 76) to afford 1.03. N-Boc deprotection followed by treatment with appropriate isocyanate gave the urea 1.05. Hydrolysis of the methyl ester provided the acid 1.06. Peptide coupling of the acid 1.06 with the appropriate P$_1$-P' primary amide moiety afforded the hydroxyl amide 1.07. Oxidation (Moffatt, or Dess-Martin's) resulted in the target compound 1.08.

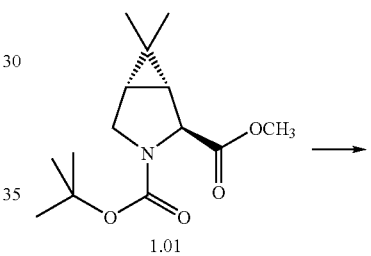

1.01

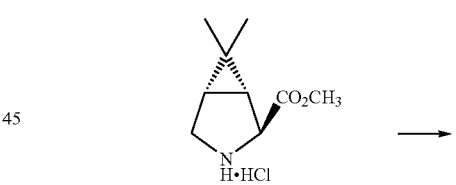

1.02

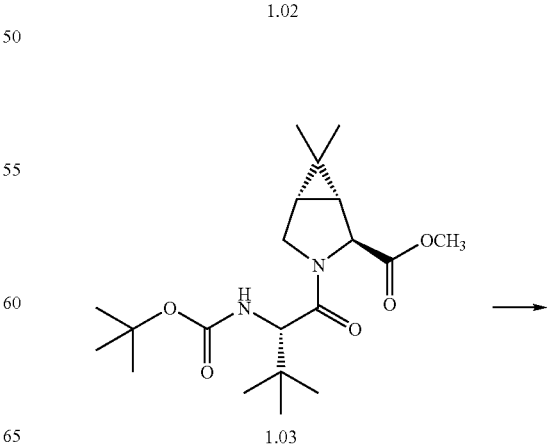

1.03

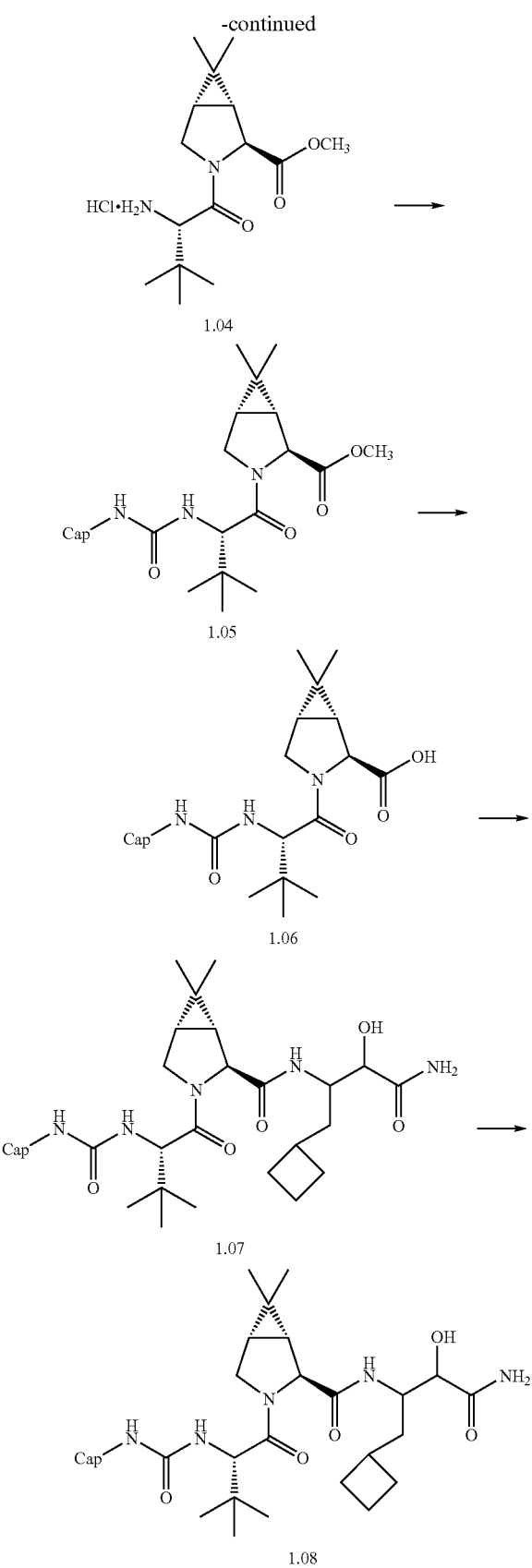

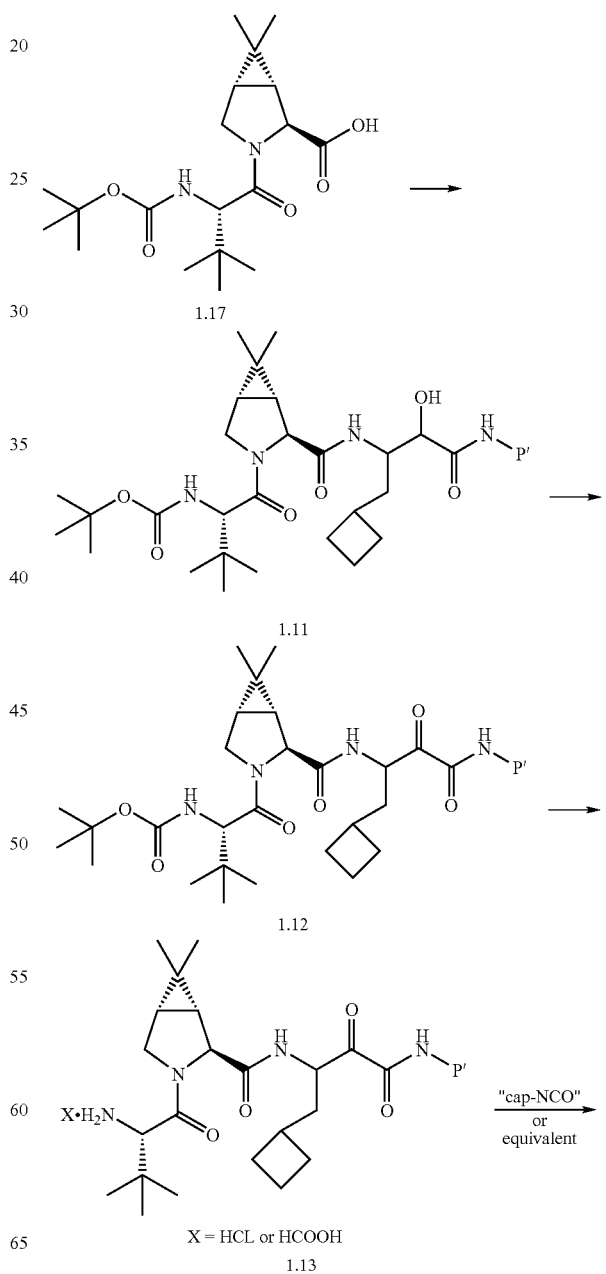

Method B

Peptide coupling of the acid 1.06 with the appropriate P$_1$-P' secondary amide moiety afforded the hydroxylamide 1.09. Oxidation (Moffatt or Dess-Martin's) resulted in the target compound 1.10.

Method C

In another variation, peptide coupling of the N-Boc-P2-P$_3$-acid 1.03 with the appropriate P$_1$-P' amide moiety afforded the hydroxylamide 1.11. Oxidation (Moffatt or Dess-Martin's) resulted in the keto-amide 1.12. Deprotection of the N-Boc using either formic acid or 4 M HCl in dioxane gave the formate or hydrochloride salt 1.13. Treatment with a suitable isocyanate (or isocyanate equivalent) resulted in the target compound 1.14.

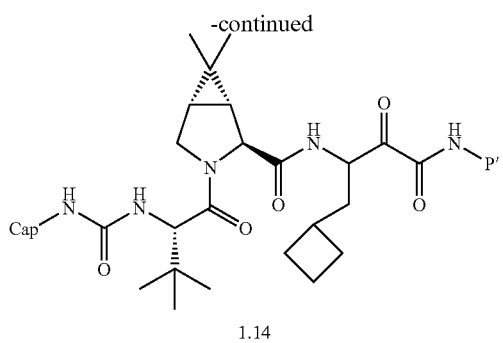

1.14

Method D

In yet another variation, the hydrochloride salt 1.13 was converted to the 4-nitrophenyl carbamate 1.15 by reaction with 4-nitrophenyl chloroformate. Subsequent treatment with an amine (or amine hydrochloride salt) of choice provided the target compound 1.14.

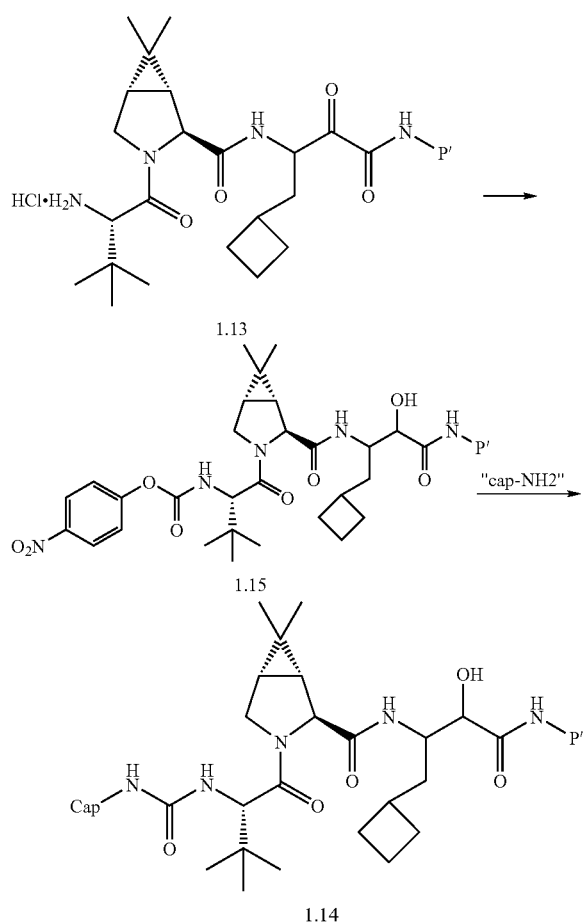

Method E

In yet another variation, the dipeptide hydrochloride salt 1.04 was converted to the 4-nitrophenyl carbamate as described above. Treatment with an amine (or amine hydrochloride salt) of choice provided the urea derivative 1.05. Hydrolysis and further elaboration as described in Methods A/B provided the target compounds 1.14.

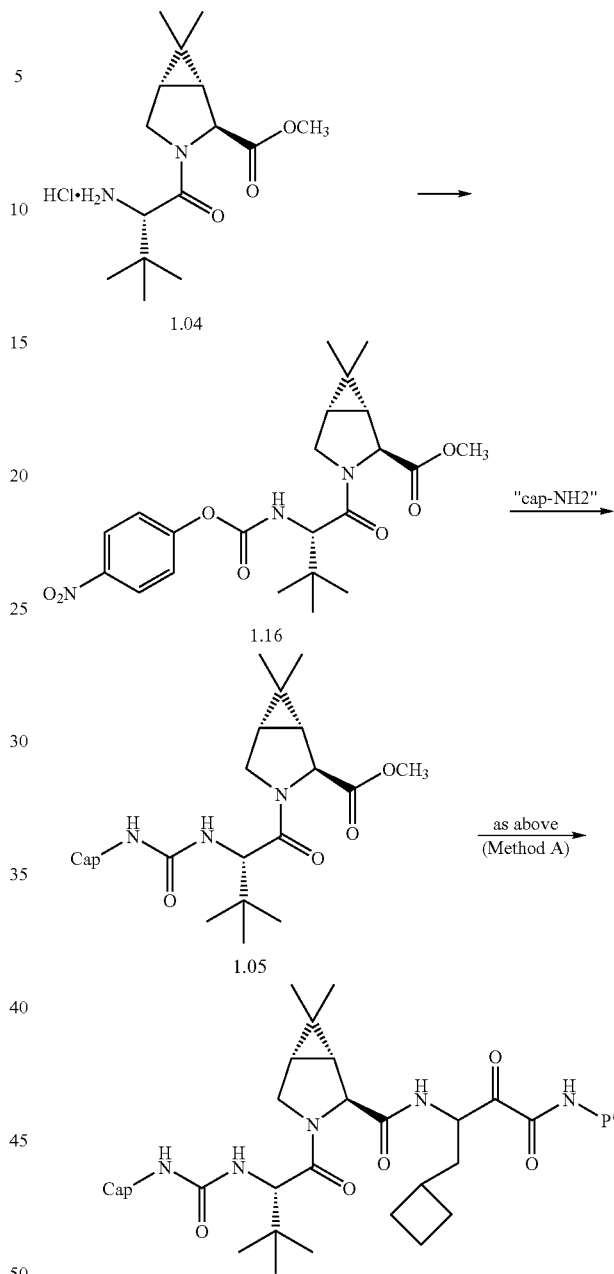

The Following Experimental Section Applies for the Preparation of the Compounds of Formula XII:

Abbreviations which are used in the descriptions of the schemes, preparations and the examples that follow are:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate MeOH: Methanol
EtOH: Ethanol
Et$_2$O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
iBoc: isobutoxycarbonyl
iPr: isopropyl
$^t$Bu or Bu$^t$: tert-Butyl
Boc: tert-Butyloxycarbonyl
Cbz: Benzyloxycarbonyl
Cp: Cylcopentyldienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate General Schemes for Preparation of Target Compounds Compounds of the present invention were synthesized using the general schemes (Methods A-E) described below.

Method A:

Deprotection of the N-Boc functionality of 1.01 under acidic conditions provided the hydrochloride salt 1.02 which was subsequently coupled with N-Boc-tert-leucine under peptide coupling methodology to afford 1.03. N-Boc deprotection followed by treatment with appropriate isocyanate gave the urea 1.05. Hydrolysis of the methyl ester provided the acid 1.06. Peptide coupling of the acid 1.06 with the appropriate P$_1$-P' primary amide moiety afforded the hydroxylamide 1.07. Oxidation (Moffatt or related process—T. T. Tidwell, *Synthesis*, 1990, 857; or Dess-Martin's—*J. Org. Chem.*, 1983, 48, 4155) resulted in the target compound 1.08.

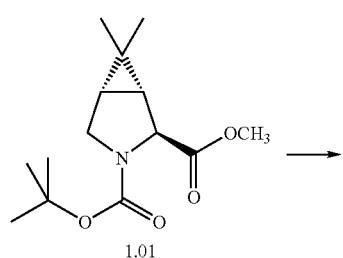

1.01

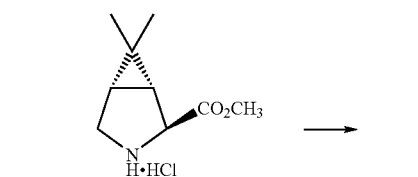

1.02

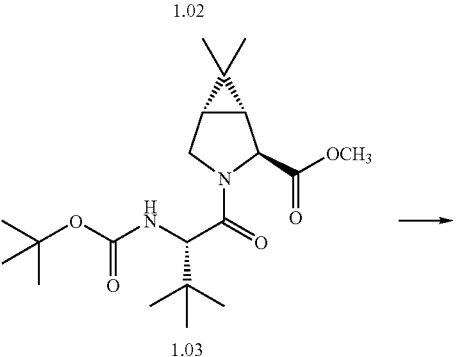

1.03

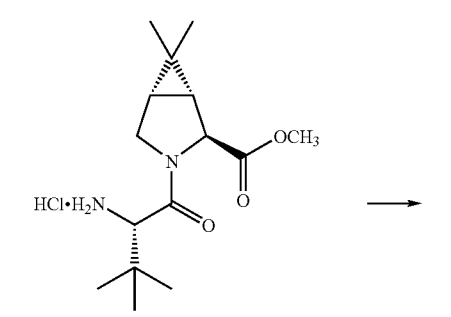

1.04

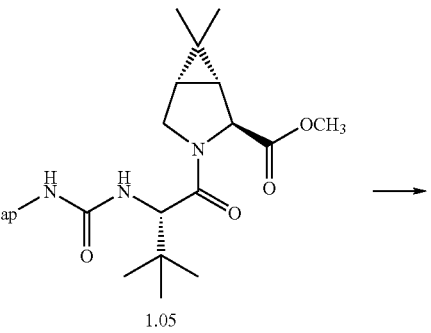

1.05

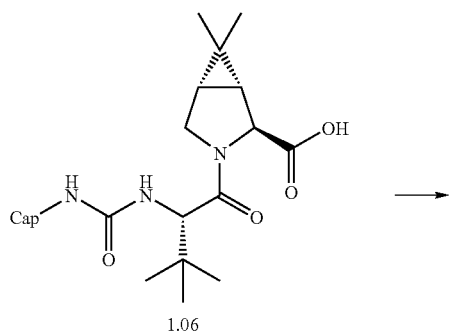

1.06

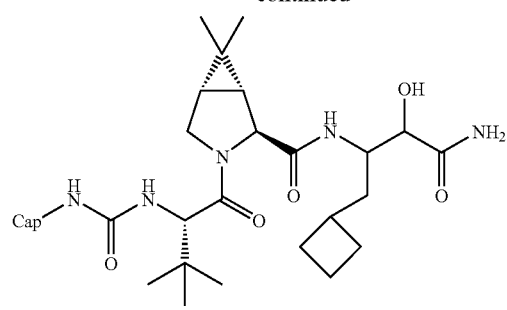

1.07

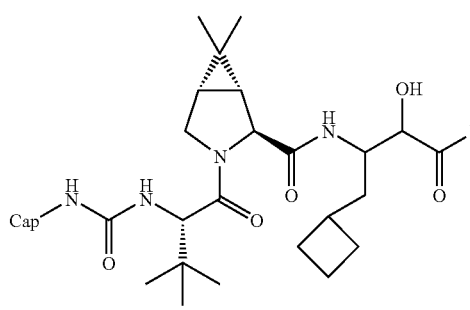

1.08

Method B

Peptide coupling of the acid 1.06 with the appropriate P1-P' secondary amide moiety afforded the hydroxylamide 1.09. Oxidation (Moffatt or Dess-Martin's) resulted in the target compound 1.10.

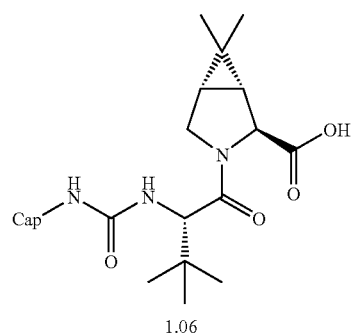

1.06

1.09

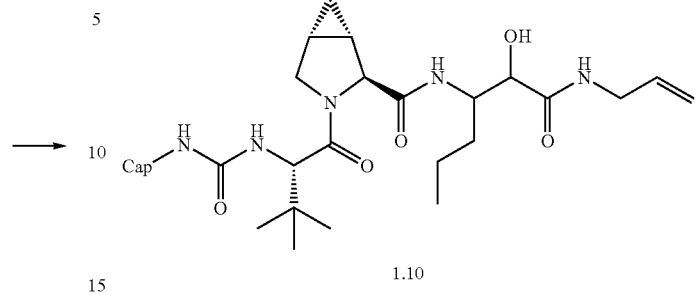

1.10

Method C

In another variation, peptide coupling of the N-Boc-$P_2$—$P_3$-acid 1.17 with the appropriate $P_1$-P' amide moiety afforded the hydroxylamide 1.11. Oxidation (Moffatt or Dess-Martin's) resulted in the keto amide 1.12. Deprotection of the N-Boc functionality gave the hydrochloride salt 1.13. Treatment with a suitable isocyanate (or isocyanate equivalent) resulted in the target compound 1.14.

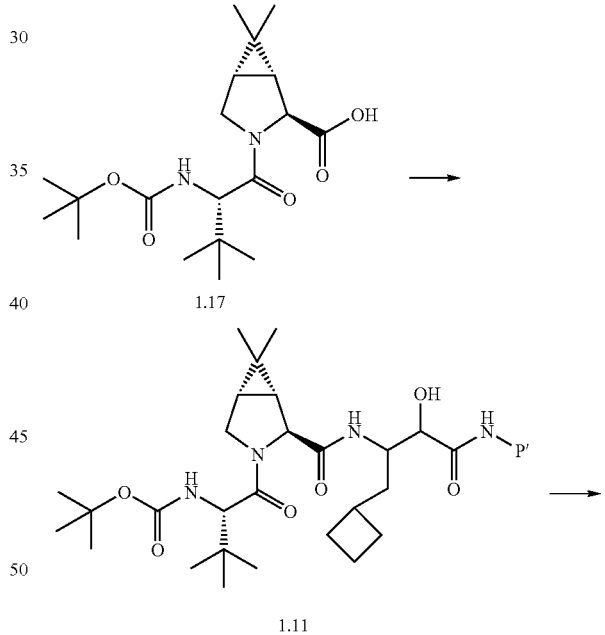

1.17

1.11

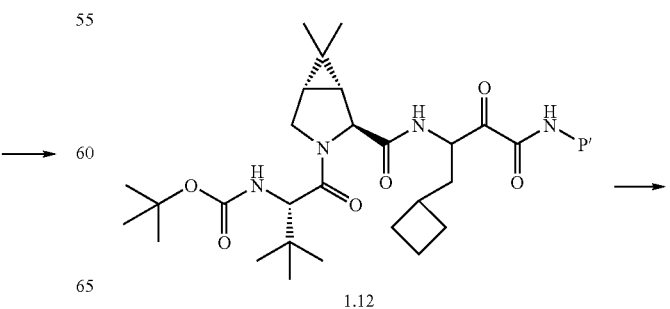

1.12

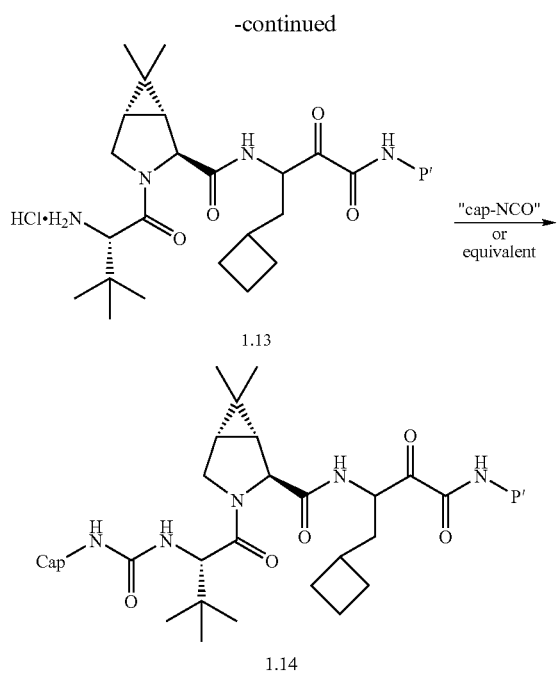

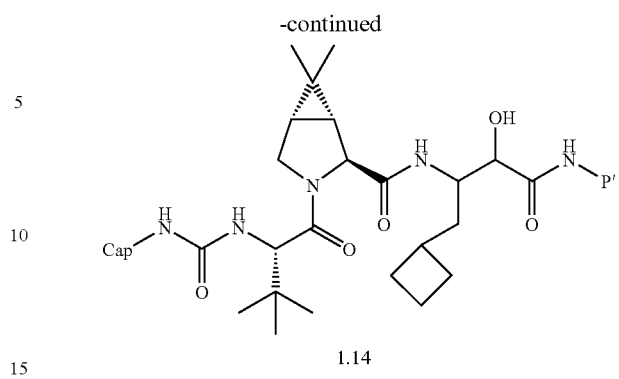

Method D

In yet another variation, the hydrochloride salt 1.13 was converted to the 4-nitrophenyl carbamate 1.15 by reaction with 4-nitrophenyl chloroformate. Subsequent treatment with an amine (or amine hydrochloride salt) of choice provided the target compound 1.14.

Method E

In yet another variation, the dipeptide hydrochloride salt 1.03 was converted to the 4-nitrophenyl carbamate as described above. Treatment with an amine (or amine hydrochloride salt) of choice provided the urea derivative 1.05. Hydrolysis and further elaboration as described in Methods A/B provided the target compounds 1.14.

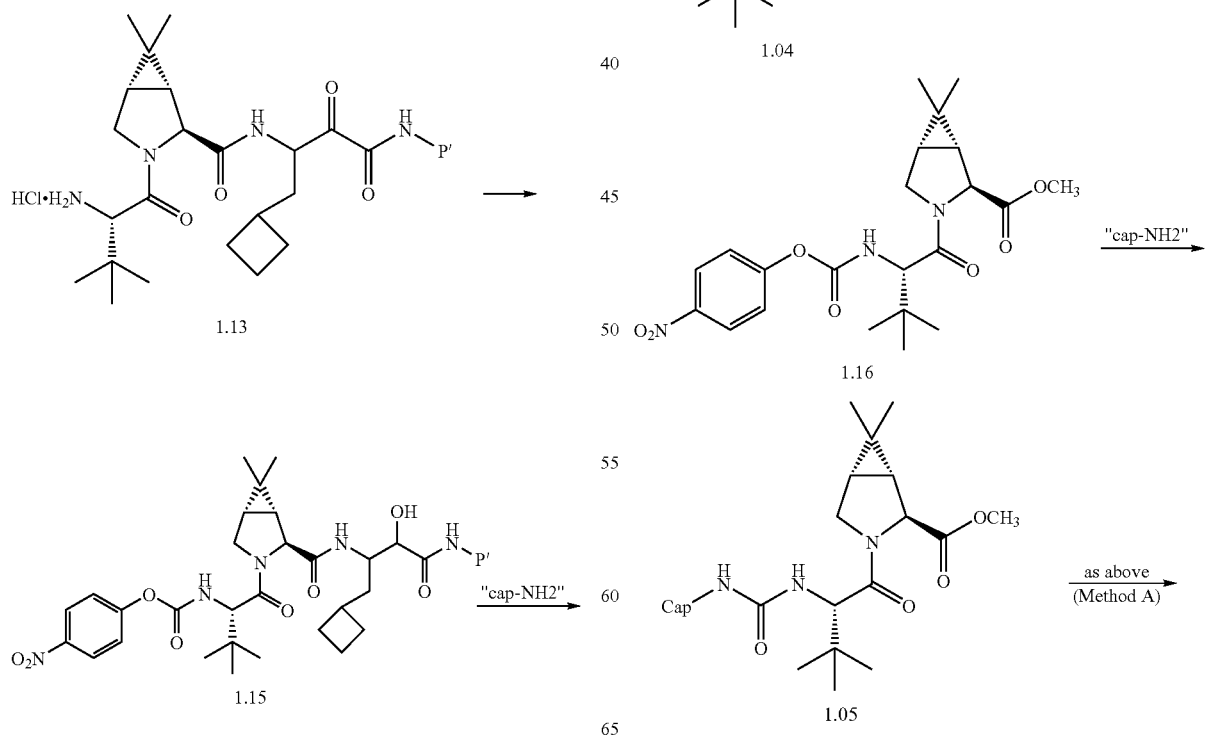

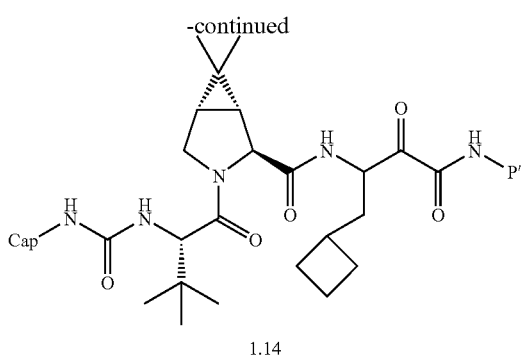

1.14 the Following Experimental Section Applies for the Preparation of the Compounds of FORMULA XIII:

Abbreviations which are used in the descriptions of the schemes, preparations and the examples that follow are:
THF: Tetrahydrofuran
DMF: N,N-Dimethylformamide
EtOAc: Ethyl acetate
ACOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
DIAD: Diisopropylazodicarboxylate
MeOH: Methanol
EtOH: Ethanol
$Et_2O$: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bz: Benzyl
Et: Ethyl
Ph: Phenyl
iBoc: isobutoxycarbonyl
iPr: isopropyl
$^tBu$ or $Bu^t$: tert-Butyl
Boc: tert-Butyloxycarbonyl
Cbz: Benzyloxycarbonyl
Cp: Cylcopentyldienyl
Ts: p-toluenesulfonyl
Me: Methyl
Ms or Mesyl: Methane sulfonyl
HATU: O-(7-azabenzotriazol-1-yl)-1,1,3,3-tetramethyluronium hexafluorophosphate
DMAP: 4-N,N-Dimethylaminopyridine
Bop: Benzotriazol-1-yl-oxy-tris(dimethylamino)hexafluorophosphate
PCC: Pyridiniumchlorochromate
DIBAL-H: diisopropyl aluminum hydride
rt or RT: Room temperature
quant.: Quantitative yield
h or hr: hour min: minute
TFA: Trifluoroacetic acid General Schemes for Preparation of Target Compounds Compounds of the present invention were synthesized using the general schemes (Methods A-E) described below.

Method A

Deprotection of the N-Boc functionality of 1.01 under acidic conditions provided the hydrochloride salt 1.02 which was subsequently coupled with N-Boc-tert-leucine under peptide coupling methodology to afford 1.03. N-Boc deprotection followed by treatment with appropriate isocyanate gave the urea 1.05. Hydrolysis of the methyl ester provided the acid 1.06. Peptide coupling of the acid 1.06 with the appropriate $P_1$-$P'$ primary amide moiety afforded the hydroxylamide 1.07. Oxidation (Moffatt or related process— T. T. Tidwell, Synthesis, 1990, 857; or Dess-Martin's periodinane (J. Org. Chem., 1983, 48, 4155) resulted in the target compound 1.08.

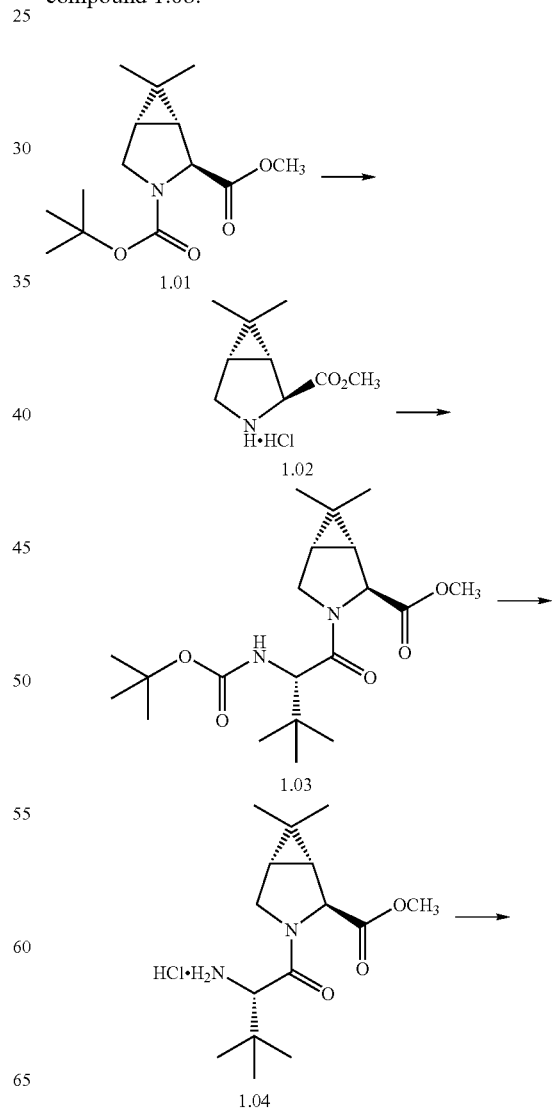

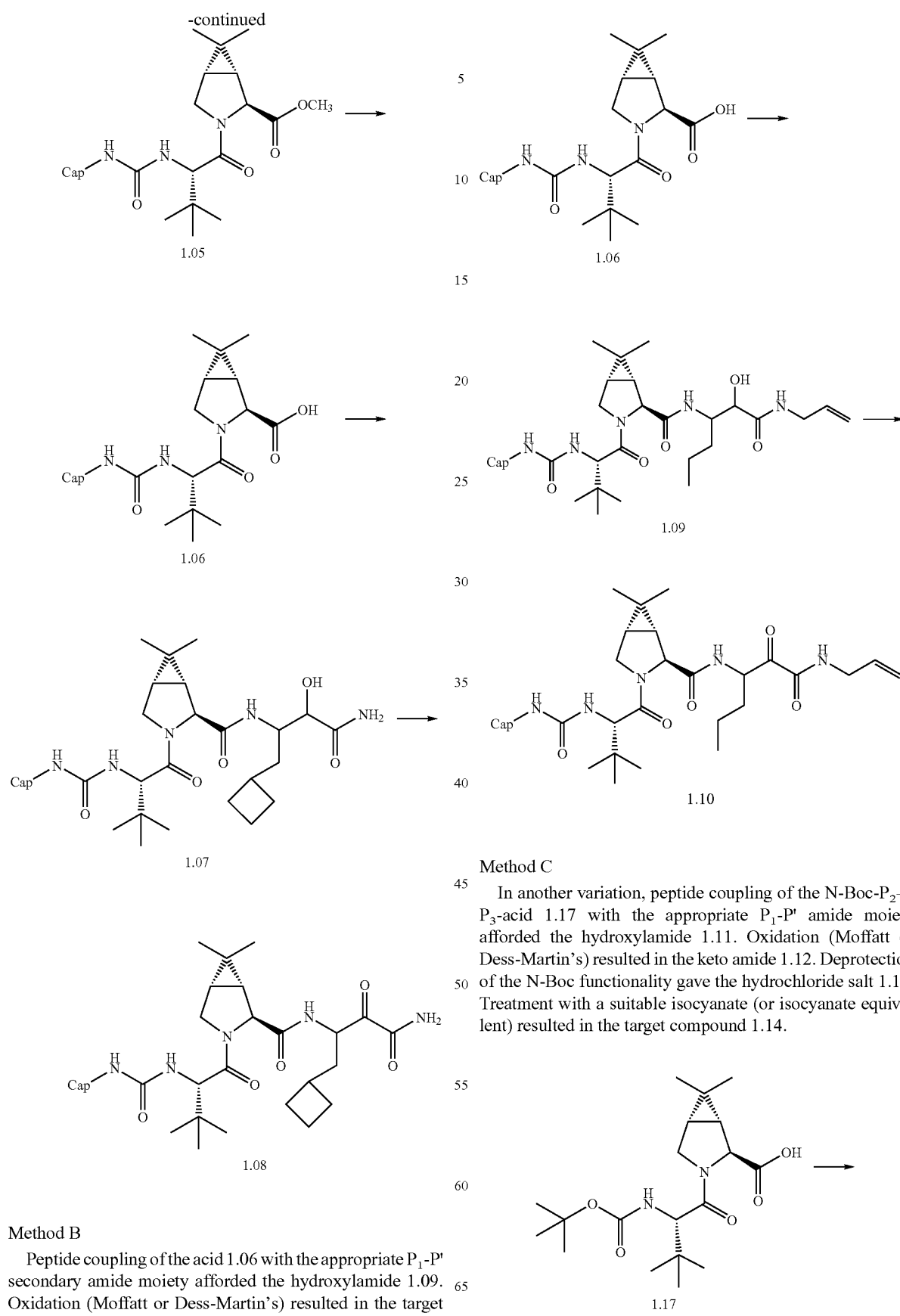

Method B

Peptide coupling of the acid 1.06 with the appropriate $P_1$-$P'$ secondary amide moiety afforded the hydroxylamide 1.09. Oxidation (Moffatt or Dess-Martin's) resulted in the target compound 1.10.

Method C

In another variation, peptide coupling of the N-Boc-$P_2$—$P_3$-acid 1.17 with the appropriate $P_1$-$P'$ amide moiety afforded the hydroxylamide 1.11. Oxidation (Moffatt or Dess-Martin's) resulted in the keto amide 1.12. Deprotection of the N-Boc functionality gave the hydrochloride salt 1.13. Treatment with a suitable isocyanate (or isocyanate equivalent) resulted in the target compound 1.14.

-continued

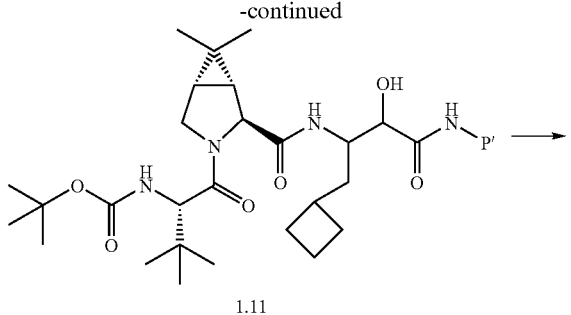
1.11

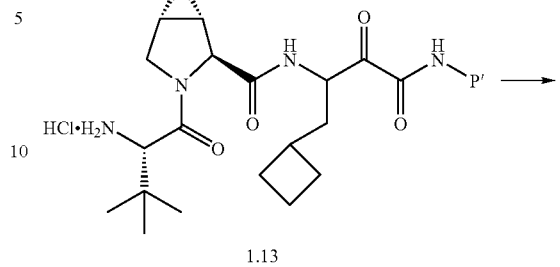
1.13

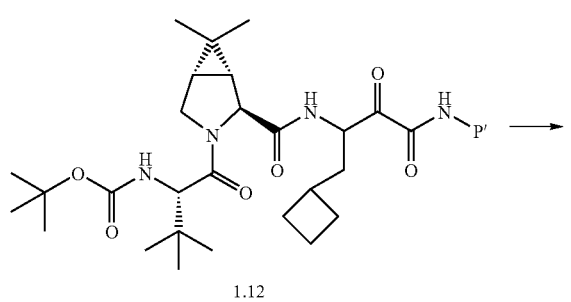
1.12

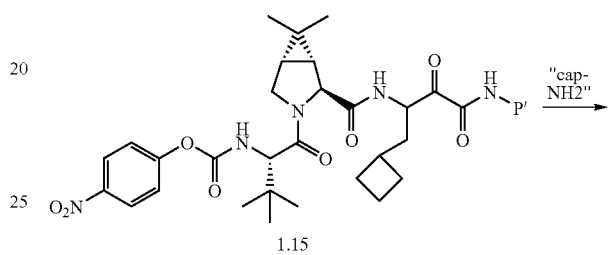
"cap-NH2"
1.15

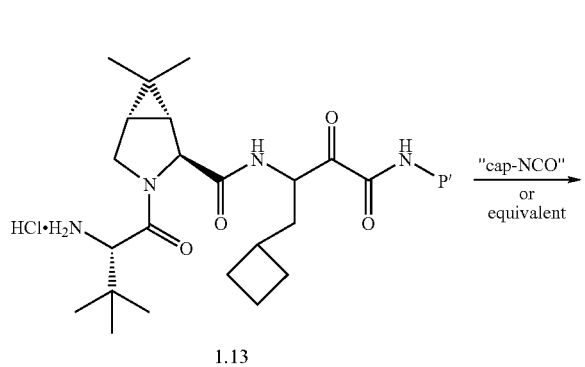
"cap-NCO" or equivalent
1.13

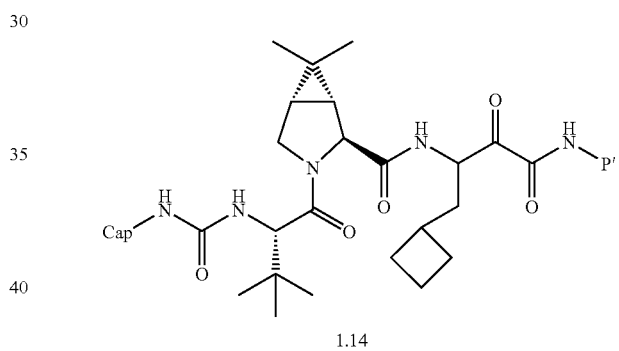
1.14

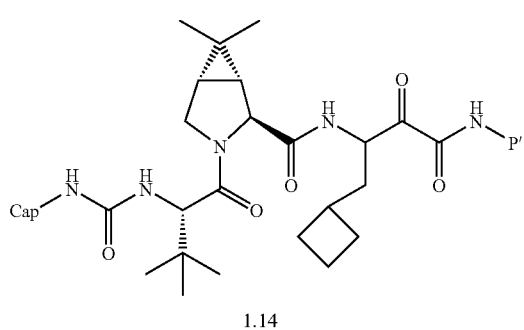
1.14

Method D

In yet another variation, the hydrochloride salt 1.13 was converted to the 4-nitrophenyl carbamate 1.15 by reaction with 4-nitrophenyl chloroformate. Subsequent treatment with an amine (or amine hydrochloride salt) of choice provided the target compound 1.14.

Method E

In yet another variation, the dipeptide hydrochloride salt 1.03 was converted to the 4-nitrophenyl carbamate as described above. Treatment with an amine (or amine hydrochloride salt) of choice provided the urea derivative 1.05. Hydrolysis and further elaboration as described in Methods A/B provided the target compounds 1.14.

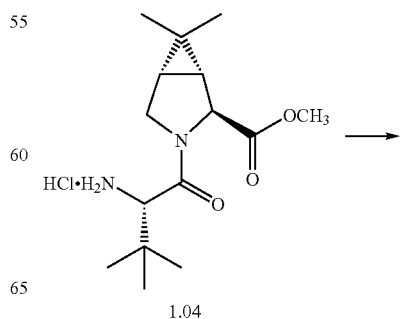
1.04

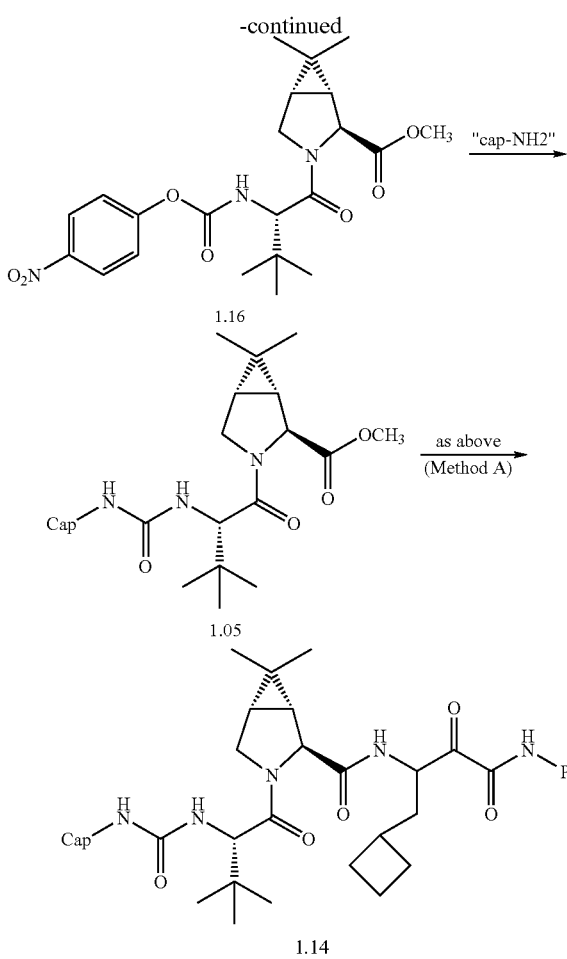

The Following Experimental Section Applies for the Preparation of the Compounds of Formula XIV:

For the procedures described below, the following abbreviations are used:
THF: Tetrahydrofuran
DMF: N,N-Dimethylformamide
EtOAc: Ethyl acetate
ACOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et2O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
DM F-DMA: N,N-Dimethylformamide-dimethylacetal
iBoc: isobutoxycarbonyl
iPr: isopropyl
tBu or But: tert-Butyl
Boc: tert-Butyloxycarbonyl
Cbz: Benzyloxycarbonyl
Cp: Cylcopentyidienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate
KHMDS: Potassium Hexamethyldisilazide or Potassium bis(trimethylsilylamide)
NaHMDS: Sodium Hexamethyldisilazide or Sodium bis(trimethylsilylamide)
LiHMDS: Lithium Hexamethyldisilazide or Lithium bis(trimethylsilylamide)
10% Pd/C: 10% Palladium on carbon (by weight).
TG: Thioglycerol General Schemes for Preparation of Target Compounds Compounds of the present invention were synthesized using the general schemes (Methods A-E) described below.

Method A

Deprotection of the N-Boc functionality of 1.01 under acidic conditions provided the hydrochloride salt 1.02 which was subsequently coupled with N-Boc-tert-leucine under peptide coupling methodology to afford 1.03. N-Boc deprotection followed by treatment with appropriate isocyanate gave the urea 1.05. Hydrolysis of the methyl ester provided the acid 1.06. Peptide coupling of the acid 1.06 with the appropriate P1-P' primary amide moiety afforded the hydroxylamide 1.07. Oxidation (Moffatt oxidation or related process—see, T. T. Tidwell, *Synthesis,* 1990, 857), or Dess-Martin Periodinane—*J. Org. Chem.*, (1983) 48, 4155) resulted in the target compound 1.08.

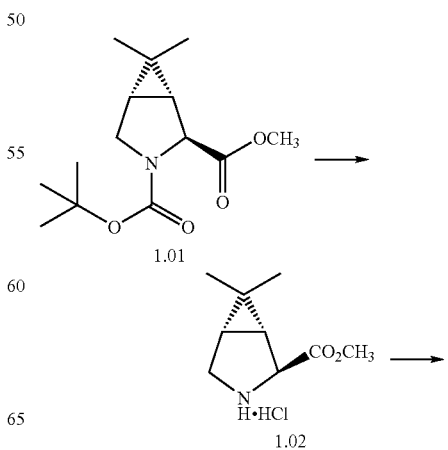

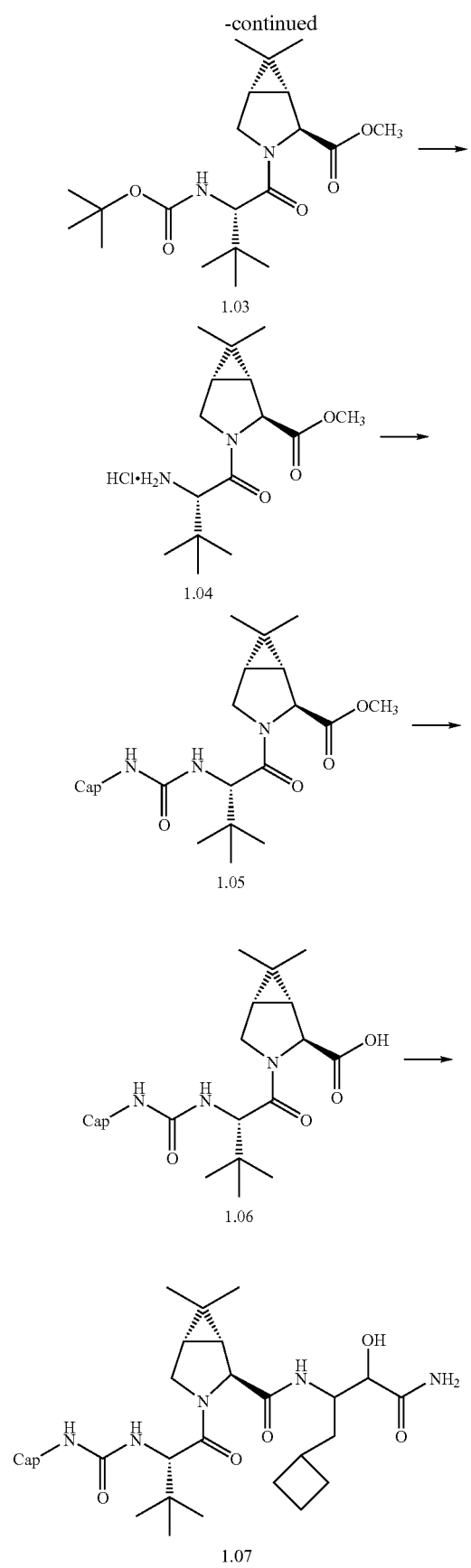

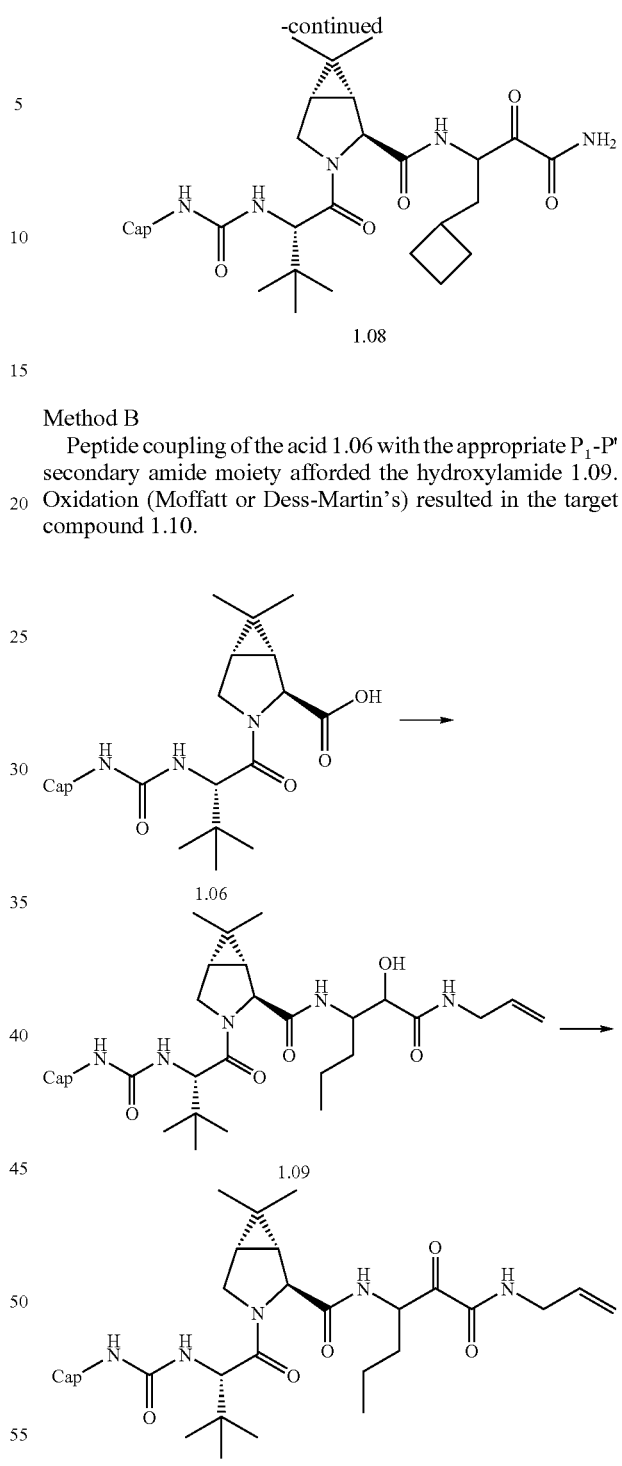

Method B
Peptide coupling of the acid 1.06 with the appropriate P₁-P′ secondary amide moiety afforded the hydroxylamide 1.09. Oxidation (Moffatt or Dess-Martin's) resulted in the target compound 1.10.

Method C
In another variation, peptide coupling of the N-Boc-P2-P₃-acid 1.17 with the appropriate P₁-P′ amide moiety afforded the hydroxylamide 1.11. Oxidation (Moffatt or Dess-Martin Periodinane) resulted in the keto amide 1.12. Deprotection of the N—Boc functionality gave the hydrochloride salt 1.13. Treatment with a suitable isocyanate (or isocyanate equivalent) resulted in the target compound 1.14.

821

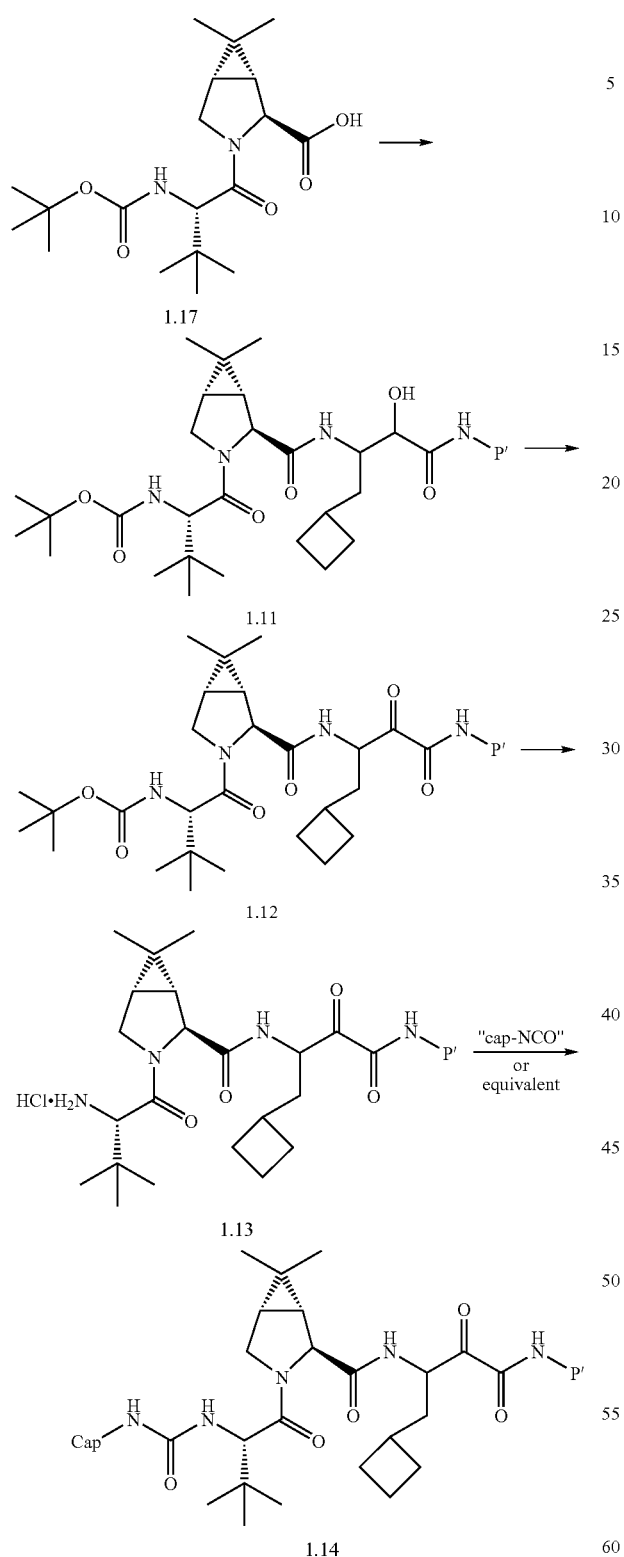

Method D

In yet another variation, the hydrochloride salt 1.13 was converted to the 4-nitrophenyl carbamate 1.15 by reaction with 4-nitrophenyl chloroformate. Subsequent treatment

822 with an amine (or amine hydrochloride salt) of choice provided the target compound 1.14.

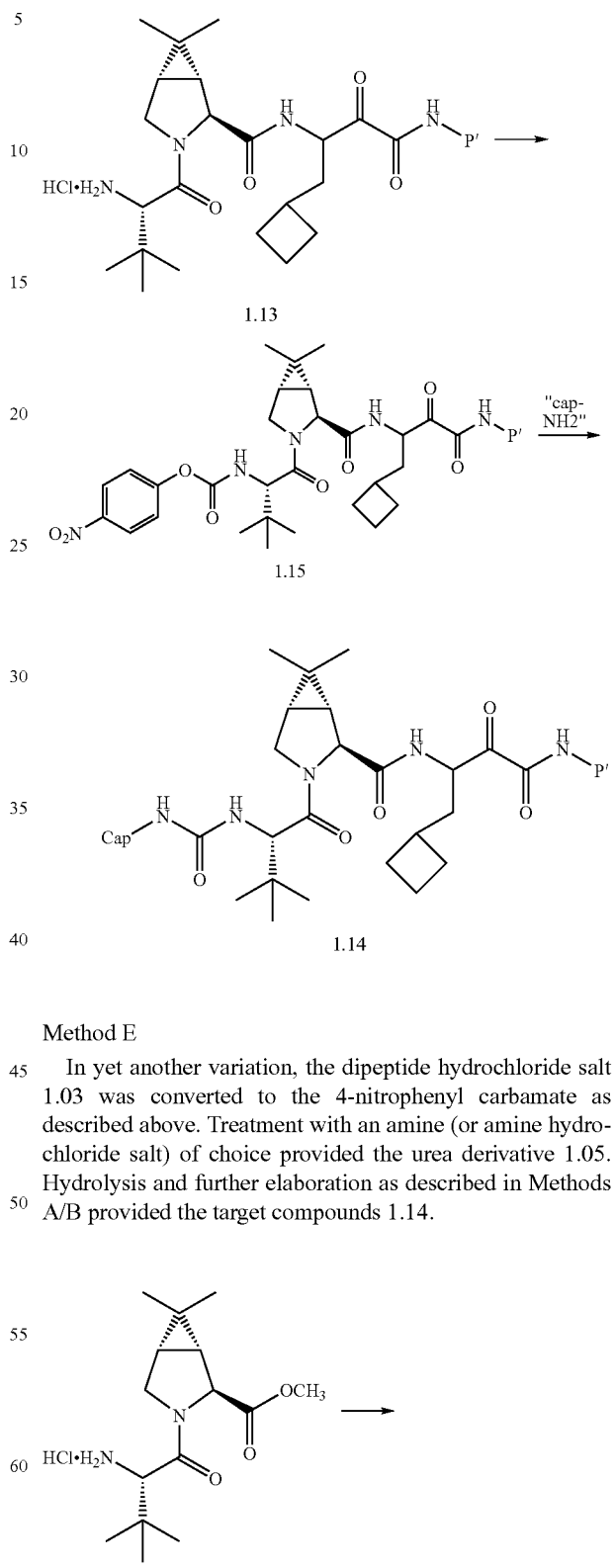

Method E

In yet another variation, the dipeptide hydrochloride salt 1.03 was converted to the 4-nitrophenyl carbamate as described above. Treatment with an amine (or amine hydrochloride salt) of choice provided the urea derivative 1.05. Hydrolysis and further elaboration as described in Methods A/B provided the target compounds 1.14.

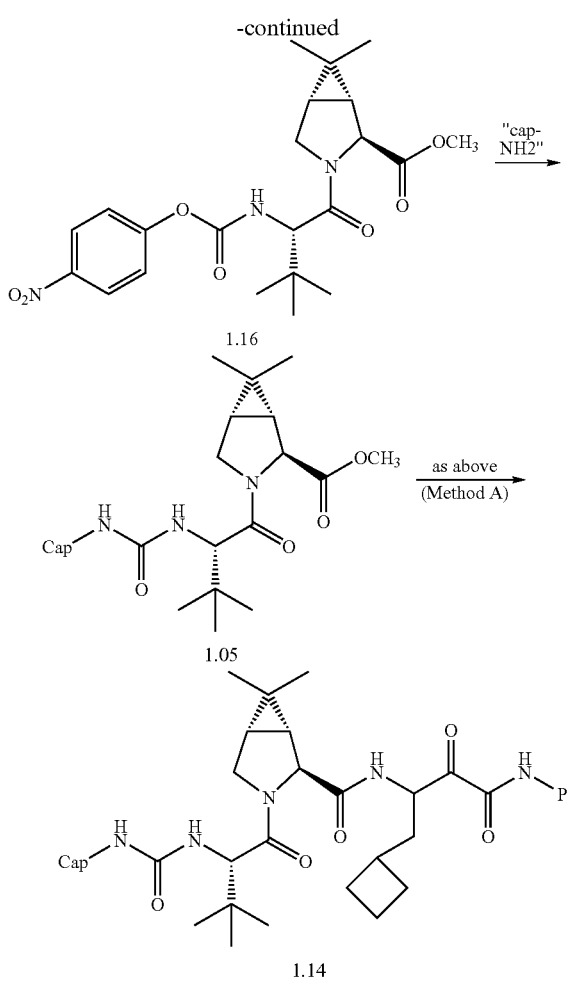

The Following Experimental Section Applies for the Preparation of the Compounds of Formula XV:

For the procedures described below, the following abbreviations are used:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et2O: Diethyl ether
DMSO: Dimethylsulfoxide
HOBt: N-Hydroxybenzotriazole
PyBrOP: B romo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
iBoc: isobutoxycarbonyl
iPr: isopropyl
tBu or Bu$^t$: tert-Butyl
Boc: tert-Butyloxycarbonyl
Cbz: Benzyloxycarbonyl
Cp: Cylcopentyldienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate
KHMDS: Potassium Hexamethyldisilazide or Potassium bis(trimethylsilylamide)
NaHMDS: Sodium Hexamethyldisilazide or Sodium bis(trimethylsilylamide)
LiHMDS: Lithium Hexamethyldisilazide or Lithium bis(trimethylsilylamide)
10% Pd/C: 10% Palladium on carbon (by weight).

PREPARATIVE EXAMPLE 1

Step A

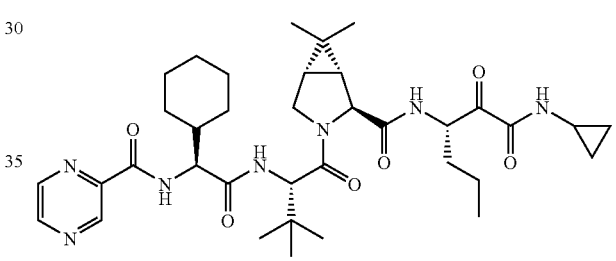

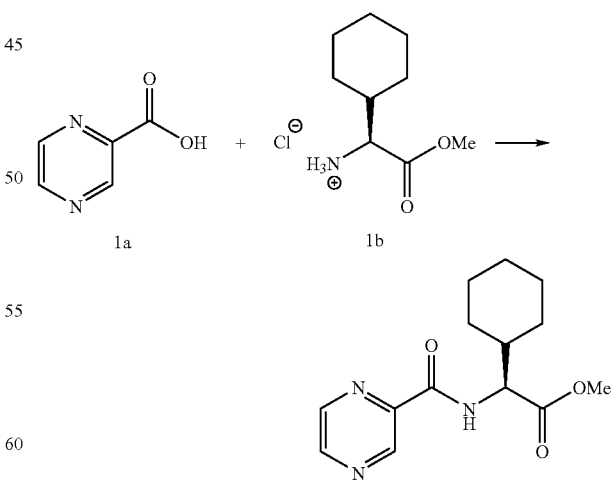

A solution of pyrazinecarboxylic acid 1a (3 g) in 150 mL of dry dichloromethane and 150 mL of dry DMF was stirred at 0° C. and treated with HATU (1.4 eq, 6.03 g). L-cyclohexylglycine hydrochloride 1b (1.2 eq, 6.03 g) was added in small portions. Then, N-methylmorpholine (4 eq, 10 mL, d 0.920) was added dropwise. The reaction mixture was gradually warmed to room temperature and stirred for 20 h. All the volatiles were removed under vacuum and the residue was dissolved in 500 mL of ethyl acetate. The organic layer was washed with water (100 mL), aqueous 1N HCl (100 mL), aqueous saturated sodium bicarbonate solution (100 mL), and brine (100 mL). The organic layer was dried over magnesium sulfate, filtered and concentrated under reduced pressure. The residue was chromatographed on silica gel (gradient: acetone/hexanes; 5:95 to 3:7) to afford the product 1c as a white solid.

Step B

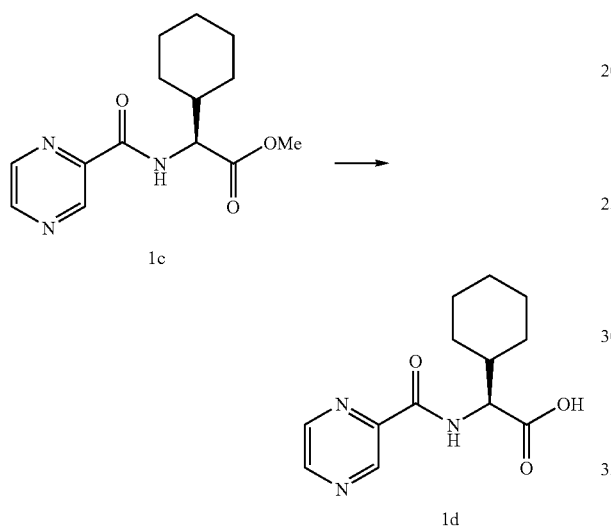

A solution of methyl ester 1c (6.5 g) in 270 mL of a 1:1:1 mixture of THF/MeOH/water was cooled to 0° C. and treated with lithium hydroxide monohydrate (2.5 eq, 2.45 g). The mixture was stirred and monitored by TLC (acetone/hexanes; 2:8). When all the starting material had been consumed, the reaction mixture was treated with 100 mL of aqueous 1N HCl and the mixture was concentrated on the rotavap. Dichloromethane (250 mL) was added and layers separated. The aqueous layer was extracted with dichloromethane (3×80 mL). The combined organic layers were dried over magnesium sulfate, filtered, and concentrated to afford the product 1d as a white solid.

Step C

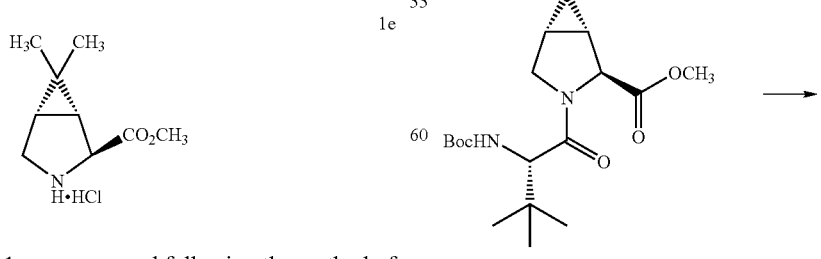

The amino ester 1e was prepared following the method of R. Zhang and J. S. Madalengoitia (*J. Org. Chem.* 1999, 64, 330), with the exception that the Boc group was cleaved by the reaction of the Boc-protected amino acid with methanolic HCl (4M HCl in dioxane was also employed for the deprotection).

(Note: In a variation of the reported synthesis, the sulfonium ylide was replaced with the corresponding phosphonium ylide).

Step D

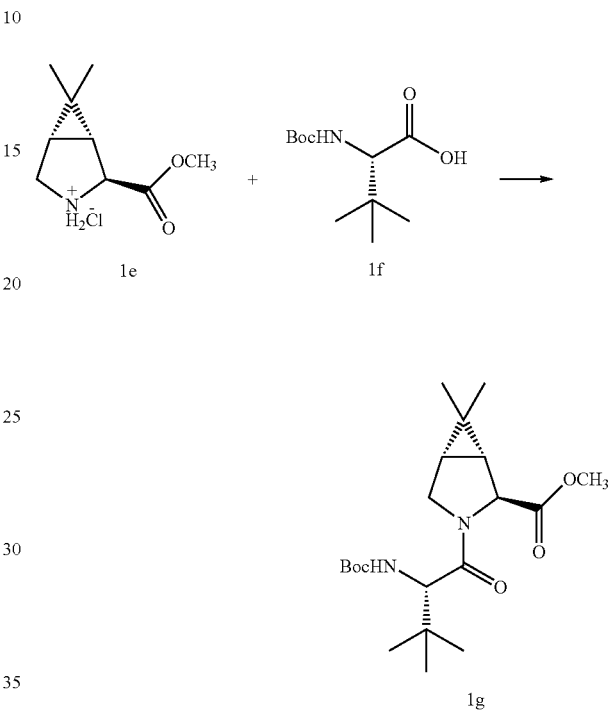

A solution of Boc-tert-Leu 1f (Fluka, 5.0 g, 21.6 mmol) in dry $CH_2Cl_2$/DMF (50 mL, 1:1) was cooled to 0° C. and treated with the amine hydrochloride 1e (5.3 g, 25.7 mmol), NMM (6.5 g, 64.8 mmol) and BOP reagent (11.6 g, 25.7 mmol). The reaction was stirred at rt. for 24 h, diluted with aqueous HCl (1 M) and extracted with $CH_2Cl_2$. The combined organic layers were washed with aqueous 1M HCl, saturated $NaHCO_3$, brine, dried ($MgSO_4$), filtered and concentrated in vacuo and purified by chromatography ($SiO_2$, Acetone/Hexane 1:5) to yield 1 g as a colorless solid.

Step E

-continued

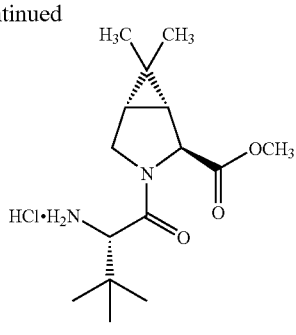

1h

A solution of methyl ester 1g (4.0 g, 10.46 mmol) was dissolved in 4M HCl in dioxane and stirred at rt. for 3 h. The reaction mixture was concentrated in vacuo to obtain the amine hydrochloride salt, 1 h which was used without purification.

Step F

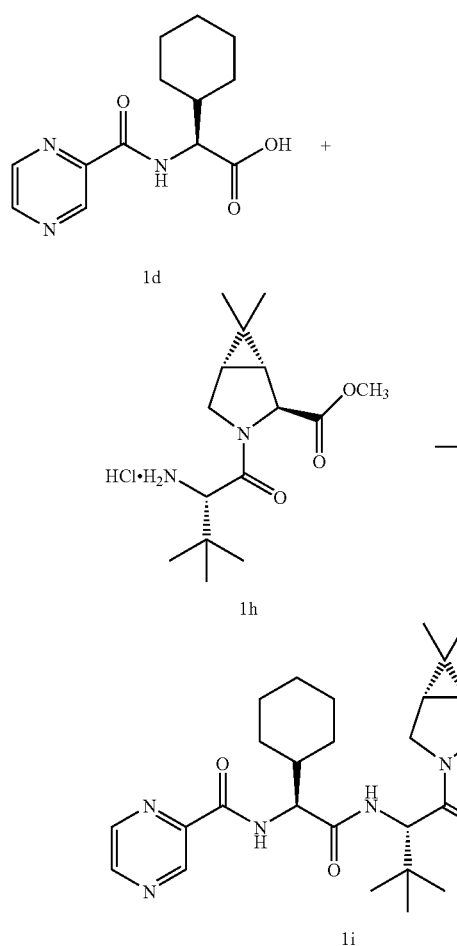

A solution of acid 1d (100 mg) in 5 mL of dry dichloromethane and 5 mL of dry DMF was stirred at 0° C. and treated with HATU (1.4 eq, 202 mg). The amine hydrochloride 1h (1.2 eq, 146 mg) was added. Then, N-methylmorpholine (4 eq, 0.17 mL, d 0.920) was also added. The reaction mixture was stirred at 0° C. overnight. All the volatiles were removed under vacuum and the residue was dissolved in 80 mL of ethyl acetate. The organic layer was washed with water (10 mL), aqueous 1N HCl (10 mL), aqueous saturated sodium bicarbonate solution (10 mL), and brine (10 mL). The organic layer was dried over magnesium sulfate, filtered and concentrated under reduced pressure. The residue was chromatographed on silica gel (gradient: acetone/hexanes; 1:9 to 4:6) to afford the product 1i as a white solid.

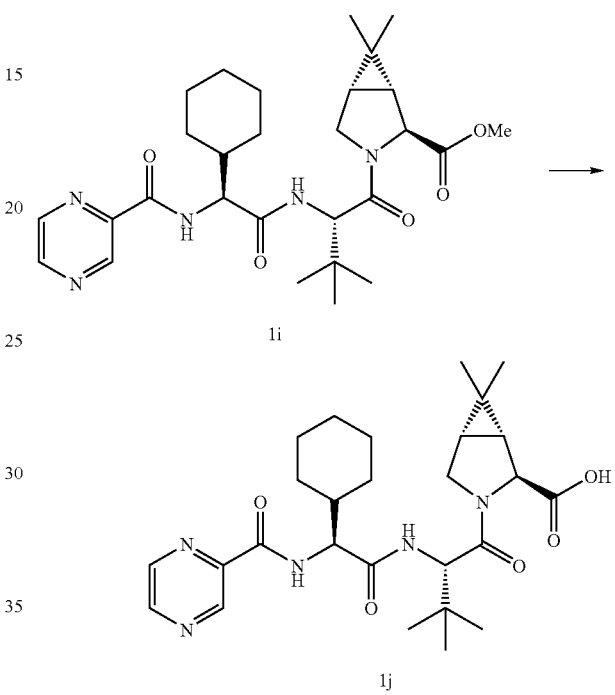

A solution of methyl ester 1i (180 mg) in 9 mL of a 1:1:1 mixture of THF/MeOH/water was cooled to 0° C. and treated with lithium hydroxide monohydrate (2.5 eq, 35 mg). The mixture was stirred and monitored by TLC (acetone/hexanes; 3:7). When all the starting material had been consumed, the reaction mixture was treated with 50 mL of aqueous 1N HCl and the mixture was concentrated on the rotavap. Dichloromethane (80 mL) was added and layers separated. The aqueous layer was extracted with dichloromethane (3×50 mL). The combined organic layers were dried over magnesium sulfate, filtered, and concentrated to afford the product 1j as a white solid.

Step H

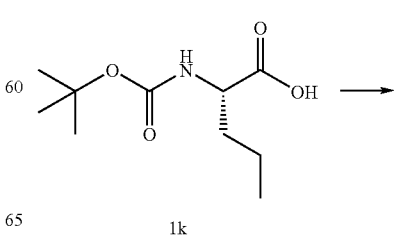

1k

-continued

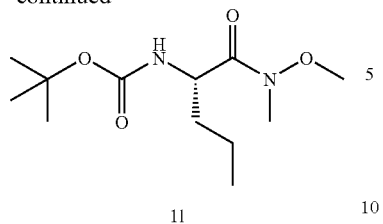

11

A solution of acid 1k (2 g) in 100 mL of dry dichloromethane and 5 mL of DMF was treated with N,O-dimethylhydroxylamine hydrochloride (1.1 eq, 986 mg), BOP reagent (1.1 eq, 4.47 g), and N-methylmorpholine (3.3 eq, 3.3 mL, d 0.920) in that order. The mixture was heated to 50° C. overnight. The reaction mixture was concentrated to half its volume and diluted with 400 mL of ethyl acetate. The organic layer was washed with water (80 mL), aqueous 1M HCl (80 mL), aqueous saturated sodium bicarbonate solution (80 mL), and brine (80 mL). The organic layer was dried over magnesium sulfate, filtered, and concentrated under reduced pressure. The residue was chromatographed on silica gel (gradient: acetone/hexanes; 5:95 to 3:7) to afford the product 11 as a clear oil.

Step I

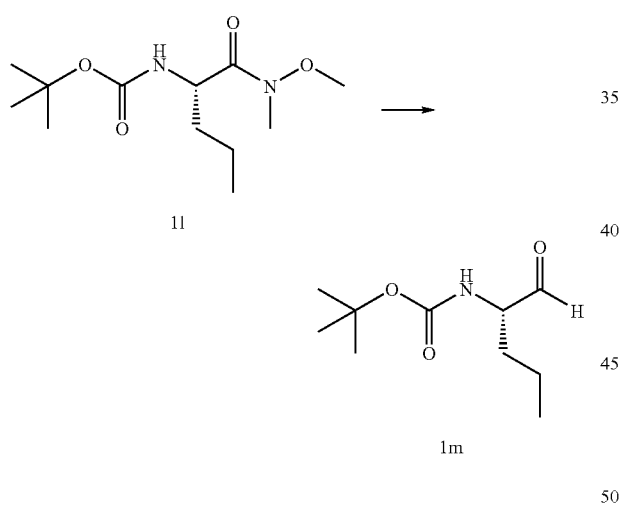

A solution of amide 11 (2.2 g) in 100 mL of dry THF was cooled to ° C. Lithium aluminum hydride solution (1.3 eq) was added dropwise. The cooling bath was removed after 5 min and the mixture was allowed to reach room temperature. TLC analysis (ethyl acetate/hexanes; 2:8) showed that all the starting material had been consumed. The excess LAH was carefully quenched by addition of drops of aqueous saturated sodium hydrogen sulfate. The mixture was diluted with 200 mL of ether and aqueous saturated sodium hydrogen sulfate was added in small portions until a white solid precipitated. The mixture was filtered thru celite and the filtrate was washed with 50 mL of brine. The organic layer was dried over magnesium sulfate, filtered and concentrated. The residue was chromatographed on silica gel (gradient: ethyl acetate/hexanes; 5:95 to 4:6) to afford the aldehyde product 1m as a colorless oil.

Step J

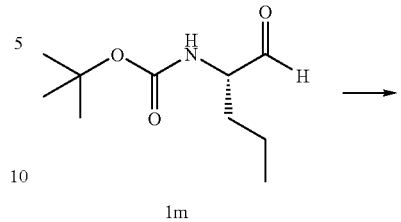

1m

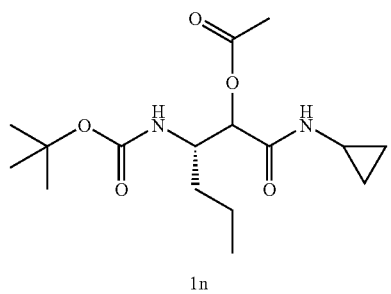

1n

A solution of aldehyde 1m (1.8 g) in 100 mL of dry dichloromethane was treated with isonitrile (1.1 eq, 680 mg) and acetic acid (2 eq, 1.02 mL, d 1.0149). The mixture was stirred overnight. All the volatiles were removed under vacuum and the residue was chromatographed on silica gel (gradient: ethyl acetate/hexanes; 2:8 to 6:4) to afford the product 1 n as a white solid.

Step K

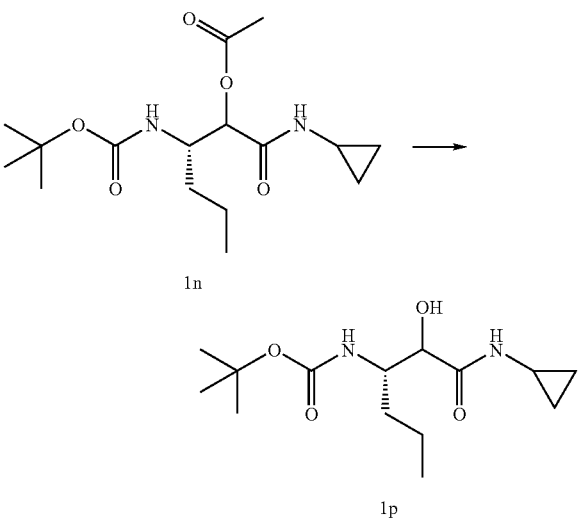

A solution of acetate in (1.6 g) in 60 mL of a 1:1:1 mixture of THF/MeOH/water was treated with lithium hydroxide monohydrate and stirred for approximately 1 h until all the starting material had been consumed as determined by TLC analysis (ethyl acetate/hexanes; 1:1). The volatiles were removed in rotavap and the residue was diluted with dichloromethane (150 mL). The layers were separated and the aqueous layer was diluted with 30 mL of aqueous saturated sodium bicarbonate solution and extracted with dichloromethane (3×80 mL). The combined organic layers were dried over magnesium sulfate, filtered and concentrated to afford the product 1p as a white solid.

Step L
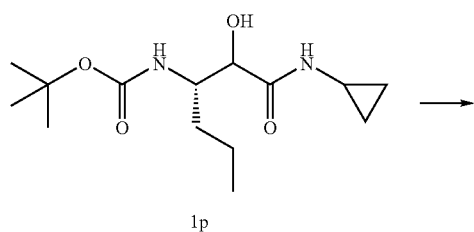
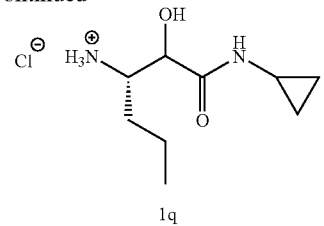
The N-Boc protected amine 1p (1.5 g) was dissolved in 20 mL of 4M HCl in dioxane. The reaction mixture was stirred for about 1 h until all the starting material had been consumed. All the volatiles were removed under vacuum to afford the product 1q as a white solid.
Step M
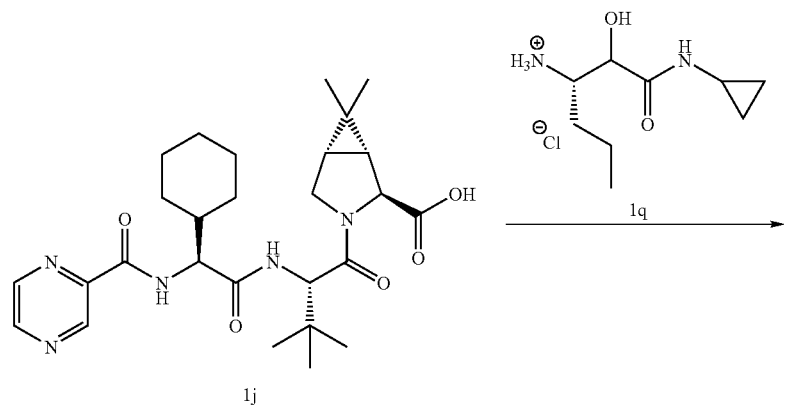
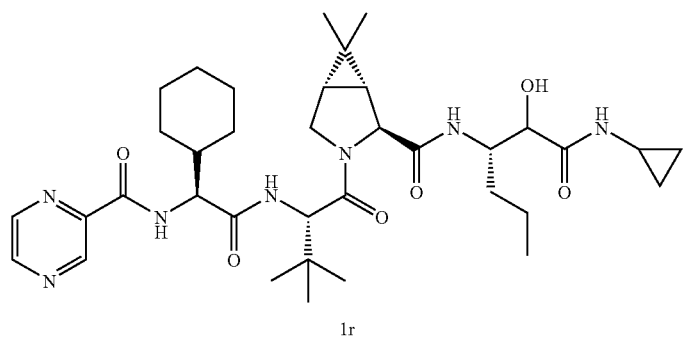

A solution of acid 1j (50 mg) in 2 mL of dry dichloromethane and 2 mL of dry DMF was stirred at 0° C. and treated with HATU (1.4 eq, 52 mg). The amine hydrochloride 1q (1.2 eq, 26 mg) was added. Then, N-methylmorpholine (4 eq, 0.042 mL, d 0.920) was also added. The reaction mixture was stirred at 0° C. overnight. All the volatiles were removed under vacuum and the residue was dissolved in 80 mL of ethyl acetate. The organic layer was washed with water (10 mL), aqueous 1N HCl (10 mL), aqueous saturated sodium bicarbonate solution (10 mL), and brine (10 mL). The organic layer was dried over magnesium sulfate, filtered and concentrated under reduced pressure. The product 1r was used without further purification.

Step N

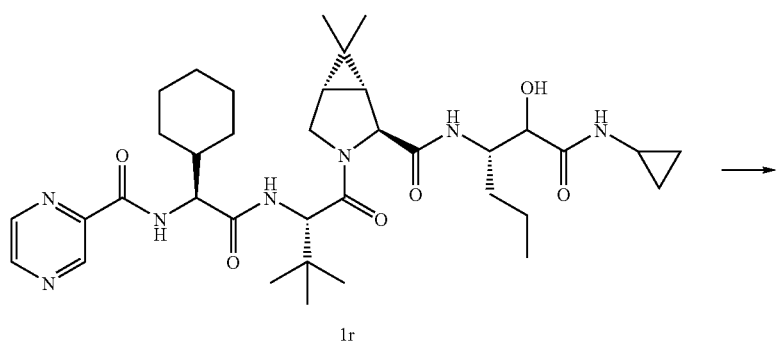

1r

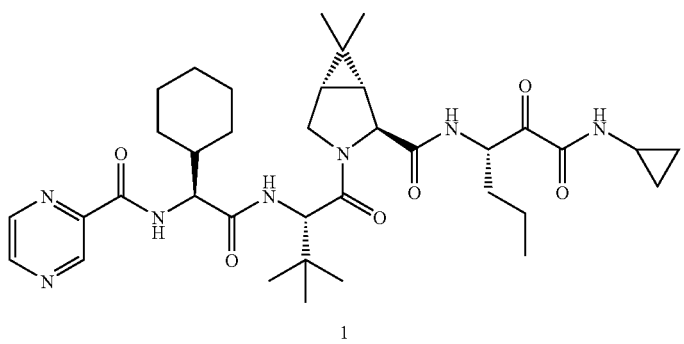

1

A solution of alcohol 1r (65 mg) in 5 mL of dry dichloromethane was treated with Dess-Martin periodinane (3 eq, 121 mg). Reaction mixture was stirred at room temperature for 45 min. The mixture was treated with aqueous 1M sodium thiosulfate solution (10 mL) and aqueous saturated sodium bicarbonate solution (10 mL) and stirred for 15 min. The mixture was extracted with dichloromethane (3×20 mL). The combined organic layers were dried over magnesium sulfate, filtered, and concentrated. The residue was chromatographed on silica gel (gradient: acetone/hexanes; 2:8 to 5:5) to afford the product 1 as a white solid.

One skilled in the art would understand that other suitable compounds of Formula XV can be prepared in a similar manner to that disclosed above.

The Following Experimental Section Applies for the Preparation of the Compounds of Formula XVI:

PREPARATIVE EXAMPLE A

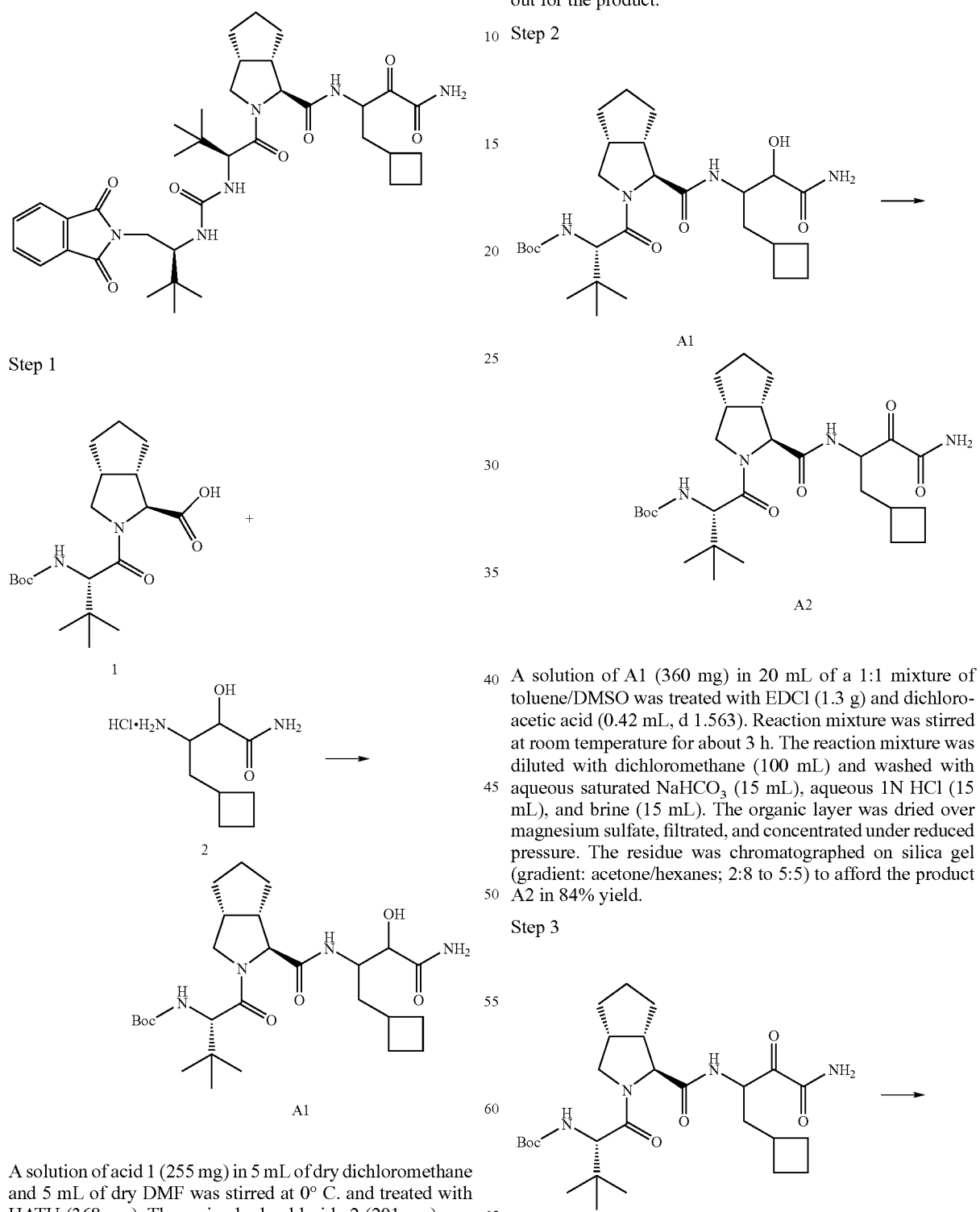

Step 1

A solution of acid 1 (255 mg) in 5 mL of dry dichloromethane and 5 mL of dry DMF was stirred at 0° C. and treated with HATU (368 mg). The amine hydrochloride 2 (201 mg) was added followed by addition of N-methylmorpholine (0.42 mL). The reaction mixture was gradually warmed to room temperature and stirred overnight. All the volatiles were removed under vacuum and the residue was taken into 100 mL of ethyl acetate. The organic layer was washed with aqueous 1N HCl (15 mL), aqueous saturated NaHCO3 (15 mL), water (15 mL), brine (15 mL), dried over MgSO4, filtered, and concentrated under reduced pressure to afford the desired product A1. No further purification was carried out for the product.

Step 2

A solution of A1 (360 mg) in 20 mL of a 1:1 mixture of toluene/DMSO was treated with EDCl (1.3 g) and dichloroacetic acid (0.42 mL, d 1.563). Reaction mixture was stirred at room temperature for about 3 h. The reaction mixture was diluted with dichloromethane (100 mL) and washed with aqueous saturated $NaHCO_3$ (15 mL), aqueous 1N HCl (15 mL), and brine (15 mL). The organic layer was dried over magnesium sulfate, filtrated, and concentrated under reduced pressure. The residue was chromatographed on silica gel (gradient: acetone/hexanes; 2:8 to 5:5) to afford the product A2 in 84% yield.

Step 3

-continued

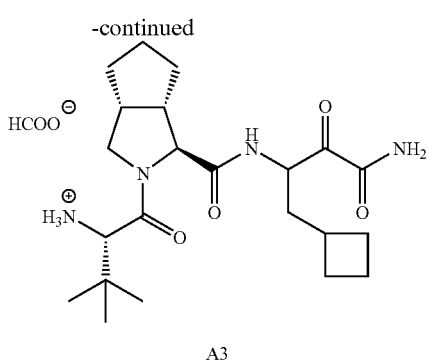

A3

The N-Boc protected amine A2 was treated with 10 mL of formic acid. The resulting solution was stirred for 2 h. All the volatiles were removed under reduced pressure. No further purification was done for the product A3.

Step 4

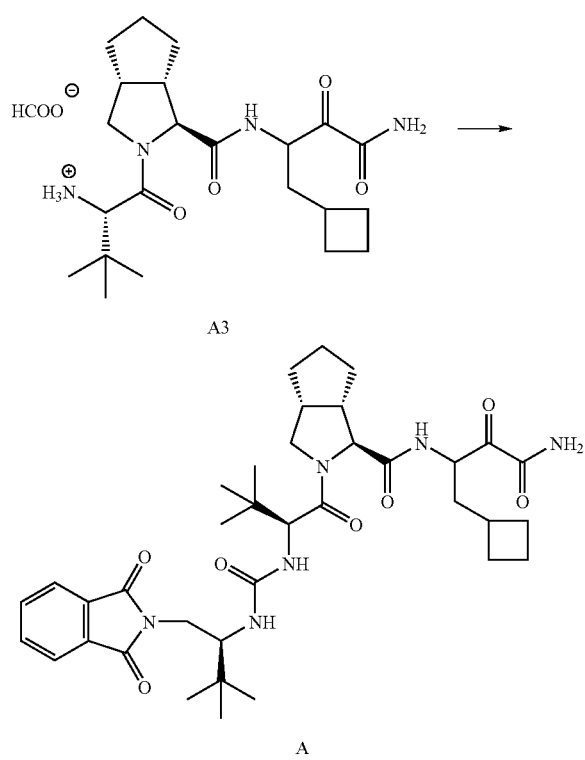

To a solution of the amine salt A3 in 1 mL of dry methylene chloride was added N-methylmorpholine (0.037 mL, d 0.920). The resulting solution was cooled in an ice-water bath and a solution of isocyanate in toluene (2.5 mL of a 0.135M soln) was slowly added. The mixture was stirred for 2 h (temp 0 to 25° C.). The reaction mixture was diluted with 60 mL of dichloromethane and washed with 15 mL of aqueous 1N HCl. Aqueous layer was back extracted with dichloromethane (2×20 mL). Combined organic layers were dried over magnesium sulfate, filtered and concentrated under reduced pressure. The residue was chromatographed on Silica gel (gradient: acetone/hexanes; 1:9 to 6:4) to give the product A (15 mg)

as a white solid in 20% yield. HRMS (FAB) calcd for $C_{37}H_{53}N_6O_7$ [M+H] 693.3976; found 693.3987.

One skilled in the art would understand that other suitable compounds of Formula XVI can be prepared in a similar manner to that disclosed above.

The Following Experimental Section Applies for the Preparation of the Compounds of Formula XVII:

Abbreviations which are used in the descriptions of the schemes, preparations and the examples that follow are:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et2O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
iBoc: isobutoxycarbonyl
iPr: isopropyl
$^t$Bu or Bu$^t$: tert-Butyl
Boc: tert-Butyloxycarbonyl
Cbz: Benzyloxycarbonyl
Cp: Cylcopentyldienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate
KHMDS: Potassium Hexamethyldisilazide or Potassium bis (trimethylsilylamide)
NaHMDS: Sodium Hexamethyldisilazide or Sodium bis(trimethylsilylamide)
LiHMDS: Lithium Hexamethyldisilazide or Lithium bis(trimethylsilylamide)
10% Pd/C: 10% Palladium on carbon (by weight).
TG: Thioglycerol General Schemes for Preparation of Target Compounds Compounds of the present invention were synthesized using the general schemes (Methods A-E) described below.

Method A

Deprotection of the N-Boc functionality of 1.01 under acidic conditions provided the hydrochloride salt 1.02 which was subsequently coupled with N-Boc-tert-leucine under peptide coupling methodology to afford 1.03. N-Boc deprotection followed by treatment with appropriate isocyanate gave the urea 1.05. Hydrolysis of the methyl ester provided the acid 1.06. Peptide coupling of the acid 1.06 with the appropriate P₁-P' primary amide moiety afforded the hydroxylamide 1.07. Oxidation (Moffatt oxidation or related process—see, T. T. Tidwell, *Synthesis,* 1990, 857), or Dess-Martin Periodinane—*J. Org. Chem.*, (1983) 48, 4155) resulted in the target compound 1.08.

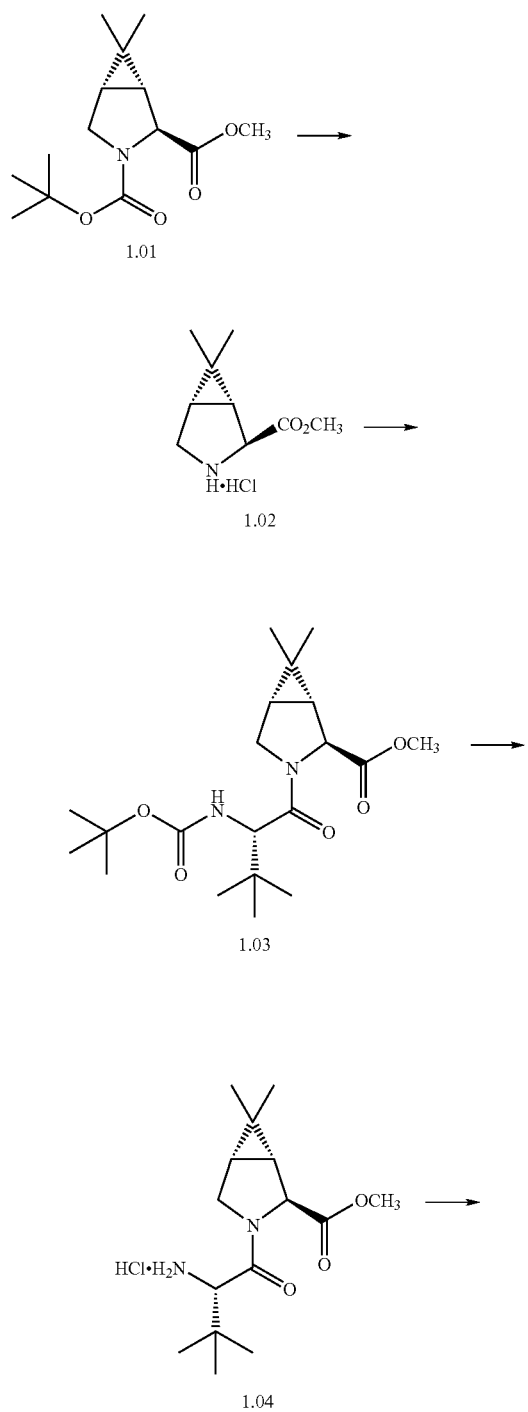

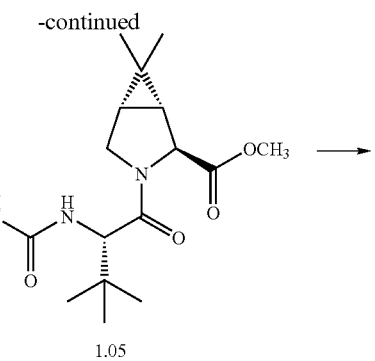

Method B

Peptide coupling of the acid 1.06 with the appropriate P₁-P' secondary amide moiety afforded the hydroxylamide 1.09. Oxidation (Moffatt or Dess-Martin's) resulted in the target compound 1.10.

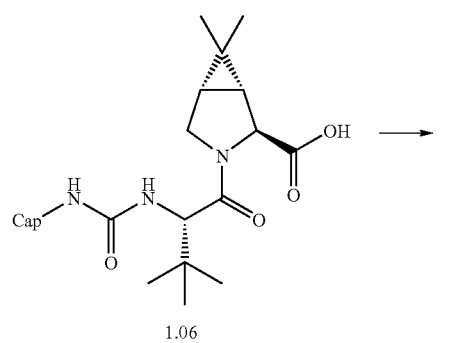
1.06

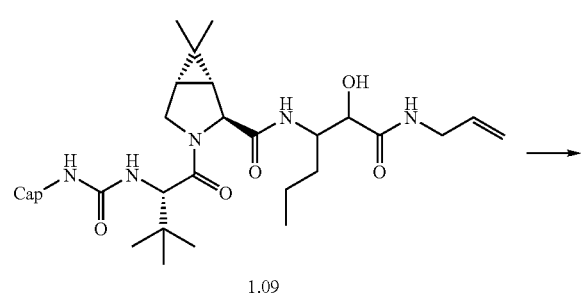
1.09

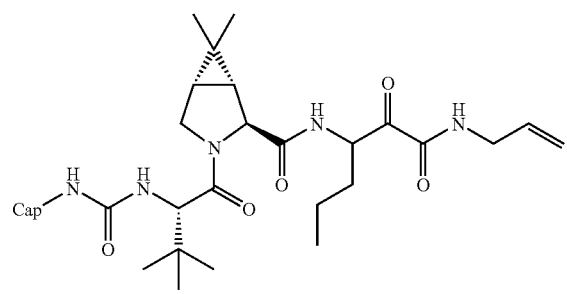
1.10

Method C

In another variation, peptide coupling of the N-Boc-P2-P$_3$-acid 1.17 with the appropriate P$_1$-P' amide moiety afforded the hydroxylamide 1.11. Oxidation (Moffatt or Dess-Martin Periodinane) resulted in the keto amide 1.12. Deprotection of the N—Boc functionality gave the hydrochloride salt 1.13. Treatment with a suitable isocyanate (or isocyanate equivalent) resulted in the target compound 1.14.

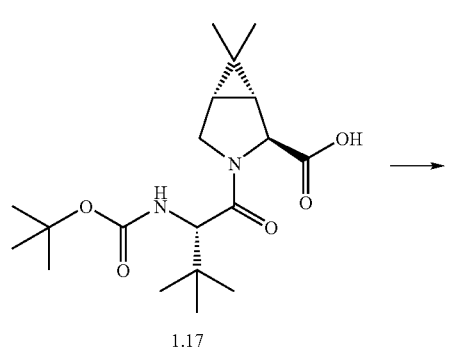
1.17

-continued

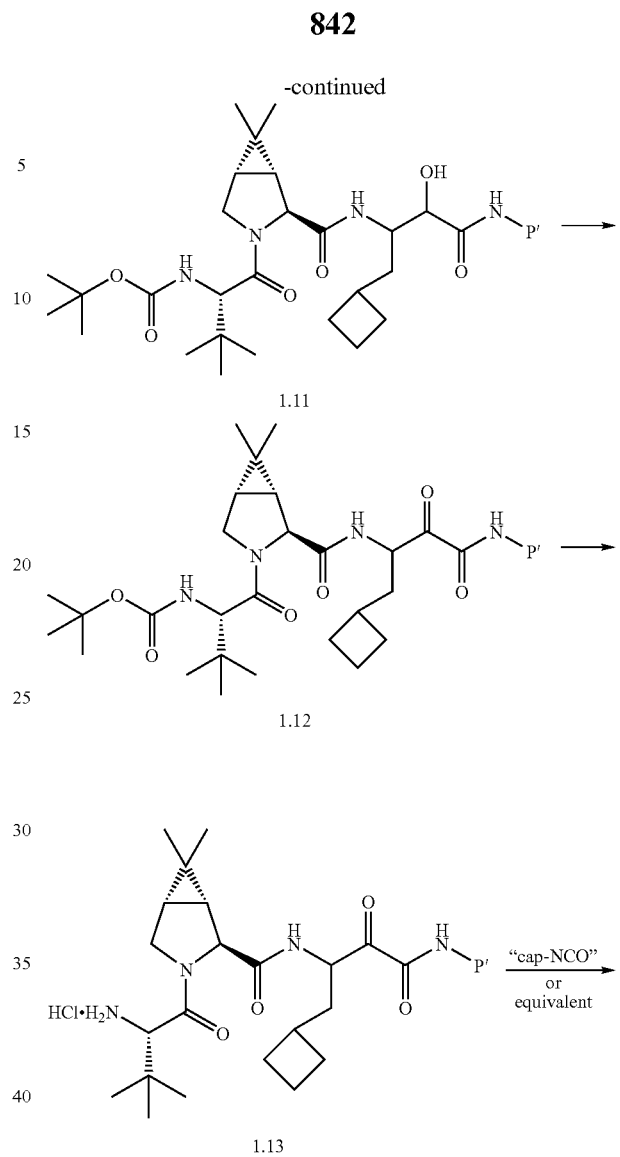

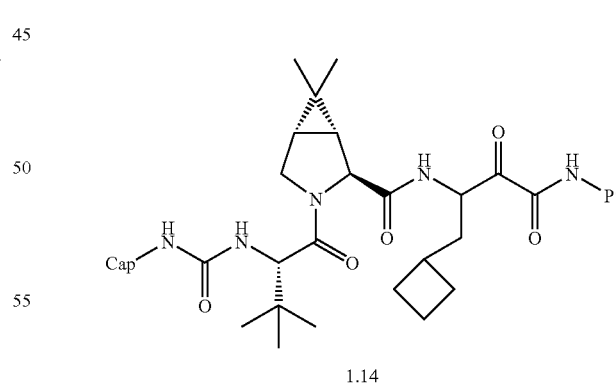
1.14

Method D

In yet another variation, the hydrochloride salt 1.13 was converted to the 4-nitrophenyl carbamate 1.15 by reaction with 4-nitrophenyl chloroformate. Subsequent treatment with an amine (or amine hydrochloride salt) of choice provided the target compound 1.14.

843

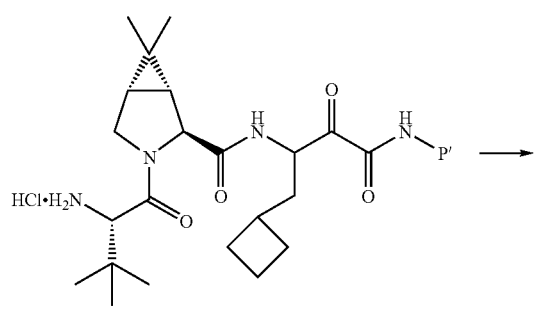

1.13

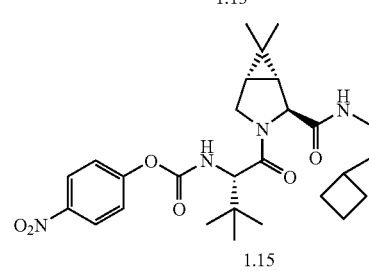

1.15

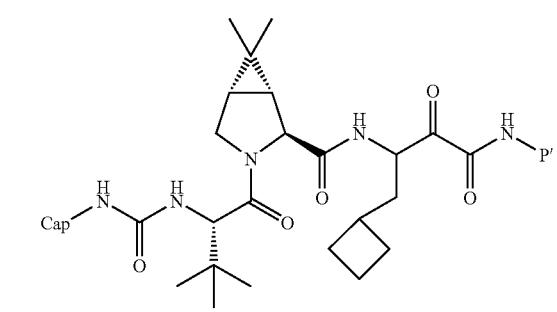

1.14

Method E

In yet another variation, the dipeptide hydrochloride salt 1.03 was converted to the 4-nitrophenyl carbamate as described above. Treatment with an amine (or amine hydrochloride salt) of choice provided the urea derivative 1.05. Hydrolysis and further elaboration as described in Methods A/B provided the target compounds 1.14.

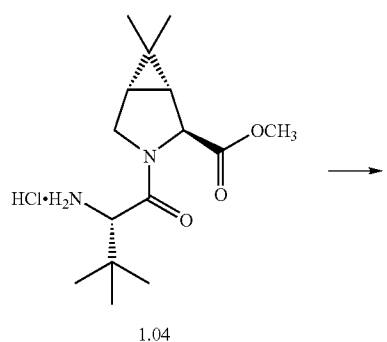

1.04

844

-continued

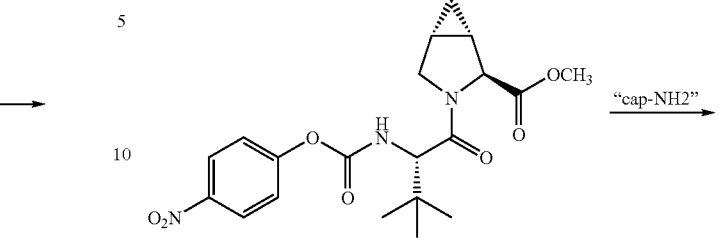

1.16

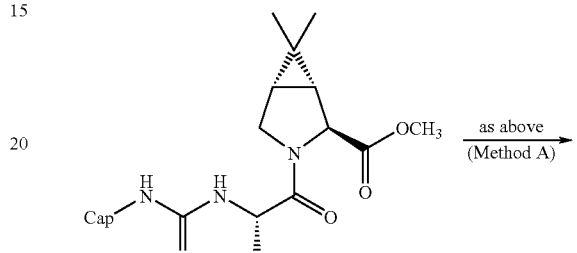

1.05

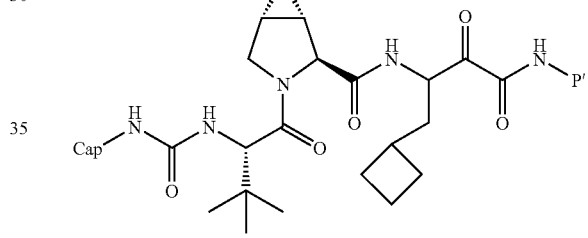

1.14

The Following Experimental Section Applies for the Preparation of the Compounds of Formula XVIII:

EXAMPLE 3

Preparation of Compound of Formula 3

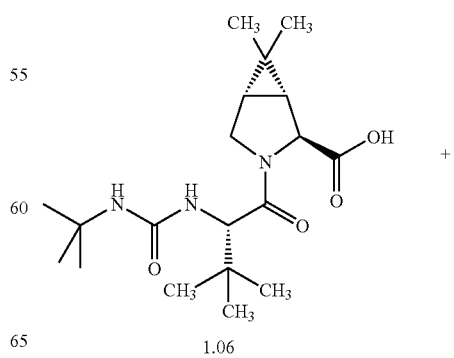

1.06

-continued

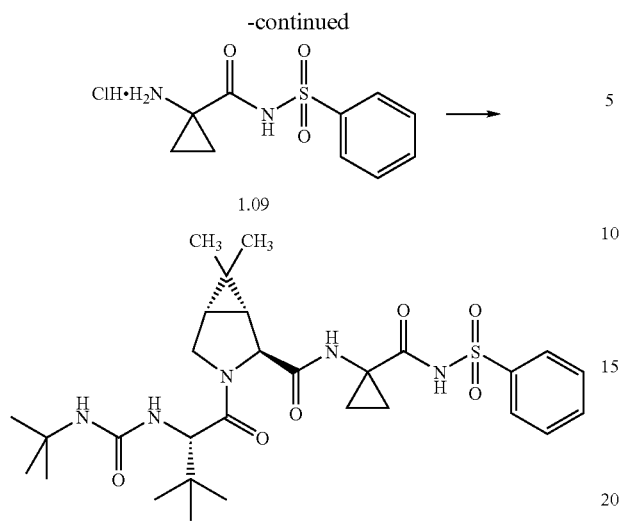

To a cooled solution (0° C.) of the intermediates 1.06 (75.0 mg, 0.2 mmol) and 1.09 (100.0 mg, 0.36 mmol) in DMF (5.0 mL) was added HATU (Aldrich, 76.05 mg, 0.20 mmol), followed by DIPEA (0.102 mL, 6 mmol). The reaction mixture was stirred for two days then warmed up to room temperature, diluted with ethyl acetate (40.0 mL), washed with 5% KH$_2$PO$_4$ containing 0.05 vol. of 1M H$_3$PO$_4$ and brine. Organic layer was dried over MgSO$_4$, filtered and concentrated to dryness. Residue was purified over silica gel using acetone-CH$_2$Cl$_2$ (1:9 to 1:1) to get 8.0 mg of product of formula 3 (6.5% yield); LCMS: (590.1).

One skilled in the art would understand that other suitable compounds of Formula XVIII can be prepared in a similar manner to that disclosed above.

The Following Experimental Section Applies for the Preparation of the Compounds of Formula XIX:

SYNTHESIS OF PREPARATIVE EXAMPLES

Synthesis of Example 101

Step 1

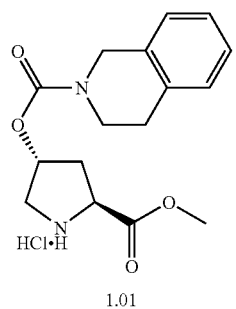

-continued

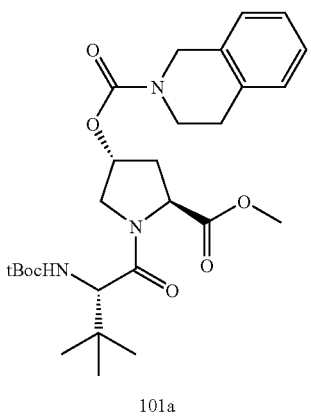

To a stirred solution of the proline derivative 1.01 (3.66 mmol, prepared as described above) in dichloromethane (20 mL) and DMF (15 mL) at 0° C. was added L-boc-tert-leucine (930 mg, 4.03 mmol), DIPEA (2.02 mL, 10.98 mmol) and HATU (1.8 g, 4.76 mmol). After 15 minutes at that temperature, the reaction flask was stored in the freezer (−20° C.), overnight (16 hr). The reaction mixture was diluted with dichloromethane (80 mL) and washed with saturated sodium bicarbonate solution (80 mL), 10% aq. citric acid solution (80 mL), brine (80 mL), dried (Na$_2$SO$_4$), filtered and concentrated. The crude material was purified by silica chromatography using 25/75 to 50/50 EtOAc/hexanes to provide 1.77 g of the required material, 101a. LC-MS: 518.1 (M+H)$^+$.

Step 2

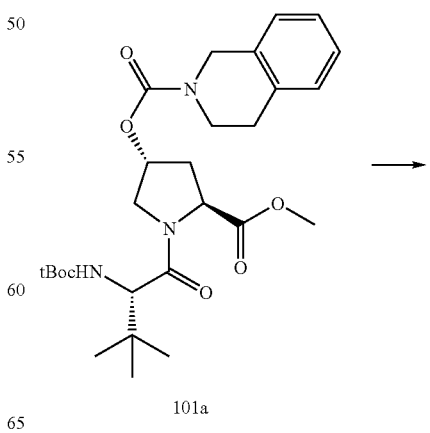

-continued

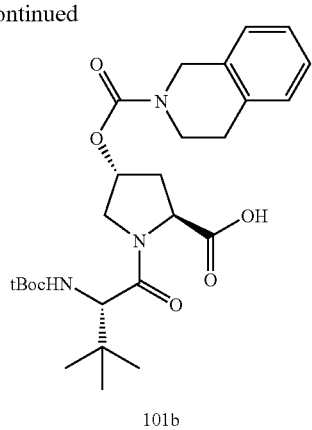

101b

To a solution of the methyl ester 101a (1.21 g, 2.34 mmol) in THF (10 mL) and MeOH (5 mL) was added aq. 1M LiOH solution (5 mL). The reaction mixture was stirred at RT for 4 h. It was then concentrated, diluted with water (50 mL) and acidified with solid citric acid (pH approximately 3) when white solid material crashed out. This solid was filtered off, washed with water and dried in vacuo to afford 970 mg of 101 b. LC-MS: 504.1 $(M+H)^+$.

Step 3

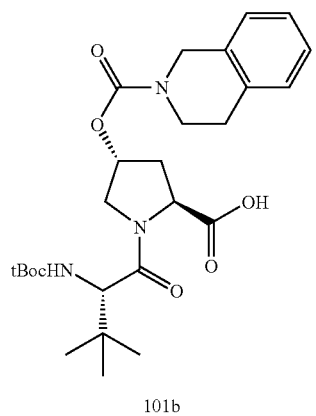

101b

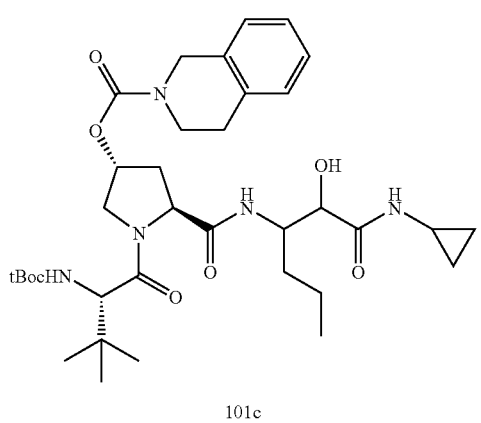

101c

The acid 101b (503 mg, 1 mmol) was coupled with intermediate 13.06 (334 mg, 1.5 mmol) using essentially procedure described above (Step 1, preparation of 101a) to provide 101c which was used without purification. MS: 672.37 $(M+H)^+$.

Step 4

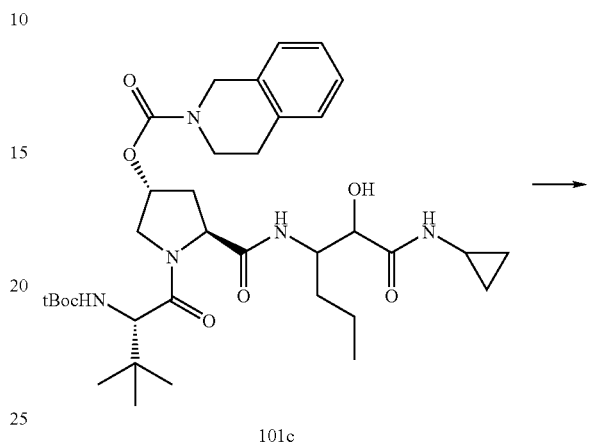

101c

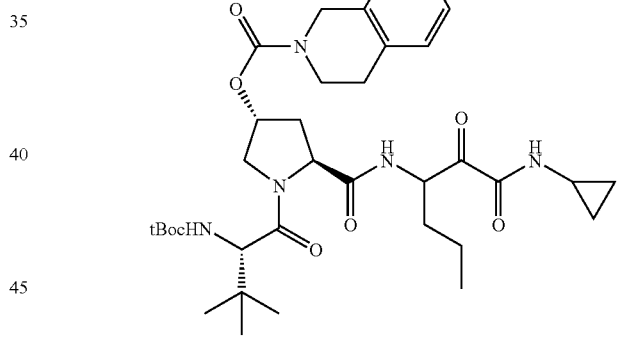

101d

To a solution of the hydroxyl compound 101c from above in dichloromethane (15 mL) was added Dess-Martin's periodinane (848 mg, 2 mmol) and the reaction mixture was stirred at RT for 5 h. At this time, the reaction mixture was diluted with dichloromethane (30 mL) and washed with 1:1 mixture of aq. 10% sodium thiosulfate solution and saturated sodium bicarbonate solution (2×25 mL each), brine (50 mL), dried (Na$_2$SO$_4$), filtered and concentrated. The crude material was purified by silica chromatography using 15/85 to 50/50 acetone/hexanes to provide 410 mg of the required material, 101d. LC-MS: 670.2 $(M+H)^+$.

Step 5

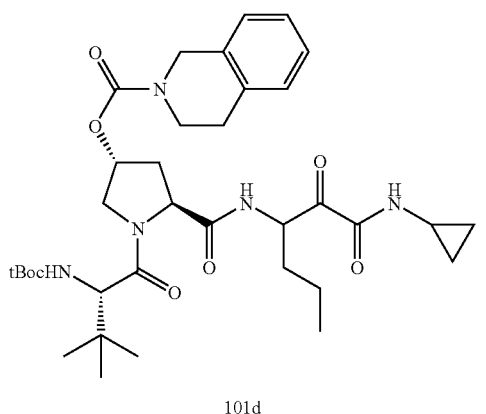

101d

To a solution of the amine salt 101e (60 mg, 0.1 mmol) in dichloromethane (2 mL) at 0° C. was added DIPEA (0.06 mL, 0.3 mmol) followed by the isocyanate intermediate 65.01 (0.25 M solution in toluene, 0.8 mL, 0.2 mmol). After 15 minutes at that temperature, the reaction flask was stored in the freezer (−20° C.), overnight (16 hr). The reaction mixture was diluted with dichloromethane (20 mL) and washed with saturated ammonium chloride solution (20 mL), brine (20 mL), dried ($Na_2SO_4$), filtered and concentrated. The crude material was purified by silica chromatography using 15/85 to 50/50 acetone/hexanes to provide the required compound 101 (53 mg); LC-MS: 872.2 $(M+H)^+$.

One skilled in the art would understand that other suitable compounds of Formula XIX can be prepared in a similar manner to that disclosed above.

The Following Experimental Section Applies for the Preparation of the Compounds of Formulae Ia, Ib and Ic:

Abbreviations:

Abbreviations which are used in the descriptions of the schemes, preparations and the examples that follow are:

THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
MeOH: Methanol
EtOH: Ethanol
Et2O: Diethyl ether
DMSO: Dimethylsulfoxide
K$^t$BuO: Potassium tert-butoxide
DCM: Dichloromethane
Chg: Cyclohexylglycine
Bn: Benzyl
Et: Ethyl
Ph: Phenyl
iPr: isopropyl
$^t$Bu or Bu$^t$: tert-Butyl
Boc: tert-Butyloxycarbonyl
Cbz: Benzyloxycarbonyl 101e Deprotection of the N-boc functionality of 101d to provide the required material 101e was carried out as described for intermediate 1.01, Step 3 (reaction time=2 h). LC-MS: 570.1 $(M+H)^+$.

Step 6

101e →

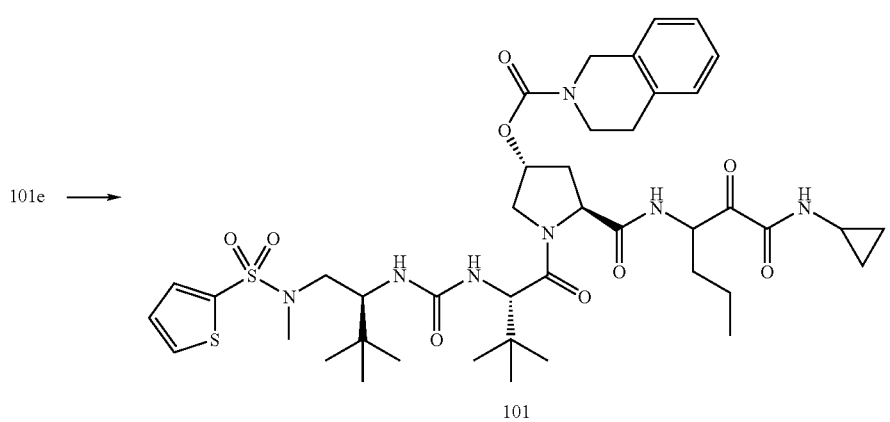

101

HATU: O-(7-azabenzotriazol-1-yl)-1,1,3,3-tetramethyluronium hexafluorophosphate
BOP: Benzotriazol-1-yl-oxy-tris(dimethylamino)hexafluorophosphate
10% Pd/C: 10% Palladium on carbon (by weight).

EXAMPLE

Synthesis of (1R,5S)-N-[3-Amino-1-(Cyclobutylmethyl)-2,3-Dioxopropyl]-3-[2(S)-[[[(1,1-Dimethylethyl)Amino]Carbonyl]Amino]-3,3-Dimethyl-1-Oxobutyl]-6,6-Dimethyl-3-Azabicyclo[3.1.0]Hexan-2(S)-Carboxamide (Structure Ia):

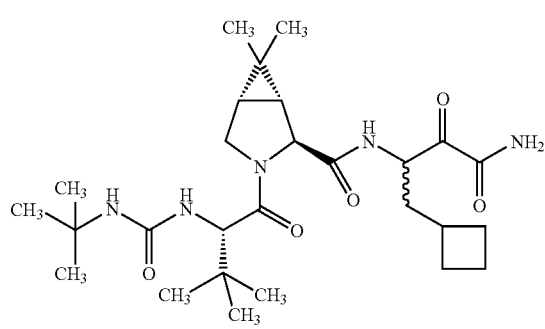

Step 1.

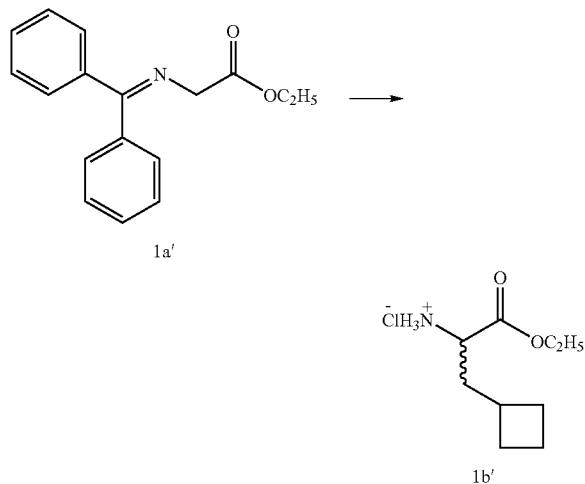

A stirred solution of the ketimime 1a' (50 g, 187.1 mmol, available from Aldrich Chemical Company, Milwaukee, Wis.) under $N_2$ in dry THF (400 mL) was cooled to −78° C. and treated with 1 M solution of K-$^t$BuO (220 mL, 1.15 equiv.) in THF. The reaction mixture was warmed to 0° C. and stirred for 1 h and treated with bromomethylcyclobutane (28 mL, 249 mmol). The reaction mixture was stirred at room temperature for 48 h and concentrated in vacuo. The residue was dissolved in $Et_2O$ (300 mL) and treated with aq. HCl (2 M, 300 mL) The resulting solution was stirred at room temperature for 5 h and extracted with $Et_2O$ (1 L). The aqueous layer was made basic to pH~12-14 with aq. NaOH (50%) and extracted with $CH_2Cl_2$ (3×300 mL). The combined organic layers were dried ($MgSO_4$), filtered, and concentrated to give pure amine (1b', 18 g) as a colorless oil.

Step 2.

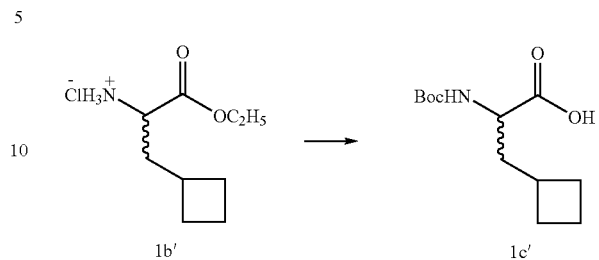

A solution of the amine 1b' (18 g, 105.2 mmol) at 0° C. in $CH_2Cl_2$ (350 mL) was treated with di-tert-butyldicarbonate (23 g, 105.4 mmol) and stirred at rt. for 12 h. After the completion of the reaction (TLC), the reaction mixture was concentrated in vacuo and the residue was dissolved in THF/$H_2O$ (200 ml, 1:1) and treated with $LiOH.H_2O$ (6.5 g, 158.5 mmol) and stirred at room temperature for 3 h. The reaction mixture was concentrated and the basic aqueous layer was extracted with $Et_2O$. The aqueous layer was acidified with conc. HCl to pH~1-2 and extracted with $CH_2Cl_2$. The combined organic layers were dried ($MgSO_4$), filtered, and concentrated in vacuo to yield 1c' as a colorless viscous oil which was used for next step without any further purification.

Step 3.

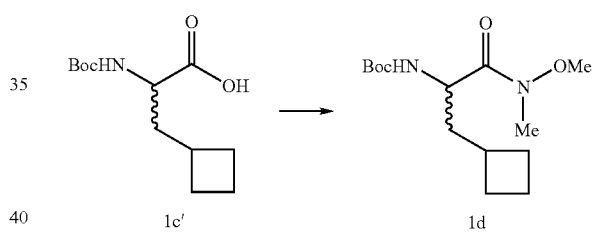

A solution of the acid 1c' (15.0 g, 62 mmol) in $CH_2Cl_2$ (250 mL) was treated with BOP reagent (41.1 g, 93 mmol), N-methylmorpholine (27 mL), N,O-dimethyl hydroxylamine hydrochloride (9.07 g, 93 mmol) and stirred overnight at rt. The reaction mixture was diluted with 1 N aq. HCl (250 mL), and the layers were separated and the aqueous layer was extracted with $CH_2Cl_2$ (3×300 ml). The combined organic layers were dried ($MgSO_4$), filtered, concentrated in vacuo and purified by chromatography ($SiO_2$, EtOAc/Hex 2:3) to yield the amide 1d (15.0 g) as a colorless solid.

Step 4.

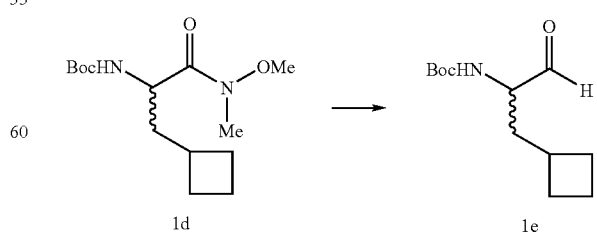

A solution of the amide 1d (15 g, 52.1 mmol) in dry THF (200 mL) was treated dropwise with a solution of $LiAlH_4$ (1M, 93 mL, 93 mmol) at 0° C. The reaction mixture was stirred at room temperature for 1 h and carefully quenched at 0° C. with a solution of KHSO$_4$ (10% aq.) and stirred for 0.5 h. The reaction mixture was diluted with aq. HCl (1 M, 150 mL) and extracted with CH$_2$Cl$_2$ (3×200 mL), The combined organic layers were washed with aq. HCl (1 M), saturated NaHCO$_3$, brine, and dried (MgSO$_4$). The mixture was filtered and concentrated in vacuo to yield 1e as viscous colorless oil (14 g).

Step 5.

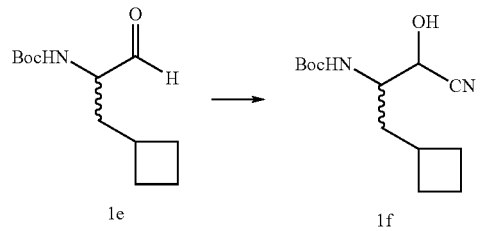

A solution of the aldehyde 1e (14 g, 61.6 mmol) in CH$_2$Cl$_2$ (50 mL), was treated with Et$_3$N (10.73 mL, 74.4 mmol), and acetone cyanohydrin (10.86 g, 127.57 mmol) and stirred at room temperature for 24 hrs. The reaction mixture was concentrated in vacuo and diluted with aq. HCl (1 M, 200 mL) and extracted into CH$_2$Cl$_2$ (3×200 mL). The combined organic layer were washed with H$_2$O, brine, dried (MgSO$_4$), filtered, concentrated in vacuo and purified by chromatography (SiO$_2$, EtOAc/Hex 1:4) to yield 1f (10.3 g) as a colorless liquid as a mixture of diastereomers.

Step 6.

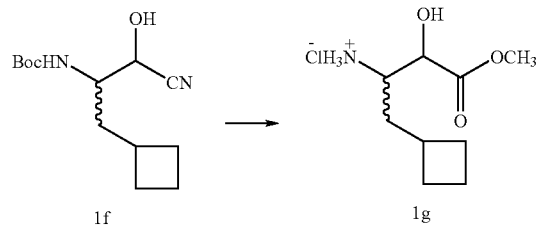

Methanol saturated with HCl*, prepared by bubbling HCl gas to CH$_3$OH (700 ml) at 0° C., was treated with cyanohydrin 1f and heated to reflux for 24 h. The reaction was concentrated in vacuo to yield 1g, which was used in the next step without purification. Alternatively 6M HCl prepared by addition of AcCl to dry methanol can also be used.

Step 7.

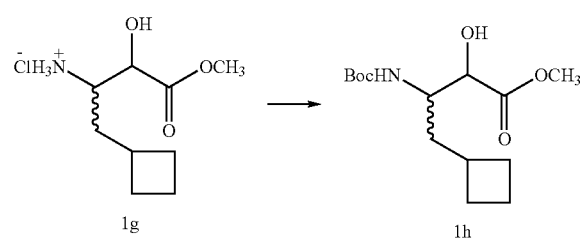

A solution of the amine hydrochloride 1g in CH$_2$Cl$_2$ (200 mL) was treated with Et$_3$N (45.0 mL, 315 mmol) and Boc$_2$O (45.7 g, 209 mmol) at −78° C. The reaction mixture was then stirred at room temperature overnight and diluted with HCl (2 M, 200 mL) and extracted into CH$_2$Cl$_2$. The combined organic layers were dried (MgSO$_4$) filtered, concentrated in vacuo and purified by chromatography (EtOAc/Hex 1:4) to yield hydroxy ester 1h.

Step 8.

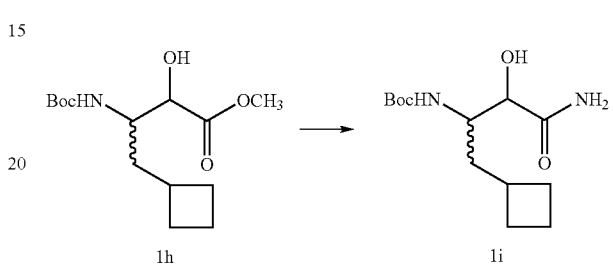

A solution of methyl ester 1h (3 g, 10.5 mmol) in THF/H$_2$O (1:1) was treated with LiOH.H$_2$O (645 mg, 15.75 mmol) and stirred at rt. for 2 h. The reaction mixture was acidified with aq HCl (1 M, 15 mL) and concentrated in vacuo. The residue was dried in vacuum.

A solution of the acid in CH$_2$Cl$_2$ (50 mL) and DMF (25 mL) was treated with NH$_4$Cl (2.94 g, 5.5 mmol), EDCl (3.15 g, 16.5 mmol), HOOBt (2.69 g, 16.5 mmol), and NMM (4.4 g, 44 mmol). The reaction mixture was stirred at room temperature for 3 d. The solvents were removed under vacuo and the residue was diluted with aq. HCl (250 mL) and extracted with CH$_2$Cl$_2$. The combined organic layers were washed with aq. saturated NaHCO$_3$, dried (MgSO$_4$) filtered concentrated in vacuo to obtain 1l, which was used as it is in the following steps. (Alternatively 1i can also be obtained directly by the reaction of 1f (4.5 g, 17.7 mmol) with aq. H$_2$O$_2$ (10 mL), LiOH.H$_2$O (820 mg, 20.8 mmol) at 0° C. in 50 mL of CH$_3$OH for 0.5 h.)

Step 9.

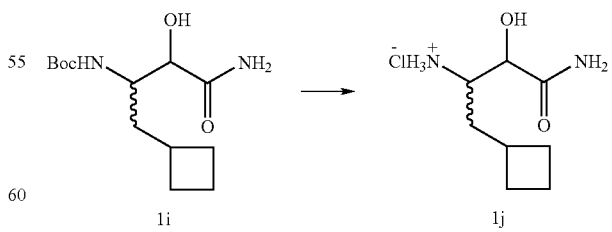

A solution of 1i obtained in the previous step was dissolved in 4 N HCl in dioxane and stirred at rt. for 2 h. The reaction mixture was concentrated in vacuo to give 1j as a solid, which was used without further purification.

Step 10.

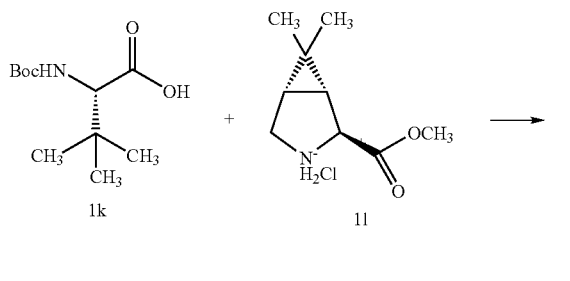

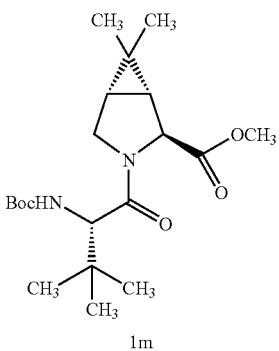

The amino ester 11 was prepared following the method of R. Zhang and J. S. Madalengoitia (*J. Org. Chem.* 1999, 64, 330), with the exception that the Boc group was cleaved by the reaction of the Boc-protected amino acid with methanolic HCl.

A solution of Boc-tert-Lue 1 k (Fluka, 5.0 g 21.6 mmol) in dry CH$_2$Cl$_2$/DMF (50 mL, 1:1) was cooled to 0° C. and treated with the amine 11 (5.3 g, 25.7 mmol), NMM (6.5 g, 64.8 mmol) and BOP reagent (11.6 g, 25.7 mmol). The reaction was stirred at rt. for 24 hrs, diluted with aq. HCl (1 M) and extracted with CH$_2$Cl$_2$. The combined organic layers were washed with HCl (aq, 1 M), saturated NaHCO$_3$, brine, dried (MgSO$_4$), filtered and concentrated in vacuo and purified by chromatography (SiO$_2$, acetone/hexane 1:5) to yield 1m as a colorless solid.

Step 11.

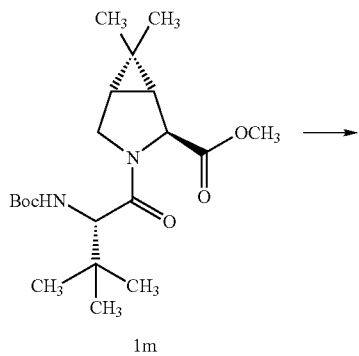

-continued

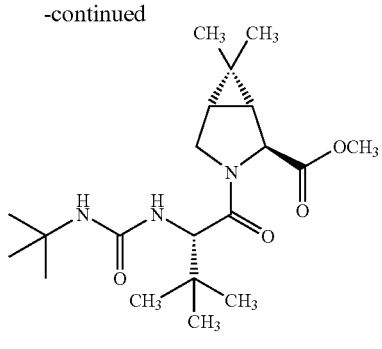

A solution of methyl ester 1m (4.0 g, 10.46 mmol) was dissolved in HCl (4 M solution in dioxane) and stirred at rt. for 3 h. The reaction mixture was concentrated in vacuo to obtain the amine hydrochloride salt used in the next step without further purification.

A solution of the amine hydrochloride salt (397 mg, 1.24 mmol) in CH$_2$Cl$_2$ (10 mL) was cooled to −78° C. and treated with tert-butyl isocyanate (250 mg, 2.5 mmol) and stirred at rt. overnight. The reaction mixture was concentrated in vacuo and the residue was diluted with aq. HCl (1M) and extracted with CH$_2$Cl$_2$. The combined organic layers were washed with aq. HCl (1M), saturated NaHCO$_3$ and brine. The organic layers were dried, filtered and concentrated in vacuo and the residue was purified by chromatography (SiO$_2$, acetone/Hex 1:4) to yield 1n as a colorless solid.

Step 12.

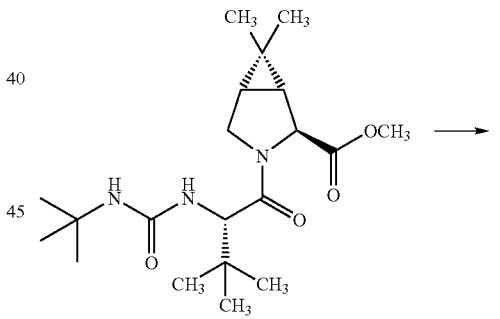

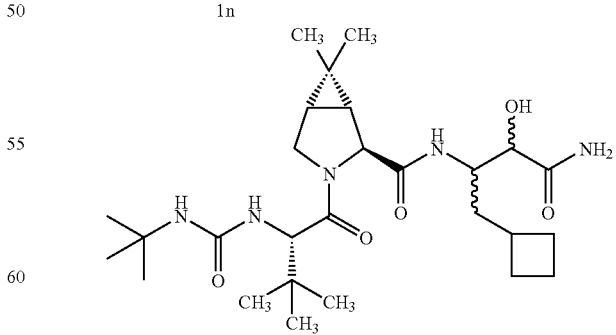

A solution of methyl ester 1n (381 mg, 1.0 mmol) in THF/H$_2$O (1:1, 5 mL) was treated with LiOH.H$_2$O (62 mg, 1.5 mmol) and stirred at rt. for 3 h. The reaction mixture was acidified with aq. HCl and concentrated in vacuo to obtain the free acid.

A solution of acid (254.9 mg, 0.69 mmol) in DMF/CH₂Cl₂ (1:1, 5.0 mL) was treated with amine 1j (159 mg, 0.763 mmol), EDCl (199 mg, 1.04 mmol), HOOBt (169.5 mg, 1.04 mmol) and NMM (280 mg, 2.77 mmol) at −20° C. The reaction mixture was stirred at −20° C. for 48 h and concentrated in vacuo. The residue was diluted with aq. 1M HCl and extracted with EtOAc, The combined organic layers were extracted with aq. NaHCO₃, aq. HCl, brine, dried (MgSO₄) filtered, concentrated in vacuo to obtain 1o (470 mg) as a tan colored solid that was used in the next reaction without further purification.

Step 13.

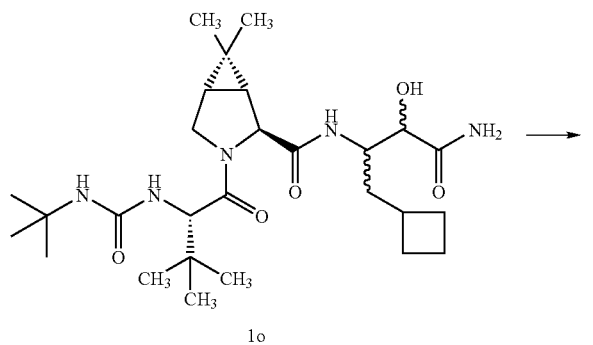

1o

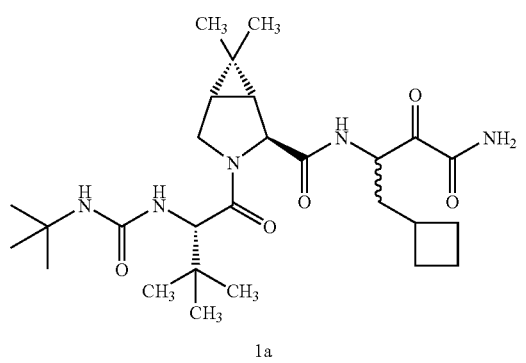

1a

A solution of amide 1o (470 mg, 0.9 mmol) in toluene and DMSO (1:1 20 mL) at 0° C. was treated with EDCl (1.72 g, 9.0 mmol) and dichloroacetic acid (0.37 mL, 4.5 mmol) and stirred at 0° C. for 4 hrs. The reaction mixture was diluted with CH₂Cl₂, and washed with saturated NaHCO₃, and brine. The organic layer was dried (MgSO₄), filtered, concentrated, in vacuo and purified by chromatography (SiO₂, acetone/hexanes 3:7) to yield 1a as a colorless solid.

Separation of the Compound of Formula 1 into Diastereomers of Formulas Ib and Ic:

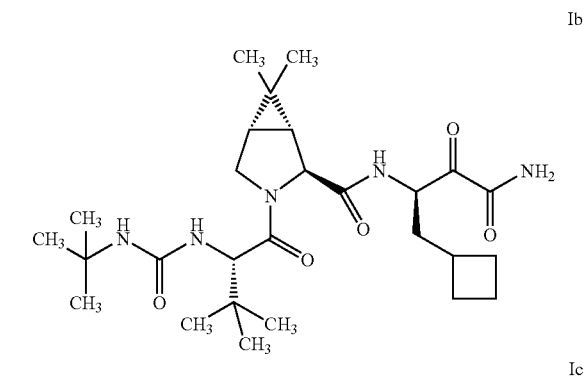

Ib

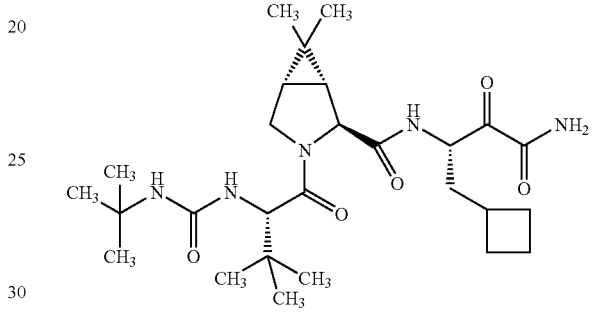

Ic

Preparative HPLC Condition for Separation

COLUMN USED: NORMAL PHASE YMC DIOL-NP COLUMN 120 Å, S-10/20; 50 mm×500 mm I.D/length
SOLVENT A: Hexanes
SOLVENT B: To make 4 L of solvent (1.7 L Isopropanol+300 mL of CH₃CN+2 L of CH₂Cl₂)
HPLC CONDITIONS: 12% of Solvent B/88% of Solvent A
FLOW: 120 mL/min Procedure: 1 g of compound 1a was dissolved in 10 mL of CH₂Cl₂/25 mL of Hexanes and injected into the column. It was eluted with 120 mL/min and two peaks were independently collected and concentrated. The solid residue was further dried in high vacuum and analyzed by analytical HPLC. Since the polar (second isomer) contained 2.6% of nonpolar diastereomer (First isomer), it was purified once more to isolate the pure diastereomers.

Analytical Conditions for Analysis of Diastereomeric Purity

COLUMN USED: NORMAL PHASE YMC DIOL-NP COLUMN 200 Å, S-5 □M; 150 mm×3 mm length/I.D
SOLVENT A: Hexanes
SOLVENT B: To make 4 L of solvent (1.7 L Isopropanol+300 mL of CH₃CN+2 L of CH₂Cl₂)
HPLC CONDITIONS: 8.5% of Solvent B/91.5% of Solvent A
FLOW: 0.7 mL/min
Rt Nonpolar isomer (compound Ib)=13.2 min Polar isomer (compound Ic)=16.1 min 2.5 mg of compound in 1 mL was used and 20 μL was injected and analyzed with a U.V detector at □=254 nm.

Analytical Data for Compounds 2 and 3.

Compound 3 [Polar Diastereomer]

$^1$H NMR (d$_6$-dmso, 500 MHz): ☐ 8.26 (d, 1 H, J=7.0 Hz), 8.00 (s, 1 H), 7.75 (s, 1 H), 5.96 (s, 1 H), 5.84 (d, 1 H, J=10 Hz), 4.96 (m, 1 H), 4.28 (s, 1H), 4.11 (d, 1 H, J=11 Hz), 3.94 (d, 1H, J=10 Hz), 3.73 (dd, 1 H, J=10 & 5 Hz), 2.48 (m, 1 H), 1.95 (m, 2H), 1.61 (m, 1 H), 1.59 (m, 1 H), 1.77(m, 1 H), 1.57 (m, 1 H), 1.74 (m, 2 H), 1.42 (dd, 1 H, J=7.5 & 5 Hz), 1.28 (d, 1 H, J=7.5 Hz), 1.17 (s, 9 H), 1.01 (s, 3 H), 0.90 (s, 9 H), 0.85 (s, 3 H). $^{13}$C NMR (d$_6$-dmso, 125 MHζ): ☐ 197.8, 170.9, 170.8, 162.8, 157.4, 59.1, 56.8, 51.8, 48.9, 47.4, 36.7, 34.0, 32.0, 30.6, 29.1, 27.8, 27.3, 27.1, 26.4, 26.1, 18.5, 17.7, 12.5. MS [FAB] 520 (55), 421 (100), 308 (75), 213 (90). HRMS calcd for C$_{27}$H$_{46}$O$_5$N$_5$ [M+1]$^+$ 520.3499; observed: 520.3505.

Compound 2 [Non-polar Diastereomer]

$^1$H NMR (d$_6$-dmso, 500 MHz): ☐ 8.15 (d, 1 H, J=7.0 Hz), 7.96 (s, 1 H), 7.74 (s, 1 H), 5.96 (s, 1 H), 5.86 (d, 1 H, J=10 Hz), 4.85 (m, 1 H), 4.27 (s, 1H), 4.13 (d, 1 H, J=11.0 Hz), 3.97 (d, 1H, J=10 Hz), 3.76 (dd, 1 H, J=10 & 5 Hz), 2.36 (m, 1 H), 1.97 (m, 2H), 1.60 (m, 2 H), 1.78 (m, 1 H), 1.64 (m, 1 H), 1.75 (m, 2 H), 1.44 (dd, 1 H, J=7.5 & 5 Hz), 1.27 (d, 1 H, J=7.5 Hz), 1.17 (s, 9 H), 1.00 (s, 3 H), 0.89 (s, 9 H), 0.82 (s, 3 H). $^{13}$C NMR (d$_6$-dmso125 MHζ): δ 197.1, 171.1, 170.7, 163.0, 157.3, 59.4, 56.9, 52.1, 48.9, 47.4, 36.6, 34.0, 32.1, 30.5, 29.1, 27.9, 27.4, 26.8, 26.4, 26.1, 18.5, 17.8, 12.4. MS [FAB] 520 (40), 421 (100), 308 (60), 213 (65). HRMS calcd. for C$_{27}$H$_{46}$O$_5$N$_5$ [M+1]$^+$ 520.3499; observed: 520.3514.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Each document (including granted patents, published patent applications, and nonpatent publications such as journal articles) referred to in this application is incorporated in its entirety by reference for all purposes.

What is claimed is:

1. A pharmaceutical formulation comprising:
   (a) at least one surfactant present in an amount of about 0.1 to about 10% by weight; and
   (b) at least one compound wherein said compound is present in an amount of about 50 to about 1000 mg which is:

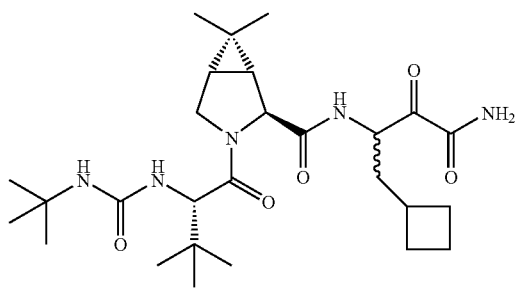

Formula Ia

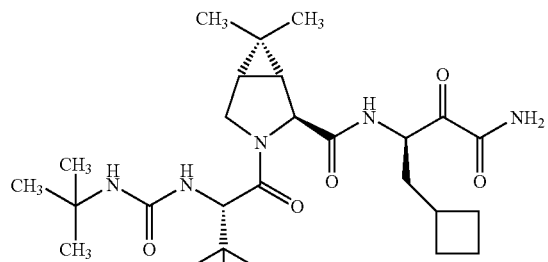

Formula Ib

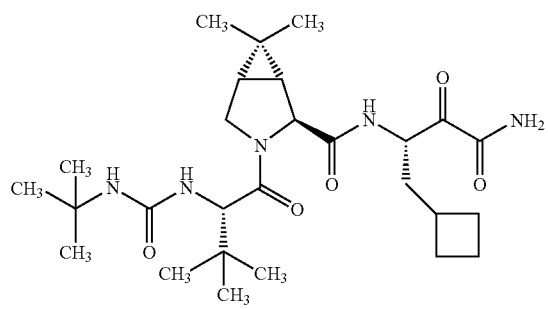

Formula Ic

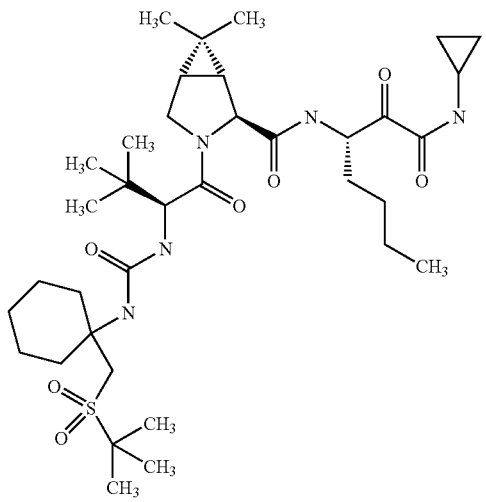

Formula Id or a pharmaceutically acceptable salt thereof, wherein said at least one surfactant is selected from the group consisting of sodium lauryl sulfate, monoethanolamine, docusate sodium, poloxamer, lecithin, sorbitan fatty acid esters, polyoxyethylene sorbitan fatty acid esters, ethoxylated aliphatic alcohols, propylene glycol monocaprylate, glycerol monostearate, medium chain triglycerides, polyoxyethylene alkyl ethers, and polyoxyethylene stearates.

2. The pharmaceutical formulation of claim 1 wherein said at least one surfactant comprises sodium lauryl sulfate.

3. The pharmaceutical formulation of claim 1 wherein said formulation is in capsule form.

4. A method of treating HCV infection comprising administering an effective amount of the pharmaceutical formulation of claim 1 to a subject in need of such treatment.

5. A method of treating a capthesin-associated disorder comprising administering an effective amount of the pharmaceutical formulation of claim 1 to a subject in need of such treatment.

6. The pharmaceutical formulation of claim 2 further comprising 0.1 to 15% by weight of a lubricant.

7. The pharmaceutical formulation of claim 6 wherein the lubricant is magnesium stearate.

8. The pharmaceutical formulation of claim 1 further comprising one or more carriers, binders or disintegrants, or a mixture of two or more thereof.

9. The pharmaceutical formulation of claim 2, further comprising magnesium stearate and one or more carriers, binders or disintegrants, or a mixture of two or more thereof.

10. A pharmaceutical formulation, comprising;
 (a) a surfactant which is sodium lauryl sulfate present in an amount of about 0.1 to about 10% by weight and
 (b) at least one compound wherein said compound is present in an amount of about 50 to about 1000 mg which is:

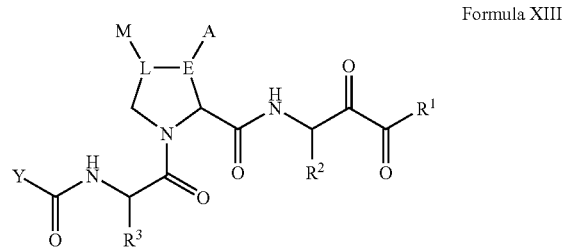

Formula XIII or a pharmaceutically acceptable salt thereof.

* * * * *

UNITED STATES PATENT AND TRADEMARK OFFICE
CERTIFICATE OF CORRECTION

PATENT NO. : 7,772,178 B2  
APPLICATION NO. : 11/444078  
DATED : August 10, 2010  
INVENTOR(S) : Bruce A. Malcolm et al.

Page 1 of 1

It is certified that error appears in the above-identified patent and that said Letters Patent is hereby corrected as shown below:

Claim 10, at Column 862, lines 3-16, replace:
"which is:

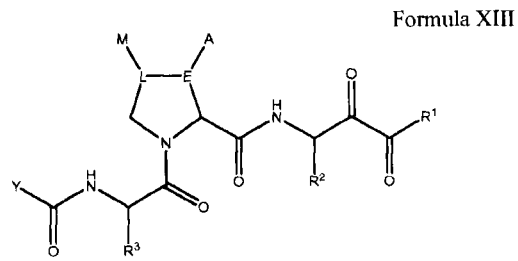

Formula XIII or a pharmaceutically acceptable salt thereof."

with the following:

--which is:

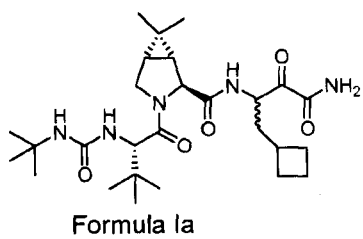

Formula Ia

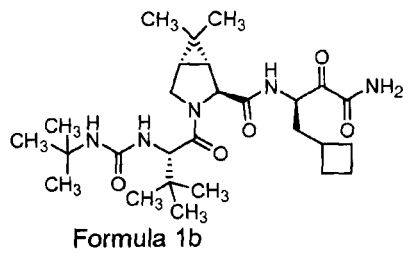

Formula Ib

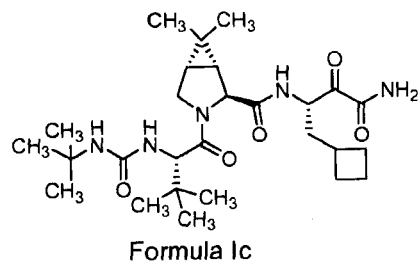

Formula Ic or a pharmaceutically acceptable salt thereof.--

Signed and Sealed this  
First Day of February, 2011

David J. Kappos  
*Director of the United States Patent and Trademark Office*